US007704720B2

(12) United States Patent
Tang et al.

(10) Patent No.: US 7,704,720 B2
(45) Date of Patent: Apr. 27, 2010

(54) METAPNEUMOVIRUS STRAINS AND THEIR USE IN VACCINE FORMULATIONS AND AS VECTORS FOR EXPRESSION OF ANTIGENIC SEQUENCES AND METHODS FOR PROPAGATING VIRUS

(75) Inventors: Roderick Tang, San Mateo, CA (US); Jeanne H. Schickli, Sunnyvale, CA (US)

(73) Assignees: MedImmune, LLC, Gaithersburg, MD (US); ViroNovative BV, Rotterdam (NL)

( * ) Notice: Subject to any disclaimer, the term of this patent is extended or adjusted under 35 U.S.C. 154(b) by 1623 days.

(21) Appl. No.: 10/831,780

(22) Filed: Apr. 23, 2004

(65) Prior Publication Data

US 2005/0019891 A1 Jan. 27, 2005

Related U.S. Application Data

(60) Provisional application No. 60/465,811, filed on Apr. 25, 2003, provisional application No. 60/466,776, filed on Apr. 30, 2003, provisional application No. 60/480,658, filed on Jun. 20, 2003, provisional application No. 60/498,640, filed on Aug. 28, 2003, provisional application No. 60/550,911, filed on Mar. 5, 2004.

(51) Int. Cl.
*C12N 7/00* (2006.01)
*C12N 7/02* (2006.01)
*C12N 7/04* (2006.01)

(52) U.S. Cl. ..................... 435/235.1; 435/236; 435/239

(58) Field of Classification Search ............... 435/235.1
See application file for complete search history.

(56) References Cited

U.S. PATENT DOCUMENTS

| | | | | |
|---|---|---|---|---|
| 5,166,057 | A | 11/1992 | Palese et al. | |
| 5,824,307 | A | 10/1998 | Johnson | |
| 5,854,037 | A | 12/1998 | Palese et al. | |
| 5,869,036 | A | 2/1999 | Belshe et al. | |
| 6,146,642 | A | 11/2000 | Garcia-Sastre et al. | |
| 6,180,398 | B1 | 1/2001 | Klein et al. | |
| 2002/0155581 | A1 | 10/2002 | Murphy et al. | |
| 2003/0232061 | A1 | 12/2003 | Fouchier et al. | |
| 2003/0232326 | A1 | 12/2003 | Fouchier et al. | |
| 2004/0005544 | A1 | 1/2004 | Fouchier et al. | |
| 2004/0005545 | A1 | 1/2004 | Fouchier et al. | |
| 2004/0229219 | A1 | 11/2004 | Gallagher et al. | |
| 2004/0241188 | A1 * | 12/2004 | Collins et al. | 424/199.1 |
| 2005/0053919 | A1 | 3/2005 | De Jong et al. | |
| 2005/0118195 | A1 | 6/2005 | De Jong et al. | |
| 2005/0142148 | A1 | 6/2005 | Fouchier et al. | |

FOREIGN PATENT DOCUMENTS

| | | |
|---|---|---|
| EP | 0 702 085 A1 | 2/1996 |
| EP | 0 780 475 A1 | 6/1997 |
| EP | 01200213.5 | 1/2001 |
| EP | 01203985.5 | 10/2001 |
| FR | 2 801 607 A1 | 11/1999 |
| WO | WO 89/10405 | 11/1989 |
| WO | WO 93/14207 | 7/1993 |
| WO | WO 96/34625 | 11/1996 |
| WO | WO 97/06270 | 2/1997 |
| WO | WO 97/12032 | 4/1997 |
| WO | WO 97/34008 | 9/1997 |
| WO | WO 98/02530 | 1/1998 |
| WO | WO 98/13501 | 4/1998 |
| WO | WO 98/53078 | 11/1998 |
| WO | WO 99/02657 | 1/1999 |
| WO | WO 99/15672 | 4/1999 |
| WO | WO 00/20600 | 4/2000 |
| WO | WO 01/04320 | 1/2001 |
| WO | WO 01/38497 | 5/2001 |
| WO | WO 01/42445 | 6/2001 |
| WO | WO 02/057302 | 7/2002 |
| WO | WO 03/043587 | 5/2003 |

(Continued)

OTHER PUBLICATIONS

Schickli et al. Journal of Virology 2005 vol. 79 No. 16, pp. 10678-10689.*

(Continued)

*Primary Examiner*—Mary E Mosher
*Assistant Examiner*—Myron G Hill
(74) *Attorney, Agent, or Firm*—Jones Day

(57) ABSTRACT

The present invention provides an isolated mammalian negative strand RNA virus, *metapneumovirus* (MPV), within the sub-family *Pneumoviridae*, of the family Paramyxoviridae. The invention also provides isolated mammalian negative strand RNA viruses identifiable as phylogenetically corresponding or relating to the genus *Metapneumovirus* and components thereof. In particular the invention provides a mammalian MPV, subgroups and variants thereof. The invention relates to genomic nucleotide sequences of different isolates of mammalian *metapneumoviruses*, in particular human *metapneumoviruses*. The invention relates to the use of the sequence information of different isolates of mammalian *metapneumoviruses* for diagnostic and therapeutic methods. The present invention relates to nucleotide sequences encoding the genome of a *metapneumovirus* or a portion thereof, including both mammalian and avian *metapneumovirus*. The invention further encompasses chimeric or recombinant viruses encoded by said nucleotide sequences. The invention also relates to chimeric and recombinant mammalian MPV that comprise one or more non-native or heterologous sequences. The invention further relates to vaccine formulations comprising mammalian or avian *metapneumovirus*, including recombinant and chimeric forms of said viruses. The vaccine preparations of the invention encompass multivalent vaccines, including bivalent and trivalent vaccine preparations. The invention also provide methods for propagating virus.

6 Claims, 147 Drawing Sheets

FOREIGN PATENT DOCUMENTS

Figure 3:
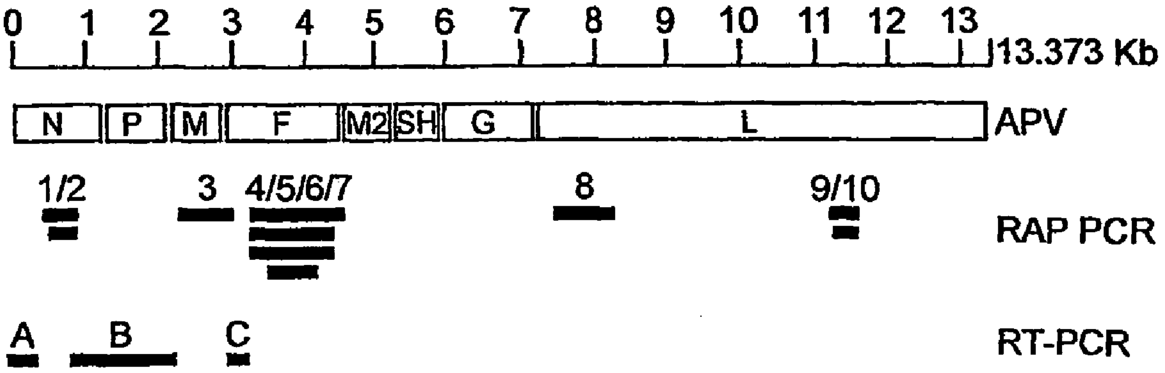

| | | |
|---|---|---|
| WO | WO 03/072720 | 9/2003 |
| WO | WO 03/097089 | 11/2003 |
| WO | WO 2004/057021 | 7/2004 |
| WO | WO 2005/014626 | 2/2005 |

OTHER PUBLICATIONS

Williams et al., 2006, "The role of human metapneumovirus in upper respiratory tract infections in children: a 20-year experience," J Infect Dis. 193(3):387-95.
Nissen et al., 2002, "Evidence of human metapneumovirus in Australian children," Med J Aust. Feb. 18, 2002;176(4):188.
Bastien et al., 2003, "Sequence analysis of the N, P, M and F genes of Canadian human metapneumovirus strains," Virus Res. 93(1):51-62.
Greensill et al., 2003, "Human metapneumovirus in severe respiratory syncytial virus bronchiolitis," Emerg. Infect. Dis. 9(3):372-5.
Schmidt et al., 2001, "Recombinant bovine/human parainfluenza virus type 3 (B/HPIV3) expressing the respiratory syncytial virus (RSV) G and F proteins can be used to achieve simultaneous mucosal immunization against RSV and HPIV3," J. Virol. 75(10):4594-603.
Tang et al., 2003, "Effects of human metapneumovirus and respiratory syncytial virus antigen insertion in two 3' proximal genome positions of bovine/human parainfluenza virus type 3 on virus replication and immunogenicity," J. Virol. 77(20):10819-28.
Database EMBL Online, 2001, Database Accession No. AF371337.
Database EMBL Online, 2002, Database Accession No. AY145294.
Bailly et al., 2000, "A recombinant human parainfluenza virus type 3 (PIV3) in which the nucleocapsid N protein has been replaced by that of bovine PIV3 is attenuated in primates," J. Virol. 74: 3188-3195.
Barr, 1991, "Mammalian subtilisins: the long-sought dibasic processing endoproteases," Cell 66: 1-3.
Bastien et al., 2003, "Human metapneumovirus infection in the Canadian population," J. Clin. Microbiol. 41: 4642-4646.
Boivin et al., 2002, "Virological features and clinical manifestations associated with human metapeumovirus: a new paramyxovirus responsible for acute respiratory-tract infections in all age groups," J. Infect. Dis. 186: 1330-1334.
Boivin et al., 2003, "Human metapneumovirus infections in hospitalized children," Emerg. Infect. Dis. 9: 634-640.
Bosch et al., 1981, "Proteolytic cleavage of influenza virus hemagglutinin. Primary structure of the connecting peptide between HA1 and HA2 determines proteolytic cleavability and pathogenicity of avian influenza viruses," Virology 113: 725-735.
Botts et al., 1984, "On the mechanism of energy transduction in myosin subfragment 1," PNAS USA 81: 2060-2064.
Breker-Klassen et al. 1996, "Comparisons of the F and HN gene sequences of different strains of bovine parainfluenza virus type 3: relationship to phenotype and pathogenicity," Can. J. Vet. Res. 60:228-236.
Chanock et al., 1989, "Respiratory Syncytial Virus," Chapter 20 in: Viral Infections of Humans. Epidemiology and Control, 3rd ed., Evans, ed., Plenum Publishing Corp., New York, NY pp. 525-544.
Clements et al. 1991, "Evaluation of bovine, cold-adapted human, and wild-type human parainfluenza type 3 viruses in adult volunteers and in chimpanzees," J. Clin. Microbiol. 29(6):1175-1182.
Collins et al., 1991, "Post translational processing and oligomerization of the fusion glycoprotein of human respiratory syncytial virus," J. Gen. Virol. 72: 3095-4101.
Collins et al., 1993, "Deduced amino acid sequences at the fusion protein cleavage site of Newcastle disease viruses showing variation in antigenicity and pathogenicity," Arch. Virol. 128: 363-370.
Collins et al., 1996, "Respiratory Syncytial Virus," Chapter 44 in: Fields Virology, Third Ed., Fields, Knipe & Howley, eds., Lippencott-Raven, Philadelphia PA, pp. 1313-1351.
Collins et al., 2001, "Respiratory Syncytial Virus," Chapter 45 in: Fields Virology, Fourth Ed., Knipe & Howley, eds., Lippincott Williams and Wilkins, Philadelphia, PA, pp. 1443-1486.
Collins, 1991, "The Molecular Biology of Human Respiratory Syncytial Virus (RSV) of the Genus Pneumovirus," Chapter 4 in: The Paramyxoviruses, D.W. Kingsbury, ed. Plenum Press, New York, pp. 103-162.
Cook et al., 1999, "Preliminary antigenic characterization of an avian pneumovirus isolated from turkeys in Colorado, USA," Avian Pathol. 28:607-617.
Cook, 2000, "Avian rhinotracheitis," Rev. Sci. Tech. 19: 602-613.
Crookshanks et al., 1984, "Evaluation of cold-adapted and temperature-sensitive mutants of parainfluenza virus type 3 in weanling hamsters," J Med Virol. 13: 243-249.
Dimock et al., 1993, "Rescue of synthetic analogs of genomic RNA and replicative-intermediate RNA of human parainfluenza virus type 3," J Virol. 67: 2772-8.
Glickman et al., 1988, "Quantitative basic residue requirements in the cleavage-activation site of the fusion glycoprotein as a determinant of virulence for Newcastle disease virus," J. Virol. 62: 354-356.
Gonzalez-Reyes et al., 2001, "Cleavage of the human respiratory syncytial virus fusion protein at two distinct sites is required for activation of membrane fusion," PNAS 98: 9859-9864.
Hall, 1987, "Respiratory Syncytial Virus", in: Textbook of Pediatric Infectious Diseases, Second Ed., Feigin and Cherry, authors, W.B. Saunders Co., Philadelphia, PA, pp. 1653-1676.
Haller et al. 2000, "Expression of the surface glycoproteins of human parainfluenza virus type 3 by bovine parainfluenza virus type 3, a novel attenuated virus vaccine vector," J. Virol. 74:11626-11635.
Hamelin et al., 2004, "Human metapneumovirus: a new player among respiratory viruses," Clinical Infectious Diseases 38: 983-990.
Herfst, 2004, "Recovery of human metapneumovirus genetic lineages A and B from cloned cDNA," J. Virol. 78:8264-8270.
Hoffmann et al. 2000, "Unidirectional RNA polymerase I-polymerase II transcription system for the generation of influenza A virus from eight plasmids," J. Gen. Virol. (Pt 12):2843-2847.
Howe, 2002, "Australian find suggests worldwide reach for metapneumovirus," Lancet Infect. Dis. 2:202.
Ijpma et al., 2004, "Human metapneumovirus infection in hospital referred South African children," J. Med. Virol. 73: 486-493.
Ishida et al., 1978, "Sendai virus," Adv. Virus Res. 23: 349-383.
Johnson et al. 1997, "Development of a humanized monoclonal antibody (MEDI-493) with potent in vitro and in vivo activity against respiratory syncytial virus," J Infect Dis. 176:1215-1224.
Karron et al., 1995, "A live attenuated bovine parainfluenza virus type 3 vaccine is safe, infectious, immunogenic, and phenotypically stable in infants and children," J. Infect. Dis. 171:1107-1114.
Karron et al., 1996, "Evaluation of a live attenuated bovine parainfluenza type 3 vaccine in two- to six-month-old infants," Pediatr. Infect. Dis. J. 15: 650-654.
Kawaoka et al., 1984, "Is virulence of H5N2 influenza viruses in chickens associated with loss of carbohydrate from the hemagglutinin?" Virology 139: 303-316.
Kido et al., 1992, "Isolation and characterization of a novel trypsin-like protease found in rat bronchiolar epithelial Clara cells: a possible activator of the viral fusion glycoprotein," J. Biol. Chem. 267: 13573-13579.
Kido et al., 1996, "Cellular proteases involved in the pathogenicity of enveloped animal viruses, human immunodeficiency virus, influenza virus A and Sendai virus," Adv. Enzyme Regul. 36: 325-47.
Klenk et al., 1988, "The molecular biology of influenza virus pathogenicity," Adv. Virus Res. 34: 247-281.
Klenk et al., 1994, "Host cell proteases controlling virus pathogenicity," Trends Microbiol. 2: 39-43.
Klippmark et al., 1990, "Antigenic variation of human and bovine parainfluenza virus type 3 strains," J. Gen. Virol. 71 ( Pt 7):1577-80.
Kunkel et al., 1985, "Rapid and efficient site-specific mutagenesis without phenotypic selection," Proc Natl Acad Sci U S A. 82: 488-492.
Lamb, 1993, "Paramyxovirus fusion: A hypothesis for changes," Virology 197: 1-11.
Maggi et al., 2003, "Human metapneumovirus associated with respiratory tract infections in a 3-year study of nasal swabs from infants in Italy," J. Clinical Microbiology 41: 2987-2991.
Morrison, 2003, "Structure and function of a paramyxovirus fusion protein," Biochimica Et Biophysica Acta 1614: 73-84.
Nagai et al., 1989, "Molecular biology of Newcastle disease virus," Prog. Vet. Microbiol. Immunol. 5:16-64.

New Vaccine Development, Establishing Priorities, vol. 1, 1985, National Academy Press, Washington DC pp. 397-409.
Oomens et al., 2003, "Recovery of infectious human respiratory syncytial virus lacking all transmembrane glycoprotein genes via trans-complementation," 12th Int'l. Conf. on Negative Strand Viruses, Pisa, Italy, Abstr# 205.
Osterhaus et al., 2000, "Influenza B virus in seals," Science 288(5468):1051-3.
Peiris et al., 2003, "Children with respiratory disease associated with metapneumovirus in Hong Kong," Emerg. Infect. Dis. 9: 628-633.
Peret et al., 2004, "Sequence polymorphism of the predicted human metapneumovirus G glycoprotein," J. Infect. Dis. 85: 679-686.
Russell et al., 2001, "Membrane fusion machines of paramyxoviruses: capture of intermediates of fusion," EMBO J. 20: 4024-4034.
Scheid et al., 1974, "Identification of the biological activities of paramyxovirus glycoproteins. Activation of cell fusion, hemolysis and infectivity by proteolytic cleavage of an inactive precursor protein of Sendaivirus," Virology 57:475-490.
Scheid et al., 1977, "Two disulfide linked polypeptide chains constitute the active F protein of paramyxoviruses," Virology 80: 54-66.
Schickli et al., 2005, "An S101P substitution in the putative cleavage motif of the human metapneumovirus fusion protein is a major determinant for trypsin-independent growth in vero cells and does not alter tissue tropism in hamsters," J. Virol. 79(16):10678-89.
Schmidt et al., 2000, "Bovine parainfluenza virus type 3 (BPIV3) fusion and hemagglutinin-neuraminidase glycoproteins make an important contribution to the restricted replication of BPIV3 in primates," J Virol. 74:8922-8929.
Schmidt et al., 2002, "Mucosal immunization of Rhesus monkeys against respiratory syncytial virus subgroups A and B and human parainfluenza virus type 3 by using a live cDNA-derived vaccine based on a host range-attenuated bovine parainfluenza virus type 3 vector backbone," J. Virol. 76 :1089-1099.
Seal, 2000, "Avian pneumoviruses and emergence of a new type in the United States of America," Anim. Health Res. Rev. 1: 67-72.
Shibuta, 1977, "Characterization of bovine parainfluenza virus type 3," Microbiol. Immunol. 23: 617-628.
Skiadopoulos et al., 2001, "A chimeric human-bovine parainfluenza virus type 3 expressing measles virus hemagglutinin is attenuated for replication but is still immunogenic in rhesus monkeys," J Virol. 75:10498-504.
Skiadopoulos, 2004, "The two major human metapneumovirus genetic lineages are highly related antigenically, and the fusion (F) protein is a major contributor to this antigenic relatedness," J. Virol. 78: 6927-6937.
Stockton et al., 2002, "Human metapneumovirus as a cause of community-acquired respiratory illness," Emerg. Infect. Dis. 8, 897-901.
Tao et al., 2000, "Replacement of the ectodomains of the hemagglutinin-neuraminidase and fusion glycoproteins of recombinant parainfluenza virus type 3 (PIV3) with their counterparts from PIV2 yields attenuated PIV2 vaccine candidates," J. Virol. 74: 6448-58.
Tashiro et al., 1983, "Pneumotropism of Sendai virus in relation to protease-mediated activation in mouse lungs," Infect. Immun. 39: 879-888.
Tashiro et al., 1988, "Characterization of a pantropic variant of Sendai virus derived from a host-range mutant," Virology 165: 577-583.
Toquin et al., 2003, "Subgroup C avian metapneumovirus (MPV) and the recently isolated human MPV exhibit a common organization but have extensive sequence divergence in their putative SH and G genes," J. Gen. Virol. 84: 2169-2178.
Towatari et al., 2002, "Identification of ectopic anionic trypsin I in rat lungs potentiating pneumotropic virus infectivity and increased enzyme level after virus infection," Eur. J. Biochem. 269: 2613-2621.
Toyoda et al., 1987, "Structural comparison of the cleavage-activation site of the fusion glycoprotein between virulent and avirulent strains of Newcastle disease virus," Virology 158: 242-247.
Van Den Hoogen et al., 2003, "Prevalence and clinical symptoms of human metapneumovirus infection in hospitalized patients," J. Infect. Dis. 188: 1571-1577.
Van Den Hoogen et al., 2004, "Clinical impact and diagnosis of hMPV infections," Pediatr. Infect. Dis. J. 23: S25-32.
Van Den Hoogen et al., 2004, "Antigenic and genetic variability of human metapneumoviruses," Emerging Infectious Diseases 10: 658-666.
Van Wyke Coelingh et al., 1990, "Antibody responses of humans and nonhuman primates to individual antigenic sites of the hemagglutinin-neuraminidase and fusion glycoproteins after primary infection or reinfection with parainfluenza type 3 virus," J Virol. 64: 3833-3843.
White, 1990, "Viral and cellular membrane fusion proteins," Annu. Rev. Physiol. 52: 675-697.
Williams et al., 2004, "Human metapneumovirus and lower respiratory tract disease in otherwise healthy infants and children," N. Engl. J. Med. 350: 443-450.
Wolf et al., D., 2003, "High seroprevalence of human metapneumovirus among young children in Israel," J. Inf. Dis. 188: 1865-1867.
Tang, et al., 2003, "Effects of human rmetapneumovirus and respiratory syncytial antigen insertion in two 3'proximal genome positions of bovine/human parainfluenza virus type 3 on virus replication and immunogenicity," J. Virol. 77(20):10819-20.
Abman et al. Role of respiratory syncytial virus in early hospitalizations for respiratory distress of young infants with cystic fibrosis. J Pediatr. Nov. 1988;113(5):826-30.
Ahmadian et al. Detection and characterization of proteins encoded by the second ORF of the M2 gene of pneumoviruses. J Gen Virol. Aug. 1999;80 ( Pt 8):2011-2016.
Bayon-Auboyer et al. Comparison of F-, G- and N-based RT-PCR protocols with conventional virological procedures for the detection and typing of turkey rhinotracheitis virus. Arch Virol. 1999;144(6):1091-1109.
Bayon-Auboyer et al. Nucleotide sequences of the F, L and G protein genes of two non-A/non-B avian pneumoviruses (APV) reveal a novel APV subgroup. J Gen Virol. Nov. 2000;81(Pt 11):2723-2733.
Beare et al. Trials in man with live recombinants made from A/PR/8/34 (H0 N1) and wild H3 N2 influenza viruses. Lancet. Oct. 18, 1975;2(7938):729-32.
Beeler et al. Neutralization epitopes of the F glycoprotein of respiratory syncytial virus: effect of mutation upon fusion function. J Virol. Jul. 1989;63(7):2941-50.
Bentley et al. Human immunoglobulin variable region genes—DNA sequences of two V kappa genes and a pseudogene. Nature. Dec. 25, 1980;288(5792):730-3.
Botts and Takashi et al. On the mechanism of energy transduction in myosin subfragment 1. Proc Natl Acad Sci U S A. Apr. 1984;81(7):2060-4.
Bridgen et al. Rescue of a segmented negative-strand RNA virus entirely from cloned complementary DNAs. Proc Natl Acad Sci U S A. Dec. 24, 1996;93(26):15400-4.
Buchholz et al. Generation of bovine respiratory syncytial virus (BRSV) from cDNA: BRSV NS2 is not essential for virus replication in tissue culture, and the human RSV leader region acts as a functional BRSV genome promoter. J Virol. Jan. 1999;73(1):251-9.
Buys et al. 1980, Turkey 28:36-46.
Cavanagh et al. Pneumovirus-like characteristics of the mRNA and proteins of turkey rhinotracheitis virus. Virus Res. Oct. 1988;11(3):241-56.
Collins et al. Characterization of a virus associated with turkey rhinotracheitis. J Gen Virol. Apr. 1988;69 ( Pt 4):909-16.
Collins et al. Production of infectious human respiratory syncytial virus from cloned cDNA confirms an essential role for the transcription elongation factor from the 5' proximal open reading frame of the M2 mRNA in gene expression and provides a capability for vaccine development. Proc Natl Acad Sci U S A. Dec. 5, 1995;92(25):11563-7.
Collins et al., 1993, Avian Pathology, 22:469-79.
Cook et al., Avian Pathol. 1988, 17:403-10.
Cook et al., 1993, Avian Pathology, 22:257-73.
Domachowske et al. Respiratory syncytial virus infection: immune response, immunopathogenesis, and treatment. Clin Microbiol Rev. Apr. 1999;12(2):298-309. Review.
Durbin et al. Human parainfluenza virus type 3 (PIV3) expressing the hemagglutinin protein of measles virus provides a potential method for immunization against measles virus and PIV3 in early infancy. J Virol. Aug. 2000;74(15):6821-31.
Durbin et al. Recovery of infectious human parainfluenza virus type 3 from cDNA. Virology. Sep. 1, 1997;235(2):323-32.
Ennis et al. Recombination of influenza A virus strains: effect on pathogenicity. Dev Biol Stand. 1976;33:220-5.
Evans AS (ed.) Viral infections of Humans, Epidemiology and Control. 3rd edition, pp. 22-28, Plenum Publishing Corp. New York, 1989.
Falsey AR., Noninfluenza respiratory virus infection in long-term care facilities. Infect Control Hosp Epidemiol. Oct. 1991;12(10):602-8. Review.
Fields et al., eds, *Fields Virology*, 2nd ed., vol. 1, Raven Press, New York, 1990, pp. 1045-1072.
Flint et al., *Principles of virology, Molecular Biology, Pathogenesis and Control*. ASM Press 2000, pp. 25-56.
Florent et al. RNAs of influenza virus recombinants derived from parents of known virulence for man. Arch Virol. 1977;54(1-2):19-28.
Garvie et al. Outbreak of respiratory syncytial virus infection in the elderly. Br Med J. Nov. 8, 1980;281(6250):1253-4.
Giraud et al. Turkey rhinotracheitis in France: preliminary investigations on a ciliostatic virus. Vet Rec. Dec. 13, 1986;119(24):606-7.
Glezen et al. Risk of respiratory syncytial virus infection for infants from low-income families in relationship to age, sex, ethnic group, and maternal antibody level. J Pediatr. May 1981;98(5):708-15.
Groothuis et al. Respiratory syncytial virus infection in children with bronchopulmonary dysplasia. Pediatrics. Aug. 1988;82(2):199-203.
Groothuis et al. Prophylactic administration of respiratory syncytial virus immune globulin to high-risk infants and young children. The Respiratory Syncytial Virus Immune Globulin Study Group. N Engl J Med. Nov. 18, 1993;329(21):1524-30.
Hall et al. Neonatal respiratory syncytial virus infection. N Engl J Med. Feb. 22, 1979;300(8):393-6.
Hall, Contemp. Pediatr. 1993, 10:92-110.
Heckert et al. Absence of antibodies to avian pneumovirus in Canadian poultry. Vet Rec. Feb. 13, 1993;132(7):172.
Hemming et al. Studies of passive immunotherapy for infections of respiratory syncytial virus in the respiratory tract of a primate model. J Infect Dis. Nov. 1985;152(5):1083-7.
Henderson et al. Respiratory-syncytial-virus infections, reinfections and immunity. A prospective, longitudinal study in young children. N Engl J Med. Mar. 8, 1979;300(10):530-4.
Hertz et al. Respiratory syncytial virus-induced acute lung injury in adult patients with bone marrow transplants: a clinical approach and review of the literature. Medicine (Baltimore). Sep. 1989;68(5):269-81. Review.
Hoffmann et al. A DNA transfection system for generation of influenza A virus from eight plasmids. Proc Natl Acad Sci U S A. May 23, 2000;97(11):6108-13.
Huygelen et al. Laboratory and clinical evaluation of new live influenza virus vaccines. Need for minimum requirements. Dev Biol Stand. Jun. 1-3, 1977;39:155-60.
Inoue et al. An improved method for recovering rabies virus from cloned cDNA. J Virol Methods. Feb. 2003;107(2):229-36.
Ishiguro et al., 2004, "High genetic diversity of the attachment (G) protein of human metapneumovirus," J. Clin. Microbiol. 42(8):3406-3414.
Johnson et al. The G glycoprotein of human respiratory syncytial viruses of subgroups A and B: extensive sequence divergence between antigenically related proteins. Proc Natl Acad Sci U S A. Aug. 1987;84(16):5625-9.
Juhasz et al. Extensive sequence variation in the attachment (G) protein gene of avian pneumovirus: evidence for two distinct subgroups. J Gen Virol. Nov. 1994;75 ( Pt 11):2873-80.
Kapikian et al. An epidemiologic study of altered clinical reactivity to respiratory syncytial (RS) virus infection in children previously vaccinated with an inactivated RS virus vaccine. Am J Epidemiol. Apr. 1969;89(4):405-21.
Kim et al. Respiratory syncytial virus disease in infants despite prior administration of antigenic inactivated vaccine. Am J Epidemiol. Apr. 1969;89(4):422-34.
Krempl et al. Recombinant respiratory syncytial virus with the G and F genes shifted to the promoter-proximal positions. J Virol. Dec. 2002;76(23):11931-42.
Krystal et al. Expression of the three influenza virus polymerase proteins in a single cell allows growth complementation of viral mutants. Proc Natl Acad Sci U S A. Apr. 1986;83(8):2709-13.
Lamprecht et al. Role of maternal antibody in pneumonia and bronchiolitis due to respiratory syncytial virus. J Infect Dis. Sep. 1976;134(3):211-7.
Ling et al. Sequence analysis of the 22K, SH and G genes of turkey rhinotracheitis virus and their intergenic regions reveals a gene order different from that of other pneumoviruses. J Gen Virol. Jul. 1992;73 ( Pt 7):1709-15.
Lopez et al. Antigenic structure of human respiratory syncytial virus fusion glycoprotein. J Virol. Aug. 1998;72(8):6922-8.
MacDonald et al. Respiratory syncytial viral infection in infants with congenital heart disease. N Engl J Med. Aug. 12, 1982;307(7):397-400.
Marriott AC, Easton AJ. Reverse genetics of the Paramyxoviridae. Adv Virus Res. 1999;53:321-40.
Marriott et al. Fidelity of leader and trailer sequence usage by the respiratory syncytial virus and avian pneumovirus replication complexes. J Virol. Jul. 2001;75(14):6265-72.
Morell et al., eds., *Clinical Use of Intravenous Immunoglobulins*. Academic Press, London 1986, pp. 285-294.
Murphy et al. An update on approaches to the development of respiratory syncytial virus (RSV) and parainfluenza virus type 3 (PIV3) vaccines. Virus Res. Apr. 1994;32(1):13-36. Review.
Murphy et al. Passive transfer of respiratory syncytial virus (RSV) antiserum suppresses the immune response to the RSV fusion (F) and large (G) glycoproteins expressed by recombinant vaccinia viruses. J Virol. Oct. 1988;62(10):3907-10.
Murphy et al. Effect of passive antibody on the immune response of cotton rats to purified F and G glycoproteins of respiratory syncytial virus (RSV). Vaccine. Mar. 1991;9(3):185-9.
Navas et al. Improved outcome of respiratory syncytial virus infection in a high-risk hospitalized population of Canadian children. Pediatric Investigators Collaborative Network on Infections in Canada. J Pediatr. Sep. 1992;121(3):348-54.
Naylor et al. The ectodomains but not the transmembrane domains of the fusion proteins of subtypes A and B avian pneumovirus are conserved to a similar extent as those of human respiratory syncytial virus. J Gen Virol. Jun. 1998;79 ( Pt 6):1393-8.
Neumann et al. Reverse genetics demonstrates that proteolytic processing of the Ebola virus glycoprotein is not essential for replication in cell culture. J Virol. Jan. 2002;76(1):406-10.
Nissen et al., 2002, "Evidence of human metapneumovirus in Australian children," Med. J. Australia 176(4):188.
O'Brien JD. Swollen head syndrome in broiler breeders. Vet Rec. Dec. 7, 1985;117(23):619-20.
Ogra et al. Respiratory syncytial virus infection and the immunocompromised host. Pediatr Infect Dis J. Apr. 1988;7(4):246-9.
Palese et al. Negative-strand RNA viruses: genetic engineering and applications. Proc Natl Acad Sci U S A. Oct. 15, 1996;93(21):11354-8. Review.
Peeters et al. Rescue of Newcastle disease virus from cloned cDNA: evidence that cleavability of the fusion protein is a major determinant for virulence. J Virol. Jun. 1999;73(6):5001-9.
Peret et al. Characterization of human metapneumoviruses isolated from patients in North America. J Infect Dis. Jun. 1, 2002;185(11):1660-3. Epub May 3, 2002.
Poch et al. Sequence comparison of five polymerases (L proteins) of unsegmented negative-strand RNA viruses: theoretical assignment of functional domains. J Gen Virol. May 1990;71 ( Pt 5):1153-62.
Poch et al., Identification of four conserved motifs among the RNA-dependent polymerase encoding elements. EMBO J. Dec. 1, 1989;8(12):3867-74.
Pohl et al. Respiratory syncytial virus infections in pediatric liver transplant recipients. J Infect Dis. Jan. 1992;165(1):166-9.
Press et al. The amino acid sequences of the Fd fragments of two human gamma-1 heavy chains. Biochem J. May 1970;117(4):641-60.

Prince et al. Immunoprophylaxis and immunotherapy of respiratory syncytial virus infection in the cotton rat. Virus Res. Oct. 1985;3(3):193-206.
Prince et al. Mechanism of antibody-mediated viral clearance in immunotherapy of respiratory syncytial virus infection of cotton rats. J Virol. Jun. 1990;64(6):3091-2.
Prince et al. Mechanisms of immunity to respiratory syncytial virus in cotton rats. Infect Immun. Oct. 1983;42(1):81-7.
Prince et al. Quantitative aspects of passive immunity to respiratory syncytial virus infection in infant cotton rats. J Virol. Sep. 1985;55(3):517-20.
Prince, GA, Ph.D. diss., University of California, LA 1975.
Pringle CR. Virus taxonomy—San Diego 1998. Arch Virol. 1998;143(7):1449-59.
Pringle et al. Virus taxonomy at the XIth International Congress of Virology, Sydney, Australia, 1999. Arch Virol. 1999;144(10):2065-70.
Randhawa et al. Rescue of synthetic minireplicons establishes the absence of the NS1 and NS2 genes from avian pneumovirus. J Virol. Dec. 1997;71(12):9849-54.
Ruuskanen et al. Respiratory syncytial virus. Curr Probl Pediatr. Feb. 1993;23(2):50-79. Review.
Schnell et al. Infectious rabies viruses from cloned cDNA. EMBO J. Sep. 15, 1994;13(18):4195-203.
Seal BS. Matrix protein gene nucleotide and predicted amino acid sequence demonstrate that the first US avian pneumovirus isolate is distinct from European strains. Virus Res. Nov. 1998;58(1-2):45-52.
Senne et al., 1998, In: Proc.. $47^{th}$ WPDC, CA, pp. 67-68.
Skiadopoulos et al. Three amino acid substitutions in the L protein of the human parainfluenza virus type 3 cp45 live attenuated vaccine candidate contribute to its temperature-sensitive and attenuation phenotypes. J Virol. Mar. 1998;72(3):1762-8.
Sullender et al. Respiratory syncytial virus genetic and antigenic diversity. Clin Microbiol Rev. Jan. 2000;13(1):1-15, table of contents. Review.
Takashi et al. Angiomyolipoma of the kidney: report of three cases and a statistical study of 194 cases in Japan Hinyokika Kiyo. Jan. 1984;30(1):65-75.
Tao et al. A live attenuated chimeric recombinant parainfluenza virus (PIV) encoding the internal proteins of PIV type 3 and the surface glycoproteins of PIV type 1 induces complete resistance to PIV1 challenge and partial resistance to PIV3 challenge. Vaccine. Mar. 5, 1999;17(9-10):1100-8.
Tao et al. Recovery of a fully viable chimeric human parainfluenza virus (PIV) type 3 in which the hemagglutinin-neuraminidase and fusion glycoproteins have been replaced by those of PIV type 1. J Virol. Apr. 1998;72(4):2955-61.
Teng et al. Recombinant respiratory syncytial virus that does not express the NS1 or M2-2 protein is highly attenuated and immunogenic in chimpanzees. J Virol. Oct. 2000;74(19):9317-21.
van den Hoogen et al. A newly discovered human pneumovirus isolated from young children with respiratory tract disease. Nat Med. Jun. 2001; 7(6):719-24.
van den Hoogen et al. Analysis of the genomic sequence of a human metapneumovirus. Virology. Mar. 30, 2002;295(1):119-32.
Volchkov et al. Recovery of infectious Ebola virus from complementary DNA: RNA editing of the GP gene and viral cytotoxicity. Science. Mar 9, 2001;291(5510):1965-9.
Yu et al. Cloning and sequencing of the matrix protein (M) gene of turkey rhinotracheitis virus reveal a gene order different from that of respiratory syncytial virus. Virology. Feb. 1992;186(2):426-34.
Yu et al. Sequence and in vitro expression of the M2 gene of turkey rhinotracheitis pneumovirus. J Gen Virol. Jun. 1992;73 ( Pt 6):1355-63.
Yu et al., 1991, "Deduced amino acid sequence of the fusion glycoprotein of turkey rhinotracheitis virus has a greater identity with that of human respiratory syncytial virus, a pneumovirus, than that of paramyxoviruses and morbilliviruses," J. Gen. Virol. 72:75-81.
Database EBI 'Online! SWALL; Dec. 1, 2001 "Nucleoprotein" Database accession No. Q91F57.
Database EBI 'Online! SWALL; May 1, 2000 "Nucleocapsid protein" Database accession No. Q9QF48.
Database EBI 'Online! SWALL; Dec. 1, 2001 "Phosphoprotein," Database accession No. Q91KZ5.
Database EBI 'Online! SWALL; May 1, 2000 "Phosphoprotein," Database accession No. Q9QF47.
Database EBI 'Online! SWALL; Dec. 1, 2001 "Matrix protein," Database accession No. Q91F56.
Database EBI 'Online! SWALL; Nov. 1, 1998 "Matrix protein," Database accession No. O90244.
Database EBI 'Online! SWALL; Dec. 1, 2001 "Fusion protein," Database accession No. Q91F55.
Database EBI 'Online! SWALL; May 1, 2000 "Fusion protein," Database accession No. Q9QDI1.
Database EBI 'Online! SWALL; Dec. 1, 2001 "RNA-dependent RNA polymerase," Database accession No. Q91L20.
Database EBI 'Online! SWALL; May 1, 1997 "RNA-dependent RNA polymerase," Database accession No. P87509.
Biacchesi, S. et al., 2003, "Genetic diversity between human metapneumovirus subgroups." Virol. 315(1): 1-9.
Randhawa J.S. et al., 1996 "Nucleotide sequence of the gene encoding the viral polymerase of avian pneumovirus." J. Gen. Virol. 77: 3047-3051.
Seal, B.S. et al, 2000, "Fusion protein predicted amino acid sequence of the first US avian pneumovirus isolate and lack of heterogeneity among other US isolates." Virus Res. 66: 139-147.
Wang, E. et al., 2003, "Both heptad repeats of human respiratory syncytial virus fusion protein are potent inhibitors of viral fusion." BBRC. 302: 469-475.
Office Action dated May 11, 2007 for U.S. Appl. No. 10/373,567.
Office Action dated Aug. 23, 2007 for U.S. Appl. No. 10/373,567.
Office Action dated May 11, 2007 for U.S. Appl. No. 10/371,099.
Office Action dated Sep. 7, 2006 for U.S. Appl. No. 10/371,099.
Office Action dated Jun. 13, 2007 for U.S. Appl. No. 10/371,264.
Office Action dated Sep. 8, 2006 for U.S. Appl. No. 10/371,264.
Office Action dated Jan. 24, 2006 for U.S. Appl. No. 10/371,264.
Office Action dated May 4, 2005 for U.S. Appl. No. 10/371,264.
Office Action dated Jun. 13, 2007 for U.S. Appl. No. 10/831,781.
Biacchesi et al., 2006, "Modification of the Trypsin-Dependent Cleavage Activation Site of the Human Metapneumovirus Fusion Protein To Be Trypsin Independent Does Not Increase Replication or Spread in Rodents or Nonhuman Primates" in J. Virology; 80(12):5798-5806.
Notice of Allowance dated Sep. 19, 2007 of U.S. Appl. No. 10/373,567.
Notice of Allowance dated Nov. 21, 2007 of U.S. Appl. No. 10/371,099.
Notice of Allowance dated Jun. 19, 2008 of U.S. Appl. No. 10/371,099.
Office Action dated Aug. 25, 2006 of U.S. Appl. No. 10/371,122.
Office Action dated Oct. 5, 2006 of U.S. Appl. No. 10/722,045.
Office Action dated Mar. 1, 2007 of U.S. Appl. No. 10/371,122.
Office Action dated Apr. 5, 2007 of U.S. Appl. No. 10/466,811.
Office Action dated Nov. 28, 2007 of U.S. Appl. No. 10/371,122.
Office Action dated Dec. 31, 2007 of U.S. Appl. No. 10/722,045.
Office Action dated Feb. 20, 2008 of U.S. Appl. No. 10/831,781.
Office Action dated Feb. 20, 2008 of U.S. Appl. No. 10/466,811.
Office Action dated Feb. 26, 2008 of U.S. Appl. No. 10/371,264.
Office Action dated Mar. 26, 2008 of U.S. Appl. No. 10/373,567.
Database NIH (USA) Jun. 17, 2001 "Human Metapneumovirus isolate 99-1 nucleoprotein (N) gene, partial cds" Database accession No. AF371361.
Database NIH (USA) Jun. 17, 2001 "Human Metapneumovirus isolate 99-1 matrix (M) gene, partial cds" Database accession No. AF371352.
Database NIH (USA) Jun. 17, 2001 "Human Metapneumovirus isolate 99-1 fusion (F) gene, partial cds" Database accession No. AF371344.
Database NIH (USA) Jun. 17, 2001 "Human Metapneumovirus isolate 99-1 RNA-dependent RNA polymerase (L) gene, partial cds" Database accession No. AF371335.
Office Action dated Sep. 5, 2008 of U.S. Appl. No. 10/466,811.
Office Action dated Aug. 20, 2008 of U.S. Appl. No. 10/722,045.
Office Action dated Aug. 8, 2008 of U.S. Appl. No. 10/371,099.
Office Action dated Sep. 24, 2008 of U.S. Appl. No. 10/831,781.

Notice of Allowance dated Sep. 25, 2008 of U.S. Appl. No. 10/371,264.

Notice of Allowance dated Oct. 1, 2008 of U.S. Appl. No. 10/371,122.

Tashiro et al. 1992, "Budding site of sendai virus in polarized epithelial cells is one of the determinants for tropism and pathogenicity in mice", Virology, 187(2): pp. 413-422.

* cited by examiner

M

| | 00-1 | hRSV | bRSV | PMV | APV-A | APV-C | APV-B |
|---|---|---|---|---|---|---|---|
| 00-1 | 1,00 | 0,37 | 0,37 | 0,37 | 0,77 | 0,87 | 0,75 |
| hRSV | --- | 1,00 | 0,91 | 0,41 | 0,37 | 0,37 | 0,37 |
| bRSV | --- | --- | 1,00 | 0,42 | 0,35 | 0,36 | 0,35 |
| PMV | --- | --- | --- | 1,00 | 0,37 | 0,38 | 0,38 |
| APV-A | --- | --- | --- | --- | 1,00 | 0,78 | 0,89 |
| APV-C | --- | --- | --- | --- | --- | 1,00 | 0,77 |
| APV-B | --- | --- | --- | --- | --- | --- | 1,00 |

N

| | 00-1 | hRSV | bRSV | PVM | APV-A | APV-C | APV-B |
|---|---|---|---|---|---|---|---|
| 00-1 | 1,00 | 0,20 | 0,22 | 0,21 | 0,40 | 0,52 | 0,40 |
| hRSV | --- | 1,00 | 0,59 | 0,30 | 0,18 | 0,21 | 0,18 |
| bRSV | --- | --- | 1,00 | 0,31 | 0,21 | 0,23 | 0,21 |
| PVM | --- | --- | --- | 1,00 | 0,21 | 0,23 | 0,21 |
| APVA | --- | --- | --- | --- | 1,00 | 0,42 | 1,00 |
| APVC | --- | --- | --- | --- | --- | 1,00 | 0,42 |
| APVB | --- | --- | --- | --- | --- | --- | 1,00 |

F

| | 00-1 | hRSV | bRSV | PVM | APV-A | APV-C | APV-B |
|---|---|---|---|---|---|---|---|
| 00-1 | 1,00 | 0,32 | 0,33 | 0,37 | 0,67 | 0,80 | 0,66 |
| hRSV | --- | 1,00 | 0,82 | 0,40 | 0,35 | 0,35 | 0,35 |
| bRSV | --- | --- | 1,00 | 0,41 | 0,34 | 0,36 | 0,34 |
| PVM | --- | --- | --- | 1,00 | 0,38 | 0,38 | 0,39 |
| APV-A | --- | --- | --- | --- | 1,00 | 0,72 | 0,84 |
| APV-C | --- | --- | --- | --- | --- | 1,00 | 0,72 |
| APV-B | --- | --- | --- | --- | --- | --- | 1,00 |

P

| | 00-1 | hRSV | bRSV | PMV | APV-A | APV-C |
|---|---|---|---|---|---|---|
| 00-1 | 1,00 | 0,25 | 0,26 | 0,27 | 0,55 | 0,67 |
| hRSV | --- | 1,00 | 0,81 | 0,30 | 0,28 | 0,26 |
| bRSV | --- | --- | 1,00 | 0,29 | 0,28 | 0,26 |
| PMV | --- | --- | --- | 1,00 | 0,23 | 0,27 |
| APV-A | --- | --- | --- | --- | 1,00 | 0,52 |
| APV-C | --- | --- | --- | --- | --- | 1,00 |

L8

| | 00-1 | hRSV | bRSV | APV-A |
|---|---|---|---|---|
| 00-1 | 1,00 | 0,36 | 0,35 | 0,56 |
| hRSV | --- | 1,00 | 0,79 | 0,36 |
| bRSV | --- | --- | 1,00 | 0,35 |
| APV-A | --- | --- | --- | 1,00 |

L9/10

| | 00-1 | hRSV | bRSV | APV-A |
|---|---|---|---|---|
| 00-1 | 1,00 | 0,30 | 0,30 | 0,53 |
| hRSV | --- | 1,00 | 0,83 | 0,34 |
| bRSV | --- | --- | 1,00 | 0,32 |
| APV-A | --- | --- | --- | 1,00 |

FIGURE 1

Seroprevalence of hMPV in humans categorised by age group using immunofluorescence and virus neutralisation assays

| | Immunofluorescence assays | | Virus neutralisation assays | | |
|---|---|---|---|---|---|
| Age (Years) | N tested | N positive | N tested | N positive | Titre range |
| < 1 | 20 | 5 | 12 | 3 | 16-32 |
| 1-2 | 20 | 11 | 13 | 4 | 16-32 |
| 2-5 | 20 | 14 | 8 | 3 | 16-512 |
| 5-10 | 20 | 20 | 4 | 4 | 32-256 |
| 10-20 | 20 | 20 | 4 | 3 | 32-128 |
| > 20 | 20 | 20 | 4 | 3 | 32-128 |
| 8-99[1] | 72 | 72 | 11 | 11 | 16-128 |

[1]Sero-archeological analysis using sera collected in 1958

FIGURE 2

Nucleo protein

```
00-1 NP MSLQGIHLSDLSYKHAILKESQYTIKRDVGTTTAVTPSSLQQEITLLCGEILYAKHADYKYAAEIGIQYISTALGSERVQQILRNSGSEVQVVLTRTYSL 10
APV A   ...ES.R....E......ED.....R....A...I...E..PQVST...MV.F...T..EP...V.M.........AD.T....K.......G.M.KIVT. 10
APV B   ......Q.................................R.VS...........T..SH...V.M..V..T..A..T....K.......A...K.... 10
APV C   ......Q.................................R.VS...........T..SH...V.M..V..T..A..T....K.......A...K.... 10
bRSV    .A.SKVK.N.TFN.DQL.ST.K...Q.ST.DNIDIPNYDV.KHLNK...ML.ITED.NH.FTGL..ML.AMSR..R.DTLK..KDA.YQ.RANGVDVITH 10
hRSV    .A.SKVK.N.TLN.DQL.SS.K...Q.ST.DNIDTPNYDV.KHLNK...ML.ITED.NH.FTGL..ML.AMSR..R.DTIK..KDA.YH.KANGVDITTY 10
PVM     ...DRLK.N.V.N.DSL.SNCK.SVT.ST.DV.S.SGHAM.KALARTL.MF.LTAFNRCEEV....L..AMSL..RDDSIK...EA.YN.KC.D.QLKDF 10

00-1 NP GKIKNNKGEDLQMLDIHGVEKSWVEEIDKEARKTMATLLKESSGNIPQNQRPSAPDTPIILLCVGALIFTKLASTIEVGLETTVRRANRVLSDALKRYPR 20
APV A   SAEGSVRKREV—.N..D.GVG.ADDVERTT.EA.GAMVR.KV-QLTK..K...L.A.V....I...........V......AI...S.......IS.... 19
APV B   ..G..S...E..........R..I..V.........SAT.DN..P........S..A......I.................A........N.....F.. 20
APV C   ..G..S...E..........R..I..V.........SAT.DN..P........S..A......I.................A........N.....F.. 20
bRSV    RQDV.G.EMKFEV.TLVSLTSEVQGN.EI.S..SYKKM...M-.EVAPEY.HDS..CGM.V...A..VI....AGDRS..TAVI....N..RNEM...KG 19
hRSV    RQDI.G.EMKFEV.TLSSLTSEIQVN.EI.S..SYKKM...M-.EVAPEY.HDS..CGM.I..IA..VI....AGDRS..TAVI....N..KNEI...KG 19
PVM     TIKLQG.EYKI.V...V.IDAANLADLEIQ..GVV.KE..TG-ARL.D.R.HD...CGV.V..IA..VVS...AGDRG..DAVE...LN..KAEKA...N 19

00-1 NP MDIPKIARSFYDLFEQKVYHRSLFIEYGKALGSSSTGSKAESLFVNIFMQAYGAGQTMLRWGVIARSSNNIMLGHVSVQAELKQVTEVYDLVREMGPESG 30
APV A   ....R..K..FE...K...Y.N............T....RM..............................................R..S.......K..... 29
APV B   I.................Y.................................................................................. 30
APV C   I.................Y.................................................................................. 30
bRSV    LIPKD..N...EV..KYPHYIDV.VHF.I.QS.TRG..RV.GI.AGL..N......V......L.K.VK......A.....ME..V...EYAQKL.G.A. 29
hRSV    LIPKD..N...EV..KHPHLIDV.VHF.I.QS.TRG..RV.GI.AGL..N...S..V......L.K.VK......A.....ME..V...EYAQKL.G.A. 29
PVM     .EVKQ..E.......R.P.YIDV..TF.L.QS.VRG...V.G..SGL..N......V.....LL.K.VK......A.....ME..V...EYAQKQ.G.A. 29

00-1 NP LLHLRQSPKAGLLSLANCPNFASVVLGNASGLGIIGMYRGRVPNTELFSAAESYAKSLKESNKINFSSLGLTDEEKEAAEHFLNVSDDSQNDYE 39
APV A   ...............T.............A........K..A..L...A......RT.R.N....LAA.....D.R...TSY.GGD.ERSSKF. 39
APV B   ......N.........................L.............A......R.................E.......N...INEEG..... 39
APV C   ......N.........................L.............A......R.................E.......N...INEEG..... 39
bRSV    FY.ILNN...S....TQF...S.......A....M.E...TPR.QD.YD..KA..EQ...NGV..Y.V.D..T..L..IKNQ..PK.N—DVEL 39
hRSV    FY.ILNN...S....TQF...S.......A....M.E...TPR.QD.YD..KA..EQ...NGV..Y.V.D..A..L..IKNQ..PKE.—DVEL 39
PVM     FY.I.NN...S....T.....T.......A......S.K.APR.R...D..KD..ER..DN.V..Y.A.N..A..R.LISQQ..IV..TPD.DI 39
```

Phospho protein

```
00-1 P MS-FPEGKDILFMGNEAAKLAEAF--------QKSLRKPGHKRSQSIIGEKVNTVSETLELPTISRPAKPTIPSEPKLAWTDKGGATKTEIKQAIKVMDP 91
APV-A  ..-........M..S....M.D.Y--------.R...NTSAG-GR..S..PI..IA.KVP..PLCN.TT.------------..SCI.PNKAPVP..K-- 76
APV-C  ..-........L.......A....————————.R..K.I..R.T...V.D.II.....V.K....KST.V.T.P.R.N..GE.PDT.RSQTEE.RNEAT. 91
bRSV   .——————————.........———————.......................................................................... 80
hRSV   .EK.APE----.H.ED.NNK.TK.LES——————————————————————IKGKF———————————————————ASSKDPKK.DS.ISVNS 45
PVM    .EK.APE----.V.ED.N.K..E.LKHRSFPSE.P.AGIPNTATHVTKYNMPPILRSSFK..SPRVA.NL.E..A.----PTTPPP.PPQN.EEQPKESD 92

00-1 P IEEEESTEKKVLPSSDGKTPAEKKLKPSTNT————KKKVSPTPNEP——GKYTKLEKDALDLLSDNEEEDAE-SSILTFEE—RDTSSLSIEARLESIE 18
APV-A  —.I..IYP.LPTAPVATDTYTSTSTE.AKK————S...K.DNPKV——.......EEG.E....P..DND.K........—K..A.T.......A.. 16
APV-C  EDASRLY.EVFA.T.........GKETPEKP————....T.KND.S——.R.....ME..E......DD...-..V.....—K...A..L.......D 18
bRSV   ............................——............——..............................-.........—................ 16
hRSV   .DI.VTK.SPITSGTNIIN.TSEADSTPETKANYPR.PL...KEDLTPSDNPFS..Y.ETIETF——DNN——.EE.SYSY..INDQ.-NDN.T...DR.D 13
PVM    VDI.TMHVC..PDNPEHSKKPCCSDDTD.KKT——R.PM.T.VEP.EKFV.LGAS.YRETMQTF——AADGYDEE.N.S...TNQEPG.S.V.Q..DR.. 18

00-1 P EKLSMILGLLRTLNIATAGPTAARDGIRDAMIGVREELIADIIKEA——KGKAAEM——MEEEMXQRSKIGNGSVKLTEKAKELNKIVEDESTSGESEEE 27
APV-A  ........M.K.........................M.....NS.MT..——.D.I...——.K..DT..A...D...............L..Q.S.....S. 25
APV-C  ..............V.................V.L............——.......——.K..AK.K........G.......................... 27
bRSV   ...............................................——.......——.....X........................................ 26
hRSV   ....E...M.H..VV.S....S.........V.L...M.EK.RA..IMTNDRLEA.ARLRN..SEKMA.DTSDE.P.NPTS.K.SDLL..N———————— 23
PVM    ....Y.I...N.IMV......T...E....L..T.....EM.KSDILTVNDRIVA.EKLRD..CSRADTDDGSACY..DR.RI.D...SSNA———————— 27

00-1 P EEPKDTQDNSQEDDIY———QLIM.          29
APV-A  ..SGESESDEE.S...NLDL-.L           28
APV-C  ..EE.EEESNPD..L.SLTM-.LIKN        29
bRSV   ................———.....          28
hRSV   ———.SDNDLSL.———————DF.            24
PVM    ——EEAKEDLDV...MGINF-.LI           29
```

FIGURE 4

Matrix protein

FIGURE 4, contd.

```
00-1 matrix MESYLVDTYQGIPYTAAVQVDLIEKDLLPASLTIWFPLFQANTPPAVLLDQLKTLTITTLYAASQNGPILKVNASAQGAAMFVLPKKFEVNATVAKDEYS 10
APV-B       ....II.....V..........V...NN..K..V......SS..AP.........S...Q.TV.PE..V.Q...T......SA.....S.S.AA.L.... 10
APV-A       ....II.....V..............SN..T..V......SS..AP.........S...Q.T..PE..V.Q...A......SA.....A.S.A..L.... 10
APV-C       ...........V.......T..V...Q...R..V.V....T....T...E...........T...................SA...S.D.S.S..L.D.. 10
bRSV        ..T.VNKLHE.ST......YNV....DD.......V.M..SSISADL.IKE.INVN.LVRQISTLK..S..IMINSRS.VLAQM.S..TIS.N.SL..R. 10
hRSV        ..T.VNKLHE.ST......YNVL...DD.......V.M..SSV.ADL.IKE.ASIN.LVKQISTPK..S.R.TINSRS.VLAQM.SN.IIS.N.SL..R. 10
PVM         ..A...EM.H.V.......LN.V..HSANI...V.I.M..TSL.KNSVM.L.HDV.VICTQISTVH..MI..DL.SSN.GLATM.RQ.LI..II.L.DWG 10

00-1 matrix KLEFDKLTVCEVKTVYLTTMKPYGMVSKFVSSAKSVGKKTHDLIALCDFMDLEKNTPVTIPAFIKSVSIKESESATVEAAISSEADQALTQAKIAPYAGL 20
APV-B       ..D.GV....D.RA.....L.........I.TNMNT..R...........I.M.RGI......Y..A....D...........G.....I...R....... 20
APV-A       R...GT....D.RSI....L.........IMTDVR...R...........I.I..GV.I....Y..A....D...........G.....I...R....... 20
APV-C       ...........L.A.................N...A..............L....GV......Y....................G.....I...R....... 20
bRSV        ..AY.IT.P..I.ACS..CL.VKN.LTTVKDLTMKTFNP..EI....E.ENIMTSKR.V..T.LR.INV.AKDLDSL.NIATT.FKN.I.N...I..... 20
hRSV        ..AY.VT.P..I.ACS..CL.VKS.LTTVKDLTMKTFNP..EI....E.ENIMTSKR.I..TYLRPI.V.NKDLNSL.NIATT.FKN.I.N...I..... 20
PVM         NMDYEVPVAFDK.SFCV.IL..KN.LYTVP.ITPTN-RP..E...V.S.HNRVTLKSFN..V..RALY.RQQGLDS..Q....DV.H.I.T.RV...... 19

00-1 matrix IMIMTMNNPKGIFKKLGAGTQVIVELGAYVQAESISKICKTWSHQGTRYVLKSR.                                             25
APV-B       .LL.A........R..............P......LG......N..R...------I-------L--K-----SR                         25
APV-A       .L..................M........P......LG......N..R.....R..-.GYPK-A.-IC.C-YSQ.K                        27
APV-C       ...................V...............R..RN............----------------------R                         25
bRSV        VLVI.VTDN..A..YIKPQS.F..D....LEK...YYVTTN.K.TA.KFSI.P-------------------IED.                        25
hRSV        VLVI.VTDN..A..YIKPQS.F..D....LEK...YYVTTN.K.TA..FSI.P-------------------LED.                        25
PVM         TLVINITST..A..L.K..S.IIA...P.LTQV.LHDVIMN.K.T..S.I...SS-----------------TSG.                        25
```

Fusion protein

```
00-1 F MSW---KVVIXFSLLI-------TPXHGLKESYLEESCSTITEGYLSVLRTGWYTNVFTLEVGDVENLTCADGPS---LIKTELDLTKSALRELRTVSADQ 88
APV-A  .DV---RICLLLF.IS-------N.SSCIQ.T.N......V.R..K............N..I.N...I..N....---..D...V...N.....K...... 88
APV-B  .YL---.LLLIIY.VV-------GASGKIQ.T.S......V.R..K............N..I.N...I..N....---..S...S..QN..Q......... 88
APV-C  ...---...LLLV..A-------..TG..E.......Y..V.R..........................T....---..R...E...N..E..K...... 88
bRSV   .ATTAMRMI.SIIFISTYVTHI.LCQNIT.EFYQST..AVSR....A.......S.V.I.LSKIQKNV.KSTD.KVK...Q..ERYNN.VV..QSIMQNE 10
hRSV   .ELLIHRLSAI.LT.AINALYL.SSQNIT.EFYQST..AVSR..F.A.......S.I.I.LSNIKETK.NGTDTKVK...Q...KY.N.VT..QLIMQNT 10
PVM    .----IPGR.FLV..VIFNTKPIHPNT.T.K.Y.ST..VE.A..K.A.....HMT.MSIKLSQINIES.KSSN.---.LAH..AIYS..VD....L.SNA 93

00-1 F LAREEQ------------------------IENPRQSRFVLGAIALGVATAAAVTAGVAIAKTIRLESEVTAIKNALKKTNEAVSTLGNGVRVLATAVRELK 16
APV-A V.K.SR------------------------LSS..RR........................L.......G..K......RN..................ND.. 16
APV-B ITK.NR------------------------.LSR.KK.............T........L.......G..K...L..RS.............I.....ND.. 16
APV-C ..K.AR------------------------.MS..KA...............................G..A...G..R...................ND.. 16
bRSV  P.SFSRAKRGIPELIHYTRNSTKKFYGLMGKK.KR..L--GFL..IG--S..AS...VS.VLH..G..NK.....LS..K..VS.S...S..TSK.LD.. 19
hRSV  P.ANNRARREAPQYMNYTINTTKNLNVS.SKK.KR..L--GFL...G--S.IAS.I.VS.VLH..G..NK.....LS..K..VS.S...S..TSK.LD.. 19
PVM   ------------------------------LKSK.KK..L--GLI..LG--........L...VQ....IAL.RD.VRN.....VS.T..MS...KV.DD.. 16

00-1 F DFVSKNLTRAINKNKCDIADLKMAVSFSQFNRRFLNVVRQFSDNAGITPAISLDLMTDAELARAVSNMPTSAGQIKLMLENRAMVRRKGFGFLIGVYGSS 26
APV-A E.I..K..P...Q...N...I...I..G.N.............S....S.V.......D..V..INR....S...S...N...........I.....DGT 26
APV-B E.I..K..P...Q...N...IR..I..G.N.............S....S.V..........VK.INR....S...S...N...........I......GT 25
APV-C ..I..K..P...R.....S........G.Y.............................V.........S...N...............I........ 26
bRSV  NYID.E.LPQV.NHD.R.SNIETVIE.Q.K.N.L.EIA.E..V.....TPL.TYML.NS..LSLIND..ITND.K...SS.VQI..QQSYSIMSV.KEEV 29
hRSV  NYINNQ.LPIV.QQS.R.SNIETVIE.Q.K.S.L.EIN.E..V...V.TPL.TYML.NS..LSLIND..ITND.K...SS.VQI..QQSYSIMSIIKEEV 29
PVM   N.I..E.LPK..RVS..VH.ITAVIR.Q.L.K.L.E.S.E..S...L.HTV.SFML..R..TSI.GG.AV....KEI..SSK.IM..N.LAI.SS.NADT 26

00-1 F VIXMVQLPIFGVIDTPCWIVKAAPSC---SGKKGNYACLLREDQGWYCQNAGSTVYYPNEKDCETRGDHVFCDTAAGINVAEQSXECNINISTTNYPCKVS 36
APV-A .VY..........E....R.V...L.---RKE......I..........T.....A....KD...V.D.Y............LEVEQ..Y....SK...... 36
APV-B .VY..........E....R.V...L.---RHERES..............T.....A.....D...V.D.Y............SEVEQ..H....ST...... 36
APV-C .VYI...............K.....L.---..D..........................E...V.S...............KE.E...R.....K...... 36
bRSV  LAYV.....Y........KLHTS.L.TTDN.E.SNI..T.T.R....D....VSFF.QTET.KVQSNR.....MNSLTLPTDVNL..TD.FN.K.D..IM 39
hRSV  LAYV.....Y........KLHTS.L.TINI.E.SNI..T.T.R....D....VSFF.QADT.KVQSNR.....MNSLTLPSEVSL..TD.FNSK.D..IM 39
PVM   LVYVI...L...M..D..VIRSSID.---HNIADK....A.A.N....H....LS.F.SPT...IHNGYA....LKSLT.PVT.R...S.MY....D..I. 35

00-1 F TGRHPISMVALSPLGALVACYKGVSCSIGSNRVGIIKQLNKGCSYITNQDADTVTIDNTVYQLSKVEGEQHVIKGRPVSSSFDPVKFPEDQFNVALDQVF 46
APV-A .....V.....T...G..S..ES.........K.......G...TH.P.NE...I............V...RT...A..VNN.N.IL............... 46
APV-B .....V.....T...G..S..E..........K............TH.P.NE...I.....I......V...RT...A..VNN.N.LL............... 46
APV-C .....................D.M.......K....RP.G......S...........................T...K....N...IE.......I...... 46
bRSV  .SKTD..SSVITSI..I.S..GKTK.TASNKNR....TFSN..D.VS.KGV...SVG..L.YVN.L..KALY....E.IINYY..LV..S.E.DASIA..N 49
hRSV  .SKTD..SSVITS....I.S..GKTK.TASNKNR....TFSN..D.VS.KGV...SVG..L.YVN.L..KNLYV...E.IINYY..LV..S.E.DASIS..N 49
PVM   .SKTYV.TAV.TIM.C..S..GHN..TVIN.DK...RT.PD..H..S.KGV.R.QVG....Y...EV.KSI.VR.E.LVLKY..LS..D.K.D..IRD.E 45

00-1 F ESIENSQALVDQSNRILS----SAEKGNTGFII--VIILIAVLGSTMILVSVFIIIKKTKRPTGAP-PELSGVTNNGFIPH-N.                  54
APV-A ...DR..D.I.K..DL.G----ADA.SKA.IA.--A.VVLVI..IFFL.AVIYYCSRVR.TKPKHDY.ATT.HSSMAYV---------------S       53
APV-B ..VIK.KD.I.K..DL.D----IEV.S.I.AAL--A.TILV..SMLI.VGIAYYVV..R.AK.SNGY.KTT.QS.M.Y.S.                    53
APV-C ..V.K..N.I....K..D----.I....A..V.--..V..VL.MLAAVG.G..FVV..R.AAPKF.-M.MN..N.K....-.-F.LLKKKKKKKKK       55
bRSV  AK.NQ.L.FIRR.DEL.H--SVDVG.ST.NVV.TTI..V.V.VILML.A.GLLFYC.TKST.IMLGKDQ...IN.LS.S--------------K.        57
hRSV  .K.NQ.L.FIRR.DEL.H--NVNTG.ST.NIM.TTI..V.I.VLLSL.AIGLLLYC.AKNT.VTLSKDQ...IN.IA.S--------------K.        57
PVM   H..NQTRTFFKA.DQL.DLSENREN.NLNKSY.LTTLLFVVM.III.AVIGFILYKVLK----MIRDNK.KSKSTP.LT--------------VLS      53
```

L polymerase RAP PCR fragment 8

```
00-1 fragment 8 --------TVNVYLPDSYLKGVISFSETNAIGSCLLKRPYLKNDNTAKVAIENPVIEHVRLKNAVNSKMKISDYK-----IVEPVNMQHE 77
APV-A           ME-ISNESV.........................V.N...I.D.Y..H..MT......Q..RALEK.LTISRE.R----V...LMI.K. 84
bRSV            MDTLIHENST....T............C..L..Y..DG......Y.NIISRQK.L...IN..KLSIIQSFVTK.NKGELGLE..TYF.SL 90
hRSV            MDPIINGNSA....T.G..........C..L..YIFNG......Y.NLISRQ..L...MN..KLNITQSL..K.HKGEIKLE..TYF.SL 90

00-1 fragment 8 IM--KNVHSCEL----TLLKQFLTRSKNISTLKLNMICDWLQLK----------STSDDTSILSFIDVEFI------------------ 13
APV-A           LL--.VAAGAR.----KK..KW.G...D..EV..K.VT...K.S----------Q.PGRGK.IDR.Q..NL------------------ 13
bRSV            L.TY.SLSTS..ITTT..F.KIIR.AIE..DV.VYA.LNK.G..EKGKVDRC---DDTN.TLSNIVRDNILSVISDNTPSTKKPNNSSCK 17
hRSV            L.TY.SMT.S.QIATTN...KIIR.AIE..DV.VYA.LNK.G..EKDKIKSNNGQDE.NSV.TTI.KDDILSAVKDNQSHLKADKNHSTK 18

00-1 fragment 8 ---------------------PSWVSNWFSNWYNLNKLILEFRKEEVIRTGSIL--CRSLGKLVFVVSSYGCIVKSNKSKRVSFFTYNQLL 20
APV-A           ---------------------.D.LEH..DS.LI..DV.QSY.CL..SQ.SA..--RK.SLNFF.A...F...II.R..R.IC.C...... 20
bRSV            PDQPIKTTILCKLLSSMSHP.T.LIH..NLYTK..DILTQY.TN.ARNH.Y..IDT.T..EFQ.ILNQ.....YHK.L.KITIT....F. 26
hRSV            QKDTIKTTLLKKLMCSMQHP...LIH..NLYTK..NILTQY.SN..KNH.FT.IDNQT.SGFQ.ILNQ.....YHKEL..ITVT....F. 27

00-1 fragment 8 TWKDVMLSRFNANFCIWVSNSLNENQEGVGLRSNL-------Q                                               23
APV-A           ....LA.......L.V....C..SA.D.L....K.VGELLNR                                                24
bRSV            ....IS...L.VCMIT.I..C..TLNKSL...C                                                         30
hRSV            ....IS...L.VCLIT.I..C..TLNKSL.                                                            30
```

L polymerase RAP-PCR fragment 9/10

```
00-1 fragment 9/10 --KLVDKITSDQHIFSPDKIDMLTLGKMLMP--TIKGQKTDQ----FLNKRENYFHGNNLIESLSAALAXHWCGILTEQC 72
APV-A              -F.S.R..VT.....N..H..LVM...L.L.--.VRSNINNN-----KPAT..F.N...IV.A.TSC..C...TV.ILLT 72
bRSV               -ICKLNQVIQK..M.L....SLSQYVELFLSNK.L.NSPHISSNLVLVH.MSD..LHKYV---..TN..G..IM.IQLMK 76
hRSV               DIHKLKQVIQK..M.L....SLTQYVELFLSNK.L.SGSHVNSNLILAH.ISD...NTYI---..TN..G..IL.IQLMK 77

00-1 fragment 9/10 IENNIFKKDWGDGFISDHAFMDFKIFLCVFKTKLLC                                             10
APV-A              T..S..Q.E......T....IN.TW..MS...Y...HW                                           11
bRSV               DSKG..E....E.Y.T..M.L.LNV.FDAY..Y.                                               11
hRSV               DSKG..E....E.Y.T..M.INL.V.FNAY..Y                                                11
```

FIGURE 4, contd.

```
                                                              50
HMPV   MSLQGIHLSDLSYKHAILKESQYTIKRDVGTTTAVTPSSLQQEITLLCGE
APVC   ......Q................................R.VS.....
APVB   ...ES.R....E......D......R....A...I...E..PKVST...M
APVA   ...ES.R....E......ED.....R....A...I...E..PQVST...M
HRSVA  .A.SKVK.N.TLN.DQL.SS.K...Q.ST.DSIDTPNYDV.KH.NK...M
HRSVB  .A.SKVK.N.TLN.DQL.SS.K...Q.ST.DNIDTPNYDV.KHLNK...M
BRSV   .A.SKVK.N.TFN.DQL.ST.K...Q.ST.DNIDIPNYDV.KHLNK...M
PVM    ...DRLK.N.V.N.DSL.SNCK.SVT.ST.DV.S.SGHAM.KALARTL.M
                                                             100
HMPV   ILYAKHADYKYAAEIGIQYISTALGSERVQQILRNSGSEVQVVLTRTYSL
APVC   ......T..SH...V.M..V..T..A..T....K.......A...K....
APVB   ..F......EP..QV.M.........ADKT....KS......G.M.KIVT.
APVA   V.F...T..EP...V.M........AD.T....K.......G.M.KIVT.
HRSVA  L.ITED.NH.FTGL..ML.AMSR..R.DTIK...DA.YH.KANGVDVTTH
HRSVB  L.ITED.NH.FTGL..ML.AMSR..R.DTIK..KDA.YH.KANGVDITTY
BRSV   L.ITED.NH.FTGL..ML.AMSR..R.DTLK..KDA.YQ.RANGVDVITH
PVM    F.LTAFNRCEEV....L..AMSL..RDDSIK...EA.YN.KC.D.QLKDF
                                                             150
HMPV   GKIKNNKGEDLQMLDIHGVEKSWVEEIDKEARKTMATLLKESSGNIPQNQ
APVC   ..G..S...E..........R..I..V.........SAT.DN..P.....
APVB   PAEGPIR--KREV.N..DIGPA.ADNVERT..E..SLMV..K-AQ..K..
APVA   SAEGSVR--KREV.N..D.GVG.ADDVERTT.EA.GAMVR.K-VQLTK..
HRSVA  RQDI.G.EMKFEV.TLASLTTEIQIN.EI.S..SYKKM...M-.EVAPEY
HRSVB  RQDI.G.EMKFEV.TLSSLTSEIQVN.EI.S..SYKKM...M-.EVAPEY
BRSV   RQDV.G.EMKFEV.TLVSLTSEVQGN.EI.S..SYKKM...M-.EVAPEY
PVM    TIKLQG.EYKI.V...V.IDAANLADLEIQ..GVV.KE..TG-ARL.D.R
                     A                                       200
HMPV   RPSAPDTPIILLCVGALIFTKLASTIEVGLETTVRRANRVLSDALKRYPR
APVC   ...S..A.......I.........................A........N.....F..
APVB   K...L.A.V....I.........V......AI...S......IS....
APVA   K...L.A.V....I.........V......AI...S......IS....
HRSVA  .HDS..CGM.I..IA..VI....AGDRS..TAVI....N..KNEM...KG
HRSVB  .HDS..CGM.I..IA..VI....AGDRS..TAVI....N..KNEI...KG
BRSV   .HDS..CGM.V...A..VI....AGDRS..TAVI....N..RNEM...KG
PVM    .HD...CGV.V..IA..VVS...AGDRG..DAVE...LN..KAEKA...N
                                                             250
HMPV   MDIPKIARSFYDLFEQKVYHRSLFIEYGKALGSSSTGSKAESLFVNIFMQ
APVC   I.............Y..............................
APVB   ....R..K..FE...K...Y.N...........T.S..RM..........
APVA   ....R..K..FE...K...Y.N...........T....RM..........
HRSVA  LLPKD..N...EV..KHPHFIDV.VHF.I.QS.TRG..RV.GI.AGL..N
HRSVB  LIPKD..N...EV..KHPHLIDV.VHF.I.QS.TRG..RV.GI.AGL..N
BRSV   LIPKD..N...EV..KYPHYIDV.VHF.I.QS.TRG..RV.GI.AGL..N
PVM    .EVKQ..E.......R.P.YIDV..TF.L.QS.VRG...V.G..SGL..N
           B                                      C          300
HMPV   AYGAGQTMLRWGVIARSSNNIMLGHVSVQAELKQVTEVYDLVREMGPESG
APVC   ..................................................
APVB   ..........R..V............ .....R..S.......K......
APVA   ...........................  .....R..S.......K......
HRSVA  ......V......L.K.VK......A....ME..V...EYAQKL.G.A.
HRSVB  ...S..V......L.K.VK......A....ME..V...EYAQKL.G.A.
BRSV   ......V......L.K.VK......A....ME..V...EYAQKL.G.A.
PVM    ......V.....IL.K.VK......A....ME..V...EYAQKQ.G.A.
                                                             350
HMPV   LLHLRQSPKAGLLSLANCPNFASVVLGNASGLGIIGMYRGRVPNTELFSA
APVC   ......N.......................L...........A.
APVB   ...............TS..........A........K..A..L.....
APVA   ...............T...........A........K..A..L...A.
HRSVA  FY.ILNN...S....TQF.H.S......A....M.E...TPR.QD.YD.
HRSVB  FY.ILNN...S....TQF...S......A....M.E...TPR.QD.YD.
BRSV   FY.ILNN...S....TQF...S......A....M.E...TPR.QD.YD.
PVM    FY.I.NN...S....T.....T......A......S.K.APR.R...D.
                                                        395
HMPV   AESYAKSLKESNKINFSSLGLTDEEKEAAEHFLNVSDDS-QNDYE
APVC   .....R...............E.......N...INEEG-.....
APVB   .....R..........LAA....ED.R...TSY.GGDE.K-SQKF.
APVA   .....RT.R.N....LAA.....D.R...TSY.GGD.ER-SSKF.
HRSVA  .KA..EQ...NGV..Y.V.D..A..L..IK.Q..PK.N--DVEL-
HRSVB  .KA..EQ...NGV..Y.V.D..A..L..IKNQ..PKE.--DVEL-
BRSV   .KA..EQ...NGV..Y.V.D..T..L..IKNQ..PK.N--DVEL-
PVM    .KD..ER..DN.V..Y.A.N..A..R.LISQQ..IV..TPDD.I-
```

FIGURE 5

```
                                                                  50
HMPV   MSFPEGKDILFMGNEAAKLAEAFQKSLRKPGHKRS---------QSIIGEK
APVC   ..........L.......A.....R..K.I..R.T---------...V.D.
APVB   ..L.......M..S........Y.Q.IKNSTSV.---------R..S.DP
APVA   ..........M..S....M.D.Y.R...NTSAGG---------R..S..P
HRSVA  ---M.KFAPE.H.ED.NNR.TK.LE.-----------------------
HRSVB  ---M.KFAPE.H.ED.NNK.TK.LE.-----------------------
BRSV   ---M.KFAPE.H.ED.NTK.TK.LE.-----------------------
PVM    ---M.KFAPE.V.ED.N.K..E.L.HRSF.SE.PLAGIPNTATHVTKYNM
                                                                 100
HMPV   VNTVSETLELPTISRPAKPTIPSEPKLAWTDKGGATKTEIKQAIKVMDPI
APVC   II.....V.K....KST.V.T.P.R.N..GE.PDT.RSQTEE.RNEAT.E
APVB   .S....KVP..PLCSSETS------------R.ACIRPT-.STLPPIK--
APVA   I..IA.KVP..PLCN.TT.------------..SCI.PN-.APVPKVK--
HRSVA  ---IKGKFTS.----------------------KDPKK.DS.ISVNS.
HRSVB  ---IKGKFASS----------------------KDPKK.DS.ISVNS.
BRSV   ---LKGKFTSS----------------------KDSRK.DS.ISVNSV
PVM    PPILRSSFK..SPRVA.NL.E..A.P----TTPPP.PPQN.EEQPKESDV
                                                                 150
HMPV   EEEESTEKKVLPSSDGKTPAEKKLKPSTNTKKK-----VSFTPNEPGKYT
APVC   DASRLY.EVFA.T.........GKETPEKP...-----.T.KND.S.R..
APVB   .V.SIYP.LPTAPP.AMIETAHPIGAPKKAQ.R-----.K.ESSKA....
APVA   .I.SIYP.LPTAPVATD.YTSTSTESAKKS..------.K.DNPKV....
HRSVA  DI.VTK.SPITSN.TIIN.TNETDDTAG.KPNYQRKPL...KEDPTPSDN
HRSVB  DI.VTK.SPITSGTNIIN.TSEADSTPETKANYPRKPL...KEDLTPSDN
BRSV   DI.LPK.SPITSTNQNINQPSEINDTIATNQVHIRKPL...KEEL.SSEN
PVM    DI.TMHVC..PDNPEHSKKPCCSDDTD.KKT---RKPM.T.VEP.EKFVG
                                                                 200
HMPV   KLEKDALDLLSD-NEEEDAESSILTFEERD--TSSLSIEARLESIEEKLS
APVC   ...ME..E....-..DD.....V.....K.--..A..L.......D....
APVB   ...EE..E....PD.DN.EK..V.....K.--NAPS.......A......
APVA   ...EEG.E....PE.DN.EK........K.--.A.T.......A......
HRSVA  PFS.LYKETIETFDNN--E.E.SYSY..INDQ.NDN-.T...DR.D....
HRSVB  PFS.LYKETIETFDNN--E.E.SYSY..INDQ.NDN-.T...DR.D....
BRSV   PFTRLYKETIETFDNN--E.E.SYSYD.INDQ.NDN-.T...DR.D....
PVM    LGASLYRETMQTFAADGYD.E.N.S...TNQEPG.S.V.Q..DR......
                                                                 250
HMPV   MILGLLRTLNIATAGPTAARDGIRDAMIGVREELIADIIKEAKGK-----
APVC   ..........V...............V.L............----
APVB   ....M.K..S................V.......NS.MA......-----
APVA   ....M.K...................M.....NS.MT...D.-----
HRSVA  E...M.H..VV.S....S...........L...M.EK.RT..LMTNDRLE
HRSVB  E...M.H..VV.S....S.........V.L...M.EK.RA..LMTNDRLE
BRSV   E.I.M.H..VV.S.............V.L...M.EK.RS..LMTNDRLE
PVM    Y.I...N.IMV......T...E....L..T.....EM.KSDILTVNDRIV
                                                                 300
HMPV   -AAEMMEEEMSQRSKIGNGSVKLTEKAKELNKIVEDESTSGESEEEEEPK
APVC   -.....K..AK.K........G...........................EE
APVB   -I..IIK..DA..A...D.........R...RML..Q.S........S.ET
APVA   -I....K..DT..A...D..............L..Q.S.........SG
HRSVA  AM.RLRN..SEKMA.DTSDE.S.NPTSEK..NLL.G--------------N
HRSVB  AM.RLRN..SEKMA.DTSDE.P.NPTS.K.SDLL..--------------N
BRSV   AM.RLRD..SEKMT.DTSDE....PTSEK..MVL..--------------E
PVM    AMEKLRD..C.RADTDDGSACY..DR.RI.D...SSNA-----------E
                  316
HMPV   DTQDNSQEDDIYQLIM
APVC   .HEESNPD..L.S.T.
APVB   EPDTDGEN....SFD.
APVA   ESESDEELS...N.DL
HRSVA  .SDNDLSLE.F-----
HRSVB  .SDNDLSL..F-----
BRSV   SSDNDLSLE.F-----
PVM    EAKEDLDV...MGINF
```

FIGURE 6

```
                                                        50
HMPV   MESYLVDTYQGIPYTAAVQVDLIEKDLLPASLTIWFPLFQANTPPAVLLD
APVC   ...........V.......T..V...Q...R..V.V....T....T...E
APVB   ....II.....V..........V...NN..K..V......SS..AP....
APVA   ....II.....V...............SN..T..V......SS..AP....
HRSVA  ..T.VNKLHE.ST......YNVL...DD.......V.M..SSM.ADL.IK
HRSVB  ..T.VNKLHE.ST......YNVL...DD.......V.M..SSV.ADL.IK
BRSV   ..T.VNKLHE.ST......YNV....DD.......V.M..SSISADL.IK
PVM    ..A...EM.H.V.......LN.V..HSANI...V.I.M..TSL.KNSVM.
                                                       100
HMPV   QLKTLTITTLYAASQNGPILKVNASAQGAAMSVLPKKFEVNATVALDEYS
APVC   ...........T....................A...S.D.S.S....D..
APVB   .....S...Q.TV.PE..V.Q...T.......A.....S.S.AA......
APVA   .....S...Q.T..PE..V.Q...A.......A.....A.S.A.......
HRSVA  E.ANVN.LVKQISTPK..S.R.MINSRS.VLAQM.S..TIC.N.S...R.
HRSVB  E.ASIN.LVKQISTPK..S.R.TINSRS.VLAQM.SN.IIS.N.S...R.
BRSV   E.INVN.LVRQISTLK..S..IMINSRS.VLAQM.S..TIS.N.S...R.
PVM    L.HDV.VICTQISTVH..MI..DL.SSN.GLATM.RQ.LI..II...DWG
                                                       150
HMPV   KLEFDKLTVCEVKTVYLTTMKPYGMVSKFVSSAKSVGKKTHDLIALCDFM
APVC   ...........L.A................N...A...............L
APVB   ..D.GV....D.RA.....L........I.TNMNT..R............I
APVA   R...GT....D.RSI....L........IMTDVR...R............I
HRSVA  ..AY.VT.P..I.ACS..CL.SKN.LTTVKDLTMKTLNP...I....E.E
HRSVB  ..AY.VT.P..I.ACS..CL.VKS.LTTVKDLTMKTFNP..EI....E.E
BRSV   ..AY.IT.P..I.ACS..CL.VKN.LTTVKDLTMKTFNP..EI....E.E
PVM    NMDYEVPVAFDK.SFCV.IL..KN.LYTVP.ITP-TNRP..E...V.S.H
                                                       200
HMPV   DLEKNTPVTIPAFIKSVSIKESESATVEAAISSEADQALTQAKIAPYAGL
APVC   ....GV......Y...................G.....I...R.......
APVB   .M.RGI......Y..A....D...........G.....I...R.......
APVA   .I..GV.I....Y..A....D...........G.....I...R.......
HRSVA  NIVTSKK.I..TYLR.I.VRNKDLN.L.NITTT.FKN.I.N...I..S..
HRSVB  NIMTSKR.I..TYLRPI.V.NKDLNSL.NIATT.FKN.I.N...I.....
BRSV   NIMTSKR.V..T.LR.INV.AKDLDSL.NIATT.FKN.I.N...I.....
PVM    NRVTLKSFN..V..RALY.RQQGLDS..Q....DV.H.I.T.RV......
                                                       250
HMPV   IMIMTMNNPKGIFKKLGAGTQVIVELGAYVQAESISKICKTWSHQGTRYV
APVC   ....................V...............R..RN.........
APVB   .LL.A........R..............P......LG......N..R...I
APVA   .L..................M.......P......LG......N..R....
HRSVA  LLVI.VTDN..A..YIKPQS.F..D....LEK...YYVTTN.K.TA..FA
HRSVB  VLVI.VTDN..A..YIKPQS.F..D....LEK...YYVTTN.K.TA..FS
BRSV   VLVI.VTDN..A..YIKPQS.F..D....LEK...YYVTTN.K.TA.KFS
PVM    TLVINITST..A..L.K..S.ILA...P.LTQV.LHDVIMN.K.T..S.I
              258
HMPV   LKSR----
APVC   ....----
APVB   ....----
APVA   .R..----
HRSVA  I.PMED--
HRSVB  I.PLED--
BRSV   I.PIED--
PVM    ...SSTSG
```

FIGURE 7

```
               Signal peptide                                                             100
HMPV   ---------MSWKVVIIFSLLITPQHGLKESYLEESCSTITEGYLSVLRTGWYTNVFTLEVGDVENLTCADGPS---LIKTELDLTKSALRELRTVSADQ
APVC   ---------.....LLLV..A..TG..E......Y..V.R.......................T....---..R...E...N..E..K......
APVB   ---------.YL.LLL.IY.VVGASGKIQ.T.S.....V.R..K...........N..I.N...I..N....---..S...S..QN..Q.........
APVA   ---------.DVRICLLLF.ISN.SSCIQ.T.N.....V.R..K...........N..I.N...I..N....---..D...V...N.....K......
HRSVA  MELLILKANAITTILTAVTFCFASGQNIT.EFYQST..AVSK....A.......S.I.I.LSNIKENK.NGTDAKVK...Q...KY.N.VT..QLLMQST
HRSVB  MELLIHRLSAIFLTLA.NA.YL.SSQNIT.EFYQST..AVSR..F.A.......S.I.I.LSNIKETK.NGTDTKVK...Q...KY.N.VT..QLLMQNT
BRSV   MATTAMRMII.IIFISTYVTH..LCQNIT.EFYQST..AVSR....A.......S.V.I.LSKIQKNV.KSTD.KVK...Q..ERYNN.VV..QSLMQNE
PVM    ----MIPGRIFLVLLV..NTKPIHPNT.T.K.Y.ST..VE.A..K.A....HMT.MSIKLSQINIES.KSSN.---.LAH..AIYS..VD....L.SN-

                                                    Fusion domain                       HRA        200
HMPV   LAREEQ-----------------------IENPRQSRFVLGAIALGVATAAAVTAGVAIAKTIRLESEVTAIKNALKKTNEAVSTLGNGVRVLATAVRELK
APVC   ..K.AR-----------------------.MS..KA...........................G..A...G..R....................ND..
APVB   ITK.NR-----------------------.LSH.KK............T........L.......G..K...L..RS.............I.....ND..
APVA   V.K.SR-----------------------LSS..RR.....................L.......G..K......RN...................ND..
HRSVA  PPTNNRARRELPRFMNYTLNNAKKTNVTLSKK.KR..LG--FL...G--S.IAS...VS.VLH..G..NK..S..LS..K..VS.S...S..TSK.LD..
HRSVB  P.ANNRARREAPQYMNYTINTTKNLNVS.SKK.KR..LG--FL...G--S.IAS.I.VS.VLH..G..NK.....LS..K..VS.S...S..TSK.LD..
BRSV   P.SFSRAKRGIPELIHYTRNSTKKFYGLMGKK.KR..LG--FL..IG--S..AS...VS.VLH..G..NK.....LS..K..VS.S...S..TSK.LD..
PVM    -------------------------ALKSK-..KK..LG--LI..LG--........L...VQ....IAL.RD.VRN.....VS.T..MS...KV.DD..

                                                                                                 300
HMPV   DFVSKNLTRAINKNKCDIADLKMAVSFSQFNRRFLNVVRQFSDNAGITPAISLDIMTDAELARAVSNMPTSAGQIKLMLENRAMVRRKGFGFLIGVYGSS
APVC   ..I..K..P...R.....S........G.Y..........................V.........S...N..................I........
APVB   E.I..K..P...Q....N...IR..I..G.N.............S....S.V..........VK.INR....S...S...N............I......GT
APVA   E.I..K..P...Q....N...I...I..G.N.............S....S.V.......D..V..INR....S...S...N............I.....DGT
HRSVA  NYID.Q.LPIV..QS.S.SNIETVIE.Q.K.N.L.EIT.E..V...V.TPV.TYML.NS..LSLIND..ITND.K...SN.VQI..QQSYSIMSIIKEEV
HRSVB  NYINNQ.LPIV.QQS.R.SNIETVIE.Q.K.S.L.EIN.E..V...V.TPL.TYML.NS..LSLIND..ITND.K...SS.VQI..QQSYSIMSIIKEEV
BRSV   NYID.E.LPQV.NHD.R.SNIETVIE.Q.K.N.L.EIA.E..V.....TPL.TYML.NS..LSLIND..ITND.K...SS.VQI..QQSYSIMSV.KEEV
PVM    N.I..E.LPK..RVS..VH.ITAVIR.Q.L.K.L.E.S.E..S...L.HTV.SFML..R..TSI.GG.AV....KEI..SSK.IM..N.LAI.SS.NADT

                                                                                                 400
HMPV   VIYMVQLPIFGVIDTPCWIVKAAPSCSG--KKGNYACLLREDQGWYCQNAGSTVYYPNEKDCETRGDHVFCDTAAGINVAEQSKECNINISTTNYPCKVS
APVC   .V.I..............K.....I..--.D..........................E...V.S...............KE.E...R....K.......
APVB   .V..........E.....R.V...I.RH--ERES................T....A.....D...V.D.Y...............SEVEC..H....ST.......
APVA   .V..........E.....R.V...I.RK--E........I..........T....A....KD...V.D.Y...............LEVEC..Y....SK.......
HRSVA  LA.V....LY.........KLHTS.I.TTNT.E.SNI..T.T.R.....D...VSFF.QAET.KVQSNR......MNSLTLPSEINI..VD.FNPK.I...IM
HRSVB  LA.V.....Y.........KLHTS.I.TTNI.E.SNI..T.T.R.....D...VSFF.QADT.KVQSNR......MNSLTLPSEVSI..TD.FNSK.I...IM
BRSV   IA.V.....Y.........KLHTS.I.TTDN.E.SNI..T.T.R.....D...VSFF.QTET.KVQSNR......MNSLTLPTDVNI..TD.FN.K.I...IM
PVM    LV.VI...L...M..I...VIRSSII.HN--IADK....A.A.N.....H...LS.F.SPT...IHNGYA.....LKSLT.PVT.R....S.MY....I..I.

                                                                                                 500
HMPV   TGRHPISMVALSPLGALVACYKGVSCSIGSNRVGIIKQLNKGCSYITNQDADTVTIDNTVYQLSKVEGEQHVIKGRPVSSSFDPVKFPEDQFNVALDQVF
APVC   ..................D.M.......K...RP.G......S.......................T...K....N...IE.......I......
APVB   .....V.....T...G.S..E........K...........TH.P.NE...I.....I......V...RT...A..VNN.N.LL.............
APVA   .....V.....T...G.S..ES.......K......G....TH.P.NE...I............V...RT...A..VNN.N.IL.............
HRSVA  .SKTDV.SSVITS...I.S..GKTK.TASNKNR....TFSN..D.VS.KGM...SVG..L.YVN.Q..KSLYV..E.IINFY..LV..S.E.DASIS..N
HRSVB  .SKTD..SSVITS...I.S..GKTK.TASNKNR....TFSN..D.VS.KGV...SVG..L.YVN.L..KNLYV..E.IINYY..LV..S.E.DASIS..N
BRSV   .SKTD..SSVITSI..I.S..GKTK.TASNKNR....TFSN..D.VS.KGV...SVG..L.YVN.L..KALY...E.IINYY..LV..S.E.DASIA..N
PVM    .SKTYV.TAV.TTM.C..S..GHN..TVIN.DK...RT.PD..H..S.KGV.R.QVG....Y...EV.KSI.VR.E.LVLKY..LS..D.K.D..IRD.E

             HRB                       Membrane anchor                     583
HMPV   ESIENSQALVDQSNRILSSAE----KGNTGFIIVIILIAVLGSTMILVSVFIIIKKTKKPTG---AP-PELSGVTNNGFIPHN
APVC   ..V.K..N.I....K..D.I.----...A..V...V..VL.MLAAVG.G..FVV..R.AAPK---F.-M.MN..N.K....--
APVB   ..VDK.KD.I.K..DL.DIEV----.S.I.AALA.TILV..SMLI.VGIAYYVV..R.AK.S---NGY.KTT.QS.M.Y.S--
APVA   ...DR..D.I.K..DL.GADA----.SKA.IA.A.VVLVI..IFFL.AVIYYCSRVR.TKPK---HDY.ATT.HSSMAYVS--
HRSVA  .K.NQ.L.FIRK.DEL.HNVN--AG.ST.NIM.TT.I.VIIVILLS.IA.GLLLYCKARS.P-VTLSKDQ...IN.IA.SN--
HRSVB  .K.NQ.L.FIRR.DEL.HNVN--TG.ST.NIM.TT.I.VIIVVLLS.IAIGLLLYCKA.N.P-VTLSKDQ...IN.IA.SK--
BRSV   AK.NQ.L.FIRR.DEL.H.VD--VG.ST.NVV.TT.I.VIVVVILM.IA.GLLFYCKT.S.P-IMLGKDQ...IN.LS.SK--
PVM    H..NQTRTFFKA.DQL.DLS.NREN.NLNKSY.LTT.LF.VMLII.MAVIGF.LY.VL.MIRDNKLKSKSTP.L.VLS-----
```

FIGURE 9

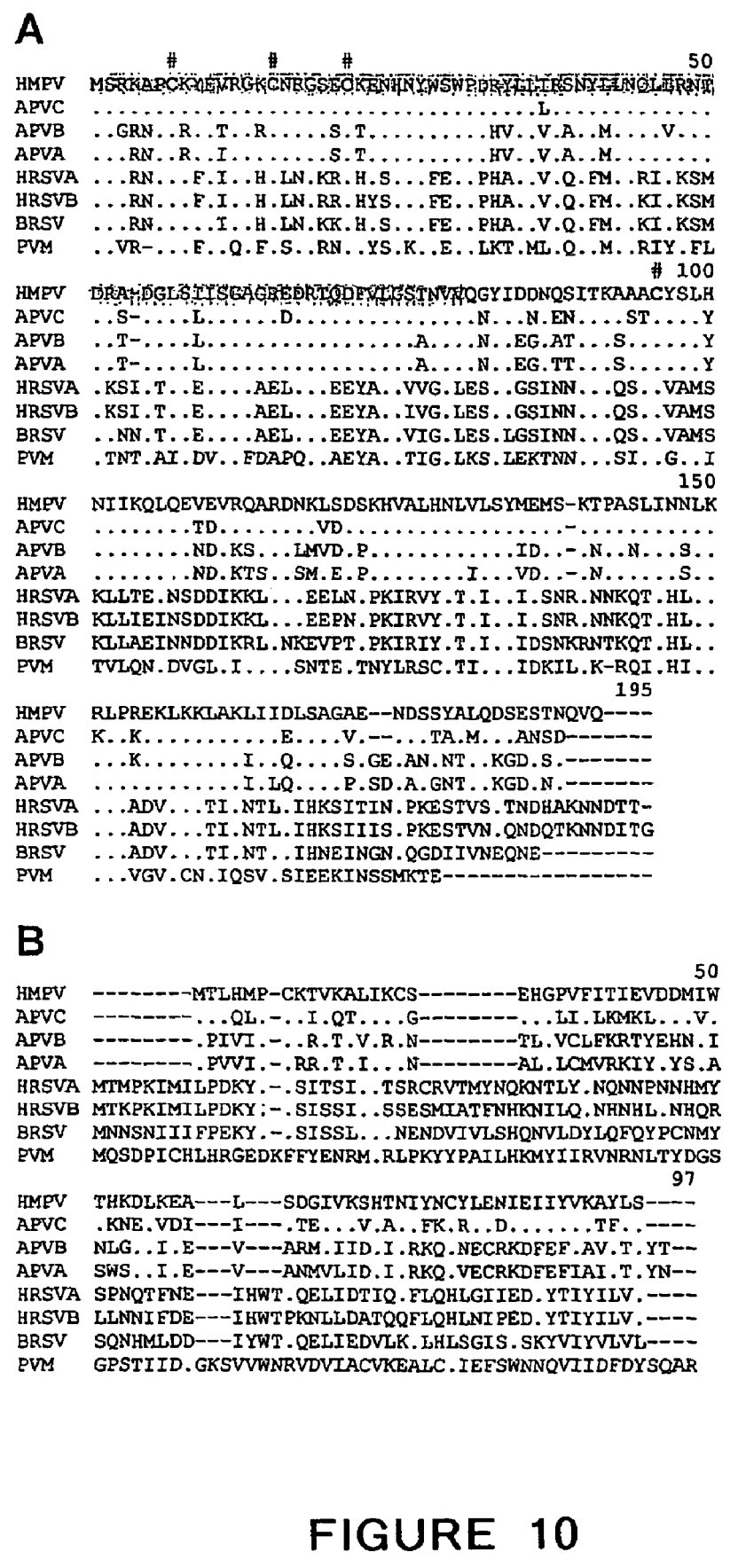

A

```
                #       #     #                             50
HMPV   MSRKAPCKYEVRGKCNRGSECKFNHNYWSWPDRYLLIRSNYLLNQLLRNT
APVC   ...................................L..............
APVB   ..GRN..R..T..R.....S.T..........HV..V.A..M....V...
APVA   ...RN..R..I........S.T..........HV..V.A..M........
HRSVA  ...RN...F.I..H.LN.KR.H.S...FE..PHA..V.Q.FM..RI.KSM
HRSVB  ...RN...F.I..H.LN.RR.HYS...FE..PHA..V.Q.FM..KI.KSM
BRSV   ...RN.....I..H.LN.KK.H.S...FE..PHA..V.Q.FM..KI.KSM
PVM    ..VR-...F..Q.F.S..RN..YS.K..E..LKT.ML.Q..M..RIY.FL
                                                  # 100
HMPV   DRA-DGLSIISGAGREDRTQDFVLGSTNVVQGYIDDNQSITKAAACYSLH
APVC   ..S-....L.....D...............N...N.EN....ST....Y
APVB   ..T-....L.................A....N..EG.AT...S......Y
APVA   ..T-....L.................A....N..EG.TT...S......Y
HRSVA  .KSI.T..E....AEL...EEYA..VVG.LES..GSINN...QS..VAMS
HRSVB  .KSI.T..E....AEL...EEYA..IVG.LES..GSINN...QS..VAMS
BRSV   ..NN.T..E....AEL...EEYA..VIG.LES.LGSINN...QS..VAMS
PVM    .TNT.AI.DV..FDAPQ..AEYA..TIG.LKS.LEKTNN...SI..G..I
                                                    150
HMPV   NIIKQLQEVEVRQARDNKLSDSKHVALHNLVLSYMEMS-KTPASLINNLK
APVC   ........TD........VD.................-...........
APVB   ........ND.KS...LMVD.P............ID..-.N..N...S..
APVA   ........ND.KTS..SM.E.P........I...VD..-.N......S..
HRSVA  KLLTE.NSDDIKKL...EELN.PKIRVY.T.I..I.SNR.NNKQT.HL..
HRSVB  KLLIEINSDDIKKL...EEPN.PKIRVY.T.I..I.SNR.NNKQT.HL..
BRSV   KLLAEINNDDIKRL.NKEVPT.PKIRIY.T.I..IDSNKRNTKQT.HL..
PVM    TVLQN.DVGL.I....SNTE.TNYLRSC.TI...IDKIL.K-RQI.HI..
                                               195
HMPV   RLPREKLKKLAKLIIDLSAGAE--NDSSYALQDSESTNQVQ----
APVC   K..K............E....V.--...TA.M...ANSD-------
APVB   ...K.........I..Q....S.GE.AN.NT..KGD.S.-------
APVA   .............I.LQ....P.SD.A.GNT..KGD.N.-------
HRSVA  ...ADV...TI.NTL.IHKSITIN.PKESTVS.TNDHAKNNDTT-
HRSVB  ...ADV...TI.NTL.IHKSIIIS.PKESTVN.QNDQTKNNDITG
BRSV   ...ADV...TI.NT..IHNEINGN.QGDIIVNEQNE---------
PVM    ...VGV.CN.IQSV.SIEEKINSSMKTE-----------------
```

B

```
                                                          50
HMPV   --------MTLHMP-CKTVKALIKCS--------EHGPVFITIEVDDMIW
APVC   --------...QL.-..I.QT....G--------...LI.LKMKL...V.
APVB   --------.PIVI.-..R.T.V.R.N--------TL.VCLFKRTYEHN.I
APVA   --------.PVVI.-.RR.T.I...N--------AL.LCMVRKIY.YS.A
HRSVA  MTMPKIMILPDKY.-.SITSI..TSRCRVTMYNQKNTLY.NQNNPNNHMY
HRSVB  MTKPKIMILPDKY;-.SISSI..SSESMIATFNHKNILQ.NHNHL.NHQR
BRSV   MNNSNIIIFPEKY.-.SISSL...NENDVIVLSHQNVLDYLQFQYPCNMY
PVM    MQSDPICHLHRGEDKFFYENRM.RLPKYYPAILHKMYIIRVNRNLTYDGS
                                                    97
HMPV   THKDLKEA---L---SDGIVKSHTNIYNCYLENIEIIYVKAYLS----
APVC   .KNE.VDI---I---.TE...V.A..FK.R..D.......TF..----
APVB   NLG..I.E---V---ARM.IID.I.RKQ.NECRKDFEF.AV.T.YT--
APVA   SWS..I.E---V---ANMVLID.I.RKQ.VECRKDFEFIAI.T.YN--
HRSVA  SPNQTFNE---IHWT.QELIDTIQ.FLQHLGIIED.YTIYILV.----
HRSVB  LLNNIFDE---IHWTPKNLLDATQQFLQHLNIPED.YTIYILV.----
BRSV   SQNHMLDD---IYWT.QELIEDVLK.LHLSGIS.SKYVIYVLVL----
PVM    GPSTIID.GKSVVWNRVDVIACVKEALC.IEFSWNNQVIIDFDYSQAR
```

FIGURE 10

A

```
                                                           50
MITLDVIKSDGSSKTCTHLKKIIKDHSGKVLIVLKLILALLTFLTVTITI
                                                          100
NYIKVENNLQICQSKTESDKKDSSSNTTSVTTKTTLNHDITQYFKSLIQR
                                                          150
YTNSAINSDTCWKINRNQCTNITTYKFLCFKSEDTKTNNCDKLTDLCRNK
                                          183
PKPAVGVYHIVECHCIYTVKWKCYHYPTDETQS
```

B

A

50
MEVKVENIRTIDMLKARVKNRVARSKCFKNASLVLIGITTLSIALNIYLI
100
INYKMQKNTSESEHHTSSSPMESSRETPTVPTDNSDTNSSPQHPTQQSTE
150
GSTLYFAASASSPETEPTSTPDTTNRPPFVDTHTTPPSASRTKTSPAVHT
200
KNNPRTSSRTHSPPRATTRTARRTTTLRTSSTRKRPSTASVQPDISATTH
236
KNEEASPASPQTSASTTRIQRKSVEANTSTTYNQTS

B

```
                 A                              674
HMPV   NYIARASIVTDLSKFNQAFRYETTAICADVADELHGTQSLFCWLHLIVPM
APVA   ..........................SV...................T.SS
HRSVA  ...SKC..I.............SC..S..L.....V....F....AI.H
HRSVB  ...SKC..I.............SC..S..L.....V....S....TI.L
BRSV   ...SKC..I.............SC..S..L.....V....S....TI.F
HPIV2  FELSACF.T...A.YCLQW..Q.IIHF.RTLNRMY.VPH..E.I..RLIR
NDV    RRRVATF.T...Q.YCLNW..Q.IKLF.HAINQ.M.LPHF.E.I..RLMD
SV     YETLSCFLT...K.YCLNW.F.S..LFGQRCN.IF.FKTF.N.M.PVLEK
HPIV3  YETVSCFLT...K.YCLNW...S..LFGETCNQIF.LNK..N...PRLEG
MV     YETVS.F.T...K.YCLNW....ISLF.QRLN.IY.LP.F.Q...KRLET
NIPAH  FDTVS.FLT...K..CLNW...SM..F.ERL..IY.LPGF.N.M.KRLER
                                      B           723
HMPV   TTMICAYRHAPPETKG-EYDIDKIEEQSGLYRYHMGGIEGWCQKLWTMEA
APVA   .....T......D.G.-I....Q.P.......F...........M.....
HRSVA  V.I..T......YIRDHIV.LNNVD.....................I..
HRSVB  V.I..T......FI.DHVVNLNEVD.....................I..
BRSV   A.V..T......YIRNHIT.LN.VD.....................I..
HPIV2  S.LYVGDPFN..AATD-AF.L..VLNGDIFIVSK-.....L...M...IS
NDV    ...FVGDPFN..SDPT-DC.LSRVPNDDIYIVSAR.....L.......IS
SV     C.IYVGDPYC.VADRM-HRQLQDHADSGIFIHNPR.....Y.......LIS
HPIV3  S.IYVGDPYC..SD.E-HISLEDHPDSGFYVHNPR.....F.......LIS
MV     SVLYVSDP.C..DLDA-HIPLY.VPNDQIFIK.P......Y.......IST
NIPAH  SVIYV.DPNC..NIDK-HMELE.TP.DDIFIH.PK.....YS..T..IAT
                     C                            772
HMPV   ISLIDVVSVKTRCQMTSLLNGDNQSIDVSKPVKLSEG-LDEVKADYSLAV
APVA   ..........RN.V.L..............R.TGA-QT.IQ......I
HRSVA  .....LI.L.GKFSI.A.I........I....R.M..-QTHAQ...L..L
HRSVB  .....LI.L.GKFSI.A.I........I....R.I..-QTHAQ...L..L
BRSV   .....LI.I.GKFSI.A.I........I...I..N..-QTHAQ...L..L
HPIV2  ..VIILS.AESKTRVM.MVQ....A.A.TTR.PR.LPSIQKKELA.AASK
NDV    .AAIQLAAARSH.RVACMVQ....V.A.TRE.RSDDSPEMVLTQLHQASD
SV     ..AIHLAA.RVGVRVSAMVQ....A.A.TSR.PVAQTYKQKKNHV.EEIT
HPIV3  ..AIHLAA.RIGVRV.AMVQ....A.A.TTR.PNNYDYRIKKEIV.KDV.
MV     .PY.YLAAYESGVRLA..VQ....T.A.T.R.PSTWPYNLKKREAARVTR
NIPAH  .PF.FLSAYE.NTRIAAIVQ...E..AITQK.HPNLPYKVKKEICAKQ.Q
                                              D    822
HMPV   KMLKEIRDAYRNIGHKLKEGETYISRDLQFISKVIQSEGVMHPTPIKKIL
APVA   ...TAV....Y............V......M..T.......Y.AA...V.
HRSVA  NS..LLYKE.AG......GT.......M..M..T..HN..YY.AS...V.
HRSVB  NS..LLYKE.AG......GT.......M..M..T..HN..YY.AS...V.
BRSV   .S..LLYKE.AS......GT.......M..M..T..HN..YY.AS...V.
HPIV2  LFFERL.ANNYGL..Q..AQ..I..STFFIY..RVFYQ.RILTQAL.NAS
NDV    NFF..LIHVNHL...N..DR..IR.DTFFIY..R.FKD.AILSQVL.NSS
SV     RYFGAL.HVMFD...E..LN..I..SKMFVY..R.YYD.KIL.QCL.AIT
HPIV3  RFFDSL.EVMDDL..E..LN..I..SKMFIY..R.YYD.RIL.QAL.AIS
MV     DYFVIL.QRLHD...H..AN..IV.SHFFVY..G.YYD.LLVSQSL.S.A
NIPAH  LYFERL.MNL.AL..N..AT..I..TH.FIY..K.HYD.AVLSQAL.SMS
                         847
HMPV   RVGPWINTILDDIKTSAESIGSLCQ
APVA   ...............M.A......
HRSVA  ............F.V.L......T.
HRSVB  ............F.V.L......T.
BRSV   ............F.V.M......T.
HPIV2  KLCLTADVLGECTQA.CSNSATTIM
NDV    KLVLVSGDLSENTVM.CAN.A.TVA
SV     .CVF.SE.LV.ENRSACSN.STSIA
HPIV3  .CVF.SE.VI.ETRSASSNLATSFA
MV     .CVF.SE..V.ETRAACSN.ATTMA
NIPAH  .CCF.SE.LV.ETRSACSN.STTIA
```

FIGURE 13

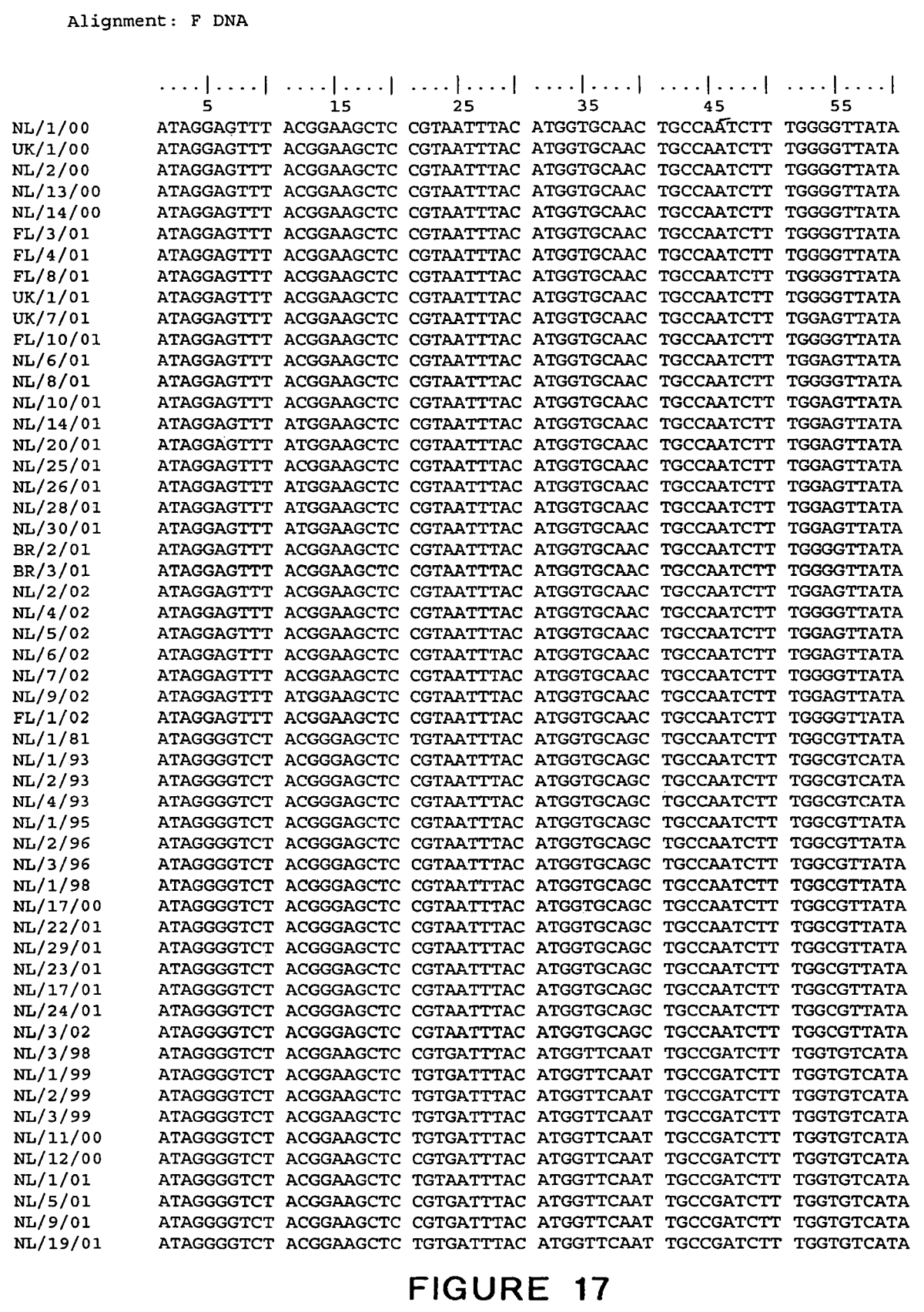

Alignment: F DNA

| | 5 | 15 | 25 | 35 | 45 | 55 |
|---|---|---|---|---|---|---|
| NL/1/00 | ATAGGAGTTT | ACGGAAGCTC | CGTAATTTAC | ATGGTGCAAC | TGCCAATCTT | TGGGGTTATA |
| UK/1/00 | ATAGGAGTTT | ACGGAAGCTC | CGTAATTTAC | ATGGTGCAAC | TGCCAATCTT | TGGGGTTATA |
| NL/2/00 | ATAGGAGTTT | ACGGAAGCTC | CGTAATTTAC | ATGGTGCAAC | TGCCAATCTT | TGGGGTTATA |
| NL/13/00 | ATAGGAGTTT | ACGGAAGCTC | CGTAATTTAC | ATGGTGCAAC | TGCCAATCTT | TGGGGTTATA |
| NL/14/00 | ATAGGAGTTT | ACGGAAGCTC | CGTAATTTAC | ATGGTGCAAC | TGCCAATCTT | TGGGGTTATA |
| FL/3/01 | ATAGGAGTTT | ACGGAAGCTC | CGTAATTTAC | ATGGTGCAAC | TGCCAATCTT | TGGGGTTATA |
| FL/4/01 | ATAGGAGTTT | ACGGAAGCTC | CGTAATTTAC | ATGGTGCAAC | TGCCAATCTT | TGGGGTTATA |
| FL/8/01 | ATAGGAGTTT | ACGGAAGCTC | CGTAATTTAC | ATGGTGCAAC | TGCCAATCTT | TGGGGTTATA |
| UK/1/01 | ATAGGAGTTT | ACGGAAGCTC | CGTAATTTAC | ATGGTGCAAC | TGCCAATCTT | TGGGGTTATA |
| UK/7/01 | ATAGGAGTTT | ACGGAAGCTC | CGTAATTTAC | ATGGTGCAAC | TGCCAATCTT | TGGAGTTATA |
| FL/10/01 | ATAGGAGTTT | ACGGAAGCTC | CGTAATTTAC | ATGGTGCAAC | TGCCAATCTT | TGGGGTTATA |
| NL/6/01 | ATAGGAGTTT | ACGGAAGCTC | CGTAATTTAC | ATGGTGCAAC | TGCCAATCTT | TGGAGTTATA |
| NL/8/01 | ATAGGAGTTT | ACGGAAGCTC | CGTAATTTAC | ATGGTGCAAC | TGCCAATCTT | TGGGGTTATA |
| NL/10/01 | ATAGGAGTTT | ACGGAAGCTC | CGTAATTTAC | ATGGTGCAAC | TGCCAATCTT | TGGAGTTATA |
| NL/14/01 | ATAGGAGTTT | ATGGAAGCTC | CGTAATTTAC | ATGGTGCAAC | TGCCAATCTT | TGGAGTTATA |
| NL/20/01 | ATAGGAGTTT | ATGGAAGCTC | CGTAATTTAC | ATGGTGCAAC | TGCCAATCTT | TGGAGTTATA |
| NL/25/01 | ATAGGAGTTT | ACGGAAGCTC | CGTAATTTAC | ATGGTGCAAC | TGCCAATCTT | TGGAGTTATA |
| NL/26/01 | ATAGGAGTTT | ATGGAAGCTC | CGTAATTTAC | ATGGTGCAAC | TGCCAATCTT | TGGAGTTATA |
| NL/28/01 | ATAGGAGTTT | ATGGAAGCTC | CGTAATTTAC | ATGGTGCAAC | TGCCAATCTT | TGGAGTTATA |
| NL/30/01 | ATAGGAGTTT | ATGGAAGCTC | CGTAATTTAC | ATGGTGCAAC | TGCCAATCTT | TGGAGTTATA |
| BR/2/01 | ATAGGAGTTT | ACGGAAGCTC | CGTAATTTAC | ATGGTGCAAC | TGCCAATCTT | TGGGGTTATA |
| BR/3/01 | ATAGGAGTTT | ACGGAAGCTC | CGTAATTTAC | ATGGTGCAAC | TGCCAATCTT | TGGGGTTATA |
| NL/2/02 | ATAGGAGTTT | ACGGAAGCTC | CGTAATTTAC | ATGGTGCAAC | TGCCAATCTT | TGGAGTTATA |
| NL/4/02 | ATAGGAGTTT | ACGGAAGCTC | CGTAATTTAC | ATGGTGCAAC | TGCCAATCTT | TGGGGTTATA |
| NL/5/02 | ATAGGAGTTT | ACGGAAGCTC | CGTAATTTAC | ATGGTGCAAC | TGCCAATCTT | TGGAGTTATA |
| NL/6/02 | ATAGGAGTTT | ACGGAAGCTC | CGTAATTTAC | ATGGTGCAAC | TGCCAATCTT | TGGAGTTATA |
| NL/7/02 | ATAGGAGTTT | ACGGAAGCTC | CGTAATTTAC | ATGGTGCAAC | TGCCAATCTT | TGGGGTTATA |
| NL/9/02 | ATAGGAGTTT | ATGGAAGCTC | CGTAATTTAC | ATGGTGCAAC | TGCCAATCTT | TGGAGTTATA |
| FL/1/02 | ATAGGAGTTT | ACGGAAGCTC | CGTAATTTAC | ATGGTGCAAC | TGCCAATCTT | TGGGGTTATA |
| NL/1/81 | ATAGGGGTCT | ACGGGAGCTC | TGTAATTTAC | ATGGTGCAGC | TGCCAATCTT | TGGCGTTATA |
| NL/1/93 | ATAGGGGTCT | ACGGGAGCTC | CGTAATTTAC | ATGGTGCAGC | TGCCAATCTT | TGGCGTCATA |
| NL/2/93 | ATAGGGGTCT | ACGGGAGCTC | CGTAATTTAC | ATGGTGCAGC | TGCCAATCTT | TGGCGTCATA |
| NL/4/93 | ATAGGGGTCT | ACGGGAGCTC | CGTAATTTAC | ATGGTGCAGC | TGCCAATCTT | TGGCGTCATA |
| NL/1/95 | ATAGGGGTCT | ACGGGAGCTC | CGTAATTTAC | ATGGTGCAGC | TGCCAATCTT | TGGCGTTATA |
| NL/2/96 | ATAGGGGTCT | ACGGGAGCTC | CGTAATTTAC | ATGGTGCAGC | TGCCAATCTT | TGGCGTTATA |
| NL/3/96 | ATAGGGGTCT | ACGGGAGCTC | CGTAATTTAC | ATGGTGCAGC | TGCCAATCTT | TGGCGTTATA |
| NL/1/98 | ATAGGGGTCT | ACGGGAGCTC | CGTAATTTAC | ATGGTGCAGC | TGCCAATCTT | TGGCGTTATA |
| NL/17/00 | ATAGGGGTCT | ACGGGAGCTC | CGTAATTTAC | ATGGTGCAGC | TGCCAATCTT | TGGCGTTATA |
| NL/22/01 | ATAGGGGTCT | ACGGGAGCTC | CGTAATTTAC | ATGGTGCAGC | TGCCAATCTT | TGGCGTTATA |
| NL/29/01 | ATAGGGGTCT | ACGGGAGCTC | CGTAATTTAC | ATGGTGCAGC | TGCCAATCTT | TGGCGTTATA |
| NL/23/01 | ATAGGGGTCT | ACGGGAGCTC | CGTAATTTAC | ATGGTGCAGC | TGCCAATCTT | TGGCGTTATA |
| NL/17/01 | ATAGGGGTCT | ACGGGAGCTC | CGTAATTTAC | ATGGTGCAGC | TGCCAATCTT | TGGCGTTATA |
| NL/24/01 | ATAGGGGTCT | ACGGGAGCTC | CGTAATTTAC | ATGGTGCAGC | TGCCAATCTT | TGGCGTTATA |
| NL/3/02 | ATAGGGGTCT | ACGGGAGCTC | CGTAATTTAC | ATGGTGCAGC | TGCCAATCTT | TGGCGTTATA |
| NL/3/98 | ATAGGGGTCT | ACGGAAGCTC | CGTGATTTAC | ATGGTTCAAT | TGCCGATCTT | TGGTGTCATA |
| NL/1/99 | ATAGGGGTCT | ACGGAAGCTC | TGTGATTTAC | ATGGTTCAAT | TGCCGATCTT | TGGTGTCATA |
| NL/2/99 | ATAGGGGTCT | ACGGAAGCTC | TGTGATTTAC | ATGGTTCAAT | TGCCGATCTT | TGGTGTCATA |
| NL/3/99 | ATAGGGGTCT | ACGGAAGCTC | TGTGATTTAC | ATGGTTCAAT | TGCCGATCTT | TGGTGTCATA |
| NL/11/00 | ATAGGGGTCT | ACGGAAGCTC | TGTGATTTAC | ATGGTTCAAT | TGCCGATCTT | TGGTGTCATA |
| NL/12/00 | ATAGGGGTCT | ACGGAAGCTC | CGTGATTTAC | ATGGTTCAAT | TGCCGATCTT | TGGTGTCATA |
| NL/1/01 | ATAGGGGTCT | ACGGAAGCTC | TGTAATTTAC | ATGGTTCAAT | TGCCGATCTT | TGGTGTCATA |
| NL/5/01 | ATAGGGGTCT | ACGGAAGCTC | CGTGATTTAC | ATGGTTCAAT | TGCCGATCTT | TGGTGTCATA |
| NL/9/01 | ATAGGGGTCT | ACGGAAGCTC | CGTGATTTAC | ATGGTTCAAT | TGCCGATCTT | TGGTGTCATA |
| NL/19/01 | ATAGGGGTCT | ACGGAAGCTC | TGTGATTTAC | ATGGTTCAAT | TGCCGATCTT | TGGTGTCATA |

FIGURE 17

```
NL/21/01    ATAGGGGTCT ACGGAAGCTC CGTGATTTAC ATGGTTCAAT TGCCGATCTT TGGTGTCATA
UK/11/01    ATAGGGGTCT ACGGAAGCTC TGTGATTTAC ATGGTTCAAT TGCCGATCTT TGGGGTCATA
FL/1/01     ATAGGGGTCT ACGGAAGCTC TGTGATTTAC ATGGTTCAAT TGCCGATCTT TGGTGTCATA
FL/2/01     ATAGGGGTCT ACGGAAGCTC TGTGATTTAC ATGGTTCAAT TGCCGATCTT TGGTGTCATA
FL/5/01     ATAGGGGTCT ACGGAAGCTC TGTGATTTAC ATGGTTCAAT TGCCGATCTT TGGTGTCATA
FL/7/01     ATAGGGGTCT ACGGAAGCTC CGTGATTTAC ATGGTTCAAT TGCCGATCTT TGGTGTCATA
FL/9/01     ATAGGGGTCT ACGGAAGCTC TGTGATTTAC ATGGTTCAAT TGCCGATCTT TGGTGTCATA
UK/10/01    ATAGGGGTCT ACGGAAGCTC TGTGATTTAC ATGGTTCAAT TGCCGATCTT TGGTGTCATA
NL/1/02     ATAGGGGTCT ACGGAAGCTC CGTGATTTAC ATGGTTCAAT TGCCGATCTT TGGTGTCATA
NL/1/94     ATAGGGGTCT ACGGAAGCTC TGTGATTTAC ATGGTCCAGC TGCCGATCTT TGGTGTCATA
NL/1/96     ATAGGGGTCT ACGGAAGCTC TGTGATTTAC ATGGTCCAGC TGCCGATCTT TGGTGTCATA
NL/6/97     ATAGGGGTCT ACGGAAGCTC TGTGATTTAC ATGGTCCAGC TGCCGATCTT TGGTGTCATA
NL/7/00     ATAGGGGTCT ACGGAAGCTC CGTGATTTAC ATGGTCCAGC TGCCGATCTT TGGTGTCATA
NL/9/00     ATAGGGGTCT ACGGAAGCTC CGTGATTTAC ATGGTCCAGC TACCGATCTT TGGTGTCATA
NL/19/00    ATAGGGGTCT ACGGAAGCTC CGTGATTTAC ATGGTCCAGC TGCCGATCTT TGGTGTCATA
NL/28/00    ATAGGGGTCT ACGGAAGCTC CGTGATTTAC ATGGTCCAGC TGCCGATCTT TGGTGTCATA
NL/3/01     ATAGGGGTCT ACGGAAGCTC CGTGATTTAC ATGGTCCAGC TGCCGATCTT TGGTGTCATA
NL/4/01     ATAGGGGTCT ACGGAAGCTC CGTGATTTAC ATGGTCCAGC TGCCGATCTT TGGTGTCATA
NL/11/01    ATAGGGGTCT ACGGAAGCTC CGTGATTTAC ATGGTCCAGC TGCCGATCTT TGGTGTCATA
NL/15/01    ATAGGGGTCT ACGGAAGCTC CGTGATTTAC ATGGTCCAGC TGCCGATCTT TGGTGTCATA
NL/18/01    ATAGGGGTCT ACGGAAGCTC CGTGATTTAC ATGGTCCAGC TGCCGATCTT TGGTGTCATA
FL/6/01     ATAGGGGTCT ACGGAAGCTC CGTGATTTAC ATGGTCCAGC TGCCGATCTT TGGTGTCATA
UK/5/01     ATAGGGGTCT ACGGAAGCTC TGTGATTTAC ATGGTCCAGC TGCCGATCTT TGGTGTCATA
UK/8/01     ATAGGGGTCT ACGGAAGCTC TGTGATTTAC ATGGTCCAGC TGCCGATCTT TGGTGTCATA
NL/12/02    ATAGGGGTCT ACGGAAGCTC CGTGATTTAC ATGGTCCAGC TGCCGATCTT tGGTGTCATA
HK/1/02     ATAGGGGTCT ACGGAAGCTC CGTGATTTAC ATGGTCCAGC TGCCGATCTT TGGTGTCATA

            ....|....| ....|....| ....|....| ....|....| ....|....| ....|....|
                 65         75         85         95        105        115
NL/1/00     GACACGCCTT GCTGGATAGT AAAAGCAGCC CCTTCTTGTT CAGGAAAAAA GGGAAACTAT
UK/1/00     GACACGCCTT GCTGGATAGT AAAAGCAGCC CCTTCTTGCT CAGAAAAAAA GGGAAACTAT
NL/2/00     GACACGCCTT GCTGGATAGT AAAAGCAGCC CCTTCTTGCT CAGAAAAAAA GGGAAACTAT
NL/13/00    GACACGCCTT GCTGGATAGT AAAAGCAGCC CCTTCTTGCT CAGAAAAAAA GGGAAACTAT
NL/14/00    GACACGCCTT GCTGGATAGT AAAAGCAGCC CCTTCTTGCT CAGAAAAAAA GGGAAACTAT
FL/3/01     GACACGCCTT GCTGGATAGT AAAAGCAGCC CCTTCTTGTT CAGAAAAAAA GGGAAACTAT
FL/4/01     GACACGCCTT GCTGGATAGT AAAAGCAGCC CCTTCTTGTT CAGAAAAAAA GGGAAACTAT
FL/8/01     GACACGCCTT GCTGGATAGT AAAAGCAGCC CCTTCTTGTT CAGAAAAAAA GGGAAACTAT
UK/1/01     GACACGCCTT GCTGGATAGT AAAAGCAGCC CCTTCTTGCT CAGAAAAAAA GGGAAACTAT
UK/7/01     GACACGCCTT GCTGGATAGT AAAAGCAGCC CCTTCTTGCT CAGAAAAAAA GGGAAACTAT
FL/10/01    GACACGCCTT GTTGGATAGT AAAAGCAGCC CCTTCTTGCT CAGAAAAAAA GGGGAACTAT
NL/6/01     GACACGCCTT GCTGGATAGT AAAAGCGGCC CCTTCTTGCT CAGAAAAAAA GGGAAACTAT
NL/8/01     GACACGCCTT GCTGGATAGT AAAAGCAGCC CCTTCTTGCT CAGAAAAAAA GGGAAACTAT
NL/10/01    GACACGCCTT GCTGGATAGT AAAAGCGGCC CCTTCTTGCT CGGAAAAAAA GGGAAACTAT
NL/14/01    GACACGCCTT GCTGGATAGT AAAAGCGGCC CCTTCTTGCT CAGAAAAAAA GGGAAACTAT
NL/20/01    GACACGCCTT GCTGGATAGT AAAAGCGGCC CCTTCTTGCT CAGAAAAAAA GGGAAACTAT
NL/25/01    GACACGCCTT GCTGGATAGT AAAAGCGGCC CCTTCTTGCT CAGAAAAAAA GGGAAACTAT
NL/26/01    GACACGCCTT GCTGGATAGT AAAAGCGGCC CCTTCTTGCT CAGAAAAAAA GGGAAACTAT
NL/28/01    GACACGCCTT GCTGGATAGT AAAAGCGGCC CCTTCTTGCT CAGAAAAAAA GGGAAACTAT
NL/30/01    GACACGCCTT GCTGGATAGT AAAAGCGGCC CCTTCTTGCT CAGAAAAAAA GGGAAACTAT
BR/2/01     GACACGCCTT GCTGGATAGT AAAAGCAGCC CCTTCTTGTT CAGGAAAAAA GGGAAACTAT
BR/3/01     GACACGCCTT GCTGGATAGT AAAAGCAGCC CCTTCTTGTT CAGGAAAAAA GGGAAACTAT
NL/2/02     GACACGCCTT GCTGGATAGT AAAAGCGGCC CCTTCTTGCT CAGAAAAAAA GGGAAACTAT
NL/4/02     GACACGCCTT GCTGGATAGT AAAAGCAGCC CCTTCTTGCT CAGAAAAAAA GGGAAACTAT
NL/5/02     GACACGCCTT GCTGGATAGT AAAAGCGGCC CCTTCTTGCT CAGAAAAAAA GGGAAACTAT
NL/6/02     GACACGCCTT GCTGGATAGT AAAAGCGGCC CCTTCTTGCT CAGAAAAAAA GGGAAACTAT
NL/7/02     GACACGCCTT GCTGGATAGT AAAAGCAGCC CCTTCTTGTT CAGGAAAAAA GGGAAACTAT
NL/9/02     GACACGCCTT GCTGGATAGT AAAAGCGGCC CCTTCTTGCT CAGAAAAAAA GGGAAACTAT
FL/1/02     GACACGCCTT GCTGGATAGT AAAAGCAGCC CCTTCTTGTT CAGGAAAAAA GGGAAACTAT
NL/1/81     GACACGCCTT GCTGGATAGT AAAAGCAGCC CCCTCTTGTT CCGAAAAAAA GGGAAACTAT
NL/1/93     GACACGCCTT GCTGGATAGT AAAAGCAGCC CCCTCTTGTT CCGAAAAAAA GGGAAACTAT
NL/2/93     GACACGCCTT GCTGGATAGT AAAAGCAGCC CCCTCTTGTT CCGAAAAAAA GGGAAACTAT
```

Figure 17 con't

```
NL/4/93     GACACGCCTT GCTGGATAGT AAAAGCAGCC CCCTCTTGTT CCGAAAAAAA GGGAAACTAT
NL/1/95     GACACGCCCT GCTGGATAGT AAAAGCAGCC CCCTCTTGTT CCGAAAAAAA GGGAAACTAT
NL/2/96     GACACGCCTT GCTGGATAGT AAAAGCAGCC CCCTCTTGTT CCGAAAAAAA GGGAAACTAT
NL/3/96     GACACGCCCT GCTGGATAGT AAAAGCAGCC CCCTCTTGTT CCGAAAAAAA GGGAAACTAT
NL/1/98     GACACGCCTT GCTGGATAGT AAAAGCAGCC CCTTCTTGTT CCGAAAAAAA GGGAAACTAT
NL/17/00    GACACGCCTT GCTGGATAGT AAAAGCAGCC CCTTCTTGTT CCGAAAAAAA GGGAAACTAT
NL/22/01    GACACGCCTT GCTGGATAGT AAAAGCAGCC CCTTCTTGTT CCGAAAAAAA GGGAAACTAT
NL/29/01    GACACGCCTT GCTGGATAGT AAAAGCAGCC CCTTCTTGTT CCGAAAAAAA GGGAAACTAT
NL/23/01    GACACGCCTT GCTGGATAGT AAAAGCAGCC CCTTCTTGTT CCGAAAAAAA GGGAAACTAT
NL/17/01    GACACACCTT GCTGGATAGT AAAAGCAGCC CCTTCTTGTT CCGAAAAAAA GGGAAATTAT
NL/24/01    GACACGCCTT GCTGGATAGT AAAAGCAGCC CCTTCTTGTT CCGAAAAAAA GGGAAACTAT
NL/3/02     GACACGCCTT GCTGGATAGT AAAAGCAGCC CCTTCTTGTT CCGAAAAAAA GGGAAACTAT
NL/3/98     GATACACCTT GTTGGATAAT CAAGGCAGCT CCCTCTTGCT CAGAAAAAAA CGGGAATTAT
NL/1/99     GATACACCTT GTTGGATCAT CAAGGCAGCT CCCTCTTGCT CAGAAAAAAA CGGGAATTAT
NL/2/99     GATACACCTT GTTGGATCAT CAAGGCAGCT CCCTCTTGCT CAGAAAAAAA CGGGAATTAT
NL/3/99     GATACACCTT GTTGGATCAT CAAGGCAGCT CCCTCTTGCT CAGAAAAAAA CGGGAATTAT
NL/11/00    GATACACCTT GTTGGATAAT CAAGGCAGCT CCCTCTTGCT CAGAAAAAAA CGGGAATTAT
NL/12/00    GATACACCTT GTTGGATAAT CAAGGCAGCT CCCTCTTGCT CAGAAAAAAA CGGGAATTAT
NL/1/01     GATACACCTT GTTGGATAAT CAAGGCAGCT CCCTCTTGCT CAGAAAAAAA CGGGAATTAT
NL/5/01     GATACACCTT GTTGGATAAT CAAGGCAGCT CCCTCTTGCT CAGAAAAAAA CGGGAATTAT
NL/9/01     GATACACCTT GTTGGATAAT CAAGGCAGCT CCCTCTTGCT CAGAAAAAAA CGGGAATTAT
NL/19/01    GATACACCTT GTTGGATAAT CAAGGCAGCT CCCTCTTGCT CAGAAAAAAA CGGGAATTAT
NL/21/01    GATACACCTT GTTGGATAAT CAAGGCAGCT CCCTCTTGCT CAGAAAAAAA CGGGAATTAT
UK/11/01    GATACACCTT GTTGGATAAT CAAGGCAGCT CCCTCTTGCT CAGAAAAAAA CGGGAATTAT
FL/1/01     GATACACCTT GTTGGATAAT CAAGGCAGCC CCCTCTTGCT CAGAGAAAAA CGGGAATTAT
FL/2/01     GATACACCTT GTTGGATAAT CAAGGCAGCT CCCTCTTGCT CAGAGAAAAA CGGGAATTAT
FL/5/01     GATACACCTT GTTGGATAAT CAAGGCAGCT CCCTCTTGCT CAGAAAAAAA CGGGAATTAT
FL/7/01     GATACACCTT GTTGGATAAT CAAGGCAGCT CCCTCTTGCT CAGAAAAAAA CGGGAATTAT
FL/9/01     GATACACCTT GTTGGATAAT CAAGGCAGCT CCCTCTTGCT CAGAGAAAAA CGGGAATTAT
UK/10/01    GATACACCTT GTTGGATAAT CAAGGCAGCT CCCTCTTGCT CAGAAAAAAA CGGGAATTAT
NL/1/02     GATACACCTT GTTGGATAAT CAAGGCAGCT CCCTCTTGCT CAGAAAAAAA CGGGAATTAT
NL/1/94     GATACACCTT GTTGGATAAT CAAGGCAGCT CCCTCTTGTT CAGAAAAAGA TGGAAATTAT
NL/1/96     GATACACCTT GTTGGATAAT CAAGGCAGCT CCCTCTTGTT CAGAAAAAGA TGGAAATTAT
NL/6/97     GATACACCTT GTTGGATAAT CAAGGCAGCT CCCTCTTGTT CAGAAAAAGA TGGAAATTAT
NL/7/00     GATACACCTT GTTGGATAAT CAAGGCAGCT CCCTCTTGTT CAGAAAAAGA TGGAAATTAT
NL/9/00     GATACACCTT GTTGGATAAT CAAGGCAGCT CCCTCTTGTT CAGAAAAAGA TGGAAATTAT
NL/19/00    GATACACCTT GTTGGATAAT CAAGGCAGCT CCCTCTTGTT CAGAAAAAGA TGGAAATTAT
NL/28/00    GATACACCTT GTTGGATAAT CAAGGCAGCT CCCTCTTGTT CAGAAAAAGA TGGAAATTAT
NL/3/01     GATACACCTT GTTGGATAAT CAAGGCAGCT CCCTCTTGTT CAGAAAAAGA TGGAAATTAT
NL/4/01     GATACACCTT GTTGGATAAT CAAGGCAGCT CCCTCTTGTT CAGAAAAAGA TGGAAATTAT
NL/11/01    GATACACCTT GTTGGATAAT CAAGGCAGCT CCCTCTTGTT CAGAAAAAGA TGGAAATTAT
NL/15/01    GATACACCTT GTTGGATAAT CAAGGCAGCT CCCTCTTGTT CAGAAAAAGA TGGAAATTAT
NL/18/01    GATACACCTT GTTGGATAAT CAAGGCAGCT CCCTCTTGTT CAGAAAAAGA TGGAAATTAT
FL/6/01     GATACACCTT GTTGGATAAT CAAGGCAGCT CCCTCTTGTT CAGAAAAAGA TGGAAATTAT
UK/5/01     GATACACCTT GTTGGATAAT CAAGGCAGCT CCCTCTTGTT CAGAAAAAGA TGGAAATTAT
UK/8/01     GATACACCTT GTTGGATAAT CAAGGCAGCT CCCTCTTGTT CAGAAAAAGA TGGAAATTAT
NL/12/02    GATACACCTT GTTGGATAAT CAAGGCAGCT CCCTCTTGTT CAGAAAAAGA TGGAAATTAT
HK/1/02     GATACACCTT GTTGGATAAT CAAGGCAGCT CCCTCTTGTT CAGAAAAAGA TGGAAATTAT

            ....|....| ....|....| ....|....| ....|....| ....|....| ....|....|
                125        135        145        155        165        175
NL/1/00     GCTTGCCTCT TAAGAGAAGA CCAAGGATGG TATTGTCAAA ATGCAGGGTC AACTGTTTAC
UK/1/00     GCTTGCCTCT TAAGAGAAGA TCAAGGATGG TATTGTCAGA ATGCAGGGTC AACTGTTTAC
NL/2/00     GCTTGCCTCT TAAGAGAAGA TCAAGGATGG TATTGTCAGA ATGCAGGGTC AACTGTTTAC
NL/13/00    GCTTGCCTCT TAAGAGAAGA TCAAGGATGG TATTGTCAGA ATGCAGGGTC AACTGTTTAC
NL/14/00    GCTTGCCTCT TAAGAGAAGA TCAAGGATGG TATTGTCAGA ATGCAGGGTC AACTGTTTAC
FL/3/01     GCTTGCCTCT TAAGAGAAGA CCAAGGATGG TATTGTCAGA ATGCAGGGTC AACTGTTTAC
FL/4/01     GCTTGCCTCT TAAGAGAAGA CCAAGGATGG TATTGTCAGA ATGCAGGGTC AACTGTTTAC
FL/8/01     GCTTGCCTCT TAAGAGAAGA CCAAGGATGG TATTGTCAGA ATGCAGGGTC AACTGTTTAC
UK/1/01     GCTTGCCTCT TAAGAGAAGA TCAGGGATGG TATTGTCAGA ATGCAGGGTC AACTGTTTAC
UK/7/01     GCTTGCCTCT TAAGAGAAGA TCAAGGATGG TATTGTCAGA ATGCAGGGTC AACTGTTTAC
```

Figure 17 con't

| | | | | | | |
|---|---|---|---|---|---|---|
| FL/10/01 | GCTTGCCTCT | TAAGAGAAGA | TCAAGGATGG | TATTGTCAGA | ATGCAGGGTC | AACTGTTTAC |
| NL/6/01 | GCTTGCCTCT | TAAGAGAAGA | TCAAGGATGG | TATTGTCAGA | ATGCAGGGTC | AACTGTTTAC |
| NL/8/01 | GCTTGCCTTT | TAAGAGAAGA | TCAAGGATGG | TATTGTCAGA | ATGCAGGGTC | AACTGTTTAC |
| NL/10/01 | GCTTGCCTCT | TAAGAGAAGA | TCAAAGATGG | TATTGTCAGA | ATGCAGGGTC | AACTGTTTAC |
| NL/14/01 | GCTTGCCTCT | TAAGAGAAGA | TCAAGGATGG | TATTGTCAGA | ATGCAGGGTC | AACTGTTTAC |
| NL/20/01 | GCTTGCCTCT | TAAGAGAAGA | TCAAGGATGG | TATTGTCAGA | ATGCAGGGTC | AACTGTTTAC |
| NL/25/01 | GCTTGCCTCT | TAAGAGAAGA | TCAAGGATGG | TATTGTCAGA | ATGCAGGGTC | AACTGTTTAC |
| NL/26/01 | GCTTGCCTCT | TAAGAGAAGA | TCAAGGATGG | TATTGTCAGA | ATGCAGGGTC | AACTGTTTAC |
| NL/28/01 | GCTTGCCTCT | TAAGAGAAGA | TCAAGGATGG | TATTGTCAGA | ATGCAGGGTC | AACTGTTTAC |
| NL/30/01 | GCTTGCCTCT | TAAGAGAAGA | TCAAGGATGG | TATTGTCAGA | ATGCAGGGTC | AACTGTTTAC |
| BR/2/01 | GCTTGCCTCT | TAAGAGAAGA | CCAAGGATGG | TATTGTCAAA | ATGCAGGGTC | AACTGTTTAC |
| BR/3/01 | GCTTGCCTCT | TAAGAGAAGA | CCAAGGATGG | TATTGTCAAA | ATGCAGGGTC | AACTGTTTAC |
| NL/2/02 | GCTTGCCTCT | TAAGAGAAGA | TCAAGGATGG | TATTGTCAGA | ATGCAGGGTC | AACTGTTTAC |
| NL/4/02 | GCTTGCCTCT | TAAGAGAAGA | TCAAGGATGG | TATTGTCAGA | ATGCAGGGTC | AACTGTTTAC |
| NL/5/02 | GCTTGCCTCT | TAAGAGAAGA | TCAAGGATGG | TATTGTCAGA | ATGCAGGGTC | AACTGTTTAC |
| NL/6/02 | GCTTGCCTCT | TAAGAGAAGA | TCAAGGATGG | TATTGTCAGA | ATGCAGGGTC | AACTGTTTAC |
| NL/7/02 | GCTTGCCTCT | TAAGAGAAGA | CCAAGGATGG | TATTGTCAAA | ATGCAGGGTC | AACTGTTTAC |
| NL/9/02 | GCTTGCCTCT | TAAGAGAAGA | TCAAGGATGG | TATTGTCAGA | ATGCAGGGTC | AACTGTTTAC |
| FL/1/02 | GCTTGCCTCT | TAAGAGAAGA | CCAAGGATGG | TATTGTCAAA | ATGCAGGGTC | AACTGTTTAC |
| NL/1/81 | GCTTGCCTCT | TAAGAGAAGA | CCAAGGGTGG | TATTGTCAGA | ATGCAGGGTC | AACTGTTTAC |
| NL/1/93 | GCTTGCCTTT | TAAGAGAAGA | TCAAGGGTGG | TATTGTCAGA | ATGCAGGGTC | AACTGTTTAC |
| NL/2/93 | GCTTGCCTTT | TAAGAGAAGA | TCAAGGGTGG | TATTGTCAGA | ATGCAGGGTC | AACTGTTTAC |
| NL/4/93 | GCTTGCCTTT | TAAGAGAAGA | TCAAGGGTGG | TATTGTCAGA | ATGCAGGGTC | AACTGTTTAC |
| NL/1/95 | GCTTGCCTTC | TAAGAGAAGA | CCAAGGGTGG | TATTGTCAGA | ATGCAGGGTC | AACTGTTTAC |
| NL/2/96 | GCTTGCCTCT | TAAGAGAAGA | CCAAGGGTGG | TATTGTCAGA | ATGCAGGGTC | AACTGTTTAC |
| NL/3/96 | GCTTGCCTTC | TAAGAGAAGA | CCAAGGGTGG | TATTGTCAGA | ATGCAGGGTC | AACTGTTTAC |
| NL/1/98 | GCTTGCCTCT | TAAGAGAAGA | CCAAGGGTGG | TATTGTCAGA | ATGCAGGGTC | AACTGTTTAC |
| NL/17/00 | GCTTGCCTCT | TAAGAGAAGA | CCAAGGGTGG | TATTGTCAGA | ATGCAGGGTC | AACTGTTTAC |
| NL/22/01 | GCTTGCCTCT | TAAGAGAAGA | CCAAGGATGG | TATTGTCAGA | ATGCAGGGTC | AACTGTTTAC |
| NL/29/01 | GCTTGCCTCT | TAAGAGAAGA | CCAAGGGTGG | TATTGTCAGA | ATGCAGGGTC | AACTGTTTAC |
| NL/23/01 | GCTTGCCTCT | TAAGAGAAGA | CCAAGGATGG | TATTGTCAGA | ATGCAGGGTC | AACTGTTTAC |
| NL/17/01 | GCTTGCCTCT | TAAGAGAAGA | CCAAGGGTGG | TATTGTCAGA | ATGCAGGGTC | AACTGTTTAC |
| NL/24/01 | GCTTGCCTCT | TAAGAGAAGA | CCAAGGATGG | TATTGTCAGA | ATGCAGGGTC | AACTGTTTAC |
| NL/3/02 | GCTTGCCTCT | TAAGAGAAGA | CCAAGGGTGG | TATTGTCAGA | ATGCAGGGTC | AACTGTTTAC |
| NL/3/98 | GCTTGCCTCC | TAAGAGAGGA | TCAAGGGTGG | TATTGTAAAA | ATGCAGGATC | CACTGTTTAC |
| NL/1/99 | GCTTGCCTCC | TAAGAGAGGA | TCAAGGGTGG | TATTGTAAAA | ATGCAGGATC | TACTGTTTAC |
| NL/2/99 | GCTTGCCTCC | TAAGAGAGGA | TCAAGGGTGG | TATTGTAAAA | ATGCAGGATC | TACTGTTTAC |
| NL/3/99 | GCTTGCCTCC | TAAGAGAGGA | TCAAGGGTGG | TATTGTAAAA | ATGCAGGATC | TACTGTTTAC |
| NL/11/00 | GCTTGCCTCC | TAAGAGAGGA | TCAAGGGTGG | TATTGCAAAA | ATGCAGGATC | CACTGTTTAC |
| NL/12/00 | GCTTGCCTCC | TAAGAGAGGA | TCAAGGGTGG | TATTGTAAAA | ATGCAGGATC | CACTGTTTAC |
| NL/1/01 | GCTTGCCTCC | TAAGAGAGGA | TCAAGGGTGG | TATTGTAAAA | ATGCAGGATC | CACTGTTTAC |
| NL/5/01 | GCTTGCCTCC | TAAGAGAGGA | TCAAGGGTGG | TATTGTAAAA | ATGCAGGATC | CACTGTTTAC |
| NL/9/01 | GCTTGCCTCC | TAAGAGAGGA | TCAAGGGTGG | TATTGTAAAA | ATGCAGGATC | CACTGTTTAC |
| NL/19/01 | GCTTGCCTCC | TAAGAGAGGA | TCAAGGGTGG | TATTGTAAAA | ATGCAGGATC | CACTGTTTAC |
| NL/21/01 | GCTTGCCTCC | TAAGAGAGGA | TCAAGGGTGG | TACTGTAAAA | ATGCAGGATC | CACTGTTTAC |
| UK/11/01 | GCTTGCCTCC | TAAGAGAGGA | TCAAGGGTGG | TATTGTAAAA | ATGCAGGATC | CACTGTTTAC |
| FL/1/01 | GCTTGCCTCC | TAAGAGAGGA | TCAAGGGTGG | TATTGTAAAA | ATGCAGGATC | CACTGTTTAC |
| FL/2/01 | GCTTGCCTCC | TAAGAGAGGA | TCAAGGGTGG | TATTGTAAAA | ATGCAGGATC | CACTGTTTAC |
| FL/5/01 | GCTTGCCTCC | TAAGAGAGGA | TCAAGGGTGG | TATTGTAAAA | ATGCAGGATC | CACTGTTTAC |
| FL/7/01 | GCTTGCCTCC | TAAGAGAGGA | TCAAGGGTGG | TATTGTAAAA | ATGCAGGATC | CACTGTTTAC |
| FL/9/01 | GCTTGCCTCC | TAAGAGAGGA | TCAAGGGTGG | TATTGTAAAA | ATGCAGGATC | CACTGTTTAC |
| UK/10/01 | GCTTGCCTCC | TAAGAGAGGA | TCAAGGGTGG | TATTGTAAAA | ATGCAGGATC | CACTGTTTAC |
| NL/1/02 | GCTTGCCTCC | TAAGAGAGGA | TCAAGGGTGG | TACTGTAAAA | ATGCAGGATC | CACTGTTTAC |
| NL/1/94 | GCTTGCCTCC | TAAGAGAGGA | TCAAGGGTGG | TATTGCAAAA | ATGCAGGATC | CACTGTTTAC |
| NL/1/96 | GCTTGCCTCC | TAAGAGAGGA | TCAAGGGTGG | TATTGTAAAA | ATGCAGGATC | CACTGTTTAC |
| NL/6/97 | GCTTGCCTCC | TAAGAGAGGA | TCAAGGGTGG | TATTGTAAAA | ATGCAGGATC | CACTGTTTAC |
| NL/7/00 | GCTTGCCTCC | TAAGAGAGGA | CCAAGGGTGG | TATTGTAAAA | ATGCGGGATC | CACTGTTTAC |
| NL/9/00 | GCTTGCCTCC | TAAGAGAGGA | TCAAGGGTGG | TATTGTAAAA | ATGCAGGATC | CACTGTTTAC |
| NL/19/00 | GCTTGCCTCC | TAAGAGAGGA | TCAAGGGTGG | TATTGTAAAA | ATGCAGGATC | CACTGTTTAC |
| NL/28/00 | GCTTGCCTCC | TAAGAGAGGA | TCAAGGGTGG | TATTGTAAAA | ATGCAGGATC | CACTGTTTAC |
| NL/3/01 | GCTTGCCTCC | TAAGAGAGGA | CCAAGGGTGG | TATTGTAAAA | ATGCGGGATC | CACTGTTTAC |

Figure 17 con't

```
NL/4/01     GCTTGCCTCC TAAGAGAGGA TCAAGGGTGG TATTGTAAAA ATGCAGGATC CACTGTTTAC
NL/11/01    GCTTGCCTCC TAAGAGAGGA TCAAGGGTGG TATTGTAAAA ATGCAGGATC CACTGTTTAC
NL/15/01    GCTTGCCTCC TAAGAGAGGA TCAAGGGTGG TATTGTAAAA ATGCAGGATC CACTGTTTAC
NL/18/01    GCTTGCCTCC TAAGAGAGGA TCAAGGGTGG TATTGTAAAA ATGCAGGATC CACTGTTTAC
FL/6/01     GCTTGCCTCC TAAGAGAGGA TCAAGGGTGG TATTGTAAAA ATGCAGGATC CACTGTTTAC
UK/5/01     GCTTGCCTCC TAAGAGAGGA TCAAGGGTGG TATTGTAAAA ATGCAGGATC CACTGTTTAC
UK/8/01     GCTTGCCTCC TAAGAGAGGA TCAAGGGTGG TATTGTAAAA ATGCAGGATC CACTGTTTAC
NL/12/02    GCTTGCCTCC TAAGAGAGGA TCAAGGGTGG TATTGTAAAA ATGCAGGATC CACTGTTTAC
HK/1/02     GCTTGCCTCC TAAGAGAGGA TCAAGGGTGG TATTGTAAAA ATGCAGGATC CACTGTTTAC

            ....|....| ....|....| ....|....| ....|....| ....|....| ....|....|
                185        195        205        215        225        235
NL/1/00     TACCCAAATG AAAAAGACTG TGAAACAAGA GGAGACCATG TCTTTTGCGA CACAGCAGCA
UK/1/00     TACCCAAATG AAAAAGACTG CGAAACAAGA GGAGACCATG TCTTTTGCGA CACAGCAGCA
NL/2/00     TACCCAAATG AAAAAGATTG CGAAACAAGA GGAGACCATG TCTTTTGCGA CACAGCAGCA
NL/13/00    TACCCAAATG AAAAAGACTG CGAAACAAGA GGAGACCATG TCTTTTGCGA CACAGCAGCA
NL/14/00    TACCCAAATG AAAAAGATTG CGAAACAAGA GGAGACCATG TCTTTTGCGA CACAGCAGCA
FL/3/01     TACCCAAATG AAAAAGACTG TGAAACAAGA GGAGACCATG TCTTTTGCGA CACAGCAGCA
FL/4/01     TACCCAAATG AAAAAGACTG TGAAACAAGA GGAGACCATG TCTTTTGCGA CACAGCAGCA
FL/8/01     TACCCAAATG AAAAAGACTG TGAAACAAGA GGAGACCATG TCTTTTGCGA CACAGCAGCA
UK/1/01     TACCCAAATG AAAAAGACTG TGAAACAAGA GGAGACCATG TCTTTTGCGA CACAGCAGCA
UK/7/01     TACCCAAATG AAAAAGACTG CGAAACAAGA GGAGACCATG TCTTTTGCGA CACAGCAGCA
FL/10/01    TACCCAAATG AAAAAGACTG CGAAACAAGA GGAGACCATG TCTTTTGCGA CACAGCAGCA
NL/6/01     TACCCAAATG AAAAAGACTG CGAAACAAGA GGAGACCATG TCTTTTGCGA CACAGCAGCA
NL/8/01     TACCCAAATG AAAAAGACTG CGAAACAAGA GGAGACCATG TCTTTTGCGA CACAGCAGCA
NL/10/01    TACCCAAATG AAAAAGACTG CGAAACAAGA GGAGACCATG TCTTTTGCGA CACAGCAGCA
NL/14/01    TACCCAAATG AAAAAGACTG CGAAACAAGA GGAGACCATG TCTTTTGCGA CACAGCAGCA
NL/20/01    TACCCAAATG AAAAAGACTG CGAAACAAGA GGAGACCATG TCTTTTGCGA CACAGCAGCA
NL/25/01    TACCCAAATG AAAAAGACTG CGAAACAAGA GGAGACCATG TCTTTTGCGA CACAGCAGCA
NL/26/01    TACCCAAATG AAAAAGACTG CGAAACAAGA GGAGACCATG TCTTTTGCGA CACAGCAGCA
NL/28/01    TACCCAAATG AAAAAGACTG CGAAACAAGA GGAGACCATG TCTTTTGCGA CACAGCAGCA
NL/30/01    TACCCAAATG AAAAAGACTG CGAAACAAGA GGAGACCATG TCTTTTGCGA CACAGCAGCA
BR/2/01     TACCCAAATG AAAAAGACTG TGAAACAAGA GGAGACCATG TCTTTTGCGA CACAGCAGCA
BR/3/01     TACCCAAATG AAAAAGACTG TGAAACAAGA GGAGACCATG TCTTTTGCGA CACAGCAGCA
NL/2/02     TACCCAAATG AAAAAGACTG CGAAACAAGA GGAGACCATG TCTTTTGCGA CACAGCAGCA
NL/4/02     TACCCAAATG AAAAAGACTG CGAAACAAGA GGAGACCATG TCTTTTGCGA CACAGCAGCA
NL/5/02     TACCCAAATG AAAAAGACTG CGAAACAAGA GGAGACCATG TCTTTTGCGA CACAGCAGCA
NL/6/02     TACCCAAATG AAAAAGACTG CGAAACAAGA GGAGACCATG TCTTTTGCGA CACAGCAGCA
NL/7/02     TACCCAAATG AAAAAGACTG TGAAACAAGA GGAGACCATG TCTTTTGCGA CACAGCAGCA
NL/9/02     TACCCAAATG AAAAAGACTG CGAAACAAGA GGAGACCATG TCTTTTGCGA CACAGCAGCA
FL/1/02     TACCCAAATG AAAAAGACTG TGAAACAAGA GGAGACCATG TCTTTTGCGA CACAGCAGCA
NL/1/81     TACCCAAATG AGAAAGACTG TGAAACAAGA GGAGACCATG TCTTTTGCGA CACAGCAGCA
NL/1/93     TACCCAAATG AGAAAGACTG TGAAACAAGA GGAGACCATG TCTTTTGCGA CACAGCAGCA
NL/2/93     TACCCAAATG AGAAAGACTG TGAAACAAGA GGAGACCATG TCTTTTGCGA CACAGTAGCA
NL/4/93     TACCCAAATG AGAAAGACTG TGAAACAAGA GGAGACCATG TCTTTTGCGA CACAGCAGCA
NL/1/95     TACCCAAATG AGAAGGACTG TGAAACAAGA GGAGACCATG TCTTTTGCGA CACAGCAGCA
NL/2/96     TACCCAAATG AGAAAGACTG TGAAACAAGA GGAGACCATG TCTTTTGCGA CACAGCAGCA
NL/3/96     TACCCAAATG AGAAGGACTG TGAAACAAGA GGAGACCATG TCTTTTGCGA CACAGCAGCA
NL/1/98     TACCCAAATG AGAAAGACTG TGAAACAAGA GGAGACCATG TCTTTTGCGA CACAGCAGCA
NL/17/00    TACCCAAATG AGAAAGACTG TGAAACAAGA GGAGACCATG TCTTTTGCGA CACAGCAGCA
NL/22/01    TACCCAAATG AGAAAGACTG TGAAACAAGA GGAGACCATG TCTTTTGCGA CACAGCAGCA
NL/29/01    TACCCAAATG AGAAAGACTG TGAAACAAGA GGAGACCATG TCTTTTGCGA CACAGCAGCA
NL/23/01    TACCCAAATG AGAAAGACTG TGAAACAAGA GGAGACCATG TCTTTTGCGA CACAGCAGCA
NL/17/01    TACCCAAATG AGAAAGACTG TGAAACAAGA GGAGACCATG TCTTTTGCGA CACAGCAGCA
NL/24/01    TACCCAAATG AGAAAGACTG TGAAACAAGA GGAGACCATG TCTTTTGCGA CACAGCAGCA
NL/3/02     TACCCAAATG AGAAAGACTG TGAAACAAGA GGAGACCATG TCTTTTGCGA CACAGCAGCA
NL/3/98     TACCCAAATG AAAAAGACTG CGAAACAAGA GGTGATCATG TTTTTTGTGA CACAGCAGCA
NL/1/99     TACCCAAATG AAAAAGACTG CGAAACAAGA GGTGATCATG TTTTTTGTGA CACAGCAGCA
NL/2/99     TACCCAAATG AAAAAGACTG CGAAACAAGA GGTGATCATG TTTTTTGTGA CACAGCAGCA
NL/3/99     TACCCAAATG AAAAAGACTG CGAAACAAGA GGTGATCATG TTTTTTGTGA CACAGCAGCA
NL/11/00    TACCCAAATG AAAAAGACTG CGAAACAAGA GGTGATCATG TTTTTTGTGA CACAGCAGCA
```

Figure 17 con't

| | | | | | | |
|---|---|---|---|---|---|---|
| NL/12/00 | TACCCAAATG | AAAAAGACTG | CGAAACAAGA | GGTGATCATG | TTTTTTGTGA | CACAGCAGCA |
| NL/1/01 | TACCCAAATG | AAAAAGACTG | CGAAACAAGA | GGTGATCATG | TTTTTTGTGA | CACAGCAGCA |
| NL/5/01 | TACCCAAATG | AAAAAGACTG | CGAAACAAGA | GGTGATCATG | TTTTTTGTGA | CACAGCAGCA |
| NL/9/01 | TACCCAAATG | AAAAAGACTG | CGAAACAAGA | GGTGATCATG | TTTTTTGTGA | CACAGCAGCA |
| NL/19/01 | TACCCAAATG | AAAAAGACTG | TGAAACAAGA | GGTGATCATG | TTTTTTGTGA | CACAGCAGCA |
| NL/21/01 | TACCCAAATG | AAAAAGACTG | CGAAACAAGA | GGTGATCATG | TTTTTTGTGA | CACAGCAGCA |
| UK/11/01 | TACCCAAATG | AAAAAGACTG | CGAAACAAGA | GGTGATCATG | TTTTTTGTGA | TACAGCAGCA |
| FL/1/01 | TACCCAAATG | AAAAAGACTG | CGAAACAAGA | GGTGATCATG | TGTTTTGTGA | CACAGCAGCA |
| FL/2/01 | TACCCAAATG | AAAAAGACTG | CGAAACAAGA | GGTGATCATG | TGTTTTGTGA | CACAGCAGCA |
| FL/5/01 | TACCCAAATG | AAAAAGACTG | TGAAACAAGA | GGTGATCATG | TTTTTTGTGA | CACAGCAGCA |
| FL/7/01 | TACCCAAATG | AAAAAGACTG | CGAAACAAGA | GGTGATCATG | TTTTTTGTGA | CACAGCAGCA |
| FL/9/01 | TACCCAAATG | AAAAAGACTG | CGAAACAAGA | GGTGATCATG | TGTTTTGTGA | CACAGCAGCA |
| UK/10/01 | TACCCAAATG | AAAAAGACTG | CGAAACAAGA | GGTGATCATG | TTTTTTGTGA | TACAGCAGCA |
| NL/1/02 | TACCCAAATG | AAAAAGACTG | CGAAACAAGA | GGTGATCATG | TTTTTTGTGA | CACAGCAGCA |
| NL/1/94 | TACCCAAATG | AAAAAGACTG | CGAAACAAGA | GGTGATCATG | TTTTTTGTGA | CACAGCAGCA |
| NL/1/96 | TACCCAAATG | AAAAAGACTG | CGAAACAAGA | GGTGATCATG | TTTTTTGTGA | CACAGCAGCA |
| NL/6/97 | TACCCAAATG | AAAAAGACTG | CGAAACAAGA | GGTGATCATG | TTTTTTGTGA | CACAGCAGCA |
| NL/7/00 | TACCCAAATG | AAAAAGACTG | CGAAACAAGA | GGTGATCATG | TTTTTTGTGA | CACAGCAGCA |
| NL/9/00 | TACCCAAATG | AAAAAGACTG | CGAAACAAGA | GGTGATCATG | TTTTTTGTGA | CACAGCTGCA |
| NL/19/00 | TACCCAAATG | AAAAAGACTG | CGAAACAAGA | GGTGATCATG | TTTTTTGTGA | CACAGCAGCA |
| NL/28/00 | TACCCAAATG | AAAAAGACTG | TGAAACAAGA | GGTGATCATG | TTTTTTGTGA | CACAGCAGCA |
| NL/3/01 | TACCCAAATG | AAAAAGACTG | CGAAACAAGA | GGTGATCATG | TTTTTTGTGA | CACAGCAGCA |
| NL/4/01 | TACCCAAATG | AAAAAGACTG | CGAAACAAGA | GGTGATCATG | TTTTTTGTGA | CACAGCAGCA |
| NL/11/01 | TACCCAAATG | AAAAAGACTG | TGAAACAAGA | GGTGATCATG | TTTTTTGTGA | CACAGCAGCA |
| NL/15/01 | TACCCAAATG | AAAAAGACTG | CGAAACAAGA | GGTGATCATG | TTTTTTGTGA | CACAGCTGCA |
| NL/18/01 | TACCCAAATG | AAAAAGACTG | CGAAACAAGA | GGTGATCATG | TTTTTTGTGA | CACAGCTGCA |
| FL/6/01 | TACCCAAATG | AAAAAGACTG | CGAAACAAGA | GGTGATCATG | TTTTTTGTGA | CACAGCTGCA |
| UK/5/01 | TACCCAAATG | AAAAAGACTG | CGAAACAAGA | GGTGATCATG | TTTTTTGTGA | CACAGCTGCA |
| UK/8/01 | TACCCAAATG | AAAAAGACTG | CGAAACAAGA | GGTGATCATG | TTTTTTGTGA | CACAGCAGCA |
| NL/12/02 | TACCCAAATG | AAAAAGACTG | CGAAACAAGA | GGTGATCATG | TTTTTTGTGA | CACAGCTGCA |
| HK/1/02 | TACCCAAATG | AAAAAGACTG | CGAAACAAGA | GGTGATCATG | TTTTTTGTGA | CACAGCAGCA |
| | 245 | 255 | 265 | 275 | 285 | 295 |
| NL/1/00 | GGAATCAATG | TTGCTGAGCA | GTCAAAGGAG | TGCAACATAA | ACATATCTAC | TACTAATTAC |
| UK/1/00 | GGAATCAATG | TTGCTGAGCA | GTCAAAGGAG | TGCAACATCA | ACATATCCAC | TACTAATTAC |
| NL/2/00 | GGAATCAATG | TTGCTGAGCA | GTCAAAGGAG | TGCAACATCA | ACATATCCAC | TACTAATTAC |
| NL/13/00 | GGAATCAATG | TTGCTGAGCA | GTCAAAGGAG | TGCAACATCA | ACATATCCAC | TACTAATTAC |
| NL/14/00 | GGAATCAATG | TTGCTGAGCA | GTCAAAGGAG | TGCAACATCA | ACATATCCAC | TACTAATTAC |
| FL/3/01 | GGAATCAATG | TTGCTGAGCA | GTCAAAGGAG | TGCAACATAA | ACATATCTAC | TACTAATTAC |
| FL/4/01 | GGAATCAATG | TTGCTGAGCA | GTCAAAGGAG | TGCAACATAA | ACATATCTAC | TACTAATTAC |
| FL/8/01 | GGAATCAATG | TTGCTGAGCA | GTCAAAGGAG | TGCAACATAA | ACATATCTAC | TACTAATTAC |
| UK/1/01 | GGAATCAATG | TTGCTGAGCA | GTCAAAGGAG | TGCAACATCA | ACATATCCAC | TACTAATTAC |
| UK/7/01 | GGAATCAATG | TTGCTGAGCA | GTCAAAGGAG | TGCAACATCA | ACATATCCAC | TACTAATTAC |
| FL/10/01 | GGAATCAATG | TTGCTGAGCA | GTCAAAGGAG | TGCAACATCA | ACATATCCAC | TACTAATTAC |
| NL/6/01 | GGAATCAATG | TTGCTGAGCA | GTCAAAGGAG | TGCAACATCA | ACATATCCAC | TACTAATTAC |
| NL/8/01 | GGAATCAATG | TTGCTGAGCA | GTCAAAGGAG | TGCAACATCA | ATATATCCAC | TACTAATTAC |
| NL/10/01 | GGAATCAATG | TTGCTGAGCA | GTCAAAGGAG | TGCAACATCA | ACATATCCAC | TACTAATTAC |
| NL/14/01 | GGAATCAATG | TTGCTGAGCA | GTCAAAGGAG | TGCAACATCA | ACATATCCAC | TACTAATTAC |
| NL/20/01 | GGAATCAATG | TTGCTGAGCA | GTCAAAGGAG | TGCAACATCA | ACATATCCAC | TACTAATTAC |
| NL/25/01 | GGAATCAATG | TTGCTGAGCA | GTCAAAGGAG | TGCAACATCA | ACATATCCAC | CACTAATTAC |
| NL/26/01 | GGAATCAATG | TTGCTGAGCA | GTCAAAGGAG | TGCAACATCA | ACATATCCAC | TACTAATTAC |
| NL/28/01 | GGAATCAATG | TTGCTGAGCA | GTCAAAGGAG | TGCAACATCA | ACATATCCAC | TACTAATTAC |
| NL/30/01 | GGAATCAATG | TTGCTGAGCA | GTCAAAGGAG | TGCAACATCA | ACATATCCAC | TACTAATTAC |
| BR/2/01 | GGAATCAATG | TTGCTGAGCA | GTCAAAGGAG | TGCAACATAA | ACATATCTAC | TACTAATTAC |
| BR/3/01 | GGAATCAATG | TTGCTGAGCA | GTCAAAGGAG | TGCAACATAA | ACATATCTAC | TACTAATTAC |
| NL/2/02 | GGAATCAATG | TTGCTGAGCA | GTCAAAGGAG | TGCAACATCA | ACATATCCAC | CACTAATTAC |
| NL/4/02 | GGAATCAATG | TTGCTGAGCA | GTCAAAGGAG | TGCAACATCA | ACATATCCAC | TACTAATTAC |
| NL/5/02 | GGAATCAATG | TTGCTGAGCA | GTCAAAGGAG | TGCAACATCA | ACATATCCAC | CACTAATTAC |
| NL/6/02 | GGAATCAATG | TTGCTGAGCA | GTCAAAGGAG | TGCAACATCA | ACATATCCAC | CACTAATTAC |
| NL/7/02 | GGAATCAATG | TTGCTGAGCA | GTCAAAGGAG | TGCAACATAA | ACATATCTAC | TACTAATTAC |

Figure 17 con't

| | | | | | | |
|---|---|---|---|---|---|---|
| NL/9/02 | GGAATCAATG | TTGCTGAGCA | GTCAAAGGAG | TGCAACATCA | ACATATCCAC | TACTAATTAC |
| FL/1/02 | GGAATCAATG | TTGCTGAGCA | GTCAAAGGAG | TGCAACATAA | ACATATCTAC | TACTAATTAC |
| NL/1/81 | GGAATTAATG | TTGCTGAGCA | ATCAAAGGAG | TGCAACATCA | ACATATCCAC | TACAAATTAC |
| NL/1/93 | GGAATTAATG | TTGCTGAGCA | ATCAAAAGAG | TGCAACATCA | ACATATCCAC | TACAAATTAC |
| NL/2/93 | GGAATTAATG | TTGCTGAGCA | ATCAAAAGAG | TGCAACATCA | ACATATCCAC | TACAAATTAC |
| NL/4/93 | GGAATTAATG | TTGCTGAGCA | ATCAAAAGAG | TGCAACATCA | ACATATCCAC | TACAAATTAC |
| NL/1/95 | GGAATTAATG | TTGCTGAGCA | ATCAAAGGAG | TGCAACATCA | ACATATCCAC | CACAAATTAC |
| NL/2/96 | GGAATTAATG | TTGCTGAGCA | ATCAAAGGAG | TGCAACATCA | ACATATCCAC | TACAAATTAC |
| NL/3/96 | GGAATTAATG | TTGCTGAGCA | ATCAAAGGAG | TGCAACATCA | ACATATCCAC | CACAAATTAC |
| NL/1/98 | GGAATTAATG | TTGCTGAGCA | ATCAAAGGAG | TGCAACATCA | ACATATCCAC | TACAAATTAC |
| NL/17/00 | GGAATTAATG | TTGCTGAGCA | ATCAAAGGAG | TGCAACATCA | ACATATCCAC | TACAAATTAC |
| NL/22/01 | GGAATTAATG | TTGCTGAGCA | ATCAAAGGAG | TGCAACATCA | ACATATCCAC | CACAAATTAC |
| NL/29/01 | GGAATTAATG | TTGCTGAGCA | ATCAAAGGAG | TGCAACATCA | ACATATCCAC | TACAAATTAC |
| NL/23/01 | GGAATTAATG | TTGCTGAGCA | ATCAAAGGAG | TGCAACATCA | ACATATCCAC | CACAAATTAC |
| NL/17/01 | GGAATTAATG | TTGCTGAGCA | ATCAAAGGAA | TGCAACATCA | ACATATCCAC | TACAAATTAC |
| NL/24/01 | GGAATTAATG | TTGCTGAGCA | ATCAAAGGAG | TGCAACATCA | ACATATCCAC | CACAAATTAC |
| NL/3/02 | GGAATTAATG | TTGCTGAGCA | ATCAAAGGAG | TGCAACATCA | ACATATCCAC | TACAAATTAC |
| NL/3/98 | GGGATCAATG | TTGCTGAGCA | ATCAAGAGAA | TGCAACATCA | ACATATCTAC | TACCAACTAC |
| NL/1/99 | GGGATCAATG | TTGCTGAGCA | ATCAAGAGAA | TGCAACATCA | ACATATCTAC | TACCAACTAC |
| NL/2/99 | GGGATCAATG | TTGCTGAGCA | ATCAAGAGAA | TGCAACATCA | ACATATCTAC | TACCAACTAC |
| NL/3/99 | GGGATCAATG | TTGCTGAGCA | ATCAAGAGAA | TGCAACATCA | ACATATCTAC | TACCAACTAC |
| NL/11/00 | GGGATCAATG | TTGCTGAGCA | ATCAAGAGAA | TGCAACATCA | ACATATCTAC | TACCAACTAC |
| NL/12/00 | GGGATCAATG | TTGCTGAGCA | ATCAAGAGAA | TGCAACATCA | ACATATCTAC | TACCAACTAC |
| NL/1/01 | GGGATCAATG | TTGCTGAGCA | ATCAAGAGAA | TGCAACATCA | ACATATCTAC | TACCAACTAC |
| NL/5/01 | GGGATCAATG | TTGCTGAGCA | ATCAAGAGAA | TGCAACATCA | ACATATCTAC | TACCAACTAC |
| NL/9/01 | GGGATCAATG | TTGCTGAGCA | ATCAAGAGAA | TGCAACATCA | ACATATCTAC | TACCAACTAC |
| NL/19/01 | GGGATCAATG | TTGCTGAGCA | ATCAAGAGAA | TGCAACATCA | ACATATCTAC | TACCAACTAC |
| NL/21/01 | GGGATCAATG | TTGCTGAGCA | ATCAAGAGAA | TGCAACATCA | ACATATCTAC | TACCAACTAC |
| UK/11/01 | GGGATCAATG | TTGCTGAGCA | ATCAAGAGAA | TGCAACATCA | ACATATCTAC | TACCAACTAC |
| FL/1/01 | GGGATCAATG | TTGCTGAGCA | ATCAAGAGAA | TGCAACATCA | ACATATCTAC | TACCAACTAC |
| FL/2/01 | GGGATCAATG | TTGCTGAGCA | ATCAAGAGAA | TGCAACATCA | ACATATCTAC | TACCAACTAC |
| FL/5/01 | GGGATCAATG | TTGCTGAGCA | ATCAAGAGAA | TGCAACATCA | ACATATCTAC | TACCAACTAC |
| FL/7/01 | GGGATCAATG | TTGCTGAGCA | ATCAAGAGAA | TGCAACATCA | ACATATCTAC | TACCAACTAC |
| FL/9/01 | GGGATCAATG | TTGCTGAGCA | ATCAAGAGAA | TGCAACATCA | ACATATCTAC | TACCAACTAC |
| UK/10/01 | GGGATCAATG | TTGCTGAGCA | ATCAAGAGAA | TGCAACATCA | ACATATCTAC | TACCAACTAC |
| NL/1/02 | GGGATCAATG | TTGCTGAGCA | ATCAAGAGAA | TGCAACATCA | ACATATCTAC | TACCAACTAC |
| NL/1/94 | GGGATCAATG | TTGCTGAGCA | ATCAAGAGAA | TGCAACATCA | ACATATCTAC | CACCAACTAC |
| NL/1/96 | GGGATCAATG | TTGCTGAGCA | ATCAAGAGAA | TGCAACATCA | ACATATCTAC | CACCAACTAC |
| NL/6/97 | GGGATCAATG | TTGCTGAGCA | ATCAAGAGAA | TGCAACATCA | ACATATCTAC | CACCAACTAC |
| NL/7/00 | GGGATCAATG | TTGCTGAGCA | ATCAAGAGAA | TGCAACATCA | ACATATCTAC | AACCAACTAC |
| NL/9/00 | GGGATCAATG | TTGCTGAGCA | ATCAAGAGAA | TGCAACATCA | ACATATCCAC | AACCAACTAC |
| NL/19/00 | GGGATCAATG | TTGCTGAGCA | ATCAAGAGAA | TGCAACATCA | ACATATCTAC | TACCAACTAC |
| NL/28/00 | GGGATCAATG | TTGCTGAGCA | ATCAAGAGAA | TGCAACATCA | ACATATCTAC | AACCAACTAC |
| NL/3/01 | GGGATCAATG | TTGCTGAGCA | ATCAAGAGAA | TGCAACATCA | ACATATCTAC | AACCAACTAC |
| NL/4/01 | GGGATCAATG | TTGCTGAGCA | ATCAAGAGAA | TGCAACATCA | ACATATCTAC | AACCAACTAC |
| NL/11/01 | GGGATCAATG | TTGCTGAGCA | ATCAAGAGAA | TGCAACATCA | ACATATCTAC | AACCAACTAC |
| NL/15/01 | GGGATCAATG | TTGCTGAGCA | ATCAAGAGAA | TGCAACATCA | ACATATCTAC | AACCAACTAC |
| NL/18/01 | GGGATCAATG | TTGCTGAGCA | ATCAAGAGAA | TGCAACATCA | ACATATCTAC | AACCAACTAC |
| FL/6/01 | GGGATCAATG | TTGCTGAGCA | ATCAAGAGAA | TGCAACATCA | ACATATCTAC | AACCAACTAC |
| UK/5/01 | GGGATCAATG | TTGCTGAGCA | ATCAAGAGAA | TGCAACATCA | ACATATCCAC | AACCAACTAC |
| UK/8/01 | GGGATCAACG | TTGCTGAGCA | ATCAAGAGAA | TGCAACATCA | ACATATCTAC | CACCAACTAT |
| NL/12/02 | GGGATCAATG | TTGCTGAGCA | ATCAAGAGAA | TGCAACATCA | ACATATCTAC | AACCAACTAC |
| HK/1/02 | GGGATCAATG | TTGCTGAGCA | ATCAAGAGAA | TGCAACATCA | ACATATCTAC | AACCAACTAC |
| | ....\|....\| | ....\|....\| | ....\|....\| | ....\|....\| | ....\|....\| | ....\|....\| |
| | 305 | 315 | 325 | 335 | 345 | 355 |
| NL/1/00 | CCATGCAAAG | TTAGCACAGG | AAGACATCCT | ATCAGTATGG | TTGCACTATC | TCCTCTTGGG |
| UK/1/00 | CCATGCAAAG | TTAGCACAGG | AAGACATCCT | ATCAGTATGG | TTGCACTGTC | TCCTCTTGGG |
| NL/2/00 | CCATGCAAAG | TTAGCACAGG | AAGACATCCT | ATCAGTATGG | TTGCACTGTC | TCCTCTTGGG |
| NL/13/00 | CCATGCAAAG | TTAGCACAGG | AAGACATCCT | ATCAGTATGG | TTGCACTGTC | TCCTCTTGGG |
| NL/14/00 | CCATGCAAAG | TTAGCACAGG | AAGACATCCT | ATCAGTATGG | TTGCACTGTC | TCCTCTTGGG |

Figure 17 con't

| | | | | | | |
|---|---|---|---|---|---|---|
| FL/3/01 | CCATGCAAAG | TTAGCACAGG | AAGACATCCT | ATCAGTATGG | TTGCACTGTC | TCCTCTTGGG |
| FL/4/01 | CCATGCAAAG | TTAGCACAGG | AAGACATCCT | ATCAGTATGG | TTGCACTGTC | TCCTCTTGGG |
| FL/8/01 | CCATGCAAAG | TTAGCACAGG | AAGACATCCT | ATCAGTATGG | TTGCACTGTC | TCCTCTTGGG |
| UK/1/01 | CCATGCAAAG | TTAGCACAGG | AAGACATCCT | ATCAGTATGG | TTGCACTGTC | TCCTCTTGGG |
| UK/7/01 | CCATGCAAAG | TTAGCACAGG | AAGACATCCT | ATCAGTATGG | TTGCACTGTC | TCCTCTTGGG |
| FL/10/01 | CCATGCAAAG | TTAGCACAGG | AAGACATCCT | ATCAGTATGG | TTGCACTGTC | TCCTCTTGGG |
| NL/6/01 | CCATGCAAAG | TTAGCACAGG | AAGACATCCT | ATCAGTATGG | TTGCACTGTC | TCCTCTTGGG |
| NL/8/01 | CCATGCAAAG | TTAGCACAGG | AAGACATCCT | ATCAGTATGG | TTGCACTGTC | TCCTCTTGGG |
| NL/10/01 | CCATGCAAAG | TTAGCACAGG | AAGACATCCT | ATCAGTATGG | TTGCACTGTC | TCCTCTTGGG |
| NL/14/01 | CCATGCAAAG | TTAGCACAGG | AAGACATCCT | ATCAGTATGG | TTGCACTGTC | TCCTCTTGGG |
| NL/20/01 | CCATGCAAAG | TTAGCACAGG | AAGACATCCT | ATCAGTATGG | TTGCACTGTC | TCCTCTTGGG |
| NL/25/01 | CCATGCAAAG | TTAGCACAGG | AAGACATCCT | ATCAGTATGG | TTGCACTGTC | TCCTCTTGGG |
| NL/26/01 | CCATGCAAAG | TTAGCACAGG | AAGACATCCT | ATCAGTATGG | TTGCACTGTC | TCCTCTTGGG |
| NL/28/01 | CCATGCAAAG | TTAGCACAGG | AAGACATCCT | ATCAGTATGG | TTGCACTGTC | TCCTCTTGGG |
| NL/30/01 | CCATGCAAAG | TTAGCACAGG | AAGACATCCT | ATCAGTATGG | TTGCACTGTC | TCCTCTTGGG |
| BR/2/01 | CCATGCAAAG | TTAGCACAGG | AAGACATCCT | ATCAGTATGG | TTGCACTATC | TCCTCTTGGG |
| BR/3/01 | CCATGCAAAG | TTAGCACAGG | AAGACATCCT | ATCAGTATGG | TTGCACTATC | TCCTCTTGGG |
| NL/2/02 | CCATGCAAAG | TTAGCACAGG | AAGACATCCT | ATCAGTATGG | TTGCACTGTC | TCCTCTTGGG |
| NL/4/02 | CCATGCAAAG | TTAGCACAGG | AAGACATCCT | ATCAGTATGG | TTGCACTGTC | TCCTCTTGGG |
| NL/5/02 | CCATGCAAAG | TTAGCACAGG | AAGACATCCT | ATCAGTATGG | TTGCACTGTC | TCCTCTTGGG |
| NL/6/02 | CCATGCAAAG | TTAGCACAGG | AAGACATCCT | ATCAGTATGG | TTGCACTGTC | TCCTCTTGGG |
| NL/7/02 | CCATGCAAAG | TTAGCACAGG | AAGACATCCT | ATCAGTATGG | TTGCACTATC | TCCTCTTGGG |
| NL/9/02 | CCATGCAAAG | TTAGCACAGG | AAGACATCCT | ATCAGTATGG | TTGCACTGTC | TCCTCTTGGG |
| FL/1/02 | CCATGCAAAG | TTAGCACAGG | AAGACATCCT | ATCAGTATGG | TTGCACTATC | TCCTCTTGGG |
| NL/1/81 | CCATGCAAAG | TCAGCACAGG | AAGACATCCT | ATCAGTATGG | TTGCACTGTC | CCCTCTTGGG |
| NL/1/93 | CCATGCAAAG | TCAGCACAGG | AAGACATCCT | ATCAGTATGG | TTGCACTGTC | CCCTCTTGGG |
| NL/2/93 | CCATGCAAAG | TCAGCACAGG | AAGACATCCT | ATCAGTATGG | TTGCACTGTC | CCCTCTTGGG |
| NL/4/93 | CCATGCAAAG | TCAGCACAGG | AAGACATCCT | ATCAGTATGG | TTGCACTGTC | CCCTCTTGGG |
| NL/1/95 | CCATGCAAAG | TCAGCACAGG | AAGGCATCCT | ATCAGTATGG | TTGCACTGTC | CCCTCTTGGG |
| NL/2/96 | CCATGCAAAG | TCAGCACAGG | AAGACATCCT | ATCAGTATGG | TTGCACTGTC | TCCTCTTGGG |
| NL/3/96 | CCATGCAAAG | TCAGCACAGG | AAGGCATCCT | ATCAGTATGG | TTGCACTGTC | CCCTCTTGGG |
| NL/1/98 | CCATGCAAAG | TCAGCACAGG | AAGACATCCT | ATCAGTATGG | TTGCACTGTC | TCCTCTTGGG |
| NL/17/00 | CCATGCAAAG | TCAGCACAGG | AAGACATCCT | ATCAGTATGG | TTGCACTGTC | TCCTCTTGGG |
| NL/22/01 | CCATGCAAAG | TCAGCACAGG | AAGGCATCCT | ATCAGTATGG | TTGCACTGTC | CCCTCTCGGG |
| NL/29/01 | CCATGCAAAG | TCAGCACAGG | AAGACATCCT | ATCAGTATGG | TTGCACTGTC | TCCTCTTGGG |
| NL/23/01 | CCATGCAAAG | TCAGCACAGG | AAGGCATCCT | ATCAGTATGG | TTGCACTGTC | CCCTCTCGGG |
| NL/17/01 | CCATGCAAAG | TCAGCACAGG | AAGACATCCT | ATCAGTATGG | TTGCACTGTC | TCCTCTTGGG |
| NL/24/01 | CCATGCAAAG | TCAGCACAGG | AAGGCATCCT | ATCAGTATGG | TTGCACTGTC | CCCTCTCGGG |
| NL/3/02 | CCATGCAAAG | TCAGCACAGG | AAGACATCCT | ATCAGTATGG | TTGCACTGTC | TCCTCTTGGG |
| NL/3/98 | CCATGCAAAG | TCAGCACAGG | AAGACACCCT | ATAAGCATGG | TTGCACTATC | ACCTCTCGGT |
| NL/1/99 | CCATGCAAAG | TCAGCACAGG | AAGACACCCT | ATAAGCATGG | TTGCACTATC | ACCTCTCGGT |
| NL/2/99 | CCATGCAAAG | TCAGCACAGG | AAGACACCCT | ATAAGCATGG | TTGCACTATC | ACCTCTCGGT |
| NL/3/99 | CCATGCAAAG | TCAGCACAGG | AAGACACCCT | ATAAGCATGG | TTGCACTATC | ACCTCTCGGT |
| NL/11/00 | CCATGCAAAG | TCAGCACAGG | AAGACACCCT | ATAAGCATGG | TTGCACTATC | ACCTCTCGGT |
| NL/12/00 | CCATGCAAAG | TCAGCACAGG | AAGACACCCT | ATAAGCATGG | TTGCACTATC | ACCTCTCGGT |
| NL/1/01 | CCATGCAAAG | TCAGCACAGG | AAGACACCCT | ATAAGCATGG | TTGCACTATC | ACCTCTCGGT |
| NL/5/01 | CCATGCAAAG | TCAGCACAGG | AAGACACTCT | ATAAGCATGG | TTGCACTATC | ACCTCTCGGT |
| NL/9/01 | CCATGCAAAG | TCAGCACAGG | AAGACACCCT | ATAAGCATGG | TtGCACTATC | ACCTCTCGGT |
| NL/19/01 | CCATGCAAAG | TCAGCACAGG | AAGACACCCT | ATAAGCATGG | TTGCACTATC | ACCTCTCGGT |
| NL/21/01 | CCATGCAAAG | TCAGCACAGG | AAGACACCCT | ATAAGCATGG | TTGCACTATC | ACCTCTCGGT |
| UK/11/01 | CCATGCAAAG | TCAGCACAGG | AAGACACCCT | ATAAGCATGG | TTGCACTATC | ACCTCTCGGT |
| FL/1/01 | CCATGCAAAG | TCAGCACAGG | AAGACACCCT | ATAAGCATGG | TTGCACTATC | ACCTCTCGGT |
| FL/2/01 | CCATGCAAAG | TCAGCACAGG | AAGACACCCT | ATAAGCATGG | TTGCACTATC | ACCTCTCGGT |
| FL/5/01 | CCATGCAAAG | TCAGCACAGG | AAGACACCCT | ATAAGCATGG | TTGCACTATC | ACCTCTCGGT |
| FL/7/01 | CCATGCAAAG | TCAGCACAGG | AAGACACCCT | ATAAGCATGG | TTGCACTATC | ACCTCTCGGT |
| FL/9/01 | CCATGCAAAG | TCAGCACAGG | AAGACACCCT | ATAAGCATGG | TTGCACTATC | ACCTCTCGGT |
| UK/10/01 | CCATGCAAAG | TCAGCACAGG | AAGACACCCT | ATAAGCATGG | TTGCACTATC | ACCTCTCGGT |
| NL/1/02 | CCATGCAAAG | TCAGCACAGG | AAGACACCCT | ATAAGCATGG | TTGCACTATC | ACCTCTCGGT |
| NL/1/94 | CCATGCAAAG | TCAGCACAGG | AAGACACCCT | ATCAGCATGG | TTGCACTATC | ACCTCTCGGT |
| NL/1/96 | CCATGCAAAG | TCAGCACAGG | AAGACACCCC | ATCAGCATGG | TTGCACTATC | ACCTCTCGGT |
| NL/6/97 | CCATGCAAAG | TCAGCACAGG | AAGACACCCT | ATCAGCATGG | TTGCACTATC | ACCTCTCGGT |

Figure 17 con't

| | | | | | | |
|---|---|---|---|---|---|---|
| NL/7/00 | CCATGCAAAG | TCAGCACAGG | AAGACACCCT | ATCAGCATGG | TTGCACTATC | ACCTCTCGGT |
| NL/9/00 | CCATGCAAAG | TCAGCACAGG | AAGACACCCT | ATCAGCATGG | TTGCACTGTC | ACCTCTCGGC |
| NL/19/00 | CCATGCAAAG | TCAGCACAGG | AAGACACCCT | ATCAGCATGG | TTGCACTATC | ACCTCTCGGT |
| NL/28/00 | CCATGCAAAG | TCAGCACAGG | AAGACACCCT | ATCAGCATGG | TTGCACTATC | ACCTCTCGGT |
| NL/3/01 | CCATGCAAAG | TCAGCACAGG | AAGACACCCT | ATCAGCATGG | TTGCACTATC | ACCTCTCGGT |
| NL/4/01 | CCATGCAAAG | TCAGCACAGG | AAGACACCCT | ATCAGCATGG | TTGCACTATC | ACCTCTCGGT |
| NL/11/01 | CCATGCAAAG | TCAGCACAGG | AAGACACCCT | ATCAGCATGG | TTGCACTATC | ACCTCTCGGT |
| NL/15/01 | CCATGCAAAG | TCAGCACAGG | AAGACACCCT | ATCAGCATGG | TTGCACTATC | ACCTCTCGGT |
| NL/18/01 | CCATGCAAAG | TCAGCACAGG | AAGACACCCT | ATCAGCATGG | TTGCACTATC | ACCTCTCGGT |
| FL/6/01 | CCATGCAAAG | TCAGCACAGG | AAGACACCCT | ATCAGCATGG | TTGCACTATC | ACCTCTCGGT |
| UK/5/01 | CCATGCAAAG | TCAGCACAGG | AAGACACCCT | ATCAGCATGG | TTGCACTGTC | ACCTCTCGGC |
| UK/8/01 | CCGTGCAAAG | TCAGCACAGG | AAGACACCCT | ATCAGCATGG | TTGCACTATC | ACCTCTCGGT |
| NL/12/02 | CCATGCAAAG | TCAGCACAGG | AAGACACCCT | ATCAGCATGG | TTGCACTATC | ACCTCTCGGT |
| HK/1/02 | CCATGCAAAG | TCAGCACAGG | AAGACACCCT | ATCAGCATGG | TTGCACTATC | ACCTCTCGGT |

| | ....\|....\| 365 | ....\|....\| 375 | ....\|....\| 385 | ....\|....\| 395 | ....\|....\| 405 | ....\|....\| 415 |
|---|---|---|---|---|---|---|
| NL/1/00 | GCTTTGGTTG | CTTGCTACAA | GGGAGTGAGC | TGTTCCATTG | GCAGCAACAG | AGTAGGGATC |
| UK/1/00 | GCTTTGGTTG | CTTGCTACAA | GGGAGTGAGC | TGTTCCATTG | GCAGCAACAG | AGTAGGGATC |
| NL/2/00 | GCTTTGGTTG | CTTGCTACAA | GGGAGTGAGC | TGTTCCATTG | GCAGCAACAG | AGTAGGGATC |
| NL/13/00 | GCTTTGGTTG | CTTGCTACAA | GGGAGTGAGC | TGTTCCATTG | GCAGCAACAG | AGTAGGGATC |
| NL/14/00 | GCTTTGGTTG | CTTGCTACAA | GGGAGTGAGC | TGTTCCATTG | GTAGCAACAG | AGTAGGGATC |
| FL/3/01 | GCTTTGGTTG | CTTGCTACAA | GGGAGTGAGC | TGTTCCATTG | GCAGCAACAG | AGTAGGGATC |
| FL/4/01 | GCTTTGGTTG | CTTGCTACAA | GGGAGTGAGC | TGTTCCATTG | GCAGCAACAG | AGTAGGGATC |
| FL/8/01 | GCTTTGGTTG | CTTGCTACAA | GGGAGTGAGC | TGTTCCATTG | GCAGCAACAG | AGTAGGGATC |
| UK/1/01 | GCTTTGGTTG | CTTGCTACAA | GGGAGTGAGC | TGTTCCATTG | GCAGCAACAG | AGTAGGAATC |
| UK/7/01 | GCTTTGGTTG | CTTGCTACAA | GGGAGTGAGC | TGTTCCATTG | GCAGCAACAG | AGTAGGGATC |
| FL/10/01 | GCTTTGGTTG | CTTGCTACAA | GGGAGTGAGC | TGTTCCATTG | GCAGCAACAG | AGTAGGGATC |
| NL/6/01 | GCTTTGGTTG | CTTGCTACAA | GGGAGTGAGC | TGTTCCATTG | GCAGCAACAG | AGTAGGGATC |
| NL/8/01 | GCTTTGGTTG | CTTGCTACAA | GGGAGTGAGC | TGTTCCATTG | GCAGCAACAG | AGTAGGGATC |
| NL/10/01 | GCTTTGGTTG | CTTGCTACAA | GGGAGTGAGC | TGTTCCATTG | GCAGCAACAG | AGTAGGGATC |
| NL/14/01 | GCTTTGGTTG | CTTGCTACAA | GGGAGTGAGC | TGTTCTATTG | GCAGCAACAG | AGTAGGGATC |
| NL/20/01 | GCTTTGGTTG | CTTGCTACAA | GGGAGTGAGC | TGTTCCATTG | GCAGCAACAG | AGTAGGGATC |
| NL/25/01 | GCTTTGGTTG | CTTGCTACAA | GGGAGTGAGC | TGTTCCATTG | GCAGCAACAG | AGTAGGGATC |
| NL/26/01 | GCTTTGGTTG | CTTGCTACAA | GGGAGTGAGC | TGTTCCATTG | GCAGCAACAG | AGTAGGGATC |
| NL/28/01 | GCTTTGGTTG | CTTGCTACAA | GGGAGTGAGC | TGTTCCATTG | GCAGCAACAG | AGTAGGGATC |
| NL/30/01 | GCTTTGGTTG | CTTGCTACAA | GGGAGTGAGC | TGTTCCATTG | GCAGCAACAG | AGTAGGGATC |
| BR/2/01 | GCTTTGGTTG | CTTGCTaCAA | GGGAGTGAGC | TGTTCCATTG | GCAGCAACAG | AGTAGGGATC |
| BR/3/01 | GCTTTGGTTG | CTTGCTACAA | GGGAGTGAGC | TGTTCCATTG | GCAGCAACAG | AGTAGGGATC |
| NL/2/02 | GCTTTGGTTG | CTTGCTACAA | GGGAGTGAGC | TGTTCCATTG | GCAGCAACAG | AGTAGGGATC |
| NL/4/02 | GCTCTGGTTG | CTTGCTACAA | GGGAGTGAGC | TGCTCCATTG | GCAGCAACAG | AGTAGGGATC |
| NL/5/02 | GCTTTGGTTG | CTTGCTACAA | GGGAGTGAGC | TGTTCCATTG | GCAGCAACAG | AGTAGGGATC |
| NL/6/02 | GCTTTGGTTG | CTTGCTACAA | GGGAGTGAGC | TGTTCCATTG | GCAGCAACAG | AGTAGGGATC |
| NL/7/02 | GCTTTGGTTG | CTTGCTACAA | GGGAGTGAGC | TGTTCCATTG | GCAGCAACAG | AGTAGGGATC |
| NL/9/02 | GCTTTGGTTG | CTTGCTACAA | GGGAGTGAGC | TGTTCCATTG | GCAGCAACAG | AGTAGGGATC |
| FL/1/02 | GCTTTGGTTG | CTTGCTACAA | GGGAGTGAGC | TGTTCCATTG | GCAGCAACAG | AGTAGGGATC |
| NL/1/81 | GCTCTGGTTG | CTTGCTACAA | AGGAGTAAGC | TGTTCCATTG | GCAGCAATAG | AGTAGGGATT |
| NL/1/93 | GCTCTAGTTG | CTTGCTACAA | AGGAGTAAGC | TGTTCCATTG | GCAGCAATAG | AGTAGGGATC |
| NL/2/93 | GCTCTAGTTG | CTTGCTACAA | AGGAGTAAGC | TGTTCCATTG | GCAGCAATAG | AGTAGGGATC |
| NL/4/93 | GCTCTAGTTG | CTTGCTACAA | AGGAGTAAGC | TGTTCCATTG | GCAGCAATAG | AGTAGGGATC |
| NL/1/95 | GCTCTGGTTG | CTTGTTACAA | AGGAGTAAGC | TGTTCTATTG | GCAGCAATAG | AGTAGGGATC |
| NL/2/96 | GCTCTAGTTG | CTTGCTACAA | AGGAGTAAGC | TGTTCCATTG | GCAGCAACAG | AGTAGGGATC |
| NL/3/96 | GCTCTGGTTG | CTTGTTACAA | AGGAGTAAGC | TGTTCTATTG | GCAGCAATAG | AGTAGGGATC |
| NL/1/98 | GCTCTGGTTG | CTTGCTACAA | AGGAGTAAGC | TGTTCCATTG | GCAGCAACAG | AGTAGGGATC |
| NL/17/00 | GCTCTGGTTG | CTTGCTACAA | AGGAGTAAGC | TGTTCCATTG | GCAGCAACAG | AGTAGGGATC |
| NL/22/01 | GCTCTGGTTG | CCTGTTACAA | AGGAGTAAGT | TGTTCCATTG | GCAGCAATAG | AGTAGGGATC |
| NL/29/01 | GCTCTGGTTG | CTTGCTACAA | AGGAGTAAGC | TGTTCCATTG | GCAGCAACAG | AGTAGGGATC |
| NL/23/01 | GCTCTGGTTG | CCTGTTACAA | AGGAGTAAGT | TGTTCCATTG | GCAGCAATAG | AGTAGGGATC |
| NL/17/01 | GCTCTGGTTG | CTTGCTACAA | AGGAGTAAGC | TGTTCCATTG | GCAGCAACAG | AGTAGGGATC |
| NL/24/01 | GCTCTGGTTG | CCTGTTACAA | AGGAGTAAGT | TGTTCCATTG | GCAGCAATAG | AGTAGGGATC |
| NL/3/02 | GCTCTGGTTG | CTTGCTACAA | AGGAGTAAGC | TGTTCCATTG | GCAGCAACAG | AGTAGGGATC |

Figure 17 con't

| | | | | | | |
|---|---|---|---|---|---|---|
| NL/3/98 | GCTTTGGTGG | CTTGCTATAA | AGGGGTAAGC | TGCTCGATTG | GCAGCAATCG | GGTTGGAATC |
| NL/1/99 | GCTTTGGTGG | CTTGCTATAA | AGGGGTAAGC | TGCTCGATTG | GCAGCAATTG | GGTTGGAATC |
| NL/2/99 | GCTTTGGTGG | CTTGCTATAA | AGGGGTAAGC | TGCTCGATTG | GCAGCAATCG | GGTTGGAATC |
| NL/3/99 | GCTTTGGTGG | CTTGCTATAA | AGGGGTAAGC | TGCTCGATTG | GCAGCAATCG | GGTTGGAATC |
| NL/11/00 | GCTTTGGTGG | CTTGCTATAA | AGGGGTAAGC | TGCTCGATTG | GCAGCAATCG | GGTTGGAATC |
| NL/12/00 | GCTTTGGTGG | CTTGCTATAA | AGGGGTAAGC | TGCTCGATTG | GCAGCAATCG | GGTTGGAATC |
| NL/1/01 | GCTTTGGTGG | CTTGCTATAA | AGGGGTAAGC | TGCTCGATTG | GCAGCAATCG | GGTTGGAATC |
| NL/5/01 | GCTTTGGTGG | CTTGCTATAA | AGGGGTAAGC | TGCTCGATTG | GCAGCAATCG | GGTTGGAATC |
| NL/9/01 | GCTTTGGTGG | CTTGCTATAA | AGGGGTAAGC | TGCTCGATTG | GCAGCAATCG | GGTTGGAATC |
| NL/19/01 | GCTTTGGTGG | CTTGCTATAA | AGGGGTAAGC | TGCTCGATTG | GCAGCAATCG | GGTTGGAATC |
| NL/21/01 | GCTTTGGTGG | CTTGCTATAA | AGGGGTAAGC | TGCTCGATTG | GCAGCAATCG | GGTTGGAATC |
| UK/11/01 | GCTTTGGTGG | CTTGCTATAA | AGGGGTAAGC | TGCTCGATTG | GCAGCAATCG | GGTTGGAATC |
| FL/1/01 | GCTTTGGTGG | CTTGCTATAA | AGGGGTAAGC | TGCTCGATTG | GCAGCAATCG | GGTTGGAATT |
| FL/2/01 | GCTTTGGTGG | CTTGCTATAA | AGGGGTAAGC | TGCTCGATTG | GCAGCAATCG | GGTTGGAATC |
| FL/5/01 | GCTTTGGTGG | CTTGCTATAA | AGGGGTAAGC | TGCTCGATTG | GCAGCAATCG | GGTTGGAATC |
| FL/7/01 | GCTTTGGTGG | CTTGCTATAA | AGGGGTAAGC | TGCTCGATTG | GCAGCAATCG | GGTTGGAATC |
| FL/9/01 | GCTTTGGTGG | CTTGCTATAA | AGGGGTAAGC | TGCTCGATTG | GCAGCAATCG | GGTTGGAATC |
| UK/10/01 | GCTTTGGTGG | CTTGCTATAA | AGGGGTAAGC | TGCTCGATTG | GCAGCAATCG | GGTTGGAATC |
| NL/1/02 | GCTTTGGTGG | CTTGCTATAA | AGGGGTAAGC | TGCTCGATTG | GCAGCAATCG | GGTTGGAATC |
| NL/1/94 | GCTTTGGTaG | CTTGcTaCaA | GGGGGTTAGC | TGCTCGATTG | GCAGTAATCG | GGTTGGAATA |
| NL/1/96 | GCTTTGGTAG | CTTGCTACAA | AGGGGTTAGC | TGCTCGATTG | GCAGTAATCG | GGTTGGAATA |
| NL/6/97 | GCTTTGGTAG | CTTGCTACAA | AGGGGTTAGC | TGCTCGATTG | GCAGTAATCG | GGTTGGAATA |
| NL/7/00 | GCTTTGGTAG | CTTGCTACAA | AGGGGTTAGC | TGTTCGATTG | GCAGTAATCG | GGTTGGAATA |
| NL/9/00 | GCTTTGGTAG | CTTGCTACAA | AGGGGTTAGC | TGTTCGATTG | GCAGTAATCG | GGTTGGAATA |
| NL/19/00 | GCTTTGGTAG | CTTGCTACAA | AGGGGTTAGC | TGTTCGATTG | GCAGTAATCG | GGTTGGAATA |
| NL/28/00 | GCTTTGGTAG | CTTGCTACAA | AGGGGTTAGC | TGTTCGATTG | GCAGTAATCG | GGTTGGAATA |
| NL/3/01 | GCTTTGGTAG | CTTGCTACAA | AGGGGTTAGC | TGTTCGATTG | GCAGTAATCG | GGTTGGAATA |
| NL/4/01 | GCTTTGGTAG | CTTGCTACAA | AGGGGTTAGC | TGTTCGATTG | GCAGTAATCG | GGTTGGAATA |
| NL/11/01 | GCTTTGGTAG | CTTGCTACAA | AGGGGTTAGC | TGTTCGATTG | GCAGTAATCG | GGTTGGAATA |
| NL/15/01 | GCTTTGGTAG | CTTGCTACAA | AGGGGTTAGC | TGTTCAATTG | GCAGTAATCG | GGTTGGAATA |
| NL/18/01 | GCTTTGGTAG | CTTGCTACAA | AGGGGTTAGC | TGTTCAATTG | GCAGTAATCG | GGTTGGAATA |
| FL/6/01 | GCTTTGGTAG | CTTGCTACAA | GGGGGTTAGC | TGTTCGATTG | GCAGTAATCG | GGTTGGAATA |
| UK/5/01 | GCTTTGGTAG | CTTGCTACAA | AGGGGTTAGC | TGTTCGATTG | GCAGTAATCG | GGTTGGAATA |
| UK/8/01 | GCTTTGGTAG | CTTGCTACAA | AGGGGTTAGC | TGCTCGATTG | GCAGTAATCG | GGTTGGAATA |
| NL/12/02 | GCTTTGGTAG | CTTGCTACAA | AGGGGTTAGC | TGTTCAATTG | GCAGTAATCG | GGTTGGAATA |
| HK/1/02 | GCTTTGGTAG | CTTGCTACAA | AGGGGTTAGC | TGTTCGATTG | GCAGTAATCG | GGTTGGAATA |

| | | | |
|---|---|---|---|
| | ....\|....\| | ....\|....\| | ....\|.... |
| | 425 | 435 | 445 |
| NL/1/00 | ATCAAGCAAC | TGAACAAAGG | CTGCTCTTA |
| UK/1/00 | ATCAAGCAAC | TGAACAAAGG | CTGCTCTTA |
| NL/2/00 | ATCAAGCAAC | TGAACAAAGG | CTGCTCTTA |
| NL/13/00 | ATCAAGCAAC | TGAACAAAGG | CTGCTCTTA |
| NL/14/00 | ATCAAGCAAC | TGAACAAAGG | CTGCTCTTA |
| FL/3/01 | ATCAAGCAAC | TGAACAAAGG | CTGCTCTTA |
| FL/4/01 | ATCAAGCAAC | TGAACAAAGG | CTGCTCTTA |
| FL/8/01 | ATCAAGCAAC | TGAACAAAGG | CTGCTCTTA |
| UK/1/01 | ATCAAGCAAC | TGAACAAAGG | CTGCTCTTA |
| UK/7/01 | ATCAAGCAAC | TGAACAAAGG | CTGCTCTTA |
| FL/10/01 | ATCAAGCAAC | TGAACAAAGG | CTGCTCTTA |
| NL/6/01 | ATCAAGCAAC | TGAACAAAGG | CTGCTCTTA |
| NL/8/01 | ATCAAGCAAC | TGAACAAAGG | CTGCTCTTA |
| NL/10/01 | ATCAAGCAAC | TGAACAAAGG | CTGCTCTTA |
| NL/14/01 | ATCAAGCAAC | TGAACAAAGG | CTGCTCTTA |
| NL/20/01 | ATCAAGCAAC | TGAACAAAGG | CTGCTCTTA |
| NL/25/01 | ATCAAGCAAC | TGAACAAAGG | CTGCTCTTA |
| NL/26/01 | ATCAAGCAAC | TGAACAAAGG | CTGCTCTTA |
| NL/28/01 | ATCAAGCAAC | TGAACAAAGG | CTGCTCTTA |
| NL/30/01 | ATCAAGCAAC | TGAACAAAGG | CTGCTCTTA |
| BR/2/01 | ATCAAGCAAC | TGAACAAAGG | CTGCTCTTA |
| BR/3/01 | ATCAAGCAAC | TGAACAAAGG | CTGCTCTTA |

Figure 17 con't

| | | | |
|---|---|---|---|
| NL/2/02 | ATCAAGCAAC | TGAACAAAGG | CTGCTCTTA |
| NL/4/02 | ATCAAGCAAC | TGAACAAAGG | CTGCTCTTA |
| NL/5/02 | ATCAAGCAAC | TGAACAAAGG | CTGCTCTTA |
| NL/6/02 | ATCAAGCAAC | TGAACAAAGG | CTGCTCTTA |
| NL/7/02 | ATCAAGCAAC | TGAACAAAGG | CTGCTCTTA |
| NL/9/02 | ATCAAGCAAC | TGAACAAAGG | CTGCTCTTA |
| FL/1/02 | ATCAAGCAAC | TGAACAAAGG | CTGCTCTTA |
| NL/1/81 | ATCAAGCAGC | TGAACAAAGG | TTGCTCTTA |
| NL/1/93 | ATCAAGCAGC | TGAACAAAGG | TTGCTCCTA |
| NL/2/93 | ATCAAGCAGC | TGAACAAAGG | TTGCTCCTA |
| NL/4/93 | ATCAAGCAGC | TGAACAAAGG | TTGCTCCTA |
| NL/1/95 | ATCAAGCAGC | TGAACAAAGG | TTGCTCTTA |
| NL/2/96 | ATCAAGCAGC | TGAACAAAGG | TTGCTCCTA |
| NL/3/96 | ATCAAGCAGC | TGAACAAAGG | TTGCTCTTA |
| NL/1/98 | ATCAAGCAGC | TGAACAAAGG | TTGCTCCTA |
| NL/17/00 | ATCAAGCAGC | TGAACAAAGG | TTGCTCCTA |
| NL/22/01 | ATCAAGCAGC | TGAACAAAGG | TTGCTCTTA |
| NL/29/01 | ATAAAGCAGC | TGAACAAAGG | TTGCTCCTA |
| NL/23/01 | ATCAAGCAGC | TGAACAAAGG | TTGCTCTTA |
| NL/17/01 | ATCAAGCAGC | TGAACAAAGG | TTGCTCCTA |
| NL/24/01 | ATCAAGCAGC | TGAACAAAGG | TTGCTCTTA |
| NL/3/02 | ATAAAGCAGC | TGAACAAAGG | TTGCTCCTA |
| NL/3/98 | ATCAAACAAT | TACCTAAAGG | CTGCTCATA |
| NL/1/99 | ATCAAACAAT | TACCCAAAGG | CTGCTCATA |
| NL/2/99 | ATCAAACAAT | TACCCAAAGG | CTGCTCATA |
| NL/3/99 | ATCAAACAAT | TACCCAAAGG | CTGCTCATA |
| NL/11/00 | ATCAAACAAT | TACCTAAAGG | CTGCTCATA |
| NL/12/00 | ATCAAACAAT | TACCTAAAGG | CTGCTCATA |
| NL/1/01 | ATCAAACAAT | TACCTAAAGG | CTGCTCATA |
| NL/5/01 | ATCAAACAAT | TACCTAAAGG | CTGCTCATA |
| NL/9/01 | ATCAAACAAT | TACCTAAAGG | CTGCTCATA |
| NL/19/01 | ATCAAACAAT | TACCTAAAGG | CTGCTCATA |
| NL/21/01 | ATCAAACAAT | TACCTAAAGG | CTGCTCATA |
| UK/11/01 | ATCAAACAAT | TACCCAAAGG | CTGCTCATA |
| FL/1/01 | ATCAAACAAT | TACCTAAAGG | CTGCTCATA |
| FL/2/01 | ATCAAACAAT | TACCTAAAGG | CTGCTCATA |
| FL/5/01 | ATCAAACAAT | TACCTAAAGG | CTGCTCATA |
| FL/7/01 | ATCAAACAAT | TACCTAAAGG | CTGCTCATA |
| FL/9/01 | ATCAAACAAT | TACCTAAAGG | CTGCTCATA |
| UK/10/01 | ATCAAACAAT | TACCCAAAGG | CTGCTCATA |
| NL/1/02 | ATCAAACAAT | TACCTAAAGG | CTGCTCATA |
| NL/1/94 | ATCAAACAAC | TACCTAAAGG | CTGCTCATA |
| NL/1/96 | ATCAAACAAC | TACCTAAAGG | CTGCTCATA |
| NL/6/97 | ATCAAACAAC | TACCTAAAGG | CTGCTCATA |
| NL/7/00 | ATCAAACAAC | TACCTAAAGG | CTGCTCATA |
| NL/9/00 | ATCAAACAAC | TACCTAAAGG | CTGCTCATA |
| NL/19/00 | ATCAAACAAC | TACCTAAAGG | CTGCTCATA |
| NL/28/00 | ATCAAACAAC | TACCTAAAGG | CTGCTCATA |
| NL/3/01 | ATCAAACAAC | TACCTAAAGG | CTGCTCATA |
| NL/4/01 | ATCAAACAAC | TACCTAAAGG | CTGCTCATA |
| NL/11/01 | ATCAAACAAC | TACCTAAAGG | CTGCTCATA |
| NL/15/01 | ATCAAACAAC | TACCTAAAGG | CTGCTCATA |
| NL/18/01 | ATCAAACAAC | TACCTAAAGG | CTGCTCATA |
| FL/6/01 | ATCAAACAAC | TACCTAAAGG | CTGCTCATA |
| UK/5/01 | ATCAAACAAC | TACCTAAAGG | CTGCTCATA |
| UK/8/01 | ATCAAACAAC | TACCTAAAGG | CTGCTCATA |
| NL/12/02 | ATCAAACAAC | TACCTAAAGG | CTGCTCATA |
| HK/1/02 | ATCAAACAAC | TACCTAAAGG | CTGCTCATA |

Figure 17 con't

Alignment: F proteins

```
              ....|....| ....|....| ....|....| ....|....| ....|....| ....|....|
                  5         15         25         35         45         55
NL/1/00       IGVYGSSVIY MVQLPIFGVI DTPCWIVKAA PSCSGKKGNY ACLLREDQGW YCQNAGSTVY
UK/1/00       IGVYGSSVIY MVQLPIFGVI DTPCWIVKAA PSCSEKKGNY ACLLREDQGW YCQNAGSTVY
NL/2/00       IGVYGSSVIY MVQLPIFGVI DTPCWIVKAA PSCSEKKGNY ACLLREDQGW YCQNAGSTVY
NL/13/00      IGVYGSSVIY MVQLPIFGVI DTPCWIVKAA PSCSEKKGNY ACLLREDQGW YCQNAGSTVY
NL/14/00      IGVYGSSVIY MVQLPIFGVI DTPCWIVKAA PSCSEKKGNY ACLLREDQGW YCQNAGSTVY
FL/3/01       IGVYGSSVIY MVQLPIFGVI DTPCWIVKAA PSCSEKKGNY ACLLREDQGW YCQNAGSTVY
FL/4/01       IGVYGSSVIY MVQLPIFGVI DTPCWIVKAA PSCSEKKGNY ACLLREDQGW YCQNAGSTVY
FL/8/01       IGVYGSSVIY MVQLPIFGVI DTPCWIVKAA PSCSEKKGNY ACLLREDQGW YCQNAGSTVY
UK/1/01       IGVYGSSVIY MVQLPIFGVI DTPCWIVKAA PSCSEKKGNY ACLLREDQGW YCQNAGSTVY
UK/7/01       IGVYGSSVIY MVQLPIFGVI DTPCWIVKAA PSCSEKKGNY ACLLREDQGW YCQNAGSTVY
FL/10/01      IGVYGSSVIY MVQLPIFGVI DTPCWIVKAA PSCSEKKGNY ACLLREDQGW YCQNAGSTVY
NL/6/01       IGVYGSSVIY MVQLPIFGVI DTPCWIVKAA PSCSEKKGNY ACLLREDQGW YCQNAGSTVY
NL/8/01       IGVYGSSVIY MVQLPIFGVI DTPCWIVKAA PSCSEKKGNY ACLLREDQGW YCQNAGSTVY
NL/10/01      IGVYGSSVIY MVQLPIFGVI DTPCWIVKAA PSCSEKKGNY ACLLREDQRW YCQNAGSTVY
NL/14/01      IGVYGSSVIY MVQLPIFGVI DTPCWIVKAA PSCSEKKGNY ACLLREDQGW YCQNAGSTVY
NL/20/01      IGVYGSSVIY MVQLPIFGVI DTPCWIVKAA PSCSEKKGNY ACLLREDQGW YCQNAGSTVY
NL/25/01      IGVYGSSVIY MVQLPIFGVI DTPCWIVKAA PSCSEKKGNY ACLLREDQGW YCQNAGSTVY
NL/26/01      IGVYGSSVIY MVQLPIFGVI DTPCWIVKAA PSCSEKKGNY ACLLREDQGW YCQNAGSTVY
NL/28/01      IGVYGSSVIY MVQLPIFGVI DTPCWIVKAA PSCSEKKGNY ACLLREDQGW YCQNAGSTVY
NL/30/01      IGVYGSSVIY MVQLPIFGVI DTPCWIVKAA PSCSEKKGNY ACLLREDQGW YCQNAGSTVY
BR/2/01       IGVYGSSVIY MVQLPIFGVI DTPCWIVKAA PSCSGKKGNY ACLLREDQGW YCQNAGSTVY
BR/3/01       IGVYGSSVIY MVQLPIFGVI DTPCWIVKAA PSCSGKKGNY ACLLREDQGW YCQNAGSTVY
NL/2/02       IGVYGSSVIY MVQLPIFGVI DTPCWIVKAA PSCSEKKGNY ACLLREDQGW YCQNAGSTVY
NL/4/02       IGVYGSSVIY MVQLPIFGVI DTPCWIVKAA PSCSEKKGNY ACLLREDQGW YCQNAGSTVY
NL/5/02       IGVYGSSVIY MVQLPIFGVI DTPCWIVKAA PSCSEKKGNY ACLLREDQGW YCQNAGSTVY
NL/6/02       IGVYGSSVIY MVQLPIFGVI DTPCWIVKAA PSCSEKKGNY ACLLREDQGW YCQNAGSTVY
NL/7/02       IGVYGSSVIY MVQLPIFGVI DTPCWIVKAA PSCSGKKGNY ACLLREDQGW YCQNAGSTVY
NL/9/02       IGVYGSSVIY MVQLPIFGVI DTPCWIVKAA PSCSEKKGNY ACLLREDQGW YCQNAGSTVY
A1  FL/1/02   IGVYGSSVIY MVQLPIFGVI DTPCWIVKAA PSCSGKKGNY ACLLREDQGW YCQNAGSTVY
A2  NL/1/81   IGVYGSSVIY MVQLPIFGVI DTPCWIVKAA PSCSEKKGNY ACLLREDQGW YCQNAGSTVY
NL/1/93       IGVYGSSVIY MVQLPIFGVI DTPCWIVKAA PSCSEKKGNY ACLLREDQGW YCQNAGSTVY
NL/2/93       IGVYGSSVIY MVQLPIFGVI DTPCWIVKAA PSCSEKKGNY ACLLREDQGW YCQNAGSTVY
NL/4/93       IGVYGSSVIY MVQLPIFGVI DTPCWIVKAA PSCSEKKGNY ACLLREDQGW YCQNAGSTVY
NL/1/95       IGVYGSSVIY MVQLPIFGVI DTPCWIVKAA PSCSEKKGNY ACLLREDQGW YCQNAGSTVY
NL/2/96       IGVYGSSVIY MVQLPIFGVI DTPCWIVKAA PSCSEKKGNY ACLLREDQGW YCQNAGSTVY
NL/3/96       IGVYGSSVIY MVQLPIFGVI DTPCWIVKAA PSCSEKKGNY ACLLREDQGW YCQNAGSTVY
NL/1/98       IGVYGSSVIY MVQLPIFGVI DTPCWIVKAA PSCSEKKGNY ACLLREDQGW YCQNAGSTVY
NL/17/00      IGVYGSSVIY MVQLPIFGVI DTPCWIVKAA PSCSEKKGNY ACLLREDQGW YCQNAGSTVY
NL/22/01      IGVYGSSVIY MVQLPIFGVI DTPCWIVKAA PSCSEKKGNY ACLLREDQGW YCQNAGSTVY
NL/29/01      IGVYGSSVIY MVQLPIFGVI DTPCWIVKAA PSCSEKKGNY ACLLREDQGW YCQNAGSTVY
NL/23/01      IGVYGSSVIY MVQLPIFGVI DTPCWIVKAA PSCSEKKGNY ACLLREDQGW YCQNAGSTVY
NL/17/01      IGVYGSSVIY MVQLPIFGVI DTPCWIVKAA PSCSEKKGNY ACLLREDQGW YCQNAGSTVY
NL/24/01      IGVYGSSVIY MVQLPIFGVI DTPCWIVKAA PSCSEKKGNY ACLLREDQGW YCQNAGSTVY
NL/3/02       IGVYGSSVIY MVQLPIFGVI DTPCWIVKAA PSCSEKKGNY ACLLREDQGW YCQNAGSTVY
NL/3/98       IGVYGSSVIY MVQLPIFGVI DTPCWIIKAA PSCSEKNGNY ACLLREDQGW YCKNAGSTVY
NL/1/99       IGVYGSSVIY MVQLPIFGVI DTPCWIIKAA PSCSEKNGNY ACLLREDQGW YCKNAGSTVY
NL/2/99       IGVYGSSVIY MVQLPIFGVI DTPCWIIKAA PSCSEKNGNY ACLLREDQGW YCKNAGSTVY
NL/3/99       IGVYGSSVIY MVQLPIFGVI DTPCWIIKAA PSCSEKNGNY ACLLREDQGW YCKNAGSTVY
NL/11/00      IGVYGSSVIY MVQLPIFGVI DTPCWIIKAA PSCSEKNGNY ACLLREDQGW YCKNAGSTVY
NL/12/00      IGVYGSSVIY MVQLPIFGVI DTPCWIIKAA PSCSEKNGNY ACLLREDQGW YCKNAGSTVY
NL/1/01       IGVYGSSVIY MVQLPIFGVI DTPCWIIKAA PSCSEKNGNY ACLLREDQGW YCKNAGSTVY
NL/5/01       IGVYGSSVIY MVQLPIFGVI DTPCWIIKAA PSCSEKNGNY ACLLREDQGW YCKNAGSTVY
NL/9/01       IGVYGSSVIY MVQLPIFGVI DTPCWIIKAA PSCSEKNGNY ACLLREDQGW YCKNAGSTVY
NL/19/01      IGVYGSSVIY MVQLPIFGVI DTPCWIIKAA PSCSEKNGNY ACLLREDQGW YCKNAGSTVY
```

FIGURE 18

| | | | | | | |
|---|---|---|---|---|---|---|
| NL/21/01 | IGVYGSSVIY | MVQLPIFGVI | DTPCWIIKAA | PSCSEKNGNY | ACLLREDQGW | YCKNAGSTVY |
| UK/11/01 | IGVYGSSVIY | MVQLPIFGVI | DTPCWIIKAA | PSCSEKNGNY | ACLLREDQGW | YCKNAGSTVY |
| FL/1/01 | IGVYGSSVIY | MVQLPIFGVI | DTPCWIIKAA | PSCSEKNGNY | ACLLREDQGW | YCKNAGSTVY |
| FL/2/01 | IGVYGSSVIY | MVQLPIFGVI | DTPCWIIKAA | PSCSEKNGNY | ACLLREDQGW | YCKNAGSTVY |
| FL/5/01 | IGVYGSSVIY | MVQLPIFGVI | DTPCWIIKAA | PSCSEKNGNY | ACLLREDQGW | YCKNAGSTVY |
| FL/7/01 | IGVYGSSVIY | MVQLPIFGVI | DTPCWIIKAA | PSCSEKNGNY | ACLLREDQGW | YCKNAGSTVY |
| FL/9/01 | IGVYGSSVIY | MVQLPIFGVI | DTPCWIIKAA | PSCSEKNGNY | ACLLREDQGW | YCKNAGSTVY |
| UK/10/01 | IGVYGSSVIY | MVQLPIFGVI | DTPCWIIKAA | PSCSEKNGNY | ACLLREDQGW | YCKNAGSTVY |
| NL/1/02 | IGVYGSSVIY | MVQLPIFGVI | DTPCWIIKAA | PSCSEKNGNY | ACLLREDQGW | YCKNAGSTVY |
| NL/1/94 | IGVYGSSVIY | MVQLPIFGVI | DTPCWIIKAA | PSCSEKDGNY | ACLLREDQGW | YCKNAGSTVY |
| NL/1/96 | IGVYGSSVIY | MVQLPIFGVI | DTPCWIIKAA | PSCSEKDGNY | ACLLREDQGW | YCKNAGSTVY |
| NL/6/97 | IGVYGSSVIY | MVQLPIFGVI | DTPCWIIKAA | PSCSEKDGNY | ACLLREDQGW | YCKNAGSTVY |
| NL/7/00 | IGVYGSSVIY | MVQLPIFGVI | DTPCWIIKAA | PSCSEKDGNY | ACLLREDQGW | YCKNAGSTVY |
| NL/9/00 | IGVYGSSVIY | MVQLPIFGVI | DTPCWIIKAA | PSCSEKDGNY | ACLLREDQGW | YCKNAGSTVY |
| NL/19/00 | IGVYGSSVIY | MVQLPIFGVI | DTPCWIIKAA | PSCSEKDGNY | ACLLREDQGW | YCKNAGSTVY |
| NL/28/00 | IGVYGSSVIY | MVQLPIFGVI | DTPCWIIKAA | PSCSEKDGNY | ACLLREDQGW | YCKNAGSTVY |
| NL/3/01 | IGVYGSSVIY | MVQLPIFGVI | DTPCWIIKAA | PSCSEKDGNY | ACLLREDQGW | YCKNAGSTVY |
| NL/4/01 | IGVYGSSVIY | MVQLPIFGVI | DTPCWIIKAA | PSCSEKDGNY | ACLLREDQGW | YCKNAGSTVY |
| NL/11/01 | IGVYGSSVIY | MVQLPIFGVI | DTPCWIIKAA | PSCSEKDGNY | ACLLREDQGW | YCKNAGSTVY |
| NL/15/01 | IGVYGSSVIY | MVQLPIFGVI | DTPCWIIKAA | PSCSEKDGNY | ACLLREDQGW | YCKNAGSTVY |
| NL/18/01 | IGVYGSSVIY | MVQLPIFGVI | DTPCWIIKAA | PSCSEKDGNY | ACLLREDQGW | YCKNAGSTVY |
| FL/6/01 | IGVYGSSVIY | MVQLPIFGVI | DTPCWIIKAA | PSCSEKDGNY | ACLLREDQGW | YCKNAGSTVY |
| UK/5/01 | IGVYGSSVIY | MVQLPIFGVI | DTPCWIIKAA | PSCSEKDGNY | ACLLREDQGW | YCKNAGSTVY |
| UK/8/01 | IGVYGSSVIY | MVQLPIFGVI | DTPCWIIKAA | PSCSEKDGNY | ACLLREDQGW | YCKNAGSTVY |
| NL/12/02 | IGVYGSSVIY | MVQLPIFGVI | DTPCWIIKAA | PSCSEKDGNY | ACLLREDQGW | YCKNAGSTVY |
| HK/1/02 | IGVYGSSVIY | MVQLPIFGVI | DTPCWIIKAA | PSCSEKDGNY | ACLLREDQGW | YCKNAGSTVY |
| | ....\|....\| | ....\|....\| | ....\|....\| | ....\|....\| | ....\|....\| | ....\|....\| |
| | 65 | 75 | 85 | 95 | 105 | 115 |
| NL/1/00 | YPNEKDCETR | GDHVFCDTAA | GINVAEQSKE | CNINISTTNY | PCKVSTGRHP | ISMVALSPLG |
| UK/1/00 | YPNEKDCETR | GDHVFCDTAA | GINVAEQSKE | CNINISTTNY | PCKVSTGRHP | ISMVALSPLG |
| NL/2/00 | YPNEKDCETR | GDHVFCDTAA | GINVAEQSKE | CNINISTTNY | PCKVSTGRHP | ISMVALSPLG |
| NL/13/00 | YPNEKDCETR | GDHVFCDTAA | GINVAEQSKE | CNINISTTNY | PCKVSTGRHP | ISMVALSPLG |
| NL/14/00 | YPNEKDCETR | GDHVFCDTAA | GINVAEQSKE | CNINISTTNY | PCKVSTGRHP | ISMVALSPLG |
| FL/3/01 | YPNEKDCETR | GDHVFCDTAA | GINVAEQSKE | CNINISTTNY | PCKVSTGRHP | ISMVALSPLG |
| FL/4/01 | YPNEKDCETR | GDHVFCDTAA | GINVAEQSKE | CNINISTTNY | PCKVSTGRHP | ISMVALSPLG |
| FL/8/01 | YPNEKDCETR | GDHVFCDTAA | GINVAEQSKE | CNINISTTNY | PCKVSTGRHP | ISMVALSPLG |
| UK/1/01 | YPNEKDCETR | GDHVFCDTAA | GINVAEQSKE | CNINISTTNY | PCKVSTGRHP | ISMVALSPLG |
| UK/7/01 | YPNEKDCETR | GDHVFCDTAA | GINVAEQSKE | CNINISTTNY | PCKVSTGRHP | ISMVALSPLG |
| FL/10/01 | YPNEKDCETR | GDHVFCDTAA | GINVAEQSKE | CNINISTTNY | PCKVSTGRHP | ISMVALSPLG |
| NL/6/01 | YPNEKDCETR | GDHVFCDTAA | GINVAEQSKE | CNINISTTNY | PCKVSTGRHP | ISMVALSPLG |
| NL/8/01 | YPNEKDCETR | GDHVFCDTAA | GINVAEQSKE | CNINISTTNY | PCKVSTGRHP | ISMVALSPLG |
| NL/10/01 | YPNEKDCETR | GDHVFCDTAA | GINVAEQSKE | CNINISTTNY | PCKVSTGRHP | ISMVALSPLG |
| NL/14/01 | YPNEKDCETR | GDHVFCDTAA | GINVAEQSKE | CNINISTTNY | PCKVSTGRHP | ISMVALSPLG |
| NL/20/01 | YPNEKDCETR | GDHVFCDTAA | GINVAEQSKE | CNINISTTNY | PCKVSTGRHP | ISMVALSPLG |
| NL/25/01 | YPNEKDCETR | GDHVFCDTAA | GINVAEQSKE | CNINISTTNY | PCKVSTGRHP | ISMVALSPLG |
| NL/26/01 | YPNEKDCETR | GDHVFCDTAA | GINVAEQSKE | CNINISTTNY | PCKVSTGRHP | ISMVALSPLG |
| NL/28/01 | YPNEKDCETR | GDHVFCDTAA | GINVAEQSKE | CNINISTTNY | PCKVSTGRHP | ISMVALSPLG |
| NL/30/01 | YPNEKDCETR | GDHVFCDTAA | GINVAEQSKE | CNINISTTNY | PCKVSTGRHP | ISMVALSPLG |
| BR/2/01 | YPNEKDCETR | GDHVFCDTAA | GINVAEQSKE | CNINISTTNY | PCKVSTGRHP | ISMVALSPLG |
| BR/3/01 | YPNEKDCETR | GDHVFCDTAA | GINVAEQSKE | CNINISTTNY | PCKVSTGRHP | ISMVALSPLG |
| NL/2/02 | YPNEKDCETR | GDHVFCDTAA | GINVAEQSKE | CNINISTTNY | PCKVSTGRHP | ISMVALSPLG |
| NL/4/02 | YPNEKDCETR | GDHVFCDTAA | GINVAEQSKE | CNINISTTNY | PCKVSTGRHP | ISMVALSPLG |
| NL/5/02 | YPNEKDCETR | GDHVFCDTAA | GINVAEQSKE | CNINISTTNY | PCKVSTGRHP | ISMVALSPLG |
| NL/6/02 | YPNEKDCETR | GDHVFCDTAA | GINVAEQSKE | CNINISTTNY | PCKVSTGRHP | ISMVALSPLG |
| NL/7/02 | YPNEKDCETR | GDHVFCDTAA | GINVAEQSKE | CNINISTTNY | PCKVSTGRHP | ISMVALSPLG |
| NL/9/02 | YPNEKDCETR | GDHVFCDTAA | GINVAEQSKE | CNINISTTNY | PCKVSTGRHP | ISMVALSPLG |
| FL/1/02 | YPNEKDCETR | GDHVFCDTAA | GINVAEQSKE | CNINISTTNY | PCKVSTGRHP | ISMVALSPLG |
| NL/1/81 | YPNEKDCETR | GDHVFCDTAA | GINVAEQSKE | CNINISTTNY | PCKVSTGRHP | ISMVALSPLG |
| NL/1/93 | YPNEKDCETR | GDHVFCDTAA | GINVAEQSKE | CNINISTTNY | PCKVSTGRHP | ISMVALSPLG |
| NL/2/93 | YPNEKDCETR | GDHVFCDTVA | GINVAEQSKE | CNINISTTNY | PCKVSTGRHP | ISMVALSPLG |

Figure 18 con't

| | | | | | | |
|---|---|---|---|---|---|---|
| NL/4/93 | YPNEKDCETR | GDHVFCDTAA | GINVAEQSKE | CNINISTTNY | PCKVSTGRHP | ISMVALSPLG |
| NL/1/95 | YPNEKDCETR | GDHVFCDTAA | GINVAEQSKE | CNINISTTNY | PCKVSTGRHP | ISMVALSPLG |
| NL/2/96 | YPNEKDCETR | GDHVFCDTAA | GINVAEQSKE | CNINISTTNY | PCKVSTGRHP | ISMVALSPLG |
| NL/3/96 | YPNEKDCETR | GDHVFCDTAA | GINVAEQSKE | CNINISTTNY | PCKVSTGRHP | ISMVALSPLG |
| NL/1/98 | YPNEKDCETR | GDHVFCDTAA | GINVAEQSKE | CNINISTTNY | PCKVSTGRHP | ISMVALSPLG |
| NL/17/00 | YPNEKDCETR | GDHVFCDTAA | GINVAEQSKE | CNINISTTNY | PCKVSTGRHP | ISMVALSPLG |
| NL/22/01 | YPNEKDCETR | GDHVFCDTAA | GINVAEQSKE | CNINISTTNY | PCKVSTGRHP | ISMVALSPLG |
| NL/29/01 | YPNEKDCETR | GDHVFCDTAA | GINVAEQSKE | CNINISTTNY | PCKVSTGRHP | ISMVALSPLG |
| NL/23/01 | YPNEKDCETR | GDHVFCDTAA | GINVAEQSKE | CNINISTTNY | PCKVSTGRHP | ISMVALSPLG |
| NL/17/01 | YPNEKDCETR | GDHVFCDTAA | GINVAEQSKE | CNINISTTNY | PCKVSTGRHP | ISMVALSPLG |
| NL/24/01 | YPNEKDCETR | GDHVFCDTAA | GINVAEQSKE | CNINISTTNY | PCKVSTGRHP | ISMVALSPLG |
| NL/3/02 | YPNEKDCETR | GDHVFCDTAA | GINVAEQSKE | CNINISTTNY | PCKVSTGRHP | ISMVALSPLG |
| NL/3/98 | YPNEKDCETR | GDHVFCDTAA | GINVAEQSRE | CNINISTTNY | PCKVSTGRHP | ISMVALSPLG |
| NL/1/99 | YPNEKDCETR | GDHVFCDTAA | GINVAEQSRE | CNINISTTNY | PCKVSTGRHP | ISMVALSPLG |
| NL/2/99 | YPNEKDCETR | GDHVFCDTAA | GINVAEQSRE | CNINISTTNY | PCKVSTGRHP | ISMVALSPLG |
| NL/3/99 | YPNEKDCETR | GDHVFCDTAA | GINVAEQSRE | CNINISTTNY | PCKVSTGRHP | ISMVALSPLG |
| NL/11/00 | YPNEKDCETR | GDHVFCDTAA | GINVAEQSRE | CNINISTTNY | PCKVSTGRHP | ISMVALSPLG |
| NL/12/00 | YPNEKDCETR | GDHVFCDTAA | GINVAEQSRE | CNINISTTNY | PCKVSTGRHP | ISMVALSPLG |
| NL/1/01 | YPNEKDCETR | GDHVFCDTAA | GINVAEQSRE | CNINISTTNY | PCKVSTGRHP | ISMVALSPLG |
| NL/5/01 | YPNEKDCETR | GDHVFCDTAA | GINVAEQSRE | CNINISTTNY | PCKVSTGRHS | ISMVALSPLG |
| NL/9/01 | YPNEKDCETR | GDHVFCDTAA | GINVAEQSRE | CNINISTTNY | PCKVSTGRHP | ISMVALSPLG |
| NL/19/01 | YPNEKDCETR | GDHVFCDTAA | GINVAEQSRE | CNINISTTNY | PCKVSTGRHP | ISMVALSPLG |
| NL/21/01 | YPNEKDCETR | GDHVFCDTAA | GINVAEQSRE | CNINISTTNY | PCKVSTGRHP | ISMVALSPLG |
| UK/11/01 | YPNEKDCETR | GDHVFCDTAA | GINVAEQSRE | CNINISTTNY | PCKVSTGRHP | ISMVALSPLG |
| FL/1/01 | YPNEKDCETR | GDHVFCDTAA | GINVAEQSRE | CNINISTTNY | PCKVSTGRHP | ISMVALSPLG |
| FL/2/01 | YPNEKDCETR | GDHVFCDTAA | GINVAEQSRE | CNINISTTNY | PCKVSTGRHP | ISMVALSPLG |
| FL/5/01 | YPNEKDCETR | GDHVFCDTAA | GINVAEQSRE | CNINISTTNY | PCKVSTGRHP | ISMVALSPLG |
| FL/7/01 | YPNEKDCETR | GDHVFCDTAA | GINVAEQSRE | CNINISTTNY | PCKVSTGRHP | ISMVALSPLG |
| FL/9/01 | YPNEKDCETR | GDHVFCDTAA | GINVAEQSRE | CNINISTTNY | PCKVSTGRHP | ISMVALSPLG |
| UK/10/01 | YPNEKDCETR | GDHVFCDTAA | GINVAEQSRE | CNINISTTNY | PCKVSTGRHP | ISMVALSPLG |
| NL/1/02 | YPNEKDCETR | GDHVFCDTAA | GINVAEQSRE | CNINISTTNY | PCKVSTGRHP | ISMVALSPLG |
| NL/1/94 | YPNEKDCETR | GDHVFCDTAA | GINVAEQSRE | CNINISTTNY | PCKVSTGRHP | ISMVALSPLG |
| NL/1/96 | YPNEKDCETR | GDHVFCDTAA | GINVAEQSRE | CNINISTTNY | PCKVSTGRHP | ISMVALSPLG |
| NL/6/97 | YPNEKDCETR | GDHVFCDTAA | GINVAEQSRE | CNINISTTNY | PCKVSTGRHP | ISMVALSPLG |
| NL/7/00 | YPNEKDCETR | GDHVFCDTAA | GINVAEQSRE | CNINISTTNY | PCKVSTGRHP | ISMVALSPLG |
| NL/9/00 | YPNEKDCETR | GDHVFCDTAA | GINVAEQSRE | CNINISTTNY | PCKVSTGRHP | ISMVALSPLG |
| NL/19/00 | YPNEKDCETR | GDHVFCDTAA | GINVAEQSRE | CNINISTTNY | PCKVSTGRHP | ISMVALSPLG |
| NL/28/00 | YPNEKDCETR | GDHVFCDTAA | GINVAEQSRE | CNINISTTNY | PCKVSTGRHP | ISMVALSPLG |
| NL/3/01 | YPNEKDCETR | GDHVFCDTAA | GINVAEQSRE | CNINISTTNY | PCKVSTGRHP | ISMVALSPLG |
| NL/4/01 | YPNEKDCETR | GDHVFCDTAA | GINVAEQSRE | CNINISTTNY | PCKVSTGRHP | ISMVALSPLG |
| NL/11/01 | YPNEKDCETR | GDHVFCDTAA | GINVAEQSRE | CNINISTTNY | PCKVSTGRHP | ISMVALSPLG |
| NL/15/01 | YPNEKDCETR | GDHVFCDTAA | GINVAEQSRE | CNINISTTNY | PCKVSTGRHP | ISMVALSPLG |
| NL/18/01 | YPNEKDCETR | GDHVFCDTAA | GINVAEQSRE | CNINISTTNY | PCKVSTGRHP | ISMVALSPLG |
| FL/6/01 | YPNEKDCETR | GDHVFCDTAA | GINVAEQSRE | CNINISTTNY | PCKVSTGRHP | ISMVALSPLG |
| UK/5/01 | YPNEKDCETR | GDHVFCDTAA | GINVAEQSRE | CNINISTTNY | PCKVSTGRHP | ISMVALSPLG |
| UK/8/01 | YPNEKDCETR | GDHVFCDTAA | GINVAEQSRE | CNINISTTNY | PCKVSTGRHP | ISMVALSPLG |
| NL/12/02 | YPNEKDCETR | GDHVFCDTAA | GINVAEQSRE | CNINISTTNY | PCKVSTGRHP | ISMVALSPLG |
| HK/1/02 | YPNEKDCETR | GDHVFCDTAA | GINVAEQSRE | CNINISTTNY | PCKVSTGRHP | ISMVALSPLG |

| | | | |
|---|---|---|---|
| | ....\|....\| | ....\|....\| | ....\|.... |
| | 125 | 135 | 145 |
| NL/1/00 | ALVACYKGVS | CSIGSNRVGI | IKQLNKGCS |
| UK/1/00 | ALVACYKGVS | CSIGSNRVGI | IKQLNKGCS |
| NL/2/00 | ALVACYKGVS | CSIGSNRVGI | IKQLNKGCS |
| NL/13/00 | ALVACYKGVS | CSIGSNRVGI | IKQLNKGCS |
| NL/14/00 | ALVACYKGVS | CSIGSNRVGI | IKQLNKGCS |
| FL/3/01 | ALVACYKGVS | CSIGSNRVGI | IKQLNKGCS |
| FL/4/01 | ALVACYKGVS | CSIGSNRVGI | IKQLNKGCS |
| FL/8/01 | ALVACYKGVS | CSIGSNRVGI | IKQLNKGCS |
| UK/1/01 | ALVACYKGVS | CSIGSNRVGI | IKQLNKGCS |
| UK/7/01 | ALVACYKGVS | CSIGSNRVGI | IKQLNKGCS |

Figure 18 con't

| | | | |
|---|---|---|---|
| FL/10/01 | ALVACYKGVS | CSIGSNRVGI | IKQLNKGCS |
| NL/6/01 | ALVACYKGVS | CSIGSNRVGI | IKQLNKGCS |
| NL/8/01 | ALVACYKGVS | CSIGSNRVGI | IKQLNKGCS |
| NL/10/01 | ALVACYKGVS | CSIGSNRVGI | IKQLNKGCS |
| NL/14/01 | ALVACYKGVS | CSIGSNRVGI | IKQLNKGCS |
| NL/20/01 | ALVACYKGVS | CSIGSNRVGI | IKQLNKGCS |
| NL/25/01 | ALVACYKGVS | CSIGSNRVGI | IKQLNKGCS |
| NL/26/01 | ALVACYKGVS | CSIGSNRVGI | IKQLNKGCS |
| NL/28/01 | ALVACYKGVS | CSIGSNRVGI | IKQLNKGCS |
| NL/30/01 | ALVACYKGVS | CSIGSNRVGI | IKQLNKGCS |
| BR/2/01 | ALVACYKGVS | CSIGSNRVGI | IKQLNKGCS |
| BR/3/01 | ALVACYKGVS | CSIGSNRVGI | IKQLNKGCS |
| NL/2/02 | ALVACYKGVS | CSIGSNRVGI | IKQLNKGCS |
| NL/4/02 | ALVACYKGVS | CSIGSNRVGI | IKQLNKGCS |
| NL/5/02 | ALVACYKGVS | CSIGSNRVGI | IKQLNKGCS |
| NL/6/02 | ALVACYKGVS | CSIGSNRVGI | IKQLNKGCS |
| NL/7/02 | ALVACYKGVS | CSIGSNRVGI | IKQLNKGCS |
| NL/9/02 | ALVACYKGVS | CSIGSNRVGI | IKQLNKGCS |
| FL/1/02 | ALVACYKGVS | CSIGSNRVGI | IKQLNKGCS |
| NL/1/81 | ALVACYKGVS | CSIGSNRVGI | IKQLNKGCS |
| NL/1/93 | ALVACYKGVS | CSIGSNRVGI | IKQLNKGCS |
| NL/2/93 | ALVACYKGVS | CSIGSNRVGI | IKQLNKGCS |
| NL/4/93 | ALVACYKGVS | CSIGSNRVGI | IKQLNKGCS |
| NL/1/95 | ALVACYKGVS | CSIGSNRVGI | IKQLNKGCS |
| NL/2/96 | ALVACYKGVS | CSIGSNRVGI | IKQLNKGCS |
| NL/3/96 | ALVACYKGVS | CSIGSNRVGI | IKQLNKGCS |
| NL/1/98 | ALVACYKGVS | CSIGSNRVGI | IKQLNKGCS |
| NL/17/00 | ALVACYKGVS | CSIGSNRVGI | IKQLNKGCS |
| NL/22/01 | ALVACYKGVS | CSIGSNRVGI | IKQLNKGCS |
| NL/29/01 | ALVACYKGVS | CSIGSNRVGI | IKQLNKGCS |
| NL/23/01 | ALVACYKGVS | CSIGSNRVGI | IKQLNKGCS |
| NL/17/01 | ALVACYKGVS | CSIGSNRVGI | IKQLNKGCS |
| NL/24/01 | ALVACYKGVS | CSIGSNRVGI | IKQLNKGCS |
| NL/3/02 | ALVACYKGVS | CSIGSNRVGI | IKQLNKGCS |
| NL/3/98 | ALVACYKGVS | CSIGSNRVGI | IKQLPKGCS |
| NL/1/99 | ALVACYKGVS | CSIGSNWVGI | IKQLPKGCS |
| NL/2/99 | ALVACYKGVS | CSIGSNRVGI | IKQLPKGCS |
| NL/3/99 | ALVACYKGVS | CSIGSNRVGI | IKQLPKGCS |
| NL/11/00 | ALVACYKGVS | CSIGSNRVGI | IKQLPKGCS |
| NL/12/00 | ALVACYKGVS | CSIGSNRVGI | IKQLPKGCS |
| NL/1/01 | ALVACYKGVS | CSIGSNRVGI | IKQLPKGCS |
| NL/5/01 | ALVACYKGVS | CSIGSNRVGI | IKQLPKGCS |
| NL/9/01 | ALVACYKGVS | CSIGSNRVGI | IKQLPKGCS |
| NL/19/01 | ALVACYKGVS | CSIGSNRVGI | IKQLPKGCS |
| NL/21/01 | ALVACYKGVS | CSIGSNRVGI | IKQLPKGCS |
| UK/11/01 | ALVACYKGVS | CSIGSNRVGI | IKQLPKGCS |
| FL/1/01 | ALVACYKGVS | CSIGSNRVGI | IKQLPKGCS |
| FL/2/01 | ALVACYKGVS | CSIGSNRVGI | IKQLPKGCS |
| FL/5/01 | ALVACYKGVS | CSIGSNRVGI | IKQLPKGCS |
| FL/7/01 | ALVACYKGVS | CSIGSNRVGI | IKQLPKGCS |
| FL/9/01 | ALVACYKGVS | CSIGSNRVGI | IKQLPKGCS |
| UK/10/01 | ALVACYKGVS | CSIGSNRVGI | IKQLPKGCS |
| NL/1/02 | ALVACYKGVS | CSIGSNRVGI | IKQLPKGCS |
| NL/1/94 | ALVACYKGVS | CSIGSNRVGI | IKQLPKGCS |
| NL/1/96 | ALVACYKGVS | CSIGSNRVGI | IKQLPKGCS |
| NL/6/97 | ALVACYKGVS | CSIGSNRVGI | IKQLPKGCS |
| NL/7/00 | ALVACYKGVS | CSIGSNRVGI | IKQLPKGCS |
| NL/9/00 | ALVACYKGVS | CSIGSNRVGI | IKQLPKGCS |
| NL/19/00 | ALVACYKGVS | CSIGSNRVGI | IKQLPKGCS |
| NL/28/00 | ALVACYKGVS | CSIGSNRVGI | IKQLPKGCS |
| NL/3/01 | ALVACYKGVS | CSIGSNRVGI | IKQLPKGCS |

Figure 18 con't

| | | | |
|---|---|---|---|
| NL/4/01 | ALVACYKGVS | CSIGSNRVGI | IKQLPKGCS |
| NL/11/01 | ALVACYKGVS | CSIGSNRVGI | IKQLPKGCS |
| NL/15/01 | ALVACYKGVS | CSIGSNRVGI | IKQLPKGCS |
| NL/18/01 | ALVACYKGVS | CSIGSNRVGI | IKQLPKGCS |
| FL/6/01 | ALVACYKGVS | CSIGSNRVGI | IKQLPKGCS |
| UK/5/01 | ALVACYKGVS | CSIGSNRVGI | IKQLPKGCS |
| UK/8/01 | ALVACYKGVS | CSIGSNRVGI | IKQLPKGCS |
| NL/12/02 | ALVACYKGVS | CSIGSNRVGI | IKQLPKGCS |
| HK/1/02 | ALVACYKGVS | CSIGSNRVGI | IKQLPKGCS |

Figure 18 con't

Alignment: G DNA

```
              ....|....| ....|....| ....|....| ....|....| ....|....| ....|....|
                  5          15         25         35         45         55
NL/1/00 (p    ATGGAGGTGA AAGTGGAGAA CATTCGAACA ATAGATATGC TCAAAGCAAG AGTAAAAAAT
BR/2/01 (A    ATGGAGGTGA AAGTGGAGAA CATTCGAACA ATAGATATGC TCAAAGCAAG TGTAAAAAAT
FL/4/01 (A    ATGGAGGTGA AAGTGGAGAA CATTCGAACA ATAGATATGC TCAAAGCAAG AGTAAAAAAT
FL/3/01 (A    ATGGAGGTGA AAGTGGAGAA CATTCGAACA ATAGATATGC TCAAAGCAAG AGTAAAAAAT
FL/8/01 (A    ATGGAGGTGA AAGTGGAGAA CATTCGAACA ATAGATATGC TCAAAGCAAG AGTAAAAAAT
FL/10/01 (    ATGGAGGTGA AAGTGGAGAA CATTCGAACA ATAGATATGC TCAAAGCAAG AGTGAAAAAT
NL/10/01 (    ATGGAGGTGA AAGTGGAGAA CATTCGAACA ATAGATATGC TCAAAGCAAG AGTGAAAAAT
NL/2/02 (A    ATGGAGGTGA AAGTGGAGAA CATTCGAACA ATAGATATGC TCAAAGCAAG AGTGAAAAAT
NL/17/00 (    ATGGAGGTGA AAGTAGAGAA CATTCGAGCA ATAGACATGC TCAAAGCAAG AGTGAAAAAT
NL/1/81 (A    ATGGAGGTGA AAGTAGAGAA CATTCGAGCA ATAGACATGC TCAAAGCAAG AGTGAAAAAT
NL/1/93 (A    ATGGAGGTGA AAGTAGAGAA CATCCGAGCA GTAGACATGC TCAAAGCAAG AGTCAAAAAT
NL/2/93 (A    ATGGAGGTGA AAGTAGAGAA CATCCGAGCA GTAGACATGC TCAAAGCAAG AGTTAAAAAT
NL/3/93 (A    ATGGAGGTGA AAGTAGAGAA CATTCGAGCA ATAGACATGC TCAAAGCAAG AATGAAAAAT
NL/1/95 (A    ATGGAGGTGA AAGTAGAGAA CATTCGAGCA ATAGACATGC TCAAAGCAAG AGTGAAAAAT
NL/2/96 (A    ATGGAGGTGA AAGTAGAGAA CATTCGAGCA ATAGACATGC TCAAAGCAAG AGTGAAAAAT
NL/3/96 (A    ATGGAGGTGA AAGTAGAGAA CATTCGAGCA ATAGACATGC TCAAAGCAAG AGTGAAAAAT
NL/22/01 (    ATGGAGGTGA AAGTAGAGAA CATTCGAGCA ATAGACATGC TCAAAGCAAG AGTGAAAAAT
NL/24/01 (    ATGGAGGTGA AAGTAGAGAA CATTCGAGCA ATAGACATGC TCAAAGCAAG AGTGAAAAAT
NL/23/01 (    ATGGAGGTGA AAGTAGAGAA TATTCGAGCA ATAGACATGC TCAAAGCAAG AGTGAAAAAT
NL/29/01 (    ATGGAGGTGA AAGTAGAGAA CATTCGAGCA ATAGACATGC TCAAAGCAAG AGTGAAAAAT
NL/3/02 (A    ATGGAGGTGA AAGTAGAGAA CATTCGAGCA ATAGACATGC TCAAAGCAAG AGTGAAAAAT
NL/1/99 (p    ATGGAAGTAA GAGTGGAGAA CATTCGAGCG ATAGACATGT TCAAAGCAAA GATAAAAAAC
NL/11/00 (    ATGGAAGTAA GAGTGGAGAA CATTCGAGCG ATAGACATGT TCAAAGCAAA GATAAAGAAC
NL/12/00 (    ATGGAAGTAA GAGTGGAGAA CATTCGAGCG ATAGACATGT TCAAAGCAAA GATAAAAAAC
NL/5/01 (B    ATGGAAGTAA GAGTGGAGAA CATTCGAGCG ATAGACATGT TCAAAGCAAA GATAAAAAAC
NL/9/01 (B    ATGGAAGTAA GAGTGGAGAA CATTCGAGCG ATAGACATGT TCAAAGCAAA GATAAAAAAC
NL/21/01 (    ATGGAAGTAA GAGTGGAGAA CATTCGAGCG ATAGACATGT TCAAAGCAAA GATAAAAAAC
NL/1/94 (p    ATGGAAGTAA GAGTGGAGAA CATTCGGGCA ATAGACATGT TCAAAGCAAA AATGAAAAAC
NL/1/82 (B    ATGGAAGTAA GAGTGGAGAA CATTCGGACA ATAGACATGT TCAAAGCAAA GATGAAAAAC
NL/1/96 (B    ATGGAAGTAA GAGTGGAGAA CATTCGGGCA ATAGACATGT TCAAAGCAAA GATGAAAAAC
NL/6/97 (B    ATGGAAGTAA GAGTGGAGAA CATTCGGGCA ATAGACATGT TCAAAGCAAA GATGAAAAAC
NL/9/00 (B    ATGGAAGTAA GAGTGGAGAA CATTCGGGCA ATAGACATGT TCAAAGCAAA GATGAAAAAC
NL/3/01 (B    ATGGAAGTAA GAGTGGAGAA CATTCGGGCA ATAGACATGT TCAAAGCAAA GATGAAAAAC
NL/4/01 (B    ATGGAAGTAA GAGTGGAGAA CATTCGGGCA ATAGACATGT TCAAAGCAAA GATGAAAAAC
UK/5/01 (B    ATGGAAGTAA GAGTGGAGAA CATTCGGGCA ATAGACATGT TCAAAGCAAA GATGAAAAAC

              ....|....| ....|....| ....|....| ....|....| ....|....| ....|....|
                  65         75         85         95        105        115
NL/1/00 (p    CGTGTGGCAC GCAGCAAATG CTTTAAAAAT GCCTCTTTGG TCCTCATAGG AATAACTACA
BR/2/01 (A    CGTGTGGCAC GCAGCAAATG CTTTAAAAAT GCCTCTTTGG TCCTCATAGG AATAACTACA
FL/4/01 (A    CGTGTGGCAC GCAGCAAATG CTTTAAAAAT GCCTCTTTGG TCCTCATAGG AATAACTACA
FL/3/01 (A    CGTGTGGCAC GCAGCAAATG CTTTAAAAAT GCCTCTTTGG TCCTCATAGG AATAACTACA
FL/8/01 (A    CGTGTGGCAC GCAGCAAATG CTTTAAAAAT GCCTCTTTGG TCCTCATAGG AATAACTACA
FL/10/01 (    CGTGTGGCAC GCAGCAAATG CTTTAAAAAT GCCTCTTTGA TCCTAATAGG AATAACTACA
NL/10/01 (    CGTGTGGCAC GCAGCAAATG CTTTAAAAAT GCCTCTTTGA TCCTAATAGG AATAACTACA
NL/2/02 (A    CGTGTGGCAC GCAGCAAATG CTTTAAAAAT GCCTCTTTGA TCCTAATAGG AATAACTACA
NL/17/00 (    CGTGTGGCAC GTAGCAAATG CTTTAAAAAT GCTTCTTTAA TCCTCATAGG AATAACTACA
NL/1/81 (A    CGTGTGGCAC GCAGCAAATG CTTTAAAAAT GCTTCTTTAA TCCTCATAGG AATAACTACA
NL/1/93 (A    CGTGTGGCAC GCAGCAAATG CTTTAAAAAT GCCTCCTTAA TCCTCGTAGG AATAACTACA
NL/2/93 (A    CGTGTGGCAC GCAGCAAATG CTTTAAAAAT GCCTCTTTAA TCCTCGTAGG AATAACTACA
NL/3/93 (A    CGTGTGGCAC GCAGCAAATG CTTTAAAAAT GCTTCTTTAA TCCTCATAGG AATAACTACT
NL/1/95 (A    CGTGTGGCAC GCAGCAAATG CTTTAAAAAT GCTTCTTTAA TCCTCATAGG AATAACTACT
NL/2/96 (A    CGTGTGGCAC GTAGCAAATG CTTTAAAAAT GCTTCTTTAA TCCTCATAGG AATAACTACA
NL/3/96 (A    CGTGTGGCAC GCAGCAAATG CTTTAAAAAT GCTTCTTTAA TCCTCATAGG AATAACTACT
NL/22/01 (    CGTGTGGCAC GCAGCAAATG CTTTAAAAAT GCTTCTTTAA TCCTCATAGG AATAACTACT
```

FIGURE 19

```
NL/24/01 (   CGTGTGGCAC GCAGCAAATG CTTTAAAAAT GCTTCTTTAA TCCTCATAGG AATAACTACT
NL/23/01 (   CGTGTGGCAC GCAGCAAATG CTTTAAAAAT GCTTCTTTAA TCCTCATAGG AATAACTACT
NL/29/01 (   CGTGTGGCAC GTAGCAAATG CTTTAAAAAT GCTTCTTTAA TCCTCATAGG AATAACTACA
NL/3/02 (A   CGTGTGGCAC GTAGCAAATG CTTTAAAAAT GCTTCTTTAA TCCTCATAGG AATAACTACA
NL/1/99 (p   CGTATAAGAA GCAGCAGGTG CTATAGAAAT GCTACACTGA TCCTTATTGG ACTAACAGCG
NL/11/00 (   CGTATAAGAA GCAGCAGGTG CTATAGAAAT GCTACACTGA TCCTTATTGG ACTAACAGCG
NL/12/00 (   CGTATAAGAA GCAGCAGGTG CTATAGAAAT GCTACACTGA TCCTTATTGG ACTAACAGCG
NL/5/01 (B   CGTATAAGAA GCAGCAGGTG CTATAGAAAT GCTACACTGA TCCTTATTGG ACTAACAGCG
NL/9/01 (B   CGTATAAGAA GCAGCAGGTG CTATAGAAAT GCTACATTGA TCCTTATTGG ACTAACAGCG
NL/21/01 (   CGTATAAGAA GCAGCAGGTG CTATAGAAAT GCTACACTGA TCCTTATTGG ACTAACAGCG
NL/1/94 (p   CGTATAAGAA GTAGCAAGTG CTATAGAAAT GCTACACTGA TCCTTATTGG ATTAACAGCA
NL/1/82 (B   CGTATAAGAA GCAGCAAGTG CTATAGAAAT GCTACACTGA TCCTTATTGG ACTGACAGCA
NL/1/96 (B   CGTATAAGAA GTAGCAAGTG CTATAGAAAT GCTACACTGA TCCTTATTGG ATTAACAGCA
NL/6/97 (B   CGCATAAGAA GTAGCAAGTG CTATAGAAAT GCTACACTGA TCCTTATTGG ATTAACAGCA
NL/9/00 (B   CGTATAAGAA GTAGCAAGTG CTATAGAAAT GCTACACTGA TCCTTATTGG ATTAACAGCA
NL/3/01 (B   CGTATAAGAA GTAGCAAGTG CTATAGAAAT GCTACACTGA TCCTTATTGG ATTATCAGCA
NL/4/01 (B   CGTATAAGAA GTAGCAAGTG CTATAGAAAT GCTACACTGA TCCTTATTGG ATTATCAGCA
UK/5/01 (B   CGTATAAGAA GTAGCAAGTG CTATAGAAAT GCTACACTGA TCCTTATTGG ATTAACAGCA

             ....|....| ....|....| ....|....| ....|....| ....|....| ....|....|
                125        135        145        155        165        175
NL/1/00 (p   TTGAGTATTG CCCTCAATAT CTATCTGATC ATAAACTATA AAATGCAAAA AAACACATCT
BR/2/01 (A   TTGAGTATTG CCCTCAATAT CTATCTGATC ATAAACTATA AAATGCAAAA AAACACATCT
FL/4/01 (A   CTGAGTATTG CCCTCAATAT CTATCTGATC ATAAACTATA AAATGCAAAA AAACACATCT
FL/3/01 (A   TTGAGTATTG CCCTCAATAT CTATCTGATC ATAAACTATA AAATGCAAAA AAACACATCT
FL/8/01 (A   TTGAGTATTG CCCTCAATAT CTATCTGATC ATAAACTATA AAATGCAAAA AAACACATCT
FL/10/01 (   TTGAGTATAG CCCTCAATAT CTATCTGATC ATAAACTATA CAATGCAAGA AAACACATCC
NL/10/01 (   TTGAGTATAG CCCTCAATAT CTATCTGATC ATAAACTATA CAATGCAAGA AAACACATCC
NL/2/02 (A   TTGAGTATAG CCCTCAATAT CTATCTGATC ATAAACTATA CAATGCAAGA AAACACATCC
NL/17/00 (   CTGAGTATAG CTCTCAATAT CTATCTGATC ATAAACTACA CAATACAAAA AACCACATCC
NL/1/81 (A   CTGAGTATAG CCCTCAATAT CTATCTGATC ATAAACTACA CAATACAAAA AACCACATCT
NL/1/93 (A   CTGAGCATAG CCCTCAATAT CTATCTGATC GTAAACTACA CAATACAAAA AACCACATCC
NL/2/93 (A   CTGAGTATAG CCCTCAATAT CTATCTGATC GTAAACTACA CAATACAAAA AACCACATCC
NL/3/93 (A   CTGAGTATAG CCCTCAATAT CTATCTGATC ATAAACTACA CAATACAAAA AACCACATCT
NL/1/95 (A   CTGAGTATAG CCCTCAACAT CTATCTGATC ATAAACTACA CAATACAAAA AACCACATCT
NL/2/96 (A   CTGAGTATAG CTCTCAATAT CTATCTGATC ATAAACTACA CAATACAAAA AACCACATCT
NL/3/96 (A   CTGAGTATAG CCCTCAACAT CTATCTGATC ATAAACTACA CAATACAAAA AACCACATCT
NL/22/01 (   CTGAGTATAG CCCTCAATAT CTATCTGATC ATAAACTACA CAATACAAAA AACCACATCT
NL/24/01 (   CTGAGTATAG CCCTCAATAT CTATCTGATC ATAAACTACA CAATACAAAA AACCACATCT
NL/23/01 (   CTGAGTATAG CCCTCAATAT CTATCTGATC ATAAACTACA CAATACAAAA AACCACATCT
NL/29/01 (   CTGAGCATAG CCCTCAATAT CTATCTGATC ATAAACTACA CAATACAACA AACCACATCT
NL/3/02 (A   CTGAGCATAG CCCTCAATAT CTATCTGATC ATAAACTACA CAATACAAAA AACCACATCT
NL/1/99 (p   TTAAGCATGG CACTTAATAT TTTCCTGATC ATCGATCATG CAACATTAAG AAACATGATC
NL/11/00 (   TTAAGCATGG CACTTAATAT TTTCCTGATC ATTGATCATG CAACATTAAG AAACATGATC
NL/12/00 (   TTAAGCATGG CACTTAATAT TTTCCTGATC ATCGATCATG CAACATTAAG AAACATGATC
NL/5/01 (B   TTAAGCATGG CACTTAATAT TTTCCTGATC ATCGATCATG CAACATTAAG AAACATGATC
NL/9/01 (B   TTAAGCATGG CACTTAATAT TTTCCTGATC ATCGATCATG CAACATTAAG AAACATGATC
NL/21/01 (   TTAAGCATGG CACTTAATAT TTTCCTGATC ATCGATCATG CAACATTAAG AAACATGATC
NL/1/94 (p   TTAAGTATGG CACTTAATAT TTTTTTAATC ATTGATTATG CAATGTTAAA AAACATGACC
NL/1/82 (B   TTAAGTATGG CACTTAATAT TTTCTTGATC ATCGATTATG CAACATTTAA AAACATGACC
NL/1/96 (B   TTAAGTATGG CACTTAATAT TTTTTTAATC ATTGATTATG CAATGTTAAA AAACATGACC
NL/6/97 (B   TTAAGTATGG CACTTAATAT TTTTTTAATC ATTGATTATG CAACATTAAA AAACATGACC
NL/9/00 (B   CTAAGTATGG CACTTAATAT TTTTTTAATC ATTGATTATG CAACATTAAA AAACATGACC
NL/3/01 (B   CTAAGTATGG CACTTAATAT TTTTTTAATC ATTGATTATG CAAAATCAAA AAACATGACC
NL/4/01 (B   CTAAGTATGG CACTTAATAT TTTTTTAATC ATTGATTATG CAAAATCAAA AACCATGACC
UK/5/01 (B   CTAAGTATGG CACTTAATAT TTTTTTAATC ATTGATTATG CAACATTAAA AAACATGACC

             ....|....| ....|....| ....|....| ....|....| ....|....| ....|....|
                185        195        205        215        225        235
NL/1/00 (p   GAATCAGAAC ATCACACCAG CTCATCACCC ATGGAATCCA GCAGAGAAAC TCCAACGGTC
BR/2/01 (A   GAATCAGAAC ATCACACCAG CTCATCACCC ATGGAATCCA GCAGAGAAAC TCCAACGGTC
```

Figure 19 con't

```
FL/4/01 (A    GAATCAGAAC ATCACACCAG CTCATCACCC ATGGAATCCA GCAGAGAAAC TCCAACGGTC
FL/3/01 (A    GAATCAGAAC ATCACACCAG CTCATCACCC ATGGAATCCA GCAGAGAAAC TCCAACGGTC
FL/8/01 (A    GAATCAGAAC ATCACACCAG CTCATCACCC ATGGAATCCA GCAGAGAAAC TCCAACGGTC
FL/10/01 (    GAATCAGAAC ATCACACCAG CTCATCACCC ATGGAATCCA GCAGGGAAAC TCCAACGGTC
NL/10/01 (    GAATCAGAAC ATCACACCAG TTCATCACCC ATGGAATCCA GCAGGGAAAC TCCAACGGTC
NL/2/02 (A    GAATCAGAAC ATCACACCAG CTCATCACCC ATGGAATCCA GCAGAGAAAC TCCAACGGTC
NL/17/00 (    GAATCAGAAC ACCACACCAG CTCACCACCC ACAGAACCCA ACAAGGAAGC TTCAACAATC
NL/1/81 (A    GAATCAGAAC ACCACACTAG CTCACCACCC ACAGAATCCA ACAAAGAAAC TTCAACAATC
NL/1/93 (A    GAATCAGAAC ACCACACCAG CTCATCACCC ACAGAATCCA ACAAAGGAAC TTCAACAATC
NL/2/93 (A    GAATCAGAAC ACCACACTAG CTCATCACCC ACAGAATCCA ACAAAGGAAC TTCAACAATC
NL/3/93 (A    GAATCAGAAC ACCACACTAG CTCACCACCC ACAGAATCCA ACAAAGAAAC TTCAACAATC
NL/1/95 (A    GAATCAGAAC ACCACACTAG CTCACCACCC ACAGAATCTA ACAAAGAAAC TTCAACAATC
NL/2/96 (A    GAATCAGAAC ACCACACCAG CTCACCACCC ACAGAATCCA ACAAGGAAGC TTCAACAATC
NL/3/96 (A    GAATCAGAAC ACCACACTAG CTCACCACCC ACAGAATCTA ACAAAGAAAC TTCAACAATC
NL/22/01 (    GAATCAGAAC ACCACACTAG CTCACCACCC ACAGAATCTA ACAAGGAAAC TTCAACAATC
NL/24/01 (    GAATCAGAAC ACCACACTAG CTCACCACCC ACAGAATCTA ACAAGGAAAC TTCAACAATC
NL/23/01 (    GAATCAGAAC ACCACACTAG CTCACCACCC ACAGAATCTA ACAAGGAAAC TTCAACAATC
NL/29/01 (    GAATCAGAAC ACCACACCAG CTCACCACCC ACAGAATCCA ACAAGGAAGC TTCAACAATC
NL/3/02 (A    GAATCAGAAC ACCACACCAG CTCACCACCC ACAGAATCCA ACAAGGAAGC TTCAACAATC
NL/1/99 (p    AAAACAGAAA ACTGTGCTAA CATGCCGTCG GCAGAACCAA GCAAAAAGAC CCCAATGACC
NL/11/00 (    AAAACAGAAA ACTGTGCTAA CATGCCATCG GCAGAACCAA GCAAAAAGAC CCCAATGACC
NL/12/00 (    AAAACAGAAA ATTGTGCTAA CATGCCGCCG GCAGAACCAA GCAAAAAGAC CCCAATGACC
NL/5/01 (B    AAAACAGAAA ATTGTGCTAA CATGCCGCCG GCAGAACCAA GCAGAAAGAC CCCAATGACC
NL/9/01 (B    AAAACAGAAA ATTGTGCTAA CATGCCACCG GCAGAACCAA GCAAAAAGAC CCCAATGACC
NL/21/01 (    AAAACAGAAA ATTGTGCTAA CATGCCGCCG GCAGAACCAA GCAAAAAGAC CCCAATGACC
NL/1/94 (p    AAAGTGGAAC ACTGTGTTAA TATGCCGCCG GTAGAACCAA GCAAGAAGAC CCCAATGACC
NL/1/82 (B    AAAGTGGAAC ACTGTGCTAA TATGCCGCCG GTAGAACCGA GTAAGAAGAC CCCAATGACC
NL/1/96 (B    AAAGTGGAAC ACTGTGTTAA TATGCCGCCG GTAGAACCAA GCAAGAAGAC CCCAATGACC
NL/6/97 (B    AAAGTGGAAC ACTGTGTTAA TATGCCGCCG GTAGAACCAA GCAAGAAGAC CCCAATGACC
NL/9/00 (B    AAAGTGGAAC ACTGTGTTAA TATGCCGCCG GTAGAACCAA GCAAGAAGAC CCCAATGACC
NL/3/01 (B    AGAGTGGAAC ACTGTGTCAA TATGCCGCCG GTAGAACCAA GCAAGAAGAC CCCAATGACC
NL/4/01 (B    AGAGTGGAAC ACTGTGTTAA TATGCCGCCG GTAGAACCAA GCAAGAAGAC CCCAATGACC
UK/5/01 (B    AAAGTGGAAC ACTGTGTTAA TATGCCGCCG GTAGAACCAA GCAAGAAGAC CCCAATGACC

              ....|....| ....|....| ....|....| ....|....| ....|....| ....|....|
                  245        255        265        275        285        295
NL/1/00 (p    CCCACAGACA ACTCAGACAC CAACTCAAGC CCACAGCATC CAACTCAACA GTCCACAGAA
BR/2/01 (A    CCCACAGACA ACTCAGACAC CAACTCAAGC CCACAGCATC CAACTCAACA GTCCACAGAA
FL/4/01 (A    CCCACAGATA ATTCAGACAC CAACTCAAGC CCACAACATC CAACTCAACA GTCCACAGAA
FL/3/01 (A    CCCACAGATA ATTCAGACAC CAACTCAAGC CCACAACATC CAACTCAACA GTCCACAGAA
FL/8/01 (A    CCCACAGATA ATTCAGACAC CAACTCAAGC CCACAACATC CAACTCAACA GTCCACAGAA
FL/10/01 (    CCCATAGACA ACTCAGACAC CAATCCAGGC TCACAGTATC CAACTCAACA GTCCACAGAA
NL/10/01 (    CCTATGGACA ACTCAGACAC CAATCCAGGC TCACAGTATC CAACTCAACA GTCCACAGAA
NL/2/02 (A    CCTATGGACA ACTCAGACAC CAATCCAGGC TCACAGTATC CAACTCAACA GTCCACAGAA
NL/17/00 (    TCCACAGACA ACCCAGACAT CAATCCAAGC TCACAGCATC CAACTCAACA GTCCACAGAA
NL/1/81 (A    CCCATAGACA ACCCAGACAT CAATCCAAAC TCACAGCATC CAACCCAACA GTCCACAGAA
NL/1/93 (A    CCCACAGACA ACCCAGACAT CAATCCAAAT TCACAACATC CAACTCAACA GTCCACAGAA
NL/2/93 (A    CC-ACAGACA ACCCAGACAT CAATCCAAAT TCACAACATC CAACTCAACA GTCCACAGAA
NL/3/93 (A    CCTATAGACA ACCCAGACAT CAATCCAAAC TCACAGCATC CAACTCAACA GTCCACAGAA
NL/1/95 (A    TCTATAGACA ACCCAGACAT CAATCCAAAC TCACAGCATC CAACTCAACA GTCCACAGAA
NL/2/96 (A    TCCACAGACA ATCCAGACAT CAATCCAAAC TCACAGCATC CAACTCAACA GTCCACAGAA
NL/3/96 (A    TCTATAGACA ACTCAGACAT CAATCCAAAC TCACAGCATC CAACTCAACA GTCCACAGAA
NL/22/01 (    CCTATAGACA ACCCAGACAT CAATCCAAAC TCACAGCATC CAACTCAACA GTCCACAGAA
NL/24/01 (    CCTATAGACA ACCCAGACAT CAATCCAAAC TCACAGCATC CAACTCAACA GTCCGCAGAA
NL/23/01 (    CCTATAGACA ACCCAGACAT CAATCCAAAC TCACAGCATC CAACTCAACA GTCCACAGAA
NL/29/01 (    TCCACAGACA ACCCAGACAT CAATCCAAAC TCACAGCATC CAACTCAACA GTCCACAGAA
NL/3/02 (A    TCCACAGACA ACCCAGACAT CAATCCAAAC TCACAGCATC CAACTCAACA GTCCACAGAA
NL/1/99 (p    TCCACAGCAG GCCCAAACAC CAAACCCAAT CCACAGCAAG CAACACAGTG GACCACAGAG
NL/11/00 (    TCCACAGCAG GCCCAAGCAC CGAACCCAAT CCACAGCAAG CAACACAATG GACCACAGAG
NL/12/00 (    TCTACAGCAG GCCCAAACAC CAAACCCAAT CCACAGCAAG CAACACAGTG GACCACGGAG
NL/5/01 (B    TCCACAGCAG GCCCAAACAC CAAACCCAAT CCACAGCAAG CAACACAGTG GACCACGGAG
```

Figure 19 con't

```
NL/9/01  (B    TCCACAGCAG GCCTAAACAC TAAACCCAAT CCACAGCAAG CAACACAGTG GACCACGGAG
NL/21/01 (     TCCACAGCAG GCCCAAACAC CAAACCCAAT CCACAGCAAG CAACACAGTG GACCACGGAG
NL/1/94  (p    TCTGCAGTAG ACTTAAACAC CAAACCCAAT CCACAGCAGG CAACACAGTT GGCCGCAGAG
NL/1/82  (B    TCTACAGTAG ACTCAAGCAC CGGACCCAAT CCACAGCAGA CAACACAGTG GACCACAGAG
NL/1/96  (B    TCTGCAGTAG ACTTAAACAC CAAACTCAAT CCACAGCAGG CAACACAGTT GACCACAGAG
NL/6/97  (B    TCTGCAGTAG ACTTAAACAC CAAACTCAAT CCACAGCAGG CAACACAGTT GACCACAGAG
NL/9/00  (B    TCTGCAGTAG ACTCAAACAC CAAACCCAAT CCACAGCAGG CAACACAGTT GACCACAGAG
NL/3/01  (B    TCTGCAGTAG ACTTAAACAC CAAACCCAAT CCACAGCGGG CAACACAGTT GACCACAGAG
NL/4/01  (B    TCTGCAGTAG ACTTAAACAC CAAACCCAAT CCACAGCAGG CAACACAGTT GACCACAGAG
UK/5/01  (B    TCTGCAGTAG ACTTAAACAC CAAACCCAAT CCACAGCAGG CAACACAGTT GACCACAGAG

               ....|....| ....|....| ....|....| ....|....| ....|....| ....|....|
                   305        315        325        335        345        355
NL/1/00  (p    GGCTCCACAC TCTACTTTGC AGCCTCAGCA AGCTCACCAG AGACAGAACC AACATCAACA
BR/2/01  (A    GGCTCCACAC TCTACTTTGC AGCCTCAGCA AGCTCACCAG AGACAGAACC AACATCAACA
FL/4/01  (A    GGCTCCACAC TCTACTTTGC AGCCTCAGCA AACTCACCAG AGACAGAACC AACATCAACA
FL/3/01  (A    GGCTCCACAC TCTACTTTGC AGCCTCAGCA AACTCACCAG AGACAGAACC AACATCAACA
FL/8/01  (A    GGCTCCACAC TCTACTTTGC AGCCTCAGCA AGCTCACCAG AGACAGAACC AACATCAACA
FL/10/01 (     GACTCCACAC TCCACTCTGC AGCTTCAGCA AGCTCACCAG AGACAGAACC AACATCAACA
NL/10/01 (     GGCTCCACAC TCCACTTTGC AGCCTCAGCA AGCTCACCAG AGACAGAACC AACATCAACA
NL/2/02  (A    GGCTCCACAC TCCACTTTGC AGCCTCAGCA AGCTCACCAG AGACAGAACC AACATCAACA
NL/17/00 (     AACCCCACAC TCAACCCCGC AGCATCAGCG AGCCCATCAG AAACAGAACC AGCATCAACA
NL/1/81  (A    AGCCCCACAC TCAACCCCGC AGCCTCGGTG AGCCCATCAG AAACAGAACC AGCATCAACA
NL/1/93  (A    AGCCCCACAC TCAACACCGC AGCCTCGGTG AGCCCATCAG AAACAGAACC AGCATCAACA
NL/2/93  (A    AGCCCCACAC TCAACACCGC AGCCTCGGTG AGCCCATCAG AAACAGAACC AGCATCAACA
NL/3/93  (A    AGCCTCACAC TCAACCCCGC AGCCTCGGTG AGCCCATCAG AAACAGAACC AGCATCAACA
NL/1/95  (A    AGCCTCACAC TCAGCCCCAC AGCCTCGGTG AGCCCATCAG AAACAGAACC AGCATCAACA
NL/2/96  (A    AACCCCACAC TAAACCCCGC AGCATCGGTG AGCTCATCAG AAACAGAACC AGCATCAACA
NL/3/96  (A    AGCCTCACAC TCAGCCCCAC AGCCTCGGTG AGCCCATCAG AAACAGAACC AGCATCAACA
NL/22/01 (     AGCCTCACAC TCTACCCCAC ATCCTCGGTG AGCTCATCAG AAACAGAACC AGCATCAACA
NL/24/01 (     AGCCTCACAC TCTACCCCAC ATCCTCGGTG AGCTCATCAG AAACAGAACC AGCATCAACA
NL/23/01 (     AGCCTCACAC TCTACCCCAC ATCCTCGGTG AGCTCATCAG AAACAGAACC AGCATCAACA
NL/29/01 (     AACCCCACAC TCAACCCAGC AGCATCAGCG AGCCCATCAG AAACAGAATC AGCATCAACA
NL/3/02  (A    AACCCCACAC TCAACCCAGC AGCATCAGCG AGCCCATCAG AAACAGAATC AGCATCAACA
NL/1/99  (p    AACTCAACAT CCCCAGTAGC AACCCCAGAG GGCCATCCAT ACACAGGGAC AACTCAAACA
NL/11/00 (     AACTCAACAT CCCCAGCAGC AACCCTAGAG AGCCATCCAT ACACAGGGAC AACCCAAACA
NL/12/00 (     AACTCAACAT TCCCAGCAGC AACCTCAGAG GGCCATCTAC ACACAGGGAC AACTCAAACA
NL/5/01  (B    AACTCAACAT CCCCAGCAGC AACCCCAGAG GGCCATCTAC ACACAGGGAC AACTCAAACA
NL/9/01  (B    AACTCAACAT CCCCAGCAGC AACCCCAGAG GGCCATCTAC ACACAGGGAC AACTCAAACA
NL/21/01 (     AACTCAACAT CCCCAGCAGC AACCCCAGAG GGCCATCTAC ACACAGGGAC AACTCAAACA
NL/1/94  (p    GATTCAACAT CTCTAGCAGC AACCTCAGAG GACCATCTAC ACACAGGGAC AACTCCAACA
NL/1/82  (B    GATTCAACAT CTCTAGCAGC AACCTCAGAG GACCATCTAC ACACAGGGAC AACTCCAACA
NL/1/96  (B    GATTCAACAT CTCTAGCAGC AACCTCGGAG GATCATTTAC TCACAGGGAC AACTCCAACA
NL/6/97  (B    GATTCAACAT CTCTAGCAGC AACCTCAGAG GGCCATCCAC ACACAGGAAC AACTCCAACA
NL/9/00  (B    GATTCTACAT CTTTAGCAGC AACCCTAGAG GACCATCCAC ACACAGGGAC AACTCCAACA
NL/3/01  (B    GATTCAACAT CTCTAGCAGC AACCCTAGAG GGCCATCTAC ACACAGGGAC AACTCCAACA
NL/4/01  (B    GATTCAACAT CTCCAGCAGC AACCCTAGAG GGCCATCTAC ACACAGGGAC AACTCCAACA
UK/5/01  (B    GACTCTACAT CTTTAGCAGC AACCCTAGAG GACCATCCAC ACACAGGGAC AACTCCAACA

               ....|....| ....|....| ....|....| ....|....| ....|....| ....|....|
                   365        375        385        395        405        415
NL/1/00  (p    CCAGATACAA CAAACCGCCC GCCCTTCGTC GACACACACA CAACACCACC AAGCGCAAGC
BR/2/01  (A    CCAGATACAA CAAACCGCCC GCCCTTCGTC GACACACACA CAACACCACC AAGCGCAAGC
FL/4/01  (A    CCAGACACAA CAAACCGCCC GCCCTTCGTC GACACACACA CAACACCACC AAGCGCAAGC
FL/3/01  (A    CCAGACACAA CAGACCGCCC GCCCTTCGTC GACACACACA CAACACCACC AAGCGCAAGC
FL/8/01  (A    CCAGACACAA CAGACCGCCC GCCCTTCGTC GACACACACA CAACACCACC AAGCGCAAGC
FL/10/01 (     CCAGACACAA CAAGCCGCCC GCCCTTCGTC GACACACACA CAACACCACC AAGTGCAAGC
NL/10/01 (     CCAGACACAA CAAGCCGCCC GCCCTTCGTC GACACACACA CAACACCATC AAGTGCAAGC
NL/2/02  (A    CCAGACACAA CAAGCCGCCC GCCCTTCGTC GACACACACA CAACACCATC AAGTGCAAGC
NL/17/00 (     CCAGACACAA CAAACCGCCT GTCCTCCGTA GACAGGTCCA CAGCACAACC AAGTGAAAGC
NL/1/81  (A    CCAGACACAA CAAACCGCCT GTCCTCCGTA GACAGATCCA CAACACAACC AAGTGAAAGC
```

Figure 19 con't

```
NL/1/93  (A    CCAGACACAA CAAACCGCCT GTCCTCCGCA GACAGATCCA CAACACAACC AAGTGAAAGC
NL/2/93  (A    CCAGACACAA CAAACCGCCT GTCCTCCGCA GACAGATCCA CAACACAACC AAGTGAAAGC
NL/3/93  (A    CCAGACACAA CAAACCGCCT GTCCTCCGTA GACAGATCCA CAACACAACC AAGTGAAAGC
NL/1/95  (A    TCAGACACAA CAAGCCGCCT GTCTTCCGTA GACAGATCCA CAACACAACC AAGTGAAAGC
NL/2/96  (A    CCAGACACAA CAAACCGCCT GTCCTCCGTA GACAGGTCCA CAGCACAACC AAGTGAAAGC
NL/3/96  (A    TCAGACACAA CAAACCGCCT GTCTTCCGTA GACAGATCCA CAACACAACC AAGTGAAAGC
NL/22/01 (     CCAGGCATAA CAAACCACCT GTCCTTTGTA GACAGATCCA CAACACAACC AAGTGAAAGC
NL/24/01 (     CCAGGCATAA CAAACCACCT GTCCTTTGTA GACAGATCCA CAACACAACC AAGTGAAAGC
NL/23/01 (     CCAGGCATAA CAAACCACCT GTCCTTTGTA GACAGATCCA CAACACAACC AAGTGAAAGC
NL/29/01 (     CCAGATACAA CAAACCGCCT GTCCTCCGTA GACAGGTCCA CGGTACAACC AAGTGAAAAC
NL/3/02  (A    CCAGATACAA CAAACCGCCT GTCCTCCGTA GACAGGTCCA CGGTACAACC AAGTGAAAAC
NL/1/99  (p    TCAGACACAA CAGCTCCCCA GCAAACCACA GACAAACACA CAGCACCGCT AAAATCAACC
NL/11/00 (     CCAGACATAA CAGCTCCCCA ACAAACCACA GACAAACACA CAGCACTGCC AAAATCAACC
NL/12/00 (     CCAGACACAA CAGCTCCTCA GCAAACCACA GACAAACACA CAGCACTGCC AAAATCAACC
NL/5/01  (B    CCAGACACAA CAGCTCCTCA GCAAACCACA GACAAACACA CAGCACTGCC AAAATCAACC
NL/9/01  (B    CCAGACACAA CAGCTCCTCA GCAAACCACA GACAAGCACA CAGCACTGCC AAAATCAACC
NL/21/01 (     CCAGACACAA CAGCTCCTCA GCAAACCACA GACAAACACA CAGCACTGCC AAAATCAACC
NL/1/94  (p    CCAGATGCAA CAGTCTCTCA GCAAACCACA GACGAGTACA CAACATTGCT GAGATCAACC
NL/1/82  (B    CTAGATGCAA CAGTTTCTCA GCAAACCCCA GACAAGCACA CAACACCGCT GAGATCAACC
NL/1/96  (B    CCAGATGCAA CAGTCTCTCA GCAAACCACA GACGAGCACA CAACACTGCT GAGATCAACC
NL/6/97  (B    CCAGACGCAA CAGTCTCTCA GCAAACCACA GACGAGCACA CAACACTGCT GAGATCAACC
NL/9/00  (B    CCAGATGCAA CAGTCTCTCA GCAAACCACA GACGAGCACA CAACACTGCT GAGATCAACC
NL/3/01  (B    CCAGATGTAA CAGTCTCTCA GCAAACCACA GACGAGCACA CAACACTGCT GAGATCAACC
NL/4/01  (B    CCAGATGCAA CAGTCTCTCA GCAAACCACA GACGAGCACA CAACACTGCT GAGATCAACC
UK/5/01  (B    CCAGATGCAA CAGTCTCTCA GCAAACCACA GACGAGCACA CAACACTGCT GAGATCAACC

               ....|....| ....|....| ....|....| ....|....| ....|....| ....|....|
                   425        435        445        455        465        475
NL/1/00  (p    AGAACAAAGA CAAGTCCGGC AGTC-CACAC AAAAAA-CAA CCCAAGGACA AGCTCTAG--
BR/2/01  (A    AGAACAAAGA CAAGTCCGGC AGTC-CACAC AAAAAA-CAA CCCAAGGACA AGCTCTAG--
FL/4/01  (A    AGAACAAAGA CAAGTCCGGC AGTC-CACAC AAAAAA-CAA CCCAAGGATA AGCTCCAG--
FL/3/01  (A    AGAACAAAGA CAAGTCCGGC AGTC-CACAC AAAAAA-CAA CCCAAGGATA AGCTCCAG--
FL/8/01  (A    AGAACAAAGA CAAGTCCGGC AGTC-CACAC AAAAAA-CAA CCCAAGGATA AGCTCCAG--
FL/10/01 (     AGGACAAGGA CAAGTCCGGC AGTC-CACAC AAAAAA-CAA TCCAAGGGTA AGCCCCAG--
NL/10/01 (     AGAACAAAGA CAAGTCCGGC AGTC-CACAC AAAAAA-CAA TCTAAGGATA AGCCCCAG--
NL/2/02  (A    AGAATAAGGA CAAGTCCGGC AGTC-CACAC AAAAAA-CAA TCTAAGGATA AGCCCCAG--
NL/17/00 (     AGAACAAAGA CAAAACCGAC AGTC-CACAC AATCAA-CAA CCCAAACACA GCTTCCAG--
NL/1/81  (A    AGAACAAAGA CAAAACCAAC AGTC-CACAC AAAAAA-CAA TCCAAGTACA GTTTCCAG--
NL/1/93  (A    AGAACAAAGA CAAAGCTGAC AGTC-CACAC AAAAAA-CAA CCTAAGTACA GCCTCCAG--
NL/2/93  (A    AGAACAAAGA CAAAGCTGAC AGTC-CACAC AAAAAA-CAA CCTAAGTACA GCCTCCAG--
NL/3/93  (A    AGAACAAAGA CAAAACTGAC AGTC-CACAA AAAAAA-CAT CCCAAGTACA GTCTCTAG--
NL/1/95  (A    AGAGCAAGGA CAAAACCGAC AGTC-CACAA GAAAAA-CAT CCCAAGTACA GTTTCTAG--
NL/2/96  (A    AGAACAAAGA CAAAACCGAC AGTC-CACAC AAGAAA-CAA CCCAAGCACA GCTTCCAG--
NL/3/96  (A    AGAGCAAGAA CAAAACCGAC AGTC-CACAA GAAAAA-CAT CCCAAGTACA GTTTCTAG--
NL/22/01 (     AGAACAAAGA CAAACCGGAC AGTC-CACAA AAAAAA-CAT CTCAAGTACA GTTTCTAG--
NL/24/01 (     AGAACAAAGA CAAACCGGAC AGTC-CACAA AAAAAA-CAT CTCAAGTACA GTTTCTAG--
NL/23/01 (     AGAACAAAGA CAAACCGGAC AGTC-CACAA AAAAAA-CAT CTCAAGTACA GTTTCTAG--
NL/29/01 (     AGAACAAAGA CAAAACTGAC AGTC-CACAC AAGAAA-CAA CCTAAGCACA GCCTCCAG--
NL/3/02  (A    AGAACAAAGA CAAAACTGAC AGTC-CACAC AAGAAA-CAA CCTAAGCACA GCCTCCAG--
NL/1/99  (p    AATGAACAGA TCACCCAGAC AACCACAGAG AAAAAGACAA TCAGAGCAAC AACCCAAAAA
NL/11/00 (     AATGAACAGA TCACCCAGAC AACCACAGAG AAAAAGACAA CCAGAGCAAC AACCCAAAAA
NL/12/00 (     AATGAACAAA TCACCCAGAC AACCACAGAG AAAAAGACAA CCAGAGCAAC AACCCAAAGA
NL/5/01  (B    AATGAACAGA TCACCCAGGC AACCACAGAG AAAAAGACAA CCAGAGAAAC AACCCAAAGA
NL/9/01  (B    AATGAACAGA TCACCCAGAC AACCACAGAG AAAAAGACAA CCAGAGCAAC AACCCAAAGA
NL/21/01 (     AATGAACAGA TCACCCAGAC AACCACAGAG AAAAAGACAA CCAGAGCAAC AACCCAAAGA
NL/1/94  (p    AACAGACAGA CCACCCAAAC AACCACAGAG AAAAAGCCAA CCGGAGCAAC AACCAAAA--
NL/1/82  (B    AATGGACAGA CCACCCAGAC AACCACAGAG AAAAAGCCAA CCAGAGCAAT AGCCAAAA--
NL/1/96  (B    AACAGACAGA CCACCCAAAC AACCACAGAG AAAAAGCCAA CCGGAGCAAC AACCAAAA--
NL/6/97  (B    AACAGACAGA CCACCCAAAC AGCCACAGAG AAAAAGCCAA CTGGAGCAAC AACCAAAA--
NL/9/00  (B    AACAGACAGA CCACCCAAAC AACTGCAGAG AAAAAGCCAA CCAGGGCAAC AACCAAAA--
NL/3/01  (B    AACAGACAGA CCACCCAAAC AGCCGCAGAG AAAAAGCCAA CCAGAGTAAC AACTAACA--
```

Figure 19 con't

```
NL/4/01 (B    AACAGACAGA CCACCCAAAC AACCGCAGAG AAAAAGCCAA CCAGAGCAAC AACCAAAA--
UK/5/01 (B    AACAGACAGA CCACCCAAAC AACTGCAGAG AAAAAGCCAA CCAGAGCAAC AACCAAAA--

              ....|....| ....|....| ....|....| ....|....| ....|....| ....|....|
                   485        495        505        515        525        535
NL/1/00 (p    ---------- -AACACATTC TCCACCACGG GCAACGACAA GGACGGC--A CGCAG-AACC
BR/2/01 (A    ---------- -AACACATTC TCCACCACGG GCAACGACAA GGACGGC--A CGCAGGAACC
FL/4/01 (A    ---------- -AACACACTC TCCACCATGG GCAACGACAA GGACGGC--A CGCAG-AACC
FL/3/01 (A    ---------- -AACACATTC TCCACCATGG GCAACGACAA GGACGGC--A CGCAG-AACC
FL/8/01 (A    ---------- -AACACATTC TCCACCATGG GCAACGACAA GGACGGC--A CGCAG-AACC
FL/10/01 (    ---------- -AACACATTC CCCACCATGG GCAATGACAA GGACGGT--C CGCGG-AACC
NL/10/01 (    ---------- -AACACATTC CCCACCATGG GCAATGACAA GGACGGT--C CGTGG-AACC
NL/2/02 (A    ---------- -AACACATTC CCCACCATGG GCAATGACAA GGACGGT--C CGTGG-AACC
NL/17/00 (    ---------- -TACACAATC CCCACCACGG ACAACAACGA AGGCAAT--C CGCAG-AGCC
NL/1/81 (A    ---------- -AACACAATC CCCACTACGG GCAACAACGA AGGCGGT--C CTCAG-AGCC
NL/1/93 (A    ---------- -AACACAATC ACCACCACGG GCAACAACGA AGGCGGT--C CTCAG-AGAC
NL/2/93 (A    ---------- -AACACAATC ACCACCACGG GCAACAACGA AGGCGGT--C CTCAG-AGAC
NL/3/93 (A    ---------- -AACACAATC CTCAATACGG GCAACAACGA AGGCGGT--C CTCAG-AGCC
NL/1/95 (A    ---------- -AACACAATC CCCACTACGG GCAACAACGA AGGCGGT--C CTCAG-AGCC
NL/2/96 (A    ---------- -CACACAATC CCCACCACGG GTAACAACGA AGGCAAT--C CTCAG-AGCC
NL/3/96 (A    ---------- -AACACAATC CCCACTACGG GCAACAACGA AGGCGGT--C CTCAG-AGCC
NL/22/01 (    ---------- -AACACAGTC CCCACCACGG ACAACAGCGA AGGCGGT--C CCCAG-AGCC
NL/24/01 (    ---------- -AACACAGTC CCCACCACGG ACAACAGCGA AGGCGGT--C CCCAG-AGCC
NL/23/01 (    ---------- -AACACAGTC CCCACCACGG ACAACAGCGA AGGCGGT--C CCCAG-AGCC
NL/29/01 (    ---------- -TACACAATC CCCACCACGG GCAACAACGA AGGCAAT--C CGCAG-AGCC
NL/3/02 (A    ---------- -TACACAATC CCCACCACGG GCAACAACGA AGGCAAT--C CGCAG-AGCC
NL/1/99 (p    AGGGAAAAAG GAAAAGAAAA CACAAACCAA ACCACAAGCA CAGCTGCAAC CCAAACAACC
NL/11/00 (    AGGGAAAAAG AAAAAGAAAA CACAAACCAA ACCACAAGCA CAGCTGCAAC CCAAACAACC
NL/12/00 (    AGGGAAAAAG GGAAAGAAAA CACAAACCAA ACCACAAGCA CAGCTGCTAC CCAAACAACC
NL/5/01 (B    AGGGAAAAAG GAAAAGAAAA CACAAACCAA ACCACAAGCA CAGCTGCAAC CCAAACAACC
NL/9/01 (B    AGGGAAAAAG GAAAAGAAAA CACAAACCAA ACCACAAGCA CAGCTGCAAC CCAAACAACC
NL/21/01 (    AGGGAAAAAG GAAAAGAAAA CACAAACCAA ACCACAAGCA CAGCTGCAAC CCAAACAACC
NL/1/94 (p    ---------- ---AAGAAAC CACAACTCGA ACTACAAGCA CAGCTGCAAC CCAAACACTC
NL/1/82 (B    ---------- ---AAGAAAC CACAAACCAA ACCACAAGCA CAGCTGCAAC CCAAACATTC
NL/1/96 (B    ---------- ---AAGAAAC CACAACTCGA ACCACAAGCA CAGCTGCAAC CCAAACACTC
NL/6/97 (B    ---------- ---AAGAAAC CACAACCCGA ACTACAAGTA CAGCTGCAAC CCAAACACCC
NL/9/00 (B    ---------- ---AAGAAAC CACAACTCGA ACCACAAGCA CAGCTGCAAC CCAAACACTC
NL/3/01 (B    ---------- ---AAGAAAC CATAACTCGA ACCACAAGCA CAGCCGCAAC CCAAACACTC
NL/4/01 (B    ---------- ---AAGAAAC CATAACTCGA ACCACAAGCA CAGCTGCAAC CCAAACACTC
UK/5/01 (B    ---------- ---AAGAAAC CACAACTCGA ACCACAAGCA CAGCTGCAAC CCAAACACTC

              ....|....| ....|....| ....|....| ....|....| ....|....| ....|....|
                   545        555        565        575        585        595
NL/1/00 (p    ACCACTCTCC GCACAAGCAG CACAAGAAAG AGACCGTCCA CAGCATCAGT CCAACCTGAC
BR/2/01 (A    ACCACTCTCC GCACAAGCAG CACAAGAAAG AGACCGTCCA CAGCATCAGT CCAACCTGAC
FL/4/01 (A    ACCACTCTCC GCACAAGCAG CACAAGAAAG AGACCGTCCA CAGCATCAGC CCAACCCGAC
FL/3/01 (A    ACCACTCTCC GCACAAGCAG CACAAGAAAG AGACCGTCCA CAGCATCAGT CCAACCCGAC
FL/8/01 (A    ACCACTCTCC GCACAAGCAG CACAAGAAAG AGACCGTCCA CAGCATCAGT CCAACCCGAC
FL/10/01 (    ACCACTCTCC GCACAAGCAG CACAAGAAAA AGACTGTCTA CAGCATCAGT CCAACCCGAC
NL/10/01 (    ACCACTCTCC GCACAAGCAG CATAAGAAAA AGACCGTCCA CAGCATCAGT CCAACCTGAC
NL/2/02 (A    ACCACTCTCC GCACAAGCAG CATAAGAAAA AGACCGTCCA CAGCATCAGT CCAACCTGAC
NL/17/00 (    ACCACTTTCC GCATGAGCAG CACAGGAAAA AGACCAACCA CAACATTAGT CCAGTCCGAC
NL/1/81 (A    ACCGCTTTCC GCACGAGCAG CACAAGAAAA AGACCAACCA CAACATCAGT CCAGTCTGAC
NL/1/93 (A    ACCGCCTTCC ACACGAGCAG CACAGGAAAA AGACCAACCA CAACATCAGT CCAGTCTGGC
NL/2/93 (A    ACCGCCTTCC ACACGAGCAG CACAGGAAAA AGACCAACCA CAACATCAGT CCAGTCTGGC
NL/3/93 (A    ACCGCCTTTC GCACGAGCAG CACAGGAGAA AGACCAACTA CAACATCAGT CCAGTCTGAC
NL/1/95 (A    ACCGCCTTTC GCACGAGCAG CACAGGAGAG GGACCAACCA CAACATCGGT CCAGTCTGAC
NL/2/96 (A    ACCGTCTTCC GCATGAGCAG CACAGGAAAA AGACCAGCCA CAACATTAGT CCAGTCCGAC
NL/3/96 (A    ACCGCCTTTC GCATGAGCAG CACAGGAGAG GGACCAACCA CAACATCGGT CCAGTCTGAC
NL/22/01 (    ACCGCCCTTC GCACGAGCAG CACAGGAGAA AGACCAACCA CAACACCAGT CCAGCCCGAT
NL/24/01 (    ACCGCCCTTC GCACGAGCAG CACAGGAGAA AGACCAACCA CAACACCAGT CCAGCCCGAT
```

Figure 19 con't

```
NL/23/01 (    ACCGCCCTTC GCACGAGCAG CACAGGAGAA AGACCAACCA CAACACCAGT CCAGCCCGAT
NL/29/01 (    ACCACCCTCC GCATGAGCAG CACAGGAAGA AGACCAACCA CAACACTAGT CCAGTCCGAC
NL/3/02  (A   ACCACCCTCC GCATGAGCAG CACAGGAAGA AGACCAACCA CAACACTAGT CCAGTCCGAC
NL/1/99  (p   AACACCACCA ACCAAATCAG AAATGCAAGT GAGACAATCA CAACATCCGA CAGACCCAGA
NL/11/00 (    AACACCACCA ACCAAACCAG AAATGCAAGT GAGACAATCA CAACATCCGA CAGACCCAGA
NL/12/00 (    AACACCACCA ACCAAATCAG AAATGCAAGC GAGACAATCA CAACATCCGA CAGACCCAGA
NL/5/01  (B   AACACCACCA ACCAAATCAG AAATGCAAGC GAGACAATCA CAACATCCGA CAGACCCAGA
NL/9/01  (B   AACACCACCA ACCAAATCAG AAATGCAAGC GAGACAATCA CAACATCCGA CAGACCCAGA
NL/21/01 (    AACACCACCA ACCAAATCAG AAATGCAATT GAGACAATCA CAACATCCGA CAGACCCAGA
NL/1/94  (p   AACACTACCA ACCAAACTAG CTATGTGAGA GAGGCAACCA CAACATCCGC CAGATCCAGA
NL/1/82  (B   AACACCACCA ATCAAACCAG AAATGGAAGA GAGACAACCA TAACATCTGC CAGATCCAGA
NL/1/96  (B   AACACCACCA ACCAAACTAG CAATGGAAGA GAGGCAACCA CAACATCCAC CAGATCCAGA
NL/6/97  (B   AACACCACCA ACCAAACCAG CAATGGAAGA GAGGCAACCA CAACATCCGC CAGGTCCAGA
NL/9/00  (B   AACACCACCA ACCAAACTAG CAATGGAAGA GAGGCAACCA CAACATCTGC CAGATCCAGA
NL/3/01  (B   AACACCACCA ACCAAACCAA CAATGGAAGA GAGGCAACCA CAACATCTGC CAGATCCAGA
NL/4/01  (B   AACACCACCA ACCAAACCAG CAATGGAAGA GAGGCAACCA CAACATCTGC CAGATCCAGA
UK/5/01  (B   AACACCACCA ACCAAACTAG CAATGGAAGA GAGGCAACCA CAACATCTGC CAGATCCAGA

              ....|....| ....|....| ....|....| ....|....| ....|....| ....|....|
                 605        615        625        635        645        655
NL/1/00  (p   ATCAGCGCAA CAACCCACAA AAACGAAGAA GCAAGTCCAG CGAGCCCACA AACATCTGCA
BR/2/01  (A   ATCAGCGCAA CAACCCACAA AAACGAAGAA GCAAGTCCAG CGAGCCCACA AACATCTGCA
FL/4/01  (A   ATCAGCGCAA CAACCCACAA AAACGAAGAA GCAAGTCCAG CGAGCCCACA AACATCTGCA
FL/3/01  (A   ATCAGCGCAA CAACCCACAA AAACGAAGAA GCAAGTCCAG CGAGCCCACA AACATCTGCA
FL/8/01  (A   ATCAGCGCAA CAACCCACAA AAACGAAGAA GCAAGTCCAG CGAGCCCACA AACATCTGCA
FL/10/01 (    AGCAGCGCAA CAACCCACAA ACACGAAGAA ACAAGCCCAG TGAGCCCACA AACATCTGCA
NL/10/01 (    AGCAGCGCAA CAACCCACAA ACACGAAGAA GCAAGCCCAG TGAGCCCGCA AGCATCTGCA
NL/2/02  (A   AGCAGCGCAA CAACCCACAA ACACGAAGAA GCAAGCCCAG TGAGCCCGCA AGCATCTGCA
NL/17/00 (    AGCAGCACCA CAACCCAAAA TCATGAAGAA ACAGGTTCAG CGAACCCACA GGCGTCTGCA
NL/1/81  (A   AGCAGCACCA CAACCCAAAA TCATGAAGAA ACAAGTTCAG CGAACCCACA GGCATCTGCA
NL/1/93  (A   AGCAGCACCA CAACTCAAAA TCATGAAGAA ACAAGTTCAT CGAACCCACA GGCATCTGCA
NL/2/93  (A   AGCAGCACCA CAACTCAAAA TCATGAAGAA ACAAGTTCAT CGAACCCACA GGCATCTGCA
NL/3/93  (A   AGCAGCACCA CAACCCAAAA TCATGAAGAA ACAGGTTCAG CGAACCCACA GGCATCTGCA
NL/1/95  (A   AGCAGCACCA CAACCCAAAA TCATGAAGAA ACAGGTTCAG CGAACCCACA GGCATCTGCA
NL/2/96  (A   AGCAGCACCA CAACCCAAAA TCATGAAGAA ACAGGTTCAG CAAACTCACA GGCATCTGCA
NL/3/96  (A   AGCAGCACCA CAACCCAAAA TCATGAAGAA ACAGGCTCAG CGAACCCACA GGCATCTGCA
NL/22/01 (    AGCAGCACCA CAACACAAAA TCATGAAGAA ACAGGCTCAG CGAACCCACA GGCATCCGCA
NL/24/01 (    AGCAGCACCA CAACACAAAA TCATGAAGAA ACAGGCTCAG CGAACCCACA GGCATCCGCA
NL/23/01 (    AGCAGCACCA CAACACAAAA TCATGAAGAA ACAGGCTCAG CGAACCCACA GGCATCCGCA
NL/29/01 (    AGCAGCACCA CAACCCAAAA TCATGAAGAA ACAGGCTCAG CGAACCCACA GGCATCTGCA
NL/3/02  (A   AGCAGCACCA CAACCCAAAA TCATGAAGAA ACAGGCTCAG CGAACCCACA GGCATCTGCA
NL/1/99  (p   ACTGACACCA CAACCCAAAG CAGCGAACAG ACAA-CCCGG GCAACAGACC CAAGCTCCCC
NL/11/00 (    ATTGACACCA CAACCCAAAG CAGCGATCAG ACAA-CCCGG GCAACAGACC CAAGCTCCCC
NL/12/00 (    ACTGACTCCA CAACCCAAAG CAGCGAACAG ACAA-CCCGG GCAACAGACC CAAGCTCCCC
NL/5/01  (B   ACTGACTCCA CAACCCAAAG CAGCGAACAG ACAA-CCCAG GCAACAGACC CAAGCTCCCC
NL/9/01  (B   ACTGACTCCA CAACCCAAAG CAGCGAACAG ACAA-CCCGG GCAACAGACC CAAGCTCCCC
NL/21/01 (    ACTGACTCCA CAACCCAAAG CAGCGAACAG ACAA-CCCGG GCAACAGACC CAAGCTCCCA
NL/1/94  (p   AACAGTGCCA CAACTCAAAG CAGCGACCAA ACAA-CCCAG GCAGCAGACC CAAGCTCCCA
NL/1/82  (B   AACGACGCCA CAACTCAAAG CAGCGAACAA ACAA-ACCAG ACAACAGACC CAAGCTCCCA
NL/1/96  (B   AACGGTGCCA CAACTCAAAA CAGCGATCAA ACAA-CCTAG ACAGCAGACC CAAGCTCCCA
NL/6/97  (B   AACGGTGCCA CAACTCAAAA CAGCGATCAA ATAA-CCCAG GCAGCAGACT CAAGCTCCCA
NL/9/00  (B   AACAATGCCA CAACTCAAAG CAGCGATCAA ACAA-CCCAG GCAGCAGAAC CAAGCTCCCA
NL/3/01  (B   AACAATGCCA CAACTCAAAG CAGCGACCAA ACAA-CCCAG GCAGCAGACC CAAGCTCCCA
NL/4/01  (B   AACAATGCCA CAACTCAAAG CAGCGACCAA ACAA-CCCAG GCAGCAGACC CAAGCTCCCA
UK/5/01  (B   AACAATGCCA CAACTCAAAG CAGCGATCAA ACAA-CCCAA GCAGCAGAAC CAAACTCCCA

              ....|....| ....|....| ....|....| ....|....| ....|....| ....|....|
                 665        675        685        695        705        715
NL/1/00  (p   AGCACAACAA GAATACAAAG GAAAAGCGTG GAGGCCAACA CATCAACAAC ATACAACCAA
BR/2/01  (A   AGCACAACAA GAATACAAAG GAAAAGCGTG GAGGCCAACA CATCAACAAC ATACAACCAA
FL/4/01  (A   AGCACAACAA GAACACAAAG GAAAAGCGTG GAGGCCAACA CATCAACAAC ATACAACCAA
```

Figure 19 con't

```
FL/3/01 (A    AGCACAACAA GAACACAAAG GAAAAGCGTG GAGGCCAACA CATCAACAAC ATACAACCAA
FL/8/01 (A    AGCACAACAA GAACACAAAG GAAAAGCGTG GAGGCCAACA CATCAACAAC ATACAACCAA
FL/10/01 (    AGCACAGCAA GACCACAAAG GAAGGGCATG GAGGCCAGCA CATCAACAAC ATACAACCAA
NL/10/01 (    AGCACAGCAA GACCACAAAG GAAGGGCATG GAGGCCAGCA CATCAACAAC ATACAACCAA
NL/2/02 (A    AGCACAGCAA GACCACAAAG GAAGGGCATG GAGGCCAGCA CATCAACAAC ATACAACCAA
NL/17/00 (    AGCACAATG- -----CAAAA ---------- ----CTAGCA CACCAATAAT ATAAAACCAA
NL/1/81 (A    AGCACAATG- -----CAAAG ---------- ----CCAGCA CACCAACAAC ATAAAACCAA
NL/1/93 (A    AGCACAATG- -----CAAGA ---------- ----CCAGGA CACCAACAAT ACAAAACAAA
NL/2/93 (A    AGCACAATG- -----CAAGA ---------- ----CCAGGA CACCAACAAT ACAAAACAAA
NL/3/93 (A    AGCACAATG- -----CAAAA ---------- ----CTAGCA CACCAACATT GTAAAACCAA
NL/1/95 (A    AGCACAATG- -----CAAAA ---------- ----CTAGCA CACCAACATT GTAAAACCAA
NL/2/96 (A    AGCACAATG- -----CAAAA ---------- ----CTAGCA CTCCAACAAT ATAAAACCAA
NL/3/96 (A    AGCACAATG- -----CAAAA ---------- ----CCAGCA CACCAACATT GCAAAACCAA
NL/22/01 (    AGCACAATG- -----CAAAA ---------- ----CCAGCA CACCAACATT GCAAGACCAA
NL/24/01 (    AGCACAATG- -----CAAAA ---------- ----CCAGCA CACCAACATT GCAAGACCAA
NL/23/01 (    AGCACAATG- -----CAAAA ---------- ----CCAGCA CACCAACATT GCAAGACCAA
NL/29/01 (    AGCACAATG- -----CAAAA ---------- ----CCAGCA CACCAACAAT ATAAAACCAA
NL/3/02 (A    AGCACAATG- -----CAAAA ---------- ----CCAGCA CACCAACAAT ATAAAACCAA
NL/1/99 (p    ACCACACCAT GCATAGAGAG GTGCA----- -AAACTCAAA TGAGCACAAC ACACAAACAT
NL/11/00 (    ACCACACCAT GCACAGAGTG GTGCA----- -AAACCCAAA TGAACACAAC ACACAAACAT
NL/12/00 (    ACCACATCAT GCACAGGGAA GTGCA----- -AAACCCAAA TGAACACAAC ACACAAACAT
NL/5/01 (B    AGCACACCAT GCACAGGGAA GTGCA----- -AAACCCAAA TGAACACAAC ACACAAACAT
NL/9/01 (B    ACCACACCAT GCACAGGGAA GTGCA----- -AAACCCAAA TGAACACAAC ACACAAACAT
NL/21/01 (    CCCACACCAT GCACAGGGAA GTGCA----- -AAACCCAAA TGAACACAAC ACACAAACAT
NL/1/94 (p    ACCACACCAT ACACAGAAAA GCACA----- -ACAACAACA T----ACAAC ACAGACACAT
NL/1/82 (B    ACCACATCAT GCATAGATAA GCACA----- -ATAACAATA TGAACACAAC ACAGACACAT
NL/1/96 (B    ACCACACCAT ACACAGAAAA GCACA----- -ACAACAACA T----ACAAC ACAGACACAT
NL/6/97 (B    ACCACACCAT ACACAGAAAA GCACA----- -ACAACAGCA T----ACAAC ACAGACACAT
NL/9/00 (B    ATCACAACAT ACACAGAAAA GCACA----- -ACAACAACA T----ACAAC ACAGACACAT
NL/3/01 (B    ATCACAACAT ACACAGAAAA GCATA----- -ACAACAACA T----ACAAC ACAGACACAT
NL/4/01 (B    ATCACAACAT ACAAAGAAAA GCACA----- -ACAACAACA T----ACAAC ACAGACACAT
UK/5/01 (B    ATCACAACAT ACACAGAAAA GCACA----- -ACAACAACA T----ACAAC ACAGACACAT

              ....|....| ....|....| ....|....| ....|....| ....|....| ....|....|
                   725        735        745        755        765        775
NL/1/00 (p    ACTAGTTAAC AAAAAATACA AAATAACTCT AAGATAAACC ATGCAGACAC CAACAATGGA
BR/2/01 (A    ACTAGTTAAC AAAAAATACA AAATAACTCT AAGATAAACC ATGCAGACAC CAACAATGGA
FL/4/01 (A    ACTAGTTAAC AAAAAATACA AAATAACTCT AAGATAAACC ATGCAGACAC CAACAATGGA
FL/3/01 (A    ACTAGTTAAC AAAAAATACA AAATAACTCT AAGATAAACC ATGCAGACAC CAACAATGGA
FL/8/01 (A    ACTAGTTAAC AAAAAATACA AAATAACTCT AAGATAAACC ATGCAGACAC CAACAATGGA
FL/10/01 (    ACTAGTTAAC AAAAAATACA AAATAACTCT AAGATAAACC ATGTAGACAC CAACAATTGA
NL/10/01 (    ACTAGTTAAC AAAAAATATA AAATAACTCT AAGATAAACC ATGTAGACAC CAACAATTGA
NL/2/02 (A    ACTAGTTAAC AAAAAATATA CAATAACTCT AAGATAAACC ATGTAGACAC CAACAATTGA
NL/17/00 (    ATTAGTTAAC AAAAAATGCG AGATAGCTCT AAAGCAAAAC ATGTAGGTAC CAACAATCAA
NL/1/81 (A    ATTAGTTAAC AAAAAATACG AGATAGCTCT AAAGTAAAAC ATGTAGGTAC CAACAATCAA
NL/1/93 (A    ATTAGTTAAC AAAAAATACA AGATAGCTCT AAAGTAAAAC ATGTAGGTAC CAACAGTAAA
NL/2/93 (A    ATTAGTTAAC AAAAAATACA AGATAGCTCT AAAGTAAAAC ATGTAGGTAC CAACAGTAAA
NL/3/93 (A    ATTAGTTAAC AAAAAATATG AAATAGCTCT AAAGTAAAAC ATGTAGGTGC TAACAATCAA
NL/1/95 (A    ATTAGTTAAC AAAAAATATG AAATAGTTCT AAAGTAAAAC ATGTAGGTGC TAACAATCAA
NL/2/96 (A    ATTAGTTAAC AAAAAATACG AGATAGCTCT AAAGTAAAAC ATGTAGGCAC CAACAATCAG
NL/3/96 (A    ATTAGTTAAC AAAAAATATG AAATAGTTCT AAAGTAAAAC ATGTAGGTGC CAACAATCAA
NL/22/01 (    ATTAGTTAAC AAAAAATATG AAATAGCTCT AAAGTAAAAC ATGTAGGTGC CAACAATCAA
NL/24/01 (    ATTAGTTAAC AAAAAATATG AAATAGCTCT AAAGTAAAAC ATGTAGGTGC CAACAATCAA
NL/23/01 (    ATTAGTTAAC AAAAAATATG AAATAGCTCT AAAGTAAAAC ATGTAGGTGC CAACAATCAA
NL/29/01 (    ATTAGTTAAC AAAAAATACG AGATAGCTCT AAAGTAAAAC ATGTAGGCAC CAACAATCAA
NL/3/02 (A    ATTAGTTAAC AAAAAATACG AGATAGCTCT AAAGTAAAAC ATGTAGGCAC CAACAATCAA
NL/1/99 (p    CCCATCCAAG TAGTTA-ACA AAAAA-CCAC AAAATAA-CC TTGAAAAC-C AAAAAA--CC
NL/11/00 (    CTCATCCAAG TAGTTA-ACA AAAAA-CCAC AAAATAA-CC TTGAAAAC-C AAAAAA--CC
NL/12/00 (    CCCATCCAAG TAGTTA-ACA AAAAA----- ---------- ---------- ----------
NL/5/01 (B    CCCATCCAAG TAGTTA-ACA AAAAA-A--- ---------- ---------- ----------
NL/9/01 (B    CCCATCCAAG TAGTTA-ACA AAAAA----- ---------- ---------- ----------
```

Figure 19 con't

```
NL/21/01 (   CCCATCCAAG TAGTTA-ACA AAAAA----- ---------- ---------- ----------
NL/1/94  (p  CCTCTCCAAG TAGTTA-ACA AAAAAACTAT AAAATAA-TC ATGAAAAC-C GAAAAA-CTA
NL/1/82  (B  CTTCTCCAAG TAGTTA-ACA AAAAA-CTAT AAAATAA-CC ATGAAAAC-C AAAAAA-CTA
NL/1/96  (B  CTTCTCCAAG TAGTTA-ACA AAAAA-CTAT AAAATAA-CC ATGAAAAC-T AAAAAA-CTA
NL/6/97  (B  CTTTTCCAAG TAGTTA-ACA AAAAA-CTAT AAAATAA-CC ATGAAAAC-C AAAAAA-CTA
NL/9/00  (B  CTTCTCTAAG TAGTTA-ACA AAAAAACTAT AAAATAA-CC ATGAAAAC-C AAAAAA-CTA
NL/3/01  (B  CTTCTCCAAG TAGTTA-ACA AAAAAACTAT AAAATAA-CC ATGAAAAC-C AAAAAAACTA
NL/4/01  (B  CTTCTCCAAG TAGTTA-ACA AAAAAACTAT AAAATAA-CC ATGAAAAC-C AAAAAAACTA
UK/5/01  (B  CTTCTCTAAG TAGTTA-ACA AAAAAACTAT AAAATAA-CC ATGAAAAC-C AAAAAA-CTA

             ....|....| ....|....| ....|....| ....|....| ....|....| ....|....|
                 785        795        805        815        825        835
NL/1/00  (p  GAAGCCAAAA GACAATTCAC AATCTCCCCA AAAAGGCAAC AACACCATAT TAGC--TCTG
BR/2/01  (A  GAAGCCAAAA GACAATTCAC AATCTCCCCA AAAAGGCAAC AACACCATAT TAGC--TCTG
FL/4/01  (A  GAAGTCAAAA GACAATTCAC AATCTCCCCA AAAAGGCAAC AACACCATAT TAGC--TCTG
FL/3/01  (A  GAAGTCAAAA GACAATTCAC AATCTCCCCA AAAAGGCAAC AACACCATAT TAGC--TCTG
FL/8/01  (A  GAAGTCAAAA GACAATTCAC AATCTCCCCA AAAAGGCAAC AACACCATAT TAGC--TCTG
FL/10/01 (   GAAGCCAAAA GGCAATTCAC AATCTCCC-A AAAAAGCAAC AACACCATAT TAGC--TCCG
NL/10/01 (   GAAGCCAAAA GGCAATTCAC AATCTCCCCA AAAAGGCAAC AACACCATAT TAGC--TCCG
NL/2/02  (A  GAAGCCAAAA GGCAATTCAC AATCTCCCCA AAAAGGCAAC AACACCATAT TAGC--TCCG
NL/17/00 (   GAAACCAAAA GACAACTCAC AATCTCCCCA AAACAGCAAC GACACCATGT CAGC--TTTG
NL/1/81  (A  GGAATCAAAA GACAACTCAC AATCTCCCTA AAACAGCAAC GACACCATGT CAGC--TTTG
NL/1/93  (A  GAAATCAAAA GACAACTCAC AATCTCCCCA AAACAGCAAC AACATCATGT CAGT--TTTG
NL/2/93  (A  GAAATCAAAA GACAACTCAT AATCTCCCCA AAACAGCAAC AACATCATGT CAGC--TTCG
NL/3/93  (A  GAAATCAAAA GACATCTCAT AATCTCTCCA AAACAGCAAC AACATCATGT CAAC--TTTG
NL/1/95  (A  GAAATCAAAA GACAACTCAT AATCTCCCTA AAACAGCAAC AACATCATGT CAAC--TTTG
NL/2/96  (A  GAAATTAAAA GACAACTCAC AACCTCCCTA AAACAGCAAC GACACCATGT CAAC--TTTG
NL/3/96  (A  GAAATCAAAA GACAACTCAC AATCTCCCTA AAACAGCAAC AACATCATGC CAAC--TTTG
NL/22/01 (   GAAATCAAAA GATAACTCAT AATCTCTCTA AAACATCAAC AACATCATGT TAAC--TTTG
NL/24/01 (   GAAATCAAAA GATAACTCAT AATCTCTCTA AAACATCAAC AACATCATGT TAAC--TTTG
NL/23/01 (   GAAATCAAAA GATAACTCAT AATCTCTCTA AAACATCAAC AACATCATGT TAAC--TTTG
NL/29/01 (   GAAACCAAAA GATAACTCAC AATCCCCCCA AAACAGCAAC GACACCATGT CAGC--TTTG
NL/3/02  (A  GAAACCAAAA GATAACTCAC AATCCCCCCA AAACAGCAAC GACACCATGT CAGC--TTTG
NL/1/99  (p  A-----AAAC ATAAACCCAG A---CCCAGA AA--AACATA GACACCATAT GGAAGGTTCT
NL/11/00 (   A-----AACC ACAAACTTAG A---CCCAGA AA--AACATA GACACTATAT GGAAGGTTTG
NL/12/00 (   ---------- ------TCAG A---CCCAGA AA--AACATA GACACTATAT GGAAGGTCCG
NL/5/01  (B  ---------- ------TCAG A---CCCAGA AA--AACACA GACACTATAT GGAAGGTCCG
NL/9/01  (B  ---------- ------TCAG A---CCCAGA AA--AACATA GACACTATAT GGAAGGTCCG
NL/21/01 (   ---------- ------TCAG A---CCCAGA AA--AACATA GACACTATAT GGAAGGTCCG
NL/1/94  (p  G-----AAAA GTTAATTTGA A---CTCAGA AAAGAACACA AACACTATAT GAATTGTTTG
NL/1/82  (B  G-----AAAA GTAAATTTGA A---CTCAGA AAAGAACACA AACACTAAAT GAATTGTTTG
NL/1/96  (B  G-----AAAA GTTAATTTGA A---CTCAGA AAAGAACACA AACACTATAT GAATTGTTTG
NL/6/97  (B  G-----AAAA GTTAATTTGA A---CTCAGA AAAGAACACA AACACTATAT GAATTGTTTG
NL/9/00  (B  G-----AAAA GTTAATTTGA A---CTCAGA AAAGAACACA AACACTATAT GAATTATTTG
NL/3/01  (B  G-----AAAA GTTAATTTGA A---CTCAGA AAAGAACACA AACACTATAT GAATTGTTTG
NL/4/01  (B  G-----AAAA GTTAATTTGA A---CTCAGA AAAGAACACA AACACTATAT GAATTGTTTG
UK/5/01  (B  G-----AAAA GTTAATTTGA A---CTCAGA AAGGAACACA AACACTATAT GAATTATTTG

             ....|....| ....|....| ....|....| ....|....| ....|....| ....|....|
                 845        855        865        875        885        895
NL/1/00  (p  CCCAAATCTC CCTGGAAAA- AACACTCGCC CATATACCAA AAATACCACA ACCACCCCAA
BR/2/01  (A  CCCAAATCTC CCTGGAAAA- AACACTCGCC CATATACCAA AAATACCACA ACCACCCCAA
FL/4/01  (A  CCCAAATCTC CCTGGAAAA- AACACTCGCC CATATACCAA AAATACCACA ACCACCCCAA
FL/3/01  (A  CCCAAATCTC CCTGGAAAA- AACACTCGCC CATATACCAA AAATACCACA ACCACCCCAA
FL/8/01  (A  CCCAAATCTC CCTGGAAAA- AACACTCGCC CATATACCAA AAATACCACA ACCACCCCAA
FL/10/01 (   CTTAAATCTC CCTGAAAAA- AACACTCACC CATATACCAA CTATACCACA ACCATCCCAA
NL/10/01 (   CTTAAATCTC CCTGGAAAA- AACACTCGCC CATATACCAA CTATACCACA ACCATCCCAA
NL/2/02  (A  CTTAAGTCTC CCTGGAAAA- AACACTCGCC CATATACCAA CTATACCACA ACCATCCAAA
NL/17/00 (   CTCAAATCTC TCTGGGAGA- AACTTCTACC CACATACTAA CAACATCACA ACCATCTCAA
NL/1/81  (A  CTCAAATCTC CCTGGGAGA- AACTTTCGCC CACATACTAA CAACATCACA ACCATCTCAA
NL/1/93  (A  CTCAAATCTC CCTGGGAGA- AACTCTCGCC CACATACTAA CAACATCACA ACTATCTCAA
```

Figure 19 con't

```
NL/2/93 (A    CTCAAATCTC CCTGGGAGA- AACTCTCGCC CACATACTAA CAACATCACA ACTATCTCAA
NL/3/93 (A    CTCAAATCTC CCTGGGAGA- AACTTTCGCC CCCATACTGA CAACATCACA ATCATCTCAA
NL/1/95 (A    CTCAAATCTC CCTGGGAGA- AACTTTCGCC CCCATACTGA CAACATCACA ATCATCTCAA
NL/2/96 (A    CTCAAATCTC TCTGGGAGA- AACTTTTGCC CACATACTAA CAACATCACA ATCATCTCAA
NL/3/96 (A    CTCAAATCTC CCTGGGAGA- AACCCTCGCC CCCATACTGA CAACATCACA ATCATCTCAA
NL/22/01 (    CTCAAATCTC TCTGGGAGA- AACCTTCGCC CCCATACTGG CAACATCACA ATCATCTCAA
NL/24/01 (    CTCAAATCTC TCTGGGAGA- AACCTTCGCC CCCATACTGG CAACATCACA ATCATCTCAA
NL/23/01 (    CTCAAATCTC TCTGGGAGA- AACCTTCGCC CCCATACTGG CAACATCACA ATCATCTCAA
NL/29/01 (    CTCAAATCTC TCTGGGAGA- AACTTTTGCC CACATACTAA CAACATCACA ACCATCTCAA
NL/3/02 (A    CTCAAATCTC TCTGGGAGA- AACTTTTGCC CACATACTAA CAACATCACA ACCATCTCAA
NL/1/99 (p    AGCATATGCA CCAATGAGAT GGCATCTGTT CATGTATCAA TAGCACCACC ATCAT-TCAA
NL/11/00 (    AGCATATGCA CCAATGAAAT GGTATCTGTT CATGTATCAA TAGCGCCACC ATTAT-TTAA
NL/12/00 (    AGCATATGCA CCGATGAAAT GGCATTTGTT CATGTATCAA TAGCGCCACC ATTAT-TTAA
NL/5/01 (B    AGCATATGCA CCGATGAAAT GGCATCTGTT CATGTATCAA TAGCACCACC ATTAT-TTAA
NL/9/01 (B    AGCATATGCA CCGATGAAAT GGCATCTGTT CATGTATCAA TAGCGCCACC ATTAT-TTAA
NL/21/01 (    AGCATATGCA CCGATGAAAT GGCATCTGTT CATGTATCAA TAGCGCCACC ATTAT-TTAA
NL/1/94 (p    AGCGTATATA CTAATGAAAT AGCATCTGTT TGTGCATCAA TAATACCATC ATTAT-TTAA
NL/1/82 (B    AGCATATATA CTAATGAAAT AGCATCTGTT CATGCATCAA TAATACCATC ATTAC-TTAA
NL/1/96 (B    AGCGTATATA CTAATGAAAT AGCATCTGTT TGTGCATCAA TAATACCATC ATTAT-TTAA
NL/6/97 (B    AGCGTATATA CTAATGAAAT AGCATCTGTT TGTGCATCAA TAATACCATC ATTAT-TTAA
NL/9/00 (B    AGCGTATATA CTAATGAAAT AGCATCTGTT TGTGCATCAA TAATACCATC ATTAT-TTAA
NL/3/01 (B    AGCGTATATA CTAATGAAAT AGCATCTGTT TGTGCATCAA TAATACCATC ATTAT-TTAA
NL/4/01 (B    AGCGTATATA CTAATGAAAT AGCATCTGTT TGTGCATCAA TAATACCATC ATTAT-TTAA
UK/5/01 (B    AGCGTATATA CTAATGAAAT AGCATCTGTT TGTGCATCAA TAATACCATC ATTAT-TTAA

              ....|....| ....|....| ....|....
                 905        915        925
NL/1/00 (p    GAAAAAAA-C TGGGCAAAAC AACACCCAA
BR/2/01 (A    GAAAAAAA-C TGGGCAAAAC AACACCCAA
FL/4/01 (A    GAAAAAAA-C TGGGCAAAAC AACACCCAA
FL/3/01 (A    GAAAAAAA-C TGGGCAAAAC AACACCCAA
FL/8/01 (A    GAAAAAAA-C TGGGCAAAAC AACACCCAA
FL/10/01 (    GAAAAAAGGC TGGGCAAAAC AACACCCAA
NL/10/01 (    GGAAAAAAGC TGGGTAAAAC AACACCCAA
NL/2/02 (A    GAAAAAAAGC TGGGCAAAAC AACACCCAA
NL/17/00 (    GAAAAGAAAC TGGGCAAAAC AGCATCCAA
NL/1/81 (A    GAAAAGAAAC TGGGCAAAAC AGCACCCAA
NL/1/93 (A    GAAAAGAAAC TGGGCAAAAA AACACTCAA
NL/2/93 (A    GAAAAGAAAC TGGGCAAAAA AACACTCAA
NL/3/93 (A    GAAAAGAAAC TGGGCAAAAC AGCACCAAA
NL/1/95 (A    GAAAAGAAAC TGGGCAAAAC AGCACCAAA
NL/2/96 (A    GAAAAGAAAC TGGGCAAAAC AGCATCCAA
NL/3/96 (A    GAAAAGAAAC TGGGCAAAAC AGCACCAAA
NL/22/01 (    GAAAAGAAAC TGGGCAAAAC AACACCAAA
NL/24/01 (    GAAAAGAAAC TGGGCAAAAC AACACCAAA
NL/23/01 (    GAAAAGAAAC TGGGCAAAAC AACACCCAA
NL/29/01 (    GAAAAGAAAC TGGGCAAAAC AGCATCCAA
NL/3/02 (A    GAAAAGAAAC TGGGCAAAAC AGCATCCAA
NL/1/99 (p    GGAATAAGAA GAGGCGAAA- ---ATTTAA
NL/11/00 (    GGAATAAGAA GAGGCAAAA- ---ATTCAA
NL/12/00 (    GGAATAAGAA GAGGCAAAA- ---ATTCAA
NL/5/01 (B    GGAATAAGAA GAGGCAAAA- ---ATTCAA
NL/9/01 (B    GGAATAAGAA GAGGCAAAA- ---ATTCAA
NL/21/01 (    GGAATAAGAA GAGGCAAGA- ---ATTCAA
NL/1/94 (p    GAAATAAGAA GAAGCTAAA- ---ATTCAA
NL/1/82 (B    GAAATAAGAA GAAGCAAAA- ---ATTCAA
NL/1/96 (B    GAAATAAGAA GAAGCTAAA- ---ATTCAA
NL/6/97 (B    GAAATAAGAA GAAGCTAAA- ---ATTCAA
NL/9/00 (B    GAAATAAGAA GAAGCTAAA- ---ATTCAA
NL/3/01 (B    GAATTAAGAA GAAGCTAAA- ---ATTCAA
NL/4/01 (B    GAATTAAGAA GAAGCTAAA- ---ATTCAA
```

Figure 19 con't

UK/5/01 (B GAAATAAGAA GAAGCTAAA- ---ATTCAA

Figure 19 con't

Alignment: G Protein

```
              ....|....| ....|....| ....|....| ....|....| ....|....| ....|....|
                  5         15         25         35         45         55
NL/1/00  (p   MEVKVENIRT IDMLKARVKN RVARSKCFKN ASLVLIGITT LSIALNIYLI INYKMQKNTS
BR/2/01  (A   MEVKVENIRT IDMLKASVKN RVARSKCFKN ASLVLIGITT LSIALNIYLI INYKMQKNTS
FL/4/01  (A   MEVKVENIRT IDMLKARVKN RVARSKCFKN ASLVLIGITT LSIALNIYLI INYKMQKNTS
FL/3/01  (A   MEVKVENIRT IDMLKARVKN RVARSKCFKN ASLVLIGITT LSIALNIYLI INYKMQKNTS
FL/8/01  (A   MEVKVENIRT IDMLKARVKN RVARSKCFKN ASLVLIGITT LSIALNIYLI INYKMQKNTS
FL/10/01 (    MEVKVENIRT IDMLKARVKN RVARSKCFKN ASLILIGITT LSIALNIYLI INYTMQENTS
NL/10/01 (    MEVKVENIRT IDMLKARVKN RVARSKCFKN ASLILIGITT LSIALNIYLI INYTMQENTS
NL/2/02  (A   MEVKVENIRT IDMLKARVKN RVARSKCFKN ASLILIGITT LSIALNIYLI INYTMQENTS
NL/17/00 (    MEVKVENIRA IDMLKARVKN RVARSKCFKN ASLILIGITT LSIALNIYLI INYTIQKTTS
NL/1/81  (A   MEVKVENIRA IDMLKARVKN RVARSKCFKN ASLILIGITT LSIALNIYLI INYTIQKTTS
NL/1/93  (A   MEVKVENIRA VDMLKARVKN RVARSKCFKN ASLILVGITT LSIALNIYLI VNYTIQKTTS
NL/2/93  (A   MEVKVENIRA VDMLKARVKN RVARSKCFKN ASLILVGITT LSIALNIYLI VNYTIQKTTS
NL/3/93  (A   MEVKVENIRA IDMLKARMKN RVARSKCFKN ASLILIGITT LSIALNIYLI INYTIQKTTS
NL/1/95  (A   MEVKVENIRA IDMLKARVKN RVARSKCFKN ASLILIGITT LSIALNIYLI INYTIQKTTS
NL/2/96  (A   MEVKVENIRA IDMLKARVKN RVARSKCFKN ASLILIGITT LSIALNIYLI INYTIQKTTS
NL/3/96  (A   MEVKVENIRA IDMLKARVKN RVARSKCFKN ASLILIGITT LSIALNIYLI INYTIQKTTS
NL/22/01 (    MEVKVENIRA IDMLKARVKN RVARSKCFKN ASLILIGITT LSIALNIYLI INYTIQKTTS
NL/24/01 (    MEVKVENIRA IDMLKARVKN RVARSKCFKN ASLILIGITT LSIALNIYLI INYTIQKTTS
NL/23/01 (    MEVKVENIRA IDMLKARVKN RVARSKCFKN ASLILIGITT LSIALNIYLI INYTIQKTTS
NL/29/01 (    MEVKVENIRA IDMLKARVKN RVARSKCFKN ASLILIGITT LSIALNIYLI INYTIQQTTS
NL/3/02  (A   MEVKVENIRA IDMLKARVKN RVARSKCFKN ASLILIGITT LSIALNIYLI INYTIQKTTS
NL/1/99  (p   MEVRVENIRA IDMFKAKIKN RIRSSRCYRN ATLILIGLTA LSMALNIFLI IDHATLRNMI
NL/11/00 (    MEVRVENIRA IDMFKAKIKN RIRSSRCYRN ATLILIGLTA LSMALNIFLI IDHATLRNMI
NL/12/00 (    MEVRVENIRA IDMFKAKIKN RIRSSRCYRN ATLILIGLTA LSMALNIFLI IDHATLRNMI
NL/5/01  (B   MEVRVENIRA IDMFKAKIKN RIRSSRCYRN ATLILIGLTA LSMALNIFLI IDHATLRNMI
NL/9/01  (B   MEVRVENIRA IDMFKAKIKN RIRSSRCYRN ATLILIGLTA LSMALNIFLI IDHATLRNMI
NL/21/01 (    MEVRVENIRA IDMFKAKIKN RIRSSRCYRN ATLILIGLTA LSMALNIFLI IDHATLRNMI
NL/1/94  (p   MEVRVENIRA IDMFKAKMKN RIRSSKCYRN ATLILIGLTA LSMALNIFLI IDYAMLKNMT
NL/1/82  (B   MEVRVENIRT IDMFKAKMKN RIRSSKCYRN ATLILIGLTA LSMALNIFLI IDYATFKNMT
NL/1/96  (B   MEVRVENIRA IDMFKAKMKN RIRSSKCYRN ATLILIGLTA LSMALNIFLI IDYAMLKNMT
NL/6/97  (B   MEVRVENIRA IDMFKAKMKN RIRSSKCYRN ATLILIGLTA LSMALNIFLI IDYATLKNMT
NL/9/00  (B   MEVRVENIRA IDMFKAKMKN RIRSSKCYRN ATLILIGLTA LSMALNIFLI IDYATLKNMT
NL/3/01  (B   MEVRVENIRA IDMFKAKMKN RIRSSKCYRN ATLILIGLSA LSMALNIFLI IDYAKSKNMT
NL/4/01  (B   MEVRVENIRA IDMFKAKMKN RIRSSKCYRN ATLILIGLSA LSMALNIFLI IDYAKSKTMT
UK/5/01  (B   MEVRVENIRA IDMFKAKMKN RIRSSKCYRN ATLILIGLTA LSMALNIFLI IDYATLKNMT

              ....|....| ....|....| ....|....| ....|....| ....|....| ....|....|
                  65         75         85         95        105        115
NL/1/00  (p   ESEHHTSSSP MESSRETPTV PTDNSDTNSS PQHPTQQSTE GSTLYFAASA SSPETEPTST
BR/2/01  (A   ESEHHTSSSP MESSRETPTV PTDNSDTNSS PQHPTQQSTE GSTLYFAASA SSPETEPTST
FL/4/01  (A   ESEHHTSSSP MESSRETPTV PTDNSDTNSS PQHPTQQSTE GSTLYFAASA NSPETEPTST
FL/3/01  (A   ESEHHTSSSP MESSRETPTV PTDNSDTNSS PQHPTQQSTE GSTLYFAASA NSPETEPTST
FL/8/01  (A   ESEHHTSSSP MESSRETPTV PTDNSDTNSS PQHPTQQSTE GSTLYFAASA SSPETEPTST
FL/10/01 (    ESEHHTSSSP MESSRETPTV PIDNSDTNPG SQYPTQQSTE DSTLHSAASA SSPETEPTST
NL/10/01 (    ESEHHTSSSP MESSRETPTV PMDNSDTNPG SQYPTQQSTE GSTLHFAASA SSPETEPTST
NL/2/02  (A   ESEHHTSSSP MESSRETPTV PMDNSDTNPG SQYPTQQSTE GSTLHFAASA SSPETEPTST
NL/17/00 (    ESEHHTSSPP TEPNKEASTI STDNPDINPS SQHPTQQSTE NPTLNPAASA SPSETEPAST
NL/1/81  (A   ESEHHTSSPP TESNKETSTI PIDNPDINPN SQHPTQQSTE SPTLNPAASV SPSETEPAST
NL/1/93  (A   ESEHHTSSSP TESNKGTSTI PTDNPDINPN SQHPTQQSTE SPTLNTAASV SPSETEPAST
NL/2/93  (A   ESEHHTSSSP TESNKGTSTI XTDNPDINPN SQHPTQQSTE SPTLNTAASV SPSETEPAST
NL/3/93  (A   ESEHHTSSPP TESNKETSTI PIDNPDINPN SQHPTQQSTE SLTLNPAASV SPSETEPAST
NL/1/95  (A   ESEHHTSSPP TESNKETSTI SIDNPDINPN SQHPTQQSTE SLTLSPTASV SPSETEPAST
NL/2/96  (A   ESEHHTSSPP TESNKEASTI STDNPDINPN SQHPTQQSTE NPTLNPAASV SSSETEPAST
NL/3/96  (A   ESEHHTSSPP TESNKETSTI SIDNSDINPN SQHPTQQSTE SLTLSPTASV SPSETEPAST
NL/22/01 (    ESEHHTSSPP TESNKETSTI PIDNPDINPN SQHPTQQSTE SLTLYPTSSV SSSETEPAST
```

FIGURE 20

```
NL/24/01 (   ESEHHTSSPP TESNKETSTI PIDNPDINPN SQHPTQQSAE SLTLYPTSSV SSSETEPAST
NL/23/01 (   ESEHHTSSPP TESNKETSTI PIDNPDINPN SQHPTQQSTE SLTLYPTSSV SSSETEPAST
NL/29/01 (   ESEHHTSSPP TESNKEASTI STDNPDINPN SQHPTQQSTE NPTLNPAASA SPSETESAST
NL/3/02  (A  ESEHHTSSPP TESNKEASTI STDNPDINPN SQHPTQQSTE NPTLNPAASA SPSETESAST
NL/1/99  (p  KTENCANMPS AEPSKKTPMT STAGPNTKPN PQQATQWTTE NSTSPVATPE GHPYTGTTQT
NL/11/00 (   KTENCANMPS AEPSKKTPMT STAGPSTEPN PQQATQWTTE NSTSPAATLE SHPYTGTTQT
NL/12/00 (   KTENCANMPP AEPSKKTPMT STAGPNTKPN PQQATQWTTE NSTFPAATSE GHLHTGTTQT
NL/5/01  (B  KTENCANMPP AEPSRKTPMT STAGPNTKPN PQQATQWTTE NSTSPAATPE GHLHTGTTQT
NL/9/01  (B  KTENCANMPP AEPSKKTPMT STAGLNTKPN PQQATQWTTE NSTSPAATPE GHLHTGTTQT
NL/21/01 (   KTENCANMPP AEPSKKTPMT STAGPNTKPN PQQATQWTTE NSTSPAATPE GHLHTGTTQT
NL/1/94  (p  KVEHCVNMPP VEPSKKTPMT SAVDLNTKPN PQQATQLAAE DSTSLAATSE DHLHTGTTPT
NL/1/82  (B  KVEHCANMPP VEPSKKTPMT STVDSSTGPN PQQTTQWTTE DSTSLAATSE DHLHTGTTPT
NL/1/96  (B  KVEHCVNMPP VEPSKKTPMT SAVDLNTKLN PQQATQLTTE DSTSLAATSE DHLLTGTTPT
NL/6/97  (B  KVEHCVNMPP VEPSKKTPMT SAVDLNTKLN PQQATQLTTE DSTSLAATSE GHPHTGTTPT
NL/9/00  (B  KVEHCVNMPP VEPSKKTPMT SAVDSNTKPN PQQATQLTTE DSTSLAATLE DHPHTGTTPT
NL/3/01  (B  RVEHCVNMPP VEPSKKTPMT SAVDLNTKPN PQRATQLTTE DSTSLAATLE GHLHTGTTPT
NL/4/01  (B  RVEHCVNMPP VEPSKKTPMT SAVDLNTKPN PQQATQLTTE DSTSPAATLE GHLHTGTTPT
UK/5/01  (B  KVEHCVNMPP VEPSKKTPMT SAVDLNTKPN PQQATQLTTE DSTSLAATLE DHPHTGTTPT

             ....|....| ....|....| ....|....| ....|....| ....|....| ....|....|
                125        135        145        155        165        175
NL/1/00  (p  PDTTNRPPFV DTHTTPPSAS RTKTSPAVHT KNNPRTSSR- -----THSPP RATTRTARRT
BR/2/01  (A  PDTTNRPPFV DTHTTPPSAS RTKTSPAVHT KNNPRTSSR- -----THSPP RATTRTARRT
FL/4/01  (A  PDTTNRPPFV DTHTTPPSAS RTKTSPAVHT KNNPRISSR- -----THSPP WATTRTARRT
FL/3/01  (A  PDTTDRPPFV DTHTTPPSAS RTKTSPAVHT KNNPRISSR- -----THSPP WATTRTARRT
FL/8/01  (A  PDTTDRPPFV DTHTTPPSAS RTKTSPAVHT KNNPRISSR- -----THSPP WATTRTARRT
FL/10/01 (   PDTTSRPPFV DTHTTPPSAS RTRTSPAVHT KNNPRVSPR- -----THSPP WAMTRTVRGT
NL/10/01 (   PDTTSRPPFV DTHTTPSSAS RTKTSPAVHT KNNLRISPR- -----THSPP WAMTRTVRGT
NL/2/02  (A  PDTTSRPPFV DTHTTPSSAS RIRTSPAVHT KNNLRISPR- -----THSPP WAMTRTVRGT
NL/17/00 (   PDTTNRLSSV DRSTAQPSES RTKTKPTVHT INNPNTASS- -----TQSPP RTTTKAIRRA
NL/1/81  (A  PDTTNRLSSV DRSTTQPSES RTKTKPTVHT KNNPSTVSR- -----TQSPL RATTKAVLRA
NL/1/93  (A  PDTTNRLSSA DRSTTQPSES RTKTKLTVHT KNNLSTASR- -----TQSPP RATTKAVLRD
NL/2/93  (A  PDTTNRLSSA DRSTTQPSES RTKTKLTVHT KNNLSTASR- -----TQSPP RATTKAVLRD
NL/3/93  (A  PDTTNRLSSV DRSTTQPSES RTKTKLTVHK KNIPSTVSR- -----TQSSI RATTKAVLRA
NL/1/95  (A  SDTTSRLSSV DRSTTQPSES RARTKPTVHK KNIPSTVSR- -----TQSPL RATTKAVLRA
NL/2/96  (A  PDTTNRLSSV DRSTAQPSES RTKTKPTVHT RNNPSTASS- -----TQSPP RVTTKAILRA
NL/3/96  (A  SDTTNRLSSV DRSTTQPSES RARTKPTVHK KNIPSTVSR- -----TQSPL RATTKAVLRA
NL/22/01 (   PGITNHLSFV DRSTTQPSES RTKTNRTVHK KNISSTVSR- -----TQSPP RTTAKAVPRA
NL/24/01 (   PGITNHLSFV DRSTTQPSES RTKTNRTVHK KNISSTVSR- -----TQSPP RTTAKAVPRA
NL/23/01 (   PGITNHLSFV DRSTTQPSES RTKTNRTVHK KNISSTVSR- -----TQSPP RTTAKAVPRA
NL/29/01 (   PDTTNRLSSV DRSTVQPSEN RTKTKLTVHT RNNLSTASS- -----TQSPP RATTKAIRRA
NL/3/02  (A  PDTTNRLSSV DRSTVQPSEN RTKTKLTVHT RNNLSTASS- -----TQSPP RATTKAIRRA
NL/1/99  (p  SDTTAPQQTT DKHTAPLKST NEQITQTTTE KKTIRATTQK REKGKENTNQ TTSTAATQTT
NL/11/00 (   PDITAPQQTT DKHTALPKST NEQITQTTTE KKTTRATTQK REKEKENTNQ TTSTAATQTT
NL/12/00 (   PDTTAPQQTT DKHTALPKST NEQITQTTTE KKTTRATTQR REKGKENTNQ TTSTAATQTT
NL/5/01  (B  PDTTAPQQTT DKHTALPKST NEQITQATTE KKTTRETTQR REKGKENTNQ TTSTAATQTT
NL/9/01  (B  PDTTAPQQTT DKHTALPKST NEQITQTTTE KKTTRATTQR REKGKENTNQ TTSTAATQTT
NL/21/01 (   PDTTAPQQTT DKHTALPKST NEQITQTTTE KKTTRATTQR REKGKENTNQ TTSTAATQTT
NL/1/94  (p  PDATVSQQTT DEYTTLLRST NRQTTQTTTE KKPTGATTK- ----KETTTR TTSTAATQTL
NL/1/82  (B  LDATVSQQTP DKHTTPLRST NGQTTQTTTE KKPTRAIAK- ----KETTNQ TTSTAATQTF
NL/1/96  (B  PDATVSQQTT DEHTTLLRST NRQTTQTTTE KKPTGATTK- ----KETTTR TTSTAATQTL
NL/6/97  (B  PDATVSQQTT DEHTTLLRST NRQTTQTATE KKPTGATTK- ----KETTTR TTSTAATQTP
NL/9/00  (B  PDATVSQQTT DEHTTLLRST NRQTTQTTAE KKPTRATTK- ----KETTTR TTSTAATQTL
NL/3/01  (B  PDVTVSQQTT DEHTTLLRST NRQTTQTAAE KKPTRVTTN- ----KETITR TTSTAATQTL
NL/4/01  (B  PDATVSQQTT DEHTTLLRST NRQTTQTTAE KKPTRATTK- ----KETITR TTSTAATQTL
UK/5/01  (B  PDATVSQQTT DEHTTLLRST NRQTTQTTAE KKPTRATTK- ----KETTTR TTSTAATQTL

             ....|....| ....|....| ....|....| ....|....| ....|....| ....|....|
                185        195        205        215        225        235
NL/1/00  (p  TTLRTSSTRK RPSTASVQPD ISATTHKNEE ASPASPQTSA STTRIQRKSV EANTSTTYNQ
BR/2/01  (A  TTLRTSSTRK RPSTASVQPD ISATTHKNEE ASPASPQTSA STTRIQRKSV EANTSTTYNQ
```

Figure 20 con't

```
FL/4/01 (A    TTLRTSSTRK RPSTASAQPD ISATTHKNEE ASPASPQTSA STTRTQRKSV EANTSTTYNQ
FL/3/01 (A    TTLRTSSTRK RPSTASVQPD ISATTHKNEE ASPASPQTSA STTRTQRKSV EANTSTTYNQ
FL/8/01 (A    TTLRTSSTRK RPSTASVQPD ISATTHKNEE ASPASPQTSA STTRTQRKSV EANTSTTYNQ
FL/10/01 (    TTLRTSSTRK RLSTASVQPD SSATTHKHEE TSPVSPQTSA STARPQRKGM EASTSTTYNQ
NL/10/01 (    TTLRTSSIRK RPSTASVQPD SSATTHKHEE ASPVSPQASA STARPQRKGM EASTSTTYNQ
NL/2/02 (A    TTLRTSSIRK RPSTASVQPD SSATTHKHEE ASPVSPQASA STARPQRKGM EASTSTTYNQ
NL/17/00 (    TTFRMSSTGK RPTTTLVQSD SSTTTQNHEE TGSANPQASA STMQN----- ----HTNNIK
NL/1/81 (A    TAFRTSSTRK RPTTTSVQSD SSTTTQNHEE TSSANPQASA STMQSQ---- ----HTNNIK
NL/1/93 (A    TAFHTSSTGK RPTTTSVQSG SSTTTQNHEE TSSSNPQASA STMQDQ---- ----DTNNTK
NL/2/93 (A    TAFHTSSTGK RPTTTSVQSG SSTTTQNHEE TSSSNPQASA STMQDQ---- ----DTNNTK
NL/3/93 (A    TAFRTSSTGE RPTTTSVQSD SSTTTQNHEE TGSANPQASA STMQN----- ----HTNIVK
NL/1/95 (A    TAFRTSSTGE GPTTTSVQSD SSTTTQNHEE TGSANPQASA STMQN----- ----HTNIVK
NL/2/96 (A    TVFRMSSTGK RPATTLVQSD SSTTTQNHEE TGSANSQASA STMQN----- ----HSNNIK
NL/3/96 (A    TAFRMSSTGE GPTTTSVQSD SSTTTQNHEE TGSANPQASA STMQNQ---- ----HTNIAK
NL/22/01 (    TALRTSSTGE RPTTTPVQPD SSTTTQNHEE TGSANPQASA STMQNQ---- ----HTNIAR
NL/24/01 (    TALRTSSTGE RPTTTPVQPD SSTTTQNHEE TGSANPQASA STMQNQ---- ----HTNIAR
NL/23/01 (    TALRTSSTGE RPTTTPVQPD SSTTTQNHEE TGSANPQASA STMQNQ---- ----HTNIAR
NL/29/01 (    TTLRMSSTGR RPTTTLVQSD SSTTTQNHEE TGSANPQASA STMQNQ---- ----HTNNIK
NL/3/02 (A    TTLRMSSTGR RPTTTLVQSD SSTTTQNHEE TGSANPQASA STMQNQ---- ----HTNNIK
NL/1/99 (p    NTTNQIRNAS ETITTSDRPR TDTTTQSSEQ TTRATDPSSP PHHAR----- ----GAKLK-
NL/11/00 (    NTTNQTRNAS ETITTSDRPR IDTTTQSSDQ TTRATDPSSP PHHAQS---- ----GAKPK-
NL/12/00 (    NTTNQIRNAS ETITTSDRPR TDSTTQSSEQ TTRATDPSSP PHHAQG---- ----SAKPK-
NL/5/01 (B    NTTNQIRNAS ETITTSDRPR TDSTTQSSEQ TTQATDPSSP AHHAQG---- ----SAKPK-
NL/9/01 (B    NTTNQIRNAS ETITTSDRPR TDSTTQSSEQ TTRATDPSSP PHHAQG---- ----SAKPK-
NL/21/01 (    NTTNQIRNAI ETITTSDRPR TDSTTQSSEQ TTRATDPSSH PHHAQG---- ----SAKPK-
NL/1/94 (p    NTTNQTSYVR EATTTSARSR NSATTQSSDQ TTQAADPSSQ PHHTQK---- ----STTTTY
NL/1/82 (B    NTTNQTRNGR ETTITSARSR NDATTQSSEQ TNQTTDPSSQ PHHAIS---- ----TITITQ
NL/1/96 (B    NTTNQTSNGR EATTTSTRSR NGATTQNSDQ TT-TADPSSQ PHHTQK---- ----STTTTY
NL/6/97 (B    NTTNQTSNGR EATTTSARSR NGATTQNSDQ ITQAADSSSQ PHHTQK---- ----STTTAY
NL/9/00 (B    NTTNQTSNGR EATTTSARSR NNATTQSSDQ TTQAAEPSSQ SQHTQK---- ----STTTTY
NL/3/01 (B    NTTNQTNNGR EATTTSARSR NNATTQSSDQ TTQAADPSSQ SQHTQK---- ----SITTTY
NL/4/01 (B    NTTNQTSNGR EATTTSARSR NNATTQSSDQ TTQAADPSSQ SQHTKK---- ----STTTTY
UK/5/01 (B    NTTNQTSNGR EATTTSARSR NNATTQSSDQ TTQAAEPNSQ SQHTQK---- ----STTTTY

              ....|....
                245
NL/1/00 (p    TS-------
BR/2/01 (A    TS-------
FL/4/01 (A    TS-------
FL/3/01 (A    TS-------
FL/8/01 (A    TS-------
FL/10/01 (    TS-------
NL/10/01 (    TS-------
NL/2/02 (A    TS-------
NL/17/00 (    PN-------
NL/1/81 (A    PN-------
NL/1/93 (A    QN-------
NL/2/93 (A    QN-------
NL/3/93 (A    PN-------
NL/1/95 (A    PN-------
NL/2/96 (A    PN-------
NL/3/96 (A    PN-------
NL/22/01 (    PN-------
NL/24/01 (    PN-------
NL/23/01 (    PN-------
NL/29/01 (    PN-------
NL/3/02 (A    PN-------
NL/1/99 (p    ---------
NL/11/00 (    ---------
NL/12/00 (    ---------
NL/5/01 (B    ---------
```

Figure 20 con't

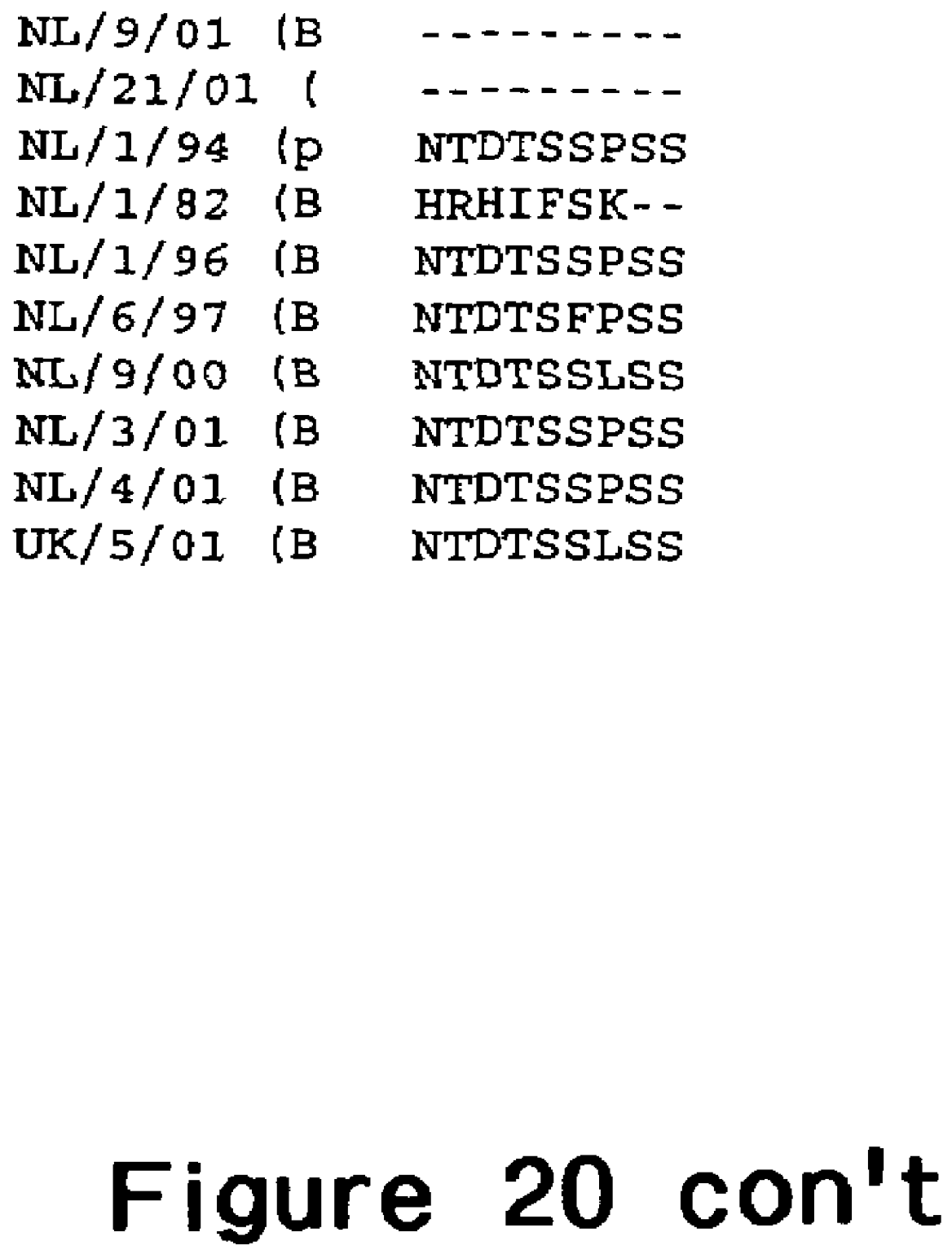

```
NL/9/01   (B    ----------
NL/21/01  (     ---------
NL/1/94   (p    NTDTSSPSS
NL/1/82   (B    HRHIFSK--
NL/1/96   (B    NTDTSSPSS
NL/6/97   (B    NTDTSFPSS
NL/9/00   (B    NTDTSSLSS
NL/3/01   (B    NTDTSSPSS
NL/4/01   (B    NTDTSSPSS
UK/5/01   (B    NTDTSSLSS
```

Figure 20 con't

Phylogenetic analysis of hMPV F sequences

Phylogenetic analysis of G sequences

AccI

CATATTGTAATACGACTCACTATAGGACGGCAAAAAAACCGTATACATCCAATTATAATTTCTTATTTTTAATAAA 76
GTATAACATTATGCTGAGTGATATCCTGCCGTTTTTTTGGCATATGTAGGTTAATATTAAAGAATAAAAATTATTT

P-T7 Tr

PacI

CTTAATGACAGTTGTTAGTTTCTAACTTTTGATTTTTAGTTTTTAATTAACTATTACATAATTGCATAATCAAATG 152
GAATTACTGTCAACAATCAAAGATTGAAAACTAAAAATCAAAAATTAATTGATAATGTATTAACGTATTAGTTTAC

Tr

ATTACTTTGGAATAGTATGAAGTTGTCACCTATTTTATCATTTTTATCATTTTTTACGCCCCGCCCTGCCACTCAT 228
TAATGAAACCTTATCATACTTCAACAGTGGATAAAATAGTAAAAATAGTAAAAAATGCGGGGCGGGACGGTGAGTA

Tr A G G Q W E D
CAT

ScaI

CGCAGTACTGTTGTAATTCATTAAGCATTCTGCCGACATGGAAGCCATCACAAACGGCATGATGAACCTGAATCGC 304
GCGTCATGACAACATTAAGTAATTCGTAAGACGGCTGTACCTTCGGTAGTGTTTGCCGTACTACTTGGACTTAGCG

C Y Q Q L E N L M R G V H F G D C V A H H V Q I A
CAT

SspI NcoI

CAGCGGCATCAGCACCTTGTCGCCTTGCGTATAATATTTGCCCATGGTGAAAACGGGGGCGAAGAAGTTGTCCATA 380
GTCGCCGTAGTCGTGGAACAGCGGAACGCATATTATAAACGGGTACCACTTTTGCCCCCGCTTCTTCAACAGGTAT

L P M L V K D G Q T Y Y K G M T F V P A F F N D M
CAT

MscI DraI BsmBI

TTGGCCACGTTTAAATCAAAACTGGTGAAACTCACCCAGGGATTGGCTGAGACGAAAAACATATTCTCAATAAACC 456
AACCGGTGCAAATTTAGTTTTGACCACTTTGAGTGGGTCCCTAACCGACTCTGCTTTTTGTATAAGAGTTATTTGG

N A V N L D F S T F S V W P N A S V F F M N E I F G
CAT

FIGURE 24

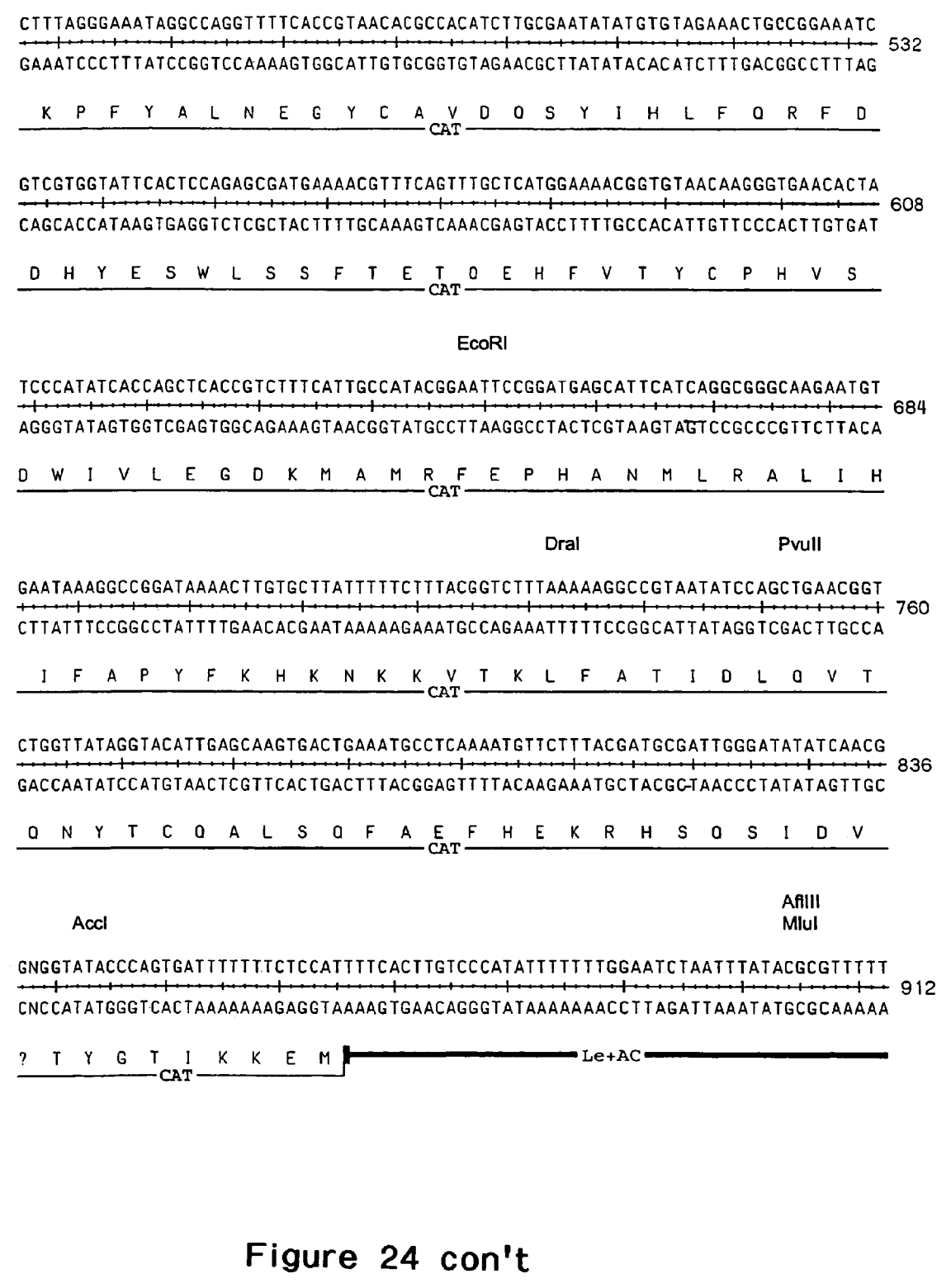

```
CTTTAGGGAAATAGGCCAGGTTTTCACCGTAACACGCCACATCTTGCGAATATATGTGTAGAAACTGCCGGAAATC
                                                                              532
GAAATCCCTTTATCCGGTCCAAAAGTGGCATTGTGCGGTGTAGAACGCTTATATACACATCTTTGACGGCCTTTAG

 K  P  F  Y  A  L  N  E  G  Y  C  A  V  D  Q  S  Y  I  H  L  F  Q  R  F  D
                                    CAT

GTCGTGGTATTCACTCCAGAGCGATGAAAACGTTTCAGTTTGCTCATGGAAAACGGTGTAACAAGGGTGAACACTA
                                                                              608
CAGCACCATAAGTGAGGTCTCGCTACTTTTGCAAAGTCAAACGAGTACCTTTTGCCACATTGTTCCCACTTGTGAT

D  H  Y  E  S  W  L  S  S  F  T  E  T  Q  E  H  F  V  T  Y  C  P  H  V  S
                                    CAT

                                      EcoRI
TCCCATATCACCAGCTCACCGTCTTTCATTGCCATACGGAATTCCGGATGAGCATTCATCAGGCGGGCAAGAATGT
                                                                              684
AGGGTATAGTGGTCGAGTGGCAGAAAGTAACGGTATGCCTTAAGGCCTACTCGTAAGTAGTCCGCCCGTTCTTACA

D  W  I  V  L  E  G  D  K  M  A  M  R  F  E  P  H  A  N  M  L  R  A  L  I  H
                                    CAT

                                            DraI                 PvuII
GAATAAAGGCCGGATAAAACTTGTGCTTATTTTTCTTTACGGTCTTTAAAAAGGCCGTAATATCCAGCTGAACGGT
                                                                              760
CTTATTTCCGGCCTATTTTGAACACGAATAAAAAGAAATGCCAGAAATTTTTCCGGCATTATAGGTCGACTTGCCA

 I  F  A  P  Y  F  K  H  K  N  K  K  V  T  K  L  F  A  T  I  D  L  Q  V  T
                                    CAT

CTGGTTATAGGTACATTGAGCAAGTGACTGAAATGCCTCAAAATGTTCTTTACGATGCGATTGGGATATATCAACG
                                                                              836
GACCAATATCCATGTAACTCGTTCACTGACTTTACGGAGTTTTACAAGAAATGCTACGCTAACCCTATATAGTTGC

Q  N  Y  T  C  Q  A  L  S  Q  F  A  E  F  H  E  K  R  H  S  Q  S  I  D  V
                                    CAT

                                                                 AflIII
   AccI                                                          MluI
GNGGTATACCCAGTGATTTTTTTCTCCATTTTCACTTGTCCCATATTTTTTTGGAATCTAATTTATACGCGTTTTT
                                                                              912
CNCCATATGGGTCACTAAAAAAAGAGGTAAAAGTGAACAGGGTATAAAAAAACCTTAGATTAAATATGCGCAAAAA

?  T  Y  G  T  I  K  K  E  M  ---------------- Le+AC ----------------
           CAT
```

Figure 24 con't

KasI
NgoMIV NgoMIV

TTCGCGTGGCCGGCATGGTCCCAGCCTCCTCGCTGGCGCCGGCTGGGCAACATTCCGAGGGGACCGTCCCCTCGGT 988
AAGCGCACCGGCCGTACCAGGGTCGGAGGAGCGACCGCGGCCGACCCGTTGTAAGGCTCCCCTGGCAGGGGAGCCA

Le+AC Hep-d Ribo

BamHI

AATGGCGAATGGGACGGATCCGGCTGCTAACAAAGCCCGAAA 1030
TTACCGCTTACCCTGCCTAGGCCGACGATTGTTTCGGGCTTT

Hep-d Ribo T-T7

Figure 24 con't hMPV full length clones

Figure 30:
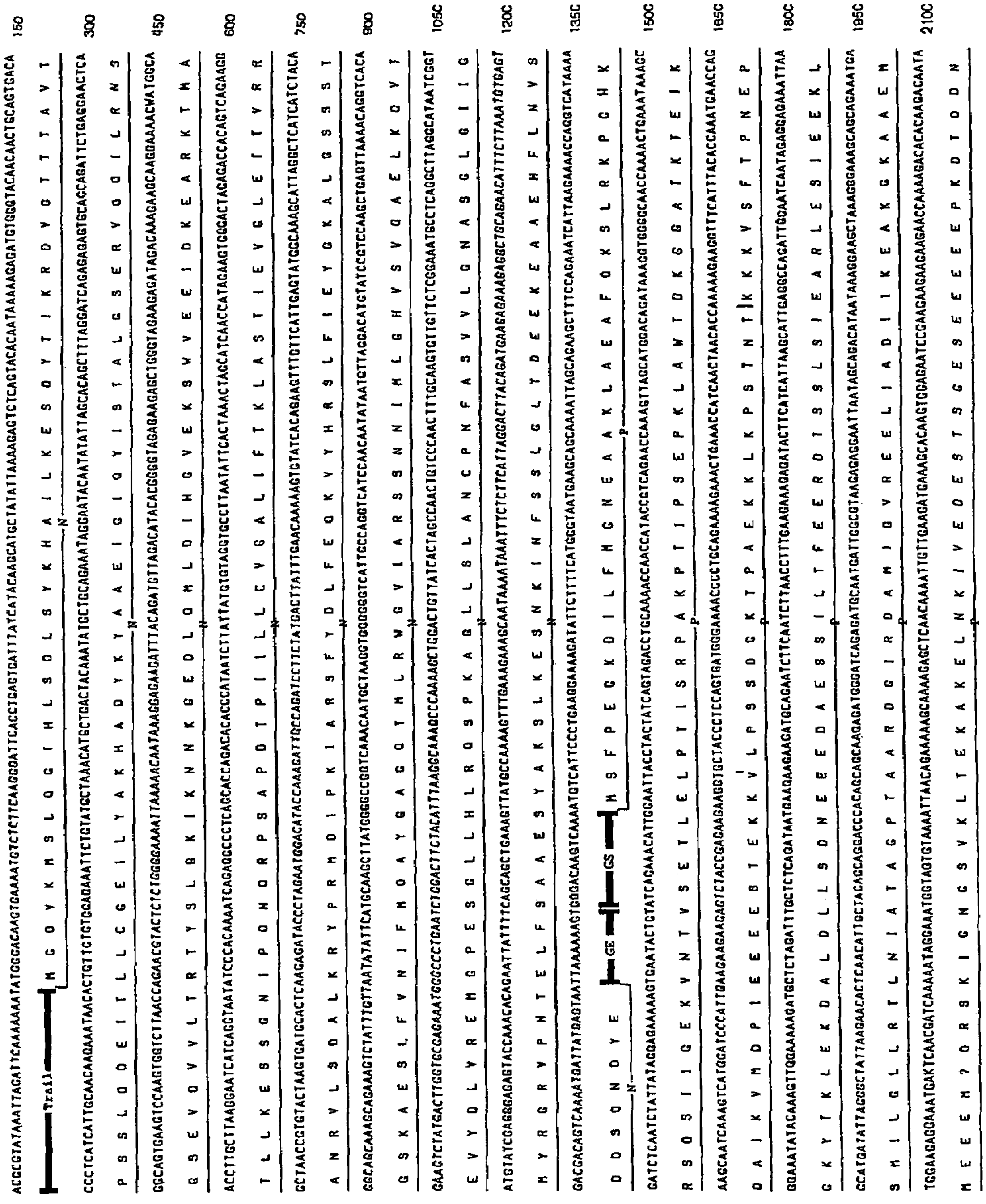

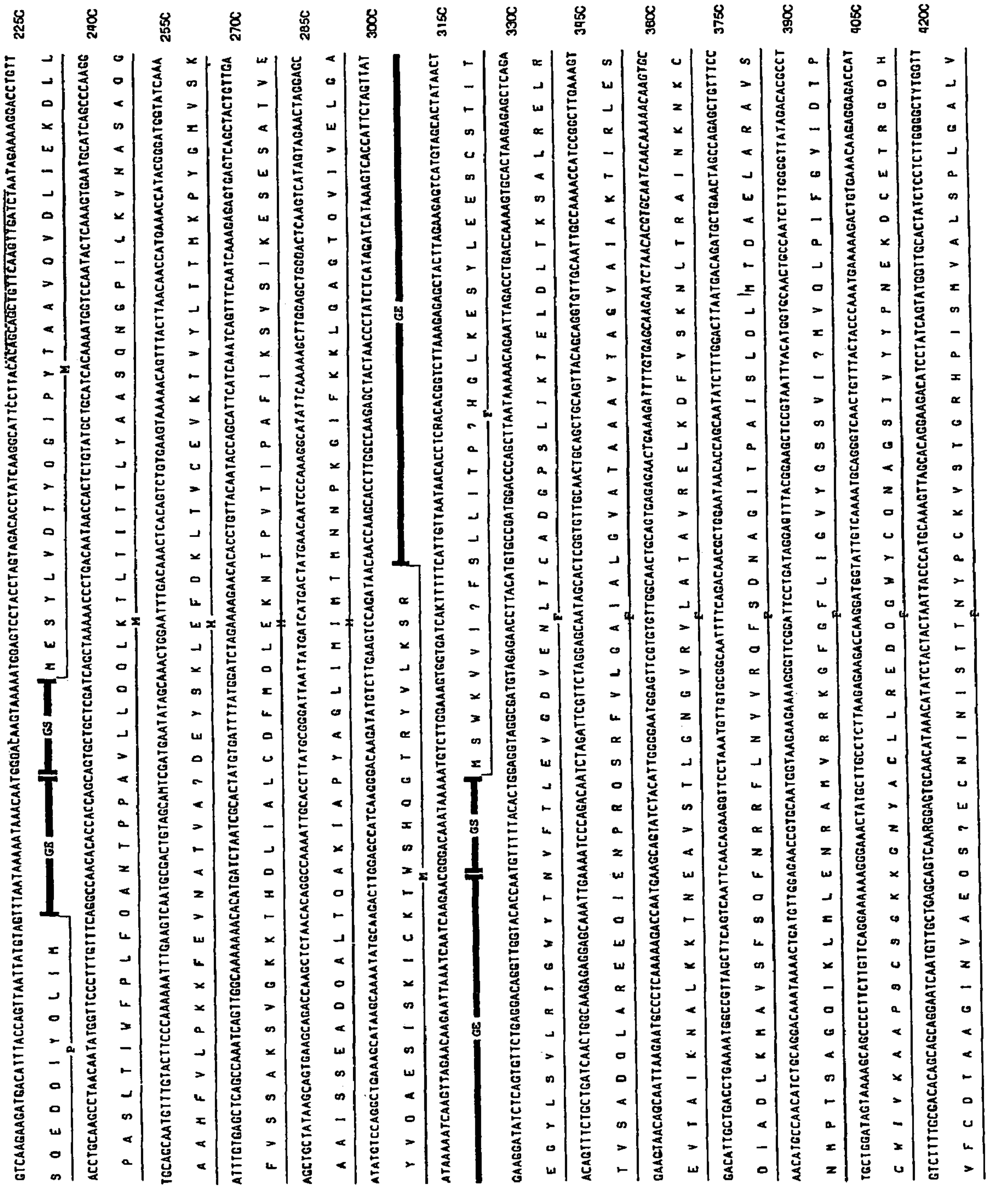
FIGURE 30 contd.

FIGURE 30 contd.

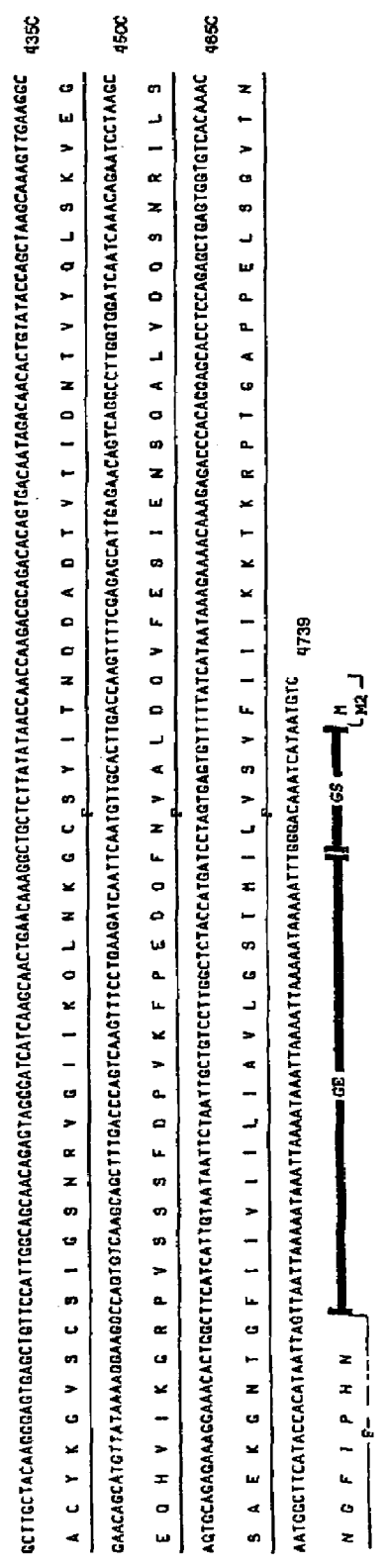

GCTTGCTACAAGGGAGTGAGCTGTTCCATTGGCAGCAACAGAGTAGGGATCATCAAGCAACTGAACAAAGGCTGCTCTTATATAACCAACCAAGACGCAGACACAGTGACAATAGACAACACTGTATACCAGCTAAGCAAAGTTGAAGGC 4350

A C Y K G V S C S I G S N R V G I I K Q L N K G C S Y I T N Q D A D T V T I D N T V Y Q L S K V E G

F

GAACAGCATGTTATAAAAGGAAGGCCAGTGTCAAGCAGCTTTGACCCAGTCAAGTTTCCTGAAGATCAATTCAATGTTGCACTTGACCAAGTTTTCGAGAGCATTGAGAACAGTCAGGCCTTGGTGGATCAATCAAACAGAATCCTAAGC 4500

E Q H V I K G R P V S S S F D P V K F P E D Q F N V A L D Q V F E S I E N S Q A L V D Q S N R I L S

F

AGTGCAGAGAAAGGAAACACTGGCTTCATCATTGTAATAATTCTAATTGCTGTCCTTGGCTCTACCATGATCCTAGTGAGTGTTTTTATCATAATAAAGAAAACAAAGAGACCCACAGGAGCACCTCCAGAGCTGAGTGGTGTCACAAAC 4650

S A E K G N T G F I I V I I L I A V L G S T M I L V S V F I I I K K T K R P T G A P P E L S G V T N

F

AATGGCTTCATACCACATAATTAGTTAATTAAAAATAAATTAAAATAAATTAAAATTAAAAATAAAAATTTGGGACAAATCATAATGTC 4739

N G F I P H N

F

GE

GS

M

M2

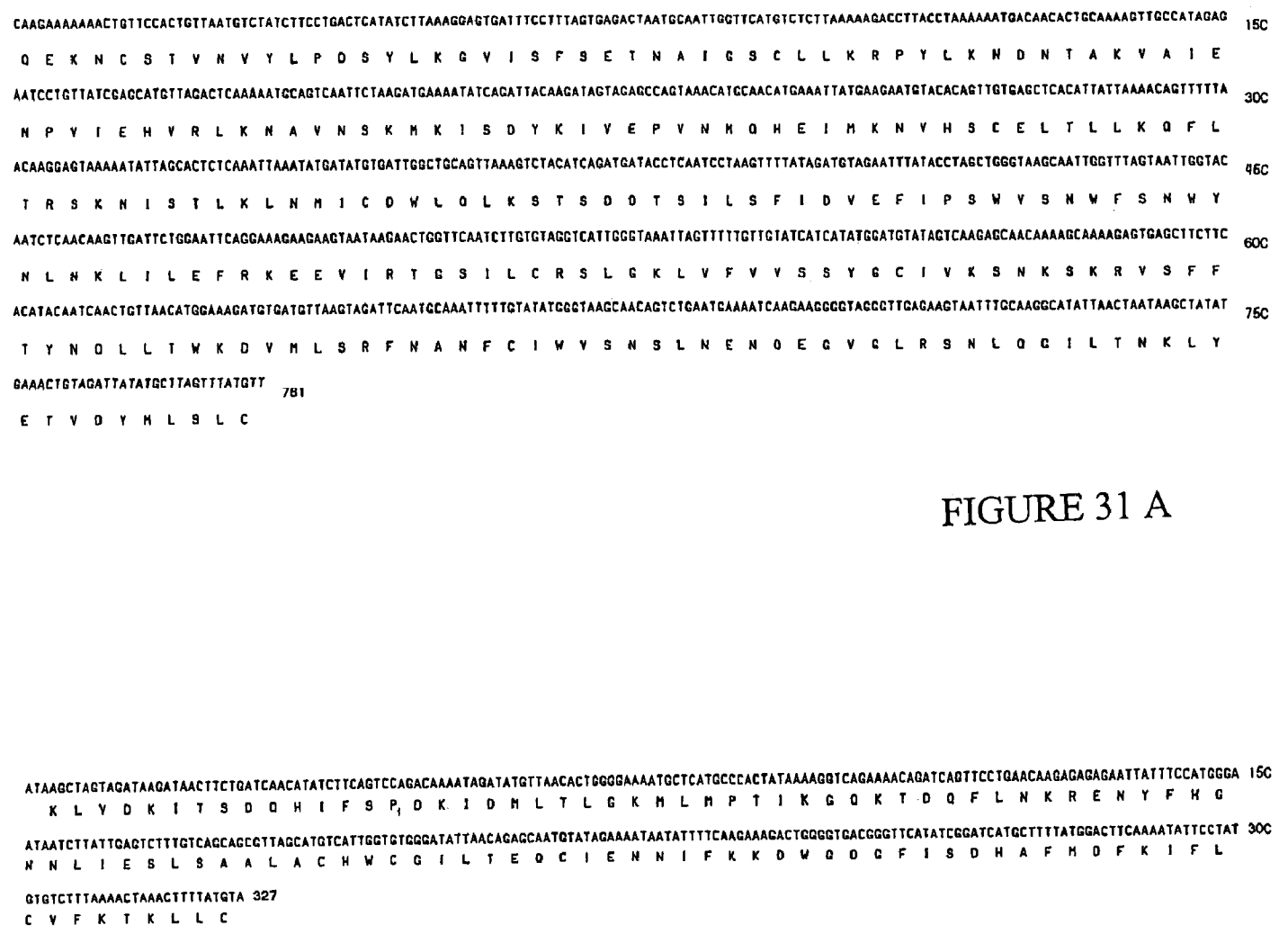

CAAGAAAAAAACTGTTCCACTGTTAATGTCTATCTTCCTGACTCATATCTTAAAGGAGTGATTTCCTTTAGTGAGACTAATGCAATTGGTTCATGTCTCTTAAAAAGACCTTACCTAAAAAATGACAACACTGCAAAAGTTGCCATAGAG 15C

Q E K N C S T V N V Y L P D S Y L K G V I S F S E T N A I G S C L L K R P Y L K N D N T A K V A I E

AATCCTGTTATCGAGCATGTTAGACTCAAAAATGCAGTCAATTCTAAGATGAAAATATCAGATTACAAGATAGTAGAGCCAGTAAACATGCAACATGAAATTATGAAGAATGTACACAGTTGTGAGCTCACATTATTAAAACAGTTTTTA 30C

N P Y I E H V R L K N A V N S K M K I S D Y K I V E P V N M Q H E I M K N V H S C E L T L L K Q F L

ACAAGGAGTAAAAATATTAGCACTCTCAAATTAAATATGATATGTGATTGGCTGCAGTTAAAGTCTACATCAGATGATACCTCAATCCTAAGTTTTATAGATGTAGAATTTATACCTAGCTGGGTAAGCAATTGGTTTAGTAATTGGTAC 45C

T R S K N I S T L K L N M I C D W L Q L K S T S D D T S I L S F I D V E F I P S W V S N W F S N W Y

AATCTCAACAAGTTGATTCTGGAATTCAGGAAAGAAGAAGTAATAAGAACTGGTTCAATCTTGTGTAGGTCATTGGGTAAATTAGTTTTTGTTGTATCATCATATGGATGTATAGTCAAGAGCAACAAAAGCAAAAGAGTGAGCTTCTTC 60C

N L N K L I L E F R K E E V I R T G S I L C R S L G K L V F V V S S Y G C I V K S N K S K R V S F F

ACATACAATCAACTGTTAACATGGAAAGATGTGATGTTAAGTAGATTCAATGCAAATTTTTGTATATGGGTAAGCAACAGTCTGAATGAAAATCAAGAAGGCGTAGGCTTGAGAAGTAATTTGCAAGGCATATTAACTAATAAGCTATAT 75C

T Y N Q L L T W K D V M L S R F N A N F C I W V S N S L N E N Q E G V G L R S N L Q G I L T N K L Y

GAAACTGTAGATTATATGCTTAGTTTATGTT 781

E T V D Y M L S L C

FIGURE 31 A

ATAAGCTAGTAGATAAGATAACTTCTGATCAACATATCTTCAGTCCAGACAAAATAGATATGTTAACACTGGGGAAAATGCTCATGCCCACTATAAAAGGTCAGAAAACAGATCAGTTCCTGAACAAGAGAGAGAATTATTTCCATGGGA 15C

K L V D K I T S D Q H I F S P D K I D M L T L G K M L M P T I K G Q K T D Q F L N K R E N Y F H G

ATAATCTTATTGAGTCTTTGTCAGCAGCGTTAGCATGTCATTGGTGTGGGATATTAACAGAGCAATGTATAGAAAATAATATTTTCAAGAAAGACTGGGGTGACGGGTTCATATCGGATCATGCTTTTATGGACTTCAAAATATTCCTAT 30C

N N L I E S L S A A L A C H W C G I L T E Q C I E N N I F K K D W G D G F I S D H A F M D F K I F L

GTGTCTTTAAAACTAAACTTTTATGTA 327

C V F K T K L L C

FIGURE 31 B

+ = positive; - = negative; T = throatswabs; NO = nose swab; N = not done; ? = not sure; D = dead; 0 to 12: days post infection. 2e infection is only tested on nose swabs.

| nr | 1e infection | swab | 0 | 1 | 2 | 3 | 4 | 5 | 8 | 10 | 11 | 12 | 2e infection | 0 | 1 | 2 | 3 | 4 | 5 |
|---|---|---|---|---|---|---|---|---|---|---|---|---|---|---|---|---|---|---|---|
| 1 | 00-1 | T | - | + | + | + | - | + | + | + | - | - | 99-1 | N | N | N | N | N | N |
| | | NO | - | + | + | + | + | + | N | + | - | - | | - | - | - | - | - | - |
| 2 | 00-1 | T | - | + | + | + | + | + | - | - | - | D | | N | N | N | N | N | N |
| | | NO | | + | + | + | + | + | N | + | - | D | | - | - | - | - | - | - |
| 3 | 00-1 | T | - | - | ? | - | - | - | - | - | - | N | 99-1 | N | N | ? | N | N | N |
| | | NO | | + | ? | ? | | - | N | - | - | - | | - | - | ? | + | + | - |
| 4 | 00-1 | T | - | + | + | + | + | + | - | ? | - | N | 00-1 | N | N | N | N | N | N |
| | | NO | - | + | + | + | + | + | N | ? | - | - | | - | - | - | + | - | - |
| 5 | 00-1 | T | - | ? | + | + | + | + | + | + | - | N | 00-1 | N | N | N | N | N | N |
| | | NO | | + | + | + | + | + | N | + | - | - | | - | - | - | - | - | - |
| 6 | 00-1 | T | - | - | + | + | + | + | - | + | - | N | 00-1 | N | N | N | N | N | N |
| | | NO | - | + | + | + | + | + | N | + | + | ? | | - | - | - | - | - | - |
| 7 | 99-1 | T | - | - | - | + | + | - | + | D | - | - | | N | N | N | N | N | N |
| | | NO | - | - | -- | + | + | + | N | D | - | - | | - | - | - | - | - | - |
| 8 | 99-1 | T | - | - | + | + | - | - | - | - | - | N | 00-1 | N | N | N | N | N | N |
| | | NO | - | ? | - | + | + | ? | N | - | - | -- | | - | - | + | + | + | + |
| 9 | 99-1 | T | - | - | - | - | - | - | - | - | - | N | 00-1 | N | N | N | N | N | N |
| | | NO | - | - | - | - | + | + | N | - | - | -- | | - | ? | + | + | - | - |
| 10 | 99-1 | T | - | - | - | + | + | - | - | - | - | N | 99-1 | N | N | N | N | N | N |
| | | NO | - | + | + | + | + | + | N | - | - | -- | | - | - | - | - | - | - |
| 11 | 99-1 | T | - | - | + | + | + | - | - | - | - | N | 99-1 | N | N | N | N | N | N |
| | | NO | - | + | ? | + | + | + | N | - | - | - | | - | - | - | + | - | - |
| 12 | 99-1 | T | - | - | + | + | ? | - | - | - | - | N | 99-1 | N | N | N | N | N | N |
| | | NO | - | + | + | + | + | + | N | - | - | - | | - | - | - | - | - | - |

FIGURE 32

| | Against 00-1 | Against 99-1 | Against APV-C |
|---|---|---|---|
| 1 infection with 00-1 | 20-60 | < 10 | < 10 |
| 2 infections with 00-1 | >320-1280 | 40-80 | < 10-60 |
| 1infection with 99-1 | <10-60 | 10-80 | < 10 |
| 2 infections with | 20-40 | 80-400 | <10-40 |

FIGURE 37

+ = positive; - = negative; N = not done; ? = not sure; 0 to 10: days post infection

| nr | 1st infection | 0 | 2 | 3 | 4 | 5 | 6 | 7 | 8 | 9 | 11 | 2nd infect ion | 0 | 1 | 2 | 3 | 4 | 5 | 7 | 10 |
|---|---|---|---|---|---|---|---|---|---|---|---|---|---|---|---|---|---|---|---|---|
| 3 | 00-1 | - | - | - | + | + | + | + | + | N | - | | - | + | + | + | + | - | ? | - |
| 6 | 00-1 | - | + | + | + | + | + | + | - | - | - | | - | + | + | + | + | + | - | - |

FIGURE 38

FIGURE 41

Comparison of two prototypic hMPV isolates with APV-A and APV-C

DNA similarity matrices

| N | 00-1 | 99-1 | APVC | APVA |
|---|---|---|---|---|
| 00-1 | 1,000 | 0,862 | 0,757 | 0,660 |
| 99-1 | --- | 1,000 | 0,757 | 0,663 |
| APVC | --- | --- | 1,000 | 0,656 |
| APVA | --- | --- | --- | 1,000 |

| P | 00-1 | 99-1 | APVC | APVA |
|---|---|---|---|---|
| 00-1 | 1,000 | 0,811 | 0,677 | 0,588 |
| 99-1 | --- | 1,000 | 0,674 | 0,593 |
| APVC | --- | --- | 1,000 | 0,584 |
| APVA | --- | --- | --- | 1,000 |

| M | 00-1 | 99-1 | APVC | APVA |
|---|---|---|---|---|
| 00-1 | 1,000 | 0,865 | 0,766 | 0,695 |
| 99-1 | --- | 1,000 | 0,773 | 0,707 |
| APVC | --- | --- | 1,000 | 0,705 |
| APVA | --- | --- | --- | 1,000 |

| F | 00-1 | 99-1 | APVC | APVA |
|---|---|---|---|---|
| 00-1 | 1,000 | 0,838 | 0,706 | 0,662 |
| 99-1 | --- | 1,000 | 0,716 | 0,655 |
| APVC | --- | --- | 1,000 | 0,685 |
| APVA | --- | --- | --- | 1,000 |

| M2-1 | 00-1 | 99-1 | APVC | APVA |
|---|---|---|---|---|
| 00-1 | 1,000 | 0,863 | 0,764 | 0,668 |
| 99-1 | --- | 1,000 | 0,744 | 0,657 |
| APVC | --- | --- | 1,000 | 0,670 |
| APVA | --- | --- | --- | 1,000 |

| M2-2 | 00-1 | 99-1 | APVC | APVA |
|---|---|---|---|---|
| 00-1 | 1,000 | 0,861 | 0,648 | 0,486 |
| 99-1 | --- | 1,000 | 0,675 | 0,486 |
| APVC | --- | --- | 1,000 | 0,463 |
| APVA | --- | --- | --- | 1,000 |

| SH | 00-1 | 99-1 | APVC | APVA |
|---|---|---|---|---|
| 00-1 | 1,000 | 0,688 | N.A. | 0,421 |
| 99-1 | --- | 1,000 | N.A. | 0,380 |
| APVC | --- | --- | N.A. | N.A. |
| APVA | --- | --- | --- | 1,000 |

| G | 00-1 | 99-1 | APVC | APVA |
|---|---|---|---|---|
| 00-1 | 1,000 | 0,543 | N.A. | 0,262 |
| 99-1 | --- | 1,000 | N.A. | 0,263 |
| APVC | --- | --- | N.A. | N.A. |
| APVA | --- | --- | --- | 1,000 |

| 5'L | 00-1 | 99-1 | APVC | APVA |
|---|---|---|---|---|
| 00-1 | 1,000 | 0,835 | N.A. | 0,596 |
| 99-1 | --- | 1,000 | N.A. | 0,605 |
| APVC | --- | --- | N.A. | N.A. |
| APVA | --- | --- | --- | 1,000 |

5'L: only the first 1500 nucleotides of 99-1 were available.
N.A.: sequence not available.

Figure 41 con't

Protein similarity matrices

| N | 00-1 | 99-1 | APVC | APVA |
|---|---|---|---|---|
| 00-1 | 1,000 | 0,949 | 0,880 | 0,685 |
| 99-1 | --- | 1,000 | 0,883 | 0,682 |
| APVC | --- | --- | 1,000 | 0,700 |
| APVA | --- | --- | --- | 1,000 |

| P | 00-1 | 99-1 | APVC | APVA |
|---|---|---|---|---|
| 00-1 | 1,000 | 0,860 | 0,683 | 0,552 |
| 99-1 | --- | 1,000 | 0,676 | 0,549 |
| APVC | --- | --- | 1,000 | 0,528 |
| APVA | --- | --- | --- | 1,000 |

| M | 00-1 | 99-1 | APVC | APVA |
|---|---|---|---|---|
| 00-1 | 1,000 | 0,976 | 0,874 | 0,775 |
| 99-1 | --- | 1,000 | 0,874 | 0,763 |
| APVC | --- | --- | 1,000 | 0,775 |
| APVA | --- | --- | --- | 1,000 |

| F | 00-1 | 99-1 | APVC | APVA |
|---|---|---|---|---|
| 00-1 | 1,000 | 0,938 | 0,810 | 0,677 |
| 99-1 | --- | 1,000 | 0,803 | 0,674 |
| APVC | --- | --- | 1,000 | 0,719 |
| APVA | --- | --- | --- | 1,000 |

| M2-1 | 00-1 | 99-1 | APVC | APVA |
|---|---|---|---|---|
| 00-1 | 1,000 | 0,946 | 0,844 | 0,719 |
| 99-1 | --- | 1,000 | 0,834 | 0,703 |
| APVC | --- | --- | 1,000 | 0,704 |
| APVA | --- | --- | --- | 1,000 |

| M2-2 | 00-1 | 99-1 | APVC | APVA |
|---|---|---|---|---|
| 00-1 | 1,000 | 0,901 | 0,563 | 0,246 |
| 99-1 | --- | 1,000 | 0,577 | 0,232 |
| APVC | --- | --- | 1,000 | 0,191 |
| APVA | --- | --- | --- | 1,000 |

| SH | 00-1 | 99-1 | APVC | APVA |
|---|---|---|---|---|
| 00-1 | 1,000 | 0,570 | N.A. | 0,178 |
| 99-1 | --- | 1,000 | N.A. | 0,162 |
| APVC | --- | --- | N.A. | N.A. |
| APVA | --- | --- | --- | 1,000 |

| G | 00-1 | 99-1 | APVC | APVA |
|---|---|---|---|---|
| 00-1 | 1,000 | 0,326 | N.A. | 0,094 |
| 99-1 | --- | 1,000 | N.A. | 0,107 |
| APVC | --- | --- | N.A. | N.A. |
| APVA | --- | --- | --- | 1,000 |

| 5'L | 00-1 | 99-1 | APVC | APVA |
|---|---|---|---|---|
| 00-1 | 1,000 | 0,921 | N.A. | 0,600 |
| 99-1 | --- | 1,000 | N.A. | 0,594 |
| APVC | --- | --- | N.A. | N.A. |
| APVA | --- | --- | --- | 1,000 |

5'L: only the first 500 amino acid residues of 99-1 were available.
N.A.: sequence not available.

FIGURE 42A

Comparison of the coding sequences of 4 hMPV prototypes

| N nt | NL/17/00 | NL/1/99 | NL/1/94 |
|---|---|---|---|
| NL/1/00 | 0.938 | 0.864 | 0.854 |
| NL/17/00 | | 0.870 | 0.861 |
| NL/1/99 | | | 0.944 |

| N aa | NL/17/00 | NL/1/99 | NL/1/94 |
|---|---|---|---|
| NL/1/00 | 0.994 | 0.954 | 0.961 |
| NL/17/00 | | 0.956 | 0.964 |
| NL/1/99 | | | 0.984 |

| P nt | NL/17/00 | NL/1/99 | NL/1/94 |
|---|---|---|---|
| NL/1/00 | 0.923 | 0.812 | 0.818 |
| NL/17/00 | | 0.807 | 0.811 |
| NL/1/99 | | | 0.932 |

| P aa | NL/17/00 | NL/1/99 | NL/1/94 |
|---|---|---|---|
| NL/1/00 | 0.955 | 0.863 | 0.867 |
| NL/17/00 | | 0.857 | 0.863 |
| NL/1/99 | | | 0.959 |

| M nt | NL/17/00 | NL/1/99 | NL/1/94 |
|---|---|---|---|
| NL/1/00 | 0.938 | 0.860 | 0.861 |
| NL/17/00 | | 0.848 | 0.852 |
| NL/1/99 | | | 0.942 |

| M aa | NL/17/00 | NL/1/99 | NL/1/94 |
|---|---|---|---|
| NL/1/00 | 0.988 | 0.976 | 0.976 |
| NL/17/00 | | 0.972 | 0.972 |
| NL/1/99 | | | 1.000 |

| F nt | NL/17/00 | NL/1/99 | NL/1/94 |
|---|---|---|---|
| NL/1/00 | 0.937 | 0.840 | 0.840 |
| NL/17/00 | | 0.838 | 0.840 |
| NL/1/99 | | | 0.943 |

| F aa | NL/17/00 | NL/1/99 | NL/1/94 |
|---|---|---|---|
| NL/1/00 | 0.979 | 0.940 | 0.946 |
| NL/17/00 | | 0.942 | 0.949 |
| NL/1/99 | | | 0.987 |

| M2 nt | NL/17/00 | NL/1/99 | NL/1/94 |
|---|---|---|---|
| NL/1/00 | 0.943 | 0.854 | 0.854 |
| NL/17/00 | | 0.863 | 0.851 |
| NL/1/99 | | | 0.943 |

| M2.1 nt | NL/17/00 | NL/1/99 | NL/1/94 |
|---|---|---|---|
| NL/1/00 | 0.943 | 0.863 | 0.861 |
| NL/17/00 | | 0.870 | 0.852 |
| NL/1/99 | | | 0.939 |

| M2.1 aa | NL/17/00 | NL/1/99 | NL/1/94 |
|---|---|---|---|
| NL/1/00 | 0.983 | 0.946 | 0.951 |
| NL/17/00 | | 0.951 | 0.957 |
| NL/1/99 | | | 0.978 |

| M2.2 nt | NL/17/00 | NL/1/99 | NL/1/94 |
|---|---|---|---|
| NL/1/00 | 0.953 | 0.861 | 0.865 |
| NL/17/00 | | 0.870 | 0.875 |
| NL/1/99 | | | 0.967 |

| M2.2 aa | NL/17/00 | NL/1/99 | NL/1/94 |
|---|---|---|---|
| NL/1/00 | 0.957 | 0.901 | 0.915 |
| NL/17/00 | | 0.887 | 0.901 |
| NL/1/99 | | | 0.985 |

| SH nt | NL/17/00 | NL/1/99 | NL/1/94 |
|---|---|---|---|
| NL/1/00 | 0.884 | 0.682 | 0.673 |
| NL/17/00 | | 0.688 | 0.685 |
| NL/1/99 | | | 0.887 |

| SH aa | NL/17/00 | NL/1/99 | NL/1/94 |
|---|---|---|---|
| NL/1/00 | 0.836 | 0.570 | 0.576 |
| NL/17/00 | | 0.605 | 0.622 |
| NL/1/99 | | | 0.830 |

| G nt | NL/17/00 | NL/1/99 | NL/1/94 |
|---|---|---|---|
| NL/1/00 | 0.762 | 0.530 | 0.575 |
| NL/17/00 | | 0.573 | 0.546 |
| NL/1/99 | | | 0.765 |

| G aa | NL/17/00 | NL/1/99 | NL/1/94 |
|---|---|---|---|
| NL/1/00 | 0.652 | 0.309 | 0.341 |
| NL/17/00 | | 0.337 | 0.338 |
| NL/1/99 | | | 0.651 |

| L nt | NL/17/00 | NL/1/99 | NL/1/94 |
|---|---|---|---|
| NL/1/00 | 0.944 | 0.843 | 0.843 |
| NL/17/00 | | 0.843 | 0.843 |
| NL/1/99 | | | 0.952 |

| L aa | NL/17/00 | NL/1/99 | NL/1/94 |
|---|---|---|---|
| NL/1/00 | 0.986 | 0.942 | 0.938 |
| NL/17/00 | | 0.944 | 0.939 |
| NL/1/99 | | | 0.985 |

FIGURE 42B

Amino acid sequence alignment of two prototype hMPV isolates

Nucleoprotein (N)

```
                10        20        30        40        50        60
        ....|....|....|....|....|....|....|....|....|....|....|....|
00-1    MSLQGIHLSDLSYKHAILKESQYTIKRDVGTTTAVTPSSLQQEITLLCGEILYAKHADYK 60
99-1    MSLQGIHLSDLSYKHAILKESQYTIKRDVGTTTAVTPSSLQQEITLLCGEILYTKHTDYK 60

                70        80        90       100       110       120
        ....|....|....|....|....|....|....|....|....|....|....|....|
00-1    YAAEIGIQYISTALGSERVQQILRNSGSEVQVVLTRTYSLGKIKNNKGEDLQMLDIHGVE 120
99-1    YAAEIGIQYICTALGSERVQQILRNSGSEVQVVLTKTYSLGKGKNSKGEELQMLDIHGVE 120

               130       140       150       160       170       180
        ....|....|....|....|....|....|....|....|....|....|....|....|
00-1    KSWVEEIDKEARKTMATLLKESSGNIPQNQRPSAPDTPIILLCVGALIFTKLASTIEVGL 180
99-1    KSWIEEIDKEARKTMVTLLKESSGNIPQNQRPSAPDTPIILLCVGALIFTKLASTIEVGL 180

               190       200       210       220       230       240
        ....|....|....|....|....|....|....|....|....|....|....|....|
00-1    ETTVRRANRVLSDALKRYPRMDIPKIARSFYDLFEQKVYHRSLFIEYGKALGSSSTGSKA 240
99-1    ETTVRRANRVLSDALKRYPRIDIPKIARSFYELFEQKVYYRSLFIEYGKALGSSSTGSKA 240

               250       260       270       280       290       300
        ....|....|....|....|....|....|....|....|....|....|....|....|
00-1    ESLFVNIFMQAYGAGQTMLRWGVIARSSNNIMLGHVSVQAELKQVTEVYDLVREMGPESG 300
99-1    ESLFVNIFMQAYGAGQTLLRWGVIARSSNNIMLGHVSVQSELKQVTEVYDLVREMGPESG 300

               310       320       330       340       350       360
        ....|....|....|....|....|....|....|....|....|....|....|....|
00-1    LLHLRQSPKAGLLSLANCPNFASVVLGNASGLGIIGMYRGRVPNTELFSAAESYAKSLKE 360
99-1    LLHLRQSPKAGLLSLANCPNFASVVLGNASGLGIIGMYRGRVPNTELFSAAESYARSLKE 360

               370       380       390
        ....|....|....|....|....|....|....
00-1    SNKINFSSLGLTDEEKEAAEHFLNVSDDSQNDYE 394
99-1    SNKINFSSLGLTDEEKEAAEHFLNMSGDNQDDYE 394
```

FIGURE 43

Phosphoprotein (P)

```
              10         20         30         40         50         60
        ....|....|....|....|....|....|....|....|....|....|....|....|
00-1    MSFPEGKDILFMGNEAAKLAEAFQKSLRKPGHKRSQSIIGEKVNTVSETLELPTISRPAK  60
99-1    MSFPEGKDILFMGNEAAKIAEAFQKSLKKSGHKRTQSIVGEKVNTISETLELPTISKPAR  60

              70         80         90        100        110        120
        ....|....|....|....|....|....|....|....|....|....|....|....|
00-1    PTIPSEPKLAWTDKGGATKTEIKQAIKVMDPIEEEESTEKKVLPSSDGKTPAEKKLKPST 120
99-1    SSTLLEPKLAWADNSGITKITEKPATKTTDPVEEEEFNEKKVLPSSDGKTPAEKKSKFST 120

             130        140        150        160        170        180
        ....|....|....|....|....|....|....|....|....|....|....|....|
00-1    NTKKKVSFTPNEPGKYTKLEKDALDLLSDNEEEDAESSILTFEERDTSSLSIEARLESIE 180
99-1    SVKKKVSFTSNEPGKYTKLEKDALDLLSDNEEEDAESSILTFEEKDTSSLSIEARLESIE 180

             190        200        210        220        230        240
        ....|....|....|....|....|....|....|....|....|....|....|....|
00-1    EKLSMILGLLRTLNIATAGPTAARDGIRDAMIGVREELIADIIKEAKGKAAEMMEEEMSQ 240
99-1    EKLSMILGLLRTLNIATAGPTAARDGIRDAMIGIREELIAEIIKEAKGKAAEMMEEEMNQ 240

             250        260        270        280        290
        ....|....|....|....|....|....|....|....|....|....|....|....
00-1    RSKIGNGSVKLTEKAKELNKIVEDESTSGESEEEEEPKDTQDNSQEDDIYQLIM       294
99-1    RSKIGNGSVKLTEKAKELNKIVEDESTSGESEEEEEPKETQDNNQGEDIYQLIM       294
```

FIGURE 44

Matrix protein (M)

```
                10        20        30        40        50        60
        ....|....|....|....|....|....|....|....|....|....|....|....|
00-1    MESYLVDTYQGIPYTAAVQVDLIEKDLLPASLTIWFPLFQANTPPAVLLDQLKTLTITTL 60
99-1    MESYLVDTYQGIPYTAAVQVDLVEKDLLPASLTIWFPLFQANTPPAVLLDQLKTLTITTL 60

                70        80        90       100       110       120
        ....|....|....|....|....|....|....|....|....|....|....|....|
00-1    YAASQNGPILKVNASAQGAAMSVLPKKFEVNATVALDEYSKLEFDKLTVCEVKTVYLTTM 120
99-1    YAASQNGPILKVNASAQGAAMSVLPKKFEVNATVALDEYSKLDFDKLTVCDVKTVYLTTM 120

               130       140       150       160       170       180
        ....|....|....|....|....|....|....|....|....|....|....|....|
00-1    KPYGMVSKFVSSAKSVGKKTHDLIALCDFMDLEKNIPVTIPAFIKSVSIKESESATVEAA 180
99-1    KPYGMVSKFVSSAKSVGKKTHDLIALCDFMDLEKNIPVTIPAFIKSVSIKESESATVEAA 180

               190       200       210       220       230       240
        ....|....|....|....|....|....|....|....|....|....|....|....|
00-1    ISSEADQALTQAKIAPYAGLIMIMTMNNPKGIFKKLGAGTQVIVELGAYVQAESISKICK 240
99-1    ISSEADQALTQAKIAPYAGLIMIMTMNNPKGIFKKLGAGTQVIVELGAYVQAESISRICK 240

               250
        ....|....|....
00-1    TWSHQGTRYVLKSR 254
99-1    SWSHQGTRYVLKSR 254
```

FIGURE 45

Fusion protein (F)

```
              10        20        30        40        50        60
      ....|....|....|....|....|....|....|....|....|....|....|....|
00-1  MSWKVVIIFSLLITPQHGLKESYLEESCSTITEGYLSVLRTGWYTNVFTLEVGDVENLTC 60
99-1  MSWKVMIIISLLITPQHGLKESYLEESCSTITEGYLSVLRTGWYTNVFTLEVGDVENLTC 60

              70        80        90       100       110       120
      ....|....|....|....|....|....|....|....|....|....|....|....|
00-1  ADGPSLIKTELDLTKSALRELRTVSADQLAREEQIENPRQSRFVLGAIALGVATAAAVTA 120
99-1  TDGPSLIKTELDLTKSALRELKTVSADQLAREEQIENPRQSRFVLGAIALGVATAAAVTA 120

             130       140       150       160       170       180
      ....|....|....|....|....|....|....|....|....|....|....|....|
00-1  GVAIAKTIRLESEVTAIKNALKKTNEAVSTLGNGVRVLATAVRELKDFVSKNLTRAINKN 180
99-1  GIAIAKTIRLESEVNAIKGALKQTNEAVSTLGNGVRVLATAVRELKEFVSKNLTSAINRN 180

             190       200       210       220       230       240
      ....|....|....|....|....|....|....|....|....|....|....|....|
00-1  KCDIADLKMAVSFSQFNRRFLNVVRQFSDNAGITPAISLDLMTDAELARAVSNMPTSAGQ 240
99-1  KCDIADLKMAVSFSQFNRRFLNVVRQFSDNAGITPAISLDLMTDAELARAVSYMPTSAGQ 240

             250       260       270       280       290       300
      ....|....|....|....|....|....|....|....|....|....|....|....|
00-1  IKLMLENRAMVRRKGFGFLIGVYGSSVIYMVQLPIFGVIDTPCWIVKAAPSCSGKKGNYA 300
99-1  IKLMLENRAMVRRKGFGILIGVYGSSVIYMVQLPIFGVIDTPCWIIKAAPSCSEKNGNYA 300

             310       320       330       340       350       360
      ....|....|....|....|....|....|....|....|....|....|....|....|
00-1  CLLREDQGWYCQNAGSTVYYPNEKDCETRGDHVFCDTAAGINVAEQSKECNINISTTNYP 360
99-1  CLLREDQGWYCKNAGSTVYYPNEKDCETRGDHVFCDTAAGINVAEQSRECNINISTTNYP 360

             370       380       390       400       410       420
      ....|....|....|....|....|....|....|....|....|....|....|....|
00-1  CKVSTGRHPISMVALSPLGALVACYKGVSCSIGSNRVGIIKQLNKGCSYITNQDADTVTI 420
99-1  CKVSTGRHPISMVALSPLGALVACYKGVSCSIGSNWVGIIKQLPKGCSYITNQDADTVTI 420

             430       440       450       460       470       480
      ....|....|....|....|....|....|....|....|....|....|....|....|
00-1  DNTVYQLSKVEGEQHVIKGRPVSSSFDPVKFPEDQFNVALDQVFESIENSQALVDQSNRI 480
99-1  DNTVYQLSKVEGEQHVIKGRPVSSSFDPIKFPEDQFNVALDQVFESIENSQALVDQSNKI 480

             490       500       510       520       530
      ....|....|....|....|....|....|....|....|....|....|....|....
00-1  LSSAEKGNTGFIIVIILIAVLGSTMILVSVFIIIKKTKKPTGAPPELSGVTNNGFIPHN 539
99-1  LNSAEKGNTGFIIVVILVAVLGLTMISVSIIIIIKKTRKPTGAPPELNGVTNGGFIPHS 539
```

FIGURE 46

22K protein (M2-1)

```
             10        20        30        40        50        60
     ....|....|....|....|....|....|....|....|....|....|....|....|
00-1 MSRKAPCKYEVRGKCNRGSECKFNHNYWSWPDRYLLIRSNYLLNQLLRNTDRADGLSIIS 60
99-1 MSRKAPCKYEVRGKCNRGSDCKFNHNYWSWPDRYLLLRSNYLLNQLLRNTDKADGLSIIS 60

             70        80        90       100       110       120
     ....|....|....|....|....|....|....|....|....|....|....|....|
00-1 GAGREDRTQDFVLGSTNVVQGYIDDNQSITKAAACYSLHNIIKQLQEVEVRQARDNKLSD 120
99-1 GAGREDRTQDFVLGSTNVVQGYIDDNQGITKAAACYSLHNIIKQLQETEVRQARDNKLSD 120

            130       140       150       160       170       180
     ....|....|....|....|....|....|....|....|....|....|....|....|
00-1 SKHVALHNLVLSYMEMSKTPASLINNLKRLPREKLKKLAKLIIDLSAGAENDSSYALQDS 180
99-1 SKHVALHNLILSYMEMSKTPASLINNLKKLPREKLKKLARLIIDLSAGTDNDSSYALQDS 180

     ....|..
00-1 ESTNQVQ 187
99-1 ESTNQVQ 187
```

FIGURE 47

M2-2 protein (M2-2)

```
                  10        20        30        40        50        60
         ....|....|....|....|....|....|....|....|....|....|....|....|
00-1     MTLHMPCKTVKALIKCSEHGPVFITIEVDDMIWTHKDLKEALSDGIVKSHTNIYNCYLEN 60
99-1     MTLHMPCKTVKALIKCSKHGPKFITIEADDMIWTHKELKETLSDGIVKSHTNIYSCYLEN 60

                  70
         ....|....|.
00-1     IEIIYVKAYLS 71
99-1     IEIIYVKTYLS 71
```

FIGURE 48

Short hydrophobic protein (SH)

```
                10        20        30        40        50        60
        ....|....|....|....|....|....|....|....|....|....|....|....|
00-1    MITLDVIKSDGSSKTCTHLKKIIKDHSGKVLIVLKLILALLTFLTVTITINYIKVENNLQ 60
99-1    MKTLDVIKSDGSSETCNQLKKIIKKHSGKVLIALKLILALLTFFTATITVNYIKVENNLQ 60

                70        80        90       100       110       120
        ....|....|....|....|....|....|....|....|....|....|....|....|
00-1    ICQSKTESDKKDSSSNTTSVTTKTTLNHDITQYFKSLIQRYTNSAIN-SDTCWKINRNQC 119
99-1    ACQPKNESDKKVTKPNTTSITIRPTPDPTVVHHLKRLIQRHTNSVTKDSDTCWRIHKNQR 120

               130       140       150       160       170       180
        ....|....|....|....|....|....|....|....|....|....|....|....|
00-1    TNITTYKFLCFKSEDTKTNNCDKLTDLCRNKPKPAVGVYHIVECHCIYTVKWKCYHYPTD 179
99-1    TNIKIYKFLCSGFTNSKGTDCEEPTALCDKKLKTIVEKHRKAECHCLHTTEWGCLHP--- 177

        ....
00-1    ETQS 183
99-1    ---- 177
```

FIGURE 49

Attachment glycoprotein (G)

```
              10        20        30        40        50        60
      ....|....|....|....|....|....|....|....|....|....|....|....|
00-1  MEVKVENIRTIDMLKARVKNRVARSKCFKNASLVLIGITTLSIALNIYLIINYKMQKNTS 60
99-1  MEVRVENIRAIDMFKAKIKNRIRSSRCYRNATLILIGLTALSMALNIFLIIDHATLRNMI 60

              70        80        90       100       110       120
      ....|....|....|....|....|....|....|....|....|....|....|....|
00-1  ESEHHTSSSPMESSRETPTVPTDNSDTNSSPQHPTQQSTEGSTLYFAASASSPETEPTST 120
99-1  KTENCANMPSAEPSKKTPMTSTAGPNTKPNPQQATQWTTENSTSPVATPEGHPYTGTTQT 120

             130       140       150       160       170       180
      ....|....|....|....|....|....|....|....|....|....|....|....|
00-1  PDTTNRPPFVDTHTTPPSASRTKTSPAVHTKNNPRTSSRTHSPPRATTRTARRTTTLRTS 180
99-1  SDTTAPQQTTDKHTAPLKSTNEQITQTTTEKKTIRATTQKREKGKENTNQTTSTAATQTT 180

             190       200       210       220       230
      ....|....|....|....|....|....|....|....|....|....|....|.
00-1  STRKRPSTASVQPDISATTHKNEEASPASPQTSASTTRIQRKSVEANTSTTYNQTS 236
99-1  NTTNQIRNASET-----ITTSDRPRTDTTQSSEQTTRATDPSSPPHHA-------- 224
```

FIGURE 50

N-terminus of polymerase protein (L)

```
                 10        20        30        40        50        60
         ....|....|....|....|....|....|....|....|....|....|....|....|
00-1     MDPLNESTVNVYLPDSYLKGVISFSETNAIGSCLLKRPYLKNDNTAKVAIENPVIEHVRL 60
99-1     MDPFCESTVNVYLPDSYLKGVISFSETNAIGSCLLKRPYLKNDNTAKVAVENPVVEHVRL 60

                 70        80        90       100       110       120
         ....|....|....|....|....|....|....|....|....|....|....|....|
00-1     KNAVNSKMKISDYKIVEPVNMQHEIMKNVHSCELTLLKQFLTRSKNISTLKLNMICDWLQ 120
99-1     RNAVMTKMKISDYKVVEPVNMQHEIMKNIHSCELTLLKQFLTRSKNISSLKLNMICDWLQ 120

                130       140       150       160       170       180
         ....|....|....|....|....|....|....|....|....|....|....|....|
00-1     LKSTSDDTSILSFIDVEFIPSWVSNWFSNWYNLNKLILEFRKEEVIRTGSILCRSLGKLV 180
99-1     LKSTSDNTSILNFIDVEFIPVWVSNWFSNWYNLNKLILEFRREEVIRTGSILCRSLGKLV 180

                190       200       210       220       230       240
         ....|....|....|....|....|....|....|....|....|....|....|....|
00-1     FVVSSYGCIVKSNKSKRVSFFTYNQLLTWKDVMLSRFNANFCIWVSNSLNENQEGLGLRS 240
99-1     FIVSSYGCVVKSNKSKRVSFFTYNQLLTWKDVMLSRFNANFCIWVSNNLNKNQEGLGLRS 240

                250       260       270       280       290       300
         ....|....|....|....|....|....|....|....|....|....|....|....|
00-1     NLQGILTNKLYETVDYMLSLCCNEGFSLVKEFEGFIMSEILRITEHAQFSTRFRNTLLNG 300
99-1     NLQGMLTNKLYETVDYMLSLCCNEGFSLVKEFEGFIMSEILKITEHAQFSTRFRNTLLNG 300

                310       320       330       340       350       360
         ....|....|....|....|....|....|....|....|....|....|....|....|
00-1     LTDQLTKLKNKNRLRVHGTVLENNDYPMYEVVLKLLGDTLRCIKLLINKNLENAAELYYI 360
99-1     LTEQLSVLKAKNRSRVLGTILENNNYPMYEVVLKLLGDTLKSIKLLINKNLENAAELYYI 360

                370       380       390       400       410       420
         ....|....|....|....|....|....|....|....|....|....|....|....|
00-1     FRIFGHPMVDERDAMDAVKLNNEITKILRWESLTELRGAFILRIIKGFVDNNKRWPKIKN 420
99-1     FRIFGHPMVDEREAMDAVKLNNEITKILKLESLTELRGAFILRIIKGFVDNNKRWPKIKN 420

                430       440       450       460       470       480
         ....|....|....|....|....|....|....|....|....|....|....|....|
00-1     LKVLSKRWTMYFKAKSYPSQLELSEQDFLELAAIQFEQEFSVPEKTNLEMVLNDKAISPP 480
99-1     LKVLSKRWAMYFKAKSYPSQLELSVQDFLELAAVQFEQEFSVPEKTNLEMVLNDKAISPP 480

                490
         ....|....|....|....
00-1     KRLIWSVYPKNYLPEKIKN 499
99-1     KKLIWSVYPKNYLPETIKN 499
```

FIGURE 51

A

| Pos., ORF | Stop | Non-coding sequence | Gene start | Start | Pos., ORF |
|---|---|---|---|---|---|
| 1, Le | | ACGAGAAAAAAACGCGUAUAAAUUAGAUUCCAAAAAAAUAU........................... | GGGACAAGUGAAA | AUG | 55, N |
| 1237, N | UAA | UUAAAAAAGU........................................................ | GGGACAAGUCAAA | AUG | 1263, P |
| 2145, P | UAG | UUUAAUAAAAAUAAACAAU.................................................. | GGGACAAGUAAAA | AUG | 2180, M |
| 2942, M | UAA | CAACCAAGCACCUUGGCCAAGAGCUACUAACCCUAUCUCAUAGAUCAUAAAGUCACCAUUCUAGUUAUAU AAAAAUCAAGUUAGAACAAGAAUUAAAUCAAUCAAGAAC.............................. | GGGACAAAUAAAA | AUG | 3067, F |
| 4684, F | UAG | UUAAUUAAAAAUAAAGUAAAUUAAAAUAAAUUAAAAUUAAAAAUAAAAAUUU................. | GGGACAAAUCAUA | AUG | 4752, M2 |
| 5476, M2 | UAG | UAAAAACACAUCAGAGU.................................................... | GGGAUAAAUGACA | AUG | 5509, SH |
| 6058, SH | UAA | AUGUUAACACCAGAUUAGGAUCCAUCCAAGUCUGUUAGUUCAACAAUUUAGUUAUUUAAAAAUAUUUUGA AAACAAGUAAGUUUCUAUGAUACUUCAUAAUAAUAAGUAAUAAUUAAUUGCUUAAUCAUCAUCACAACAU UAUUCGAAACCAUAACUAUUCAAUUUAAAAAGUAAAAAACAAUAACAU..................... | GGGACAAGUAGUU | AUG | 6262, G |
| 6970, G | UAA | CAAAAAAUACAAAAUAACUCUAAGAUAAACCAUGCAGACACCAACAAUGGAGAAGCCAAAAGACAAUUCA CAAUCUCCCCAAAAAGGCAACAACACCAUAUUAGCUCUGCCCAAAUCUCCCUGGAAAAAACACUCGCCCA UAUACCAAAAAUACCACAACCACCCCAAGAAAAAAACUGGGCAAAACAACACCCAA.............. | GAGACAAAUAACA | AUG | 7182, L |
| 13197, L | UGA | AAAAUGAUAAAAAUGAUAAAAUAGGUGACAACUUCAUACUAUUCCAAAGUAAUCAUUUGAUUAUGCAAUU AUGUAAUAGUUAAUUAAAAACUAAAAAUCAAAAGUUAGAAACUAACAACUGUCAUUAAGUUUAUUAAAAA UAAGAAAUUAUAAUUGGAUGUAUACGGUUUUUUUCUCGU | | | 13378, Tr |

B

```
hMPV Le: 3' UGCUCUUUUUUUGCGCAUAUUUAAUCUAAGGUUUUUUUAUACCCU
            ||||||||||||| |||||| ||    ||| ||       |||   |
hMPV Tr: 5' ACGAGAAAAAAAC CGUAUACAUCCAAUUAUAAUUUCUUAUUUUU hMPV Tr: 5' ACGAGAAAAAAACCGUAUACAUCCAAUUAUAAUUUCUUAUUUUUA
            |||||||||||||||||| |||| |||| | |  | ||| ||||
APV  Tr: 5' ACGAGAAAAAAACCGUAUUCAUCAAAUUUUUAGCUUUUAGUUUUU hMPV Le: 3' UGCUCUUUUUUUGCGCAUAUUUAAUCUAAGGUUUUUUUAU-ACCC
            ||||||||||||||| | | ||  || ||| | ||||||| ||||
APV  Le: 3' UGCUCUUUUUUUGCGUA-AGUUCGUCCAAGAUCUUUUUAUUACCC
```

```
              1 . . . . . . . . . 10   . . . . . . . . . . 20   . . . . . . . . . . 30
00-1 1-9000   - - - - - - - - - -      - - - - - G T A T A      A A T T A G A T T C
99-1 1-9000   A C G C G A A A A A      A A C G C G T A T A      A A T T A A A T T C

              . . . . . . . . . . 40   . . . . . . . . . . 50   . . . . . . . . . . 60
00-1 1-9000   C A A A A A A A T A      T G G G A C A A G T      G A A A A T G T C T
99-1 1-9000   C A A A C A A A - A      C G G G A C A A A T      A A A A A T G T C T

              . . . . . . . . . . 70   . . . . . . . . . . 80   . . . . . . . . . . 90
00-1 1-9000   C T T C A A G G G A      T T C A C C T G A G      T G A T T T A T C A
99-1 1-9000   C T T C A A G G G A      T T C A C C T A A G      T G A T C T A T C A

              . . . . . . . . . . 100  . . . . . . . . . . 110  . . . . . . . . . . 120
00-1 1-9000   T A C A A G C A T G      C T A T A T T A A A      A G A G T C T C A G
99-1 1-9000   T A T A A A C A T G      C T A T A T T A A A      A G A G T C T C A A

              . . . . . . . . . . 130  . . . . . . . . . . 140  . . . . . . . . . . 150
00-1 1-9000   T A C A C A A T A A      A A A G A G A T G T      G G G T A C A A C A
99-1 1-9000   T A C A C A A T A A      A A A G A G A T G T      A G G C A C C A C A

              . . . . . . . . . . 160  . . . . . . . . . . 170  . . . . . . . . . . 180
00-1 1-9000   A C T G C A G T G A      C A C C C T C A T C      A T T G C A A C A A
99-1 1-9000   A C T G C A G T G A      C A C C T T C A T C      A T T A C A A C A A

              . . . . . . . . . . 190  . . . . . . . . . . 200  . . . . . . . . . . 210
00-1 1-9000   G A A A T A A C A C      T G T T G T G T G G      A G A A A T T C T G
99-1 1-9000   G A A A T A A C A C      T T T T G T G T G G      G G A A A T A C T T

              . . . . . . . . . . 220  . . . . . . . . . . 230  . . . . . . . . . . 240
00-1 1-9000   T A T G C T A A A C      A T G C T G A C T A      C A A A T A T G C T
99-1 1-9000   T A C A C T A A A C      A C A C T G A T T A      C A A A T A T G C T

              . . . . . . . . . . 250  . . . . . . . . . . 260  . . . . . . . . . . 270
00-1 1-9000   G C A G A A A T A G      G A A T A C A A T A      T A T T A G C A C A
99-1 1-9000   G C T G A G A T A G      G A A T A C A A T A      T A T T T G C A C A

              . . . . . . . . . . 280  . . . . . . . . . . 290  . . . . . . . . . . 300
00-1 1-9000   G C T T T A G G A T      C A G A G A G A G T      G C A G C A G A T T
99-1 1-9000   G C T C T A G G A T      C A G A A A G A G T      A C A A C A G A T T

              . . . . . . . . . . 310  . . . . . . . . . . 320  . . . . . . . . . . 330
00-1 1-9000   C T G A G G A A C T      C A G G C A G T G A      A G T C C A A G T G
99-1 1-9000   T T G A G A A A C T      C A G G T A G T G A      A G T T C A G G T G

              . . . . . . . . . . 340  . . . . . . . . . . 350  . . . . . . . . . . 360
00-1 1-9000   G T C T T A A C C A      G A A C G T A C T C      T C T G G G G A A A
99-1 1-9000   G T T C T A A C C A      A A A C A T A C T C      C T T A G G G A A A

              . . . . . . . . . . 370  . . . . . . . . . . 380  . . . . . . . . . . 390
00-1 1-9000   A T T A A A A A C A      A T A A A G G A G A      A G A T T T A C A G
99-1 1-9000   G G C A A A A A C A      G T A A A G G G G A      A G A G C T G C A G
```

| | 400 | 410 | 420 |
|---|---|---|---|
| 00-1 1-9000 | ATGTTAGACA | TACACGGGGT | AGAGAAGAGC |
| 99-1 1-9000 | ATGTTAGATA | TACATGGAGT | GGAAAAGAGT |
| | **430** | **440** | **450** |
| 00-1 1-9000 | TGGGTAGAAG | AGATAGACAA | AGAAGCAAGG |
| 99-1 1-9000 | TGGATAGAAG | AAATAGACAA | AGAGGCAAGA |
| | **460** | **470** | **480** |
| 00-1 1-9000 | AAAACAATGG | CAACCTTGCT | TAAGGAATCA |
| 99-1 1-9000 | AAGACAATGG | TAACTTTGCT | TAAGGAATCA |
| | **490** | **500** | **510** |
| 00-1 1-9000 | TCAGGTAATA | TCCCACAAAA | TCAGAGGCCC |
| 99-1 1-9000 | TCAGGTAACA | TCCCACAAAA | CCAGAGACCT |
| | **520** | **530** | **540** |
| 00-1 1-9000 | TCAGCACCAG | ACACACCCAT | AATCTTATTA |
| 99-1 1-9000 | TCAGCACCAG | ACACACCAAT | AATTTTATTA |
| | **550** | **560** | **570** |
| 00-1 1-9000 | TGTGTAGGTG | CCTTAATATT | CACTAAACTA |
| 99-1 1-9000 | TGTGTAGGTG | CCCTAATATT | CACTAAACTA |
| | **580** | **590** | **600** |
| 00-1 1-9000 | GCATCAACCA | TAGAAGTGGG | ACTAGAGACC |
| 99-1 1-9000 | GCATCAACAA | TAGAAGTTGG | ATTAGAGACT |
| | **610** | **620** | **630** |
| 00-1 1-9000 | ACAGTCAGAA | GGGCTAACCG | TGTACTAAGT |
| 99-1 1-9000 | ACAGTTAGAA | GAGCTAATAG | AGTGCTAAGT |
| | **640** | **650** | **660** |
| 00-1 1-9000 | GATGCACTCA | AGAGATACCC | TAGAATGGAC |
| 99-1 1-9000 | GATGCACTCA | AAAGATACCC | AAGGATAGAT |
| | **670** | **680** | **690** |
| 00-1 1-9000 | ATACCAAAGA | TTGCCAGATC | CTTCTATGAC |
| 99-1 1-9000 | ATACCAAAGA | TTGCTAGATC | TTTTTATGAA |
| | **700** | **710** | **720** |
| 00-1 1-9000 | TTATTTGAAC | AAAAAGTGTA | TCACAGAAGT |
| 99-1 1-9000 | CTATTTGAAC | AAAAAGTGTA | CTACAGAAGT |
| | **730** | **740** | **750** |
| 00-1 1-9000 | TTGTTCATTG | AGTATGGCAA | AGCATTAGGC |
| 99-1 1-9000 | TTATTCATTG | AGTACGGAAA | AGCTTTAGGC |
| | **760** | **770** | **780** |
| 00-1 1-9000 | TCATCATCTA | CAGGCAGCAA | AGCAGAAAGT |
| 99-1 1-9000 | TCATCTTCAA | CAGGAAGCAA | AGCAGAAAGT |

Figure 53 con't

| | 790 | 800 | 810 |
|---|---|---|---|
| 00-1 1-9000 | C T A T T T G T T A | A T A T A T T C A T | G C A A G C T T A T |
| 99-1 1-9000 | T T G T T T G T A A | A T A T A T T T A T | G C A A G C T T A T |

| | 820 | 830 | 840 |
|---|---|---|---|
| 00-1 1-9000 | G G G G C C G G T C | A A A C A A T G C T | A A G G T G G G G G |
| 99-1 1-9000 | G G A G C T G G C C | A A A C A C T G C T | A A G G T G G G G T |

| | 850 | 860 | 870 |
|---|---|---|---|
| 00-1 1-9000 | G T C A T T G C C A | G G T C A T C C A A | C A A T A T A A T G |
| 99-1 1-9000 | G T C A T T G C C A | G A T C A T C C A A | C A A C A T A A T G |

| | 880 | 890 | 900 |
|---|---|---|---|
| 00-1 1-9000 | T T A G G A C A T G | T A T C C G T C C A | A G C T G A G T T A |
| 99-1 1-9000 | C T A G G G C A T G | T A T C T G T G C A | A T C T G A A T T G |

| | 910 | 920 | 930 |
|---|---|---|---|
| 00-1 1-9000 | A A A C A G G T C A | C A G A A G T C T A | T G A C T T G G T G |
| 99-1 1-9000 | A A G C A A G T T A | C A G A G G T T T A | T G A C T T G G T G |

| | 940 | 950 | 960 |
|---|---|---|---|
| 00-1 1-9000 | C G A G A A A T G G | G C C C T G A A T C | T G G A C T T C T A |
| 99-1 1-9000 | A G A G A A A T G G | G T C C T G A A T C | T G G G C T T T T A |

| | 970 | 980 | 990 |
|---|---|---|---|
| 00-1 1-9000 | C A T T T A A G G C | A A A G C C C A A A | A G C T G G A C T G |
| 99-1 1-9000 | C A T C T A A G A C | A A A G T C C A A A | G G C A G G G C T G |

| | 1000 | 1010 | 1020 |
|---|---|---|---|
| 00-1 1-9000 | T T A T C A C T A G | C C A A C T G T C C | C A A C T T T G C A |
| 99-1 1-9000 | T T A T C A T T G G | C C A A T T G C C C | C A A T T T T G C T |

| | 1030 | 1040 | 1050 |
|---|---|---|---|
| 00-1 1-9000 | A G T G T T G T T C | T C G G A A A T G C | C T C A G G C T T A |
| 99-1 1-9000 | A G T G T T G T T C | T T G G C A A T G C | T T C A G G T C T A |

| | 1060 | 1070 | 1080 |
|---|---|---|---|
| 00-1 1-9000 | G G C A T A A T C G | G T A T G T A T C G | A G G G A G A G T A |
| 99-1 1-9000 | G G C A T A A T C G | G A A T G T A C A G | A G G G A G A G T A |

| | 1090 | 1100 | 1110 |
|---|---|---|---|
| 00-1 1-9000 | C C A A A C A C A G | A A T T A T T T T C | A G C A G C T G A A |
| 99-1 1-9000 | C C A A A C A C A G | A G C T A T T T T C | T G C A G C A G A A |

| | 1120 | 1130 | 1140 |
|---|---|---|---|
| 00-1 1-9000 | A G T T A T G C C A | A A A G T T T G A A | A G A A A G C A A T |
| 99-1 1-9000 | A G T T A T G C C A | G A A G C T T A A A | A G A A A G C A A T |

| | 1150 | 1160 | 1170 |
|---|---|---|---|
| 00-1 1-9000 | A A A A T A A A T T | T C T C T T C A T T | A G G A C T T A C A |
| 99-1 1-9000 | A A A A T C A A C T | T C T C T T C G T T | A G G G C T T A C A |

Figure 53 con't

| | 1180 | 1190 | 1200 |
|---|---|---|---|
| 00-1 1-9000 | G A T G A A G A G A | A A G A G G C T G C | A G A A C A T T T C |
| 99-1 1-9000 | G A T G A A G A A A | A A G A A G C T G C | A G A A C A C T T C |
| | 1210 | 1220 | 1230 |
| 00-1 1-9000 | T T A A A T G T G A | G T G A C G A C A G | T C A A A A T G A T |
| 99-1 1-9000 | T T A A A C A T G A | G T G G T G A C A A | T C A A G A T G A T |
| | 1240 | 1250 | 1260 |
| 00-1 1-9000 | T A T G A G T A A T | T A A A A A A G T G | G G A C A A G T C A |
| 99-1 1-9000 | T A T G A G T A A T | T A A A A A A C T G | G G A C A A G T C A |
| | 1270 | 1280 | 1290 |
| 00-1 1-9000 | A A A T G T C A T T | C C C T G A A G G A | A A A G A T A T T C |
| 99-1 1-9000 | A A A T G T C A T T | C C C T G A A G G A | A A G G A T A T T C |
| | 1300 | 1310 | 1320 |
| 00-1 1-9000 | T T T T C A T G G G | T A A T G A A G C A | G C A A A A T T A G |
| 99-1 1-9000 | T G T T C A T G G G | T A A T G A A G C A | G C A A A A A T A G |
| | 1330 | 1340 | 1350 |
| 00-1 1-9000 | C A G A A G C T T T | C C A G A A A T C A | T T A A G A A A A C |
| 99-1 1-9000 | C C G A A G C T T T | C C A G A A A T C A | C T G A A A A A A T |
| | 1360 | 1370 | 1380 |
| 00-1 1-9000 | C A G G T C A T A A | A A G A T C T C A A | T C T A T T A T A G |
| 99-1 1-9000 | C A G G T C A C A A | G A G A A C T C A A | T C T A T T G T A G |
| | 1390 | 1400 | 1410 |
| 00-1 1-9000 | G A G A A A A A G T | G A A T A C T G T A | T C A G A A A C A T |
| 99-1 1-9000 | G G G A A A A A G T | T A A C A C T A T A | T C A G A A A C T C |
| | 1420 | 1430 | 1440 |
| 00-1 1-9000 | T G G A A T T A C C | T A C T A T C A G T | A G A C C T G C A A |
| 99-1 1-9000 | T A G A A C T A C C | T A C C A T C A G C | A A A C C T G C A C |
| | 1450 | 1460 | 1470 |
| 00-1 1-9000 | A A C C A A C C A T | A C C G T C A G A A | C C A A A G T T A G |
| 99-1 1-9000 | G A T C A T C T A C | A C T G C T G G A A | C C A A A A T T G G |
| | 1480 | 1490 | 1500 |
| 00-1 1-9000 | C A T G G A C A G A | T A A A G G T G G G | G C A A C C A A A A |
| 99-1 1-9000 | C A T G G G C A G A | C A A C A G C G G A | A T C A C C A A A A |
| | 1510 | 1520 | 1530 |
| 00-1 1-9000 | C T G A A A T A A A | G C A A G C A A T C | A A A G T C A T G G |
| 99-1 1-9000 | T C A C A G A A A A | A C C A G C A A C C | A A A A C A A C A G |
| | 1540 | 1550 | 1560 |
| 00-1 1-9000 | A T C C C A T T G A | A G A A G A A G A G | T C T A C C G A G A |
| 99-1 1-9000 | A T C C T G T T G A | A G A A G A G G A A | T T C A A T G A A A |

Figure 53 con't

| | 1570 | 1580 | 1590 |
|---|---|---|---|
| 00-1 1-9000 | A G A A G G T G C T | A C C C T C C A G T | G A T G G G A A A A |
| 99-1 1-9000 | A G A A A G T G T T | A C C T T C C A G T | G A T G G G A A G A |

| | 1600 | 1610 | 1620 |
|---|---|---|---|
| 00-1 1-9000 | C C C C T G C A G A | A A A G A A A C T G | A A A C C A T C A A |
| 99-1 1-9000 | C T C C T G C A G A | G A A A A A A T C A | A A G T T T T C A A |

| | 1630 | 1640 | 1650 |
|---|---|---|---|
| 00-1 1-9000 | C T A A C A C C A A | A A A G A A G G T T | T C A T T T A C A C |
| 99-1 1-9000 | C C A G T G T A A A | A A A G A A A G T T | T C C T T T A C A T |

| | 1660 | 1670 | 1680 |
|---|---|---|---|
| 00-1 1-9000 | C A A A T G A A C C | A G G G A A A T A T | A C A A A G T T G G |
| 99-1 1-9000 | C A A A T G A A C C | A G G G A A A T A C | A C C A A A C T A G |

| | 1690 | 1700 | 1710 |
|---|---|---|---|
| 00-1 1-9000 | A A A A A G A T G C | T C T A G A T T T G | C T C T C A G A T A |
| 99-1 1-9000 | A G A A A G A T G C | C C T A G A T T T G | C T C T C A G A C A |

| | 1720 | 1730 | 1740 |
|---|---|---|---|
| 00-1 1-9000 | A T G A A G A A G A | A G A T G C A G A A | T C T T C A A T C T |
| 99-1 1-9000 | A T G A G G A A G A | A G A C G C A G A A | T C C T C A A T C C |

| | 1750 | 1760 | 1770 |
|---|---|---|---|
| 00-1 1-9000 | T A A C C T T T G A | A G A A A G A G A T | A C T T C A T C A T |
| 99-1 1-9000 | T A A C T T T T G A | G G A G A A A G A T | A C A T C A T C A C |

| | 1780 | 1790 | 1800 |
|---|---|---|---|
| 00-1 1-9000 | T A A G C A T T G A | G G C C A G A T T G | G A A T C A A T A G |
| 99-1 1-9000 | T A A G C A T T G A | A G C T A G A C T A | G A A T C T A T A G |

| | 1810 | 1820 | 1830 |
|---|---|---|---|
| 00-1 1-9000 | A G G A G A A A T T | A A G C A T G A T A | T T A G G G C T A T |
| 99-1 1-9000 | A A G A G A A G T T | G A G C A T G A T A | T T A G G A C T G C |

| | 1840 | 1850 | 1860 |
|---|---|---|---|
| 00-1 1-9000 | T A A G A A C A C T | C A A C A T T G C T | A C A G C A G G A C |
| 99-1 1-9000 | T T C G T A C A C T | T A A C A T T G C A | A C A G C A G G A C |

| | 1870 | 1880 | 1890 |
|---|---|---|---|
| 00-1 1-9000 | C C A C A G C A G C | A A G A G A T G G G | A T C A G A G A T G |
| 99-1 1-9000 | C A A C A G C T G C | A C G A G A T G G A | A T T A G G G A T G |

| | 1900 | 1910 | 1920 |
|---|---|---|---|
| 00-1 1-9000 | C A A T G A T T G G | C G T A A G A G A G | G A A T T A A T A G |
| 99-1 1-9000 | C A A T G A T T G G | T A T A A G A G A A | G A G C T A A T A G |

| | 1930 | 1940 | 1950 |
|---|---|---|---|
| 00-1 1-9000 | C A G A C A T A A T | A A A G G A A G C T | A A A G G G A A A G |
| 99-1 1-9000 | C A G A G A T A A T | T A A G G A A G C C | A A G G G A A A A G |

Figure 53 con't

| | 1960 | 1970 | 1980 |
|---|---|---|---|
| 00-1 1-9000 | C A G C A G A A A T | G A T G G A A G A G | G A A A T G A G T C |
| 99-1 1-9000 | C A G C T G A A A T | G A T G G A A G A A | G A G A T G A A T C |

| | 1990 | 2000 | 2010 |
|---|---|---|---|
| 00-1 1-9000 | A A C G A T C A A A | A A T A G G A A A T | G G T A G T G T A A |
| 99-1 1-9000 | A A A G A T C A A A | A A T A G G A A A T | G G C A G T G T A A |

| | 2020 | 2030 | 2040 |
|---|---|---|---|
| 00-1 1-9000 | A A T T A A C A G A | A A A A G C A A A A | G A G C T C A A C A |
| 99-1 1-9000 | A A C T A A C C G A | G A A G G C A A A A | G A G C T C A A C A |

| | 2050 | 2060 | 2070 |
|---|---|---|---|
| 00-1 1-9000 | A A A T T G T T G A | A G A T G A A A G C | A C A A G T G G A G |
| 99-1 1-9000 | A A A T T G T T G A | A G A C G A G A G C | A C A A G C G G T G |

| | 2080 | 2090 | 2100 |
|---|---|---|---|
| 00-1 1-9000 | A A T C C G A A G A | A G A A G A A G A A | C C A A A A G A C A |
| 99-1 1-9000 | A A T C A G A A G A | A G A A G A A G A A | C C A A A A G A A A |

| | 2110 | 2120 | 2130 |
|---|---|---|---|
| 00-1 1-9000 | C A C A A G A C A A | T A G T C A A G A A | G A T G A C A T T T |
| 99-1 1-9000 | C T C A G G A T A A | C A A T C A A G G A | G A A G A T A T T T |

| | 2140 | 2150 | 2160 |
|---|---|---|---|
| 00-1 1-9000 | A C C A G T T A A T | T A T G T A G T T T | A A T A A A A A T A |
| 99-1 1-9000 | A T C A G T T A A T | C A T G T A G T T T | A A T A A A A A T A |

| | 2170 | 2180 | 2190 |
|---|---|---|---|
| 00-1 1-9000 | A A C A A T G G G A | C A A G T A A A A A | T G G A G T C C T A |
| 99-1 1-9000 | A A C A A T G G G A | C A A G T C A A G A | T G G A G T C C T A |

| | 2200 | 2210 | 2220 |
|---|---|---|---|
| 00-1 1-9000 | C C T A G T A G A C | A C C T A T C A A G | G C A T T C C T T A |
| 99-1 1-9000 | T C T A G T A G A C | A C T T A T C A A G | G C A T T C C A T A |

| | 2230 | 2240 | 2250 |
|---|---|---|---|
| 00-1 1-9000 | C A C A G C A G C T | G T T C A A G T T G | A T C T A A T A G A |
| 99-1 1-9000 | T A C A G C T G C T | G T T C A A G T T G | A C C T G G T A G A |

| | 2260 | 2270 | 2280 |
|---|---|---|---|
| 00-1 1-9000 | A A A G G A C C T G | T T A C C T G C A A | G C C T A A C A A T |
| 99-1 1-9000 | A A A A G A T T T A | C T G C C A G C A A | G T T T G A C A A T |

| | 2290 | 2300 | 2310 |
|---|---|---|---|
| 00-1 1-9000 | A T G G T T C C C T | T T G T T T C A G G | C C A A C A C A C C |
| 99-1 1-9000 | A T G G T T T C C T | T T A T T T C A G G | C C A A C A C A C C |

| | 2320 | 2330 | 2340 |
|---|---|---|---|
| 00-1 1-9000 | A C C A G C A G T G | C T G C T C G A T C | A G C T A A A A A C |
| 99-1 1-9000 | A C C A G C A G T T | C T G C T T G A T C | A G C T A A A A A C |

Figure 53 con't

| | 2350 | 2360 | 2370 |
|---|---|---|---|
| 00-1 1-9000 | C C T G A C A A T A | A C C A C T C T G T | A T G C T G C A T C |
| 99-1 1-9000 | C C T G A C A A T A | A C C A C T C T G T | A T G C T G C A T C |

| | 2380 | 2390 | 2400 |
|---|---|---|---|
| 00-1 1-9000 | A C A A A A T G G T | C C A A T A C T C A | A A G T G A A T G C |
| 99-1 1-9000 | A C A G A A T G G T | C C A A T A C T C A | A G G T A A A T G C |

| | 2410 | 2420 | 2430 |
|---|---|---|---|
| 00-1 1-9000 | A T C A G C C C A A | G G T G C A G C A A | T G T C T G T A C T |
| 99-1 1-9000 | A T C T G C C C A A | G G T G C T G C C A | T G T C T G T A C T |

| | 2440 | 2450 | 2460 |
|---|---|---|---|
| 00-1 1-9000 | T C C C A A A A A A | T T T G A A G T C A | A T G C G A C T G T |
| 99-1 1-9000 | T C C C A A A A A A | T T C G A G G T A A | A T G C A A C T G T |

| | 2470 | 2480 | 2490 |
|---|---|---|---|
| 00-1 1-9000 | A G C A C T C G A T | G A A T A T A G C A | A A C T G G A A T T |
| 99-1 1-9000 | A G C A C T T G A T | G A A T A C A G T A | A A C T T G A T T T |

| | 2500 | 2510 | 2520 |
|---|---|---|---|
| 00-1 1-9000 | T G A C A A A C T C | A C A G T C T G T G | A A G T A A A A A C |
| 99-1 1-9000 | T G A C A A G C T G | A C G G T C T G C G | A T G T T A A A A C |

| | 2530 | 2540 | 2550 |
|---|---|---|---|
| 00-1 1-9000 | A G T T T A C T T A | A C A A C C A T G A | A A C C A T A C G G |
| 99-1 1-9000 | A G T T T A T T T G | A C A A C T A T G A | A A C C G T A C G G |

| | 2560 | 2570 | 2580 |
|---|---|---|---|
| 00-1 1-9000 | G A T G G T A T C A | A A A T T T G T G A | G C T C A G C C A A |
| 99-1 1-9000 | G A T G G T G T C A | A A A T T T G T G A | G T T C A G C C A A |

| | 2590 | 2600 | 2610 |
|---|---|---|---|
| 00-1 1-9000 | A T C A G T T G G C | A A A A A A A C A C | A T G A T C T A A T |
| 99-1 1-9000 | A T C A G T T G G C | A A A A A G A C A C | A T G A T C T A A T |

| | 2620 | 2630 | 2640 |
|---|---|---|---|
| 00-1 1-9000 | C G C A C T A T G T | G A T T T T A T G G | A T C T A G A A A A |
| 99-1 1-9000 | T G C A C T A T G T | G A C T T C A T G G | A C C T A G A G A A |

| | 2650 | 2660 | 2670 |
|---|---|---|---|
| 00-1 1-9000 | G A A C A C A C C T | G T T A C A A T A C | C A G C A T T C A T |
| 99-1 1-9000 | A A A T A T A C C T | G T G A C A A T A C | C A G C A T T C A T |

| | 2680 | 2690 | 2700 |
|---|---|---|---|
| 00-1 1-9000 | C A A A T C A G T T | T C A A T C A A A G | A G A G T G A G T C |
| 99-1 1-9000 | A A A G T C A G T T | T C A A T C A A A G | A G A G T G A A T C |

| | 2710 | 2720 | 2730 |
|---|---|---|---|
| 00-1 1-9000 | A G C T A C T G T T | G A A G C T G C T A | T A A G C A G T G A |
| 99-1 1-9000 | A G C C A C T G T T | G A A G C T G C A A | T A A G C A G C G A |

Figure 53 con't

| | 2740 | 2750 | 2760 |
|---|---|---|---|
| 00-1 1-9000 | A G C A G A C C A A | G C T C T A A C A C | A G G C C A A A A T |
| 99-1 1-9000 | A G C C G A C C A A | G C C T T G A C A C | A A G C C A A G A T |
| | **2770** | **2780** | **2790** |
| 00-1 1-9000 | T G C A C C T T A T | G C G G G A T T A A | T T A T G A T C A T |
| 99-1 1-9000 | T G C G C C C T A T | G C A G G A C T A A | T T A T G A T C A T |
| | **2800** | **2810** | **2820** |
| 00-1 1-9000 | G A C T A T G A A C | A A T C C C A A A G | G C A T A T T C A A |
| 99-1 1-9000 | G A C C A T G A A C | A A T C C A A A A G | G T A T A T T C A A |
| | **2830** | **2840** | **2850** |
| 00-1 1-9000 | A A A G C T T G G A | G C T G G G A C T C | A A G T C A T A G T |
| 99-1 1-9000 | G A A A C T A G G G | G C T G G A A C A C | A A G T G A T A G T |
| | **2860** | **2870** | **2880** |
| 00-1 1-9000 | A G A A C T A G G A | G C A T A T G T C C | A G G C T G A A A G |
| 99-1 1-9000 | A G A G C T G G G G | G C A T A T G T T C | A G G C T G A G A G |
| | **2890** | **2900** | **2910** |
| 00-1 1-9000 | C A T A A G C A A A | A T A T G C A A G A | C T T G G A G C C A |
| 99-1 1-9000 | C A T C A G T A G G | A T C T G C A A G A | G C T G G A G T C A |
| | **2920** | **2930** | **2940** |
| 00-1 1-9000 | T C A A G G G A C A | A G A T A T G T C T | T G A A G T C C A G |
| 99-1 1-9000 | C C A A G G A A C A | A G A T A C G T A C | T A A A A T C C A G |
| | **2950** | **2960** | **2970** |
| 00-1 1-9000 | A T A A C A A C C A | A G C A C C T T G G | C C A A G A G C T A |
| 99-1 1-9000 | A T A A - A A A T A | A C T G T C T T A A | T C A A T A A T T G |
| | **2980** | **2990** | **3000** |
| 00-1 1-9000 | C T A A C C C T A T | C T C A T A G A T C | A - T A A A G T C A |
| 99-1 1-9000 | C T T A T A T A A C | T C T A G A G A T T | A A T A A G C T T A |
| | **3010** | **3020** | **3030** |
| 00-1 1-9000 | C C A T T C T A G T | T A T A T A A A A A | T C A A G T T A G A |
| 99-1 1-9000 | T T A T T A T A G T | T A T A T A A A A A | T - A A A T T A G A |
| | **3040** | **3050** | **3060** |
| 00-1 1-9000 | A C A A G A A T T A | A A T C A A T C A A | G A A C G G G A C A |
| 99-1 1-9000 | A T T A G A A G G G | C A T C A A T A G A | A A G C G G G A C A |
| | **3070** | **3080** | **3090** |
| 00-1 1-9000 | A A T A A A A A T G | T C T T G G A A A G | T G G T G A T C A T |
| 99-1 1-9000 | A A T A A A A A T G | T C T T G G A A A G | T G A T G A T C A T |
| | **3100** | **3110** | **3120** |
| 00-1 1-9000 | T T T T T C A T T G | T T A A T A A C A C | C T C A A C A C G G |
| 99-1 1-9000 | C A T T T C G T T A | C T C A T A A C A C | C C C A G C A C G G |

Figure 53 con't

| | 3130 | 3140 | 3150 |
|---|---|---|---|
| 00-1 1-9000 | TCTTAAAGAG | AGCTACTTAG | AAGAGTCATG |
| 99-1 1-9000 | GCTAAAGGAG | AGTTATTTGG | AAGAATCATG |

| | 3160 | 3170 | 3180 |
|---|---|---|---|
| 00-1 1-9000 | TAGCACTATA | ACTGAAGGAT | ATCTCAGTGT |
| 99-1 1-9000 | TAGTACTATA | ACTGAGGGAT | ACCTCAGTGT |

| | 3190 | 3200 | 3210 |
|---|---|---|---|
| 00-1 1-9000 | TCTGAGGACA | GGTTGGTACA | CCAATGTTTT |
| 99-1 1-9000 | TTTAAGAACA | GGCTGGTACA | CTAATGTCTT |

| | 3220 | 3230 | 3240 |
|---|---|---|---|
| 00-1 1-9000 | TACACTGGAG | GTAGGCGATG | TAGAGAACCT |
| 99-1 1-9000 | CACATTAGAA | GTTGGTGATG | TTGAAAATCT |

| | 3250 | 3260 | 3270 |
|---|---|---|---|
| 00-1 1-9000 | TACATGTGCC | GATGGACCCA | GCTTAATAAA |
| 99-1 1-9000 | TACATGTACT | GATGGACCTA | GCTTAATCAA |

| | 3280 | 3290 | 3300 |
|---|---|---|---|
| 00-1 1-9000 | AACAGAATTA | GACCTGACCA | AAAGTGCACT |
| 99-1 1-9000 | AACAGAACTT | GATCTAACAA | AAAGTGCTTT |

| | 3310 | 3320 | 3330 |
|---|---|---|---|
| 00-1 1-9000 | AAGAGAGCTC | AGAACAGTTT | CTGCTGATCA |
| 99-1 1-9000 | AAGGGAACTC | AAAACAGTCT | CTGCTGATCA |

| | 3340 | 3350 | 3360 |
|---|---|---|---|
| 00-1 1-9000 | ACTGGCAAGA | GAGGAGCAAA | TTGAAAATCC |
| 99-1 1-9000 | GTTGGCGAGA | GAGGAGCAAA | TTGAAAATCC |

| | 3370 | 3380 | 3390 |
|---|---|---|---|
| 00-1 1-9000 | CAGACAATCT | AGATTCGTTC | TAGGAGCAAT |
| 99-1 1-9000 | CAGACAATCA | AGATTTGTCT | TAGGTGCGAT |

| | 3400 | 3410 | 3420 |
|---|---|---|---|
| 00-1 1-9000 | AGCACTCGGT | GTTGCAACTG | CAGCTGCAGT |
| 99-1 1-9000 | AGCTCTCGGA | GTTGCTACAG | CAGCAGCAGT |

| | 3430 | 3440 | 3450 |
|---|---|---|---|
| 00-1 1-9000 | TACAGCAGGT | GTTGCAATTG | CCAAAACCAT |
| 99-1 1-9000 | CACAGCAGGC | ATTGCAATAG | CCAAAACCAT |

| | 3460 | 3470 | 3480 |
|---|---|---|---|
| 00-1 1-9000 | CCGGCTTGAA | AGTGAAGTAA | CAGCAATTAA |
| 99-1 1-9000 | AAGGCTTGAG | AGTGAGGTGA | ATGCAATTAA |

| | 3490 | 3500 | 3510 |
|---|---|---|---|
| 00-1 1-9000 | GAATGCCCTC | AAAAAGACCA | ATGAAGCAGT |
| 99-1 1-9000 | AGGTGCTCTC | AAACAAACTA | ATGAAGCAGT |

Figure 53 con't

| | 3520 | 3530 | 3540 |
|---|---|---|---|
| 00-1 1-9000 | ATCTACATTG | GGGAATGGAG | TTCGTGTGTT |
| 99-1 1-9000 | ATCCACATTA | GGGAATGGTG | TGCGGGTCCT |
| | 3550 | 3560 | 3570 |
| 00-1 1-9000 | GGCAACTGCA | GTGAGAGAGC | TGAAAGATTT |
| 99-1 1-9000 | AGCCACTGCA | GTGAGAGAGC | TAAAAGAATT |
| | 3580 | 3590 | 3600 |
| 00-1 1-9000 | TGTGAGCAAG | AATCTAACAC | GTGCAATCAA |
| 99-1 1-9000 | TGTGAGCAAA | AACCTGACTA | GTGCAATCAA |
| | 3610 | 3620 | 3630 |
| 00-1 1-9000 | CAAAAACAAG | TGCGACATTG | CTGACCTGAA |
| 99-1 1-9000 | CAGGAACAAA | TGTGACATTG | CTGATCTGAA |
| | 3640 | 3650 | 3660 |
| 00-1 1-9000 | AATGGCCGTT | AGCTTCAGTC | AATTCAACAG |
| 99-1 1-9000 | GATGGCTGTC | AGCTTCAGTC | AATTCAACAG |
| | 3670 | 3680 | 3690 |
| 00-1 1-9000 | AAGGTTCCTA | AATGTTGTGC | GGCAATTTTC |
| 99-1 1-9000 | AAGATTTCTA | AATGTTGTGC | GGCAGTTTTC |
| | 3700 | 3710 | 3720 |
| 00-1 1-9000 | AGACAACGCT | GGAATAACAC | CAGCAATATC |
| 99-1 1-9000 | AGACAATGCA | GGGATAACAC | CAGCAATATC |
| | 3730 | 3740 | 3750 |
| 00-1 1-9000 | TTTGGACTTA | ATGACAGATG | CTGAACTAGC |
| 99-1 1-9000 | ATTGGACCTG | ATGACTGATG | CTGAGTTGGC |
| | 3760 | 3770 | 3780 |
| 00-1 1-9000 | CAGAGCTGTT | TCCAACATGC | CAACATCTGC |
| 99-1 1-9000 | CAGAGCTGTA | TCATACATGC | CAACATCTGC |
| | 3790 | 3800 | 3810 |
| 00-1 1-9000 | AGGACAAATA | AAACTGATGT | TGGAGAACCG |
| 99-1 1-9000 | AGGGCAGATA | AAACTGATGT | TGGAGAACCG |
| | 3820 | 3830 | 3840 |
| 00-1 1-9000 | TGCAATGGTA | AGAAGAAAAG | GGTTCGGATT |
| 99-1 1-9000 | CGCAATGGTA | AGGAGAAAAG | GATTTGGAAT |
| | 3850 | 3860 | 3870 |
| 00-1 1-9000 | CCTGATAGGA | GTTTACGGAA | GCTCCGTAAT |
| 99-1 1-9000 | CCTGATAGGG | GTCTACGGAA | GCTCTGTGAT |
| | 3880 | 3890 | 3900 |
| 00-1 1-9000 | TTACATGGTG | CAACTGCCAA | TCTTTGGGGT |
| 99-1 1-9000 | TTACATGGTT | CAATTGCCGA | TCTTTGGTGT |

Figure 53 con't

| | | | |
|---|---|---|---|
| | 3910 | 3920 | 3930 |
| 00-1 1-9000 | TATAGACACG | CCTTGCTGGA | TAGTAAAAGC |
| 99-1 1-9000 | CATAGATACA | CCTTGTTGGA | TCATCAAGGC |
| | 3940 | 3950 | 3960 |
| 00-1 1-9000 | AGCCCCTTCT | TGTTCAGGAA | AAAAGGGAAA |
| 99-1 1-9000 | AGCTCCCTCT | TGCTCAGAAA | AAAACGGGAA |
| | 3970 | 3980 | 3990 |
| 00-1 1-9000 | CTATGCTTGC | CTCTTAAGAG | AAGACCAAGG |
| 99-1 1-9000 | TTATGCTTGC | CTCCTAAGAG | AGGATCAAGG |
| | 4000 | 4010 | 4020 |
| 00-1 1-9000 | ATGGTATTGT | CAAAATGCAG | GGTCAACTGT |
| 99-1 1-9000 | GTGGTATTGT | AAAAATGCAG | GATCTACTGT |
| | 4030 | 4040 | 4050 |
| 00-1 1-9000 | TTACTACCCA | AATGAAAAAG | ACTGTGAAAC |
| 99-1 1-9000 | TTACTACCCA | AATGAAAAAG | ACTGCGAAAC |
| | 4060 | 4070 | 4080 |
| 00-1 1-9000 | AAGAGGAGAC | CATGTCTTTT | GCGACACAGC |
| 99-1 1-9000 | AAGAGGTGAT | CATGTTTTTT | GTGACACAGC |
| | 4090 | 4100 | 4110 |
| 00-1 1-9000 | AGCAGGAATC | AATGTTGCTG | AGCAGTCAAA |
| 99-1 1-9000 | AGCAGGGATC | AATGTTGCTG | AGCAATCAAG |
| | 4120 | 4130 | 4140 |
| 00-1 1-9000 | GGAGTGCAAC | ATAAACATAT | CTACTACTAA |
| 99-1 1-9000 | AGAATGCAAC | ATCAACATAT | CTACTACCAA |
| | 4150 | 4160 | 4170 |
| 00-1 1-9000 | TTACCCATGC | AAAGTTAGCA | CAGGAAGACA |
| 99-1 1-9000 | CTACCCATGC | AAAGTCAGCA | CAGGAAGACA |
| | 4180 | 4190 | 4200 |
| 00-1 1-9000 | TCCTATCAGT | ATGGTTGCAC | TATCTCCTCT |
| 99-1 1-9000 | CCCTATAAGC | ATGGTTGCAC | TATCACCTCT |
| | 4210 | 4220 | 4230 |
| 00-1 1-9000 | TGGGGCTTTG | GTTGCTTGCT | ACAAGGGAGT |
| 99-1 1-9000 | CGGTGCTTTG | GTGGCTTGCT | ATAAAGGGGT |
| | 4240 | 4250 | 4260 |
| 00-1 1-9000 | GAGCTGTTCC | ATTGGCAGCA | ACAGAGTAGG |
| 99-1 1-9000 | AAGCTGCTCG | ATTGGCAGCA | ATTGGGTTGG |
| | 4270 | 4280 | 4290 |
| 00-1 1-9000 | GATCATCAAG | CAACTGAACA | AAGGCTGCTC |
| 99-1 1-9000 | AATCATCAAA | CAATTACCCA | AAGGCTGCTC |

Figure 53 con't

| | 4300 | 4310 | 4320 |
|---|---|---|---|
| 00-1 1-9000 | T T A T A T A A C C | A A C C A A G A C G | C A G A C A C A G T |
| 99-1 1-9000 | A T A C A T A A C C | A A C C A G G A T G | C A G A C A C T G T |
| | **4330** | **4340** | **4350** |
| 00-1 1-9000 | G A C A A T A G A C | A A C A C T G T A T | A C C A G C T A A G |
| 99-1 1-9000 | A A C A A T T G A C | A A T A C C G T G T | A T C A A C T A A G |
| | **4360** | **4370** | **4380** |
| 00-1 1-9000 | C A A A G T T G A A | G G C G A A C A G C | A T G T T A T A A A |
| 99-1 1-9000 | C A A A G T T G A A | G G T G A A C A G C | A T G T A A T A A A |
| | **4390** | **4400** | **4410** |
| 00-1 1-9000 | A G G A A G G C C A | G T G T C A A G C A | G C T T T G A C C C |
| 99-1 1-9000 | A G G G A G A C C A | G T T T C A A G C A | G T T T T G A T C C |
| | **4420** | **4430** | **4440** |
| 00-1 1-9000 | A G T C A A G T T T | C C T G A A G A T C | A A T T C A A T G T |
| 99-1 1-9000 | A A T C A A G T T T | C C T G A G G A T C | A G T T C A A T G T |
| | **4450** | **4460** | **4470** |
| 00-1 1-9000 | T G C A C T T G A C | C A A G T T T T C G | A G A G C A T T G A |
| 99-1 1-9000 | T G C G C T T G A T | C A A G T C T T C G | A A A G C A T T G A |
| | **4480** | **4490** | **4500** |
| 00-1 1-9000 | G A A C A G T C A G | G C C T T G G T G G | A T C A A T C A A A |
| 99-1 1-9000 | G A A C A G T C A G | G C A C T A G T G G | A C C A G T C A A A |
| | **4510** | **4520** | **4530** |
| 00-1 1-9000 | C A G A A T C C T A | A G C A G T G C A G | A G A A A G G A A A |
| 99-1 1-9000 | C A A A A T T C T A | A A C A G T G C A G | A A A A A G G A A A |
| | **4540** | **4550** | **4560** |
| 00-1 1-9000 | C A C T G G C T T C | A T C A T T G T A A | T A A T T C T A A T |
| 99-1 1-9000 | C A C T G G T T T C | A T T A T C G T A G | T A A T T T T G G T |
| | **4570** | **4580** | **4590** |
| 00-1 1-9000 | T G C T G T C C T T | G G C T C T A C C A | T G A T C C T A G T |
| 99-1 1-9000 | T G C T G T T C T T | G G T C T A A C C A | T G A T T T C A G T |
| | **4600** | **4610** | **4620** |
| 00-1 1-9000 | G A G T G T T T T T | A T C A T A A T A A | A G A A A A C A A A |
| 99-1 1-9000 | G A G C A T C A T C | A T C A T A A T C A | A G A A A A C A A G |
| | **4630** | **4640** | **4650** |
| 00-1 1-9000 | G A A A C C C A C A | G G A G C A C C T C | C A G A G C T G A G |
| 99-1 1-9000 | G A A G C C C A C A | G G A G C A C C T C | C A G A G C T G A A |
| | **4660** | **4670** | **4680** |
| 00-1 1-9000 | T G G T G T C A C A | A A C A A T G G C T | T C A T A C C A C A |
| 99-1 1-9000 | T G G T G T C A C C | A A C G G C G G T T | T C A T A C C A C A |

Figure 53 con't

| | | | |
|---|---|---|---|
| | 4690 | 4700 | 4710 |
| 00-1 1-9000 | T A A T T A G T T A | A T T A A A A A T A | A A G T A A A T T A |
| 99-1 1-9000 | T A G T T A G T T A | A T T A A A A A - - | - - - - - A - - - - |
| | 4720 | 4730 | 4740 |
| 00-1 1-9000 | A A A T A A A T T A | A A A T T A A A A A | T A A A A A T T T G |
| 99-1 1-9000 | - - - - - - - - - - | - - - - - - - - - - | - - - - - - - - T G |
| | 4750 | 4760 | 4770 |
| 00-1 1-9000 | G G A C A A A T C A | T A A T G T C T C G | C A A G G C T C C G |
| 99-1 1-9000 | G G A C A A A T C A | T C A T G T C T C G | T A A G G C T C C A |
| | 4780 | 4790 | 4800 |
| 00-1 1-9000 | T G C A A A T A T G | A A G T G C G G G G | C A A A T G C A A T |
| 99-1 1-9000 | T G C A A A T A T G | A A G T G C G G G G | C A A A T G C A A C |
| | 4810 | 4820 | 4830 |
| 00-1 1-9000 | A G A G G A A G T G | A G T G C A A G T T | T A A C C A C A A T |
| 99-1 1-9000 | A G A G G G A G T G | A T T G C A A A T T | C A A T C A C A A T |
| | 4840 | 4850 | 4860 |
| 00-1 1-9000 | T A C T G G A G T T | G G C C A G A T A G | A T A C T T A T T A |
| 99-1 1-9000 | T A C T G G A G T T | G G C C T G A T A G | A T A T T T A T T G |
| | 4870 | 4880 | 4890 |
| 00-1 1-9000 | A T A A G A T C A A | A T T A T T T A T T | A A A T C A A C T T |
| 99-1 1-9000 | T T A A G A T C A A | A T T A T C T C T T | A A A T C A G C T T |
| | 4900 | 4910 | 4920 |
| 00-1 1-9000 | T T A A G G A A C A | C T G A T A G A G C | T G A T G G C T T A |
| 99-1 1-9000 | T T A A G A A A C A | C A G A T A A G G C | T G A T G G T T T G |
| | 4930 | 4940 | 4950 |
| 00-1 1-9000 | T C A A T A A T A T | C A G G A G C A G G | C A G A G A A G A T |
| 99-1 1-9000 | T C A A T A A T A T | C A G G A G C A G G | T A G A G A A G A T |
| | 4960 | 4970 | 4980 |
| 00-1 1-9000 | A G G A C A C A A G | A T T T T G T C C T | A G G T T C C A C C |
| 99-1 1-9000 | A G A A C T C A A G | A C T T T G T T C T | T G G T T C T A C T |
| | 4990 | 5000 | 5010 |
| 00-1 1-9000 | A A T G T G G T T C | A A G G T T A T A T | T G A T G A T A A C |
| 99-1 1-9000 | A A T G T G G T T C | A A G G G T A C A T | T G A T G A C A A C |
| | 5020 | 5030 | 5040 |
| 00-1 1-9000 | C A A A G C A T A A | C A A A A G C T G C | A G C C T G T T A C |
| 99-1 1-9000 | C A A G G A A T A A | C C A A G G C T G C | A G C T T G C T A T |
| | 5050 | 5060 | 5070 |
| 00-1 1-9000 | A G T C T A C A T A | A T A T A A T C A A | A C A A C T A C A A |
| 99-1 1-9000 | A G T C T A C A C A | A C A T A A T C A A | G C A A C T A C A A |

Figure 53 con't

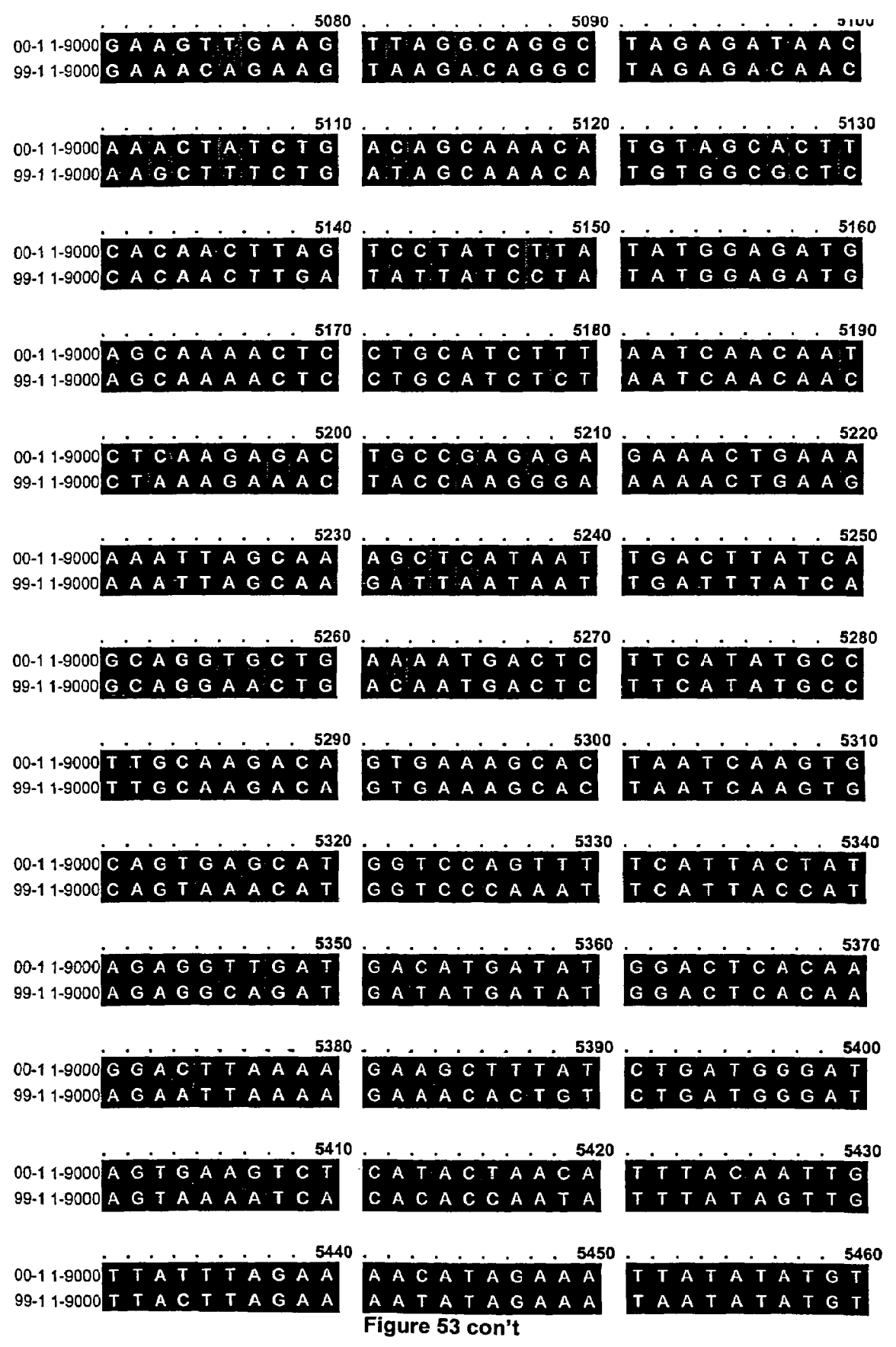

| | 5080 | 5090 | 5100 |
|---|---|---|---|
| 00-1 1-9000 | G A A G T T G A A G | T T A G G C A G G C | T A G A G A T A A C |
| 99-1 1-9000 | G A A A C A G A A G | T A A G A C A G G C | T A G A G A C A A C |
| | 5110 | 5120 | 5130 |
| 00-1 1-9000 | A A A C T A T C T G | A C A G C A A A C A | T G T A G C A C T T |
| 99-1 1-9000 | A A G C T T T C T G | A T A G C A A A C A | T G T G G C G C T C |
| | 5140 | 5150 | 5160 |
| 00-1 1-9000 | C A C A A C T T A G | T C C T A T C T T A | T A T G G A G A T G |
| 99-1 1-9000 | C A C A A C T T G A | T A T T A T C C T A | T A T G G A G A T G |
| | 5170 | 5180 | 5190 |
| 00-1 1-9000 | A G C A A A A C T C | C T G C A T C T T T | A A T C A A C A A T |
| 99-1 1-9000 | A G C A A A A C T C | C T G C A T C T C T | A A T C A A C A A C |
| | 5200 | 5210 | 5220 |
| 00-1 1-9000 | C T C A A G A G A C | T G C C G A G A G A | G A A A C T G A A A |
| 99-1 1-9000 | C T A A A G A A A C | T A C C A A G G G A | A A A A C T G A A G |
| | 5230 | 5240 | 5250 |
| 00-1 1-9000 | A A A T T A G C A A | A G C T C A T A A T | T G A C T T A T C A |
| 99-1 1-9000 | A A A T T A G C A A | G A T T A A T A A T | T G A T T T A T C A |
| | 5260 | 5270 | 5280 |
| 00-1 1-9000 | G C A G G T G C T G | A A A A T G A C T C | T T C A T A T G C C |
| 99-1 1-9000 | G C A G G A A C T G | A C A A T G A C T C | T T C A T A T G C C |
| | 5290 | 5300 | 5310 |
| 00-1 1-9000 | T T G C A A G A C A | G T G A A A G C A C | T A A T C A A G T G |
| 99-1 1-9000 | T T G C A A G A C A | G T G A A A G C A C | T A A T C A A G T G |
| | 5320 | 5330 | 5340 |
| 00-1 1-9000 | C A G T G A G C A T | G G T C C A G T T T | T C A T T A C T A T |
| 99-1 1-9000 | C A G T A A A C A T | G G T C C C A A A T | T C A T T A C C A T |
| | 5350 | 5360 | 5370 |
| 00-1 1-9000 | A G A G G T T G A T | G A C A T G A T A T | G G A C T C A C A A |
| 99-1 1-9000 | A G A G G C A G A T | G A T A T G A T A T | G G A C T C A C A A |
| | 5380 | 5390 | 5400 |
| 00-1 1-9000 | G G A C T T A A A A | G A A G C T T T A T | C T G A T G G G A T |
| 99-1 1-9000 | A G A A T T A A A A | G A A A C A C T G T | C T G A T G G G A T |
| | 5410 | 5420 | 5430 |
| 00-1 1-9000 | A G T G A A G T C T | C A T A C T A A C A | T T T A C A A T T G |
| 99-1 1-9000 | A G T A A A A T C A | C A C A C C A A T A | T T T A T A G T T G |
| | 5440 | 5450 | 5460 |
| 00-1 1-9000 | T T A T T T A G A A | A A C A T A G A A A | T T A T A T A T G T |
| 99-1 1-9000 | T T A C T T A G A A | A A T A T A G A A A | T A A T A T A T G T |

Figure 53 con't

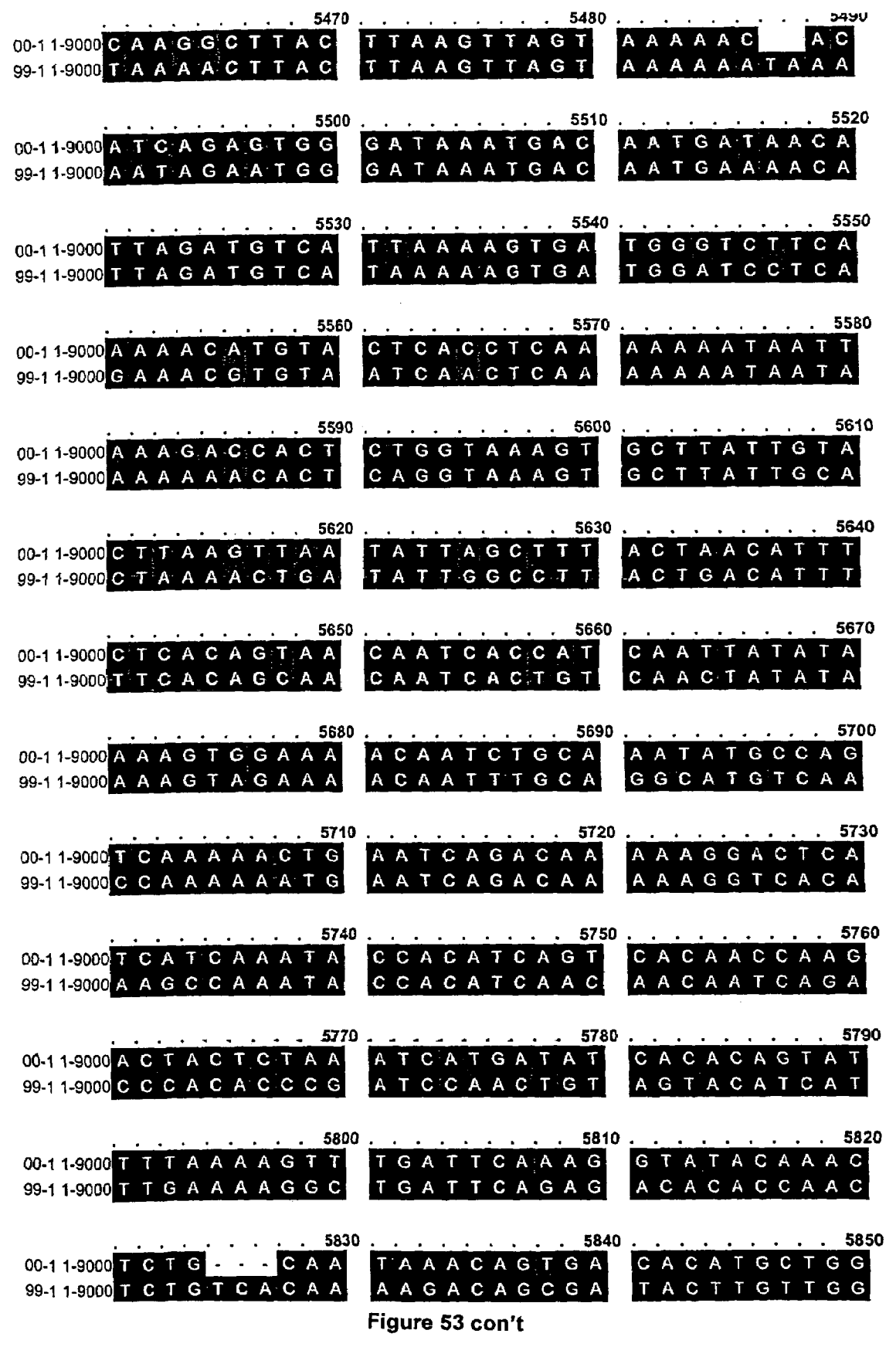

| | | | |
|---|---|---|---|
| | 5470 | 5480 | 5490 |
| 00-1 1-9000 | C A A G G C T T A C | T T A A G T T A G T | A A A A A C     A C |
| 99-1 1-9000 | T A A A A C T T A C | T T A A G T T A G T | A A A A A A T A A A |
| | 5500 | 5510 | 5520 |
| 00-1 1-9000 | A T C A G A G T G G | G A T A A A T G A C | A A T G A T A A C A |
| 99-1 1-9000 | A A T A G A A T G G | G A T A A A T G A C | A A T G A A A A C A |
| | 5530 | 5540 | 5550 |
| 00-1 1-9000 | T T A G A T G T C A | T T A A A A G T G A | T G G G T C T T C A |
| 99-1 1-9000 | T T A G A T G T C A | T A A A A A G T G A | T G G A T C C T C A |
| | 5560 | 5570 | 5580 |
| 00-1 1-9000 | A A A A C A T G T A | C T C A C C T C A A | A A A A A T A A T T |
| 99-1 1-9000 | G A A A C G T G T A | A T C A A C T C A A | A A A A A T A A T A |
| | 5590 | 5600 | 5610 |
| 00-1 1-9000 | A A A G A C C A C T | C T G G T A A A G T | G C T T A T T G T A |
| 99-1 1-9000 | A A A A A A C A C T | C A G G T A A A G T | G C T T A T T G C A |
| | 5620 | 5630 | 5640 |
| 00-1 1-9000 | C T T A A G T T A A | T A T T A G C T T T | A C T A A C A T T T |
| 99-1 1-9000 | C T A A A A C T G A | T A T T G G C C T T | A C T G A C A T T T |
| | 5650 | 5660 | 5670 |
| 00-1 1-9000 | C T C A C A G T A A | C A A T C A C C A T | C A A T T A T A T A |
| 99-1 1-9000 | T T C A C A G C A A | C A A T C A C T G T | C A A C T A T A T A |
| | 5680 | 5690 | 5700 |
| 00-1 1-9000 | A A A G T G G A A A | A C A A T C T G C A | A A T A T G C C A G |
| 99-1 1-9000 | A A A G T A G A A A | A C A A T T T G C A | G G C A T G T C A A |
| | 5710 | 5720 | 5730 |
| 00-1 1-9000 | T C A A A A A C T G | A A T C A G A C A A | A A A G G A C T C A |
| 99-1 1-9000 | C C A A A A A A T G | A A T C A G A C A A | A A A G G T C A C A |
| | 5740 | 5750 | 5760 |
| 00-1 1-9000 | T C A T C A A A T A | C C A C A T C A G T | C A C A A C C A A G |
| 99-1 1-9000 | A A G C C A A A T A | C C A C A T C A A C | A A C A A T C A G A |
| | 5770 | 5780 | 5790 |
| 00-1 1-9000 | A C T A C T C T A A | A T C A T G A T A T | C A C A C A G T A T |
| 99-1 1-9000 | C C C A C A C C C G | A T C C A A C T G T | A G T A C A T C A T |
| | 5800 | 5810 | 5820 |
| 00-1 1-9000 | T T T A A A A G T T | T G A T T C A A A G | G T A T A C A A A C |
| 99-1 1-9000 | T T G A A A A G G C | T G A T T C A G A G | A C A C A C C A A C |
| | 5830 | 5840 | 5850 |
| 00-1 1-9000 | T C T G - - - C A A | T A A A C A G T G A | C A C A T G C T G G |
| 99-1 1-9000 | T C T G T C A C A A | A A G A C A G C G A | T A C T T G T T G G |

Figure 53 con't

| | | | |
|---|---|---|---|
| | 5860 | 5870 | 5880 |
| 00-1 1-9000 | A A A A T A A A C A | G A A A T C A A T G | C A C A A A T A T A |
| 99-1 1-9000 | A G A A T A C A C A | A G A A T C A A C G | T A C A A A T A T A |
| | 5890 | 5900 | 5910 |
| 00-1 1-9000 | A C A A C A T A C A | A A T T T T T A T G | T T T T A A A T C T |
| 99-1 1-9000 | A A A A T A T A C A | A G T T C T T A T G | C T C T G G G T T C |
| | 5920 | 5930 | 5940 |
| 00-1 1-9000 | G A A G A C A C A A | A A A C C A A C A A | T T G T G A T A A A |
| 99-1 1-9000 | A C A A A T T C A A | A A G G T A C A G A | T T G T G A G G A A |
| | 5950 | 5960 | 5970 |
| 00-1 1-9000 | C T G A C A G A T T | T A T G C A G A A A | C A A A C C A A A A |
| 99-1 1-9000 | C C A A C A G C C C | T A T G C G A C A A | A A A G T T A A A A |
| | 5980 | 5990 | 6000 |
| 00-1 1-9000 | C C A G C A G T T G | G A G T G T A T C A | C A T A G T A G A A |
| 99-1 1-9000 | A C C A T A G T A G | A A A A A C A T A G | A A A A G C A G A A |
| | 6010 | 6020 | 6030 |
| 00-1 1-9000 | T G C C A T T G T A | T A T A C A C A G T | T A A A T G G A A G |
| 99-1 1-9000 | T G T C A C T G T C | T A C A T A C A A C | C G A G T G G G G G |
| | 6040 | 6050 | 6060 |
| 00-1 1-9000 | T G C T A T C A T T | A C C C A A C C G A | T G A A A C C C A A |
| 99-1 1-9000 | T G C C T T C A T C | C C T A A A A T - - | - - - A A C A C G G |
| | 6070 | 6080 | 6090 |
| 00-1 1-9000 | T C C T A A A T G T | T A A C A C C A G A | T T A G G A T C C A |
| 99-1 1-9000 | C T T T C A A C A T | T A A A A T C A G A | A C A A C C T C C A |
| | 6100 | 6110 | 6120 |
| 00-1 1-9000 | T C C A A G T C T G | T T A G T T C A A C | A A T T T A G T T A |
| 99-1 1-9000 | C C C A G G T C T A | T C A A T A C A G T | G G T T T A G C C A |
| | 6130 | 6140 | 6150 |
| 00-1 1-9000 | T T T A A A A A T A | T T T T G A A A A C | A A G T A A G T T T |
| 99-1 1-9000 | T T T A A A A A - - | - - C C G A A T A T | T A T C T A G G C T |
| | 6160 | 6170 | 6180 |
| 00-1 1-9000 | C T A T G A T A C T | T C A T A A T A A T | A A G T A A T A A T |
| 99-1 1-9000 | G C A C G A C A C T | T T G C A A T A A T | A T G C A A T A G T |
| | 6190 | 6200 | 6210 |
| 00-1 1-9000 | T A A T T G C T T A | A T C A T C A T C A | C A A C A T T A T T |
| 99-1 1-9000 | C A A T A G T T A A | A C C A C T G C T G | C A A A C T C A T C |
| | 6220 | 6230 | 6240 |
| 00-1 1-9000 | C G A A A C C A T A | A C T A T T C A A T | T T A A A A A G T A |
| 99-1 1-9000 | C A T A A T - A T A | A T C A C T G A G T | - - - - - A A T A C |

Figure 53 con't

| | | | |
|---|---|---|---|
| | 6250 | 6260 | 6270 |
| 00-1 1-9000 | A A A A A C A A T A | A C A T G G G A C A | A G T A G T T A T G |
| 99-1 1-9000 | A A A A T C A A G A | A A A T G G G A C A | A G T G G C T A T G |
| | 6280 | 6290 | 6300 |
| 00-1 1-9000 | G A G G T G A A A G | T G G A G A A C A T | T C G A A C A A T A |
| 99-1 1-9000 | G A A G T A A G A G | T G G A G A A C A T | T C G A G C G A T A |
| | 6310 | 6320 | 6330 |
| 00-1 1-9000 | G A T A T G C T C A | A A G C A A G A G T | A A A A A A T C G T |
| 99-1 1-9000 | G A C A T G T T C A | A A G C A A A G A T | A A A A A A C C G T |
| | 6340 | 6350 | 6360 |
| 00-1 1-9000 | G T G G C A C G C A | G C A A A T G C T T | T A A A A A T G C C |
| 99-1 1-9000 | A T A A G A A G C A | G C A G G T G C T A | T A G A A A T G C T |
| | 6370 | 6380 | 6390 |
| 00-1 1-9000 | T C T T T G G T C C | T C A T A G G A A T | A A C T A C A T T G |
| 99-1 1-9000 | A C A C T G A T C C | T T A T T G G A C T | A A C A G C G T T A |
| | 6400 | 6410 | 6420 |
| 00-1 1-9000 | A G T A T T G C C C | T C A A T A T C T A | T C T G A T C A T A |
| 99-1 1-9000 | A G C A T G G C A C | T T A A T A T T T T | C C T G A T C A T C |
| | 6430 | 6440 | 6450 |
| 00-1 1-9000 | A A C T A T A A A A | T G C A A A A A A A | C A C A T C T G A A |
| 99-1 1-9000 | G A T C A T G C A A | C A T T A A G A A A | C A T G A T C A A A |
| | 6460 | 6470 | 6480 |
| 00-1 1-9000 | T C A G A A C A T C | A C A C C A G C T C | A T C A C C C A T G |
| 99-1 1-9000 | A C A G A A A A C T | G T G C T A A C A T | G C C G T C G G C A |
| | 6490 | 6500 | 6510 |
| 00-1 1-9000 | G A A T C C A G C A | G A G A A A C T C C | A A C G G T C C C C |
| 99-1 1-9000 | G A A C C A A G C A | A A A A G A C C C C | A A T G A C C T C C |
| | 6520 | 6530 | 6540 |
| 00-1 1-9000 | A C A G A C A A C T | C A G A C A C C A A | C T C A A G C C C A |
| 99-1 1-9000 | A C A G C A G G C C | C A A A C A C C A A | A C C C A A T C C A |
| | 6550 | 6560 | 6570 |
| 00-1 1-9000 | C A G C A T C C A A | C T C A A C A G T C | C A C A G A A G G C |
| 99-1 1-9000 | C A G C A A G C A A | C A C A G T G G A C | C A C A G A G A A C |
| | 6580 | 6590 | 6600 |
| 00-1 1-9000 | T C C A C A C T C T | A C T T T G C A G C | C T C A G C A A G C |
| 99-1 1-9000 | T C A A C A T C C C | C A G T A G C A A C | C C C A G A G G G C |
| | 6610 | 6620 | 6630 |
| 00-1 1-9000 | T C A C C A G A G A | C A G A A C C A A C | A T C A A C A C C A |
| 99-1 1-9000 | C A T C C A T A C A | C A G G G A C A A C | T C A A A C A T C A |

Figure 53 con't

| | | | |
|---|---|---|---|
| | 6640 | 6650 | 6660 |
| 00-1 1-9000 | GATACAACAA | ACCGCCCGCC | CTTCGTCGAC |
| 99-1 1-9000 | GACACAACAG | CTCCCCAGCA | AACCACAGAC |
| | 6670 | 6680 | 6690 |
| 00-1 1-9000 | ACACACACAA | CACCACCAAG | CGCAAGCAGA |
| 99-1 1-9000 | AAACACACAG | CACCGCTAAA | ATCAACCAAT |
| | 6700 | 6710 | 6720 |
| 00-1 1-9000 | ACAAAGACAA | GTCCGGCAGT | C-CACACAAA |
| 99-1 1-9000 | GAACAGATCA | CCCAGACAAC | CACAGAGAAA |
| | 6730 | 6740 | 6750 |
| 00-1 1-9000 | AA-ACAACCC | AAGGACAAGC | TCTAGAACAC |
| 99-1 1-9000 | AAGACAATCA | GAGCAACAAC | CCAAAAAAGG |
| | 6760 | 6770 | 6780 |
| 00-1 1-9000 | --------AT | TCTCCACCAC | GGGC--AACG |
| 99-1 1-9000 | GAAAAAGGAA | AAGAAAACAC | AAACCAAACC |
| | 6790 | 6800 | 6810 |
| 00-1 1-9000 | ACAAGGACGG | C----ACGCA | GA--ACCACC |
| 99-1 1-9000 | ACAAGCACAG | CTGCAACCCA | AACAACCAAC |
| | 6820 | 6830 | 6840 |
| 00-1 1-9000 | ACTCTCCGCA | CAAGCAGCAC | AAGAAAGAGA |
| 99-1 1-9000 | ACCACCAACC | AAATCAGAAA | TGCAAGTGAG |
| | 6850 | 6860 | 6870 |
| 00-1 1-9000 | CCGTCCACAG | CATCAGTCCA | ACCTGACATC |
| 99-1 1-9000 | ACAATCACAA | CATCCGACAG | ACCCAGAACT |
| | 6880 | 6890 | 6900 |
| 00-1 1-9000 | AGCGCAACAA | CCCACAAAAA | CGAAGAAGCA |
| 99-1 1-9000 | GACACCACAA | CCCAAAGCAG | CGAACAGACA |
| | 6910 | 6920 | 6930 |
| 00-1 1-9000 | AGTCCAGCGA | GCCCACAAAC | ATCTGCAAGC |
| 99-1 1-9000 | A-CCCGGGCA | ACAGACCCAA | GCTCCCCACC |
| | 6940 | 6950 | 6960 |
| 00-1 1-9000 | ACAACAAGAA | TACAAAGGAA | AAGCGTGGAG |
| 99-1 1-9000 | ACACCATGCA | TAGAGAGGTG | CAAAACTCAA |
| | 6970 | 6980 | 6990 |
| 00-1 1-9000 | GCCAACACAT | CA-ACAA-CA | TACAACCAAA |
| 99-1 1-9000 | ATGAGCACAA | CACACAAACA | TCCCATCCAA |
| | 7000 | 7010 | 7020 |
| 00-1 1-9000 | CTAGTTAACA | AAAAAT-ACA | AAATAACTCT |
| 99-1 1-9000 | GTAGTTAACA | AAAAACCACA | AAATAACCTT |

Figure 53 con't

| | 7030 | 7040 | 7050 |
|---|---|---|---|
| 00-1 1-9000 | AAGATAAACC | ATGCAGACAC | CAACAATGGA |
| 99-1 1-9000 | GA---AAACC | A-------A- | -------A-- |

| | 7060 | 7070 | 7080 |
|---|---|---|---|
| 00-1 1-9000 | GAAGCCAAAA | GACAATTCAC | AATCTCCCCA |
| 99-1 1-9000 | -AAACCAAAA | CATAAACCCA | GA----CCCA |

| | 7090 | 7100 | 7110 |
|---|---|---|---|
| 00-1 1-9000 | AAAAGGCAAC | AACACCATAT | TA---GCTCT |
| 99-1 1-9000 | GAAAAACATA | GACACCATAT | GGAAGGTTCT |

| | 7120 | 7130 | 7140 |
|---|---|---|---|
| 00-1 1-9000 | GCCCAAATCT | CCCTGGAAAA | AACACTCGCC |
| 99-1 1-9000 | AGCATATGCA | CCAATGAGAT | GGCATCTGTT |

| | 7150 | 7160 | 7170 |
|---|---|---|---|
| 00-1 1-9000 | CATATACCAA | AAATACCACA | ACCACCCCAA |
| 99-1 1-9000 | CATGTATCAA | TAGCACCACC | ATCATTCAAG |

| | 7180 | 7190 | 7200 |
|---|---|---|---|
| 00-1 1-9000 | GAAAAAAACT | GGGCAAAACA | ACACCCAAGA |
| 99-1 1-9000 | GAATAAGAAG | AGGCGAAA-- | --ATTTAAGG |

| | 7210 | 7220 | 7230 |
|---|---|---|---|
| 00-1 1-9000 | GACAAATAAC | AATGGATCCT | CTCAATGAAT |
| 99-1 1-9000 | GATAAATGAC | AATGGATCCC | TTTTGTGAAT |

| | 7240 | 7250 | 7260 |
|---|---|---|---|
| 00-1 1-9000 | CCACTGTTAA | TGTCTATCTT | CCTGACTCAT |
| 99-1 1-9000 | CTACTGTTAA | TGTTTATCTC | CCTGATTCAT |

| | 7270 | 7280 | 7290 |
|---|---|---|---|
| 00-1 1-9000 | ATCTTAAAGG | AGTGATTTCC | TTTAGTGAGA |
| 99-1 1-9000 | ATCTCAAAGG | AGTAATATCT | TTTAGTGAAA |

| | 7300 | 7310 | 7320 |
|---|---|---|---|
| 00-1 1-9000 | CTAATGCAAT | TGGTTCATGT | CTCTTAAAAA |
| 99-1 1-9000 | CCAATGCAAT | TGGATCATGT | CTTTTGAAAA |

| | 7330 | 7340 | 7350 |
|---|---|---|---|
| 00-1 1-9000 | GACCTTACCT | AAAAAATGAC | AACACTGCAA |
| 99-1 1-9000 | GACCCTATCT | AAAAAATGAC | AACACTGCCA |

| | 7360 | 7370 | 7380 |
|---|---|---|---|
| 00-1 1-9000 | AAGTTGCCAT | AGAGAATCCT | GTTATCGAGC |
| 99-1 1-9000 | AAGTTGCTGT | AGAAAACCCT | GTTGTTGAAC |

| | 7390 | 7400 | 7410 |
|---|---|---|---|
| 00-1 1-9000 | ATGTTAGACT | CAAAAATGCA | GTCAATTCTA |
| 99-1 1-9000 | ATGTGAGGCT | TAGAAATGCA | GTCATGACCA |

Figure 53 con't

| | | | |
|---|---|---|---|
| | . . . . . . . . . . 7420 | . . . . . . . . . . 7430 | . . . . . . . . . . 7440 |
| 00-1 1-9000 | A G A T G A A A A T | A T C A G A T T A C | A A G A T A G T A G |
| 99-1 1-9000 | A A A T G A A G A T | A T C A G A T T A T | A A A G T G G T T G |
| | . . . . . . . . . . 7450 | . . . . . . . . . . 7460 | . . . . . . . . . . 7470 |
| 00-1 1-9000 | A G C C A G T A A A | C A T G C A A C A T | G A A A T T A T G A |
| 99-1 1-9000 | A A C C A G T T A A | T A T G C A G C A T | G A A A T A A T G A |
| | . . . . . . . . . . 7480 | . . . . . . . . . . 7490 | . . . . . . . . . . 7500 |
| 00-1 1-9000 | A G A A T G T A C A | C A G T T G T G A G | C T C A C A T T A T |
| 99-1 1-9000 | A A A A T A T A C A | T A G T T G T G A G | C T T A C A T T A T |
| | . . . . . . . . . . 7510 | . . . . . . . . . . 7520 | . . . . . . . . . . 7530 |
| 00-1 1-9000 | T A A A A C A G T T | T T T A A C A A G G | A G T A A A A A T A |
| 99-1 1-9000 | T A A A A C A A T T | C T T A A C G A G A | A G C A A A A A C A |
| | . . . . . . . . . . 7540 | . . . . . . . . . . 7550 | . . . . . . . . . . 7560 |
| 00-1 1-9000 | T T A G C A C T C T | C A A A T T A A A T | A T G A T A T G T G |
| 99-1 1-9000 | T T A G C T C T C T | A A A A T T A A A T | A T G A T A T G T G |
| | . . . . . . . . . . 7570 | . . . . . . . . . . 7580 | . . . . . . . . . . 7590 |
| 00-1 1-9000 | A T T G G C T G C A | G T T A A A G T C T | A C A T C A G A T G |
| 99-1 1-9000 | A T T G G T T A C A | G T T A A A A T C C | A C T T C A G A T A |
| | . . . . . . . . . . 7600 | . . . . . . . . . . 7610 | . . . . . . . . . . 7620 |
| 00-1 1-9000 | A T A C C T C A A T | C C T A A G T T T T | A T A G A T G T A G |
| 99-1 1-9000 | A C A C A T C A A T | T C T C A A T T T T | A T A G A T G T G G |
| | . . . . . . . . . . 7630 | . . . . . . . . . . 7640 | . . . . . . . . . . 7650 |
| 00-1 1-9000 | A A T T T A T A C C | T A G C T G G G T A | A G C A A T T G G T |
| 99-1 1-9000 | A G T T C A T A C C | C G T T T G G G T A | A G C A A T T G G T |
| | . . . . . . . . . . 7660 | . . . . . . . . . . 7670 | . . . . . . . . . . 7680 |
| 00-1 1-9000 | T T A G T A A T T G | G T A C A A T C T C | A A C A A G T T G A |
| 99-1 1-9000 | T C A G T A A C T G | G T A T A A T C T C | A A T A A A T T A A |
| | . . . . . . . . . . 7690 | . . . . . . . . . . 7700 | . . . . . . . . . . 7710 |
| 00-1 1-9000 | T T C T G G A A T T | C A G G A A A G A A | G A A G T A A T A A |
| 99-1 1-9000 | T C T T A G A G T T | T A G A A G A G A A | G A A G T A A T A A |
| | . . . . . . . . . . 7720 | . . . . . . . . . . 7730 | . . . . . . . . . . 7740 |
| 00-1 1-9000 | G A A C T G G T T C | A A T C T T G T G T | A G G T C A T T G G |
| 99-1 1-9000 | G A A C T G G T T C | A A T T T T A T G T | A G A T C A C T A G |
| | . . . . . . . . . . 7750 | . . . . . . . . . . 7760 | . . . . . . . . . . 7770 |
| 00-1 1-9000 | G T A A A T T A G T | T T T T G T T G T A | T C A T C A T A T G |
| 99-1 1-9000 | G C A A G T T A G T | T T T T A T T G T A | T C A T C T T A T G |
| | . . . . . . . . . . 7780 | . . . . . . . . . . 7790 | . . . . . . . . . . 7800 |
| 00-1 1-9000 | G A T G T A T A G T | C A A G A G C A A C | A A A A G C A A A A |
| 99-1 1-9000 | G A T G T G T A G T | A A A A A G C A A C | A A A A G T A A A A |

Figure 53 con't

| | | | |
|---|---|---|---|
| | 7810 | 7820 | 7830 |
| 00-1 1-9000 | G A G T G A G C T T | C T T C A C A T A C | A A T C A A C T G T |
| 99-1 1-9000 | G A G T G A G C T T | T T T C A C C T A T | A A C C A A C T G T |
| | 7840 | 7850 | 7860 |
| 00-1 1-9000 | T A A C A T G G A A | A G A T G T G A T G | T T A A G T A G A T |
| 99-1 1-9000 | T A A C A T G G A A | A G A T G T G A T G | T T A A G T A G A T |
| | 7870 | 7880 | 7890 |
| 00-1 1-9000 | T C A A T G C A A A | T T T T T G T A T A | T G G G T A A G C A |
| 99-1 1-9000 | T C A A T G C A A A | C T T T T G T A T A | T G G G T A A G T A |
| | 7900 | 7910 | 7920 |
| 00-1 1-9000 | A C A G T C T G A A | T G A A A A T C A A | G A A G G G C T A G |
| 99-1 1-9000 | A C A A C C T G A A | C A A A A A T C A A | G A A G G A C T A G |
| | 7930 | 7940 | 7950 |
| 00-1 1-9000 | G G T T G A G A A G | T A A T C T G C A A | G G C A T A T T A A |
| 99-1 1-9000 | G A C T T A G A A G | C A A T C T G C A A | G G T A T G T T A A |
| | 7960 | 7970 | 7980 |
| 00-1 1-9000 | C T A A T A A G C T | A T A T G A A A C T | G T A G A T T A T A |
| 99-1 1-9000 | C C A A T A A A T T | A T A T G A A A C T | G T T G A T T A C A |
| | 7990 | 8000 | 8010 |
| 00-1 1-9000 | T G C T T A G T T T | A T G T T G C A A T | G A A G G T T T C T |
| 99-1 1-9000 | T G C T A A G C C T | A T G C T G C A A T | G A A G G A T T C T |
| | 8020 | 8030 | 8040 |
| 00-1 1-9000 | C A C T T G T G A A | A G A G T T C G A A | G G C T T T A T T A |
| 99-1 1-9000 | C T C T G G T G A A | A G A G T T T G A A | G G A T T T A T T A |
| | 8050 | 8060 | 8070 |
| 00-1 1-9000 | T G A G T G A A A T | T C T T A G G A T T | A C T G A A C A T G |
| 99-1 1-9000 | T G A G T G A A A T | T C T A A A A A T T | A C T G A G C A T G |
| | 8080 | 8090 | 8100 |
| 00-1 1-9000 | C T C A A T T C A G | T A C T A G A T T T | A G A A A T A C T T |
| 99-1 1-9000 | C T C A G T T C A G | T A C T A G G T T T | A G G A A T A C T T |
| | 8110 | 8120 | 8130 |
| 00-1 1-9000 | T A T T A A A T G G | A T T A A C T G A T | C A A T T A A C A A |
| 99-1 1-9000 | T A T T G A A T G G | G T T A A C T G A A | C A A T T A T C A G |
| | 8140 | 8150 | 8160 |
| 00-1 1-9000 | A A T T A A A A A A | T A A A A A C A G A | C T C A G A G T T C |
| 99-1 1-9000 | T G T T G A A A G C | T A A G A A C A G A | T C T A G A G T T C |
| | 8170 | 8180 | 8190 |
| 00-1 1-9000 | A T G G T A C C G T | G T T A G A A A A T | A A T G A T T A T C |
| 99-1 1-9000 | T T G G A A C T A T | A T T A G A A A A C | A A C A A T T A C C |

Figure 53 con't

| | | | |
|---|---|---|---|
| | 8200 | 8210 | 8220 |
| 00-1 1-9000 | C A A T G T A C G A | A G T T G T A C T T | A A G T T A T T A G |
| 99-1 1-9000 | C T A T G T A C G A | A G T A G T A C T T | A A A T T A T T A G |
| | 8230 | 8240 | 8250 |
| 00-1 1-9000 | G A G A T A C T T T | G A G A T G T A T T | A A A T T A T T A A |
| 99-1 1-9000 | G G G A C A C C T T | G A A A A G C A T A | A A G T T A T T A A |
| | 8260 | 8270 | 8280 |
| 00-1 1-9000 | T C A A T A A A A A | C T T A G A G A A T | G C T G C T G A A T |
| 99-1 1-9000 | T T A A C A A G A A | T T T A G A A A A T | G C T G C A G A A T |
| | 8290 | 8300 | 8310 |
| 00-1 1-9000 | T A T A C T A T A T | A T T T A G A A T A | T T C G G T C A C C |
| 99-1 1-9000 | T A T A T T A T A T | A T T C A G A A T T | T T T G G A C A C C |
| | 8320 | 8330 | 8340 |
| 00-1 1-9000 | C A A T G G T A G A | T G A A A G A G A T | G C A A T G G A T G |
| 99-1 1-9000 | C T A T G G T A G A | T G A G A G G G A A | G C A A T G G A T G |
| | 8350 | 8360 | 8370 |
| 00-1 1-9000 | C T G T C A A A T T | A A A C A A T G A A | A T C A C A A A A A |
| 99-1 1-9000 | C T G T T A A A T T | A A A C A A T G A G | A T T A C A A A A A |
| | 8380 | 8390 | 8400 |
| 00-1 1-9000 | T C C T T A G G T G | G G A G A G C T T G | A C A G A A C T A A |
| 99-1 1-9000 | T T C T T A A A T T | A G A G A G T T T A | A C A G A A C T A A |
| | 8410 | 8420 | 8430 |
| 00-1 1-9000 | G A G G G G C A T T | C A T A T T A A G G | A T T A T C A A A G |
| 99-1 1-9000 | G A G G A G C A T T | T A T A C T A A G A | A T T A T A A A A G |
| | 8440 | 8450 | 8460 |
| 00-1 1-9000 | G A T T T G T A G A | C A A C A A C A A A | A G A T G G C C C A |
| 99-1 1-9000 | G G T T T G T A G A | C A A T A A T A A A | A G A T G G C C T A |
| | 8470 | 8480 | 8490 |
| 00-1 1-9000 | A A A T T A A A A A | C T T A A A A G T G | C T T A G T A A G A |
| 99-1 1-9000 | A A A T T A A G A A | T T T A A A A G T G | C T C A G C A A A A |
| | 8500 | 8510 | 8520 |
| 00-1 1-9000 | G A T G G A C T A T | G T A C T T C A A A | G C A A A A A G T T |
| 99-1 1-9000 | G A T G G G C T A T | G T A T T T C A A A | G C T A A A A G T T |
| | 8530 | 8540 | 8550 |
| 00-1 1-9000 | A C C C C A G T C A | A C T T G A A T T A | A G C G A A C A A G |
| 99-1 1-9000 | A C C C T A G C C A | A C T T G A G C T A | A G T G T A C A A G |
| | 8560 | 8570 | 8580 |
| 00-1 1-9000 | A T T T T T T A G A | G C T T G C T G C A | A T A C A G T T T G |
| 99-1 1-9000 | A T T T T T T A G A | A C T T G C T G C A | G T A C A A T T T G |

Figure 53 con't

```
                 8590        8600        8610
00-1 1-9000  AACAAGAGTT  TTCTGTCCCT  GAAAAAACCA
99-1 1-9000  AGCAGGAATT  CTCTGTACCT  GAAAAAACCA

                 8620        8630        8640
00-1 1-9000  ACCTTGAGAT  GGTATTAAAT  GATAAAGCTA
99-1 1-9000  ACCTTGAGAT  GGTATTAAAT  GATAAAGCAA

                 8650        8660        8670
00-1 1-9000  TATCACCTCC  TAAAAGATTA  ATATGGTCTG
99-1 1-9000  TATCACCTCC  AAAAAAGCTA  ATATGGTCTG

                 8680        8690        8700
00-1 1-9000  TGTATCCAAA  AAATTACTTA  CCTGAGAAAA
99-1 1-9000  TATATCCAAA  AAACTACCTG  CCTGAAACTA

                 8710        8720        8730
00-1 1-9000  TAAAAAATCG  ATATCTAGAA  GAGACTTTCA
99-1 1-9000  TAAAAAATCA  ATATTTAGAA  GAGGCTTTCA

                 8740        8750        8760
00-1 1-9000  ATGCAAGTGA  TAGTCTCAAA  ACAAGAAGAG
99-1 1-9000  ATGCAAGTGA  CAGCCAAAGA  ACAAGGAGAG

                 8770        8780        8790
00-1 1-9000  TACTAGAGTA  CTATTTGAAA  GATAATAAAT
99-1 1-9000  TCTTAGAATT  TTACTTAAAA  GATTGTAAAT

                 8800        8810        8820
00-1 1-9000  TCGACCAAAA  AGAACTTAAA  AGTTATGTTG
99-1 1-9000  TTGATCAAAA  AGAACTTAAA  CGTTATGTAA

                 8830        8840        8850
00-1 1-9000  TTAAACAAGA  ATATTTAAAT  GATAAGGATC
99-1 1-9000  TTAAACAAGA  GTATCTGAAT  GACAAAGACC

                 8860        8870        8880
00-1 1-9000  ATATTGTCTC  GCTAACTGGA  AAAGAAAGAG
99-1 1-9000  ACATTGTCTC  GTTAACTGGG  AAGGAAAGAG

                 8890        8900        8910
00-1 1-9000  AATTAAGTGT  AGGTAGAATG  TTTGCTATGC
99-1 1-9000  AATTAAGTGT  AGGTAGGATG  TTTGCAATGC

                 8920        8930        8940
00-1 1-9000  AACCAGGAAA  ACAGCGACAA  ATACAAATAT
99-1 1-9000  AACCAGGAAA  ACAAAGACAG  ATACAGATAT

                 8950        8960        8970
00-1 1-9000  TGGCTGAAAA  ATTGTTAGCT  GATAATATTG
99-1 1-9000  TAGCTGAGAA  ACTTCTAGCT  GATAATATTG
```

Figure 53 con't

7682-112

| | 8980 | 8990 | 9000 |
|---|---|---|---|
| 00-1 1-9000 | T A C C T T T T T T | C C C A G A A A C C | T T A A C A A A G T |
| 99-1 1-9000 | T A C C T T T T T T | C C C A G A A A C T | T T A A C A A A G T |

| | 9010 | 9020 | 9030 |
|---|---|---|---|
| 00-1 1-9000 | A T G G T G A T C T | A G A T C T T C A G | A G A A T A A T G G |
| 99-1 1-9000 | A T G G T G A C T T | A G A T C T C C A A | A G A A T T A T G G |

| | 9040 | 9050 | 9060 |
|---|---|---|---|
| 00-1 1-9000 | A A A T C A A A T C | G G A A C | |
| 99-1 1-9000 | A A A T A A A A T C | A G A A C T T T C T | T C C A T T A A A A |

| | 9070 | 9080 | 9090 |
|---|---|---|---|
| 00-1 1-9000 | | | |
| 99-1 1-9000 | C T A G A A A G A A | T G A T A G C T A C | A A C A A T T |

Figure 53 con't

| Position | Sequence | | | |
|---|---|---|---|---|
| 1–30 | 00-1 7001-13350 | ACAATGGAGA | AGCCAAAAGA | CAATTCACAA |
| | 99-1 7001-13294 | ---------- | ---------- | ---------- |
| 31–60 | 00-1 7001-13350 | TCTCCCCAAA | AAGGCAACAA | CACCATATTA |
| | 99-1 7001-13294 | ---------- | -AAACATAGA | CACCATATGG |
| 61–90 | 00-1 7001-13350 | ---GCTCTGC | CCAAATCTCC | CTGGAAAAAA |
| | 99-1 7001-13294 | AAGGTTCTAG | CATATGCACC | AATGAGATGG |
| 91–120 | 00-1 7001-13350 | CACTCGCCCA | TATACCAAAA | ATACCACAAC |
| | 99-1 7001-13294 | CATCTGTTCA | TGTATCAATA | GCACCACCAT |
| 121–150 | 00-1 7001-13350 | CACCCCAAGA | AAAAAACTGG | GCAAAACAAC |
| | 99-1 7001-13294 | CATTCAAGGA | ATAAGAAGAG | GCGAAA---- |
| 151–180 | 00-1 7001-13350 | ACCCAAGAGA | CAAATAACAA | TGGATCCTCT |
| | 99-1 7001-13294 | ATTTAAGGGA | TAAATGACAA | TGGATCCCTT |
| 181–210 | 00-1 7001-13350 | CAATGAATCC | ACTGTTAATG | TCTATCTTCC |
| | 99-1 7001-13294 | TTGTGAATCT | ACTGTTAATG | TTTATCTCCC |
| 211–240 | 00-1 7001-13350 | TGACTCATAT | CTTAAAGGAG | TGATTTCCTT |
| | 99-1 7001-13294 | TGATTCATAT | CTCAAAGGAG | TAATATCTTT |
| 241–270 | 00-1 7001-13350 | TAGTGAGACT | AATGCAATTG | GTTCATGTCT |
| | 99-1 7001-13294 | TAGTGAAACC | AATGCAATTG | GATCATGTCT |
| 271–300 | 00-1 7001-13350 | CTTAAAAAGA | CCTTACCTAA | AAAATGACAA |
| | 99-1 7001-13294 | TTTGAAAAGA | CCCTATCTAA | AAAATGACAA |
| 301–330 | 00-1 7001-13350 | CACTGCAAAA | GTTGCCATAG | AGAATCCTGT |
| | 99-1 7001-13294 | CACTGCCAAA | GTTGCTGTAG | AAAACCCTGT |
| 331–360 | 00-1 7001-13350 | TATCGAGCAT | GTTAGACTCA | AAAATGCAGT |
| | 99-1 7001-13294 | TGTTGAACAT | GTGAGGCTTA | GAAATGCAGT |
| 361–390 | 00-1 7001-13350 | CAATTCTAAG | ATGAAAATAT | CAGATTACAA |
| | 99-1 7001-13294 | CATGACCAAA | ATGAAGATAT | CAGATTATAA |

Figure 53 con't

| | 400 | 410 | 420 |
|---|---|---|---|
| 00-1 7001-13350 | G A T A G T A G A G | C C A G T A A A C A | T G C A A C A T G A |
| 99-1 7001-13294 | A G T G G T T G A A | C C A G T T A A T A | T G C A G C A T G A |
| | 430 | 440 | 450 |
| 00-1 7001-13350 | A A T T A T G A A G | A A T G T A C A C A | G T T G T G A G C T |
| 99-1 7001-13294 | A A T A A T G A A A | A A T A T A C A T A | G T T G T G A G C T |
| | 460 | 470 | 480 |
| 00-1 7001-13350 | C A C A T T A T T A | A A A C A G T T T T | T A A C A A G G A G |
| 99-1 7001-13294 | T A C A T T A T T A | A A A C A A T T C T | T A A C G A G A A G |
| | 490 | 500 | 510 |
| 00-1 7001-13350 | T A A A A A T A T T | A G C A C T C T C A | A A T T A A A T A T |
| 99-1 7001-13294 | C A A A A A C A T T | A G C T C T C T A A | A A T T A A A T A T |
| | 520 | 530 | 540 |
| 00-1 7001-13350 | G A T A T G T G A T | T G G C T G C A G T | T A A A G T C T A C |
| 99-1 7001-13294 | G A T A T G T G A T | T G G T T A C A G T | T A A A A T C C A C |
| | 550 | 560 | 570 |
| 00-1 7001-13350 | A T C A G A T G A T | A C C T C A A T C C | T A A G T T T T A T |
| 99-1 7001-13294 | T T C A G A T A A C | A C A T C A A T T C | T C A A T T T T A T |
| | 580 | 590 | 600 |
| 00-1 7001-13350 | A G A T G T A G A A | T T T A T A C C T A | G C T G G G T A A G |
| 99-1 7001-13294 | A G A T G T G G A G | T T C A T A C C C G | T T T G G G T A A G |
| | 610 | 620 | 630 |
| 00-1 7001-13350 | C A A T T G G T T T | A G T A A T T G G T | A C A A T C T C A A |
| 99-1 7001-13294 | C A A T T G G T T C | A G T A A C T G G T | A T A A T C T C A A |
| | 640 | 650 | 660 |
| 00-1 7001-13350 | C A A G T T G A T T | C T G G A A T T C A | G G A A A G A A G A |
| 99-1 7001-13294 | T A A A T T A A T C | T T A G A G T T T A | G A A G A G A A G A |
| | 670 | 680 | 690 |
| 00-1 7001-13350 | A G T A A T A A G A | A C T G G T T C A A | T C T T G T G T A G |
| 99-1 7001-13294 | A G T A A T A A G A | A C T G G T T C A A | T T T T A T G T A G |
| | 700 | 710 | 720 |
| 00-1 7001-13350 | G T C A T T G G G T | A A A T T A G T T T | T T G T T G T A T C |
| 99-1 7001-13294 | A T C A C T A G G C | A A G T T A G T T T | T T A T T G T A T C |
| | 730 | 740 | 750 |
| 00-1 7001-13350 | A T C A T A T G G A | T G T A T A G T C A | A G A G C A A C A A |
| 99-1 7001-13294 | A T C T T A T G G A | T G T G T A G T A A | A A A G C A A C A A |
| | 760 | 770 | 780 |
| 00-1 7001-13350 | A A G C A A A A G A | G T G A G C T T C T | T C A C A T A C A A |
| 99-1 7001-13294 | A A G T A A A A G A | G T G A G C T T T T | T C A C C T A T A A |

Figure 53 con't

| | | | |
|---|---|---|---|
| | 790 | 800 | 810 |
| 00-1 7001-13350 | T C A A C T G T T A | A C A T G G A A A G | A T G T G A T G T T |
| 99-1 7001-13294 | C C A A C T G T T A | A C A T G G A A A G | A T G T G A T G T T |
| | 820 | 830 | 840 |
| 00-1 7001-13350 | A A G T A G A T T C | A A T G C A A A T T | T T T G T A T A T G |
| 99-1 7001-13294 | A A G T A G A T T C | A A T G C A A A C T | T T T G T A T A T G |
| | 850 | 860 | 870 |
| 00-1 7001-13350 | G G T A A G C A A C | A G T C T G A A T G | A A A A T C A A G A |
| 99-1 7001-13294 | G G T A A G T A A C | A A C C T G A A C A | A A A A T C A A G A |
| | 880 | 890 | 900 |
| 00-1 7001-13350 | A G G G C T A G G G | T T G A G A A G T A | A T C T G C A A G G |
| 99-1 7001-13294 | A G G A C T A G G A | C T T A G A A G C A | A T C T G C A A G G |
| | 910 | 920 | 930 |
| 00-1 7001-13350 | C A T A T T A A C T | A A T A A G C T A T | A T G A A A C T G T |
| 99-1 7001-13294 | T A T G T T A A C C | A A T A A A T T A T | A T G A A A C T G T |
| | 940 | 950 | 960 |
| 00-1 7001-13350 | A G A T T A T A T G | C T T A G T T T A T | G T T G C A A T G A |
| 99-1 7001-13294 | T G A T T A C A T G | C T A A G C C T A T | G C T G C A A T G A |
| | 970 | 980 | 990 |
| 00-1 7001-13350 | A G G T T T C T C A | C T T G T G A A A G | A G T T C G A A G G |
| 99-1 7001-13294 | A G G A T T C T C T | C T G G T G A A A G | A G T T T G A A G G |
| | 1000 | 1010 | 1020 |
| 00-1 7001-13350 | C T T T A T T A T G | A G T G A A A T T C | T T A G G A T T A C |
| 99-1 7001-13294 | A T T T A T T A T G | A G T G A A A T T C | T A A A A A T T A C |
| | 1030 | 1040 | 1050 |
| 00-1 7001-13350 | T G A A C A T G C T | C A A T T C A G T A | C T A G A T T T A G |
| 99-1 7001-13294 | T G A G C A T G C T | C A G T T C A G T A | C T A G G T T T A G |
| | 1060 | 1070 | 1080 |
| 00-1 7001-13350 | A A A T A C T T T A | T T A A A T G G A T | T A A C T G A T C A |
| 99-1 7001-13294 | G A A T A C T T T A | T T G A A T G G G T | T A A C T G A A C A |
| | 1090 | 1100 | 1110 |
| 00-1 7001-13350 | A T T A A C A A A A | T T A A A A A A T A | A A A A C A G A C T |
| 99-1 7001-13294 | A T T A T C A G T G | T T G A A A G C T A | A G A A C A G A T C |
| | 1120 | 1130 | 1140 |
| 00-1 7001-13350 | C A G A G T T C A T | G G T A C C G T G T | T A G A A A A T A A |
| 99-1 7001-13294 | T A G A G T T C T T | G G A A C T A T A T | T A G A A A A C A A |
| | 1150 | 1160 | 1170 |
| 00-1 7001-13350 | T G A T T A T C C A | A T G T A C G A A G | T T G T A C T T A A |
| 99-1 7001-13294 | C A A T T A C C C T | A T G T A C G A A G | T A G T A C T T A A |

Figure 53 con't

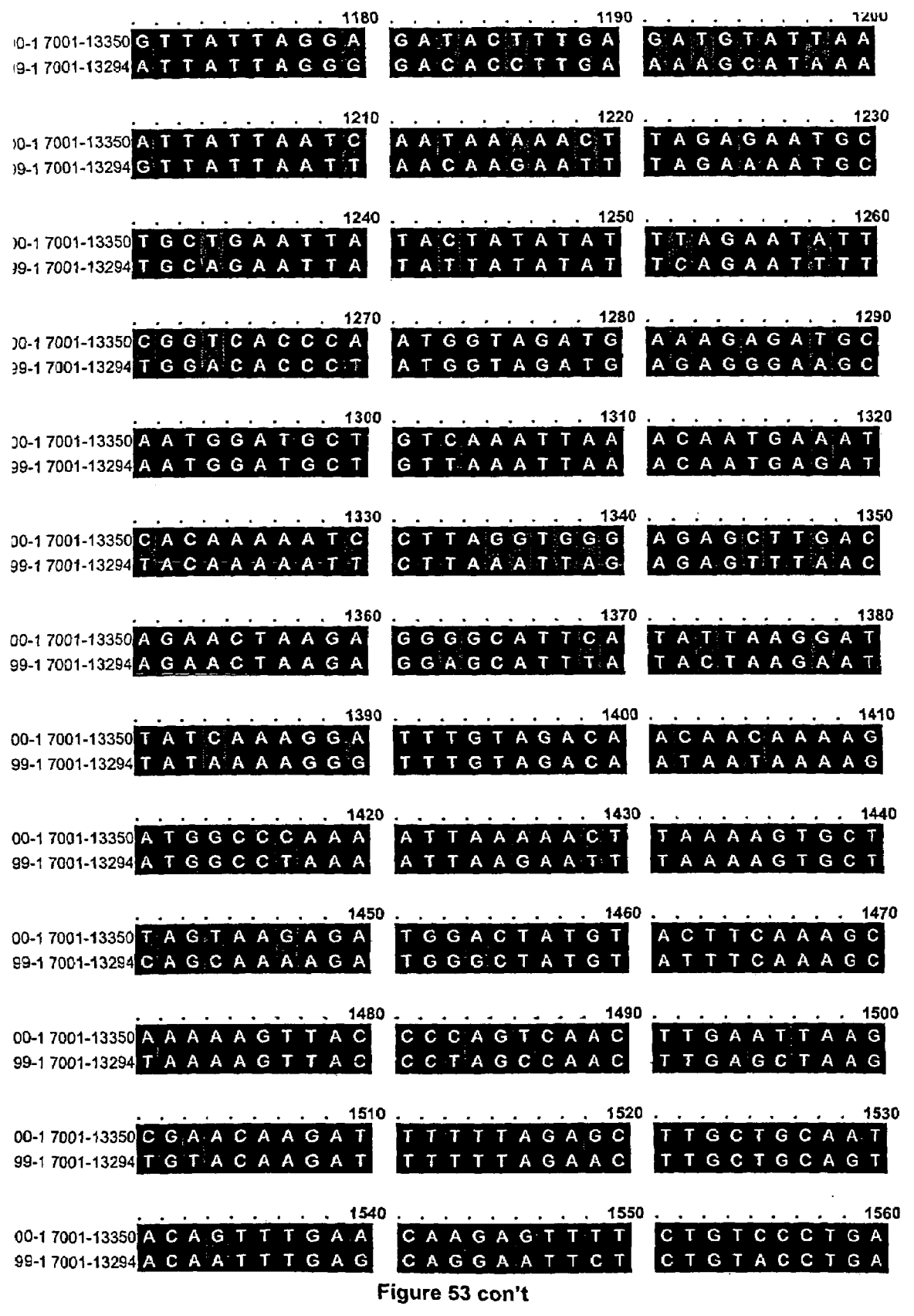

| | | | |
|---|---|---|---|
| | 1180 | 1190 | 1200 |
| i0-1 7001-13350 | G T T A T T A G G A | G A T A C T T T G A | G A T G T A T T A A |
| i9-1 7001-13294 | A T T A T T A G G G | G A C A C C T T G A | A A A G C A T A A A |
| | 1210 | 1220 | 1230 |
| )0-1 7001-13350 | A T T A T T A A T C | A A T A A A A A C T | T A G A G A A T G C |
| )9-1 7001-13294 | G T T A T T A A T T | A A C A A G A A T T | T A G A A A A T G C |
| | 1240 | 1250 | 1260 |
| )0-1 7001-13350 | T G C T G A A T T A | T A C T A T A T A T | T T A G A A T A T T |
| )9-1 7001-13294 | T G C A G A A T T A | T A T T A T A T A T | T C A G A A T T T T |
| | 1270 | 1280 | 1290 |
| )0-1 7001-13350 | C G G T C A C C C A | A T G G T A G A T G | A A A G A G A T G C |
| 99-1 7001-13294 | T G G A C A C C C T | A T G G T A G A T G | A G A G G G A A G C |
| | 1300 | 1310 | 1320 |
| 00-1 7001-13350 | A A T G G A T G C T | G T C A A A T T A A | A C A A T G A A A T |
| 99-1 7001-13294 | A A T G G A T G C T | G T T A A A T T A A | A C A A T G A G A T |
| | 1330 | 1340 | 1350 |
| 00-1 7001-13350 | C A C A A A A A T C | C T T A G G T G G G | A G A G C T T G A C |
| 99-1 7001-13294 | T A C A A A A A T T | C T T A A A T T A G | A G A G T T T A A C |
| | 1360 | 1370 | 1380 |
| 00-1 7001-13350 | A G A A C T A A G A | G G G G C A T T C A | T A T T A A G G A T |
| 99-1 7001-13294 | A G A A C T A A G A | G G A G C A T T T A | T A C T A A G A A T |
| | 1390 | 1400 | 1410 |
| 00-1 7001-13350 | T A T C A A A G G A | T T T G T A G A C A | A C A A C A A A A G |
| 99-1 7001-13294 | T A T A A A A G G G | T T T G T A G A C A | A T A A T A A A A G |
| | 1420 | 1430 | 1440 |
| 00-1 7001-13350 | A T G G C C C A A A | A T T A A A A A C T | T A A A A G T G C T |
| 99-1 7001-13294 | A T G G C C T A A A | A T T A A G A A T T | T A A A A G T G C T |
| | 1450 | 1460 | 1470 |
| 00-1 7001-13350 | T A G T A A G A G A | T G G A C T A T G T | A C T T C A A A G C |
| 99-1 7001-13294 | C A G C A A A A G A | T G G G C T A T G T | A T T T C A A A G C |
| | 1480 | 1490 | 1500 |
| 00-1 7001-13350 | A A A A A G T T A C | C C C A G T C A A C | T T G A A T T A A G |
| 99-1 7001-13294 | T A A A A G T T A C | C C T A G C C A A C | T T G A G C T A A G |
| | 1510 | 1520 | 1530 |
| 00-1 7001-13350 | C G A A C A A G A T | T T T T T A G A G C | T T G C T G C A A T |
| 99-1 7001-13294 | T G T A C A A G A T | T T T T T A G A A C | T T G C T G C A G T |
| | 1540 | 1550 | 1560 |
| 00-1 7001-13350 | A C A G T T T G A A | C A A G A G T T T T | C T G T C C C T G A |
| 99-1 7001-13294 | A C A A T T T G A G | C A G G A A T T C T | C T G T A C C T G A |

Figure 53 con't

| | 1570 | 1580 | 1590 |
|---|---|---|---|
| 00-1 7001-13350 | A A A A A C C A A C | C T T G A G A T G G | T A T T A A A T G A |
| 99-1 7001-13294 | A A A A A C C A A C | C T T G A G A T G G | T A T T A A A T G A |
| | 1600 | 1610 | 1620 |
| 00-1 7001-13350 | T A A A G C T A T A | T C A C C T C C T A | A A A G A T T A A T |
| 99-1 7001-13294 | T A A A G C A A T A | T C A C C T C C A A | A A A A G C T A A T |
| | 1630 | 1640 | 1650 |
| 00-1 7001-13350 | A T G G T C T G T G | T A T C C A A A A A | A T T A C T T A C C |
| 99-1 7001-13294 | A T G G T C T G T A | T A T C C A A A A A | A C T A C C T G C C |
| | 1660 | 1670 | 1680 |
| 00-1 7001-13350 | T G A G A A A A T A | A A A A A T C G A T | A T C T A G A A G A |
| 99-1 7001-13294 | T G A A A C T A T A | A A A A A T C A A T | A T T T A G A A G A |
| | 1690 | 1700 | 1710 |
| 00-1 7001-13350 | G A C T T T C A A T | G C A A G T G A T A | G T C T C A A A A C |
| 99-1 7001-13294 | G G C T T T C A A T | G C A A G T G A C A | G C C A A A G A A C |
| | 1720 | 1730 | 1740 |
| 00-1 7001-13350 | A A G A A G A G T A | C T A G A G T A C T | A T T T G A A A G A |
| 99-1 7001-13294 | A A G G A G A G T C | T T A G A A T T T T | A C T T A A A A G A |
| | 1750 | 1760 | 1770 |
| 00-1 7001-13350 | T A A T A A A T T C | G A C C A A A A A G | A A C T T A A A A G |
| 99-1 7001-13294 | T T G T A A A T T T | G A T C A A A A A G | A A C T T A A A C G |
| | 1780 | 1790 | 1800 |
| 00-1 7001-13350 | T T A T G T T G T T | A A A C A A G A A T | A T T T A A A T G A |
| 99-1 7001-13294 | T T A T G T A A T T | A A A C A A G A G T | A T C T G A A T G A |
| | 1810 | 1820 | 1830 |
| 00-1 7001-13350 | T A A G G A T C A T | A T T G T C T C G C | T A A C T G G A A A |
| 99-1 7001-13294 | C A A A G A C C A C | A T T G T C T C G T | T A A C T G G G A A |
| | 1840 | 1850 | 1860 |
| 00-1 7001-13350 | A G A A A G A G A A | T T A A G T G T A G | G T A G A A T G T T |
| 99-1 7001-13294 | G G A A A G A G A A | T T A A G T G T A G | G T A G G A T G T T |
| | 1870 | 1880 | 1890 |
| 00-1 7001-13350 | T G C T A T G C A A | C C A G G A A A A C | A G C G A C A A A T |
| 99-1 7001-13294 | T G C A A T G C A A | C C A G G A A A A C | A A A G A C A G A T |
| | 1900 | 1910 | 1920 |
| 00-1 7001-13350 | A C A A A T A T T G | G C T G A A A A A T | T G T T A G C T G A |
| 99-1 7001-13294 | A C A G A T A T T A | G C T G A G A A A C | T T C T A G C T G A |
| | 1930 | 1940 | 1950 |
| 00-1 7001-13350 | T A A T A T T G T A | C C T T T T T T C C | C A G A A A C C T T |
| 99-1 7001-13294 | T A A T A T T G T A | C C T T T T T T C C | C A G A A A C T T T |

Figure 53 con't

| | | | |
|---|---|---|---|
| | 1960 | 1970 | 1980 |
| 00-1 7001-13350 | A A C A A A G T A T | G G T G A T C T A G | A T C T T C A G A G |
| 99-1 7001-13294 | A A C A A A G T A T | G G T G A C T T A G | A T C T C C A A A G |
| | 1990 | 2000 | 2010 |
| 00-1 7001-13350 | A A T A A T G G A A | A T C A A A T C G G | A A C T T T C T T C |
| 99-1 7001-13294 | A A T T A T G G A A | A T A A A A T C A G | A A C T T T C T T C |
| | 2020 | 2030 | 2040 |
| 00-1 7001-13350 | T A T T A A A A C T | A G A A G A A A T G | A T A G T T A T A A |
| 99-1 7001-13294 | C A T T A A A A C T | A G A A A G A A T G | A T A G C T A C A A |
| | 2050 | 2060 | 2070 |
| 00-1 7001-13350 | T A A T T A C A T T | G C A A G A G C A T | C C A T A G T A A C |
| 99-1 7001-13294 | C A A T T A T A T T | G C A A G G G C C T | C T A T A G T A A C |
| | 2080 | 2090 | 2100 |
| 00-1 7001-13350 | A G A T T T A A G T | A A G T T C A A C C | A A G C C T T T A G |
| 99-1 7001-13294 | A G A C T T A A G T | A A G T T C A A T C | A G G C C T T T A G |
| | 2110 | 2120 | 2130 |
| 00-1 7001-13350 | G T A T G A A A C T | A C A G C G A T C T | G T G C G G A T G T |
| 99-1 7001-13294 | A T A T G A A A C C | A C A G C T A T A T | G T G C A G A T G T |
| | 2140 | 2150 | 2160 |
| 00-1 7001-13350 | A G C A G A T G A A | C T A C A T G G A A | C A C A A A G C C T |
| 99-1 7001-13294 | A G C T G A T G A G | T T A C A T G G G A | C A C A A A G C T T |
| | 2170 | 2180 | 2190 |
| 00-1 7001-13350 | A T T C T G T T G G | T T A C A T C T T A | T C G T C C C T A T |
| 99-1 7001-13294 | A T T C T G T T G G | T T A C A T C T T A | T T G T T C C C A T |
| | 2200 | 2210 | 2220 |
| 00-1 7001-13350 | G A C A A C A A T G | A T A T G T G C C T | A T A G A C A T G C |
| 99-1 7001-13294 | G A C T A C A A T G | A T A T G T G C A T | A C A G A C A T G C |
| | 2230 | 2240 | 2250 |
| 00-1 7001-13350 | A C C A C C A G A A | A C A A A A G G T G | A A T A T G A T A T |
| 99-1 7001-13294 | A C C A C C A G A A | A C A A A A G G G G | A A T A T G A T A T |
| | 2260 | 2270 | 2280 |
| 00-1 7001-13350 | A G A T A A G A T A | G A A G A G C A A A | G T G G T T T A T A |
| 99-1 7001-13294 | A G A C A A A A T A | C A A G A G C A A A | G C G G A T T A T A |
| | 2290 | 2300 | 2310 |
| 00-1 7001-13350 | T A G A T A T C A T | A T G G G T G G T A | T T G A A G G A T G |
| 99-1 7001-13294 | C A G A T A T C A T | A T G G G A G G G A | T T G A A G G G T G |
| | 2320 | 2330 | 2340 |
| 00-1 7001-13350 | G T G T C A A A A A | C T C T G G A C A A | T G G A A G C T A T |
| 99-1 7001-13294 | G T G C C A G A A G | T T A T G G A C A A | T G G A A G C A A T |

Figure 53 con't

```
                 .........2350 .........2360 .........2370
00-1 7001-13350  ATCTCTATTA    GATGTTGTAT    CTGTAAAAAC
99-1 7001-13294  ATCCTTGTTA    GATGTAGTAT    CTGTGAAGAC

                 .........2380 .........2390 .........2400
00-1 7001-13350  ACGATGTCAA    ATGACATCTT    TATTAAACGG
99-1 7001-13294  TCGCTGTCAG    ATGACCTCTC    TATTAAACGG

                 .........2410 .........2420 .........2430
00-1 7001-13350  TGACAACCAA    TCAATAGATG    TAAGTAAACC
99-1 7001-13294  AGACAATCAG    TCAATAGATG    TTAGTAAACC

                 .........2440 .........2450 .........2460
00-1 7001-13350  AGTTAAGTTA    TCTGAGGGTT    TAGATGAAGT
99-1 7001-13294  AGTAAAATTG    TCTGAAGGTA    TAGATGAAGT

                 .........2470 .........2480 .........2490
00-1 7001-13350  GAAAGCAGAT    TATAGCTTGG    CTGTAAAAAT
99-1 7001-13294  AAAAGCAGAC    TATAGCTTAG    CAATTAGAAT

                 .........2500 .........2510 .........2520
00-1 7001-13350  GTTAAAAGAA    ATAAGAGATG    CATACAGAAA
99-1 7001-13294  GCTTAAAGAA    ATAAGAGATG    CTTATAAAAA

                 .........2530 .........2540 .........2550
00-1 7001-13350  TATAGGCCAT    AAACTTAAAG    AAGGGGAAAC
99-1 7001-13294  CATTGGTCAT    AAACTCAAAG    AAGGTGAAAC

                 .........2560 .........2570 .........2580
00-1 7001-13350  ATATATATCA    AGAGATCTTC    AGTTTATAAG
99-1 7001-13294  ATATATATCA    AGGGATCTCC    AATTTATAAG

                 .........2590 .........2600 .........2610
00-1 7001-13350  TAAGGTGATT    CAATCTGAAG    GAGTAATGCA
99-1 7001-13294  TAAGGTGATT    CAATCTGAAG    GAGTCATGCA

                 .........2620 .........2630 .........2640
00-1 7001-13350  TCCTACCCCT    ATAAAAAAGA    TCTTAAGAGT
99-1 7001-13294  TCCTACCCCT    ATAAAAAAGA    TATTAAGAGT

                 .........2650 .........2660 .........2670
00-1 7001-13350  GGGACCATGG    ATAAACACAA    TATTAGATGA
99-1 7001-13294  AGGTCCTTGG    ATAAATACAA    TACTAGATGA

                 .........2680 .........2690 .........2700
00-1 7001-13350  CATTAAAACC    AGTGCAGAGT    CAATAGGGAG
99-1 7001-13294  TATTAAAACC    AGTGCAGAAT    CAATAGGAAG

                 .........2710 .........2720 .........2730
00-1 7001-13350  TCTATGTCAG    GAATTAGAAT    TTAGGGGGGA
99-1 7001-13294  TCTATGTCAA    GAACTAGAAT    TCAGAGGGGA
```

Figure 53 con't

| | 2740 | 2750 | 2760 |
|---|---|---|---|
| 00-1 7001-13350 | A A G C A T A A T A | G T T A G T C T G A | T A T T A A G G A A |
| 99-1 7001-13294 | G A G T A T A C T A | G T T A G C T T G A | T A T T A A G G A A |

| | 2770 | 2780 | 2790 |
|---|---|---|---|
| 00-1 7001-13350 | T T T T T G G C T G | T A T A A T T T A T | A C A T G C A T G A |
| 99-1 7001-13294 | T T T C T G G C T G | T A T A A C T T G T | A C A T G T A T G A |

| | 2800 | 2810 | 2820 |
|---|---|---|---|
| 00-1 7001-13350 | A T C A A A G C A A | C A C C C C C T A G | C A G G G A A G C A |
| 99-1 7001-13294 | G T C A A A A C A G | C A C C C A T T A G | C T G G G A A G C A |

| | 2830 | 2840 | 2850 |
|---|---|---|---|
| 00-1 7001-13350 | G T T A T T C A A A | C A A C T A A A T A | A A A C A T T A A C |
| 99-1 7001-13294 | A C T G T T C A A G | C A A T T G A A C A | A A A C A T T A A C |

| | 2860 | 2870 | 2880 |
|---|---|---|---|
| 00-1 7001-13350 | A T C A G T G C A G | A G A T T T T T T G | A A A T A A A A A A |
| 99-1 7001-13294 | A T C T G T G C A G | A G A T T T T T T G | A A C T G A A G A A |

| | 2890 | 2900 | 2910 |
|---|---|---|---|
| 00-1 7001-13350 | G G A A A A T G A A | G T A G T A G A T C | T A T G G A T G A A |
| 99-1 7001-13294 | A G A A A A T G A T | G T G G T T G A C C | T A T G G A T G A A |

| | 2920 | 2930 | 2940 |
|---|---|---|---|
| 00-1 7001-13350 | C A T A C C A A T G | C A G T T T G G A G | G A G G A G A T C C |
| 99-1 7001-13294 | T A T A C C A A T G | C A G T T T G G A G | G G G G A G A T C C |

| | 2950 | 2960 | 2970 |
|---|---|---|---|
| 00-1 7001-13350 | A G T A G T C T T C | T A T A G A T C T T | T C T A T A G A A G |
| 99-1 7001-13294 | A G T A G T T T T T | T A C A G A T C T T | T T T A C A G A A G |

| | 2980 | 2990 | 3000 |
|---|---|---|---|
| 00-1 7001-13350 | G A C C C C T G A T | T T T T T A A C T G | A A G C A A T C A G |
| 99-1 7001-13294 | G A C T C C C G A T | T T C C T A A C T G | A A G C A A T C A G |

| | 3010 | 3020 | 3030 |
|---|---|---|---|
| 00-1 7001-13350 | T C A T G T G G A T | A T T C T G T T A A | G A A T A T C A G C |
| 99-1 7001-13294 | C C A T G T G G A T | T T A C T G T T A A | A A G T G T C A A A |

| | 3040 | 3050 | 3060 |
|---|---|---|---|
| 00-1 7001-13350 | C A A C A T A A G A | A A T G A A G C G A | A A A T A A G T T T |
| 99-1 7001-13294 | C A A T A T C A A A | G A T G A G A C T A | A G A T A C G A T T |

| | 3070 | 3080 | 3090 |
|---|---|---|---|
| 00-1 7001-13350 | C T T C A A A G C C | T T A C T G T C A A | T A G A A A A A A A |
| 99-1 7001-13294 | T T T C A A A G C C | T T A T T A T C T A | T A G A A A A G A A |

| | 3100 | 3110 | 3120 |
|---|---|---|---|
| 00-1 7001-13350 | T G A A C G T G C T | A C A C T G A C A A | C A C T A A T G A G |
| 99-1 7001-13294 | T G A A C G T G C T | A C A T T A A C A A | C A C T A A T G A G |

Figure 53 con't

| | | | |
|---|---|---|---|
| | 3130 | 3140 | 3150 |
| 00-1 7001-13350 | A G A T C C T C A A | G C T G T T G G C T | C A G A G C G A C A |
| 99-1 7001-13294 | A G A C C C T C A G | G C A G T A G G A T | C A G A A C G A C A |
| | 3160 | 3170 | 3180 |
| 00-1 7001-13350 | A G C A A A A G T A | A C A A G T G A T A | T C A A T A G A A C |
| 99-1 7001-13294 | A G C T A A G G T A | A C A A G T G A T A | T A A A T A G A A C |
| | 3190 | 3200 | 3210 |
| 00-1 7001-13350 | A G C A G T T A C C | A G C A T C T T A A | G T C T T T C T C C |
| 99-1 7001-13294 | A G C A G T T A C C | A G C A T A C T G A | G T C T A T C T C C |
| | 3220 | 3230 | 3240 |
| 00-1 7001-13350 | A A A T C A A C T T | T T C A G C G A T A | G T G C T A T A C A |
| 99-1 7001-13294 | G A A T C A G C T C | T T C T G T G A T A | G T G C T A T A C A |
| | 3250 | 3260 | 3270 |
| 00-1 7001-13350 | C T A C A G T A G A | A A T G A A G A A G | A G G T C G G A A T |
| 99-1 7001-13294 | T T A T A G T A G A | A A T G A G G A A G | A A G T T G G G A T |
| | 3280 | 3290 | 3300 |
| 00-1 7001-13350 | C A T T G C T G A C | A A C A T A A C A C | C T G T T T A T C C |
| 99-1 7001-13294 | C A T T G C A G A C | A A C A T A A C A C | C T G T C T A T C C |
| | 3310 | 3320 | 3330 |
| 00-1 7001-13350 | T C A T G G A C T G | A G A G T T T T G T | A T G A A T C A T T |
| 99-1 7001-13294 | T C A T G G G C T G | A G A G T G C T C T | A T G A A T C A C T |
| | 3340 | 3350 | 3360 |
| 00-1 7001-13350 | A C C T T T T C A T | A A A G C T G A A A | A A G T T G T G A A |
| 99-1 7001-13294 | A C C T T T T C A T | A A G G C T G A A A | A G G T T G T C A A |
| | 3370 | 3380 | 3390 |
| 00-1 7001-13350 | T A T G A T A T C A | G G A A C G A A A T | C C A T A A C C A A |
| 99-1 7001-13294 | T A T G A T A T C A | G G C A C A A A G T | C T A T A A C T A A |
| | 3400 | 3410 | 3420 |
| 00-1 7001-13350 | C T T A T T A C A G | A G A A C A T C T G | C T A T T A A T G G |
| 99-1 7001-13294 | T C T A T T A C A G | A G A A C A T C T G | C T A T C A A T G G |
| | 3430 | 3440 | 3450 |
| 00-1 7001-13350 | T G A A G A T A T T | G A C A G A G C T G | T A T C C A T G A T |
| 99-1 7001-13294 | T G A A G A T A T T | G A T A G A G C A G | T G T C T A T G A T |
| | 3460 | 3470 | 3480 |
| 00-1 7001-13350 | G C T G G A G A A C | C T A G G A T T A T | T A T C T A G A A T |
| 99-1 7001-13294 | G T T A G A G A A C | T T A G G G T T G T | T A T C T A G A A T |
| | 3490 | 3500 | 3510 |
| 00-1 7001-13350 | A T T G T C A G T A | G T T G T T G A T A | G T A T A G A A A T |
| 99-1 7001-13294 | A T T G T C A G T A | A T A A T T A A T A | G T A T A G A A A T |

Figure 53 con't

| | 3520 | 3530 | 3540 |
|---|---|---|---|
| 00-1 7001-13350 | T C C A A C C A A A | T C T A A T G G T A | G G C T G A T A T G |
| 99-1 7001-13294 | A C C A A T C A A G | T C C A A T G G C A | G A T T G A T A T G |
| | 3550 | 3560 | 3570 |
| 00-1 7001-13350 | T T G T C A G A T A | T C T A G A A C C C | T A A G G G A G A C |
| 99-1 7001-13294 | C T G T C A A A T T | T C C A A G A C C T | T G A G A G A A A A |
| | 3580 | 3590 | 3600 |
| 00-1 7001-13350 | A T C A T G G A A T | A A T A T G G A A A | T A G T T G G A G T |
| 99-1 7001-13294 | A T C A T G G A A C | A A T A T G G A A A | T A G T A G G A G T |
| | 3610 | 3620 | 3630 |
| 00-1 7001-13350 | A A C A T C C C C T | A G C A T C A C T A | C A T G C A T G G A |
| 99-1 7001-13294 | G A C A T C T C C T | A G T A T T G T G A | C A T G T A T G G A |
| | 3640 | 3650 | 3660 |
| 00-1 7001-13350 | T G T C A T A T A T | G C A A C T A G C T | C T C A T T T G A A |
| 99-1 7001-13294 | T G T T G T G T A T | G C A A C T A G T T | C T C A T T T A A A |
| | 3670 | 3680 | 3690 |
| 00-1 7001-13350 | A G G G A T A A T C | A T T G A A A A G T | T C A G C A C T G A |
| 99-1 7001-13294 | A G G A A T A A T T | A T T G A A A A A T | T C A G T A C T G A |
| | 3700 | 3710 | 3720 |
| 00-1 7001-13350 | C A G A A C T A C A | A G A G G T C A A A | G A G G T C C A A A |
| 99-1 7001-13294 | C A A G A C C A C A | A G A G G T C A G A | G G G G A C C A A A |
| | 3730 | 3740 | 3750 |
| 00-1 7001-13350 | G A G C C C T T G G | G T A G G G T C G A | G C A C T C A A G A |
| 99-1 7001-13294 | A A G C C C C T G G | G T A G G A T C A A | G C A C T C A A G A |
| | 3760 | 3770 | 3780 |
| 00-1 7001-13350 | G A A A A A A T T A | G T T C C T G T T T | A T A A C A G A C A |
| 99-1 7001-13294 | G A A A A A A T T G | G T T C C T G T T T | A T A A T A G A C A |
| | 3790 | 3800 | 3810 |
| 00-1 7001-13350 | A A T T C T T T C A | A A A C A A C A A A | G A G A A C A G C T |
| 99-1 7001-13294 | A A T T C T T T C A | A A A C A A C A A A | A A G A G C A A C T |
| | 3820 | 3830 | 3840 |
| 00-1 7001-13350 | A G A A G C A A T T | G G A A A A A T G A | G A T G G G T A T A |
| 99-1 7001-13294 | G G A A G C A A T A | G G G A A A A T G A | G G T G G G T G T A |
| | 3850 | 3860 | 3870 |
| 00-1 7001-13350 | T A A A G G G A C A | C C A G G T T T A A | G A C G A T T A C T |
| 99-1 7001-13294 | C A A A G G A A C T | C C A G G G C T A A | G A A G A T T G C T |
| | 3880 | 3890 | 3900 |
| 00-1 7001-13350 | C A A T A A G A T T | T G T C T T G G A A | G T T T A G G C A T |
| 99-1 7001-13294 | C A A C A A G A T T | T G C A T A G G A A | G C T T A G G T A T |

Figure 53 con't

| | 3910 | 3920 | 3930 |
|---|---|---|---|
| 00-1 7001-13350 | T A G T T A C A A A | T G T G T A A A A C | C T T T A T T A C C |
| 99-1 7001-13294 | T A G C T A T A A A | T G T G T G A A A C | C T T T A T T A C C |
| | **3940** | **3950** | **3960** |
| 00-1 7001-13350 | T A G G T T T A T G | A G T G T A A A T T | T C C T A C A C A G |
| 99-1 7001-13294 | A A G A T T C A T G | A G T G T A A A C T | T C T T A C A T A G |
| | **3970** | **3980** | **3990** |
| 00-1 7001-13350 | G T T A T C T G T C | A G T A G T A G A C | C T A T G G A A T T |
| 99-1 7001-13294 | G T T A T C T G T T | A G T A G T A G A C | C C A T G G A A T T |
| | **4000** | **4010** | **4020** |
| 00-1 7001-13350 | C C C A G C A T C A | G T T C C A G C T T | A T A G A A C A A C |
| 99-1 7001-13294 | C C C A G C T T C T | G T T C C A G C T T | A C A G G A C A A C |
| | **4030** | **4040** | **4050** |
| 00-1 7001-13350 | A A A T T A C C A T | T T T G A C A C T A | G T C C T A T T A A |
| 99-1 7001-13294 | A A A T T A C C A T | T T T G A C A C T A | G T C C A A T C A A |
| | **4060** | **4070** | **4080** |
| 00-1 7001-13350 | T C A A G C A C T A | A G T G A G A G A T | T T G G G A A T G A |
| 99-1 7001-13294 | C C A A G C A T T A | A G T G A G A G G T | T C G G G A A C G A |
| | **4090** | **4100** | **4110** |
| 00-1 7001-13350 | A G A T A T T A A T | T T G G T C T T C C | A A A A T G C A A T |
| 99-1 7001-13294 | A G A C A T T A A T | T T A G T G T T C C | A A A A T G C A A T |
| | **4120** | **4130** | **4140** |
| 00-1 7001-13350 | C A G C T G T G G A | A T T A G C A T A A | T G A G T G T A G T |
| 99-1 7001-13294 | C A G C T G C G G A | A T T A G T A T A A | T G A G T G T T G T |
| | **4150** | **4160** | **4170** |
| 00-1 7001-13350 | A G A A C A A T T A | A C T G G T A G G A | G T C C A A A A C A |
| 99-1 7001-13294 | A G A A C A G T T A | A C T G G T A G A A | G C C C A A A A C A |
| | **4180** | **4190** | **4200** |
| 00-1 7001-13350 | G T T A G T T T T A | A T A C C T C A A T | T A G A A G A A A T |
| 99-1 7001-13294 | A T T A G T C C T A | A T C C C T C A A T | T A G A A G A G A T |
| | **4210** | **4220** | **4230** |
| 00-1 7001-13350 | A G A C A T T A T G | C C A C C A C C A G | T G T T T C A A G G |
| 99-1 7001-13294 | A G A T A T T A T G | C C T C C T C C T G | T A T T T C A A G G |
| | **4240** | **4250** | **4260** |
| 00-1 7001-13350 | G A A A T T C A A T | T A T A A G C T A G | T A G A T A A G A T |
| 99-1 7001-13294 | A A A A T T C A A T | T A T A A A C T A G | T T G A T A A G A T |
| | **4270** | **4280** | **4290** |
| 00-1 7001-13350 | A A C T T C T G A T | C A A C A T A T C T | T C A G T C C A G A |
| 99-1 7001-13294 | A A C C T C C G A T | C A A C A C A T C T | T C A G T C C T G A |

Figure 53 con't

| Sequence | 4300 | 4310 | 4320 |
|---|---|---|---|
| 00-1 7001-13350 | C A A A A T A G A T | A T G T T A A C A C | T G G G G A A A A T |
| 99-1 7001-13294 | C A A A A T A G A C | A T A T T A A C A C | T A G G G A A G A T |
| | **4330** | **4340** | **4350** |
| 00-1 7001-13350 | G C T C A T G C C C | A C T A T A A A A G | G T C A G A A A A C |
| 99-1 7001-13294 | G C T T A T G C C T | A C C A T A A A A G | G T C A A A A A A C |
| | **4360** | **4370** | **4380** |
| 00-1 7001-13350 | A G A T C A G T T C | C T G A A C A A G A | G A G A G A A T T A |
| 99-1 7001-13294 | T G A T C A G T T C | T T A A A T A A G A | G A G A A A A C T A |
| | **4390** | **4400** | **4410** |
| 00-1 7001-13350 | T T T C C A T G G G | A A T A A T C T T A | T T G A G T C T T T |
| 99-1 7001-13294 | T T T T C A T G G A | A A T A A T T T A A | T T G A A T C T T T |
| | **4420** | **4430** | **4440** |
| 00-1 7001-13350 | G T C A G C A G C G | T T A G C A T G T C | A T T G G T G T G G |
| 99-1 7001-13294 | A T C T G C A G C A | C T T G C A T G C C | A C T G G T G T G G |
| | **4450** | **4460** | **4470** |
| 00-1 7001-13350 | G A T A T T A A C A | G A G C A A T G T A | T A G A A A A T A A |
| 99-1 7001-13294 | G A T A T T A A C A | G A A C A G T G C A | T A G A A A A C A A |
| | **4480** | **4490** | **4500** |
| 00-1 7001-13350 | T A T T T T C A A G | A A A G A C T G G G | G T G A C G G G T T |
| 99-1 7001-13294 | T A T C T T T A G G | A A A G A T T G G G | G T G A T G G G T T |
| | **4510** | **4520** | **4530** |
| 00-1 7001-13350 | C A T A T C G G A T | C A T G C T T T T A | T G G A C T T C A A |
| 99-1 7001-13294 | C A T C T C A G A T | C A T G C C T T C A | T G G A T T T C A A |
| | **4540** | **4550** | **4560** |
| 00-1 7001-13350 | A A T A T T C C T A | T G T G T C T T T A | A A A C T A A A C T |
| 99-1 7001-13294 | G G T A T T T C T A | T G T G T A T T T A | A A A C C A A A C T |
| | **4570** | **4580** | **4590** |
| 00-1 7001-13350 | T T T A T G T A G T | T G G G G G T C C C | A A G G G A A A A A |
| 99-1 7001-13294 | T T T A T G T A G T | T G G G G A T C T C | A A G G A A A G A A |
| | **4600** | **4610** | **4620** |
| 00-1 7001-13350 | C A T T A A A G A T | G A A G A T A T A G | T A G A T G A A T C |
| 99-1 7001-13294 | T G T A A A A G A T | G A A G A T A T A A | T A G A T G A A T C |
| | **4630** | **4640** | **4650** |
| 00-1 7001-13350 | A A T A G A T A A A | C T G T T A A G G A | T T G A T A A T A C |
| 99-1 7001-13294 | C A T T G A C A A A | T T A T T A A G A A | T T G A C A A C A C |
| | **4660** | **4670** | **4680** |
| 00-1 7001-13350 | T T T T T G G A G A | A T G T T C A G C A | A G G T T A T G T T |
| 99-1 7001-13294 | C T T T T G G A G A | A T G T T C A G C A | A A G T C A T G T T |

Figure 53 con't

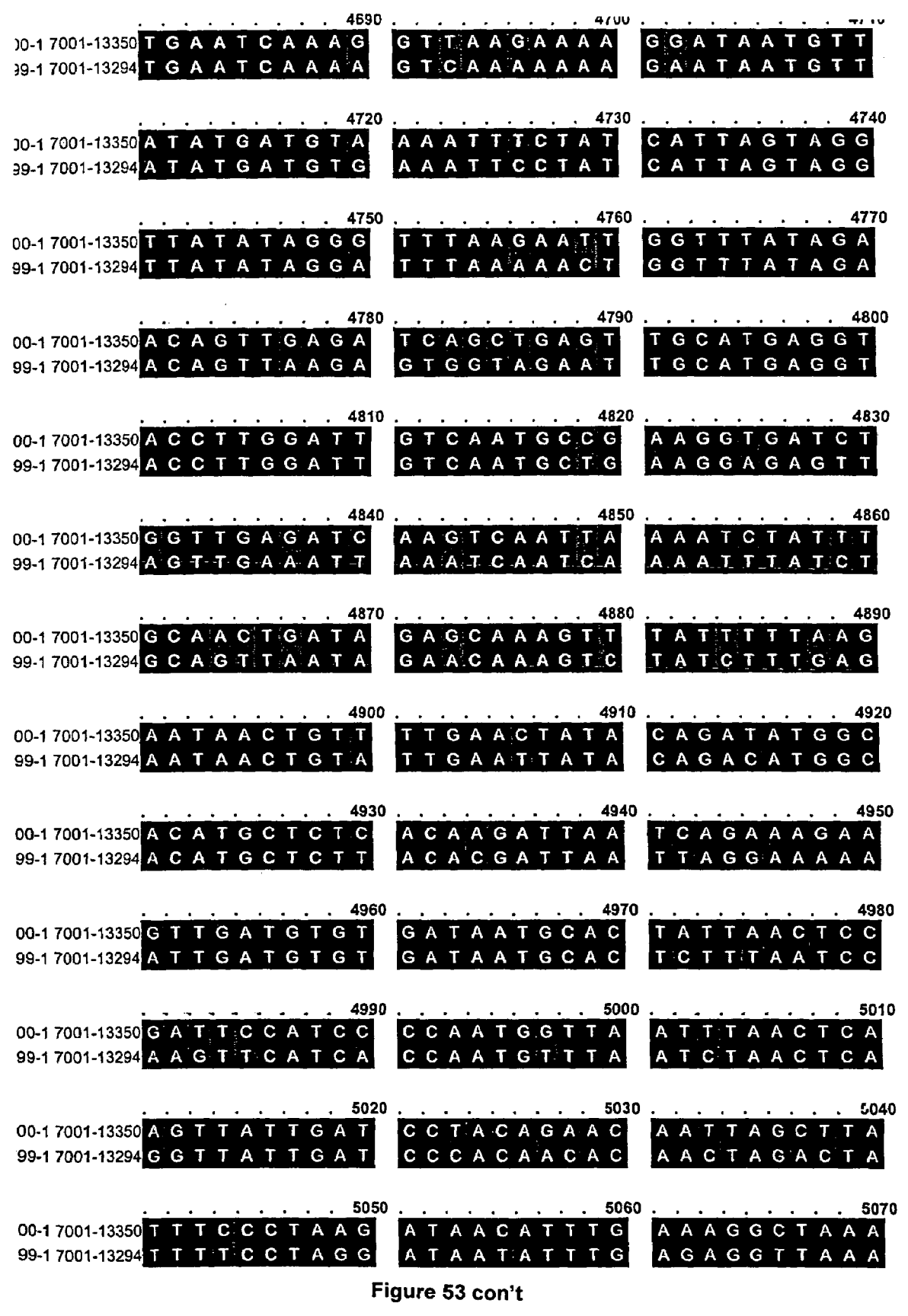

| | 4690 | 4700 | 4710 |
|---|---|---|---|
| 00-1 7001-13350 | T G A A T C A A A G | G T T A A G A A A A | G G A T A A T G T T |
| 99-1 7001-13294 | T G A A T C A A A A | G T C A A A A A A A | G A A T A A T G T T |

| | 4720 | 4730 | 4740 |
|---|---|---|---|
| 00-1 7001-13350 | A T A T G A T G T A | A A A T T T C T A T | C A T T A G T A G G |
| 99-1 7001-13294 | A T A T G A T G T G | A A A T T C C T A T | C A T T A G T A G G |

| | 4750 | 4760 | 4770 |
|---|---|---|---|
| 00-1 7001-13350 | T T A T A T A G G G | T T T A A G A A T T | G G T T T A T A G A |
| 99-1 7001-13294 | T T A T A T A G G A | T T T A A A A A C T | G G T T T A T A G A |

| | 4780 | 4790 | 4800 |
|---|---|---|---|
| 00-1 7001-13350 | A C A G T T G A G A | T C A G C T G A G T | T G C A T G A G G T |
| 99-1 7001-13294 | A C A G T T A A G A | G T G G T A G A A T | T G C A T G A G G T |

| | 4810 | 4820 | 4830 |
|---|---|---|---|
| 00-1 7001-13350 | A C C T T G G A T T | G T C A A T G C C G | A A G G T G A T C T |
| 99-1 7001-13294 | A C C T T G G A T T | G T C A A T G C T G | A A G G A G A G T T |

| | 4840 | 4850 | 4860 |
|---|---|---|---|
| 00-1 7001-13350 | G G T T G A G A T C | A A G T C A A T T A | A A A T C T A T T T |
| 99-1 7001-13294 | A G T T G A A A T T | A A A T C A A T C A | A A A T T T A T C T |

| | 4870 | 4880 | 4890 |
|---|---|---|---|
| 00-1 7001-13350 | G C A A C T G A T A | G A G C A A A G T T | T A T T T T T A A G |
| 99-1 7001-13294 | G C A G T T A A T A | G A A C A A A G T C | T A T C T T T G A G |

| | 4900 | 4910 | 4920 |
|---|---|---|---|
| 00-1 7001-13350 | A A T A A C T G T T | T T G A A C T A T A | C A G A T A T G G C |
| 99-1 7001-13294 | A A T A A C T G T A | T T G A A T T A T A | C A G A C A T G G C |

| | 4930 | 4940 | 4950 |
|---|---|---|---|
| 00-1 7001-13350 | A C A T G C T C T C | A C A A G A T T A A | T C A G A A A G A A |
| 99-1 7001-13294 | A C A T G C T C T T | A C A C G A T T A A | T T A G G A A A A A |

| | 4960 | 4970 | 4980 |
|---|---|---|---|
| 00-1 7001-13350 | G T T G A T G T G T | G A T A A T G C A C | T A T T A A C T C C |
| 99-1 7001-13294 | A T T G A T G T G T | G A T A A T G C A C | T C T T T A A T C C |

| | 4990 | 5000 | 5010 |
|---|---|---|---|
| 00-1 7001-13350 | G A T T C C A T C C | C C A A T G G T T A | A T T T A A C T C A |
| 99-1 7001-13294 | A A G T T C A T C A | C C A A T G T T T A | A T C T A A C T C A |

| | 5020 | 5030 | 5040 |
|---|---|---|---|
| 00-1 7001-13350 | A G T T A T T G A T | C C T A C A G A A C | A A T T A G C T T A |
| 99-1 7001-13294 | G G T T A T T G A T | C C C A C A A C A C | A A C T A G A C T A |

| | 5050 | 5060 | 5070 |
|---|---|---|---|
| 00-1 7001-13350 | T T T C C C T A A G | A T A A C A T T T G | A A A G G C T A A A |
| 99-1 7001-13294 | T T T T C C T A G G | A T A A T A T T T G | A G A G G T T A A A |

Figure 53 con't

| | 5080 | 5090 | 5100 |
|---|---|---|---|
| 00-1 7001-13350 | A A A T T A T G A C | A C T A G T T C A A | A T T A T G C T A A |
| 99-1 7001-13294 | A A G T T A T G A T | A C C A G T T C A G | A C T A C A A C A A |

| | 5110 | 5120 | 5130 |
|---|---|---|---|
| 00-1 7001-13350 | A G G A A A G C T A | A C A A G G A A T T | A C A T G A T A C T |
| 99-1 7001-13294 | A G G G A A G T T A | A C A A G G A A T T | A C A T G A C A T T |

| | 5140 | 5150 | 5160 |
|---|---|---|---|
| 00-1 7001-13350 | G T T G C C A T G G | C A A C A T G T T A | A T A G A T A T A A |
| 99-1 7001-13294 | A T T A C C A T G G | C A A C A C G T A A | A C A G G T A C A A |

| | 5170 | 5180 | 5190 |
|---|---|---|---|
| 00-1 7001-13350 | C T T T G T C T T T | A G T T C T A C T G | G A T G T A A A G T |
| 99-1 7001-13294 | T T T T G T C T T T | A G T T C T A C A G | G T T G T A A A G T |

| | 5200 | 5210 | 5220 |
|---|---|---|---|
| 00-1 7001-13350 | T A G T C T A A A A | A C A T G C A T T G | G A A A A C T T A T |
| 99-1 7001-13294 | C A G T T T G A A G | A C A T G C A T C G | G G A A A T T G A T |

| | 5230 | 5240 | 5250 |
|---|---|---|---|
| 00-1 7001-13350 | G A A A G A T C T A | A A C C C T A A A G | T T C T G T A C T T |
| 99-1 7001-13294 | A A A G G A T T T A | A A T C C T A A A G | T T C T T T A C T T |

| | 5260 | 5270 | 5280 |
|---|---|---|---|
| 00-1 7001-13350 | T A T T G G A G A A | G G G G C A G G A A | A T T G G A T G G C |
| 99-1 7001-13294 | T A T T G G A G A A | G G A G C A G G T A | A C T G G A T G G C |

| | 5290 | 5300 | 5310 |
|---|---|---|---|
| 00-1 7001-13350 | C A G A A C A G C A | T G T G A A T A T C | C T G A C A T C A A |
| 99-1 7001-13294 | A A G A A C A G C A | T G T G A A T A T C | C T G A T A T A A A |

| | 5320 | 5330 | 5340 |
|---|---|---|---|
| 00-1 7001-13350 | A T T T G T A T A C | A G A A G T T T A A | A A G A T G A C C T |
| 99-1 7001-13294 | A T T T G T A T A T | A G G A G T T T A A | A G G A T G A C C T |

| | 5350 | 5360 | 5370 |
|---|---|---|---|
| 00-1 7001-13350 | T G A T C A T C A T | T A T C C T T T G G | A A T A C C A G A G |
| 99-1 7001-13294 | T G A T C A C C A T | T A C C C A T T A G | A A T A T C A A A G |

| | 5380 | 5390 | 5400 |
|---|---|---|---|
| 00-1 7001-13350 | A G T T A T A G G A | G A A T T A A G C A | G G A T A A T A G A |
| 99-1 7001-13294 | G G T A A T A G G T | G A T C T A A A T A | G G G T G A T A G A |

| | 5410 | 5420 | 5430 |
|---|---|---|---|
| 00-1 7001-13350 | T A G C G G T G A A | G G G C T T T C A A | T G G A A A C A A C |
| 99-1 7001-13294 | T A G T G G T G A A | G G A T T A T C A A | T G G A A A C C A C |

| | 5440 | 5450 | 5460 |
|---|---|---|---|
| 00-1 7001-13350 | A G A T G C A A C T | C A A A A A A C T C | A T T G G G A T T T |
| 99-1 7001-13294 | A G A T G C A A C T | C A A A A A A C T C | A T T G G G A C T T |

Figure 53 con't

| | | | |
|---|---|---|---|
| | 5470 | 5480 | 5490 |
| 00-1 7001-13350 | G A T A C A C A G A | G T A A G C A A A G | A T G C T T T A T T |
| 99-1 7001-13294 | G A T A C A C A G A | A T A A G T A A A G | A T G C T T T A T T |
| | 5500 | 5510 | 5520 |
| 00-1 7001-13350 | A A T A A C T T T A | T G T G A T G C A G | A A T T T A A G G A |
| 99-1 7001-13294 | G A T A A C A T T G | T G T G A T G C A G | A A T T C A A A A A |
| | 5530 | 5540 | 5550 |
| 00-1 7001-13350 | C A G A G A T G A T | T T T T T T A A G A | T G G T A A T T C T |
| 99-1 7001-13294 | C A G A G A T G A T | T T C T T T A A G A | T G G T A A T C C T |
| | 5560 | 5570 | 5580 |
| 00-1 7001-13350 | A T G G A G G A A A | C A T G T A T T A T | C A T G C A G A A T |
| 99-1 7001-13294 | T T G G A G A A A A | C A T G T A T T A T | C T T G T A G A A T |
| | 5590 | 5600 | 5610 |
| 00-1 7001-13350 | T T G C A C T A C T | T A T G G G A C A G | A C C T C T A T T T |
| 99-1 7001-13294 | C T G T A C A G C T | T A T G G A A C A G | A T C T T T A C T T |
| | 5620 | 5630 | 5640 |
| 00-1 7001-13350 | A T T C G C A A A G | T A T C A T G C T A | A A G A C T G C A A |
| 99-1 7001-13294 | A T T T G C A A A G | T A T C A T G C G G | T G G A C T G C A A |
| | 5650 | 5660 | 5670 |
| 00-1 7001-13350 | T G T A A A A T T A | C C T T T T T T T G | T G A G A T C A G T |
| 99-1 7001-13294 | T A T A A A A T T A | C C A T T T T T T G | T A A G A T C T G T |
| | 5680 | 5690 | 5700 |
| 00-1 7001-13350 | A G C C A C C T T T | A T T A T G C A A G | G T A G T A A A C T |
| 99-1 7001-13294 | A G C T A C T T T T | A T T A T G C A A G | G A A G C A A A T T |
| | 5710 | 5720 | 5730 |
| 00-1 7001-13350 | G T C A G G C T C A | G A A T G C T A C A | T A C T C T T A A C |
| 99-1 7001-13294 | A T C A G G G T C A | G A A T G T T A C A | T A C T T T T A A C |
| | 5740 | 5750 | 5760 |
| 00-1 7001-13350 | A C T A G G C C A C | C A C A A C A A T T | T A C C C T G C C A |
| 99-1 7001-13294 | A T T A G G T C A T | C A C A A T A A T C | T A C C C T G T C A |
| | 5770 | 5780 | 5790 |
| 00-1 7001-13350 | T G G A G A A A T A | C A A A A T T C T A | A G A T G A A A A T |
| 99-1 7001-13294 | T G G A G A A A T A | C A A A A T T C C A | A A A T G A G A A T |
| | 5800 | 5810 | 5820 |
| 00-1 7001-13350 | A G C A G T G T G T | A A T G A T T T T T | A T G C T G C A A A |
| 99-1 7001-13294 | A G C A G T G T G T | A A T G A T T T C T | A T G C C T C A A A |
| | 5830 | 5840 | 5850 |
| 00-1 7001-13350 | A A A A C T T G A C | A A T A A A T C T A | T T G A A G C C A A |
| 99-1 7001-13294 | G A A A C T G G A C | A A C A A A T C A A | T T G A A G C A A A |

Figure 53 con't

| | 5860 | 5870 | 5880 |
|---|---|---|---|
| 00-1 7001-13350 | CTGTAAATCA | CTTTTATCAG | GGCTAAGAAT |
| 99-1 7001-13294 | CTGCAAATCT | CTTCTATCAG | GATTGAGAAT |
| | 5890 | 5900 | 5910 |
| 00-1 7001-13350 | ACCGATAAAT | AAGAAAGAAT | TAAATAGACA |
| 99-1 7001-13294 | ACCTATAAAC | AAAAAGGAGT | TAAATAGACA |
| | 5920 | 5930 | 5940 |
| 00-1 7001-13350 | GAGAAGGTTA | TTAACACTAC | AAAGCAACCA |
| 99-1 7001-13294 | AAAGAAATTG | TTAACACTAC | AAAGTAACCA |
| | 5950 | 5960 | 5970 |
| 00-1 7001-13350 | TTCTTCTGTA | GCAACAGTTG | GAGGTAGCAA |
| 99-1 7001-13294 | TTCTTCTATA | GCAACAGTTG | GCGGCAGTAA |
| | 5980 | 5990 | 6000 |
| 00-1 7001-13350 | GGTCATAGAG | TCTAAATGGT | TAACAAACAA |
| 99-1 7001-13294 | GATTATAGAA | TCCAAATGGT | TAAAGAATAA |
| | 6010 | 6020 | 6030 |
| 00-1 7001-13350 | GGCAAACACA | ATAATTGATT | GGTTAGAACA |
| 99-1 7001-13294 | AGCAAGTACA | ATAATTGATT | GGTTAGAGCA |
| | 6040 | 6050 | 6060 |
| 00-1 7001-13350 | TATTTTAAAT | TCTCCAAAAG | GTGAATTAAA |
| 99-1 7001-13294 | TATTTTGAAT | TCTCCAAAAG | GTGAATTAAA |
| | 6070 | 6080 | 6090 |
| 00-1 7001-13350 | TTATGATTTT | TTTGAAGCAT | TAGAAAATAC |
| 99-1 7001-13294 | CTATGATTTC | TTTGAAGCAT | TAGAGAACAC |
| | 6100 | 6110 | 6120 |
| 00-1 7001-13350 | TTACCCTAAT | ATGATTAAAC | TAATAGATAA |
| 99-1 7001-13294 | ATACCCCAAT | ATGATCAAGC | TTATAGATAA |
| | 6130 | 6140 | 6150 |
| 00-1 7001-13350 | TCTAGGGAAT | GCAGAGATAA | AAAAACTGAT |
| 99-1 7001-13294 | TTTGGGAAAT | GCAGAAATAA | AGAAACTAAT |
| | 6160 | 6170 | 6180 |
| 00-1 7001-13350 | CAAAGTAACT | GGATATATGC | TTGTAAGTAA |
| 99-1 7001-13294 | CAAGGTCACT | GGGTATATGC | TTGTGAGTAA |
| | 6190 | 6200 | 6210 |
| 00-1 7001-13350 | AAAATGAAAA | ATGATAAAAA | TGATAAAATA |
| 99-1 7001-13294 | GAAGT-AATA | ATAATGATAA | TGATTAACCA |
| | 6220 | 6230 | 6240 |
| 00-1 7001-13350 | GGTGACAACT | TCATACTATT | CC-AAAGTAA |
| 99-1 7001-13294 | -----TAATC | TCACACAACT | GAGAAAATAA |

Figure 53 con't

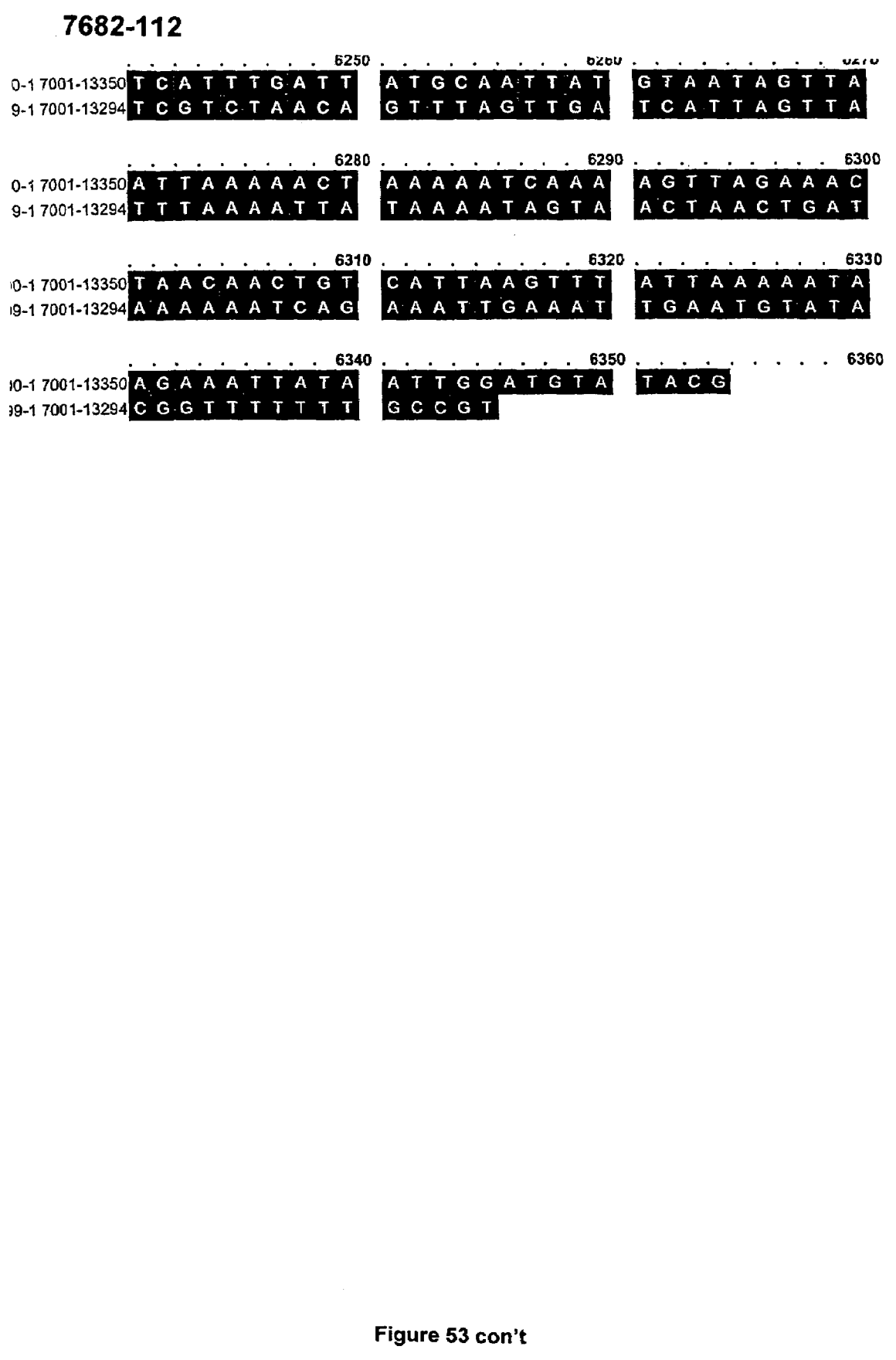

7682-112

| | . . . . . . . . . 6250 | . . . . . . . . . 6260 | . . . . . . . . . 6270 |
|---|---|---|---|
| 0-1 7001-13350 | T C A T T T G A T T | A T G C A A T T A T | G T A A T A G T T A |
| 9-1 7001-13294 | T C G T C T A A C A | G T T T A G T T G A | T C A T T A G T T A |
| | . . . . . . . . . 6280 | . . . . . . . . . 6290 | . . . . . . . . . 6300 |
| 0-1 7001-13350 | A T T A A A A A C T | A A A A A T C A A A | A G T T A G A A A C |
| 9-1 7001-13294 | T T T A A A A T T A | T A A A A T A G T A | A C T A A C T G A T |
| | . . . . . . . . . 6310 | . . . . . . . . . 6320 | . . . . . . . . . 6330 |
| 0-1 7001-13350 | T A A C A A C T G T | C A T T A A G T T T | A T T A A A A A T A |
| 9-1 7001-13294 | A A A A A A T C A G | A A A T T G A A A T | T G A A T G T A T A |
| | . . . . . . . . . 6340 | . . . . . . . . . 6350 | . . . . . . . . . 6360 |
| 0-1 7001-13350 | A G A A A T T A T A | A T T G G A T G T A | T A C G |
| 9-1 7001-13294 | C G G T T T T T T T | G C C G T | |

Figure 53 con't

5' cDNA Terminal Sequences of hMPV

Clonal Analysis of 96 PCR colonies

| | # Colony | Ratio |
|---|---|---|
| 5'-ACGCGAAAAAAACGCG | 15 | 31% |
| CGCGAAAAAAACGCG | 6 | 12% |
| GCGAAAAAAACGCG | 5 | 10% |
| CGAAAAAAACGCG | 23 | 47% |

Total 49 near full-length clones

Blank

Rescued hMPV #2

Immunostaining of hMPV (guinea pig Ab)

hMPV rescued P1, 9 day p.i. in Vero hMPV /NL/1/00 (clade A1) 8 day p.i. in Vero hMPV /NL/17/00 (clade A2) 10 day p.i. in Vero hMPV /NL/99/1 (clade B1) 10 days p.i. in Vero hMPV /NL/94/1 (clade B2) 8 day p.i. in Vero

Figure 59C:
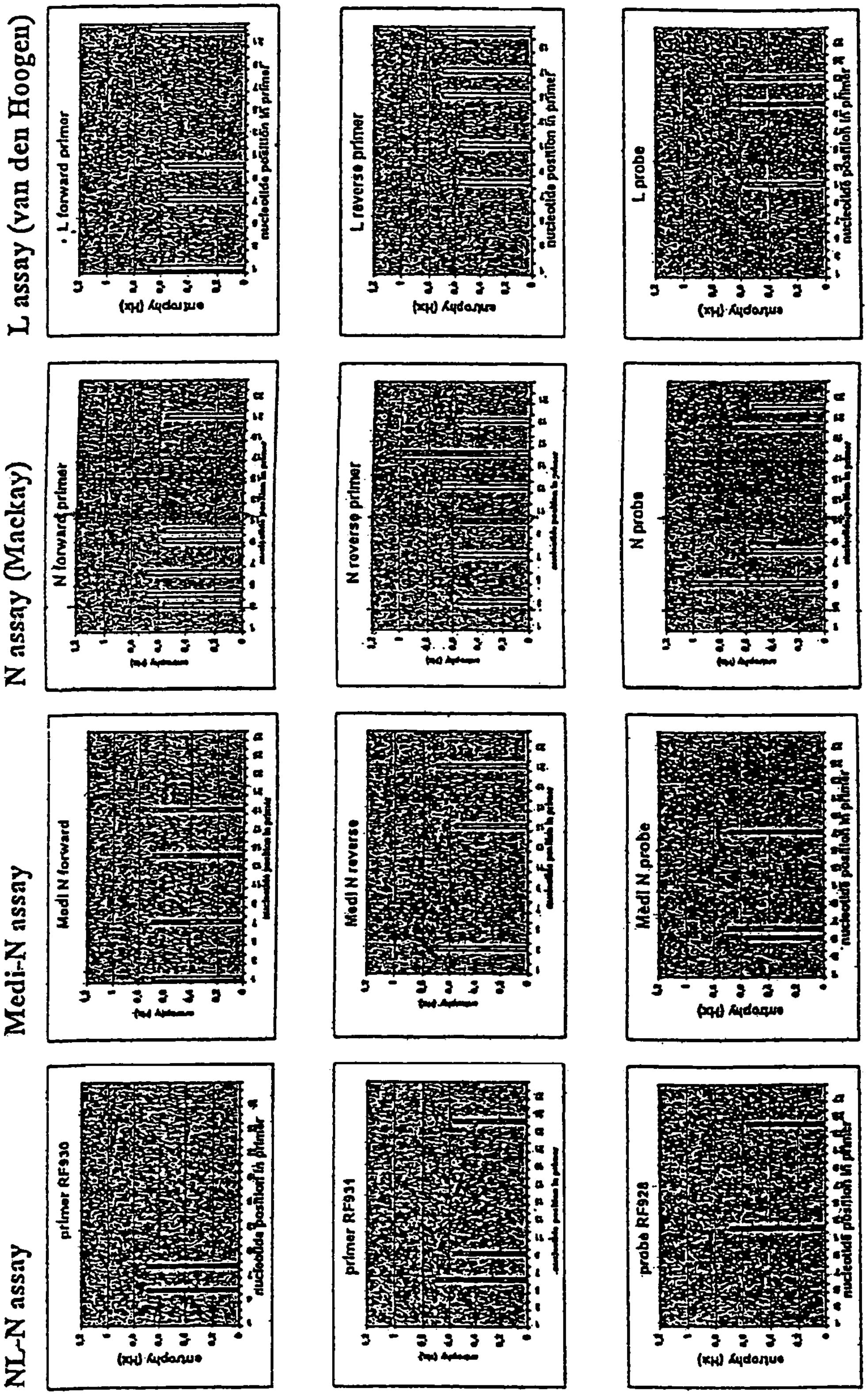
Figure 59D:
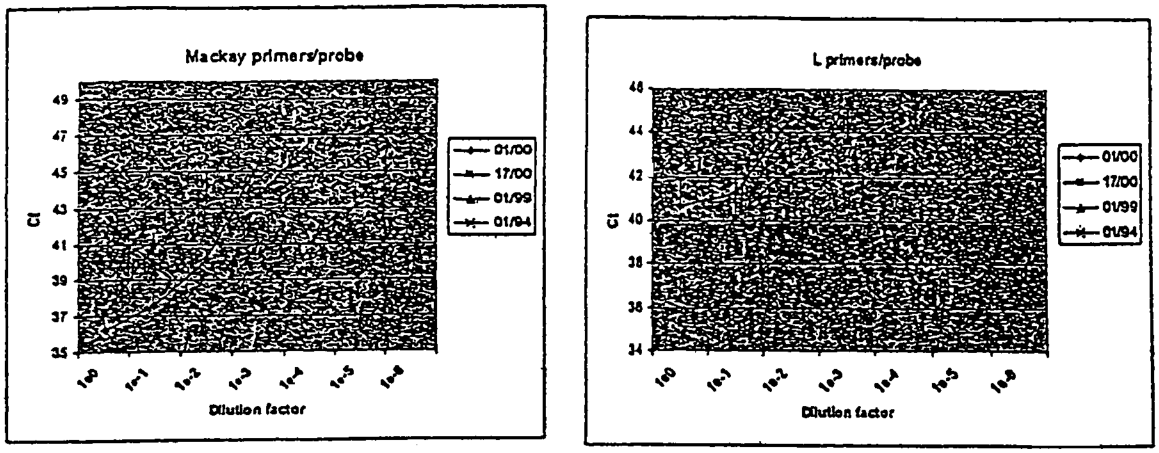

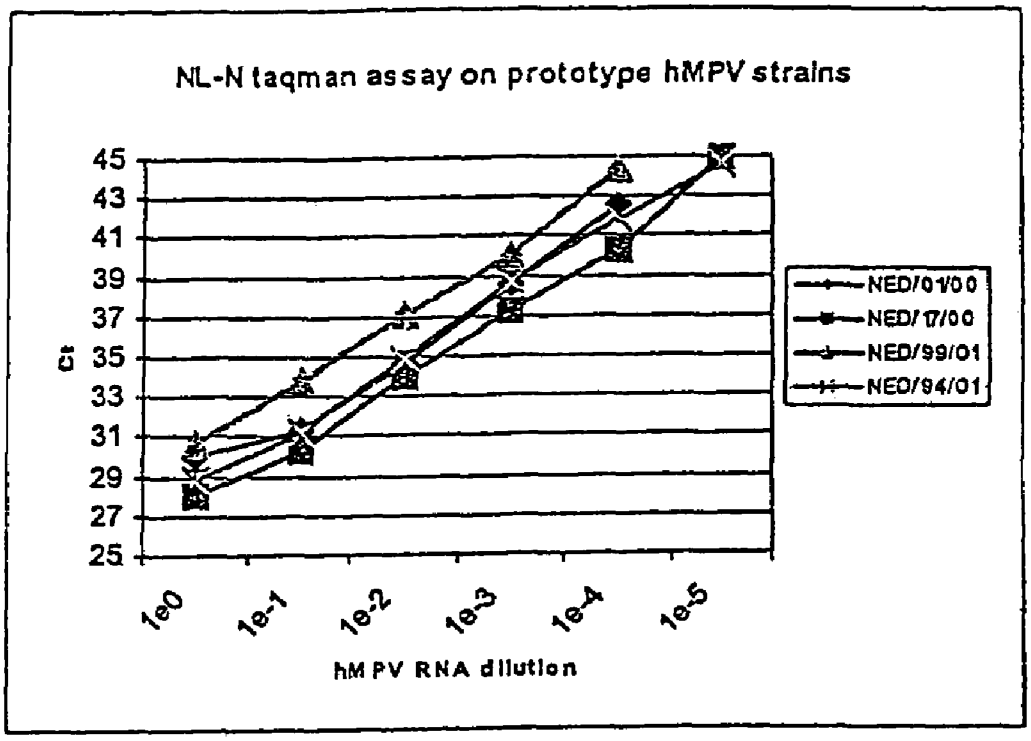
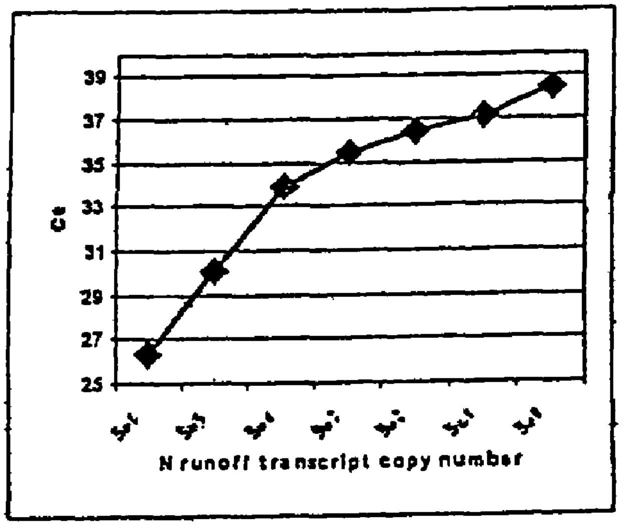
FIGURE 59 A-B

Plan for Cloning Deletions in M2 Gene

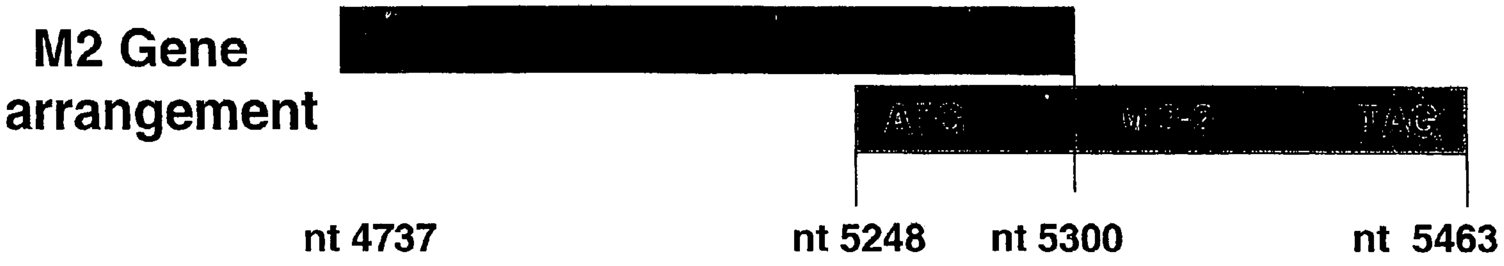

- To construct M2 deletion,
construct *Bsp* EI sites at nucleotides 4741 and 5444
and delete the intervening nucleotides.
- To construct M2-1 deletion,
construct *Nhe* I sites at nucleotides 4744 and 5241
and delete the intervening nucleotides.
- To construct M2-2 deletion,
construct *Swa* I sites at nucleotides 5311 and 5453
and delete the intervening nucleotides MedImmune, Inc.

Figure 61 hMPV Virus Growth Curves of hMPV Viruses
( With Trypsin; MOI = 0.1)
Titer (Log 10 PFU/ml)
8.00
6.00
4.00
2.00
0.00
0
1
2
3
4
5
6
Time Post Infection (days)
wt hMPV
rec hMPV (#21)
rec hMPV (C4A)(#5)
Growth Curves of hMPV Viruses
(Without Trypsin; MOI = 0.1)
Titer (Log 10 PFU/ml)
8.00
6.00
4.00
2.00
0.00
0
1
2
3
4
5
6
Time Post Infection (days)
wt hMPV
rec hMPV # 21
rec hMPV (C4A)(#5)
MedImmune, Inc.

Figure 66

| Virus [a] | Mean virus titer on day 4 post-infection ($\log_{10}$ $TCID_{50}$/g tissue ± S.E.) [b] | | |
|---|---|---|---|
| | Lungs (PFU in 100 uL) | Inoculum | Nasal turbinates |
| wt hMPV/NL/1/00 | $1.8 \times 10^{6}$ | 5.7 ± 0.5 | 5.2 ± 0.1 |
| rec hMPV/NL/1/00 (C4A) (APV-like leader and trailer) | $2 \times 10^{6}$ | 4.6 ± 1.2 | 4.5 ± 0.3 |
| rec hMPV/NL/1/00[c] (hMPV-like leader and trailer) | $4.0 \times 10^{5}$ | 4.8 ± 0.5 | 4.3 ± 0.3 |
| rec hMPV/GFP2 (APV-like leader and trailer) | $3.0 \times 10^{4}$ | no titer, no fluorescence | no titer, no fluorescence |

[a] Groups of six hamsters were inoculated intranasally
[b] Results are average ± standard error.
[c] Plaques were small compared to wt hMPV/NL/100

MedImmune, Inc.

Rec hMPVNL/1/00 (C4A) vs. wt hMPV/NL/1/00
(MOI = 1.0 in Vero cells)
Titer (Log 10 PFU/ml)
Time Post Infection (days)
wt hMPV
rec hMPV(C4A)
Rec hMPV/NL/1/00 (C4)
(APV leader and trailer)
(Mutation A3344T=E93V in F protein)
MedImmune, Inc.

SEQUENCE LISTING

```
<160> NUMBER OF SEQ ID NOS: 433

<210> SEQ ID NO 1
<211> LENGTH: 2507
<212> TYPE: DNA
<213> ORGANISM: metapneumovirus
<220> FEATURE:
<221> NAME/KEY: CDS
<222> LOCATION: (1)...(2507)
<223> OTHER INFORMATION: Human metapneumovirus isolate 00-1 matrix
      protein (M) and fusion protein (F) genes

<400> SEQUENCE: 1

atggagtcct acctagtaga cacctatcaa ggcattcctt acacagcagc tgttcaagtt     60

gatctaatag aaaaggacct gttacctgca agcctaacaa tatggttccc tttgtttcag    120

gccaacacac caccagcagt gctgctcgat cagctaaaaa ccctgacaat aaccactctg    180

tatgctgcat cacaaaatgg tccaatactc aaagtgaatg catcagccca aggtgcagca    240

atgtctgtac ttcccaaaaa atttgaagtc aatgcgactg tagcactcga tgaatatagc    300

aaactggaat ttgacaaact cacagtctgt gaagtaaaaa cagtttactt aacaaccatg    360

aaaccatacg ggatggtatc aaaatttgtg agctcagcca aatcagttgg caaaaaaaca    420

catgatctaa tcgcactatg tgattttatg gatctagaaa agaacacacc tgttacaata    480

ccagcattca tcaaatcagt ttcaatcaaa gagagtgagt cagctactgt tgaagctgct    540

ataagcagtg aagcagacca agctctaaca caggccaaaa ttgcacctta tgcgggatta    600

attatgatca tgactatgaa caatcccaaa ggcatattca aaaagcttgg agctgggact    660

caagtcatag tagaactagg agcatatgtc caggctgaaa gcataagcaa aatatgcaag    720

acttggagcc atcaagggac aagatatgtc ttgaagtcca gataacaacc aagcaccttg    780

gccaagagct actaacccta tctcatagat cataaagtca ccattctagt tatataaaaa    840

tcaagttaga acaagaatta aatcaatcaa gaacgggaca aataaaaatg tcttggaaag    900
```

-continued

```
tggtgatcat tttttcattg ttaataacac ctcaacacgg tcttaaagag agctacttag    960

aagagtcatg tagcactata actgaaggat atctcagtgt tctgaggaca ggttggtaca   1020

ccaatgtttt tacactggag gtaggcgatg tagagaacct tacatgtgcc gatggaccca   1080

gcttaataaa aacagaatta gacctgacca aaagtgcact aagagagctc agaacagttt   1140

ctgctgatca actggcaaga gaggagcaaa ttgaaaatcc cagacaatct agattcgttc   1200

taggagcaat agcactcggt gttgcaactg cagctgcagt tacagcaggt gttgcaattg   1260

ccaaaaccat ccggcttgaa agtgaagtaa cagcaattaa gaatgccctc aaaaagacca   1320

atgaagcagt atctacattg gggaatggag ttcgtgtgtt ggcaactgca gtgagagagc   1380

tgaaagattt tgtgagcaag aatctaacac gtgcaatcaa caaaaacaag tgcgacattg   1440

ctgacctgaa aatggccgtt agcttcagtc aattcaacag aaggttccta aatgttgtgc   1500

ggcaattttc agacaacgct ggaataacac cagcaatatc tttggactta atgacagatg   1560

ctgaactagc cagagctgtt tccaacatgc caacatctgc aggacaaata aaactgatgt   1620

tggagaaccg tgcaatggta agaagaaaag ggttcggatt cctgatagga gtttacggaa   1680

gctccgtaat ttacatggtg caactgccaa tctttggggt tatagacacg ccttgctgga   1740

tagtaaaagc agccccttct tgttcaggaa aaaagggaaa ctatgcttgc ctcttaagag   1800

aagaccaagg atggtattgt caaaatgcag ggtcaactgt ttactaccca aatgaaaaag   1860

actgtgaaac aagaggagac catgtctttt gcgacacagc agcaggaatc aatgttgctg   1920

agcagtcaaa ggagtgcaac ataaacatat ctactactaa ttacccatgc aaagttagca   1980

caggaagaca tcctatcagt atggttgcac tatctcctct tggggctttg gttgcttgct   2040

acaagggagt gagctgttcc attggcagca acagagtagg gatcatcaag caactgaaca   2100

aaggctgctc ttatataacc aaccaagacg cagacacagt gacaatagac aacactgtat   2160

accagctaag caaagttgaa ggcgaacagc atgttataaa aggaaggcca gtgtcaagca   2220

gctttgaccc agtcaagttt cctgaagatc aattcaatgt tgcacttgac caagttttcg   2280

agagcattga gaacagtcag gccttggtgg atcaatcaaa cagaatccta agcagtgcag   2340

agaaaggaaa cactggcttc atcattgtaa taattctaat tgctgtcctt ggctctacca   2400

tgatcctagt gagtgttttt atcataataa agaaaacaaa gagacccaca ggagcacctc   2460

cagagctgag tggtgtcaca aacaatggct tcataccaca taattag                 2507
```

<210> SEQ ID NO 2
<211> LENGTH: 1596
<212> TYPE: DNA
<213> ORGANISM: pneumvirus
<220> FEATURE:
<221> NAME/KEY: CDS
<222> LOCATION: (1)...(1596)
<223> OTHER INFORMATION: Avian pneumovirus fusion protein gene, partial
cds

<400> SEQUENCE: 2

```
atgtcttgga aagtggtact gctattggta ttgctagcta ccccaacggg ggggctagaa     60

gaaagttatc tagaggagtc atgcagtact gttactagag gatacctgag tgttttgagg    120

acaggatggt atacaaatgt gttcacactt ggggttggag atgtgaaaaa tctcacatgt    180

accgacgggc ccagcttaat aagaacagaa cttgaactga caaaaaatgc acttgaggaa    240

ctcaagacag tatcagcaga tcaattggca aaggaagcta ggataatgtc accaagaaaa    300

gcccggtttg ttctgggtgc catagcatta ggtgtggcaa ctgctgctgc tgtgacggct    360
```

-continued ggtgtagcga tagccaagac aattaggcta gaaggagaag tggctgcaat caaaggtgcg 420
ctcaggaaaa caaatgaggc tgtatctaca ttaggaaatg gcgtgagggt acttgcaaca 480
gctgtgaatg atctcaagga ctttataagt aaaaaattga cacctgcaat aaacaggaac 540
aagtgtgaca tctcagacct taagatggca gtgagctttg gacaatacaa tcggaggttc 600
ctcaatgtgg taagacagtt ttctgacaat gcaggtatta cgcctgcaat atctctagat 660
ttaatgactg acgctgagct tgtaagagct gtaagcaaca tgcccacatc ttcaggacag 720
atcaatctga tgcttgagaa tcgggcaatg gtcagaagga aaggatttgg gattttgatt 780
ggagtttatg gtagctctgt ggtctatata gtgcagcttc ctattttcgg tgtgatagat 840
acaccgtgtt ggagggtgaa ggctgctcca ttatgttcag ggaaagacgg gaattatgca 900
tgtctcttgc gagaggacca aggttggtat tgtcaaaatg ctggatccac agtttattat 960
ccaaatgagg aggactgtga agtaagaagt gatcatgtgt tttgtgacac agcagctggg 1020
ataaatgtag caaaggagtc agaagagtgc aacaggaata tctcaacaac aaagtaccct 1080
tgcaaggtaa gtacagggcg tcacccaata agcatggtgg ccttatcacc actgggtgct 1140
ttggtagcct gttatgacgg tatgagttgt tccattggaa gcaacaaggt tggaataatc 1200
agacctttgg ggaaagggtg ttcatacatc agcaatcaag atgctgacac tgttacaatt 1260
gacaacacag tgtaccaatt gagcaaagtt gaaggagaac aacacacaat taaagggaag 1320
ccagtatcta gcaattttga ccctatagag ttccctgaag atcagttcaa cgtagccctg 1380
gatcaggtgt ttgaaagtgt tgagaagagt cagaatctga tagaccagtc aaacaagata 1440
ttggatagca ttgaaaaggg gaatgcagga tttgtcatag tgatagtcct cattgtcctg 1500
ctcatgctgg cagcagttgg tgtgggtgtc ttctttgtgg ttaagaagag aaaagctgct 1560
cccaaattcc caatggaaat gaatggtgtg aacaac 1596

<210> SEQ ID NO 3
<211> LENGTH: 1666
<212> TYPE: DNA
<213> ORGANISM: pneumovirus
<220> FEATURE:
<221> NAME/KEY: CDS
<222> LOCATION: (14)...(1627)
<223> OTHER INFORMATION: Avian pneumovirus isolate 1b fusion protein
mRNA, complete cds

<400> SEQUENCE: 3
gggacaagtg aaaatgtctt ggaaagtggt actgctattg gtattgctag ctaccccaac 60 ggggggggcta gaagaaagtt atctagagga gtcatgcagt actgttacta gaggatacct 120
gagtgttttg aggacaggat ggtatacaaa tgtgttcaca cttgaggttg gagatgtgga 180
aaatctcaca tgtaccgacg ggcccagctt aataagaaca gaacttgaac tgacaaaaaa 240
tgcacttgag gaactcaaga cagtatcagc agatcaattg gcaaaggaag ctaggataat 300
gtcaccaaga aaagcccggt ttgttctggg tgccatagca ttaggtgtgg caactgctgc 360
tgctgtgacg gctggtgtag cgatagccaa gacaattagg ctagaaggag aagtggctgc 420
aatcaagggt gcgctcagga aaacaaatga ggctgtatct acattaggaa atggcgtgag 480
ggtacttgca acagctgtga atgatctcaa ggactttata agtaaaaaat tgacacctgc 540
aataaacagg aacaagtgtg acatctcaga ccttaagatg gcagtgagct ttggacaata 600
caatcggagg ttcctcaatg tggtaagaca gttttctgac aatgcaggta ttacgcctgc 660
aatatctcta gatttaatga ctgacgctga gcttgtaaga gctgtaagca acatgcccac 720

-continued

```
atcttcagga cagatcaatc tgatgcttga gaatcgggca atggtcagaa ggaaaggatt    780

tgggattttg attggagttt atggtagctc tgtggtctat atagtgcagc ttcctatttt    840

cggtgtgata gatacaccgt gttggaaggt gaaggctgct ccattatgtt cagggaaaga    900

cgggaattat gcatgtctct tgcgagagga ccaaggttgg tattgtcaaa atgctggatc    960

cacagtttat tatccaaatg aggaggactg tgaagtaaga agtgatcatg tgttttgtga   1020

cacagcagct gggataaatg tagcaaagga gtcagaagag tgcaacagga atatctcaac   1080

aacaaagtac ccttgcaagg taagtacagg gcgtcaccca ataagcatgg tggccttatc   1140

accactgggt gctttggtag cctgttatga cggtatgagt tgttccattg gaagcaacaa   1200

ggttggaata atcagacctt tggggaaagg gtgttcatac atcagcaatc aagatgctga   1260

cactgttaca attgacaaca cagtgtacca attgagcaaa gttgaaggag aacaacacac   1320

aattaaaggg aagccagtat ctagcaattt tgaccctata gagttccctg aagatcagtt   1380

caacgtagcc ctggatcagg tgtttgaaag tgttgagaag agtcagaatc tgatagacca   1440

gtcaaacaag atattggata gcattgaaaa ggggaatgca ggatttgtca tagtgatagt   1500

cctcattgtc ctgctcatgc tggcagcagt tggtgtgggt gtcttctttg tggttaagaa   1560

gagaaaagct gctcccaaat tcccaatgga aatgaatggt gtgaacaaca aaggatttat   1620

cccttaattt tagttattaa aaaaaaaaaa aaaaaaaaaa aaaaaa                  1666
```

<210> SEQ ID NO 4
<211> LENGTH: 1636
<212> TYPE: DNA
<213> ORGANISM: rhinotracheitis virus
<220> FEATURE:
<221> NAME/KEY: CDS
<222> LOCATION: (13)...(1629)
<223> OTHER INFORMATION: Turkey rhinotracheitis virus gene for fusion
      protein (F1 and F2 subunits), complete cds

<400> SEQUENCE: 4

```
gggacaagta ggatggatgt aagaatctgt ctcctattgt tccttatatc taatcctagt     60

agctgcatac aagaaacata caatgaagaa tcctgcagta ctgtaactag aggttataag    120

agtgtgttaa ggacagggtg gtatacgaat gtatttaacc tcgaaatagg gaatgttgag    180

aacatcactt gcaatgatgg acccagccta attgacactg agttagtact cacaaagaat    240

gctttgaggg agctcaaaac agtgtcagct gatcaagtgg ctaaggaaag cagactatcc    300

tcacccagga gacgtagatt tgtactgggt gcaatagcac ttggtgttgc gacagctgct    360

gccgtaacag ctggtgtagc acttgcaaag acaattagat tagagggaga ggtgaaggca    420

attaagaatg ccctccggaa cacaaatgag gcagtatcca cattagggaa tggtgtgagg    480

gtactagcaa ctgcagtcaa tgacctcaaa gaatttataa gtaaaaaatt gactcctgct    540

attaaccaga acaaatgcaa tatagcagat ataaagatgg caattagttt tggccaaaat    600

aacagaaggt tcctgaatgt ggtgaggcaa ttctctgata gtgcaggtat cacatcagct    660

gtgtctcttg atttaatgac agatgatgaa cttgttagag caattaacag aatgccaact    720

tcatcaggac agattagttt gatgttgaac aatcgtgcca tggttagaag gaaggggttt    780

ggtatattga ttggtgttta tgatggaacg gtcgtttata tggtacaact gcccatattc    840

ggcgtgattg agacaccttg ttggagggtg gtggcagcac cactctgtag gaaagagaaa    900

ggcaattatg cttgtatact gagagaagat caagggtggt actgtacaaa tgctggctct    960

acagcttatt atcctaataa agatgattgt gaggtaaggg atgattatgt attttgtgac   1020
```

-continued acagcagctg gcattaatgt ggccctagaa gttgaacagt gcaactataa catatcgact 1080
tctaaatacc catgcaaagt cagcacaggt agacaccctg tcagtatggt agccttaacc 1140
cccctagggg gtctagtgtc ttgttatgag agtgtaagtt gctccatagg tagcaataaa 1200
gtagggataa taaaacagct aggcaaaggg tgcacccaca ttcccaacaa cgaagctgac 1260
acgataacca ttgataacac tgtgtaccaa ttgagcaagg ttgtaggcga acagaggacc 1320
ataaaaggag ctccagttgt gaacaatttt aacccaatat tattccctga ggatcagttc 1380
aatgttgcac ttgaccaagt atttgagagt atagatagat ctcaggactt aatagataag 1440
tctaacgact tgctaggtgc agatgccaag agcaaggctg gaattgctat agcaatagta 1500
gtgctagtca ttctaggaat cttcttttta cttgcagtga tatattactg ttccagagtc 1560
cggaagacca aaccaaagca tgattacccg gccacgacag gtcatagcag catggcttat 1620
gtcagttaag ttattt 1636

<210> SEQ ID NO 5
<211> LENGTH: 1860
<212> TYPE: DNA
<213> ORGANISM: pneumovirus
<220> FEATURE:
<221> NAME/KEY: CDS
<222> LOCATION: (1)...(110)
<223> OTHER INFORMATION: Avian pneumovirus matrix protein (M) gene, partial cds
<220> FEATURE:
<221> NAME/KEY: CDS
<222> LOCATION: (216)...(1829)
<223> OTHER INFORMATION: Avian pneumovirus fusion glycoprotein (F) gene, complete cds

<400> SEQUENCE: 5
gagttcaggt aatagtggag ttaggggcat acgttcaagc agaaagcata agcagaatct 60
gcaggaactg gagccaccag ggtacgagat atgtcctgaa gtcaagataa acacagagag 120
tacacttacc aaatcacagt aacaatttcg tttttaaccc tctcatagtt attacctagc 180
ttgatattat ttagaaaaaa ttgggacaag tgaaaatgtc ttggaaagtg gtactgctat 240
tggtattgct agctacccca acgggggggc tagaagaaag ttatctagag gagtcatgca 300
gtactgttac tagaggatac ctgagtgttt tgaggacagg atggtataca aatgtgttca 360
cacttgaggt tggagatgtg gaaaatctca catgtaccga cgggcccagc ttaataagaa 420
cagaacttga actgacaaaa aatgcacttg aggaactcaa gacagtatca gcagatcaat 480
tggcaaagga agctaggata atgtcaccaa gaaaagcccg gtttgttctg ggtgccatag 540
cattaggtgt ggcaactgct gctgctgtga cggctggtgt agcgatagcc aagacaatta 600
ggctagaagg agaagtggct gcaatcaagg gtgcgctcag gaaaacaaat gaggctgtat 660
ctacattagg aaatggcgtg agggtacttg caacagctgt gaatgatctc aaggacttta 720
taagtaaaaa attgacacct gcaataaaca ggaacaagtg tgacatctca gaccttaaga 780
tggcagtgag ctttggacaa tacaatcgga ggttcctcaa tgtggtaaga cagttttctg 840
acaatgcagg tattacgcct gcaatatctc tagatttaat gactgacgct gagcttgtaa 900
gagctgtaag caacatgccc acatcttcag gacagatcaa tctgatgctt gagaatcggg 960
caatggtcag aaggaaagga tttgggattt tgattggagt ttatggtagc tctgtggtct 1020
atatagtgca gcttcctatt ttcggtgtga tagatacacc gtgttggaag gtgaaggctg 1080
ctccattatg ttcagggaaa gacgggaatt atgcatgtct cttgcgagag gaccaaggtt 1140
ggtattgtca aaatgctgga tccacagttt attatccaaa tgaggaggac tgtgaagtaa 1200

-continued

```
gaagtgatca tgtgttttgt gacacagcag ctgggataaa tgtagcaaag gagtcagaag   1260

agtgcaacag gaatatctca acaacaaagt acccttgcaa ggtaagtaca gggcgtcacc   1320

caataagcat ggtggcctta tcaccactgg gtgctttggt agcctgttat gacggtatga   1380

gttgttccat tggaagcaac aaggttggaa taatcagacc tttggggaaa gggtgttcat   1440

acatcagcaa tcaagatgct gacactgtta caattgacaa cacagtgtac caattgagca   1500

aagttgaagg agaacaacac acaattaaag ggaagccagt atctagcaat tttgacccta   1560

tagagttccc tgaagatcag ttcaacatag ccctggatca ggtgtttgaa agtgttgaga   1620

agagtcagaa tctgatagac cagtcaaaca agatattgga tagcattgaa aaggggaatg   1680

caggatttgt catagtgata gtcctcattg tcctgctcat gctggcagca gttggtgtgg   1740

gtgtcttctt tgtggttaag aagagaaaag ctgctcccaa attcccaatg gaaatgaatg   1800

gtgtgaacaa caaaggattt atcccttaat tttagttact aaaaaattgg gacaagtgaa   1860
```

```
<210> SEQ ID NO 6
<211> LENGTH: 574
<212> TYPE: PRT
<213> ORGANISM: paramyxovirus
<220> FEATURE:
<223> OTHER INFORMATION: paramyxovirus F protein hRSV B

<400> SEQUENCE: 6

Met Glu Leu Leu Ile His Arg Leu Ser Ala Ile Phe Leu Thr Leu Ala
 1               5                  10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
```

-continued

```
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 7
<211> LENGTH: 574
<212> TYPE: PRT
<213> ORGANISM: paramyxovirus
<220> FEATURE:
<223> OTHER INFORMATION: paramyxovirus F protein hRSV A2

<400> SEQUENCE: 7

Met Glu Leu Leu Ile Leu Lys Ala Asn Ala Ile Thr Thr Ile Leu Thr
 1               5                  10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
```

-continued

```
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460
```

-continued

```
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 8
<211> LENGTH: 121
<212> TYPE: PRT
<213> ORGANISM: metapneumovirus
<220> FEATURE:
<223> OTHER INFORMATION: human metapneumovirus01-71 (partial sequence)

<400> SEQUENCE: 8

Leu Leu Ile Thr Pro Gln His Gly Leu Lys Glu Ser Tyr Leu Glu Glu
 1               5                  10                  15

Ser Cys Ser Thr Ile Thr Glu Gly Tyr Leu Ser Val Leu Arg Thr Gly
            20                  25                  30

Trp Tyr Thr Asn Val Phe Thr Leu Glu Val Gly Asp Val Glu Asn Leu
        35                  40                  45

Thr Cys Ala Asp Gly Pro Ser Leu Ile Lys Thr Glu Leu Asp Leu Thr
    50                  55                  60

Lys Ser Ala Leu Arg Glu Leu Arg Thr Val Ser Ala Asp Gln Leu Ala
65                  70                  75                  80

Arg Glu Glu Gln Ile Glu Asn Pro Arg Gln Ser Arg Phe Val Leu Gly
                85                  90                  95

Ala Ile Ala Leu Gly Val Ala Thr Ala Ala Ala Val Thr Ala Gly Val
            100                 105                 110

Ala Ile Ala Lys Thr Ile Arg Leu Glu
        115                 120


<210> SEQ ID NO 9
<211> LENGTH: 539
<212> TYPE: PRT
<213> ORGANISM: metapneumovirus
<220> FEATURE:
<223> OTHER INFORMATION: Human metapneumovirus isolate 00-1 matrix
      protein (M) and fusion protein (F) genes

<400> SEQUENCE: 9

Met Ser Trp Lys Val Val Ile Ile Phe Ser Leu Leu Ile Thr Pro Gln
 1               5                  10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60
```

-continued

```
Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Phe Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
```

-continued

```
                485                 490                 495

Leu Ile Ala Val Leu Gly Ser Thr Met Ile Leu Val Ser Val Phe Ile
            500                 505                 510

Ile Ile Lys Lys Thr Lys Arg Pro Thr Gly Ala Pro Pro Glu Leu Ser
        515                 520                 525

Gly Val Thr Asn Asn Gly Phe Ile Pro His Asn
    530                 535


<210> SEQ ID NO 10
<211> LENGTH: 532
<212> TYPE: PRT
<213> ORGANISM: Avian pneumovirus
<220> FEATURE:
<223> OTHER INFORMATION: Avian pneumovirus fusion protein gene, partial
      cds

<400> SEQUENCE: 10

Met Ser Trp Lys Val Val Leu Leu Leu Val Leu Leu Ala Thr Pro Thr
 1               5                  10                  15

Gly Gly Leu Glu Glu Ser Tyr Leu Glu Glu Ser Cys Ser Thr Val Thr
            20                  25                  30

Arg Gly Tyr Leu Ser Val Leu Arg Thr Gly Trp Tyr Thr Asn Val Phe
        35                  40                  45

Thr Leu Gly Val Gly Asp Val Lys Asn Leu Thr Cys Thr Asp Gly Pro
    50                  55                  60

Ser Leu Ile Arg Thr Glu Leu Glu Leu Thr Lys Asn Ala Leu Glu Glu
65                  70                  75                  80

Leu Lys Thr Val Ser Ala Asp Gln Leu Ala Lys Glu Ala Arg Ile Met
                85                  90                  95

Ser Pro Arg Lys Ala Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Gly Glu Val Ala Ala Ile Lys Gly Ala Leu Arg Lys Thr
    130                 135                 140

Asn Glu Ala Val Ser Thr Leu Gly Asn Gly Val Arg Val Leu Ala Thr
145                 150                 155                 160

Ala Val Asn Asp Leu Lys Asp Phe Ile Ser Lys Lys Leu Thr Pro Ala
                165                 170                 175

Ile Asn Arg Asn Lys Cys Asp Ile Ser Asp Leu Lys Met Ala Val Ser
            180                 185                 190

Phe Gly Gln Tyr Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Val Arg Ala Val Ser Asn Met Pro Thr Ser Ser Gly Gln
225                 230                 235                 240

Ile Asn Leu Met Leu Glu Asn Arg Ala Met Val Arg Arg Lys Gly Phe
                245                 250                 255

Gly Ile Leu Ile Gly Val Tyr Gly Ser Ser Val Val Tyr Ile Val Gln
            260                 265                 270

Leu Pro Ile Phe Gly Val Ile Asp Thr Pro Cys Trp Arg Val Lys Ala
        275                 280                 285

Ala Pro Leu Cys Ser Gly Lys Asp Gly Asn Tyr Ala Cys Leu Leu Arg
    290                 295                 300
```

-continued

```
Glu Asp Gln Gly Trp Tyr Cys Gln Asn Ala Gly Ser Thr Val Tyr Tyr
305                 310                 315                 320

Pro Asn Glu Glu Asp Cys Glu Val Arg Ser Asp His Val Phe Cys Asp
                325                 330                 335

Thr Ala Ala Gly Ile Asn Val Ala Lys Glu Ser Glu Glu Cys Asn Arg
            340                 345                 350

Asn Ile Ser Thr Thr Lys Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Asp Gly Met Ser Cys Ser Ile Gly Ser Asn Lys Val Gly Ile Ile
385                 390                 395                 400

Arg Pro Leu Gly Lys Gly Cys Ser Tyr Ile Ser Asn Gln Asp Ala Asp
                405                 410                 415

Thr Val Thr Ile Asp Asn Thr Val Tyr Gln Leu Ser Lys Val Glu Gly
            420                 425                 430

Glu Gln His Thr Ile Lys Gly Lys Pro Val Ser Ser Asn Phe Asp Pro
        435                 440                 445

Ile Glu Phe Pro Glu Asp Gln Phe Asn Val Ala Leu Asp Gln Val Phe
    450                 455                 460

Glu Ser Val Glu Lys Ser Gln Asn Leu Ile Asp Gln Ser Asn Lys Ile
465                 470                 475                 480

Leu Asp Ser Ile Glu Lys Gly Asn Ala Gly Phe Val Ile Val Ile Val
                485                 490                 495

Leu Ile Val Leu Leu Met Leu Ala Ala Val Gly Val Gly Val Phe Phe
            500                 505                 510

Val Val Lys Lys Arg Lys Ala Ala Pro Lys Phe Pro Met Glu Met Asn
        515                 520                 525

Gly Val Asn Asn
    530


<210> SEQ ID NO 11
<211> LENGTH: 537
<212> TYPE: PRT
<213> ORGANISM: Avian pneumovirus
<220> FEATURE:
<223> OTHER INFORMATION: Avian pneumovirus isolate 1b fusion protein
      mRNA, complete cds

<400> SEQUENCE: 11

Met Ser Trp Lys Val Val Leu Leu Leu Val Leu Leu Ala Thr Pro Thr
 1               5                  10                  15

Gly Gly Leu Glu Glu Ser Tyr Leu Glu Glu Ser Cys Ser Thr Val Thr
            20                  25                  30

Arg Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro
    50                  55                  60

Ser Leu Ile Arg Thr Glu Leu Glu Leu Thr Lys Asn Ala Leu Glu Glu
65                  70                  75                  80

Leu Lys Thr Val Ser Ala Asp Gln Leu Ala Lys Glu Ala Arg Ile Met
                85                  90                  95

Ser Pro Arg Lys Ala Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125
```

-continued

```
Arg Leu Glu Gly Glu Val Ala Ala Ile Lys Gly Ala Leu Arg Lys Thr
    130                 135                 140

Asn Glu Ala Val Ser Thr Leu Gly Asn Gly Val Arg Val Leu Ala Thr
145                 150                 155                 160

Ala Val Asn Asp Leu Lys Asp Phe Ile Ser Lys Lys Leu Thr Pro Ala
                165                 170                 175

Ile Asn Arg Asn Lys Cys Asp Ile Ser Asp Leu Lys Met Ala Val Ser
            180                 185                 190

Phe Gly Gln Tyr Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Val Arg Ala Val Ser Asn Met Pro Thr Ser Ser Gly Gln
225                 230                 235                 240

Ile Asn Leu Met Leu Glu Asn Arg Ala Met Val Arg Arg Lys Gly Phe
                245                 250                 255

Gly Ile Leu Ile Gly Val Tyr Gly Ser Ser Val Val Tyr Ile Val Gln
            260                 265                 270

Leu Pro Ile Phe Gly Val Ile Asp Thr Pro Cys Trp Lys Val Lys Ala
        275                 280                 285

Ala Pro Leu Cys Ser Gly Lys Asp Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Glu Asp Cys Glu Val Arg Ser Asp His Val Phe Cys Asp
                325                 330                 335

Thr Ala Ala Gly Ile Asn Val Ala Lys Glu Ser Glu Glu Cys Asn Arg
            340                 345                 350

Asn Ile Ser Thr Thr Lys Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Asp Gly Met Ser Cys Ser Ile Gly Ser Asn Lys Val Gly Ile Ile
385                 390                 395                 400

Arg Pro Leu Gly Lys Gly Cys Ser Tyr Ile Ser Asn Gln Asp Ala Asp
                405                 410                 415

Thr Val Thr Ile Asp Asn Thr Val Tyr Gln Leu Ser Lys Val Glu Gly
            420                 425                 430

Glu Gln His Thr Ile Lys Gly Lys Pro Val Ser Ser Asn Phe Asp Pro
        435                 440                 445

Ile Glu Phe Pro Glu Asp Gln Phe Asn Val Ala Leu Asp Gln Val Phe
    450                 455                 460

Glu Ser Val Glu Lys Ser Gln Asn Leu Ile Asp Gln Ser Asn Lys Ile
465                 470                 475                 480

Leu Asp Ser Ile Glu Lys Gly Asn Ala Gly Phe Val Ile Val Ile Val
                485                 490                 495

Leu Ile Val Leu Leu Met Leu Ala Ala Val Gly Val Gly Val Phe Phe
            500                 505                 510

Val Val Lys Lys Arg Lys Ala Ala Pro Lys Phe Pro Met Glu Met Asn
        515                 520                 525

Gly Val Asn Asn Lys Gly Phe Ile Pro
    530                 535
```

-continued

```
<210> SEQ ID NO 12
<211> LENGTH: 538
<212> TYPE: PRT
<213> ORGANISM: Turkey rhinotracheitis virus
<220> FEATURE:
<223> OTHER INFORMATION: Turkey rhinotracheitis virus gene for fusion
      protein (F1 and F2 subunits), complete cds

<400> SEQUENCE: 12

Met Asp Val Arg Ile Cys Leu Leu Leu Phe Leu Ile Ser Asn Pro Ser
 1               5                  10                  15

Ser Cys Ile Gln Glu Thr Tyr Asn Glu Glu Ser Cys Ser Thr Val Thr
            20                  25                  30

Arg Gly Tyr Lys Ser Val Leu Arg Thr Gly Trp Tyr Thr Asn Val Phe
        35                  40                  45

Asn Leu Glu Ile Gly Asn Val Glu Asn Ile Thr Cys Asn Asp Gly Pro
    50                  55                  60

Ser Leu Ile Asp Thr Glu Leu Val Leu Thr Lys Asn Ala Leu Arg Glu
65                  70                  75                  80

Leu Lys Thr Val Ser Ala Asp Gln Val Ala Lys Glu Ser Arg Leu Ser
                85                  90                  95

Ser Pro Arg Arg Arg Arg Phe Val Leu Gly Ala Ile Ala Leu Gly Val
            100                 105                 110

Ala Thr Ala Ala Ala Val Thr Ala Gly Val Ala Leu Ala Lys Thr Ile
        115                 120                 125

Arg Leu Glu Gly Glu Val Lys Ala Ile Lys Asn Ala Leu Arg Asn Thr
    130                 135                 140

Asn Glu Ala Val Ser Thr Leu Gly Asn Gly Val Arg Val Leu Ala Thr
145                 150                 155                 160

Ala Val Asn Asp Leu Lys Glu Phe Ile Ser Lys Lys Leu Thr Pro Ala
                165                 170                 175

Ile Asn Gln Asn Lys Cys Asn Ile Ala Asp Ile Lys Met Ala Ile Ser
            180                 185                 190

Phe Gly Gln Asn Asn Arg Arg Phe Leu Asn Val Val Arg Gln Phe Ser
        195                 200                 205

Asp Ser Ala Gly Ile Thr Ser Ala Val Ser Leu Asp Leu Met Thr Asp
    210                 215                 220

Asp Glu Leu Val Arg Ala Ile Asn Arg Met Pro Thr Ser Ser Gly Gln
225                 230                 235                 240

Ile Ser Leu Met Leu Asn Asn Arg Ala Met Val Arg Arg Lys Gly Phe
                245                 250                 255

Gly Ile Leu Ile Gly Val Tyr Asp Gly Thr Val Val Tyr Met Val Gln
            260                 265                 270

Leu Pro Ile Phe Gly Val Ile Glu Thr Pro Cys Trp Arg Val Val Ala
        275                 280                 285

Ala Pro Leu Cys Arg Lys Glu Lys Gly Asn Tyr Ala Cys Ile Leu Arg
    290                 295                 300

Glu Asp Gln Gly Trp Tyr Cys Thr Asn Ala Gly Ser Thr Ala Tyr Tyr
305                 310                 315                 320

Pro Asn Lys Asp Asp Cys Glu Val Arg Asp Asp Tyr Val Phe Cys Asp
                325                 330                 335

Thr Ala Ala Gly Ile Asn Val Ala Leu Glu Val Glu Gln Cys Asn Tyr
            340                 345                 350

Asn Ile Ser Thr Ser Lys Tyr Pro Cys Lys Val Ser Thr Gly Arg His
        355                 360                 365
```

-continued

Pro Val Ser Met Val Ala Leu Thr Pro Leu Gly Gly Leu Val Ser Cys
370 375 380

Tyr Glu Ser Val Ser Cys Ser Ile Gly Ser Asn Lys Val Gly Ile Ile
385 390 395 400

Lys Gln Leu Gly Lys Gly Cys Thr His Ile Pro Asn Asn Glu Ala Asp
405 410 415

Thr Ile Thr Ile Asp Asn Thr Val Tyr Gln Leu Ser Lys Val Val Gly
420 425 430

Glu Gln Arg Thr Ile Lys Gly Ala Pro Val Val Asn Asn Phe Asn Pro
435 440 445

Ile Leu Phe Pro Glu Asp Gln Phe Asn Val Ala Leu Asp Gln Val Phe
450 455 460

Glu Ser Ile Asp Arg Ser Gln Asp Leu Ile Asp Lys Ser Asn Asp Leu
465 470 475 480

Leu Gly Ala Asp Ala Lys Ser Lys Ala Gly Ile Ala Ile Ala Ile Val
485 490 495

Val Leu Val Ile Leu Gly Ile Phe Phe Leu Leu Ala Val Ile Tyr Tyr
500 505 510

Cys Ser Arg Val Arg Lys Thr Lys Pro Lys His Asp Tyr Pro Ala Thr
515 520 525

Thr Gly His Ser Ser Met Ala Tyr Val Ser
530 535

<210> SEQ ID NO 13
<211> LENGTH: 537
<212> TYPE: PRT
<213> ORGANISM: Avian penumovirus
<220> FEATURE:
<223> OTHER INFORMATION: Avian pneumovirus fusion glycoprotein (F) gene, complete cds

<400> SEQUENCE: 13

Met Ser Trp Lys Val Val Leu Leu Leu Val Leu Leu Ala Thr Pro Thr
1 5 10 15

Gly Gly Leu Glu Glu Ser Tyr Leu Glu Glu Ser Cys Ser Thr Val Thr
20 25 30

Arg Gly Tyr Leu Ser Val Leu Arg Thr Gly Trp Tyr Thr Asn Val Phe
35 40 45

Thr Leu Glu Val Gly Asp Val Glu Asn Leu Thr Cys Thr Asp Gly Pro
50 55 60

Ser Leu Ile Arg Thr Glu Leu Glu Leu Thr Lys Asn Ala Leu Glu Glu
65 70 75 80

Leu Lys Thr Val Ser Ala Asp Gln Leu Ala Lys Glu Ala Arg Ile Met
85 90 95

Ser Pro Arg Lys Ala Arg Phe Val Leu Gly Ala Ile Ala Leu Gly Val
100 105 110

Ala Thr Ala Ala Ala Val Thr Ala Gly Val Ala Ile Ala Lys Thr Ile
115 120 125

Arg Leu Glu Gly Glu Val Ala Ala Ile Lys Gly Ala Leu Arg Lys Thr
130 135 140

Asn Glu Ala Val Ser Thr Leu Gly Asn Gly Val Arg Val Leu Ala Thr
145 150 155 160

Ala Val Asn Asp Leu Lys Asp Phe Ile Ser Lys Lys Leu Thr Pro Ala
165 170 175

Ile Asn Arg Asn Lys Cys Asp Ile Ser Asp Leu Lys Met Ala Val Ser

-continued

```
            180                 185                 190

Phe Gly Gln Tyr Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Val Arg Ala Val Ser Asn Met Pro Thr Ser Ser Gly Gln
225                 230                 235                 240

Ile Asn Leu Met Leu Glu Asn Arg Ala Met Val Arg Arg Lys Gly Phe
                245                 250                 255

Gly Ile Leu Ile Gly Val Tyr Gly Ser Ser Val Val Tyr Ile Val Gln
            260                 265                 270

Leu Pro Ile Phe Gly Val Ile Asp Thr Pro Cys Trp Lys Val Lys Ala
        275                 280                 285

Ala Pro Leu Cys Ser Gly Lys Asp Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Glu Asp Cys Glu Val Arg Ser Asp His Val Phe Cys Asp
                325                 330                 335

Thr Ala Ala Gly Ile Asn Val Ala Lys Glu Ser Glu Glu Cys Asn Arg
            340                 345                 350

Asn Ile Ser Thr Thr Lys Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Asp Gly Met Ser Cys Ser Ile Gly Ser Asn Lys Val Gly Ile Ile
385                 390                 395                 400

Arg Pro Leu Gly Lys Gly Cys Ser Tyr Ile Ser Asn Gln Asp Ala Asp
                405                 410                 415

Thr Val Thr Ile Asp Asn Thr Val Tyr Gln Leu Ser Lys Val Glu Gly
            420                 425                 430

Glu Gln His Thr Ile Lys Gly Lys Pro Val Ser Ser Asn Phe Asp Pro
        435                 440                 445

Ile Glu Phe Pro Glu Asp Gln Phe Asn Ile Ala Leu Asp Gln Val Phe
    450                 455                 460

Glu Ser Val Glu Lys Ser Gln Asn Leu Ile Asp Gln Ser Asn Lys Ile
465                 470                 475                 480

Leu Asp Ser Ile Glu Lys Gly Asn Ala Gly Phe Val Ile Val Ile Val
                485                 490                 495

Leu Ile Val Leu Leu Met Leu Ala Ala Val Gly Val Gly Val Phe Phe
            500                 505                 510

Val Val Lys Lys Arg Lys Ala Ala Pro Lys Phe Pro Met Glu Met Asn
        515                 520                 525

Gly Val Asn Asn Lys Gly Phe Ile Pro
    530                 535
```

<210> SEQ ID NO 14
<211> LENGTH: 1193
<212> TYPE: DNA
<213> ORGANISM: rhinotracheitis virus
<220> FEATURE:
<221> NAME/KEY: CDS
<222> LOCATION: (16)...(1191)
<223> OTHER INFORMATION: Turkey rhinotracheitis virus (strain CVL14/1)
      attachment protien (G) mRNA, complete cds -continued

<400> SEQUENCE: 14
gggacaagta tctctatggg gtccaaacta tatatggctc agggcaccag tgcatatcaa 60
actgcagtgg ggttctggct ggacatcggg aggaggtaca tattggctat agtcctatca 120
gctttcgggc tgacctgcac agtcactatt gcactcactg ttagcgtcat agttgaacag 180
tcagtgttag aggagtgcag aaactacaat ggaggagata gagattggtg gtcaaccacc 240
caggagcagc caactactgc accaagtgcg actccagcag gaaattatgg aggattacaa 300
acggctcgaa caagaaagtc tgaaagctgt ttgcatgtgc aaatttctta tggtgatatg 360
tatagccgca gtgatactgt actgggtggt tttgattgta tgggcttatt ggttctttgc 420
aaatcaggac caatttgtca gcgagataat caagttgacc caacagccct ctgccattgc 480
agggtagatc tttcaagtgt ggactgctgc aaggtgaaca agattagcac taacagcagc 540
accacctctg agccccagaa gaccaacccg gcatggccta gccaagacaa cacagactcc 600
gatccaaatc cccaaggcat aaccaccagc acagccactc tgctctcaac aagtctgggc 660
ctcatgctca catcgaagac tgggacacac aaatcagggc ccccccaagc cttgccgggg 720
agcaacacca acggaaaaac aaccacagac cgagaaccag ggcccacaaa ccaaccaaat 780
tcaaccacca atgggcaaca caataaacac acccaacgaa tgacaccccc gccaagtcac 840
gacaacacaa gaaccatcct ccagcacaca acaccctggg aaaagacatt cagtacatac 900
aagcccacac actctccgac caacgaatca gatcaatccc tccccacaac tcaaaacagc 960
atcaactgtg aacattttga cccccaaggc aaggaaaaaa tctgctacag agtaggttct 1020
tacaactcca atattacaaa gcaatgcaga attgatgtgc ctttgtgttc cacttatagc 1080
acagtgtgca tgaaaacata ctataccgaa ccattcaact gttggaggcg tatctggcgt 1140
tgcttgtgtg atgacggagt tggtctggtt gagtggtgtt gcactagtta act 1193

<210> SEQ ID NO 15
<211> LENGTH: 1260
<212> TYPE: DNA
<213> ORGANISM: rhinotracheitis virus
<220> FEATURE:
<221> NAME/KEY: CDS
<222> LOCATION: (16)...(1260)
<223> OTHER INFORMATION: Turkey rhinotracheitis virus (strain 6574)
attachment protein (G), complete cds

<400> SEQUENCE: 15
gggacaagta tccagatggg gtcagagctc tacatcatag agggggtgag ctcatctgaa 60
atagtcctca agcaagtcct cagaaggagc caaaaaaatac tgttaggact ggtgttatca 120
gccttaggct tgacgctcac tagcactatt gttatatcta tttgtattag tgtagaacag 180
gtcaaattac gacagtgtgt ggacacttat tgggcggaaa atggatcctt acatccagga 240
cagtcaacag aaaatacttc aacaagaggt aagactacaa caaaagaccc tagaagatta 300
caggcgactg gagcaggaaa gtttgagagc tgtgggtatg tgcaagttgt tgatggtgat 360
atgcatgatc gcagttatgc tgtactgggt ggtgttgatt gtttgggctt attggctctt 420
tgtgaatcag gaccaatttg tcagggagat acttggtctg aagacggaaa cttctgccga 480 tgcactttttt cttcccatgg ggtgagttgc tgcaaaaaac ccaaaagcaa ggcaaccact 540
gcccagagga actccaaacc agctaacagc aaatcaactc ctccggtaca ttcagacagg 600
gccagcaaag aacataatcc ctcccaaggg gagcaacccc gcagggggcc aaccagcagc 660
aagacaacta ttgctagcac cccttcaaca gaggacactg ctaaaccaac gattagcaaa 720

-continued

```
cctaaactca ccatcaggcc ctcgcaaaga ggtccatccg gcagcacaaa agcagcctcc    780

agcaccccca gccacaagac caacaccaga ggcaccagca agacgaccga ccagagaccc    840

cgcaccggac ccactcccga aaggcccaga caaacccaca gcacagcaac tccgcccccc    900

acaaccccaa tccacaaggg ccgggcccca acccccaaac caacaacaga cctcaaggtc    960

aacccaaggg aaggcagcac aagcccaact gcaatacaga aaaacccaac cacacaaagt   1020

aatcttgttg actgcacact gtctgatcca gatgagccac aaaggatttg ttaccaggta   1080

ggaacttaca atcctagtca atcgggaacc tgcaacatag aggttccaaa atgttccact   1140

tatgggcatg cttgtatggc tacattatat gacaccccat tcaactgctg gcgcaggacc   1200

aggagatgca tctgtgattc cggaggggag ctgattgagt ggtgctgtac tagtcaataa   1260


<210> SEQ ID NO 16
<211> LENGTH: 391
<212> TYPE: PRT
<213> ORGANISM: Turkey rhinotracheitis virus
<220> FEATURE:
<223> OTHER INFORMATION: Turkey rhinotracheitis virus (strain CVL14/1)
      attachment protien (G) mRNA, complete cds

<400> SEQUENCE: 16

Met Gly Ser Lys Leu Tyr Met Ala Gln Gly Thr Ser Ala Tyr Gln Thr
 1               5                  10                  15

Ala Val Gly Phe Trp Leu Asp Ile Gly Arg Arg Tyr Ile Leu Ala Ile
            20                  25                  30

Val Leu Ser Ala Phe Gly Leu Thr Cys Thr Val Thr Ile Ala Leu Thr
        35                  40                  45

Val Ser Val Ile Val Glu Gln Ser Val Leu Glu Glu Cys Arg Asn Tyr
    50                  55                  60

Asn Gly Gly Asp Arg Asp Trp Trp Ser Thr Thr Gln Glu Gln Pro Thr
65                  70                  75                  80

Thr Ala Pro Ser Ala Thr Pro Ala Gly Asn Tyr Gly Gly Leu Gln Thr
                85                  90                  95

Ala Arg Thr Arg Lys Ser Glu Ser Cys Leu His Val Gln Ile Ser Tyr
            100                 105                 110

Gly Asp Met Tyr Ser Arg Ser Asp Thr Val Leu Gly Gly Phe Asp Cys
        115                 120                 125

Met Gly Leu Leu Val Leu Cys Lys Ser Gly Pro Ile Cys Gln Arg Asp
    130                 135                 140

Asn Gln Val Asp Pro Thr Ala Leu Cys His Cys Arg Val Asp Leu Ser
145                 150                 155                 160

Ser Val Asp Cys Cys Lys Val Asn Lys Ile Ser Thr Asn Ser Ser Thr
                165                 170                 175

Thr Ser Glu Pro Gln Lys Thr Asn Pro Ala Trp Pro Ser Gln Asp Asn
            180                 185                 190

Thr Asp Ser Asp Pro Asn Pro Gln Gly Ile Thr Thr Ser Thr Ala Thr
        195                 200                 205

Leu Leu Ser Thr Ser Leu Gly Leu Met Leu Thr Ser Lys Thr Gly Thr
    210                 215                 220

His Lys Ser Gly Pro Pro Gln Ala Leu Pro Gly Ser Asn Thr Asn Gly
225                 230                 235                 240

Lys Thr Thr Thr Asp Arg Glu Pro Gly Pro Thr Asn Gln Pro Asn Ser
                245                 250                 255

Thr Thr Asn Gly Gln His Asn Lys His Thr Gln Arg Met Thr Pro Pro
            260                 265                 270
```

-continued

```
Pro Ser His Asp Asn Thr Arg Thr Ile Leu Gln His Thr Thr Pro Trp
        275                 280                 285

Glu Lys Thr Phe Ser Thr Tyr Lys Pro Thr His Ser Pro Thr Asn Glu
    290                 295                 300

Ser Asp Gln Ser Leu Pro Thr Thr Gln Asn Ser Ile Asn Cys Glu His
305                 310                 315                 320

Phe Asp Pro Gln Gly Lys Glu Lys Ile Cys Tyr Arg Val Gly Ser Tyr
                325                 330                 335

Asn Ser Asn Ile Thr Lys Gln Cys Arg Ile Asp Val Pro Leu Cys Ser
            340                 345                 350

Thr Tyr Ser Thr Val Cys Met Lys Thr Tyr Tyr Thr Glu Pro Phe Asn
        355                 360                 365

Cys Trp Arg Arg Ile Trp Arg Cys Leu Cys Asp Asp Gly Val Gly Leu
    370                 375                 380

Val Glu Trp Cys Cys Thr Ser
385                 390


<210> SEQ ID NO 17
<211> LENGTH: 414
<212> TYPE: PRT
<213> ORGANISM: rhinotracheitis virus
<220> FEATURE:
<223> OTHER INFORMATION: Turkey rhinotracheitis virus (strain 6574)
      attachment protein (G), complete cds

<400> SEQUENCE: 17

Met Gly Ser Glu Leu Tyr Ile Ile Glu Gly Val Ser Ser Ser Glu Ile
 1               5                  10                  15

Val Leu Lys Gln Val Leu Arg Arg Ser Gln Lys Ile Leu Leu Gly Leu
            20                  25                  30

Val Leu Ser Ala Leu Gly Leu Thr Leu Thr Ser Thr Ile Val Ile Ser
        35                  40                  45

Ile Cys Ile Ser Val Glu Gln Val Lys Leu Arg Gln Cys Val Asp Thr
    50                  55                  60

Tyr Trp Ala Glu Asn Gly Ser Leu His Pro Gly Gln Ser Thr Glu Asn
65                  70                  75                  80

Thr Ser Thr Arg Gly Lys Thr Thr Thr Lys Asp Pro Arg Arg Leu Gln
                85                  90                  95

Ala Thr Gly Ala Gly Lys Phe Glu Ser Cys Gly Tyr Val Gln Val Val
            100                 105                 110

Asp Gly Asp Met His Asp Arg Ser Tyr Ala Val Leu Gly Gly Val Asp
        115                 120                 125

Cys Leu Gly Leu Leu Ala Leu Cys Glu Ser Gly Pro Ile Cys Gln Gly
    130                 135                 140

Asp Thr Trp Ser Glu Asp Gly Asn Phe Cys Arg Cys Thr Phe Ser Ser
145                 150                 155                 160

His Gly Val Ser Cys Cys Lys Lys Pro Lys Ser Lys Ala Thr Thr Ala
                165                 170                 175

Gln Arg Asn Ser Lys Pro Ala Asn Ser Lys Ser Thr Pro Pro Val His
            180                 185                 190

Ser Asp Arg Ala Ser Lys Glu His Asn Pro Ser Gln Gly Glu Gln Pro
        195                 200                 205

Arg Arg Gly Pro Thr Ser Ser Lys Thr Thr Ile Ala Ser Thr Pro Ser
    210                 215                 220

Thr Glu Asp Thr Ala Lys Pro Thr Ile Ser Lys Pro Lys Leu Thr Ile
```

-continued

```
225                 230                 235                 240

Arg Pro Ser Gln Arg Gly Pro Ser Gly Ser Thr Lys Ala Ala Ser Ser
                245                 250                 255

Thr Pro Ser His Lys Thr Asn Thr Arg Gly Thr Ser Lys Thr Thr Asp
            260                 265                 270

Gln Arg Pro Arg Thr Gly Pro Thr Pro Glu Arg Pro Arg Gln Thr His
        275                 280                 285

Ser Thr Ala Thr Pro Pro Pro Thr Thr Pro Ile His Lys Gly Arg Ala
    290                 295                 300

Pro Thr Pro Lys Pro Thr Thr Asp Leu Lys Val Asn Pro Arg Glu Gly
305                 310                 315                 320

Ser Thr Ser Pro Thr Ala Ile Gln Lys Asn Pro Thr Thr Gln Ser Asn
                325                 330                 335

Leu Val Asp Cys Thr Leu Ser Asp Pro Asp Glu Pro Gln Arg Ile Cys
            340                 345                 350

Tyr Gln Val Gly Thr Tyr Asn Pro Ser Gln Ser Gly Thr Cys Asn Ile
        355                 360                 365

Glu Val Pro Lys Cys Ser Thr Tyr Gly His Ala Cys Met Ala Thr Leu
    370                 375                 380

Tyr Asp Thr Pro Phe Asn Cys Trp Arg Arg Thr Arg Arg Cys Ile Cys
385                 390                 395                 400

Asp Ser Gly Gly Glu Leu Ile Glu Trp Cys Cys Thr Ser Gln
                405                 410


<210> SEQ ID NO 18
<211> LENGTH: 13294
<212> TYPE: DNA
<213> ORGANISM: human metapneumo virus
<220> FEATURE:
<221> NAME/KEY: misc_feature
<222> LOCATION: (0)...(0)
<223> OTHER INFORMATION: human MPV protein

<400> SEQUENCE: 18

acgcgaaaaa aacgcgtata aattaaattc caaacaaaac gggacaaata aaaatgtctc     60

ttcaagggat tcacctaagt gatctatcat ataaacatgc tatattaaaa gagtctcaat    120

acacaataaa aagagatgta ggcaccacaa ctgcagtgac accttcatca ttacaacaag    180

aaataacact tttgtgtggg gaaatacttt acactaaaca cactgattac aaatatgctg    240

ctgagatagg aatacaatat atttgcacag ctctaggatc agaaagagta caacagattt    300

tgagaaactc aggtagtgaa gttcaggtgg ttctaaccaa aacatactcc ttagggaaag    360

gcaaaaacag taaaggggaa gagctgcaga tgttagatat acatggagtg gaaaagagtt    420

ggatagaaga aatagacaaa gaggcaagaa agacaatggt aactttgctt aaggaatcat    480

caggtaacat cccacaaaac cagagacctt cagcaccaga cacaccaata attttattat    540

gtgtaggtgc cctaatattc actaaactag catcaacaat agaagttgga ttagagacta    600

cagttagaag agctaataga gtgctaagtg atgcactcaa aagataccca aggatagata    660

taccaaagat tgctagatct ttttatgaac tatttgaaca aaaagtgtac tacagaagtt    720

tattcattga gtacggaaaa gctttaggct catcttcaac aggaagcaaa gcagaaagtt    780

tgtttgtaaa tatatttatg caagcttatg gagctggcca aacactgcta aggtggggtg    840

tcattgccag atcatccaac aacataatgc tagggcatgt atctgtgcaa tctgaattga    900

agcaagttac agaggtttat gacttggtga gagaaatggg tcctgaatct gggcttttac    960
```

-continued atctaagaca aagtccaaag gcagggctgt tatcattggc caattgcccc aattttgcta 1020
gtgttgttct tggcaatgct tcaggtctag gcataatcgg aatgtacaga gggagagtac 1080
caaacacaga gctattttct gcagcagaaa gttatgccag aagcttaaaa gaaagcaata 1140
aaatcaactt ctcttcgtta gggcttacag atgaagaaaa agaagctgca gaacacttct 1200
taaacatgag tggtgacaat caagatgatt atgagtaatt aaaaaactgg gacaagtcaa 1260
aatgtcattc cctgaaggaa aggatattct gttcatgggt aatgaagcag caaaaatagc 1320
cgaagctttc cagaaatcac tgaaaaaatc aggtcacaag agaactcaat ctattgtagg 1380
ggaaaaagtt aacactatat cagaaactct agaactacct accatcagca aacctgcacg 1440
atcatctaca ctgctggaac caaaattggc atgggcagac aacagcggaa tcaccaaaat 1500
cacagaaaaa ccagcaacca aaacaacaga tcctgttgaa gaagaggaat tcaatgaaaa 1560
gaaagtgtta ccttccagtg atgggaagac tcctgcagag aaaaaatcaa agttttcaac 1620
cagtgtaaaa aagaaagttt cctttacatc aaatgaacca gggaaataca ccaaactaga 1680
gaaagatgcc ctagatttgc tctcagacaa tgaggaagaa gacgcagaat cctcaatcct 1740
aacttttgag gagaaagata catcatcact aagcattgaa gctagactag aatctataga 1800
agagaagttg agcatgatat taggactgct tcgtacactt aacattgcaa cagcaggacc 1860
aacagctgca cgagatggaa ttagggatgc aatgattggt ataagagaag agctaatagc 1920
agagataatt aaggaagcca agggaaaagc agctgaaatg atggaagaag agatgaatca 1980
aagatcaaaa ataggaaatg gcagtgtaaa actaaccgag aaggcaaaag agctcaacaa 2040
aattgttgaa gacgagagca caagcggtga atcagaagaa gaagaagaac caaaagaaac 2100
tcaggataac aatcaaggag aagatattta tcagttaatc atgtagttta ataaaaataa 2160
acaatgggac aagtcaagat ggagtcctat ctagtagaca cttatcaagg cattccatat 2220
acagctgctg ttcaagttga cctggtagaa aaagatttac tgccagcaag tttgacaata 2280
tggtttcctt tatttcaggc caacacacca ccagcagttc tgcttgatca gctaaaaacc 2340
ctgacaataa ccactctgta tgctgcatca cagaatggtc caatactcaa ggtaaatgca 2400
tctgcccaag gtgctgccat gtctgtactt cccaaaaaat tcgaggtaaa tgcaactgta 2460
gcacttgatg aatacagtaa acttgatttt gacaagctga cggtctgcga tgttaaaaca 2520
gtttatttga caactatgaa accgtacggg atggtgtcaa aatttgtgag ttcagccaaa 2580
tcagttggca aaaagacaca tgatctaatt gcactatgtg acttcatgga cctagagaaa 2640
aatatacctg tgacaatacc agcattcata aagtcagttt caatcaaaga gagtgaatca 2700
gccactgttg aagctgcaat aagcagcgaa gccgaccaag ccttgacaca agccaagatt 2760
gcgccctatg caggactaat tatgatcatg accatgaaca atccaaaagg tatattcaag 2820
aaactagggg ctggaacaca agtgatagta gagctggggg catatgttca ggctgagagc 2880
atcagtagga tctgcaagag ctggagtcac caaggaacaa gatacgtact aaaatccaga 2940
taaaaataac tgtcttaatc aataattgct tatataactc tagagattaa taagcttatt 3000
attatagtta tataaaaata aattagaatt agaagggcat caatagaaag cgggacaaat 3060
aaaaatgtct tggaaagtga tgatcatcat ttcgttactc ataacacccc agcacgggct 3120
aaaggagagt tatttggaag aatcatgtag tactataact gagggatacc tcagtgtttt 3180
aagaacaggc tggtacacta atgtcttcac attagaagtt ggtgatgttg aaaatcttac 3240
atgtactgat ggacctagct taatcaaaac agaacttgat ctaacaaaaa gtgctttaag 3300
ggaactcaaa acagtctctg ctgatcagtt ggcgagagag gagcaaattg aaaatcccag 3360

-continued acaatcaaga tttgtcttag gtgcgatagc tctcggagtt gctacagcag cagcagtcac 3420
agcaggcatt gcaatagcca aaaccataag gcttgagagt gaggtgaatg caattaaagg 3480
tgctctcaaa caaactaatg aagcagtatc cacattaggg aatggtgtgc gggtcctagc 3540
cactgcagtg agagagctaa aagaatttgt gagcaaaaac ctgactagtg caatcaacag 3600
gaacaaatgt gacattgctg atctgaagat ggctgtcagc ttcagtcaat tcaacagaag 3660
atttctaaat gttgtgcggc agttttcaga caatgcaggg ataacaccag caatatcatt 3720
ggacctgatg actgatgctg agttggccag agctgtatca tacatgccaa catctgcagg 3780
gcagataaaa ctgatgttgg agaaccgcgc aatggtaagg agaaaaggat ttggaatcct 3840
gataggggtc tacggaagct ctgtgattta catggttcaa ttgccgatct ttggtgtcat 3900
agatacacct tgttggatca tcaaggcagc tccctcttgc tcagaaaaaa acgggaatta 3960
tgcttgcctc ctaagagagg atcaagggtg gtattgtaaa aatgcaggat ctactgttta 4020
ctacccaaat gaaaaagact gcgaaacaag aggtgatcat gtttttgtg acacagcagc 4080
agggatcaat gttgctgagc aatcaagaga atgcaacatc aacatatcta ctaccaacta 4140
cccatgcaaa gtcagcacag gaagacaccc tataagcatg gttgcactat cacctctcgg 4200
tgctttggtg gcttgctata aaggggtaag ctgctcgatt ggcagcaatt gggttggaat 4260
catcaaacaa ttacccaaag gctgctcata cataaccaac caggatgcag acactgtaac 4320
aattgacaat accgtgtatc aactaagcaa agttgaaggt gaacagcatg taataaaagg 4380
gagaccagtt tcaagcagtt ttgatccaat caagtttcct gaggatcagt tcaatgttgc 4440
gcttgatcaa gtcttcgaaa gcattgagaa cagtcaggca ctagtggacc agtcaaacaa 4500
aattctaaac agtgcagaaa aaggaaacac tggtttcatt atcgtagtaa ttttggttgc 4560
tgttcttggt ctaaccatga tttcagtgag catcatcatc ataatcaaga aaacaaggaa 4620
gcccacagga gcacctccag agctgaatgg tgtcaccaac ggcggtttca taccacatag 4680
ttagttaatt aaaaaatggg acaaatcatc atgtctcgta aggctccatg caaatatgaa 4740
gtgcggggca aatgcaacag agggagtgat tgcaaattca atcacaatta ctggagttgg 4800
cctgatagat atttattgtt aagatcaaat tatctcttaa atcagctttt aagaaacaca 4860
gataaggctg atggtttgtc aataatatca ggagcaggta gagaagatag aactcaagac 4920
tttgttcttg gttctactaa tgtggttcaa gggtacattg atgacaacca aggaataacc 4980
aaggctgcag cttgctatag tctacacaac ataatcaagc aactacaaga aacagaagta 5040
agacaggcta gagacaacaa gctttctgat agcaaacatg tggcgctcca caacttgata 5100
ttatcctata tggagatgag caaaactcct gcatctctaa tcaacaacct aaagaaacta 5160
ccaagggaaa aactgaagaa attagcaaga ttaataattg atttatcagc aggaactgac 5220
aatgactctt catatgcctt gcaagacagt gaaagcacta atcaagtgca gtaaacatgg 5280
tcccaaattc attaccatag aggcagatga tatgatatgg actcacaaag aattaaaaga 5340
aacactgtct gatgggatag taaaatcaca caccaatatt tatagttgtt acttagaaaa 5400
tatagaaata atatatgtta aaacttactt aagttagtaa aaaataaaaa tagaatggga 5460
taaatgacaa tgaaaacatt agatgtcata aaaagtgatg gatcctcaga aacgtgtaat 5520
caactcaaaa aaataataaa aaaacactca ggtaaagtgc ttattgcact aaaactgata 5580
ttggccttac tgacattttt cacagcaaca atcactgtca actatataaa agtagaaaac 5640
aatttgcagg catgtcaacc aaaaaatgaa tcagacaaaa aggtcacaaa gccaaatacc 5700

-continued

```
acatcaacaa caatcagacc cacacccgat ccaactgtag tacatcattt gaaaaggctg   5760
attcagagac acaccaactc tgtcacaaaa gacagcgata cttgttggag aatacacaag   5820
aatcaacgta caaatataaa aatatacaag ttcttatgct ctgggttcac aaattcaaaa   5880
ggtacagatt gtgaggaacc aacagcccta tgcgacaaaa agttaaaaac catagtagaa   5940
aaacatagaa aagcagaatg tcactgtcta catacaaccg agtgggggtg ccttcatccc   6000
taaaataaca cggctttcaa cattaaaatc agaacaacct ccacccaggt ctatcaatac   6060
agtggtttag ccatttaaaa accgaatatt atctaggctg cacgacactt tgcaataata   6120
tgcaatagtc aatagttaaa ccactgctgc aaactcatcc ataatataat cactgagtaa   6180
tacaaaatca agaaaatggg acaagtggct atggaagtaa gagtggagaa cattcgagcg   6240
atagacatgt tcaaagcaaa gataaaaaac cgtataagaa gcagcaggtg ctatagaaat   6300
gctacactga tccttattgg actaacagcg ttaagcatgg cacttaatat tttcctgatc   6360
atcgatcatg caacattaag aaacatgatc aaaacagaaa actgtgctaa catgccgtcg   6420
gcagaaccaa gcaaaaagac cccaatgacc tccacagcag gcccaaacac caaacccaat   6480
ccacagcaag caacacagtg gaccacagag aactcaacat ccccagtagc aaccccagag   6540
ggccatccat acacagggac aactcaaaca tcagacacaa cagctcccca gcaaaccaca   6600
gacaaacaca cagcaccgct aaaatcaacc aatgaacaga tcacccagac aaccacagag   6660
aaaaagacaa tcagagcaac aacccaaaaa agggaaaaag gaaaagaaaa cacaaaccaa   6720
accacaagca cagctgcaac ccaaacaacc aacaccacca accaaatcag aaatgcaagt   6780
gagacaatca caacatccga cagacccaga actgacacca caacccaaag cagcgaacag   6840
acaacccggg caacagaccc aagctcccca ccacaccatg catagagagg tgcaaaactc   6900
aaatgagcac aacacacaaa catcccatcc aagtagttaa caaaaaacca caaaataacc   6960
ttgaaaacca aaaaaccaaa acataaaccc agacccagaa aaacatagac accatatgga   7020
aggttctagc atatgcacca atgagatggc atctgttcat gtatcaatag caccaccatc   7080
attcaaggaa taagaagagg cgaaaattta agggataaat gacaatggat cccttttgtg   7140
aatctactgt taatgtttat ctccctgatt catatctcaa aggagtaata tcttttagtg   7200
aaaccaatgc aattggatca tgtcttttga aaagaccct a tctaaaaaat gacaacactg   7260
ccaaagttgc tgtagaaaac cctgttgttg aacatgtgag gcttagaaat gcagtcatga   7320
ccaaaatgaa gatatcagat tataaagtgg ttgaaccagt taatatgcag catgaaataa   7380
tgaaaaatat acatagttgt gagcttacat tattaaaaca attcttaacg agaagcaaaa   7440
acattagctc tctaaaatta aatatgatat gtgattggtt acagttaaaa tccacttcag   7500
ataacacatc aattctcaat tttatagatg tggagttcat acccgtttgg gtaagcaatt   7560
ggttcagtaa ctggtataat ctcaataaat taatcttaga gtttagaaga gaagaagtaa   7620
taagaactgg ttcaatttta tgtagatcac taggcaagtt agtttttatt gtatcatctt   7680
atggatgtgt agtaaaaagc aacaaaagta aaagagtgag ctttttcacc tataaccaac   7740
tgttaacatg gaaagatgtg atgttaagta gattcaatgc aaacttttgt atatgggtaa   7800
gtaacaacct gaacaaaaat caagaaggac taggacttag aagcaatctg caaggtatgt   7860
taaccaataa attatatgaa actgttgatt acatgctaag cctatgctgc aatgaaggat   7920
tctctctggt gaaagagttt gaaggattta ttatgagtga aattctaaaa attactgagc   7980
atgctcagtt cagtactagg tttaggaata ctttattgaa tgggttaact gaacaattat   8040
cagtgttgaa agctaagaac agatctagag ttcttggaac tatattagaa aacaacaatt   8100
```

-continued

```
accctatgta cgaagtagta cttaaattat taggggacac cttgaaaagc ataaagttat   8160
taattaacaa gaatttagaa aatgctgcag aattatatta tatattcaga atttttggac   8220
accctatggt agatgagagg gaagcaatgg atgctgttaa attaaacaat gagattacaa   8280
aaattcttaa attagagagt ttaacagaac taagaggagc atttatacta agaattataa   8340
aagggtttgt agacaataat aaaagatggc ctaaaattaa gaatttaaaa gtgctcagca   8400
aaagatgggc tatgtatttc aaagctaaaa gttaccctag ccaacttgag ctaagtgtac   8460
aagatttttt agaacttgct gcagtacaat ttgagcagga attctctgta cctgaaaaaa   8520
ccaaccttga gatggtatta aatgataaag caatatcacc tccaaaaaag ctaatatggt   8580
ctgtatatcc aaaaaactac ctgcctgaaa ctataaaaaa tcaatattta gaagaggctt   8640
tcaatgcaag tgacagccaa agaacaagga gagtcttaga attttactta aaagattgta   8700
aatttgatca aaaagaactt aaacgttatg taattaaaca agagtatctg aatgacaaag   8760
accacattgt ctcgttaact gggaaggaaa gagaattaag tgtaggtagg atgtttgcaa   8820
tgcaaccagg aaaacaaaga cagatacaga tattagctga gaaacttcta gctgataata   8880
ttgtaccttt tttcccagaa actttaacaa agtatggtga cttagatctc caaagaatta   8940
tggaaataaa atcagaactt tcttccatta aaactagaaa gaatgatagc tacaacaatt   9000
atattgcaag ggcctctata gtaacagact taagtaagtt caatcaggcc tttagatatg   9060
aaaccacagc tatatgtgca gatgtagctg atgagttaca tgggacacaa agcttattct   9120
gttggttaca tcttattgtt cccatgacta caatgatatg tgcatacaga catgcaccac   9180
cagaaacaaa aggggaatat gatatagaca aaatacaaga gcaaagcgga ttatacagat   9240
atcatatggg agggattgaa gggtggtgcc agaagttatg gacaatggaa gcaatatcct   9300
tgttagatgt agtatctgtg aagactcgct gtcagatgac ctctctatta aacggagaca   9360
atcagtcaat agatgttagt aaaccagtaa aattgtctga aggtatagat gaagtaaaag   9420
cagactatag cttagcaatt agaatgctta aagaaataag agatgcttat aaaaacattg   9480
gtcataaact caaagaaggt gaaacatata tatcaaggga tctccaattt ataagtaagg   9540
tgattcaatc tgaaggagtc atgcatccta cccctataaa aaagatatta agagtaggtc   9600
cttggataaa tacaatacta gatgatatta aaaccagtgc agaatcaata ggaagtctat   9660
gtcaagaact agaattcaga ggggagagta tactagttag cttgatatta aggaatttct   9720
ggctgtataa cttgtacatg tatgagtcaa aacagcaccc attagctggg aagcaactgt   9780
tcaagcaatt gaacaaaaca ttaacatctg tgcagagatt ttttgaactg aagaaagaaa   9840
atgatgtggt tgacctatgg atgaatatac caatgcagtt tggaggggga gatccagtag   9900
tttttacag atctttttac agaaggactc ccgatttcct aactgaagca atcagccatg   9960
tggatttact gttaaaagtg tcaaacaata tcaaagatga gactaagata cgatttttca  10020
aagccttatt atctatagaa aagaatgaac gtgctacatt aacaacacta atgagagacc  10080
ctcaggcagt aggatcagaa cgacaagcta aggtaacaag tgatataaat agaacagcag  10140
ttaccagcat actgagtcta tctccgaatc agctcttctg tgatagtgct atacattata  10200
gtagaaatga ggaagaagtt gggatcattg cagacaacat aacacctgtc tatcctcatg  10260
ggctgagagt gctctatgaa tcactacctt ttcataaggc tgaaaaggtt gtcaatatga  10320
tatcaggcac aaagtctata actaatctat tacagagaac atctgctatc aatggtgaag  10380
atattgatag agcagtgtct atgatgttag agaacttagg gttgttatct agaatattgt  10440
```

-continued

```
cagtaataat taatagtata gaaataccaa tcaagtccaa tggcagattg atatgctgtc  10500
aaatttccaa gaccttgaga gaaaaatcat ggaacaatat ggaaatagta ggagtgacat  10560
ctcctagtat tgtgacatgt atggatgttg tgtatgcaac tagttctcat ttaaaaggaa  10620
taattattga aaaattcagt actgacaaga ccacaagagg tcagagggga ccaaaaagcc  10680
cctgggtagg atcaagcact caagagaaaa aattggttcc tgtttataat agacaaattc  10740
tttcaaaaca acaaaaagag caactggaag caatagggaa aatgaggtgg gtgtacaaag  10800
gaactccagg gctaagaaga ttgctcaaca agatttgcat aggaagctta ggtattagct  10860
ataaatgtgt gaaaccttta ttaccaagat tcatgagtgt aaacttctta cataggttat  10920
ctgttagtag tagacccatg gaattcccag cttctgttcc agcttacagg acaacaaatt  10980
accatttga cactagtcca atcaaccaag cattaagtga gaggttcggg aacgaagaca  11040
ttaatttagt gttccaaaat gcaatcagct gcggaattag tataatgagt gttgtagaac  11100
agttaactgg tagaagccca aaacaattag tcctaatccc tcaattagaa gagatagata  11160
ttatgcctcc tcctgtattt caaggaaaat tcaattataa actagttgat aagataacct  11220
ccgatcaaca catcttcagt cctgacaaaa tagacatatt aacactaggg aagatgctta  11280
tgcctaccat aaaaggtcaa aaaactgatc agttcttaaa taagagagaa aactattttc  11340
atggaaataa tttaattgaa tctttatctg cagcacttgc atgccactgg tgtgggatat  11400
taacagaaca gtgcatagaa aacaatatct ttaggaaaga ttggggtgat gggttcatct  11460
cagatcatgc cttcatggat ttcaaggtat ttctatgtgt atttaaaacc aaacttttat  11520
gtagttgggg atctcaagga aagaatgtaa aagatgaaga tataatagat gaatccattg  11580
acaaattatt aagaattgac aacacctttt ggagaatgtt cagcaaagtc atgtttgaat  11640
caaaagtcaa aaaaagaata atgttatatg atgtgaaatt cctatcatta gtaggttata  11700
taggatttaa aaactggttt atagaacagt taagagtggt agaattgcat gaggtacctt  11760
ggattgtcaa tgctgaagga gagttagttg aaattaaatc aatcaaaatt tatctgcagt  11820
taatagaaca aagtctatct ttgagaataa ctgtattgaa ttatacagac atggcacatg  11880
ctcttacacg attaattagg aaaaaattga tgtgtgataa tgcactcttt aatccaagtt  11940
catcaccaat gtttaatcta actcaggtta ttgatcccac aacacaacta gactattttc  12000
ctaggataat atttgagagg ttaaaaagtt atgataccag ttcagactac aacaaaggga  12060
agttaacaag gaattacatg acattattac catggcaaca cgtaaacagg tacaattttg  12120
tctttagttc tacaggttgt aaagtcagtt tgaagacatg catcgggaaa ttgataaagg  12180
atttaaatcc taaagttctt tactttattg gagaaggagc aggtaactgg atggcaagaa  12240
cagcatgtga atatcctgat ataaaatttg tatataggag tttaaaggat gaccttgatc  12300
accattaccc attagaatat caaagggtaa taggtgatct aaatagggtg atagatagtg  12360
gtgaaggatt atcaatggaa accacagatg caactcaaaa aactcattgg gacttgatac  12420
acagaataag taaagatgct ttattgataa cattgtgtga tgcagaattc aaaaacagag  12480
atgatttctt taagatggta atcctttgga gaaaacatgt attatcttgt agaatctgta  12540
cagcttatgg aacagatctt tacttatttg caaagtatca tgcggtggac tgcaatataa  12600
aattaccatt ttttgtaaga tctgtagcta cttttattat gcaaggaagc aaattatcag  12660
ggtcagaatg ttacatactt ttaacattag gtcatcacaa taatctaccc tgtcatggag  12720
aaatacaaaa ttccaaaatg agaatagcag tgtgtaatga tttctatgcc tcaaagaaac  12780
tggacaacaa atcaattgaa gcaaactgca aatctcttct atcaggattg agaataccta  12840
```

```
taaacaaaaa ggagttaaat agacaaaaga aattgttaac actacaaagt aaccattctt  12900

ctatagcaac agttggcggc agtaagatta tagaatccaa atggttaaag aataaagcaa  12960

gtacaataat tgattggtta gagcatattt tgaattctcc aaaaggtgaa ttaaactatg  13020

atttctttga agcattagag aacacatacc ccaatatgat caagcttata gataatttgg  13080

gaaatgcaga aataaagaaa ctaatcaagg tcactgggta tatgcttgtg agtaagaagt  13140

aataataatg ataatgatta accataatct cacacaactg agaaaataat cgtctaacag  13200

tttagttgat cattagttat ttaaaattat aaaatagtaa ctaactgata aaaaatcaga  13260

aattgaaatt gaatgtatac ggtttttttg ccgt                              13294
```

<210> SEQ ID NO 19
<211> LENGTH: 13350
<212> TYPE: DNA
<213> ORGANISM: human metapneumo virus

<400> SEQUENCE: 19

```
gtataaatta gattccaaaa aaatatggga caagtgaaaa tgtctcttca agggattcac     60

ctgagtgatt tatcatacaa gcatgctata ttaaaagagt ctcagtacac aataaaaaga    120

gatgtgggta caacaactgc agtgacaccc tcatcattgc aacaagaaat aacactgttg    180

tgtggagaaa ttctgtatgc taaacatgct gactacaaat atgctgcaga aataggaata    240

caatatatta gcacagcttt aggatcagag agagtgcagc agattctgag gaactcaggc    300

agtgaagtcc aagtggtctt aaccagaacg tactctctgg ggaaaattaa aaacaataaa    360

ggagaagatt tacagatgtt agacatacac ggggtagaga agagctgggt agaagagata    420

gacaaagaag caaggaaaac aatggcaacc ttgcttaagg aatcatcagg taatatccca    480

caaaatcaga ggccctcagc accagacaca cccataatct tattatgtgt aggtgcctta    540

atattcacta aactagcatc aaccatagaa gtgggactag agaccacagt cagaagggct    600

aaccgtgtac taagtgatgc actcaagaga taccctagaa tggacatacc aaagattgcc    660

agatccttct atgacttatt tgaacaaaaa gtgtatcaca gaagtttgtt cattgagtat    720

ggcaaagcat taggctcatc atctacaggc agcaaagcag aaagtctatt tgttaatata    780

ttcatgcaag cttatggggc cggtcaaaca atgctaaggt ggggggtcat tgccaggtca    840

tccaacaata taatgttagg acatgtatcc gtccaagctg agttaaaaca ggtcacagaa    900

gtctatgact tggtgcgaga aatgggccct gaatctggac ttctacattt aaggcaaagc    960

ccaaaagctg gactgttatc actagccaac tgtcccaact ttgcaagtgt tgttctcgga   1020

aatgcctcag gcttaggcat aatcggtatg tatcgaggga gagtaccaaa cacagaatta   1080

ttttcagcag ctgaaagtta tgccaaaagt ttgaaagaaa gcaataaaat aaatttctct   1140

tcattaggac ttacagatga agagaaagag gctgcagaac atttcttaaa tgtgagtgac   1200

gacagtcaaa atgattatga gtaattaaaa aagtgggaca agtcaaaatg tcattccctg   1260

aaggaaaaga tattcttttc atgggtaatg aagcagcaaa attagcagaa gctttccaga   1320

aatcattaag aaaaccaggt cataaaagat ctcaatctat tataggagaa aaagtgaata   1380

ctgtatcaga aacattggaa ttacctacta tcagtagacc tgcaaaacca accataccgt   1440

cagaaccaaa gttagcatgg acagataaag gtggggcaac caaaactgaa ataaagcaag   1500

caatcaaagt catggatccc attgaagaag aagagtctac cgagaagaag gtgctaccct   1560

ccagtgatgg gaaaacccct gcagaaaaga aactgaaacc atcaactaac accaaaaaga   1620
```

-continued

```
aggtttcatt tacaccaaat gaaccaggga aatatacaaa gttggaaaaa gatgctctag   1680
atttgctctc agataatgaa gaagaagatg cagaatcttc aatcttaacc tttgaagaaa   1740
gagatacttc atcattaagc attgaggcca gattggaatc aatagaggag aaattaagca   1800
tgatattagg gctattaaga acactcaaca ttgctacagc aggacccaca gcagcaagag   1860
atgggatcag agatgcaatg attggcgtaa gagaggaatt aatagcagac ataataaagg   1920
aagctaaagg gaaagcagca gaaatgatgg aagaggaaat gagtcaacga tcaaaaatag   1980
gaaatggtag tgtaaaatta acagaaaaag caaaagagct caacaaaatt gttgaagatg   2040
aaagcacaag tggagaatcc gaagaagaag aagaaccaaa agacacacaa gacaatagtc   2100
aagaagatga catttaccag ttaattatgt agtttaataa aaataaacaa tgggacaagt   2160
aaaaatggag tcctacctag tagacaccta tcaaggcatt ccttacacag cagctgttca   2220
agttgatcta atagaaaagg acctgttacc tgcaagccta acaatatggt tccctttgtt   2280
tcaggccaac acaccaccag cagtgctgct cgatcagcta aaaaccctga caataaccac   2340
tctgtatgct gcatcacaaa atggtccaat actcaaagtg aatgcatcag cccaaggtgc   2400
agcaatgtct gtacttccca aaaaatttga agtcaatgcg actgtagcac tcgatgaata   2460
tagcaaactg gaatttgaca aactcacagt ctgtgaagta aaaacagttt acttaacaac   2520
catgaaacca tacgggatgg tatcaaaatt tgtgagctca gccaaatcag ttggcaaaaa   2580
aacacatgat ctaatcgcac tatgtgattt tatggatcta gaaaagaaca cacctgttac   2640
aataccagca ttcatcaaat cagtttcaat caaagagagt gagtcagcta ctgttgaagc   2700
tgctataagc agtgaagcag accaagctct aacacaggcc aaaattgcac cttatgcggg   2760
attaattatg atcatgacta tgaacaatcc caaaggcata ttcaaaaagc ttggagctgg   2820
gactcaagtc atagtagaac taggagcata tgtccaggct gaaagcataa gcaaaatatg   2880
caagacttgg agccatcaag ggacaagata tgtcttgaag tccagataac aaccaagcac   2940
cttggccaag agctactaac cctatctcat agatcataaa gtcaccattc tagttatata   3000
aaaatcaagt tagaacaaga attaaatcaa tcaagaacgg gacaaataaa aatgtcttgg   3060
aaagtggtga tcattttttc attgttaata acacctcaac acggtcttaa agagagctac   3120
ttagaagagt catgtagcac tataactgaa ggatatctca gtgttctgag gacaggttgg   3180
tacaccaatg tttttacact ggaggtaggc gatgtagaga accttacatg tgccgatgga   3240
cccagcttaa taaaaacaga attagacctg accaaaagtg cactaagaga gctcagaaca   3300
gtttctgctg atcaactggc aagagaggag caaattgaaa atcccagaca atctagattc   3360
gttctaggag caatagcact cggtgttgca actgcagctg cagttacagc aggtgttgca   3420
attgccaaaa ccatccggct tgaaagtgaa gtaacagcaa ttaagaatgc cctcaaaaag   3480
accaatgaag cagtatctac attggggaat ggagttcgtg tgttggcaac tgcagtgaga   3540
gagctgaaag attttgtgag caagaatcta acacgtgcaa tcaacaaaaa caagtgcgac   3600
attgctgacc tgaaaatggc cgttagcttc agtcaattca acagaaggtt cctaaatgtt   3660
gtgcggcaat tttcagacaa cgctggaata acaccagcaa tatctttgga cttaatgaca   3720
gatgctgaac tagccagagc tgtttccaac atgccaacat ctgcaggaca aataaaactg   3780
atgttggaga accgtgcaat ggtaagaaga aaagggttcg gattcctgat aggagtttac   3840
ggaagctccg taatttacat ggtgcaactg ccaatctttg ggttatagac acgccttgc    3900
tggatagtaa aagcagcccc ttcttgttca ggaaaaaagg gaaactatgc ttgcctctta   3960
agagaagacc aaggatggta ttgtcaaaat gcagggtcaa ctgtttacta cccaaatgaa   4020
```

-continued

```
aaagactgtg aaacaagagg agaccatgtc ttttgcgaca cagcagcagg aatcaatgtt   4080
gctgagcagt caaaggagtg caacataaac atatctacta ctaattaccc atgcaaagtt   4140
agcacaggaa gacatcctat cagtatggtt gcactatctc ctcttggggc tttggttgct   4200
tgctacaagg gagtgagctg ttccattggc agcaacagag tagggatcat caagcaactg   4260
aacaaaggct gctcttatat aaccaaccaa gacgcagaca cagtgacaat agacaacact   4320
gtataccagc taagcaaagt tgaaggcgaa cagcatgtta taaaaggaag gccagtgtca   4380
agcagctttg acccagtcaa gtttcctgaa gatcaattca atgttgcact tgaccaagtt   4440
ttcgagagca ttgagaacag tcaggccttg gtggatcaat caaacagaat cctaagcagt   4500
gcagagaaag gaaacactgg cttcatcatt gtaataattc taattgctgt ccttggctct   4560
accatgatcc tagtgagtgt ttttatcata ataaagaaaa caaagaaacc cacaggagca   4620
cctccagagc tgagtggtgt cacaaacaat ggcttcatac cacataatta gttaattaaa   4680
aataaagtaa attaaaataa attaaaatta aaaataaaaa tttgggacaa atcataatgt   4740
ctcgcaaggc tccgtgcaaa tatgaagtgc ggggcaaatg caatagagga agtgagtgca   4800
agtttaacca caattactgg agttggccag atagatactt attaataaga tcaaattatt   4860
tattaaatca acttttaagg aacactgata gagctgatgg cttatcaata atatcaggag   4920
caggcagaga agataggaca caagattttg tcctaggttc caccaatgtg gttcaaggtt   4980
atattgatga taaccaaagc ataacaaaag ctgcagcctg ttacagtcta cataatataa   5040
tcaaacaact acaagaagtt gaagttaggc aggctagaga taacaaacta tctgacagca   5100
aacatgtagc acttcacaac ttagtcctat cttatatgga gatgagcaaa actcctgcat   5160
ctttaatcaa caatctcaag agactgccga gagagaaact gaaaaaatta gcaaagctca   5220
taattgactt atcagcaggt gctgaaaatg actcttcata tgccttgcaa gacagtgaaa   5280
gcactaatca agtgcagtga gcatggtcca gttttcatta ctatagaggt tgatgacatg   5340
atatggactc acaaggactt aaaagaagct ttatctgatg ggatagtgaa gtctcatact   5400
aacatttaca attgttattt agaaaacata gaaattatat atgtcaaggc ttacttaagt   5460
tagtaaaaac acatcagagt gggataaatg acaatgataa cattagatgt cattaaaagt   5520
gatgggtctt caaaaacatg tactcacctc aaaaaaataa ttaaagacca ctctggtaaa   5580
gtgcttattg tacttaagtt aatattagct ttactaacat ttctcacagt aacaatcacc   5640
atcaattata taaaagtgga aaacaatctg caaatatgcc agtcaaaaac tgaatcagac   5700
aaaaaggact catcatcaaa taccacatca gtcacaacca agactactct aaatcatgat   5760
atcacacagt attttaaaag tttgattcaa aggtatacaa actctgcaat aaacagtgac   5820
acatgctgga aaataaacag aaatcaatgc acaaatataa caacatacaa atttttatgt   5880
tttaaatctg aagacacaaa aaccaacaat tgtgataaac tgacagattt atgcagaaac   5940
aaaccaaaac cagcagttgg agtgtatcac atagtagaat gccattgtat atacacagtt   6000
aaatggaagt gctatcatta cccaaccgat gaaacccaat cctaaatgtt aacaccagat   6060
taggatccat ccaagtctgt tagttcaaca atttagttat ttaaaaatat tttgaaaaca   6120
agtaagtttc tatgatactt cataataata agtaataatt aattgcttaa tcatcatcac   6180
aacattattc gaaaccataa ctattcaatt taaaaagtaa aaaacaataa catgggacaa   6240
gtagttatgg aggtgaaagt ggagaacatt cgaacaatag atatgctcaa agcaagagta   6300
aaaaatcgtg tggcacgcag caaatgcttt aaaaatgcct ctttggtcct cataggaata   6360
```

-continued

```
actacattga gtattgccct caatatctat ctgatcataa actataaaat gcaaaaaaac   6420
acatctgaat cagaacatca caccagctca tcacccatgg aatccagcag agaaactcca   6480
acggtcccca cagacaactc agacaccaac tcaagcccac agcatccaac tcaacagtcc   6540
acagaaggct ccacactcta ctttgcagcc tcagcaagct caccagagac agaaccaaca   6600
tcaacaccag atacaacaaa ccgcccgccc ttcgtcgaca cacacacaac accaccaagc   6660
gcaagcagaa caaagacaag tccggcagtc cacacaaaaa acaacccaag gacaagctct   6720
agaacacatt ctccaccacg ggcaacgaca aggacggcac gcagaaccac cactctccgc   6780
acaagcagca caagaaagag accgtccaca gcatcagtcc aacctgacat cagcgcaaca   6840
acccacaaaa acgaagaagc aagtccagcg agcccacaaa catctgcaag cacaacaaga   6900
atacaaagga aaagcgtgga ggccaacaca tcaacaacat acaaccaaac tagttaacaa   6960
aaaatacaaa ataactctaa gataaaccat gcagacacca acaatggaga agccaaaaga   7020
caattcacaa tctccccaaa aaggcaacaa caccatatta gctctgccca aatctccctg   7080
gaaaaaacac tcgcccatat accaaaaata ccacaaccac cccaagaaaa aaactgggca   7140
aaacaacacc caagagacaa ataacaatgg atcctctcaa tgaatccact gttaatgtct   7200
atcttcctga ctcatatctt aaaggagtga tttcctttag tgagactaat gcaattggtt   7260
catgtctctt aaaaagacct tacctaaaaa atgacaacac tgcaaaagtt gccatagaga   7320
atcctgttat cgagcatgtt agactcaaaa atgcagtcaa ttctaagatg aaaatatcag   7380
attacaagat agtagagcca gtaaacatgc aacatgaaat tatgaagaat gtacacagtt   7440
gtgagctcac attattaaaa cagtttttaa caaggagtaa aaatattagc actctcaaat   7500
taaatatgat atgtgattgg ctgcagttaa agtctacatc agatgatacc tcaatcctaa   7560
gttttataga tgtagaattt atacctagct gggtaagcaa ttggtttagt aattggtaca   7620
atctcaacaa gttgattctg gaattcagga aagaagaagt aataagaact ggttcaatct   7680
tgtgtaggtc attgggtaaa ttagtttttg ttgtatcatc atatggatgt atagtcaaga   7740
gcaacaaaag caaaagagtg agcttcttca catacaatca actgttaaca tggaaagatg   7800
tgatgttaag tagattcaat gcaaattttt gtatatgggt aagcaacagt ctgaatgaaa   7860
atcaagaagg gctagggttg agaagtaatc tgcaaggcat attaactaat aagctatatg   7920
aaactgtaga ttatatgctt agtttatgtt gcaatgaagg tttctcactt gtgaaagagt   7980
tcgaaggctt tattatgagt gaaattctta ggattactga acatgctcaa ttcagtacta   8040
gatttagaaa tactttatta aatggattaa ctgatcaatt aacaaaatta aaaaataaaa   8100
acagactcag agttcatggt accgtgttag aaaataatga ttatccaatg tacgaagttg   8160
tacttaagtt attaggagat actttgagat gtattaaatt attaatcaat aaaaacttag   8220
agaatgctgc tgaattatac tatatattta gaatattcgg tcacccaatg gtagatgaaa   8280
gagatgcaat ggatgctgtc aaattaaaca atgaaatcac aaaaatcctt aggtgggaga   8340
gcttgacaga actaagaggg gcattcatat taaggattat caaaggattt gtagacaaca   8400
acaaaagatg gcccaaaatt aaaaacttaa aagtgcttag taagagatgg actatgtact   8460
tcaaagcaaa aagttacccc agtcaacttg aattaagcga acaagatttt ttagagcttg   8520
ctgcaataca gtttgaacaa gagttttctg tccctgaaaa aaccaacctt gagatggtat   8580
taaatgataa agctatatca cctcctaaaa gattaatatg gtctgtgtat ccaaaaaatt   8640
acttacctga gaaaataaaa aatcgatatc tagaagagac tttcaatgca agtgatagtc   8700
tcaaaacaag aagagtacta gagtactatt tgaaagataa taaattcgac caaaaagaac   8760
```

-continued

```
ttaaaagtta tgttgttaaa caagaatatt taaatgataa ggatcatatt gtctcgctaa   8820
ctggaaaaga aagagaatta agtgtaggta gaatgtttgc tatgcaacca ggaaaacagc   8880
gacaaataca aatattggct gaaaaattgt tagctgataa tattgtacct tttttcccag   8940
aaaccttaac aaagtatggt gatctagatc ttcagagaat aatggaaatc aaatcggaac   9000
tttcttctat taaaactaga agaaatgata gttataataa ttacattgca agagcatcca   9060
tagtaacaga tttaagtaag ttcaaccaag cctttaggta tgaaactaca gcgatctgtg   9120
cggatgtagc agatgaacta catggaacac aaagcctatt ctgttggtta catcttatcg   9180
tccctatgac aacaatgata tgtgcctata gacatgcacc accagaaaca aaaggtgaat   9240
atgatataga taagatagaa gagcaaagtg gtttatatag atatcatatg ggtggtattg   9300
aaggatggtg tcaaaaactc tggacaatgg aagctatatc tctattagat gttgtatctg   9360
taaaaacacg atgtcaaatg acatctttat taaacggtga caaccaatca atagatgtaa   9420
gtaaaccagt taagttatct gagggtttag atgaagtgaa agcagattat agcttggctg   9480
taaaaatgtt aaaagaaata agagatgcat acagaaatat aggccataaa cttaaagaag   9540
gggaaacata tatatcaaga gatcttcagt ttataagtaa ggtgattcaa tctgaaggag   9600
taatgcatcc taccccctata aaaaagatct taagagtggg accatggata aacacaatat   9660
tagatgacat taaaaccagt gcagagtcaa tagggagtct atgtcaggaa ttagaattta   9720
ggggggaaag cataatagtt agtctgatat taaggaattt ttggctgtat aatttataca   9780
tgcatgaatc aaagcaacac cccctagcag ggaagcagtt attcaaacaa ctaaataaaa   9840
cattaacatc agtgcagaga ttttttgaaa taaaaaagga aaatgaagta gtagatctat   9900
ggatgaacat accaatgcag tttggaggag gagatccagt agtcttctat agatctttct   9960
atagaaggac ccctgatttt ttaactgaag caatcagtca tgtggatatt ctgttaagaa  10020
tatcagccaa cataagaaat gaagcgaaaa taagtttctt caaagcctta ctgtcaatag  10080
aaaaaaatga acgtgctaca ctgacaacac taatgagaga tcctcaagct gttggctcag  10140
agcgacaagc aaaagtaaca agtgatatca atagaacagc agttaccagc atcttaagtc  10200
tttctccaaa tcaacttttc agcgatagtg ctatacacta cagtagaaat gaagaagagg  10260
tcggaatcat tgctgacaac ataacacctg tttatcctca tggactgaga gttttgtatg  10320
aatcattacc ttttcataaa gctgaaaaag ttgtgaatat gatatcagga acgaaatcca  10380
taaccaactt attacagaga acatctgcta ttaatggtga agatattgac agagctgtat  10440
ccatgatgct ggagaaccta ggattattat ctagaatatt gtcagtagtt gttgatagta  10500
tagaaattcc aaccaaatct aatggtaggc tgatatgttg tcagatatct agaaccctaa  10560
gggagacatc atggaataat atggaaatag ttggagtaac atcccctagc atcactacat  10620
gcatggatgt catatatgca actagctctc atttgaaagg gataatcatt gaaaagttca  10680
gcactgacag aactacaaga ggtcaaagag gtccaaagag cccttgggta gggtcgagca  10740
ctcaagagaa aaaattagtt cctgtttata acagacaaat tctttcaaaa caacaaagag  10800
aacagctaga agcaattgga aaaatgagat gggtatataa agggacacca ggtttaagac  10860
gattactcaa taagatttgt cttggaagtt taggcattag ttacaaatgt gtaaaacctt  10920
tattacctag gtttatgagt gtaaatttcc tacacaggtt atctgtcagt agtagaccta  10980
tggaattccc agcatcagtt ccagcttata gaacaacaaa ttaccatttt gacactagtc  11040
ctattaatca agcactaagt gagagatttg ggaatgaaga tattaatttg gtcttccaaa  11100
```

-continued

```
atgcaatcag ctgtggaatt agcataatga gtgtagtaga acaattaact ggtaggagtc  11160
caaaacagtt agttttaata cctcaattag aagaaataga cattatgcca ccaccagtgt  11220
ttcaagggaa attcaattat aagctagtag ataagataac ttctgatcaa catatcttca  11280
gtccagacaa aatagatatg ttaacactgg ggaaaatgct catgcccact ataaaaggtc  11340
agaaaacaga tcagttcctg aacaagagag agaattattt ccatgggaat aatcttattg  11400
agtctttgtc agcagcgtta gcatgtcatt ggtgtgggat attaacagag caatgtatag  11460
aaaataatat tttcaagaaa gactggggtg acgggttcat atcggatcat gcttttatgg  11520
acttcaaaat attcctatgt gtctttaaaa ctaaactttt atgtagttgg gggtcccaag  11580
ggaaaaacat taaagatgaa gatatagtag atgaatcaat agataaactg ttaaggattg  11640
ataatacttt ttggagaatg ttcagcaagg ttatgtttga atcaaaggtt aagaaaagga  11700
taatgttata tgatgtaaaa tttctatcat tagtaggtta tatagggttt aagaattggt  11760
ttatagaaca gttgagatca gctgagttgc atgaggtacc ttggattgtc aatgccgaag  11820
gtgatctggt tgagatcaag tcaattaaaa tctatttgca actgatagag caaagtttat  11880
ttttaagaat aactgttttg aactatacag atatggcaca tgctctcaca agattaatca  11940
gaaagaagtt gatgtgtgat aatgcactat taactccgat tccatcccca atggttaatt  12000
taactcaagt tattgatcct acagaacaat tagcttattt ccctaagata acatttgaaa  12060
ggctaaaaaa ttatgacact agttcaaatt atgctaaagg aaagctaaca aggaattaca  12120
tgatactgtt gccatggcaa catgttaata gatataactt tgtctttagt tctactggat  12180
gtaaagttag tctaaaaaca tgcattggaa aacttatgaa agatctaaac cctaaagttc  12240
tgtactttat tggagaaggg gcaggaaatt ggatggccag aacagcatgt gaatatcctg  12300
acatcaaatt tgtatacaga agtttaaaag atgaccttga tcatcattat cctttggaat  12360
accagagagt tataggagaa ttaagcagga taatagatag cggtgaaggg ctttcaatgg  12420
aaacaacaga tgcaactcaa aaaactcatt gggatttgat acacagagta agcaaagatg  12480
ctttattaat aactttatgt gatgcagaat ttaaggacag agatgatttt tttaagatgg  12540
taattctatg gaggaaacat gtattatcat gcagaatttg cactacttat gggacagacc  12600
tctatttatt cgcaaagtat catgctaaag actgcaatgt aaaattacct ttttttgtga  12660
gatcagtagc cacctttatt atgcaaggta gtaaactgtc aggctcagaa tgctacatac  12720
tcttaacact aggccaccac aacaatttac cctgccatgg agaaatacaa aattctaaga  12780
tgaaaatagc agtgtgtaat gatttttatg ctgcaaaaaa acttgacaat aaatctattg  12840
aagccaactg taaatcactt ttatcagggc taagaatacc gataaataag aaagaattaa  12900
atagacagag aaggttatta acactacaaa gcaaccattc ttctgtagca acagttggag  12960
gtagcaaggt catagagtct aaatggttaa caaacaaggc aaacacaata attgattggt  13020
tagaacatat tttaaattct ccaaaaggtg aattaaatta tgattttttt gaagcattag  13080
aaaatactta ccctaatatg attaaactaa tagataatct agggaatgca gagataaaaa  13140
aactgatcaa agtaactgga tatatgcttg taagtaaaaa atgaaaaatg ataaaaatga  13200
taaaataggt gacaacttca tactattcca aagtaatcat ttgattatgc aattatgtaa  13260
tagttaatta aaaactaaaa atcaaaagtt agaaactaac aactgtcatt aagtttatta  13320
aaaataagaa attataattg gatgtatacg                                    13350
```

<210> SEQ ID NO 20
<211> LENGTH: 13215

-continued

<212> TYPE: DNA
<213> ORGANISM: human metapneumo virus

<400> SEQUENCE: 20
acgcgaaaaa aacgcgtata aattaagtta caaaaaacca tgggacaagt gaaaatgtct 60
cttcaaggga ttcacctgag tgatctatca tacaagcatg ctatattaaa agagtctcag 120
tatacaataa agagagatgt aggcacaaca accgcagtga caccctcatc attgcaacaa 180
gaaataacac tattgtgtgg agaaattcta tatgctaagc atgctgatta caaatatgct 240
gcagaaatag gaatacaata tattagcaca gctctaggat cagagagagt acagcagatt 300
ctaagaaact caggtagtga agtccaagtg gttttaacca gaacgtactc cttggggaaa 360
gttaaaaaca acaaaggaga agatttacag atgttagaca tacacggagt agagaaaagc 420
tgggtggaag agatagacaa agaagcaaga aaaacaatgg caactttgct taaagaatca 480
tcaggcaata ttccacaaaa tcagaggcct tcagcaccag acacacccat aatcttatta 540
tgtgtaggtg ccttaatatt taccaaacta gcatcaacta tagaagtggg attagagacc 600
acagtcagaa gagctaaccg tgtactaagt gatgcactca aaagataccc taggatggac 660
ataccaaaaa tcgctagatc tttctatgac ttatttgaac aaaaagtgta ttacagaagt 720
ttgttcattg agtatggcaa agcattaggc tcatcctcta caggcagcaa agcagaaagt 780
ttattcgtta atatattcat gcaagcttac ggtgctggtc aaacaatgct gaggtgggga 840
gtcattgcca ggtcatctaa caatataatg ttaggacatg tatctgttca agctgagtta 900
aaacaagtca cagaagtcta tgacctggtg cgagaaatgg gccctgaatc tgggctccta 960
catttaaggc aaagcccaaa agctggactg ttatcactag ccaattgtcc caactttgct 1020
agtgttgttc tcggcaatgc ctcaggctta ggcataatag gtatgtatcg cgggagagtg 1080
ccaaacacag aactattttc agcagcagaa agctatgcca agagtttgaa agaaagcaat 1140
aaaattaact ttcttcatt aggactcaca gatgaagaaa aagaggctgc agaacacttc 1200
ctaaatgtga gtgacgacag tcaaaatgat tatgagtaat taaaaaaatg ggacaagtca 1260
aaatgtcatt ccctgaagga aaagatattc ttttcatggg taatgaagca gcaaaattgg 1320
cagaagcttt tcaaaaatca ttaagaaaac ctaatcataa aagatctcaa tctattatag 1380
gagaaaaagt gaacactgta tctgaaacat tggaattacc tactatcagt agacctacca 1440
aaccgaccat attgtcagag ccgaagttag catggacaga caaaggtggg gcaatcaaaa 1500
ctgaagcaaa gcaaacaatc aaagttatgg atcctattga agaagaagag tttactgaga 1560
aaagggtgct gccctccagt gatgggaaaa ctcctgcaga aaagaagttg aaaccatcaa 1620
ccaacactaa aaagaaggtc tcatttacac caaatgaacc aggaaaatac acaaagttgg 1680
agaaagatgc tctagacttg ctttcagaca atgaagaaga agatgcagaa tcctcaatct 1740
taaccttcga agaaagagat acttcatcat taagcattga agccagacta gaatcgattg 1800
aggagaaatt aagcatgata ttagggctat taagaacact caacattgct acagcaggac 1860
ccacagcagc aagagatggg atcagagatg caatgattgg cataagggag gaactaatag 1920
cagacataat aaaagaagcc aagggaaaag cagcagaaat gatggaagaa gaaatgaacc 1980
agcggacaaa aataggaaac ggtagtgtaa aattaactga aaaggcaaag gagctcaaca 2040
aaattgttga agacgaaagc acaagtggtg aatccgaaga agaagaagaa ccaaaagaca 2100
cacaggaaaa taatcaagaa gatgacattt accagttaat tatgtagttt aataaaaata 2160
aaaatgggac aagtgaaaat ggagtcctat ctggtagaca cttatcaagg catcccttac 2220

-continued

```
acagcagctg ttcaagttga tctagtagaa aaggacctgt tacctgcaag cctaacaata   2280
tggttcccct tgtttcaggc caatacacca ccagcagttc tgcttgatca gctaaagact   2340
ctgactataa ctactctgta tgctgcatca caaagtggtc caatactaaa agtgaatgca   2400
tcagcccagg gtgcagcaat gtctgtactt cccaaaaagt ttgaagtcaa tgcgactgta   2460
gcacttgacg aatatagcaa attagaattt gacaaactta cagtctgtga agtaaaaaca   2520
gtttacttaa caaccatgaa accatatggg atggtatcaa agtttgtgag ctcggccaaa   2580
tcagttggca aaaaaacaca tgatctaatc gcattatgtg attttatgga tctagaaaag   2640
aacacaccag ttacaatacc agcatttatc aaatcagttt ctatcaagga gagtgaatca   2700
gccactgttg aagctgcaat aagcagtgaa gcagaccaag ctctaacaca agccaaaatt   2760
gcaccttatg cgggactgat catgattatg accatgaaca atcccaaagg catattcaag   2820
aagcttggag ctgggaccca agttatagta gaactaggag catatgtcca ggctgaaagc   2880
ataagtaaaa tatgcaagac ttggagccat caaggaacaa gatatgtgct gaagtccagt   2940
taacagccaa gcaacctggc caagaactac caactctatt ctatagacta aaaagtcgcc   3000
attttagtta tataaaaatc aagttagaat aagaattaaa tcaatcaaga acgggacaaa   3060
taaaaatgtc ttggaaagtg gtgatcattt tttcattgct aataacacct caacacggtc   3120
ttaaagagag ctacctagaa gaatcatgta gcactataac tgagggatat cttagtgttc   3180
tgaggacagg ttggtatacc aacgttttta cattagaggt gggtgatgta gaaaacctta   3240
catgttctga tggacctagc ctaataaaaa cagaattaga tctgaccaaa agtgcactaa   3300
gagagctcaa aacagtctct gctgaccaat tggcaagaga ggaacaaatt gagaatccca   3360
gacaatctag gtttgttcta ggagcaatag cactcggtgt tgcaacagca gctgcagtca   3420
cagcaggtgt tgcaattgcc aaaaccatcc ggcttgagag tgaagtcaca gcaattaaga   3480
atgccctcaa aacgaccaat gaagcagtat ctacattggg gaatggagtt cgagtgttgg   3540
caactgcagt gagagagcta aaagactttg tgagcaagaa tttaactcgt gcaatcaaca   3600
aaaacaagtg cgacattgat gacctaaaaa tggctgttag cttcagtcaa ttcaacagaa   3660
ggtttctaaa tgttgtgcgg caattttcag acaatgctgg aataacacca gcaatatctt   3720
tggacttaat gacagatgct gaactagcca gggccgtttc taacatgccg acatctgcag   3780
gacaaataaa attgatgttg gagaaccgtg cgatggtgcg aagaaagggg ttcggaatcc   3840
tgataggggt ctacgggagc tccgtaattt acacggtgca gctgccaatc tttggcgtta   3900
tagacacgcc ttgctggata gtaaaagcag ccccttcttg ttccgaaaaa aagggaaact   3960
atgcttgcct cttaagagaa gaccaagggt ggtattgtca gaatgcaggg tcaactgttt   4020
actacccaaa tgagaaagac tgtgaaacaa gaggagacca tgtcttttgc gacacagcag   4080
caggaattaa tgttgctgag caatcaaagg agtgcaacat caacatatcc actacaaatt   4140
acccatgcaa agtcagcaca ggaagacatc ctatcagtat ggttgcactg tctcctcttg   4200
gggctctggt tgcttgctac aaaggagtaa gctgttccat tggcagcaac agagtaggga   4260
tcatcaagca gctgaacaaa ggttgctcct atataaccaa ccaagatgca gacacagtga   4320
caatagacaa cactgtatat cagctaagca aagttgaggg tgaacagcat gttataaaag   4380
gcagaccagt gtcaagcagc tttgatccaa tcaagtttcc tgaagatcaa ttcaatgttg   4440
cacttgacca agtttttgag aacattgaaa acagccaggc cttagtagat caatcaaaca   4500
gaatcctaag cagtgcagag aaagggaata ctggctttat cattgtaata attctaattg   4560
ctgtccttgg ctctagcatg atcctagtga gcatcttcat tataatcaag aaaacaaaga   4620
```

-continued

```
aaccaacggg agcacctcca gagctgagtg gtgtcacaaa caatggcttc ataccacaca   4680
gttagttaat taaaaataaa ataaaatttg ggacaaatca taatgtctcg caaggctcca   4740
tgcaaatatg aagtgcgggg caaatgcaac agaggaagtg agtgtaagtt taaccacaat   4800
tactggagtt ggccagatag atacttatta ataagatcaa actatctatt aaatcagctt   4860
ttaaggaaca ctgatagagc tgatggccta tcaataatat caggcgcagg cagagaagac   4920
agaacgcaag attttgttct aggttccacc aatgtggttc aaggttatat tgatgataac   4980
caaagcataa caaaagctgc agcctgctac agtctacaca acataatcaa gcaactacaa   5040
gaagttgaag ttaggcaggc tagagatagc aaactatctg acagcaagca tgtggcactc   5100
cataacttaa tcttatctta catggagatg agcaaaactc ccgcatcttt aatcaacaat   5160
cttaaaagac tgccgagaga aaaactgaaa aaattagcaa agctgataat tgacttatca   5220
gcaggcgctg acaatgactc ttcatatgcc ctgcaagaca gtgaaagcac taatcaagtg   5280
cagtgagcat ggtcctgttt tcattactat agaggttgat gaaatgatat ggactcaaaa   5340
agaattaaaa gaagctttgt ccgatgggat agtgaagtct cacaccaaca tttacaattg   5400
ttatttagaa aacatagaaa ttatatatgt caaggcttac ttaagttagt aaaaacacac   5460
atcagagtgg gataagtgac aatgataaca ttagatgtca ttaaaagtga tgggtcttca   5520
aaaacatgta ctcacctcaa aaaaataatc aaagaccatt ctggtaaagt gcttattgca   5580
cttaagttaa tattagcttt actaacattt ttcacaataa caatcactat aaattacata   5640
aaagtagaaa acaatctaca aatatgccag tcaaaaactg aatcagacaa agaagactca   5700
ccatcaaata ccacatccgt cacaaccaag actactctag accatgatat aacacagtat   5760
tttaaaagat taattcaaag gtatacagat tctgtgataa acaaggacac atgctggaaa   5820
ataagcagaa atcaatgcac aaatataaca acatataaat ttttatgctt taaacctgag   5880
gactcaaaaa tcaacagttg tgatagactg acagatctat gcagaaacaa atcaaaatca   5940
gcagctgaag catatcatac agtagaatgc cattgcatat acacaattga gtggaagtgc   6000
tatcaccacc caatagatta aacccaattt tgaatgttaa aactagacta ggatccgtct   6060
aagactatca gttcaatagt ttagttattt aaaaatattt gagaacaggt aagtttctat   6120
ggcacttcat agcaataggt aataattaac agcttaatta taattaaaac attatttaaa   6180
accgtaacta tttaatttac aaagtaaaaa caaaaaatatg ggacaagtag ttatggaggt   6240
gaaagtagag aacattcgag caatagacat gctcaaagca agagtgaaaa atcgtgtggc   6300
acgtagcaaa tgctttaaaa atgcttcttt aatcctcata ggaataacta cactgagtat   6360
agctctcaat atctatctga tcataaacta cacaatacaa aaaaccacat ccgaatcaga   6420
acaccacacc agctcaccac ccacagaacc caacaaggaa gcttcaacaa tctccacaga   6480
caacccagac atcaatccaa gctcacagca tccaactcaa cagtccacag aaaaccccac   6540
actcaacccc gcagcatcag cgagcccatc agaaacagaa ccagcatcaa caccagacac   6600
aacaaaccgc ctgtcctccg tagacaggtc cacagcacaa ccaagtgaaa gcagaacaaa   6660
gacaaaaccg acagtccaca caatcaacaa cccaaacaca gcttccagta cacaatcccc   6720
accacggaca acaacgaagg caatccgcag agccaccact ttccgcatga gcagcacagg   6780
aaaaagacca accacaacat tagtccagtc cgacagcagc accacaaccc aaaatcatga   6840
agaaacaggt tcagcgaacc cacaggcgtc tgcaagcaca atgcaaaact agcacaccaa   6900
taatataaaa ccaaattagt taacaaaaaa tgcgagatag ctctaaagca aaacatgtag   6960
```

-continued

```
gtaccaacaa tcaagaaacc aaaagacaac tcacaatctc cctaaaacag caacgacacc   7020
atgtcagctt tgctcaaatc tctctgggag aaacttctac ccacatacta acaacatcac   7080
aaccatctca agaaaagaaa ctgggcaaaa cagcatccaa gagacaaata gcaatggatc   7140
ctcttaatga atccactgtt aatgtctatc tccctgattc gtaccttaaa ggagtaattt   7200
cttttagtga aactaatgca attggttcat gtctcttaaa aagaccttac ttaaaaaatg   7260
acaacactgc aaaagttgcc atagagaatc ctgttattga gcatgtgaga ctcaaaaatg   7320
cagtcaattc taaaatgaaa atatcagatt acaaggtagt agagccagta aacatgcaac   7380
atgaaataat gaagaatgta cacagttgtg agctcacact attgaaacag tttttaacaa   7440
ggagtaaaaa cattagcact ctcaaattaa atatgatatg tgattggctg caattaaagt   7500
ctacatcaga tgatacctca atcctaagtt tcatagatgt agaatttata cctagttggg   7560
taagcaactg gtttagtaat tggtacaatc tcaataagtt aattttggaa ttcagaagag   7620
aggaagtaat aagaaccggt tcaatcttat gcaggtcatt gggtaaatta gtttttattg   7680
tatcatcata cggatgtatc gtcaagagca acaaaagcaa aagagtgagc ttcttcacat   7740
acaatcaact gttaacatgg aaagatgtga tgttaagtag atttaatgcg aatttttgta   7800
tatgggtaag caatagtctg aatgaaaatc aggaagggct agggttaaga agtaatctac   7860
aaggtatgtt aactaataaa ctatatgaaa ctgtagatta tatgctaagt ttatgttgca   7920
atgaaggttt ctcacttgta aaagagttcg aaggttttat tatgagtgaa atccttagga   7980
ttactgaaca tgctcaattc agtactagat ttagaaatac tttattaaat ggattaacag   8040
atcaattaac aaaattaaaa aataaaaaca gactcagagt tcatggtacc gtattagaaa   8100
ataatgatta tccaatgtat gaagttgtac ttaaattatt aggagatact ttgagatgta   8160
tcaaattatt aatcaataaa aacttagaga atgctgcaga attatactat atattcagaa   8220
tttttggtca tccaatggta gatgaaagag atgcaatgga tgctgtcaaa ttaaacaatg   8280
aaatcacaaa aatcctaagg ttggagagct tgacagaact aagaggagca ttcatattaa   8340
ggattatcaa aggatttgtg gacaacaaca aaaggtggcc caaaattaaa aatttaatag   8400
tgcttagcaa aagatggact atgtacttca aagctaaaaa ttatcccagt caactcgaat   8460
taagtgaaca agactttcta gagcttgctg caatacaatt tgaacaagag ttttctgttc   8520
ctgaaaaaac caatcttgag atggtattaa atgacaaagc catatcacct cctaaaagat   8580
taatatggtc tgtgtatcca aagaattact tacctgagac gataaaaaat cgatatttag   8640
aagaaacttt caatgcgagt gatagtctca aaacaagaag agtactagag tactatttaa   8700
aagacaataa atttgatcaa aaggaactta aaagttatgt agttagacaa gaatatttaa   8760
atgataagga gcacattgtc tcattaactg gaaaagaaag agaattaagt gtaggtagaa   8820
tgtttgctat gcaaccagga aaacagcgac aaatacaaat attggcagaa aaattgttag   8880
ctgataacat tgtacctttc ttcccggaaa ccttaacaaa gtatggtgat ctagatcttc   8940
agagaataat ggaaatcaaa tcagaacttt cttctatcaa aaccagaaga aatgacagtt   9000
ataataatta cattgcaaga gcatccatag taacagattt gagcaagttc aaccaagcct   9060
ttagatatga aactacagcg atctgtgcgg atgtagcaga cgaattacat ggaacacaaa   9120
gcttattctg ttggttacat cttatcgttc ctatgactac aatgatatgt gcctatagac   9180
atgcaccacc agaaacaaaa ggtgaaatatg atatagataa gatagaagag caaagtggtc   9240
tatatagata tcacatgggc ggtattgaag gatggtgtca aaaactctgg acaatggaag   9300
ctatatcttt attggatgtt gtatctgtaa agacacggtg tcaaatgaca tctttattaa   9360
```

-continued

```
acggtgataa ccaatcaata gatgtaagta aaccagtcaa gttatctgaa ggtttagatg   9420
aagtgaaggc agattatcgc ttagcaataa aaatgctaaa agaaataaga gatgcataca   9480
gaaatatagg ccataaactt aaagaagggg aaacatatat atcaagggat cttcaattta   9540
taagcaaggt gattcaatct gaaggagtga tgcatcctac ccctataaaa aaggtcttga   9600
gagtaggacc atggataaac acaatattag atgacattaa aactagtgct gagtcaatag   9660
ggagtctatg tcaagaatta gaatttaggg gagaaagcat aatagttagt ctgatattaa   9720
gaaacttctg gctgtataac ttatacatgc atgaatcaaa gcaacatcct ttggcaggga   9780
aacagttatt caaacaacta aataaaacat taacatcagt gcagagattt tttgaaatta   9840
aaaaggaaaa tgaggtagta gatctatgga tgaacatacc aatgcaattt ggaggaggag   9900
atccagtagt cttctataga tctttctata gaaggacccc tgattttta actgaggcaa   9960
tcagccatgt agatattctg ttaaaaatat cagctaacat aaaaaatgaa acgaaagtaa  10020
gtttcttcaa agccttacta tcaatagaaa aaaatgaacg tgctacactg acaacgctaa  10080
tgagagatcc tcaagctgtt ggatcagaac gacaagcaaa agtaacaagt gacatcaata  10140
gaacagcagt taccagtatc ttaagtcttt ccccaaatca acttttcagt gatagtgcta  10200
tacactatag caggaatgaa gaagaagtgg gaatcattgc agaaaacata acacctgttt  10260
atcctcatgg gctgagagta ttatatgaat cattgccctt tcacaaagct gaaaaagttg  10320
taaacatgat atcagggaca aaatctataa ccaacttatt acagagaaca tccgctatta  10380
atggtgaaga tattgacagg gctgtatcta tgatgttgga gaatctagga ttattatcta  10440
gaatattgtc agtagttgtt gatagtatag aaattccaat caaatctaat ggtaggctga  10500
tatgttgtca aatctctagg actttaagag agacatcatg gaataatatg gaaatagttg  10560
gagtaacatc tcctagcatc actacatgta tggatgtcat atatgcaact agttctcatt  10620
tgaaggggat aattatagaa aagttcagca ctgacagaac tacaaggggt caaagaggtc  10680
caaaaagccc ttgggtaggg tcgagtactc aagagaaaaa attagtacct gtttataaca  10740
gacaaattct ttcaaaacaa caaagagaac agctagaagc aattggaaaa atgagatggg  10800
tgtataaagg gacaccaggc ttgcgacgat tactcaacaa gatctgtctt gggagtttag  10860
gcattagtta caaatgtgta aaacctttat tacctaggtt tatgagtgta aatttcttac  10920
ataggttatc tgtcagtagt agacctatgg aattcccagc atcagttcca gcttatagaa  10980
caacaaatta ccatttcgac actagtccta ttaatcaagc actaagtgag agatttggga  11040
atgaagatat taacttggtc ttccaaaatg cgatcagctg tggaattagc ataatgagtg  11100
tagtagaaca attaacaggt agaagcccaa aacagttagt tttaataccc caattagaag  11160
aaatagacat tatgccacca ccagtgtttc aagggaaatt caattataaa ttagtagata  11220
agataacttc tgatcaacat atcttcagtc cggacaaaat agatatgtta acactaggga  11280
aaatgctcat gcctactata aaaggtcaga aaacagatca gttcttaaat aagagagaga  11340
attatttcca tgggaacaat cttattgagt ctttatcagc agcattagca tgtcattggt  11400
gtgggatatt aacagaacaa tgcatagaaa ataatatttt caagaaggac tggggtgacg  11460
ggtttatatc agatcatgct tttatggact tcaaaatatt cctatgtgtc tttaaaacta  11520
aactttttatg tagttgggga tcccaaggga aaaacattaa agatgaagat atagtagatg  11580
aatcaataga taaattgtta aggattgaca atacttttg gagaatgttc agcaaagtta  11640
tgtttgaacc aaaagttaag aaaaggataa tgttatatga tgtaaaattc ctatcactag  11700
```

-continued

```
taggctacat agggtttaag aactggttta tagagcagtt gagatcagct gaattgcatg  11760

aaataccttg gattgtcaat gccgaaggtg atttggttga gatcaagtca attaaaatct  11820

atttgcaact gatagaacaa agcttatttt taagaataac tgttttgaac tatacagata  11880

tggcacatgc tctcacacga ttaatcagaa agaagttaat gtgtgataat gcactgttaa  11940

ccccaatttc atccccaatg gttaacttaa ctcaagttat tgatcccaca acacaattag  12000

attacttccc caagataaca ttcgaaaggc taaaaaatta tgacacaagt tcaaattatg  12060

ctaaaggaaa gctaacaaga aattacatga tactattgcc atggcagcat gttaatagat  12120

ataactttgt ctttagttct actggatgta aagttagtct gaaaacatgt attggaaaac  12180

ttatgaaaga cttaaatcct aaagttttgt actttattgg agaaggagca ggaaattgga  12240

tggccagaac agcatgtgaa tatcctgata ttaaatttgt atatagaagt ctgaaagatg  12300

accttgatca tcattatcct ctggaatacc agagagtgat aggtgaatta agcagaatca  12360

tagatagtgg tgaaggactt tcaatggaaa caacagacgc aactcaaaaa actcattggg  12420

atttgataca cagggtaagc aaagatgctt tattaataac tttatgtgat gcagaattta  12480

aggacagaga tgattttttt aagatggtaa ttctatggag aaaacatgta ttatcatgca  12540

gaatttgcac tacttatggg acggacctct atttattcgc aaagtatcat gctaaagact  12600

gcaatgtaaa attacctttt tttgtgagat cagttgctac tttcattatg cagggtagta  12660

agctgtcagg ttcagaatgc tacatactct taacactagg ccaccacaac agtttacctt  12720

gccatggaga aatacaaaat tctaagatga aaatagcagt gtgtaatgat ttttatgctg  12780

caaaaaaact cgacaataaa tcaattgaag ctaattgtaa atcacttttg tcagggctaa  12840

gaatacctat aaataagaag gaactagata gacagagaag attattaaca ctacaaagca  12900

atcattcttc tgtggcaaca gttggcggta gcaagatcat agagtctaaa tggttaacaa  12960

acaaagcaag tacaataatt gattggttag aacatatttt aaattctcca aagggcgaat  13020

taaattatga ttttttgaa gcattggaga acacttaccc taatatgatt aaactaatag  13080

ataacttagg gaatgcagag attaaaaaac ttatcaaagt aacaggatac atgcttgtaa  13140

gtaaaaaatg aaaaatgatg aagatgacaa aatagatgac aacttcatac tattctaaat  13200

taattatttg attat                                                   13215
```

<210> SEQ ID NO 21
<211> LENGTH: 13135
<212> TYPE: DNA
<213> ORGANISM: human metapneumo virus

<400> SEQUENCE: 21

```
acgcgaaaaa aacgcgtata aattaaattc caaacaaaac gggacaaata aaaatgtctc     60

ttcaagggat tcacctaagt gatctgtcat ataaacatgc tatattaaaa gagtctcaat    120

acacaataaa aagagatgta ggcaccacaa ctgcagtgac accttcatca ttgcagcaag    180

agataacact tttgtgtgga gagattcttt acactaaaca tactgattac aaatatgctg    240

cagagatagg gatacaatat atttgcacag ctctaggatc agaaagagta caacagattt    300

taagaaattc aggtagtgag gttcaggtgg ttctaaccaa gacatactct ttagggaaag    360

gtaaaaatag taaaggggaa gagttgcaaa tgttagatat acatggagtg gaaaagagtt    420

gggtagaaga aatagacaaa gaggcaagaa aaacaatggt gactttgcta aaggaatcat    480

caggcaacat cccacaaaac cagaggcctt cagcaccaga cacaccaata attttattgt    540

gtgtaggtgc tttaatattc actaaactag catcaacaat agaagttgga ctagagacta    600
```

-continued

```
cagttagaag ggctaacaga gtgttaagtg atgcgctcaa aagataccct agggtagata    660
taccaaagat tgctagatct ttttatgaac tatttgagca gaaagtgtat tacaggagtc    720
tattcattga gtatgggaaa gctttaggct catcttcaac aggaagcaaa gcagaaagtt    780
tgtttgtaaa tatatttatg caagcttatg gagccggtca gacaatgcta aggtggggtg    840
tcattgccag atcatctaac aacataatgc tagggcatgt atctgtgcaa gctgaattga    900
aacaagttac agaggtttat gatttggtaa gagaaatggg tcctgaatct gggcttttac    960
atctaagaca aagtccaaag gcaggactgt tatcgttggc taattgcccc aattttgcta   1020
gtgttgttct tggtaatgct tcaggtctag gtataatcgg aatgtacagg ggaagagtgc   1080
caaacacaga gctattttct gcagcagaaa gttatgccag aagcttaaaa gaaagcaaca   1140
aaatcaactt ctcctcatta gggctcacag acgaagaaaa agaagctgca gaacacttct   1200
taaacatgag tgatgacaat caagatgatt atgagtaatt aaaaaactgg gacaagtcaa   1260
aatgtcattc cctgaaggaa aagatatcct gttcatgggt aatgaagcag caaaaaatagc  1320
agaagctttc cagaaatcac taaaaagatc aggtcacaaa agaacccagt ctattgtagg   1380
ggaaaaagta aacactatat cagaaactct agagctacct accatcagca aacctgcacg   1440
atcatctaca ctgctagagc caaaattggc atgggcagac agcagcggag ccaccaaaac   1500
cacagaaaaa caaacaacca aaacaacaga tcctgttgaa gaagaggaac tcaatgaaaa   1560
gaaggtatca ccttccagtg atgggaagac tcctgcagag aaaaaatcaa aatctccaac   1620
caatgtaaaa aagaaagttt ccttcacatc aaatgaacca gggaaatata ctaaactaga   1680
aaaagatgcc ctagatttgc tctcagacaa tgaggaagaa gacgcagagt cctcaatcct   1740
aacctttgaa gagagagaca catcatcact aagcattgag gctagactag aatcaataga   1800
agagaagcta agcatgatat taggactgct tcgtacactt aacattgcaa cagcaggacc   1860
aacggctgca agggatggaa tcagagatgc aatgattggt ataagagaag aactaatagc   1920
agaaataata aaagaagcaa agggaaaagc agccgaaatg atggaagagg aaatgaatca   1980
aaggtcaaaa ataggtaatg gcagtgtaaa actaaccgag aaggcaaaag aacttaataa   2040
aattgttgaa gacgagagca caagtggtga atcagaagaa gaagaagaac caaaagaaac   2100
tcaggataac aatcaaggag aagatatcta ccagttaatc atgtagttta ataaaaataa   2160
acaatgggac aagtcaagat ggagtcctat ctagtggaca cttatcaagg cattccctac   2220
acagctgctg ttcaagttga tctggtagaa aaagacttac taccagcaag tttgacaata   2280
tggtttcctc tattccaagc caacacacca ccagcggttt tgctcgatca gctaaaaacc   2340
ttgactataa caactctgta tgctgcatca cagaatggtc caatactcaa agtaaatgca   2400
tcagctcagg gtgctgctat gtctgtactt cccaaaaaat tcgaagtaaa tgcaactgtg   2460
gcacttgatg aatacagcaa acttgacttt gacaagttaa cggtttgcga tgttaaaaca   2520
gtttatttga caaccatgaa gccatatggg atggtgtcaa aatttgtgag ttcagccaaa   2580
tcagttggca aaaagacaca tgatctaatt gcactgtgtg acttcatgga cctagagaaa   2640
aatatacctg tgacaatacc agcattcata aagtcagttt caatcaaaga gagtgagtca   2700
gccactgttg aagctgcaat aagcagtgag gccgaccaag cattaacaca agccaaaatt   2760
gcaccctatg caggactaat catgatcatg accatgaaca atccaaaagg tatattcaag   2820
aaactaggag ctggaacaca agtgatagta gagctagggg catatgttca agccgagagc   2880
atcagcagga tctgcaagag ctggagtcac caaggaacaa gatatgtact aaaatccaga   2940
```

-continued

```
taaaaataac tgtcctaatc aataattgct tatataatcc taaagatcaa tgagcttatt   3000
attatagtta tataaaaata atttagaact agaaaggtat taatagaaag cgggacaagt   3060
aaaaatgtct tggaaagtga tgattatcat ttcgttactc ataacacctc agcacggact   3120
aaaagaaagt tatttagaag aatcatgtag tactataact gaaggatatc tcagtgtttt   3180
aagaacaggt tggtacacca atgtctttac attagaagtt ggtgatgttg aaaatcttac   3240
atgtactgat ggacctagct taatcaaaac agaacttgac ctaaccaaaa gtgctctgag   3300
agaactcaaa acagtttctg ctgatcagtt agcgagagaa gaacaaattg aaaatcccag   3360
acaatcaagg tttgtcctag gtgcaatagc tcttggagtt gccacagcag cagcagtcac   3420
agcaggcatt gcaatagcca aaaccataag acttgagagt gaagtgaatg caatcaaagg   3480
tgctctcaaa acaaccaacg aggcagtatc cacactagga aatggagtgc gagtcctagc   3540
cactgcagta agagagctga aagaatttgt gagcaaaaac ctgactagtg cgatcaacaa   3600
gaacaaatgt gacattgctg atctgaagat ggctgtcagc ttcagtcaat tcaacagaag   3660
attcctaaat gttgtgcggc agttttcaga caatgcaggg ataacaccag caatatcatt   3720
ggacctaatg actgatgctg agctggccag agctgtatca tacatgccaa catctgcagg   3780
acagataaaa ctaatgttag agaaccgtgc aatggtgagg agaaaaggat ttggaatctt   3840
gataggggtc tacggaagct ctgtgattta catggtccag ctgccgatct ttggtgtcat   3900
agatacacct tgttggataa tcaaggcagc tccctcttgt tcagaaaaag atggaaatta   3960
tgcttgcctc ctaagagagg atcaagggtg gtattgcaaa aatgcaggat ccactgttta   4020
ctacccaaat gaaaaagact gcgaaacaag aggtgatcat gtttttgtg acacagcagc    4080
agggatcaat gttgctgagc aatcaagaga atgcaacatc aacatatcta ccaccaacta   4140
cccatgcaaa gtcagcacag gaagacaccc tatcagcatg gttgcactat cacctctcgg   4200
tgctttggta gcttgctaca agggggttag ctgctcgatt ggcagtaatc gggttggaat   4260
aatcaaacaa ctacctaaag gctgctcata cataactaac caggacgcag acactgtaac   4320
aattgacaac actgtgtatc aactaagcaa agttgagggt gaacagcatg taataaaagg   4380
gagaccagtt tcaagcagtt ttgatccaat caggtttcct gaggatcagt tcaatgttgc   4440
gcttgatcaa gtctttgaaa gcattgaaaa cagtcaagca ctagtggacc agtcaaacaa   4500
aattctgaac agtgcagaaa aaggaaacac tggtttcatt attgtaataa ttttgattgc   4560
tgttcttggg ttaaccatga tttcagtgag catcatcatc ataatcaaaa aaacaaggaa   4620
gcccacaggg gcacctccag agctgaatgg tgttaccaac ggcggtttta taccgcatag   4680
ttagttaatt aaaaaatggg acaaatcatc atgtctcgca aagctccatg caaatatgaa   4740
gtacggggca agtgcaacag ggaagtgag tgcaaattca accacaatta ctggagctgg    4800
cctgataggt atttattgtt aagatcaaat tatctcttga atcagctttt aagaaacact   4860
gataaggctg atggtttgtc aataatatca ggagcaggta gagaagatag gactcaagac   4920
tttgttcttg gttctactaa tgtggttcaa gggtacattg ataacaatca aggaataaca   4980
aaggctgcag cttgctatag tctacataac ataataaaac agctacaaga aatagaagta   5040
agacaggcta gagataataa gctttctgac agcaaacatg tggcacttca caacttgata   5100
ttatcctata tggagatgag caaaactcct gcatccctga ttaataacct aaagaaacta   5160
ccaagagaaa aactgaagaa attagcgaaa ttaataattg atttatcagc aggaactgat   5220
aatgactctt catatgcctt gcaagacagt gaaagcacta atcaagtgca gtaagcatgg   5280
tcccaaattc attaccatag aggcagatga tatgatatgg acacacaaag aattaaagga   5340
```

-continued

```
gacactgtct gatgggatag taaaatcaca caccaatatt tacagttgtt atttagaaaa   5400
tatagaaata atatatgtta aagcttactt aagttagtaa aaaataaata gaatgggata   5460
aatgacaatg aaaacattag atgtcataaa aagtgatgga tcctcagaaa catgtaatca   5520
actcaaaaaa ataataaaaa aacactcagg taaattgctt attgcattaa aactgatatt   5580
ggccttattg acgtttttca cagtaacaat tactgttaac tatataaaag tagaaaacaa   5640
tttgcaggca tgtcaattaa aaaatgaatc agacaaaaag gacacaaagc taaataccac   5700
atcaacaaca atcagaccca ttcctgatct aaatgcagta cagtacttga aaaggctgat   5760
tcagaaacac accaactttg tcataaaaga cagagatacc tgttggagaa tacacacgaa   5820
tcaatgcaca aatataaaaa tatataagtt cttatgtttc gggtttatga attcaacaaa   5880
tacagactgt gaagaactaa cagttttatg tgataaaaag tcaaaaacca tgacagaaaa   5940
acataggaaa gcagagtgtc actgtctaca tacaaccgag tggtggtgtt attatcttta   6000
agagaaaact cggctttcaa cattaaaatc agaacaaatc ctatccagat ctattaatat   6060
aatagtttag tcattcaaaa actctaaata ttgtctagac ttcacaacac tttgcggtca   6120
tatgcaataa tcaatggtca aaccactgtt gcaaactcac ccataatata atcactgagt   6180
aatacaaaac aagaaaatgg gacaagtggc catggaagta agagtggaga acattcgggc   6240
aatagacatg ttcaaagcaa aaatgaaaaa ccgtataaga agtagcaagt gctatagaaa   6300
tgctacactg atccttattg gattaacagc attaagtatg gcacttaata ttttttaat    6360
cattgattat gcaatgttaa aaaacatgac caaagtggaa cactgtgtta atatgccgcc   6420
ggtagaacca agcaagaaga ccccaatgac ctctgcagta gacttaaaca ccaaacccaa   6480
tccacagcag gcaacacagt tggccgcaga ggattcaaca tctctagcag caacctcaga   6540
ggaccatcta cacacaggga caactccaac accagatgca acagtctctc agcaaaccac   6600
agacgagtac acaacattgc tgagatcaac caacagacag accacccaaa caaccacaga   6660
gaaaaagcca accggagcaa caaccaaaaa agaaaccaca actcgaacta caagcacagc   6720
tgcaacccaa acactcaaca ctaccaacca aactagctat gtgagagagg caaccacaac   6780
atccgccaga tccagaaaca gtgccacaac tcaaagcagc gaccaaacaa cccaggcagc   6840
agacccaagc tcccaaccac accatacaca gaaaagcaca acaacaacat acaacacaga   6900
cacatcctct ccaagtagtt aacaaaaaaa ctataaaata atcatgaaaa ccgaaaaact   6960
agaaaagtta atttgaactc agaaaagaac acaaacacta tatgaattgt ttgagcgtat   7020
atactaatga aatagcatct gtttgtgcat caataatacc atcattattt aagaaataag   7080
aagaagctaa aattcaaggg acaaataaca atggatccat tttgtgaatc cactgtcaat   7140
gtttatcttc ctgactcata tctcaaagga gtaatatctt tcagtgaaac caatgcaatt   7200
ggctcatgcc ttttgaaaag accctatcta aaaaaagata acactgctaa agttgctgta   7260
gaaaaccctg ttgttgaaca tgtcaggctt agaaatgcag tcatgaccaa aatgaagata   7320
tcagattata aagtggttga accaattaat atgcagcatg aaataatgaa aaatatacac   7380
agttgtgagc tcacattatt aaaacaattc ttaacaagaa gtaaaaacat tagctctcta   7440
aaattaagta tgatatgtga ttggttacag ttaaaatcca cctcagataa cacatcaatt   7500
cttaatttta tagatgtgga gtttatacct gtttgggtga gcaattggtt tagtaactgg   7560
tataatctca ataaattaat cttagagttt agaagagagg aagtaataag aactggttca   7620
attttatgta gatcactagg caagttagtt ttcattgtat catcttatgg gtgtgtagta   7680
```

-continued

```
aaaagcaaca aaagtaaaag agtaagtttt ttcacatata accaactgtt aacatggaaa   7740
gatgtgatgt taagtaggtt caatgcaaac ttttgtatat gggtaagtaa caacctgaac   7800
aaaaatcaag aaggactagg atttagaagt aatctgcaag gtatgttaac caataaatta   7860
tatgaaactg ttgattatat gttaagtcta tgtagtaatg aagggttctc actagtgaaa   7920
gagttcgaag gctttattat gagtgaaatt cttaaaatta ctgagcatgc tcaattcagt   7980
actaggttta ggaatacttt attaaatggg ttgactgaac aattatcaat gttgaaagct   8040
aaaaacagat ctagagttct tggcactata ttagaaaaca atgattaccc catgtatgaa   8100
gtagtactta aattattagg ggacactttg aaaagtataa aattattaat taacaagaat   8160
ttagaaaatg ctgcagaatt atattatata ttcagaattt ttggacaccc tatggtagat   8220
gagagggaag caatggatgc tgttaaatta aataatgaga ttacaaaaat tcttaaactg   8280
gagagcttaa cagaactaag aggagcattt atactaagaa ttataaaagg gtttgtagat   8340
aataataaaa gatggcctaa aattaagaat ttaaaagtgc tcagtaaaag atgggttatg   8400
tatttcaaag ccaaaagtta ccctagccaa cttgagctaa gtgtacaaga ttttttagaa   8460
cttgctgcag tacaattcga acaggaattt tctgtccctg aaaaaaccaa ccttgagatg   8520
gtattaaatg ataaagcaat atctcctcca aaaaagttaa tatggtcggt atatccaaaa   8580
aattatctac ctgaaattat aaaaaatcaa tatttagaag aggtcttcaa tgcaagtgac   8640
agtcaaagaa cgaggagagt cttagaattt tacttaaaag attgcaaatt tgatcaaaaa   8700
gaccttaaac gttatgtact taaacaagag tatctaaatg acaaagacca cattgtctca   8760
ttaactggga aggaaagaga attaagtgta ggcaggatgt ttgcaatgca accaggcaaa   8820
caaagacaaa tacagatact agctgagaaa cttctagctg ataatattgt accctttttc   8880
ccagaaactt taacaaagta tggtgacttg gatctccaaa gaattatgga aatgaaatca   8940
gaactttctt ccattaaaac taggaagaat gatagttaca acaattatat tgcaagagcc   9000
tccatagtaa cagacctaag taaattcaat caagccttta gatatgaaac cacagctatc   9060
tgtgcagatg tagcagatga gttacatggt acgcaaagct tattttgttg gttacatctt   9120
attgttccca tgaccacaat gatatgtgca tacagacatg caccaccaga aacaaagggg   9180
gagtatgaca tagacaaaat agaagagcaa agtgggctat acagatatca tatgggaggg   9240
attgaagggt ggtgtcagaa gttatggaca atggaagcga tatccttgtt agatgtagta   9300
tctgttaaga ctcgttgtca gatgacctct ctattaaacg gagacaatca atcaatagat   9360
gtcagtaaac cagtaaaatt gtctgaaggt atagatgaag taaaagcaga ttatagctta   9420
gcaattaaaa tgcttaaaga gataagagat gcctataaaa acattggcca taaactcaaa   9480
gaaggtgaaa catatatatc aagagatctc caatttataa gtaaggtgat tcaatctgag   9540
ggggtcatgc atcctacccc cataaaaaag atattaaggg taggtccctg gataaataca   9600
atactagatg acattaaaac cagtgcagaa tcaataggga gtctgtgtca agaactagag   9660
ttcagaggag aaagtatgct agttagcttg atattaagga atttctggct gtataactta   9720
tacatgcatg agtcaaaaca gcatccgtta gctggaaaac aactgtttaa gcaattgaac   9780
aaaacactaa catctgtgca aagatttttt gagctgaaga aagaaaatga tgtggttgac   9840
ctatggatga atataccaat gcagtttgga gggggagacc cagtagtttt ttacagatct   9900
ttttacagaa ggactcctga tttcctgact gaagcaatca gccatgtgga tttactgtta   9960
aaagtttcga acaatattaa aaatgagact aagatacgat tctttaaagc cttattatct  10020
atagaaaaga atgaacgtgc aacattaaca acactaatga gagacccccca ggcggtagga  10080
```

-continued

```
tcggaaagac aagctaaggt aacaagtgat ataaatagaa cagcagttac tagcatactg  10140
agtctatctc cgaatcagct cttttgtgat agtgctatac actatagcag aaatgaagaa  10200
gaagtcggga tcattgcaga caacataaca cctgtttatc ctcacggatt gagagtgctc  10260
tatgaatcac taccttttca taaggctgaa aaggttgtca atatgatatc aggtacaaag  10320
tctataacta acctattgca gagaacatct gctatcaatg gtgaagatat tgatagagca  10380
gtgtctatga tgttagagaa cttagggttg ttatctagga tattgtcagt aataattaat  10440
agtatagaaa taccaattaa gtccaatggc agattgatat gctgtcaaat ttctaagact  10500
ttgagagaaa aatcatggaa caatatggaa atagtaggag tgacatctcc aagtattgta  10560
acatgtatgg atgttgtgta tgcaactagt tctcatttaa aaggaataat tattgaaaaa  10620
ttcagtactg acaagaccac aagaggtcag aggggaccaa aaagcccctg ggtaggatca  10680
agcactcaag agaaaaaatt agttcctgtt tataatagac aaattctttc aaaacaacaa  10740
aaggagcaac tggaagcaat aggaaaaatg aggtgggtgt ataaaggaac tccagggcta  10800
agaagattgc tcaataagat ttgcatagga agtttaggta ttagctataa atgtgtaaaa  10860
cctctattac caagattcat gagtgtaaac ttcttacata ggttatctgt tagtagcaga  10920
cccatggaat tcccagcttc tgttccagct tataggacaa caaattacca ctttgacact  10980
agtccaatca accaagcatt aagtgagagg ttcgggaacg aagacattaa tctagtgttc  11040
caaaatgcaa tcagctgcgg aattagtata atgagtgttg tagaacagtt aactggtaga  11100
agcccaaaac aattagtctt aatccccaa ttagaagaga tagatattat gcctcctcct  11160
gtatttcaag gaaaattcaa ttataaacta gttgataaaa taacctctga tcaacacatc  11220
ttcagtcctg acaaaataga catattaaca ctagggaaga tgcttatgcc tactataaaa  11280
ggtcaaaaaa ctgatcagtt cttaaataag agagaaaact atttccatgg aaataattta  11340
attgaatctt tatctgcagc acttgcatgc cactggtgtg gaatattaac agaacagtgt  11400
gtagaaaaca atatctttag gaaagactgg ggtgatgggt tcatatcaga tcatgccttc  11460
atggatttca agatatttct atgtgtattt aaaaccaaac ttttatgtag ttggggatcc  11520
caagggaaaa atgtaaaaga tgaagatata atagatgaat ccattgacaa attattaaga  11580
attgacaaca ctttttggag aatgttcagc aaagtcatgt ttgaatcaaa ggtcaaaaaa  11640
agaataatgt tatatgatgt aaaattccta tcattagtag gttatatagg atttaaaaac  11700
tggtttatag agcagttaag agtagtagaa ttgcatgaag tgccctggat tgtcaatgct  11760
gaaggggagc tagttgaaat taaaccaatc aaaatttatt tgcagttaat agaacaaagt  11820
ctatctttaa gaataactgt tttgaattat acagacatgg cacatgctct tacacgatta  11880
attaggaaga aattgatgtg tgataatgca ctcttcaatc caagttcatc accaatgttt  11940
agtctaactc aagttatcga tcctacaaca cagctagact attttcctaa ggtgatattt  12000
gaaaggttaa aaagttatga taccagttca gactacaaca aagggaagtt aacaagaaat  12060
tacatgacat tattaccatg gcagcacgta aacaggtata attttgtctt tagttcaaca  12120
ggatgtaaaa tcagcttgaa gacatgcatc gggaaattga taaaggactt aaaccctaag  12180
gttctttact ttattggaga aggagcaggt aactggatgg caagaacagc atgtgagtat  12240
cctgacataa aatttgtata taggagttta aaggatgatc ttgatcatca ttacccatta  12300
gaatatcaaa gggtaatagg tgatttaaat agggtaatag atggtggtga aggactatca  12360
atggagacca cagatgcaac tcaaaagact cattgggact taatacacag aataagtaaa  12420
```

-continued

```
gatgctttat tgataacatt gtgtgatgca gaattcaaaa acagagatga tttctttaaa  12480

atggtaattc tttggagaaa acatgtatta tcatgtagaa tctgtacagc ttatggaaca  12540

gatctttact tatttgcaaa gtatcatgcg acggactgca atataaaatt accatttttt  12600

gtaaggtctg tagctacttt tattatgcaa ggaagcaaat tgtcaggatc agaatgttac  12660

atacttttaa cattaggtca tcacaataat ctgccatgcc atggagaaat acaaaattcc  12720

aaaatgagaa tagcagtgtg taatgatttc catgcctcaa aaaaactaga caacaaatca  12780

attgaagcta actgtaaatc tcttctatca ggattaagaa taccaataaa caaaaaagag  12840

ttaaatagac aaaagaaact gttaacacta caaagcaatc attcttccat agcaacagtt  12900

ggcggcagta agattataga atccaaatgg ttaaagaata aagcaagtac aataattgat  12960

tggttagagc atatcttgaa ttctccaaaa ggtgaattaa actatgattt ctttgaagca  13020

ttagagaaca cataccccaa tatgatcaag cttatagata acctgggaaa tgcagagata  13080

aaaaaactaa tcaaagttcc tgggtatatg cttgtgagta agaagtaata ataat       13135
```

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
aaagaattca cgagaaaaaa acgc 24

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ctgtggtctc tagtcccact tc 22

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
catgcaagct tatggggc 18

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
cagagtggtt attgtcaggg t 21

<210> SEQ ID NO 26
<211> LENGTH: 19
<212> TYPE: DNA
<213> ORGANISM: Artificial Sequence
<220> FEATURE:
<223> OTHER INFORMATION: Primer -continued

<400> SEQUENCE: 26
gtagaactag gagcatatg 19

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tccccaatgt agatactgct tc 22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gcactcaaga gataccctag 20

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
agactttctg ctttgctgcc tg 22

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ccctgacaat aaccactctg 20

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
gccaactgat ttggctgagc tc 22

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tgcctatctc ctcttggggc ttg 23

<210> SEQ ID NO 33

-continued

<211> LENGTH: 22
<212> TYPE: DNA
<213> ORGANISM: Artificial Sequence
<220> FEATURE:
<223> OTHER INFORMATION: Primer

<400> SEQUENCE: 33
tcaaagctgc ttgacactgg cc 22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
catgcccact ataaaaggtc ag 22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
caccccagtc tttcttgaaa 20

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36
tgcttgtact tcccaaag 18

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
tatttgaaca aaaagtgt 18

<210> SEQ ID NO 38
<211> LENGTH: 19
<212> TYPE: DNA
<213> ORGANISM: Artificial Sequence
<220> FEATURE:
<223> OTHER INFORMATION: Primer

<400> SEQUENCE: 38
tggtgtggga tattaacag 19

<210> SEQ ID NO 39
<211> LENGTH: 66
<212> TYPE: DNA
<213> ORGANISM: Artificial Sequence
<220> FEATURE:
<223> OTHER INFORMATION: Primer

<400> SEQUENCE: 39

-continued aagcccaaaa gctggactgt ttagccaact gtcccaactt tgcaaggttc tcggaaatgc 60
ctcagg 66

<210> SEQ ID NO 40
<211> LENGTH: 66
<212> TYPE: DNA
<213> ORGANISM: Artificial Sequence
<220> FEATURE:
<223> OTHER INFORMATION: Primer

<400> SEQUENCE: 40
aagcccaaaa gctggactgt ttagccaact gtcctaactt tgcaaggttc tcggaaatgc 60
ctcagg 66

<210> SEQ ID NO 41
<211> LENGTH: 66
<212> TYPE: DNA
<213> ORGANISM: Artificial Sequence
<220> FEATURE:
<223> OTHER INFORMATION: Primer

<400> SEQUENCE: 41
aagcccaaaa gctggactgt ttagccaatt gtcccaactt tgcaaggttc tcggcaatgc 60
ctcagg 66

<210> SEQ ID NO 42
<211> LENGTH: 66
<212> TYPE: DNA
<213> ORGANISM: Artificial Sequence
<220> FEATURE:
<223> OTHER INFORMATION: Primer

<400> SEQUENCE: 42
aagcccaaaa gctggattgt ttagccaatt gtcccaactt tgcaaggttc tcggcaatgc 60
ctcagg 66

<210> SEQ ID NO 43
<211> LENGTH: 66
<212> TYPE: DNA
<213> ORGANISM: Artificial Sequence
<220> FEATURE:
<223> OTHER INFORMATION: Primer

<400> SEQUENCE: 43
aagcccaaaa gctggactgt ttagccaatt gtcccaactt tgctaggttc tcggcaatgc 60
ctcagg 66

<210> SEQ ID NO 44
<211> LENGTH: 66
<212> TYPE: DNA
<213> ORGANISM: Artificial Sequence
<220> FEATURE:
<223> OTHER INFORMATION: Primer

<400> SEQUENCE: 44
aagtccaaag gcagggctgt ttggccaatt gccccaattt tgctaggttc ttggcaatgc 60
ttcagg 66

<210> SEQ ID NO 45
<211> LENGTH: 66
<212> TYPE: DNA

-continued

<213> ORGANISM: Artificial Sequence
<220> FEATURE:
<223> OTHER INFORMATION: Primer

<400> SEQUENCE: 45
aagtccaaag gcagggctgt ttggccaatt gccccaattt tgctaggttc ttggcaatgc 60
ttcagg 66

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
cccaccacca gagagaaa 18

<210> SEQ ID NO 47
<211> LENGTH: 18
<212> TYPE: DNA
<213> ORGANISM: Artificial Sequence
<220> FEATURE:
<223> OTHER INFORMATION: Primer

<400> SEQUENCE: 47
accaccagag agaaaccc 18

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
accagagaga aacccacc 18

<210> SEQ ID NO 49
<211> LENGTH: 18
<212> TYPE: DNA
<213> ORGANISM: Artificial Sequence
<220> FEATURE:
<223> OTHER INFORMATION: Primer

<400> SEQUENCE: 49
agagagaaac ccaccacc 18

<210> SEQ ID NO 50
<211> LENGTH: 18
<212> TYPE: DNA
<213> ORGANISM: Artificial Sequence
<220> FEATURE:
<223> OTHER INFORMATION: Primer

<400> SEQUENCE: 50
gagaaaccca ccaccaga 18

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51

-continued aaacccacca ccagagag 18

<210> SEQ ID NO 52
<211> LENGTH: 18
<212> TYPE: DNA
<213> ORGANISM: Artificial Sequence
<220> FEATURE:
<223> OTHER INFORMATION: Primer

<400> SEQUENCE: 52
ggaggcaagc gaacgcaa 18

<210> SEQ ID NO 53
<211> LENGTH: 18
<212> TYPE: DNA
<213> ORGANISM: Artificial Sequence
<220> FEATURE:
<223> OTHER INFORMATION: Primer

<400> SEQUENCE: 53
ggcaagcgaa cgcaagga 18

<210> SEQ ID NO 54
<211> LENGTH: 18
<212> TYPE: DNA
<213> ORGANISM: Artificial Sequence
<220> FEATURE:
<223> OTHER INFORMATION: Primer

<400> SEQUENCE: 54
aagcgaacgc aaggaggc 18

<210> SEQ ID NO 55
<211> LENGTH: 18
<212> TYPE: DNA
<213> ORGANISM: Artificial Sequence
<220> FEATURE:
<223> OTHER INFORMATION: Primer

<400> SEQUENCE: 55
cgaacgcaag gaggcaag 18

<210> SEQ ID NO 56
<211> LENGTH: 18
<212> TYPE: DNA
<213> ORGANISM: Artificial Sequence
<220> FEATURE:
<223> OTHER INFORMATION: Primer

<400> SEQUENCE: 56
acgcaaggag gcaagcga 18

<210> SEQ ID NO 57
<211> LENGTH: 18
<212> TYPE: DNA
<213> ORGANISM: Artificial Sequence
<220> FEATURE:
<223> OTHER INFORMATION: Primer

<400> SEQUENCE: 57
caaggaggca agcgaacg 18

<210> SEQ ID NO 58
<211> LENGTH: 20
<212> TYPE: DNA

-continued

<213> ORGANISM: Artificial Sequence
<220> FEATURE:
<223> OTHER INFORMATION: Primer

<400> SEQUENCE: 58
tgttgtcgag actattccaa 20

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
tgttgwacca gttgcagtct 20

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
tgctgcttct attgagaaac gcc 23

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
ggtgacttcy aatagggcca 20

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
ctcgaggttg tcaggatata g 21

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
ctttgggagt tgaacacagt t 21

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
ttcrgtttta gctgcttacg 20

-continued

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
aggcaaatct ctggataatg c 21

<210> SEQ ID NO 66
<211> LENGTH: 18
<212> TYPE: DNA
<213> ORGANISM: Artificial Sequence
<220> FEATURE:
<223> OTHER INFORMATION: Primer

<400> SEQUENCE: 66
tcgtaacgtc tcgtgacc 18

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
ggagatcttt ctagagtgag 20

<210> SEQ ID NO 68
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 10, 19
<223> OTHER INFORMATION: n = A,T,C or G
<220> FEATURE:
<221> NAME/KEY: misc_feature
<222> LOCATION: 10, 19
<223> OTHER INFORMATION: n = A,T,C or G

<400> SEQUENCE: 68
ccttggtgan tctatccgna g 21

<210> SEQ ID NO 69
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 17
<223> OTHER INFORMATION: n = A,T,C or G
<220> FEATURE:
<221> NAME/KEY: misc_feature
<222> LOCATION: 17
<223> OTHER INFORMATION: n = A,T,C or G

<400> SEQUENCE: 69
ctgccactgc tagttgngat aatcc 25

<210> SEQ ID NO 70

-continued

<211> LENGTH: 25
<212> TYPE: DNA
<213> ORGANISM: Artificial Sequence
<220> FEATURE:
<223> OTHER INFORMATION: Primer

<400> SEQUENCE: 70
gggcttctaa gcgacccaga tcttg 25

<210> SEQ ID NO 71
<211> LENGTH: 27
<212> TYPE: DNA
<213> ORGANISM: Artificial Sequence
<220> FEATURE:
<223> OTHER INFORMATION: Primer

<400> SEQUENCE: 71
gaatttcctt atggacaagc tctgtgc 27

<210> SEQ ID NO 72
<211> LENGTH: 25
<212> TYPE: DNA
<213> ORGANISM: Artificial Sequence
<220> FEATURE:
<223> OTHER INFORMATION: Primer

<400> SEQUENCE: 72
ggagcaggaa ctccaagacc tggag 25

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
gctcaacctc atcacatact aaccc 25

<210> SEQ ID NO 74
<211> LENGTH: 27
<212> TYPE: DNA
<213> ORGANISM: Artificial Sequence
<220> FEATURE:
<223> OTHER INFORMATION: Primer

<400> SEQUENCE: 74
gagatgggcg ggcaagtgcg gcaacag 27

<210> SEQ ID NO 75
<211> LENGTH: 28
<212> TYPE: DNA
<213> ORGANISM: Artificial Sequence
<220> FEATURE:
<223> OTHER INFORMATION: Primer

<400> SEQUENCE: 75
gcctttgcaa tcaggatcca aatttggg 28

<210> SEQ ID NO 76
<211> LENGTH: 24
<212> TYPE: DNA
<213> ORGANISM: Artificial Sequence
<220> FEATURE:
<223> OTHER INFORMATION: Primer

<400> SEQUENCE: 76

-continued ctgctgcagt tcaggaaaca tcag 24

<210> SEQ ID NO 77
<211> LENGTH: 22
<212> TYPE: DNA
<213> ORGANISM: Artificial Sequence
<220> FEATURE:
<223> OTHER INFORMATION: Primer

<400> SEQUENCE: 77
accggatgtg ctcacagaac tg 22

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
tttgttatag gcatatcatt g 21

<210> SEQ ID NO 79
<211> LENGTH: 18
<212> TYPE: DNA
<213> ORGANISM: Artificial Sequence
<220> FEATURE:
<223> OTHER INFORMATION: Primer

<400> SEQUENCE: 79
ttaaccagca aagtgtta 18

<210> SEQ ID NO 80
<211> LENGTH: 21
<212> TYPE: DNA
<213> ORGANISM: Artificial Sequence
<220> FEATURE:
<223> OTHER INFORMATION: Primer

<400> SEQUENCE: 80
ttagggcaag agatggtaag g 21

<210> SEQ ID NO 81
<211> LENGTH: 19
<212> TYPE: DNA
<213> ORGANISM: Artificial Sequence
<220> FEATURE:
<223> OTHER INFORMATION: Primer

<400> SEQUENCE: 81
ttataacaat gatggaggg 19

<210> SEQ ID NO 82
<211> LENGTH: 21
<212> TYPE: DNA
<213> ORGANISM: Artificial Sequence
<220> FEATURE:
<223> OTHER INFORMATION: Primer

<400> SEQUENCE: 82
cattaaaaag ggcacagacg c 21

<210> SEQ ID NO 83
<211> LENGTH: 17
<212> TYPE: DNA

-continued

<213> ORGANISM: Artificial Sequence
<220> FEATURE:
<223> OTHER INFORMATION: Primer

<400> SEQUENCE: 83
tggacattct ccgcagt 17

<210> SEQ ID NO 84
<211> LENGTH: 907
<212> TYPE: DNA
<213> ORGANISM: human metapneumo virus

<400> SEQUENCE: 84
atggaggtga aagtggagaa cattcgaaca atagatatgc tcaaagcaag agtaaaaaat 60
cgtgtggcac gcagcaaatg ctttaaaaat gcctctttgg tcctcatagg aataactaca 120
ttgagtattg ccctcaatat ctatctgatc ataaactata aaatgcaaaa aaacacatct 180
gaatcagaac atcacaccag ctcatcaccc atggaatcca gcagagaaac tccaacggtc 240
cccacagaca actcagacac caactcaagc ccacagcatc caactcaaca gtccacagaa 300
ggctccacac tctactttgc agcctcagca agctcaccag agacagaacc aacatcaaca 360
ccagatacaa caaaccgccc gcccttcgtc gacacacaca caacaccacc aagcgcaagc 420
agaacaaaga caagtccggc agtccacaca aaaaacaacc caaggacaag ctctagaaca 480
cattctccac cacgggcaac gacaaggacg gcacgcagaa ccaccactct ccgcacaagc 540
agcacaagaa agagaccgtc cacagcatca gtccaacctg acatcagcgc aacaacccac 600
aaaaacgaag aagcaagtcc agcgagccca caaacatctg caagcacaac aagaatacaa 660
aggaaaagcg tggaggccaa cacatcaaca acatacaacc aaactagtta acaaaaaata 720
caaaataact ctaagataaa ccatgcagac accaacaatg gagaagccaa aagacaattc 780
acaatctccc caaaaaggca acaacaccat attagctctg cccaaatctc cctggaaaaa 840
acactcgccc atataccaaa aataccacaa ccaccccaag aaaaaaactg ggcaaaacaa 900
cacccaa 907

<210> SEQ ID NO 85
<211> LENGTH: 908
<212> TYPE: DNA
<213> ORGANISM: human metapneumo virus

<400> SEQUENCE: 85
atggaggtga aagtggagaa cattcgaaca atagatatgc tcaaagcaag tgtaaaaaat 60
cgtgtggcac gcagcaaatg ctttaaaaat gcctctttgg tcctcatagg aataactaca 120
ttgagtattg ccctcaatat ctatctgatc ataaactata aaatgcaaaa aaacacatct 180
gaatcagaac atcacaccag ctcatcaccc atggaatcca gcagagaaac tccaacggtc 240
cccacagaca actcagacac caactcaagc ccacagcatc caactcaaca gtccacagaa 300
ggctccacac tctactttgc agcctcagca agctcaccag agacagaacc aacatcaaca 360
ccagatacaa caaaccgccc gcccttcgtc gacacacaca caacaccacc aagcgcaagc 420
agaacaaaga caagtccggc agtccacaca aaaaacaacc caaggacaag ctctagaaca 480
cattctccac cacgggcaac gacaaggacg gcacgcagga accaccactc tccgcacaag 540
cagcacaaga aagagaccgt ccacagcatc agtccaacct gacatcagcg caacaaccca 600
caaaaacgaa gaagcaagtc cagcgagccc acaaacatct gcaagcacaa caagaataca 660
aaggaaaagc gtggaggcca acacatcaac aacatacaac caaactagtt aacaaaaaat 720

-continued acaaaataac tctaagataa accatgcaga caccaacaat ggagaagcca aaagacaatt 780
cacaatctcc ccaaaaaggc aacaacacca tattagctct gcccaaatct ccctggaaaa 840
aacactcgcc catataccaa aaataccaca accaccccaa gaaaaaaact gggcaaaaca 900
acacccaa 908

<210> SEQ ID NO 86
<211> LENGTH: 907
<212> TYPE: DNA
<213> ORGANISM: human metapneumo virus

<400> SEQUENCE: 86
atggaggtga aagtggagaa cattcgaaca atagatatgc tcaaagcaag agtaaaaaat 60
cgtgtggcac gcagcaaatg ctttaaaaat gcctctttgg tcctcatagg aataactaca 120
ctgagtattg ccctcaatat ctatctgatc ataaactata aaatgcaaaa aaacacatct 180
gaatcagaac atcacaccag ctcatcaccc atggaatcca gcagagaaac tccaacggtc 240
cccacagata attcagacac caactcaagc ccacaacatc caactcaaca gtccacagaa 300
ggctccacac tctactttgc agcctcagca aactcaccag agacagaacc aacatcaaca 360
ccagacacaa caaaccgccc gcccttcgtc gacacacaca caacaccacc aagcgcaagc 420
agaacaaaga caagtccggc agtccacaca aaaaacaacc caaggataag ctccagaaca 480
cactctccac catgggcaac gacaaggacg gcacgcagaa ccaccactct ccgcacaagc 540
agcacaagaa agagaccgtc cacagcatca gcccaacccg acatcagcgc aacaacccac 600
aaaaacgaag aagcaagtcc agcgagccca caaacatctg caagcacaac aagaacacaa 660
aggaaaagcg tggaggccaa cacatcaaca acatacaacc aaactagtta acaaaaaata 720
caaaataact ctaagataaa ccatgcagac accaacaatg gagaagtcaa aagacaattc 780
acaatctccc caaaaaggca acaacaccat attagctctg cccaaatctc cctggaaaaa 840
acactcgccc atataccaaa aataccacaa ccaccccaag aaaaaaactg ggcaaaacaa 900
cacccaa 907

<210> SEQ ID NO 87
<211> LENGTH: 907
<212> TYPE: DNA
<213> ORGANISM: human metapneumo virus

<400> SEQUENCE: 87
atggaggtga aagtggagaa cattcgaaca atagatatgc tcaaagcaag agtaaaaaat 60
cgtgtggcac gcagcaaatg ctttaaaaat gcctctttgg tcctcatagg aataactaca 120
ttgagtattg ccctcaatat ctatctgatc ataaactata aaatgcaaaa aaacacatct 180
gaatcagaac atcacaccag ctcatcaccc atggaatcca gcagagaaac tccaacggtc 240
cccacagata attcagacac caactcaagc ccacaacatc caactcaaca gtccacagaa 300
ggctccacac tctactttgc agcctcagca aactcaccag agacagaacc aacatcaaca 360
ccagacacaa cagaccgccc gcccttcgtc gacacacaca caacaccacc aagcgcaagc 420
agaacaaaga caagtccggc agtccacaca aaaaacaacc caaggataag ctccagaaca 480
cattctccac catgggcaac gacaaggacg gcacgcagaa ccaccactct ccgcacaagc 540
agcacaagaa agagaccgtc cacagcatca gtccaacccg acatcagcgc aacaacccac 600
aaaaacgaag aagcaagtcc agcgagccca caaacatctg caagcacaac aagaacacaa 660

-continued aggaaaagcg tggaggccaa cacatcaaca acatacaacc aaactagtta acaaaaaata 720
caaaataact ctaagataaa ccatgcagac accaacaatg gagaagtcaa aagacaattc 780
acaatctccc caaaaaggca acaacaccat attagctctg cccaaatctc cctggaaaaa 840
acactcgccc atataccaaa aataccacaa ccaccccaag aaaaaaactg ggcaaaacaa 900
cacccaa 907

<210> SEQ ID NO 88
<211> LENGTH: 907
<212> TYPE: DNA
<213> ORGANISM: human metapneumo virus

<400> SEQUENCE: 88
atggaggtga aagtggagaa cattcgaaca atagatatgc tcaaagcaag agtaaaaaat 60
cgtgtggcac gcagcaaatg ctttaaaaat gcctctttgg tcctcatagg aataactaca 120
ttgagtattg ccctcaatat ctatctgatc ataaactata aaatgcaaaa aaacacatct 180
gaatcagaac atcacaccag ctcatcaccc atggaatcca gcagagaaac tccaacggtc 240
cccacagata attcagacac caactcaagc ccacaacatc caactcaaca gtccacagaa 300
ggctccacac tctactttgc agcctcagca agctcaccag agacagaacc aacatcaaca 360
ccagacacaa cagaccgccc gcccttcgtc gacacacaca caacaccacc aagcgcaagc 420
agaacaaaga caagtccggc agtccacaca aaaaacaacc caaggataag ctccagaaca 480
cattctccac catgggcaac gacaaggacg gcacgcagaa ccaccactct ccgcacaagc 540
agcacaagaa agagaccgtc cacagcatca gtccaacccg acatcagcgc aacaacccac 600
aaaaacgaag aagcaagtcc agcgagccca caaacatctg caagcacaac aagaacacaa 660
aggaaaagcg tggaggccaa cacatcaaca acatacaacc aaactagtta acaaaaaata 720
caaaataact ctaagataaa ccatgcagac accaacaatg gagaagtcaa aagacaattc 780
acaatctccc caaaaaggca acaacaccat attagctctg cccaaatctc cctggaaaaa 840
acactcgccc atataccaaa aataccacaa ccaccccaag aaaaaaactg ggcaaaacaa 900
cacccaa 907

<210> SEQ ID NO 89
<211> LENGTH: 907
<212> TYPE: DNA
<213> ORGANISM: human metapneumo virus

<400> SEQUENCE: 89
atggaggtga aagtggagaa cattcgaaca atagatatgc tcaaagcaag agtgaaaaat 60
cgtgtggcac gcagcaaatg ctttaaaaat gcctctttga tcctaatagg aataactaca 120
ttgagtatag ccctcaatat ctatctgatc ataaactata caatgcaaga aaacacatcc 180
gaatcagaac atcacaccag ctcatcaccc atggaatcca gcagggaaac tccaacggtc 240
cccatagaca actcagacac caatccaggc tcacagtatc caactcaaca gtccacagaa 300
gactccacac tccactctgc agcttcagca agctcaccag agacagaacc aacatcaaca 360
ccagacacaa caagccgccc gcccttcgtc gacacacaca caacaccacc aagtgcaagc 420
aggacaagga caagtccggc agtccacaca aaaaacaatc caagggtaag ccccagaaca 480
cattccccac catgggcaat gacaaggacg gtccgcggaa ccaccactct ccgcacaagc 540
agcacaagaa aaagactgtc tacagcatca gtccaacccg acagcagcgc aacaacccac 600
aaacacgaag aaacaagccc agtgagccca caaacatctg caagcacagc aagaccacaa 660

-continued

```
aggaagggca tggaggccag cacatcaaca acatacaacc aaactagtta acaaaaaata    720

caaaataact ctaagataaa ccatgtagac accaacaatt gagaagccaa aaggcaattc    780

acaatctccc aaaaaagcaa caacaccata ttagctccgc ttaaatctcc ctgaaaaaaa    840

cactcaccca tataccaact ataccacaac catcccaaga aaaaaggctg ggcaaaacaa    900

cacccaa                                                              907
```

<210> SEQ ID NO 90
<211> LENGTH: 908
<212> TYPE: DNA
<213> ORGANISM: human metapneumo virus

<400> SEQUENCE: 90

```
atggaggtga aagtggagaa cattcgaaca atagatatgc tcaaagcaag agtgaaaaat     60

cgtgtggcac gcagcaaatg ctttaaaaat gcctctttga tcctaatagg aataactaca    120

ttgagtatag ccctcaatat ctatctgatc ataaactata caatgcaaga aaacacatcc    180

gaatcagaac atcacaccag ttcatcaccc atggaatcca gcagggaaac tccaacggtc    240

cctatggaca actcagacac caatccaggc tcacagtatc caactcaaca gtccacagaa    300

ggctccacac tccactttgc agcctcagca agctcaccag agacagaacc aacatcaaca    360

ccagacacaa caagccgccc gcccttcgtc gacacacaca caacaccatc aagtgcaagc    420

agaacaaaga caagtccggc agtccacaca aaaaacaatc taaggataag ccccagaaca    480

cattccccac catgggcaat gacaaggacg gtccgtggaa ccaccactct ccgcacaagc    540

agcataagaa aaagaccgtc cacagcatca gtccaacctg acagcagcgc aacaacccac    600

aaacacgaag aagcaagccc agtgagcccg caagcatctg caagcacagc aagaccacaa    660

aggaagggca tggaggccag cacatcaaca acatacaacc aaactagtta acaaaaaata    720

taaaataact ctaagataaa ccatgtagac accaacaatt gagaagccaa aaggcaattc    780

acaatctccc caaaaaggca acaacaccat attagctccg cttaaatctc cctggaaaaa    840

acactcgccc atataccaac tataccacaa ccatcccaag gaaaaaagct gggtaaaaca    900

acacccaa                                                             908
```

<210> SEQ ID NO 91
<211> LENGTH: 908
<212> TYPE: DNA
<213> ORGANISM: human metapneumo virus

<400> SEQUENCE: 91

```
atggaggtga aagtggagaa cattcgaaca atagatatgc tcaaagcaag agtgaaaaat     60

cgtgtggcac gcagcaaatg ctttaaaaat gcctctttga tcctaatagg aataactaca    120

ttgagtatag ccctcaatat ctatctgatc ataaactata caatgcaaga aaacacatcc    180

gaatcagaac atcacaccag ctcatcaccc atggaatcca gcagagaaac tccaacggtc    240

cctatggaca actcagacac caatccaggc tcacagtatc caactcaaca gtccacagaa    300

ggctccacac tccactttgc agcctcagca agctcaccag agacagaacc aacatcaaca    360

ccagacacaa caagccgccc gcccttcgtc gacacacaca caacaccatc aagtgcaagc    420

agaataagga caagtccggc agtccacaca aaaaacaatc taaggataag ccccagaaca    480

cattccccac catgggcaat gacaaggacg gtccgtggaa ccaccactct ccgcacaagc    540

agcataagaa aaagaccgtc cacagcatca gtccaacctg acagcagcgc aacaacccac    600
```

-continued

```
aaacacgaag aagcaagccc agtgagcccg caagcatctg caagcacagc aagaccacaa    660

aggaagggca tggaggccag cacatcaaca acatacaacc aaactagtta acaaaaaata    720

tacaataact ctaagataaa ccatgtagac accaacaatt gagaagccaa aaggcaattc    780

acaatctccc caaaaaggca acaacaccat attagctccg cttaagtctc cctggaaaaa    840

acactcgccc atataccaac tataccacaa ccatccaaag aaaaaaagct gggcaaaaca    900

acacccaa                                                             908
```

<210> SEQ ID NO 92
<211> LENGTH: 888
<212> TYPE: DNA
<213> ORGANISM: human metapneumo virus

<400> SEQUENCE: 92

```
atggaggtga aagtagagaa cattcgagca atagacatgc tcaaagcaag agtgaaaaat     60

cgtgtggcac gtagcaaatg ctttaaaaat gcttctttaa tcctcatagg aataactaca    120

ctgagtatag ctctcaatat ctatctgatc ataaactaca caatacaaaa aaccacatcc    180

gaatcagaac accacaccag ctcaccaccc acagaaccca acaaggaagc ttcaacaatc    240

tccacagaca acccagacat caatccaagc tcacagcatc caactcaaca gtccacagaa    300

aaccccacac tcaaccccgc agcatcagcg agcccatcag aaacagaacc agcatcaaca    360

ccagacacaa caaaccgcct gtcctccgta gacaggtcca cagcacaacc aagtgaaagc    420

agaacaaaga caaaaccgac agtccacaca atcaacaacc caaacacagc ttccagtaca    480

caatccccac cacggacaac aacgaaggca atccgcagag ccaccacttt ccgcatgagc    540

agcacaggaa aaagaccaac cacaacatta gtccagtccg acagcagcac cacaacccaa    600

aatcatgaag aaacaggttc agcgaaccca caggcgtctg caagcacaat gcaaaactag    660

cacaccaata atataaaacc aaattagtta acaaaaaatg cgagatagct ctaaagcaaa    720

acatgtaggt accaacaatc aagaaaccaa aagacaactc acaatctccc taaaacagca    780

acgacaccat gtcagctttg ctcaaatctc tctgggagaa acttctaccc acatactaac    840

aacatcacaa ccatctcaag aaaagaaact gggcaaaaca gcatccaa                888
```

<210> SEQ ID NO 93
<211> LENGTH: 888
<212> TYPE: DNA
<213> ORGANISM: human metapneumo virus

<400> SEQUENCE: 93

```
atggaggtga aagtagagaa cattcgagca atagacatgc tcaaagcaag agtgaaaaat     60

cgtgtggcac gcagcaaatg ctttaaaaat gcttctttaa tcctcatagg aataactaca    120

ctgagtatag ccctcaatat ctatctgatc ataaactaca caatacaaaa aaccacatct    180

gaatcagaac accacactag ctcaccaccc acagaatcca acaaagaaac ttcaacaatc    240

cccatagaca acccagacat caatccaaac tcacagcatc caacccaaca gtccacagaa    300

agccccacac tcaaccccgc agcctcggtg agcccatcag aaacagaacc agcatcaaca    360

ccagacacaa caaaccgcct gtcctccgta gacagatcca caacacaacc aagtgaaagc    420

agaacaaaga caaaaccaac agtccacaca aaaaacaatc caagtacagt ttccagaaca    480

caatccccac tacgggcaac aacgaaggcg gtcctcagag ccaccgcttt ccgcacgagc    540

agcacaagaa aaagaccaac cacaacatca gtccagtctg acagcagcac cacaacccaa    600

aatcatgaag aaacaagttc agcgaaccca caggcatctg caagcacaat gcaaagccag    660
```

-continued cacaccaaca acataaaacc aaattagtta acaaaaaata cgagatagct ctaaagtaaa 720
acatgtaggt accaacaatc aaggaatcaa aagacaactc acaatctccc taaaacagca 780
acaacatcat gtcagttttg ctcaaatctc cctgggagaa actttcgccc acatactaac 840
aacatcacaa ccatctcaag aaaagaaact gggcaaaaca gcacccaa 888

<210> SEQ ID NO 94
<211> LENGTH: 888
<212> TYPE: DNA
<213> ORGANISM: human metapneumo virus

<400> SEQUENCE: 94
atggaggtga aagtagagaa catccgagca gtagacatgc tcaaagcaag agtcaaaaat 60
cgtgtggcac gcagcaaatg ctttaaaaat gcctccttaa tcctcgtagg aataactaca 120
ctgagcatag ccctcaatat ctatctgatc gtaaactaca caatacaaaa aaccacatcc 180
gaatcagaac accacaccag ctcatcaccc acagaatcca acaaaggaac ttcaacaatc 240
cccacagaca acccagacat caatccaaat tcacaacatc caactcaaca gtccacagaa 300
agccccacac tcaacaccgc agcctcggtg agcccatcag aaacagaacc agcatcaaca 360
ccagacacaa caaaccgcct gtcctccgca gacagatcca caacacaacc aagtgaaagc 420
agaacaaaga caaagctgac agtccacaca aaaaacaacc taagtacagc ctccagaaca 480
caatcaccac cacgggcaac aacgaaggcg gtcctcagag acaccgcctt ccacacgagc 540
agcacaggaa aaagaccaac cacaacatca gtccagtctg gcagcagcac cacaactcaa 600
aatcatgaag aaacaagttc atcgaaccca caggcatctg caagcacaat gcaagaccag 660
gacaccaaca atacaaaaca aaattagtta acaaaaaata caagatagct ctaaagtaaa 720
acatgtaggt accaacagta aagaaatcaa aagacaactc acaatctccc caaaacagca 780
acaacatcat gtcagcttcg ctcaaatctc cctgggagaa actctcgccc acatactaac 840
aacatcacaa ctatctcaag aaaagaaact gggcaaaaaa acactcaa 888

<210> SEQ ID NO 95
<211> LENGTH: 887
<212> TYPE: DNA
<213> ORGANISM: human metapneumo virus

<400> SEQUENCE: 95
atggaggtga aagtagagaa catccgagca gtagacatgc tcaaagcaag agttaaaaat 60
cgtgtggcac gcagcaaatg ctttaaaaat gcctctttaa tcctcgtagg aataactaca 120
ctgagtatag ccctcaatat ctatctgatc gtaaactaca caatacaaaa aaccacatcc 180
gaatcagaac accacactag ctcatcaccc acagaatcca acaaaggaac ttcaacaatc 240
ccacagacaa cccagacatc aatccaaatt cacaacatcc aactcaacag tccacagaaa 300
gccccacact caacaccgca gcctcggtga gcccatcaga aacagaacca gcatcaacac 360
cagacacaac aaaccgcctg tcctccgcag acagatccac aacacaacca agtgaaagca 420
gaacaaagac aaagctgaca gtccacacaa aaaacaacct aagtacagcc tccagaacac 480
aatcaccacc acgggcaaca acgaaggcgg tcctcagaga caccgccttc cacacgagca 540
gcacaggaaa aagaccaacc acaacatcag tccagtctgg cagcagcacc acaactcaaa 600
atcatgaaga aacaagttca tcgaacccac aggcatctgc aagcacaatg caagaccagg 660
acaccaacaa tacaaaacaa aattagttaa caaaaaatac aagatagctc taaagtaaaa 720

-continued

```
catgtaggta ccaacagtaa agaaatcaaa agacaactca taatctcccc aaaacagcaa    780

caacatcatg tcagcttcgc tcaaatctcc ctgggagaaa ctctcgccca catactaaca    840

acatcacaac tatctcaaga aaagaaactg ggcaaaaaaa cactcaa                  887
```

<210> SEQ ID NO 96
<211> LENGTH: 888
<212> TYPE: DNA
<213> ORGANISM: human metapneumo virus

<400> SEQUENCE: 96

```
atggaggtga aagtagagaa cattcgagca atagacatgc tcaaagcaag aatgaaaaat     60

cgtgtggcac gcagcaaatg ctttaaaaat gcttctttaa tcctcatagg aataactact    120

ctgagtatag ccctcaatat ctatctgatc ataaactaca caatacaaaa aaccacatct    180

gaatcagaac accacactag ctcaccaccc acagaatcca acaaagaaac ttcaacaatc    240

cctatagaca acccagacat caatccaaac tcacagcatc caactcaaca gtccacagaa    300

agcctcacac tcaaccccgc agcctcggtg agcccatcag aaacagaacc agcatcaaca    360

ccagacacaa caaaccgcct gtcctccgta gacagatcca caacacaacc aagtgaaagc    420

agaacaaaga caaaactgac agtccacaaa aaaaacatcc caagtacagt ctctagaaca    480

caatcctcaa tacgggcaac aacgaaggcg gtcctcagag ccaccgcctt tcgcacgagc    540

agcacaggag aaagaccaac tacaacatca gtccagtctg acagcagcac cacaacccaa    600

aatcatgaag aaacaggttc agcgaaccca caggcatctg caagcacaat gcaaaactag    660

cacaccaaca ttgtaaaacc aaattagtta acaaaaaata tgaaatagct ctaaagtaaa    720

acatgtaggt gctaacaatc aagaaatcaa aagacatctc ataatctctc caaaacagca    780

acaacatcat gtcaactttg ctcaaatctc cctgggagaa actttcgccc ccatactgac    840

aacatcacaa tcatctcaag aaaagaaact gggcaaaaca gcaccaaa                 888
```

<210> SEQ ID NO 97
<211> LENGTH: 888
<212> TYPE: DNA
<213> ORGANISM: human metapneumo virus

<400> SEQUENCE: 97

```
atggaggtga aagtagagaa cattcgagca atagacatgc tcaaagcaag agtgaaaaat     60

cgtgtggcac gcagcaaatg ctttaaaaat gcttctttaa tcctcatagg aataactact    120

ctgagtatag ccctcaacat ctatctgatc ataaactaca caatacaaaa aaccacatct    180

gaatcagaac accacactag ctcaccaccc acagaatcta acaaagaaac ttcaacaatc    240

tctatagaca acccagacat caatccaaac tcacagcatc caactcaaca gtccacagaa    300

agcctcacac tcagccccac agcctcggtg agcccatcag aaacagaacc agcatcaaca    360

tcagacacaa caagccgcct gtcttccgta gacagatcca caacacaacc aagtgaaagc    420

agagcaagga caaaaccgac agtccacaag aaaaacatcc caagtacagt ttctagaaca    480

caatccccac tacgggcaac aacgaaggcg gtcctcagag ccaccgcctt tcgcacgagc    540

agcacaggag agggaccaac cacaacatcg gtccagtctg acagcagcac cacaacccaa    600

aatcatgaag aaacaggttc agcgaaccca caggcatctg caagcacaat gcaaaactag    660

cacaccaaca ttgtaaaacc aaattagtta acaaaaaata tgaaatagtt ctaaagtaaa    720

acatgtaggt gctaacaatc aagaaatcaa aagacaactc ataatctccc taaaacagca    780

acaacatcat gtcaactttg ctcaaatctc cctgggagaa actttcgccc ccatactgac    840
```

-continued

```
aacatcacaa tcatctcaag aaaagaaact gggcaaaaca gcaccaaa                888
```

<210> SEQ ID NO 98
<211> LENGTH: 888
<212> TYPE: DNA
<213> ORGANISM: human metapneumo virus

<400> SEQUENCE: 98

```
atggaggtga aagtagagaa cattcgagca atagacatgc tcaaagcaag agtgaaaaat     60
cgtgtggcac gtagcaaatg ctttaaaaat gcttctttaa tcctcatagg aataactaca    120
ctgagtatag ctctcaatat ctatctgatc ataaactaca caatacaaaa aaccacatct    180
gaatcagaac accacaccag ctcaccaccc acagaatcca acaaggaagc ttcaacaatc    240
tccacagaca atccagacat caatccaaac tcacagcatc caactcaaca gtccacagaa    300
aaccccacac taaaccccgc agcatcggtg agctcatcag aaacagaacc agcatcaaca    360
ccagacacaa caaaccgcct gtcctccgta gacaggtcca cagcacaacc aagtgaaagc    420
agaacaaaga caaaaccgac agtccacaca agaaacaacc caagcacagc ttccagcaca    480
caatccccac cacgggtaac aacgaaggca atcctcagag ccaccgtctt ccgcatgagc    540
agcacaggaa aaagaccagc cacaacatta gtccagtccg acagcagcac cacaacccaa    600
aatcatgaag aaacaggttc agcaaactca caggcatctg caagcacaat gcaaaactag    660
cactccaaca atataaaacc aaattagtta acaaaaaata cgagatagct ctaaagtaaa    720
acatgtaggc accaacaatc aggaaattaa aagacaactc acaacctccc taaaacagca    780
acgacaccat gtcaactttg ctcaaatctc tctgggagaa acttttgccc acatactaac    840
aacatcacaa tcatctcaag aaaagaaact gggcaaaaca gcatccaa                888
```

<210> SEQ ID NO 99
<211> LENGTH: 888
<212> TYPE: DNA
<213> ORGANISM: human metapneumo virus

<400> SEQUENCE: 99

```
atggaggtga aagtagagaa cattcgagca atagacatgc tcaaagcaag agtgaaaaat     60
cgtgtggcac gcagcaaatg ctttaaaaat gcttctttaa tcctcatagg aataactact    120
ctgagtatag ccctcaacat ctatctgatc ataaactaca caatacaaaa aaccacatct    180
gaatcagaac accacactag ctcaccaccc acagaatcta acaaagaaac ttcaacaatc    240
tctatagaca actcagacat caatccaaac tcacagcatc caactcaaca gtccacagaa    300
agcctcacac tcagccccac agcctcggtg agcccatcag aaacagaacc agcatcaaca    360
tcagacacaa caaaccgcct gtcttccgta gacagatcca caacacaacc aagtgaaagc    420
agagcaagaa caaaaccgac agtccacaag aaaaacatcc caagtacagt ttctagaaca    480
caatccccac tacgggcaac aacgaaggcg gtcctcagag ccaccgcctt tcgcatgagc    540
agcacaggag agggaccaac cacaacatcg gtccagtctg acagcagcac cacaacccaa    600
aatcatgaag aaacaggctc agcgaaccca caggcatctg caagcacaat gcaaaaccag    660
cacaccaaca ttgcaaaacc aaattagtta acaaaaaata tgaaatagtt ctaaagtaaa    720
acatgtaggt gccaacaatc aagaaatcaa aagacaactc acaatctccc taaaacagca    780
acaacatcat gccaactttg ctcaaatctc cctgggagaa accctcgccc ccatactgac    840
aacatcacaa tcatctcaag aaaagaaact gggcaaaaca gcaccaaa                888
```

-continued

<210> SEQ ID NO 100
<211> LENGTH: 888
<212> TYPE: DNA
<213> ORGANISM: human metapneumo virus

<400> SEQUENCE: 100
atggaggtga aagtagagaa cattcgagca atagacatgc tcaaagcaag agtgaaaaat 60
cgtgtggcac gcagcaaatg ctttaaaaat gcttctttaa tcctcatagg aataactact 120
ctgagtatag ccctcaatat ctatctgatc ataaactaca caatacaaaa aaccacatct 180
gaatcagaac accacactag ctcaccaccc acagaatcta acaaggaaac ttcaacaatc 240
cctatagaca acccagacat caatccaaac tcacagcatc caactcaaca gtccacagaa 300
agcctcacac tctaccccac atcctcggtg agctcatcag aaacagaacc agcatcaaca 360
ccaggcataa caaaccacct gtcctttgta gacagatcca caacacaacc aagtgaaagc 420
agaacaaaga caaaccggac agtccacaaa aaaaacatct caagtacagt ttctagaaca 480
cagtccccac cacggacaac agcgaaggcg gtccccagag ccaccgccct tcgcacgagc 540
agcacaggag aaagaccaac cacaacacca gtccagcccg atagcagcac cacaacacaa 600
aatcatgaag aaacaggctc agcgaaccca caggcatccg caagcacaat gcaaaaccag 660
cacaccaaca ttgcaagacc aaattagtta acaaaaaata tgaaatagct ctaaagtaaa 720
acatgtaggt gccaacaatc aagaaatcaa aagataactc ataatctctc taaaacatca 780
acaacatcat gttaactttg ctcaaatctc tctgggagaa accttcgccc ccatactggc 840
aacatcacaa tcatctcaag aaaagaaact gggcaaaaca acaccaaa 888

<210> SEQ ID NO 101
<211> LENGTH: 888
<212> TYPE: DNA
<213> ORGANISM: human metapneumo virus

<400> SEQUENCE: 101
atggaggtga aagtagagaa cattcgagca atagacatgc tcaaagcaag agtgaaaaat 60
cgtgtggcac gcagcaaatg ctttaaaaat gcttctttaa tcctcatagg aataactact 120
ctgagtatag ccctcaatat ctatctgatc ataaactaca caatacaaaa aaccacatct 180
gaatcagaac accacactag ctcaccaccc acagaatcta acaaggaaac ttcaacaatc 240
cctatagaca acccagacat caatccaaac tcacagcatc caactcaaca gtccgcagaa 300
agcctcacac tctaccccac atcctcggtg agctcatcag aaacagaacc agcatcaaca 360
ccaggcataa caaaccacct gtcctttgta gacagatcca caacacaacc aagtgaaagc 420
agaacaaaga caaaccggac agtccacaaa aaaaacatct caagtacagt ttctagaaca 480
cagtccccac cacggacaac agcgaaggcg gtccccagag ccaccgccct tcgcacgagc 540
agcacaggag aaagaccaac cacaacacca gtccagcccg atagcagcac cacaacacaa 600
aatcatgaag aaacaggctc agcgaaccca caggcatccg caagcacaat gcaaaaccag 660
cacaccaaca ttgcaagacc aaattagtta acaaaaaata tgaaatagct ctaaagtaaa 720
acatgtaggt gccaacaatc aagaaatcaa aagataactc ataatctctc taaaacatca 780
acaacatcat gttaactttg ctcaaatctc tctgggagaa accttcgccc ccatactggc 840
aacatcacaa tcatctcaag aaaagaaact gggcaaaaca acaccaaa 888

<210> SEQ ID NO 102
<211> LENGTH: 888

<212> TYPE: DNA
<213> ORGANISM: human metapneumo virus

<400> SEQUENCE: 102
atggaggtga aagtagagaa tattcgagca atagacatgc tcaaagcaag agtgaaaaat 60
cgtgtggcac gcagcaaatg ctttaaaaat gcttctttaa tcctcatagg aataactact 120
ctgagtatag ccctcaatat ctatctgatc ataaactaca caatacaaaa aaccacatct 180
gaatcagaac accacactag ctcaccaccc acagaatcta acaaggaaac ttcaacaatc 240
cctatagaca acccagacat caatccaaac tcacagcatc caactcaaca gtccacagaa 300
agcctcacac tctaccccac atcctcggtg agctcatcag aaacagaacc agcatcaaca 360
ccaggcataa caaaccacct gtcctttgta gacagatcca caacacaacc aagtgaaagc 420
agaacaaaga caaaccggac agtccacaaa aaaaacatct caagtacagt ttctagaaca 480
cagtccccac cacggacaac agcgaaggcg gtccccagag ccaccgccct tcgcacgagc 540
agcacaggag aaagaccaac cacaacacca gtccagcccg atagcagcac cacaacacaa 600
aatcatgaag aaacaggctc agcgaaccca caggcatccg caagcacaat gcaaaaccag 660
cacaccaaca ttgcaagacc aaattagtta acaaaaaata tgaaatagct ctaaagtaaa 720
acatgtaggt gccaacaatc aagaaatcaa aagataactc ataatctctc taaaacatca 780
acaacatcat gttaactttg ctcaaatctc tctgggagaa accttcgccc ccatactggc 840
aacatcacaa tcatctcaag aaaagaaact gggcaaaaca acacccaa 888

<210> SEQ ID NO 103
<211> LENGTH: 888
<212> TYPE: DNA
<213> ORGANISM: human metapneumo virus

<400> SEQUENCE: 103
atggaggtga aagtagagaa cattcgagca atagacatgc tcaaagcaag agtgaaaaat 60
cgtgtggcac gtagcaaatg ctttaaaaat gcttctttaa tcctcatagg aataactaca 120
ctgagcatag ccctcaatat ctatctgatc ataaactaca caatacaaca aaccacatct 180
gaatcagaac accacaccag ctcaccaccc acagaatcca acaaggaagc ttcaacaatc 240
tccacagaca acccagacat caatccaaac tcacagcatc caactcaaca gtccacagaa 300
aaccccacac tcaacccagc agcatcagcg agcccatcag aaacagaatc agcatcaaca 360
ccagatacaa caaaccgcct gtcctccgta gacaggtcca cggtacaacc aagtgaaaac 420
agaacaaaga caaaactgac agtccacaca agaaacaacc taagcacagc ctccagtaca 480
caatccccac cacgggcaac aacgaaggca atccgcagag ccaccaccct ccgcatgagc 540
agcacaggaa gaagaccaac cacaacacta gtccagtccg acagcagcac cacaacccaa 600
aatcatgaag aaacaggctc agcgaaccca caggcatctg caagcacaat gcaaaaccag 660
cacaccaaca atataaaacc aaattagtta acaaaaaata cgagatagct ctaaagtaaa 720
acatgtaggc accaacaatc aagaaaccaa aagataactc acaatccccc caaaacagca 780
acgacaccat gtcagctttg ctcaaatctc tctgggagaa acttttgccc acatactaac 840
aacatcacaa ccatctcaag aaaagaaact gggcaaaaca gcatccaa 888

<210> SEQ ID NO 104
<211> LENGTH: 888
<212> TYPE: DNA
<213> ORGANISM: human metapneumo virus -continued

<400> SEQUENCE: 104
atggaggtga aagtagagaa cattcgagca atagacatgc tcaaagcaag agtgaaaaat 60
cgtgtggcac gtagcaaatg ctttaaaaat gcttctttaa tcctcatagg aataactaca 120
ctgagcatag ccctcaatat ctatctgatc ataaactaca caatacaaaa aaccacatct 180
gaatcagaac accacaccag ctcaccaccc acagaatcca acaaggaagc ttcaacaatc 240
tccacagaca acccagacat caatccaaac tcacagcatc caactcaaca gtccacagaa 300
aaccccacac tcaacccagc agcatcagcg agcccatcag aaacagaatc agcatcaaca 360
ccagatacaa caaaccgcct gtcctccgta gacaggtcca cggtacaacc aagtgaaaac 420
agaacaaaga caaaactgac agtccacaca agaaacaacc taagcacagc ctccagtaca 480
caatccccac cacgggcaac aacgaaggca atccgcagag ccaccaccct ccgcatgagc 540
agcacaggaa gaagaccaac cacaacacta gtccagtccg acagcagcac cacaacccaa 600
aatcatgaag aaacaggctc agcgaaccca caggcatctg caagcacaat gcaaaaccag 660
cacaccaaca atataaaacc aaattagtta acaaaaaata cgagatagct ctaaagtaaa 720
acatgtaggc accaacaatc aagaaaccaa aagataactc acaatccccc caaaacagca 780
acgacaccat gtcagctttg ctcaaatctc tctgggagaa acttttgccc acatactaac 840
aacatcacaa ccatctcaag aaaagaaact gggcaaaaca gcatccaa 888

<210> SEQ ID NO 105
<211> LENGTH: 901
<212> TYPE: DNA
<213> ORGANISM: human metapneumo virus

<400> SEQUENCE: 105
atggaagtaa gagtggagaa cattcgagcg atagacatgt tcaaagcaaa gataaaaaac 60
cgtataagaa gcagcaggtg ctatagaaat gctacactga tccttattgg actaacagcg 120
ttaagcatgg cacttaatat tttcctgatc atcgatcatg caacattaag aaacatgatc 180
aaaacagaaa actgtgctaa catgccgtcg gcagaaccaa gcaaaaagac cccaatgacc 240
tccacagcag gcccaaacac caaacccaat ccacagcaag caacacagtg gaccacagag 300
aactcaacat ccccagtagc aaccccagag ggccatccat acacagggac aactcaaaca 360
tcagacacaa cagctcccca gcaaaccaca gacaaacaca cagcaccgct aaaatcaacc 420
aatgaacaga tcacccagac aaccacagag aaaaagacaa tcagagcaac aacccaaaaa 480
agggaaaaag gaaaagaaaa cacaaaccaa accacaagca cagctgcaac ccaaacaacc 540
aacaccacca accaaatcag aaatgcaagt gagacaatca caacatccga cagacccaga 600
actgacacca caacccaaag cagcgaacag acaacccggg caacagaccc aagctcccca 660
ccacaccatg catagagagg tgcaaaactc aaatgagcac aacacacaaa catcccatcc 720
aagtagttaa caaaaaacca caaaataacc ttgaaaacca aaaaaccaaa acataaaccc 780
agacccagaa aaacatagac accatatgga aggttctagc atatgcacca atgagatggc 840
atctgttcat gtatcaatag caccaccatc attcaaggaa taagaagagg cgaaaattta 900
a 901

<210> SEQ ID NO 106
<211> LENGTH: 901
<212> TYPE: DNA
<213> ORGANISM: human metapneumo virus

<400> SEQUENCE: 106

-continued

```
atggaagtaa gagtggagaa cattcgagcg atagacatgt tcaaagcaaa gataaagaac     60
cgtataagaa gcagcaggtg ctatagaaat gctacactga tccttattgg actaacagcg    120
ttaagcatgg cacttaatat tttcctgatc attgatcatg caacattaag aaacatgatc    180
aaaacagaaa actgtgctaa catgccatcg gcagaaccaa gcaaaaagac cccaatgacc    240
tccacagcag gcccaagcac cgaacccaat ccacagcaag caacacaatg gaccacagag    300
aactcaacat ccccagcagc aaccctagag agccatccat acacagggac aacccaaaca    360
ccagacataa cagctcccca acaaaccaca gacaaacaca cagcactgcc aaaatcaacc    420
aatgaacaga tcacccagac aaccacagag aaaaagacaa ccagagcaac aacccaaaaa    480
agggaaaaag aaaaagaaaa cacaaaccaa accacaagca cagctgcaac ccaaacaacc    540
aacaccacca accaaaccag aaatgcaagt gagacaatca caacatccga cagacccaga    600
attgacacca caacccaaag cagcgatcag acaacccggg caacagaccc aagctcccca    660
ccacaccatg cacagagtgg tgcaaaaccc aaatgaacac aacacacaaa catctcatcc    720
aagtagttaa caaaaaacca caaaataacc ttgaaaacca aaaaaccaaa ccacaaactt    780
agacccagaa aaacatagac actatatgga aggtttgagc atatgcacca atgaaatggt    840
atctgttcat gtatcaatag cgccaccatt atttaaggaa taagaagagg caaaaattca    900
a                                                                    901
```

<210> SEQ ID NO 107
<211> LENGTH: 860
<212> TYPE: DNA
<213> ORGANISM: human metapneumo virus

<400> SEQUENCE: 107

```
atggaagtaa gagtggagaa cattcgagcg atagacatgt tcaaagcaaa gataaaaaac     60
cgtataagaa gcagcaggtg ctatagaaat gctacactga tccttattgg actaacagcg    120
ttaagcatgg cacttaatat tttcctgatc atcgatcatg caacattaag aaacatgatc    180
aaaacagaaa attgtgctaa catgccgccg gcagaaccaa gcaaaaagac cccaatgacc    240
tctacagcag gcccaaacac caaacccaat ccacagcaag caacacagtg gaccacggag    300
aactcaacat tcccagcagc aacctcagag ggccatctac acacagggac aactcaaaca    360
ccagacacaa cagctcctca gcaaaccaca gacaaacaca cagcactgcc aaaatcaacc    420
aatgaacaaa tcacccagac aaccacagag aaaaagacaa ccagagcaac aacccaaaga    480
agggaaaaag ggaaagaaaa cacaaaccaa accacaagca cagctgctac ccaaacaacc    540
aacaccacca accaaatcag aaatgcaagc gagacaatca caacatccga cagacccaga    600
actgactcca caacccaaag cagcgaacag acaacccggg caacagaccc aagctcccca    660
ccacatcatg cacagggaag tgcaaaaccc aaatgaacac aacacacaaa catcccatcc    720
aagtagttaa caaaaaatca gacccagaaa aacatagaca ctatatggaa ggtccgagca    780
tatgcaccga tgaaatggca tttgttcatg tatcaatagc gccaccatta tttaaggaat    840
aagaagaggc aaaaattcaa                                                860
```

<210> SEQ ID NO 108
<211> LENGTH: 861
<212> TYPE: DNA
<213> ORGANISM: human metapneumo virus

<400> SEQUENCE: 108

-continued

```
atggaagtaa gagtggagaa cattcgagcg atagacatgt tcaaagcaaa gataaaaaac     60

cgtataagaa gcagcaggtg ctatagaaat gctacactga tccttattgg actaacagcg    120

ttaagcatgg cacttaatat tttcctgatc atcgatcatg caacattaag aaacatgatc    180

aaaacagaaa attgtgctaa catgccgccg gcagaaccaa gcagaaagac cccaatgacc    240

tccacagcag gcccaaacac caaacccaat ccacagcaag caacacagtg gaccacggag    300

aactcaacat ccccagcagc aaccccagag ggccatctac acacagggac aactcaaaca    360

ccagacacaa cagctcctca gcaaaccaca gacaaacaca cagcactgcc aaaatcaacc    420

aatgaacaga tcacccaggc aaccacagag aaaaagacaa ccagagaaac aacccaaaga    480

agggaaaaag gaaaagaaaa cacaaaccaa accacaagca cagctgcaac ccaaacaacc    540

aacaccacca accaaatcag aaatgcaagc gagacaatca caacatccga cagacccaga    600

actgactcca caacccaaag cagcgaacag acaacccagg caacagaccc aagctcccca    660

gcacaccatg cacagggaag tgcaaaaccc aaatgaacac aacacacaaa catcccatcc    720

aagtagttaa caaaaaaatc agacccagaa aaacacagac actatatgga aggtccgagc    780

atatgcaccg atgaaatggc atctgttcat gtatcaatag caccaccatt atttaaggaa    840

taagaagagg caaaaattca a                                               861
```

<210> SEQ ID NO 109
<211> LENGTH: 860
<212> TYPE: DNA
<213> ORGANISM: human metapneumo virus

<400> SEQUENCE: 109

```
atggaagtaa gagtggagaa cattcgagcg atagacatgt tcaaagcaaa gataaaaaac     60

cgtataagaa gcagcaggtg ctatagaaat gctacattga tccttattgg actaacagcg    120

ttaagcatgg cacttaatat tttcctgatc atcgatcatg caacattaag aaacatgatc    180

aaaacagaaa attgtgctaa catgccaccg gcagaaccaa gcaaaaagac cccaatgacc    240

tccacagcag gcctaaacac taaacccaat ccacagcaag caacacagtg gaccacggag    300

aactcaacat ccccagcagc aaccccagag ggccatctac acacagggac aactcaaaca    360

ccagacacaa cagctcctca gcaaaccaca gacaagcaca cagcactgcc aaaatcaacc    420

aatgaacaga tcacccagac aaccacagag aaaaagacaa ccagagcaac aacccaaaga    480

agggaaaaag gaaaagaaaa cacaaaccaa accacaagca cagctgcaac ccaaacaacc    540

aacaccacca accaaatcag aaatgcaagc gagacaatca caacatccga cagacccaga    600

actgactcca caacccaaag cagcgaacag acaacccggg caacagaccc aagctcccca    660

ccacaccatg cacagggaag tgcaaaaccc aaatgaacac aacacacaaa catcccatcc    720

aagtagttaa caaaaaatca gacccagaaa aacatagaca ctatatggaa ggtccgagca    780

tatgcaccga tgaaatggca tctgttcatg tatcaatagc gccaccatta tttaaggaat    840

aagaagaggc aaaaattcaa                                                 860
```

<210> SEQ ID NO 110
<211> LENGTH: 860
<212> TYPE: DNA
<213> ORGANISM: human metapneumo virus

<400> SEQUENCE: 110

```
atggaagtaa gagtggagaa cattcgagcg atagacatgt tcaaagcaaa gataaaaaac     60

cgtataagaa gcagcaggtg ctatagaaat gctacactga tccttattgg actaacagcg    120
```

-continued

```
ttaagcatgg cacttaatat tttcctgatc atcgatcatg caacattaag aaacatgatc    180
aaaacagaaa attgtgctaa catgccgccg gcagaaccaa gcaaaaagac cccaatgacc    240
tccacagcag gcccaaacac caaacccaat ccacagcaag caacacagtg gaccacggag    300
aactcaacat ccccagcagc aaccccagag ggccatctac acacagggac aactcaaaca    360
ccagacacaa cagctcctca gcaaaccaca gacaaacaca cagcactgcc aaaatcaacc    420
aatgaacaga tcacccagac aaccacagag aaaaagacaa ccagagcaac aacccaaaga    480
agggaaaaag gaaaagaaaa cacaaaccaa accacaagca cagctgcaac ccaaacaacc    540
aacaccacca accaaatcag aaatgcaatt gagacaatca caacatccga cagacccaga    600
actgactcca caacccaaag cagcgaacag acaacccggg caacagaccc aagctcccac    660
ccacaccatg cacagggaag tgcaaaaccc aaatgaacac aacacacaaa catcccatcc    720
aagtagttaa caaaaaatca gacccagaaa aacatagaca ctatatggaa ggtccgagca    780
tatgcaccga tgaaatggca tctgttcatg tatcaatagc gccaccatta tttaaggaat    840
aagaagaggc aagaattcaa                                                860
```

<210> SEQ ID NO 111
<211> LENGTH: 886
<212> TYPE: DNA
<213> ORGANISM: human metapneumo virus

<400> SEQUENCE: 111

```
atggaagtaa gagtggagaa cattcgggca atagacatgt tcaaagcaaa aatgaaaaac     60
cgtataagaa gtagcaagtg ctatagaaat gctacactga tccttattgg attaacagca    120
ttaagtatgg cacttaatat ttttttaatc attgattatg caatgttaaa aaacatgacc    180
aaagtggaac actgtgttaa tatgccgccg gtagaaccaa gcaagaagac cccaatgacc    240
tctgcagtag acttaaacac caaacccaat ccacagcagg caacacagtt ggccgcagag    300
gattcaacat ctctagcagc aacctcagag gaccatctac acacagggac aactccaaca    360
ccagatgcaa cagtctctca gcaaaccaca gacgagtaca caacattgct gagatcaacc    420
aacagacaga ccacccaaac aaccacagag aaaaagccaa ccggagcaac aaccaaaaaa    480
gaaaccacaa ctcgaactac aagcacagct gcaacccaaa cactcaacac taccaaccaa    540
actagctatg tgagagaggc aaccacaaca tccgccagat ccagaaacag tgccacaact    600
caaagcagcg accaaacaac ccaggcagca gacccaagct cccaaccaca ccatacacag    660
aaaagcacaa caacaacata caacacagac acatcctctc caagtagtta acaaaaaaac    720
tataaaataa tcatgaaaac cgaaaaacta gaaaagttaa tttgaactca gaaaagaaca    780
caaacactat atgaattgtt tgagcgtata tactaatgaa atagcatctg tttgtgcatc    840
aataatacca tcattattta agaaataaga agaagctaaa attcaa                   886
```

<210> SEQ ID NO 112
<211> LENGTH: 889
<212> TYPE: DNA
<213> ORGANISM: human metapneumo virus

<400> SEQUENCE: 112

```
atggaagtaa gagtggagaa cattcggaca atagacatgt tcaaagcaaa gatgaaaaac     60
cgtataagaa gcagcaagtg ctatagaaat gctacactga tccttattgg actgacagca    120
ttaagtatgg cacttaatat tttcttgatc atcgattatg caacatttaa aaacatgacc    180
```

-continued

```
aaagtggaac actgtgctaa tatgccgccg gtagaaccga gtaagaagac cccaatgacc    240
tctacagtag actcaagcac cggacccaat ccacagcaga caacacagtg gaccacagag    300
gattcaacat ctctagcagc aacctcagag gaccatctac acacagggac aactccaaca    360
ctagatgcaa cagtttctca gcaaacccca gacaagcaca caacaccgct gagatcaacc    420
aatggacaga ccacccagac aaccacagag aaaaagccaa ccagagcaat agccaaaaaa    480
gaaaccacaa accaaaccac aagcacagct gcaacccaaa cattcaacac caccaatcaa    540
accagaaatg gaagagagac aaccataaca tctgccagat ccagaaacga cgccacaact    600
caaagcagcg aacaaacaaa ccagacaaca gacccaagct cccaaccaca tcatgcatag    660
ataagcacaa taacaatatg aacacaacac agacacatct tctccaagta gttaacaaaa    720
aactataaaa taaccatgaa aaccaaaaaa ctagaaaagt aaatttgaac tcagaaaaga    780
acacaaacac taaatgaatt gtttgagcat atatactaat gaaatagcat ctgttcatgc    840
atcaataata ccatcattac ttaagaaata agaagaagca aaaattcaa                889
```

<210> SEQ ID NO 113
<211> LENGTH: 885
<212> TYPE: DNA
<213> ORGANISM: human metapneumo virus

<400> SEQUENCE: 113

```
atggaagtaa gagtggagaa cattcgggca atagacatgt tcaaagcaaa gatgaaaaac     60
cgtataagaa gtagcaagtg ctatagaaat gctacactga tccttattgg attaacagca    120
ttaagtatgg cacttaatat ttttttaatc attgattatg caatgttaaa aaacatgacc    180
aaagtggaac actgtgttaa tatgccgccg gtagaaccaa gcaagaagac cccaatgacc    240
tctgcagtag acttaaacac caaactcaat ccacagcagg caacacagtt gaccacagag    300
gattcaacat ctctagcagc aacctcggag gatcatttac tcacagggac aactccaaca    360
ccagatgcaa cagtctctca gcaaaccaca gacgagcaca caacactgct gagatcaacc    420
aacagacaga ccacccaaac aaccacagag aaaaagccaa ccggagcaac aaccaaaaaa    480
gaaaccacaa ctcgaaccac aagcacagct gcaacccaaa cactcaacac caccaaccaa    540
actagcaatg gaagagaggc aaccacaaca tccaccagat ccagaaacgg tgccacaact    600
caaaacagcg atcaaacaac ctagacagca gacccaagct cccaaccaca ccatacacag    660
aaaagcacaa caacaacata caacacagac acatcttctc caagtagtta acaaaaaact    720
ataaaataac catgaaaact aaaaaactag aaaagttaat ttgaactcag aaaagaacac    780
aaacactata tgaattgttt gagcgtatat actaatgaaa tagcatctgt ttgtgcatca    840
ataataccat cattatttaa gaaataagaa gaagctaaaa ttcaa                    885
```

<210> SEQ ID NO 114
<211> LENGTH: 885
<212> TYPE: DNA
<213> ORGANISM: human metapneumo virus

<400> SEQUENCE: 114

```
atggaagtaa gagtggagaa cattcgggca atagacatgt tcaaagcaaa gatgaaaaac     60
cgcataagaa gtagcaagtg ctatagaaat gctacactga tccttattgg attaacagca    120
ttaagtatgg cacttaatat ttttttaatc attgattatg caacattaaa aaacatgacc    180
aaagtggaac actgtgttaa tatgccgccg gtagaaccaa gcaagaagac cccaatgacc    240
tctgcagtag acttaaacac caaactcaat ccacagcagg caacacagtt gaccacagag    300
```

-continued gattcaacat ctctagcagc aacctcagag ggccatccac acacaggaac aactccaaca 360
ccagacgcaa cagtctctca gcaaaccaca gacgagcaca caacactgct gagatcaacc 420
aacagacaga ccacccaaac agccacagag aaaaagccaa ctggagcaac aaccaaaaaa 480
gaaaccacaa cccgaactac aagtacagct gcaacccaaa cacccaacac caccaaccaa 540
accagcaatg gaagagaggc aaccacaaca tccgccaggt ccagaaacgg tgccacaact 600
caaaacagcg atcaaataac ccaggcagca gactcaagct cccaaccaca ccatacacag 660
aaaagcacaa caacagcata caacacagac acatcttttc caagtagtta acaaaaaact 720
ataaaataac catgaaaacc aaaaaactag aaaagttaat ttgaactcag aaaagaacac 780
aaacactata tgaattgttt gagcgtatat actaatgaaa tagcatctgt ttgtgcatca 840
ataataccat cattatttaa gaaataagaa gaagctaaaa ttcaa 885

<210> SEQ ID NO 115
<211> LENGTH: 886
<212> TYPE: DNA
<213> ORGANISM: human metapneumo virus

<400> SEQUENCE: 115
atggaagtaa gagtggagaa cattcgggca atagacatgt tcaaagcaaa gatgaaaaac 60
cgtataagaa gtagcaagtg ctatagaaat gctacactga tccttattgg attaacagca 120
ctaagtatgg cacttaatat ttttttaatc attgattatg caacattaaa aaacatgacc 180
aaagtggaac actgtgttaa tatgccgccg gtagaaccaa gcaagaagac cccaatgacc 240
tctgcagtag actcaaacac caaacccaat ccacagcagg caacacagtt gaccacagag 300
gattctacat ctttagcagc aaccctagag gaccatccac acacagggac aactccaaca 360
ccagatgcaa cagtctctca gcaaaccaca gacgagcaca caacactgct gagatcaacc 420
aacagacaga ccacccaaac aactgcagag aaaaagccaa ccagggcaac aaccaaaaaa 480
gaaaccacaa ctcgaaccac aagcacagct gcaacccaaa cactcaacac caccaaccaa 540
actagcaatg gaagagaggc aaccacaaca tctgccagat ccagaaacaa tgccacaact 600
caaagcagcg atcaaacaac ccaggcagca gaaccaagct cccaatcaca acatacacag 660
aaaagcacaa caacaacata caacacagac acatcttctc taagtagtta acaaaaaaac 720
tataaaataa ccatgaaaac caaaaaacta gaaaagttaa tttgaactca gaaaagaaca 780
caaacactat atgaattatt tgagcgtata tactaatgaa atagcatctg tttgtgcatc 840
aataatacca tcattattta agaaataaga agaagctaaa attcaa 886

<210> SEQ ID NO 116
<211> LENGTH: 887
<212> TYPE: DNA
<213> ORGANISM: human metapneumo virus

<400> SEQUENCE: 116
atggaagtaa gagtggagaa cattcgggca atagacatgt tcaaagcaaa gatgaaaaac 60
cgtataagaa gtagcaagtg ctatagaaat gctacactga tccttattgg attatcagca 120
ctaagtatgg cacttaatat ttttttaatc attgattatg caaaatcaaa aaacatgacc 180
agagtggaac actgtgtcaa tatgccgccg gtagaaccaa gcaagaagac cccaatgacc 240
tctgcagtag acttaaacac caaacccaat ccacagcggg caacacagtt gaccacagag 300
gattcaacat ctctagcagc aaccctagag ggccatctac acacagggac aactccaaca 360

-continued

```
ccagatgtaa cagtctctca gcaaaccaca gacgagcaca caacactgct gagatcaacc    420

aacagacaga ccacccaaac agccgcagag aaaaagccaa ccagagtaac aactaacaaa    480

gaaaccataa ctcgaaccac aagcacagcc gcaacccaaa cactcaacac caccaaccaa    540

accaacaatg gaagagaggc aaccacaaca tctgccagat ccagaaacaa tgccacaact    600

caaagcagcg accaaacaac ccaggcagca gacccaagct cccaatcaca acatacacag    660

aaaagcataa caacaacata caacacagac acatcttctc caagtagtta acaaaaaaac    720

tataaaataa ccatgaaaac caaaaaaact agaaaagtta atttgaactc agaaaagaac    780

acaaacacta tatgaattgt ttgagcgtat atactaatga aatagcatct gtttgtgcat    840

caataatacc atcattattt aagaattaag aagaagctaa aattcaa                  887
```

<210> SEQ ID NO 117
<211> LENGTH: 887
<212> TYPE: DNA
<213> ORGANISM: human metapneumo virus

<400> SEQUENCE: 117

```
atggaagtaa gagtggagaa cattcgggca atagacatgt tcaaagcaaa gatgaaaaac     60

cgtataagaa gtagcaagtg ctatagaaat gctacactga tccttattgg attatcagca    120

ctaagtatgg cacttaatat ttttttaatc attgattatg caaaatcaaa aaccatgacc    180

agagtggaac actgtgttaa tatgccgccg gtagaaccaa gcaagaagac cccaatgacc    240

tctgcagtag acttaaacac caaacccaat ccacagcagg caacacagtt gaccacagag    300

gattcaacat ctccagcagc aaccctagag ggccatctac acacagggac aactccaaca    360

ccagatgcaa cagtctctca gcaaaccaca gacgagcaca caacactgct gagatcaacc    420

aacagacaga ccacccaaac aaccgcagag aaaaagccaa ccagagcaac aaccaaaaaa    480

gaaaccataa ctcgaaccac aagcacagct gcaacccaaa cactcaacac caccaaccaa    540

accagcaatg gaagagaggc aaccacaaca tctgccagat ccagaaacaa tgccacaact    600

caaagcagcg accaaacaac ccaggcagca gacccaagct cccaatcaca acatacaaag    660

aaaagcacaa caacaacata caacacagac acatcttctc caagtagtta acaaaaaaac    720

tataaaataa ccatgaaaac caaaaaaact agaaaagtta atttgaactc agaaaagaac    780

acaaacacta tatgaattgt ttgagcgtat atactaatga aatagcatct gtttgtgcat    840

caataatacc atcattattt aagaattaag aagaagctaa aattcaa                  887
```

<210> SEQ ID NO 118
<211> LENGTH: 886
<212> TYPE: DNA
<213> ORGANISM: human metapneumo virus

<400> SEQUENCE: 118

```
atggaagtaa gagtggagaa cattcgggca atagacatgt tcaaagcaaa gatgaaaaac     60

cgtataagaa gtagcaagtg ctatagaaat gctacactga tccttattgg attaacagca    120

ctaagtatgg cacttaatat ttttttaatc attgattatg caacattaaa aaacatgacc    180

aaagtggaac actgtgttaa tatgccgccg gtagaaccaa gcaagaagac cccaatgacc    240

tctgcagtag acttaaacac caaacccaat ccacagcagg caacacagtt gaccacagag    300

gactctacat ctttagcagc aaccctagag gaccatccac acacagggac aactccaaca    360

ccagatgcaa cagtctctca gcaaaccaca gacgagcaca caacactgct gagatcaacc    420

aacagacaga ccacccaaac aactgcagag aaaaagccaa ccagagcaac aaccaaaaaa    480
```

-continued

```
gaaaccacaa ctcgaaccac aagcacagct gcaacccaaa cactcaacac caccaaccaa    540
actagcaatg gaagagaggc aaccacaaca tctgccagat ccagaaacaa tgccacaact    600
caaagcagcg atcaaacaac ccaagcagca gaaccaaact cccaatcaca acatacacag    660
aaaagcacaa caacaacata caacacagac acatcttctc taagtagtta acaaaaaaac    720
tataaaataa ccatgaaaac caaaaaacta gaaaagttaa tttgaactca gaaaggaaca    780
caaacactat atgaattatt tgagcgtata tactaatgaa atagcatctg tttgtgcatc    840
aataatacca tcattattta agaaataaga agaagctaaa attcaa                   886
```

<210> SEQ ID NO 119
<211> LENGTH: 236
<212> TYPE: PRT
<213> ORGANISM: human metapneumo virus

<400> SEQUENCE: 119

```
Met Glu Val Lys Val Glu Asn Ile Arg Thr Ile Asp Met Leu Lys Ala
 1               5                  10                  15

Arg Val Lys Asn Arg Val Ala Arg Ser Lys Cys Phe Lys Asn Ala Ser
            20                  25                  30

Leu Val Leu Ile Gly Ile Thr Thr Leu Ser Ile Ala Leu Asn Ile Tyr
        35                  40                  45

Leu Ile Ile Asn Tyr Lys Met Gln Lys Asn Thr Ser Glu Ser Glu His
    50                  55                  60

His Thr Ser Ser Ser Pro Met Glu Ser Ser Arg Glu Thr Pro Thr Val
65                  70                  75                  80

Pro Thr Asp Asn Ser Asp Thr Asn Ser Ser Pro Gln His Pro Thr Gln
                85                  90                  95

Gln Ser Thr Glu Gly Ser Thr Leu Tyr Phe Ala Ala Ser Ala Ser Ser
            100                 105                 110

Pro Glu Thr Glu Pro Thr Ser Thr Pro Asp Thr Thr Asn Arg Pro Pro
        115                 120                 125

Phe Val Asp Thr His Thr Thr Pro Pro Ser Ala Ser Arg Thr Lys Thr
    130                 135                 140

Ser Pro Ala Val His Thr Lys Asn Asn Pro Arg Thr Ser Ser Arg Thr
145                 150                 155                 160

His Ser Pro Pro Arg Ala Thr Thr Arg Thr Ala Arg Arg Thr Thr Thr
                165                 170                 175

Leu Arg Thr Ser Ser Thr Arg Lys Arg Pro Ser Thr Ala Ser Val Gln
            180                 185                 190

Pro Asp Ile Ser Ala Thr Thr His Lys Asn Glu Glu Ala Ser Pro Ala
        195                 200                 205

Ser Pro Gln Thr Ser Ala Ser Thr Thr Arg Ile Gln Arg Lys Ser Val
    210                 215                 220

Glu Ala Asn Thr Ser Thr Thr Tyr Asn Gln Thr Ser
225                 230                 235
```

<210> SEQ ID NO 120
<211> LENGTH: 236
<212> TYPE: PRT
<213> ORGANISM: human metapneumo virus

<400> SEQUENCE: 120

```
Met Glu Val Lys Val Glu Asn Ile Arg Thr Ile Asp Met Leu Lys Ala
 1               5                  10                  15
```

-continued

```
Ser Val Lys Asn Arg Val Ala Arg Ser Lys Cys Phe Lys Asn Ala Ser
            20                  25                  30

Leu Val Leu Ile Gly Ile Thr Thr Leu Ser Ile Ala Leu Asn Ile Tyr
        35                  40                  45

Leu Ile Ile Asn Tyr Lys Met Gln Lys Asn Thr Ser Glu Ser Glu His
    50                  55                  60

His Thr Ser Ser Ser Pro Met Glu Ser Ser Arg Glu Thr Pro Thr Val
65                  70                  75                  80

Pro Thr Asp Asn Ser Asp Thr Asn Ser Ser Pro Gln His Pro Thr Gln
                85                  90                  95

Gln Ser Thr Glu Gly Ser Thr Leu Tyr Phe Ala Ala Ser Ala Ser Ser
            100                 105                 110

Pro Glu Thr Glu Pro Thr Ser Thr Pro Asp Thr Thr Asn Arg Pro Pro
        115                 120                 125

Phe Val Asp Thr His Thr Thr Pro Pro Ser Ala Ser Arg Thr Lys Thr
    130                 135                 140

Ser Pro Ala Val His Thr Lys Asn Asn Pro Arg Thr Ser Ser Arg Thr
145                 150                 155                 160

His Ser Pro Pro Arg Ala Thr Thr Arg Thr Ala Arg Arg Thr Thr Thr
                165                 170                 175

Leu Arg Thr Ser Ser Thr Arg Lys Arg Pro Ser Thr Ala Ser Val Gln
            180                 185                 190

Pro Asp Ile Ser Ala Thr Thr His Lys Asn Glu Glu Ala Ser Pro Ala
        195                 200                 205

Ser Pro Gln Thr Ser Ala Ser Thr Thr Arg Ile Gln Arg Lys Ser Val
    210                 215                 220

Glu Ala Asn Thr Ser Thr Thr Tyr Asn Gln Thr Ser
225                 230                 235


<210> SEQ ID NO 121
<211> LENGTH: 236
<212> TYPE: PRT
<213> ORGANISM: human metapneumo virus

<400> SEQUENCE: 121

Met Glu Val Lys Val Glu Asn Ile Arg Thr Ile Asp Met Leu Lys Ala
 1               5                  10                  15

Arg Val Lys Asn Arg Val Ala Arg Ser Lys Cys Phe Lys Asn Ala Ser
            20                  25                  30

Leu Val Leu Ile Gly Ile Thr Thr Leu Ser Ile Ala Leu Asn Ile Tyr
        35                  40                  45

Leu Ile Ile Asn Tyr Lys Met Gln Lys Asn Thr Ser Glu Ser Glu His
    50                  55                  60

His Thr Ser Ser Ser Pro Met Glu Ser Ser Arg Glu Thr Pro Thr Val
65                  70                  75                  80

Pro Thr Asp Asn Ser Asp Thr Asn Ser Ser Pro Gln His Pro Thr Gln
                85                  90                  95

Gln Ser Thr Glu Gly Ser Thr Leu Tyr Phe Ala Ala Ser Ala Asn Ser
            100                 105                 110

Pro Glu Thr Glu Pro Thr Ser Thr Pro Asp Thr Thr Asn Arg Pro Pro
        115                 120                 125

Phe Val Asp Thr His Thr Thr Pro Pro Ser Ala Ser Arg Thr Lys Thr
    130                 135                 140

Ser Pro Ala Val His Thr Lys Asn Asn Pro Arg Ile Ser Ser Arg Thr
145                 150                 155                 160
```

-continued

```
His Ser Pro Pro Trp Ala Thr Thr Arg Thr Ala Arg Arg Thr Thr Thr
                165                 170                 175

Leu Arg Thr Ser Ser Thr Arg Lys Arg Pro Ser Thr Ala Ser Ala Gln
            180                 185                 190

Pro Asp Ile Ser Ala Thr Thr His Lys Asn Glu Glu Ala Ser Pro Ala
        195                 200                 205

Ser Pro Gln Thr Ser Ala Ser Thr Thr Arg Thr Gln Arg Lys Ser Val
    210                 215                 220

Glu Ala Asn Thr Ser Thr Thr Tyr Asn Gln Thr Ser
225                 230                 235


<210> SEQ ID NO 122
<211> LENGTH: 236
<212> TYPE: PRT
<213> ORGANISM: human metapneumo virus

<400> SEQUENCE: 122

Met Glu Val Lys Val Glu Asn Ile Arg Thr Ile Asp Met Leu Lys Ala
 1               5                  10                  15

Arg Val Lys Asn Arg Val Ala Arg Ser Lys Cys Phe Lys Asn Ala Ser
            20                  25                  30

Leu Val Leu Ile Gly Ile Thr Thr Leu Ser Ile Ala Leu Asn Ile Tyr
        35                  40                  45

Leu Ile Ile Asn Tyr Lys Met Gln Lys Asn Thr Ser Glu Ser Glu His
    50                  55                  60

His Thr Ser Ser Ser Pro Met Glu Ser Ser Arg Glu Thr Pro Thr Val
65                  70                  75                  80

Pro Thr Asp Asn Ser Asp Thr Asn Ser Ser Pro Gln His Pro Thr Gln
                85                  90                  95

Gln Ser Thr Glu Gly Ser Thr Leu Tyr Phe Ala Ala Ser Ala Asn Ser
            100                 105                 110

Pro Glu Thr Glu Pro Thr Ser Thr Pro Asp Thr Thr Asp Arg Pro Pro
        115                 120                 125

Phe Val Asp Thr His Thr Thr Pro Pro Ser Ala Ser Arg Thr Lys Thr
    130                 135                 140

Ser Pro Ala Val His Thr Lys Asn Asn Pro Arg Ile Ser Ser Arg Thr
145                 150                 155                 160

His Ser Pro Pro Trp Ala Thr Thr Arg Thr Ala Arg Arg Thr Thr Thr
                165                 170                 175

Leu Arg Thr Ser Ser Thr Arg Lys Arg Pro Ser Thr Ala Ser Val Gln
            180                 185                 190

Pro Asp Ile Ser Ala Thr Thr His Lys Asn Glu Glu Ala Ser Pro Ala
        195                 200                 205

Ser Pro Gln Thr Ser Ala Ser Thr Thr Arg Thr Gln Arg Lys Ser Val
    210                 215                 220

Glu Ala Asn Thr Ser Thr Thr Tyr Asn Gln Thr Ser
225                 230                 235


<210> SEQ ID NO 123
<211> LENGTH: 236
<212> TYPE: PRT
<213> ORGANISM: human metapneumo virus

<400> SEQUENCE: 123

Met Glu Val Lys Val Glu Asn Ile Arg Thr Ile Asp Met Leu Lys Ala
 1               5                  10                  15
```

-continued

Arg Val Lys Asn Arg Val Ala Arg Ser Lys Cys Phe Lys Asn Ala Ser
            20                  25                  30

Leu Val Leu Ile Gly Ile Thr Thr Leu Ser Ile Ala Leu Asn Ile Tyr
        35                  40                  45

Leu Ile Ile Asn Tyr Lys Met Gln Lys Asn Thr Ser Glu Ser Glu His
    50                  55                  60

His Thr Ser Ser Ser Pro Met Glu Ser Ser Arg Glu Thr Pro Thr Val
65                  70                  75                  80

Pro Thr Asp Asn Ser Asp Thr Asn Ser Ser Pro Gln His Pro Thr Gln
                85                  90                  95

Gln Ser Thr Glu Gly Ser Thr Leu Tyr Phe Ala Ala Ser Ala Ser Ser
            100                 105                 110

Pro Glu Thr Glu Pro Thr Ser Thr Pro Asp Thr Thr Asp Arg Pro Pro
        115                 120                 125

Phe Val Asp Thr His Thr Thr Pro Pro Ser Ala Ser Arg Thr Lys Thr
    130                 135                 140

Ser Pro Ala Val His Thr Lys Asn Asn Pro Arg Ile Ser Ser Arg Thr
145                 150                 155                 160

His Ser Pro Pro Trp Ala Thr Thr Arg Thr Ala Arg Arg Thr Thr Thr
                165                 170                 175

Leu Arg Thr Ser Ser Thr Arg Lys Arg Pro Ser Thr Ala Ser Val Gln
            180                 185                 190

Pro Asp Ile Ser Ala Thr Thr His Lys Asn Glu Glu Ala Ser Pro Ala
        195                 200                 205

Ser Pro Gln Thr Ser Ala Ser Thr Thr Arg Thr Gln Arg Lys Ser Val
    210                 215                 220

Glu Ala Asn Thr Ser Thr Thr Tyr Asn Gln Thr Ser
225                 230                 235

<210> SEQ ID NO 124
<211> LENGTH: 236
<212> TYPE: PRT
<213> ORGANISM: human metapneumo virus

<400> SEQUENCE: 124

Met Glu Val Lys Val Glu Asn Ile Arg Thr Ile Asp Met Leu Lys Ala
1               5                   10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Met Gln Glu Asn Thr Ser Glu Ser Glu His
    50                  55                  60

His Thr Ser Ser Ser Pro Met Glu Ser Ser Arg Glu Thr Pro Thr Val
65                  70                  75                  80

Pro Ile Asp Asn Ser Asp Thr Asn Pro Gly Ser Gln Tyr Pro Thr Gln
                85                  90                  95

Gln Ser Thr Glu Asp Ser Thr Leu His Ser Ala Ala Ser Ala Ser Ser
            100                 105                 110

Pro Glu Thr Glu Pro Thr Ser Thr Pro Asp Thr Thr Ser Arg Pro Pro
        115                 120                 125

Phe Val Asp Thr His Thr Thr Pro Pro Ser Ala Ser Arg Thr Arg Thr
    130                 135                 140

Ser Pro Ala Val His Thr Lys Asn Asn Pro Arg Val Ser Pro Arg Thr

-continued

```
145                 150                 155                 160

His Ser Pro Pro Trp Ala Met Thr Arg Thr Val Arg Gly Thr Thr Thr
                165                 170                 175

Leu Arg Thr Ser Ser Thr Arg Lys Arg Leu Ser Thr Ala Ser Val Gln
            180                 185                 190

Pro Asp Ser Ser Ala Thr Thr His Lys His Glu Glu Thr Ser Pro Val
        195                 200                 205

Ser Pro Gln Thr Ser Ala Ser Thr Ala Arg Pro Gln Arg Lys Gly Met
    210                 215                 220

Glu Ala Ser Thr Ser Thr Thr Tyr Asn Gln Thr Ser
225                 230                 235


<210> SEQ ID NO 125
<211> LENGTH: 236
<212> TYPE: PRT
<213> ORGANISM: human metapneumo virus

<400> SEQUENCE: 125

Met Glu Val Lys Val Glu Asn Ile Arg Thr Ile Asp Met Leu Lys Ala
 1               5                  10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Met Gln Glu Asn Thr Ser Glu Ser Glu His
    50                  55                  60

His Thr Ser Ser Ser Pro Met Glu Ser Ser Arg Glu Thr Pro Thr Val
65                  70                  75                  80

Pro Met Asp Asn Ser Asp Thr Asn Pro Gly Ser Gln Tyr Pro Thr Gln
                85                  90                  95

Gln Ser Thr Glu Gly Ser Thr Leu His Phe Ala Ala Ser Ala Ser Ser
            100                 105                 110

Pro Glu Thr Glu Pro Thr Ser Thr Pro Asp Thr Thr Ser Arg Pro Pro
        115                 120                 125

Phe Val Asp Thr His Thr Thr Pro Ser Ser Ala Ser Arg Thr Lys Thr
    130                 135                 140

Ser Pro Ala Val His Thr Lys Asn Asn Leu Arg Ile Ser Pro Arg Thr
145                 150                 155                 160

His Ser Pro Pro Trp Ala Met Thr Arg Thr Val Arg Gly Thr Thr Thr
                165                 170                 175

Leu Arg Thr Ser Ser Ile Arg Lys Arg Pro Ser Thr Ala Ser Val Gln
            180                 185                 190

Pro Asp Ser Ser Ala Thr Thr His Lys His Glu Glu Ala Ser Pro Val
        195                 200                 205

Ser Pro Gln Ala Ser Ala Ser Thr Ala Arg Pro Gln Arg Lys Gly Met
    210                 215                 220

Glu Ala Ser Thr Ser Thr Thr Tyr Asn Gln Thr Ser
225                 230                 235


<210> SEQ ID NO 126
<211> LENGTH: 236
<212> TYPE: PRT
<213> ORGANISM: human metapneumo virus

<400> SEQUENCE: 126

Met Glu Val Lys Val Glu Asn Ile Arg Thr Ile Asp Met Leu Lys Ala
```

-continued

```
1               5                   10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Met Gln Glu Asn Thr Ser Glu Ser Glu His
    50                  55                  60

His Thr Ser Ser Ser Pro Met Glu Ser Ser Arg Glu Thr Pro Thr Val
65                  70                  75                  80

Pro Met Asp Asn Ser Asp Thr Asn Pro Gly Ser Gln Tyr Pro Thr Gln
                85                  90                  95

Gln Ser Thr Glu Gly Ser Thr Leu His Phe Ala Ala Ser Ala Ser Ser
            100                 105                 110

Pro Glu Thr Glu Pro Thr Ser Thr Pro Asp Thr Thr Ser Arg Pro Pro
        115                 120                 125

Phe Val Asp Thr His Thr Thr Pro Ser Ser Ala Ser Arg Ile Arg Thr
    130                 135                 140

Ser Pro Ala Val His Thr Lys Asn Asn Leu Arg Ile Ser Pro Arg Thr
145                 150                 155                 160

His Ser Pro Pro Trp Ala Met Thr Arg Thr Val Arg Gly Thr Thr Thr
                165                 170                 175

Leu Arg Thr Ser Ser Ile Arg Lys Arg Pro Ser Thr Ala Ser Val Gln
            180                 185                 190

Pro Asp Ser Ser Ala Thr Thr His Lys His Glu Glu Ala Ser Pro Val
        195                 200                 205

Ser Pro Gln Ala Ser Ala Ser Thr Ala Arg Pro Gln Arg Lys Gly Met
    210                 215                 220

Glu Ala Ser Thr Ser Thr Thr Tyr Asn Gln Thr Ser
225                 230                 235


<210> SEQ ID NO 127
<211> LENGTH: 228
<212> TYPE: PRT
<213> ORGANISM: Human metapneumo virus
<220> FEATURE:
<221> NAME/KEY: VARIANT
<222> LOCATION: 220
<223> OTHER INFORMATION: Xaa = unknown amino acid or other

<400> SEQUENCE: 127

Met Glu Val Lys Val Glu Asn Ile Arg Ala Ile Asp Met Leu Lys Ala
1               5                   10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Pro Asn Lys Glu Ala Ser Thr Ile
65                  70                  75                  80

Ser Thr Asp Asn Pro Asp Ile Asn Pro Ser Ser Gln His Pro Thr Gln
                85                  90                  95

Gln Ser Thr Glu Asn Pro Thr Leu Asn Pro Ala Ala Ser Ala Ser Pro
            100                 105                 110

Ser Glu Thr Glu Pro Ala Ser Thr Pro Asp Thr Thr Asn Arg Leu Ser
        115                 120                 125
```

-continued

```
Ser Val Asp Arg Ser Thr Ala Gln Pro Ser Glu Ser Arg Thr Lys Thr
    130                 135                 140

Lys Pro Thr Val His Thr Ile Asn Asn Pro Asn Thr Ala Ser Ser Thr
145                 150                 155                 160

Gln Ser Pro Pro Arg Thr Thr Thr Lys Ala Ile Arg Arg Ala Thr Thr
                165                 170                 175

Phe Arg Met Ser Ser Thr Gly Lys Arg Pro Thr Thr Thr Leu Val Gln
            180                 185                 190

Ser Asp Ser Ser Thr Thr Thr Gln Asn His Glu Glu Thr Gly Ser Ala
        195                 200                 205

Asn Pro Gln Ala Ser Ala Ser Thr Met Gln Asn Xaa His Thr Asn Asn
    210                 215                 220

Ile Lys Pro Asn
225


<210> SEQ ID NO 128
<211> LENGTH: 228
<212> TYPE: PRT
<213> ORGANISM: human metapneumo virus

<400> SEQUENCE: 128

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Thr Ser Thr Ile
65                  70                  75                  80

Pro Ile Asp Asn Pro Asp Ile Asn Pro Asn Ser Gln His Pro Thr Gln
                85                  90                  95

Gln Ser Thr Glu Ser Pro Thr Leu Asn Pro Ala Ala Ser Val Ser Pro
            100                 105                 110

Ser Glu Thr Glu Pro Ala Ser Thr Pro Asp Thr Thr Asn Arg Leu Ser
        115                 120                 125

Ser Val Asp Arg Ser Thr Thr Gln Pro Ser Glu Ser Arg Thr Lys Thr
    130                 135                 140

Lys Pro Thr Val His Thr Lys Asn Asn Pro Ser Thr Val Ser Arg Thr
145                 150                 155                 160

Gln Ser Pro Leu Arg Ala Thr Thr Lys Ala Val Leu Arg Ala Thr Ala
                165                 170                 175

Phe Arg Thr Ser Ser Thr Arg Lys Arg Pro Thr Thr Thr Ser Val Gln
            180                 185                 190

Ser Asp Ser Ser Thr Thr Thr Gln Asn His Glu Glu Thr Ser Ser Ala
        195                 200                 205

Asn Pro Gln Ala Ser Ala Ser Thr Met Gln Ser Gln His Thr Asn Asn
    210                 215                 220

Ile Lys Pro Asn
225


<210> SEQ ID NO 129
<211> LENGTH: 228
<212> TYPE: PRT
```

-continued

<213> ORGANISM: human metapneumo virus

<400> SEQUENCE: 129

Met Glu Val Lys Val Glu Asn Ile Arg Ala Val Asp Met Leu Lys Ala
1 5 10 15

Arg Val Lys Asn Arg Val Ala Arg Ser Lys Cys Phe Lys Asn Ala Ser
20 25 30

Leu Ile Leu Val Gly Ile Thr Thr Leu Ser Ile Ala Leu Asn Ile Tyr
35 40 45

Leu Ile Val Asn Tyr Thr Ile Gln Lys Thr Thr Ser Glu Ser Glu His
50 55 60

His Thr Ser Ser Ser Pro Thr Glu Ser Asn Lys Gly Thr Ser Thr Ile
65 70 75 80

Pro Thr Asp Asn Pro Asp Ile Asn Pro Asn Ser Gln His Pro Thr Gln
85 90 95

Gln Ser Thr Glu Ser Pro Thr Leu Asn Thr Ala Ala Ser Val Ser Pro
100 105 110

Ser Glu Thr Glu Pro Ala Ser Thr Pro Asp Thr Thr Asn Arg Leu Ser
115 120 125

Ser Ala Asp Arg Ser Thr Thr Gln Pro Ser Glu Ser Arg Thr Lys Thr
130 135 140

Lys Leu Thr Val His Thr Lys Asn Asn Leu Ser Thr Ala Ser Arg Thr
145 150 155 160

Gln Ser Pro Pro Arg Ala Thr Thr Lys Ala Val Leu Arg Asp Thr Ala
165 170 175

Phe His Thr Ser Ser Thr Gly Lys Arg Pro Thr Thr Thr Ser Val Gln
180 185 190

Ser Gly Ser Ser Thr Thr Thr Gln Asn His Glu Glu Thr Ser Ser Ser
195 200 205

Asn Pro Gln Ala Ser Ala Ser Thr Met Gln Asp Gln Asp Thr Asn Asn
210 215 220

Thr Lys Gln Asn
225

<210> SEQ ID NO 130
<211> LENGTH: 228
<212> TYPE: PRT
<213> ORGANISM: human metapneumo virus
<220> FEATURE:
<221> NAME/KEY: VARIANT
<222> LOCATION: 81
<223> OTHER INFORMATION: Xaa = Any Amino Acid

<400> SEQUENCE: 130

Met Glu Val Lys Val Glu Asn Ile Arg Ala Val Asp Met Leu Lys Ala
1 5 10 15

Arg Val Lys Asn Arg Val Ala Arg Ser Lys Cys Phe Lys Asn Ala Ser
20 25 30

Leu Ile Leu Val Gly Ile Thr Thr Leu Ser Ile Ala Leu Asn Ile Tyr
35 40 45

Leu Ile Val Asn Tyr Thr Ile Gln Lys Thr Thr Ser Glu Ser Glu His
50 55 60

His Thr Ser Ser Ser Pro Thr Glu Ser Asn Lys Gly Thr Ser Thr Ile
65 70 75 80

Xaa Thr Asp Asn Pro Asp Ile Asn Pro Asn Ser Gln His Pro Thr Gln
85 90 95

-continued

```
Gln Ser Thr Glu Ser Pro Thr Leu Asn Thr Ala Ala Ser Val Ser Pro
            100                 105                 110

Ser Glu Thr Glu Pro Ala Ser Thr Pro Asp Thr Thr Asn Arg Leu Ser
        115                 120                 125

Ser Ala Asp Arg Ser Thr Thr Gln Pro Ser Glu Ser Arg Thr Lys Thr
    130                 135                 140

Lys Leu Thr Val His Thr Lys Asn Asn Leu Ser Thr Ala Ser Arg Thr
145                 150                 155                 160

Gln Ser Pro Pro Arg Ala Thr Thr Lys Ala Val Leu Arg Asp Thr Ala
                165                 170                 175

Phe His Thr Ser Ser Thr Gly Lys Arg Pro Thr Thr Thr Ser Val Gln
            180                 185                 190

Ser Gly Ser Ser Thr Thr Thr Gln Asn His Glu Glu Thr Ser Ser Ser
        195                 200                 205

Asn Pro Gln Ala Ser Ala Ser Thr Met Gln Asp Gln Asp Thr Asn Asn
    210                 215                 220

Thr Lys Gln Asn
225


<210> SEQ ID NO 131
<211> LENGTH: 228
<212> TYPE: PRT
<213> ORGANISM: Human metapneumo virus
<220> FEATURE:
<221> NAME/KEY: VARIANT
<222> LOCATION: 220
<223> OTHER INFORMATION: Xaa = unknown amino acid or other

<400> SEQUENCE: 131

Met Glu Val Lys Val Glu Asn Ile Arg Ala Ile Asp Met Leu Lys Ala
 1               5                  10                  15

Arg Met Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Thr Ser Thr Ile
65                  70                  75                  80

Pro Ile Asp Asn Pro Asp Ile Asn Pro Asn Ser Gln His Pro Thr Gln
                85                  90                  95

Gln Ser Thr Glu Ser Leu Thr Leu Asn Pro Ala Ala Ser Val Ser Pro
            100                 105                 110

Ser Glu Thr Glu Pro Ala Ser Thr Pro Asp Thr Thr Asn Arg Leu Ser
        115                 120                 125

Ser Val Asp Arg Ser Thr Thr Gln Pro Ser Glu Ser Arg Thr Lys Thr
    130                 135                 140

Lys Leu Thr Val His Lys Lys Asn Ile Pro Ser Thr Val Ser Arg Thr
145                 150                 155                 160

Gln Ser Ser Ile Arg Ala Thr Thr Lys Ala Val Leu Arg Ala Thr Ala
                165                 170                 175

Phe Arg Thr Ser Ser Thr Gly Glu Arg Pro Thr Thr Thr Ser Val Gln
            180                 185                 190

Ser Asp Ser Ser Thr Thr Thr Gln Asn His Glu Glu Thr Gly Ser Ala
        195                 200                 205

Asn Pro Gln Ala Ser Ala Ser Thr Met Gln Asn Xaa His Thr Asn Ile
```

-continued

```
    210                 215                 220

Val Lys Pro Asn
225


<210> SEQ ID NO 132
<211> LENGTH: 228
<212> TYPE: PRT
<213> ORGANISM: Human metapneumovirus
<220> FEATURE:
<221> NAME/KEY: VARIANT
<222> LOCATION: 220
<223> OTHER INFORMATION: Xaa = unknown amino acid or other

<400> SEQUENCE: 132

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Thr Ser Thr Ile
65                  70                  75                  80

Ser Ile Asp Asn Pro Asp Ile Asn Pro Asn Ser Gln His Pro Thr Gln
                85                  90                  95

Gln Ser Thr Glu Ser Leu Thr Leu Ser Pro Thr Ala Ser Val Ser Pro
            100                 105                 110

Ser Glu Thr Glu Pro Ala Ser Thr Ser Asp Thr Thr Ser Arg Leu Ser
        115                 120                 125

Ser Val Asp Arg Ser Thr Thr Gln Pro Ser Glu Ser Arg Ala Arg Thr
    130                 135                 140

Lys Pro Thr Val His Lys Lys Asn Ile Pro Ser Thr Val Ser Arg Thr
145                 150                 155                 160

Gln Ser Pro Leu Arg Ala Thr Thr Lys Ala Val Leu Arg Ala Thr Ala
                165                 170                 175

Phe Arg Thr Ser Ser Thr Gly Glu Gly Pro Thr Thr Thr Ser Val Gln
            180                 185                 190

Ser Asp Ser Ser Thr Thr Thr Gln Asn His Glu Glu Thr Gly Ser Ala
        195                 200                 205

Asn Pro Gln Ala Ser Ala Ser Thr Met Gln Asn Xaa His Thr Asn Ile
    210                 215                 220

Val Lys Pro Asn
225


<210> SEQ ID NO 133
<211> LENGTH: 228
<212> TYPE: PRT
<213> ORGANISM: Human metapneumovirus
<220> FEATURE:
<221> NAME/KEY: VARIANT
<222> LOCATION: 220
<223> OTHER INFORMATION: Xaa = unknown amino acid or other

<400> SEQUENCE: 133

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
            20                  25                  30
```

-continued

```
Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Ala Ser Thr Ile
65                  70                  75                  80

Ser Thr Asp Asn Pro Asp Ile Asn Pro Asn Ser Gln His Pro Thr Gln
                85                  90                  95

Gln Ser Thr Glu Asn Pro Thr Leu Asn Pro Ala Ala Ser Val Ser Ser
            100                 105                 110

Ser Glu Thr Glu Pro Ala Ser Thr Pro Asp Thr Thr Asn Arg Leu Ser
        115                 120                 125

Ser Val Asp Arg Ser Thr Ala Gln Pro Ser Glu Ser Arg Thr Lys Thr
    130                 135                 140

Lys Pro Thr Val His Thr Arg Asn Asn Pro Ser Thr Ala Ser Ser Thr
145                 150                 155                 160

Gln Ser Pro Pro Arg Val Thr Thr Lys Ala Ile Leu Arg Ala Thr Val
                165                 170                 175

Phe Arg Met Ser Ser Thr Gly Lys Arg Pro Ala Thr Thr Leu Val Gln
            180                 185                 190

Ser Asp Ser Ser Thr Thr Thr Gln Asn His Glu Glu Thr Gly Ser Ala
        195                 200                 205

Asn Ser Gln Ala Ser Ala Ser Thr Met Gln Asn Xaa His Ser Asn Asn
    210                 215                 220

Ile Lys Pro Asn
225


<210> SEQ ID NO 134
<211> LENGTH: 228
<212> TYPE: PRT
<213> ORGANISM: human metapneumo virus

<400> SEQUENCE: 134

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Thr Ser Thr Ile
65                  70                  75                  80

Ser Ile Asp Asn Ser Asp Ile Asn Pro Asn Ser Gln His Pro Thr Gln
                85                  90                  95

Gln Ser Thr Glu Ser Leu Thr Leu Ser Pro Thr Ala Ser Val Ser Pro
            100                 105                 110

Ser Glu Thr Glu Pro Ala Ser Thr Ser Asp Thr Thr Asn Arg Leu Ser
        115                 120                 125

Ser Val Asp Arg Ser Thr Thr Gln Pro Ser Glu Ser Arg Ala Arg Thr
    130                 135                 140

Lys Pro Thr Val His Lys Lys Asn Ile Pro Ser Thr Val Ser Arg Thr
145                 150                 155                 160

Gln Ser Pro Leu Arg Ala Thr Thr Lys Ala Val Leu Arg Ala Thr Ala
```

-continued

```
                165                 170                 175

Phe Arg Met Ser Ser Thr Gly Glu Gly Pro Thr Thr Thr Ser Val Gln
            180                 185                 190

Ser Asp Ser Ser Thr Thr Thr Gln Asn His Glu Glu Thr Gly Ser Ala
        195                 200                 205

Asn Pro Gln Ala Ser Ala Ser Thr Met Gln Asn Gln His Thr Asn Ile
    210                 215                 220

Ala Lys Pro Asn
225


<210> SEQ ID NO 135
<211> LENGTH: 228
<212> TYPE: PRT
<213> ORGANISM: human metapneumo virus

<400> SEQUENCE: 135

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Thr Ser Thr Ile
65                  70                  75                  80

Pro Ile Asp Asn Pro Asp Ile Asn Pro Asn Ser Gln His Pro Thr Gln
                85                  90                  95

Gln Ser Thr Glu Ser Leu Thr Leu Tyr Pro Thr Ser Ser Val Ser Ser
            100                 105                 110

Ser Glu Thr Glu Pro Ala Ser Thr Pro Gly Ile Thr Asn His Leu Ser
        115                 120                 125

Phe Val Asp Arg Ser Thr Thr Gln Pro Ser Glu Ser Arg Thr Lys Thr
    130                 135                 140

Asn Arg Thr Val His Lys Lys Asn Ile Ser Ser Thr Val Ser Arg Thr
145                 150                 155                 160

Gln Ser Pro Pro Arg Thr Thr Ala Lys Ala Val Pro Arg Ala Thr Ala
                165                 170                 175

Leu Arg Thr Ser Ser Thr Gly Glu Arg Pro Thr Thr Thr Pro Val Gln
            180                 185                 190

Pro Asp Ser Ser Thr Thr Thr Gln Asn His Glu Glu Thr Gly Ser Ala
        195                 200                 205

Asn Pro Gln Ala Ser Ala Ser Thr Met Gln Asn Gln His Thr Asn Ile
    210                 215                 220

Ala Arg Pro Asn
225


<210> SEQ ID NO 136
<211> LENGTH: 228
<212> TYPE: PRT
<213> ORGANISM: human metapneumo virus

<400> SEQUENCE: 136

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
```

-continued

```
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Thr Ser Thr Ile
65                  70                  75                  80

Pro Ile Asp Asn Pro Asp Ile Asn Pro Asn Ser Gln His Pro Thr Gln
                85                  90                  95

Gln Ser Ala Glu Ser Leu Thr Leu Tyr Pro Thr Ser Ser Val Ser Ser
            100                 105                 110

Ser Glu Thr Glu Pro Ala Ser Thr Pro Gly Ile Thr Asn His Leu Ser
        115                 120                 125

Phe Val Asp Arg Ser Thr Thr Gln Pro Ser Glu Ser Arg Thr Lys Thr
    130                 135                 140

Asn Arg Thr Val His Lys Lys Asn Ile Ser Ser Thr Val Ser Arg Thr
145                 150                 155                 160

Gln Ser Pro Pro Arg Thr Thr Ala Lys Ala Val Pro Arg Ala Thr Ala
                165                 170                 175

Leu Arg Thr Ser Ser Thr Gly Glu Arg Pro Thr Thr Thr Pro Val Gln
            180                 185                 190

Pro Asp Ser Ser Thr Thr Thr Gln Asn His Glu Glu Thr Gly Ser Ala
        195                 200                 205

Asn Pro Gln Ala Ser Ala Ser Thr Met Gln Asn Gln His Thr Asn Ile
    210                 215                 220

Ala Arg Pro Asn
225


<210> SEQ ID NO 137
<211> LENGTH: 228
<212> TYPE: PRT
<213> ORGANISM: human metapneumo virus

<400> SEQUENCE: 137

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Thr Ser Thr Ile
65                  70                  75                  80

Pro Ile Asp Asn Pro Asp Ile Asn Pro Asn Ser Gln His Pro Thr Gln
                85                  90                  95

Gln Ser Thr Glu Ser Leu Thr Leu Tyr Pro Thr Ser Ser Val Ser Ser
            100                 105                 110

Ser Glu Thr Glu Pro Ala Ser Thr Pro Gly Ile Thr Asn His Leu Ser
        115                 120                 125

Phe Val Asp Arg Ser Thr Thr Gln Pro Ser Glu Ser Arg Thr Lys Thr
    130                 135                 140

Asn Arg Thr Val His Lys Lys Asn Ile Ser Ser Thr Val Ser Arg Thr
145                 150                 155                 160
```

-continued

```
Gln Ser Pro Pro Arg Thr Thr Ala Lys Ala Val Pro Arg Ala Thr Ala
                165                 170                 175

Leu Arg Thr Ser Ser Thr Gly Glu Arg Pro Thr Thr Thr Pro Val Gln
            180                 185                 190

Pro Asp Ser Ser Thr Thr Thr Gln Asn His Glu Glu Thr Gly Ser Ala
        195                 200                 205

Asn Pro Gln Ala Ser Ala Ser Thr Met Gln Asn Gln His Thr Asn Ile
    210                 215                 220

Ala Arg Pro Asn
225


<210> SEQ ID NO 138
<211> LENGTH: 228
<212> TYPE: PRT
<213> ORGANISM: human metapneumo virus

<400> SEQUENCE: 138

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Gln Thr Thr Ser Glu Ser Glu His
    50                  55                  60

His Thr Ser Ser Pro Pro Thr Glu Ser Asn Lys Glu Ala Ser Thr Ile
65                  70                  75                  80

Ser Thr Asp Asn Pro Asp Ile Asn Pro Asn Ser Gln His Pro Thr Gln
                85                  90                  95

Gln Ser Thr Glu Asn Pro Thr Leu Asn Pro Ala Ala Ser Ala Ser Pro
            100                 105                 110

Ser Glu Thr Glu Ser Ala Ser Thr Pro Asp Thr Thr Asn Arg Leu Ser
        115                 120                 125

Ser Val Asp Arg Ser Thr Val Gln Pro Ser Glu Asn Arg Thr Lys Thr
    130                 135                 140

Lys Leu Thr Val His Thr Arg Asn Asn Leu Ser Thr Ala Ser Ser Thr
145                 150                 155                 160

Gln Ser Pro Pro Arg Ala Thr Thr Lys Ala Ile Arg Arg Ala Thr Thr
                165                 170                 175

Leu Arg Met Ser Ser Thr Gly Arg Arg Pro Thr Thr Thr Leu Val Gln
            180                 185                 190

Ser Asp Ser Ser Thr Thr Thr Gln Asn His Glu Glu Thr Gly Ser Ala
        195                 200                 205

Asn Pro Gln Ala Ser Ala Ser Thr Met Gln Asn Gln His Thr Asn Asn
    210                 215                 220

Ile Lys Pro Asn
225


<210> SEQ ID NO 139
<211> LENGTH: 228
<212> TYPE: PRT
<213> ORGANISM: human metapneumo virus

<400> SEQUENCE: 139

Met Glu Val Lys Val Glu Asn Ile Arg Ala Ile Asp Met Leu Lys Ala
 1               5                  10                  15
```

-continued

```
Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Ser Asn Lys Glu Ala Ser Thr Ile
65                  70                  75                  80

Ser Thr Asp Asn Pro Asp Ile Asn Pro Asn Ser Gln His Pro Thr Gln
                85                  90                  95

Gln Ser Thr Glu Asn Pro Thr Leu Asn Pro Ala Ala Ser Ala Ser Pro
            100                 105                 110

Ser Glu Thr Glu Ser Ala Ser Thr Pro Asp Thr Thr Asn Arg Leu Ser
        115                 120                 125

Ser Val Asp Arg Ser Thr Val Gln Pro Ser Glu Asn Arg Thr Lys Thr
    130                 135                 140

Lys Leu Thr Val His Thr Arg Asn Asn Leu Ser Thr Ala Ser Ser Thr
145                 150                 155                 160

Gln Ser Pro Pro Arg Ala Thr Thr Lys Ala Ile Arg Arg Ala Thr Thr
                165                 170                 175

Leu Arg Met Ser Ser Thr Gly Arg Arg Pro Thr Thr Thr Leu Val Gln
            180                 185                 190

Ser Asp Ser Ser Thr Thr Thr Gln Asn His Glu Glu Thr Gly Ser Ala
        195                 200                 205

Asn Pro Gln Ala Ser Ala Ser Thr Met Gln Asn Gln His Thr Asn Asn
    210                 215                 220

Ile Lys Pro Asn
225


<210> SEQ ID NO 140
<211> LENGTH: 231
<212> TYPE: PRT
<213> ORGANISM: Human metapneumo virus
<220> FEATURE:
<221> NAME/KEY: VARIANT
<222> LOCATION: 225
<223> OTHER INFORMATION: Xaa = unknown amino acid or other

<400> SEQUENCE: 140

Met Glu Val Arg Val Glu Asn Ile Arg Ala Ile Asp Met Phe Lys Ala
 1               5                  10                  15

Lys Ile Lys Asn Arg Ile Arg Ser Ser Arg Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp His Ala Thr Leu Arg Asn Met Ile Lys Thr Glu Asn
    50                  55                  60

Cys Ala Asn Met Pro Ser Ala Glu Pro Ser Lys Lys Thr Pro Met Thr
65                  70                  75                  80

Ser Thr Ala Gly Pro Asn Thr Lys Pro Asn Pro Gln Gln Ala Thr Gln
                85                  90                  95

Trp Thr Thr Glu Asn Ser Thr Ser Pro Val Ala Thr Pro Glu Gly His
            100                 105                 110

Pro Tyr Thr Gly Thr Thr Gln Thr Ser Asp Thr Thr Ala Pro Gln Gln
        115                 120                 125

Thr Thr Asp Lys His Thr Ala Pro Leu Lys Ser Thr Asn Glu Gln Ile
```

-continued

```
    130                 135                 140

Thr Gln Thr Thr Thr Glu Lys Lys Thr Ile Arg Ala Thr Thr Gln Lys
145                 150                 155                 160

Arg Glu Lys Gly Lys Glu Asn Thr Asn Gln Thr Thr Ser Thr Ala Ala
                165                 170                 175

Thr Gln Thr Thr Asn Thr Thr Asn Gln Ile Arg Asn Ala Ser Glu Thr
            180                 185                 190

Ile Thr Thr Ser Asp Arg Pro Arg Thr Asp Thr Thr Thr Gln Ser Ser
        195                 200                 205

Glu Gln Thr Thr Arg Ala Thr Asp Pro Ser Ser Pro Pro His His Ala
    210                 215                 220

Xaa Arg Gly Ala Lys Leu Lys
225                 230


<210> SEQ ID NO 141
<211> LENGTH: 231
<212> TYPE: PRT
<213> ORGANISM: human metapneumo virus

<400> SEQUENCE: 141

Met Glu Val Arg Val Glu Asn Ile Arg Ala Ile Asp Met Phe Lys Ala
 1               5                  10                  15

Lys Ile Lys Asn Arg Ile Arg Ser Ser Arg Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp His Ala Thr Leu Arg Asn Met Ile Lys Thr Glu Asn
    50                  55                  60

Cys Ala Asn Met Pro Ser Ala Glu Pro Ser Lys Lys Thr Pro Met Thr
65                  70                  75                  80

Ser Thr Ala Gly Pro Ser Thr Glu Pro Asn Pro Gln Gln Ala Thr Gln
                85                  90                  95

Trp Thr Thr Glu Asn Ser Thr Ser Pro Ala Ala Thr Leu Glu Ser His
            100                 105                 110

Pro Tyr Thr Gly Thr Thr Gln Thr Pro Asp Ile Thr Ala Pro Gln Gln
        115                 120                 125

Thr Thr Asp Lys His Thr Ala Leu Pro Lys Ser Thr Asn Glu Gln Ile
    130                 135                 140

Thr Gln Thr Thr Thr Glu Lys Lys Thr Thr Arg Ala Thr Thr Gln Lys
145                 150                 155                 160

Arg Glu Lys Glu Lys Glu Asn Thr Asn Gln Thr Thr Ser Thr Ala Ala
                165                 170                 175

Thr Gln Thr Thr Asn Thr Thr Asn Gln Thr Arg Asn Ala Ser Glu Thr
            180                 185                 190

Ile Thr Thr Ser Asp Arg Pro Arg Ile Asp Thr Thr Thr Gln Ser Ser
        195                 200                 205

Asp Gln Thr Thr Arg Ala Thr Asp Pro Ser Ser Pro Pro His His Ala
    210                 215                 220

Gln Ser Gly Ala Lys Pro Lys
225                 230


<210> SEQ ID NO 142
<211> LENGTH: 231
<212> TYPE: PRT
<213> ORGANISM: human metapneumo virus
```

-continued

<400> SEQUENCE: 142

Met Glu Val Arg Val Glu Asn Ile Arg Ala Ile Asp Met Phe Lys Ala
1 5 10 15

Lys Ile Lys Asn Arg Ile Arg Ser Ser Arg Cys Tyr Arg Asn Ala Thr
20 25 30

Leu Ile Leu Ile Gly Leu Thr Ala Leu Ser Met Ala Leu Asn Ile Phe
35 40 45

Leu Ile Ile Asp His Ala Thr Leu Arg Asn Met Ile Lys Thr Glu Asn
50 55 60

Cys Ala Asn Met Pro Pro Ala Glu Pro Ser Lys Lys Thr Pro Met Thr
65 70 75 80

Ser Thr Ala Gly Pro Asn Thr Lys Pro Asn Pro Gln Gln Ala Thr Gln
85 90 95

Trp Thr Thr Glu Asn Ser Thr Phe Pro Ala Ala Thr Ser Glu Gly His
100 105 110

Leu His Thr Gly Thr Thr Gln Thr Pro Asp Thr Thr Ala Pro Gln Gln
115 120 125

Thr Thr Asp Lys His Thr Ala Leu Pro Lys Ser Thr Asn Glu Gln Ile
130 135 140

Thr Gln Thr Thr Thr Glu Lys Lys Thr Thr Arg Ala Thr Thr Gln Arg
145 150 155 160

Arg Glu Lys Gly Lys Glu Asn Thr Asn Gln Thr Thr Ser Thr Ala Ala
165 170 175

Thr Gln Thr Thr Asn Thr Thr Asn Gln Ile Arg Asn Ala Ser Glu Thr
180 185 190

Ile Thr Thr Ser Asp Arg Pro Arg Thr Asp Ser Thr Thr Gln Ser Ser
195 200 205

Glu Gln Thr Thr Arg Ala Thr Asp Pro Ser Ser Pro Pro His His Ala
210 215 220

Gln Gly Ser Ala Lys Pro Lys
225 230

<210> SEQ ID NO 143
<211> LENGTH: 231
<212> TYPE: PRT
<213> ORGANISM: human metapneumo virus

<400> SEQUENCE: 143

Met Glu Val Arg Val Glu Asn Ile Arg Ala Ile Asp Met Phe Lys Ala
1 5 10 15

Lys Ile Lys Asn Arg Ile Arg Ser Ser Arg Cys Tyr Arg Asn Ala Thr
20 25 30

Leu Ile Leu Ile Gly Leu Thr Ala Leu Ser Met Ala Leu Asn Ile Phe
35 40 45

Leu Ile Ile Asp His Ala Thr Leu Arg Asn Met Ile Lys Thr Glu Asn
50 55 60

Cys Ala Asn Met Pro Pro Ala Glu Pro Ser Arg Lys Thr Pro Met Thr
65 70 75 80

Ser Thr Ala Gly Pro Asn Thr Lys Pro Asn Pro Gln Gln Ala Thr Gln
85 90 95

Trp Thr Thr Glu Asn Ser Thr Ser Pro Ala Ala Thr Pro Glu Gly His
100 105 110

Leu His Thr Gly Thr Thr Gln Thr Pro Asp Thr Thr Ala Pro Gln Gln
115 120 125

-continued

```
Thr Thr Asp Lys His Thr Ala Leu Pro Lys Ser Thr Asn Glu Gln Ile
    130                 135                 140

Thr Gln Ala Thr Thr Glu Lys Lys Thr Thr Arg Glu Thr Thr Gln Arg
145                 150                 155                 160

Arg Glu Lys Gly Lys Glu Asn Thr Asn Gln Thr Thr Ser Thr Ala Ala
                165                 170                 175

Thr Gln Thr Thr Asn Thr Thr Asn Gln Ile Arg Asn Ala Ser Glu Thr
            180                 185                 190

Ile Thr Thr Ser Asp Arg Pro Arg Thr Asp Ser Thr Thr Gln Ser Ser
        195                 200                 205

Glu Gln Thr Thr Gln Ala Thr Asp Pro Ser Ser Pro Ala His His Ala
    210                 215                 220

Gln Gly Ser Ala Lys Pro Lys
225                 230


<210> SEQ ID NO 144
<211> LENGTH: 231
<212> TYPE: PRT
<213> ORGANISM: human metapneumo virus

<400> SEQUENCE: 144

Met Glu Val Arg Val Glu Asn Ile Arg Ala Ile Asp Met Phe Lys Ala
 1               5                  10                  15

Lys Ile Lys Asn Arg Ile Arg Ser Ser Arg Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp His Ala Thr Leu Arg Asn Met Ile Lys Thr Glu Asn
    50                  55                  60

Cys Ala Asn Met Pro Pro Ala Glu Pro Ser Lys Lys Thr Pro Met Thr
65                  70                  75                  80

Ser Thr Ala Gly Leu Asn Thr Lys Pro Asn Pro Gln Gln Ala Thr Gln
                85                  90                  95

Trp Thr Thr Glu Asn Ser Thr Ser Pro Ala Ala Thr Pro Glu Gly His
            100                 105                 110

Leu His Thr Gly Thr Thr Gln Thr Pro Asp Thr Thr Ala Pro Gln Gln
        115                 120                 125

Thr Thr Asp Lys His Thr Ala Leu Pro Lys Ser Thr Asn Glu Gln Ile
    130                 135                 140

Thr Gln Thr Thr Thr Glu Lys Lys Thr Thr Arg Ala Thr Thr Gln Arg
145                 150                 155                 160

Arg Glu Lys Gly Lys Glu Asn Thr Asn Gln Thr Thr Ser Thr Ala Ala
                165                 170                 175

Thr Gln Thr Thr Asn Thr Thr Asn Gln Ile Arg Asn Ala Ser Glu Thr
            180                 185                 190

Ile Thr Thr Ser Asp Arg Pro Arg Thr Asp Ser Thr Thr Gln Ser Ser
        195                 200                 205

Glu Gln Thr Thr Arg Ala Thr Asp Pro Ser Ser Pro Pro His His Ala
    210                 215                 220

Gln Gly Ser Ala Lys Pro Lys
225                 230


<210> SEQ ID NO 145
<211> LENGTH: 231
<212> TYPE: PRT
<213> ORGANISM: human metapneumo virus
```

<400> SEQUENCE: 145

```
Met Glu Val Arg Val Glu Asn Ile Arg Ala Ile Asp Met Phe Lys Ala
 1               5                  10                  15

Lys Ile Lys Asn Arg Ile Arg Ser Ser Arg Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp His Ala Thr Leu Arg Asn Met Ile Lys Thr Glu Asn
    50                  55                  60

Cys Ala Asn Met Pro Pro Ala Glu Pro Ser Lys Lys Thr Pro Met Thr
65                  70                  75                  80

Ser Thr Ala Gly Pro Asn Thr Lys Pro Asn Pro Gln Gln Ala Thr Gln
                85                  90                  95

Trp Thr Thr Glu Asn Ser Thr Ser Pro Ala Ala Thr Pro Glu Gly His
            100                 105                 110

Leu His Thr Gly Thr Thr Gln Thr Pro Asp Thr Thr Ala Pro Gln Gln
        115                 120                 125

Thr Thr Asp Lys His Thr Ala Leu Pro Lys Ser Thr Asn Glu Gln Ile
    130                 135                 140

Thr Gln Thr Thr Thr Glu Lys Lys Thr Thr Arg Ala Thr Thr Gln Arg
145                 150                 155                 160

Arg Glu Lys Gly Lys Glu Asn Thr Asn Gln Thr Thr Ser Thr Ala Ala
                165                 170                 175

Thr Gln Thr Thr Asn Thr Thr Asn Gln Ile Arg Asn Ala Ile Glu Thr
            180                 185                 190

Ile Thr Thr Ser Asp Arg Pro Arg Thr Asp Ser Thr Thr Gln Ser Ser
        195                 200                 205

Glu Gln Thr Thr Arg Ala Thr Asp Pro Ser Ser His Pro His His Ala
    210                 215                 220

Gln Gly Ser Ala Lys Pro Lys
225                 230
```

<210> SEQ ID NO 146
<211> LENGTH: 236
<212> TYPE: PRT
<213> ORGANISM: human metapneumo virus

<400> SEQUENCE: 146

```
Met Glu Val Arg Val Glu Asn Ile Arg Ala Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp Tyr Ala Met Leu Lys Asn Met Thr Lys Val Glu His
    50                  55                  60

Cys Val Asn Met Pro Pro Val Glu Pro Ser Lys Lys Thr Pro Met Thr
65                  70                  75                  80

Ser Ala Val Asp Leu Asn Thr Lys Pro Asn Pro Gln Gln Ala Thr Gln
                85                  90                  95

Leu Ala Ala Glu Asp Ser Thr Ser Leu Ala Ala Thr Ser Glu Asp His
            100                 105                 110

Leu His Thr Gly Thr Thr Pro Thr Pro Asp Ala Thr Val Ser Gln Gln
        115                 120                 125
```

-continued

```
Thr Thr Asp Glu Tyr Thr Thr Leu Leu Arg Ser Thr Asn Arg Gln Thr
    130                 135                 140

Thr Gln Thr Thr Thr Glu Lys Lys Pro Thr Gly Ala Thr Thr Lys Lys
145                 150                 155                 160

Glu Thr Thr Thr Arg Thr Thr Ser Thr Ala Ala Thr Gln Thr Leu Asn
                165                 170                 175

Thr Thr Asn Gln Thr Ser Tyr Val Arg Glu Ala Thr Thr Thr Ser Ala
            180                 185                 190

Arg Ser Arg Asn Ser Ala Thr Thr Gln Ser Ser Asp Gln Thr Thr Gln
        195                 200                 205

Ala Ala Asp Pro Ser Ser Gln Pro His His Thr Gln Lys Ser Thr Thr
    210                 215                 220

Thr Thr Tyr Asn Thr Asp Thr Ser Ser Pro Ser Ser
225                 230                 235


<210> SEQ ID NO 147
<211> LENGTH: 236
<212> TYPE: PRT
<213> ORGANISM: Human metapneumo virus
<220> FEATURE:
<221> NAME/KEY: VARIANT
<222> LOCATION: 220, 227
<223> OTHER INFORMATION: Xaa = unknown amino acid or other

<400> SEQUENCE: 147

Met Glu Val Arg Val Glu Asn Ile Arg Thr Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp Tyr Ala Thr Phe Lys Asn Met Thr Lys Val Glu His
    50                  55                  60

Cys Ala Asn Met Pro Pro Val Glu Pro Ser Lys Lys Thr Pro Met Thr
65                  70                  75                  80

Ser Thr Val Asp Ser Ser Thr Gly Pro Asn Pro Gln Gln Thr Thr Gln
                85                  90                  95

Trp Thr Thr Glu Asp Ser Thr Ser Leu Ala Ala Thr Ser Glu Asp His
            100                 105                 110

Leu His Thr Gly Thr Thr Pro Thr Leu Asp Ala Thr Val Ser Gln Gln
        115                 120                 125

Thr Pro Asp Lys His Thr Thr Pro Leu Arg Ser Thr Asn Gly Gln Thr
    130                 135                 140

Thr Gln Thr Thr Thr Glu Lys Lys Pro Thr Arg Ala Ile Ala Lys Lys
145                 150                 155                 160

Glu Thr Thr Asn Gln Thr Thr Ser Thr Ala Ala Thr Gln Thr Phe Asn
                165                 170                 175

Thr Thr Asn Gln Thr Arg Asn Gly Arg Glu Thr Thr Ile Thr Ser Ala
            180                 185                 190

Arg Ser Arg Asn Asp Ala Thr Thr Gln Ser Ser Glu Gln Thr Asn Gln
        195                 200                 205

Thr Thr Asp Pro Ser Ser Gln Pro His His Ala Xaa Ile Ser Thr Ile
    210                 215                 220

Thr Ile Xaa Thr Gln His Arg His Ile Phe Ser Lys
225                 230                 235
```

-continued

<210> SEQ ID NO 148
<211> LENGTH: 236
<212> TYPE: PRT
<213> ORGANISM: Human metapneumo virus
<220> FEATURE:
<221> NAME/KEY: VARIANT
<222> LOCATION: 208
<223> OTHER INFORMATION: Xaa = unknown amino acid or other

<400> SEQUENCE: 148

```
Met Glu Val Arg Val Glu Asn Ile Arg Ala Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp Tyr Ala Met Leu Lys Asn Met Thr Lys Val Glu His
    50                  55                  60

Cys Val Asn Met Pro Pro Val Glu Pro Ser Lys Lys Thr Pro Met Thr
65                  70                  75                  80

Ser Ala Val Asp Leu Asn Thr Lys Leu Asn Pro Gln Gln Ala Thr Gln
                85                  90                  95

Leu Thr Thr Glu Asp Ser Thr Ser Leu Ala Ala Thr Ser Glu Asp His
            100                 105                 110

Leu Leu Thr Gly Thr Thr Pro Thr Pro Asp Ala Thr Val Ser Gln Gln
        115                 120                 125

Thr Thr Asp Glu His Thr Thr Leu Leu Arg Ser Thr Asn Arg Gln Thr
    130                 135                 140

Thr Gln Thr Thr Thr Glu Lys Lys Pro Thr Gly Ala Thr Thr Lys Lys
145                 150                 155                 160

Glu Thr Thr Thr Arg Thr Thr Ser Thr Ala Ala Thr Gln Thr Leu Asn
                165                 170                 175

Thr Thr Asn Gln Thr Ser Asn Gly Arg Glu Ala Thr Thr Thr Ser Thr
            180                 185                 190

Arg Ser Arg Asn Gly Ala Thr Thr Gln Asn Ser Asp Gln Thr Thr Xaa
        195                 200                 205

Thr Ala Asp Pro Ser Ser Gln Pro His His Thr Gln Lys Ser Thr Thr
    210                 215                 220

Thr Thr Tyr Asn Thr Asp Thr Ser Ser Pro Ser Ser
225                 230                 235
```

<210> SEQ ID NO 149
<211> LENGTH: 236
<212> TYPE: PRT
<213> ORGANISM: human metapneumo virus

<400> SEQUENCE: 149

```
Met Glu Val Arg Val Glu Asn Ile Arg Ala Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp Tyr Ala Thr Leu Lys Asn Met Thr Lys Val Glu His
    50                  55                  60

Cys Val Asn Met Pro Pro Val Glu Pro Ser Lys Lys Thr Pro Met Thr
65                  70                  75                  80
```

-continued

```
Ser Ala Val Asp Leu Asn Thr Lys Leu Asn Pro Gln Gln Ala Thr Gln
                85                  90                  95

Leu Thr Thr Glu Asp Ser Thr Ser Leu Ala Ala Thr Ser Glu Gly His
            100                 105                 110

Pro His Thr Gly Thr Thr Pro Thr Pro Asp Ala Thr Val Ser Gln Gln
        115                 120                 125

Thr Thr Asp Glu His Thr Thr Leu Leu Arg Ser Thr Asn Arg Gln Thr
    130                 135                 140

Thr Gln Thr Ala Thr Glu Lys Lys Pro Thr Gly Ala Thr Thr Lys Lys
145                 150                 155                 160

Glu Thr Thr Thr Arg Thr Thr Ser Thr Ala Ala Thr Gln Thr Pro Asn
                165                 170                 175

Thr Thr Asn Gln Thr Ser Asn Gly Arg Glu Ala Thr Thr Thr Ser Ala
            180                 185                 190

Arg Ser Arg Asn Gly Ala Thr Thr Gln Asn Ser Asp Gln Ile Thr Gln
        195                 200                 205

Ala Ala Asp Ser Ser Ser Gln Pro His His Thr Gln Lys Ser Thr Thr
    210                 215                 220

Thr Ala Tyr Asn Thr Asp Thr Ser Phe Pro Ser Ser
225                 230                 235


<210> SEQ ID NO 150
<211> LENGTH: 236
<212> TYPE: PRT
<213> ORGANISM: human metapneumo virus

<400> SEQUENCE: 150

Met Glu Val Arg Val Glu Asn Ile Arg Ala Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp Tyr Ala Thr Leu Lys Asn Met Thr Lys Val Glu His
    50                  55                  60

Cys Val Asn Met Pro Pro Val Glu Pro Ser Lys Lys Thr Pro Met Thr
65                  70                  75                  80

Ser Ala Val Asp Ser Asn Thr Lys Pro Asn Pro Gln Gln Ala Thr Gln
                85                  90                  95

Leu Thr Thr Glu Asp Ser Thr Ser Leu Ala Ala Thr Leu Glu Asp His
            100                 105                 110

Pro His Thr Gly Thr Thr Pro Thr Pro Asp Ala Thr Val Ser Gln Gln
        115                 120                 125

Thr Thr Asp Glu His Thr Thr Leu Leu Arg Ser Thr Asn Arg Gln Thr
    130                 135                 140

Thr Gln Thr Thr Ala Glu Lys Lys Pro Thr Arg Ala Thr Thr Lys Lys
145                 150                 155                 160

Glu Thr Thr Thr Arg Thr Thr Ser Thr Ala Ala Thr Gln Thr Leu Asn
                165                 170                 175

Thr Thr Asn Gln Thr Ser Asn Gly Arg Glu Ala Thr Thr Thr Ser Ala
            180                 185                 190

Arg Ser Arg Asn Asn Ala Thr Thr Gln Ser Ser Asp Gln Thr Thr Gln
        195                 200                 205

Ala Ala Glu Pro Ser Ser Gln Ser Gln His Thr Gln Lys Ser Thr Thr
```

-continued

```
    210                 215                 220

Thr Thr Tyr Asn Thr Asp Thr Ser Ser Leu Ser Ser
225                 230                 235


<210> SEQ ID NO 151
<211> LENGTH: 236
<212> TYPE: PRT
<213> ORGANISM: human metapneumo virus

<400> SEQUENCE: 151

Met Glu Val Arg Val Glu Asn Ile Arg Ala Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Ser Ala Leu Ser Met Ala Leu Asn Ile Phe
        35                  40                  45

Leu Ile Ile Asp Tyr Ala Lys Ser Lys Asn Met Thr Arg Val Glu His
    50                  55                  60

Cys Val Asn Met Pro Pro Val Glu Pro Ser Lys Lys Thr Pro Met Thr
65                  70                  75                  80

Ser Ala Val Asp Leu Asn Thr Lys Pro Asn Pro Gln Arg Ala Thr Gln
                85                  90                  95

Leu Thr Thr Glu Asp Ser Thr Ser Leu Ala Ala Thr Leu Glu Gly His
            100                 105                 110

Leu His Thr Gly Thr Thr Pro Thr Pro Asp Val Thr Val Ser Gln Gln
        115                 120                 125

Thr Thr Asp Glu His Thr Thr Leu Leu Arg Ser Thr Asn Arg Gln Thr
    130                 135                 140

Thr Gln Thr Ala Ala Glu Lys Lys Pro Thr Arg Val Thr Thr Asn Lys
145                 150                 155                 160

Glu Thr Ile Thr Arg Thr Thr Ser Thr Ala Ala Thr Gln Thr Leu Asn
                165                 170                 175

Thr Thr Asn Gln Thr Asn Asn Gly Arg Glu Ala Thr Thr Thr Ser Ala
            180                 185                 190

Arg Ser Arg Asn Asn Ala Thr Thr Gln Ser Ser Asp Gln Thr Thr Gln
        195                 200                 205

Ala Ala Asp Pro Ser Ser Gln Ser Gln His Thr Gln Lys Ser Ile Thr
    210                 215                 220

Thr Thr Tyr Asn Thr Asp Thr Ser Ser Pro Ser Ser
225                 230                 235


<210> SEQ ID NO 152
<211> LENGTH: 236
<212> TYPE: PRT
<213> ORGANISM: human metapneumo virus

<400> SEQUENCE: 152

Met Glu Val Arg Val Glu Asn Ile Arg Ala Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Ser Ala Leu Ser Met Ala Leu Asn Ile Phe
        35                  40                  45

Leu Ile Ile Asp Tyr Ala Lys Ser Lys Thr Met Thr Arg Val Glu His
    50                  55                  60

Cys Val Asn Met Pro Pro Val Glu Pro Ser Lys Lys Thr Pro Met Thr
```

-continued

```
65                  70                  75                  80

Ser Ala Val Asp Leu Asn Thr Lys Pro Asn Pro Gln Gln Ala Thr Gln
                85                  90                  95

Leu Thr Thr Glu Asp Ser Thr Ser Pro Ala Ala Thr Leu Glu Gly His
            100                 105                 110

Leu His Thr Gly Thr Thr Pro Thr Pro Asp Ala Thr Val Ser Gln Gln
        115                 120                 125

Thr Thr Asp Glu His Thr Thr Leu Leu Arg Ser Thr Asn Arg Gln Thr
    130                 135                 140

Thr Gln Thr Thr Ala Glu Lys Lys Pro Thr Arg Ala Thr Thr Lys Lys
145                 150                 155                 160

Glu Thr Ile Thr Arg Thr Thr Ser Thr Ala Ala Thr Gln Thr Leu Asn
                165                 170                 175

Thr Thr Asn Gln Thr Ser Asn Gly Arg Glu Ala Thr Thr Thr Ser Ala
            180                 185                 190

Arg Ser Arg Asn Asn Ala Thr Thr Gln Ser Ser Asp Gln Thr Thr Gln
        195                 200                 205

Ala Ala Asp Pro Ser Ser Gln Ser Gln His Thr Lys Lys Ser Thr Thr
    210                 215                 220

Thr Thr Tyr Asn Thr Asp Thr Ser Ser Pro Ser Ser
225                 230                 235


<210> SEQ ID NO 153
<211> LENGTH: 236
<212> TYPE: PRT
<213> ORGANISM: human metapneumo virus

<400> SEQUENCE: 153

Met Glu Val Arg Val Glu Asn Ile Arg Ala Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp Tyr Ala Thr Leu Lys Asn Met Thr Lys Val Glu His
    50                  55                  60

Cys Val Asn Met Pro Pro Val Glu Pro Ser Lys Lys Thr Pro Met Thr
65                  70                  75                  80

Ser Ala Val Asp Leu Asn Thr Lys Pro Asn Pro Gln Gln Ala Thr Gln
                85                  90                  95

Leu Thr Thr Glu Asp Ser Thr Ser Leu Ala Ala Thr Leu Glu Asp His
            100                 105                 110

Pro His Thr Gly Thr Thr Pro Thr Pro Asp Ala Thr Val Ser Gln Gln
        115                 120                 125

Thr Thr Asp Glu His Thr Thr Leu Leu Arg Ser Thr Asn Arg Gln Thr
    130                 135                 140

Thr Gln Thr Thr Ala Glu Lys Lys Pro Thr Arg Ala Thr Thr Lys Lys
145                 150                 155                 160

Glu Thr Thr Thr Arg Thr Thr Ser Thr Ala Ala Thr Gln Thr Leu Asn
                165                 170                 175

Thr Thr Asn Gln Thr Ser Asn Gly Arg Glu Ala Thr Thr Thr Ser Ala
            180                 185                 190

Arg Ser Arg Asn Asn Ala Thr Thr Gln Ser Ser Asp Gln Thr Thr Gln
        195                 200                 205
```

-continued

Ala Ala Glu Pro Asn Ser Gln Ser Gln His Thr Gln Lys Ser Thr Thr
    210                 215                 220

Thr Thr Tyr Asn Thr Asp Thr Ser Ser Leu Ser Ser
225                 230                 235

<210> SEQ ID NO 154
<211> LENGTH: 449
<212> TYPE: DNA
<213> ORGANISM: human metapneumo virus

<400> SEQUENCE: 154
ataggagttt acggaagctc cgtaatttac atggtgcaac tgccaatctt tggggttata 60
gacacgcctt gctggatagt aaaagcagcc ccttcttgtt caggaaaaaa gggaaactat 120
gcttgcctct taagagaaga ccaaggatgg tattgtcaaa atgcagggtc aactgtttac 180
tacccaaatg aaaaagactg tgaaacaaga ggagaccatg tcttttgcga cacagcagca 240
ggaatcaatg ttgctgagca gtcaaaggag tgcaacataa acatatctac tactaattac 300
ccatgcaaag ttagcacagg aagacatcct atcagtatgg ttgcactatc tcctcttggg 360
gctttggttg cttgctacaa gggagtgagc tgttccattg gcagcaacag agtagggatc 420
atcaagcaac tgaacaaagg ctgctctta 449

<210> SEQ ID NO 155
<211> LENGTH: 449
<212> TYPE: DNA
<213> ORGANISM: human metapneumo virus

<400> SEQUENCE: 155
ataggagttt acggaagctc cgtaatttac atggtgcaac tgccaatctt tggggttata 60
gacacgcctt gctggatagt aaaagcagcc ccttcttgct cagaaaaaaa gggaaactat 120
gcttgcctct taagagaaga tcaaggatgg tattgtcaga atgcagggtc aactgtttac 180
tacccaaatg aaaaagactg cgaaacaaga ggagaccatg tcttttgcga cacagcagca 240
ggaatcaatg ttgctgagca gtcaaaggag tgcaacatca acatatccac tactaattac 300
ccatgcaaag ttagcacagg aagacatcct atcagtatgg ttgcactgtc tcctcttggg 360
gctttggttg cttgctacaa gggagtgagc tgttccattg gcagcaacag agtagggatc 420
atcaagcaac tgaacaaagg ctgctctta 449

<210> SEQ ID NO 156
<211> LENGTH: 449
<212> TYPE: DNA
<213> ORGANISM: human metapneumo virus

<400> SEQUENCE: 156
ataggagttt acggaagctc cgtaatttac atggtgcaac tgccaatctt tggggttata 60
gacacgcctt gctggatagt aaaagcagcc ccttcttgct cagaaaaaaa gggaaactat 120
gcttgcctct taagagaaga tcaaggatgg tattgtcaga atgcagggtc aactgtttac 180
tacccaaatg aaaaagattg cgaaacaaga ggagaccatg tcttttgcga cacagcagca 240
ggaatcaatg ttgctgagca gtcaaaggag tgcaacatca acatatccac tactaattac 300
ccatgcaaag ttagcacagg aagacatcct atcagtatgg ttgcactgtc tcctcttggg 360
gctttggttg cttgctacaa gggagtgagc tgttccattg gcagcaacag agtagggatc 420
atcaagcaac tgaacaaagg ctgctctta 449

-continued

<210> SEQ ID NO 157
<211> LENGTH: 449
<212> TYPE: DNA
<213> ORGANISM: human metapneumo virus

<400> SEQUENCE: 157
ataggagttt acggaagctc cgtaatttac atggtgcaac tgccaatctt tggggttata 60
gacacgcctt gctggatagt aaaagcagcc ccttcttgct cagaaaaaaa gggaaactat 120
gcttgcctct taagagaaga tcaaggatgg tattgtcaga atgcagggtc aactgtttac 180
tacccaaatg aaaaagactg cgaaacaaga ggagaccatg tcttttgcga cacagcagca 240
ggaatcaatg ttgctgagca gtcaaaggag tgcaacatca acatatccac tactaattac 300
ccatgcaaag ttagcacagg aagacatcct atcagtatgg ttgcactgtc tcctcttggg 360
gctttggttg cttgctacaa gggagtgagc tgttccattg gcagcaacag agtagggatc 420
atcaagcaac tgaacaaagg ctgctctta 449

<210> SEQ ID NO 158
<211> LENGTH: 449
<212> TYPE: DNA
<213> ORGANISM: human metapneumo virus

<400> SEQUENCE: 158
ataggagttt acggaagctc cgtaatttac atggtgcaac tgccaatctt tggggttata 60
gacacgcctt gctggatagt aaaagcagcc ccttcttgct cagaaaaaaa gggaaactat 120
gcttgcctct taagagaaga tcaaggatgg tattgtcaga atgcagggtc aactgtttac 180
tacccaaatg aaaaagattg cgaaacaaga ggagaccatg tcttttgcga cacagcagca 240
ggaatcaatg ttgctgagca gtcaaaggag tgcaacatca acatatccac tactaattac 300
ccatgcaaag ttagcacagg aagacatcct atcagtatgg ttgcactgtc tcctcttggg 360
gctttggttg cttgctacaa gggagtgagc tgttccattg gtagcaacag agtagggatc 420
atcaagcaac tgaacaaagg ctgctctta 449

<210> SEQ ID NO 159
<211> LENGTH: 449
<212> TYPE: DNA
<213> ORGANISM: human metapneumo virus

<400> SEQUENCE: 159
ataggagttt acggaagctc cgtaatttac atggtgcaac tgccaatctt tggggttata 60
gacacgcctt gctggatagt aaaagcagcc ccttcttgtt cagaaaaaaa gggaaactat 120
gcttgcctct taagagaaga ccaaggatgg tattgtcaga atgcagggtc aactgtttac 180
tacccaaatg aaaaagactg tgaaacaaga ggagaccatg tcttttgcga cacagcagca 240
ggaatcaatg ttgctgagca gtcaaaggag tgcaacataa acatatctac tactaattac 300
ccatgcaaag ttagcacagg aagacatcct atcagtatgg ttgcactgtc tcctcttggg 360
gctttggttg cttgctacaa gggagtgagc tgttccattg gcagcaacag agtagggatc 420
atcaagcaac tgaacaaagg ctgctctta 449

<210> SEQ ID NO 160
<211> LENGTH: 449
<212> TYPE: DNA
<213> ORGANISM: human metapneumo virus

<400> SEQUENCE: 160

-continued

```
ataggagttt acggaagctc cgtaatttac atggtgcaac tgccaatctt tggggttata     60

gacacgcctt gctggatagt aaaagcagcc ccttcttgtt cagaaaaaaa gggaaactat    120

gcttgcctct taagagaaga ccaaggatgg tattgtcaga atgcagggtc aactgtttac    180

tacccaaatg aaaaagactg tgaaacaaga ggagaccatg tcttttgcga cacagcagca    240

ggaatcaatg ttgctgagca gtcaaaggag tgcaacataa acatatctac tactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420

atcaagcaac tgaacaaagg ctgctctta                                       449
```

<210> SEQ ID NO 161
<211> LENGTH: 449
<212> TYPE: DNA
<213> ORGANISM: human metapneumo virus

<400> SEQUENCE: 161

```
ataggagttt acggaagctc cgtaatttac atggtgcaac tgccaatctt tggggttata     60

gacacgcctt gctggatagt aaaagcagcc ccttcttgtt cagaaaaaaa gggaaactat    120

gcttgcctct taagagaaga ccaaggatgg tattgtcaga atgcagggtc aactgtttac    180

tacccaaatg aaaaagactg tgaaacaaga ggagaccatg tcttttgcga cacagcagca    240

ggaatcaatg ttgctgagca gtcaaaggag tgcaacataa acatatctac tactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420

atcaagcaac tgaacaaagg ctgctctta                                       449
```

<210> SEQ ID NO 162
<211> LENGTH: 449
<212> TYPE: DNA
<213> ORGANISM: human metapneumo virus

<400> SEQUENCE: 162

```
ataggagttt acggaagctc cgtaatttac atggtgcaac tgccaatctt tggggttata     60

gacacgcctt gctggatagt aaaagcagcc ccttcttgct cagaaaaaaa gggaaactat    120

gcttgcctct taagagaaga tcagggatgg tattgtcaga atgcagggtc aactgtttac    180

tacccaaatg aaaaagactg tgaaacaaga ggagaccatg tcttttgcga cacagcagca    240

ggaatcaatg ttgctgagca gtcaaaggag tgcaacatca acatatccac tactaattac    300

ccatgcaaag ttagcacagg aagacatcct atcagtatgg ttgcactgtc tcctcttggg    360

gctttggttg cttgctacaa gggagtgagc tgttccattg gcagcaacag agtaggaatc    420

atcaagcaac tgaacaaagg ctgctctta                                       449
```

<210> SEQ ID NO 163
<211> LENGTH: 449
<212> TYPE: DNA
<213> ORGANISM: human metapneumo virus

<400> SEQUENCE: 163

```
ataggagttt acggaagctc cgtaatttac atggtgcaac tgccaatctt tggagttata     60

gacacgcctt gctggatagt aaaagcagcc ccttcttgct cagaaaaaaa gggaaactat    120

gcttgcctct taagagaaga tcaaggatgg tattgtcaga atgcagggtc aactgtttac    180

tacccaaatg aaaaagactg cgaaacaaga ggagaccatg tcttttgcga cacagcagca    240
```

-continued

```
ggaatcaatg ttgctgagca gtcaaaggag tgcaacatca acatatccac tactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420

atcaagcaac tgaacaaagg ctgctctta                                      449
```

<210> SEQ ID NO 164
<211> LENGTH: 449
<212> TYPE: DNA
<213> ORGANISM: human metapneumo virus

<400> SEQUENCE: 164

```
ataggagttt acggaagctc cgtaatttac atggtgcaac tgccaatctt tggggttata     60

gacacgcctt gttggatagt aaaagcagcc ccttcttgct cagaaaaaaa ggggaactat    120

gcttgcctct taagagaaga tcaaggatgg tattgtcaga atgcagggtc aactgtttac    180

tacccaaatg aaaaagactg cgaaacaaga ggagaccatg tcttttgcga cacagcagca    240

ggaatcaatg ttgctgagca gtcaaaggag tgcaacatca acatatccac tactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420

atcaagcaac tgaacaaagg ctgctctta                                      449
```

<210> SEQ ID NO 165
<211> LENGTH: 449
<212> TYPE: DNA
<213> ORGANISM: human metapneumo virus

<400> SEQUENCE: 165

```
ataggagttt acggaagctc cgtaatttac atggtgcaac tgccaatctt tggagttata     60

gacacgcctt gctggatagt aaaagcggcc ccttcttgct cagaaaaaaa gggaaactat    120

gcttgcctct taagagaaga tcaaggatgg tattgtcaga atgcagggtc aactgtttac    180

tacccaaatg aaaaagactg cgaaacaaga ggagaccatg tcttttgcga cacagcagca    240

ggaatcaatg ttgctgagca gtcaaaggag tgcaacatca acatatccac tactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420

atcaagcaac tgaacaaagg ctgctctta                                      449
```

<210> SEQ ID NO 166
<211> LENGTH: 449
<212> TYPE: DNA
<213> ORGANISM: human metapneumo virus

<400> SEQUENCE: 166

```
ataggagttt acggaagctc cgtaatttac atggtgcaac tgccaatctt tggggttata     60

gacacgcctt gctggatagt aaaagcagcc ccttcttgct cagaaaaaaa gggaaactat    120

gcttgccttt taagagaaga tcaaggatgg tattgtcaga atgcagggtc aactgtttac    180

tacccaaatg aaaaagactg cgaaacaaga ggagaccatg tcttttgcga cacagcagca    240

ggaatcaatg ttgctgagca gtcaaaggag tgcaacatca atatatccac tactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420
```

-continued

```
atcaagcaac tgaacaaagg ctgctctta                                   449

<210> SEQ ID NO 167
<211> LENGTH: 449
<212> TYPE: DNA
<213> ORGANISM: human metapneumo virus

<400> SEQUENCE: 167

ataggagttt acggaagctc cgtaatttac atggtgcaac tgccaatctt tggagttata    60

gacacgcctt gctggatagt aaaagcggcc ccttcttgct cggaaaaaaa gggaaactat   120

gcttgcctct taagagaaga tcaaagatgg tattgtcaga atgcagggtc aactgtttac   180

tacccaaatg aaaaagactg cgaaacaaga ggagaccatg tcttttgcga cacagcagca   240

ggaatcaatg ttgctgagca gtcaaaggag tgcaacatca acatatccac tactaattac   300

ccatgcaaag ttagcacagg aagacatcct atcagtatgg ttgcactgtc tcctcttggg   360

gctttggttg cttgctacaa gggagtgagc tgttccattg gcagcaacag agtagggatc   420

atcaagcaac tgaacaaagg ctgctctta                                   449

<210> SEQ ID NO 168
<211> LENGTH: 449
<212> TYPE: DNA
<213> ORGANISM: human metapneumo virus

<400> SEQUENCE: 168

ataggagttt atggaagctc cgtaatttac atggtgcaac tgccaatctt tggagttata    60

gacacgcctt gctggatagt aaaagcggcc ccttcttgct cagaaaaaaa gggaaactat   120

gcttgcctct taagagaaga tcaaggatgg tattgtcaga atgcagggtc aactgtttac   180

tacccaaatg aaaaagactg cgaaacaaga ggagaccatg tcttttgcga cacagcagca   240

ggaatcaatg ttgctgagca gtcaaaggag tgcaacatca acatatccac tactaattac   300

ccatgcaaag ttagcacagg aagacatcct atcagtatgg ttgcactgtc tcctcttggg   360

gctttggttg cttgctacaa gggagtgagc tgttctattg gcagcaacag agtagggatc   420

atcaagcaac tgaacaaagg ctgctctta                                   449

<210> SEQ ID NO 169
<211> LENGTH: 449
<212> TYPE: DNA
<213> ORGANISM: human metapneumo virus

<400> SEQUENCE: 169

ataggagttt atggaagctc cgtaatttac atggtgcaac tgccaatctt tggagttata    60

gacacgcctt gctggatagt aaaagcggcc ccttcttgct cagaaaaaaa gggaaactat   120

gcttgcctct taagagaaga tcaaggatgg tattgtcaga atgcagggtc aactgtttac   180

tacccaaatg aaaaagactg cgaaacaaga ggagaccatg tcttttgcga cacagcagca   240

ggaatcaatg ttgctgagca gtcaaaggag tgcaacatca acatatccac tactaattac   300

ccatgcaaag ttagcacagg aagacatcct atcagtatgg ttgcactgtc tcctcttggg   360

gctttggttg cttgctacaa gggagtgagc tgttccattg gcagcaacag agtagggatc   420

atcaagcaac tgaacaaagg ctgctctta                                   449

<210> SEQ ID NO 170
<211> LENGTH: 449
<212> TYPE: DNA
<213> ORGANISM: human metapneumo virus
```

-continued

<400> SEQUENCE: 170

```
ataggagttt acggaagctc cgtaatttac atggtgcaac tgccaatctt tggagttata     60
gacacgcctt gctggatagt aaaagcggcc ccttcttgct cagaaaaaaa gggaaactat    120
gcttgcctct taagagaaga tcaaggatgg tattgtcaga atgcagggtc aactgtttac    180
tacccaaatg aaaaagactg cgaaacaaga ggagaccatg tcttttgcga cacagcagca    240
ggaatcaatg ttgctgagca gtcaaaggag tgcaacatca acatatccac cactaattac    300
ccatgcaaag ttagcacagg aagacatcct atcagtatgg ttgcactgtc tcctcttggg    360
gctttggttg cttgctacaa gggagtgagc tgttccattg gcagcaacag agtagggatc    420
atcaagcaac tgaacaaagg ctgctctta                                      449
```

<210> SEQ ID NO 171
<211> LENGTH: 449
<212> TYPE: DNA
<213> ORGANISM: human metapneumo virus

<400> SEQUENCE: 171

```
ataggagttt atggaagctc cgtaatttac atggtgcaac tgccaatctt tggagttata     60
gacacgcctt gctggatagt aaaagcggcc ccttcttgct cagaaaaaaa gggaaactat    120
gcttgcctct taagagaaga tcaaggatgg tattgtcaga atgcagggtc aactgtttac    180
tacccaaatg aaaaagactg cgaaacaaga ggagaccatg tcttttgcga cacagcagca    240
ggaatcaatg ttgctgagca gtcaaaggag tgcaacatca acatatccac tactaattac    300
ccatgcaaag ttagcacagg aagacatcct atcagtatgg ttgcactgtc tcctcttggg    360
gctttggttg cttgctacaa gggagtgagc tgttccattg gcagcaacag agtagggatc    420
atcaagcaac tgaacaaagg ctgctctta                                      449
```

<210> SEQ ID NO 172
<211> LENGTH: 449
<212> TYPE: DNA
<213> ORGANISM: human metapneumo virus

<400> SEQUENCE: 172

```
ataggagttt atggaagctc cgtaatttac atggtgcaac tgccaatctt tggagttata     60
gacacgcctt gctggatagt aaaagcggcc ccttcttgct cagaaaaaaa gggaaactat    120
gcttgcctct taagagaaga tcaaggatgg tattgtcaga atgcagggtc aactgtttac    180
tacccaaatg aaaaagactg cgaaacaaga ggagaccatg tcttttgcga cacagcagca    240
ggaatcaatg ttgctgagca gtcaaaggag tgcaacatca acatatccac tactaattac    300
ccatgcaaag ttagcacagg aagacatcct atcagtatgg ttgcactgtc tcctcttggg    360
gctttggttg cttgctacaa gggagtgagc tgttccattg gcagcaacag agtagggatc    420
atcaagcaac tgaacaaagg ctgctctta                                      449
```

<210> SEQ ID NO 173
<211> LENGTH: 449
<212> TYPE: DNA
<213> ORGANISM: human metapneumo virus

<400> SEQUENCE: 173

```
ataggagttt atggaagctc cgtaatttac atggtgcaac tgccaatctt tggagttata     60
gacacgcctt gctggatagt aaaagcggcc ccttcttgct cagaaaaaaa gggaaactat    120
```

-continued

```
gcttgcctct taagagaaga tcaaggatgg tattgtcaga atgcagggtc aactgtttac    180

tacccaaatg aaaaagactg cgaaacaaga ggagaccatg tcttttgcga cacagcagca    240

ggaatcaatg ttgctgagca gtcaaaggag tgcaacatca acatatccac tactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420

atcaagcaac tgaacaaagg ctgctctta                                      449
```

<210> SEQ ID NO 174
<211> LENGTH: 449
<212> TYPE: DNA
<213> ORGANISM: human metapneumo virus

<400> SEQUENCE: 174

```
ataggagttt acggaagctc cgtaatttac atggtgcaac tgccaatctt tggggttata     60

gacacgcctt gctggatagt aaaagcagcc ccttcttgtt caggaaaaaa gggaaactat    120

gcttgcctct taagagaaga ccaaggatgg tattgtcaaa atgcagggtc aactgtttac    180

tacccaaatg aaaaagactg tgaaacaaga ggagaccatg tcttttgcga cacagcagca    240

ggaatcaatg ttgctgagca gtcaaaggag tgcaacataa acatatctac tactaattac    300

ccatgcaaag ttagcacagg aagacatcct atcagtatgg ttgcactatc tcctcttggg    360

gctttggttg cttgctacaa gggagtgagc tgttccattg gcagcaacag agtagggatc    420

atcaagcaac tgaacaaagg ctgctctta                                      449
```

<210> SEQ ID NO 175
<211> LENGTH: 449
<212> TYPE: DNA
<213> ORGANISM: human metapneumo virus

<400> SEQUENCE: 175

```
ataggagttt acggaagctc cgtaatttac atggtgcaac tgccaatctt tggggttata     60

gacacgcctt gctggatagt aaaagcagcc ccttcttgtt caggaaaaaa gggaaactat    120

gcttgcctct taagagaaga ccaaggatgg tattgtcaaa atgcagggtc aactgtttac    180

tacccaaatg aaaaagactg tgaaacaaga ggagaccatg tcttttgcga cacagcagca    240

ggaatcaatg ttgctgagca gtcaaaggag tgcaacataa acatatctac tactaattac    300

ccatgcaaag ttagcacagg aagacatcct atcagtatgg ttgcactatc tcctcttggg    360

gctttggttg cttgctacaa gggagtgagc tgttccattg gcagcaacag agtagggatc    420

atcaagcaac tgaacaaagg ctgctctta                                      449
```

<210> SEQ ID NO 176
<211> LENGTH: 449
<212> TYPE: DNA
<213> ORGANISM: human metapneumo virus

<400> SEQUENCE: 176

```
ataggagttt acggaagctc cgtaatttac atggtgcaac tgccaatctt tggagttata     60

gacacgcctt gctggatagt aaaagcggcc ccttcttgct cagaaaaaaa gggaaactat    120

gcttgcctct taagagaaga tcaaggatgg tattgtcaga atgcagggtc aactgtttac    180

tacccaaatg aaaaagactg cgaaacaaga ggagaccatg tcttttgcga cacagcagca    240

ggaatcaatg ttgctgagca gtcaaaggag tgcaacatca acatatccac cactaattac    300

ccatgcaaag ttagcacagg aagacatcct atcagtatgg ttgcactgtc tcctcttggg    360
```

-continued

```
gctttggttg cttgctacaa gggagtgagc tgttccattg gcagcaacag agtagggatc    420

atcaagcaac tgaacaaagg ctgctctta                                      449
```

<210> SEQ ID NO 177
<211> LENGTH: 449
<212> TYPE: DNA
<213> ORGANISM: human metapneumo virus

<400> SEQUENCE: 177

```
ataggagttt acggaagctc cgtaatttac atggtgcaac tgccaatctt tggggttata     60

gacacgcctt gctggatagt aaaagcagcc ccttcttgct cagaaaaaaa gggaaactat    120

gcttgcctct taagagaaga tcaaggatgg tattgtcaga atgcagggtc aactgtttac    180

tacccaaatg aaaaagactg cgaaacaaga ggagaccatg tcttttgcga cacagcagca    240

ggaatcaatg ttgctgagca gtcaaaggag tgcaacatca acatatccac tactaattac    300

ccatgcaaag ttagcacagg aagacatcct atcagtatgg ttgcactgtc tcctcttggg    360

gctctggttg cttgctacaa gggagtgagc tgctccattg gcagcaacag agtagggatc    420

atcaagcaac tgaacaaagg ctgctctta                                      449
```

<210> SEQ ID NO 178
<211> LENGTH: 449
<212> TYPE: DNA
<213> ORGANISM: human metapneumo virus

<400> SEQUENCE: 178

```
ataggagttt acggaagctc cgtaatttac atggtgcaac tgccaatctt tggagttata     60

gacacgcctt gctggatagt aaaagcggcc ccttcttgct cagaaaaaaa gggaaactat    120

gcttgcctct taagagaaga tcaaggatgg tattgtcaga atgcagggtc aactgtttac    180

tacccaaatg aaaaagactg cgaaacaaga ggagaccatg tcttttgcga cacagcagca    240

ggaatcaatg ttgctgagca gtcaaaggag tgcaacatca acatatccac cactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420

atcaagcaac tgaacaaagg ctgctctta                                      449
```

<210> SEQ ID NO 179
<211> LENGTH: 449
<212> TYPE: DNA
<213> ORGANISM: human metapneumo virus

<400> SEQUENCE: 179

```
ataggagttt acggaagctc cgtaatttac atggtgcaac tgccaatctt tggagttata     60

gacacgcctt gctggatagt aaaagcggcc ccttcttgct cagaaaaaaa gggaaactat    120

gcttgcctct taagagaaga tcaaggatgg tattgtcaga atgcagggtc aactgtttac    180

tacccaaatg aaaaagactg cgaaacaaga ggagaccatg tcttttgcga cacagcagca    240

ggaatcaatg ttgctgagca gtcaaaggag tgcaacatca acatatccac cactaattac    300

ccatgcaaag ttagcacagg aagacatcct atcagtatgg ttgcactgtc tcctcttggg    360

gctttggttg cttgctacaa gggagtgagc tgttccattg gcagcaacag agtagggatc    420

atcaagcaac tgaacaaagg ctgctctta                                      449
```

<210> SEQ ID NO 180

-continued

<211> LENGTH: 449
<212> TYPE: DNA
<213> ORGANISM: human metapneumo virus

<400> SEQUENCE: 180
ataggagttt acggaagctc cgtaatttac atggtgcaac tgccaatctt tggggttata 60
gacacgcctt gctggatagt aaaagcagcc ccttcttgtt caggaaaaaa gggaaactat 120
gcttgcctct taagagaaga ccaaggatgg tattgtcaaa atgcagggtc aactgtttac 180
tacccaaatg aaaaagactg tgaaacaaga ggagaccatg tcttttgcga cacagcagca 240
ggaatcaatg ttgctgagca gtcaaaggag tgcaacataa acatatctac tactaattac 300
ccatgcaaag ttagcacagg aagacatcct atcagtatgg ttgcactatc tcctcttggg 360
gctttggttg cttgctacaa gggagtgagc tgttccattg gcagcaacag agtagggatc 420
atcaagcaac tgaacaaagg ctgctctta 449

<210> SEQ ID NO 181
<211> LENGTH: 449
<212> TYPE: DNA
<213> ORGANISM: human metapneumo virus

<400> SEQUENCE: 181
ataggagttt atggaagctc cgtaatttac atggtgcaac tgccaatctt tggagttata 60
gacacgcctt gctggatagt aaaagcggcc ccttcttgct cagaaaaaaa gggaaactat 120
gcttgcctct taagagaaga tcaaggatgg tattgtcaga atgcagggtc aactgtttac 180
tacccaaatg aaaaagactg cgaaacaaga ggagaccatg tcttttgcga cacagcagca 240
ggaatcaatg ttgctgagca gtcaaaggag tgcaacatca acatatccac tactaattac 300
ccatgcaaag ttagcacagg aagacatcct atcagtatgg ttgcactgtc tcctcttggg 360
gctttggttg cttgctacaa gggagtgagc tgttccattg gcagcaacag agtagggatc 420
atcaagcaac tgaacaaagg ctgctctta 449

<210> SEQ ID NO 182
<211> LENGTH: 449
<212> TYPE: DNA
<213> ORGANISM: human metapneumo virus

<400> SEQUENCE: 182
ataggagttt acggaagctc cgtaatttac atggtgcaac tgccaatctt tggggttata 60
gacacgcctt gctggatagt aaaagcagcc ccttcttgtt caggaaaaaa gggaaactat 120
gcttgcctct taagagaaga ccaaggatgg tattgtcaaa atgcagggtc aactgtttac 180
tacccaaatg aaaaagactg tgaaacaaga ggagaccatg tcttttgcga cacagcagca 240
ggaatcaatg ttgctgagca gtcaaaggag tgcaacataa acatatctac tactaattac 300
ccatgcaaag ttagcacagg aagacatcct atcagtatgg ttgcactatc tcctcttggg 360
gctttggttg cttgctacaa gggagtgagc tgttccattg gcagcaacag agtagggatc 420
atcaagcaac tgaacaaagg ctgctctta 449

<210> SEQ ID NO 183
<211> LENGTH: 449
<212> TYPE: DNA
<213> ORGANISM: human metapneumo virus

<400> SEQUENCE: 183
ataggggtct acgggagctc tgtaatttac atggtgcagc tgccaatctt tggcgttata 60

-continued

```
gacacgcctt gctggatagt aaaagcagcc ccctcttgtt ccgaaaaaaa gggaaactat    120

gcttgcctct taagagaaga ccaagggtgg tattgtcaga atgcagggtc aactgtttac    180

tacccaaatg agaaagactg tgaaacaaga ggagaccatg tcttttgcga cacagcagca    240

ggaattaatg ttgctgagca atcaaaggag tgcaacatca acatatccac tacaaattac    300

ccatgcaaag tcagcacagg aagacatcct atcagtatgg ttgcactgtc ccctcttggg    360

gctctggttg cttgctacaa aggagtaagc tgttccattg gcagcaatag agtagggatt    420

atcaagcagc tgaacaaagg ttgctctta                                      449
```

<210> SEQ ID NO 184
<211> LENGTH: 449
<212> TYPE: DNA
<213> ORGANISM: human metapneumo virus

<400> SEQUENCE: 184

```
ataggggtct acgggagctc cgtaatttac atggtgcagc tgccaatctt tggcgtcata     60

gacacgcctt gctggatagt aaaagcagcc ccctcttgtt ccgaaaaaaa gggaaactat    120

gcttgccttt taagagaaga tcaagggtgg tattgtcaga atgcagggtc aactgtttac    180

tacccaaatg agaaagactg tgaaacaaga ggagaccatg tcttttgcga cacagcagca    240

ggaattaatg ttgctgagca atcaaaagag tgcaacatca acatatccac tacaaattac    300

ccatgcaaag tcagcacagg aagacatcct atcagtatgg ttgcactgtc ccctcttggg    360

gctctagttg cttgctacaa aggagtaagc tgttccattg gcagcaatag agtagggatc    420

atcaagcagc tgaacaaagg ttgctccta                                      449
```

<210> SEQ ID NO 185
<211> LENGTH: 449
<212> TYPE: DNA
<213> ORGANISM: human metapneumo virus

<400> SEQUENCE: 185

```
ataggggtct acgggagctc cgtaatttac atggtgcagc tgccaatctt tggcgtcata     60

gacacgcctt gctggatagt aaaagcagcc ccctcttgtt ccgaaaaaaa gggaaactat    120

gcttgccttt taagagaaga tcaagggtgg tattgtcaga atgcagggtc aactgtttac    180

tacccaaatg agaaagactg tgaaacaaga ggagaccatg tcttttgcga cacagtagca    240

ggaattaatg ttgctgagca atcaaaagag tgcaacatca acatatccac tacaaattac    300

ccatgcaaag tcagcacagg aagacatcct atcagtatgg ttgcactgtc ccctcttggg    360

gctctagttg cttgctacaa aggagtaagc tgttccattg gcagcaatag agtagggatc    420

atcaagcagc tgaacaaagg ttgctccta                                      449
```

<210> SEQ ID NO 186
<211> LENGTH: 449
<212> TYPE: DNA
<213> ORGANISM: human metapneumo virus

<400> SEQUENCE: 186

```
ataggggtct acgggagctc cgtaatttac atggtgcagc tgccaatctt tggcgtcata     60

gacacgcctt gctggatagt aaaagcagcc ccctcttgtt ccgaaaaaaa gggaaactat    120

gcttgccttt taagagaaga tcaagggtgg tattgtcaga atgcagggtc aactgtttac    180

tacccaaatg agaaagactg tgaaacaaga ggagaccatg tcttttgcga cacagcagca    240
```

-continued

```
ggaattaatg ttgctgagca atcaaaagag tgcaacatca acatatccac tacaaattac    300

ccatgcaaag tcagcacagg aagacatcct atcagtatgg ttgcactgtc ccctcttggg    360

gctctagttg cttgctacaa aggagtaagc tgttccattg gcagcaatag agtagggatc    420

atcaagcagc tgaacaaagg ttgctcccta                                     449
```

<210> SEQ ID NO 187
<211> LENGTH: 449
<212> TYPE: DNA
<213> ORGANISM: human metapneumo virus

<400> SEQUENCE: 187

```
ataggggtct acgggagctc cgtaatttac atggtgcagc tgccaatctt tggcgttata     60

gacacgccct gctggatagt aaaagcagcc ccctcttgtt ccgaaaaaaa gggaaactat    120

gcttgccttc taagagaaga ccaagggtgg tattgtcaga atgcagggtc aactgtttac    180

tacccaaatg agaaggactg tgaaacaaga ggagaccatg tcttttgcga cacagcagca    240

ggaattaatg ttgctgagca atcaaaggag tgcaacatca acatatccac cacaaattac    300

ccatgcaaag tcagcacagg aaggcatcct atcagtatgg ttgcactgtc ccctcttggg    360

gctctggttg cttgttacaa aggagtaagc tgttctattg gcagcaatag agtagggatc    420

atcaagcagc tgaacaaagg ttgctcttta                                     449
```

<210> SEQ ID NO 188
<211> LENGTH: 449
<212> TYPE: DNA
<213> ORGANISM: human metapneumo virus

<400> SEQUENCE: 188

```
ataggggtct acgggagctc cgtaatttac atggtgcagc tgccaatctt tggcgttata     60

gacacgcctt gctggatagt aaaagcagcc ccctcttgtt ccgaaaaaaa gggaaactat    120

gcttgcctct taagagaaga ccaagggtgg tattgtcaga atgcagggtc aactgtttac    180

tacccaaatg agaaagactg tgaaacaaga ggagaccatg tcttttgcga cacagcagca    240

ggaattaatg ttgctgagca atcaaaggag tgcaacatca acatatccac tacaaattac    300

ccatgcaaag tcagcacagg aagacatcct atcagtatgg ttgcactgtc tcctcttggg    360

gctctagttg cttgctacaa aggagtaagc tgttccattg gcagcaacag agtagggatc    420

atcaagcagc tgaacaaagg ttgctcccta                                     449
```

<210> SEQ ID NO 189
<211> LENGTH: 449
<212> TYPE: DNA
<213> ORGANISM: human metapneumo virus

<400> SEQUENCE: 189

```
ataggggtct acgggagctc cgtaatttac atggtgcagc tgccaatctt tggcgttata     60

gacacgccct gctggatagt aaaagcagcc ccctcttgtt ccgaaaaaaa gggaaactat    120

gcttgccttc taagagaaga ccaagggtgg tattgtcaga atgcagggtc aactgtttac    180

tacccaaatg agaaggactg tgaaacaaga ggagaccatg tcttttgcga cacagcagca    240

ggaattaatg ttgctgagca atcaaaggag tgcaacatca acatatccac cacaaattac    300

ccatgcaaag tcagcacagg aaggcatcct atcagtatgg ttgcactgtc ccctcttggg    360

gctctggttg cttgttacaa aggagtaagc tgttctattg gcagcaatag agtagggatc    420

atcaagcagc tgaacaaagg ttgctcttta                                     449
```

-continued

<210> SEQ ID NO 190
<211> LENGTH: 449
<212> TYPE: DNA
<213> ORGANISM: human metapneumo virus

<400> SEQUENCE: 190

```
ataggggtct acgggagctc cgtaatttac atggtgcagc tgccaatctt tggcgttata     60

gacacgcctt gctggatagt aaaagcagcc ccttcttgtt ccgaaaaaaa gggaaactat    120

gcttgcctct taagagaaga ccaagggtgg tattgtcaga atgcagggtc aactgtttac    180

tacccaaatg agaaagactg tgaaacaaga ggagaccatg tcttttgcga cacagcagca    240

ggaattaatg ttgctgagca atcaaaggag tgcaacatca acatatccac tacaaattac    300

ccatgcaaag tcagcacagg aagacatcct atcagtatgg ttgcactgtc tcctcttggg    360

gctctggttg cttgctacaa aggagtaagc tgttccattg gcagcaacag agtagggatc    420

atcaagcagc tgaacaaagg ttgctccta                                      449
```

<210> SEQ ID NO 191
<211> LENGTH: 449
<212> TYPE: DNA
<213> ORGANISM: human metapneumo virus

<400> SEQUENCE: 191

```
ataggggtct acgggagctc cgtaatttac atggtgcagc tgccaatctt tggcgttata     60

gacacgcctt gctggatagt aaaagcagcc ccttcttgtt ccgaaaaaaa gggaaactat    120

gcttgcctct taagagaaga ccaagggtgg tattgtcaga atgcagggtc aactgtttac    180

tacccaaatg agaaagactg tgaaacaaga ggagaccatg tcttttgcga cacagcagca    240

ggaattaatg ttgctgagca atcaaaggag tgcaacatca acatatccac tacaaattac    300

ccatgcaaag tcagcacagg aagacatcct atcagtatgg ttgcactgtc tcctcttggg    360

gctctggttg cttgctacaa aggagtaagc tgttccattg gcagcaacag agtagggatc    420

atcaagcagc tgaacaaagg ttgctccta                                      449
```

<210> SEQ ID NO 192
<211> LENGTH: 449
<212> TYPE: DNA
<213> ORGANISM: human metapneumo virus

<400> SEQUENCE: 192

```
ataggggtct acgggagctc cgtaatttac atggtgcagc tgccaatctt tggcgttata     60

gacacgcctt gctggatagt aaaagcagcc ccttcttgtt ccgaaaaaaa gggaaactat    120

gcttgcctct taagagaaga ccaaggatgg tattgtcaga atgcagggtc aactgtttac    180

tacccaaatg agaaagactg tgaaacaaga ggagaccatg tcttttgcga cacagcagca    240

ggaattaatg ttgctgagca atcaaaggag tgcaacatca acatatccac cacaaattac    300

ccatgcaaag tcagcacagg aaggcatcct atcagtatgg ttgcactgtc ccctctcggg    360

gctctggttg cctgttacaa aggagtaagt tgttccattg gcagcaatag agtagggatc    420

atcaagcagc tgaacaaagg ttgctctta                                      449
```

<210> SEQ ID NO 193
<211> LENGTH: 449
<212> TYPE: DNA
<213> ORGANISM: human metapneumo virus -continued

<400> SEQUENCE: 193 atagggggtct acgggagctc cgtaatttac atggtgcagc tgccaatctt tggcgttata 60
gacacgcctt gctggatagt aaaagcagcc ccttcttgtt ccgaaaaaaa gggaaactat 120
gcttgcctct taagagaaga ccaagggtgg tattgtcaga atgcagggtc aactgtttac 180
tacccaaatg agaaagactg tgaaacaaga ggagaccatg tcttttgcga cacagcagca 240
ggaattaatg ttgctgagca atcaaaggag tgcaacatca acatatccac tacaaattac 300
ccatgcaaag tcagcacagg aagacatcct atcagtatgg ttgcactgtc tcctcttggg 360
gctctggttg cttgctacaa aggagtaagc tgttccattg gcagcaacag agtagggatc 420
ataaagcagc tgaacaaagg ttgctcccta 449

<210> SEQ ID NO 194
<211> LENGTH: 449
<212> TYPE: DNA
<213> ORGANISM: human metapneumo virus

<400> SEQUENCE: 194 atagggggtct acgggagctc cgtaatttac atggtgcagc tgccaatctt tggcgttata 60
gacacgcctt gctggatagt aaaagcagcc ccttcttgtt ccgaaaaaaa gggaaactat 120
gcttgcctct taagagaaga ccaaggatgg tattgtcaga atgcagggtc aactgtttac 180
tacccaaatg agaaagactg tgaaacaaga ggagaccatg tcttttgcga cacagcagca 240
ggaattaatg ttgctgagca atcaaaggag tgcaacatca acatatccac cacaaattac 300
ccatgcaaag tcagcacagg aaggcatcct atcagtatgg ttgcactgtc ccctctcggg 360
gctctggttg cctgttacaa aggagtaagt tgttccattg gcagcaatag agtagggatc 420
atcaagcagc tgaacaaagg ttgctctta 449

<210> SEQ ID NO 195
<211> LENGTH: 449
<212> TYPE: DNA
<213> ORGANISM: human metapneumo virus

<400> SEQUENCE: 195 atagggggtct acgggagctc cgtaatttac atggtgcagc tgccaatctt tggcgttata 60
gacacacctt gctggatagt aaaagcagcc ccttcttgtt ccgaaaaaaa gggaaattat 120
gcttgcctct taagagaaga ccaagggtgg tattgtcaga atgcagggtc aactgtttac 180
tacccaaatg agaaagactg tgaaacaaga ggagaccatg tcttttgcga cacagcagca 240
ggaattaatg ttgctgagca atcaaaggaa tgcaacatca acatatccac tacaaattac 300
ccatgcaaag tcagcacagg aagacatcct atcagtatgg ttgcactgtc tcctcttggg 360
gctctggttg cttgctacaa aggagtaagc tgttccattg gcagcaacag agtagggatc 420
atcaagcagc tgaacaaagg ttgctcccta 449

<210> SEQ ID NO 196
<211> LENGTH: 449
<212> TYPE: DNA
<213> ORGANISM: human metapneumo virus

<400> SEQUENCE: 196 atagggggtct acgggagctc cgtaatttac atggtgcagc tgccaatctt tggcgttata 60
gacacgcctt gctggatagt aaaagcagcc ccttcttgtt ccgaaaaaaa gggaaactat 120
gcttgcctct taagagaaga ccaaggatgg tattgtcaga atgcagggtc aactgtttac 180

-continued

```
tacccaaatg agaaagactg tgaaacaaga ggagaccatg tcttttgcga cacagcagca    240

ggaattaatg ttgctgagca atcaaaggag tgcaacatca acatatccac cacaaattac    300

ccatgcaaag tcagcacagg aaggcatcct atcagtatgg ttgcactgtc ccctctcggg    360

gctctggttg cctgttacaa aggagtaagt tgttccattg gcagcaatag agtagggatc    420

atcaagcagc tgaacaaagg ttgctctta                                      449
```

<210> SEQ ID NO 197
<211> LENGTH: 449
<212> TYPE: DNA
<213> ORGANISM: human metapneumo virus

<400> SEQUENCE: 197

```
ataggggtct acgggagctc cgtaatttac atggtgcagc tgccaatctt tggcgttata     60

gacacgcctt gctggatagt aaaagcagcc ccttcttgtt ccgaaaaaaa gggaaactat    120

gcttgcctct taagagaaga ccaagggtgg tattgtcaga atgcagggtc aactgtttac    180

tacccaaatg agaaagactg tgaaacaaga ggagaccatg tcttttgcga cacagcagca    240

ggaattaatg ttgctgagca atcaaaggag tgcaacatca acatatccac tacaaattac    300

ccatgcaaag tcagcacagg aagacatcct atcagtatgg ttgcactgtc tcctcttggg    360

gctctggttg cttgctacaa aggagtaagc tgttccattg gcagcaacag agtagggatc    420

ataaagcagc tgaacaaagg ttgctccta                                      449
```

<210> SEQ ID NO 198
<211> LENGTH: 449
<212> TYPE: DNA
<213> ORGANISM: human metapneumo virus

<400> SEQUENCE: 198

```
ataggggtct acggaagctc cgtgatttac atggttcaat tgccgatctt tggtgtcata     60

gatacacctt gttggataat caaggcagct ccctcttgct cagaaaaaaa cgggaattat    120

gcttgcctcc taagagagga tcaagggtgg tattgtaaaa atgcaggatc cactgtttac    180

tacccaaatg aaaaagactg cgaaacaaga ggtgatcatg ttttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacctaaagg ctgctcata                                      449
```

<210> SEQ ID NO 199
<211> LENGTH: 449
<212> TYPE: DNA
<213> ORGANISM: human metapneumo virus

<400> SEQUENCE: 199

```
ataggggtct acggaagctc tgtgatttac atggttcaat tgccgatctt tggtgtcata     60

gatacacctt gttggatcat caaggcagct ccctcttgct cagaaaaaaa cgggaattat    120

gcttgcctcc taagagagga tcaagggtgg tattgtaaaa atgcaggatc tactgtttac    180

tacccaaatg aaaaagactg cgaaacaaga ggtgatcatg ttttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360
```

-continued

```
gctttggtgg cttgctataa aggggtaagc tgctcgattg gcagcaattg ggttggaatc    420

atcaaacaat tacccaaagg ctgctcata                                      449


<210> SEQ ID NO 200
<211> LENGTH: 449
<212> TYPE: DNA
<213> ORGANISM: human metapneumo virus

<400> SEQUENCE: 200

ataggggtct acggaagctc tgtgatttac atggttcaat tgccgatctt tggtgtcata     60

gatacacctt gttggatcat caaggcagct ccctcttgct cagaaaaaaa cgggaattat    120

gcttgcctcc taagagagga tcaagggtgg tattgtaaaa atgcaggatc tactgtttac    180

tacccaaatg aaaaagactg cgaaacaaga ggtgatcatg ttttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacccaaagg ctgctcata                                      449


<210> SEQ ID NO 201
<211> LENGTH: 449
<212> TYPE: DNA
<213> ORGANISM: human metapneumo virus

<400> SEQUENCE: 201

ataggggtct acggaagctc tgtgatttac atggttcaat tgccgatctt tggtgtcata     60

gatacacctt gttggatcat caaggcagct ccctcttgct cagaaaaaaa cgggaattat    120

gcttgcctcc taagagagga tcaagggtgg tattgtaaaa atgcaggatc tactgtttac    180

tacccaaatg aaaaagactg cgaaacaaga ggtgatcatg ttttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacccaaagg ctgctcata                                      449


<210> SEQ ID NO 202
<211> LENGTH: 449
<212> TYPE: DNA
<213> ORGANISM: human metapneumo virus

<400> SEQUENCE: 202

ataggggtct acggaagctc tgtgatttac atggttcaat tgccgatctt tggtgtcata     60

gatacacctt gttggataat caaggcagct ccctcttgct cagaaaaaaa cgggaattat    120

gcttgcctcc taagagagga tcaagggtgg tattgcaaaa atgcaggatc cactgtttac    180

tacccaaatg aaaaagactg cgaaacaaga ggtgatcatg ttttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacctaaagg ctgctcata                                      449


<210> SEQ ID NO 203
<211> LENGTH: 449
```

-continued

<212> TYPE: DNA
<213> ORGANISM: human metapneumo virus

<400> SEQUENCE: 203 atagggtct acggaagctc cgtgatttac atggttcaat tgccgatctt tggtgtcata 60
gatacacctt gttggataat caaggcagct ccctcttgct cagaaaaaaa cgggaattat 120
gcttgcctcc taagagagga tcaagggtgg tattgtaaaa atgcaggatc cactgtttac 180
tacccaaatg aaaaagactg cgaaacaaga ggtgatcatg ttttttgtga cacagcagca 240
gggatcaatg ttgctgagca atcaagagaa tgcaacatca acatatctac taccaactac 300
ccatgcaaag tcagcacagg aagacaccct ataagcatgg ttgcactatc acctctcggt 360
gctttggtgg cttgctataa aggggtaagc tgctcgattg gcagcaatcg ggttggaatc 420
atcaaacaat tacctaaagg ctgctcata 449

<210> SEQ ID NO 204
<211> LENGTH: 449
<212> TYPE: DNA
<213> ORGANISM: human metapneumo virus

<400> SEQUENCE: 204 atagggtct acggaagctc tgtaatttac atggttcaat tgccgatctt tggtgtcata 60
gatacacctt gttggataat caaggcagct ccctcttgct cagaaaaaaa cgggaattat 120
gcttgcctcc taagagagga tcaagggtgg tattgtaaaa atgcaggatc cactgtttac 180
tacccaaatg aaaaagactg cgaaacaaga ggtgatcatg ttttttgtga cacagcagca 240
gggatcaatg ttgctgagca atcaagagaa tgcaacatca acatatctac taccaactac 300
ccatgcaaag tcagcacagg aagacaccct ataagcatgg ttgcactatc acctctcggt 360
gctttggtgg cttgctataa aggggtaagc tgctcgattg gcagcaatcg ggttggaatc 420
atcaaacaat tacctaaagg ctgctcata 449

<210> SEQ ID NO 205
<211> LENGTH: 449
<212> TYPE: DNA
<213> ORGANISM: human metapneumo virus

<400> SEQUENCE: 205 atagggtct acggaagctc cgtgatttac atggttcaat tgccgatctt tggtgtcata 60
gatacacctt gttggataat caaggcagct ccctcttgct cagaaaaaaa cgggaattat 120
gcttgcctcc taagagagga tcaagggtgg tattgtaaaa atgcaggatc cactgtttac 180
tacccaaatg aaaaagactg cgaaacaaga ggtgatcatg ttttttgtga cacagcagca 240
gggatcaatg ttgctgagca atcaagagaa tgcaacatca acatatctac taccaactac 300
ccatgcaaag tcagcacagg aagacactct ataagcatgg ttgcactatc acctctcggt 360
gctttggtgg cttgctataa aggggtaagc tgctcgattg gcagcaatcg ggttggaatc 420
atcaaacaat tacctaaagg ctgctcata 449

<210> SEQ ID NO 206
<211> LENGTH: 449
<212> TYPE: DNA
<213> ORGANISM: human metapneumo virus

<400> SEQUENCE: 206 atagggtct acggaagctc cgtgatttac atggttcaat tgccgatctt tggtgtcata 60

-continued gatacacctt gttggataat caaggcagct ccctcttgct cagaaaaaaa cgggaattat 120
gcttgcctcc taagagagga tcaagggtgg tattgtaaaa atgcaggatc cactgtttac 180
tacccaaatg aaaaagactg cgaaacaaga ggtgatcatg ttttttgtga cacagcagca 240
gggatcaatg ttgctgagca atcaagagaa tgcaacatca acatatctac taccaactac 300
ccatgcaaag tcagcacagg aagacaccct ataagcatgg ttgcactatc acctctcggt 360
gctttggtgg cttgctataa aggggtaagc tgctcgattg gcagcaatcg ggttggaatc 420
atcaaacaat tacctaaagg ctgctcata 449

<210> SEQ ID NO 207
<211> LENGTH: 449
<212> TYPE: DNA
<213> ORGANISM: human metapneumo virus

<400> SEQUENCE: 207
ataggggtct acggaagctc tgtgatttac atggttcaat tgccgatctt tggtgtcata 60
gatacacctt gttggataat caaggcagct ccctcttgct cagaaaaaaa cgggaattat 120
gcttgcctcc taagagagga tcaagggtgg tattgtaaaa atgcaggatc cactgtttac 180
tacccaaatg aaaaagactg tgaaacaaga ggtgatcatg ttttttgtga cacagcagca 240
gggatcaatg ttgctgagca atcaagagaa tgcaacatca acatatctac taccaactac 300
ccatgcaaag tcagcacagg aagacaccct ataagcatgg ttgcactatc acctctcggt 360
gctttggtgg cttgctataa aggggtaagc tgctcgattg gcagcaatcg ggttggaatc 420
atcaaacaat tacctaaagg ctgctcata 449

<210> SEQ ID NO 208
<211> LENGTH: 449
<212> TYPE: DNA
<213> ORGANISM: human metapneumo virus

<400> SEQUENCE: 208
ataggggtct acggaagctc cgtgatttac atggttcaat tgccgatctt tggtgtcata 60
gatacacctt gttggataat caaggcagct ccctcttgct cagaaaaaaa cgggaattat 120
gcttgcctcc taagagagga tcaagggtgg tactgtaaaa atgcaggatc cactgtttac 180
tacccaaatg aaaaagactg cgaaacaaga ggtgatcatg ttttttgtga cacagcagca 240
gggatcaatg ttgctgagca atcaagagaa tgcaacatca acatatctac taccaactac 300
ccatgcaaag tcagcacagg aagacaccct ataagcatgg ttgcactatc acctctcggt 360
gctttggtgg cttgctataa aggggtaagc tgctcgattg gcagcaatcg ggttggaatc 420
atcaaacaat tacctaaagg ctgctcata 449

<210> SEQ ID NO 209
<211> LENGTH: 449
<212> TYPE: DNA
<213> ORGANISM: human metapneumo virus

<400> SEQUENCE: 209
ataggggtct acggaagctc tgtgatttac atggttcaat tgccgatctt tggggtcata 60
gatacacctt gttggataat caaggcagct ccctcttgct cagaaaaaaa cgggaattat 120
gcttgcctcc taagagagga tcaagggtgg tattgtaaaa atgcaggatc cactgtttac 180
tacccaaatg aaaaagactg cgaaacaaga ggtgatcatg ttttttgtga tacagcagca 240
gggatcaatg ttgctgagca atcaagagaa tgcaacatca acatatctac taccaactac 300

-continued

```
ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacccaaagg ctgctcata                                     449
```

<210> SEQ ID NO 210
<211> LENGTH: 449
<212> TYPE: DNA
<213> ORGANISM: human metapneumo virus

<400> SEQUENCE: 210

```
ataggggtct acggaagctc tgtgatttac atggttcaat tgccgatctt tggtgtcata     60

gatacacctt gttggataat caaggcagcc ccctcttgct cagagaaaaa cgggaattat    120

gcttgcctcc taagagagga tcaagggtgg tattgtaaaa atgcaggatc cactgtttac    180

tacccaaatg aaaaagactg cgaaacaaga ggtgatcatg tgttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatt    420

atcaaacaat tacctaaagg ctgctcata                                     449
```

<210> SEQ ID NO 211
<211> LENGTH: 449
<212> TYPE: DNA
<213> ORGANISM: human metapneumo virus

<400> SEQUENCE: 211

```
ataggggtct acggaagctc tgtgatttac atggttcaat tgccgatctt tggtgtcata     60

gatacacctt gttggataat caaggcagct ccctcttgct cagagaaaaa cgggaattat    120

gcttgcctcc taagagagga tcaagggtgg tattgtaaaa atgcaggatc cactgtttac    180

tacccaaatg aaaaagactg cgaaacaaga ggtgatcatg tgttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacctaaagg ctgctcata                                     449
```

<210> SEQ ID NO 212
<211> LENGTH: 449
<212> TYPE: DNA
<213> ORGANISM: human metapneumo virus

<400> SEQUENCE: 212

```
ataggggtct acggaagctc tgtgatttac atggttcaat tgccgatctt tggtgtcata     60

gatacacctt gttggataat caaggcagct ccctcttgct cagaaaaaaa cgggaattat    120

gcttgcctcc taagagagga tcaagggtgg tattgtaaaa atgcaggatc cactgtttac    180

tacccaaatg aaaaagactg tgaaacaaga ggtgatcatg tttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacctaaagg ctgctcata                                     449
```

-continued

<210> SEQ ID NO 213
<211> LENGTH: 449
<212> TYPE: DNA
<213> ORGANISM: human metapneumo virus

<400> SEQUENCE: 213

```
ataggggtct acggaagctc cgtgatttac atggttcaat tgccgatctt tggtgtcata     60

gatacacctt gttggataat caaggcagct ccctcttgct cagaaaaaaa cgggaattat    120

gcttgcctcc taagagagga tcaagggtgg tattgtaaaa atgcaggatc cactgtttac    180

tacccaaatg aaaaagactg cgaaacaaga ggtgatcatg ttttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacctaaagg ctgctcata                                      449
```

<210> SEQ ID NO 214
<211> LENGTH: 449
<212> TYPE: DNA
<213> ORGANISM: human metapneumo virus

<400> SEQUENCE: 214

```
ataggggtct acggaagctc tgtgatttac atggttcaat tgccgatctt tggtgtcata     60

gatacacctt gttggataat caaggcagct ccctcttgct cagagaaaaa cgggaattat    120

gcttgcctcc taagagagga tcaagggtgg tattgtaaaa atgcaggatc cactgtttac    180

tacccaaatg aaaaagactg cgaaacaaga ggtgatcatg tgttttgtga cacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacctaaagg ctgctcata                                      449
```

<210> SEQ ID NO 215
<211> LENGTH: 449
<212> TYPE: DNA
<213> ORGANISM: human metapneumo virus

<400> SEQUENCE: 215

```
ataggggtct acggaagctc tgtgatttac atggttcaat tgccgatctt tggtgtcata     60

gatacacctt gttggataat caaggcagct ccctcttgct cagaaaaaaa cgggaattat    120

gcttgcctcc taagagagga tcaagggtgg tattgtaaaa atgcaggatc cactgtttac    180

tacccaaatg aaaaagactg cgaaacaaga ggtgatcatg ttttttgtga tacagcagca    240

gggatcaatg ttgctgagca atcaagagaa tgcaacatca acatatctac taccaactac    300

ccatgcaaag tcagcacagg aagacaccct ataagcatgg ttgcactatc acctctcggt    360

gctttggtgg cttgctataa aggggtaagc tgctcgattg gcagcaatcg ggttggaatc    420

atcaaacaat tacccaaagg ctgctcata                                      449
```

<210> SEQ ID NO 216
<211> LENGTH: 449
<212> TYPE: DNA
<213> ORGANISM: human metapneumo virus

<400> SEQUENCE: 216

-continued atagggtct acggaagctc cgtgatttac atggttcaat tgccgatctt tggtgtcata 60
gatacacctt gttggataat caaggcagct ccctcttgct cagaaaaaaa cgggaattat 120
gcttgcctcc taagagagga tcaagggtgg tactgtaaaa atgcaggatc cactgtttac 180
tacccaaatg aaaaagactg cgaaacaaga ggtgatcatg ttttttgtga cacagcagca 240
gggatcaatg ttgctgagca atcaagagaa tgcaacatca acatatctac taccaactac 300
ccatgcaaag tcagcacagg aagacaccct ataagcatgg ttgcactatc acctctcggt 360
gctttggtgg cttgctataa aggggtaagc tgctcgattg gcagcaatcg ggttggaatc 420
atcaaacaat tacctaaagg ctgctcata 449

<210> SEQ ID NO 217
<211> LENGTH: 449
<212> TYPE: DNA
<213> ORGANISM: human metapneumo virus

<400> SEQUENCE: 217 atagggtct acggaagctc tgtgatttac atggtccagc tgccgatctt tggtgtcata 60
gatacacctt gttggataat caaggcagct ccctcttgtt cagaaaaaga tggaaattat 120
gcttgcctcc taagagagga tcaagggtgg tattgcaaaa atgcaggatc cactgtttac 180
tacccaaatg aaaaagactg cgaaacaaga ggtgatcatg ttttttgtga cacagcagca 240
gggatcaatg ttgctgagca atcaagagaa tgcaacatca acatatctac caccaactac 300
ccatgcaaag tcagcacagg aagacaccct atcagcatgg ttgcactatc acctctcggt 360
gctttggtag cttgctacaa gggggttagc tgctcgattg gcagtaatcg ggttggaata 420
atcaaacaac tacctaaagg ctgctcata 449

<210> SEQ ID NO 218
<211> LENGTH: 449
<212> TYPE: DNA
<213> ORGANISM: human metapneumo virus

<400> SEQUENCE: 218 atagggtct acggaagctc tgtgatttac atggtccagc tgccgatctt tggtgtcata 60
gatacacctt gttggataat caaggcagct ccctcttgtt cagaaaaaga tggaaattat 120
gcttgcctcc taagagagga tcaagggtgg tattgtaaaa atgcaggatc cactgtttac 180
tacccaaatg aaaaagactg cgaaacaaga ggtgatcatg ttttttgtga cacagcagca 240
gggatcaatg ttgctgagca atcaagagaa tgcaacatca acatatctac caccaactac 300
ccatgcaaag tcagcacagg aagacacccc atcagcatgg ttgcactatc acctctcggt 360
gctttggtag cttgctacaa aggggttagc tgctcgattg gcagtaatcg ggttggaata 420
atcaaacaac tacctaaagg ctgctcata 449

<210> SEQ ID NO 219
<211> LENGTH: 449
<212> TYPE: DNA
<213> ORGANISM: human metapneumo virus

<400> SEQUENCE: 219 atagggtct acggaagctc tgtgatttac atggtccagc tgccgatctt tggtgtcata 60
gatacacctt gttggataat caaggcagct ccctcttgtt cagaaaaaga tggaaattat 120
gcttgcctcc taagagagga tcaagggtgg tattgtaaaa atgcaggatc cactgtttac 180

-continued

```
tacccaaatg aaaaagactg cgaaacaaga ggtgatcatg ttttttgtga cacagcagca    240

gggatcaatg ttgctgagca atcaagagaa tgcaacatca acatatctac caccaactac    300

ccatgcaaag tcagcacagg aagacaccct atcagcatgg ttgcactatc acctctcggt    360

gctttggtag cttgctacaa aggggttagc tgctcgattg gcagtaatcg ggttggaata    420

atcaaacaac tacctaaagg ctgctcata                                     449
```

<210> SEQ ID NO 220
<211> LENGTH: 449
<212> TYPE: DNA
<213> ORGANISM: human metapneumo virus

<400> SEQUENCE: 220

```
ataggggtct acggaagctc cgtgatttac atggtccagc tgccgatctt tggtgtcata     60

gatacacctt gttggataat caaggcagct ccctcttgtt cagaaaaaga tggaaattat    120

gcttgcctcc taagagagga ccaagggtgg tattgtaaaa atgcgggatc cactgtttac    180

tacccaaatg aaaaagactg cgaaacaaga ggtgatcatg ttttttgtga cacagcagca    240

gggatcaatg ttgctgagca atcaagagaa tgcaacatca acatatctac aaccaactac    300

ccatgcaaag tcagcacagg aagacaccct atcagcatgg ttgcactatc acctctcggt    360

gctttggtag cttgctacaa aggggttagc tgttcgattg gcagtaatcg ggttggaata    420

atcaaacaac tacctaaagg ctgctcata                                     449
```

<210> SEQ ID NO 221
<211> LENGTH: 449
<212> TYPE: DNA
<213> ORGANISM: human metapneumo virus

<400> SEQUENCE: 221

```
ataggggtct acggaagctc cgtgatttac atggtccagc taccgatctt tggtgtcata     60

gatacacctt gttggataat caaggcagct ccctcttgtt cagaaaaaga tggaaattat    120

gcttgcctcc taagagagga tcaagggtgg tattgtaaaa atgcaggatc cactgtttac    180

tacccaaatg aaaaagactg cgaaacaaga ggtgatcatg ttttttgtga cacagctgca    240

gggatcaatg ttgctgagca atcaagagaa tgcaacatca acatatccac aaccaactac    300

ccatgcaaag tcagcacagg aagacaccct atcagcatgg ttgcactgtc acctctcggc    360

gctttggtag cttgctacaa aggggttagc tgttcgattg gcagtaatcg ggttggaata    420

atcaaacaac tacctaaagg ctgctcata                                     449
```

<210> SEQ ID NO 222
<211> LENGTH: 449
<212> TYPE: DNA
<213> ORGANISM: human metapneumo virus

<400> SEQUENCE: 222

```
ataggggtct acggaagctc cgtgatttac atggtccagc tgccgatctt tggtgtcata     60

gatacacctt gttggataat caaggcagct ccctcttgtt cagaaaaaga tggaaattat    120

gcttgcctcc taagagagga tcaagggtgg tattgtaaaa atgcaggatc cactgtttac    180

tacccaaatg aaaaagactg cgaaacaaga ggtgatcatg ttttttgtga cacagcagca    240

gggatcaatg ttgctgagca atcaagagaa tgcaacatca acatatctac taccaactac    300

ccatgcaaag tcagcacagg aagacaccct atcagcatgg ttgcactatc acctctcggt    360

gctttggtag cttgctacaa aggggttagc tgttcgattg gcagtaatcg ggttggaata    420
```

-continued

```
atcaaacaac tacctaaagg ctgctcata                                     449

<210> SEQ ID NO 223
<211> LENGTH: 449
<212> TYPE: DNA
<213> ORGANISM: human metapneumo virus

<400> SEQUENCE: 223

ataggggtct acggaagctc cgtgatttac atggtccagc tgccgatctt tggtgtcata     60

gatacacctt gttggataat caaggcagct ccctcttgtt cagaaaaaga tggaaattat    120

gcttgcctcc taagagagga tcaagggtgg tattgtaaaa atgcaggatc cactgtttac    180

tacccaaatg aaaaagactg tgaaacaaga ggtgatcatg tttttgtga cacagcagca    240

gggatcaatg ttgctgagca atcaagagaa tgcaacatca acatatctac aaccaactac    300

ccatgcaaag tcagcacagg aagacaccct atcagcatgg ttgcactatc acctctcggt    360

gctttggtag cttgctacaa aggggttagc tgttcgattg gcagtaatcg ggttggaata    420

atcaaacaac tacctaaagg ctgctcata                                     449

<210> SEQ ID NO 224
<211> LENGTH: 449
<212> TYPE: DNA
<213> ORGANISM: human metapneumo virus

<400> SEQUENCE: 224

ataggggtct acggaagctc cgtgatttac atggtccagc tgccgatctt tggtgtcata     60

gatacacctt gttggataat caaggcagct ccctcttgtt cagaaaaaga tggaaattat    120

gcttgcctcc taagagagga ccaagggtgg tattgtaaaa atgcgggatc cactgtttac    180

tacccaaatg aaaaagactg cgaaacaaga ggtgatcatg tttttgtga cacagcagca    240

gggatcaatg ttgctgagca atcaagagaa tgcaacatca acatatctac aaccaactac    300

ccatgcaaag tcagcacagg aagacaccct atcagcatgg ttgcactatc acctctcggt    360

gctttggtag cttgctacaa aggggttagc tgttcgattg gcagtaatcg ggttggaata    420

atcaaacaac tacctaaagg ctgctcata                                     449

<210> SEQ ID NO 225
<211> LENGTH: 449
<212> TYPE: DNA
<213> ORGANISM: human metapneumo virus

<400> SEQUENCE: 225

ataggggtct acggaagctc cgtgatttac atggtccagc tgccgatctt tggtgtcata     60

gatacacctt gttggataat caaggcagct ccctcttgtt cagaaaaaga tggaaattat    120

gcttgcctcc taagagagga tcaagggtgg tattgtaaaa atgcaggatc cactgtttac    180

tacccaaatg aaaaagactg cgaaacaaga ggtgatcatg tttttgtga cacagcagca    240

gggatcaatg ttgctgagca atcaagagaa tgcaacatca acatatctac aaccaactac    300

ccatgcaaag tcagcacagg aagacaccct atcagcatgg ttgcactatc acctctcggt    360

gctttggtag cttgctacaa aggggttagc tgttcgattg gcagtaatcg ggttggaata    420

atcaaacaac tacctaaagg ctgctcata                                     449

<210> SEQ ID NO 226
<211> LENGTH: 449
<212> TYPE: DNA
```

-continued

<213> ORGANISM: human metapneumo virus

<400> SEQUENCE: 226

```
atagggggtct acggaagctc cgtgatttac atggtccagc tgccgatctt tggtgtcata     60
gatacacctt gttggataat caaggcagct ccctcttgtt cagaaaaaga tggaaattat    120
gcttgcctcc taagagagga tcaagggtgg tattgtaaaa atgcaggatc cactgtttac    180
tacccaaatg aaaaagactg tgaaacaaga ggtgatcatg ttttttgtga cacagcagca    240
gggatcaatg ttgctgagca atcaagagaa tgcaacatca acatatctac aaccaactac    300
ccatgcaaag tcagcacagg aagacaccct atcagcatgg ttgcactatc acctctcggt    360
gctttggtag cttgctacaa aggggttagc tgttcgattg gcagtaatcg ggttggaata    420
atcaaacaac tacctaaagg ctgctcata                                      449
```

<210> SEQ ID NO 227
<211> LENGTH: 449
<212> TYPE: DNA
<213> ORGANISM: human metapneumo virus

<400> SEQUENCE: 227

```
ataggggtct acggaagctc cgtgatttac atggtccagc tgccgatctt tggtgtcata     60
gatacacctt gttggataat caaggcagct ccctcttgtt cagaaaaaga tggaaattat    120
gcttgcctcc taagagagga tcaagggtgg tattgtaaaa atgcaggatc cactgtttac    180
tacccaaatg aaaaagactg cgaaacaaga ggtgatcatg ttttttgtga cacagctgca    240
gggatcaatg ttgctgagca atcaagagaa tgcaacatca acatatctac aaccaactac    300
ccatgcaaag tcagcacagg aagacaccct atcagcatgg ttgcactatc acctctcggt    360
gctttggtag cttgctacaa aggggttagc tgttcaattg gcagtaatcg ggttggaata    420
atcaaacaac tacctaaagg ctgctcata                                      449
```

<210> SEQ ID NO 228
<211> LENGTH: 449
<212> TYPE: DNA
<213> ORGANISM: human metapneumo virus

<400> SEQUENCE: 228

```
ataggggtct acggaagctc cgtgatttac atggtccagc tgccgatctt tggtgtcata     60
gatacacctt gttggataat caaggcagct ccctcttgtt cagaaaaaga tggaaattat    120
gcttgcctcc taagagagga tcaagggtgg tattgtaaaa atgcaggatc cactgtttac    180
tacccaaatg aaaaagactg cgaaacaaga ggtgatcatg ttttttgtga cacagctgca    240
gggatcaatg ttgctgagca atcaagagaa tgcaacatca acatatctac aaccaactac    300
ccatgcaaag tcagcacagg aagacaccct atcagcatgg ttgcactatc acctctcggt    360
gctttggtag cttgctacaa aggggttagc tgttcaattg gcagtaatcg ggttggaata    420
atcaaacaac tacctaaagg ctgctcata                                      449
```

<210> SEQ ID NO 229
<211> LENGTH: 449
<212> TYPE: DNA
<213> ORGANISM: human metapneumo virus

<400> SEQUENCE: 229

```
ataggggtct acggaagctc cgtgatttac atggtccagc tgccgatctt tggtgtcata     60
gatacacctt gttggataat caaggcagct ccctcttgtt cagaaaaaga tggaaattat    120
```

-continued

```
gcttgcctcc taagagagga tcaagggtgg tattgtaaaa atgcaggatc cactgtttac    180

tacccaaatg aaaaagactg cgaaacaaga ggtgatcatg ttttttgtga cacagctgca    240

gggatcaatg ttgctgagca atcaagagaa tgcaacatca acatatctac aaccaactac    300

ccatgcaaag tcagcacagg aagacaccct atcagcatgg ttgcactatc acctctcggt    360

gctttggtag cttgctacaa gggggttagc tgttcgattg gcagtaatcg ggttggaata    420

atcaaacaac tacctaaagg ctgctcata                                      449
```

<210> SEQ ID NO 230
<211> LENGTH: 449
<212> TYPE: DNA
<213> ORGANISM: human metapneumo virus

<400> SEQUENCE: 230

```
ataggggtct acggaagctc tgtgatttac atggtccagc tgccgatctt tggtgtcata     60

gatacacctt gttggataat caaggcagct ccctcttgtt cagaaaaaga tggaaattat    120

gcttgcctcc taagagagga tcaagggtgg tattgtaaaa atgcaggatc cactgtttac    180

tacccaaatg aaaaagactg cgaaacaaga ggtgatcatg ttttttgtga cacagctgca    240

gggatcaatg ttgctgagca atcaagagaa tgcaacatca acatatccac aaccaactac    300

ccatgcaaag tcagcacagg aagacaccct atcagcatgg ttgcactgtc acctctcggc    360

gctttggtag cttgctacaa aggggttagc tgttcgattg gcagtaatcg ggttggaata    420

atcaaacaac tacctaaagg ctgctcata                                      449
```

<210> SEQ ID NO 231
<211> LENGTH: 449
<212> TYPE: DNA
<213> ORGANISM: human metapneumo virus

<400> SEQUENCE: 231

```
ataggggtct acggaagctc tgtgatttac atggtccagc tgccgatctt tggtgtcata     60

gatacacctt gttggataat caaggcagct ccctcttgtt cagaaaaaga tggaaattat    120

gcttgcctcc taagagagga tcaagggtgg tattgtaaaa atgcaggatc cactgtttac    180

tacccaaatg aaaaagactg cgaaacaaga ggtgatcatg ttttttgtga cacagcagca    240

gggatcaacg ttgctgagca atcaagagaa tgcaacatca acatatctac caccaactat    300

ccgtgcaaag tcagcacagg aagacaccct atcagcatgg ttgcactatc acctctcggt    360

gctttggtag cttgctacaa aggggttagc tgctcgattg gcagtaatcg ggttggaata    420

atcaaacaac tacctaaagg ctgctcata                                      449
```

<210> SEQ ID NO 232
<211> LENGTH: 449
<212> TYPE: DNA
<213> ORGANISM: human metapneumo virus

<400> SEQUENCE: 232

```
ataggggtct acggaagctc cgtgatttac atggtccagc tgccgatctt tggtgtcata     60

gatacacctt gttggataat caaggcagct ccctcttgtt cagaaaaaga tggaaattat    120

gcttgcctcc taagagagga tcaagggtgg tattgtaaaa atgcaggatc cactgtttac    180

tacccaaatg aaaaagactg cgaaacaaga ggtgatcatg ttttttgtga cacagctgca    240

gggatcaatg ttgctgagca atcaagagaa tgcaacatca acatatctac aaccaactac    300
```

-continued

```
ccatgcaaag tcagcacagg aagacaccct atcagcatgg ttgcactatc acctctcggt    360

gctttggtag cttgctacaa aggggttagc tgttcaattg gcagtaatcg ggttggaata    420

atcaaacaac tacctaaagg ctgctcata                                      449
```

<210> SEQ ID NO 233
<211> LENGTH: 449
<212> TYPE: DNA
<213> ORGANISM: human metapneumo virus

<400> SEQUENCE: 233

```
ataggggtct acggaagctc cgtgatttac atggtccagc tgccgatctt tggtgtcata     60

gatacacctt gttggataat caaggcagct ccctcttgtt cagaaaaaga tggaaattat    120

gcttgcctcc taagagagga tcaagggtgg tattgtaaaa atgcaggatc cactgtttac    180

tacccaaatg aaaaagactg cgaaacaaga ggtgatcatg ttttttgtga cacagcagca    240

gggatcaatg ttgctgagca atcaagagaa tgcaacatca acatatctac aaccaactac    300

ccatgcaaag tcagcacagg aagacaccct atcagcatgg ttgcactatc acctctcggt    360

gctttggtag cttgctacaa aggggttagc tgttcgattg gcagtaatcg ggttggaata    420

atcaaacaac tacctaaagg ctgctcata                                      449
```

<210> SEQ ID NO 234
<211> LENGTH: 149
<212> TYPE: PRT
<213> ORGANISM: human metapneumo virus

<400> SEQUENCE: 234

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Gly Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145
```

<210> SEQ ID NO 235
<211> LENGTH: 149
<212> TYPE: PRT
<213> ORGANISM: human metapneumo virus

<400> SEQUENCE: 235

```
Ile Gly Val Tyr Gly Ser Ser Val Ile Tyr Met Val Gln Leu Pro Ile
 1               5                  10                  15
```

-continued

```
Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 236
<211> LENGTH: 149
<212> TYPE: PRT
<213> ORGANISM: human metapneumo virus

<400> SEQUENCE: 236

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 237
<211> LENGTH: 149
<212> TYPE: PRT
<213> ORGANISM: human metapneumo virus

<400> SEQUENCE: 237

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30
```

-continued

```
Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 238
<211> LENGTH: 149
<212> TYPE: PRT
<213> ORGANISM: human metapneumo virus

<400> SEQUENCE: 238

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 239
<211> LENGTH: 149
<212> TYPE: PRT
<213> ORGANISM: human metapneumo virus

<400> SEQUENCE: 239

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45
```

-continued

Gly Trp Tyr Cys Gln Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Lys Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Asn Lys Gly Cys Ser
145

<210> SEQ ID NO 240
<211> LENGTH: 149
<212> TYPE: PRT
<213> ORGANISM: human metapneumo virus

<400> SEQUENCE: 240

Ile Gly Val Tyr Gly Ser Ser Val Ile Tyr Met Val Gln Leu Pro Ile
1 5 10 15

Phe Gly Val Ile Asp Thr Pro Cys Trp Ile Val Lys Ala Ala Pro Ser
20 25 30

Cys Ser Glu Lys Lys Gly Asn Tyr Ala Cys Leu Leu Arg Glu Asp Gln
35 40 45

Gly Trp Tyr Cys Gln Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Lys Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Asn Lys Gly Cys Ser
145

<210> SEQ ID NO 241
<211> LENGTH: 149
<212> TYPE: PRT
<213> ORGANISM: human metapneumo virus

<400> SEQUENCE: 241

Ile Gly Val Tyr Gly Ser Ser Val Ile Tyr Met Val Gln Leu Pro Ile
1 5 10 15

Phe Gly Val Ile Asp Thr Pro Cys Trp Ile Val Lys Ala Ala Pro Ser
20 25 30

Cys Ser Glu Lys Lys Gly Asn Tyr Ala Cys Leu Leu Arg Glu Asp Gln
35 40 45

Gly Trp Tyr Cys Gln Asn Ala Gly Ser Thr Val Tyr Tyr Pro Asn Glu
50 55 60

-continued

```
Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 242
<211> LENGTH: 149
<212> TYPE: PRT
<213> ORGANISM: human metapneumo virus

<400> SEQUENCE: 242

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 243
<211> LENGTH: 149
<212> TYPE: PRT
<213> ORGANISM: human metapneumo virus

<400> SEQUENCE: 243

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80
```

-continued

```
Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 244
<211> LENGTH: 149
<212> TYPE: PRT
<213> ORGANISM: human metapneumo virus

<400> SEQUENCE: 244

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 245
<211> LENGTH: 149
<212> TYPE: PRT
<213> ORGANISM: human metapneumo virus

<400> SEQUENCE: 245

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95
```

-continued

```
Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 246
<211> LENGTH: 149
<212> TYPE: PRT
<213> ORGANISM: human metapneumo virus

<400> SEQUENCE: 246

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 247
<211> LENGTH: 149
<212> TYPE: PRT
<213> ORGANISM: human metapneumo virus

<400> SEQUENCE: 247

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Arg Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110
```

```
Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 248
<211> LENGTH: 149
<212> TYPE: PRT
<213> ORGANISM: human metapneumo virus

<400> SEQUENCE: 248

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 249
<211> LENGTH: 149
<212> TYPE: PRT
<213> ORGANISM: human metapneumo virus

<400> SEQUENCE: 249

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125
```

-continued

```
Val Ser Cys Ser Ile Gly Ser Asn Arg Val Gly Ile Ile Lys Gln Leu
    130                 135                 140

Asn Lys Gly Cys Ser
145


<210> SEQ ID NO 250
<211> LENGTH: 149
<212> TYPE: PRT
<213> ORGANISM: human metapneumo virus

<400> SEQUENCE: 250

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 251
<211> LENGTH: 149
<212> TYPE: PRT
<213> ORGANISM: human metapneumo virus

<400> SEQUENCE: 251

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140
```

-continued

```
Asn Lys Gly Cys Ser
145


<210> SEQ ID NO 252
<211> LENGTH: 149
<212> TYPE: PRT
<213> ORGANISM: human metapneumo virus

<400> SEQUENCE: 252

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 253
<211> LENGTH: 149
<212> TYPE: PRT
<213> ORGANISM: human metapneumo virus

<400> SEQUENCE: 253

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145
```

-continued

<210> SEQ ID NO 254
<211> LENGTH: 149
<212> TYPE: PRT
<213> ORGANISM: human metapneumo virus

<400> SEQUENCE: 254

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Gly Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145
```

<210> SEQ ID NO 255
<211> LENGTH: 149
<212> TYPE: PRT
<213> ORGANISM: human metapneumo virus

<400> SEQUENCE: 255

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Gly Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145
```

<210> SEQ ID NO 256
<211> LENGTH: 149

<212> TYPE: PRT
<213> ORGANISM: human metapneumo virus

<400> SEQUENCE: 256

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145
```

<210> SEQ ID NO 257
<211> LENGTH: 149
<212> TYPE: PRT
<213> ORGANISM: human metapneumo virus

<400> SEQUENCE: 257

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145
```

<210> SEQ ID NO 258
<211> LENGTH: 149
<212> TYPE: PRT
<213> ORGANISM: human metapneumo virus -continued

<400> SEQUENCE: 258

Ile Gly Val Tyr Gly Ser Ser Val Ile Tyr Met Val Gln Leu Pro Ile
1 5 10 15

Phe Gly Val Ile Asp Thr Pro Cys Trp Ile Val Lys Ala Ala Pro Ser
20 25 30

Cys Ser Glu Lys Lys Gly Asn Tyr Ala Cys Leu Leu Arg Glu Asp Gln
35 40 45

Gly Trp Tyr Cys Gln Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Lys Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Asn Lys Gly Cys Ser
145

<210> SEQ ID NO 259
<211> LENGTH: 149
<212> TYPE: PRT
<213> ORGANISM: human metapneumo virus

<400> SEQUENCE: 259

Ile Gly Val Tyr Gly Ser Ser Val Ile Tyr Met Val Gln Leu Pro Ile
1 5 10 15

Phe Gly Val Ile Asp Thr Pro Cys Trp Ile Val Lys Ala Ala Pro Ser
20 25 30

Cys Ser Glu Lys Lys Gly Asn Tyr Ala Cys Leu Leu Arg Glu Asp Gln
35 40 45

Gly Trp Tyr Cys Gln Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Lys Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Asn Lys Gly Cys Ser
145

<210> SEQ ID NO 260
<211> LENGTH: 149
<212> TYPE: PRT
<213> ORGANISM: human metapneumo virus

<400> SEQUENCE: 260

Ile Gly Val Tyr Gly Ser Ser Val Ile Tyr Met Val Gln Leu Pro Ile

-continued

```
 1               5                  10                  15

Phe Gly Val Ile Asp Thr Pro Cys Trp Ile Val Lys Ala Ala Pro Ser
            20                  25                  30

Cys Ser Gly Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 261
<211> LENGTH: 149
<212> TYPE: PRT
<213> ORGANISM: human metapneumo virus

<400> SEQUENCE: 261

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 262
<211> LENGTH: 149
<212> TYPE: PRT
<213> ORGANISM: human metapneumo virus

<400> SEQUENCE: 262

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
```

-continued

```
            20                  25                  30

Cys Ser Gly Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 263
<211> LENGTH: 149
<212> TYPE: PRT
<213> ORGANISM: human metapneumo virus

<400> SEQUENCE: 263

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 264
<211> LENGTH: 149
<212> TYPE: PRT
<213> ORGANISM: human metapneumo virus

<400> SEQUENCE: 264

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
```

-continued

```
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 265
<211> LENGTH: 149
<212> TYPE: PRT
<213> ORGANISM: human metapneumo virus

<400> SEQUENCE: 265

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Val Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 266
<211> LENGTH: 149
<212> TYPE: PRT
<213> ORGANISM: human metapneumo virus

<400> SEQUENCE: 266

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
```

```
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 267
<211> LENGTH: 149
<212> TYPE: PRT
<213> ORGANISM: human metapneumo virus

<400> SEQUENCE: 267

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 268
<211> LENGTH: 149
<212> TYPE: PRT
<213> ORGANISM: human metapneumo virus

<400> SEQUENCE: 268

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
```

-continued

```
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 269
<211> LENGTH: 149
<212> TYPE: PRT
<213> ORGANISM: human metapneumo virus

<400> SEQUENCE: 269

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 270
<211> LENGTH: 149
<212> TYPE: PRT
<213> ORGANISM: human metapneumo virus

<400> SEQUENCE: 270

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
```

-continued

```
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 271
<211> LENGTH: 149
<212> TYPE: PRT
<213> ORGANISM: human metapneumo virus

<400> SEQUENCE: 271

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 272
<211> LENGTH: 149
<212> TYPE: PRT
<213> ORGANISM: human metapneumo virus

<400> SEQUENCE: 272

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
```

-continued

```
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145
```

<210> SEQ ID NO 273
<211> LENGTH: 149
<212> TYPE: PRT
<213> ORGANISM: human metapneumo virus

<400> SEQUENCE: 273

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145
```

<210> SEQ ID NO 274
<211> LENGTH: 149
<212> TYPE: PRT
<213> ORGANISM: human metapneumo virus

<400> SEQUENCE: 274

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
```

-continued

```
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 275
<211> LENGTH: 149
<212> TYPE: PRT
<213> ORGANISM: human metapneumo virus

<400> SEQUENCE: 275

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 276
<211> LENGTH: 149
<212> TYPE: PRT
<213> ORGANISM: human metapneumo virus

<400> SEQUENCE: 276

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
```

-continued

```
    130                 135                 140

Asn Lys Gly Cys Ser
145


<210> SEQ ID NO 277
<211> LENGTH: 149
<212> TYPE: PRT
<213> ORGANISM: human metapneumo virus

<400> SEQUENCE: 277

Ile Gly Val Tyr Gly Ser Ser Val Ile Tyr Met Val Gln Leu Pro Ile
 1               5                  10                  15

Phe Gly Val Ile Asp Thr Pro Cys Trp Ile Val Lys Ala Ala Pro Ser
            20                  25                  30

Cys Ser Glu Lys Lys Gly Asn Tyr Ala Cys Leu Leu Arg Glu Asp Gln
        35                  40                  45

Gly Trp Tyr Cys Gln Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Lys Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Asn Lys Gly Cys Ser
145


<210> SEQ ID NO 278
<211> LENGTH: 149
<212> TYPE: PRT
<213> ORGANISM: human metapneumo virus

<400> SEQUENCE: 278

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
```

145

<210> SEQ ID NO 279
<211> LENGTH: 149
<212> TYPE: PRT
<213> ORGANISM: human metapneumo virus

<400> SEQUENCE: 279

Ile Gly Val Tyr Gly Ser Ser Val Ile Tyr Met Val Gln Leu Pro Ile
1 5 10 15

Phe Gly Val Ile Asp Thr Pro Cys Trp Ile Ile Lys Ala Ala Pro Ser
20 25 30

Cys Ser Glu Lys Asn Gly Asn Tyr Ala Cys Leu Leu Arg Glu Asp Gln
35 40 45

Gly Trp Tyr Cys Lys Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Arg Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Trp Val Gly Ile Ile Lys Gln Leu
130 135 140

Pro Lys Gly Cys Ser
145

<210> SEQ ID NO 280
<211> LENGTH: 149
<212> TYPE: PRT
<213> ORGANISM: human metapneumo virus

<400> SEQUENCE: 280

Ile Gly Val Tyr Gly Ser Ser Val Ile Tyr Met Val Gln Leu Pro Ile
1 5 10 15

Phe Gly Val Ile Asp Thr Pro Cys Trp Ile Ile Lys Ala Ala Pro Ser
20 25 30

Cys Ser Glu Lys Asn Gly Asn Tyr Ala Cys Leu Leu Arg Glu Asp Gln
35 40 45

Gly Trp Tyr Cys Lys Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Arg Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Pro Lys Gly Cys Ser
145

-continued

<210> SEQ ID NO 281
<211> LENGTH: 149
<212> TYPE: PRT
<213> ORGANISM: human metapneumo virus

<400> SEQUENCE: 281

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 282
<211> LENGTH: 149
<212> TYPE: PRT
<213> ORGANISM: human metapneumo virus

<400> SEQUENCE: 282

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 283
<211> LENGTH: 149
<212> TYPE: PRT

-continued

<213> ORGANISM: human metapneumo virus

<400> SEQUENCE: 283

Ile Gly Val Tyr Gly Ser Ser Val Ile Tyr Met Val Gln Leu Pro Ile
1 5 10 15

Phe Gly Val Ile Asp Thr Pro Cys Trp Ile Ile Lys Ala Ala Pro Ser
20 25 30

Cys Ser Glu Lys Asn Gly Asn Tyr Ala Cys Leu Leu Arg Glu Asp Gln
35 40 45

Gly Trp Tyr Cys Lys Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Arg Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Pro Lys Gly Cys Ser
145

<210> SEQ ID NO 284
<211> LENGTH: 149
<212> TYPE: PRT
<213> ORGANISM: human metapneumo virus

<400> SEQUENCE: 284

Ile Gly Val Tyr Gly Ser Ser Val Ile Tyr Met Val Gln Leu Pro Ile
1 5 10 15

Phe Gly Val Ile Asp Thr Pro Cys Trp Ile Ile Lys Ala Ala Pro Ser
20 25 30

Cys Ser Glu Lys Asn Gly Asn Tyr Ala Cys Leu Leu Arg Glu Asp Gln
35 40 45

Gly Trp Tyr Cys Lys Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Arg Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Pro Lys Gly Cys Ser
145

<210> SEQ ID NO 285
<211> LENGTH: 149
<212> TYPE: PRT
<213> ORGANISM: human metapneumo virus

<400> SEQUENCE: 285

-continued

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Ser Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 286
<211> LENGTH: 149
<212> TYPE: PRT
<213> ORGANISM: human metapneumo virus

<400> SEQUENCE: 286

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 287
<211> LENGTH: 149
<212> TYPE: PRT
<213> ORGANISM: human metapneumo virus

<400> SEQUENCE: 287

```
Ile Gly Val Tyr Gly Ser Ser Val Ile Tyr Met Val Gln Leu Pro Ile
 1               5                  10                  15
```

-continued

```
Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 288
<211> LENGTH: 149
<212> TYPE: PRT
<213> ORGANISM: human metapneumo virus

<400> SEQUENCE: 288

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 289
<211> LENGTH: 149
<212> TYPE: PRT
<213> ORGANISM: human metapneumo virus

<400> SEQUENCE: 289

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30
```

```
Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 290
<211> LENGTH: 149
<212> TYPE: PRT
<213> ORGANISM: human metapneumo virus

<400> SEQUENCE: 290

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 291
<211> LENGTH: 149
<212> TYPE: PRT
<213> ORGANISM: human metapneumo virus

<400> SEQUENCE: 291

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45
```

-continued

```
Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 292
<211> LENGTH: 149
<212> TYPE: PRT
<213> ORGANISM: human metapneumo virus

<400> SEQUENCE: 292

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 293
<211> LENGTH: 149
<212> TYPE: PRT
<213> ORGANISM: human metapneumo virus

<400> SEQUENCE: 293

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60
```

-continued

Lys Asp Cys Glu Thr Arg Gly Asp His Val Phe Cys Asp Thr Ala Ala
65 70 75 80

Gly Ile Asn Val Ala Glu Gln Ser Arg Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Pro Lys Gly Cys Ser
145

<210> SEQ ID NO 294
<211> LENGTH: 149
<212> TYPE: PRT
<213> ORGANISM: human metapneumo virus

<400> SEQUENCE: 294

Ile Gly Val Tyr Gly Ser Ser Val Ile Tyr Met Val Gln Leu Pro Ile
1 5 10 15

Phe Gly Val Ile Asp Thr Pro Cys Trp Ile Ile Lys Ala Ala Pro Ser
20 25 30

Cys Ser Glu Lys Asn Gly Asn Tyr Ala Cys Leu Leu Arg Glu Asp Gln
35 40 45

Gly Trp Tyr Cys Lys Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

Gly Ile Asn Val Ala Glu Gln Ser Arg Glu Cys Asn Ile Asn Ile Ser
85 90 95

Thr Thr Asn Tyr Pro Cys Lys Val Ser Thr Gly Arg His Pro Ile Ser
100 105 110

Met Val Ala Leu Ser Pro Leu Gly Ala Leu Val Ala Cys Tyr Lys Gly
115 120 125

Val Ser Cys Ser Ile Gly Ser Asn Arg Val Gly Ile Ile Lys Gln Leu
130 135 140

Pro Lys Gly Cys Ser
145

<210> SEQ ID NO 295
<211> LENGTH: 149
<212> TYPE: PRT
<213> ORGANISM: human metapneumo virus

<400> SEQUENCE: 295

Ile Gly Val Tyr Gly Ser Ser Val Ile Tyr Met Val Gln Leu Pro Ile
1 5 10 15

Phe Gly Val Ile Asp Thr Pro Cys Trp Ile Ile Lys Ala Ala Pro Ser
20 25 30

Cys Ser Glu Lys Asn Gly Asn Tyr Ala Cys Leu Leu Arg Glu Asp Gln
35 40 45

Gly Trp Tyr Cys Lys Asn Ala Gly Ser Thr Val Tyr Tyr Pro Asn Glu
50 55 60

Lys Asp Cys Glu Thr Arg Gly Asp His Val Phe Cys Asp Thr Ala Ala
65 70 75 80

-continued

```
Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 296
<211> LENGTH: 149
<212> TYPE: PRT
<213> ORGANISM: human metapneumo virus

<400> SEQUENCE: 296

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asn Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 297
<211> LENGTH: 149
<212> TYPE: PRT
<213> ORGANISM: human metapneumo virus

<400> SEQUENCE: 297

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95
```

```
Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 298
<211> LENGTH: 149
<212> TYPE: PRT
<213> ORGANISM: human metapneumo virus

<400> SEQUENCE: 298

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 299
<211> LENGTH: 149
<212> TYPE: PRT
<213> ORGANISM: human metapneumo virus

<400> SEQUENCE: 299

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110
```

-continued

```
Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 300
<211> LENGTH: 149
<212> TYPE: PRT
<213> ORGANISM: human metapneumo virus

<400> SEQUENCE: 300

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 301
<211> LENGTH: 149
<212> TYPE: PRT
<213> ORGANISM: human metapneumo virus

<400> SEQUENCE: 301

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125
```

-continued

```
Val Ser Cys Ser Ile Gly Ser Asn Arg Val Gly Ile Ile Lys Gln Leu
    130                 135                 140

Pro Lys Gly Cys Ser
145


<210> SEQ ID NO 302
<211> LENGTH: 149
<212> TYPE: PRT
<213> ORGANISM: human metapneumo virus

<400> SEQUENCE: 302

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 303
<211> LENGTH: 149
<212> TYPE: PRT
<213> ORGANISM: human metapneumo virus

<400> SEQUENCE: 303

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140
```

```
Pro Lys Gly Cys Ser
145


<210> SEQ ID NO 304
<211> LENGTH: 149
<212> TYPE: PRT
<213> ORGANISM: human metapneumo virus

<400> SEQUENCE: 304

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 305
<211> LENGTH: 149
<212> TYPE: PRT
<213> ORGANISM: human metapneumo virus

<400> SEQUENCE: 305

Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

-continued

<210> SEQ ID NO 306
<211> LENGTH: 149
<212> TYPE: PRT
<213> ORGANISM: human metapneumo virus

<400> SEQUENCE: 306

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 307
<211> LENGTH: 149
<212> TYPE: PRT
<213> ORGANISM: human metapneumo virus

<400> SEQUENCE: 307

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 308

-continued

<211> LENGTH: 149
<212> TYPE: PRT
<213> ORGANISM: human metapneumo virus

<400> SEQUENCE: 308

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 309
<211> LENGTH: 149
<212> TYPE: PRT
<213> ORGANISM: human metapneumo virus

<400> SEQUENCE: 309

```
Ile Gly Val Tyr Gly Ser Ser Val Ile Tyr Met Val Gln Leu Pro Ile
 1               5                  10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 310
<211> LENGTH: 149
<212> TYPE: PRT
<213> ORGANISM: human metapneumo virus -continued

<400> SEQUENCE: 310

```
Ile Gly Val Tyr Gly Ser Ser Val Ile Tyr Met Val Gln Leu Pro Ile
 1               5                   10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 311
<211> LENGTH: 149
<212> TYPE: PRT
<213> ORGANISM: human metapneumo virus

<400> SEQUENCE: 311

```
Ile Gly Val Tyr Gly Ser Ser Val Ile Tyr Met Val Gln Leu Pro Ile
 1               5                   10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145
```

<210> SEQ ID NO 312
<211> LENGTH: 149
<212> TYPE: PRT
<213> ORGANISM: human metapneumo virus

<400> SEQUENCE: 312

-continued

```
Ile Gly Val Tyr Gly Ser Ser Val Ile Tyr Met Val Gln Leu Pro Ile
 1              5                   10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 313
<211> LENGTH: 149
<212> TYPE: PRT
<213> ORGANISM: human metapneumo virus

<400> SEQUENCE: 313

Ile Gly Val Tyr Gly Ser Ser Val Ile Tyr Met Val Gln Leu Pro Ile
 1              5                   10                  15

Phe Gly Val Ile Asp Thr Pro Cys Trp Ile Ile Lys Ala Ala Pro Ser
            20                  25                  30

Cys Ser Glu Lys Asp Gly Asn Tyr Ala Cys Leu Leu Arg Glu Asp Gln
        35                  40                  45

Gly Trp Tyr Cys Lys Asn Ala Gly Ser Thr Val Tyr Tyr Pro Asn Glu
    50                  55                  60

Lys Asp Cys Glu Thr Arg Gly Asp His Val Phe Cys Asp Thr Ala Ala
65                  70                  75                  80

Gly Ile Asn Val Ala Glu Gln Ser Arg Glu Cys Asn Ile Asn Ile Ser
                85                  90                  95

Thr Thr Asn Tyr Pro Cys Lys Val Ser Thr Gly Arg His Pro Ile Ser
            100                 105                 110

Met Val Ala Leu Ser Pro Leu Gly Ala Leu Val Ala Cys Tyr Lys Gly
        115                 120                 125

Val Ser Cys Ser Ile Gly Ser Asn Arg Val Gly Ile Ile Lys Gln Leu
    130                 135                 140

Pro Lys Gly Cys Ser
145


<210> SEQ ID NO 314
<211> LENGTH: 539
<212> TYPE: PRT
<213> ORGANISM: human metapneumo virus

<400> SEQUENCE: 314

Met Ser Trp Lys Val Val Ile Ile Phe Ser Leu Leu Ile Thr Pro Gln
 1              5                   10                  15
```

-continued

```
His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
```

-continued

```
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535


<210> SEQ ID NO 315
<211> LENGTH: 539
<212> TYPE: PRT
<213> ORGANISM: human metapneumo virus

<400> SEQUENCE: 315

Met Ser Trp Lys Val Val Ile Ile Phe Ser Leu Leu Ile Thr Pro Gln
 1               5                  10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Thr Val Gln
            260                 265                 270
```

-continued

```
Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Ser
    530                 535


<210> SEQ ID NO 316
<211> LENGTH: 539
<212> TYPE: PRT
<213> ORGANISM: human metapneumo virus

<400> SEQUENCE: 316

Met Ser Trp Lys Val Met Ile Ile Ile Ser Leu Leu Ile Thr Pro Gln
 1               5                  10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110
```

-continued

```
Ala Thr Ala Ala Ala Val Thr Ala Gly Ile Ala Ile Ala Lys Thr Ile
        115                 120                 125

Arg Leu Glu Ser Glu Val Asn Ala Ile Lys Gly Ala Leu Lys Gln Thr
    130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                165                 170                 175

Ile Asn Arg Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Ile Lys Ala
        275                 280                 285

Ala Pro Ser Cys Ser Glu Lys Asn Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Trp Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480

Leu Asn Ser Ala Glu Lys Gly Asn Thr Gly Phe Ile Ile Val Val Ile
                485                 490                 495

Leu Val Ala Val Leu Gly Leu Thr Met Ile Ser Val Ser Ile Ile Ile
            500                 505                 510

Ile Ile Lys Lys Thr Arg Lys Pro Thr Gly Ala Pro Pro Glu Leu Asn
        515                 520                 525
```

-continued

```
Gly Val Thr Asn Gly Gly Phe Ile Pro His Ser
    530                 535


<210> SEQ ID NO 317
<211> LENGTH: 539
<212> TYPE: PRT
<213> ORGANISM: human metapneumo virus

<400> SEQUENCE: 317

Met Ser Trp Lys Val Met Ile Ile Ile Ser Leu Leu Ile Thr Pro Gln
 1               5                  10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Ile Ala Ile Ala Lys Thr Ile
        115                 120                 125

Arg Leu Glu Ser Glu Val Asn Ala Ile Lys Gly Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Ile Lys Ala
        275                 280                 285

Ala Pro Ser Cys Ser Glu Lys Asp Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
            340                 345                 350

Asn Ile Ser Thr Thr Asn Tyr Pro Cys Lys Val Ser Thr Gly Arg His
        355                 360                 365
```

-continued

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Arg Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480

Leu Asn Ser Ala Glu Lys Gly Asn Thr Gly Phe Ile Ile Val Ile Ile
                485                 490                 495

Leu Ile Ala Val Leu Gly Leu Thr Met Ile Ser Val Ser Ile Ile Ile
            500                 505                 510

Ile Ile Lys Lys Thr Arg Lys Pro Thr Gly Ala Pro Pro Glu Leu Asn
        515                 520                 525

Gly Val Thr Asn Gly Gly Phe Ile Pro His Ser
    530                 535

<210> SEQ ID NO 318
<211> LENGTH: 1620
<212> TYPE: DNA
<213> ORGANISM: human metapneumo virus

<400> SEQUENCE: 318
atgtcttgga aagtggtgat catttttca ttgttaataa cacctcaaca cggtcttaaa 60
gagagctact tagaagagtc atgtagcact ataactgaag gatatctcag tgttctgagg 120
acaggttggt acaccaatgt ttttacactg gaggtaggcg atgtagagaa ccttacatgt 180
gccgatggac ccagcttaat aaaaacagaa ttagacctga ccaaaagtgc actaagagag 240
ctcagaacag tttctgctga tcaactggca agagaggagc aaattgaaaa tcccagacaa 300
tctagattcg ttctaggagc aatagcactc ggtgttgcaa ctgcagctgc agttacagca 360
ggtgttgcaa ttgccaaaac catccggctt gaaagtgaag taacagcaat taagaatgcc 420
ctcaaaaaga ccaatgaagc agtatctaca ttggggaatg gagttcgtgt gttggcaact 480
gcagtgagag agctgaaaga ttttgtgagc aagaatctaa cacgtgcaat caacaaaaac 540
aagtgcgaca ttgctgacct gaaaatggcc gttagcttca gtcaattcaa cagaaggttc 600
ctaaatgttg tgcggcaatt ttcagacaac gctggaataa caccagcaat atctttggac 660
ttaatgacag atgctgaact agccagagct gtttccaaca tgccaacatc tgcaggacaa 720
ataaaactga tgttggagaa ccgtgcaatg gtaagaagaa aagggttcgg aatcctgata 780
ggagtttacg gaagctccgt aatttacatg gtgcaactgc caatctttgg ggttatagac 840
acgccttgct ggatagtaaa agcagcccct tcttgttcag gaaaaaaggg aaactatgct 900
tgcctcttaa gagaagacca aggatggtat tgtcaaaatg cagggtcaac tgtttactac 960
ccaaatgaaa aagactgtga aacaagagga gaccatgtct tttgcgacac agcagcagga 1020
atcaatgttg ctgagcagtc aaaggagtgc aacataaaca tatctactac taattaccca 1080
tgcaaagtta gcacaggaag acatcctatc agtatggttg cactatctcc tcttggggct 1140

-continued

```
ttggttgctt gctacaaggg agtgagctgt tccattggca gcaacagagt agggatcatc   1200

aagcaactga acaaaggctg ctcttatata accaaccaag acgcagacac agtgacaata   1260

gacaacactg tataccagct aagcaaagtt gaaggcgaac agcatgttat aaaaggaagg   1320

ccagtgtcaa gcagctttga cccagtcaag tttcctgaag atcaattcaa tgttgcactt   1380

gaccaagttt tcgagagcat tgagaacagt caggccttgg tggatcaatc aaacagaatc   1440

ctaagcagtg cagagaaagg aaacactggc ttcatcattg taataattct aattgctgtc   1500

cttggctcta ccatgatcct agtgagtgtt tttatcataa taaagaaaac aaagaaaccc   1560

acaggagcac ctccagagct gagtggtgtc acaaacaatg gcttcatacc acataattag   1620
```

<210> SEQ ID NO 319
<211> LENGTH: 1620
<212> TYPE: DNA
<213> ORGANISM: human metapneumo virus

<400> SEQUENCE: 319

```
atgtcttgga aagtggtgat cattttttca ttgctaataa cacctcaaca cggtcttaaa     60

gagagctacc tagaagaatc atgtagcact ataactgagg gatatcttag tgttctgagg    120

acaggttggt ataccaacgt tttacatta gaggtgggtg atgtagaaaa ccttacatgt    180

tctgatggac ctagcctaat aaaaacagaa ttagatctga ccaaaagtgc actaagagag    240

ctcaaaacag tctctgctga ccaattggca agagaggaac aaattgagaa tcccagacaa    300

tctaggtttg ttctaggagc aatagcactc ggtgttgcaa cagcagctgc agtcacagca    360

ggtgttgcaa ttgccaaaac catccggctt gagagtgaag tcacagcaat taagaatgcc    420

ctcaaaacga ccaatgaagc agtatctaca ttggggaatg gagttcgagt gttggcaact    480

gcagtgagag agctaaaaga ctttgtgagc aagaatttaa ctcgtgcaat caacaaaaac    540

aagtgcgaca ttgatgacct aaaaatggct gttagcttca gtcaattcaa cagaaggttt    600

ctaaatgttg tgcggcaatt ttcagacaat gctggaataa caccagcaat atctttggac    660

ttaatgacag atgctgaact agccagggcc gtttctaaca tgccgacatc tgcaggacaa    720

ataaaattga tgttggagaa ccgtgcgatg gtgcgaagaa aggggttcgg aatcctgata    780

ggggtctacg ggagctccgt aatttacacg gtgcagctgc caatctttgg cgttatagac    840

acgccttgct ggatagtaaa agcagcccct tcttgttccg aaaaaaaggg aaactatgct    900

tgcctcttaa gagaagacca agggtggtat tgtcagaatg cagggtcaac tgtttactac    960

ccaaatgaga aagactgtga aacaagagga gaccatgtct tttgcgacac agcagcagga   1020

attaatgttg ctgagcaatc aaaggagtgc aacatcaaca tatccactac aaattaccca   1080

tgcaaagtca gcacaggaag acatcctatc agtatggttg cactgtctcc tcttggggct   1140

ctggttgctt gctacaaagg agtaagctgt tccattggca gcaacagagt agggatcatc   1200

aagcagctga acaaaggttg ctcctatata accaaccaag atgcagacac agtgacaata   1260

gacaacactg tatatcagct aagcaaagtt gagggtgaac agcatgttat aaaaggcaga   1320

ccagtgtcaa gcagctttga tccaatcaag tttcctgaag atcaattcaa tgttgcactt   1380

gaccaagttt ttgagaacat tgaaaacagc caggccttag tagatcaatc aaacagaatc   1440

ctaagcagtg cagagaaagg gaatactggc tttatcattg taataattct aattgctgtc   1500

cttggctcta gcatgatcct agtgagcatc ttcattataa tcaagaaaac aaagaaacca   1560

acgggagcac ctccagagct gagtggtgtc acaaacaatg gcttcatacc acacagttag   1620
```

-continued

<210> SEQ ID NO 320
<211> LENGTH: 1620
<212> TYPE: DNA
<213> ORGANISM: human metapneumo virus

<400> SEQUENCE: 320
atgtcttgga aagtgatgat catcatttcg ttactcataa caccccagca cgggctaaag 60
gagagttatt tggaagaatc atgtagtact ataactgagg gatacctcag tgttttaaga 120
acaggctggt acactaatgt cttcacatta gaagttggtg atgttgaaaa tcttacatgt 180
actgatggac ctagcttaat caaaacagaa cttgatctaa caaaaagtgc tttaagggaa 240
ctcaaaacag tctctgctga tcagttggcg agagaggagc aaattgaaaa tcccagacaa 300
tcaagatttg tcttaggtgc gatagctctc ggagttgcta cagcagcagc agtcacagca 360
ggcattgcaa tagccaaaac cataaggctt gagagtgagg tgaatgcaat taaaggtgct 420
ctcaaacaaa ctaatgaagc agtatccaca ttagggaatg gtgtgcgggt cctagccact 480
gcagtgagag agctaaaaga atttgtgagc aaaaacctga ctagtgcaat caacaggaac 540
aaatgtgaca ttgctgatct gaagatggct gtcagcttca gtcaattcaa cagaagattt 600
ctaaatgttg tgcggcagtt ttcagacaat gcagggataa caccagcaat atcattggac 660
ctgatgactg atgctgagtt ggccagagct gtatcataca tgccaacatc tgcagggcag 720
ataaaactga tgttggagaa ccgcgcaatg gtaaggagaa aaggatttgg aatcctgata 780
ggggtctacg gaagctctgt gatttacatg gttcaattgc cgatctttgg tgtcatagat 840
acaccttgtt ggatcatcaa ggcagctccc tcttgctcag aaaaaaacgg gaattatgct 900
tgcctcctaa gagaggatca agggtggtat tgtaaaaatg caggatctac tgtttactac 960
ccaaatgaaa aagactgcga aacaagaggt gatcatgttt tttgtgacac agcagcaggg 1020
atcaatgttg ctgagcaatc aagagaatgc aacatcaaca tatctactac caactaccca 1080
tgcaaagtca gcacaggaag acaccctata agcatggttg cactatcacc tctcggtgct 1140
ttggtggctt gctataaagg ggtaagctgc tcgattggca gcaattgggt tggaatcatc 1200
aaacaattac ccaaaggctg ctcatacata accaaccagg atgcagacac tgtaacaatt 1260
gacaataccg tgtatcaact aagcaaagtt gaaggtgaac agcatgtaat aaaagggaga 1320
ccagtttcaa gcagttttga tccaatcaag tttcctgagg atcagttcaa tgttgcgctt 1380
gatcaagtct tcgaaagcat tgagaacagt caggcactag tggaccagtc aaacaaaatt 1440
ctaaacagtg cagaaaaagg aaacactggt ttcattatcg tagtaatttt ggttgctgtt 1500
cttggtctaa ccatgatttc agtgagcatc atcatcataa tcaagaaaac aaggaagccc 1560
acaggagcac ctccagagct gaatggtgtc accaacggcg gtttcatacc acatagttag 1620

<210> SEQ ID NO 321
<211> LENGTH: 1620
<212> TYPE: DNA
<213> ORGANISM: human metapneumo virus

<400> SEQUENCE: 321
atgtcttgga aagtgatgat tatcatttcg ttactcataa cacctcagca cggactaaaa 60
gaaagttatt tagaagaatc atgtagtact ataactgaag gatatctcag tgttttaaga 120
acaggttggt acaccaatgt ctttacatta gaagttggtg atgttgaaaa tcttacatgt 180
actgatggac ctagcttaat caaaacagaa cttgacctaa ccaaaagtgc tctgagagaa 240
ctcaaaacag tttctgctga tcagttagcg agagaagaac aaattgaaaa tcccagacaa 300

-continued

```
tcaaggtttg tcctaggtgc aatagctctt ggagttgcca cagcagcagc agtcacagca    360

ggcattgcaa tagccaaaac cataagactt gagagtgaag tgaatgcaat caaaggtgct    420

ctcaaaacaa ccaacgaggc agtatccaca ctaggaaatg gagtgcgagt cctagccact    480

gcagtaagag agctgaaaga atttgtgagc aaaaacctga ctagtgcgat caacaagaac    540

aaatgtgaca ttgctgatct gaagatggct gtcagcttca gtcaattcaa cagaagattc    600

ctaaatgttg tgcggcagtt ttcagacaat gcagggataa caccagcaat atcattggac    660

ctaatgactg atgctgagct ggccagagct gtatcataca tgccaacatc tgcaggacag    720

ataaaactaa tgttagagaa ccgtgcaatg gtgaggagaa aaggatttgg aatcttgata    780

ggggtctacg gaagctctgt gatttacatg gtccagctgc cgatctttgg tgtcatagat    840

acaccttgtt ggataatcaa ggcagctccc tcttgttcag aaaaagatgg aaattatgct    900

tgcctcctaa gagaggatca agggtggtat tgcaaaaatg caggatccac tgtttactac    960

ccaaatgaaa aagactgcga aacaagaggt gatcatgttt tttgtgacac agcagcaggg   1020

atcaatgttg ctgagcaatc aagagaatgc aacatcaaca tatctaccac caactaccca   1080

tgcaaagtca gcacaggaag acaccctatc agcatggttg cactatcacc tctcggtgct   1140

ttggtagctt gctacaaggg ggttagctgc tcgattggca gtaatcgggt tggaataatc   1200

aaacaactac ctaaaggctg ctcatacata actaaccagg acgcagacac tgtaacaatt   1260

gacaacactg tgtatcaact aagcaaagtt gagggtgaac agcatgtaat aaaagggaga   1320

ccagtttcaa gcagttttga tccaatcagg tttcctgagg atcagttcaa tgttgcgctt   1380

gatcaagtct ttgaaagcat tgaaaacagt caagcactag tggaccagtc aaacaaaatt   1440

ctgaacagtg cagaaaaagg aaacactggt ttcattattg taataatttt gattgctgtt   1500

cttgggttaa ccatgatttc agtgagcatc atcatcataa tcaaaaaaac aaggaagccc   1560

acaggggcac ctccagagct gaatggtgtt accaacggcg gttttatacc gcatagttag   1620
```

<210> SEQ ID NO 322
<211> LENGTH: 236
<212> TYPE: PRT
<213> ORGANISM: human metapneumo virus

<400> SEQUENCE: 322

```
Met Glu Val Lys Val Glu Asn Ile Arg Thr Ile Asp Met Leu Lys Ala
 1               5                  10                  15

Arg Val Lys Asn Arg Val Ala Arg Ser Lys Cys Phe Lys Asn Ala Ser
            20                  25                  30

Leu Val Leu Ile Gly Ile Thr Thr Leu Ser Ile Ala Leu Asn Ile Tyr
        35                  40                  45

Leu Ile Ile Asn Tyr Lys Met Gln Lys Asn Thr Ser Glu Ser Glu His
    50                  55                  60

His Thr Ser Ser Ser Pro Met Glu Ser Ser Arg Glu Thr Pro Thr Val
65                  70                  75                  80

Pro Thr Asp Asn Ser Asp Thr Asn Ser Ser Pro Gln His Pro Thr Gln
                85                  90                  95

Gln Ser Thr Glu Gly Ser Thr Leu Tyr Phe Ala Ala Ser Ala Ser Ser
            100                 105                 110

Pro Glu Thr Glu Pro Thr Ser Thr Pro Asp Thr Thr Asn Arg Pro Pro
        115                 120                 125

Phe Val Asp Thr His Thr Thr Pro Pro Ser Ala Ser Arg Thr Lys Thr
    130                 135                 140
```

-continued

```
Ser Pro Ala Val His Thr Lys Asn Asn Pro Arg Thr Ser Ser Arg Thr
145                 150                 155                 160

His Ser Pro Pro Arg Ala Thr Thr Arg Thr Ala Arg Arg Thr Thr Thr
                165                 170                 175

Leu Arg Thr Ser Ser Thr Arg Lys Arg Pro Ser Thr Ala Ser Val Gln
            180                 185                 190

Pro Asp Ile Ser Ala Thr Thr His Lys Asn Glu Glu Ala Ser Pro Ala
        195                 200                 205

Ser Pro Gln Thr Ser Ala Ser Thr Thr Arg Ile Gln Arg Lys Ser Val
    210                 215                 220

Glu Ala Asn Thr Ser Thr Thr Tyr Asn Gln Thr Ser
225                 230                 235


<210> SEQ ID NO 323
<211> LENGTH: 219
<212> TYPE: PRT
<213> ORGANISM: human metapneumo virus

<400> SEQUENCE: 323

Met Glu Val Lys Val Glu Asn Ile Arg Ala Ile Asp Met Leu Lys Ala
 1               5                  10                  15

Arg Val Lys Asn Arg Val Ala Arg Ser Lys Cys Phe Lys Asn Ala Ser
            20                  25                  30

Leu Ile Leu Ile Gly Ile Thr Thr Leu Ser Ile Ala Leu Asn Ile Tyr
        35                  40                  45

Leu Ile Ile Asn Tyr Thr Ile Gln Lys Thr Thr Ser Glu Ser Glu His
    50                  55                  60

His Thr Ser Ser Pro Pro Thr Glu Pro Asn Lys Glu Ala Ser Thr Ile
65                  70                  75                  80

Ser Thr Asp Asn Pro Asp Ile Asn Pro Ser Ser Gln His Pro Thr Gln
                85                  90                  95

Gln Ser Thr Glu Asn Pro Thr Leu Asn Pro Ala Ala Ser Ala Ser Pro
            100                 105                 110

Ser Glu Thr Glu Pro Ala Ser Thr Pro Asp Thr Thr Asn Arg Leu Ser
        115                 120                 125

Ser Val Asp Arg Ser Thr Ala Gln Pro Ser Glu Ser Arg Thr Lys Thr
    130                 135                 140

Lys Pro Thr Val His Thr Ile Asn Asn Pro Asn Thr Ala Ser Ser Thr
145                 150                 155                 160

Gln Ser Pro Pro Arg Thr Thr Thr Lys Ala Ile Arg Arg Ala Thr Thr
                165                 170                 175

Phe Arg Met Ser Ser Thr Gly Lys Arg Pro Thr Thr Thr Leu Val Gln
            180                 185                 190

Ser Asp Ser Ser Thr Thr Thr Gln Asn His Glu Glu Thr Gly Ser Ala
        195                 200                 205

Asn Pro Gln Ala Ser Ala Ser Thr Met Gln Asn
    210                 215


<210> SEQ ID NO 324
<211> LENGTH: 224
<212> TYPE: PRT
<213> ORGANISM: human metapneumo virus

<400> SEQUENCE: 324

Met Glu Val Arg Val Glu Asn Ile Arg Ala Ile Asp Met Phe Lys Ala
 1               5                  10                  15
```

-continued

```
Lys Ile Lys Asn Arg Ile Arg Ser Ser Arg Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp His Ala Thr Leu Arg Asn Met Ile Lys Thr Glu Asn
    50                  55                  60

Cys Ala Asn Met Pro Ser Ala Glu Pro Ser Lys Lys Thr Pro Met Thr
65                  70                  75                  80

Ser Thr Ala Gly Pro Asn Thr Lys Pro Asn Pro Gln Gln Ala Thr Gln
                85                  90                  95

Trp Thr Thr Glu Asn Ser Thr Ser Pro Val Ala Thr Pro Glu Gly His
            100                 105                 110

Pro Tyr Thr Gly Thr Thr Gln Thr Ser Asp Thr Thr Ala Pro Gln Gln
        115                 120                 125

Thr Thr Asp Lys His Thr Ala Pro Leu Lys Ser Thr Asn Glu Gln Ile
    130                 135                 140

Thr Gln Thr Thr Thr Glu Lys Lys Thr Ile Arg Ala Thr Thr Gln Lys
145                 150                 155                 160

Arg Glu Lys Gly Lys Glu Asn Thr Asn Gln Thr Thr Ser Thr Ala Ala
                165                 170                 175

Thr Gln Thr Thr Asn Thr Thr Asn Gln Ile Arg Asn Ala Ser Glu Thr
            180                 185                 190

Ile Thr Thr Ser Asp Arg Pro Arg Thr Asp Thr Thr Thr Gln Ser Ser
        195                 200                 205

Glu Gln Thr Thr Arg Ala Thr Asp Pro Ser Ser Pro Pro His His Ala
    210                 215                 220


<210> SEQ ID NO 325
<211> LENGTH: 236
<212> TYPE: PRT
<213> ORGANISM: human metapneumo virus

<400> SEQUENCE: 325

Met Glu Val Arg Val Glu Asn Ile Arg Ala Ile Asp Met Phe Lys Ala
 1               5                  10                  15

Lys Met Lys Asn Arg Ile Arg Ser Ser Lys Cys Tyr Arg Asn Ala Thr
            20                  25                  30

Leu Ile Leu Ile Gly Leu Thr Ala Leu Ser Met Ala Leu Asn Ile Phe
        35                  40                  45

Leu Ile Ile Asp Tyr Ala Met Leu Lys Asn Met Thr Lys Val Glu His
    50                  55                  60

Cys Val Asn Met Pro Pro Val Glu Pro Ser Lys Lys Thr Pro Met Thr
65                  70                  75                  80

Ser Ala Val Asp Leu Asn Thr Lys Pro Asn Pro Gln Gln Ala Thr Gln
                85                  90                  95

Leu Ala Ala Glu Asp Ser Thr Ser Leu Ala Ala Thr Ser Glu Asp His
            100                 105                 110

Leu His Thr Gly Thr Thr Pro Thr Pro Asp Ala Thr Val Ser Gln Gln
        115                 120                 125

Thr Thr Asp Glu Tyr Thr Thr Leu Leu Arg Ser Thr Asn Arg Gln Thr
    130                 135                 140

Thr Gln Thr Thr Thr Glu Lys Lys Pro Thr Gly Ala Thr Thr Lys Lys
145                 150                 155                 160

Glu Thr Thr Thr Arg Thr Thr Ser Thr Ala Ala Thr Gln Thr Leu Asn
```

-continued

```
                165                 170                 175

Thr Thr Asn Gln Thr Ser Tyr Val Arg Glu Ala Thr Thr Thr Ser Ala
            180                 185                 190

Arg Ser Arg Asn Ser Ala Thr Thr Gln Ser Ser Asp Gln Thr Thr Gln
        195                 200                 205

Ala Ala Asp Pro Ser Ser Gln Pro His His Thr Gln Lys Ser Thr Thr
    210                 215                 220

Thr Thr Tyr Asn Thr Asp Thr Ser Ser Pro Ser Ser
225                 230                 235


<210> SEQ ID NO 326
<211> LENGTH: 708
<212> TYPE: DNA
<213> ORGANISM: human metapneumo virus

<400> SEQUENCE: 326

gaggtgaaag tggagaacat tcgaacaata gatatgctca aagcaagagt aaaaaatcgt      60

gtggcacgca gcaaatgctt taaaaatgcc tctttggtcc tcataggaat aactacattg     120

agtattgccc tcaatatcta tctgatcata aactataaaa tgcaaaaaaa cacatctgaa     180

tcagaacatc acaccagctc atcacccatg gaatccagca gagaaactcc aacggtcccc     240

acagacaact cagacaccaa ctcaagccca cagcatccaa ctcaacagtc cacagaaggc     300

tccacactct actttgcagc ctcagcaagc tcaccagaga cagaaccaac atcaacacca     360

gatacaacaa accgcccgcc cttcgtcgac acacacacaa caccaccaag cgcaagcaga     420

acaaagacaa gtccggcagt ccacacaaaa aacaacccaa ggacaagctc tagaacacat     480

tctccaccac gggcaacgac aaggacggca cgcagaacca ccactctccg cacaagcagc     540

acaagaaaga gaccgtccac agcatcagtc caacctgaca tcagcgcaac aacccacaaa     600

aacgaagaag caagtccagc gagcccacaa acatctgcaa gcacaacaag aatacaaagg     660

aaaagcgtgg aggccaacac atcaacaaca tacaaccaaa ctagttaa                  708


<210> SEQ ID NO 327
<211> LENGTH: 660
<212> TYPE: DNA
<213> ORGANISM: human metapneumo virus

<400> SEQUENCE: 327

atggaggtga aagtagagaa cattcgagca atagacatgc tcaaagcaag agtgaaaaat      60

cgtgtggcac gtagcaaatg ctttaaaaat gcttctttaa tcctcatagg aataactaca     120

ctgagtatag ctctcaatat ctatctgatc ataaactaca caatacaaaa aaccacatcc     180

gaatcagaac accacaccag ctcaccaccc acagaaccca acaaggaagc ttcaacaatc     240

tccacagaca acccagacat caatccaagc tcacagcatc caactcaaca gtccacagaa     300

aaccccacac tcaaccccgc agcatcagcg agcccatcag aaacagaacc agcatcaaca     360

ccagacacaa caaaccgcct gtcctccgta gacaggtcca cagcacaacc aagtgaaagc     420

agaacaaaga caaaaccgac agtccacaca atcaacaacc caaacacagc ttccagtaca     480

caatccccac cacggacaac aacgaaggca atccgcagag ccaccacttt ccgcatgagc     540

agcacaggaa aaagaccaac cacaacatta gtccagtccg acagcagcac cacaacccaa     600

aatcatgaag aaacaggttc agcgaaccca caggcgtctg caagcacaat gcaaaactag     660


<210> SEQ ID NO 328
<211> LENGTH: 675
```

-continued

<212> TYPE: DNA
<213> ORGANISM: human metapneumo virus

<400> SEQUENCE: 328
atggaagtaa gagtggagaa cattcgagcg atagacatgt tcaaagcaaa gataaaaaac 60
cgtataagaa gcagcaggtg ctatagaaat gctacactga tccttattgg actaacagcg 120
ttaagcatgg cacttaatat tttcctgatc atcgatcatg caacattaag aaacatgatc 180
aaaacagaaa actgtgctaa catgccgtcg gcagaaccaa gcaaaaagac cccaatgacc 240
tccacagcag gcccaaacac caaacccaat ccacagcaag caacacagtg gaccacagag 300
aactcaacat ccccagtagc aaccccagag ggccatccat acacagggac aactcaaaca 360
tcagacacaa cagctcccca gcaaaccaca gacaaacaca cagcaccgct aaaatcaacc 420
aatgaacaga tcacccagac aaccacagag aaaaagacaa tcagagcaac aacccaaaaa 480
agggaaaaag gaaaagaaaa cacaaaccaa accacaagca cagctgcaac ccaaacaacc 540
aacaccacca accaaatcag aaatgcaagt gagacaatca caacatccga cagacccaga 600
actgacacca caacccaaag cagcgaacag acaacccggg caacagaccc aagctcccca 660
ccacaccatg catag 675

<210> SEQ ID NO 329
<211> LENGTH: 711
<212> TYPE: DNA
<213> ORGANISM: human metapneumo virus

<400> SEQUENCE: 329
atggaagtaa gagtggagaa cattcgggca atagacatgt tcaaagcaaa aatgaaaaac 60
cgtataagaa gtagcaagtg ctatagaaat gctacactga tccttattgg attaacagca 120
ttaagtatgg cacttaatat ttttttaatc attgattatg caatgttaaa aaacatgacc 180
aaagtggaac actgtgttaa tatgccgccg gtagaaccaa gcaagaagac cccaatgacc 240
tctgcagtag acttaaacac caaacccaat ccacagcagg caacacagtt ggccgcagag 300
gattcaacat ctctagcagc aacctcagag gaccatctac acacagggac aactccaaca 360
ccagatgcaa cagtctctca gcaaaccaca gacgagtaca caacattgct gagatcaacc 420
aacagacaga ccacccaaac aaccacagag aaaaagccaa ccggagcaac aaccaaaaaa 480
gaaaccacaa ctcgaactac aagcacagct gcaacccaaa cactcaacac taccaaccaa 540
actagctatg tgagagaggc aaccacaaca tccgccagat ccagaaacag tgccacaact 600
caaagcagcg accaaacaac ccaggcagca gacccaagct cccaaccaca ccatacacag 660
aaaagcacaa caacaacata caacacagac acatcctctc caagtagtta a 711

<210> SEQ ID NO 330
<211> LENGTH: 2005
<212> TYPE: PRT
<213> ORGANISM: human metapneumo virus

<400> SEQUENCE: 330

Met Asp Pro Leu Asn Glu Ser Thr Val Asn Val Tyr Leu Pro Asp Ser
1 5 10 15

Tyr Leu Lys Gly Val Ile Ser Phe Ser Glu Thr Asn Ala Ile Gly Ser
20 25 30

Cys Leu Leu Lys Arg Pro Tyr Leu Lys Asn Asp Asn Thr Ala Lys Val
35 40 45

Ala Ile Glu Asn Pro Val Ile Glu His Val Arg Leu Lys Asn Ala Val

-continued

```
    50                  55                  60

Asn Ser Lys Met Lys Ile Ser Asp Tyr Lys Ile Val Glu Pro Val Asn
65                  70                  75                  80

Met Gln His Glu Ile Met Lys Asn Val His Ser Cys Glu Leu Thr Leu
                85                  90                  95

Leu Lys Gln Phe Leu Thr Arg Ser Lys Asn Ile Ser Thr Leu Lys Leu
            100                 105                 110

Asn Met Ile Cys Asp Trp Leu Gln Leu Lys Ser Thr Ser Asp Asp Thr
        115                 120                 125

Ser Ile Leu Ser Phe Ile Asp Val Glu Phe Ile Pro Ser Trp Val Ser
    130                 135                 140

Asn Trp Phe Ser Asn Trp Tyr Asn Leu Asn Lys Leu Ile Leu Glu Phe
145                 150                 155                 160

Arg Lys Glu Glu Val Ile Arg Thr Gly Ser Ile Leu Cys Arg Ser Leu
                165                 170                 175

Gly Lys Leu Val Phe Val Val Ser Ser Tyr Gly Cys Ile Val Lys Ser
            180                 185                 190

Asn Lys Ser Lys Arg Val Ser Phe Phe Thr Tyr Asn Gln Leu Leu Thr
        195                 200                 205

Trp Lys Asp Val Met Leu Ser Arg Phe Asn Ala Asn Phe Cys Ile Trp
    210                 215                 220

Val Ser Asn Ser Leu Asn Glu Asn Gln Glu Gly Leu Gly Leu Arg Ser
225                 230                 235                 240

Asn Leu Gln Gly Ile Leu Thr Asn Lys Leu Tyr Glu Thr Val Asp Tyr
                245                 250                 255

Met Leu Ser Leu Cys Cys Asn Glu Gly Phe Ser Leu Val Lys Glu Phe
            260                 265                 270

Glu Gly Phe Ile Met Ser Glu Ile Leu Arg Ile Thr Glu His Ala Gln
        275                 280                 285

Phe Ser Thr Arg Phe Arg Asn Thr Leu Leu Asn Gly Leu Thr Asp Gln
    290                 295                 300

Leu Thr Lys Leu Lys Asn Lys Asn Arg Leu Arg Val His Gly Thr Val
305                 310                 315                 320

Leu Glu Asn Asn Asp Tyr Pro Met Tyr Glu Val Val Leu Lys Leu Leu
                325                 330                 335

Gly Asp Thr Leu Arg Cys Ile Lys Leu Leu Ile Asn Lys Asn Leu Glu
            340                 345                 350

Asn Ala Ala Glu Leu Tyr Tyr Ile Phe Arg Ile Phe Gly His Pro Met
        355                 360                 365

Val Asp Glu Arg Asp Ala Met Asp Ala Val Lys Leu Asn Asn Glu Ile
    370                 375                 380

Thr Lys Ile Leu Arg Trp Glu Ser Leu Thr Glu Leu Arg Gly Ala Phe
385                 390                 395                 400

Ile Leu Arg Ile Ile Lys Gly Phe Val Asp Asn Asn Lys Arg Trp Pro
                405                 410                 415

Lys Ile Lys Asn Leu Lys Val Leu Ser Lys Arg Trp Thr Met Tyr Phe
            420                 425                 430

Lys Ala Lys Ser Tyr Pro Ser Gln Leu Glu Leu Ser Glu Gln Asp Phe
        435                 440                 445

Leu Glu Leu Ala Ala Ile Gln Phe Glu Gln Glu Phe Ser Val Pro Glu
    450                 455                 460

Lys Thr Asn Leu Glu Met Val Leu Asn Asp Lys Ala Ile Ser Pro Pro
465                 470                 475                 480
```

-continued

```
Lys Arg Leu Ile Trp Ser Val Tyr Pro Lys Asn Tyr Leu Pro Glu Lys
                485                 490                 495

Ile Lys Asn Arg Tyr Leu Glu Glu Thr Phe Asn Ala Ser Asp Ser Leu
            500                 505                 510

Lys Thr Arg Arg Val Leu Glu Tyr Tyr Leu Lys Asp Asn Lys Phe Asp
        515                 520                 525

Gln Lys Glu Leu Lys Ser Tyr Val Val Lys Gln Glu Tyr Leu Asn Asp
    530                 535                 540

Lys Asp His Ile Val Ser Leu Thr Gly Lys Glu Arg Glu Leu Ser Val
545                 550                 555                 560

Gly Arg Met Phe Ala Met Gln Pro Gly Lys Gln Arg Gln Ile Gln Ile
                565                 570                 575

Leu Ala Glu Lys Leu Leu Ala Asp Asn Ile Val Pro Phe Phe Pro Glu
            580                 585                 590

Thr Leu Thr Lys Tyr Gly Asp Leu Asp Leu Gln Arg Ile Met Glu Ile
        595                 600                 605

Lys Ser Glu Leu Ser Ser Ile Lys Thr Arg Arg Asn Asp Ser Tyr Asn
    610                 615                 620

Asn Tyr Ile Ala Arg Ala Ser Ile Val Thr Asp Leu Ser Lys Phe Asn
625                 630                 635                 640

Gln Ala Phe Arg Tyr Glu Thr Thr Ala Ile Cys Ala Asp Val Ala Asp
                645                 650                 655

Glu Leu His Gly Thr Gln Ser Leu Phe Cys Trp Leu His Leu Ile Val
            660                 665                 670

Pro Met Thr Thr Met Ile Cys Ala Tyr Arg His Ala Pro Pro Glu Thr
        675                 680                 685

Lys Gly Glu Tyr Asp Ile Asp Lys Ile Glu Glu Gln Ser Gly Leu Tyr
    690                 695                 700

Arg Tyr His Met Gly Gly Ile Glu Gly Trp Cys Gln Lys Leu Trp Thr
705                 710                 715                 720

Met Glu Ala Ile Ser Leu Leu Asp Val Val Ser Val Lys Thr Arg Cys
                725                 730                 735

Gln Met Thr Ser Leu Leu Asn Gly Asp Asn Gln Ser Ile Asp Val Ser
            740                 745                 750

Lys Pro Val Lys Leu Ser Glu Gly Leu Asp Glu Val Lys Ala Asp Tyr
        755                 760                 765

Ser Leu Ala Val Lys Met Leu Lys Glu Ile Arg Asp Ala Tyr Arg Asn
    770                 775                 780

Ile Gly His Lys Leu Lys Glu Gly Glu Thr Tyr Ile Ser Arg Asp Leu
785                 790                 795                 800

Gln Phe Ile Ser Lys Val Ile Gln Ser Glu Gly Val Met His Pro Thr
                805                 810                 815

Pro Ile Lys Lys Ile Leu Arg Val Gly Pro Trp Ile Asn Thr Ile Leu
            820                 825                 830

Asp Asp Ile Lys Thr Ser Ala Glu Ser Ile Gly Ser Leu Cys Gln Glu
        835                 840                 845

Leu Glu Phe Arg Gly Glu Ser Ile Ile Val Ser Leu Ile Leu Arg Asn
    850                 855                 860

Phe Trp Leu Tyr Asn Leu Tyr Met His Glu Ser Lys Gln His Pro Leu
865                 870                 875                 880

Ala Gly Lys Gln Leu Phe Lys Gln Leu Asn Lys Thr Leu Thr Ser Val
                885                 890                 895
```

-continued

```
Gln Arg Phe Phe Glu Ile Lys Lys Glu Asn Glu Val Val Asp Leu Trp
            900                 905                 910

Met Asn Ile Pro Met Gln Phe Gly Gly Gly Asp Pro Val Val Phe Tyr
        915                 920                 925

Arg Ser Phe Tyr Arg Arg Thr Pro Asp Phe Leu Thr Glu Ala Ile Ser
    930                 935                 940

His Val Asp Ile Leu Leu Arg Ile Ser Ala Asn Ile Arg Asn Glu Ala
945                 950                 955                 960

Lys Ile Ser Phe Phe Lys Ala Leu Leu Ser Ile Glu Lys Asn Glu Arg
                965                 970                 975

Ala Thr Leu Thr Thr Leu Met Arg Asp Pro Gln Ala Val Gly Ser Glu
            980                 985                 990

Arg Gln Ala Lys Val Thr Ser Asp Ile Asn Arg Thr Ala Val Thr Ser
        995                 1000                1005

Ile Leu Ser Leu Ser Pro Asn Gln Leu Phe Ser Asp Ser Ala Ile His
    1010                1015                1020

Tyr Ser Arg Asn Glu Glu Glu Val Gly Ile Ile Ala Asp Asn Ile Thr
1025                1030                1035                1040

Pro Val Tyr Pro His Gly Leu Arg Val Leu Tyr Glu Ser Leu Pro Phe
                1045                1050                1055

His Lys Ala Glu Lys Val Val Asn Met Ile Ser Gly Thr Lys Ser Ile
            1060                1065                1070

Thr Asn Leu Leu Gln Arg Thr Ser Ala Ile Asn Gly Glu Asp Ile Asp
        1075                1080                1085

Arg Ala Val Ser Met Met Leu Glu Asn Leu Gly Leu Leu Ser Arg Ile
    1090                1095                1100

Leu Ser Val Val Val Asp Ser Ile Glu Ile Pro Thr Lys Ser Asn Gly
1105                1110                1115                1120

Arg Leu Ile Cys Cys Gln Ile Ser Arg Thr Leu Arg Glu Thr Ser Trp
                1125                1130                1135

Asn Asn Met Glu Ile Val Gly Val Thr Ser Pro Ser Ile Thr Thr Cys
            1140                1145                1150

Met Asp Val Ile Tyr Ala Thr Ser Ser His Leu Lys Gly Ile Ile Ile
        1155                1160                1165

Glu Lys Phe Ser Thr Asp Arg Thr Thr Arg Gly Gln Arg Gly Pro Lys
    1170                1175                1180

Ser Pro Trp Val Gly Ser Ser Thr Gln Glu Lys Lys Leu Val Pro Val
1185                1190                1195                1200

Tyr Asn Arg Gln Ile Leu Ser Lys Gln Gln Arg Glu Gln Leu Glu Ala
                1205                1210                1215

Ile Gly Lys Met Arg Trp Val Tyr Lys Gly Thr Pro Gly Leu Arg Arg
            1220                1225                1230

Leu Leu Asn Lys Ile Cys Leu Gly Ser Leu Gly Ile Ser Tyr Lys Cys
        1235                1240                1245

Val Lys Pro Leu Leu Pro Arg Phe Met Ser Val Asn Phe Leu His Arg
    1250                1255                1260

Leu Ser Val Ser Ser Arg Pro Met Glu Phe Pro Ala Ser Val Pro Ala
1265                1270                1275                1280

Tyr Arg Thr Thr Asn Tyr His Phe Asp Thr Ser Pro Ile Asn Gln Ala
                1285                1290                1295

Leu Ser Glu Arg Phe Gly Asn Glu Asp Ile Asn Leu Val Phe Gln Asn
            1300                1305                1310

Ala Ile Ser Cys Gly Ile Ser Ile Met Ser Val Val Glu Gln Leu Thr
```

-continued

```
        1315                1320                1325

Gly Arg Ser Pro Lys Gln Leu Val Leu Ile Pro Gln Leu Glu Glu Ile
    1330                1335                1340

Asp Ile Met Pro Pro Pro Val Phe Gln Gly Lys Phe Asn Tyr Lys Leu
1345                1350                1355                1360

Val Asp Lys Ile Thr Ser Asp Gln His Ile Phe Ser Pro Asp Lys Ile
                1365                1370                1375

Asp Met Leu Thr Leu Gly Lys Met Leu Met Pro Thr Ile Lys Gly Gln
            1380                1385                1390

Lys Thr Asp Gln Phe Leu Asn Lys Arg Glu Asn Tyr Phe His Gly Asn
        1395                1400                1405

Asn Leu Ile Glu Ser Leu Ser Ala Ala Leu Ala Cys His Trp Cys Gly
    1410                1415                1420

Ile Leu Thr Glu Gln Cys Ile Glu Asn Asn Ile Phe Lys Lys Asp Trp
1425                1430                1435                1440

Gly Asp Gly Phe Ile Ser Asp His Ala Phe Met Asp Phe Lys Ile Phe
                1445                1450                1455

Leu Cys Val Phe Lys Thr Lys Leu Leu Cys Ser Trp Gly Ser Gln Gly
            1460                1465                1470

Lys Asn Ile Lys Asp Glu Asp Ile Val Asp Glu Ser Ile Asp Lys Leu
        1475                1480                1485

Leu Arg Ile Asp Asn Thr Phe Trp Arg Met Phe Ser Lys Val Met Phe
    1490                1495                1500

Glu Ser Lys Val Lys Lys Arg Ile Met Leu Tyr Asp Val Lys Phe Leu
1505                1510                1515                1520

Ser Leu Val Gly Tyr Ile Gly Phe Lys Asn Trp Phe Ile Glu Gln Leu
                1525                1530                1535

Arg Ser Ala Glu Leu His Glu Val Pro Trp Ile Val Asn Ala Glu Gly
            1540                1545                1550

Asp Leu Val Glu Ile Lys Ser Ile Lys Ile Tyr Leu Gln Leu Ile Glu
        1555                1560                1565

Gln Ser Leu Phe Leu Arg Ile Thr Val Leu Asn Tyr Thr Asp Met Ala
    1570                1575                1580

His Ala Leu Thr Arg Leu Ile Arg Lys Lys Leu Met Cys Asp Asn Ala
1585                1590                1595                1600

Leu Leu Thr Pro Ile Pro Ser Pro Met Val Asn Leu Thr Gln Val Ile
                1605                1610                1615

Asp Pro Thr Glu Gln Leu Ala Tyr Phe Pro Lys Ile Thr Phe Glu Arg
            1620                1625                1630

Leu Lys Asn Tyr Asp Thr Ser Ser Asn Tyr Ala Lys Gly Lys Leu Thr
        1635                1640                1645

Arg Asn Tyr Met Ile Leu Leu Pro Trp Gln His Val Asn Arg Tyr Asn
    1650                1655                1660

Phe Val Phe Ser Ser Thr Gly Cys Lys Val Ser Leu Lys Thr Cys Ile
1665                1670                1675                1680

Gly Lys Leu Met Lys Asp Leu Asn Pro Lys Val Leu Tyr Phe Ile Gly
                1685                1690                1695

Glu Gly Ala Gly Asn Trp Met Ala Arg Thr Ala Cys Glu Tyr Pro Asp
            1700                1705                1710

Ile Lys Phe Val Tyr Arg Ser Leu Lys Asp Asp Leu Asp His His Tyr
        1715                1720                1725

Pro Leu Glu Tyr Gln Arg Val Ile Gly Glu Leu Ser Arg Ile Ile Asp
    1730                1735                1740
```

-continued

```
Ser Gly Glu Gly Leu Ser Met Glu Thr Thr Asp Ala Thr Gln Lys Thr
1745                1750                1755                1760

His Trp Asp Leu Ile His Arg Val Ser Lys Asp Ala Leu Leu Ile Thr
                1765                1770                1775

Leu Cys Asp Ala Glu Phe Lys Asp Arg Asp Asp Phe Phe Lys Met Val
            1780                1785                1790

Ile Leu Trp Arg Lys His Val Leu Ser Cys Arg Ile Cys Thr Thr Tyr
        1795                1800                1805

Gly Thr Asp Leu Tyr Leu Phe Ala Lys Tyr His Ala Lys Asp Cys Asn
    1810                1815                1820

Val Lys Leu Pro Phe Phe Val Arg Ser Val Ala Thr Phe Ile Met Gln
1825                1830                1835                1840

Gly Ser Lys Leu Ser Gly Ser Glu Cys Tyr Ile Leu Leu Thr Leu Gly
                1845                1850                1855

His His Asn Asn Leu Pro Cys His Gly Glu Ile Gln Asn Ser Lys Met
            1860                1865                1870

Lys Ile Ala Val Cys Asn Asp Phe Tyr Ala Ala Lys Lys Leu Asp Asn
        1875                1880                1885

Lys Ser Ile Glu Ala Asn Cys Lys Ser Leu Leu Ser Gly Leu Arg Ile
    1890                1895                1900

Pro Ile Asn Lys Lys Glu Leu Asn Arg Gln Arg Arg Leu Leu Thr Leu
1905                1910                1915                1920

Gln Ser Asn His Ser Ser Val Ala Thr Val Gly Gly Ser Lys Val Ile
                1925                1930                1935

Glu Ser Lys Trp Leu Thr Asn Lys Ala Asn Thr Ile Ile Asp Trp Leu
            1940                1945                1950

Glu His Ile Leu Asn Ser Pro Lys Gly Glu Leu Asn Tyr Asp Phe Phe
        1955                1960                1965

Glu Ala Leu Glu Asn Thr Tyr Pro Asn Met Ile Lys Leu Ile Asp Asn
    1970                1975                1980

Leu Gly Asn Ala Glu Ile Lys Lys Leu Ile Lys Val Thr Gly Tyr Met
1985                1990                1995                2000

Leu Val Ser Lys Lys
                2005
```

<210> SEQ ID NO 331
<211> LENGTH: 2005
<212> TYPE: PRT
<213> ORGANISM: human metapneumo virus

<400> SEQUENCE: 331

```
Met Asp Pro Leu Asn Glu Ser Thr Val Asn Val Tyr Leu Pro Asp Ser
 1               5                  10                  15

Tyr Leu Lys Gly Val Ile Ser Phe Ser Glu Thr Asn Ala Ile Gly Ser
            20                  25                  30

Cys Leu Leu Lys Arg Pro Tyr Leu Lys Asn Asp Asn Thr Ala Lys Val
        35                  40                  45

Ala Ile Glu Asn Pro Val Ile Glu His Val Arg Leu Lys Asn Ala Val
    50                  55                  60

Asn Ser Lys Met Lys Ile Ser Asp Tyr Lys Val Val Glu Pro Val Asn
65                  70                  75                  80

Met Gln His Glu Ile Met Lys Asn Val His Ser Cys Glu Leu Thr Leu
                85                  90                  95

Leu Lys Gln Phe Leu Thr Arg Ser Lys Asn Ile Ser Thr Leu Lys Leu
```

-continued

```
            100                 105                 110

Asn Met Ile Cys Asp Trp Leu Gln Leu Lys Ser Thr Ser Asp Asp Thr
        115                 120                 125

Ser Ile Leu Ser Phe Ile Asp Val Glu Phe Ile Pro Ser Trp Val Ser
    130                 135                 140

Asn Trp Phe Ser Asn Trp Tyr Asn Leu Asn Lys Leu Ile Leu Glu Phe
145                 150                 155                 160

Arg Arg Glu Glu Val Ile Arg Thr Gly Ser Ile Leu Cys Arg Ser Leu
                165                 170                 175

Gly Lys Leu Val Phe Ile Val Ser Ser Tyr Gly Cys Ile Val Lys Ser
            180                 185                 190

Asn Lys Ser Lys Arg Val Ser Phe Phe Thr Tyr Asn Gln Leu Leu Thr
        195                 200                 205

Trp Lys Asp Val Met Leu Ser Arg Phe Asn Ala Asn Phe Cys Ile Trp
    210                 215                 220

Val Ser Asn Ser Leu Asn Glu Asn Gln Glu Gly Leu Gly Leu Arg Ser
225                 230                 235                 240

Asn Leu Gln Gly Met Leu Thr Asn Lys Leu Tyr Glu Thr Val Asp Tyr
                245                 250                 255

Met Leu Ser Leu Cys Cys Asn Glu Gly Phe Ser Leu Val Lys Glu Phe
            260                 265                 270

Glu Gly Phe Ile Met Ser Glu Ile Leu Arg Ile Thr Glu His Ala Gln
        275                 280                 285

Phe Ser Thr Arg Phe Arg Asn Thr Leu Leu Asn Gly Leu Thr Asp Gln
    290                 295                 300

Leu Thr Lys Leu Lys Asn Lys Asn Arg Leu Arg Val His Gly Thr Val
305                 310                 315                 320

Leu Glu Asn Asn Asp Tyr Pro Met Tyr Glu Val Val Leu Lys Leu Leu
                325                 330                 335

Gly Asp Thr Leu Arg Cys Ile Lys Leu Leu Ile Asn Lys Asn Leu Glu
            340                 345                 350

Asn Ala Ala Glu Leu Tyr Tyr Ile Phe Arg Ile Phe Gly His Pro Met
        355                 360                 365

Val Asp Glu Arg Asp Ala Met Asp Ala Val Lys Leu Asn Asn Glu Ile
    370                 375                 380

Thr Lys Ile Leu Arg Leu Glu Ser Leu Thr Glu Leu Arg Gly Ala Phe
385                 390                 395                 400

Ile Leu Arg Ile Ile Lys Gly Phe Val Asp Asn Asn Lys Arg Trp Pro
                405                 410                 415

Lys Ile Lys Asn Leu Ile Val Leu Ser Lys Arg Trp Thr Met Tyr Phe
            420                 425                 430

Lys Ala Lys Asn Tyr Pro Ser Gln Leu Glu Leu Ser Glu Gln Asp Phe
        435                 440                 445

Leu Glu Leu Ala Ala Ile Gln Phe Glu Gln Glu Phe Ser Val Pro Glu
    450                 455                 460

Lys Thr Asn Leu Glu Met Val Leu Asn Asp Lys Ala Ile Ser Pro Pro
465                 470                 475                 480

Lys Arg Leu Ile Trp Ser Val Tyr Pro Lys Asn Tyr Leu Pro Glu Thr
                485                 490                 495

Ile Lys Asn Arg Tyr Leu Glu Glu Thr Phe Asn Ala Ser Asp Ser Leu
            500                 505                 510

Lys Thr Arg Arg Val Leu Glu Tyr Tyr Leu Lys Asp Asn Lys Phe Asp
        515                 520                 525
```

-continued

```
Gln Lys Glu Leu Lys Ser Tyr Val Val Arg Gln Glu Tyr Leu Asn Asp
    530                 535                 540

Lys Glu His Ile Val Ser Leu Thr Gly Lys Glu Arg Glu Leu Ser Val
545                 550                 555                 560

Gly Arg Met Phe Ala Met Gln Pro Gly Lys Gln Arg Gln Ile Gln Ile
                565                 570                 575

Leu Ala Glu Lys Leu Leu Ala Asp Asn Ile Val Pro Phe Phe Pro Glu
            580                 585                 590

Thr Leu Thr Lys Tyr Gly Asp Leu Asp Leu Gln Arg Ile Met Glu Ile
        595                 600                 605

Lys Ser Glu Leu Ser Ser Ile Lys Thr Arg Arg Asn Asp Ser Tyr Asn
    610                 615                 620

Asn Tyr Ile Ala Arg Ala Ser Ile Val Thr Asp Leu Ser Lys Phe Asn
625                 630                 635                 640

Gln Ala Phe Arg Tyr Glu Thr Thr Ala Ile Cys Ala Asp Val Ala Asp
                645                 650                 655

Glu Leu His Gly Thr Gln Ser Leu Phe Cys Trp Leu His Leu Ile Val
            660                 665                 670

Pro Met Thr Thr Met Ile Cys Ala Tyr Arg His Ala Pro Pro Glu Thr
        675                 680                 685

Lys Gly Glu Tyr Asp Ile Asp Lys Ile Glu Glu Gln Ser Gly Leu Tyr
    690                 695                 700

Arg Tyr His Met Gly Gly Ile Glu Gly Trp Cys Gln Lys Leu Trp Thr
705                 710                 715                 720

Met Glu Ala Ile Ser Leu Leu Asp Val Val Ser Val Lys Thr Arg Cys
                725                 730                 735

Gln Met Thr Ser Leu Leu Asn Gly Asp Asn Gln Ser Ile Asp Val Ser
            740                 745                 750

Lys Pro Val Lys Leu Ser Glu Gly Leu Asp Glu Val Lys Ala Asp Tyr
        755                 760                 765

Arg Leu Ala Ile Lys Met Leu Lys Glu Ile Arg Asp Ala Tyr Arg Asn
    770                 775                 780

Ile Gly His Lys Leu Lys Glu Gly Glu Thr Tyr Ile Ser Arg Asp Leu
785                 790                 795                 800

Gln Phe Ile Ser Lys Val Ile Gln Ser Glu Gly Val Met His Pro Thr
                805                 810                 815

Pro Ile Lys Lys Val Leu Arg Val Gly Pro Trp Ile Asn Thr Ile Leu
            820                 825                 830

Asp Asp Ile Lys Thr Ser Ala Glu Ser Ile Gly Ser Leu Cys Gln Glu
        835                 840                 845

Leu Glu Phe Arg Gly Glu Ser Ile Ile Val Ser Leu Ile Leu Arg Asn
    850                 855                 860

Phe Trp Leu Tyr Asn Leu Tyr Met His Glu Ser Lys Gln His Pro Leu
865                 870                 875                 880

Ala Gly Lys Gln Leu Phe Lys Gln Leu Asn Lys Thr Leu Thr Ser Val
                885                 890                 895

Gln Arg Phe Phe Glu Ile Lys Lys Glu Asn Glu Val Val Asp Leu Trp
            900                 905                 910

Met Asn Ile Pro Met Gln Phe Gly Gly Gly Asp Pro Val Val Phe Tyr
        915                 920                 925

Arg Ser Phe Tyr Arg Arg Thr Pro Asp Phe Leu Thr Glu Ala Ile Ser
    930                 935                 940
```

-continued

```
His Val Asp Ile Leu Leu Lys Ile Ser Ala Asn Ile Lys Asn Glu Thr
945                 950                 955                 960

Lys Val Ser Phe Phe Lys Ala Leu Leu Ser Ile Glu Lys Asn Glu Arg
                965                 970                 975

Ala Thr Leu Thr Thr Leu Met Arg Asp Pro Gln Ala Val Gly Ser Glu
            980                 985                 990

Arg Gln Ala Lys Val Thr Ser Asp Ile Asn Arg Thr Ala Val Thr Ser
        995                 1000                1005

Ile Leu Ser Leu Ser Pro Asn Gln Leu Phe Ser Asp Ser Ala Ile His
    1010                1015                1020

Tyr Ser Arg Asn Glu Glu Glu Val Gly Ile Ile Ala Glu Asn Ile Thr
1025                1030                1035                1040

Pro Val Tyr Pro His Gly Leu Arg Val Leu Tyr Glu Ser Leu Pro Phe
                1045                1050                1055

His Lys Ala Glu Lys Val Val Asn Met Ile Ser Gly Thr Lys Ser Ile
            1060                1065                1070

Thr Asn Leu Leu Gln Arg Thr Ser Ala Ile Asn Gly Glu Asp Ile Asp
        1075                1080                1085

Arg Ala Val Ser Met Met Leu Glu Asn Leu Gly Leu Leu Ser Arg Ile
    1090                1095                1100

Leu Ser Val Val Val Asp Ser Ile Glu Ile Pro Ile Lys Ser Asn Gly
1105                1110                1115                1120

Arg Leu Ile Cys Cys Gln Ile Ser Arg Thr Leu Arg Glu Thr Ser Trp
                1125                1130                1135

Asn Asn Met Glu Ile Val Gly Val Thr Ser Pro Ser Ile Thr Thr Cys
            1140                1145                1150

Met Asp Val Ile Tyr Ala Thr Ser Ser His Leu Lys Gly Ile Ile Ile
        1155                1160                1165

Glu Lys Phe Ser Thr Asp Arg Thr Thr Arg Gly Gln Arg Gly Pro Lys
    1170                1175                1180

Ser Pro Trp Val Gly Ser Ser Thr Gln Glu Lys Lys Leu Val Pro Val
1185                1190                1195                1200

Tyr Asn Arg Gln Ile Leu Ser Lys Gln Gln Arg Glu Gln Leu Glu Ala
                1205                1210                1215

Ile Gly Lys Met Arg Trp Val Tyr Lys Gly Thr Pro Gly Leu Arg Arg
            1220                1225                1230

Leu Leu Asn Lys Ile Cys Leu Gly Ser Leu Gly Ile Ser Tyr Lys Cys
        1235                1240                1245

Val Lys Pro Leu Leu Pro Arg Phe Met Ser Val Asn Phe Leu His Arg
    1250                1255                1260

Leu Ser Val Ser Ser Arg Pro Met Glu Phe Pro Ala Ser Val Pro Ala
1265                1270                1275                1280

Tyr Arg Thr Thr Asn Tyr His Phe Asp Thr Ser Pro Ile Asn Gln Ala
                1285                1290                1295

Leu Ser Glu Arg Phe Gly Asn Glu Asp Ile Asn Leu Val Phe Gln Asn
            1300                1305                1310

Ala Ile Ser Cys Gly Ile Ser Ile Met Ser Val Val Glu Gln Leu Thr
        1315                1320                1325

Gly Arg Ser Pro Lys Gln Leu Val Leu Ile Pro Gln Leu Glu Glu Ile
    1330                1335                1340

Asp Ile Met Pro Pro Pro Val Phe Gln Gly Lys Phe Asn Tyr Lys Leu
1345                1350                1355                1360

Val Asp Lys Ile Thr Ser Asp Gln His Ile Phe Ser Pro Asp Lys Ile
```

-continued

```
            1365                1370                1375

Asp Met Leu Thr Leu Gly Lys Met Leu Met Pro Thr Ile Lys Gly Gln
        1380                1385                1390

Lys Thr Asp Gln Phe Leu Asn Lys Arg Glu Asn Tyr Phe His Gly Asn
    1395                1400                1405

Asn Leu Ile Glu Ser Leu Ser Ala Ala Leu Ala Cys His Trp Cys Gly
    1410                1415                1420

Ile Leu Thr Glu Gln Cys Ile Glu Asn Asn Ile Phe Lys Lys Asp Trp
1425                1430                1435                1440

Gly Asp Gly Phe Ile Ser Asp His Ala Phe Met Asp Phe Lys Ile Phe
            1445                1450                1455

Leu Cys Val Phe Lys Thr Lys Leu Leu Cys Ser Trp Gly Ser Gln Gly
        1460                1465                1470

Lys Asn Ile Lys Asp Glu Asp Ile Val Asp Glu Ser Ile Asp Lys Leu
    1475                1480                1485

Leu Arg Ile Asp Asn Thr Phe Trp Arg Met Phe Ser Lys Val Met Phe
    1490                1495                1500

Glu Pro Lys Val Lys Lys Arg Ile Met Leu Tyr Asp Val Lys Phe Leu
1505                1510                1515                1520

Ser Leu Val Gly Tyr Ile Gly Phe Lys Asn Trp Phe Ile Glu Gln Leu
            1525                1530                1535

Arg Ser Ala Glu Leu His Glu Ile Pro Trp Ile Val Asn Ala Glu Gly
        1540                1545                1550

Asp Leu Val Glu Ile Lys Ser Ile Lys Ile Tyr Leu Gln Leu Ile Glu
    1555                1560                1565

Gln Ser Leu Phe Leu Arg Ile Thr Val Leu Asn Tyr Thr Asp Met Ala
    1570                1575                1580

His Ala Leu Thr Arg Leu Ile Arg Lys Lys Leu Met Cys Asp Asn Ala
1585                1590                1595                1600

Leu Leu Thr Pro Ile Ser Ser Pro Met Val Asn Leu Thr Gln Val Ile
            1605                1610                1615

Asp Pro Thr Thr Gln Leu Asp Tyr Phe Pro Lys Ile Thr Phe Glu Arg
        1620                1625                1630

Leu Lys Asn Tyr Asp Thr Ser Ser Asn Tyr Ala Lys Gly Lys Leu Thr
    1635                1640                1645

Arg Asn Tyr Met Ile Leu Leu Pro Trp Gln His Val Asn Arg Tyr Asn
    1650                1655                1660

Phe Val Phe Ser Ser Thr Gly Cys Lys Val Ser Leu Lys Thr Cys Ile
1665                1670                1675                1680

Gly Lys Leu Met Lys Asp Leu Asn Pro Lys Val Leu Tyr Phe Ile Gly
            1685                1690                1695

Glu Gly Ala Gly Asn Trp Met Ala Arg Thr Ala Cys Glu Tyr Pro Asp
        1700                1705                1710

Ile Lys Phe Val Tyr Arg Ser Leu Lys Asp Asp Leu Asp His His Tyr
    1715                1720                1725

Pro Leu Glu Tyr Gln Arg Val Ile Gly Glu Leu Ser Arg Ile Ile Asp
    1730                1735                1740

Ser Gly Glu Gly Leu Ser Met Glu Thr Thr Asp Ala Thr Gln Lys Thr
1745                1750                1755                1760

His Trp Asp Leu Ile His Arg Val Ser Lys Asp Ala Leu Leu Ile Thr
            1765                1770                1775

Leu Cys Asp Ala Glu Phe Lys Asp Arg Asp Asp Phe Phe Lys Met Val
        1780                1785                1790
```

-continued

```
Ile Leu Trp Arg Lys His Val Leu Ser Cys Arg Ile Cys Thr Thr Tyr
        1795                1800                1805

Gly Thr Asp Leu Tyr Leu Phe Ala Lys Tyr His Ala Lys Asp Cys Asn
    1810                1815                1820

Val Lys Leu Pro Phe Phe Val Arg Ser Val Ala Thr Phe Ile Met Gln
1825                1830                1835                1840

Gly Ser Lys Leu Ser Gly Ser Glu Cys Tyr Ile Leu Leu Thr Leu Gly
                1845                1850                1855

His His Asn Ser Leu Pro Cys His Gly Glu Ile Gln Asn Ser Lys Met
            1860                1865                1870

Lys Ile Ala Val Cys Asn Asp Phe Tyr Ala Ala Lys Lys Leu Asp Asn
        1875                1880                1885

Lys Ser Ile Glu Ala Asn Cys Lys Ser Leu Leu Ser Gly Leu Arg Ile
    1890                1895                1900

Pro Ile Asn Lys Lys Glu Leu Asp Arg Gln Arg Arg Leu Leu Thr Leu
1905                1910                1915                1920

Gln Ser Asn His Ser Ser Val Ala Thr Val Gly Gly Ser Lys Ile Ile
                1925                1930                1935

Glu Ser Lys Trp Leu Thr Asn Lys Ala Ser Thr Ile Ile Asp Trp Leu
            1940                1945                1950

Glu His Ile Leu Asn Ser Pro Lys Gly Glu Leu Asn Tyr Asp Phe Phe
        1955                1960                1965

Glu Ala Leu Glu Asn Thr Tyr Pro Asn Met Ile Lys Leu Ile Asp Asn
    1970                1975                1980

Leu Gly Asn Ala Glu Ile Lys Lys Leu Ile Lys Val Thr Gly Tyr Met
1985                1990                1995                2000

Leu Val Ser Lys Lys
                2005


<210> SEQ ID NO 332
<211> LENGTH: 2005
<212> TYPE: PRT
<213> ORGANISM: human metapneumo virus

<400> SEQUENCE: 332

Met Asp Pro Phe Cys Glu Ser Thr Val Asn Val Tyr Leu Pro Asp Ser
 1               5                  10                  15

Tyr Leu Lys Gly Val Ile Ser Phe Ser Glu Thr Asn Ala Ile Gly Ser
            20                  25                  30

Cys Leu Leu Lys Arg Pro Tyr Leu Lys Asn Asp Asn Thr Ala Lys Val
        35                  40                  45

Ala Val Glu Asn Pro Val Val Glu His Val Arg Leu Arg Asn Ala Val
    50                  55                  60

Met Thr Lys Met Lys Ile Ser Asp Tyr Lys Val Val Glu Pro Val Asn
65                  70                  75                  80

Met Gln His Glu Ile Met Lys Asn Ile His Ser Cys Glu Leu Thr Leu
                85                  90                  95

Leu Lys Gln Phe Leu Thr Arg Ser Lys Asn Ile Ser Ser Leu Lys Leu
            100                 105                 110

Asn Met Ile Cys Asp Trp Leu Gln Leu Lys Ser Thr Ser Asp Asn Thr
        115                 120                 125

Ser Ile Leu Asn Phe Ile Asp Val Glu Phe Ile Pro Val Trp Val Ser
    130                 135                 140

Asn Trp Phe Ser Asn Trp Tyr Asn Leu Asn Lys Leu Ile Leu Glu Phe
```

-continued

```
145                 150                 155                 160

Arg Arg Glu Glu Val Ile Arg Thr Gly Ser Ile Leu Cys Arg Ser Leu
                165                 170                 175

Gly Lys Leu Val Phe Ile Val Ser Ser Tyr Gly Cys Val Val Lys Ser
            180                 185                 190

Asn Lys Ser Lys Arg Val Ser Phe Phe Thr Tyr Asn Gln Leu Leu Thr
        195                 200                 205

Trp Lys Asp Val Met Leu Ser Arg Phe Asn Ala Asn Phe Cys Ile Trp
    210                 215                 220

Val Ser Asn Asn Leu Asn Lys Asn Gln Glu Gly Leu Gly Leu Arg Ser
225                 230                 235                 240

Asn Leu Gln Gly Met Leu Thr Asn Lys Leu Tyr Glu Thr Val Asp Tyr
                245                 250                 255

Met Leu Ser Leu Cys Cys Asn Glu Gly Phe Ser Leu Val Lys Glu Phe
            260                 265                 270

Glu Gly Phe Ile Met Ser Glu Ile Leu Lys Ile Thr Glu His Ala Gln
        275                 280                 285

Phe Ser Thr Arg Phe Arg Asn Thr Leu Leu Asn Gly Leu Thr Glu Gln
    290                 295                 300

Leu Ser Val Leu Lys Ala Lys Asn Arg Ser Arg Val Leu Gly Thr Ile
305                 310                 315                 320

Leu Glu Asn Asn Asn Tyr Pro Met Tyr Glu Val Val Leu Lys Leu Leu
                325                 330                 335

Gly Asp Thr Leu Lys Ser Ile Lys Leu Leu Ile Asn Lys Asn Leu Glu
            340                 345                 350

Asn Ala Ala Glu Leu Tyr Tyr Ile Phe Arg Ile Phe Gly His Pro Met
        355                 360                 365

Val Asp Glu Arg Glu Ala Met Asp Ala Val Lys Leu Asn Asn Glu Ile
    370                 375                 380

Thr Lys Ile Leu Lys Leu Glu Ser Leu Thr Glu Leu Arg Gly Ala Phe
385                 390                 395                 400

Ile Leu Arg Ile Ile Lys Gly Phe Val Asp Asn Asn Lys Arg Trp Pro
                405                 410                 415

Lys Ile Lys Asn Leu Lys Val Leu Ser Lys Arg Trp Ala Met Tyr Phe
            420                 425                 430

Lys Ala Lys Ser Tyr Pro Ser Gln Leu Glu Leu Ser Val Gln Asp Phe
        435                 440                 445

Leu Glu Leu Ala Ala Val Gln Phe Glu Gln Glu Phe Ser Val Pro Glu
    450                 455                 460

Lys Thr Asn Leu Glu Met Val Leu Asn Asp Lys Ala Ile Ser Pro Pro
465                 470                 475                 480

Lys Lys Leu Ile Trp Ser Val Tyr Pro Lys Asn Tyr Leu Pro Glu Thr
                485                 490                 495

Ile Lys Asn Gln Tyr Leu Glu Glu Ala Phe Asn Ala Ser Asp Ser Gln
            500                 505                 510

Arg Thr Arg Arg Val Leu Glu Phe Tyr Leu Lys Asp Cys Lys Phe Asp
        515                 520                 525

Gln Lys Glu Leu Lys Arg Tyr Val Ile Lys Gln Glu Tyr Leu Asn Asp
    530                 535                 540

Lys Asp His Ile Val Ser Leu Thr Gly Lys Glu Arg Glu Leu Ser Val
545                 550                 555                 560

Gly Arg Met Phe Ala Met Gln Pro Gly Lys Gln Arg Gln Ile Gln Ile
                565                 570                 575
```

-continued

Leu Ala Glu Lys Leu Leu Ala Asp Asn Ile Val Pro Phe Phe Pro Glu
580 585 590

Thr Leu Thr Lys Tyr Gly Asp Leu Asp Leu Gln Arg Ile Met Glu Ile
595 600 605

Lys Ser Glu Leu Ser Ser Ile Lys Thr Arg Lys Asn Asp Ser Tyr Asn
610 615 620

Asn Tyr Ile Ala Arg Ala Ser Ile Val Thr Asp Leu Ser Lys Phe Asn
625 630 635 640

Gln Ala Phe Arg Tyr Glu Thr Thr Ala Ile Cys Ala Asp Val Ala Asp
645 650 655

Glu Leu His Gly Thr Gln Ser Leu Phe Cys Trp Leu His Leu Ile Val
660 665 670

Pro Met Thr Thr Met Ile Cys Ala Tyr Arg His Ala Pro Pro Glu Thr
675 680 685

Lys Gly Glu Tyr Asp Ile Asp Lys Ile Gln Glu Gln Ser Gly Leu Tyr
690 695 700

Arg Tyr His Met Gly Gly Ile Glu Gly Trp Cys Gln Lys Leu Trp Thr
705 710 715 720

Met Glu Ala Ile Ser Leu Leu Asp Val Val Ser Val Lys Thr Arg Cys
725 730 735

Gln Met Thr Ser Leu Leu Asn Gly Asp Asn Gln Ser Ile Asp Val Ser
740 745 750

Lys Pro Val Lys Leu Ser Glu Gly Ile Asp Glu Val Lys Ala Asp Tyr
755 760 765

Ser Leu Ala Ile Arg Met Leu Lys Glu Ile Arg Asp Ala Tyr Lys Asn
770 775 780

Ile Gly His Lys Leu Lys Glu Gly Glu Thr Tyr Ile Ser Arg Asp Leu
785 790 795 800

Gln Phe Ile Ser Lys Val Ile Gln Ser Glu Gly Val Met His Pro Thr
805 810 815

Pro Ile Lys Lys Ile Leu Arg Val Gly Pro Trp Ile Asn Thr Ile Leu
820 825 830

Asp Asp Ile Lys Thr Ser Ala Glu Ser Ile Gly Ser Leu Cys Gln Glu
835 840 845

Leu Glu Phe Arg Gly Glu Ser Ile Leu Val Ser Leu Ile Leu Arg Asn
850 855 860

Phe Trp Leu Tyr Asn Leu Tyr Met Tyr Glu Ser Lys Gln His Pro Leu
865 870 875 880

Ala Gly Lys Gln Leu Phe Lys Gln Leu Asn Lys Thr Leu Thr Ser Val
885 890 895

Gln Arg Phe Phe Glu Leu Lys Lys Glu Asn Asp Val Val Asp Leu Trp
900 905 910

Met Asn Ile Pro Met Gln Phe Gly Gly Gly Asp Pro Val Val Phe Tyr
915 920 925

Arg Ser Phe Tyr Arg Arg Thr Pro Asp Phe Leu Thr Glu Ala Ile Ser
930 935 940

His Val Asp Leu Leu Leu Lys Val Ser Asn Asn Ile Lys Asp Glu Thr
945 950 955 960

Lys Ile Arg Phe Phe Lys Ala Leu Leu Ser Ile Glu Lys Asn Glu Arg
965 970 975

Ala Thr Leu Thr Thr Leu Met Arg Asp Pro Gln Ala Val Gly Ser Glu
980 985 990

-continued

Arg Gln Ala Lys Val Thr Ser Asp Ile Asn Arg Thr Ala Val Thr Ser
995 1000 1005

Ile Leu Ser Leu Ser Pro Asn Gln Leu Phe Cys Asp Ser Ala Ile His
1010 1015 1020

Tyr Ser Arg Asn Glu Glu Glu Val Gly Ile Ile Ala Asp Asn Ile Thr
1025 1030 1035 1040

Pro Val Tyr Pro His Gly Leu Arg Val Leu Tyr Glu Ser Leu Pro Phe
1045 1050 1055

His Lys Ala Glu Lys Val Val Asn Met Ile Ser Gly Thr Lys Ser Ile
1060 1065 1070

Thr Asn Leu Leu Gln Arg Thr Ser Ala Ile Asn Gly Glu Asp Ile Asp
1075 1080 1085

Arg Ala Val Ser Met Met Leu Glu Asn Leu Gly Leu Leu Ser Arg Ile
1090 1095 1100

Leu Ser Val Ile Ile Asn Ser Ile Glu Ile Pro Ile Lys Ser Asn Gly
1105 1110 1115 1120

Arg Leu Ile Cys Cys Gln Ile Ser Lys Thr Leu Arg Glu Lys Ser Trp
1125 1130 1135

Asn Asn Met Glu Ile Val Gly Val Thr Ser Pro Ser Ile Val Thr Cys
1140 1145 1150

Met Asp Val Val Tyr Ala Thr Ser Ser His Leu Lys Gly Ile Ile Ile
1155 1160 1165

Glu Lys Phe Ser Thr Asp Lys Thr Thr Arg Gly Gln Arg Gly Pro Lys
1170 1175 1180

Ser Pro Trp Val Gly Ser Ser Thr Gln Glu Lys Lys Leu Val Pro Val
1185 1190 1195 1200

Tyr Asn Arg Gln Ile Leu Ser Lys Gln Gln Lys Glu Gln Leu Glu Ala
1205 1210 1215

Ile Gly Lys Met Arg Trp Val Tyr Lys Gly Thr Pro Gly Leu Arg Arg
1220 1225 1230

Leu Leu Asn Lys Ile Cys Ile Gly Ser Leu Gly Ile Ser Tyr Lys Cys
1235 1240 1245

Val Lys Pro Leu Leu Pro Arg Phe Met Ser Val Asn Phe Leu His Arg
1250 1255 1260

Leu Ser Val Ser Ser Arg Pro Met Glu Phe Pro Ala Ser Val Pro Ala
1265 1270 1275 1280

Tyr Arg Thr Thr Asn Tyr His Phe Asp Thr Ser Pro Ile Asn Gln Ala
1285 1290 1295

Leu Ser Glu Arg Phe Gly Asn Glu Asp Ile Asn Leu Val Phe Gln Asn
1300 1305 1310

Ala Ile Ser Cys Gly Ile Ser Ile Met Ser Val Val Glu Gln Leu Thr
1315 1320 1325

Gly Arg Ser Pro Lys Gln Leu Val Leu Ile Pro Gln Leu Glu Glu Ile
1330 1335 1340

Asp Ile Met Pro Pro Pro Val Phe Gln Gly Lys Phe Asn Tyr Lys Leu
1345 1350 1355 1360

Val Asp Lys Ile Thr Ser Asp Gln His Ile Phe Ser Pro Asp Lys Ile
1365 1370 1375

Asp Ile Leu Thr Leu Gly Lys Met Leu Met Pro Thr Ile Lys Gly Gln
1380 1385 1390

Lys Thr Asp Gln Phe Leu Asn Lys Arg Glu Asn Tyr Phe His Gly Asn
1395 1400 1405

Asn Leu Ile Glu Ser Leu Ser Ala Ala Leu Ala Cys His Trp Cys Gly

-continued

```
    1410                1415                1420

Ile Leu Thr Glu Gln Cys Ile Glu Asn Asn Ile Phe Arg Lys Asp Trp
1425                1430                1435                1440

Gly Asp Gly Phe Ile Ser Asp His Ala Phe Met Asp Phe Lys Val Phe
                1445                1450                1455

Leu Cys Val Phe Lys Thr Lys Leu Leu Cys Ser Trp Gly Ser Gln Gly
            1460                1465                1470

Lys Asn Val Lys Asp Glu Asp Ile Ile Asp Glu Ser Ile Asp Lys Leu
        1475                1480                1485

Leu Arg Ile Asp Asn Thr Phe Trp Arg Met Phe Ser Lys Val Met Phe
    1490                1495                1500

Glu Ser Lys Val Lys Lys Arg Ile Met Leu Tyr Asp Val Lys Phe Leu
1505                1510                1515                1520

Ser Leu Val Gly Tyr Ile Gly Phe Lys Asn Trp Phe Ile Glu Gln Leu
                1525                1530                1535

Arg Val Val Glu Leu His Glu Val Pro Trp Ile Val Asn Ala Glu Gly
            1540                1545                1550

Glu Leu Val Glu Ile Lys Ser Ile Lys Ile Tyr Leu Gln Leu Ile Glu
        1555                1560                1565

Gln Ser Leu Ser Leu Arg Ile Thr Val Leu Asn Tyr Thr Asp Met Ala
    1570                1575                1580

His Ala Leu Thr Arg Leu Ile Arg Lys Lys Leu Met Cys Asp Asn Ala
1585                1590                1595                1600

Leu Phe Asn Pro Ser Ser Ser Pro Met Phe Asn Leu Thr Gln Val Ile
                1605                1610                1615

Asp Pro Thr Thr Gln Leu Asp Tyr Phe Pro Arg Ile Ile Phe Glu Arg
            1620                1625                1630

Leu Lys Ser Tyr Asp Thr Ser Ser Asp Tyr Asn Lys Gly Lys Leu Thr
        1635                1640                1645

Arg Asn Tyr Met Thr Leu Leu Pro Trp Gln His Val Asn Arg Tyr Asn
    1650                1655                1660

Phe Val Phe Ser Ser Thr Gly Cys Lys Val Ser Leu Lys Thr Cys Ile
1665                1670                1675                1680

Gly Lys Leu Ile Lys Asp Leu Asn Pro Lys Val Leu Tyr Phe Ile Gly
                1685                1690                1695

Glu Gly Ala Gly Asn Trp Met Ala Arg Thr Ala Cys Glu Tyr Pro Asp
            1700                1705                1710

Ile Lys Phe Val Tyr Arg Ser Leu Lys Asp Asp Leu Asp His His Tyr
        1715                1720                1725

Pro Leu Glu Tyr Gln Arg Val Ile Gly Asp Leu Asn Arg Val Ile Asp
    1730                1735                1740

Ser Gly Glu Gly Leu Ser Met Glu Thr Thr Asp Ala Thr Gln Lys Thr
1745                1750                1755                1760

His Trp Asp Leu Ile His Arg Ile Ser Lys Asp Ala Leu Leu Ile Thr
                1765                1770                1775

Leu Cys Asp Ala Glu Phe Lys Asn Arg Asp Asp Phe Phe Lys Met Val
            1780                1785                1790

Ile Leu Trp Arg Lys His Val Leu Ser Cys Arg Ile Cys Thr Ala Tyr
        1795                1800                1805

Gly Thr Asp Leu Tyr Leu Phe Ala Lys Tyr His Ala Val Asp Cys Asn
    1810                1815                1820

Ile Lys Leu Pro Phe Phe Val Arg Ser Val Ala Thr Phe Ile Met Gln
1825                1830                1835                1840
```

```
Gly Ser Lys Leu Ser Gly Ser Glu Cys Tyr Ile Leu Leu Thr Leu Gly
                1845                1850                1855

His His Asn Asn Leu Pro Cys His Gly Glu Ile Gln Asn Ser Lys Met
            1860                1865                1870

Arg Ile Ala Val Cys Asn Asp Phe Tyr Ala Ser Lys Lys Leu Asp Asn
        1875                1880                1885

Lys Ser Ile Glu Ala Asn Cys Lys Ser Leu Leu Ser Gly Leu Arg Ile
    1890                1895                1900

Pro Ile Asn Lys Lys Glu Leu Asn Arg Gln Lys Lys Leu Leu Thr Leu
1905                1910                1915                1920

Gln Ser Asn His Ser Ser Ile Ala Thr Val Gly Gly Ser Lys Ile Ile
                1925                1930                1935

Glu Ser Lys Trp Leu Lys Asn Lys Ala Ser Thr Ile Ile Asp Trp Leu
            1940                1945                1950

Glu His Ile Leu Asn Ser Pro Lys Gly Glu Leu Asn Tyr Asp Phe Phe
        1955                1960                1965

Glu Ala Leu Glu Asn Thr Tyr Pro Asn Met Ile Lys Leu Ile Asp Asn
    1970                1975                1980

Leu Gly Asn Ala Glu Ile Lys Lys Leu Ile Lys Val Thr Gly Tyr Met
1985                1990                1995                2000

Leu Val Ser Lys Lys
                2005


<210> SEQ ID NO 333
<211> LENGTH: 2005
<212> TYPE: PRT
<213> ORGANISM: human metapneumo virus

<400> SEQUENCE: 333

Met Asp Pro Phe Cys Glu Ser Thr Val Asn Val Tyr Leu Pro Asp Ser
 1               5                  10                  15

Tyr Leu Lys Gly Val Ile Ser Phe Ser Glu Thr Asn Ala Ile Gly Ser
            20                  25                  30

Cys Leu Leu Lys Arg Pro Tyr Leu Lys Lys Asp Asn Thr Ala Lys Val
        35                  40                  45

Ala Val Glu Asn Pro Val Val Glu His Val Arg Leu Arg Asn Ala Val
    50                  55                  60

Met Thr Lys Met Lys Ile Ser Asp Tyr Lys Val Val Glu Pro Ile Asn
65                  70                  75                  80

Met Gln His Glu Ile Met Lys Asn Ile His Ser Cys Glu Leu Thr Leu
                85                  90                  95

Leu Lys Gln Phe Leu Thr Arg Ser Lys Asn Ile Ser Ser Leu Lys Leu
            100                 105                 110

Ser Met Ile Cys Asp Trp Leu Gln Leu Lys Ser Thr Ser Asp Asn Thr
        115                 120                 125

Ser Ile Leu Asn Phe Ile Asp Val Glu Phe Ile Pro Val Trp Val Ser
    130                 135                 140

Asn Trp Phe Ser Asn Trp Tyr Asn Leu Asn Lys Leu Ile Leu Glu Phe
145                 150                 155                 160

Arg Arg Glu Glu Val Ile Arg Thr Gly Ser Ile Leu Cys Arg Ser Leu
                165                 170                 175

Gly Lys Leu Val Phe Ile Val Ser Ser Tyr Gly Cys Val Val Lys Ser
            180                 185                 190

Asn Lys Ser Lys Arg Val Ser Phe Phe Thr Tyr Asn Gln Leu Leu Thr
```

-continued

```
        195                 200                 205

Trp Lys Asp Val Met Leu Ser Arg Phe Asn Ala Asn Phe Cys Ile Trp
    210                 215                 220

Val Ser Asn Asn Leu Asn Lys Asn Gln Glu Gly Leu Gly Phe Arg Ser
225                 230                 235                 240

Asn Leu Gln Gly Met Leu Thr Asn Lys Leu Tyr Glu Thr Val Asp Tyr
                245                 250                 255

Met Leu Ser Leu Cys Ser Asn Glu Gly Phe Ser Leu Val Lys Glu Phe
            260                 265                 270

Glu Gly Phe Ile Met Ser Glu Ile Leu Lys Ile Thr Glu His Ala Gln
        275                 280                 285

Phe Ser Thr Arg Phe Arg Asn Thr Leu Leu Asn Gly Leu Thr Glu Gln
    290                 295                 300

Leu Ser Met Leu Lys Ala Lys Asn Arg Ser Arg Val Leu Gly Thr Ile
305                 310                 315                 320

Leu Glu Asn Asn Asp Tyr Pro Met Tyr Glu Val Val Leu Lys Leu Leu
                325                 330                 335

Gly Asp Thr Leu Lys Ser Ile Lys Leu Leu Ile Asn Lys Asn Leu Glu
            340                 345                 350

Asn Ala Ala Glu Leu Tyr Tyr Ile Phe Arg Ile Phe Gly His Pro Met
        355                 360                 365

Val Asp Glu Arg Glu Ala Met Asp Ala Val Lys Leu Asn Asn Glu Ile
    370                 375                 380

Thr Lys Ile Leu Lys Leu Glu Ser Leu Thr Glu Leu Arg Gly Ala Phe
385                 390                 395                 400

Ile Leu Arg Ile Ile Lys Gly Phe Val Asp Asn Asn Lys Arg Trp Pro
                405                 410                 415

Lys Ile Lys Asn Leu Lys Val Leu Ser Lys Arg Trp Val Met Tyr Phe
            420                 425                 430

Lys Ala Lys Ser Tyr Pro Ser Gln Leu Glu Leu Ser Val Gln Asp Phe
        435                 440                 445

Leu Glu Leu Ala Ala Val Gln Phe Glu Gln Glu Phe Ser Val Pro Glu
    450                 455                 460

Lys Thr Asn Leu Glu Met Val Leu Asn Asp Lys Ala Ile Ser Pro Pro
465                 470                 475                 480

Lys Lys Leu Ile Trp Ser Val Tyr Pro Lys Asn Tyr Leu Pro Glu Ile
                485                 490                 495

Ile Lys Asn Gln Tyr Leu Glu Glu Val Phe Asn Ala Ser Asp Ser Gln
            500                 505                 510

Arg Thr Arg Arg Val Leu Glu Phe Tyr Leu Lys Asp Cys Lys Phe Asp
        515                 520                 525

Gln Lys Asp Leu Lys Arg Tyr Val Leu Lys Gln Glu Tyr Leu Asn Asp
    530                 535                 540

Lys Asp His Ile Val Ser Leu Thr Gly Lys Glu Arg Glu Leu Ser Val
545                 550                 555                 560

Gly Arg Met Phe Ala Met Gln Pro Gly Lys Gln Arg Gln Ile Gln Ile
                565                 570                 575

Leu Ala Glu Lys Leu Leu Ala Asp Asn Ile Val Pro Phe Phe Pro Glu
            580                 585                 590

Thr Leu Thr Lys Tyr Gly Asp Leu Asp Leu Gln Arg Ile Met Glu Met
        595                 600                 605

Lys Ser Glu Leu Ser Ser Ile Lys Thr Arg Lys Asn Asp Ser Tyr Asn
    610                 615                 620
```

-continued

Asn Tyr Ile Ala Arg Ala Ser Ile Val Thr Asp Leu Ser Lys Phe Asn
625 630 635 640

Gln Ala Phe Arg Tyr Glu Thr Thr Ala Ile Cys Ala Asp Val Ala Asp
645 650 655

Glu Leu His Gly Thr Gln Ser Leu Phe Cys Trp Leu His Leu Ile Val
660 665 670

Pro Met Thr Thr Met Ile Cys Ala Tyr Arg His Ala Pro Pro Glu Thr
675 680 685

Lys Gly Glu Tyr Asp Ile Asp Lys Ile Glu Glu Gln Ser Gly Leu Tyr
690 695 700

Arg Tyr His Met Gly Gly Ile Glu Gly Trp Cys Gln Lys Leu Trp Thr
705 710 715 720

Met Glu Ala Ile Ser Leu Leu Asp Val Val Ser Val Lys Thr Arg Cys
725 730 735

Gln Met Thr Ser Leu Leu Asn Gly Asp Asn Gln Ser Ile Asp Val Ser
740 745 750

Lys Pro Val Lys Leu Ser Glu Gly Ile Asp Glu Val Lys Ala Asp Tyr
755 760 765

Ser Leu Ala Ile Lys Met Leu Lys Glu Ile Arg Asp Ala Tyr Lys Asn
770 775 780

Ile Gly His Lys Leu Lys Glu Gly Glu Thr Tyr Ile Ser Arg Asp Leu
785 790 795 800

Gln Phe Ile Ser Lys Val Ile Gln Ser Glu Gly Val Met His Pro Thr
805 810 815

Pro Ile Lys Lys Ile Leu Arg Val Gly Pro Trp Ile Asn Thr Ile Leu
820 825 830

Asp Asp Ile Lys Thr Ser Ala Glu Ser Ile Gly Ser Leu Cys Gln Glu
835 840 845

Leu Glu Phe Arg Gly Glu Ser Met Leu Val Ser Leu Ile Leu Arg Asn
850 855 860

Phe Trp Leu Tyr Asn Leu Tyr Met His Glu Ser Lys Gln His Pro Leu
865 870 875 880

Ala Gly Lys Gln Leu Phe Lys Gln Leu Asn Lys Thr Leu Thr Ser Val
885 890 895

Gln Arg Phe Phe Glu Leu Lys Lys Glu Asn Asp Val Val Asp Leu Trp
900 905 910

Met Asn Ile Pro Met Gln Phe Gly Gly Gly Asp Pro Val Val Phe Tyr
915 920 925

Arg Ser Phe Tyr Arg Arg Thr Pro Asp Phe Leu Thr Glu Ala Ile Ser
930 935 940

His Val Asp Leu Leu Leu Lys Val Ser Asn Asn Ile Lys Asn Glu Thr
945 950 955 960

Lys Ile Arg Phe Phe Lys Ala Leu Leu Ser Ile Glu Lys Asn Glu Arg
965 970 975

Ala Thr Leu Thr Thr Leu Met Arg Asp Pro Gln Ala Val Gly Ser Glu
980 985 990

Arg Gln Ala Lys Val Thr Ser Asp Ile Asn Arg Thr Ala Val Thr Ser
995 1000 1005

Ile Leu Ser Leu Ser Pro Asn Gln Leu Phe Cys Asp Ser Ala Ile His
1010 1015 1020

Tyr Ser Arg Asn Glu Glu Glu Val Gly Ile Ile Ala Asp Asn Ile Thr
1025 1030 1035 1040

-continued

```
Pro Val Tyr Pro His Gly Leu Arg Val Leu Tyr Glu Ser Leu Pro Phe
                1045                1050                1055

His Lys Ala Glu Lys Val Val Asn Met Ile Ser Gly Thr Lys Ser Ile
            1060                1065                1070

Thr Asn Leu Leu Gln Arg Thr Ser Ala Ile Asn Gly Glu Asp Ile Asp
        1075                1080                1085

Arg Ala Val Ser Met Met Leu Glu Asn Leu Gly Leu Leu Ser Arg Ile
    1090                1095                1100

Leu Ser Val Ile Ile Asn Ser Ile Glu Ile Pro Ile Lys Ser Asn Gly
1105                1110                1115                1120

Arg Leu Ile Cys Cys Gln Ile Ser Lys Thr Leu Arg Glu Lys Ser Trp
                1125                1130                1135

Asn Asn Met Glu Ile Val Gly Val Thr Ser Pro Ser Ile Val Thr Cys
            1140                1145                1150

Met Asp Val Val Tyr Ala Thr Ser Ser His Leu Lys Gly Ile Ile Ile
        1155                1160                1165

Glu Lys Phe Ser Thr Asp Lys Thr Thr Arg Gly Gln Arg Gly Pro Lys
    1170                1175                1180

Ser Pro Trp Val Gly Ser Ser Thr Gln Glu Lys Lys Leu Val Pro Val
1185                1190                1195                1200

Tyr Asn Arg Gln Ile Leu Ser Lys Gln Gln Lys Glu Gln Leu Glu Ala
                1205                1210                1215

Ile Gly Lys Met Arg Trp Val Tyr Lys Gly Thr Pro Gly Leu Arg Arg
            1220                1225                1230

Leu Leu Asn Lys Ile Cys Ile Gly Ser Leu Gly Ile Ser Tyr Lys Cys
        1235                1240                1245

Val Lys Pro Leu Leu Pro Arg Phe Met Ser Val Asn Phe Leu His Arg
    1250                1255                1260

Leu Ser Val Ser Ser Arg Pro Met Glu Phe Pro Ala Ser Val Pro Ala
1265                1270                1275                1280

Tyr Arg Thr Thr Asn Tyr His Phe Asp Thr Ser Pro Ile Asn Gln Ala
                1285                1290                1295

Leu Ser Glu Arg Phe Gly Asn Glu Asp Ile Asn Leu Val Phe Gln Asn
            1300                1305                1310

Ala Ile Ser Cys Gly Ile Ser Ile Met Ser Val Val Glu Gln Leu Thr
        1315                1320                1325

Gly Arg Ser Pro Lys Gln Leu Val Leu Ile Pro Gln Leu Glu Glu Ile
    1330                1335                1340

Asp Ile Met Pro Pro Pro Val Phe Gln Gly Lys Phe Asn Tyr Lys Leu
1345                1350                1355                1360

Val Asp Lys Ile Thr Ser Asp Gln His Ile Phe Ser Pro Asp Lys Ile
                1365                1370                1375

Asp Ile Leu Thr Leu Gly Lys Met Leu Met Pro Thr Ile Lys Gly Gln
            1380                1385                1390

Lys Thr Asp Gln Phe Leu Asn Lys Arg Glu Asn Tyr Phe His Gly Asn
        1395                1400                1405

Asn Leu Ile Glu Ser Leu Ser Ala Ala Leu Ala Cys His Trp Cys Gly
    1410                1415                1420

Ile Leu Thr Glu Gln Cys Val Glu Asn Asn Ile Phe Arg Lys Asp Trp
1425                1430                1435                1440

Gly Asp Gly Phe Ile Ser Asp His Ala Phe Met Asp Phe Lys Ile Phe
                1445                1450                1455

Leu Cys Val Phe Lys Thr Lys Leu Leu Cys Ser Trp Gly Ser Gln Gly
```

-continued

```
            1460                1465                1470

Lys Asn Val Lys Asp Glu Asp Ile Ile Asp Glu Ser Ile Asp Lys Leu
        1475                1480                1485

Leu Arg Ile Asp Asn Thr Phe Trp Arg Met Phe Ser Lys Val Met Phe
    1490                1495                1500

Glu Ser Lys Val Lys Lys Arg Ile Met Leu Tyr Asp Val Lys Phe Leu
1505                1510                1515                1520

Ser Leu Val Gly Tyr Ile Gly Phe Lys Asn Trp Phe Ile Glu Gln Leu
                1525                1530                1535

Arg Val Val Glu Leu His Glu Val Pro Trp Ile Val Asn Ala Glu Gly
            1540                1545                1550

Glu Leu Val Glu Ile Lys Pro Ile Lys Ile Tyr Leu Gln Leu Ile Glu
        1555                1560                1565

Gln Ser Leu Ser Leu Arg Ile Thr Val Leu Asn Tyr Thr Asp Met Ala
    1570                1575                1580

His Ala Leu Thr Arg Leu Ile Arg Lys Lys Leu Met Cys Asp Asn Ala
1585                1590                1595                1600

Leu Phe Asn Pro Ser Ser Ser Pro Met Phe Ser Leu Thr Gln Val Ile
                1605                1610                1615

Asp Pro Thr Thr Gln Leu Asp Tyr Phe Pro Lys Val Ile Phe Glu Arg
            1620                1625                1630

Leu Lys Ser Tyr Asp Thr Ser Ser Asp Tyr Asn Lys Gly Lys Leu Thr
        1635                1640                1645

Arg Asn Tyr Met Thr Leu Leu Pro Trp Gln His Val Asn Arg Tyr Asn
    1650                1655                1660

Phe Val Phe Ser Ser Thr Gly Cys Lys Ile Ser Leu Lys Thr Cys Ile
1665                1670                1675                1680

Gly Lys Leu Ile Lys Asp Leu Asn Pro Lys Val Leu Tyr Phe Ile Gly
                1685                1690                1695

Glu Gly Ala Gly Asn Trp Met Ala Arg Thr Ala Cys Glu Tyr Pro Asp
            1700                1705                1710

Ile Lys Phe Val Tyr Arg Ser Leu Lys Asp Asp Leu Asp His His Tyr
        1715                1720                1725

Pro Leu Glu Tyr Gln Arg Val Ile Gly Asp Leu Asn Arg Val Ile Asp
    1730                1735                1740

Gly Gly Glu Gly Leu Ser Met Glu Thr Thr Asp Ala Thr Gln Lys Thr
1745                1750                1755                1760

His Trp Asp Leu Ile His Arg Ile Ser Lys Asp Ala Leu Leu Ile Thr
                1765                1770                1775

Leu Cys Asp Ala Glu Phe Lys Asn Arg Asp Asp Phe Phe Lys Met Val
            1780                1785                1790

Ile Leu Trp Arg Lys His Val Leu Ser Cys Arg Ile Cys Thr Ala Tyr
        1795                1800                1805

Gly Thr Asp Leu Tyr Leu Phe Ala Lys Tyr His Ala Thr Asp Cys Asn
    1810                1815                1820

Ile Lys Leu Pro Phe Phe Val Arg Ser Val Ala Thr Phe Ile Met Gln
1825                1830                1835                1840

Gly Ser Lys Leu Ser Gly Ser Glu Cys Tyr Ile Leu Leu Thr Leu Gly
                1845                1850                1855

His His Asn Asn Leu Pro Cys His Gly Glu Ile Gln Asn Ser Lys Met
            1860                1865                1870

Arg Ile Ala Val Cys Asn Asp Phe His Ala Ser Lys Lys Leu Asp Asn
        1875                1880                1885
```

-continued

```
Lys Ser Ile Glu Ala Asn Cys Lys Ser Leu Leu Ser Gly Leu Arg Ile
    1890                1895                1900

Pro Ile Asn Lys Lys Glu Leu Asn Arg Gln Lys Lys Leu Leu Thr Leu
1905                1910                1915                1920

Gln Ser Asn His Ser Ser Ile Ala Thr Val Gly Gly Ser Lys Ile Ile
                1925                1930                1935

Glu Ser Lys Trp Leu Lys Asn Lys Ala Ser Thr Ile Ile Asp Trp Leu
            1940                1945                1950

Glu His Ile Leu Asn Ser Pro Lys Gly Glu Leu Asn Tyr Asp Phe Phe
        1955                1960                1965

Glu Ala Leu Glu Asn Thr Tyr Pro Asn Met Ile Lys Leu Ile Asp Asn
    1970                1975                1980

Leu Gly Asn Ala Glu Ile Lys Lys Leu Ile Lys Val Pro Gly Tyr Met
1985                1990                1995                2000

Leu Val Ser Lys Lys
                2005
```

<210> SEQ ID NO 334
<211> LENGTH: 6018
<212> TYPE: DNA
<213> ORGANISM: human metapneumo virus

<400> SEQUENCE: 334

```
atggatcctc tcaatgaatc cactgttaat gtctatcttc ctgactcata tcttaaagga     60

gtgatttcct ttagtgagac taatgcaatt ggttcatgtc tcttaaaaag accttaccta    120

aaaaatgaca acactgcaaa agttgccata gagaatcctg ttatcgagca tgttagactc    180

aaaaatgcag tcaattctaa gatgaaaata tcagattaca agatagtaga gccagtaaac    240

atgcaacatg aaattatgaa gaatgtacac agttgtgagc tcacattatt aaaacagttt    300

ttaacaagga gtaaaaatat tagcactctc aaattaaata tgatatgtga ttggctgcag    360

ttaaagtcta catcagatga tacctcaatc ctaagtttta tagatgtaga atttatacct    420

agctgggtaa gcaattggtt tagtaattgg tacaatctca acaagttgat tctggaattc    480

aggaaagaag aagtaataag aactggttca atcttgtgta ggtcattggg taaattagtt    540

tttgttgtat catcatatgg atgtatagtc aagagcaaca aaagcaaaag agtgagcttc    600

ttcacataca atcaactgtt aacatggaaa gatgtgatgt taagtagatt caatgcaaat    660

ttttgtatat gggtaagcaa cagtctgaat gaaaatcaag aagggctagg gttgagaagt    720

aatctgcaag gcatattaac taataagcta tatgaaactg tagattatat gcttagttta    780

tgttgcaatg aaggtttctc acttgtgaaa gagttcgaag gctttattat gagtgaaatt    840

cttaggatta ctgaacatgc tcaattcagt actagattta gaaatacttt attaaatgga    900

ttaactgatc aattaacaaa attaaaaaat aaaaacagac tcagagttca tggtaccgtg    960

ttagaaaata atgattatcc aatgtacgaa gttgtactta agttattagg agatactttg   1020

agatgtatta aattattaat caataaaaac ttagagaatg ctgctgaatt atactatata   1080

tttagaatat tcggtcaccc aatggtagat gaaagagatg caatggatgc tgtcaaatta   1140

aacaatgaaa tcacaaaaat ccttaggtgg gagagcttga cagaactaag aggggcattc   1200

atattaagga ttatcaaagg atttgtagac aacaacaaaa gatggcccaa aattaaaaac   1260

ttaaaagtgc ttagtaagag atggactatg tacttcaaag caaaaagtta ccccagtcaa   1320

cttgaattaa gcgaacaaga ttttttagag cttgctgcaa tacagtttga acaagagttt   1380
```

-continued tctgtccctg aaaaaaccaa ccttgagatg gtattaaatg ataaagctat atcacctcct 1440
aaaagattaa tatggtctgt gtatccaaaa aattacttac ctgagaaaat aaaaaatcga 1500
tatctagaag agactttcaa tgcaagtgat agtctcaaaa caagaagagt actagagtac 1560
tatttgaaag ataataaatt cgaccaaaaa gaacttaaaa gttatgttgt taaacaagaa 1620
tatttaaatg ataaggatca tattgtctcg ctaactggaa aagaaagaga attaagtgta 1680
ggtagaatgt ttgctatgca accaggaaaa cagcgacaaa tacaaatatt ggctgaaaaa 1740
ttgttagctg ataatattgt accttttttc ccagaaacct taacaaagta tggtgatcta 1800
gatcttcaga gaataatgga aatcaaatcg gaactttctt ctattaaaac tagaagaaat 1860
gatagttata ataattacat tgcaagagca tccatagtaa cagatttaag taagttcaac 1920
caagccttta ggtatgaaac tacagcgatc tgtgcggatg tagcagatga actacatgga 1980
acacaaagcc tattctgttg gttacatctt atcgtcccta tgacaacaat gatatgtgcc 2040
tatagacatg caccaccaga aacaaaaggt gaatatgata tagataagat agaagagcaa 2100
agtggtttat atagatatca tatgggtggt attgaaggat ggtgtcaaaa actctggaca 2160
atggaagcta tatctctatt agatgttgta tctgtaaaaa cacgatgtca aatgacatct 2220
ttattaaacg gtgacaacca atcaatagat gtaagtaaac cagttaagtt atctgagggt 2280
ttagatgaag tgaaagcaga ttatagcttg gctgtaaaaa tgttaaaaga aataagagat 2340
gcatacagaa atataggcca taaacttaaa gaaggggaaa catatatatc aagagatctt 2400
cagtttataa gtaaggtgat tcaatctgaa ggagtaatgc atcctacccc tataaaaaag 2460
atcttaagag tgggaccatg gataaacaca atattagatg acattaaaac cagtgcagag 2520
tcaataggga gtctatgtca ggaattagaa tttagggggg aaagcataat agttagtctg 2580
atattaagga atttttggct gtataattta tacatgcatg aatcaaagca acacccccta 2640
gcagggaagc agttattcaa acaactaaat aaaacattaa catcagtgca gagatttttt 2700
gaaataaaaa aggaaaatga agtagtagat ctatggatga acataccaat gcagtttgga 2760
ggaggagatc cagtagtctt ctatagatct ttctatagaa ggacccctga ttttttaact 2820
gaagcaatca gtcatgtgga tattctgtta agaatatcag ccaacataag aaatgaagcg 2880
aaaataagtt tcttcaaagc cttactgtca atagaaaaaa atgaacgtgc tacactgaca 2940
acactaatga gagatcctca agctgttggc tcagagcgac aagcaaaagt aacaagtgat 3000
atcaatagaa cagcagttac cagcatctta agtctttctc caaatcaact tttcagcgat 3060
agtgctatac actacagtag aaatgaagaa gaggtcggaa tcattgctga caacataaca 3120
cctgtttatc ctcatggact gagagttttg tatgaatcat taccttttca taaagctgaa 3180
aaagttgtga atatgatatc aggaacgaaa tccataacca acttattaca gagaacatct 3240
gctattaatg gtgaagatat tgacagagct gtatccatga tgctggagaa cctaggatta 3300
ttatctagaa tattgtcagt agttgttgat agtatagaaa ttccaaccaa atctaatggt 3360
aggctgatat gttgtcagat atctagaacc ctaagggaga catcatggaa taatatggaa 3420
atagttggag taacatcccc tagcatcact acatgcatgg atgtcatata tgcaactagc 3480
tctcatttga aagggataat cattgaaaag ttcagcactg acagaactac aagaggtcaa 3540
agaggtccaa agagcccttg ggtagggtcg agcactcaag agaaaaaatt agttcctgtt 3600
tataacagac aaattctttc aaaacaacaa agagaacagc tagaagcaat tggaaaaatg 3660
agatgggtat ataaagggac accaggttta agacgattac tcaataagat ttgtcttgga 3720
agtttaggca ttagttacaa atgtgtaaaa cctttattac ctaggtttat gagtgtaaat 3780

-continued

```
ttcctacaca ggttatctgt cagtagtaga cctatggaat tcccagcatc agttccagct   3840
tatagaacaa caaattacca ttttgacact agtcctatta atcaagcact aagtgagaga   3900
tttgggaatg aagatattaa tttggtcttc caaaatgcaa tcagctgtgg aattagcata   3960
atgagtgtag tagaacaatt aactggtagg agtccaaaac agttagtttt aatacctcaa   4020
ttagaagaaa tagacattat gccaccacca gtgtttcaag ggaaattcaa ttataagcta   4080
gtagataaga taacttctga tcaacatatc ttcagtccag acaaaataga tatgttaaca   4140
ctggggaaaa tgctcatgcc cactataaaa ggtcagaaaa cagatcagtt cctgaacaag   4200
agagagaatt atttccatgg gaataatctt attgagtctt tgtcagcagc gttagcatgt   4260
cattggtgtg ggatattaac agagcaatgt atagaaaata atattttcaa gaaagactgg   4320
ggtgacgggt tcatatcgga tcatgctttt atggacttca aaatattcct atgtgtcttt   4380
aaaactaaac ttttatgtag ttgggggtcc caagggaaaa acattaaaga tgaagatata   4440
gtagatgaat caatagataa actgttaagg attgataata ctttttggag aatgttcagc   4500
aaggttatgt ttgaatcaaa ggttaagaaa aggataatgt tatatgatgt aaaatttcta   4560
tcattagtag gttatatagg gtttaagaat tggtttatag aacagttgag atcagctgag   4620
ttgcatgagg taccttggat tgtcaatgcc gaaggtgatc tggttgagat caagtcaatt   4680
aaaatctatt tgcaactgat agagcaaagt ttatttttaa gaataactgt tttgaactat   4740
acagatatgg cacatgctct cacaagatta atcagaaaga agttgatgtg tgataatgca   4800
ctattaactc cgattccatc cccaatggtt aatttaactc aagttattga tcctacagaa   4860
caattagctt atttccctaa gataacattt gaaaggctaa aaaattatga cactagttca   4920
aattatgcta aaggaaagct aacaaggaat tacatgatac tgttgccatg gcaacatgtt   4980
aatagatata actttgtctt tagttctact ggatgtaaag ttagtctaaa aacatgcatt   5040
ggaaaactta tgaaagatct aaaccctaaa gttctgtact ttattggaga aggggcagga   5100
aattggatgg ccagaacagc atgtgaatat cctgacatca aatttgtata cagaagttta   5160
aaagatgacc ttgatcatca ttatcctttg gaataccaga gagttatagg agaattaagc   5220
aggataatag atagcggtga agggctttca atggaaacaa cagatgcaac tcaaaaaact   5280
cattgggatt tgatacacag agtaagcaaa gatgctttat taataacttt atgtgatgca   5340
gaatttaagg acagagatga tttttttaag atggtaattc tatggaggaa acatgtatta   5400
tcatgcagaa tttgcactac ttatgggaca gacctctatt tattcgcaaa gtatcatgct   5460
aaagactgca atgtaaaatt accttttttt gtgagatcag tagccacctt tattatgcaa   5520
ggtagtaaac tgtcaggctc agaatgctac atactcttaa cactaggcca ccacaacaat   5580
ttaccctgcc atggagaaat acaaaattct aagatgaaaa tagcagtgtg taatgatttt   5640
tatgctgcaa aaaaacttga caataaatct attgaagcca actgtaaatc acttttatca   5700
gggctaagaa taccgataaa taagaaagaa ttaaatagac agagaaggtt attaacacta   5760
caaagcaacc attcttctgt agcaacagtt ggaggtagca aggtcataga gtctaaatgg   5820
ttaacaaaca aggcaaacac aataattgat tggttagaac atattttaaa ttctccaaaa   5880
ggtgaattaa attatgattt ttttgaagca ttagaaaata cttaccctaa tatgattaaa   5940
ctaatagata atctagggaa tgcagagata aaaaaactga tcaaagtaac tggatatatg   6000
cttgtaagta aaaaatga                                                 6018
```

<210> SEQ ID NO 335

-continued

<211> LENGTH: 6018
<212> TYPE: DNA
<213> ORGANISM: human metapneumo virus

<400> SEQUENCE: 335
atggatcctc ttaatgaatc cactgttaat gtctatctcc ctgattcgta ccttaaagga 60
gtaatttctt ttagtgaaac taatgcaatt ggttcatgtc tcttaaaaag accttactta 120
aaaaatgaca acactgcaaa agttgccata gagaatcctg ttattgagca tgtgagactc 180
aaaaatgcag tcaattctaa aatgaaaata tcagattaca aggtagtaga gccagtaaac 240
atgcaacatg aaataatgaa gaatgtacac agttgtgagc tcacactatt gaaacagttt 300
ttaacaagga gtaaaaacat tagcactctc aaattaaata tgatatgtga ttggctgcaa 360
ttaaagtcta catcagatga tacctcaatc ctaagtttca tagatgtaga atttatacct 420
agttgggtaa gcaactggtt tagtaattgg tacaatctca ataagttaat tttggaattc 480
agaagagagg aagtaataag aaccggttca atcttatgca ggtcattggg taaattagtt 540
tttattgtat catcatacgg atgtatcgtc aagagcaaca aaagcaaaag agtgagcttc 600
ttcacataca atcaactgtt aacatggaaa gatgtgatgt taagtagatt taatgcgaat 660
ttttgtatat gggtaagcaa tagtctgaat gaaaatcagg aagggctagg gttaagaagt 720
aatctacaag gtatgttaac taataaacta tatgaaactg tagattatat gctaagttta 780
tgttgcaatg aaggtttctc acttgtaaaa gagttcgaag gttttattat gagtgaaatc 840
cttaggatta ctgaacatgc tcaattcagt actagattta gaaatacttt attaaatgga 900
ttaacagatc aattaacaaa attaaaaaat aaaaacagac tcagagttca tggtaccgta 960
ttagaaaata atgattatcc aatgtatgaa gttgtactta aattattagg agatactttg 1020
agatgtatca aattattaat caataaaaac ttagagaatg ctgcagaatt atactatata 1080
ttcagaattt ttggtcatcc aatggtagat gaaagagatg caatggatgc tgtcaaatta 1140
aacaatgaaa tcacaaaaat cctaaggttg gagagcttga cagaactaag aggagcattc 1200
atattaagga ttatcaaagg atttgtggac aacaacaaaa ggtggcccaa aattaaaaat 1260
ttaatagtgc ttagcaaaag atggactatg tacttcaaag ctaaaaatta tcccagtcaa 1320
ctcgaattaa gtgaacaaga ctttctagag cttgctgcaa tacaatttga acaagagttt 1380
tctgttcctg aaaaaaccaa tcttgagatg gtattaaatg acaaagccat atcacctcct 1440
aaaagattaa tatggtctgt gtatccaaag aattacttac ctgagacgat aaaaaatcga 1500
tatttagaag aaactttcaa tgcgagtgat agtctcaaaa caagaagagt actagagtac 1560
tatttaaaag acaataaatt tgatcaaaag gaacttaaaa gttatgtagt tagacaagaa 1620
tatttaaatg ataaggagca cattgtctca ttaactggaa aagaaagaga attaagtgta 1680
ggtagaatgt ttgctatgca accaggaaaa cagcgacaaa tacaaatatt ggcagaaaaa 1740
ttgttagctg ataacattgt acctttcttc ccggaaacct taacaaagta tggtgatcta 1800
gatcttcaga gaataatgga aatcaaatca gaactttctt ctatcaaaac cagaagaaat 1860
gacagttata ataattacat tgcaagagca tccatagtaa cagatttgag caagttcaac 1920
caagccttta gatatgaaac tacagcgatc tgtgcggatg tagcagacga attacatgga 1980
acacaaagct tattctgttg gttacatctt atcgttccta tgactacaat gatatgtgcc 2040
tatagacatg caccaccaga aacaaaaggt gaatatgata tagataagat agaagagcaa 2100
agtggtctat atagatatca catgggcggt attgaaggat ggtgtcaaaa actctggaca 2160
atggaagcta tatctttatt ggatgttgta tctgtaaaga cacggtgtca aatgacatct 2220

-continued ttattaaacg gtgataacca atcaatagat gtaagtaaac cagtcaagtt atctgaaggt 2280
ttagatgaag tgaaggcaga ttatcgctta gcaataaaaa tgctaaaaga aataagagat 2340
gcatacagaa atataggcca taaacttaaa gaaggggaaa catatatatc aagggatctt 2400
caatttataa gcaaggtgat tcaatctgaa ggagtgatgc atcctacccc tataaaaaag 2460
gtcttgagag taggaccatg gataaacaca atattagatg acattaaaac tagtgctgag 2520
tcaataggga gtctatgtca agaattagaa tttaggggag aaagcataat agttagtctg 2580
atattaagaa acttctggct gtataactta tacatgcatg aatcaaagca acatcctttg 2640
gcagggaaac agttattcaa acaactaaat aaaacattaa catcagtgca gagatttttt 2700
gaaattaaaa aggaaaatga ggtagtagat ctatggatga acataccaat gcaatttgga 2760
ggaggagatc cagtagtctt ctatagatct ttctatagaa ggacccctga ttttttaact 2820
gaggcaatca gccatgtaga tattctgtta aaaatatcag ctaacataaa aaatgaaacg 2880
aaagtaagtt tcttcaaagc cttactatca atagaaaaaa atgaacgtgc tacactgaca 2940
acgctaatga gagatcctca agctgttgga tcagaacgac aagcaaaagt aacaagtgac 3000
atcaatagaa cagcagttac cagtatctta agtctttccc caaatcaact tttcagtgat 3060
agtgctatac actatagcag gaatgaagaa gaagtgggaa tcattgcaga aaacataaca 3120
cctgtttatc ctcatgggct gagagtatta tatgaatcat tgccctttca caaagctgaa 3180
aaagttgtaa acatgatatc agggacaaaa tctataacca acttattaca gagaacatcc 3240
gctattaatg gtgaagatat tgacagggct gtatctatga tgttggagaa tctaggatta 3300
ttatctagaa tattgtcagt agttgttgat agtatagaaa ttccaatcaa atctaatggt 3360
aggctgatat gttgtcaaat ctctaggact ttaagagaga catcatggaa taatatggaa 3420
atagttggag taacatctcc tagcatcact acatgtatgg atgtcatata tgcaactagt 3480
tctcatttga aggggataat tatagaaaag ttcagcactg acagaactac aaggggtcaa 3540
agaggtccaa aaagcccttg ggtagggtcg agtactcaag agaaaaaatt agtacctgtt 3600
tataacagac aaattctttc aaaacaacaa agagaacagc tagaagcaat tggaaaaatg 3660
agatgggtgt ataaagggac accaggcttg cgacgattac tcaacaagat ctgtcttggg 3720
agtttaggca ttagttacaa atgtgtaaaa cctttattac ctaggtttat gagtgtaaat 3780
ttcttacata ggttatctgt cagtagtaga cctatggaat tcccagcatc agttccagct 3840
tatagaacaa caaattacca tttcgacact agtcctatta atcaagcact aagtgagaga 3900
tttgggaatg aagatattaa cttggtcttc caaaatgcga tcagctgtgg aattagcata 3960
atgagtgtag tagaacaatt aacaggtaga agcccaaaac agttagtttt aataccccaa 4020
ttagaagaaa tagacattat gccaccacca gtgtttcaag ggaaattcaa ttataaatta 4080
gtagataaga taacttctga tcaacatatc ttcagtccgg acaaaataga tatgttaaca 4140
ctagggaaaa tgctcatgcc tactataaaa ggtcagaaaa cagatcagtt cttaaataag 4200
agagagaatt atttccatgg gaacaatctt attgagtctt tatcagcagc attagcatgt 4260
cattggtgtg ggatattaac agaacaatgc atagaaaata atattttcaa gaaggactgg 4320
ggtgacgggt ttatatcaga tcatgctttt atggacttca aaatattcct atgtgtcttt 4380
aaaactaaac ttttatgtag ttggggatcc caagggaaaa acattaaaga tgaagatata 4440
gtagatgaat caatagataa attgttaagg attgacaata ctttttggag aatgttcagc 4500
aaagttatgt ttgaaccaaa agttaagaaa aggataatgt tatatgatgt aaaattccta 4560

-continued

```
tcactagtag gctacatagg gtttaagaac tggtttatag agcagttgag atcagctgaa   4620

ttgcatgaaa taccttggat tgtcaatgcc gaaggtgatt tggttgagat caagtcaatt   4680

aaaatctatt tgcaactgat agaacaaagc ttatttttaa gaataactgt tttgaactat   4740

acagatatgg cacatgctct cacacgatta atcagaaaga agttaatgtg tgataatgca   4800

ctgttaaccc caatttcatc cccaatggtt aacttaactc aagttattga tcccacaaca   4860

caattagatt acttccccaa gataacattc gaaaggctaa aaaattatga cacaagttca   4920

aattatgcta aggaaagct aacaagaaat tacatgatac tattgccatg gcagcatgtt   4980

aatagatata actttgtctt tagttctact ggatgtaaag ttagtctgaa aacatgtatt   5040

ggaaaactta tgaaagactt aaatcctaaa gttttgtact ttattggaga aggagcagga   5100

aattggatgg ccagaacagc atgtgaatat cctgatatta aatttgtata tagaagtctg   5160

aaagatgacc ttgatcatca ttatcctctg gaataccaga gagtgatagg tgaattaagc   5220

agaatcatag atagtggtga aggactttca atggaaacaa cagacgcaac tcaaaaaact   5280

cattgggatt tgatacacag ggtaagcaaa gatgctttat taataacttt atgtgatgca   5340

gaatttaagg acagagatga ttttttttaag atggtaattc tatggagaaa acatgtatta   5400

tcatgcagaa tttgcactac ttatgggacg gacctctatt tattcgcaaa gtatcatgct   5460

aaagactgca atgtaaaatt accttttttt gtgagatcag ttgctacttt cattatgcag   5520

ggtagtaagc tgtcaggttc agaatgctac atactcttaa cactaggcca ccacaacagt   5580

ttaccttgcc atggagaaat acaaaattct aagatgaaaa tagcagtgtg taatgatttt   5640

tatgctgcaa aaaaactcga caataaatca attgaagcta attgtaaatc acttttgtca   5700

gggctaagaa tacctataaa taagaaggaa ctagatagac agagaagatt attaacacta   5760

caaagcaatc attcttctgt ggcaacagtt ggcggtagca agatcataga gtctaaatgg   5820

ttaacaaaca aagcaagtac aataattgat tggttagaac atattttaaa ttctccaaag   5880

ggcgaattaa attatgattt ttttgaagca ttggagaaca cttaccctaa tatgattaaa   5940

ctaatagata acttagggaa tgcagagatt aaaaaactta tcaaagtaac aggatacatg   6000

cttgtaagta aaaaatga                                                6018
```

<210> SEQ ID NO 336
<211> LENGTH: 6018
<212> TYPE: DNA
<213> ORGANISM: human metapneumo virus

<400> SEQUENCE: 336

```
atggatccct tttgtgaatc tactgttaat gtttatctcc ctgattcata tctcaaagga     60

gtaatatctt ttagtgaaac caatgcaatt ggatcatgtc ttttgaaaag accctatcta    120

aaaaatgaca acactgccaa agttgctgta gaaaaccctg ttgttgaaca tgtgaggctt    180

agaaatgcag tcatgaccaa aatgaagata tcagattata aagtggttga accagttaat    240

atgcagcatg aaataatgaa aaatatacat agttgtgagc ttacattatt aaaacaattc    300

ttaacgagaa gcaaaaacat tagctctcta aaattaaata tgatatgtga ttggttacag    360

ttaaaatcca cttcagataa cacatcaatt ctcaatttta tagatgtgga gttcataccc    420

gtttgggtaa gcaattggtt cagtaactgg tataatctca ataaattaat cttagagttt    480

agaagagaag aagtaataag aactggttca attttatgta gatcactagg caagttagtt    540

tttattgtat catcttatgg atgtgtagta aaaagcaaca aaagtaaaag agtgagcttt    600

ttcacctata accaactgtt aacatggaaa gatgtgatgt taagtagatt caatgcaaac    660
```

-continued

```
ttttgtatat gggtaagtaa caacctgaac aaaaatcaag aaggactagg acttagaagc    720
aatctgcaag gtatgttaac caataaatta tatgaaactg ttgattacat gctaagccta    780
tgctgcaatg aaggattctc tctggtgaaa gagtttgaag gatttattat gagtgaaatt    840
ctaaaaatta ctgagcatgc tcagttcagt actaggttta ggaatacttt attgaatggg    900
ttaactgaac aattatcagt gttgaaagct aagaacagat ctagagttct tggaactata    960
ttagaaaaca acaattaccc tatgtacgaa gtagtactta aattattagg ggacaccttg   1020
aaaagcataa agttattaat taacaagaat ttagaaaatg ctgcagaatt atattatata   1080
ttcagaattt ttggacaccc tatggtagat gagagggaag caatggatgc tgttaaatta   1140
aacaatgaga ttacaaaaat tcttaaatta gagagtttaa cagaactaag aggagcattt   1200
atactaagaa ttataaaagg gtttgtagac aataataaaa gatggcctaa aattaagaat   1260
ttaaaagtgc tcagcaaaag atgggctatg tatttcaaag ctaaaagtta ccctagccaa   1320
cttgagctaa gtgtacaaga ttttttagaa cttgctgcag tacaatttga gcaggaattc   1380
tctgtacctg aaaaaaccaa ccttgagatg gtattaaatg ataaagcaat atcacctcca   1440
aaaaagctaa tatggtctgt atatccaaaa aactacctgc ctgaaactat aaaaaatcaa   1500
tatttagaag aggctttcaa tgcaagtgac agccaaagaa caaggagagt cttagaattt   1560
tacttaaaag attgtaaatt tgatcaaaaa gaacttaaac gttatgtaat taaacaagag   1620
tatctgaatg acaaagacca cattgtctcg ttaactggga aggaaagaga attaagtgta   1680
ggtaggatgt ttgcaatgca accaggaaaa caaagacaga tacagatatt agctgagaaa   1740
cttctagctg ataatattgt accttttttc ccagaaactt taacaaagta tggtgactta   1800
gatctccaaa gaattatgga aataaaatca gaactttctt ccattaaaac tagaaagaat   1860
gatagctaca acaattatat tgcaagggcc tctatagtaa cagacttaag taagttcaat   1920
caggccttta gatatgaaac cacagctata tgtgcagatg tagctgatga gttacatggg   1980
acacaaagct tattctgttg gttacatctt attgttccca tgactacaat gatatgtgca   2040
tacagacatg caccaccaga aacaaaaggg gaatatgata tagacaaaat acaagagcaa   2100
agcggattat acagatatca tatgggaggg attgaagggt ggtgccagaa gttatggaca   2160
atggaagcaa tatccttgtt agatgtagta tctgtgaaga ctcgctgtca gatgacctct   2220
ctattaaacg gagacaatca gtcaatagat gttagtaaac cagtaaaatt gtctgaaggt   2280
atagatgaag taaaagcaga ctatagctta gcaattagaa tgcttaaaga aataagagat   2340
gcttataaaa acattggtca taaactcaaa gaaggtgaaa catatatatc aagggatctc   2400
caatttataa gtaaggtgat tcaatctgaa ggagtcatgc atcctacccc tataaaaaag   2460
atattaagag taggtccttg gataaataca atactagatg atattaaaac cagtgcagaa   2520
tcaataggaa gtctatgtca agaactagaa ttcagagggg agagtatact agttagcttg   2580
atattaagga atttctggct gtataacttg tacatgtatg agtcaaaaca gcacccatta   2640
gctgggaagc aactgttcaa gcaattgaac aaaacattaa catctgtgca gagatttttt   2700
gaactgaaga aagaaaatga tgtggttgac ctatggatga atataccaat gcagtttgga   2760
gggggagatc cagtagtttt ttacagatct ttttacagaa ggactcccga tttcctaact   2820
gaagcaatca gccatgtgga tttactgtta aaagtgtcaa acaatatcaa agatgagact   2880
aagatacgat ttttcaaagc cttattatct atagaaaaga atgaacgtgc tacattaaca   2940
acactaatga gagaccctca ggcagtagga tcagaacgac aagctaaggt aacaagtgat   3000
```

-continued

```
ataaatagaa cagcagttac cagcatactg agtctatctc cgaatcagct cttctgtgat   3060
agtgctatac attatagtag aaatgaggaa gaagttggga tcattgcaga caacataaca   3120
cctgtctatc ctcatgggct gagagtgctc tatgaatcac taccttttca taaggctgaa   3180
aaggttgtca atatgatatc aggcacaaag tctataacta atctattaca gagaacatct   3240
gctatcaatg gtgaagatat tgatagagca gtgtctatga tgttagagaa cttagggttg   3300
ttatctagaa tattgtcagt aataattaat agtatagaaa taccaatcaa gtccaatggc   3360
agattgatat gctgtcaaat ttccaagacc ttgagagaaa aatcatggaa caatatggaa   3420
atagtaggag tgacatctcc tagtattgtg acatgtatgg atgttgtgta tgcaactagt   3480
tctcatttaa aaggaataat tattgaaaaa ttcagtactg acaagaccac aagaggtcag   3540
aggggaccaa aaagcccctg ggtaggatca agcactcaag agaaaaaatt ggttcctgtt   3600
tataatagac aaattctttc aaaacaacaa aaagagcaac tggaagcaat agggaaaatg   3660
aggtgggtgt acaaaggaac tccagggcta agaagattgc tcaacaagat ttgcatagga   3720
agcttaggta ttagctataa atgtgtgaaa cctttattac caagattcat gagtgtaaac   3780
ttcttacata ggttatctgt tagtagtaga cccatggaat tcccagcttc tgttccagct   3840
tacaggacaa caaattacca ttttgacact agtccaatca accaagcatt aagtgagagg   3900
ttcgggaacg aagacattaa tttagtgttc caaaatgcaa tcagctgcgg aattagtata   3960
atgagtgttg tagaacagtt aactggtaga agcccaaaac aattagtcct aatccctcaa   4020
ttagaagaga tagatattat gcctcctcct gtatttcaag gaaaattcaa ttataaacta   4080
gttgataaga taacctccga tcaacacatc ttcagtcctg acaaaataga catattaaca   4140
ctagggaaga tgcttatgcc taccataaaa ggtcaaaaaa ctgatcagtt cttaaataag   4200
agagaaaact attttcatgg aaataattta attgaatctt tatctgcagc acttgcatgc   4260
cactggtgtg ggatattaac agaacagtgc atagaaaaca atatctttag gaaagattgg   4320
ggtgatgggt tcatctcaga tcatgccttc atggatttca aggtatttct atgtgtattt   4380
aaaaccaaac ttttatgtag ttggggatct caaggaaaga atgtaaaaga tgaagatata   4440
atagatgaat ccattgacaa attattaaga attgacaaca ccttttggag aatgttcagc   4500
aaagtcatgt ttgaatcaaa agtcaaaaaa agaataatgt tatatgatgt gaaattccta   4560
tcattagtag gttatatagg atttaaaaac tggtttatag aacagttaag agtggtagaa   4620
ttgcatgagg taccttggat tgtcaatgct gaaggagagt tagttgaaat taaatcaatc   4680
aaaatttatc tgcagttaat agaacaaagt ctatctttga gaataactgt attgaattat   4740
acagacatgg cacatgctct tacacgatta attaggaaaa aattgatgtg tgataatgca   4800
ctctttaatc caagttcatc accaatgttt aatctaactc aggttattga tcccacaaca   4860
caactagact attttcctag gataatattt gagaggttaa aaagttatga taccagttca   4920
gactacaaca aagggaagtt aacaaggaat tacatgacat tattaccatg gcaacacgta   4980
aacaggtaca attttgtctt tagttctaca ggttgtaaag tcagtttgaa gacatgcatc   5040
gggaaattga taaaggattt aaatcctaaa gttctttact ttattggaga aggagcaggt   5100
aactggatgg caagaacagc atgtgaatat cctgatataa aatttgtata taggagttta   5160
aaggatgacc ttgatcacca ttacccatta gaatatcaaa gggtaatagg tgatctaaat   5220
agggtgatag atagtggtga aggattatca atggaaacca cagatgcaac tcaaaaaact   5280
cattgggact tgatacacag aataagtaaa gatgctttat tgataacatt gtgtgatgca   5340
gaattcaaaa acagagatga tttctttaag atggtaatcc tttggagaaa acatgtatta   5400
```

-continued

```
tcttgtagaa tctgtacagc ttatggaaca gatctttact tatttgcaaa gtatcatgcg   5460
gtggactgca atataaaatt accatttttt gtaagatctg tagctacttt tattatgcaa   5520
ggaagcaaat tatcagggtc agaatgttac atacttttaa cattaggtca tcacaataat   5580
ctaccctgtc atggagaaat acaaaattcc aaaatgagaa tagcagtgtg taatgatttc   5640
tatgcctcaa agaaactgga caacaaatca attgaagcaa actgcaaatc tcttctatca   5700
ggattgagaa tacctataaa caaaaaggag ttaaatagac aaaagaaatt gttaacacta   5760
caaagtaacc attcttctat agcaacagtt ggcggcagta agattataga atccaaatgg   5820
ttaaagaata aagcaagtac aataattgat tggttagagc atattttgaa ttctccaaaa   5880
ggtgaattaa actatgattt ctttgaagca ttagagaaca catacccccaa tatgatcaag   5940
cttatagata atttgggaaa tgcagaaata aagaaactaa tcaaggtcac tgggtatatg   6000
cttgtgagta agaagtaa                                                 6018
```

<210> SEQ ID NO 337
<211> LENGTH: 6018
<212> TYPE: DNA
<213> ORGANISM: human metapneumo virus

<400> SEQUENCE: 337

```
atggatccat tttgtgaatc cactgtcaat gtttatcttc ctgactcata tctcaaagga     60
gtaatatctt tcagtgaaac caatgcaatt ggctcatgcc ttttgaaaag accctatcta    120
aaaaaagata acactgctaa agttgctgta gaaaaccctg ttgttgaaca tgtcaggctt    180
agaaatgcag tcatgaccaa aatgaagata tcagattata aagtggttga accaattaat    240
atgcagcatg aaataatgaa aaatatacac agttgtgagc tcacattatt aaaacaattc    300
ttaacaagaa gtaaaaacat tagctctcta aaattaagta tgatatgtga ttggttacag    360
ttaaaatcca cctcagataa cacatcaatt cttaatttta tagatgtgga gtttatacct    420
gtttgggtga gcaattggtt tagtaactgg tataatctca ataaattaat cttagagttt    480
agaagagagg aagtaataag aactggttca attttatgta gatcactagg caagttagtt    540
ttcattgtat catcttatgg gtgtgtagta aaaagcaaca aaagtaaaag agtaagtttt    600
ttcacatata accaactgtt aacatggaaa gatgtgatgt taagtaggtt caatgcaaac    660
ttttgtatat gggtaagtaa caacctgaac aaaaatcaag aaggactagg atttagaagt    720
aatctgcaag gtatgttaac caataaatta tatgaaactg ttgattatat gttaagtcta    780
tgtagtaatg aagggttctc actagtgaaa gagttcgaag gctttattat gagtgaaatt    840
cttaaaatta ctgagcatgc tcaattcagt actaggttta ggaatacttt attaaatggg    900
ttgactgaac aattatcaat gttgaaagct aaaaacagat ctagagttct tggcactata    960
ttagaaaaca atgattaccc catgtatgaa gtagtactta aattattagg ggacactttg   1020
aaaagtataa aattattaat taacaagaat ttagaaaatg ctgcagaatt atattatata   1080
ttcagaattt ttggacaccc tatggtagat gagagggaag caatggatgc tgttaaatta   1140
aataatgaga ttacaaaaat tcttaaactg gagagcttaa cagaactaag aggagcattt   1200
atactaagaa ttataaaagg gtttgtagat aataataaaa gatggcctaa aattaagaat   1260
ttaaaagtgc tcagtaaaag atgggttatg tatttcaaag ccaaaagtta ccctagccaa   1320
cttgagctaa gtgtacaaga ttttttagaa cttgctgcag tacaattcga acaggaattt   1380
tctgtccctg aaaaaaccaa ccttgagatg gtattaaatg ataaagcaat atctcctcca   1440
```

-continued

```
aaaaagttaa tatggtcggt atatccaaaa aattatctac ctgaaattat aaaaaatcaa   1500
tatttagaag aggtcttcaa tgcaagtgac agtcaaagaa cgaggagagt cttagaattt   1560
tacttaaaag attgcaaatt tgatcaaaaa gaccttaaac gttatgtact taaacaagag   1620
tatctaaatg acaaagacca cattgtctca ttaactggga aggaaagaga attaagtgta   1680
ggcaggatgt ttgcaatgca accaggcaaa caaagacaaa tacagatact agctgagaaa   1740
cttctagctg ataatattgt acccttttc ccagaaactt taacaaagta tggtgacttg   1800
gatctccaaa gaattatgga aatgaaatca gaactttctt ccattaaaac taggaagaat   1860
gatagttaca acaattatat tgcaagagcc tccatagtaa cagacctaag taaattcaat   1920
caagccttta gatatgaaac cacagctatc tgtgcagatg tagcagatga gttacatggt   1980
acgcaaagct tattttgttg gttacatctt attgttccca tgaccacaat gatatgtgca   2040
tacagacatg caccaccaga aacaaagggg gagtatgaca tagacaaaat agaagagcaa   2100
agtgggctat acagatatca tatgggaggg attgaagggt ggtgtcagaa gttatggaca   2160
atggaagcga tatccttgtt agatgtagta tctgttaaga ctcgttgtca gatgacctct   2220
ctattaaacg gagacaatca atcaatagat gtcagtaaac cagtaaaatt gtctgaaggt   2280
atagatgaag taaaagcaga ttatagctta gcaattaaaa tgcttaaaga gataagagat   2340
gcctataaaa acattggcca taaactcaaa gaaggtgaaa catatatatc aagagatctc   2400
caatttataa gtaaggtgat tcaatctgag gggtcatgc atcctacccc cataaaaaag   2460
atattaaggg taggtccctg gataaataca atactagatg acattaaaac cagtgcagaa   2520
tcaataggga gtctgtgtca agaactagag ttcagaggag aaagtatgct agttagcttg   2580
atattaagga atttctggct gtataactta tacatgcatg agtcaaaaca gcatccgtta   2640
gctggaaaac aactgtttaa gcaattgaac aaaacactaa catctgtgca aagatttttt   2700
gagctgaaga aagaaaatga tgtggttgac ctatggatga atataccaat gcagtttgga   2760
gggggagacc cagtagtttt ttacagatct ttttacagaa ggactcctga tttcctgact   2820
gaagcaatca gccatgtgga tttactgtta aaagtttcga acaatattaa aaatgagact   2880
aagatacgat tctttaaagc cttattatct atagaaaaga atgaacgtgc aacattaaca   2940
acactaatga gagaccccca ggcggtagga tcggaaagac aagctaaggt aacaagtgat   3000
ataaatagaa cagcagttac tagcatactg agtctatctc cgaatcagct cttttgtgat   3060
agtgctatac actatagcag aaatgaagaa gaagtcggga tcattgcaga caacataaca   3120
cctgtttatc ctcacggatt gagagtgctc tatgaatcac taccttttca taaggctgaa   3180
aaggttgtca atatgatatc aggtacaaag tctataacta acctattgca gagaacatct   3240
gctatcaatg gtgaagatat tgatagagca gtgtctatga tgttagagaa cttagggttg   3300
ttatctagga tattgtcagt aataattaat agtatagaaa taccaattaa gtccaatggc   3360
agattgatat gctgtcaaat ttctaagact ttgagagaaa aatcatggaa caatatggaa   3420
atagtaggag tgacatctcc aagtattgta acatgtatgg atgttgtgta tgcaactagt   3480
tctcatttaa aaggaataat tattgaaaaa ttcagtactg acaagaccac aagaggtcag   3540
aggggaccaa aaagcccctg ggtaggatca agcactcaag agaaaaaatt agttcctgtt   3600
tataatagac aaattctttc aaaacaacaa aaggagcaac tggaagcaat aggaaaaatg   3660
aggtgggtgt ataaaggaac tccagggcta agaagattgc tcaataagat ttgcatagga   3720
agtttaggta ttagctataa atgtgtaaaa cctctattac caagattcat gagtgtaaac   3780
ttcttacata ggttatctgt tagtagcaga cccatggaat tcccagcttc tgttccagct   3840
```

-continued

```
tataggacaa caaattacca ctttgacact agtccaatca accaagcatt aagtgagagg   3900

ttcgggaacg aagacattaa tctagtgttc caaaatgcaa tcagctgcgg aattagtata   3960

atgagtgttg tagaacagtt aactggtaga agcccaaaac aattagtctt aatcccccaa   4020

ttagaagaga tagatattat gcctcctcct gtatttcaag gaaaattcaa ttataaacta   4080

gttgataaaa taacctctga tcaacacatc ttcagtcctg acaaaataga catattaaca   4140

ctagggaaga tgcttatgcc tactataaaa ggtcaaaaaa ctgatcagtt cttaaataag   4200

agagaaaact atttccatgg aaataattta attgaatctt tatctgcagc acttgcatgc   4260

cactggtgtg gaatattaac agaacagtgt gtagaaaaca atatctttag gaaagactgg   4320

ggtgatgggt tcatatcaga tcatgccttc atggatttca agatatttct atgtgtattt   4380

aaaaccaaac ttttatgtag ttggggatcc caagggaaaa atgtaaaaga tgaagatata   4440

atagatgaat ccattgacaa attattaaga attgacaaca ctttttggag aatgttcagc   4500

aaagtcatgt ttgaatcaaa ggtcaaaaaa agaataatgt tatatgatgt aaaattccta   4560

tcattagtag gttatatagg atttaaaaac tggtttatag agcagttaag agtagtagaa   4620

ttgcatgaag tgccctggat tgtcaatgct gaaggggagc tagttgaaat taaaccaatc   4680

aaaatttatt tgcagttaat agaacaaagt ctatctttaa gaataactgt tttgaattat   4740

acagacatgg cacatgctct tacacgatta attaggaaga aattgatgtg tgataatgca   4800

ctcttcaatc caagttcatc accaatgttt agtctaactc aagttatcga tcctacaaca   4860

cagctagact attttcctaa ggtgatattt gaaaggttaa aaagttatga taccagttca   4920

gactacaaca aagggaagtt aacaagaaat tacatgacat tattaccatg gcagcacgta   4980

aacaggtata attttgtctt tagttcaaca ggatgtaaaa tcagcttgaa gacatgcatc   5040

gggaaattga taaaggactt aaaccctaag gttctttact ttattggaga aggagcaggt   5100

aactggatgg caagaacagc atgtgagtat cctgacataa aatttgtata taggagttta   5160

aaggatgatc ttgatcatca ttacccatta gaatatcaaa gggtaatagg tgatttaaat   5220

agggtaatag atggtggtga aggactatca atggagacca cagatgcaac tcaaaagact   5280

cattgggact taatacacag aataagtaaa gatgctttat tgataacatt gtgtgatgca   5340

gaattcaaaa acagagatga tttctttaaa atggtaattc tttggagaaa acatgtatta   5400

tcatgtagaa tctgtacagc ttatggaaca gatctttact tatttgcaaa gtatcatgcg   5460

acggactgca atataaaatt accatttttt gtaaggtctg tagctacttt tattatgcaa   5520

ggaagcaaat tgtcaggatc agaatgttac atacttttaa cattaggtca tcacaataat   5580

ctgccatgcc atggagaaat acaaaattcc aaaatgagaa tagcagtgtg taatgatttc   5640

catgcctcaa aaaaactaga caacaaatca attgaagcta actgtaaatc tcttctatca   5700

ggattaagaa taccaataaa caaaaaagag ttaaatagac aaaagaaact gttaacacta   5760

caaagcaatc attcttccat agcaacagtt ggcggcagta agattataga atccaaatgg   5820

ttaaagaata aagcaagtac aataattgat tggttagagc atatcttgaa ttctccaaaa   5880

ggtgaattaa actatgattt ctttgaagca ttagagaaca catacccaa tatgatcaag    5940

cttatagata acctgggaaa tgcagagata aaaaaactaa tcaaagttcc tgggtatatg   6000

cttgtgagta agaagtaa                                                 6018
```

<210> SEQ ID NO 338
<211> LENGTH: 187
<212> TYPE: PRT

```
<213> ORGANISM: human metapneumo virus

<400> SEQUENCE: 338

Met Ser Arg Lys Ala Pro Cys Lys Tyr Glu Val Arg Gly Lys Cys Asn
 1               5                  10                  15

Arg Gly Ser Glu Cys Lys Phe Asn His Asn Tyr Trp Ser Trp Pro Asp
            20                  25                  30

Arg Tyr Leu Leu Ile Arg Ser Asn Tyr Leu Leu Asn Gln Leu Leu Arg
        35                  40                  45

Asn Thr Asp Arg Ala Asp Gly Leu Ser Ile Ile Ser Gly Ala Gly Arg
    50                  55                  60

Glu Asp Arg Thr Gln Asp Phe Val Leu Gly Ser Thr Asn Val Val Gln
65                  70                  75                  80

Gly Tyr Ile Asp Asp Asn Gln Ser Ile Thr Lys Ala Ala Ala Cys Tyr
                85                  90                  95

Ser Leu His Asn Ile Ile Lys Gln Leu Gln Glu Val Glu Val Arg Gln
            100                 105                 110

Ala Arg Asp Asn Lys Leu Ser Asp Ser Lys His Val Ala Leu His Asn
        115                 120                 125

Leu Val Leu Ser Tyr Met Glu Met Ser Lys Thr Pro Ala Ser Leu Ile
    130                 135                 140

Asn Asn Leu Lys Arg Leu Pro Arg Glu Lys Leu Lys Lys Leu Ala Lys
145                 150                 155                 160

Leu Ile Ile Asp Leu Ser Ala Gly Ala Glu Asn Asp Ser Ser Tyr Ala
                165                 170                 175

Leu Gln Asp Ser Glu Ser Thr Asn Gln Val Gln
            180                 185


<210> SEQ ID NO 339
<211> LENGTH: 187
<212> TYPE: PRT
<213> ORGANISM: human metapneumo virus

<400> SEQUENCE: 339

Met Ser Arg Lys Ala Pro Cys Lys Tyr Glu Val Arg Gly Lys Cys Asn
 1               5                  10                  15

Arg Gly Ser Glu Cys Lys Phe Asn His Asn Tyr Trp Ser Trp Pro Asp
            20                  25                  30

Arg Tyr Leu Leu Ile Arg Ser Asn Tyr Leu Leu Asn Gln Leu Leu Arg
        35                  40                  45

Asn Thr Asp Arg Ala Asp Gly Leu Ser Ile Ile Ser Gly Ala Gly Arg
    50                  55                  60

Glu Asp Arg Thr Gln Asp Phe Val Leu Gly Ser Thr Asn Val Val Gln
65                  70                  75                  80

Gly Tyr Ile Asp Asp Asn Gln Ser Ile Thr Lys Ala Ala Ala Cys Tyr
                85                  90                  95

Ser Leu His Asn Ile Ile Lys Gln Leu Gln Glu Val Glu Val Arg Gln
            100                 105                 110

Ala Arg Asp Ser Lys Leu Ser Asp Ser Lys His Val Ala Leu His Asn
        115                 120                 125

Leu Ile Leu Ser Tyr Met Glu Met Ser Lys Thr Pro Ala Ser Leu Ile
    130                 135                 140

Asn Asn Leu Lys Arg Leu Pro Arg Glu Lys Leu Lys Lys Leu Ala Lys
145                 150                 155                 160

Leu Ile Ile Asp Leu Ser Ala Gly Ala Asp Asn Asp Ser Ser Tyr Ala
```

-continued

```
                165                 170                 175

Leu Gln Asp Ser Glu Ser Thr Asn Gln Val Gln
            180                 185


<210> SEQ ID NO 340
<211> LENGTH: 187
<212> TYPE: PRT
<213> ORGANISM: human metapneumo virus

<400> SEQUENCE: 340

Met Ser Arg Lys Ala Pro Cys Lys Tyr Glu Val Arg Gly Lys Cys Asn
 1               5                  10                  15

Arg Gly Ser Asp Cys Lys Phe Asn His Asn Tyr Trp Ser Trp Pro Asp
            20                  25                  30

Arg Tyr Leu Leu Leu Arg Ser Asn Tyr Leu Leu Asn Gln Leu Leu Arg
        35                  40                  45

Asn Thr Asp Lys Ala Asp Gly Leu Ser Ile Ile Ser Gly Ala Gly Arg
    50                  55                  60

Glu Asp Arg Thr Gln Asp Phe Val Leu Gly Ser Thr Asn Val Val Gln
65                  70                  75                  80

Gly Tyr Ile Asp Asp Asn Gln Gly Ile Thr Lys Ala Ala Ala Cys Tyr
                85                  90                  95

Ser Leu His Asn Ile Ile Lys Gln Leu Gln Glu Thr Glu Val Arg Gln
            100                 105                 110

Ala Arg Asp Asn Lys Leu Ser Asp Ser Lys His Val Ala Leu His Asn
        115                 120                 125

Leu Ile Leu Ser Tyr Met Glu Met Ser Lys Thr Pro Ala Ser Leu Ile
    130                 135                 140

Asn Asn Leu Lys Lys Leu Pro Arg Glu Lys Leu Lys Lys Leu Ala Arg
145                 150                 155                 160

Leu Ile Ile Asp Leu Ser Ala Gly Thr Asp Asn Asp Ser Ser Tyr Ala
                165                 170                 175

Leu Gln Asp Ser Glu Ser Thr Asn Gln Val Gln
            180                 185


<210> SEQ ID NO 341
<211> LENGTH: 187
<212> TYPE: PRT
<213> ORGANISM: human metapneumo virus

<400> SEQUENCE: 341

Met Ser Arg Lys Ala Pro Cys Lys Tyr Glu Val Arg Gly Lys Cys Asn
 1               5                  10                  15

Arg Gly Ser Glu Cys Lys Phe Asn His Asn Tyr Trp Ser Trp Pro Asp
            20                  25                  30

Arg Tyr Leu Leu Leu Arg Ser Asn Tyr Leu Leu Asn Gln Leu Leu Arg
        35                  40                  45

Asn Thr Asp Lys Ala Asp Gly Leu Ser Ile Ile Ser Gly Ala Gly Arg
    50                  55                  60

Glu Asp Arg Thr Gln Asp Phe Val Leu Gly Ser Thr Asn Val Val Gln
65                  70                  75                  80

Gly Tyr Ile Asp Asn Asn Gln Gly Ile Thr Lys Ala Ala Ala Cys Tyr
                85                  90                  95

Ser Leu His Asn Ile Ile Lys Gln Leu Gln Glu Ile Glu Val Arg Gln
            100                 105                 110

Ala Arg Asp Asn Lys Leu Ser Asp Ser Lys His Val Ala Leu His Asn
```

-continued

```
        115                 120                 125

Leu Ile Leu Ser Tyr Met Glu Met Ser Lys Thr Pro Ala Ser Leu Ile
    130                 135                 140

Asn Asn Leu Lys Lys Leu Pro Arg Glu Lys Leu Lys Lys Leu Ala Lys
145                 150                 155                 160

Leu Ile Ile Asp Leu Ser Ala Gly Thr Asp Asn Asp Ser Ser Tyr Ala
                165                 170                 175

Leu Gln Asp Ser Glu Ser Thr Asn Gln Val Gln
            180                 185


<210> SEQ ID NO 342
<211> LENGTH: 564
<212> TYPE: DNA
<213> ORGANISM: human metapneumo virus

<400> SEQUENCE: 342

atgtctcgca aggctccgtg caaatatgaa gtgcggggca aatgcaatag aggaagtgag      60

tgcaagttta accacaatta ctggagttgg ccagatagat acttattaat aagatcaaat     120

tatttattaa atcaactttt aaggaacact gatagagctg atggcttatc aataatatca     180

ggagcaggca gagaagatag gacacaagat tttgtcctag gttccaccaa tgtggttcaa     240

ggttatattg atgataacca aagcataaca aaagctgcag cctgttacag tctacataat     300

ataatcaaac aactacaaga agttgaagtt aggcaggcta gagataacaa actatctgac     360

agcaaacatg tagcacttca caacttagtc ctatcttata tggagatgag caaaactcct     420

gcatctttaa tcaacaatct caagagactg ccgagagaga aactgaaaaa attagcaaag     480

ctcataattg acttatcagc aggtgctgaa aatgactctt catatgcctt gcaagacagt     540

gaaagcacta atcaagtgca gtga                                           564


<210> SEQ ID NO 343
<211> LENGTH: 564
<212> TYPE: DNA
<213> ORGANISM: human metapneumo virus

<400> SEQUENCE: 343

atgtctcgca aggctccatg caaatatgaa gtgcggggca aatgcaacag aggaagtgag      60

tgtaagttta accacaatta ctggagttgg ccagatagat acttattaat aagatcaaac     120

tatctattaa atcagctttt aaggaacact gatagagctg atggcctatc aataatatca     180

ggcgcaggca gagaagacag aacgcaagat tttgttctag gttccaccaa tgtggttcaa     240

ggttatattg atgataacca aagcataaca aaagctgcag cctgctacag tctacacaac     300

ataatcaagc aactacaaga agttgaagtt aggcaggcta gagatagcaa actatctgac     360

agcaagcatg tggcactcca taacttaatc ttatcttaca tggagatgag caaaactccc     420

gcatctttaa tcaacaatct taaaagactg ccgagagaaa aactgaaaaa attagcaaag     480

ctgataattg acttatcagc aggcgctgac aatgactctt catatgccct gcaagacagt     540

gaaagcacta atcaagtgca gtga                                           564


<210> SEQ ID NO 344
<211> LENGTH: 564
<212> TYPE: DNA
<213> ORGANISM: human metapneumo virus

<400> SEQUENCE: 344

atgtctcgta aggctccatg caaatatgaa gtgcggggca aatgcaacag agggagtgat      60
```

-continued

```
tgcaaattca atcacaatta ctggagttgg cctgatagat atttattgtt aagatcaaat    120

tatctcttaa atcagctttt aagaaacaca gataaggctg atggtttgtc aataatatca    180

ggagcaggta gagaagatag aactcaagac tttgttcttg gttctactaa tgtggttcaa    240

gggtacattg atgacaacca aggaataacc aaggctgcag cttgctatag tctacacaac    300

ataatcaagc aactacaaga aacagaagta agacaggcta gagacaacaa gctttctgat    360

agcaaacatg tggcgctcca caacttgata ttatcctata tggagatgag caaaactcct    420

gcatctctaa tcaacaacct aaagaaacta ccaagggaaa aactgaagaa attagcaaga    480

ttaataattg atttatcagc aggaactgac aatgactctt catatgcctt gcaagacagt    540

gaaagcacta atcaagtgca gtaa                                           564
```

<210> SEQ ID NO 345
<211> LENGTH: 564
<212> TYPE: DNA
<213> ORGANISM: human metapneumo virus

<400> SEQUENCE: 345

```
atgtctcgca aagctccatg caaatatgaa gtacggggca agtgcaacag gggaagtgag     60

tgcaaattca accacaatta ctggagctgg cctgataggt atttattgtt aagatcaaat    120

tatctcttga atcagctttt aagaaacact gataaggctg atggtttgtc aataatatca    180

ggagcaggta gagaagatag gactcaagac tttgttcttg gttctactaa tgtggttcaa    240

gggtacattg ataacaatca aggaataaca aaggctgcag cttgctatag tctacataac    300

ataataaaac agctacaaga aatagaagta agacaggcta gagataataa gctttctgac    360

agcaaacatg tggcacttca caacttgata ttatcctata tggagatgag caaaactcct    420

gcatccctga ttaataacct aaagaaacta ccaagagaaa aactgaagaa attagcgaaa    480

ttaataattg atttatcagc aggaactgat aatgactctt catatgcctt gcaagacagt    540

gaaagcacta atcaagtgca gtaa                                           564
```

<210> SEQ ID NO 346
<211> LENGTH: 71
<212> TYPE: PRT
<213> ORGANISM: human metapneumo virus

<400> SEQUENCE: 346

```
Met Thr Leu His Met Pro Cys Lys Thr Val Lys Ala Leu Ile Lys Cys
 1               5                  10                  15

Ser Glu His Gly Pro Val Phe Ile Thr Ile Glu Val Asp Asp Met Ile
            20                  25                  30

Trp Thr His Lys Asp Leu Lys Glu Ala Leu Ser Asp Gly Ile Val Lys
        35                  40                  45

Ser His Thr Asn Ile Tyr Asn Cys Tyr Leu Glu Asn Ile Glu Ile Ile
    50                  55                  60

Tyr Val Lys Ala Tyr Leu Ser
65                  70
```

<210> SEQ ID NO 347
<211> LENGTH: 71
<212> TYPE: PRT
<213> ORGANISM: human metapneumo virus

<400> SEQUENCE: 347

```
Met Thr Leu His Met Pro Cys Lys Thr Val Lys Ala Leu Ile Lys Cys
```

-continued

```
 1               5                   10                  15

Ser Glu His Gly Pro Val Phe Ile Thr Ile Glu Val Asp Glu Met Ile
            20                  25                  30

Trp Thr Gln Lys Glu Leu Lys Glu Ala Leu Ser Asp Gly Ile Val Lys
        35                  40                  45

Ser His Thr Asn Ile Tyr Asn Cys Tyr Leu Glu Asn Ile Glu Ile Ile
    50                  55                  60

Tyr Val Lys Ala Tyr Leu Ser
65                  70


<210> SEQ ID NO 348
<211> LENGTH: 71
<212> TYPE: PRT
<213> ORGANISM: human metapneumo virus

<400> SEQUENCE: 348

Met Thr Leu His Met Pro Cys Lys Thr Val Lys Ala Leu Ile Lys Cys
 1               5                   10                  15

Ser Lys His Gly Pro Lys Phe Ile Thr Ile Glu Ala Asp Asp Met Ile
            20                  25                  30

Trp Thr His Lys Glu Leu Lys Glu Thr Leu Ser Asp Gly Ile Val Lys
        35                  40                  45

Ser His Thr Asn Ile Tyr Ser Cys Tyr Leu Glu Asn Ile Glu Ile Ile
    50                  55                  60

Tyr Val Lys Thr Tyr Leu Ser
65                  70


<210> SEQ ID NO 349
<211> LENGTH: 71
<212> TYPE: PRT
<213> ORGANISM: human metapneumo virus

<400> SEQUENCE: 349

Met Thr Leu His Met Pro Cys Lys Thr Val Lys Ala Leu Ile Lys Cys
 1               5                   10                  15

Ser Lys His Gly Pro Lys Phe Ile Thr Ile Glu Ala Asp Asp Met Ile
            20                  25                  30

Trp Thr His Lys Glu Leu Lys Glu Thr Leu Ser Asp Gly Ile Val Lys
        35                  40                  45

Ser His Thr Asn Ile Tyr Ser Cys Tyr Leu Glu Asn Ile Glu Ile Ile
    50                  55                  60

Tyr Val Lys Ala Tyr Leu Ser
65                  70


<210> SEQ ID NO 350
<211> LENGTH: 216
<212> TYPE: DNA
<213> ORGANISM: human metapneumo virus

<400> SEQUENCE: 350

atgactcttc atatgccttg caagacagtg aaagcactaa tcaagtgcag tgagcatggt      60

ccagttttca ttactataga ggttgatgac atgatatgga ctcacaagga cttaaaagaa     120

gctttatctg atgggatagt gaagtctcat actaacattt acaattgtta tttagaaaac     180

atagaaatta tatatgtcaa ggcttactta agttag                               216


<210> SEQ ID NO 351
<211> LENGTH: 216
```

-continued

<212> TYPE: DNA
<213> ORGANISM: human metapneumo virus

<400> SEQUENCE: 351
atgactcttc atatgccctg caagacagtg aaagcactaa tcaagtgcag tgagcatggt 60
cctgttttca ttactataga ggttgatgaa atgatatgga ctcaaaaaga attaaaagaa 120
gctttgtccg atgggatagt gaagtctcac accaacattt acaattgtta tttagaaaac 180
atagaaatta tatatgtcaa ggcttactta agttag 216

<210> SEQ ID NO 352
<211> LENGTH: 216
<212> TYPE: DNA
<213> ORGANISM: human metapneumo virus

<400> SEQUENCE: 352
atgactcttc atatgccttg caagacagtg aaagcactaa tcaagtgcag taaacatggt 60
cccaaattca ttaccataga ggcagatgat atgatatgga ctcacaaaga attaaaagaa 120
acactgtctg atgggatagt aaaatcacac accaatattt atagttgtta cttagaaaat 180
atagaaataa tatatgttaa aacttactta agttag 216

<210> SEQ ID NO 353
<211> LENGTH: 216
<212> TYPE: DNA
<213> ORGANISM: human metapneumo virus

<400> SEQUENCE: 353
atgactcttc atatgccttg caagacagtg aaagcactaa tcaagtgcag taagcatggt 60
cccaaattca ttaccataga ggcagatgat atgatatgga cacacaaaga attaaaggag 120
acactgtctg atgggatagt aaaatcacac accaatattt acagttgtta tttagaaaat 180
atagaaataa tatatgttaa agcttactta agttag 216

<210> SEQ ID NO 354
<211> LENGTH: 727
<212> TYPE: DNA
<213> ORGANISM: human metapneumo virus

<400> SEQUENCE: 354
atgtctcgca aggctccgtg caaatatgaa gtgcggggca aatgcaatag aggaagtgag 60
tgcaagttta accacaatta ctggagttgg ccagatagat acttattaat aagatcaaat 120
tatttattaa atcaactttt aaggaacact gatagagctg atggcttatc aataatatca 180
ggagcaggca gagaagatag gacacaagat tttgtcctag gttccaccaa tgtggttcaa 240
ggttatattg atgataacca aagcataaca aaagctgcag cctgttacag tctacataat 300
ataatcaaac aactacaaga agttgaagtt aggcaggcta gagataacaa actatctgac 360
agcaaacatg tagcacttca caacttagtc ctatcttata tggagatgag caaaactcct 420
gcatctttaa tcaacaatct caagagactg ccgagagaga aactgaaaaa attagcaaag 480
ctcataattg acttatcagc aggtgctgaa aatgactctt catatgcctt gcaagacagt 540
gaaagcacta atcaagtgca gtgagcatgg tccagttttc attactatag aggttgatga 600
catgatatgg actcacaagg acttaaaaga agctttatct gatgggatag tgaagtctca 660
tactaacatt tacaattgtt atttagaaaa catagaaatt atatatgtca aggcttactt 720
aagttag 727

-continued

<210> SEQ ID NO 355
<211> LENGTH: 727
<212> TYPE: DNA
<213> ORGANISM: human metapneumo virus

<400> SEQUENCE: 355
atgtctcgca aggctccatg caaatatgaa gtgcggggca aatgcaacag aggaagtgag 60
tgtaagttta accacaatta ctggagttgg ccagatagat acttattaat aagatcaaac 120
tatctattaa atcagctttt aaggaacact gatagagctg atggcctatc aataatatca 180
ggcgcaggca gagaagacag aacgcaagat tttgttctag gttccaccaa tgtggttcaa 240
ggttatattg atgataacca aagcataaca aaagctgcag cctgctacag tctacacaac 300
ataatcaagc aactacaaga agttgaagtt aggcaggcta gagatagcaa actatctgac 360
agcaagcatg tggcactcca taacttaatc ttatcttaca tggagatgag caaaactccc 420
gcatctttaa tcaacaatct taaaagactg ccgagagaaa aactgaaaaa attagcaaag 480
ctgataattg acttatcagc aggcgctgac aatgactctt catatgccct gcaagacagt 540
gaaagcacta atcaagtgca gtgagcatgg tcctgttttc attactatag aggttgatga 600
aatgatatgg actcaaaaag aattaaaaga agctttgtcc gatgggatag tgaagtctca 660
caccaacatt tacaattgtt atttagaaaa catagaaatt atatatgtca aggcttactt 720
aagttag 727

<210> SEQ ID NO 356
<211> LENGTH: 727
<212> TYPE: DNA
<213> ORGANISM: human metapneumo virus

<400> SEQUENCE: 356
atgtctcgta aggctccatg caaatatgaa gtgcggggca aatgcaacag agggagtgat 60
tgcaaattca atcacaatta ctggagttgg cctgatagat atttattgtt aagatcaaat 120
tatctcttaa atcagctttt aagaaacaca gataaggctg atggtttgtc aataatatca 180
ggagcaggta gagaagatag aactcaagac tttgttcttg gttctactaa tgtggttcaa 240
gggtacattg atgacaacca aggaataacc aaggctgcag cttgctatag tctacacaac 300
ataatcaagc aactacaaga aacagaagta agacaggcta gagacaacaa gctttctgat 360
agcaaacatg tggcgctcca caacttgata ttatcctata tggagatgag caaaactcct 420
gcatctctaa tcaacaacct aaagaaacta ccaagggaaa aactgaagaa attagcaaga 480
ttaataattg atttatcagc aggaactgac aatgactctt catatgcctt gcaagacagt 540
gaaagcacta atcaagtgca gtaaacatgg tcccaaattc attaccatag aggcagatga 600
tatgatatgg actcacaaag aattaaaaga aacactgtct gatgggatag taaaatcaca 660
caccaatatt tatagttgtt acttagaaaa tatagaaata atatatgtta aaacttactt 720
aagttag 727

<210> SEQ ID NO 357
<211> LENGTH: 727
<212> TYPE: DNA
<213> ORGANISM: human metapneumo virus

<400> SEQUENCE: 357
atgtctcgca aagctccatg caaatatgaa gtacggggca agtgcaacag gggaagtgag 60
tgcaaattca accacaatta ctggagctgg cctgataggt atttattgtt aagatcaaat 120

-continued

```
tatctcttga atcagctttt aagaaacact gataaggctg atggtttgtc aataatatca    180

ggagcaggta gagaagatag gactcaagac tttgttcttg gttctactaa tgtggttcaa    240

gggtacattg ataacaatca aggaataaca aaggctgcag cttgctatag tctacataac    300

ataataaaac agctacaaga aatagaagta agacaggcta gagataataa gctttctgac    360

agcaaacatg tggcacttca caacttgata ttatcctata tggagatgag caaaactcct    420

gcatccctga ttaataacct aaagaaacta ccaagagaaa aactgaagaa attagcgaaa    480

ttaataattg atttatcagc aggaactgat aatgactctt catatgcctt gcaagacagt    540

gaaagcacta atcaagtgca gtaagcatgg tcccaaattc attaccatag aggcagatga    600

tatgatatgg acacacaaag aattaaagga gacactgtct gatgggatag taaaatcaca    660

caccaatatt tacagttgtt atttagaaaa tatagaaata atatatgtta aagcttactt    720

aagttag                                                              727
```

```
<210> SEQ ID NO 358
<211> LENGTH: 254
<212> TYPE: PRT
<213> ORGANISM: human metapneumo virus

<400> SEQUENCE: 358

Met Glu Ser Tyr Leu Val Asp Thr Tyr Gln Gly Ile Pro Tyr Thr Ala
 1               5                  10                  15

Ala Val Gln Val Asp Leu Ile Glu Lys Asp Leu Leu Pro Ala Ser Leu
            20                  25                  30

Thr Ile Trp Phe Pro Leu Phe Gln Ala Asn Thr Pro Pro Ala Val Leu
        35                  40                  45

Leu Asp Gln Leu Lys Thr Leu Thr Ile Thr Thr Leu Tyr Ala Ala Ser
    50                  55                  60

Gln Asn Gly Pro Ile Leu Lys Val Asn Ala Ser Ala Gln Gly Ala Ala
65                  70                  75                  80

Met Ser Val Leu Pro Lys Lys Phe Glu Val Asn Ala Thr Val Ala Leu
                85                  90                  95

Asp Glu Tyr Ser Lys Leu Glu Phe Asp Lys Leu Thr Val Cys Glu Val
            100                 105                 110

Lys Thr Val Tyr Leu Thr Thr Met Lys Pro Tyr Gly Met Val Ser Lys
        115                 120                 125

Phe Val Ser Ser Ala Lys Ser Val Gly Lys Lys Thr His Asp Leu Ile
    130                 135                 140

Ala Leu Cys Asp Phe Met Asp Leu Glu Lys Asn Thr Pro Val Thr Ile
145                 150                 155                 160

Pro Ala Phe Ile Lys Ser Val Ser Ile Lys Glu Ser Glu Ser Ala Thr
                165                 170                 175

Val Glu Ala Ala Ile Ser Ser Glu Ala Asp Gln Ala Leu Thr Gln Ala
            180                 185                 190

Lys Ile Ala Pro Tyr Ala Gly Leu Ile Met Ile Met Thr Met Asn Asn
        195                 200                 205

Pro Lys Gly Ile Phe Lys Lys Leu Gly Ala Gly Thr Gln Val Ile Val
    210                 215                 220

Glu Leu Gly Ala Tyr Val Gln Ala Glu Ser Ile Ser Lys Ile Cys Lys
225                 230                 235                 240

Thr Trp Ser His Gln Gly Thr Arg Tyr Val Leu Lys Ser Arg
                245                 250
```

<210> SEQ ID NO 359
<211> LENGTH: 254
<212> TYPE: PRT
<213> ORGANISM: human metapneumo virus

<400> SEQUENCE: 359

```
Met Glu Ser Tyr Leu Val Asp Thr Tyr Gln Gly Ile Pro Tyr Thr Ala
 1               5                  10                  15

Ala Val Gln Val Asp Leu Val Glu Lys Asp Leu Leu Pro Ala Ser Leu
            20                  25                  30

Thr Ile Trp Phe Pro Leu Phe Gln Ala Asn Thr Pro Pro Ala Val Leu
        35                  40                  45

Leu Asp Gln Leu Lys Thr Leu Thr Ile Thr Thr Leu Tyr Ala Ala Ser
    50                  55                  60

Gln Ser Gly Pro Ile Leu Lys Val Asn Ala Ser Ala Gln Gly Ala Ala
65                  70                  75                  80

Met Ser Val Leu Pro Lys Lys Phe Glu Val Asn Ala Thr Val Ala Leu
                85                  90                  95

Asp Glu Tyr Ser Lys Leu Glu Phe Asp Lys Leu Thr Val Cys Glu Val
            100                 105                 110

Lys Thr Val Tyr Leu Thr Thr Met Lys Pro Tyr Gly Met Val Ser Lys
        115                 120                 125

Phe Val Ser Ser Ala Lys Ser Val Gly Lys Lys Thr His Asp Leu Ile
    130                 135                 140

Ala Leu Cys Asp Phe Met Asp Leu Glu Lys Asn Thr Pro Val Thr Ile
145                 150                 155                 160

Pro Ala Phe Ile Lys Ser Val Ser Ile Lys Glu Ser Glu Ser Ala Thr
                165                 170                 175

Val Glu Ala Ala Ile Ser Ser Glu Ala Asp Gln Ala Leu Thr Gln Ala
            180                 185                 190

Lys Ile Ala Pro Tyr Ala Gly Leu Ile Met Ile Met Thr Met Asn Asn
        195                 200                 205

Pro Lys Gly Ile Phe Lys Lys Leu Gly Ala Gly Thr Gln Val Ile Val
    210                 215                 220

Glu Leu Gly Ala Tyr Val Gln Ala Glu Ser Ile Ser Lys Ile Cys Lys
225                 230                 235                 240

Thr Trp Ser His Gln Gly Thr Arg Tyr Val Leu Lys Ser Ser
                245                 250
```

<210> SEQ ID NO 360
<211> LENGTH: 254
<212> TYPE: PRT
<213> ORGANISM: human metapneumo virus

<400> SEQUENCE: 360

```
Met Glu Ser Tyr Leu Val Asp Thr Tyr Gln Gly Ile Pro Tyr Thr Ala
 1               5                  10                  15

Ala Val Gln Val Asp Leu Val Glu Lys Asp Leu Leu Pro Ala Ser Leu
            20                  25                  30

Thr Ile Trp Phe Pro Leu Phe Gln Ala Asn Thr Pro Pro Ala Val Leu
        35                  40                  45

Leu Asp Gln Leu Lys Thr Leu Thr Ile Thr Thr Leu Tyr Ala Ala Ser
    50                  55                  60

Gln Asn Gly Pro Ile Leu Lys Val Asn Ala Ser Ala Gln Gly Ala Ala
65                  70                  75                  80
```

-continued

```
Met Ser Val Leu Pro Lys Lys Phe Glu Val Asn Ala Thr Val Ala Leu
                85                  90                  95

Asp Glu Tyr Ser Lys Leu Asp Phe Asp Lys Leu Thr Val Cys Asp Val
            100                 105                 110

Lys Thr Val Tyr Leu Thr Thr Met Lys Pro Tyr Gly Met Val Ser Lys
        115                 120                 125

Phe Val Ser Ser Ala Lys Ser Val Gly Lys Lys Thr His Asp Leu Ile
    130                 135                 140

Ala Leu Cys Asp Phe Met Asp Leu Glu Lys Asn Ile Pro Val Thr Ile
145                 150                 155                 160

Pro Ala Phe Ile Lys Ser Val Ser Ile Lys Glu Ser Glu Ser Ala Thr
                165                 170                 175

Val Glu Ala Ala Ile Ser Ser Glu Ala Asp Gln Ala Leu Thr Gln Ala
            180                 185                 190

Lys Ile Ala Pro Tyr Ala Gly Leu Ile Met Ile Met Thr Met Asn Asn
        195                 200                 205

Pro Lys Gly Ile Phe Lys Lys Leu Gly Ala Gly Thr Gln Val Ile Val
    210                 215                 220

Glu Leu Gly Ala Tyr Val Gln Ala Glu Ser Ile Ser Arg Ile Cys Lys
225                 230                 235                 240

Ser Trp Ser His Gln Gly Thr Arg Tyr Val Leu Lys Ser Arg
                245                 250


<210> SEQ ID NO 361
<211> LENGTH: 254
<212> TYPE: PRT
<213> ORGANISM: human metapneumo virus

<400> SEQUENCE: 361

Met Glu Ser Tyr Leu Val Asp Thr Tyr Gln Gly Ile Pro Tyr Thr Ala
 1               5                  10                  15

Ala Val Gln Val Asp Leu Val Glu Lys Asp Leu Leu Pro Ala Ser Leu
            20                  25                  30

Thr Ile Trp Phe Pro Leu Phe Gln Ala Asn Thr Pro Pro Ala Val Leu
        35                  40                  45

Leu Asp Gln Leu Lys Thr Leu Thr Ile Thr Thr Leu Tyr Ala Ala Ser
    50                  55                  60

Gln Asn Gly Pro Ile Leu Lys Val Asn Ala Ser Ala Gln Gly Ala Ala
65                  70                  75                  80

Met Ser Val Leu Pro Lys Lys Phe Glu Val Asn Ala Thr Val Ala Leu
                85                  90                  95

Asp Glu Tyr Ser Lys Leu Asp Phe Asp Lys Leu Thr Val Cys Asp Val
            100                 105                 110

Lys Thr Val Tyr Leu Thr Thr Met Lys Pro Tyr Gly Met Val Ser Lys
        115                 120                 125

Phe Val Ser Ser Ala Lys Ser Val Gly Lys Lys Thr His Asp Leu Ile
    130                 135                 140

Ala Leu Cys Asp Phe Met Asp Leu Glu Lys Asn Ile Pro Val Thr Ile
145                 150                 155                 160

Pro Ala Phe Ile Lys Ser Val Ser Ile Lys Glu Ser Glu Ser Ala Thr
                165                 170                 175

Val Glu Ala Ala Ile Ser Ser Glu Ala Asp Gln Ala Leu Thr Gln Ala
            180                 185                 190

Lys Ile Ala Pro Tyr Ala Gly Leu Ile Met Ile Met Thr Met Asn Asn
        195                 200                 205
```

-continued

```
Pro Lys Gly Ile Phe Lys Lys Leu Gly Ala Gly Thr Gln Val Ile Val
    210                 215                 220

Glu Leu Gly Ala Tyr Val Gln Ala Glu Ser Ile Ser Arg Ile Cys Lys
225                 230                 235                 240

Ser Trp Ser His Gln Gly Thr Arg Tyr Val Leu Lys Ser Arg
                245                 250


<210> SEQ ID NO 362
<211> LENGTH: 765
<212> TYPE: DNA
<213> ORGANISM: human metapneumo virus

<400> SEQUENCE: 362

atggagtcct acctagtaga cacctatcaa ggcattcctt acacagcagc tgttcaagtt      60

gatctaatag aaaaggacct gttacctgca agcctaacaa tatggttccc tttgtttcag     120

gccaacacac caccagcagt gctgctcgat cagctaaaaa ccctgacaat aaccactctg     180

tatgctgcat cacaaaatgg tccaatactc aaagtgaatg catcagccca aggtgcagca     240

atgtctgtac ttcccaaaaa atttgaagtc aatgcgactg tagcactcga tgaatatagc     300

aaactggaat ttgacaaact cacagtctgt gaagtaaaaa cagtttactt aacaaccatg     360

aaaccatacg ggatggtatc aaaatttgtg agctcagcca aatcagttgg caaaaaaaca     420

catgatctaa tcgcactatg tgattttatg gatctagaaa agaacacacc tgttacaata     480

ccagcattca tcaaatcagt ttcaatcaaa gagagtgagt cagctactgt tgaagctgct     540

ataagcagtg aagcagacca agctctaaca caggccaaaa ttgcacctta tgcgggatta     600

attatgatca tgactatgaa caatcccaaa ggcatattca aaaagcttgg agctgggact     660

caagtcatag tagaactagg agcatatgtc caggctgaaa gcataagcaa aatatgcaag     720

acttggagcc atcaagggac aagatatgtc ttgaagtcca gataa                     765


<210> SEQ ID NO 363
<211> LENGTH: 765
<212> TYPE: DNA
<213> ORGANISM: human metapneumo virus

<400> SEQUENCE: 363

atggagtcct atctggtaga cacttatcaa ggcatccctt acacagcagc tgttcaagtt      60

gatctagtag aaaaggacct gttacctgca agcctaacaa tatggttccc cttgtttcag     120

gccaatacac caccagcagt tctgcttgat cagctaaaga ctctgactat aactactctg     180

tatgctgcat cacaaagtgg tccaatacta aaagtgaatg catcagccca gggtgcagca     240

atgtctgtac ttcccaaaaa gtttgaagtc aatgcgactg tagcacttga cgaatatagc     300

aaattagaat ttgacaaact tacagtctgt gaagtaaaaa cagtttactt aacaaccatg     360

aaaccatatg ggatggtatc aaagtttgtg agctcggcca aatcagttgg caaaaaaaca     420

catgatctaa tcgcattatg tgattttatg gatctagaaa agaacacacc agttacaata     480

ccagcattta tcaaatcagt ttctatcaag gagagtgaat cagccactgt tgaagctgca     540

ataagcagtg aagcagacca agctctaaca caagccaaaa ttgcacctta tgcgggactg     600

atcatgatta tgaccatgaa caatcccaaa ggcatattca agaagcttgg agctgggacc     660

caagttatag tagaactagg agcatatgtc caggctgaaa gcataagtaa aatatgcaag     720

acttggagcc atcaaggaac aagatatgtg ctgaagtcca gttaa                     765
```

-continued

<210> SEQ ID NO 364
<211> LENGTH: 765
<212> TYPE: DNA
<213> ORGANISM: human metapneumo virus

<400> SEQUENCE: 364

```
atggagtcct atctagtaga cacttatcaa ggcattccat atacagctgc tgttcaagtt      60

gacctggtag aaaaagattt actgccagca agtttgacaa tatggtttcc tttatttcag     120

gccaacacac caccagcagt tctgcttgat cagctaaaaa ccttgacaat aacaactctg     180

tatgctgcat cacagaatgg tccaatactc aaggtaaatg catctgccca aggtgctgcc     240

atgtctgtac ttcccaaaaa attcgaggta aatgcaactg tagcacttga tgaatacagt     300

aaacttgatt ttgacaagct gacggtctgc gatgttaaaa cagtttattt gacaactatg     360

aaaccgtacg ggatggtgtc aaaatttgtg agttcagcca aatcagttgg caaaaagaca     420

catgatctaa ttgcactatg tgacttcatg gacctagaga aaaatatacc tgtgacaata     480

ccagcattca taaagtcagt ttcaatcaaa gagagtgaat cagccactgt tgaagctgca     540

ataagcagcg aagccgacca agccttgaca caagccaaga ttgcgcccta tgcaggacta     600

attatgatca tgaccatgaa caatccaaaa ggtatattca agaaactagg ggctggaaca     660

caagtgatag tagagctggg ggcatatgtt caggctgaga gcatcagtag gatctgcaag     720

agctggagtc accaaggaac aagatacgta ctaaaatcca gataa                     765
```

<210> SEQ ID NO 365
<211> LENGTH: 765
<212> TYPE: DNA
<213> ORGANISM: human metapneumo virus

<400> SEQUENCE: 365

```
atggagtcct atctagtgga cacttatcaa ggcattccct acacagctgc tgttcaagtt      60

gatctggtag aaaaagactt actaccagca agtttgacaa tatggtttcc tctattccaa     120

gccaacacac caccagcggt tttgctcgat cagctaaaaa ccttgactat aacaactctg     180

tatgctgcat cacagaatgg tccaatactc aaagtaaatg catcagctca gggtgctgct     240

atgtctgtac ttcccaaaaa attcgaagta aatgcaactg tggcacttga tgaatacagc     300

aaacttgact ttgacaagtt aacggtttgc gatgttaaaa cagtttattt gacaaccatg     360

aagccatatg ggatggtgtc aaaatttgtg agttcagcca aatcagttgg caaaaagaca     420

catgatctaa ttgcactgtg tgacttcatg gacctagaga aaaatatacc tgtgacaata     480

ccagcattca taaagtcagt ttcaatcaaa gagagtgagt cagccactgt tgaagctgca     540

ataagcagtg aggccgacca agcattaaca caagccaaaa ttgcacccta tgcaggacta     600

atcatgatca tgaccatgaa caatccaaaa ggtatattca agaaactagg agctggaaca     660

caagtgatag tagagctagg ggcatatgtt caagccgaga gcatcagcag gatctgcaag     720

agctggagtc accaaggaac aagatatgta ctaaaatcca gataa                     765
```

<210> SEQ ID NO 366
<211> LENGTH: 394
<212> TYPE: PRT
<213> ORGANISM: human metapneumo virus

<400> SEQUENCE: 366

```
Met Ser Leu Gln Gly Ile His Leu Ser Asp Leu Ser Tyr Lys His Ala
 1               5                  10                  15

Ile Leu Lys Glu Ser Gln Tyr Thr Ile Lys Arg Asp Val Gly Thr Thr
```

-continued

```
            20                  25                  30

Thr Ala Val Thr Pro Ser Ser Leu Gln Gln Glu Ile Thr Leu Leu Cys
        35                  40                  45

Gly Glu Ile Leu Tyr Ala Lys His Ala Asp Tyr Lys Tyr Ala Ala Glu
    50                  55                  60

Ile Gly Ile Gln Tyr Ile Ser Thr Ala Leu Gly Ser Glu Arg Val Gln
65                  70                  75                  80

Gln Ile Leu Arg Asn Ser Gly Ser Glu Val Gln Val Val Leu Thr Arg
                85                  90                  95

Thr Tyr Ser Leu Gly Lys Ile Lys Asn Asn Lys Gly Glu Asp Leu Gln
            100                 105                 110

Met Leu Asp Ile His Gly Val Glu Lys Ser Trp Val Glu Glu Ile Asp
        115                 120                 125

Lys Glu Ala Arg Lys Thr Met Ala Thr Leu Leu Lys Glu Ser Ser Gly
    130                 135                 140

Asn Ile Pro Gln Asn Gln Arg Pro Ser Ala Pro Asp Thr Pro Ile Ile
145                 150                 155                 160

Leu Leu Cys Val Gly Ala Leu Ile Phe Thr Lys Leu Ala Ser Thr Ile
                165                 170                 175

Glu Val Gly Leu Glu Thr Thr Val Arg Arg Ala Asn Arg Val Leu Ser
            180                 185                 190

Asp Ala Leu Lys Arg Tyr Pro Arg Met Asp Ile Pro Lys Ile Ala Arg
        195                 200                 205

Ser Phe Tyr Asp Leu Phe Glu Gln Lys Val Tyr His Arg Ser Leu Phe
    210                 215                 220

Ile Glu Tyr Gly Lys Ala Leu Gly Ser Ser Ser Thr Gly Ser Lys Ala
225                 230                 235                 240

Glu Ser Leu Phe Val Asn Ile Phe Met Gln Ala Tyr Gly Ala Gly Gln
                245                 250                 255

Thr Met Leu Arg Trp Gly Val Ile Ala Arg Ser Ser Asn Asn Ile Met
            260                 265                 270

Leu Gly His Val Ser Val Gln Ala Glu Leu Lys Gln Val Thr Glu Val
        275                 280                 285

Tyr Asp Leu Val Arg Glu Met Gly Pro Glu Ser Gly Leu Leu His Leu
    290                 295                 300

Arg Gln Ser Pro Lys Ala Gly Leu Leu Ser Leu Ala Asn Cys Pro Asn
305                 310                 315                 320

Phe Ala Ser Val Val Leu Gly Asn Ala Ser Gly Leu Gly Ile Ile Gly
                325                 330                 335

Met Tyr Arg Gly Arg Val Pro Asn Thr Glu Leu Phe Ser Ala Ala Glu
            340                 345                 350

Ser Tyr Ala Lys Ser Leu Lys Glu Ser Asn Lys Ile Asn Phe Ser Ser
        355                 360                 365

Leu Gly Leu Thr Asp Glu Glu Lys Glu Ala Ala Glu His Phe Leu Asn
    370                 375                 380

Val Ser Asp Asp Ser Gln Asn Asp Tyr Glu
385                 390
```

```
<210> SEQ ID NO 367
<211> LENGTH: 394
<212> TYPE: PRT
<213> ORGANISM: human metapneumo virus

<400> SEQUENCE: 367
```

-continued

```
Met Ser Leu Gln Gly Ile His Leu Ser Asp Leu Ser Tyr Lys His Ala
 1               5                  10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Gln Glu Ile Thr Leu Leu Cys
        35                  40                  45

Gly Glu Ile Leu Tyr Ala Lys His Ala Asp Tyr Lys Tyr Ala Ala Glu
    50                  55                  60

Ile Gly Ile Gln Tyr Ile Ser Thr Ala Leu Gly Ser Glu Arg Val Gln
65                  70                  75                  80

Gln Ile Leu Arg Asn Ser Gly Ser Glu Val Gln Val Val Leu Thr Arg
                85                  90                  95

Thr Tyr Ser Leu Gly Lys Val Lys Asn Asn Lys Gly Glu Asp Leu Gln
            100                 105                 110

Met Leu Asp Ile His Gly Val Glu Lys Ser Trp Val Glu Glu Ile Asp
        115                 120                 125

Lys Glu Ala Arg Lys Thr Met Ala Thr Leu Leu Lys Glu Ser Ser Gly
    130                 135                 140

Asn Ile Pro Gln Asn Gln Arg Pro Ser Ala Pro Asp Thr Pro Ile Ile
145                 150                 155                 160

Leu Leu Cys Val Gly Ala Leu Ile Phe Thr Lys Leu Ala Ser Thr Ile
                165                 170                 175

Glu Val Gly Leu Glu Thr Thr Val Arg Arg Ala Asn Arg Val Leu Ser
            180                 185                 190

Asp Ala Leu Lys Arg Tyr Pro Arg Met Asp Ile Pro Lys Ile Ala Arg
        195                 200                 205

Ser Phe Tyr Asp Leu Phe Glu Gln Lys Val Tyr Tyr Arg Ser Leu Phe
    210                 215                 220

Ile Glu Tyr Gly Lys Ala Leu Gly Ser Ser Ser Thr Gly Ser Lys Ala
225                 230                 235                 240

Glu Ser Leu Phe Val Asn Ile Phe Met Gln Ala Tyr Gly Ala Gly Gln
                245                 250                 255

Thr Met Leu Arg Trp Gly Val Ile Ala Arg Ser Ser Asn Asn Ile Met
            260                 265                 270

Leu Gly His Val Ser Val Gln Ala Glu Leu Lys Gln Val Thr Glu Val
        275                 280                 285

Tyr Asp Leu Val Arg Glu Met Gly Pro Glu Ser Gly Leu Leu His Leu
    290                 295                 300

Arg Gln Ser Pro Lys Ala Gly Leu Leu Ser Leu Ala Asn Cys Pro Asn
305                 310                 315                 320

Phe Ala Ser Val Val Leu Gly Asn Ala Ser Gly Leu Gly Ile Ile Gly
                325                 330                 335

Met Tyr Arg Gly Arg Val Pro Asn Thr Glu Leu Phe Ser Ala Ala Glu
            340                 345                 350

Ser Tyr Ala Lys Ser Leu Lys Glu Ser Asn Lys Ile Asn Phe Ser Ser
        355                 360                 365

Leu Gly Leu Thr Asp Glu Glu Lys Glu Ala Ala Glu His Phe Leu Asn
    370                 375                 380

Val Ser Asp Asp Ser Gln Asn Asp Tyr Glu
385                 390
```

<210> SEQ ID NO 368
<211> LENGTH: 394
<212> TYPE: PRT

-continued

```
<213> ORGANISM: human metapneumo virus

<400> SEQUENCE: 368

Met Ser Leu Gln Gly Ile His Leu Ser Asp Leu Ser Tyr Lys His Ala
 1               5                  10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Gln Glu Ile Thr Leu Leu Cys
        35                  40                  45

Gly Glu Ile Leu Tyr Thr Lys His Thr Asp Tyr Lys Tyr Ala Ala Glu
    50                  55                  60

Ile Gly Ile Gln Tyr Ile Cys Thr Ala Leu Gly Ser Glu Arg Val Gln
65                  70                  75                  80

Gln Ile Leu Arg Asn Ser Gly Ser Glu Val Gln Val Val Leu Thr Lys
                85                  90                  95

Thr Tyr Ser Leu Gly Lys Gly Lys Asn Ser Lys Gly Glu Glu Leu Gln
            100                 105                 110

Met Leu Asp Ile His Gly Val Glu Lys Ser Trp Ile Glu Glu Ile Asp
        115                 120                 125

Lys Glu Ala Arg Lys Thr Met Val Thr Leu Leu Lys Glu Ser Ser Gly
    130                 135                 140

Asn Ile Pro Gln Asn Gln Arg Pro Ser Ala Pro Asp Thr Pro Ile Ile
145                 150                 155                 160

Leu Leu Cys Val Gly Ala Leu Ile Phe Thr Lys Leu Ala Ser Thr Ile
                165                 170                 175

Glu Val Gly Leu Glu Thr Thr Val Arg Arg Ala Asn Arg Val Leu Ser
            180                 185                 190

Asp Ala Leu Lys Arg Tyr Pro Arg Ile Asp Ile Pro Lys Ile Ala Arg
        195                 200                 205

Ser Phe Tyr Glu Leu Phe Glu Gln Lys Val Tyr Tyr Arg Ser Leu Phe
    210                 215                 220

Ile Glu Tyr Gly Lys Ala Leu Gly Ser Ser Ser Thr Gly Ser Lys Ala
225                 230                 235                 240

Glu Ser Leu Phe Val Asn Ile Phe Met Gln Ala Tyr Gly Ala Gly Gln
                245                 250                 255

Thr Leu Leu Arg Trp Gly Val Ile Ala Arg Ser Ser Asn Asn Ile Met
            260                 265                 270

Leu Gly His Val Ser Val Gln Ser Glu Leu Lys Gln Val Thr Glu Val
        275                 280                 285

Tyr Asp Leu Val Arg Glu Met Gly Pro Glu Ser Gly Leu Leu His Leu
    290                 295                 300

Arg Gln Ser Pro Lys Ala Gly Leu Leu Ser Leu Ala Asn Cys Pro Asn
305                 310                 315                 320

Phe Ala Ser Val Val Leu Gly Asn Ala Ser Gly Leu Gly Ile Ile Gly
                325                 330                 335

Met Tyr Arg Gly Arg Val Pro Asn Thr Glu Leu Phe Ser Ala Ala Glu
            340                 345                 350

Ser Tyr Ala Arg Ser Leu Lys Glu Ser Asn Lys Ile Asn Phe Ser Ser
        355                 360                 365

Leu Gly Leu Thr Asp Glu Glu Lys Glu Ala Ala Glu His Phe Leu Asn
    370                 375                 380

Met Ser Gly Asp Asn Gln Asn Asp Tyr Glu
385                 390
```

-continued

<210> SEQ ID NO 369
<211> LENGTH: 394
<212> TYPE: PRT
<213> ORGANISM: human metapneumo virus

<400> SEQUENCE: 369

```
Met Ser Leu Gln Gly Ile His Leu Ser Asp Leu Ser Tyr Lys His Ala
 1               5                  10                  15

Ile Leu Lys Glu Ser Gln Tyr Thr Ile Lys Arg Asp Val Gly Thr Thr
            20                  25                  30

Thr Ala Val Thr Pro Ser Ser Leu Gln Gln Glu Ile Thr Leu Leu Cys
        35                  40                  45

Gly Glu Ile Leu Tyr Thr Lys His Thr Asp Tyr Lys Tyr Ala Ala Glu
    50                  55                  60

Ile Gly Ile Gln Tyr Ile Cys Thr Ala Leu Gly Ser Glu Arg Val Gln
65                  70                  75                  80

Gln Ile Leu Arg Asn Ser Gly Ser Glu Val Gln Val Val Leu Thr Lys
                85                  90                  95

Thr Tyr Ser Leu Gly Lys Gly Lys Asn Ser Lys Gly Glu Glu Leu Gln
            100                 105                 110

Met Leu Asp Ile His Gly Val Glu Lys Ser Trp Val Glu Glu Ile Asp
        115                 120                 125

Lys Glu Ala Arg Lys Thr Met Val Thr Leu Leu Lys Glu Ser Ser Gly
    130                 135                 140

Asn Ile Pro Gln Asn Gln Arg Pro Ser Ala Pro Asp Thr Pro Ile Ile
145                 150                 155                 160

Leu Leu Cys Val Gly Ala Leu Ile Phe Thr Lys Leu Ala Ser Thr Ile
                165                 170                 175

Glu Val Gly Leu Glu Thr Thr Val Arg Arg Ala Asn Arg Val Leu Ser
            180                 185                 190

Asp Ala Leu Lys Arg Tyr Pro Arg Val Asp Ile Pro Lys Ile Ala Arg
        195                 200                 205

Ser Phe Tyr Glu Leu Phe Glu Gln Lys Val Tyr Tyr Arg Ser Leu Phe
    210                 215                 220

Ile Glu Tyr Gly Lys Ala Leu Gly Ser Ser Ser Thr Gly Ser Lys Ala
225                 230                 235                 240

Glu Ser Leu Phe Val Asn Ile Phe Met Gln Ala Tyr Gly Ala Gly Gln
                245                 250                 255

Thr Met Leu Arg Trp Gly Val Ile Ala Arg Ser Ser Asn Asn Ile Met
            260                 265                 270

Leu Gly His Val Ser Val Gln Ala Glu Leu Lys Gln Val Thr Glu Val
        275                 280                 285

Tyr Asp Leu Val Arg Glu Met Gly Pro Glu Ser Gly Leu Leu His Leu
    290                 295                 300

Arg Gln Ser Pro Lys Ala Gly Leu Leu Ser Leu Ala Asn Cys Pro Asn
305                 310                 315                 320

Phe Ala Ser Val Val Leu Gly Asn Ala Ser Gly Leu Gly Ile Ile Gly
                325                 330                 335

Met Tyr Arg Gly Arg Val Pro Asn Thr Glu Leu Phe Ser Ala Ala Glu
            340                 345                 350

Ser Tyr Ala Arg Ser Leu Lys Glu Ser Asn Lys Ile Asn Phe Ser Ser
        355                 360                 365

Leu Gly Leu Thr Asp Glu Glu Lys Glu Ala Ala Glu His Phe Leu Asn
    370                 375                 380
```

-continued

```
Met Ser Asp Asp Asn Gln Asp Asp Tyr Glu
385                 390
```

<210> SEQ ID NO 370
<211> LENGTH: 1185
<212> TYPE: DNA
<213> ORGANISM: human metapneumo virus

<400> SEQUENCE: 370

```
atgtctcttc aagggattca cctgagtgat ttatcataca agcatgctat attaaaagag     60
tctcagtaca caataaaaag agatgtgggt acaacaactg cagtgacacc ctcatcattg    120
caacaagaaa taacactgtt gtgtggagaa attctgtatg ctaaacatgc tgactacaaa    180
tatgctgcag aaataggaat acaatatatt agcacagctt taggatcaga gagagtgcag    240
cagattctga ggaactcagg cagtgaagtc caagtggtct taaccagaac gtactctctg    300
gggaaaatta aaaacaataa aggagaagat ttacagatgt tagacataca cggggtagag    360
aagagctggg tagaagagat agacaaagaa gcaaggaaaa caatggcaac cttgcttaag    420
gaatcatcag gtaatatccc acaaaatcag aggccctcag caccagacac acccataatc    480
ttattatgtg taggtgcctt aatattcact aaactagcat caaccataga agtgggacta    540
gagaccacag tcagaagggc taaccgtgta ctaagtgatg cactcaagag ataccctaga    600
atggacatac caaagattgc cagatccttc tatgacttat ttgaacaaaa agtgtatcac    660
agaagtttgt tcattgagta tggcaaagca ttaggctcat catctacagg cagcaaagca    720
gaaagtctat ttgttaatat attcatgcaa gcttatgggg ccggtcaaac aatgctaagg    780
tggggggtca ttgccaggtc atccaacaat ataatgttag gacatgtatc cgtccaagct    840
gagttaaaac aggtcacaga agtctatgac ttggtgcgag aaatgggccc tgaatctgga    900
cttctacatt taaggcaaag cccaaaagct ggactgttat cactagccaa ctgtcccaac    960
tttgcaagtg ttgttctcgg aaatgcctca ggcttaggca taatcggtat gtatcgaggg   1020
agagtaccaa acacagaatt attttcagca gctgaaagtt atgccaaaag tttgaaagaa   1080
agcaataaaa taaatttctc ttcattagga cttacagatg aagagaaaga ggctgcagaa   1140
catttcttaa atgtgagtga cgacagtcaa aatgattatg agtaa                   1185
```

<210> SEQ ID NO 371
<211> LENGTH: 1185
<212> TYPE: DNA
<213> ORGANISM: human metapneumo virus

<400> SEQUENCE: 371

```
atgtctcttc aagggattca cctgagtgat ctatcataca agcatgctat attaaaagag     60
tctcagtata caataaagag agatgtaggc acaacaaccg cagtgacacc ctcatcattg    120
caacaagaaa taacactatt gtgtggagaa attctatatg ctaagcatgc tgattacaaa    180
tatgctgcag aaataggaat acaatatatt agcacagctc taggatcaga gagagtacag    240
cagattctaa gaaactcagg tagtgaagtc caagtggttt taaccagaac gtactccttg    300
gggaaagtta aaaacaacaa aggagaagat ttacagatgt tagacataca cggagtagag    360
aaaagctggg tggaagagat agacaaagaa gcaagaaaaa caatggcaac tttgcttaaa    420
gaatcatcag gcaatattcc acaaaatcag aggccttcag caccagacac acccataatc    480
ttattatgtg taggtgcctt aatatttacc aaactagcat caactataga agtgggatta    540
gagaccacag tcagaagagc taaccgtgta ctaagtgatg cactcaaaag ataccctagg    600
```

-continued

```
atggacatac caaaaatcgc tagatctttc tatgacttat ttgaacaaaa agtgtattac    660

agaagtttgt tcattgagta tggcaaagca ttaggctcat cctctacagg cagcaaagca    720

gaaagtttat tcgttaatat attcatgcaa gcttacggtg ctggtcaaac aatgctgagg    780

tggggagtca ttgccaggtc atctaacaat ataatgttag gacatgtatc tgttcaagct    840

gagttaaaac aagtcacaga agtctatgac ctggtgcgag aaatgggccc tgaatctggg    900

ctcctacatt taaggcaaag cccaaaagct ggactgttat cactagccaa ttgtcccaac    960

tttgctagtg ttgttctcgg caatgcctca ggcttaggca taataggtat gtatcgcggg   1020

agagtgccaa acacagaact attttcagca gcagaaagct atgccaagag tttgaaagaa   1080

agcaataaaa ttaacttttc ttcattagga ctcacagatg aagaaaaaga ggctgcagaa   1140

cacttcctaa atgtgagtga cgacagtcaa aatgattatg agtaa                   1185
```

<210> SEQ ID NO 372
<211> LENGTH: 1185
<212> TYPE: DNA
<213> ORGANISM: human metapneumo virus

<400> SEQUENCE: 372

```
atgtctcttc aagggattca cctaagtgat ctatcatata aacatgctat attaaaagag     60

tctcaataca caataaaaag agatgtaggc accacaactg cagtgacacc ttcatcatta    120

caacaagaaa taacactttt gtgtggggaa atactttaca ctaaacacac tgattacaaa    180

tatgctgctg agataggaat acaatatatt tgcacagctc taggatcaga aagagtacaa    240

cagattttga gaaactcagg tagtgaagtt caggtggttc taaccaaaac atactcctta    300

gggaaaggca aaaacagtaa aggggaagag ctgcagatgt tagatataca tggagtggaa    360

aagagttgga tagaagaaat agacaaagag gcaagaaaga caatggtaac tttgcttaag    420

gaatcatcag gtaacatccc acaaaaccag agaccttcag caccagacac accaataatt    480

ttattatgtg taggtgccct aatattcact aaactagcat caacaataga agttggatta    540

gagactacag ttagaagagc taatagagtg ctaagtgatg cactcaaaag atacccaagg    600

atagatatac caaagattgc tagatctttt tatgaactat ttgaacaaaa agtgtactac    660

agaagtttat tcattgagta cggaaaagct ttaggctcat cttcaacagg aagcaaagca    720

gaaagtttgt ttgtaaatat atttatgcaa gcttatggag ctggccaaac actgctaagg    780

tggggtgtca ttgccagatc atccaacaac ataatgctag ggcatgtatc tgtgcaatct    840

gaattgaagc aagttacaga ggtttatgac ttggtgagag aaatgggtcc tgaatctggg    900

cttttacatc taagacaaag tccaaaggca gggctgttat cattggccaa ttgccccaat    960

tttgctagtg ttgttcttgg caatgcttca ggtctaggca taatcggaat gtacagaggg   1020

agagtaccaa acacagagct attttctgca gcagaaagtt atgccagaag cttaaaagaa   1080

agcaataaaa tcaacttctc ttcgttaggg cttacagatg aagaaaaaga agctgcagaa   1140

cacttcttaa acatgagtgg tgacaatcaa aatgattatg agtaa                   1185
```

<210> SEQ ID NO 373
<211> LENGTH: 1185
<212> TYPE: DNA
<213> ORGANISM: human metapneumo virus

<400> SEQUENCE: 373

```
atgtctcttc aagggattca cctaagtgat ctgtcatata aacatgctat attaaaagag     60
```

-continued

```
tctcaatacac aataaaaag agatgtaggc accacaactg cagtgacacc ttcatcattg    120

cagcaagaga taacactttt gtgtggagag attctttaca ctaaacatac tgattacaaa    180

tatgctgcag agatagggat acaatatatt tgcacagctc taggatcaga aagagtacaa    240

cagattttaa gaaattcagg tagtgaggtt caggtggttc taaccaagac atactcttta    300

gggaaaggta aaaatagtaa aggggaagag ttgcaaatgt tagatataca tggagtggaa    360

aagagttggg tagaagaaat agacaaagag gcaagaaaaa caatggtgac tttgctaaag    420

gaatcatcag gcaacatccc acaaaaccag aggccttcag caccagacac accaataatt    480

ttattgtgtg taggtgcttt aatattcact aaactagcat caacaataga agttggacta    540

gagactacag ttagaagggc taacagagtg ttaagtgatg cgctcaaaag ataccctagg    600

gtagatatac caaagattgc tagatctttt tatgaactat ttgagcagaa agtgtattac    660

aggagtctat tcattgagta tgggaaagct ttaggctcat cttcaacagg aagcaaagca    720

gaaagtttgt ttgtaaatat atttatgcaa gcttatggag ccggtcagac aatgctaagg    780

tggggtgtca ttgccagatc atctaacaac ataatgctag ggcatgtatc tgtgcaagct    840

gaattgaaac aagttacaga ggtttatgat ttggtaagag aaatgggtcc tgaatctggg    900

cttttacatc taagacaaag tccaaaggca ggactgttat cgttggctaa ttgccccaat    960

tttgctagtg ttgttcttgg taatgcttca ggtctaggta taatcggaat gtacaggga   1020

agagtgccaa acacagagct attttctgca gcagaaagtt atgccagaag cttaaaagaa   1080

agcaacaaaa tcaacttctc ctcattaggg ctcacagacg aagaaaaaga agctgcagaa   1140

cacttcttaa acatgagtga tgacaatcaa gatgattatg agtaa                  1185
```

<210> SEQ ID NO 374
<211> LENGTH: 294
<212> TYPE: PRT
<213> ORGANISM: human metapneumo virus

<400> SEQUENCE: 374

```
Met Ser Phe Pro Glu Gly Lys Asp Ile Leu Phe Met Gly Asn Glu Ala
 1               5                  10                  15

Ala Lys Leu Ala Glu Ala Phe Gln Lys Ser Leu Arg Lys Pro Gly His
            20                  25                  30

Lys Arg Ser Gln Ser Ile Ile Gly Glu Lys Val Asn Thr Val Ser Glu
        35                  40                  45

Thr Leu Glu Leu Pro Thr Ile Ser Arg Pro Ala Lys Pro Thr Ile Pro
    50                  55                  60

Ser Glu Pro Lys Leu Ala Trp Thr Asp Lys Gly Gly Ala Thr Lys Thr
65                  70                  75                  80

Glu Ile Lys Gln Ala Ile Lys Val Met Asp Pro Ile Glu Glu Glu Glu
                85                  90                  95

Ser Thr Glu Lys Lys Val Leu Pro Ser Ser Asp Gly Lys Thr Pro Ala
            100                 105                 110

Glu Lys Lys Leu Lys Pro Ser Thr Asn Thr Lys Lys Lys Val Ser Phe
        115                 120                 125

Thr Pro Asn Glu Pro Gly Lys Tyr Thr Lys Leu Glu Lys Asp Ala Leu
    130                 135                 140

Asp Leu Leu Ser Asp Asn Glu Glu Glu Asp Ala Glu Ser Ser Ile Leu
145                 150                 155                 160

Thr Phe Glu Glu Arg Asp Thr Ser Ser Leu Ser Ile Glu Ala Arg Leu
                165                 170                 175
```

-continued

```
Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Val Arg Glu Glu Leu Ile Ala Asp Ile Ile Lys
    210                 215                 220

Glu Ala Lys Gly Lys Ala Ala Glu Met Met Glu Glu Glu Met Ser Gln
225                 230                 235                 240

Arg Ser Lys Ile Gly Asn Gly Ser Val Lys Leu Thr Glu Lys Ala Lys
                245                 250                 255

Glu Leu Asn Lys Ile Val Glu Asp Glu Ser Thr Ser Gly Glu Ser Glu
            260                 265                 270

Glu Glu Glu Glu Pro Lys Asp Thr Gln Asp Asn Ser Gln Glu Asp Asp
        275                 280                 285

Ile Tyr Gln Leu Ile Met
    290


<210> SEQ ID NO 375
<211> LENGTH: 294
<212> TYPE: PRT
<213> ORGANISM: human metapneumo virus

<400> SEQUENCE: 375

Met Ser Phe Pro Glu Gly Lys Asp Ile Leu Phe Met Gly Asn Glu Ala
 1               5                  10                  15

Ala Lys Leu Ala Glu Ala Phe Gln Lys Ser Leu Arg Lys Pro Asn His
            20                  25                  30

Lys Arg Ser Gln Ser Ile Ile Gly Glu Lys Val Asn Thr Val Ser Glu
        35                  40                  45

Thr Leu Glu Leu Pro Thr Ile Ser Arg Pro Thr Lys Pro Thr Ile Leu
    50                  55                  60

Ser Glu Pro Lys Leu Ala Trp Thr Asp Lys Gly Gly Ala Ile Lys Thr
65                  70                  75                  80

Glu Ala Lys Gln Thr Ile Lys Val Met Asp Pro Ile Glu Glu Glu Glu
                85                  90                  95

Phe Thr Glu Lys Arg Val Leu Pro Ser Ser Asp Gly Lys Thr Pro Ala
            100                 105                 110

Glu Lys Lys Leu Lys Pro Ser Thr Asn Thr Lys Lys Lys Val Ser Phe
        115                 120                 125

Thr Pro Asn Glu Pro Gly Lys Tyr Thr Lys Leu Glu Lys Asp Ala Leu
    130                 135                 140

Asp Leu Leu Ser Asp Asn Glu Glu Glu Asp Ala Glu Ser Ser Ile Leu
145                 150                 155                 160

Thr Phe Glu Glu Arg Asp Thr Ser Ser Leu Ser Ile Glu Ala Arg Leu
                165                 170                 175

Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Ile Arg Glu Glu Leu Ile Ala Asp Ile Ile Lys
    210                 215                 220

Glu Ala Lys Gly Lys Ala Ala Glu Met Met Glu Glu Glu Met Asn Gln
225                 230                 235                 240

Arg Thr Lys Ile Gly Asn Gly Ser Val Lys Leu Thr Glu Lys Ala Lys
                245                 250                 255
```

-continued

```
Glu Leu Asn Lys Ile Val Glu Asp Glu Ser Thr Ser Gly Glu Ser Glu
            260                 265                 270

Glu Glu Glu Glu Pro Lys Asp Thr Gln Glu Asn Asn Gln Glu Asp Asp
        275                 280                 285

Ile Tyr Gln Leu Ile Met
    290


<210> SEQ ID NO 376
<211> LENGTH: 294
<212> TYPE: PRT
<213> ORGANISM: human metapneumo virus

<400> SEQUENCE: 376

Met Ser Phe Pro Glu Gly Lys Asp Ile Leu Phe Met Gly Asn Glu Ala
 1               5                  10                  15

Ala Lys Ile Ala Glu Ala Phe Gln Lys Ser Leu Lys Lys Ser Gly His
            20                  25                  30

Lys Arg Thr Gln Ser Ile Val Gly Glu Lys Val Asn Thr Ile Ser Glu
        35                  40                  45

Thr Leu Glu Leu Pro Thr Ile Ser Lys Pro Ala Arg Ser Ser Thr Leu
    50                  55                  60

Leu Glu Pro Lys Leu Ala Trp Ala Asp Asn Ser Gly Ile Thr Lys Ile
65                  70                  75                  80

Thr Glu Lys Pro Ala Thr Lys Thr Thr Asp Pro Val Glu Glu Glu Glu
                85                  90                  95

Phe Asn Glu Lys Lys Val Leu Pro Ser Ser Asp Gly Lys Thr Pro Ala
            100                 105                 110

Glu Lys Lys Ser Lys Phe Ser Thr Ser Val Lys Lys Lys Val Ser Phe
        115                 120                 125

Thr Ser Asn Glu Pro Gly Lys Tyr Thr Lys Leu Glu Lys Asp Ala Leu
    130                 135                 140

Asp Leu Leu Ser Asp Asn Glu Glu Glu Asp Ala Glu Ser Ser Ile Leu
145                 150                 155                 160

Thr Phe Glu Glu Lys Asp Thr Ser Ser Leu Ser Ile Glu Ala Arg Leu
                165                 170                 175

Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Ile Arg Glu Glu Leu Ile Ala Glu Ile Ile Lys
    210                 215                 220

Glu Ala Lys Gly Lys Ala Ala Glu Met Met Glu Glu Glu Met Asn Gln
225                 230                 235                 240

Arg Ser Lys Ile Gly Asn Gly Ser Val Lys Leu Thr Glu Lys Ala Lys
                245                 250                 255

Glu Leu Asn Lys Ile Val Glu Asp Glu Ser Thr Ser Gly Glu Ser Glu
            260                 265                 270

Glu Glu Glu Glu Pro Lys Glu Thr Gln Asp Asn Asn Gln Gly Glu Asp
        275                 280                 285

Ile Tyr Gln Leu Ile Met
    290


<210> SEQ ID NO 377
<211> LENGTH: 294
<212> TYPE: PRT
```

-continued

<213> ORGANISM: human metapneumo virus

<400> SEQUENCE: 377

```
Met Ser Phe Pro Glu Gly Lys Asp Ile Leu Phe Met Gly Asn Glu Ala
 1               5                  10                  15

Ala Lys Ile Ala Glu Ala Phe Gln Lys Ser Leu Lys Arg Ser Gly His
            20                  25                  30

Lys Arg Thr Gln Ser Ile Val Gly Glu Lys Val Asn Thr Ile Ser Glu
        35                  40                  45

Thr Leu Glu Leu Pro Thr Ile Ser Lys Pro Ala Arg Ser Ser Thr Leu
    50                  55                  60

Leu Glu Pro Lys Leu Ala Trp Ala Asp Ser Ser Gly Ala Thr Lys Thr
65                  70                  75                  80

Thr Glu Lys Gln Thr Thr Lys Thr Thr Asp Pro Val Glu Glu Glu Glu
                85                  90                  95

Leu Asn Glu Lys Lys Val Ser Pro Ser Ser Asp Gly Lys Thr Pro Ala
            100                 105                 110

Glu Lys Lys Ser Lys Ser Pro Thr Asn Val Lys Lys Lys Val Ser Phe
        115                 120                 125

Thr Ser Asn Glu Pro Gly Lys Tyr Thr Lys Leu Glu Lys Asp Ala Leu
    130                 135                 140

Asp Leu Leu Ser Asp Asn Glu Glu Glu Asp Ala Glu Ser Ser Ile Leu
145                 150                 155                 160

Thr Phe Glu Glu Arg Asp Thr Ser Ser Leu Ser Ile Glu Ala Arg Leu
                165                 170                 175

Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Ile Arg Glu Glu Leu Ile Ala Glu Ile Ile Lys
    210                 215                 220

Glu Ala Lys Gly Lys Ala Ala Glu Met Met Glu Glu Glu Met Asn Gln
225                 230                 235                 240

Arg Ser Lys Ile Gly Asn Gly Ser Val Lys Leu Thr Glu Lys Ala Lys
                245                 250                 255

Glu Leu Asn Lys Ile Val Glu Asp Glu Ser Thr Ser Gly Glu Ser Glu
            260                 265                 270

Glu Glu Glu Glu Pro Lys Glu Thr Gln Asp Asn Asn Gln Gly Glu Asp
        275                 280                 285

Ile Tyr Gln Leu Ile Met
    290
```

<210> SEQ ID NO 378
<211> LENGTH: 885
<212> TYPE: DNA
<213> ORGANISM: human metapneumo virus

<400> SEQUENCE: 378

```
atgtcattcc ctgaaggaaa agatattctt ttcatgggta atgaagcagc aaaattagca      60

gaagctttcc agaaatcatt aagaaaacca ggtcataaaa gatctcaatc tattatagga     120

gaaaaagtga atactgtatc agaaacattg gaattaccta ctatcagtag acctgcaaaa     180

ccaaccatac cgtcagaacc aaagttagca tggacagata aaggtggggc aaccaaaact     240

gaaataaagc aagcaatcaa agtcatggat cccattgaag aagaagagtc taccgagaag     300
```

-continued

```
aaggtgctac cctccagtga tgggaaaacc cctgcagaaa agaaactgaa accatcaact    360

aacaccaaaa agaaggtttc atttacacca aatgaaccag ggaaatatac aaagttggaa    420

aaagatgctc tagatttgct ctcagataat gaagaagaag atgcagaatc ttcaatctta    480

acctttgaag aaagagatac ttcatcatta agcattgagg ccagattgga atcaatagag    540

gagaaattaa gcatgatatt agggctatta agaacactca acattgctac agcaggaccc    600

acagcagcaa gagatgggat cagagatgca atgattggcg taagagagga attaatagca    660

gacataataa aggaagctaa agggaaagca gcagaaatga tggaagagga aatgagtcaa    720

cgatcaaaaa taggaaatgg tagtgtaaaa ttaacagaaa aagcaaaaga gctcaacaaa    780

attgttgaag atgaaagcac aagtggagaa tccgaagaag aagaagaacc aaaagacaca    840

caagacaata gtcaagaaga tgacatttac cagttaatta tgtag                   885
```

<210> SEQ ID NO 379
<211> LENGTH: 885
<212> TYPE: DNA
<213> ORGANISM: human metapneumo virus

<400> SEQUENCE: 379

```
atgtcattcc ctgaaggaaa agatattctt ttcatgggta atgaagcagc aaaattggca     60

gaagcttttc aaaaatcatt aagaaaacct aatcataaaa gatctcaatc tattatagga    120

gaaaaagtga acactgtatc tgaaacattg gaattaccta ctatcagtag acctaccaaa    180

ccgaccatat tgtcagagcc gaagttagca tggacagaca aaggtggggc aatcaaaact    240

gaagcaaagc aaacaatcaa agttatggat cctattgaag aagaagagtt tactgagaaa    300

agggtgctgc cctccagtga tgggaaaact cctgcagaaa agaagttgaa accatcaacc    360

aacactaaaa agaaggtctc atttacacca aatgaaccag gaaaatacac aaagttggag    420

aaagatgctc tagacttgct ttcagacaat gaagaagaag atgcagaatc ctcaatctta    480

accttcgaag aaagagatac ttcatcatta agcattgaag ccagactaga atcgattgag    540

gagaaattaa gcatgatatt agggctatta agaacactca acattgctac agcaggaccc    600

acagcagcaa gagatgggat cagagatgca atgattggca taagggagga actaatagca    660

gacataataa aagaagccaa gggaaaagca gcagaaatga tggaagaaga aatgaaccag    720

cggacaaaaa taggaaacgg tagtgtaaaa ttaactgaaa aggcaaagga gctcaacaaa    780

attgttgaag acgaaagcac aagtggtgaa tccgaagaag aagaagaacc aaaagacaca    840

caggaaaata atcaagaaga tgacatttac cagttaatta tgtag                   885
```

<210> SEQ ID NO 380
<211> LENGTH: 885
<212> TYPE: DNA
<213> ORGANISM: human metapneumo virus

<400> SEQUENCE: 380

```
atgtcattcc ctgaaggaaa ggatattctg ttcatgggta atgaagcagc aaaaatagcc     60

gaagctttcc agaaatcact gaaaaaatca ggtcacaaga gaactcaatc tattgtaggg    120

gaaaaagtta acactatatc agaaactcta gaactaccta ccatcagcaa acctgcacga    180

tcatctacac tgctggaacc aaaattggca tgggcagaca acagcggaat caccaaaatc    240

acagaaaaac cagcaaccaa aacaacagat cctgttgaag aagaggaatt caatgaaaag    300

aaagtgttac cttccagtga tgggaagact cctgcagaga aaaaatcaaa gttttcaacc    360

agtgtaaaaa agaaagtttc ctttacatca aatgaaccag ggaaatacac caaactagag    420
```

-continued

```
aaagatgccc tagatttgct ctcagacaat gaggaagaag acgcagaatc ctcaatccta    480

acttttgagg agaaagatac atcatcacta agcattgaag ctagactaga atctatagaa    540

gagaagttga gcatgatatt aggactgctt cgtacactta acattgcaac agcaggacca    600

acagctgcac gagatggaat tagggatgca atgattggta taagagaaga gctaatagca    660

gagataatta aggaagccaa gggaaaagca gctgaaatga tggaagaaga gatgaatcaa    720

agatcaaaaa taggaaatgg cagtgtaaaa ctaaccgaga aggcaaaaga gctcaacaaa    780

attgttgaag acgagagcac aagcggtgaa tcagaagaag aagaagaacc aaaagaaact    840

caggataaca atcaaggaga agatatttat cagttaatca tgtag                    885
```

```
<210> SEQ ID NO 381
<211> LENGTH: 885
<212> TYPE: DNA
<213> ORGANISM: human metapneumo virus

<400> SEQUENCE: 381

atgtcattcc ctgaaggaaa agatatcctg ttcatgggta atgaagcagc aaaaatagca     60

gaagctttcc agaaatcact aaaaaagatca ggtcacaaaa gaacccagtc tattgtaggg    120

gaaaaagtaa acactatatc agaaactcta gagctaccta ccatcagcaa acctgcacga    180

tcatctacac tgctagagcc aaaattggca tgggcagaca gcagcggagc caccaaaacc    240

acagaaaaac aaacaaccaa aacaacagat cctgttgaag aagaggaact caatgaaaag    300

aaggtatcac cttccagtga tgggaagact cctgcagaga aaaaatcaaa atctccaacc    360

aatgtaaaaa agaaagtttc cttcacatca aatgaaccag ggaaatatac taaactagaa    420

aaagatgccc tagatttgct ctcagacaat gaggaagaag acgcagagtc ctcaatccta    480

acctttgaag agagagacac atcatcacta agcattgagg ctagactaga atcaatagaa    540

gagaagctaa gcatgatatt aggactgctt cgtacactta acattgcaac agcaggacca    600

acggctgcaa gggatggaat cagagatgca atgattggta taagagaaga actaatagca    660

gaaataataa aagaagcaaa gggaaaagca gccgaaatga tggaagagga aatgaatcaa    720

aggtcaaaaa taggtaatgg cagtgtaaaa ctaaccgaga aggcaaaaga acttaataaa    780

attgttgaag acgagagcac aagtggtgaa tcagaagaag aagaagaacc aaaagaaact    840

caggataaca atcaaggaga agatatctac cagttaatca tgtag                    885
```

```
<210> SEQ ID NO 382
<211> LENGTH: 183
<212> TYPE: PRT
<213> ORGANISM: human metapneumo virus

<400> SEQUENCE: 382

Met Ile Thr Leu Asp Val Ile Lys Ser Asp Gly Ser Ser Lys Thr Cys
1               5                   10                  15

Thr His Leu Lys Lys Ile Ile Lys Asp His Ser Gly Lys Val Leu Ile
            20                  25                  30

Val Leu Lys Leu Ile Leu Ala Leu Leu Thr Phe Leu Thr Val Thr Ile
        35                  40                  45

Thr Ile Asn Tyr Ile Lys Val Glu Asn Asn Leu Gln Ile Cys Gln Ser
    50                  55                  60

Lys Thr Glu Ser Asp Lys Lys Asp Ser Ser Ser Asn Thr Thr Ser Val
65                  70                  75                  80

Thr Thr Lys Thr Thr Leu Asn His Asp Ile Thr Gln Tyr Phe Lys Ser
```

-continued

```
                85                  90                  95

Leu Ile Gln Arg Tyr Thr Asn Ser Ala Ile Asn Ser Asp Thr Cys Trp
            100                 105                 110

Lys Ile Asn Arg Asn Gln Cys Thr Asn Ile Thr Thr Tyr Lys Phe Leu
        115                 120                 125

Cys Phe Lys Ser Glu Asp Thr Lys Thr Asn Asn Cys Asp Lys Leu Thr
    130                 135                 140

Asp Leu Cys Arg Asn Lys Pro Lys Pro Ala Val Gly Val Tyr His Ile
145                 150                 155                 160

Val Glu Cys His Cys Ile Tyr Thr Val Lys Trp Lys Cys Tyr His Tyr
                165                 170                 175

Pro Thr Asp Glu Thr Gln Ser
            180


<210> SEQ ID NO 383
<211> LENGTH: 179
<212> TYPE: PRT
<213> ORGANISM: human metapneumo virus

<400> SEQUENCE: 383

Met Ile Thr Leu Asp Val Ile Lys Ser Asp Gly Ser Ser Lys Thr Cys
 1               5                  10                  15

Thr His Leu Lys Lys Ile Ile Lys Asp His Ser Gly Lys Val Leu Ile
            20                  25                  30

Ala Leu Lys Leu Ile Leu Ala Leu Leu Thr Phe Phe Thr Ile Thr Ile
        35                  40                  45

Thr Ile Asn Tyr Ile Lys Val Glu Asn Asn Leu Gln Ile Cys Gln Ser
    50                  55                  60

Lys Thr Glu Ser Asp Lys Glu Asp Ser Pro Ser Asn Thr Thr Ser Val
65                  70                  75                  80

Thr Thr Lys Thr Thr Leu Asp His Asp Ile Thr Gln Tyr Phe Lys Arg
                85                  90                  95

Leu Ile Gln Arg Tyr Thr Asp Ser Val Ile Asn Lys Asp Thr Cys Trp
            100                 105                 110

Lys Ile Ser Arg Asn Gln Cys Thr Asn Ile Thr Thr Tyr Lys Phe Leu
        115                 120                 125

Cys Phe Lys Pro Glu Asp Ser Lys Ile Asn Ser Cys Asp Arg Leu Thr
    130                 135                 140

Asp Leu Cys Arg Asn Lys Ser Lys Ser Ala Ala Glu Ala Tyr His Thr
145                 150                 155                 160

Val Glu Cys His Cys Ile Tyr Thr Ile Glu Trp Lys Cys Tyr His His
                165                 170                 175

Pro Ile Asp


<210> SEQ ID NO 384
<211> LENGTH: 177
<212> TYPE: PRT
<213> ORGANISM: human metapneumo virus

<400> SEQUENCE: 384

Met Lys Thr Leu Asp Val Ile Lys Ser Asp Gly Ser Ser Glu Thr Cys
 1               5                  10                  15

Asn Gln Leu Lys Lys Ile Ile Lys Lys His Ser Gly Lys Val Leu Ile
            20                  25                  30

Ala Leu Lys Leu Ile Leu Ala Leu Leu Thr Phe Phe Thr Ala Thr Ile
        35                  40                  45
```

-continued

```
Thr Val Asn Tyr Ile Lys Val Glu Asn Asn Leu Gln Ala Cys Gln Pro
    50                  55                  60

Lys Asn Glu Ser Asp Lys Lys Val Thr Lys Pro Asn Thr Thr Ser Thr
65                  70                  75                  80

Thr Ile Arg Pro Thr Pro Asp Pro Thr Val Val His His Leu Lys Arg
                85                  90                  95

Leu Ile Gln Arg His Thr Asn Ser Val Thr Lys Asp Ser Asp Thr Cys
            100                 105                 110

Trp Arg Ile His Lys Asn Gln Arg Thr Asn Ile Lys Ile Tyr Lys Phe
        115                 120                 125

Leu Cys Ser Gly Phe Thr Asn Ser Lys Gly Thr Asp Cys Glu Glu Pro
    130                 135                 140

Thr Ala Leu Cys Asp Lys Lys Leu Lys Thr Ile Val Glu Lys His Arg
145                 150                 155                 160

Lys Ala Glu Cys His Cys Leu His Thr Thr Glu Trp Gly Cys Leu His
                165                 170                 175

Pro


<210> SEQ ID NO 385
<211> LENGTH: 177
<212> TYPE: PRT
<213> ORGANISM: human metapneumo virus

<400> SEQUENCE: 385

Met Lys Thr Leu Asp Val Ile Lys Ser Asp Gly Ser Ser Glu Thr Cys
 1               5                  10                  15

Asn Gln Leu Lys Lys Ile Ile Lys Lys His Ser Gly Lys Leu Leu Ile
            20                  25                  30

Ala Leu Lys Leu Ile Leu Ala Leu Leu Thr Phe Phe Thr Val Thr Ile
        35                  40                  45

Thr Val Asn Tyr Ile Lys Val Glu Asn Asn Leu Gln Ala Cys Gln Leu
    50                  55                  60

Lys Asn Glu Ser Asp Lys Lys Asp Thr Lys Leu Asn Thr Thr Ser Thr
65                  70                  75                  80

Thr Ile Arg Pro Ile Pro Asp Leu Asn Ala Val Gln Tyr Leu Lys Arg
                85                  90                  95

Leu Ile Gln Lys His Thr Asn Phe Val Ile Lys Asp Arg Asp Thr Cys
            100                 105                 110

Trp Arg Ile His Thr Asn Gln Cys Thr Asn Ile Lys Ile Tyr Lys Phe
        115                 120                 125

Leu Cys Phe Gly Phe Met Asn Ser Thr Asn Thr Asp Cys Glu Glu Leu
    130                 135                 140

Thr Val Leu Cys Asp Lys Lys Ser Lys Thr Met Thr Glu Lys His Arg
145                 150                 155                 160

Lys Ala Glu Cys His Cys Leu His Thr Thr Glu Trp Trp Cys Tyr Tyr
                165                 170                 175

Leu


<210> SEQ ID NO 386
<211> LENGTH: 552
<212> TYPE: DNA
<213> ORGANISM: human metapneumo virus

<400> SEQUENCE: 386

atgataacat tagatgtcat taaaagtgat gggtcttcaa aaacatgtac tcacctcaaa      60
```

-continued

```
aaaataatta aagaccactc tggtaaagtg cttattgtac ttaagttaat attagcttta    120

ctaacatttc tcacagtaac aatcaccatc aattatataa aagtggaaaa caatctgcaa    180

atatgccagt caaaaactga atcagacaaa aaggactcat catcaaatac cacatcagtc    240

acaaccaaga ctactctaaa tcatgatatc acacagtatt ttaaaagttt gattcaaagg    300

tatacaaact ctgcaataaa cagtgacaca tgctggaaaa taaacagaaa tcaatgcaca    360

aatataacaa catacaaatt tttatgtttt aaatctgaag acacaaaaac caacaattgt    420

gataaactga cagatttatg cagaaacaaa ccaaaaccag cagttggagt gtatcacata    480

gtagaatgcc attgtatata cacagttaaa tggaagtgct atcattaccc aaccgatgaa    540

acccaatcct aa                                                        552
```

```
<210> SEQ ID NO 387
<211> LENGTH: 540
<212> TYPE: DNA
<213> ORGANISM: human metapneumo virus

<400> SEQUENCE: 387

atgataacat tagatgtcat taaaagtgat gggtcttcaa aaacatgtac tcacctcaaa     60

aaaataatca aagaccattc tggtaaagtg cttattgcac ttaagttaat attagcttta    120

ctaacatttt tcacaataac aatcactata aattacataa aagtagaaaa caatctacaa    180

atatgccagt caaaaactga atcagacaaa gaagactcac catcaaatac cacatccgtc    240

acaaccaaga ctactctaga ccatgatata acacagtatt ttaaaagatt aattcaaagg    300

tatacagatt ctgtgataaa caaggacaca tgctggaaaa taagcagaaa tcaatgcaca    360

aatataacaa catataaatt tttatgcttt aaacctgagg actcaaaaat caacagttgt    420

gatagactga cagatctatg cagaaacaaa tcaaaatcag cagctgaagc atatcataca    480

gtagaatgcc attgcatata cacaattgag tggaagtgct atcaccaccc aatagattaa    540
```

```
<210> SEQ ID NO 388
<211> LENGTH: 534
<212> TYPE: DNA
<213> ORGANISM: human metapneumo virus

<400> SEQUENCE: 388

atgaaaacat tagatgtcat aaaaagtgat ggatcctcag aaacgtgtaa tcaactcaaa     60

aaaataataa aaaaacactc aggtaaagtg cttattgcac taaaactgat attggcctta    120

ctgacatttt tcacagcaac aatcactgtc aactatataa aagtagaaaa caatttgcag    180

gcatgtcaac caaaaaatga atcagacaaa aaggtcacaa agccaaatac cacatcaaca    240

acaatcagac ccacacccga tccaactgta gtacatcatt tgaaaaggct gattcagaga    300

cacaccaact ctgtcacaaa agacagcgat acttgttgga gaatacacaa gaatcaacgt    360

acaaatataa aaatatacaa gttcttatgc tctgggttca caaattcaaa aggtacagat    420

tgtgaggaac caacagccct atgcgacaaa aagttaaaaa ccatagtaga aaaacataga    480

aaagcagaat gtcactgtct acatacaacc gagtgggggt gccttcatcc ctaa          534
```

```
<210> SEQ ID NO 389
<211> LENGTH: 534
<212> TYPE: DNA
<213> ORGANISM: human metapneumo virus

<400> SEQUENCE: 389
```

-continued

```
atgaaaacat tagatgtcat aaaaagtgat ggatcctcag aaacatgtaa tcaactcaaa      60

aaaataataa aaaaacactc aggtaaattg cttattgcat taaaactgat attggcctta     120

ttgacgtttt tcacagtaac aattactgtt aactatataa aagtagaaaa caatttgcag     180

gcatgtcaat taaaaaatga atcagacaaa aaggacacaa agctaaatac cacatcaaca     240

acaatcagac ccattcctga tctaaatgca gtacagtact tgaaaaggct gattcagaaa     300

cacaccaact ttgtcataaa agacagagat acctgttgga gaatacacac gaatcaatgc     360

acaaatataa aaatatataa gttcttatgt ttcgggttta tgaattcaac aaatacagac     420

tgtgaagaac taacagtttt atgtgataaa aagtcaaaaa ccatgacaga aaaacatagg     480

aaagcagagt gtcactgtct acatacaacc gagtggtggt gttattatct ttaa           534


<210> SEQ ID NO 390

<400> SEQUENCE: 390

000


<210> SEQ ID NO 391

<400> SEQUENCE: 391

000


<210> SEQ ID NO 392

<400> SEQUENCE: 392

000


<210> SEQ ID NO 393
<211> LENGTH: 7
<212> TYPE: DNA
<213> ORGANISM: human metapneumo virus
<220> FEATURE:
<221> NAME/KEY: VARIANT
<222> LOCATION: 7
<223> OTHER INFORMATION: h = u or a or c
<220> FEATURE:
<223> OTHER INFORMATION: Non-coding sequence of hMPV islolate 00-1 (A1)

<400> SEQUENCE: 393

uaaaaah                                                                 7


<210> SEQ ID NO 394
<211> LENGTH: 20
<212> TYPE: DNA
<213> ORGANISM: Artificial Sequence
<220> FEATURE:
<223> OTHER INFORMATION: Leader region sequence of hMPV

<400> SEQUENCE: 394

acgcgaaaaa aacgcgtata                                                  20


<210> SEQ ID NO 395
<211> LENGTH: 4
<212> TYPE: PRT
<213> ORGANISM: human metapneumo virus

<400> SEQUENCE: 395

Arg Gln Ser Arg
 1
```

-continued

```
<210> SEQ ID NO 396
<211> LENGTH: 4
<212> TYPE: PRT
<213> ORGANISM: human metapneumo virus

<400> SEQUENCE: 396

Arg Gln Pro Arg
 1


<210> SEQ ID NO 397
<211> LENGTH: 49
<212> TYPE: PRT
<213> ORGANISM: human metapneumo virus
<220> FEATURE:
<221> NAME/KEY: VARIANT
<222> LOCATION: 2-22
<223> OTHER INFORMATION: Xaa = any amino acid
<220> FEATURE:
<221> NAME/KEY: VARIANT
<222> LOCATION: 29-48
<223> OTHER INFORMATION: Xaa = any amino acid

<400> SEQUENCE: 397

Lys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Gly Glu Gly Ala Gly Asn Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Lys


<210> SEQ ID NO 398
<211> LENGTH: 49
<212> TYPE: PRT
<213> ORGANISM: human metapneumo virus
<220> FEATURE:
<221> NAME/KEY: VARIANT
<222> LOCATION: 2-23
<223> OTHER INFORMATION: Xaa = any amino acid
<220> FEATURE:
<221> NAME/KEY: VARIANT
<222> LOCATION: 30-48
<223> OTHER INFORMATION: Xaa = any amino acid

<400> SEQUENCE: 398

Lys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Gly Glu Gly Ala Gly Asn Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Lys


<210> SEQ ID NO 399
<211> LENGTH: 20
<212> TYPE: DNA
<213> ORGANISM: Artificial sequence
<220> FEATURE:
<223> OTHER INFORMATION: L-forward primer sequence of hMPV

<400> SEQUENCE: 399

caccccagtc tttcttgaaa                                                  20


<210> SEQ ID NO 400
<211> LENGTH: 22
```

-continued

<212> TYPE: DNA
<213> ORGANISM: Artificial sequence
<220> FEATURE:
<223> OTHER INFORMATION: N-forward primer sequence of hMPV

<400> SEQUENCE: 400
catgctatat taaaagagtc tc 22

<210> SEQ ID NO 401
<211> LENGTH: 21
<212> TYPE: DNA
<213> ORGANISM: Artificial sequence
<220> FEATURE:
<223> OTHER INFORMATION: N-reverse primer sequence of hMPV

<400> SEQUENCE: 401
tctgcagcat atttgtaatc a 21

<210> SEQ ID NO 402
<211> LENGTH: 29
<212> TYPE: DNA
<213> ORGANISM: Artificial sequence
<220> FEATURE:
<223> OTHER INFORMATION: Biotin-labeled N-probe sequence

<400> SEQUENCE: 402
acaactgcag tgacaccttc atcattgca 29

<210> SEQ ID NO 403
<211> LENGTH: 28
<212> TYPE: DNA
<213> ORGANISM: Artificial sequence
<220> FEATURE:
<223> OTHER INFORMATION: Biotin-labeled L-probe sequence

<400> SEQUENCE: 403
ctgttaatat cccacaccag tggcatgc 28

<210> SEQ ID NO 404
<211> LENGTH: 27
<212> TYPE: DNA
<213> ORGANISM: Artificial sequence
<220> FEATURE:
<223> OTHER INFORMATION: Medi-N-foward Taqman primer

<400> SEQUENCE: 404
caacaacata atgctaggac atgtatc 27

<210> SEQ ID NO 405
<211> LENGTH: 24
<212> TYPE: DNA
<213> ORGANISM: Artificial sequence
<220> FEATURE:
<223> OTHER INFORMATION: Medi-N-reverse Taqman primer

<400> SEQUENCE: 405
ccgagaacaa cactagcaaa gttg 24

<210> SEQ ID NO 406
<211> LENGTH: 28
<212> TYPE: DNA
<213> ORGANISM: Artificial sequence
<220> FEATURE:
<223> OTHER INFORMATION: Medi-N-probe sequence

<400> SEQUENCE: 406

-continued tggtgcgaga aatgggtcct gaatctgg 28

<210> SEQ ID NO 407
<211> LENGTH: 30
<212> TYPE: DNA
<213> ORGANISM: Artificial sequence
<220> FEATURE:
<223> OTHER INFORMATION: RF930 primer sequence for assay NL-N

<400> SEQUENCE: 407
catataagca tgctatatta aaagagtctc 30

<210> SEQ ID NO 408
<211> LENGTH: 28
<212> TYPE: DNA
<213> ORGANISM: Artificial sequence
<220> FEATURE:
<223> OTHER INFORMATION: RF931 primer for assay NL-N

<400> SEQUENCE: 408
cctatttctg cagcatattt gtaatcag 28

<210> SEQ ID NO 409
<211> LENGTH: 28
<212> TYPE: DNA
<213> ORGANISM: Artificial sequence
<220> FEATURE:
<223> OTHER INFORMATION: RF928 primer sequence for assay NL-N
<220> FEATURE:
<221> NAME/KEY: variation
<222> LOCATION: 3
<223> OTHER INFORMATION: y = c or t

<400> SEQUENCE: 409
tgyaatgatg agggtgtcac tgcggttg 28

<210> SEQ ID NO 410
<211> LENGTH: 46
<212> TYPE: PRT
<213> ORGANISM: human metapneumo virus

<400> SEQUENCE: 410

```
Lys Thr Ile Arg Leu Glu Ser Glu Val Thr Ala Ile Lys Asn Ala Leu
 1               5                  10                  15

Lys Lys Thr Asn Glu Ala Val Ser Thr Leu Gly Asn Gly Val Arg Val
            20                  25                  30

Leu Ala Thr Ala Val Arg Glu Leu Lys Asp Phe Val Ser Lys
        35                  40                  45
```

<210> SEQ ID NO 411
<211> LENGTH: 46
<212> TYPE: PRT
<213> ORGANISM: human metapneumo virus

<400> SEQUENCE: 411

```
Lys Thr Ile Arg Leu Glu Ser Glu Val Thr Ala Ile Lys Asn Ala Leu
 1               5                  10                  15

Lys Thr Thr Asn Glu Ala Val Ser Thr Leu Gly Asn Gly Val Arg Val
            20                  25                  30

Leu Ala Thr Ala Val Arg Glu Leu Lys Asp Phe Val Ser Lys
        35                  40                  45
```

<210> SEQ ID NO 412
<211> LENGTH: 46

-continued

```
<212> TYPE: PRT
<213> ORGANISM: human metapneumo virus

<400> SEQUENCE: 412

Lys Thr Ile Arg Leu Glu Ser Glu Val Asn Ala Ile Lys Gly Ala Leu
 1               5                  10                  15

Lys Gln Thr Asn Glu Ala Val Ser Thr Leu Gly Asn Gly Val Arg Val
            20                  25                  30

Leu Ala Thr Ala Val Arg Glu Leu Lys Glu Phe Val Ser Lys
        35                  40                  45


<210> SEQ ID NO 413
<211> LENGTH: 46
<212> TYPE: PRT
<213> ORGANISM: human metapneumo virus

<400> SEQUENCE: 413

Lys Thr Ile Arg Leu Glu Ser Glu Val Asn Ala Ile Lys Gly Ala Leu
 1               5                  10                  15

Lys Thr Thr Asn Glu Ala Val Ser Thr Leu Gly Asn Gly Val Arg Val
            20                  25                  30

Leu Ala Thr Ala Val Arg Glu Leu Lys Glu Phe Val Ser Lys
        35                  40                  45


<210> SEQ ID NO 414
<211> LENGTH: 29
<212> TYPE: PRT
<213> ORGANISM: human metapneumo virus

<400> SEQUENCE: 414

Asn Val Ala Leu Asp Gln Val Phe Glu Ser Ile Glu Asn Ser Gln Ala
 1               5                  10                  15

Leu Val Asp Gln Ser Asn Arg Ile Leu Ser Ser Ala Glu
            20                  25


<210> SEQ ID NO 415
<211> LENGTH: 29
<212> TYPE: PRT
<213> ORGANISM: human metapneumo virus

<400> SEQUENCE: 415

Asn Val Ala Leu Asp Gln Val Phe Glu Asn Ile Glu Asn Ser Gln Ala
 1               5                  10                  15

Leu Val Asp Gln Ser Asn Arg Ile Leu Ser Ser Ala Glu
            20                  25


<210> SEQ ID NO 416
<211> LENGTH: 29
<212> TYPE: PRT
<213> ORGANISM: human metapneumo virus

<400> SEQUENCE: 416

Asn Val Ala Leu Asp Gln Val Phe Glu Ser Ile Glu Asn Ser Gln Ala
 1               5                  10                  15

Leu Val Asp Gln Ser Asn Lys Ile Leu Asn Ser Ala Glu
            20                  25


<210> SEQ ID NO 417
<211> LENGTH: 29
<212> TYPE: PRT
<213> ORGANISM: human metapneumo virus
```

-continued

```
<400> SEQUENCE: 417

Asn Val Ala Leu Asp Gln Val Phe Glu Ser Ile Glu Asn Ser Gln Ala
 1               5                  10                  15

Leu Val Asp Gln Ser Asn Lys Ile Leu Asn Ser Ala Glu
            20                  25


<210> SEQ ID NO 418
<211> LENGTH: 33
<212> TYPE: DNA
<213> ORGANISM: Artificial Sequence
<220> FEATURE:
<223> OTHER INFORMATION: hMPV, BspEI, +4741 primer sequence

<400> SEQUENCE: 418

ggacaaatca taacgttccg gaaggctccg tgc                                    33


<210> SEQ ID NO 419
<211> LENGTH: 33
<212> TYPE: DNA
<213> ORGANISM: Artificial Sequence
<220> FEATURE:
<223> OTHER INFORMATION: hMPV, BspEI,  - 4741 primer sequence

<400> SEQUENCE: 419

gcacggagcc ttccggaacg ttatgatttg tcc                                    33


<210> SEQ ID NO 420
<211> LENGTH: 37
<212> TYPE: DNA
<213> ORGANISM: Artificial Sequence
<220> FEATURE:
<223> OTHER INFORMATION: hMPV, BspEI, +5444 primer sequence

<400> SEQUENCE: 420

catagaaatt atatatgtcc ggacttactt aagttag                                37


<210> SEQ ID NO 421
<211> LENGTH: 33
<212> TYPE: DNA
<213> ORGANISM: Artificial Sequence
<220> FEATURE:
<223> OTHER INFORMATION: hMPV, BspEI, -5444 primer sequence

<400> SEQUENCE: 421

ctaacttaag taagtccgga catatataat ttc                                    33


<210> SEQ ID NO 422
<211> LENGTH: 33
<212> TYPE: DNA
<213> ORGANISM: Artificial Sequence
<220> FEATURE:
<223> OTHER INFORMATION: hMPV, Nhe I, + 4744 primer sequence

<400> SEQUENCE: 422

ggacaaatca taacggctag caaggctccg tgc                                    33


<210> SEQ ID NO 423
<211> LENGTH: 33
<212> TYPE: DNA
<213> ORGANISM: Artificial Sequence
<220> FEATURE:
<223> OTHER INFORMATION: hMPV, Nhe I, -4744 primer sequence

<400> SEQUENCE: 423

gcacggagcc ttgctagccg ttatgatttg tcc                                    33
```

-continued

<210> SEQ ID NO 424
<211> LENGTH: 36
<212> TYPE: DNA
<213> ORGANISM: Artificial Sequence
<220> FEATURE:
<223> OTHER INFORMATION: hMPV, NheI, +5241 primer sequence

<400> SEQUENCE: 424
cttatcagca ggtgctagca atgactcttc atatgc 36

<210> SEQ ID NO 425
<211> LENGTH: 36
<212> TYPE: DNA
<213> ORGANISM: Artificial Sequence
<220> FEATURE:
<223> OTHER INFORMATION: hMPV, NheI, -5241 primer sequence

<400> SEQUENCE: 425
gcatatgaag agtcattgct agcacctgct gataag 36

<210> SEQ ID NO 426
<211> LENGTH: 35
<212> TYPE: DNA
<213> ORGANISM: Artificial Sequence
<220> FEATURE:
<223> OTHER INFORMATION: hMPV,SwaI,+5311 primer sequence

<400> SEQUENCE: 426
cagtgagcat ggtccaattt aaattactat agagg 35

<210> SEQ ID NO 427
<211> LENGTH: 35
<212> TYPE: DNA
<213> ORGANISM: Artificial Sequence
<220> FEATURE:
<223> OTHER INFORMATION: hMPV,SwaI, -5311 primer sequence

<400> SEQUENCE: 427
cctctatagt aatttaaatt ggaccatgct cactg 35

<210> SEQ ID NO 428
<211> LENGTH: 37
<212> TYPE: DNA
<213> ORGANISM: Artificial Sequence
<220> FEATURE:
<223> OTHER INFORMATION: hMPV,SwaI,+5453 primer sequence

<400> SEQUENCE: 428
catagaaatt atatatgtca aggcttattt aaattag 37

<210> SEQ ID NO 429
<211> LENGTH: 37
<212> TYPE: DNA
<213> ORGANISM: Artificial Sequence
<220> FEATURE:
<223> OTHER INFORMATION: hMPV,SwaI, -5453 primer sequence

<400> SEQUENCE: 429
ctaatttaaa taagccttga catatataat ttctatg 37

<210> SEQ ID NO 430
<211> LENGTH: 45
<212> TYPE: DNA
<213> ORGANISM: Artificial Sequence
<220> FEATURE:

-continued

```
<223> OTHER INFORMATION: hMPV SacII +5472  primer sequence

<400> SEQUENCE: 430

ggcttactta agttagtaaa aacaccgcgg agtgggataa atgac                 45


<210> SEQ ID NO 431
<211> LENGTH: 45
<212> TYPE: DNA
<213> ORGANISM: Artificial Sequence
<220> FEATURE:
<223> OTHER INFORMATION: hMPV SacII -5472  primer sequence

<400> SEQUENCE: 431

gtcatttatc ccactccgcg gtgtttttac taacttaagt aagcc                 45


<210> SEQ ID NO 432
<211> LENGTH: 42
<212> TYPE: DNA
<213> ORGANISM: Artificial Sequence
<220> FEATURE:
<223> OTHER INFORMATION: hMPV SacII +6026 primer sequence

<400> SEQUENCE: 432

ctatcattac ccaaccgcgg aaacccaatc ctaaatgtta ac                    42


<210> SEQ ID NO 433
<211> LENGTH: 42
<212> TYPE: DNA
<213> ORGANISM: Artificial Sequence
<220> FEATURE:
<223> OTHER INFORMATION: hMPV SacII -6026 primer sequence

<400> SEQUENCE: 433

gttaacattt aggattgggt ttccgcggtt gggtaatgat ag                    42
```

METAPNEUMOVIRUS STRAINS AND THEIR USE IN VACCINE FORMULATIONS AND AS VECTORS FOR EXPRESSION OF ANTIGENIC SEQUENCES AND METHODS FOR PROPAGATING VIRUS

RELATED APPLICATIONS

This application claims the benefit of priority of U.S. provisional application Nos. 60/465,811 filed Apr. 25, 2003; 60/466,776 filed Apr. 30, 2003; 60/480,658 filed Jun. 20, 2003; 60/498,640 filed Aug. 28, 2003; and 60/550,911 filed Mar. 5, 2004, the entire disclosures of which are incorporated by reference herein in their entireties.

1. INTRODUCTION

The invention relates to an isolated mammalian negative strand RNA virus, *metapneumovirus* (MPV), within the sub-family *Pneumoviridae*, of the family Paramyxoviridae. The present invention also relates to isolated mammalian negative strand RNA viruses identifiable as phylogenetically corresponding or relating to the genus *Metapneumovirus* and components thereof. The invention relates to genomic nucleotide sequences of different isolates of mammalian *metapneumoviruses*, in particular human *metapneumoviruses*. The invention relates to the use of the sequence information of different isolates of mammalian *metapneumoviruses* for diagnostic and therapeutic methods. The present invention relates to nucleotide sequences encoding the genome of a *metapneumovirus* or a portion thereof, including both mammalian and avian *metapneumovirus*. The invention further encompasses chimeric or recombinant viruses encoded by said nucleotide sequences. The invention also relates to chimeric and recombinant mammalian MPV that comprise one or more non-native or heterologous sequences. The invention further relates to vaccine formulations comprising mammalian or avian *metapneumovirus*, including recombinant and chimeric forms of said viruses. The vaccine preparations of the invention encompass multivalent vaccines, including bivalent and trivalent vaccine preparations.

A copy of the Sequence Listing is herein described in this application as Table 15.

2. BACKGROUND OF THE INVENTION

Classically, as devastating agents of disease, *paramyxoviruses* account for many animal and human deaths worldwide each year. The Paramyxoviridae form a family within the order of Mononegavirales (negative-sense single stranded RNA viruses), consisting of the sub-families Paramyxovirinae and *Pneumovirinae*. The latter sub-family is at present taxonomically divided in the genera *Pneumovirus* and *Metapneumovirus* (Pringle, 1999, Arch. Virol. 144/2, 2065-2070). Human respiratory syncytial virus (hRSV), a species of the *Pneumovirus* genus, is the single most important cause of lower respiratory tract infections during infancy and early childhood worldwide (Domachowske, & Rosenberg, 1999, Clin. Microbio. Rev. 12(2): 298-309). Other members of the *Pneumovirus* genus include the bovine and ovine respiratory syncytial viruses and pneumonia virus of mice (PVM).

In the past decades several etiological agents of mammalian disease, in particular of respiratory tract illnesses (RTI), in particular of humans, have been identified (Evans, In: Viral Infections of Humans, Epidemiology and Control. 3th edn. (ed. Evans, A. S) 22-28 (Plenum Publishing Corporation, New York, 1989)). Classical etiological agents of RTI with mammals are respiratory syncytial viruses belonging to the genus *Pneumovirus* found with humans (hRSV) and ruminants such as cattle or sheep (bRSV and/or oRSV). In human RSV differences in reciprocal cross neutralization assays, reactivity of the G proteins in immunological assays and nucleotide sequences of the G gene are used to define two hRSV antigenic subgroups. Within the subgroups the amino acid sequences show 94% (subgroup A) or 98% (subgroup B) identity, while only 53% amino acid sequence identity is found between the subgroups. Additional variability is observed within subgroups based on monoclonal antibodies, RT-PCR assays and RNAse protection assays. Viruses from both subgroups have a worldwide distribution and may occur during a single season. Infection may occur in the presence of pre-existing immunity and the antigenic variation is not strictly required to allow re-infection. See, for example Sullender, 2000, Clinical Microbiology Reviews 13(1): 1-15; Collins et al. Fields Virology, ed. B. N. Knipe, Howley, P. M. 1996, Philadelphia: Lippencott-Raven. 1313-1351; Johnson et al., 1987, (Proc Natl Acad Sci USA, 84(16): 5625-9; Collins, in The *Paramyxoviruses*, D. W. Kingsbury, Editor. 1991, Plenum Press: New York. p. 103-153.

Another classical *Pneumovirus* is the pneumonia virus of mice (PVM), in general only found with laboratory mice. However, a proportion of the illnesses observed among mammals can still not be attributed to known pathogens.

2.1 Avian *Metapneumovirus*

Respiratory disease caused by an avian *pneumovirus* (APV) was first described in South Africa in the late 1970s (Buys et al., 1980, Turkey 28:36-46) where it had a devastating effect on the turkey industry. The disease in turkeys was characterized by sinusitis and rhinitis and was called turkey rhinotracheitis (TRT). The European isolates of APV have also been strongly implicated as factors in swollen head syndrome (SHS) in chickens (O'Brien, 1985, Vet. Rec. 117:619-620). Originally, the disease appeared in broiler chicken flocks infected with Newcastle disease virus (NDV) and was assumed to be a secondary problem associated with Newcastle disease (ND). Antibody against European APV was detected in affected chickens after the onset of SHS (Cook et al., 1988, Avian Pathol. 17:403-410), thus implicating APV as the cause.

Avian *pneumovirus* (APV) also known as turkey rhinotracheitis virus (TRTV), the aetiological agent of avian rhinotracheitis, an upper respiratory tract infection of turkeys (Giraud et al., 1986, Vet. Res. 119:606-607), is the sole member of the recently assigned *Metapneumovirus* genus, which, as said was until now not associated with infections, or what is more, with disease of mammals. Serological subgroups of APV can be differentiated on the basis of nucleotide or amino acid sequences of the G glycoprotein and neutralization tests using monoclonal antibodies that also recognize the G glycoprotein. However, other differences in the nucleotide and amino acid sequences can be used to distinguish serological subgroups of APV. Within subgroups A, B and D, the G protein shows 98.5 to 99.7% aa sequence identity within subgroups while between the subgroups only 31.2-38% aa identity is observed. See for example Collins et al., 1993, Avian Pathology, 22: p. 469-479; Cook et al., 1993, Avian Pathology, 22: 257-273; Bayon-Auboyer et al., J Gen Virol, 81(Pt 11): 2723-33; Seal, 1998, Virus Res, 58(1-2): 45-52; Bayon-Auboyer et al., 1999, Arch Virol, 144(6): 91-109; Juhasz, et al., 1994, J Gen Virol, 75(Pt 11): 2873-80.

A further serotype of APV is provided in WO00/20600, incorporated by reference herein, which describes the Colorado isolate of APV and compared it to known APV or TRT strains with in vitro serum neutralization tests. First, the Colorado isolate was tested against monospecific polyclonal antisera to recognized TRT isolates. The Colorado isolate was not neutralized by monospecific antisera to any of the TRT strains. It was, however, neutralized by a hyperimmune antiserum raised against a subgroup A strain. This antiserum neutralized the homologous virus to a titre of 1:400 and the Colorado isolate to a titer of 1:80. Using the above method, the Colorado isolate was then tested against TRT monoclonal antibodies. In each case, the reciprocal neutralization titer was <10. Monospecific antiserum raised to the Colorado isolate was also tested against TRT strains of both subgroups. None of the TRT strains tested were neutralized by the antiserum to the Colorado isolate.

The Colorado strain of APV does not protect SPF chicks against challenge with either a subgroup A or a subgroup B strain of TRT virus. These results suggest that the Colorado isolate may be the first example of a further serotype of avian *pneumovirus* (See, Bayon-Auboyer et al., 2000, J. Gen. Vir. 81:2723-2733).

The avian *pneumovirus* is a single stranded, non-segmented RNA virus that belongs to the sub-family *Pneumovirinae* of the family Paramyxoviridae, genus *metapneumovirus* (Cavanagh and Barrett, 1988, Virus Res. 11:241-256; Ling et al., 1992, J. Gen. Virol. 73:1709-1715; Yu et al., 1992, J. Gen. Virol. 73:1355-1363). The Paramyxoviridae family is divided into two sub-families: the Paramyxovirinae and *Pneumovirinae*. The subfamily Paramyxovirinae includes, but is not limited to, the genera: *Paramyxovirus, Rubulavirus*, and *Morbillivirus*. Recently, the sub-family *Pneumovirinae* was divided into two genera based on gene order, and sequence homology, i.e. *pneumovirus* and *metapneumovirus* (Naylor et al., 1998, J. Gen. Virol., 79:1393-1398; Pringle, 1998, Arch. Virol. 143:1449-1159). The *pneumovirus* genus includes, but is not limited to, human respiratory syncytial virus (hRSV), bovine respiratory syncytial virus (bRSV), ovine respiratory syncytial virus, and mouse *pneumovirus*. The *metapneumovirus* genus includes, but is not limited to, European avian *pneumovirus* (subgroups A and B), which is distinguished from hRSV, the type species for the genus *pneumovirus* (Naylor et al., 1998, J. Gen. Virol., 79:1393-1398; Pringle, 1998, Arch. Virol. 143:1449-1159). The US isolate of APV represents a third subgroup (subgroup C) within *metapneumovirus* genus because it has been found to be antigenically and genetically different from European isolates (Seal, 1998, Virus Res. 58:45-52; Senne et al., 1998, In: Proc. 47th WPDC, California, pp. 67-68).

Electron microscopic examination of negatively stained APV reveals pleomorphic, sometimes spherical, virions ranging from 80 to 200 nm in diameter with long filaments ranging from 1000 to 2000 nm in length (Collins and Gough, 1988, J. Gen. Virol. 69:909-916). The envelope is made of a membrane studded with spikes 13 to 15 nm in length. The nucleocapsid is helical, 14 nm in diameter and has 7 nm pitch. The nucleocapsid diameter is smaller than that of the genera *Paramyxovirus* and *Morbillivirus*, which usually have diameters of about 18 nm.

Avian *pneumovirus* infection is an emerging disease in the USA despite its presence elsewhere in the world in poultry for many years. In May 1996, a highly contagious respiratory disease of turkeys appeared in Colorado, and an APV was subsequently isolated at the National Veterinary Services Laboratory (NVSL) in Ames, Iowa (Senne et al., 1997, Proc. 134th Ann. Mtg., AVMA, pp. 190). Prior to this time, the United States and Canada were considered free of avian *pneumovirus* (Pearson et al., 1993, In: Newly Emerging and Re-emerging Avian Diseases: Applied Research and Practical Applications for Diagnosis and Control, pp. 78-83; Hecker and Myers, 1993, Vet. Rec. 132:172). Early in 1997, the presence of APV was detected serologically in turkeys in Minnesota. By the time the first confirmed diagnosis was made, APV infections had already spread to many farms. The disease is associated with clinical signs in the upper respiratory tract: foamy eyes, nasal discharge and swelling of the sinuses. It is exacerbated by secondary infections. Morbidity in infected birds can be as high as 100%. The mortality can range from 1 to 90% and is highest in six to twelve week old poults.

Avian *pneumovirus* is transmitted by contact. Nasal discharge, movement of affected birds, contaminated water, contaminated equipment; contaminated feed trucks and load-out activities can contribute to the transmission of the virus. Recovered turkeys are thought to be carriers. Because the virus is shown to infect the epithelium of the oviduct of laying turkeys and because APV has been detected in young poults, egg transmission is considered a possibility.

2.2 PIV Infections

Parainfluenza viral infection results in serious respiratory tract disease in infants and children. (Tao et al., 1999, Vaccine 17: 1100-08). Infectious parainfluenza viral infections account for approximately 20% of all hospitalizations of pediatric patients suffering from respiratory tract infections worldwide. Id.

PIV is a member of the genus *respirovirus* (PIV1, PIV3) or *rubulavirus* (PIV2, PIV4) of the paramyxoviridae family. PIV is made up of two structural modules: (1) an internal ribonucleoprotein core, or nucleocapsid, containing the viral genome, and (2) an outer, roughly spherical lipoprotein envelope. Its genome is a single strand of negative sense RNA, approximately 15,456 nucleotides in length, encoding at least eight polypeptides. These proteins include, but are not limited to, the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins of unknown function. Id.

The parainfluenza nucleocapsid protein (NP, NC, or N) consists of two domains within each protein unit including an amino-terminal domain, comprising about two-thirds of the molecule, which interacts directly with the RNA, and a carboxyl-terminal domain, which lies on the surface of the assembled nucleocapsid. A hinge is thought to exist at the junction of these two domains thereby imparting some flexibility to this protein (see Fields et al. (ed.), 1991, Fundamental Virology, Second Edition, Raven Press, New York, incorporated by reference herein in its entirety). The matrix protein (M), is apparently involved with viral assembly and interacts with both the viral membrane as well as the nucleocapsid proteins. The phosphoprotein (P), which is subject to phosphorylation, is thought to play a regulatory role in transcription, and may also be involved in methylation, phosphorylation and polyadenylation. The fusion glycoprotein (F) interacts with the viral membrane and is first produced as an inactive precursor, then cleaved post-translationally to produce two disulfide linked polypeptides. The active F protein is also involved in penetration of the parainfluenza virion into host cells by facilitating fusion of the viral envelope with the host cell plasma membrane. Id. The glycoprotein, hemagglutinin-neuraminidase (HN), protrudes from the envelope allowing the virus to contain both hemagglutinin and neuraminidase activities. HN is strongly hydrophobic at its amino terminal which functions to anchor the HN protein into the lipid bilayer. Id. Finally, the large polymerase protein (L) plays an important role in both transcription and replication. Id.

2.3 RSV Infections

Respiratory syncytial virus (RSV) is the leading cause of serious lower respiratory tract disease in infants and children (Feigen et al., eds., 1987, In: Textbook of Pediatric Infectious Diseases, W B Saunders, Philadelphia at pages 1653-1675; New Vaccine Development, Establishing Priorities, Vol. 1, 1985, National Academy Press, Washington D.C. at pages 397-409; and Ruuskanen et al., 1993, Curr. Probl. Pediatr. 23:50-79). The yearly epidemic nature of RSV infection is evident worldwide, but the incidence and severity of RSV disease in a given season vary by region (Hall, 1993, Contemp. Pediatr. 10:92-110). In temperate regions of the northern hemisphere, it usually begins in late fall and ends in late spring. Primary RSV infection occurs most often in children from 6 weeks to 2 years of age and uncommonly in the first 4 weeks of life during nosocomial epidemics (Hall et al., 1979, New Engl. J. Med. 300:393-396). Children at increased risk for RSV infection include, but are not limited to, preterm infants (Hall et al., 1979, New Engl. J. Med. 300:393-396) and children with bronchopulmonary dysplasia (Groothuis et al., 1988, Pediatrics 82:199-203), congenital heart disease (MacDonald et al., New Engl. J. Med. 307:397-400), congenital or acquired immunodeficiency (Ogra et al., 1988, Pediatr. Infect. Dis. J. 7:246-249; and Pohl et al., 1992, J. Infect. Dis. 165:166-169), and cystic fibrosis (Abman et al., 1988, J. Pediatr. 113:826-830). The fatality rate in infants with heart or lung disease who are hospitalized with RSV infection is 3%-4% (Navas et al., 1992, J. Pediatr. 121:348-354).

RSV infects adults as well as infants and children. In healthy adults, RSV causes predominantly upper respiratory tract disease. It has recently become evident that some adults, especially the elderly, have symptomatic RSV infections more frequently than had been previously reported (Evans, A. S., eds., 1989, Viral Infections of Humans. Epidemiology and Control, 3rd ed., Plenum Medical Book, New York at pages 525-544). Several epidemics also have been reported among nursing home patients and institutionalized young adults (Falsey, A. R., 1991, Infect. Control Hosp. Epidemiol. 12:602-608; and Garvie et al., 1980, Br. Med. J. 281:1253-1254). Finally, RSV may cause serious disease in immunosuppressed persons, particularly bone marrow transplant patients (Hertz et al., 1989, Medicine 68:269-281).

Treatment options for established RSV disease are limited. Severe RSV disease of the lower respiratory tract often requires considerable supportive care, including administration of humidified oxygen and respiratory assistance (Fields et al., eds, 1990, Fields Virology, 2nd ed., Vol. 1, Raven Press, New York at pages 1045-1072).

While a vaccine might prevent RSV infection, and/or RSV-related disease, no vaccine is yet licensed for this indication. A major obstacle to vaccine development is safety. A formalin-inactivated vaccine, though immunogenic, unexpectedly caused a higher and more severe incidence of lower respiratory tract disease due to RSV in immunized infants than in infants immunized with a similarly prepared trivalent parainfluenza vaccine (Kim et al., 1969, Am. J. Epidemiol. 89:422-434; and Kapikian et al., 1969, Am. J. Epidemiol. 89:405-421). Several candidate RSV vaccines have been abandoned and others are under development (Murphy et al., 1994, Virus Res. 32:13-36), but even if safety issues are resolved, vaccine efficacy must also be improved. A number of problems remain to be solved. Immunization would be required in the immediate neonatal period since the peak incidence of lower respiratory tract disease occurs at 2-5 months of age. The immaturity of the neonatal immune response together with high titers of maternally acquired RSV antibody may be expected to reduce vaccine immunogenicity in the neonatal period (Murphy et al., 1988, J. Virol. 62:3907-3910; and Murphy et al., 1991, Vaccine 9:185-189). Finally, primary RSV infection and disease do not protect well against subsequent RSV disease (Henderson et al., 1979, New Engl. J. Med. 300:530-534).

Currently, the only approved approach to prophylaxis of RSV disease is passive immunization. Initial evidence suggesting a protective role for IgG was obtained from observations involving maternal antibody in ferrets (Prince, G. A., Ph.D. diss., University of California, Los Angeles, 1975) and humans (Lambrecht et al, 1976, J. Infect. Dis. 134:211-217; and Glezen et al., 1981, J. Pediatr. 98:708-715). Hemming et al. (Morell et al., eds., 1986, Clinical Use of Intravenous Immunoglobulins, Academic Press, London at pages 285-294) recognized the possible utility of RSV antibody in treatment or prevention of RSV infection during studies involving the pharmacokinetics of an intravenous immune globulin (IVIG) in newborns suspected of having neonatal sepsis. In this study, it was noted that one infant, whose respiratory secretions yielded RSV, recovered rapidly after IVIG infusion. Subsequent analysis of the IVIG lot revealed an unusually high titer of RSV neutralizing antibody. This same group of investigators then examined the ability of hyperimmune serum or immune globulin, enriched for RSV neutralizing antibody, to protect cotton rats and primates against RSV infection (Prince et al., 1985, Virus Res. 3:193-206; Prince et al., 1990, J. Virol. 64:3091-3092; Hemming et al., 1985, J. Infect. Dis. 152:1083-1087; Prince et al., 1983, Infect. Immun. 42:81-87; and Prince et al., 1985, J. Virol. 55:517-520). Results of these studies indicate that IVIG may be used to prevent RSV infection, in addition to treating or preventing RSV-related disorders.

Recent clinical studies have demonstrated the ability of this passively administered RSV hyperimmune globulin (RSV IVIG) to protect at-risk children from severe lower respiratory infection by RSV (Groothius et al., 1993, New Engl. J. Med. 329:1524-1530; and The PREVENT Study Group, 1997, Pediatrics 99:93-99). While this is a major advance in preventing RSV infection, this treatment poses certain limitations in its widespread use. First, RSV IVIG must be infused intravenously over several hours to achieve an effective dose. Second, the concentrations of active material in hyperimmune globulins are insufficient to treat adults at risk or most children with comprised cardiopulmonary function. Third, intravenous infusion necessitates monthly hospital visits during the RSV season. Finally, it may prove difficult to select sufficient donors to produce a hyperimmune globulin for RSV to meet the demand for this product. Currently, only approximately 8% of normal donors have RSV neutralizing antibody titers high enough to qualify for the production of hyperimmune globulin.

One way to improve the specific activity of the immunoglobulin would be to develop one or more highly potent RSV neutralizing monoclonal antibodies (MAbs). Such MAbs should be human or humanized in order to retain favorable pharmacokinetics and to avoid generating a human anti-mouse antibody response, as repeat dosing would be required throughout the RSV season. Two glycoproteins, F and G, on the surface of RSV have been shown to be targets of neutralizing antibodies (Fields et al., 1990, supra; and Murphy et al., 1994, supra).

A humanized antibody directed to an epitope in the A antigenic site of the F protein of RSV, SYNAGIS®, is approved for intramuscular administration to pediatric patients for prevention of serious lower respiratory tract disease caused by RSV at recommended monthly doses of 15 mg/kg of body weight throughout the RSV season (November through April in the northern hemisphere). SYNAGIS® is a composite of human (95%) and murine (5%) antibody sequences. See, Johnson et al., 1997, J. Infect. Diseases 176: 1215-1224 and U.S. Pat. No. 5,824,307, the entire contents of which are incorporated herein by reference. The human heavy chain sequence was derived from the constant domains of human IgG1 and the variable framework regions of the VH genes of Cor (Press et al., 1970, Biochem. J. 117:641-660) and Cess (Takashi et al., 1984, Proc. Natl. Acad. Sci. USA 81:194-198). The human light chain sequence was derived from the constant domain of $C_k$ and the variable framework regions of the VL gene K104 with $J_k$-4 (Bentley et al., 1980, Nature 288:5194-5198). The murine sequences derived from a murine monoclonal antibody, Mab 1129 (Beeler et al., 1989, J. Virology 63:2941-2950), in a process which involved the grafting of the murine complementarity determining regions into the human antibody frameworks.

A significant portion of human respiratory disease is caused by members of the viral sub-families Paramyxovirinae and *Pneumovirinae*. The identification of another mammalian *Pneumovirinae* that infects humans, hMPV, is described for the first time herein. There still remains a need for an effective vaccine to confer protection against a variety of viruses that result in respiratory tract infection.

2.4 Virus Entry Into Host Cell

It is emerging that some of the enveloped viruses, e.g., *retrovirus, orthomyxovirus, filovirus*, and *paramyxovirus*, might use a fusion mechanism to gain entry into a host cell (Eckert et. al., 2001, Annu. Rev. Biochem. 70:777-810; Weissenhorn et. al., 1999, Mol. Membr. Biol. 16:3-9; Lamb et. al., 1999, Mol. Membr. Biol. 16:11-19; Skehel et. al., 2000, Annu. Rev. Biochem. 69:531-569; Bentz, J., 2000, Biophys J. 78:886-900; Peisajovich et. al., 2002, Trends Biochem. Sci. 27:183-190). Under this model, fusion proteins undergo conformational changes and the fusion peptide located at the N-terminus of the F protein of *paramyxovirus*, for example, is exposed to insert into the cell membrane (Wang et. al., 2003, Biochem. Biophys. Res. Comm. 302:469-475). The highly conserved heptad repeat (HR) regions have been implicated in facilitation of the fusion process (Wang et. al., 2003, Biochem. Biophys. Res. Comm. 302:469-475). Therefore, the heptad repeats are an attractive target for the prevention of virus infection and/or propagation through the inhibition of fusion with a host cell.

Citation or discussion of a reference herein shall not be construed as an admission that such is prior art to the present invention.

3. SUMMARY OF THE INVENTION

The invention relates to an isolated mammalian negative strand RNA virus, *metapneumovirus* (MPV), within the subfamily *Pneumovirinae*, of the family Paramyxoviridae. The present invention also relates to isolated mammalian negative strand RNA viruses identifiable as phylogenitically corresponding or relating to the genus *Metapneumovirus* and components thereof. In particular, the invention relates to a mammalian MPV that is phylogenetically more closely related to a virus isolate deposited as I-2614 with CNCM, Paris than it is related to APV type C. In more specific embodiments, the mammalian MPV can be a variant A1, A2, B1 or B2 mammalian MPV. However, the mammalian MPVs of the present invention may encompass additional variants yet to be identified, and are not limited to variants A1, A2, B1 or B2.

The invention relates to genomic nucleotide sequences of different isolates of mammalian *metapneumoviruses*, in particular human *metapneumoviruses*. The invention relates to the use of the sequence information of different isolates of mammalian *metapneumoviruses* for diagnostic and therapeutic methods. The present invention relates to the differences of the genomic nucleotide sequences among the different *metapneumovirus*-isolates, and their use in the diagnostic and therapeutic methods of the invention. In specific embodiments, the nucleotide sequence of a mammalian MPV that encodes for the N, M, F, L, P, M2-1, M2-2, SH or G ORFs may be used to identify a virus of the invention. In other specific embodiments, the nucleotide sequence of mammalian MPV that encodes for the N, M, F, L, P, M2-1, M2-2, SH or G ORFs used to classify a mammalian MPV into variant A1, A2, B1 or B2. In a specific embodiment, the invention relates to the use of the single nucleotide polymorphisms (SNPs) among different *metapneumovirus* isolates for diagnostic purposes.

The invention relates to recombinant and chimeric viruses that are derived from a mammalian MPV or avian *pneumovirus* (APV). In accordance with the present invention, a recombinant virus is one derived from a mammalian MPV or an APV that is encoded by endogenous or native genomic sequences or non-native genomic sequences. In accordance with the invention, a non-native sequence is one that is different from the native or endogenous genomic sequence due to one or more mutations, including, but not limited to, point mutations, rearrangements, insertions, deletions etc., to the genomic sequence that may or may not result in a phenotypic change. In accordance with the invention, a chimeric virus of the invention is a recombinant MPV or APV which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences. In certain embodiments, a chimeric virus of the invention is derived from a MPV or APV in which one or more of the ORFs or a portion thereof is replaced by a homologous ORF or a portion thereof from another strain of *metapneumovirus*. In an exemplary embodiment, the ORF of the F gene of a mammalian MPV is replaced by the ORF of the F gene of an APV. In certain other embodiments, a chimeric virus of the invention is derived from an APV in which one or more of the ORFs is replaced by a homologous ORF of a mammalian MPV.

The present invention relates to nucleotide sequences encoding the genome of a *metapneumovirus* (including mammalian and avian strains) or a portion thereof. The present invention relates to nucleotide sequences encoding gene products of a *metapneumovirus*. In particular, the invention relates to, but is not limited to, nucleotide sequences encoding an F protein, a G protein, an M protein, an SH protein, an N protein, a P protein, an M2 protein, or an L protein of a MPV. In particular the invention relates to nucleotide sequences encoding an F protein, a G protein, an M protein, an SH protein, an N protein, a P protein, an M2 protein, or an L protein of a variant of mammalian MPV, such as but not limited to variant A1, A2, B1 or B2 of a MPV. The present invention further relates to a cDNA or RNA that encodes the genome or a portion thereof of a *metapneumovirus*, including both mammalian and avian, in addition to a nucleotide sequence which is heterologous or non-native to the viral genome. The invention further encompasses chimeric or recombinant viruses encoded by said cDNAs or RNAs.

The invention further relates to polypeptides and amino acid sequences of an F protein, a G protein, an M protein, an SH protein, an N protein, a P protein, an M2 protein, or an L protein of a mammalian MPV and different variants of mammalian MPV. The invention further relates to antibodies against an F protein, a G protein, an M protein, an SH protein, an N protein, a P protein, an M2 protein, or an L protein of a mammalian MPV and different variants of mammalian MPV. The antibodies can be used for diagnostic and therapeutic methods. In certain more specific embodiments, the antibodies are specific to mammalian MPV. In certain embodiments, the antibodies are specific to a variant of mammalian MPV. The invention further relates to vaccine formulations and immunogenic compositions comprising one or more of the following: an F protein, a G protein, an M protein, an SH protein, an N protein, a P protein, an M2 protein, and/or an L protein of a mammalian MPV.

The invention further relates to vaccine formulations and immunogenic compositions comprising mammalian or avian *metapneumovirus*, including recombinant and chimeric forms of said viruses. In particular, the present invention encompasses vaccine preparations comprising recombinant or chimeric forms of MPV and/or APV. The invention further relates to vaccines comprising chimeric MPV wherein the chimeric MPV encodes one or more APV proteins and wherein the chimeric MPV optionally additionally expresses one or more heterologous or non-native sequences. The invention also relates to vaccines comprising chimeric APV wherein the chimeric APV encodes one or more hMPV proteins and wherein the chimeric APV optionally additionally expresses one or more heterologous or non-native sequences. The present invention also relates to multivalent vaccines, including bivalent and trivalent vaccines. In particular, multivalent vaccines of the invention encompass two or more antigenic polypeptides expressed by the same or different pneumoviral vectors. The antigenic polypeptides of the multivalent vaccines include but are not limited to, antigenic polypeptides of MPV, APV, PIV, RSV, influenza or another negative strand RNA virus, or another virus, such as *morbillivirus.*

The invention further relates to methods for treating a respiratory tract infection in a subject. In certain embodiments, the invention relates to treating a respiratory tract infection in a subject by administering to the subject a vaccine formulation comprising a mammalian MPV. In specific embodiments, the methods for treating a respiratory tract infection in a subject comprise administering to the subject a vaccine formulation or an immunogenic composition comprising a recombinant or a chimeric mammalian MPV or APV. In more specific embodiments, the recombinant or chimeric mammalian MPV is attenuated. In a specific embodiment, the invention relates to treating a respiratory tract infection in a human patient comprising administering to the human patient a vaccine formulation comprising a recombinant or chimeric APV, or a nucleotide sequence encoding an F protein, a G protein, an M protein, an SH protein, an N protein, a P protein, an M2 protein, or an L protein of APV.

The invention provides an isolated negative-sense single stranded RNA virus MPV belonging to the sub-family *Pneumovirinae* of the family Paramyxoviridae and identifiable as phylogenetically corresponding to the genus *Metapneumovirus*, wherein the virus is phylogenetically more closely related to a virus isolate comprising the nucleotide sequence of SEQ ID NO:18, SEQ ID NO:19, SEQ ID NO:20, or SEQ ID NO:21 than it is related to turkey rhinotracheitis virus, the etiological agent of avian rhinotracheitis. In certain embodiments, the invention provides an isolated negative-sense single stranded RNA *metapneumovirus*, wherein the genome of the virus comprises a nucleotide sequence of SEQ ID NO:18. In certain embodiments, the invention providesa n isolated negative-sense single stranded RNA *metapneumovirus*, wherein the genome of the virus comprises a nucleotide sequence of SEQ ID NO:19. In certain embodiments, the invention provides an isolated negative-sense single stranded RNA *metapneumovirus*, wherein the genome of the virus comprises a nucleotide sequence of SEQ ID NO:20. In certain embodiments, the invention provides an isolated negative-sense single stranded RNA *metapneumovirus*, wherein the genome of the virus comprises a nucleotide sequence of SEQ ID NO:21. In certain embodiments, the invention provides an isolated nucleic acid, wherein the nucleic acid has a nucleotide sequence that is at least 70% identical to SEQ ID NO:18, SEQ ID NO:19, SEQ ID NO:20 or SEQ ID NO:21, wherein sequence identity is determined over the entire length of SEQ ID NO:18, SEQ ID NO:19, SEQ ID NO:20 or SEQ ID NO:21. In certain embodiments, the invention providesa n isolated nucleic acid, wherein the nucleic acid encodes a protein comprising (i) an amino acid sequence that is at least 66% identical to the G protein of a mammalian MPV variant B1 (SEQ ID NO:324); (ii) an amino acid sequence that is at least 98.5% identical to the N protein of a mammalian MPV variant B1 (SEQ ID NO:368);

(iii) an amino acid sequence that is at least 96% identical the P protein of a mammalian MPV variant B1 (SEQ ID NO:376); (iv) an amino acid sequence that is identical the M protein of a mammalian MPV variant B1 (SEQ ID NO:360); (v) an amino acid sequence that is at least 99% identical the F protein of a mammalian MPV variant B1 (SEQ ID NO:316); (vi) an amino acid sequence that is at least 98% identical the M2-1 protein of a mammalian MPV variant B1 (SEQ ID NO:340); (vii) an amino acid sequence that is at least 99% identical the M2-2 protein of a mammalian MPV variant B1 (SEQ ID NO:348); (viii) an amino acid sequence that is at least 83% identical the SH protein of a mammalian MPV variant B1 (SEQ ID NO:384); or (ix) an amino acid sequence that is at least 99% identical the L protein a mammalian MPV variant B1 (SEQ ID NO:332). In certain embodiments, the invention provides an isolated nucleic acid, wherein the nucleic acid encodes a protein comprising (i) an amino acid sequence that is at least 66% identical to the G protein of a mammalian MPV variant A1 (SEQ ID NO:322); (ii) an amino acid sequence that is at least 99.5% identical to the N protein of a mammalian MPV variant A1 (SEQ ID NO:366); (iii) an amino acid sequence that is at least 96% identical to the P protein of a mammalian MPV variant A1 (SEQ ID NO:374); (iv) an amino acid sequence that is at least 99% identical to the M protein of a mammalian MPV variant A1 (SEQ ID NO:358); (v) an amino acid sequence that is at least 98% identical to the F protein of a mammalian MPV variant A1 (SEQ ID NO:314); (vi) an amino acid sequence that is at least 99% identical to the M2-1 protein of a mammalian MPV variant A1 (SEQ ID NO:338) (vii) an amino acid sequence that is at least 96% identical to the M2-2 protein of a mammalian MPV variant A1 (SEQ ID NO:346) (viii) an amino acid sequence that is at least 84% identical to the SH protein of a mammalian MPV variant A1 (SEQ ID NO:382); or (ix) an amino acid sequence that is at least 99% identical to the L protein of a virus of a mammalian MPV variant A1 (SEQ ID NO:330). In certain embodiments, the invention provides n isolated nucleic acid, wherein the nucleic acid encodes a protein comprising (i) an amino acid sequence that is at least 66% identical to the G protein of a mammalian MPV variant A2 (SEQ ID NO:332); (ii) an amino acid sequence that is at least 99.5% identical to the N protein of a mammalian MPV variant A2 (SEQ ID NO:367); (iii) an amino acid sequence that is at least 96% identical to the P protein of a mammalian MPV variant A2 (SEQ ID NO:375); (iv) an amino acid sequence that is at least 99% identical to the M protein of a mammalian MPV variant A2 (SEQ ID NO:359); (v) an amino acid sequence that is at least 98% identical to the F protein of a mammalian MPV variant A2 (SEQ ID NO:315); (vi) an amino acid sequence that is at least 99% identical to the M2-1 protein of a mammalian MPV variant A2 (SEQ ID NO: 339); (vii) an amino acid sequence that is at least 96% identical to the M2-2 protein of a mammalian MPV variant A2 (SEQ ID NO:347); (viii) an amino acid sequence that is at least 84% identical to the SH protein of a mammalian MPV variant A2 (SEQ ID NO:383); or (ix) an amino acid sequence that is at least 99% identical to the L protein of a mammalian MPV variant A2 (SEQ ID NO:331). In certain embodiments, the invention provides an isolated nucleic acid, wherein the nucleic acid encodes a protein comprising (i) an amino acid sequence that is at least 66% identical to the G protein of a mammalian MPV variant B2 (SEQ ID NO:325); (ii) an amino acid sequence that is at least 97% identical to the N protein of a mammalian MPV variant B2 (SEQ ID NO:369); (iii) an amino acid sequence that is at least 96% identical to the P protein of a mammalian MPV variant B2 (SEQ ID NO:377); (iv) an amino acid sequence that is identical to the M protein of a mammalian MPV variant B2 (SEQ ID NO:361) (v) an amino acid sequence that is at least 99% identical to the F protein of a mammalian MPV variant B2 (SEQ ID NO:317); (vi) an amino acid sequence that is at least 98% identical to the M2-1 protein of a mammalian MPV variant B2 (SEQ ID NO:341); (vii) an amino acid sequence that is at least 99% identical to the M2-2 protein of a mammalian MPV variant B2 (SEQ ID NO:349); (viii) an amino acid sequence that is at least 84% identical to the SH protein of a mammalian MPV variant B2 (SEQ ID NO:385); or (ix) an amino acid sequence that is at least 99% identical to the L protein of a mammalian MPV variant B2 (SEQ ID NO:333). In certain embodiments, the invention provides an isolated nucleic acid, wherein the nucleic acid hybridizes specifically under high stringency, medium stringency, or low stringency conditions to a nucleic acid of a mammalian MPV.

In certain embodiments, the invention provides a virus comprising the nucleotide sequence of SEQ ID NO: 18-21 or a fragment thereof.

In certain embodiments, the invention provides an isolated protein, wherein the protein comprises (i) an amino acid sequence that is at least 66% identical to the G protein of a mammalian MPV variant B1 (SEQ ID NO:324); (ii) an amino acid sequence that is at least 98.5% identical to the N protein of a mammalian MPV variant B1 (SEQ ID NO:368); (iii) an amino acid sequence that is at least 96% identical the P protein of a mammalian MPV variant B1 (SEQ ID NO:376); (iv) an amino acid sequence that is identical the M protein of a mammalian MPV variant B1 (SEQ ID NO:360); (v) an amino acid sequence that is at least 99% identical the F protein of a mammalian MPV variant B1 (SEQ ID NO:316) (vi) an amino acid sequence that is at least 98% identical the M2-1 protein of a mammalian MPV variant B1 (SEQ ID NO:340); (vii) an amino acid sequence that is at least 99% identical the M2-2 protein of a mammalian MPV variant B1 (SEQ ID NO:348); (viii) an amino acid sequence that is at least 83% identical the SH protein of a mammalian MPV variant B1 (SEQ ID NO:384); or (ix) an amino acid sequence that is at least 99% identical the L protein a mammalian MPV variant B1 (SEQ ID NO:332). In certain embodiments, the invention provides an isolated protein, wherein the protein comprises: (i) an amino acid sequence that is at least 66% identical to the G protein of a mammalian MPV variant A1 (SEQ ID NO:322); (ii) an amino acid sequence that is at least 99.5% identical to the N protein of a mammalian MPV variant A1 (SEQ ID NO:366) (iii) an amino acid sequence that is at least 96% identical to the P protein of a mammalian MPV variant A1 (SEQ ID NO:374); (iv) an amino acid sequence that is at least 99% identical to the M protein of a mammalian MPV variant A1 (SEQ ID NO:358); (v) an amino acid sequence that is at least 98% identical to the F protein of a mammalian MPV variant A1 (SEQ ID NO:314); (vi) an amino acid sequence that is at least 99% identical to the M2-1 protein of a mammalian MPV variant A1 (SEQ ID NO:338) (vii) an amino acid sequence that is at least 96% identical to the M2-2 protein of a mammalian MPV variant A1 (SEQ ID NO:346) (viii) an amino acid sequence that is at least 84% identical to the SH protein of a mammalian MPV variant A1 (SEQ ID NO:382); or (ix) an amino acid sequence that is at least 99% identical to the L protein of a virus of a mammalian MPV variant A1 (SEQ ID NO:330) In certain embodiments, the invention provides isolated protein, wherein the protein comprises (i) an amino acid sequence that is at least 66% identical to the G protein of a mammalian MPV variant A2 (SEQ ID NO:323); (ii) an amino acid sequence that is at least 99.5% identical to the N protein of a mammalian MPV variant A2 (SEQ ID NO:367); (iii) an amino acid sequence that is at least 96% identical to the P protein of a mammalian MPV variant A2 (SEQ ID NO:375) (iv) an amino acid sequence that is at least 99% identical to the M protein of a mammalian MPV variant A2 (SEQ ID NO:359); (v) an amino acid sequence that is at least 98% identical to the F protein of a mammalian MPV variant A2 (SEQ ID NO:315) (vi) an amino acid sequence that is at least 99% identical to the M2-1 protein of a mammalian MPV variant A2 (SEQ ID NO: 339); (vii) an amino acid sequence that is at least 96% identical to the M2-2 protein of a mammalian MPV variant A2 (SEQ ID NO:347) (viii) an amino acid sequence that is at least 84% identical to the SH protein of a mammalian MPV variant A2 (SEQ ID NO:383); or (ix)an amino acid sequence that is at least 99% identical to the L protein of a mammalian MPV variant A2(SEQ ID NO:331). In certain embodiments, the invention provides an isolated protein, wherein the protein comprises: (i) an amino acid sequence that is at least 66% identical to the G protein of a mammalian MPV variant B2 (SEQ ID NO:325); (ii) an amino acid sequence that is at least 97% identical to the N protein of a mammalian MPV variant B2 (SEQ ID NO:369) (iii) an amino acid sequence that is at least 96% identical to the P protein of a mammalian MPV variant B2 (SEQ ID NO:377) (iv) an amino acid sequence that is identical to the M protein of a mammalian MPV variant B2 (SEQ ID NO:361); (v) an amino acid sequence that is at least 99% identical to the F protein of a mammalian MPV variant B2 (SEQ ID NO:317); (vi) an amino acid sequence that is at least 98% identical to the M2-1 protein of a mammalian MPV variant B2 (SEQ ID NO:341); (vii) an amino acid sequence that is at least 99% identical to the M2-2 protein of a mammalian MPV variant B2 (SEQ ID NO:349); (viii) an amino acid sequence that is at least 84% identical to the SH protein of a mammalian MPV variant B2 (SEQ ID NO:385); or (ix) an amino acid sequence that is at least 99% identical to the L protein of a mammalian MPV variant B2 (SEQ ID NO:333). In certain embodiments, the invention provides an antibody, wherein the antibody binds specifically to a protein consisting of (i) an amino acid sequence that is at least 66% identical to the G protein of a mammalian MPV variant B1 (SEQ ID NO:324); (ii) an amino acid sequence that is at least 98.5% identical to the N protein of a mammalian MPV variant B1 (SEQ ID NO:368); (iii) an amino acid sequence that is at least 96% identical the P protein of a mammalian MPV variant B1 (SEQ ID NO:376) (iv an amino acid sequence that is identical the M protein of a mammalian MPV variant B1 (SEQ ID NO:360); (v) an amino acid sequence that is at least 99% identical the F protein of a mammalian MPV variant B1 (SEQ ID NO:316); (vi) an amino acid sequence that is at least 98% identical the M2-1 protein of a mammalian MPV variant B1 (SEQ ID NO:340) (vii) an amino acid sequence that is at least 99% identical the M2-2 protein of a mammalian MPV variant B1 (SEQ ID NO:348); (viii) an amino acid sequence that is at least 83% identical the SH protein of a mammalian MPV variant B1 (SEQ ID NO:384); (ix) an amino acid sequence that is at least 99% identical the L protein a mammalian MPV variant B1 (SEQ ID NO:332). In certain embodiments, the invention provides an antibody, wherein the antibody binds specifically to a protein consisting of: (i) an amino acid sequence that is at least 66% identical to the G protein of a mammalian MPV variant A1 (SEQ ID NO:322); (ii) an amino acid sequence that is at least 99.5% identical to the N protein of a mammalian MPV variant A1 (SEQ ID NO:366); (iii an amino acid sequence that is at least 96% identical to the P protein of a mammalian MPV variant A1 (SEQ ID NO:374); (iv) an amino acid sequence that is at least 99% identical to the M protein of a mammalian MPV variant A1 (SEQ ID NO:358); (v) an amino acid sequence that is at least 98% identical to the F protein of a mammalian MPV variant A1 (SEQ ID NO:314); (vi) an amino acid sequence that is at least 99% identical to the M2-1 protein of a mammalian MPV variant A1 (SEQ ID NO:338); (vii) an amino acid sequence that is at least 96% identical to the M2-2 protein of a mammalian MPV variant A1 (SEQ ID NO:346); (viii) an amino acid sequence that is at least 84% identical to the SH protein of a mammalian MPV variant A1 (SEQ ID NO:382); (ix) an amino acid sequence that is at least 99% identical to the L protein of a virus of a mammalian MPV variant A1 (SEQ ID NO:330). In certain embodiments, the invention providesa n antibody, wherein the antibody binds specifically to a protein consisting of: (i) an amino acid sequence that is at least 66% identical to the G protein of a mammalian MPV variant A2 (SEQ ID NO:323); (ii) an amino acid sequence that is at least 96% identical to the N protein of a mammalian MPV variant A2 (SEQ ID NO:367) (iii) an amino acid sequence that is at least 96% identical to the P protein of a mammalian MPV variant A2 (SEQ ID NO:375); (iv) an amino acid sequence that is at least 99% identical to the M protein of a mammalian MPV variant A2 (SEQ ID NO:359); (v) an amino acid sequence that is at least 98% identical to the F protein of a mammalian MPV variant A2 (SEQ ID NO:315) (vi) an amino acid sequence that is at least 99% identical to the M2-1 protein of a mammalian MPV variant A2 (SEQ ID NO: 339); (vii) an amino acid sequence that is at least 96% identical to the M2-2 protein of a mammalian MPV variant A2 (SEQ ID NO:347); (viii) an amino acid sequence that is at least 84% identical to the SH protein of a mammalian MPV variant A2 (SEQ ID NO:383); (ix) an amino acid sequence that is at least 99% identical to the L protein of a mammalian MPV variant A2 (SEQ ID NO:331) In certain embodiments, the invention provides an antibody, wherein the antibody binds specifically to a protein consisting of: (i) an amino acid sequence that is at least 66% identical to the G protein of a mammalian MPV variant B2 (SEQ ID NO:325); (ii) an amino acid sequence that is at least 97% identical to the N protein of a mammalian MPV variant B2 (SEQ ID NO:369); (iii) an amino acid sequence that is at least 96% identical to the P protein of a mammalian MPV variant B2 (SEQ ID NO:377) (iv) an amino acid sequence that is identical to the M protein of a mammalian MPV variant B2 (SEQ ID NO:361); (v) an amino acid sequence that is at least 99% identical to the F protein of a mammalian MPV variant B2 (SEQ ID NO:317); (vi) an amino acid sequence that is at least 98% identical to the M2-1 protein of a mammalian MPV variant B2 (SEQ ID NO:341); (vii) an amino acid sequence that is at least 99% identical to the M2-2 protein of a mammalian MPV variant B2 (SEQ ID NO:349) (viii) an amino acid sequence that is at least 84% identical to the SH protein of a mammalian MPV variant B2 (SEQ ID NO:385); or (ix) an amino acid sequence that is at least 99% identical to the L protein of a mammalian MPV variant B2 (SEQ ID NO:333). In certain embodiments, the invention provides a method for detecting a variant B1 mammalian MPV in a sample, wherein said method comprises contacting the sample with the antibody of specific to a variant B1. In certain embodiments, the invention provides method for detecting a variant A1 mammalian MPV in a sample, wherein said method comprises contacting the sample with the antibody specific to variant A1. In certain embodiments, the invention provides a method for detecting a variant A2 mammalian MPV in a sample, wherein said method comprises contacting the sample with the antibody specific to variant A2. In certain embodiments, the invention provides a method for detecting a variant B2 mammalian MPV in a sample, wherein said method comprises contacting the sample with the antibody specific to B2.

In certain embodiments, the invention provides a method for identifying a viral isolate as a mammalian MPV, wherein said method comprises contacting said isolate or a component thereof with the antibody specific to a mammalian MPV. In certain embodiments, the invention provides method for virologically diagnosing a MPV infection of a mammal comprising determining in a sample of said mammal the presence of a viral isolate or component thereof by contacting the sample with the antibody specific to a MPV. In certain embodiments, the invention provides method for virologically diagnosing a mammalian MPV infection of a subject, wherein said method comprises obtaining a sample from the subject and contacting the sample with an antibody specific to MPV wherein if the antibody binds to the sample the subject is infected with mammalian MPV.

In certain embodiments, the invention provides an infectious recombinant virus, wherein the recombinant virus comprises the genome of a mammalian MPV and further comprises a non-native MPV sequence. In certain embodiments, the invention provides a recombinant nucleic acid, wherein the recombinant nucleic acid comprises (i) a nucleic acid encoding a G polypeptide of an MPV A1 variant; and (ii) a nucleic acid encoding a non-native MPV polypeptide. In certain embodiments, the invention provides recombinant nucleic acid, wherein the recombinant nucleic acid comprises (i) a nucleic acid encoding a G polypeptide of an MPV A2 variant; and (ii) a nucleic acid encoding a non-native MPV polypeptide. In certain embodiments, the invention provides s recombinant nucleic acid, wherein the recombinant nucleic acid comprises (i) a nucleic acid encoding a G polypeptide of an MPV B1 variant; and (ii) a nucleic acid encoding a non-native MPV polypeptide. In certain embodiments, the invention provides a recombinant nucleic acid, wherein the recombinant nucleic acid comprises (i) a nucleic acid encoding a G polypeptide of an MPV B2 variant; and (ii) a nucleic acid encoding a non-native MPV polypeptide.

In certain embodiments, the invention provides an infectious chimeric virus, wherein the chimeric virus comprises the genome of a mammalian MPV of a first variant, wherein one or more of the open reading frames in the genome of the mammalian MPV of the first variant have been replaced by the analogous open reading frame from a mammalian MPV of a second variant. In certain embodiments, the invention provides an infectious chimeric virus, wherein the chimeric virus comprises the genome of a mammalian MPV of a first variant, wherein one or more of open reading frames of a mammalian MPV of a second variant are inserted into the genome of the mammalian MPV of the first variant.

In certain embodiments, the invention provides an infectious chimeric virus, wherein the chimeric virus comprises the genome of a mammalian MPV, wherein one or more of the open reading frames in the genome of the mammalian MPV have been replaced by an ORF which encodes one or more of an avian MPV F protein; an avian MPV G protein (iii) an avian MPV SH protein; (iv) an avian MPV N protein (v) an avian MPV P protein; (vi) an avian MPV M2 protein; (vii) an avian MPV M2-1 protein; (viii) an avian MPV M2-2 protein; or (ix) an avian MPV L protein. In certain embodiments, the invention provides an infectious chimeric virus, wherein the chimeric virus comprises the genome of an avian MPV, wherein one or more of the open reading frames in the genome of the avian MPV have been replaced by an ORF which encodes one or more of (i) a mammalian MPV F protein (ii) a mammalian MPV G protein; (iii) a mammalian MPV SH protein; (iv) a mammalian MPV N protein; (v) a mammalian MPV P protein; (vi) a mammalian MPV M2 protein; (vii) a mammalian MPV M2-1 protein; (viii) a mammalian MPV M2-2 protein; or (ix) a mammalian MPV L protein.

In certain embodiments, the invention provides an infectious chimeric or recombinant virus, wherein the chimeric or recombinant virus is rescued using an interspecies or intraspecies polymerase. In one embodiment, the invention provides a chimeric or recombinant virus, wherein the chimeric or recombinant virus is rescued using MPV polymerase. In one embodiment, the invention uses a polymerase from a virus different from the polymerase of the virus to be rescued, i.e., from a different clade, subtype, or other species. In another embodiment, the invention provides an infectious chimeric or recombinant virus, wherein the chimeric or recombinant virus is rescued using the polymerase from another virus, including, but not limited to the polymerase of PIV, APV or RSV. By way of example, and not meant to limited the possible combinations, RSV polymerase can be used to rescue MPV; MPV polymerase can be used to rescue RSV; or PIV polymerase can be used to rescue MPV. In yet another embodiment of the invention, the polymerase complex that is used to rescue the recombinant virus is encoded by polymerase proteins from different viruses. By way of example, and not meant to limit the possible combinations, in one embodiment, the polymerase complex proteins are encoded by the N gene of MPV, the L gene of PIV, the P gene of RSV and the M2-1 gene of MPV. In other embodiments, the M2-1 gene is not a component of the polymerase complex. In another embodiment of the invention, and meant by way of example, the polymerase complex proteins are encoded by the N gene of RSV, the L gene of RSV, the P gene of APV, and the M2-1 gene of RSV. In another embodiment of the invention, the M2-1 gene is not required to rescue the recombinant virus of the invention. One skilled in the art would be familiar with the types of combinations that can be used to encode the polymerase complex proteins so that the recombinant chimeric virus of the invention is rescued.

In certain embodiments, the invention provides an immunogenic composition, wherein the immunogenic composition comprises the infectious recombinant virus of the invention.

In certain embodiments, the invention provides a method for detecting a mammalian MPV in a sample, wherein the method comprises contacting the sample with a nucleic acid sequence of the invention. In certain embodiments, the invention provides a pharmaceutical composition, wherein the pharmaceutical composition comprises the infectious recombinant virus of the invention.

In certain embodiments, the invention provides a method for detecting a mammalian MPV in a sample, wherein the method comprises amplifying or probing for MPV related nucleic acids, processed products, or derivatives thereof. In a more specific embodiment, the invention provides polymerase chain reaction based methods for the detection of MPV in a sample. In an even further embodiment, the invention provides oligonucleotide probes that can be used to specifically detect the presence of MPV related nucleic acids, processed products, or derivatives thereof. In yet another embodiment, the invention provides diagnostic methods for the detection of MPV antibodies in a host that is infected with the virus.

In certain embodiments, the invention provides a method for treating or preventing a respiratory tract infection in a mammal, said method comprising administering a vaccine comprising a mammalian *metapneumovirus.*

In certain embodiments, the invention provides an method for treating or preventing a respiratory tract infection in a mammal, said method comprising administering a vaccine comprising the recombinant mammalian *metapneumovirus* of the invention.

In certain embodiments, the invention provides an method for treating or preventing a respiratory tract infection in a mammal, said method comprising administering a vaccine comprising avian *metapneumovirus*. In certain embodiments, the invention provides a method for treating or preventing a respiratory tract infection in a human, said method comprising administering a vaccine comprising avian *metapneumovirus*. In certain embodiments, the invention provides a method for treating or preventing a respiratory tract infection in a subject, said method comprising administering to the subject the composition of the invention.

In certain embodiments, the invention provides a method for identifying a compound useful for the treatment of infections with mammalian MPV, wherein the method comprises: (a) infecting an animal with a mammalian MPV; (b) Administering to the animal a test compound; and (c) determining the effect of the test compound on the infection of the animal, wherein a test compound that reduces the extent of the infection or that ameliorates the symptoms associated with the infection is identified as a compound useful for the treatment of infections with mammalian MPV. In certain embodiments, the invention provides a method for identifying a compound useful for the treatment of infections with mammalian MPV, wherein the method comprises (a) infecting a cell culture with a mammalian MPV (b) incubating the cell culture with a test compound; and (c) determining the effect of the test compound on the infection of the cell culture, wherein a test compound that reduces the extent of the infection is identified as a compound useful for the treatment of infections with mammalian MPV. In certain embodiments, the invention provides a method for diagnosing a mammalian MPV infection of an animal, wherein the method comprises determining in a sample of said animal the presence of a viral isolate or component thereof by reacting said sample with a nucleic acid or an antibody reactive with a component of an avian *pneumovirus*, said nucleic acid or antibody being cross-reactive with a component of MPV.

In certain embodiments, the invention provides a method for serologically diagnosing a mammalian MPV infection of an animal, wherein the method comprises contacting a sample from the animal with the protein of the invention. In certain embodiments, the invention provides a method for serologically diagnosing a mammalian MPV infection of an animal, wherein the method comprises contacting a sample from the animal with a protein of an APV. In certain embodiments, the invention provides an method for diagnosing an APV infection of a bird comprising contacting a sample from the animal with the protein of the invention.

In certain embodiments, the invention provides an isolated negative-sense single stranded RNA virus MPV belonging to the sub-family *Pneumovirinae* of the family Paramyxoviridae and identifiable as phylogenetically corresponding to the genus *Metapneumovirus*, wherein the virus is phylogenetically more closely related to a virus isolate deposited as I-2614 with CNCM, Paris than to turkey rhinotracheitis virus, the etiological agent of avian rhinotracheitis.

3.1 Conventions and Abbreviations

| | |
|---|---|
| cDNA | complementary DNA |
| L | large protein |
| M | matrix protein (lines inside of envelope) |
| F | fusion glycoprotein |
| HN | hemagglutinin-neuraminidase glycoprotein |
| N, NP or NC | nucleoprotein (associated with RNA and required for polymerase activity) |
| P | Phosphoprotein |
| MOI | multiplicity of infection |
| NA | neuraminidase (envelope glycoprotein) |
| PIV | parainfluenza virus |
| hPIV | human parainfluenza virus |
| hPIV3 | human parainfluenza virus type 3 |
| APV/hMPV | recombinant APV with hMPV sequences |
| hMPV/APV | recombinant hMPV with APV sequences |
| Mammalian MPV | mammalian metapneumovirus |
| nt | nucleotide |
| RNP | ribonucleoprotein |
| rRNP | recombinant RNP |
| vRNA | genomic virus RNA |
| cRNA | antigenomic virus RNA |
| hMPV | human metapneumovirus |
| APV | avian pneumovirus |
| MVA | modified vaccinia virus Ankara |
| FACS | Fluorescence Activated Cell Sorter |
| CPE | cytopathic effects |
| Position 1 | Position of the first gene of the viral genome to be transcribed |
| Position 2 | Position between the first and the second open reading frame of the native viral genome, or alternatively, the position of the second gene of the viral genome to be transcribed |
| Position 3 | Position between the second and the third open reading frame of the native viral genome, or alternatively, the position of the third gene of the viral genome to be transcribed. |
| Position 4 | Position between the third and the fourth open reading frame of the native viral genome, or alternatively, the position of the fourth gene of the viral genome to be transcribed. |
| Position 5 | Position between the fourth and the fifth open reading frame of the native viral genome, or alternatively, the position of the fifth gene of the viral genome to be transcribed. |
| Position 6 | Position between the fifth and the sixth open reading frame of the native viral genome, or alternatively, the position of the sixth gene of the viral genome to be transcribed. |

dpi (days post-infection);
F (fusion);
HAI (hemagglutination-inhibition);
HN (hemagglutinin-neuraminidase);
hpi (hours post-infection);
MOI (multiplicity of infection);
POI (point of infection);
bPIV-3 (bovine parainfluenza virus type 3);
hPIV-3 (human parainfluenza virus type 3);
RSV (respiratory syncytial virus);
SFM (serum-free medium);
$TCID_{50}$ (50% tissue culture infective dose)

4. DESCRIPTION OF THE FIGURES

FIG. 1: Percentage homology found between the amino acid sequence of isolate 00-1 and other members of the *Pneumovirinae*. Percentages (×100) are given for the amino acid sequences of N, P, M, F and two RAP-PCR fragments in L (8 and 9/10).

FIG. 2: Seroprevalence of MPV in humans categorized by age group, using immunofluorescence and virus neutralisation assays.

FIG. 3: Schematic representation of the genome of APV with the location and size of the fragments obtained with RAP-PCR and RT-PCR on virus isolate 00-1 (A1). Fragments 1 to 10 were obtained using RAP-PCR. Fragment A was obtained with a primer in RAP-PCR fragment 1 and 2 and a primer that was designed based on alignment of leader and trailer sequences of APV and RSV (Randhawa et al., 1997, J.Virol. 71:9849-9854). Fragment B was obtained using primers designed in RAP-PCR fragment 1 and 2 and RAP-PCR fragment 3. Fragment C was obtained with primers designed in RAP-PCR fragment 3 and RAP-PCR fragments 4, 5, 6, and 7.

FIG. 4: Comparison of the N, P, M and F ORFs of members of the subfamily *Pneumovirinae* and virus isolate 00-1 (A1). The alignment shows the amino acid sequence of the complete N, F, M and P proteins and partial L proteins of virus isolate 00-1 (A1). Amino acids that differ between isolate 00-1 (A1) and the other viruses are shown, identical amino acids are represented by periods. Gaps are represented as dashes. Numbers correspond to amino acid positions in the proteins. Abbreviations are as follows: APV-A, B or C: Avian Pneumovirus type A, B or C; hRSV: bovine or human respiratory syncytial virus; PVM: pneumonia virus of mice. L8: fragment 8 obtained with RAP-PCR located in L, L 9/10: consensus of fragment 9 and 10 obtained with RAP-PCR, located in L. For the L alignment only bRSV, hRSV and APV-A sequences were available.

FIG. 5: Alignment of the predicted amino acid sequence of the nucleoprotein of MPV with those of other *pneumoviruses*. The conserved regions are represented by boxes and labeled A, B, and C. The conserved region among *pneumoviruses* is shown in gray and shaded. Gaps are represented by dashes, periods indicate the positions of identical amino acid residues compared to MPV.

FIG. 6: Amino acid sequence comparison of the phosphoprotein of MPV with those of other *pneumoviruses*. The region of high similarity is boxed, and the glutamate rich region is in grey and shaded. Gaps are represented by dashes. Periods indicate the position of identical amino acid residues compared to MPV.

FIG. 7: Comparison of the deduced amino acid sequence of the matrix protein of MPV with those of other *pneumoviruses*. The conserved hexapeptide sequence is in grey and shaded. Gaps are represented by dashes. Periods indicate the position of identical amino acid residues relative to MPV.

Figure 8:
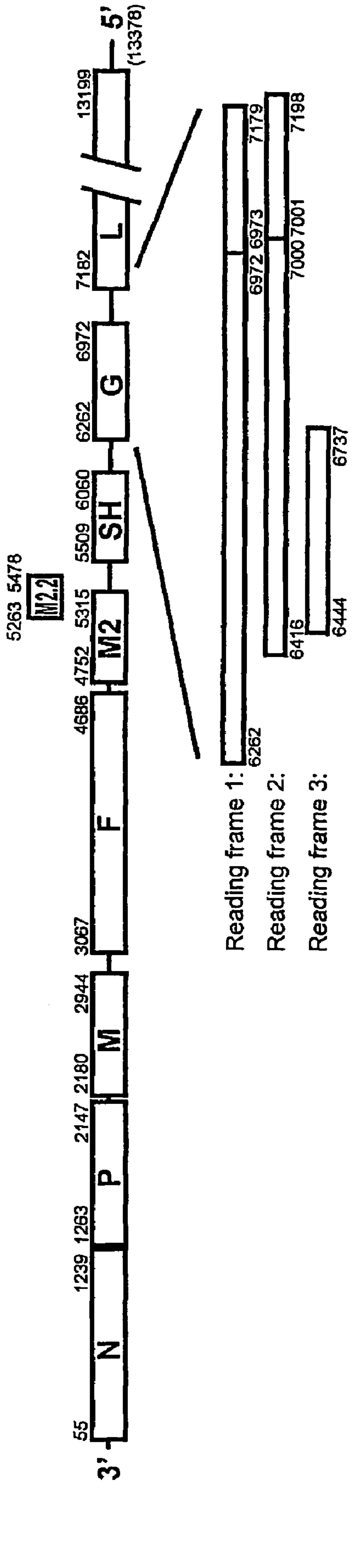

FIG. 8: Genomic map of MPV isolate 00-1 (A1). The nucleotide positions of the start and stop codons are indicated under each ORF. The double lines which cross the L ORF indicate the shortened representation of the L gene. The three reading frames below the map indicate the primary G ORF (nt 6262-6972) and overlapping potential secondary ORFs.

FIG. 9: Alignment of the predicted amino acid sequence of the fusion protein of MPV with those of other *pneumoviruses*. The conserved cysteine residues are boxed. N-linked glycosylation sites are underlined. The cleavage site of F0 is double underlined; the fusion peptide, signal peptide, and membrane anchor domain are shown in grey and shaded. Gaps are represented by dashes, and periods indicate the position of identical amino acids relative to MPV.

FIG. 10: Comparison of amino acid sequences of the M2 ORFs of MPV with those of other *pneumoviruses*. The alignment of M2-1 ORFs is shown in panel A, with the conserved amino terminus shown in grey and shaded. The three conserved cysteine residues are printed bold face and indicated by #. The alignment of the M2-2 ORFs is shown in panel B. Gaps are represented by dashes and periods indicate the position of identical amino acids relative to MPV.

Figure 11:
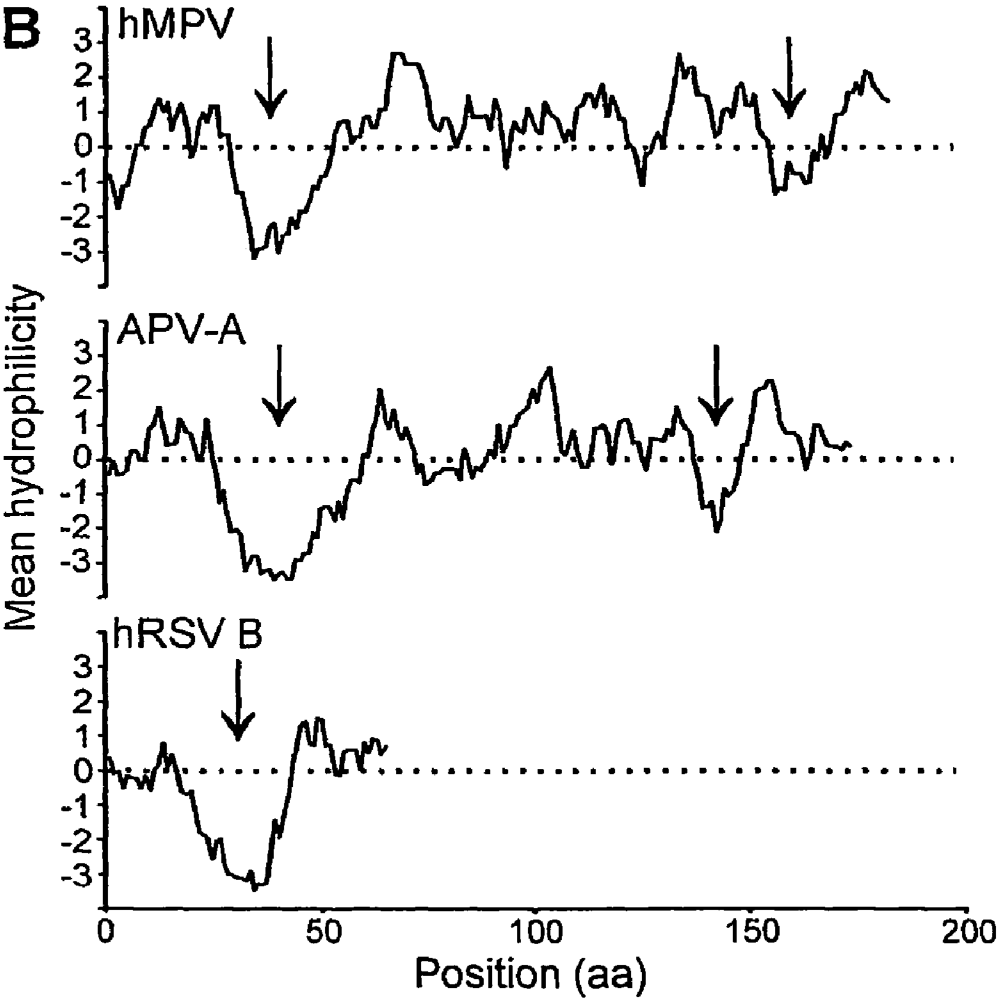

FIG. 11: Amino acid sequence analyses of the SH ORF of MPV. (A) Amino acid sequence of the SH ORF of MPV, with the serine and threonine residues in grey and shaded, cysteine residues in bold face, and the hydrophobic region doubly underlined. Potential N-linked glycosylation sites are single underlined. Arrows indicate the positions of the basic amino acids flanking the hydrophobic domain. (B) Alignment of the hydrophobicity plots of the SH proteins of MPV, APV-A and hRSV-B. A window of 17 amino acids was used. Arrows indicate a strong hydrophobic domain. Positions within the ORF are given on the X-axis.

Figure 12:
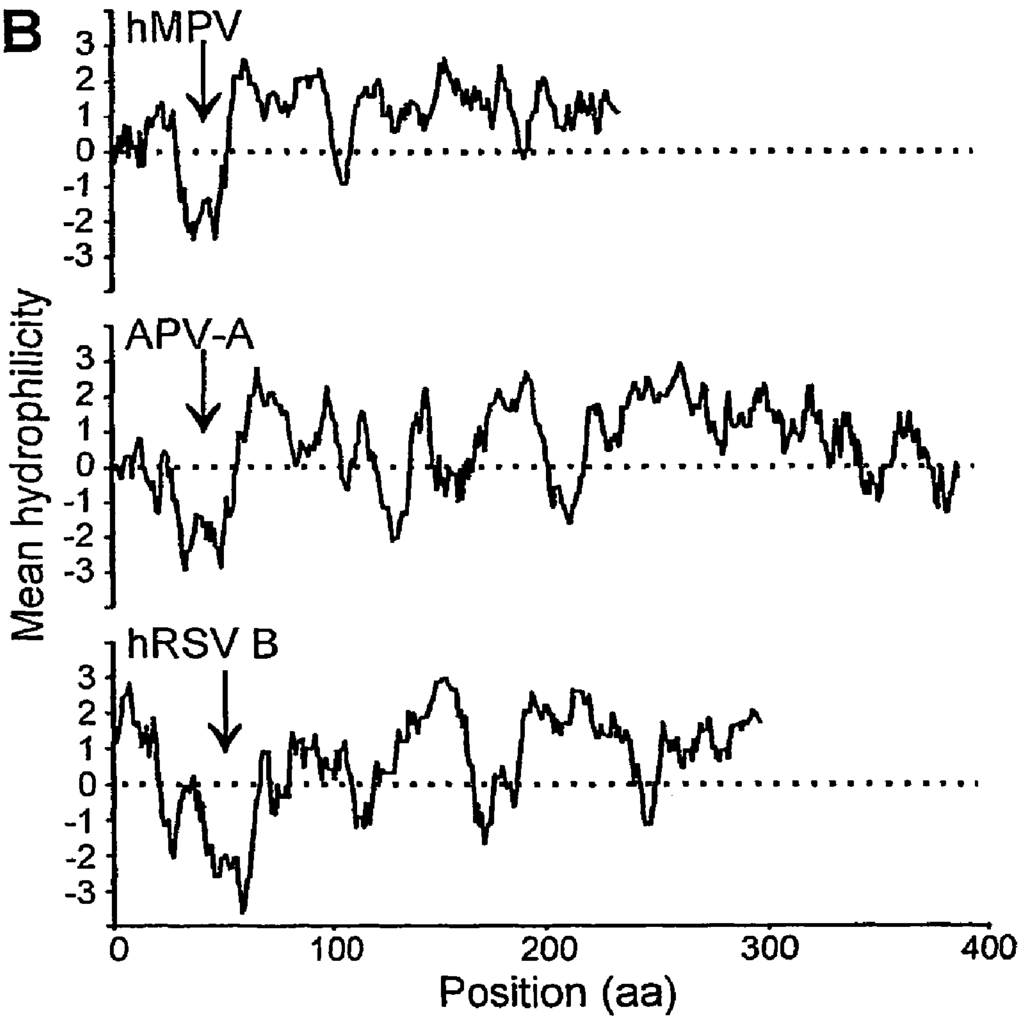

FIG. 12: Amino acid sequence analyses of the G ORF of MPV. (A) Amino acid sequence of the G ORF of MPV, with serine, threonine, and proline residues in grey and shaded. The cysteine residue is in bold face, and the hydrophobic region is doubly underlined. The potential N-linked glycosylation sites are singly underlined. (B) Alignment of the hydrophobicity plots of the G proteins of MPV, APV-A and hRSV-B. A window of 17 amino acids was used. Arrows indicate the hydrophobic region, and positions within the ORF are given at the X-axis.

FIG. 13: Comparison of the amino acid sequences of a conserved domain of the polymerase gene of MPV and other *paramyxoviruses*. Domain III is shown with the four conserved polymerase motifs (A, B, C, D) in domain III (Poch et al., 1989 EMBO J 8:3867-74; Poch et al., 1990, J. Gen. Virol 71:1153-62) boxed. Gaps are represented by dashes and periods indicate the position of identical amino acid residues relative to MPV. Abbreviations used are as follows: hPIV-3: human parainfluenza virus type 3; SV: sendai virus; hPIV-2: human parainfluenza virus type 2; NDV: New castle disease virus; MV: measles virus; nipah: Nipah virus.

Figure 14:
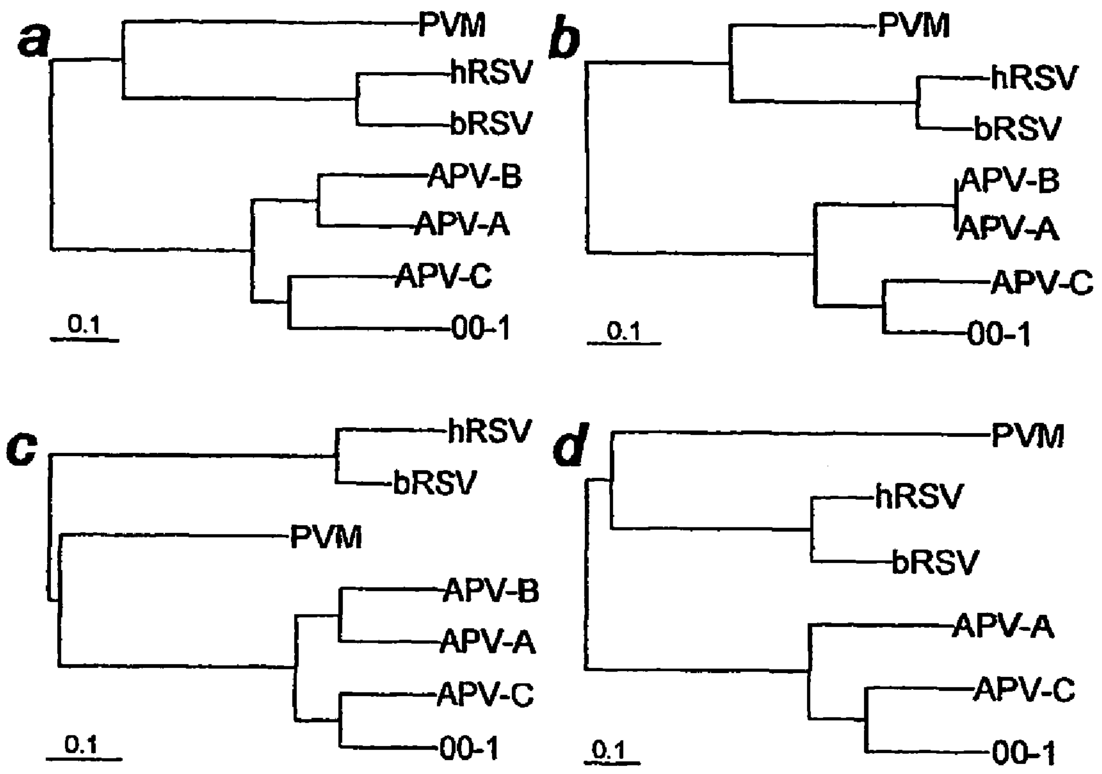

FIG. 14: Phylogenetic analyses of the N, F, M, and F ORFs of members of the genus *Pneumovirinae* and virus isolate 00-1 (A1). Phylogenetic analysis was performed on viral sequences from the following genes: F (panel A), N (panel B), M (panel C), and P (panel D). The phylogenetic trees are based on maximum likelihood analyses using 100 bootstraps and 3 jumbles. The scale representing the number of nucleotide changes is shown for each tree.

Figure 15:
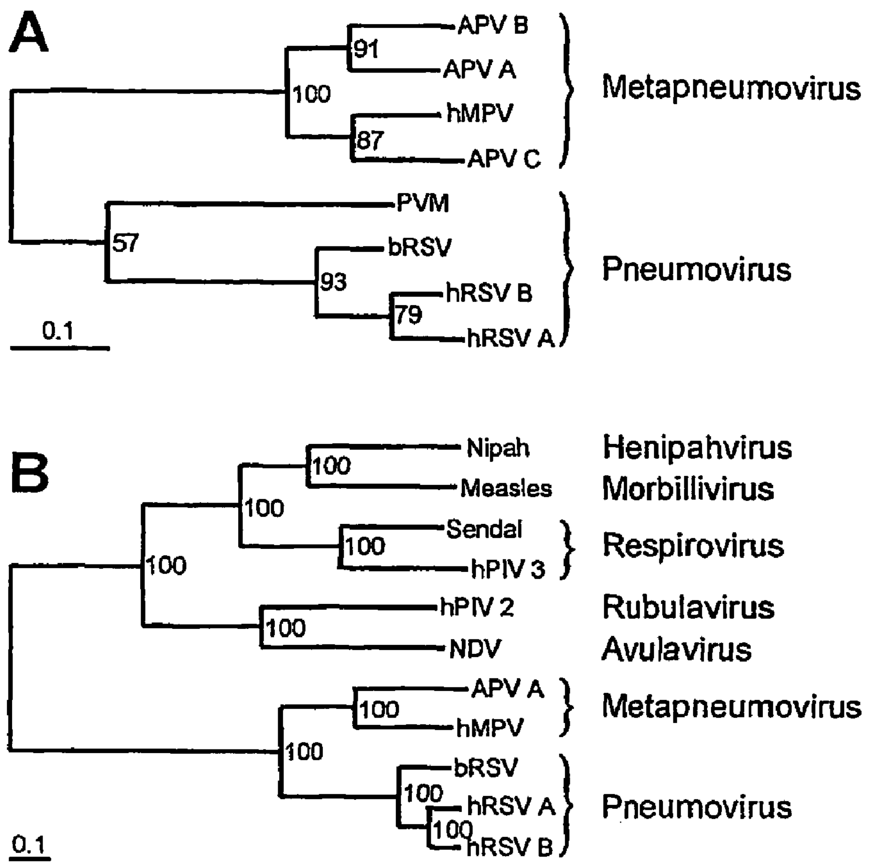

FIG. 15: Phylogenetic analyses of the M2-1 and L ORFs of MPV and selected *paramyxoviruses*. The M2-1 ORF was aligned with the M2-1 ORFs of other members of the genus *Pneumovirinae* (A) and the L ORF was aligned with L ORFs members of the genus *pneumovirinae* and selected other *paramyxoviruses* as described in the legend of FIG. 13. Phylogenetic trees were generated by maximum likelihood analyses using 100 bootstraps and 3 jumbles. The scale representing the number of nucleotide changes is shown for each tree. Numbers in the trees represent bootstrap values based on the consensus trees.

Figure 16:
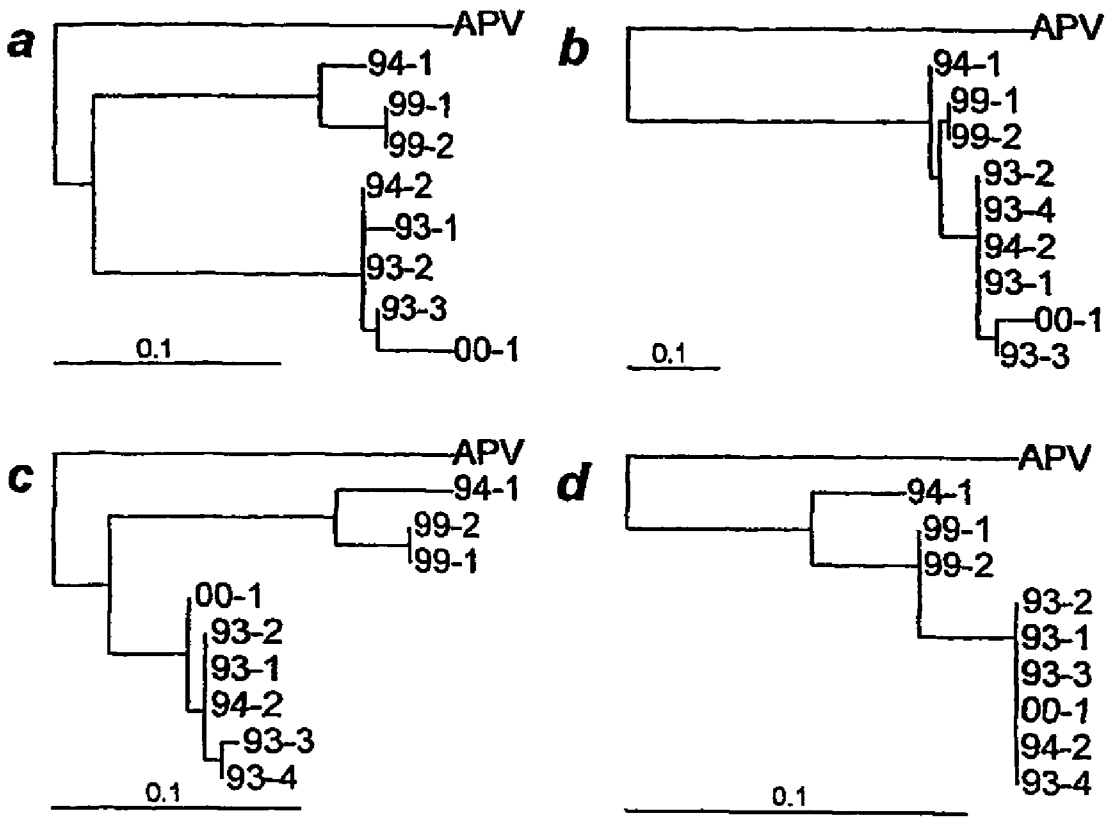

FIG. 16: Phylogenetic relationship for parts of the F (panel A), N (panel B), M (panel C) 20 and L (panel D) ORFs of nine of the primary MPV isolates with APV-C, its closest relative genetically. The phylogenetic trees are based on maximum likelihood analyses. The scale representing the number of nucleotide changes is shown for each tree. Accession numbers for APV-C: panel A: D00850; panel B: U39295; panel C: X58639; and panel D: U65312.

FIG. 17: Alignment of the F genes of different isolates of hMPV of all four variants, variant A1, A2, B1, or B2.

FIG. 18: Alignment of the F proteins of different isolates of hMPV of all four variants, variant A1, A2, B1, or B2.

FIG. 19: Alignment of the G genes of different isolates of hMPV of all four variants, variant A1, A2, B1, or B2.

FIG. 20: Alignment of the G proteins of different isolates of hMPV of all four variants, variant A1, A2, B1, or B2.

Figure 21:
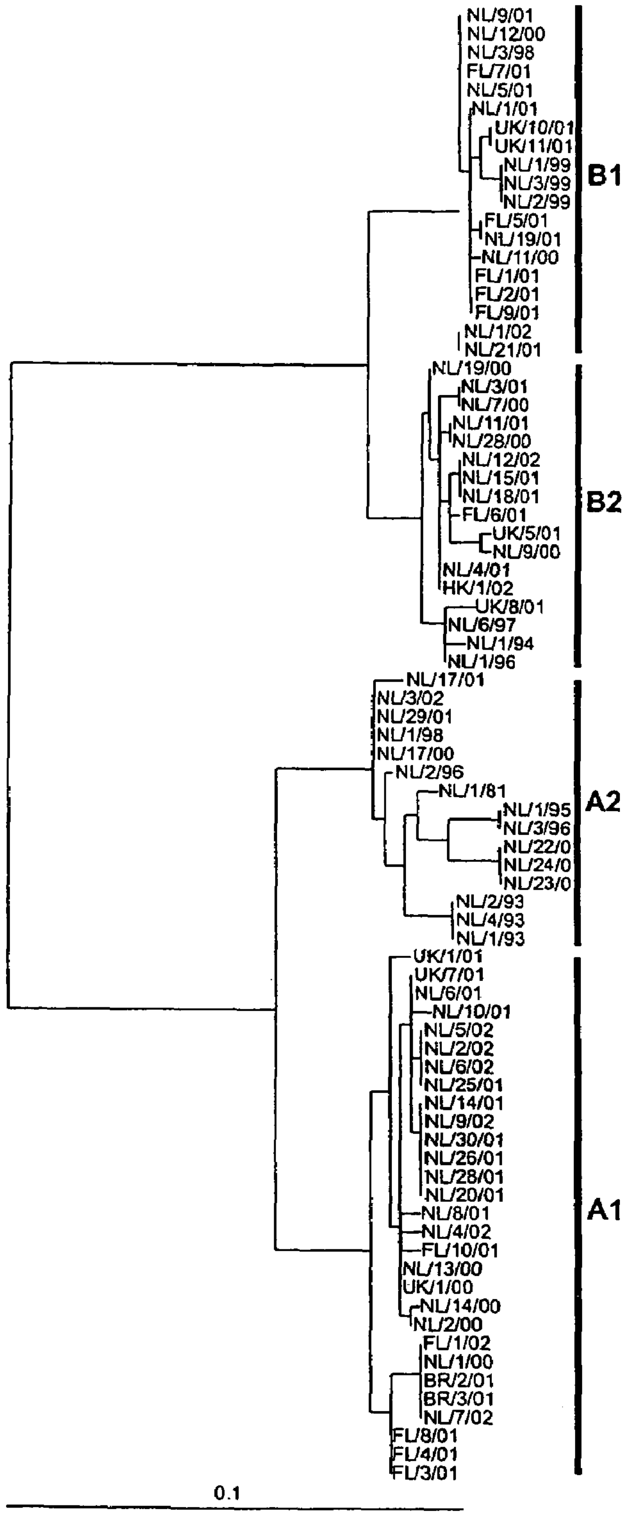

FIG. 21: Phylogenetic tree based on the F gene sequences showing the phylogenetic relationship of the different hMPV isolates with the respective variants of hMPV.

Figure 22:
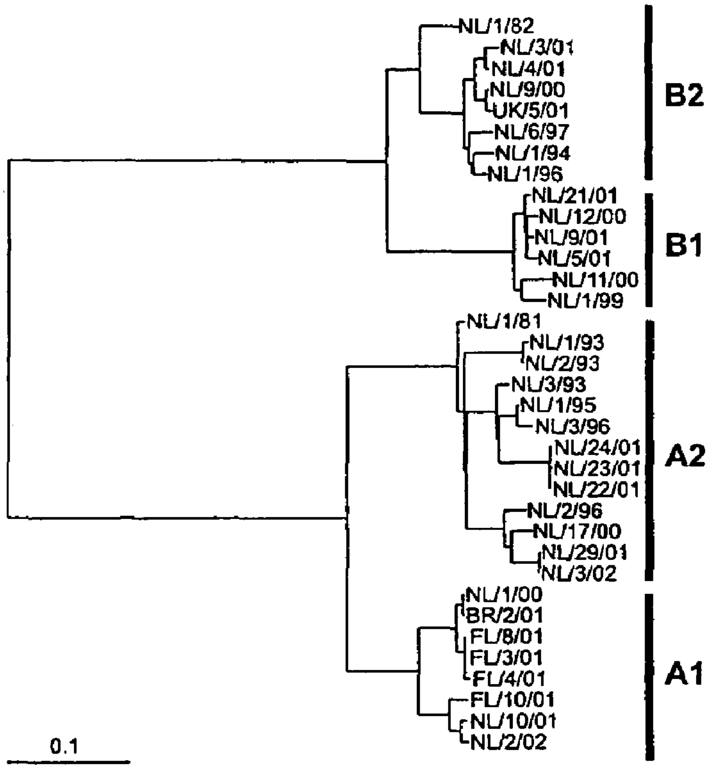

FIG. 22: Phylogenetic tree based on the G gene sequences showing the phylogenetic relationship of the different hMPV isolates with the respective variants of hMPV is shown in FIG. 13.

Figure 23:
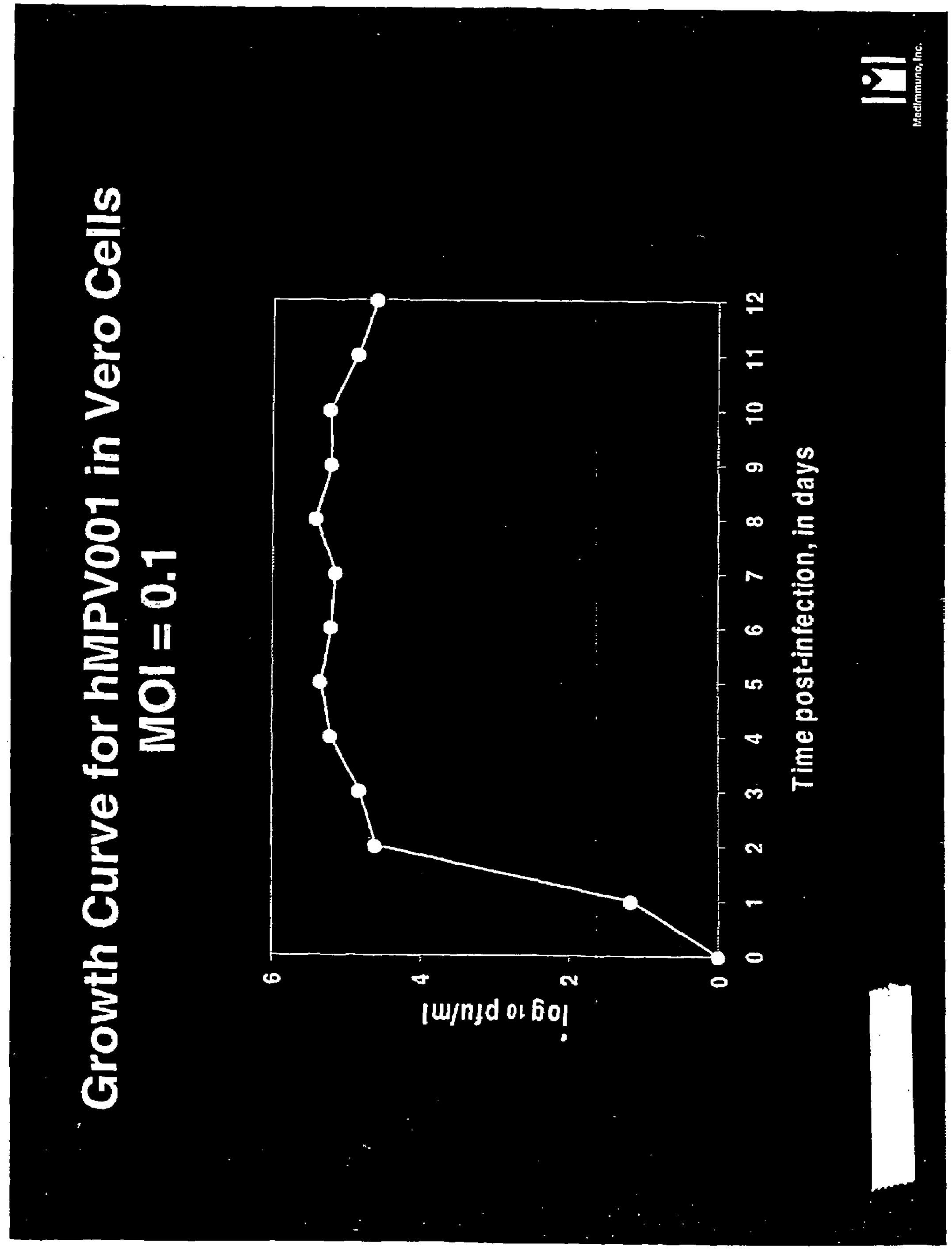

FIG. 23: Growth curve of hMPV isolate 00-1 (A1) in Vero cells. The Vero cells were infected at a MOI of 0.1.

FIG. 24: Sequence of CAT-hMPV minireplicon construct. The function encoded by a segment of sequence is indicated underneath the sequence.

Figure 25:
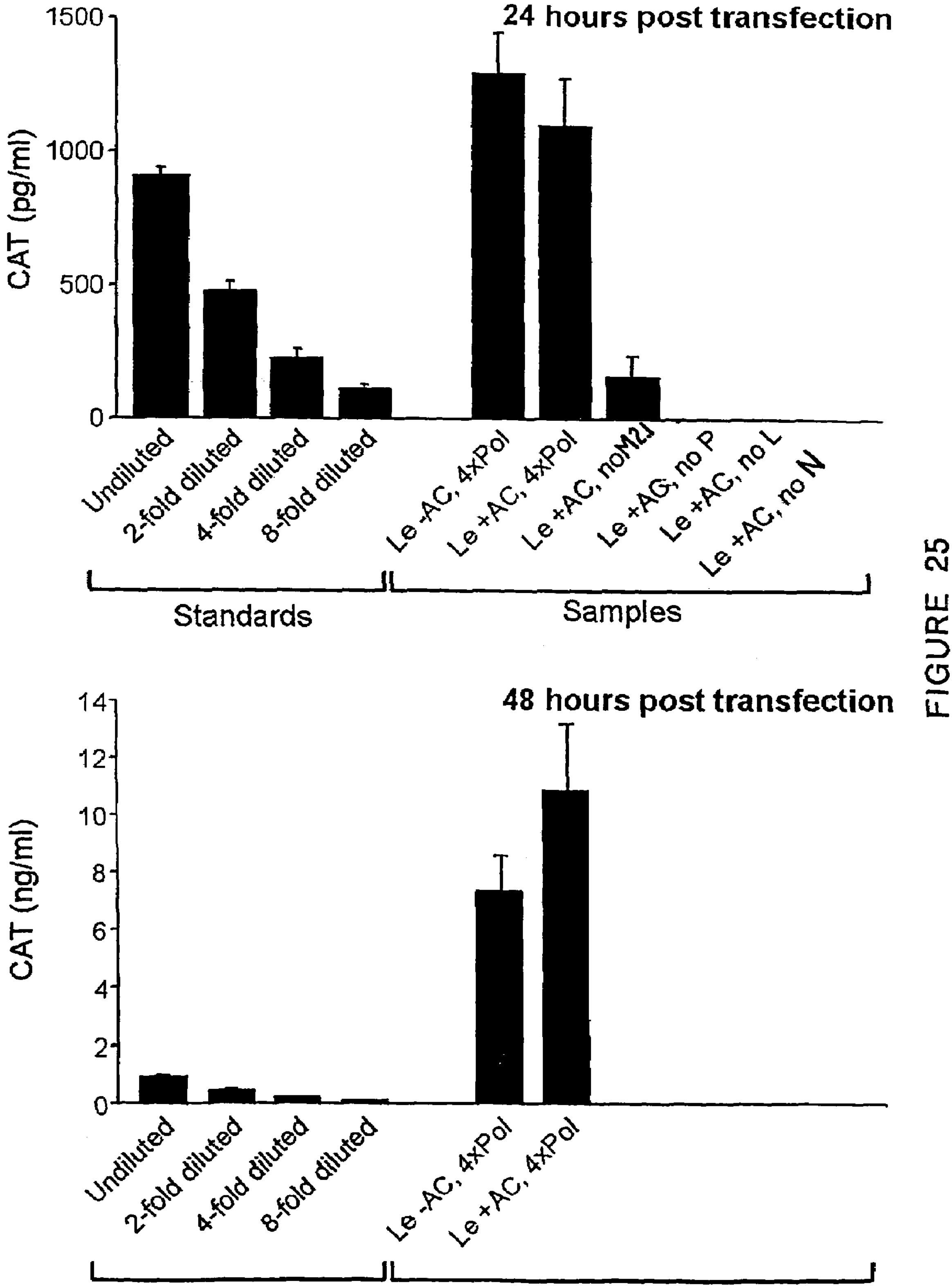

FIG. 25: Expression of CAT from the CAT-hMPV minireplicon. The different constructs used for transfection are indicated on the x-axis; the amount of CAT expression is indicated on the y-axis. The Figure shows CAT expression 24 hours after transfection and CAT expression 48 hours after transfection. Standards were dilutions of CAT protein.

Figure 26:
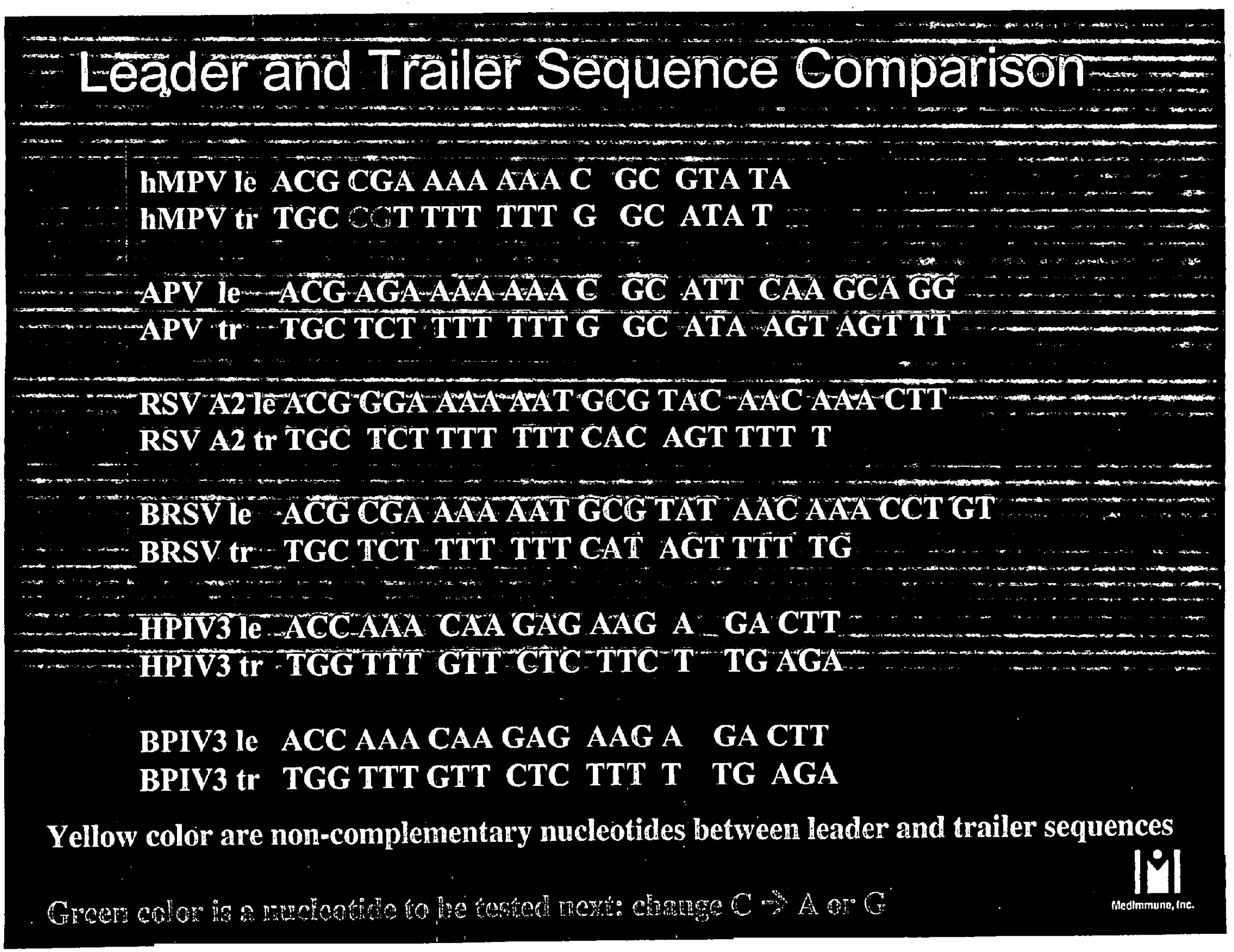

FIG. 26: Leader and Trailer Sequence Comparison: Alignments of the leader and trailer sequences of different viruses as indicated are shown.

Figure 27:
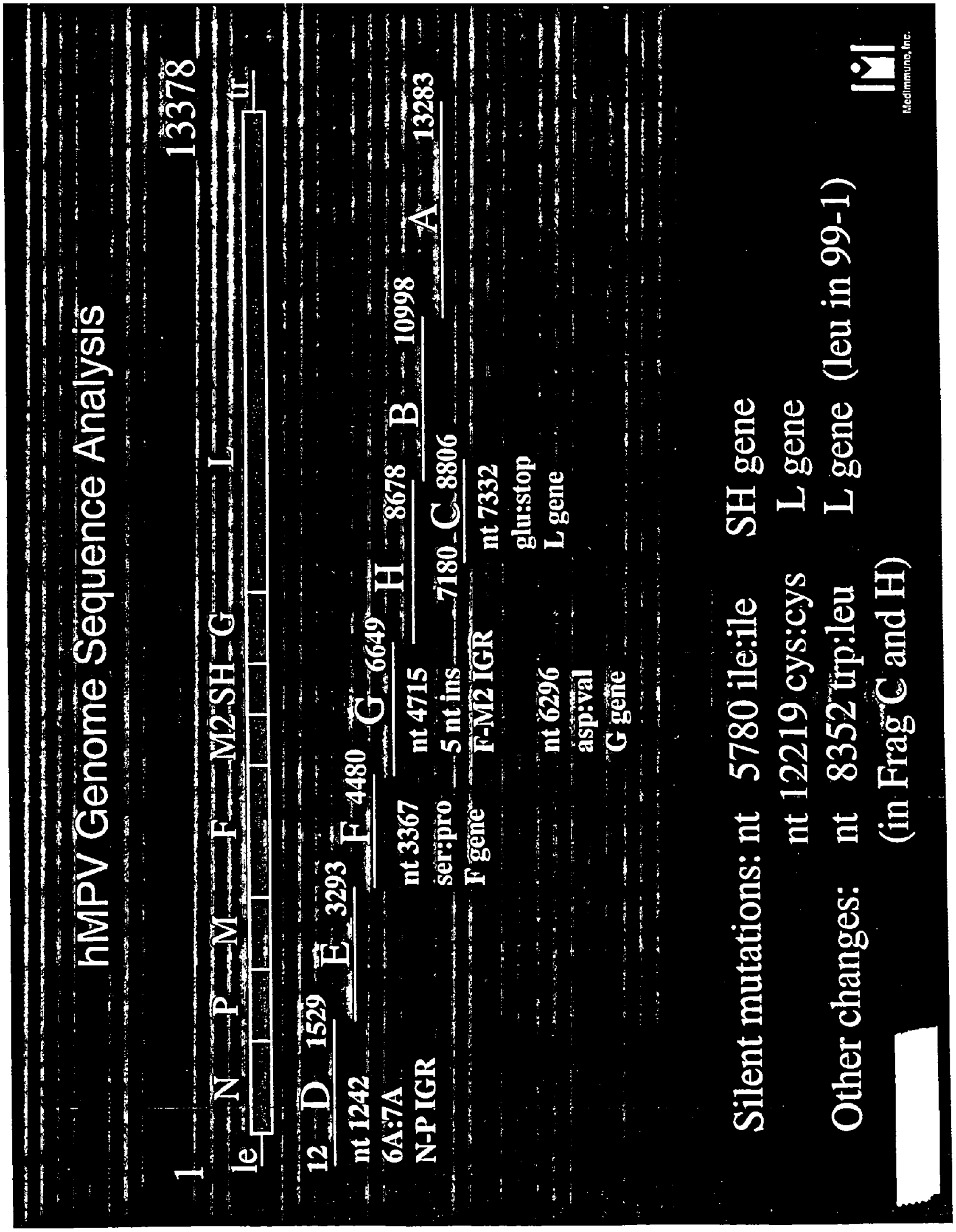

FIG. 27: hMPV genome analysis: PCR fragments of hMPV genomic sequence relative to the hMPV genomic organization are shown. The position of mutations are shown underneath the vertical bars indicating the PCR fragments.

Figure 28:
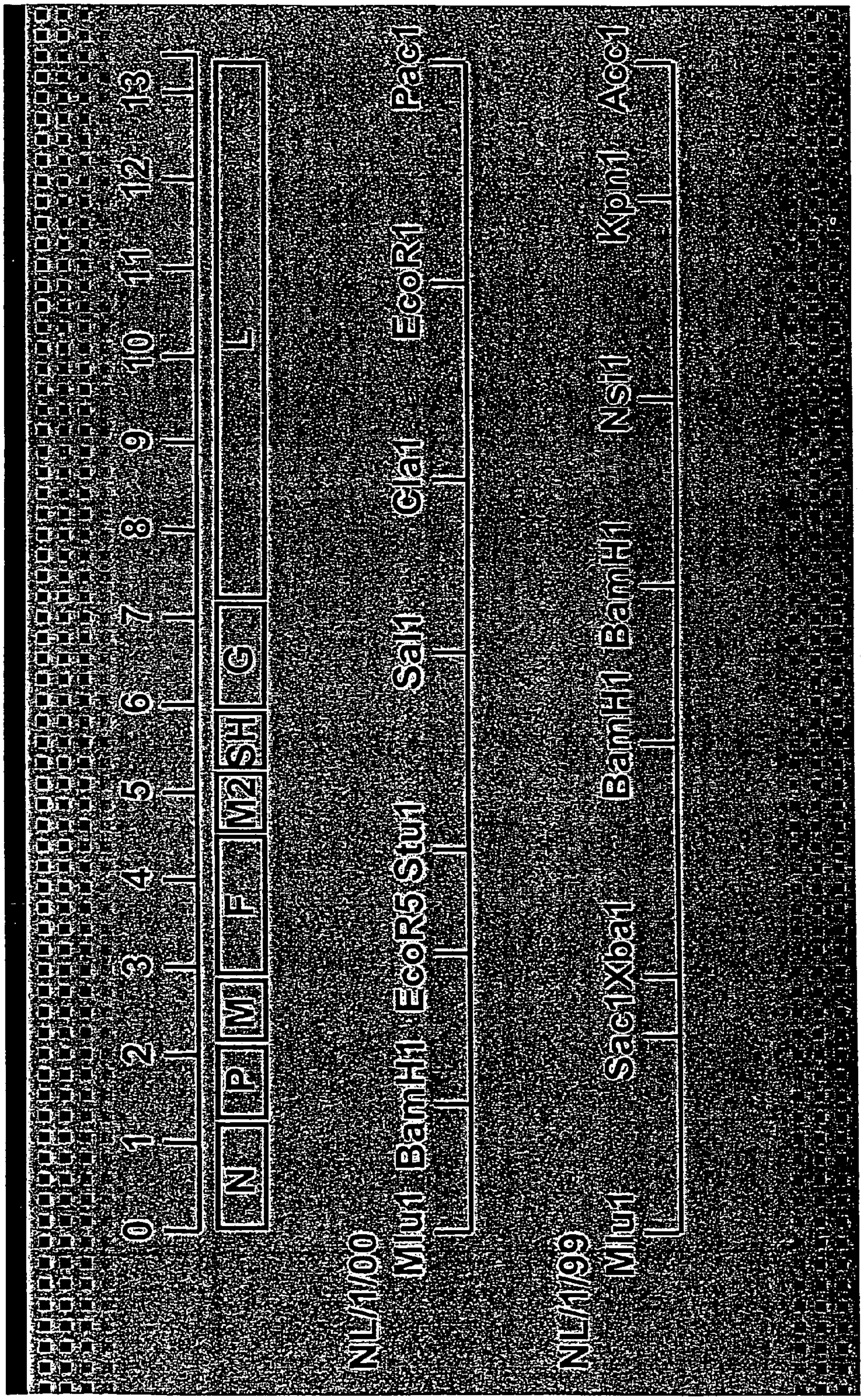

FIG. 28: Restriction maps of hMPV isolate 00-1 (A1) and hMPV isolate 99-1 (B1). Restriction sites in the respective isolates are indicated underneath the diagram showing the genomic organization of hMPV. The scale on top of the diagram indicates the position in the hMPV genome in kb.

Figure 29A:
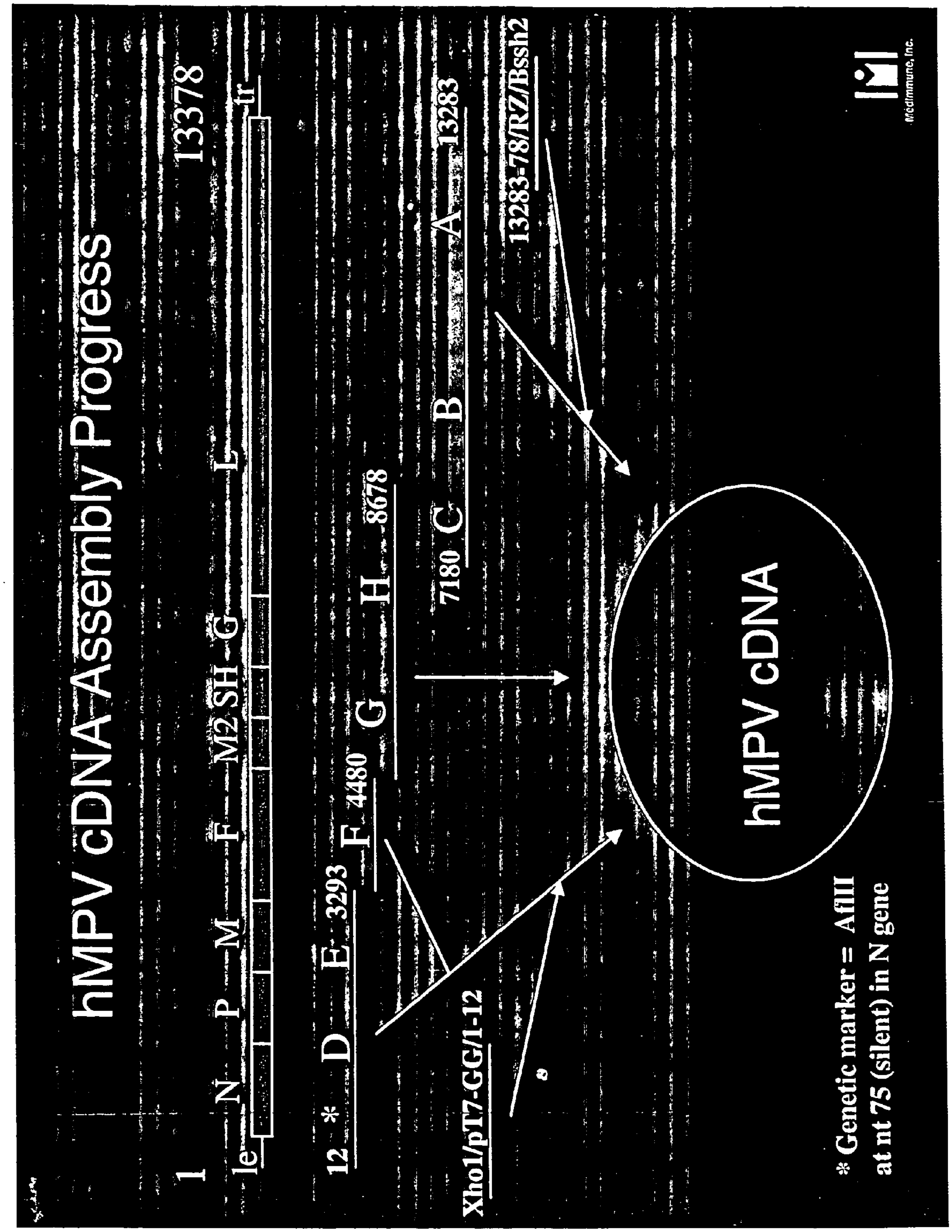
Figure 29B:
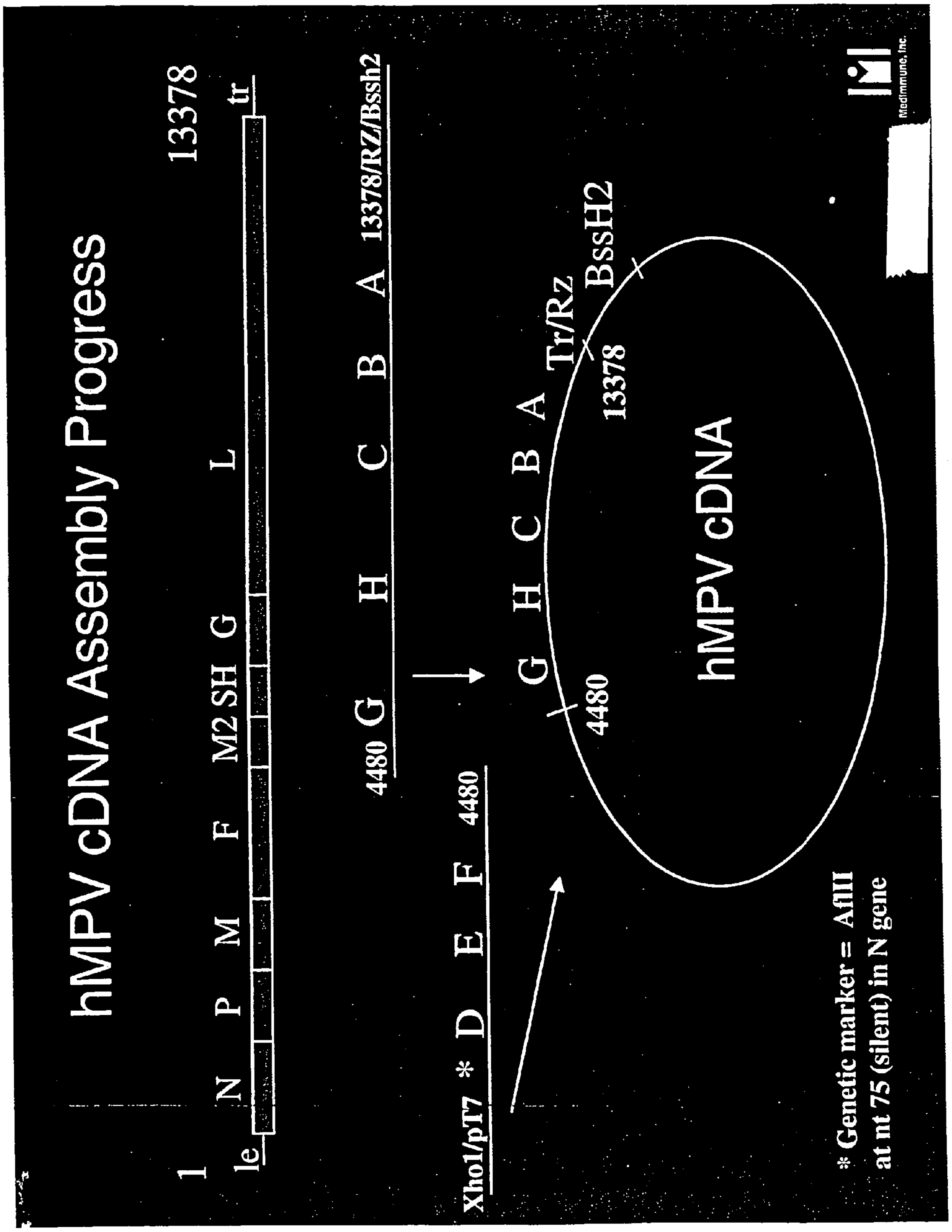

FIGS. 29A and 29B: hMPV cDNA assembly. The diagram on top shows the genomic organization of hMPV, the bars underneath indicate the PCR fragments (see FIG. 27) that are assembled to result in a full length cDNA encoding the virus. The numbers on top of the bars representing the PCR fragments indicate the position in the viral genome in basepairs.

FIG. 30: Nucleotide and amino acid sequence information from the 3' end of the genome of MPV isolate 00-1 (A1). ORFs are given. N: ORF for nucleoprotein; P: ORF for phosphoprotein; M: ORF for matrix protein; F: ORF for fusion protein; GE: gene end; GS: gene start.

FIGS. 31 A and B: Nucleotide and amino acid sequence information from obtained fragments in the polymerase gene (L) of MPV isolates 00-1 (A1). Positioning of the fragments in L is based on protein homologies with APV-A (accession number U65312). The translated fragment 8 (FIG. 31 A) is located at amino acid number 8 to 243, and the consensus of fragments 9 and 10 (FIG. 31 B) is located at amino acid number 1358 to 1464 of the APV-A L ORF.

FIG. 32: Results of RT-PCR assays on throat and nose swabs of 12 guinea pigs 15 inoculated with ned/00/01 (A1) and/or ned/99/01 (B1).

Figure 33A:
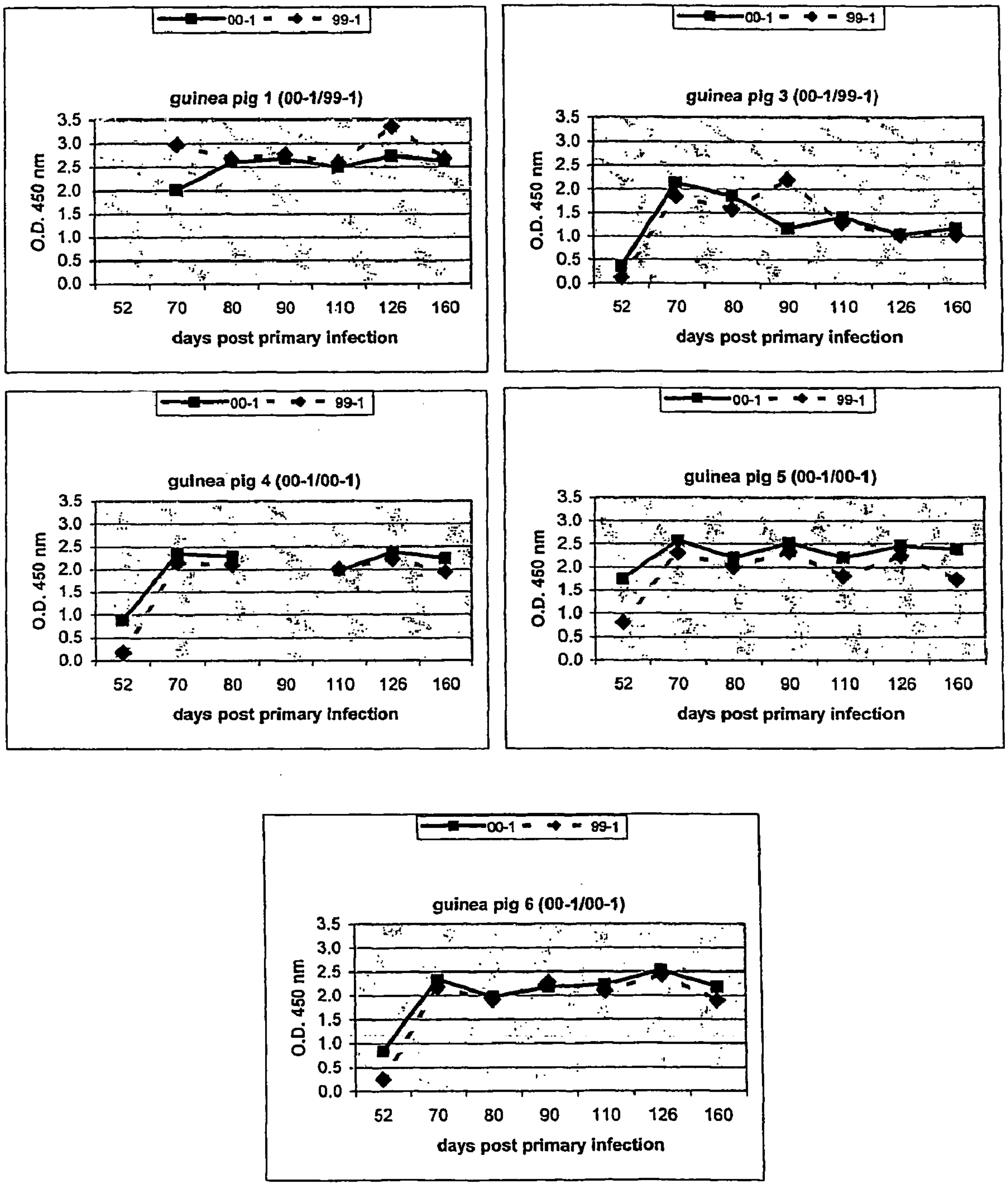

FIG. 33A: IgG response against ned/00/01 (A1) and ned/99/01 (B1) for guinea pigs infected with ned/00/01 (A1) and re-infected with ned/00/01 (A1) (GP 4, 5 and 6) or ned/99/01 (B1) (GP 1 and 3).

Figure 33B:
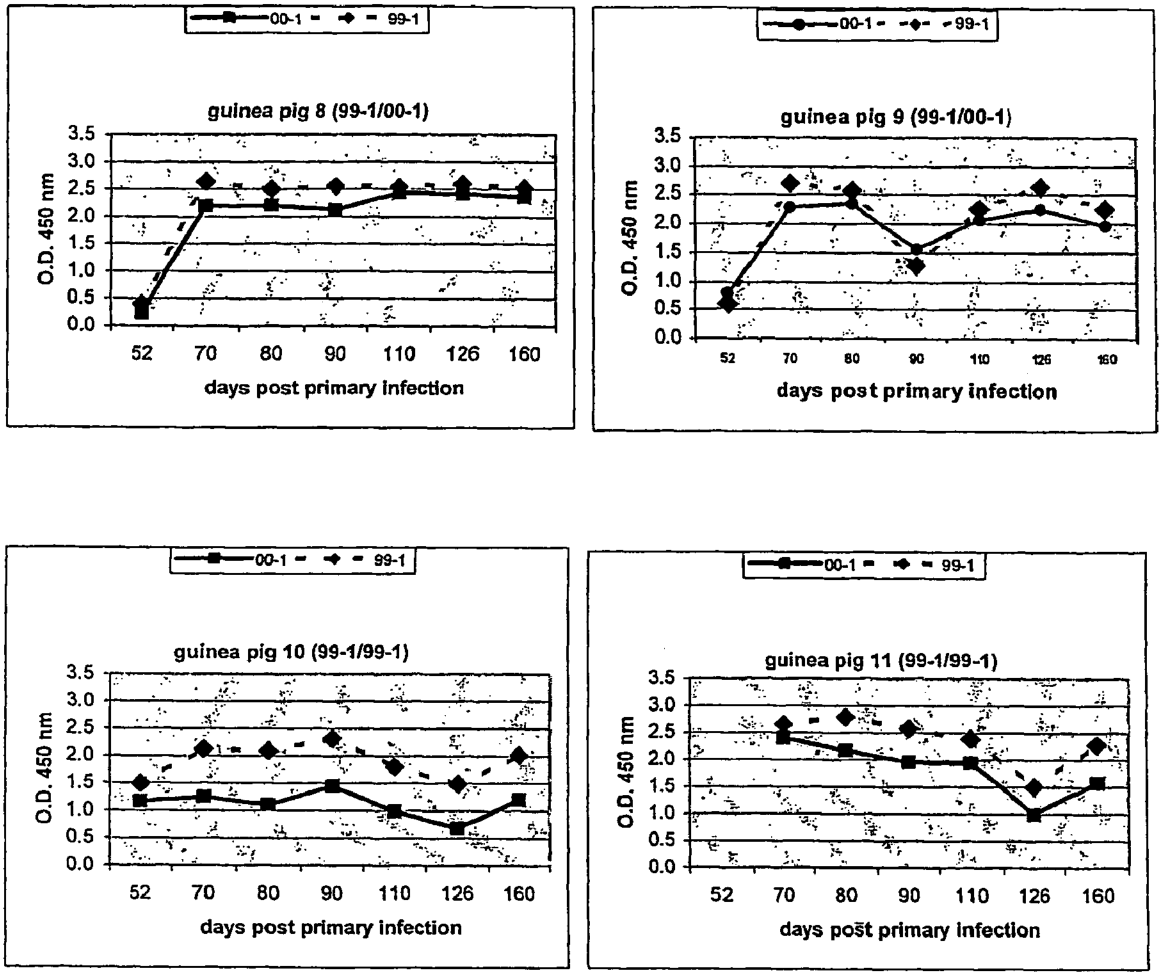

FIG. 33B: IgG response against ned/00/01 (A1) and ned/99/01 (B1) for guinea pigs infected with ned/99/01 and re-infected with either ned/00/01 (A1) (GP's 8 and 9) or with ned/99/01 (B1) (GP's 10, 11, 12).

Figure 34:
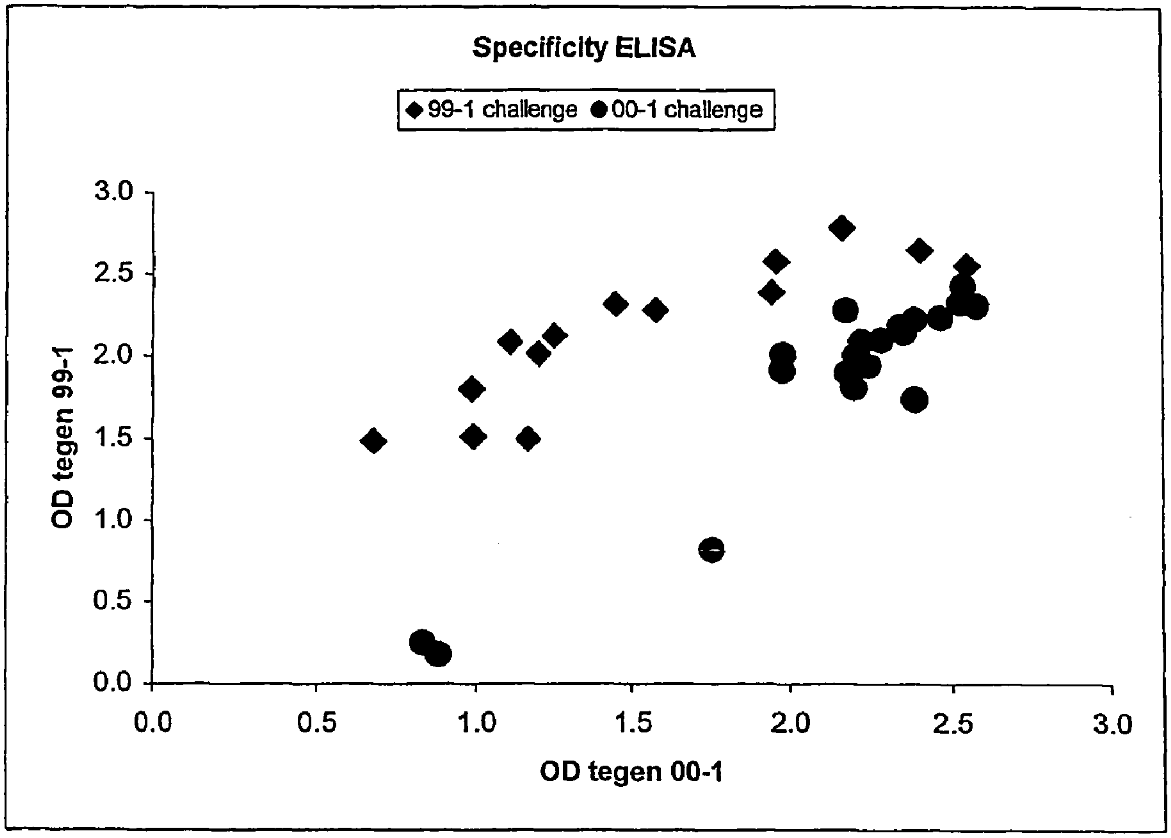

FIG. 34: Specificity of the ned/00/01 (A1) and ned/99/01 (B1) ELISA on sera taken from guinea pigs infected with either ned/00/01 (A1) or ned/99/01 (B1).

Figure 35:
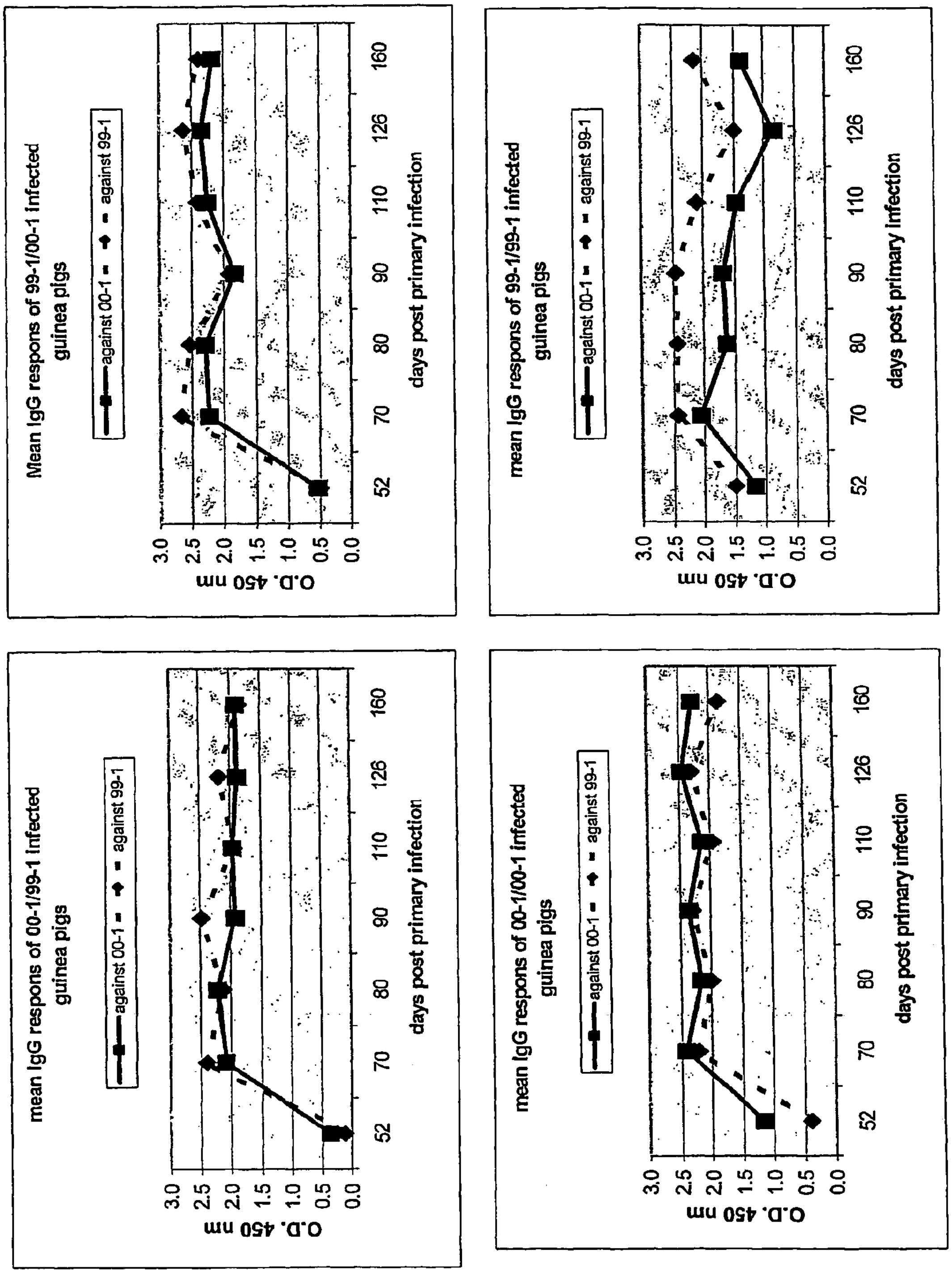

FIG. 35: Mean IgG response against ned/00/01 (A1) and ned/99/01 (B1) ELISA of 3 homologous (00-1/00-1), 2 homologous (99-1/99-1), 2 heterologous (99-1/00-1) and 2 heterologous (00-1/99-1) infected guinea pigs.

Figure 36:
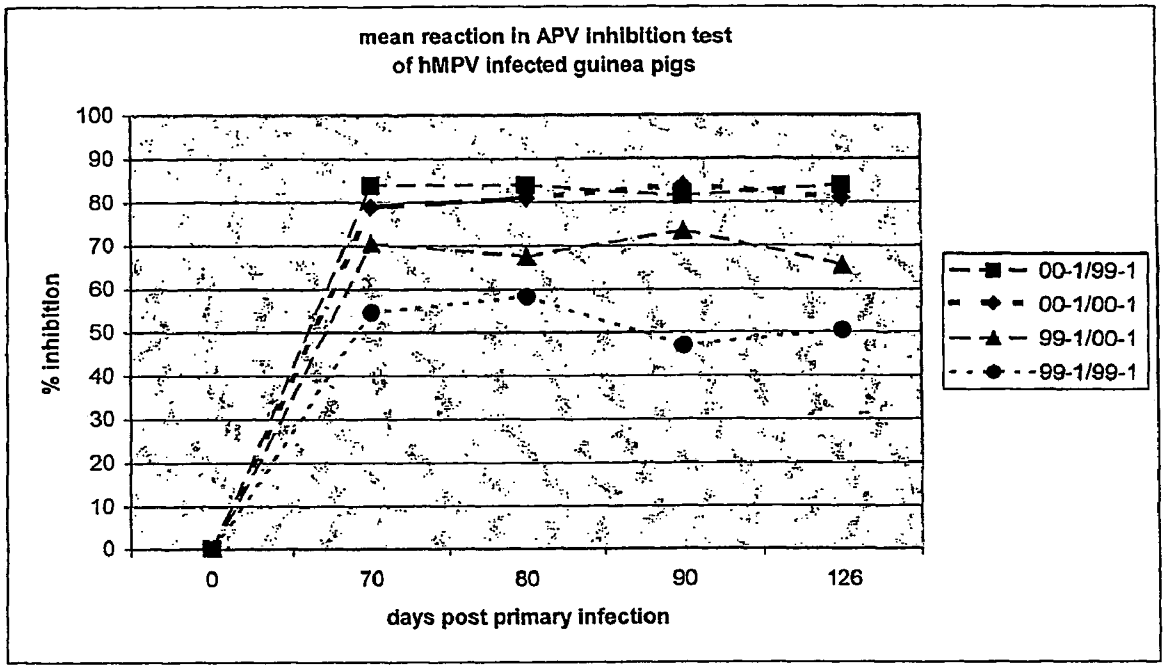

FIG. 36: Mean percentage of APV inhibition of hMPV infected guinea pigs.

FIG. 37: Virus neutralization titers of ned/00/01 (A1) and ned/99/01 (B1) infected guinea pigs against ned/00/01 (A1), ned/99/01 (B1) and APV-C.

FIG. 38: Results of RT-PCR assays on throat swabs of cynomolgous macaques inoculated (twice) with ned/00/01 (A1).

Figure 39A:
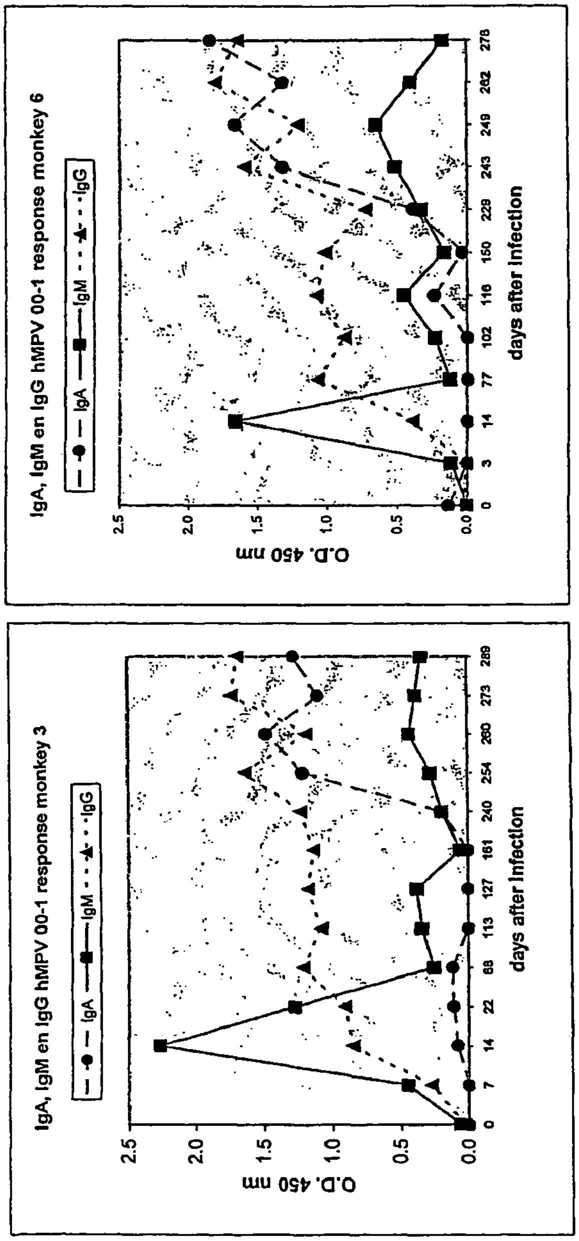

FIG. 39A (top two panels): IgA, IgM and IgG response against ned/00/01 (A1) of 2 cynomologous macaques (re) infected with ned/00/01 (A1).

Figure 39B:
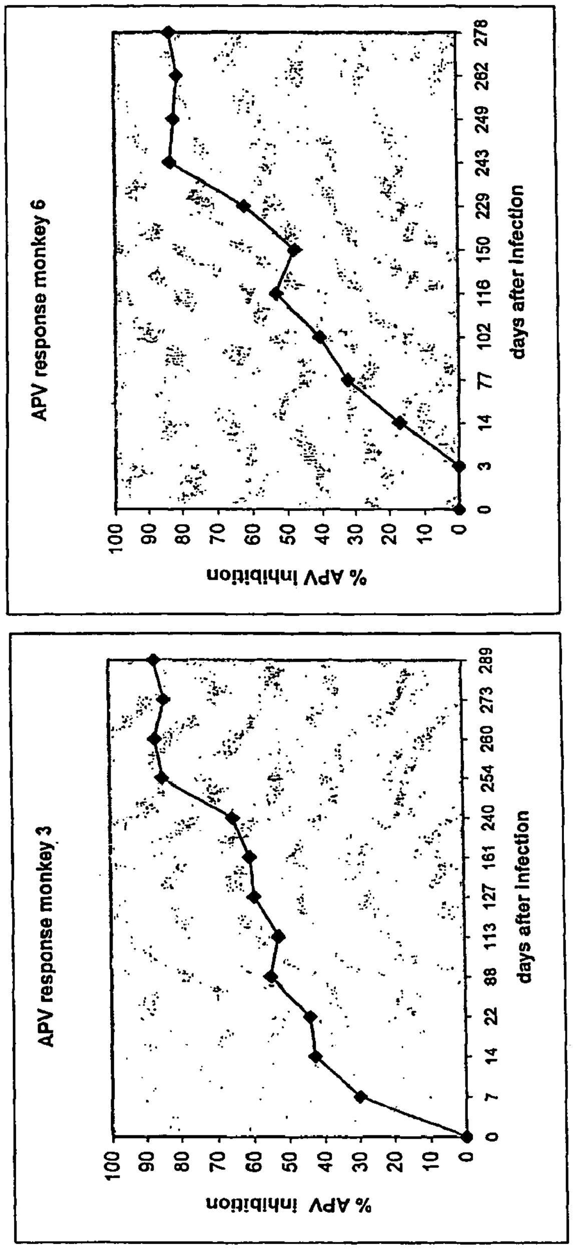

FIG. 39B (bottom panels): IgG response against APV of 2 Cynomologous macaques infected with ned/00/01 (A1).

Figure 40:
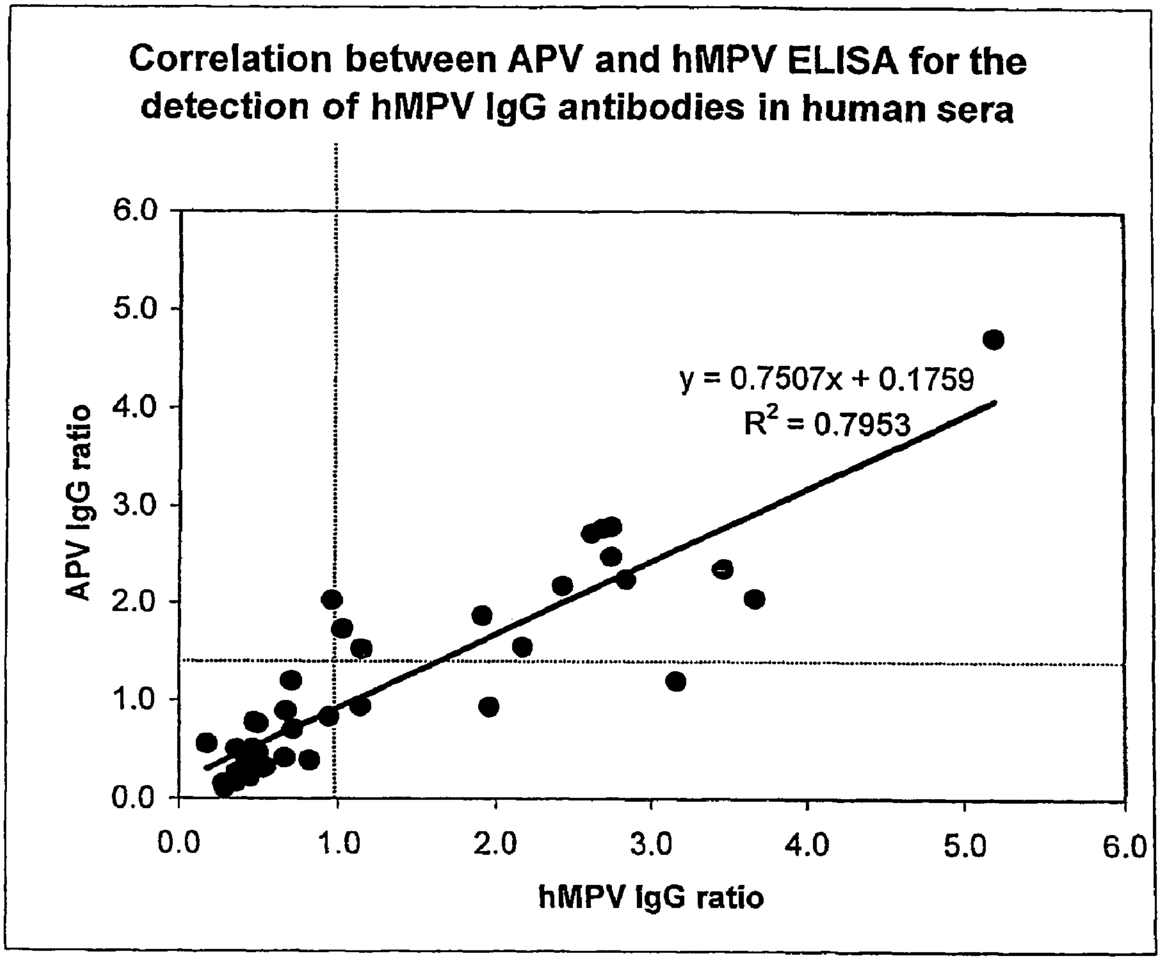

FIG. 40: Comparison of the use of the hMPV ELISA and the APV inhibition ELISA for the detection of IgG antibodies in human sera.

FIG. 41: Comparison of two prototypic hMPV isolates with APV-A and APV-C; DNA similarity matrices for nucleic acids encoding the various viral proteins.

FIG. 42*a*: Comparison of two prototypic hMPV isolates with APV-A and APV-C; protein similarity matrices for the various viral proteins.

FIG. 42*b*: Comparison of the coding sequences of four prototypes of mammalian MPV. The left column shows nucleic acid sequence comparisons and the right column shows amino acid sequence comparisons. NL/1/00 is the prototype of variant A1 (SEQ ID NO: 19). NL/17/00 is the prototype of variant A2 (SEQ ID NO:20). NL/1/99 the prototype of variant B1 (SEQ ID NO:18). NL/1/94 is the prototype of variant B2 (SEQ ID NO:21).

FIG. 43: Amino acid alignment of the nucleoprotein of two prototype hMPV isolates.

FIG. 44: Amino acid alignment of the phosphoprotein of two prototype hMPV isolates.

FIG. 45: Amino acid alignment of the matrix protein of two prototype hMPV isolates.

FIG. 46: Amino acid alignment of the fusion protein of two prototype hMPV isolates.

FIG. 47: Amino acid alignment of the M2-1 protein of two prototype hMPV isolates.

FIG. 48: Amino acid alignment of the M2-2 protein of two prototype hMPV isolates.

FIG. 49: Amino acid alignment of the short hydrophobic protein of two prototype hMPV isolates.

FIG. 50: Amino acid alignment of the attachment glycoprotein of two prototype hMPV isolates.

FIG. 51: Amino acid alignment of the N-terminus of the polymerase protein of two prototype hMPV isolates.

FIG. 52: Noncoding sequences of hMPV isolate 00-1 (A1). (A) The noncoding sequences between the ORFs and at the genomic termini are shown in the positive sense. From left to right, stop codons of indicated ORFs are shown, followed by the noncoding sequences, the gene start signals and start codons of the indicated subsequent ORFs. Numbers indicate the first position of start and stop codons in the hMPV map. Sequences that display similarity to published gene end signals are underlined and sequences that display similarity to UAAAAAU/A/C (SEQ ID NO: 393) are represented with a line above the sequence. (B) Nucleotide sequences of the genomic termini of hMPV. The genomic termini of hMPV are aligned with each other and with those of APV. Underlined regions represent the primer sequences used in RT-PCR assays which are based on the 3' and 5' end sequences of APV and RSV. Bold italicized nucleotides are part of the gene start signal of the N gene. Le: leader, Tr: trailer.

FIG. 53: Sequence comparison of the genomic sequence of hMPV isolate 00-1 (A1) with hMPV isolate 99-1 (B1).

Figure 54:
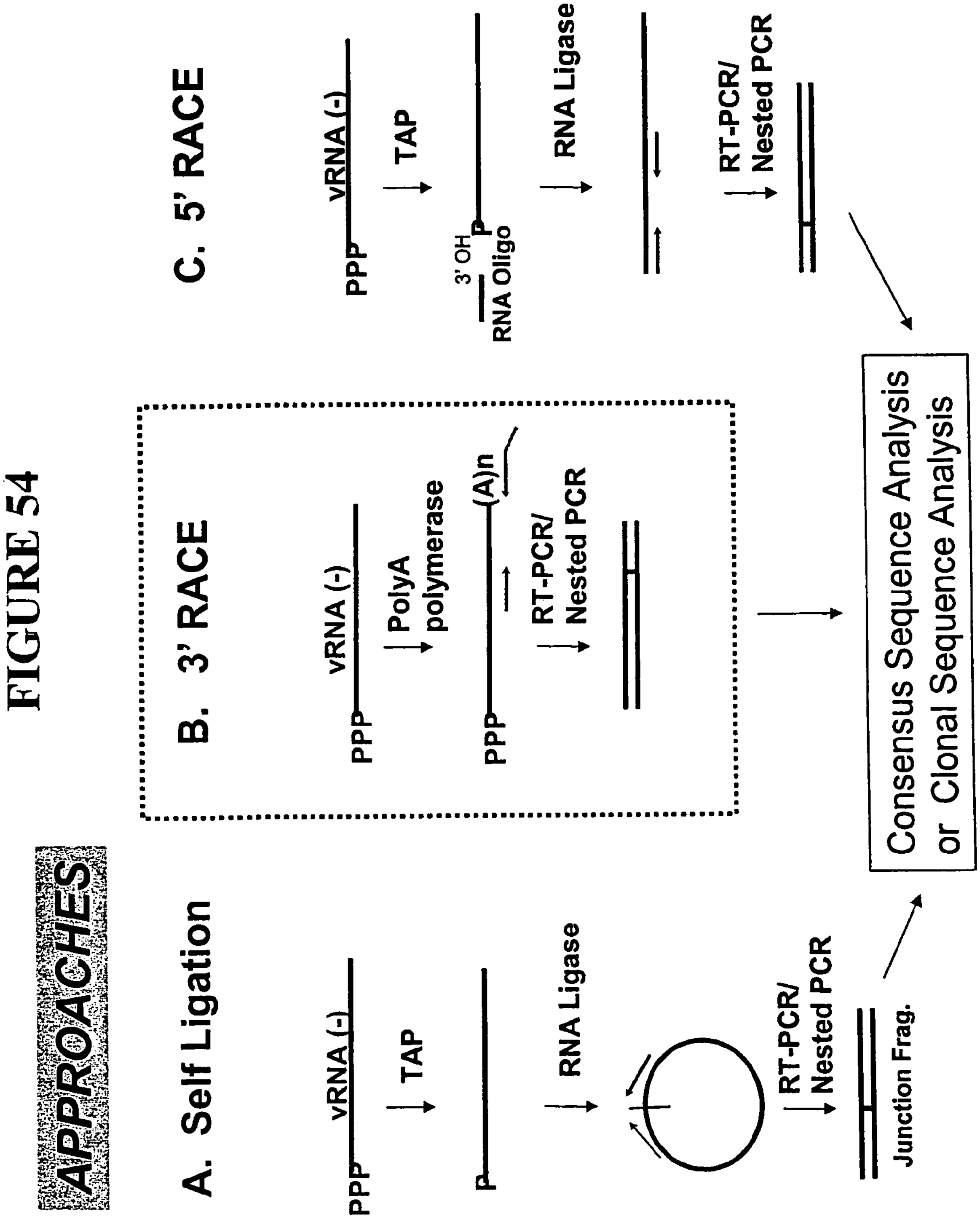

FIG. 54: Leader sequences of human *metapneumovirus* (hMPV) NL/1/00 (A1) genomic RNA was determined using a combination of polyadenylation and 3' RACE methods.

Figure 55:
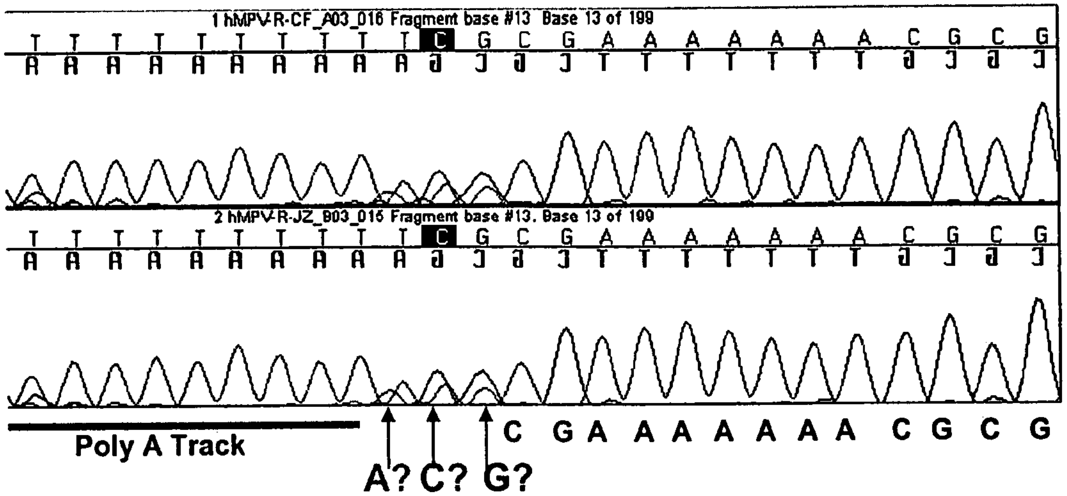

FIG. 55: Sequencing analyses on PCR products directly and on PCR clones both indicated that the leader region of hMPV consisted of 5' ACG CGA AAA AAA CGC GTA TA (SEQ ID NO:394) (expressed as positive sense cDNA orientation) at the 3' most proximal 20 nucleotides in the leader sequence. The two newly identified nucleotides are underlined.

Figure 56:
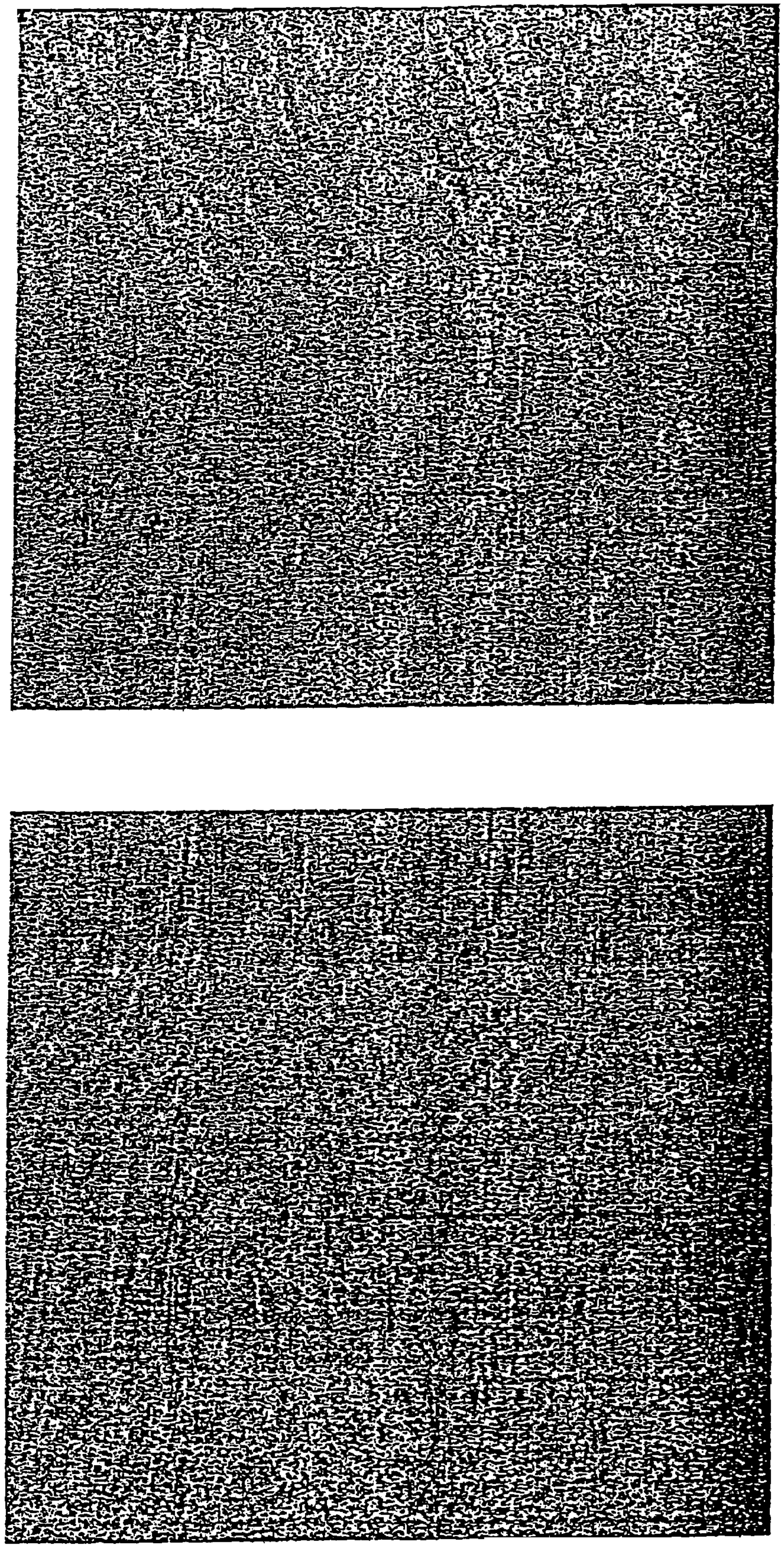

FIG. 56: Plaque formation resulting from successful rescue of infectious virus from the recombinant hMPV clone #2 which has the APV leader and trailer.

Figure 57:
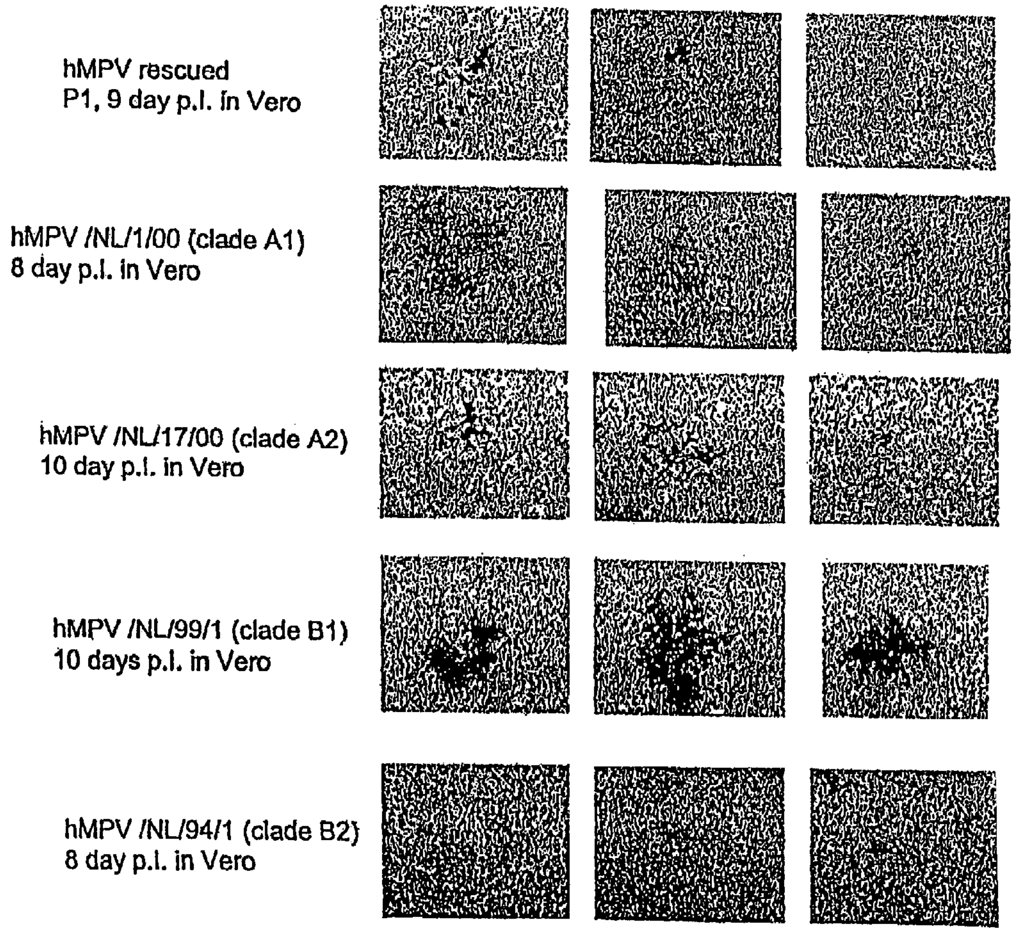

FIG. 57: Immunostaining of rescued recombinant hMPV. Guinea pig polyclonal antibody followed by anti-guinea pig HRP and the DAKO AEC substrate was used for immunostaining. Positive immunostaining was evident for hMPV from various clades, i.e., A1, A2, B1, and B2, indicating that successful rescue was achieved in all subgroups. (pI=post infection)

Figure 58:
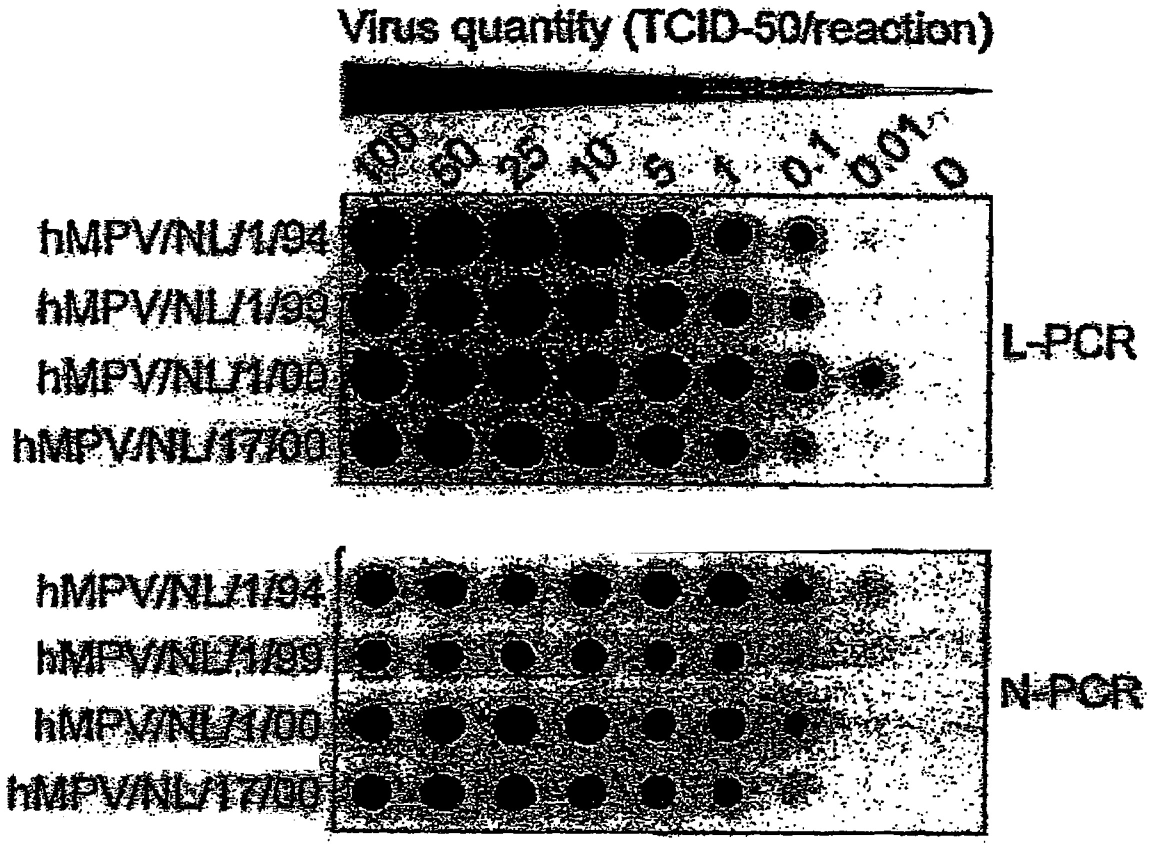

FIG. 58: Results of RT-PCR and DNA blotting assay used to detect the presence of hMPV in a sample. RT-PCR products using primers specific for the L and N genes of hMPV were transferred to a membrane and subsequently probed with an oligonucleotide specific for the L gene or the N gene respectively. Hydbridization was detected using streptavidinperoxidase. The results indicate that the assay was sensitive for the detection of both the L and N genes of hMPV.

FIG. 59: Taqman assay results used to detect hMPV. A) NL-N Taqman assay on titrated viral RNA from the four hMPV prototype virus strains showing the equivalent sensitivity of the assay for all four prototype strains of hMPV. B) Quantitation of RNA transcripts demonstrated that as low as 5 RNA copies yielded a positive signal in the Taqman RT-PCR assay. C) Entropy plots of oligonucleotide-annealing sites for the four prototype hMPV strains for the different primer/probe sets tested. D) Amplification of viral cDNA of the four prototype cDNA strains using previously published assays showed lower sensitivity than the NL-N assay for the hMPV A viruses, and a lack of detection for the hMPV B viruses.

Figure 60:
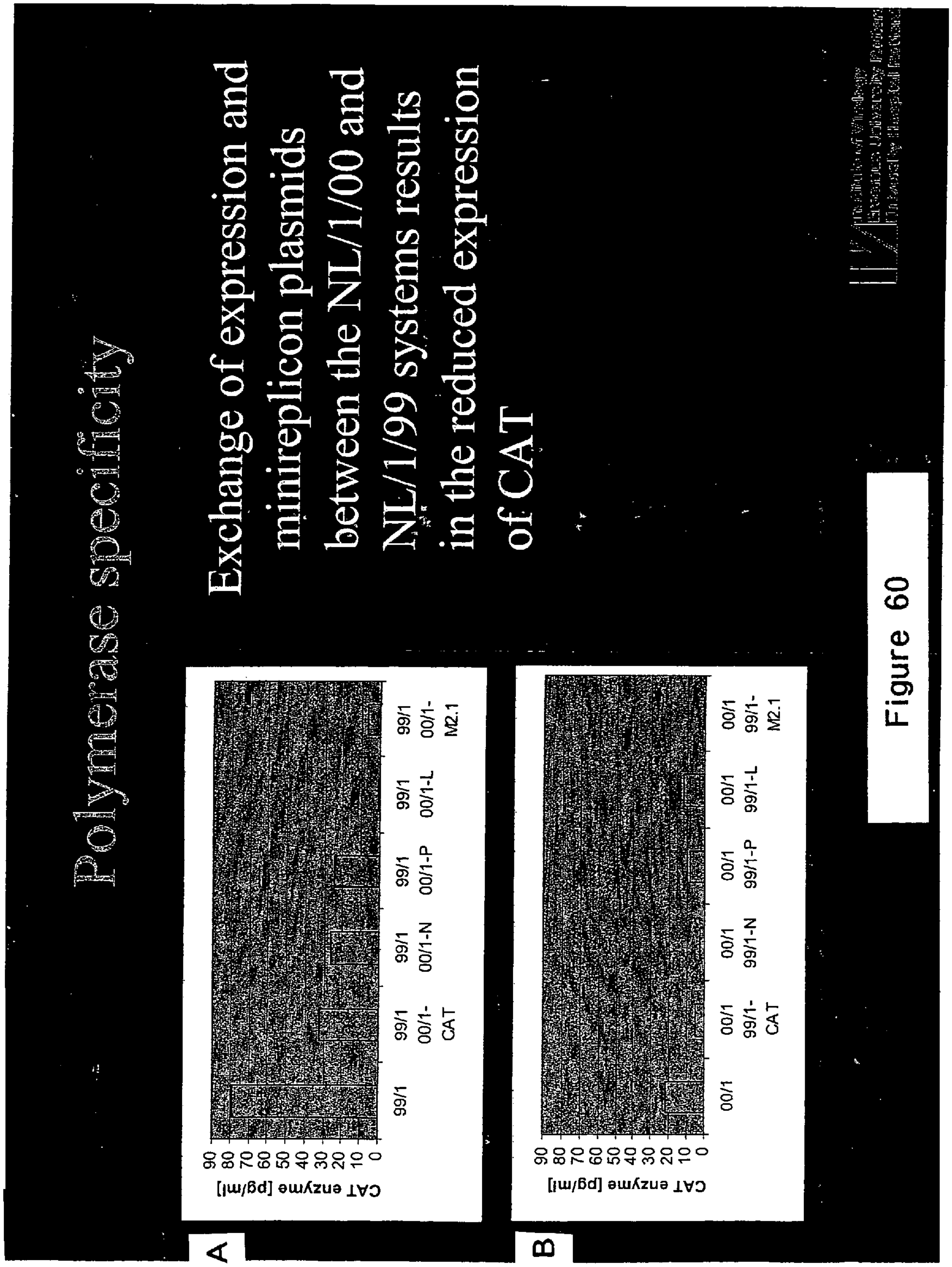

FIG. 60: Attenuation of human *metapneumovirus* resulting from substitution of different viral genes. A) Shows the levels of CAT enzyme in different chimeric forms of hMPV that were generated by substituting different genes of the isolate 99-1 of hMPV (SEQ ID NO:18) with the respective analogous gene of isolate 00-1 of hMPV (SEQ ID NO:19). B) Shows the levels of CAT enzyme in different chimeric forms of hMPV that were generated by substituting different genes of the isolate 00-1 of hMPV (SEQ ID NO:19) with the respective analogous gene of isolate 99-1 of hMPV (SEQ ID NO:18).

FIG. 61: Generation of M2 deletion mutants.

Figure 62:
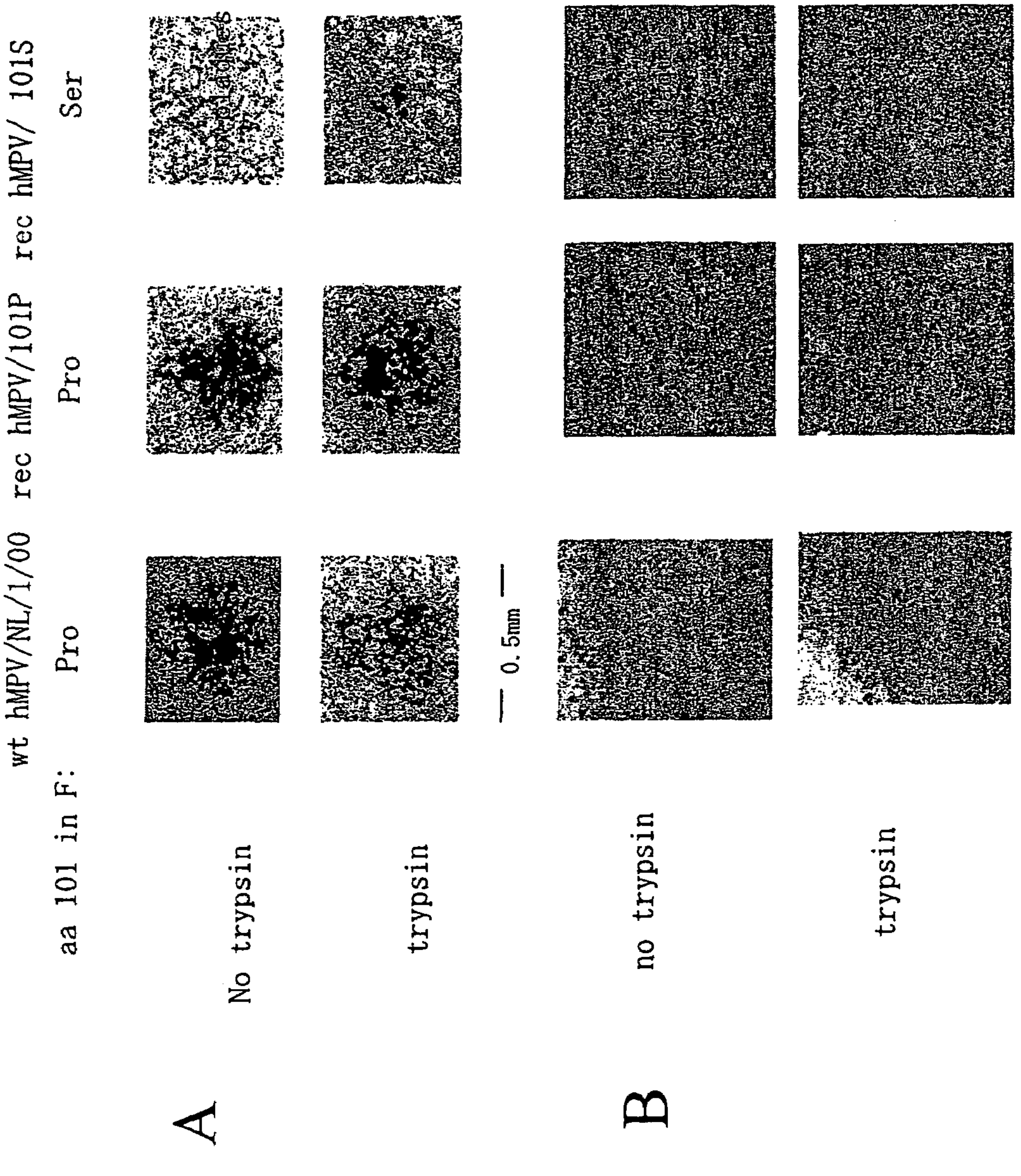

FIG. 62: A: Shows plaques in Vero cells of wild type hMPV (wt hMPV/NL/1/00), recombinant hMPV with proline at the 101 position of the F protein (rec hMPV/101P), and recombinant hMPV with serine at the 101 position of the F protein (rec hMPV/101S). Growth of the virus was either in the presence or the absence of Trypsin. B: Shows plaques 6 days after infection under methyl cellulose of wild type hMPV, recombinant hMPV with proline at the 101 position of the F protein, and recombinant hMPV with serine at the 101 position of the F protein. Growth of the virus was either in the presence or the absence of Trypsin.

Figure 63:
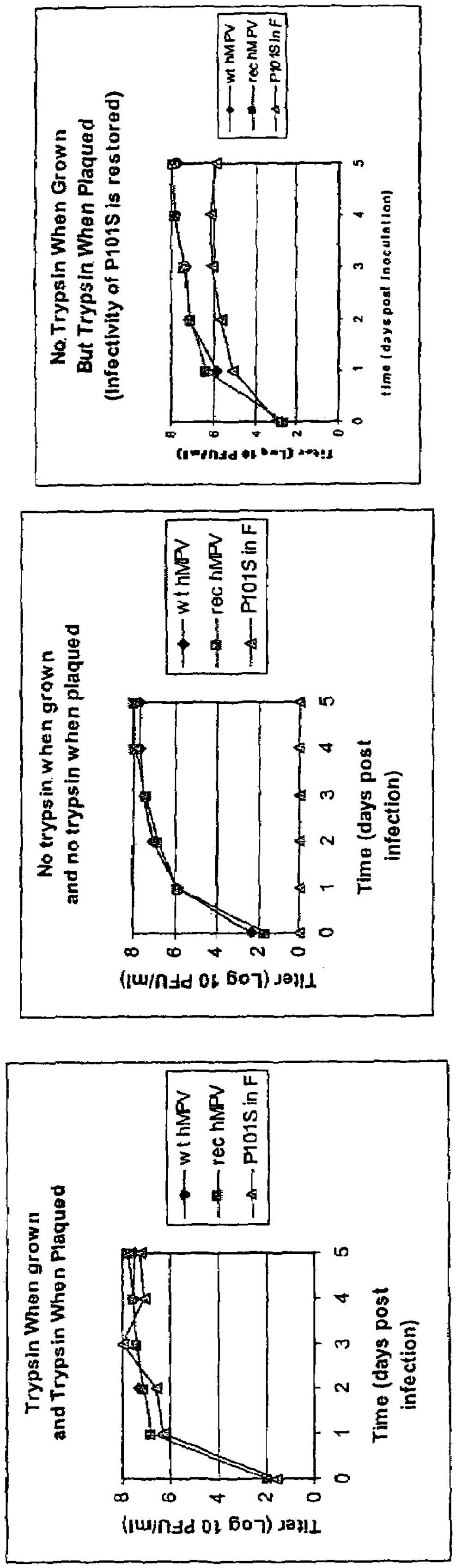

FIG. 63: Shows growth curves of wild type hMPV (wt hMPV), recombinant hMPV with proline at the 101 position of the F protein (rec hMPV), and recombinant hMPV with serine at the 101 position of the F protein (P101S in F). Presence or the absence of Trypsin during different phases of the experiment are indicated on top of the graphs.

Figure 64:
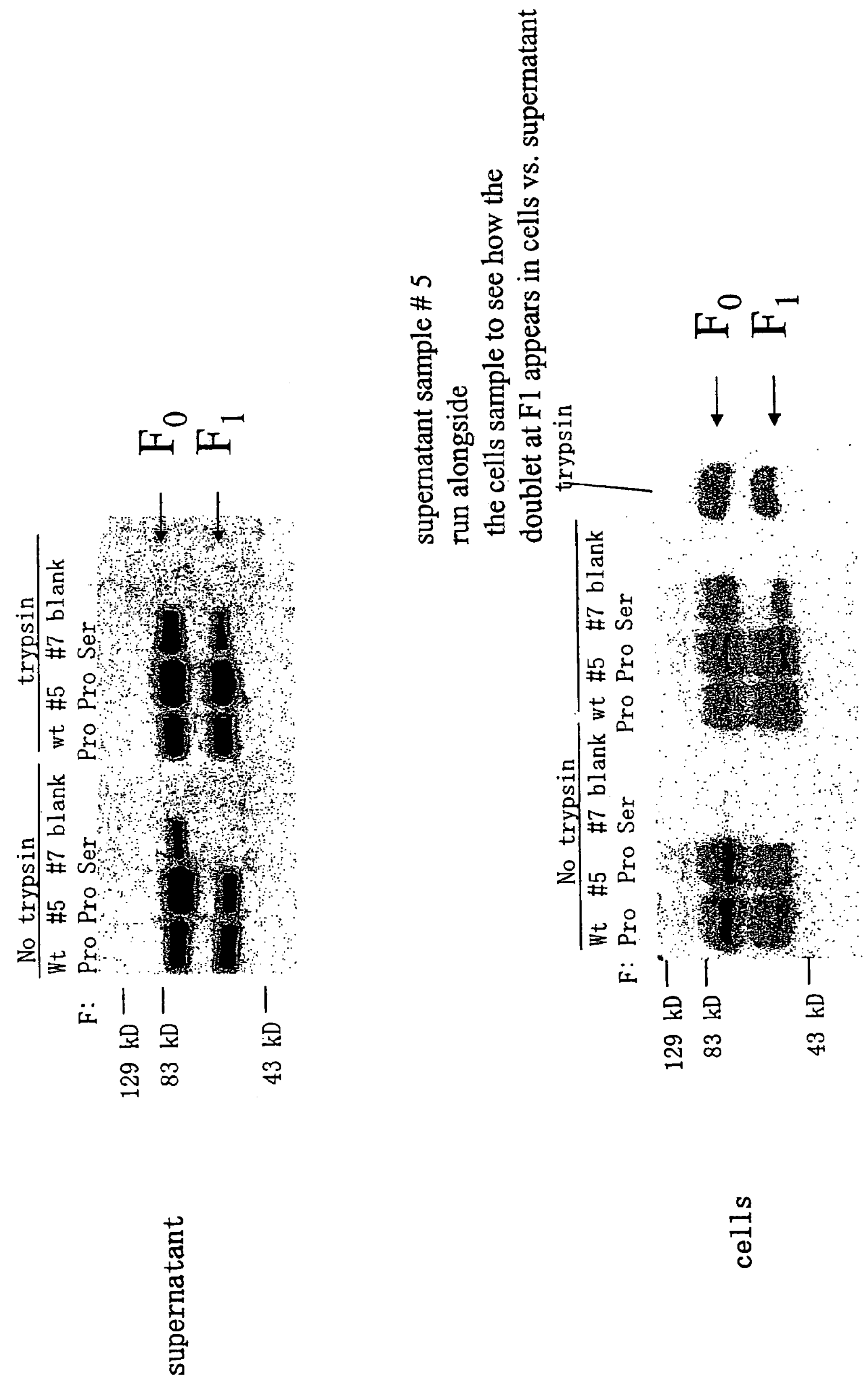

FIG. 64 Western blot analysis of the supernatant (A) or cells (B) of Vero cells infected with wild type hMPV (wt Pro), recombinant hMPV with proline at the 101 position of the F protein (#5 Pro), and recombinant hMPV with serine at the 101 position of the F protein (#7 Ser) grown either in the presence or absence of Trypsin. The uncleaved $F_0$ protein and the cleavage product $F_1$ are indicated by arrows.

Figure 65:
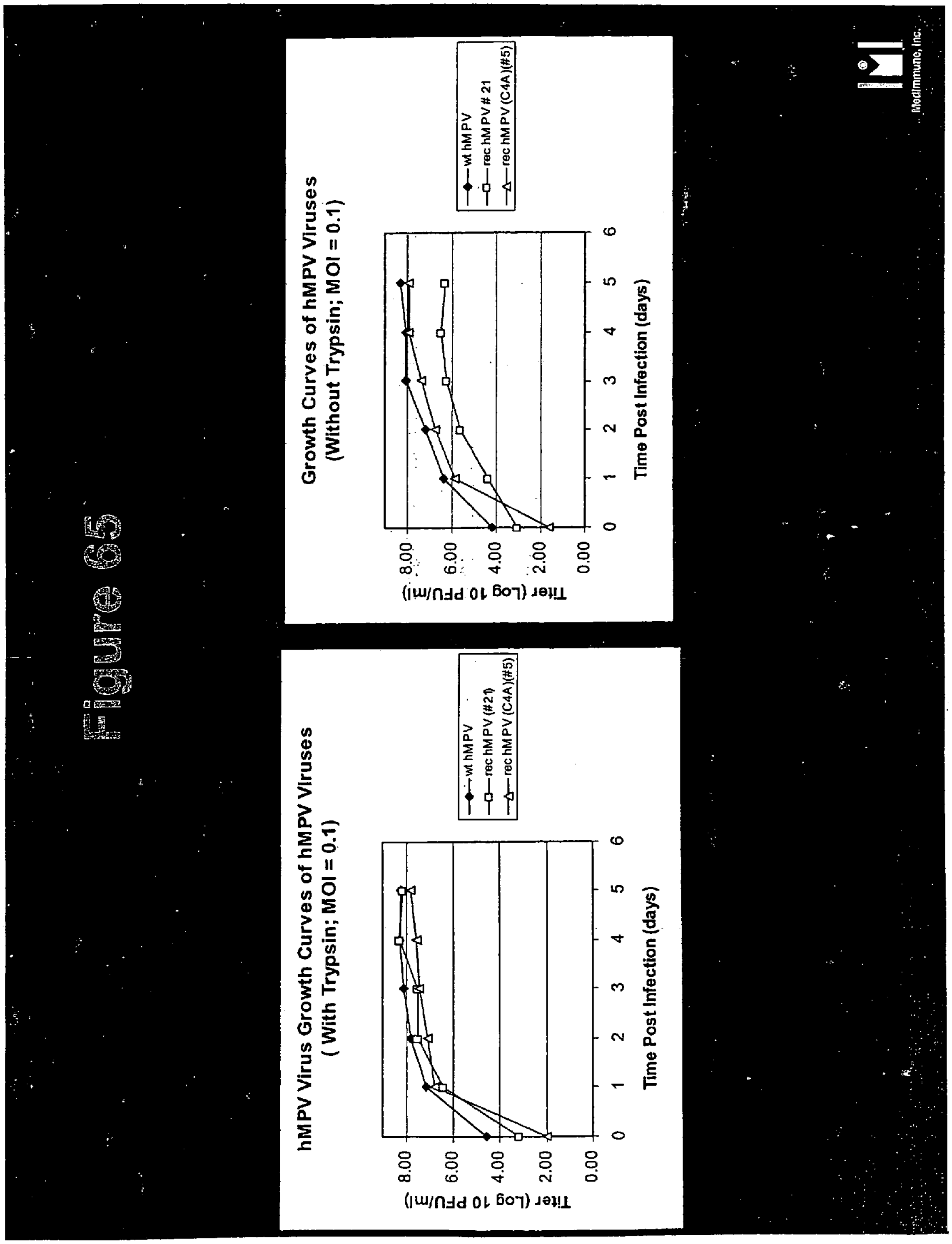

FIG. 65. Growth curves of recombinant hMPV/NL/1/00 in the presence and absence of Trypsin. wt hMPV=wild type hMPV/NL/1/00; rec hMPV (#21)=recombinant virus with the sequence of hMPV/NL/1/00; rec hMPV (C4A)(#5) recombinant virus with the sequence of hMPV/NL/1/00.

FIG. 66. Replication of wild type and recombinant hMPV in the upper and lower respiratory tract of hamsters.

Figure 67:
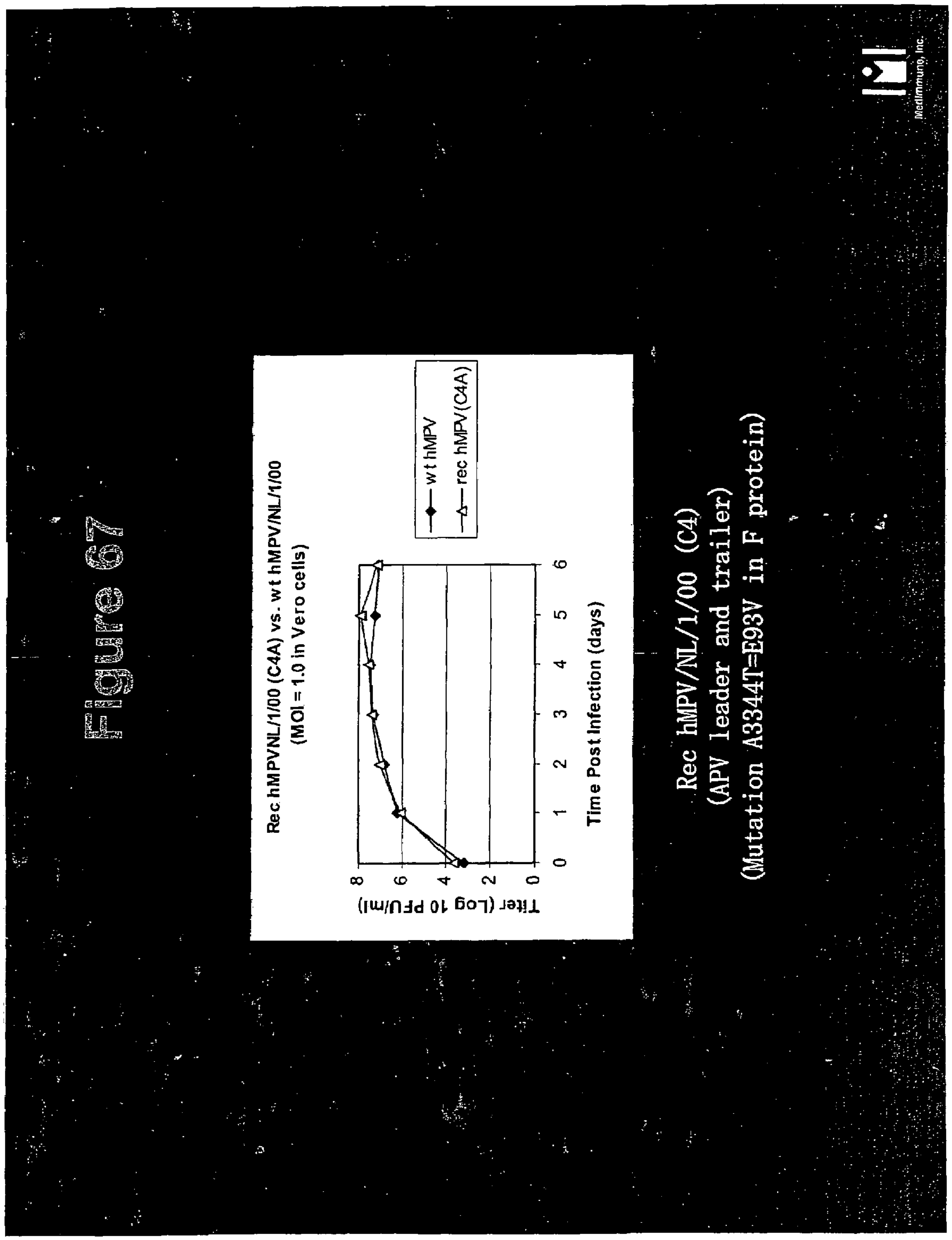

FIG. 67. Growth curves of recombinant hMPV/NL/1/00 in the presence and absence of Trypsin. wt hMPV=wild type hMPV/NL/1/00; rec hMPV (#21)=recombinant virus with the sequence of hMPV/NL/1/00; rec hMPV (C4A)(#5) recombinant virus with the sequence of hMPV/NL/1/00.

Figure 68:
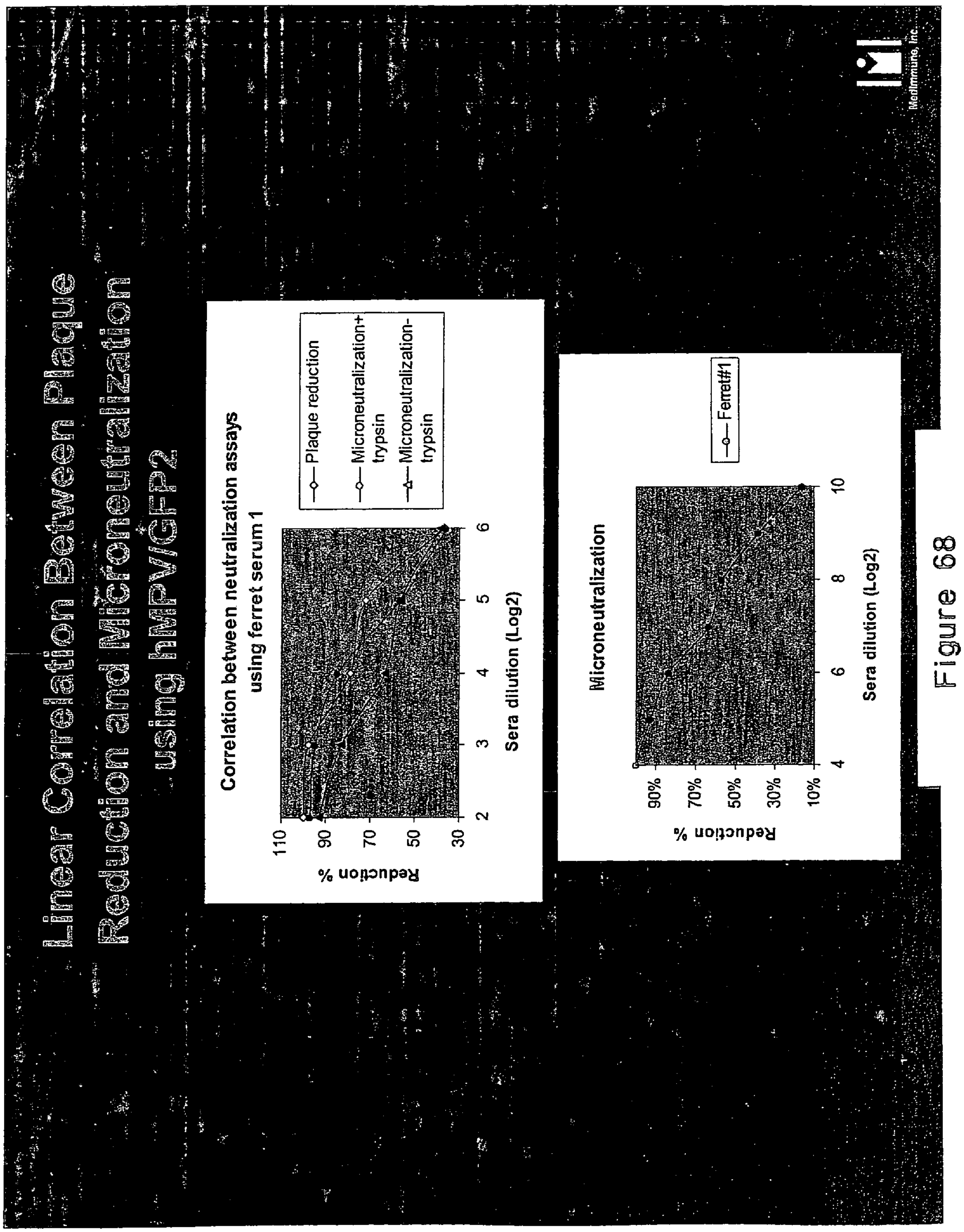

FIG. 68. Linear Correlation Between Plaque Reduction and Microneutralization using hMPV/GFP2.

5. DETAILED DESCRIPTION OF THE INVENTION

The invention relates to an isolated mammalian negative strand RNA virus, *metapneumovirus* (MPV) and variants thereof, within the sub-family *Pneumovirinae*, of the family Paramyxoviridae. The present invention also relates to isolated mammalian negative strand RNA viruses identifiable as phylogenetically corresponding or relating to the genus *metapneumovirus* and components thereof. The mammalian MPVs of the invention can be a variant A1, A2, B1 or B2 mammalian MPV. However, the mammalian MPVs of the present invention may encompass additional variants of MPV yet to be identified, and are not limited to variants A1, A2, B1 or B2.

The invention relates to genomic nucleotide sequences of different variants of isolates of mammalian *metapneumoviruses* (MPV), in particular human *metapneumoviruses* including isolates of variants A1, A2, B1 and B2. The invention relates to the use of the sequence information of different isolates of mammalian *metapneumoviruses* for diagnostic and therapeutic methods. The present invention relates to the differences of the genomic nucleotide sequences among the different *metapneumovirus*-isolates, and their use in the diagnostic and therapeutic methods of the invention. In particular, the invention relates to the use of the single nucleotide polymorphisms (SNPs) among different *metapneumovirus* isolates for diagnostic and therapeutic methods. The present invention also relates to the use serological characterization of the different isolates of mammalian *metapneumoviruses*, alone or in combination with the sequence information of the different isolates, for diagnostic and therapeutic methods.

The present invention relates to nucleotide sequences encoding the genome of a *metapneumovirus* or a portion thereof, including both mammalian and avian *metapneumovirus* (APV). The present invention relates to nucleotide sequences encoding gene products of a *metapneumovirus*, including both mammalian and avian *metapneumoviruses*. The present invention further relates to nucleic acids, including DNA and RNA, that encodes the genome or a portion thereof of a *metapneumovirus*, including both mammalian and avian, in addition to a nucleotide sequence which is heterologous or non-native to the viral genome. The invention further encompasses recombinant or chimeric viruses encoded by said nucleotide sequences.

In accordance with the present invention, a recombinant virus is one derived from a mammalian MPV or an APV that is encoded by endogenous or native genomic sequences or non-native genomic sequences. In accordance with the invention, a non-native sequence is one that is different from the native or endogenous genomic sequence due to one or more mutations, including, but not limited to, point mutations, rearrangements, insertions, deletions etc., the genomic sequence that may or may not result in a phenotypic change. In accordance with the invention, a chimeric virus is a recombinant MPV or APV which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

The invention further relates to vaccine formulations comprising mammalian or avian *metapneumovirus*, including recombinant forms of said viruses. In particular, the present invention encompasses vaccine preparations comprising recombinant or chimeric forms of MPV or APV that express antigenic glycoproteins, including glycoproteins of MPV, or APV and/or non-native MPV or APV glycoproteins. The invention also encompasses vaccine preparations comprising recombinant forms of MPV or APV that encode antigenic sequences of another negative strand RNA virus, including PIV or RSV, or a heterologous glycoprotein of another species or strain of *metapneumovirus*. The invention further relates to vaccines comprising chimeric hMPV wherein the chimeric hMPV encodes one or more APV proteins and wherein the chimeric hMPV optionally additionally expresses one or more heterologous or non-native sequences. The invention also relates to vaccines comprising chimeric APV wherein the chimeric APV encodes one or more hMPV proteins and wherein the chimeric APV optionally additionally expresses one or more heterologous or non-native sequences. The present invention also relates to multivalent vaccines, including bivalent and trivalent vaccines. In particular, the bivalent and trivalent vaccines of the invention encompass two or more antigenic polypeptides expressed by the same or different pneumoviral vectors encoding antigenic proteins of MPV, APV, PIV, RSV, influenza or another negative strand RNA virus, or *morbillivirus*.

5.1 Mammalian *Metapneumovirus* Structural Characteristics of a Mammalian *Metapneumovirus*

The invention provides a mammalian MPV. The mammalian MPV is a negative-sense single stranded RNA virus belonging to the sub-family *Pneumovirinae* of the family Paramyxoviridae. Moreover, the mammalian MPV is identifiable as phylogenetically corresponding to the genus *Metapneumovirus*, wherein the mammalian MPV is phylogenetically more closely related to a virus isolate deposited as I-2614 with CNCM, Paris (SEQ ID NO:19) than to turkey rhinotracheitis virus, the etiological agent of avian rhinotracheitis. A virus is identifiable as phylogenetically corresponding to the genus *Metapneumovirus* by, e.g., obtaining nucleic acid sequence information of the virus and testing it in phylogenetic analyses. Any technique known to the skilled artisan can be used to determine phylogenetic relationships between strains of viruses. For exemplary methods see section 5.9. Other techniques are disclosed in International Patent Application PCT/NL02/00040, published as WO 02/057302, which is incorporated by reference in its entirety herein. In particular, PCT/NL02/00040 discloses nucleic acid sequences that are suitable for phylogenetic analysis at page 12, line 27 to page 19, line 29, which are incorporated by reference herein. A virus can further be identified as a mammalian MPV on the basis of sequence similarity as described in more detail below.

In addition to phylogenetic relatedness and sequence similarity of a virus to a mammalian MPV as disclosed herein, the similarity of the genomic organization of a virus to the genomic organization of a mammalian MPV disclosed herein can also be used to identify the virus as a mammalian MPV. For a representative genomic organization of a mammalian MPV see FIG. 27. In certain embodiments, the genomic organization of a mammalian MPV is different from the genomic organization of *pneumoviruses* within the sub-family *Pneumovirinae* of the family Paramyxoviridae. The classification of the two genera, *metapneumovirus* and *pneumovirus*, is based primarily on their gene constellation; *metapneumoviruses* generally lack non-structural proteins such as NS1 or NS2 (see also Randhawa et al., 1997, J. Virol. 71:9849-9854) and the gene order is different from that of *pneumoviruses* (RSV: '3-NS1-NS2-N-P-M-SH-G-F-M2-L-5', APV: '3-N-P-M-F-M2-SH-G-L-5') (Lung, et al., 1992, J. Gen. Virol. 73:1709-17 15; Yu, et al., 1992, *Virology* 186:426-434; Randhawa, et al., 1997, J. Virol. 71:9849-9854).

Further, a mammalian MPV of the invention can be identified by its immunological properties. In certain embodiments, specific anti-sera can be raised against mammalian MPV that can neutralize mammalian MPV. Monoclonal and polyclonal antibodies can be raised against MPV that can also neutralize mammalian MPV. (See, PCT WO 02/057302 at pages ______ to ______, which is incorporated by reference herein.

The mammalian MPV of the invention is further characterized by its ability to infect a mammalian host, i.e., a mammalian cultured cell or a mammal. Unlike APV, mammalian MPV does not replicate or replicates only at low levels in chickens and turkeys. Mammalian MPV replicates, however, in mammalian hosts, such as cynomolgous macaques. In certain, more specific, embodiments, a mammalian MPV is further characterized by its ability to replicate in a mammalian host. In certain, more specific embodiments, a mammalian MPV is further characterized by its ability to cause the mammalian host to express proteins encoded by the genome of the mammalian MPV. In even more specific embodiments, the viral proteins expressed by the mammalian MPV are inserted into the cytoplasmic membranes of the mammalian host. In certain embodiments, the mammalian MPV of the invention can infect a mammalian host and cause the mammalian host to produce new infectious viral particles of the mammalian MPV. For a more detailed description of the functional characteristics of the mammalian MPV of the invention, see section 5.1.2.

In certain embodiments, the appearance of a virus in an electron microscope or its sensitivity to chloroform can be used to identify the virus as a mammalian MPV. The mammalian MPV of the invention appears in an electron microscope as *paramyxovirus*-like particle. Consistently, a mammalian MPV is sensitive to treatment with chloroform; a mammalian MPV is cultured optimally on tMK cells or cells functionally equivalent thereto and it is essentially trypsine dependent in most cell cultures. Furthermore, a mammalian MPV has a typical cytopathic effects (CPE) and lacks haemagglutinating activity against species of red blood cells. The CPE induced by MPV isolates are similar to the CPE induced by hRSV, with characteristic syncytia formation followed by rapid internal disruption of the cells and subsequent detachment from the culture plates. Although most *paramyxoviruses* have haemagglutinating activity, most of the *pneumoviruses* do not (Pringle, C. R. In: *The Paramyxoviruses*; (ed. D. W. Kingsbury) 1-39 (Plenum Press, New York, 1991)). A mammalian MPV contains a second overlapping ORF (M2-2) in the nucleic acid fragment encoding the M2 protein. The occurrence of this second overlapping ORF occurs in other *pneumoviruses* as shown in Ahmadian et al., 1999, *J Gen. Vir.* 80:2011-2016.

In certain embodiments, the invention provides methods to identify a viral isolate as a mammalian MPV. A test sample can, e.g., be obtained from an animal or human. The sample is then tested for the presence of a virus of the sub-family *Pneumovirinae*. If a virus of the sub-family *Pneumovirinae* is present, the virus can be tested for any of the characteristics of a mammalian MPV as discussed herein, such as, but not limited to, phylogenetic relatedness to a mammalian MPV, nucleotide sequence identity to a nucleotide sequence of a mammalian MPV, amino acid sequence identity/homology to a amino acid sequence of a mammalian MPV, and genomic organization. Furthermore, the virus can be identified as a mammalian MPV by cross-hybridization experiments using nucleic acid sequences from a MPV isolate, RT-PCR using primers specific to mammalian MPV, or in classical cross-serology experiments using antibodies directed against a mammalian MPV isolate. In certain other embodiments, a mammalian MPV can be identified on the basis of its immunological distinctiveness, as determined by quantitative neutralization with animal antisera. The antisera can be obtained from, e.g., ferrets, pigs or macaques that are infected with a mammalian MPV (see, e.g., Example 8).

In certain embodiments, the serotype does not cross-react with viruses other than mammalian MPV. In other embodiments, the serotype shows a homologous-to-heterologous titer ratio >16 in both directions If neutralization shows a certain degree of cross-reaction between two viruses in either or both directions (homologous-to-heterologous titer ration of eight or sixteen), distinctiveness of serotype is assumed if substantial biophysical/biochemical differences of DNA sequences exist. If neutralization shows a distinct degree of cross-reaction between two viruses in either or both directions (homologous-to-heterologous titer ratio of smaller than eight), identity of serotype of the isolates under study is assumed. Isolate I-2614, herein also known as MPV isolate 00-1, can be used as prototype.

In certain embodiments, a virus can be identified as a mammalian MPV by means of sequence homology/identity of the viral proteins or nucleic acids in comparison with the amino acid sequence and nucleotide sequences of the viral isolates disclosed herein by sequence or deposit. In particular, a virus is identified as a mammalian MPV when the genome of the virus contains a nucleic acid sequence that has a percentage nucleic acid identity to a virus isolate deposited as I-2614 with CNCM, Paris which is higher than the percentages identified herein for the nucleic acids encoding the L protein, the M protein, the N protein, the P protein, or the F protein as identified herein below in comparison with APV-C (see Table 1). (See, PCT WO 02/05302, at pp. 12 to 19, which is incorporated by reference herein. Without being bound by theory, it is generally known that viral species, especially RNA virus species, often constitute a quasi species wherein the members of a cluster of the viruses display sequence heterogeneity. Thus, it is expected that each individual isolate may have a somewhat different percentage of sequence identity when compared to APV-C.

The highest amino sequence identity between the proteins of MPV and any of the known other viruses of the same family to date is the identity between APV-C and human MPV. Between human MPV and APV-C, the amino acid sequence identity for the matrix protein is 87%, 88% for the nucleoprotein, 68% for the phosphoprotein, 81% for the fusion protein and 56-64% for parts of the polymerase protein, as can be deduced when comparing the sequences given in FIG. 30, see also Table 1. Viral isolates that contain ORFs that encode proteins with higher homology compared to these maximum values are considered mammalian MPVs. It should be noted that, similar to other viruses, a certain degree of variation is found between different isolated of mammalian MPVs.

TABLE 1

Amino acid sequence identity between the ORFs of MPV and those of other paramyxoviruses.

| | N | P | M | F | M2-1 | M2-2 | L |
|---|---|---|---|---|---|---|---|
| APV A | 69 | 55 | 78 | 67 | 72 | 26 | 64 |
| APV B | 69 | 51 | 76 | 67 | 71 | 27 | –[2] |
| APV C | 88 | 68 | 87 | 81 | 84 | 56 | –[2] |
| hRSV A | 42 | 24 | 38 | 34 | 36 | 18 | 42 |
| hRSV B | 41 | 23 | 37 | 33 | 35 | 19 | 44 |
| bRSV | 42 | 22 | 38 | 34 | 35 | 13 | 44 |
| PVM | 45 | 26 | 37 | 39 | 33 | 12 | –[2] |
| others[3] | 7-11 | 4-9 | 7-10 | 10-18 | –[4] | –[4] | 13-14 |

Footnotes:
[1]No sequence homologies were found with known G and SH proteins and were thus excluded
[2]Sequences not available.
[3]others: human parainfluenza virus type 2 and 3, Sendai virus, measles virus, nipah virus, phocine distemper virus, and New Castle Disease virus.
[4]ORF absent in viral genome.

In certain embodiments, the invention provides a mammalian MPV, wherein the amino acid sequence of the SH protein of the mammalian MPV is at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or at least 99.5% identical to the amino acid sequence of SEQ ID NO:382 (SH protein of isolate NL/1/00; see Table 14). The isolated negative-sense single stranded RNA *metapneumovirus* that comprises the SH protein that is at least 30% identical to SEQ ID NO:382 (SH protein of isolate NL/1/00; see Table 14) is capable of infecting a mammalian host. In certain embodiments, the isolated negative-sense single stranded RNA *metapneumovirus* that comprises the SH protein that is at least 30% identical to SEQ ID NO:382 (SH protein of isolate NL/1/00; see Table 14) is capable of replicating in a mammalian host. In certain embodiments, a mammalian MPV contains a nucleotide sequence that encodes a SH protein that is at least 30% identical to SEQ ID NO:382 (SH protein of isolate NL/1/00; see Table 14).

In certain embodiments, the invention provides a mammalian MPV, wherein the amino acid sequence of the G protein of the mammalian MPV is at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or at least 99.5% identical to the amino acid sequence of SEQ ID NO:322 (G protein of isolate NL/1/00; see Table 14). The isolated negative-sense single stranded RNA *metapneumovirus* that comprises the G protein that is at least 20% identical to SEQ ID NO:322 (G protein of isolate NL/1/00; see Table 14) is capable of infecting a mammalian host. In certain embodiments, the isolated negative-sense single stranded RNA *metapneumovirus* that comprises the G protein that is at least 20% identical to SEQ ID NO:322 (G protein of isolate NL/1/00; see Table 14) is capable of replicating in a mammalian host. In certain embodiments, a mammalian MPV contains a nucleotide sequence that encodes a G protein that is at least 20% identical to SEQ ID NO:322 (G protein of isolate NL/1/00; see Table 14).

In certain embodiments, the invention provides a mammalian MPV, wherein the amino acid sequence of the L protein of the mammalian MPV is at least 85%, at least 90%, at least 95%, at least 98%, at least 99%, or at least 99.5% identical to the amino acid sequence of SEQ ID NO:330 (L protein of isolate NL/1/00; see Table 14). The isolated negative-sense single stranded RNA *metapneumovirus* that comprises the L protein that is at least 85% identical to SEQ ID NO:330 (L protein of isolate NL/1/00; see Table 14) is capable of infecting a mammalian host. In certain embodiments, the isolated negative-sense single stranded RNA *metapneumovirus* that comprises the L protein that is at least 85% identical to SEQ ID NO:330 (L protein of isolate NL/1/00; see Table 14) is capable of replicating in a mammalian host. In certain embodiments, a mammalian MPV contains a nucleotide sequence that encodes a L protein that is at least 20% identical to SEQ ID NO:330 (L protein of isolate NL/1/00; see Table 14).

In certain embodiments, the invention provides a mammalian MPV, wherein the amino acid sequence of the N protein of the mammalian MPV is at least 90%, at least 95%, or at least 98% identical to the amino acid sequence of SEQ ID NO:366. The isolated negative-sense single stranded RNA *metapneumovirus* that comprises the N protein that is at least 90% identical in amino acid sequence to SEQ ID NO:366 is capable of infecting mammalian host. In certain embodiments, the isolated negative-sense single stranded RNA *metapneumovirus* that comprises the N protein that is 90% identical in amino acid sequence to SEQ ID NO:366 is capable of replicating in a mammalian host. The amino acid identity is calculated over the entire length of the N protein. In certain embodiments, a mammalian MPV contains a nucleotide sequence that encodes a N protein that is at least 90%, at least 95%, or at least 98% identical to the amino acid sequence of SEQ ID NO:366.

The invention further provides mammalian MPV, wherein the amino acid sequence of the P protein of the mammalian MPV is at least 70%, at least 80%, at least 90%, at least 95% or at least 98% identical to the amino acid sequence of SEQ ID NO:374. The mammalian MPV that comprises the P protein that is at least 70% identical in amino acid sequence to SEQ ID NO:374 is capable of infecting a mammalian host. In certain embodiments, the mammalian MPV that comprises the P protein that is at least 70% identical in amino acid sequence to SEQ ID NO:374 is capable of replicating in a mammalian host. The amino acid identity is calculated over the entire length of the P protein. In certain embodiments, a mammalian MPV contains a nucleotide sequence that encodes a P protein that is at least 70%, at least 80%, at least 90%, at least 95% or at least 98% identical to the amino acid sequence of SEQ ID NO:374.

The invention further provides, mammalian MPV, wherein the amino acid sequence of the M protein of the mammalian MPV is at least 90%, at least 95% or at least 98% identical to the amino acid sequence of SEQ ID NO:358. The mammalian MPV that comprises the M protein that is at least 90% identical in amino acid sequence to SEQ ID NO:358 is capable of infecting mammalian host. In certain embodiments, the isolated negative-sense single stranded RNA *metapneumovirus* that comprises the M protein that is 90% identical in amino acid sequence to SEQ ID NO:358 is capable of replicating in a mammalian host. The amino acid identity is calculated over the entire length of the M protein. In certain embodiments, a mammalian MPV contains a nucleotide sequence that encodes a M protein that is at least 90%, at least 95% or at least 98% identical to the amino acid sequence of SEQ ID NO:358.

The invention further provides mammalian MPV, wherein the amino acid sequence of the F protein of the mammalian MPV is at least 85%, at least 90%, at least 95% or at least 98% identical to the amino acid sequence of SEQ ID NO:314. The mammalian MPV that comprises the F protein that is at least 85% identical in amino acid sequence to SEQ ID NO:314 is capable of infecting a mammalian host. In certain embodiments, the isolated negative-sense single stranded RNA *metapneumovirus* that comprises the F protein that is 85% identical in amino acid sequence to SEQ ID NO:314 is capable of replicating in mammalian host. The amino acid identity is calculated over the entire length of the F protein. In certain embodiments, a mammalian MPV contains a nucleotide sequence that encodes a F protein that is at least 85%, at least 90%, at least 95% or at least 98% identical to the amino acid sequence of SEQ ID NO:314.

The invention further provides mammalian MPV, wherein the amino acid sequence of the M2-1 protein of the mammalian MPV is at least 85%, at least 90%, at least 95% or at least 98% identical to the amino acid sequence of SEQ ID NO:338. The mammalian MPV that comprises the M2-1 protein that is at least 85% identical in amino acid sequence to SEQ ID NO:338 is capable of infecting a mammalian host. In certain embodiments, the isolated negative-sense single stranded RNA *metapneumovirus* that comprises the M2-1 protein that is 85% identical in amino acid sequence to SEQ ID NO:338 is capable of replicating in a mammalian host. The amino acid identity is calculated over the entire length of the M2-1 protein. In certain embodiments, a mammalian MPV contains a nucleotide sequence that encodes a M2-1 protein that is at least 85%, at least 90%, at least 95% or at least 98% identical to the amino acid sequence of SEQ ID NO:338.

The invention further provides mammalian MPV, wherein the amino acid sequence of the M2-2 protein of the mammalian MPV is at least 60%, at least 70%, at least 80%, at least 90%, at least 95% or at least 98% identical to the amino acid sequence of SEQ ID NO:346 The isolated mammalian MPV that comprises the M2-2 protein that is at least 60% identical in amino acid sequence to SEQ ID NO:346 is capable of infecting mammalian host. In certain embodiments, the isolated negative-sense single stranded RNA *metapneumovirus* that comprises the M2-2 protein that is 60% identical in amino acid sequence to SEQ ID NO:346 is capable of replicating in a mammalian host. The amino acid identity is calculated over the entire length of the M2-2 protein. In certain embodiments, a mammalian MPV contains a nucleotide sequence that encodes a M2-1 protein that is at least 60%, at least 70%, at least 80%, at least 90%, at least 95% or at least 98% identical to the amino acid sequence of SEQ ID NO:346.

In certain embodiments, the invention provides mammalian MPV, wherein the negative-sense single stranded RNA *metapneumovirus* encodes at least two proteins, at least three proteins, at least four proteins, at least five proteins, or six proteins selected from the group consisting of (i) a N protein with at least 90% amino acid sequence identity to SEQ ID NO:366; (ii) a P protein with at least 70% amino acid sequence identity to SEQ ID NO:374 (iii) a M protein with at least 90% amino acid sequence identity to SEQ ID NO:358 (iv) a F protein with at least 85% amino acid sequence identity to SEQ ID NO:314 (v) a M2-1 protein with at least 85% amino acid sequence identity to SEQ ID NO:338; and (vi) a M2-2 protein with at least 60% amino acid sequence identity to SEQ ID NO:346.

The invention provides two subgroups of mammalian MPV, subgroup A and subgroup B. The invention also provides four variants A1, A2, B1 and B2. A mammalian MPV can be identified as a member of subgroup A if it is phylogenetically closer related to the isolate 00-1 (SEQ ID NO:19) than to the isolate 99-1 (SEQ ID NO:18). A mammalian MPV can be identified as a member of subgroup B if it is phylogenetically closer related to the isolate 99-1 (SEQ ID NO:18) than to the isolate 00-1 (SEQ ID NO:19). In other embodiments, nucleotide or amino acid sequence homologies of individual ORFs can be used to classify a mammalian MPV as belonging to subgroup A or B.

The different isolates of mammalian MPV can be divided into four different variants, variant A1, variant A2, variant B1 and variant B2 (see FIGS. 21 and 22). The isolate 00-1 (SEQ ID NO:19) is an example of the variant A1 of mammalian MPV. The isolate 99-1 (SEQ ID NO:18) is an example of the variant B1 of mammalian MPV. A mammalian MPV can be grouped into one of the four variants using a phylogenetic analysis. Thus, a mammalian MPV belongs to a specific variant if it is phylogenetically closer related to a known member of that variant than it is phylogenetically related to a member of another variant of mammalian MPV. The sequence of any ORF and the encoded polypeptide may be used to type a MPV isolate as belonging to a particular subgroup or variant, including N, P, L, M, SH, G, M2 or F polypeptides. In a specific embodiment, the classification of a mammalian MPV into a variant is based on the sequence of the G protein. Without being bound by theory, the G protein sequence is well suited for phylogenetic analysis because of the high degree of variation among G proteins of the different variants of mammalian MPV.

In certain embodiments of the invention, sequence homology may be determined by the ability of two sequences to hybridize under certain conditions, as set forth below. A nucleic acid which is hybridizable to a nucleic acid of a mammalian MPV, or to its reverse complement, or to its complement can be used in the methods of the invention to determine their sequence homology and identities to each other. In certain embodiments, the nucleic acids are hybridized under conditions of high stringency.

It is well-known to the skilled artisan that hybridization conditions, such as, but not limited to, temperature, salt concentration, pH, formamide concentration (see, e.g., Sambrook et al., 1989, Chapters 9 to 11, Molecular Cloning, A Laboratory Manual, 2d Ed., Cold Spring Harbor Laboratory Press, Cold Spring Harbor, N.Y., incorporated herein by reference in its entirety). In certain embodiments, hybridization is performed in aqueous solution and the ionic strength of the solution is kept constant while the hybridization temperature is varied dependent on the degree of sequence homology between the sequences that are to be hybridized. For DNA sequences that 100% identical to each other and are longer than 200 basebairsi, hybridization is carried out at approximately 15-25° C. below the melting temperature (Tm) of the perfect hybrid. The melting temperature (Tm) can be calculated using the following equation (Bolton and McCarthy, 1962, Proc. Natl. Acad. Sci. USA 84:1390):

$$Tm=81.5° \text{ C.}-16.6(\log 10[Na+])+(\%\ G+C)-0.63(\% \text{ formamide})-(600/l)$$

Wherein (Tm) is the melting temperature, [Na+] is the sodium concentration, G+C is the Guanine and Cytosine content, and l is the length of the hybrid in basepairs. The effect of mismatches between the sequences can be calculated using the formula by Bonner et al. (Bonner et al., 1973, J. Mol. Biol. 81:123-135): for every 1% of mismatching of bases in the hybrid, the melting temperature is reduced by 1-1.5° C. Thus, by determining the temperature at which two sequences hybridize, one of skill in the art can estimate how similar a sequence is to a known sequence. This can be done, e.g., by comparison of the empirically determined hybridization temperature with the hybridization temperature calculated for the know sequence to hybridize with its perfect match. Through the use of the formula by Bonner et al., the relationship between hybridization temperature and per cent mismatch can be exploited to provide information about sequence similarity.

By way of example and not limitation, procedures using such conditions of high stringency are as follows. Prehybridization of filters containing DNA is carried out for 8 h to overnight at 65 C in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65 C in prehybridization mixture containing 100 μg/ml denatured salmon sperm DNA and 5-20×106 cpm of 32P-labeled probe. Washing of filters is done at 37 C for 1 h in a solution containing 2×SSC, 0.01% PVP, 0.01% Ficoll, and 0.01% BSA. This is followed by a wash in 0.1×SSC at 50 C for 45 min before autoradiography. Other conditions of high stringency which may be used are well known in the art. In other embodiments of the invention, hybridization is performed under moderate of low stringency conditions, such conditions are well-known to the skilled artisan (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols,© 1994-1997 John Wiley and Sons, Inc., each of which is incorporated by reference herein in their entirety). An illustrative low stringency condition is provided by the following system of buffers: hybridization in a buffer comprising 35% formamide, 5×SSC, 50 mM Tris-HCl (pH 7.5), 5 mM EDTA, 0.02% PVP, 0.02% Ficoll, 0.2% BSA, 100 g/ml denatured salmon sperm DNA, and 10% (wt/vol) dextran sulfate for 18-20 hours at 40□C, washing in a buffer consisting of 2×SSC, 25 mM Tris-HCl (pH 7.4), 5 mM EDTA, and 0.1% SDS for 1.5 hours at 55□C, and washing in a buffer consisting of 2×SSC, 25 mM Tris-HCl (pH 7.4), 5 mM EDTA, and 0.1% SDS for 1.5 hours at 60□C.

In certain embodiments, a mammalian MPV can be classified into one of the variant using probes that are specific for a specific variant of mammalian MPV. Such probes include primers for RT-PCR and antibodies. Illustrative methods for identifying a mammalian MPV as a member of a specific variant are described in section 5.9 below.

In certain embodiments of the invention, the different variants of mammalian MPV can be distinguished from each other by way of the amino acid sequences of the different viral proteins (see, e.g., FIG. 42*b*). In other embodiments, the different variants of mammalian MPV can be distinguished from each other by way of the nucleotide sequences of the different ORFs encoded by the viral genome (see, e.g., FIG. 42*b*). A variant of mammalian MPV can be, but is not limited to, A1, A2, B1 or B2. The invention, however, also contemplates isolates of mammalian MPV that are members of another variant yet to be identified. The invention also contemplates that a virus may have one or more ORF that are closer related to one variant and one or more ORFs that are closer phylogenetically related to another variant. Such a virus would be classified into the variant to which the majority of its ORFs are closer phylogenetically related. Non-coding sequences may also be used to determine phylogenetic relatedness.

An isolate of mammalian MPV is classified as a variant B1 if it is phylogenetically closer related to the viral isolate NL/1/99 (SEQ ID NO:18) than it is related to any of the following other viral isolates: NL/1/00 (SEQ ID NO:19), NL/17/00 (SEQ ID NO:20) and NL/1/94 (SEQ ID NO:21).

One or more of the ORFs of a mammalian MPV can be used to classify the mammalian MPV into a variant. A mammalian MPV can be classified as an MPV variant B1, if the amino acid sequence of its G protein is at least 66%, at least 70%, at least 75%, at least 80%, at least 85%, at least 90%, at least 95%, at least 98%, or at least 99% or at least 99.5% identical to the G protein of a mammalian MPV variant B1 as represented by the prototype NL/1/99 (SEQ ID NO:324); if the amino acid sequence of its N proteint is at least 98.5% or at least 99% or at least 99.5% identical to the N protein of a mammalian MPV variant B1 as represented by the prototype NL/1/99 (SEQ ID NO:368); if the amino acid sequence of its P protein is at least 96%, at least 98%, or at least 99% or at least 99.5% identical to the P protein of a mammalian MPV variant B1 as represented by the prototype NL/1/99 (SEQ ID NO:376); if the amino acid sequence of its M protein is identical to the M protein of a mammalian MPV variant B1 as represented by the prototype NL/1/99 (SEQ ID NO:360); if the amino acid sequence of its F protein is at least 99% identical to the F protein of a mammalian MPV variant B1 as represented by the prototype NL/1/99 (SEQ ID NO:316); if the amino acid sequence of its M2-1 protein is at least 98% or at least 99% or at least 99.5% identical to the M2-1 protein of a mammalian MPV variant B1 as represented by the prototype NL/1/99 (SEQ ID NO:340); if the amino acid sequence of its M2-2 protein is at least 99% or at least 99.5% identical to the M2-2 protein of a mammalian MPV variant B1 as represented by the prototype NL/1/99 (SEQ ID NO:348); if the amino acid sequence of its SH protein is at least 83%, at least 85%, at least 90%, at least 95%, at least 98%, or at least 99% or at least 99.5% identical to the SH protein of a mammalian MPV variant B1 as represented by the prototype NL/1/99 (SEQ ID NO:384); and/or if the amino acid sequence of its L protein is at least 99% or at least 99.5% identical to the L protein a mammalian MPV variant B1 as represented by the prototype NL/1/99 (SEQ ID NO:332).

An isolate of mammalian MPV is classified as a variant A1 if it is phylogenetically closer related to the viral isolate NL/1/00 (SEQ ID NO:19) than it is related to any of the following other viral isolates: NL/1/99 (SEQ ID NO:18), NL/17/00 (SEQ ID NO:20) and NL/1/94 (SEQ ID NO:21). One or more of the ORFs of a mammalian MPV can be used to classify the mammalian MPV into a variant. A mammalian MPV can be classified as an MPV variant A1, if the amino acid sequence of its G protein is at least 66%, at least 70%, at least 75%, at least 80%, at least 85%, at least 90%, at least 95%, at least 98%, or at least 99% or at least 99.5% identical to the G protein of a mammalian MPV variant A1 as represented by the prototype NL/1/00 (SEQ ID NO:322); if the amino acid sequence of its N protein is at least 99.5% identical to the N protein of a mammalian MPV variant A1 as represented by the prototype NL/1/00 (SEQ ID NO:366); if the amino acid sequence of its P protein is at least 96%, at least 98%, or at least 99% or at least 99.5% identical to the P protein of a mammalian MPV variant A1 as represented by the prototype NL/1/00 (SEQ ID NO:374); if the amino acid sequence of its M protein is at least 99% or at least 99.5% identical to the M protein of a mammalian MPV variant A1 as represented by the prototype NL/1/00 (SEQ ID NO:358); if the amino acid sequence of its F protein is at least 98% or at least 99% or at least 99.5% identical to the F protein of a mammalian MPV variant A1 as represented by the prototype NL/1/00 (SEQ ID NO:314); if the amino acid sequence of its M2-1 protein is at least 99% or at least 99.5% identical to the M2-1 protein of a mammalian MPV variant A1 as represented by the prototype NL/1/00 (SEQ ID NO:338); if the amino acid sequence of its M2-2 protein is at least 96% or at least 99% or at least 99.5% identical to the M2-2 protein of a mammalian MPV variant A1 as represented by the prototype NL/1/00 (SEQ ID NO:346); if the amino acid sequence of its SH protein is at least 84%, at least 90%, at least 95%, at least 98%, or at least 99% or at least 99.5% identical to the SH protein of a mammalian MPV variant A1 as represented by the prototype NL/1/00 (SEQ ID NO:382); and/or if the amino acid sequence of its L protein is at least 99% or at least 99.5% identical to the L protein of a virus of a mammalian MPV variant A1 as represented by the prototype NL/1/00 (SEQ ID NO:330).

An isolate of mammalian MPV is classified as a variant A2 if it is phylogenetically closer related to the viral isolate NL/17/00 (SEQ ID NO:20) than it is related to any of the following other viral isolates: NL/1/99 (SEQ ID NO:18), NL/1/00 (SEQ ID NO:19) and NL/1/94 (SEQ ID NO:21). One or more of the ORFs of a mammalian MPV can be used to classify the mammalian MPV into a variant. A mammalian MPV can be classified as an MPV variant A2, if the amino acid sequence of its G protein is at least 66%, at least 70%, at least 75%, at least 80%, at least 85%, at least 90%, at least 95%, at least 98%, at least 99% or at least 99.5% identical to the G protein of a mammalian MPV variant A2 as represented by the prototype NL/17/00 (SEQ ID NO:323); if the amino acid sequence of its N protein is at least 99.5% identical to the N protein of a mammalian MPV variant A2 as represented by the prototype NL/17/00 (SEQ ID NO:367); if the amino acid sequence of its P protein is at least 96%, at least 98%, at least 99% or at least 99.5% identical to the P protein of a mammalian MPV variant A2 as represented by the prototype NL/17/00 (SEQ ID NO:375); if the amino acid sequence of its M protein is at least 99%, or at least 99.5% identical to the M protein of a mammalian MPV variant A2 as represented by the prototype NL/17/00 (SEQ ID NO:359); if the amino acid sequence of its F protein is at least 98%, at least 99% or at least 99.5% identical to the F protein of a mammalian MPV variant A2 as represented by the prototype NL/17/00 (SEQ ID NO:315); if the amino acid sequence of its M2-1 protein is at least 99%, or at least 99.5% identical to the M2-1 protein of a mammalian MPV variant A2 as represented by the prototype NL/17/00 (SEQ ID NO: 339); if the amino acid sequence of its M2-2 protein is at least 96%, at least 98%, at least 99% or at least 99.5% identical to the M2-2 protein of a mammalian MPV variant A2 as represented by the prototype NL/17/00 (SEQ ID NO:347); if the amino acid sequence of its SH protein is at least 84%, at least 85%, at least 90%, at least 95%, at least 98%, at least 99% or at least 99.5% identical to the SH protein of a mammalian MPV variant A2 as represented by the prototype NL/17/00 (SEQ ID NO:383); if the amino acid sequence of its L protein is at least 99% or at least 99.5% identical to the L protein of a mammalian MPV variant A2 as represented by the prototype NL/17/00 (SEQ ID NO:331).

An isolate of mammalian MPV is classified as a variant B2 if it is phylogenetically closer related to the viral isolate NL/1/94 (SEQ ID NO:21) than it is related to any of the following other viral isolates: NL/1/99 (SEQ ID NO:18), NL/1/00 (SEQ ID NO:19) and NL/17/00 (SEQ ID NO:20). One or more of the ORFs of a mammalian MPV can be used to classify the mammalian MPV into a variant. A mammalian MPV can be classified as an MPV variant B2, if the amino acid sequence of its G protein is at least 66%, at least 70%, at least 75%, at least 80%, at least 85%, at least 90%, at least 95%, at least 98%, or at least 99% or at least 99.5% identical to the G protein of a mammalian MPV variant B2 as represented by the prototype NL/1/94 (SEQ ID NO:325); if the amino acid sequence of its N protein is at least 99% or at least 99.5% identical to the N protein of a mammalian MPV variant B2 as represented by the prototype NL/1/94 (SEQ ID NO:369); if the amino acid sequence of its P protein is at least 96%, at least 98%, or at least 99% or at least 99.5% identical to the P protein of a mammalian MPV variant B2 as represented by the prototype NL/1/94 (SEQ ID NO:377); if the amino acid sequence of its M protein is identical to the M protein of a mammalian MPV variant B2 as represented by the prototype NL/1/94 (SEQ ID NO:361); if the amino acid sequence of its F protein is at least 99% or at least 99.5% identical to the F protein of a mammalian MPV variant B2 as represented by the prototype NL/1/94 (SEQ ID NO:317); if the amino acid sequence of the M2-1 protein is at least 98% or at least 99% or at least 99.5% identical to the M2-1 protein of a mammalian MPV variant B2 as represented by the prototype NL/1/94 (SEQ ID NO:341); if the amino acid sequence that is at least 99% or at least 99.5% identical to the M2-2 protein of a mammalian MPV variant B2 as represented by the prototype NL/1/94 (SEQ ID NO:349); if the amino acid sequence of its SH protein is at least 84%, at least 85%, at least 90%, at least 95%, at least 98%, or at least 99% or at least 99.5% identical to the SH protein of a mammalian MPV variant B2 as represented by the prototype NL/1/94 (SEQ ID NO:385); and/or if the amino acid sequence of its L protein is at least 99% or at least 99.5% identical to the L protein of a mammalian MPV variant B2 as represented by the prototype NL/1/94 (SEQ ID NO:333).

In certain embodiments, the percentage of sequence identity is based on an alignment of the full length proteins. In other embodiments, the percentage of sequence identity is based on an alignment of contiguous amino acid sequences of the proteins, wherein the amino acid sequences can be 25 amino acids, 50 amino acids, 75 amino acids, 100 amino acids, 125 amino acids, 150 amino acids, 175 amino acids, 200 amino acids, 225 amino acids, 250 amino acids, 275 amino acids, 300 amino acids, 325 amino acids, 350 amino acids, 375 amino acids, 400 amino acids, 425 amino acids, 450 amino acids, 475 amino acids, 500 amino acids, 750 amino acids, 1000 amino acids, 1250 amino acids, 1500 amino acids, 1750 amino acids, 2000 amino acids or 2250 amino acids in length.

5.2 Functional Characteristics of a Mammalian MPV

In addition to the structural definitions of the mammalian MPV, a mammalian MPV can also be defined by its functional characteristics. In certain embodiments, the mammalian MPV of the invention is capable of infecting a mammalian host. The mammalian host can be a mammalian cell, tissue, organ or a mammal. In a specific embodiment, the mammalian host is a human or a human cell, tissue or organ. Any method known to the skilled artisan can be used to test whether the mammalian host has been infected with the mammalian MPV. In certain embodiments, the virus is tested for its ability to attach to a mammalian cell. In certain other embodiments, the virus is tested for its ability to transfer its genome into the mammalian cell. In an illustrative embodiment, the genome of the virus is detectably labeled, e.g., radioactively labeled. The virus is then incubated with a mammalian cell for at least 1 minute, at least 5 minutes at least 15 minutes, at least 30 minutes, at least 1 hour, at least 2 hours, at least 5 hours, at least 12 hours, or at least 1 day. The cells are subsequently washed to remove any viral particles from the cells and the cells are then tested for the presence of the viral genome by virtue of the detectable label. In another embodiment, the presence of the viral genome in the cells is detected using RT-PCR using mammalian MPV specific primers. (See PCT WO 02/057302 at pp. 37 to 44, which is incorporated by reference herein).

In certain embodiments, the mammalian virus is capable to infect a mammalian host and to cause proteins of the mammalian MPV to be inserted into the cytoplasmic membrane of the mammalian host. The mammalian host can be a cultured mammalian cell, organ, tissue or mammal. In an illustrative embodiment, a mammalian cell is incubated with the mammalian virus. The cells are subsequently washed under conditions that remove the virus from the surface of the cell. Any technique known to the skilled artisan can be used to detect the newly expressed viral protein inserted in the cytoplasmic membrane of the mammalian cell. For example, after infection of the cell with the virus, the cells are maintained in medium comprising a detectably labeled amino acid. The cells are subsequently harvested, lysed, and the cytoplasmic fraction is separated from the membrane fraction. The proteins of the membrane fraction are then solubilized and then subjected to an immunoprecipitation using antibodies specific to a protein of the mammalian MPV, such as, but not limited to, the F protein or the G protein. The immunoprecipitated proteins are then subjected to SDS PAGE. The presence of viral protein can then be detected by autoradiography. In another embodiment, the presence of viral proteins in the cytoplasmic membrane of the host cell can be detected by immunocytochemistry using one or more antibodies specific to proteins of the mammalian MPV.

In even other embodiments, the mammalian MPV of the invention is capable of infecting a mammalian host and of replicating in the mammalian host. The mammalian host can be a cultured mammalian cell, organ, tissue or mammal. Any technique known to the skilled artisan can be used to determine whether a virus is capable of infecting a mammalian cell and of replicating within the mammalian host. In a specific embodiment, mammalian cells are infected with the virus. The cells are subsequently maintained for at least 30 minutes, at least 1 hour, at least 2 hours, at least 5 hours, at least 12 hours, at least 1 day, or at least 2 days. The level of viral genomic RNA in the cells can be monitored using Northern blot analysis, RT-PCR or in situ hybridization using probes that are specific to the viral genome. An increase in viral genomic RNA demonstrates that the virus can infect a mammalian cell and can replicate within a mammalian cell.

In even other embodiments, the mammalian MPV of the invention is capable of infecting a mammalian host, wherein the infection causes the mammalian host to produce new infectious mammalian MPV. The mammalian host can be a cultured mammalian cell or a mammal. Any technique known to the skilled artisan can be used to determine whether a virus is capable of infecting a mammalian host and cause the mammalian host to produce new infectious viral particles. In an illustrative example, mammalian cells are infected with a mammalian virus. The cells are subsequently washed and incubated for at least 30 minutes, at least 1 hour, at least 2 hours, at least 5 hours, at least 12 hours, at least 1 day, at least 2 days, at least one week, or at least twelve days. The titer of virus can be monitored by any method known to the skilled artisan. For exemplary methods see section 5.8.

In certain, specific embodiments, the mammalian MPV is a human MPV. The tests described in this section can also be performed with a human MPV. In certain embodiments, the human MPV is capable of infecting a mammalian host, such as a mammal or a mammalian cultured cell.

In certain embodiments, the human MPV is capable to infect a mammalian host and to cause proteins of the human MPV to be inserted into the cytoplasmic membrane of the mammalian host.

In even other embodiments, the human MPV of the invention is capable of infecting a mammalian host and of replicating in the mammalian host.

In even other embodiments, the human MPV of the invention is capable of infecting a mammalian host and of replicating in the mammalian host, wherein the infection and replication causes the mammalian host to produce and package new infectious human MPV.

In certain embodiments, the mammalian MPV, even though it is capable of infecting a mammalian host, is also capable of infecting an avian host, such as a bird or an avian cultured cell. In certain embodiments, the mammalian MPV is capable to infect an avian host and to cause proteins of the mammalian MPV to be inserted into the cytoplasmic membrane of the avian host. In even other embodiments, the mammalian MPV of the invention is capable of infecting an avian host and of replicating in the avian host. In even other embodiments, the mammalian MPV of the invention is capable of infecting an avian host and of replicating in the avian host, wherein the infection and replication causes the avian host to produce and package new infectious mammalian MPV.

5.3 Recombinant and Chimeric *Metapneumovirus*

The present invention encompasses recombinant or chimeric viruses encoded by viral vectors derived from the genomes of *metapneumovirus*, including both mammalian and avian variants. In accordance with the present invention a recombinant virus is one derived from a mammalian MPV or an APV that is encoded by endogenous or native genomic sequences or non-native genomic sequences. In accordance with the invention, a non-native sequence is one that is different from the native or endogenous genomic sequence due to one or more mutations, including, but not limited to, point mutations, rearrangements, insertions, deletions etc., to the genomic sequence that may or may not result in a phenotypic change. The recombinant viruses of the invention encompass those viruses encoded by viral vectors derived from the genomes of *metapneumovirus*, including both mammalian and avian variants, and may or may not, include nucleic acids that are non-native to the viral genome. In accordance with the present invention, a viral vector which is derived from the genome of a *metapneumovirus* is one that contains a nucleic acid sequence that encodes at least a part of one ORF of a mammalian *metapneumovirus*, wherein the polypeptides encoded by the ORF have amino acid sequence identity as set forth in Section 5.1. supra, and Table 1.

In accordance with the present invention, the recombinant viruses of the invention encompass those viruses encoded by viral vectors derived from the genome of a mammalian *metapneumovirus* (MPV), in particular a human *metapneumovirus*. In particular embodiments of the invention, the viral vector is derived from the genome of a *metapneumovirus* A1, A2, B1 or B2 variant. In accordance with the present invention, these viral vectors may or may not include nucleic acids that are non-native to the viral genome In accordance with the present invention, the recombinant viruses of the invention encompass those viruses encoded by viral vectors derived from the genome of an avian *pneumovirus* (APV), also known as turkey rhinotracheitis virus (TRTV). In particular embodiments of the invention, the viral vector is derived from the genome of an APV subgroup A, B, C or D. In a preferred embodiment, a viral vector derived from the genome of an APV subgroup C. In accordance with the present invention these viral vectors may or may not include nucleic acids that are non-native to the viral genome.

In another preferred embodiment of the invention, the recombinant viruses of the invention encompass those viruses encoded by a viral vector derived from the genome of an APV that contains a nucleic acid sequence that encodes a F-ORF of APV subgroup C. In certain embodiments, a viral vector derived from the genome of an APV is one that contains a nucleic acid sequence that encodes at least a N-ORF, a P-ORF, a M-ORF, a F-ORF, a M2-1-ORF, a M2-2-ORF or a L-ORF of APV.

In accordance with the invention, a chimeric virus is a recombinant MPV or APV which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

In accordance with the invention, the chimeric viruses are encoded by the viral vectors of the invention which further comprise a heterologous nucleotide sequence. In accordance with the present invention a chimeric virus is encoded by a viral vector that may or may not include nucleic acids that are non-native to the viral genome. In accordance with the invention a chimeric virus is encoded by a viral vector to which heterologous nucleotide sequences have been added, inserted or substituted for native or non-native sequences. In accordance with the present invention, the chimeric virus may be encoded by nucleotide sequences derived from different strains of mammalian MPV. In particular, the chimeric virus is encoded by nucleotide sequences that encode antigenic polypeptides derived from different strains of MPV.

In accordance with the present invention, the chimeric virus may be encoded by a viral vector derived from the genome of an APV, in particular subgroup C, that additionally encodes a heterologous sequence that encodes antigenic polypeptides derived from one or more strains of MPV.

A chimeric virus may be of particular use for the generation of recombinant vaccines protecting against two or more viruses (Tao et al., J. Virol. 72, 2955-2961; Durbin et al., 2000, J.Virol. 74, 6821-6831; Skiadopoulos et al., 1998, J. Virol. 72, 1762-1768; Teng et al., 2000, J.Virol. 74, 9317-9321). For example, it can be envisaged that a MPV or APV virus vector expressing one or more proteins of another negative strand RNA virus, e.g., RSV or a RSV vector expressing one or more proteins of MPV will protect individuals vaccinated with such vector against both virus infections. A similar approach can be envisaged for PIV or other *paramyxoviruses*. Attenuated and replication-defective viruses may be of use for vaccination purposes with live vaccines as has been suggested for other viruses. (See, PCT WO 02/057302, at pp. 6 and 23, incorporated by reference herein).

In accordance with the present invention the heterologous sequence to be incorporated into the viral vectors encoding the recombinant or chimeric viruses of the invention include sequences obtained or derived from different strains of *metapneumovirus*, strains of avian *pneumovirus*, and other negative strand RNA viruses, including, but not limited to, RSV, PIV and influenza virus, and other viruses, including *morbillivirus*.

In certain embodiments of the invention, the chimeric or recombinant viruses of the invention are encoded by viral vectors derived from viral genomes wherein one or more sequences, intergenic regions, termini sequences, or portions or entire ORF have been substituted with a heterologous or non-native sequence. In certain embodiments of the invention, the chimeric viruses of the invention are encoded by viral vectors derived from viral genomes wherein one or more heterologous sequences have been added to the vector.

In certain embodiments, the virus of the invention contains heterologous nucleic acids. In a preferred embodiment, the heterologous nucleotide sequence is inserted or added at Position 1 of the viral genome. In another preferred embodiment, the heterologous nucleotide sequence is inserted or added at Position 2 of the viral genome. In even another preferred embodiment, the heterologous nucleotide sequence is inserted or added at Position 3 of the viral genome. Insertion or addition of nucleic acid sequences at the lower-numbered positions of the viral genome results in stronger or higher levels of expression of the heterologous nucleotide sequence compared to insertion at higher-numbered positions due to a transcriptional gradient across the genome of the virus. Thus, inserting or adding heterologous nucleotide sequences at lower-numbered positions is the preferred embodiment of the invention if high levels of expression of the heterologous nucleotide sequence is desired.

Without being bound by theory, the position of insertion or addition of the heterologous sequence affects the replication rate of the recombinant or chimeric virus. The higher rates of replication can be achieved if the heterologous sequence is inserted or added at Position 2 or Position 1 of the viral genome. The rate of replication is reduced if the heterologous sequence is inserted or added at Position 3, Position 4, Position 5, or Position 6.

Without being bound by theory, the size of the intergenic region between the viral gene and the heterologous sequence further determines rate of replication of the virus and expression levels of the heterologous sequence.

In certain embodiments, the viral vector of the invention contains two or more different heterologous nucleotide sequences. In a preferred embodiment, one heterologous nucleotide sequence is at Position 1 and a second heterologous nucleotide sequence is at Position 2 of the viral genome. In another preferred embodiment, one heterologous nucleotide sequence is at Position 1 and a second heterologous nucleotide sequence is at Position 3 of the viral genome. In even another preferred embodiment, one heterologous nucleotide sequence is at Position 2 and a second heterologous nucleotide sequence is at Position 3 of the viral genome. In certain other embodiments, a heterologous nucleotide sequence is inserted at other, higher-numbered positions of the viral genome. In accordance with the present invention, the position of the heterologous sequence refers to the order in which the sequences are transcribed from the viral genome, e.g., a heterologous sequence at Position 1 is the first gene sequence to be transcribed from the genome.

The selection of the viral vector may depend on the species of the subject that is to be treated or protected from a viral infection. If the subject is human, then an attenuated mammalian *metapneumovirus* or an avian *pneumovirus* can be used to provide the antigenic sequences.

In accordance with the present invention, the viral vectors can be engineered to provide antigenic sequences which confer protection against infection by a *metapneumovirus*, including sequences derived from mammalian *metapneumovirus*, human *metapneumovirus*, MPV variants A1, A2, B1 or B2, sequences derived from avian *pneumovirus*, including APV subgroups A, B, C or D, although C is preferred. The viral vectors can be engineered to provide antigenic sequences which confer protection against infection or disease by another virus, including negative strand RNA virus, including influenza, RSV or PIV, including PIV3. The viral vectors may be engineered to provide one, two, three or more antigenic sequences. In accordance with the present invention the antigenic sequences may be derived from the same virus, from different strains or variants of the same type of virus, or from different viruses, including *morbillivirus*.

In certain embodiments of the invention, the heterologous nucleotide sequence to be inserted into the genome of the virus of the invention is derived from a *metapneumovirus*. In certain specific embodiments of the invention, the heterologous nucleotide sequence is derived from a human *metapneumovirus*. In another specific embodiment, the heterologous nucleotide sequence is derived from an avian *pneumovirus*. More specifically, the heterologous nucleotide sequence of the invention encodes a F gene of a human *metapneumovirus*. More specifically, the heterologous nucleotide sequence of the invention encodes an G gene of a human *metapneumovirus*. More specifically, the heterologous nucleotide sequence of the invention encodes a F gene of an avian *pneumovirus*. More specifically, the heterologous nucleotide sequence of the invention encodes a G gene of an avian *pneumovirus*. In specific embodiments, a heterologous nucleotide sequences can be any one of SEQ ID NO:1 through SEQ ID NO:5, SEQ ID NO:14, and SEQ ID NO:15. In certain specific embodiments, the nucleotide sequence encodes a protein of any one of SEQ ID NO:6 through SEQ ID NO:13, SEQ ID NO:16, and SEQ ID NO:17.

In a specific embodiment of the invention, the heterologous nucleotide sequence encodes a chimeric F protein. In an illustrative embodiment, the ectodomain of the chimeric F-protein is the ectodomain of a human MPV and the transmembrane domain and the luminal domain are derived from the F-protein of an avian *metapneumovirus*. Without being bound by theory, a chimeric human MPV that encodes the chimeric F-protein consisting of the human ectodomain and the avian luminol/transmembrane domain is attenuated because of the avian part of the F-protein, yet highly immunogenic against hMPV because of the human ectodomain.

In certain embodiments, two different heterologous nucleotide sequences are inserted or added to the viral vectors of the invention, derived from *metapneumoviral* genomes, including mammalian and avian. For example, the heterologous nucleotide sequence is derived from a human *metapneumovirus*, an avian *pneumovirus*, RSV, PIV, or influenza. In a preferred embodiment, the heterologous sequence encodes the F-protein of human *metapneumovirus*, avian *pneumovirus*, RSV or PIV respectively. In another embodiment, the heterologous sequence encodes the HA protein of influenza.

In certain embodiments, the viral vector of the invention contains two different heterologous nucleotide sequences wherein a first heterologous nucleotide sequence is derived from a *metapneumovirus*, such as a human *metapneumovirus* or an avian *pneumovirus*, and a second nucleotide sequence is derived from a respiratory syncytial virus (see Table 2). In specific embodiments, the heterologous nucleotide sequence derived from respiratory syncytial virus is a F gene of a respiratory syncytial virus. In other specific embodiments, the heterologous nucleotide sequence derived from respiratory syncytial virus is a G gene of a respiratory syncytial virus. In a specific embodiment, the heterologous nucleotide sequence derived from a *metapneumovirus* is inserted at a lower-numbered position than the heterologous nucleotide sequence derived from a respiratory syncytial virus. In another specific embodiment, the heterologous nucleotide sequence derived from a *metapneumovirus* is inserted at a higher-numbered position than the heterologous nucleotide sequence derived from a respiratory syncytial virus.

In certain embodiments, the virus of the invention contains two different heterologous nucleotide sequences wherein a first heterologous nucleotide sequence is derived from a *metapneumovirus*, such as a human *metapneumovirus* or an avian *pneumovirus*, and a second nucleotide sequence is derived from a parainfluenza virus, such as, but not limited to PIV3 (see Table 2). In specific embodiments, the heterologous nucleotide sequence derived from PIV is a F gene of PIV. In other specific embodiments, the heterologous nucleotide sequence derived from PIV is a G gene of a PIV. In a specific embodiment, the heterologous nucleotide sequence derived from a *metapneumovirus* is inserted at a lower-numbered position than the heterologous nucleotide sequence derived from a PIV. In another specific embodiment, the heterologous nucleotide sequence derived from a *metapneumovirus* is inserted at a higher-numbered position than the heterologous nucleotide sequence derived from a PIV.

The expression products and/or recombinant or chimeric virions obtained in accordance with the invention may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders. In particular, the chimeric virions of the present invention may be engineered to create vaccines for the protection of a subject from infections with PIV, RSV, and/or *metapneumovirus*.

In another embodiment, the chimeric virions of the present invention may be engineered to create anti-HIV vaccines, wherein an immunogenic polypeptide from gp 160, and/or from internal proteins of HIV is engineered into the glycoprotein HN protein to construct a vaccine that is able to elicit both vertebrate humoral and cell-mediated immune responses. In yet another embodiment, the invention relates to recombinant *metapneumoviral* vectors and viruses which are engineered to encode mutant antigens. A mutant antigen has at least one amino acid substitution, deletion or addition relative to the wild-type viral protein from which it is derived.

In certain embodiments, the invention relates to trivalent vaccines comprising a recombinant or chimeric virus of the invention. In specific embodiments, the virus used as backbone for a trivalent vaccine is a chimeric avian-human *metapneumovirus* or a chimeric human-avian *metapneumovirus* containing a first heterologous nucleotide sequence derived from a RSV and a second heterologous nucleotide sequence derived from PIV. In an exemplary embodiment, such a trivalent vaccine will be specific to (a) the gene products of the F gene and/or the G gene of the human *metapneumovirus* or avian *pneumovirus*, respectively, dependent on whether chimeric avian-human or chimeric human-avian *metapneumovirus* is used; (b) the protein encoded by the heterologous nucleotide sequence derived from a RSV; and (c) the protein encoded by the heterologous nucleotide sequence derived from PIV. In a specific embodiment, the first heterologous nucleotide sequence is the F gene of the respiratory syncytial virus and is inserted in Position 1, and the second heterologous nucleotide sequence is the F gene of the PIV and is inserted in Position 3. Many more combinations are encompassed by the present invention and some are shown by way of example in Table 2. Further, nucleotide sequences encoding chimeric F proteins could be used (see supra). In some less preferred embodiments, the heterologous nucleotide sequence can be inserted at higher-numbered positions of the viral genome.

TABLE 2

Exemplary arrangements of heterologous nucleotide sequences in the viruses used for trivalent vaccines.

| Combination | Position 1 | Position 2 | Position 3 |
|---|---|---|---|
| 1 | F-gene of PIV | F-gene of RSV | — |
| 2 | F-gene of RSV | F-gene of PIV | — |
| 3 | — | F-gene of PIV | F-gene of RSV |
| 4 | — | F-gene of RSV | F-gene of PIV |
| 5 | F-gene of PIV | — | F-gene of RSV |
| 6 | F-gene of RSV | — | F-gene of PIV |
| 7 | HN-gene of PIV | G-gene of RSV | — |
| 8 | G-gene of RSV | HN-gene of PIV | — |
| 9 | — | HN-gene of PIV | G-gene of RSV |
| 10 | — | G-gene of RSV | HN-gene of PIV |
| 11 | HN-gene of PIV | — | G-gene of RSV |
| 12 | G-gene of RSV | — | HN-gene of PIV |
| 13 | F-gene of PIV | G-gene of RSV | — |
| 14 | G-gene of RSV | F-gene of PIV | — |
| 15 | — | F-gene of PIV | G-gene of RSV |
| 16 | — | G-gene of RSV | F-gene of PIV |
| 17 | F-gene of PIV | — | G-gene of RSV |
| 18 | G-gene of RSV | — | F-gene of PIV |
| 19 | HN-gene of PIV | F-gene of RSV | — |
| 20 | F-gene of RSV | HN-gene of PIV | — |
| 21 | — | HN-gene of PIV | F-gene of RSV |
| 22 | — | F-gene of RSV | HN-gene of PIV |
| 23 | HN-gene of PIV | — | F-gene of RSV |
| 24 | F-gene of RSV | — | HN-gene of PIV |

In certain embodiments, the expression products and recombinant or chimeric virions of the present invention may be engineered to create vaccines against a broad range of pathogens, including viral antigens, tumor antigens and auto antigens involved in autoimmune disorders. One way to achieve this goal involves modifying existing *metapneumoviral* genes to contain foreign sequences in their respective external domains. Where the heterologous sequences are epitopes or antigens of pathogens, these chimeric viruses may be used to induce a protective immune response against the disease agent from which these determinants are derived.

Thus, the present invention relates to the use of viral vectors and recombinant or chimeric viruses to formulate vaccines against a broad range of viruses and/or antigens. The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs, goats, dogs, cats, avian species and rodents.

The invention may be divided into the following stages solely for the purpose of description and not by way of limitation: (a) construction of recombinant cDNA and RNA templates; (b) expression of heterologous gene products using recombinant cDNA and RNA templates; (c) rescue of the heterologous gene in recombinant virus particles; and (d) generation and use of vaccines comprising the recombinant virus particles of the invention.

5.4 Construction of the Recombinant cDNA and RNA

In certain embodiments, the viral vectors are derived from the genomes of human or mammalian *metapneumovirus* of the invention. In other embodiments, the viral vectors are derived from the genome of avian *pneumovirus*. In certain embodiments, viral vectors contain sequences derived from mammalian MPV and APV, such that a chimeric human MPV/APV virus is encoded by the viral vector. In an exemplary embodiment, the F-gene and/or the G-gene of human *metapneumovirus* have been replaced with the F-gene and/or the G-gene of avian *pneumovirus* to construct chimeric hMPV/APV virus. In other embodiments, viral vectors contain sequences derived from APV and mammalian MPV, such that a chimeric APV/hMPV virus is encoded by the viral vector. In more exemplary embodiments, the F-gene and/or the G-gene of avian *pneumovirus* have been replaced with the F-gene and/or the G-gene of human *metapneumovirus* to construct the chimeric APV/hMPV virus.

The present invention also encompasses recombinant viruses comprising a viral vector derived from a mammalian MPV or APV genome containing sequences endogenous or native to the viral genome, and may or may not contain sequences non-native to the viral genome. Non-native sequences include those that are different from native or endogenous sequences which may or may not result in a phenotypic change. The recombinant viruses of the invention may contain sequences which result in a virus having a phenotype more suitable for use in vaccine formulations, e.g., attenuated phenotype or enhanced antigenicity. The mutations and modifications can be in coding regions, in intergenic regions and in the leader and trailer sequences of the virus.

In certain embodiments the viral vectors of the invention comprise nucleotide sequences derived from hMPV, APV, hMPV/APV or APV/hMPV, in which native nucleotide sequences have been substituted with heterologous sequences or in which heterologous sequences have been added to the native *metapneumoviral* sequences.

In a more specific embodiment, a chimeric virus comprises a viral vector derived from MPV, APV, APV/hMPV, or hMPV/APV in which heterologous sequences derived from PIV have been added. In a more specific embodiment, a recombinant virus comprises a viral vector derived from MPV, APV, APV/hMPV, or hMPV/APV in which sequences have been replaced by heterologous sequences derived from PIV. In other specific embodiments, a chimeric virus comprises a viral vector derived from MPV, APV, APV/hMPV, or hMPV/APV in which heterologous sequences derived from RSV have been added. In a more specific embodiment, a chimeric virus comprises a viral vector derived from MPV, APV, APV/hMPV, or hMPV/APV in which sequences have been replaced by heterologous sequences derived from RSV.

Heterologous gene coding sequences flanked by the complement of the viral polymerase binding site/promoter, e.g., the complement of 3'-hMPV virus terminus of the present invention, or the complements of both the 3'- and 5'-hMPV virus termini may be constructed using techniques known in the art. In more specific embodiments, a recombinant virus of the invention contains the leader and trailer sequence of hMPV or APV. In certain embodiments, the intergenic regions are obtained from hMPV or APV. The resulting RNA templates may be of the negative-polarity and contain appropriate terminal sequences which enable the viral RNA-synthesizing apparatus to recognize the template. Alternatively, positive-polarity RNA templates which contain appropriate terminal sequences which enable the viral RNA-synthesizing apparatus to recognize the template, may also be used. Recombinant DNA molecules containing these hybrid sequences can be cloned and transcribed by a DNA-directed RNA polymerase, such as bacteriophage T7, T3, the SP6 polymerase or eukaryotic polymerase such as polymerase I and the like, to produce in vitro or in vivo the recombinant RNA templates which possess the appropriate viral sequences that allow for viral polymerase recognition and activity. In a more specific embodiment, the RNA polymerase is fowlpox virus T7 RNA polymerase or a MVA T7 RNA polymerase.

An illustrative approach for constructing these hybrid molecules is to insert the heterologous nucleotide sequence into a DNA complement of a hMPV, APV, APV/hMPV or hMPV/APV genome, so that the heterologous sequence is flanked by the viral sequences required for viral polymerase activity; i.e., the viral polymerase binding site/promoter, hereinafter referred to as the viral polymerase binding site, and a polyadenylation site. In a preferred embodiment, the heterologous coding sequence is flanked by the viral sequences that comprise the replication promoters of the 5' and 3' termini, the gene start and gene end sequences, and the packaging signals that are found in the 5' and/or the 3' termini. In an alternative approach, oligonucleotides encoding the viral polymerase binding site, e.g., the complement of the 3'-terminus or both termini of the virus genomic segment can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82; 488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophage T3, T7 or SP6) and the hybrid sequence containing the heterologous gene and the PIV polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase.

In addition, one or more nucleotides can be added in the untranslated region to adhere to the "Rule of Six" which may be important in obtaining virus rescue. The "Rule of Six" applies to many *paramyxoviruses* and states that the RNA nucleotide genome must be divisible by six to be functional. The addition of nucleotides can be accomplished by techniques known in the art such as using a commercial mutagenesis kits such as the QuikChange mutagenesis kit (Stratagene). After addition of the appropriate number of nucleotides, the correct DNA fragment can then be isolated by digestion with appropriate restriction enzyme and gel purification. Sequence requirements for viral polymerase activity and constructs which may be used in accordance with the invention are described in the subsections below.

Without being bound by theory, several parameters affect the rate of replication of the recombinant virus and the level of expression of the heterologous sequence. In particular, the position of the heterologous sequence in hMPV, APV, hMPV/APV or APV/hMPV and the length of the intergenic region that flanks the heterologous sequence determine rate of replication and expression level of the heterologous sequence.

In certain embodiments, the leader and or trailer sequence of the virus are modified relative to the wild type virus. In certain more specific embodiments, the lengths of the leader and/or trailer are altered. In other embodiments, the sequence(s) of the leader and/or trailer are mutated relative to the wild type virus. For more detail, see section 5.7.

The production of a recombinant virus of the invention relies on the replication of a partial or full-length copy of the negative sense viral RNA (vRNA) genome or a complementary copy thereof (cRNA). This vRNA or cRNA can be isolated from infectious virus, produced upon in-vitro transcription, or produced in cells upon transfection of nucleic acids. Second, the production of recombinant negative strand virus relies on a functional polymerase complex. Typically, the polymerase complex of *pneumoviruses* consists of N, P, L and possibly M2 proteins, but is not necessarily limited thereto.

Polymerase complexes or components thereof can be isolated from virus particles, isolated from cells expressing one or more of the components, or produced upon transfection of specific expression vectors.

Infectious copies of MPV can be obtained when the above mentioned vRNA, cRNA, or vectors expressing these RNAs are replicated by the above mentioned polymerase complex 16 (Schnell et al., 1994, EMBO J 13: 4195-4203; Collins, et al., 1995, PNAS 92: 11563-11567; Hoffmann, et al., 2000, PNAS 97: 6108-6113; Bridgen, et al., 1996, PNAS 93: 15400-15404; Palese, et al., 1996, PNAS 93: 11354-11358; Peeters, et al., 1999, J. Virol. 73: 5001-5009; Durbin, et al., 1997, Virology 235: 323-332).

The invention provides a host cell comprising a nucleic acid or a vector according to the invention. Plasmid or viral vectors containing the polymerase components of MPV (presumably N, P, L and M2, but not necessarily limited thereto) are generated in prokaryotic cells for the expression of the components in relevant cell types (bacteria, insect cells, eukaryotic cells). Plasmid or viral vectors containing full-length or partial copies of the MPV genome will be generated in prokaryotic cells for the expression of viral nucleic acids in-vitro or in-vivo. The latter vectors may contain other viral sequences for the generation of chimeric viruses or chimeric virus proteins, may lack parts of the viral genome for the generation of replication defective virus, and may contain mutations, deletions or insertions for the generation of attenuated viruses.

Infectious copies of MPV (being wild type, attenuated, replication-defective or chimeric) can be produced upon co-expression of the polymerase components according to the state-of-the-art technologies described above.

In addition, eukaryotic cells, transiently or stably expressing one or more full-length or partial MPV proteins can be used. Such cells can be made by transfection (proteins or nucleic acid vectors), infection (viral vectors) or transduction (viral vectors) and may be useful for complementation of mentioned wild type, attenuated, replication-defective or chimeric viruses.

5.4.1 Heterologous Gene Sequences to be Inserted

In accordance with the present invention the viral vectors of the invention may be further engineered to express a heterologous sequence. In an embodiment of the invention, the heterologous sequence is derived from a source other than the viral vector. By way of example, and not by limitation, the heterologous sequence encodes an antigenic protein, polypeptide or peptide of a virus belonging to a different species, subgroup or variant of *metapneumovirus* than the species, subgroup or variant from which the viral vector is derived. By way of example, and not by limitation, the heterologous sequence encodes an antigenic protein, polypeptide or peptide of a virus other than a *metapneumovirus*. By way of example, and not by limitation, the heterologous sequence is not viral in origin. In accordance with this embodiment, the heterologous sequence may encode a moiety, peptide, polypeptide or protein possessing a desired biological property or activity. Such a heterologous sequence may encode a tag or marker. Such a heterologous sequence may encode a biological response modifier, examples of which include, lymphokines, interleukines, granulocyte macrophage colony stimulating factor and granulocyte colony stimulating factor.

In certain embodiments, the heterologous nucleotide sequence to be inserted is derived from a *metapneumovirus*. More specifically, the heterologous nucleotide sequence to be inserted is derived from a human *metapneumovirus* and/or an avian *pneumovirus*.

In certain embodiments, the heterologous sequence encodes PIV nucleocapsid phosphoprotein, PIV L protein, PIV matrix protein, PIV HN glycoprotein, PIV RNA-dependent RNA polymerase, PIV Y1 protein, PIV D protein, PIV C protein, PIV F protein or PIV P protein. In certain embodiments, the heterologous nucleotide sequence encodes a protein that is at least 90%, at least 95%, at least 98%, or at least 99% homologous to PIV nucleocapsid phosphoprotein, PIV L protein, PIV matrix protein, PIV HN glycoprotein, PIV RNA-dependent RNA polymerase, PIV Y1 protein, PIV D protein, PIV C protein, PIV F protein or PIV P protein. The heterologous sequence can be obtained from PIV type 1, PIV type 2, or PIV type 3. In more specific embodiments, the heterologouse sequence is obtained from human PIV type 1, PIV type 2, or PIV type 3. In other embodiments, the heterologous sequence encodes RSV nucleoprotein, RSV phosphoprotein, RSV matrix protein, RSV small hydrophobic protein, RSV RNA-dependent RNA polymerase, RSV F protein, RSV G protein, or RSV M2-1 or M2-2 protein. In certain embodiments, the heterologous sequence encodes a protein that is at least 90%, at least 95%, at least 98%, or at least 99% homologous to RSV nucleoprotein, RSV phosphoprotein, RSV matrix protein, RSV small hydrophobic protein, RSV RNA-dependent RNA polymerase, RSV F protein, or RSV G protein. The heterologous sequence can be obtained from RSV subtype A and RSV subtype B. In more specific embodiments, the heterologouse sequence is obtained from human RSV subtype A and RSV subtype B. In other embodiments, the heterologous sequence encodes APV nucleoprotein, APV phosphoprotein, APV matrix protein, APV small hydrophobic protein, APV RNA-dependent RNA polymerase, APV F protein, APV G protein or APV M2-1 or M2-2 protein. In certain embodiments, the heterologous sequence encodes a protein that is at least 90%, at least 95%, at least 98%, or at least 99% homologous to APV nucleoprotein, APV phosphoprotein, APV matrix protein, APV small hydrophobic protein, APV RNA-dependent RNA polymerase, APV F protein, or APV G protein. The avian *pneumovirus* can be APV subgroup A, APV subgroup B, or APV subgroup C. In other embodiments, the heterologous sequence encodes hMPV nucleoprotein, hMPV phosphoprotein, hMPV matrix protein, hMPV small hydrophobic protein, hMPV RNA-dependent RNA polymerase, hMPV F protein, hMPV G protein or hMPV M2-1 or M2-2. In certain embodiments, the heterologous sequence encodes a protein that is at least 90%, at least 95%, at least 98%, or at least 99% homologous to hMPV nucleoprotein, hMPV phosphoprotein, hMPV matrix protein, hMPV small hydrophobic protein, hMPV RNA-dependent RNA polymerase, hMPV F protein, or hMPV G protein. The human *metapneumovirus* can be hMPV variant A1, hMPV variant A2, hMPV variant B1, or hMPV variant B2.

In certain embodiments, any combination of different heterologous sequence from PIV, RSV, human *metapneumovirus*, or avian *pneumovirus* can be inserted into the virus of the invention.

In certain preferred embodiments of the invention, the heterologous nucleotide sequence to be inserted is derived from a F gene from RSV, PIV, APV or hMPV.

In certain embodiments, the heterologous nucleotide sequence encodes a chimeric protein. In more specific embodiments, the heterologous nucleotide sequence encodes a chimeric F protein of RSV, PIV, APV or hMPV. A chimeric F protein can comprise parts of F proteins from different viruses, such as a human *metapneumovirus*, avian *pneumovirus*, respiratory syncytial virus, and parainfluenza virus. In certain other embodiments, the heterologous sequence encodes a chimeric G protein. A chimeric G protein comprises parts of G proteins from different viruses, such as a human *metapneumovirus*, avian *pneumovirus*, respiratory syncytial virus, and parainfluenza virus. In a specific embodiment, the F protein comprises an ectodomain of a F protein of a *metapneumovirus*, a transmembrane domain of a F protein of a parainfluenza virus, and luminal domain of a F protein of a parainfluenza virus.

In certain specific embodiments, the heterologous nucleotide sequence of the invention is any one of SEQ ID NO:1 through SEQ ID NO:5, SEQ ID NO:14, and SEQ ID NO:15. In certain specific embodiments, the nucleotide sequence encodes a protein of any one of SEQ ID NO:6 through SEQ ID NO:13, SEQ ID NO:16, and SEQ ID NO:17.

For heterologous nucleotide sequences derived from respiratory syncytial virus see, e.g., PCT/US98/20230, which is hereby incorporated by reference in its entirety.

In a preferred embodiment, heterologous gene sequences that can be expressed into the recombinant viruses of the invention include but are not limited to antigenic epitopes and glycoproteins of viruses which result in respiratory disease, such as influenza glycoproteins, in particular hemagglutinin H5, H7, respiratory syncytial virus epitopes, New Castle Disease virus epitopes, Sendai virus and infectious Laryngotracheitis virus (ILV). In a preferred embodiment, the heterologous nucleotide sequences are derived from a RSV or PIV. In yet another embodiment of the invention, heterologous gene sequences that can be engineered into the chimeric viruses of the invention include, but are not limited to, viral epitopes and glycoproteins of viruses, such as hepatitis B virus surface antigen, hepatitis A or C virus surface glycoproteins of Epstein Barr virus, glycoproteins of human papilloma virus, simian virus 5 or mumps virus, West Nile virus, Dengue virus, glycoproteins of herpes viruses, VPI of *poliovirus*, and sequences derived from a *lentivirus*, preferably, but not limited to human immunodeficiency virus (HIV) type 1 or type 2. In yet another embodiment, heterologous gene sequences that can be engineered into chimeric viruses of the invention include, but are not limited to, Marek's Disease virus (MDV) epitopes, epitopes of infectious Bursal Disease virus (IBDV), epitopes of Chicken Anemia virus, infectious laryngotracheitis virus (ILV), Avian Influenza virus (AIV), rabies, feline leukemia virus, canine distemper virus, vesicular stomatitis virus, and swinepox virus (see Fields et al., (ed.), 1991, *Fundamental Virology, Second Edition*, Raven Press, New York, incorporated by reference herein in its entirety).

Other heterologous sequences of the present invention include antigens that are characteristic of autoimmune disease. These antigens will typically be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discold lupus erythromatosus.

Antigens that are allergens generally include proteins or glycoproteins, including antigens derived from pollens, dust, molds, spores, dander, insects and foods. In addition, antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In one specific embodiment of the invention, the heterologous sequences are derived from the genome of human immunodeficiency virus (HIV), preferably human immunodeficiency virus-1 or human immunodeficiency virus-2. In another embodiment of the invention, the heterologous coding sequences may be inserted within a gene coding sequence of the viral backbone such that a chimeric gene product is expressed which contains the heterologous peptide sequence within the metapneumoviral protein. In such an embodiment of the invention, the heterologous sequences may also be derived from the genome of a human immunodeficiency virus, preferably of human immunodeficiency virus-1 or human immunodeficiency virus-2.

In instances whereby the heterologous sequences are HIV-derived, such sequences may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25) tat, rev, nef, vif, vpu, vpr, and/or vpx.

In yet another embodiment, heterologous gene sequences that can be engineered into the chimeric viruses include those that encode proteins with immunopotentiating activities. Examples of immunopotentiating proteins include, but are not limited to, cytokines, interferon type 1, gamma interferon, colony stimulating factors, and interleukin-1, -2, -4, -5, -6, -12.

In addition, other heterologous gene sequences that may be engineered into the chimeric viruses include antigens derived from bacteria such as bacterial surface glycoproteins, antigens derived from fungi, and antigens derived from a variety of other pathogens and parasites. Examples of heterologous gene sequences derived from bacterial pathogens include, but are not limited to, antigens derived from species of the following genera: *Salmonella, Shigella, Chlamydia, Helicobacter, Yersinia, Bordatella, Pseudomonas, Neisseria, Vibrio, Haemophilus, Mycoplasma, Streptomyces, Treponema, Coxiella, Ehrlichia, Brucella, Streptobacillus, Fusospirocheta, Spirillum, Ureaplasma, Spirochaeta, Mycoplasma, Actinomycetes, Borrelia, Bacteroides, Trichomoras, Branhamella, Pasteurella, Clostridium, Corynebacterium, Listeria, Bacillus, Erysipelothrix, Rhodococcus, Escherichia, Klebsiella, Pseudomanas, Enterobacter, Serratia, Staphylococcus, Streptococcus, Legionella, Mycobacterium, Proteus, Campylobacter, Enterococcus, Acinetobacter, Morganella, Moraxella, Citrobacter, Rickettsia, Rochlimeae*, as well as bacterial species such as: *P. aeruginosa; E. coli, P. cepacia, S.*

*epidermis, E. faecalis, S. pneumonias, S. aureus, N. meningitidis, S. pyogenes, Pasteurella multocida, Treponema pallidum*, and *P. mirabilis.*

Examples of heterologous gene sequences derived from pathogenic fungi, include, but are not limited to, antigens derived from fungi such as *Cryptococcus neoformans; Blastomyces dermatitidis; Aiellomyces dermatitidis; Histoplasma capsulatum; Coccidioides immitis; Candida* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata; Trichophyton* species, *Microsporum* species and *Dermatophyres* species, as well as any other yeast or fungus now known or later identified to be pathogenic.

Finally, examples of heterologous gene sequences derived from parasites include, but are not limited to, antigens derived from members of the Apicomplexa phylum such as, for example, *Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus* and *Gregarina* spp.; *Pneumocystis carinii*; members of the Microspora phylum such as, for example, *Nosema, Enterocytozoon, Encephalitozoon, Septata, Mrazekia, Amblyospora, Ameson, Glugea, Pleistophora* and *Microsporidium* spp.; and members of the Ascetospora phylum such as, for example, *Haplosporidium* spp., as well as species including *Plasmodium falciparum, P. vivax, P. ovale, P. malaria; Toxoplasma gondii; Leishmania mexicana, L. tropica, L. major, L. aethiopica, L. donovani, Trypanosoma cruzi, T brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidium parvum; Pneumocytis carinii, Babesia bovis, B. divergens, B. microti, Isospora belli, L hominis; Dientamoeba fragilis; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineas, G. Viverini, Fasciola hepatica, Sarcoptes scabiei, Pediculus humanus; Phthirlus pubis*; and *Dermatobia hominis*, as well as any other parasite now known or later identified to be pathogenic.

5.4.2 Insertion of the Heterologous Gene Sequence

Insertion of a foreign gene sequence into a viral vector of the invention can be accomplished by either a complete replacement of a viral coding region with a heterologous sequence or by a partial replacement or by adding the heterologous nucleotide sequence to the viral genome. Complete replacement would probably best be accomplished through the use of PCR-directed mutagenesis. Briefly, PCR-primer A would contain, from the 5' to 3' end: a unique restriction enzyme site, such as a class IIS restriction enzyme site (i.e., a "shifter" enzyme; that recognizes a specific sequence but cleaves the DNA either upstream or downstream of that sequence); a stretch of nucleotides complementary to a region of the gene that is to be replaced; and a stretch of nucleotides complementary to the carboxy-terminus coding portion of the heterologous sequence. PCR-primer B would contain from the 5' to 3' end: a unique restriction enzyme site; a stretch of nucleotides complementary to the gene that is to be replaced; and a stretch of nucleotides corresponding to the 5' coding portion of the heterologous or non-native gene. After a PCR reaction using these primers with a cloned copy of the heterologous or non-native gene, the product may be excised and cloned using the unique restriction sites. Digestion with the class IIS enzyme and transcription with the purified phage polymerase would generate a RNA molecule containing the exact untranslated ends of the viral gene that carries now a heterologous or non-native gene insertion. In an alternate embodiment, PCR-primed reactions could be used to prepare double-stranded DNA containing the bacteriophage promoter sequence, and the hybrid gene sequence so that RNA templates can be transcribed directly without cloning.

A heterologous nucleotide sequence can be added or inserted at various positions of the virus of the invention. In one embodiment, the heterologous nucleotide sequence is added or inserted at position 1. In another embodiment, the heterologous nucleotide sequence is added or inserted at position 2. In another embodiment, the heterologous nucleotide sequence is added or inserted at position 3. In another embodiment, the heterologous nucleotide sequence is added or inserted at position 4. In another embodiment, the heterologous nucleotide sequence is added or inserted at position 5. In yet another embodiment, the heterologous nucleotide sequence is added or inserted at position 6. As used herein, the term "position" refers to the position of the heterologous nucleotide sequence on the viral genome to be transcribed, e.g., position 1 means that it is the first gene to be transcribed, and position 2 means that it is the second gene to be transcribed. Inserting heterologous nucleotide sequences at the lower-numbered positions of the virus generally results in stronger expression of the heterologous nucleotide sequence compared to insertion at higher-numbered positions due to a transcriptional gradient that occurs across the genome of the virus. However, the transcriptional gradient also yields specific ratios of viral mRNAs. Insertion of foreign genes will perturb these ratios and result in the synthesis of different amounts of viral proteins that may influence virus replication. Thus, both the transcriptional gradient and the replication kinetics must be considered when choosing an insertion site. Inserting heterologous nucleotide sequences at lower-numbered positions is the preferred embodiment of the invention if strong expression of the heterologous nucleotide sequence is desired. In a preferred embodiment, the heterologous sequence is added or inserted at position 1, 2 or 3.

When inserting a heterologous nucleotide sequence into the virus of the invention, the intergenic region between the end of the coding sequence of the heterologous gene and the start of the coding sequence of the downstream gene can be altered to achieve a desired effect. As used herein, the term "intergenic region" refers to nucleotide sequence between the stop signal of one gene and the start codon (e.g., AUG) of the coding sequence of the next downstream open reading frame. An intergenic region may comprise a non-coding region of a gene, i.e., between the transcription start site and the start of the coding sequence (AUG) of the gene. This non-coding region occurs naturally in some viral genes.

In various embodiments, the intergenic region between the heterologous nucleotide sequence and the downstream gene can be engineered, independently from each other, to be at least 10 nt in length, at least 20 nt in length, at least 30 nt in length, at least 50 nt in length, at least 75 nt in length, at least 100 nt in length, at least 125 nt in length, at least 150 nt in length, at least 175 nt in length or at least 200 nt in length. In certain embodiments, the intergenic region between the heterologous nucleotide sequence and the downstream gene can be engineered, independently from each other, to be at most 10 nt in length, at most 20 nt in length, at most 30 nt in length, at most 50 nt in length, at most 75 nt in length, at most 100 nt in length, at most 125 nt in length, at most 150 nt in length, at most 175 nt in length or at most 200 nt in length. In various embodiments, the non-coding region of a desired gene in a virus genome can also be engineered, independently from each other, to be at least 10 nt in length, at least 20 nt in length, at least 30 nt in length, at least 50 nt in length, at least 75 nt in length, at least 100 nt in length, at least 125 nt in length, at least 150 nt in length, at least 175 nt in length or at least 200 nt in length. In certain embodiments, the non-coding region of a desired gene in a virus genome can also be engineered, independently from each other, to be at most 10 nt in length, at most 20 nt in length, at most 30 nt in length, at most 50 nt in length, at most 75 nt in length, at most 100 nt in length, at most 125 nt in length, at most 150 nt in length, at most 175 nt in length or at most 200 nt in length.

When inserting a heterologous nucleotide sequence, the positional effect and the intergenic region manipulation can be used in combination to achieve a desirable effect. For example, the heterologous nucleotide sequence can be added or inserted at a position selected from the group consisting of position 1, 2, 3, 4, 5, and 6, and the intergenic region between the heterologous nucleotide sequence and the next downstream gene can be altered (see Table 3). Some of the combinations encompassed by the present invention are shown by way of example in Table 3.

reporter gene, such as Green Fluorescence Protein (GFP) or enhanced Green Fluorescence Protein (eGFP), integrated to the viral genome the same fashion as the interested heterologous gene to observe the protein expression), or a combination thereof. Procedures of performing these assays are well known in the art (see, e.g., Flint et al., Principles Of Virology, Molecular Biology, Pathogenesis, And Control, 2000, ASM Press pp 25-56, the entire text is incorporated herein by reference), and non-limiting examples are given in the Example sections, infra.

For example, expression levels can be determined by infecting cells in culture with a virus of the invention and subsequently measuring the level of protein expression by, e.g., Western blot analysis or ELISA using antibodies specific to the gene product of the heterologous sequence, or measuring the level of RNA expression by, e.g., Northern blot analysis using probes specific to the heterologous sequence. Similarly, expression levels of the heterologous sequence can be determined by infecting an animal model and measuring the level of protein expressed from the heterologous sequence of the recombinant virus of the invention in the animal model. The protein level can be measured by obtaining a tissue sample from the infected animal and then subjecting the tissue sample to Western blot analysis or ELISA, using antibodies specific to the gene product of the heterologous sequence. Further, if an animal model is used, the titer of antibodies produced by the animal against the gene product of the heterologous sequence can be determined by any technique known to the skilled artisan, including but not limited to, ELISA.

TABLE 3

Examples of mode of insertion of heterologous nucleotide sequences

| | Position 1 | Position 2 | Position 3 | Position 4 | Position 5 | Position 6 |
|---|---|---|---|---|---|---|
| IGR[a] | 10-20 | 10-20 | 10-20 | 10-20 | 10-20 | 10-20 |
| IGR | 21-40 | 21-40 | 21-40 | 21-40 | 21-40 | 21-40 |
| IGR | 41-60 | 41-60 | 41-60 | 41-60 | 41-60 | 41-60 |
| IGR | 61-80 | 61-80 | 61-80 | 61-80 | 61-80 | 61-80 |
| IGR | 81-100 | 81-100 | 81-100 | 81-100 | 81-100 | 81-100 |
| IGR | 101-120 | 101-120 | 101-120 | 101-120 | 101-120 | 101-120 |
| IGR | 121-140 | 121-140 | 121-140 | 121-140 | 121-140 | 121-140 |
| IGR | 141-160 | 141-160 | 141-160 | 141-160 | 141-160 | 141-160 |
| IGR | 161-180 | 161-180 | 161-180 | 161-180 | 161-180 | 161-180 |
| IGR | 181-200 | 181-200 | 181-200 | 181-200 | 181-200 | 181-200 |
| IGR | 201-220 | 201-220 | 201-220 | 201-220 | 201-220 | 201-220 |
| IGR | 221-240 | 221-240 | 221-240 | 221-240 | 221-240 | 221-240 |
| IGR | 241-260 | 241-260 | 241-260 | 241-260 | 241-260 | 241-260 |
| IGR | 261-280 | 261-280 | 261-280 | 261-280 | 261-280 | 261-280 |
| IGR | 281-300 | 281-300 | 281-300 | 281-300 | 281-300 | 281-300 |

[a]Intergenic Region, measured in nucleotide.

Depending on the purpose (e.g., to have strong immunogenicity) of the inserted heterologous nucleotide sequence, the position of the insertion and the length of the intergenic region of the inserted heterologous nucleotide sequence can be determined by various indexes including, but not limited to, replication kinetics and protein or mRNA expression levels, measured by following non-limiting examples of assays: plaque assay, fluorescent-focus assay, infectious center assay, transformation assay, endpoint dilution assay, efficiency of plating, electron microscopy, hemagglutination, measurement of viral enzyme activity, viral neutralization, hemagglutination inhibition, complement fixation, immunostaining, immunoprecipitation and immunoblotting, enzyme-linked immunosorbent assay, nucleic acid detection (e.g., Southern blot analysis, Northern blot analysis, Western blot analysis), growth curve, employment of a reporter gene (e.g., using a As the heterologous sequences can be homologous to a nucleotide sequence in the genome of the virus, care should be taken that the probes and the antibodies are indeed specific to the heterologous sequence or its gene product.

In certain specific embodiments, expression levels of F-protein of hMPV from chimeric avian-human *metapneumovirus* can be determined by any technique known to the skilled artisan. Expression levels of the F-protein can be determined by infecting cells in a culture with the chimeric virus of the invention and measuring the level of protein expression by, e.g., Western blot analysis or ELISA using antibodies specific to the F-protein and/or the G-protein of hMPV, or measuring the level of RNA expression by, e.g., Northern blot analysis using probes specific to the F-gene and/or the G-gene of human *metapneumovirus*. Similarly, expression levels of the heterologous sequence can be determined using an animal model by infecting an animal and measuring the level of F-protein and/or G-protein in the animal model. The protein level can be measured by obtaining a tissue sample from the infected animal and then subjecting the tissue sample to Western blot analysis or ELISA using antibodies specific to F-protein and/or G-protein of the heterologous sequence. Further, if an animal model is used, the titer of antibodies produced by the animal against F-protein and/or G-protein can be determined by any technique known to the skilled artisan, including but not limited to, ELISA.

The rate of replication of a recombinant virus of the invention can be determined by any technique known to the skilled artisan.

In certain embodiments, to facilitate the identification of the optimal position of the heterologous sequence in the viral genome and the optimal length of the intergenic region, the heterologous sequence encodes a reporter gene. Once the optimal parameters are determined, the reporter gene is replaced by a heterologous nucleotide sequence encoding an antigen of choice. Any reporter gene known to the skilled artisan can be used with the methods of the invention. For more detail, see section 5.8.

The rate of replication of the recombinant virus can be determined by any standard technique known to the skilled artisan. The rate of replication is represented by the growth rate of the virus and can be determined by plotting the viral titer over the time post infection. The viral titer can be measured by any technique known to the skilled artisan. In certain embodiments, a suspension containing the virus is incubated with cells that are susceptible to infection by the virus. Cell types that can be used with the methods of the invention include, but are not limited to, Vero cells, LLC-MK-2 cells, Hep-2 cells, LF 1043 (HEL) cells, MRC-5 cells, WI-38 cells, tMK cells, 293 T cells, QT 6 cells, QT 35 cells, or chicken embryo fibroblasts (CEF). Subsequent to the incubation of the virus with the cells, the number of infected cells is determined. In certain specific embodiments, the virus comprises a reporter gene. Thus, the number of cells expressing the reporter gene is representative of the number of infected cells. In a specific embodiment, the virus comprises a heterologous nucleotide sequence encoding for eGFP, and the number of cells expressing eGFP, i.e., the number of cells infected with the virus, is determined using FACS.

In certain embodiments, the replication rate of the recombinant virus of the invention is at most 20% of the replication rate of the wild type virus from which the recombinant virus is derived under the same conditions. The same conditions refer to the same initial titer of virus, the same strain of cells, the same incubation temperature, growth medium, number of cells and other test conditions that may affect the replication rate. For example, the replication rate of APV/hMPV with PIV's F gene in position 1 is at most 20% of the replication rate of APV.

In certain embodiments, the replication rate of the recombinant virus of the invention is at most 5%, at most 10%, at most 20%, at most 30%, at most 40%, at most 50%, at most 75%, at most 80%, at most 90% of the replication rate of the wild type virus from which the recombinant virus is derived under the same conditions. In certain embodiments, the replication rate of the recombinant virus of the invention is at least 5%, at least 10%, at least 20%, at least 30%, at least 40%, at least 50%, at least 75%, at least 80%, at least 90% of the replication rate of the wild type virus from which the recombinant virus is derived under the same conditions. In certain embodiments, the replication rate of the recombinant virus of the invention is between 5% and 20%, between 10% and 40%, between 25% and 50%, between 40% and 75%, between 50% and 80%, or between 75% and 90% of the replication rate of the wild type virus from which the recombinant virus is derived under the same conditions.

In certain embodiments, the expression level of the heterologous sequence in the recombinant virus of the invention is at most 20% of the expression level of the F-protein of the wild type virus from which the recombinant virus is derived under the same conditions. The same conditions refer to the same initial titer of virus, the same strain of cells, the same incubation temperature, growth medium, number of cells and other test conditions that may affect the replication rate. For example, the expression level of the heterologous sequence of the F-protein of PIV3 in position 1 of hMPV is at most 20% of the expression level of the F-protein of hMPV.

In certain embodiments, the expression level of the heterologous sequence in the recombinant virus of the invention is at most 5%, at most 10%, at most 20%, at most 30%, at most 40%, at most 50%, at most 75%, at most 80%, at most 90% of the expression level of the F-protein of the wild type virus from which the recombinant virus is derived under the same conditions. In certain embodiments, the expression level of the heterologous sequence in the recombinant virus of the invention is at least 5%, at least 10%, at least 20%, at least 30%, at least 40%, at least 50%, at least 75%, at least 80%, at least 90% of the expression level of the F-protein of the wild type virus from which the recombinant virus is derived under the same conditions. In certain embodiments, the expression level of the heterologous sequence in the recombinant virus of the invention is between 5% and 20%, between 10% and 40%, between 25% and 50%, between 40% and 75%, between 50% and 80%, or between 75% and 90% of the expression level of the F-protein of the wild type virus from which the recombinant virus is derived under the same conditions.

5.4.3 Insertion of the Heterologous Gene Sequence Into the G Gene

The G protein is a transmembrane protein of *metapneumoviruses*. In a specific embodiment, the heterologous sequence is inserted into the region of the G-ORF that encodes for the ectodomain, such that it is expressed on the surface of the viral envelope. In one approach, the heterologous sequence may be inserted within the antigenic site without deleting any viral sequences. In another approach, the heterologous sequences replaces sequences of the G-ORF. Expression products of such constructs may be useful in vaccines against the foreign antigen, and may indeed circumvent problems associated with propagation of the recombinant virus in the vaccinated host. An intact G molecule with a substitution only in antigenic sites may allow for G function and thus allow for the construction of a viable virus. Therefore, this virus can be grown without the need for additional helper functions. The virus may also be attenuated in other ways to avoid any danger of accidental escape.

Other hybrid constructions may be made to express proteins on the cell surface or enable them to be released from the cell.

5.4.4 Construction of Bicistronic RNA

Bicistronic MRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with MPV packaging limitations. Thus, it is preferable that the IRES chosen for such a bicistronic approach be no more than 500 nucleotides in length. In a specific embodiment, the IRES is derived from a *picornavirus* and does not include any additional *picornaviral* sequences. Specific IRES elements include, but are not limited to the mammalian BiP IRES and the hepatitis C virus IRES.

Alternatively, a foreign protein may be expressed from a new internal transcriptional unit in which the transcriptional unit has an initiation site and polyadenylation site. In another embodiment, the foreign gene is inserted into a MPV gene such that the resulting expressed protein is a fusion protein.

5.5 Expression of Heterologous Gene Products Using Recombinant cDNA and RNA Templates The viral vectors and recombinant templates prepared as described above can be used in a variety of ways to express the heterologous gene products in appropriate host cells or to create chimeric viruses that express the heterologous gene products. In one embodiment, the recombinant cDNA can be used to transfect appropriate host cells and the resulting RNA may direct the expression of the heterologous gene product at high levels. Host cell systems which provide for high levels of expression include continuous cell lines that supply viral functions such as cell lines superinfected with APV or MPV, respectively, cell lines engineered to complement APV or MPV functions, etc.

In an alternate embodiment of the invention, the recombinant templates may be used to transfect cell lines that express a viral polymerase protein in order to achieve expression of the heterologous gene product. To this end, transformed cell lines that express a polymerase protein such as the L protein may be utilized as appropriate host cells. Host cells may be similarly engineered to provide other viral functions or additional functions such as G or N.

In another embodiment, a helper virus may provide the RNA polymerase protein utilized by the cells in order to achieve expression of the heterologous gene product. In yet another embodiment, cells may be transfected with vectors encoding viral proteins such as the N, P, L, and M2-1 proteins.

5.6 Rescue of Recombinant Virus Particles

In order to prepare the chimeric and recombinant viruses of the invention, a cDNA encoding the genome of a recombinant or chimeric virus of the invention in the plus or minus sense may be used to transfect cells which provide viral proteins and functions required for replication and rescue. Alternatively, cells may be transfected with helper virus before, during, or after transfection by the DNA or RNA molecule coding for the recombinant virus of the invention. The synthetic recombinant plasmid DNAs and RNAs of the invention can be replicated and rescued into infectious virus particles by any number of techniques known in the art, as described, e.g., in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

In one embodiment, of the present invention, synthetic recombinant viral RNAs may be prepared that contain the non-coding regions (leader and trailer) of the negative strand virus RNA which are essential for the recognition by viral polymerases and for packaging signals necessary to generate a mature virion. There are a number of different approaches which may be used to apply the reverse genetics approach to rescue negative strand RNA viruses. First, the recombinant RNAs are synthesized from a recombinant DNA template and reconstituted in vitro with purified viral polymerase complex to form recombinant ribonucleoproteins (RNPs) which can be used to transfect cells. In another approach, a more efficient transfection is achieved if the viral polymerase proteins are present during transcription of the synthetic RNAs either in vitro or in vivo. With this approach the synthetic RNAs may be transcribed from cDNA plasmids which are either co-transcribed in vitro with cDNA plasmids encoding the polymerase proteins, or transcribed in vivo in the presence of polymerase proteins, i.e., in cells which transiently or constitutively express the polymerase proteins.

In additional approaches described herein, infectious chimeric or recombinant virus may be replicated in host cell systems that express a *metapneumoviral* polymerase protein (e.g., in virus/host cell expression systems; transformed cell lines engineered to express a polymerase protein, etc.), so that infectious chimeric or recombinant virus are replicated and rescued. In this instance, helper virus need not be utilized since this function is provided by the viral polymerase proteins expressed.

In accordance with the present invention, any technique known to those of skill in the art may be used to achieve replication and rescue of recombinant and chimeric viruses. One approach involves supplying viral proteins and functions required for replication in vitro prior to transfecting host cells. In such an embodiment, viral proteins may be supplied in the form of wildtype virus, helper virus, purified viral proteins or recombinantly expressed viral proteins. The viral proteins may be supplied prior to, during or post transcription of the synthetic cDNAs or RNAs encoding the chimeric virus. The entire mixture may be used to transfect host cells. In another approach, viral proteins and functions required for replication may be supplied prior to or during transcription of the synthetic cDNAs or RNAs encoding the chimeric virus. In such an embodiment, viral proteins and functions required for replication are supplied in the form of wildtype virus, helper virus, viral extracts, synthetic cDNAs or RNAs which express the viral proteins are introduced into the host cell via infection or transfection. This infection/transfection takes place prior to or simultaneous to the introduction of the synthetic cDNAs or RNAs encoding the chimeric virus genome.

In a particularly desirable approach, cells engineered to express all viral genes or chimeric or recombinant virus of the invention, i.e., APV, MPV, MPV/APV or APV/MPV, may result in the production of infectious virus which contain the desired genotype; thus eliminating the need for a selection system. Theoretically, one can replace any one of the ORFs or part of any one of the ORFs encoding structural proteins of MPV with a foreign sequence. However, a necessary part of this equation is the ability to propagate the defective virus (defective because a normal viral gene product is missing or altered). A number of possible approaches exist to circumvent this problem. In one approach a virus having a mutant protein can be grown in cell lines which are constructed to constitutively express the wild type version of the same protein. By this way, the cell line complements the mutation in the virus. Similar techniques may be used to construct transformed cell lines that constitutively express any of the MPV genes. These cell lines which are made to express the viral protein may be used to complement the defect in the chimeric or recombinant virus and thereby propagate it. Alternatively, certain natural host range systems may be available to propagate chimeric or recombinant virus.

In yet another embodiment, viral proteins and functions required for replication may be supplied as genetic material in the form of synthetic cDNAs or RNAs so that they are co-transcribed with the synthetic cDNAs or RNAs encoding the chimeric virus. In a particularly desirable approach, plasmids which express the chimeric virus and the viral polymerase and/or other viral functions are co-transfected into host cells. For example, plasmids encoding the genomic or antigenomic APV, MPV, MPV/APV or APV/MPV RNA, with or without one or more heterologous sequences, may be co-transfected into host cells with plasmids encoding the metapneumoviral polymerase proteins N, P, L, or M2-1. Alternatively, rescue of the recombinant viruses of the invention may be accomplished by the use of Modified Vaccinia Virus Ankara (MVA) encoding T7 RNA polymerase, or a combination of MVA and plasmids encoding the polymerase proteins (N, P, and L). For example, MVA-T7 or Fowl Pox-T7 can be infected into Vero cells, LLC-MK-2 cells, HEp-2 cells, LF 1043 (HEL) cells, tMK cells, LLC-MK2, HUT 292, FRHL-2 (rhesus), FCL-1 (green monkey), WI-38 (human), MRC-5 (human) cells, 293 T cells, QT 6 cells, QT 35 cells and CEF cells. After infection with MVA-T7 or Fowl Pox-T7, a full length antigenomic or genomic cDNA encoding the recombinant virus of the invention may be transfected into the cells together with the N, P, L, and M2-1 encoding expression plasmids. Alternatively, the polymerase may be provided by plasmid transfection. The cells and cell supernatant can subsequently be harvested and subjected to a single freeze-thaw cycle. The resulting cell lysate may then be used to infect a fresh Vero cell monolayer in the presence of 1-beta-D-arabinofuranosylcytosine (ara C), a replication inhibitor of vaccinia virus, to generate a virus stock. The supernatant and cells from these plates can then be harvested, freeze-thawed once and the presence of recombinant virus particles of the invention can be assayed by immunostaining of virus plaques using antiserum specific to the particular virus.

Another approach to propagating the chimeric or recombinant virus may involve co-cultivation with wild-type virus. This could be done by simply taking recombinant virus and co-infecting cells with this and another wild-type virus. The wild-type virus should complement for the defective virus gene product and allow growth of both the wild-type and recombinant virus. Alternatively, a helper virus may be used to support propagation of the recombinant virus.

In another approach, synthetic templates may be replicated in cells co-infected with recombinant viruses that express the *metapneumovirus* polymerase protein. In fact, this method may be used to rescue recombinant infectious virus in accordance with the invention. To this end, the *metapneumovirus* polymerase protein may be expressed in any expression vector/host cell system, including but not limited to viral expression vectors (e.g., vaccinia virus, *adenovirus, baculovirus*, etc.) or cell lines that express a polymerase protein (e.g., see Krystal et al., 1986, Proc. Natl. Acad. Sci. USA 83: 2709-2713). Moreover, infection of host cells expressing all *metapneumovirus* proteins may result in the production of infectious chimeric virus particles. It should be noted that it may be possible to construct a recombinant virus without altering virus viability. These altered viruses would then be growth competent and would not need helper functions to replicate.

In order to recombinantly generate viruses in accordance with the methods of the invention, the genetic material encoding the viral genome must be transcribed (transcription step). This step can be accomplished either in vitro (outside the host cell) or in vivo (in a host cell). The viral genome can be transcribed from the genetic material to generate either a positive sense copy of the viral genome (antigenome copy) or a negative sense copy of the viral genome (genomic copy). The next step requires replication of the viral genome and packaging of the replicated genome into viral particles (replication and packaging step). This step occurs intracellularly in a host cell which has been engineered to provide sufficient levels of viral polymerase and structural proteins necessary for viral replication and packaging.

When the transcription step occurs in vitro, it is followed by intracellular replication and packaging of the viral genome. When the transcription step occurs in vivo, transcription of the viral genome can occur prior to, concurrently or subsequently to expression of the viral genetic material encoding the viral genome can be obtained or generated from a variety of sources and using a variety of methods known to one skilled in the art. The genetic material may be isolated from the virus itself. For example, a complex of the viral RNA genome and the polymerase proteins, ribonucleoprotein complexes (RNP), may be isolated from whole virus. The viral RNA genome is then stripped of the associated proteins, e.g., viral RNA polymerase and nuclear proteins.

The genetic material encoding the viral genome can be generated using standard recombinant techniques. The genetic material may encode the full length viral genome or a portion thereof. Alternatively, the genetic material may code for a heterologous sequence flanked by the leader and/or trailer sequences of the viral genome. A full-length viral genome can be assembled from several smaller PCR fragments using techniques known in the art. Restriction maps of different isolates of hMPV are shown in FIG. 28. The restriction sites can be used to assemble the full-length construct. In certain embodiments, PCR primers are designed such that the fragment resulting from the PCR reaction has a restriction site close to its 5' end and a restriction site close to it 3' end. The PCR product can then be digested with the respective restriction enzymes and subsequently ligated to the neighboring PCR fragments.

In order to achieve replication and packaging of the viral genome, it is important that the leader and trailer sequences retain the signals necessary for viral polymerase recognition. The leader and trailer sequences for the viral RNA genome can be optimized or varied to improve and enhance viral replication and rescue. Alternatively, the leader and trailer sequences can be modified to decrease the efficiency of viral replication and packaging, resulting in a rescued virus with an attenuated phenotype. Examples of different leader and trailer sequences, include, but are not limited to, leader and trailer sequences of a *paramyxovirus*. In a specific embodiment of the invention, the leader and trailer sequence is that of a wild type or mutated hMPV. In another embodiment of the invention, the leader and trailer sequence is that of a PIV, APV, or an RSV. In yet another embodiment of the invention, the leader and trailer sequence is that of a combination of different virus origins. By way of example and not meant to limit the possible combination, the leader and trailer sequence can be a combination of any of the leader and trailer sequences of hMPV, PIV, APV, RSV, or any other *paramyxovirus*. Examples of modifications to the leader and trailer sequences include varying the spacing relative to the viral promoter, varying the sequence, e.g., varying the number of G residues (typically 0 to 3), and defining the 5' or 3' end using ribozyme sequences, including, Hepatitis Delta Virus (HDV) ribozyme sequence, Hammerhead ribozyme sequences, or fragments thereof, which retain the ribozyme catalytic activity, and using restriction enzymes for run-off RNA produced in vitro.

In an alternative embodiment, the efficiency of viral replication and rescue may be enhanced if the viral genome is of hexamer length. In order to ensure that the viral genome is of the appropriate length, the 5' or 3' end may be defined using ribozyme sequences, including, Hepatitis Delta Virus (HDV) ribozyme sequence, Hammerhead ribozyme sequences, or fragments thereof, which retain the ribozyme catalytic activity, and using restriction enzymes for run-off RNA produced in vitro.

In order for the genetic material encoding the viral genome to be transcribed, the genetic material is engineered to be placed under the control of appropriate transcriptional regulatory sequences, e.g., promoter sequences recognized by a polymerase. In preferred embodiments, the promoter sequences are recognized by a T7, Sp6 or T3 polymerase. In yet another embodiment, the promoter sequences are recognized by cellular DNA dependent RNA polymerases, such as RNA polymerase I (Pol I) or RNA polymerase II (Pol II). The genetic material encoding the viral genome may be placed under the control of the transcriptional regulatory sequences, so that either a positive or negative strand copy of the viral genome is transcribed. The genetic material encoding the viral genome is recombinantly engineered to be operatively linked to the transcriptional regulatory sequences in the context of an expression vector, such as a plasmid based vector, e.g. a plasmid with a pol II promoter such as the immediate early promoter of CMV, a plasmid with a T7 promoter, or a viral based vector, e.g., pox viral vectors, including vaccinia vectors, MVA-T7, and Fowl pox vectors.

The genetic material encoding the viral genome may be modified to enhance expression by the polymerase of choice, e.g., varying the number of G residues (typically 0 to 3) upstream of the leader or trailer sequences to optimize expression from a T7 promoter.

Replication and packaging of the viral genome occurs intracellularly in a host cell permissive for viral replication and packaging. There are a number of methods by which the host cell can be engineered to provide sufficient levels of the viral polymerase and structural proteins necessary for replication and packaging, including, host cells infected with an appropriate helper virus, host cells engineered to stably or constitutively express the viral polymerase and structural proteins, or host cells engineered to transiently or inducibly express the viral polymerase and structural proteins.

Protein function required for MPV viral replication and packaging includes, but not limited to, the polymerase proteins P, N, L, and M2-1.

In one embodiment, the proteins expressed are native or wild type MPV proteins. In another embodiment, the proteins expressed may be modified to enhance their level of expression and/or polymerase activity, using standard recombinant techniques. Alternatively, fragments, derivatives, analogs or truncated versions of the polymerase proteins that retain polymerase activity may be expressed. In yet another embodiment, analogous polymerase proteins from other *pneumoviruses*, such as APV, or from any other *paramyxovirus* may be expressed. Moreover, an attenuated virus can be produced by expressing proteins of one strain of MPV along with the genome of another strain. For example, a polymerase protein of one strain of MPV can be expressed with the genome of another strain to produce an attenuated phenotype.

The viral polymerase proteins can be provided by helper viruses. Helper viruses that may be used in accordance with the invention, include those that express the polymerase viral proteins natively, such as MPV or APV. Alternatively, helper viruses may be used that have been recombinantly engineered to provide the polymerase viral proteins Alternatively the viral polymerase proteins can be provided by expression vectors. Sequences encoding the viral polymerase proteins are engineered to be placed under the control of appropriate transcriptional regulatory sequences, e.g., promoter sequences recognized by a polymerase. In preferred embodiments, the promoter sequences are recognized by a T7, Sp6 or T3 polymerase. In yet another embodiment, the promoter sequences are recognized by a Pol I or Pol II polymerase. Alternatively, the promoter sequences are recognized by a viral polymerase, such as CMV. The sequences encoding the viral polymerase proteins are recombinantly engineered to be operatively linked to the transcriptional regulatory sequences in the context of an expression vector, such as a plasmid based vector, e.g. a CMV driven plasmid, a T7 driven plasmid, or a viral based vector, e.g., pox viral vectors, including vaccinia vectors, MVA-T7, and Fowl pox vectors.

In order to achieve efficient viral replication and packaging, high levels of expression of the polymerase proteins is preferred. Such levels are obtained using 100-200 ng L/pCITE, 200-400 ng N/pCITE, 200-400 ng P/pCITE, and 100-200 ng M2-1/pCITE plasmids encoding *paramyxovirus* proteins together with 2-4 ug of plasmid encoding the full-length viral cDNA transfected into cells infected with MVA-T7. In another embodiment, 0.1-2.0 μg of pSH25 (CAT expressing), 0.1-3.0 μg of pRF542 (expressing T7 polymerase), 0.1-0.8 μg pCITE vector with N cDNA insert, and 0.1-1.0 μg of each of three pCITE vectors containing P, L and M2-1 cDNA insert are used. Alternatively, one or more polymerase and structural proteins can be introduced into the cells in conjunction with the genetic material by transfecting cells with purified ribonucleoproteins. Host cells that are permissive for MPV viral replication and packaging are preferred. Examples of preferred host cells include, but are not limited to, 293T, Vero, tMK, and BHK. Other examples of host cells include, but are not limited to, LLC-MK-2 cells, Hep-2 cells, LF 1043 (HEL) cells, LLC-MK2, HUT 292, FRHL-2 (rhesus), FCL-1 (green monkey), WI-38 (human), MRC-5 (human) cells, QT 6 cells, QT 35 cells and CEF cells.

In alternative embodiments of the invention, the host cells can be treated using a number of methods in order to enhance the level of transfection and/or infection efficiencies, protein expression, in order to optimize viral replication and packaging. Such treatment methods, include, but are not limited to, sonication, freeze/thaw, and heat shock. Furthermore, standard techniques known to the skilled artisan can be used to optimize the transfection and/or infection protocol, including, but are not limited to, DEAE-dextran-mediated transfection, calcium phosphate precipitation, lipofectin treatment, liposome-mediated transfection and electroporation. The skilled artisan would also be familiar with standard techniques available for the optimization of transfection/infection protocols. By way of example, and not meant to limit the available techniques, methods that can be used include, manipulating the timing of infection relative to transfection when a virus is used to provide a necessary protein, manipulating the timing of transfections of different plasmids, and affecting the relative amounts of viruses and transfected plasmids.

In another embodiment, the invention relates to the rescue or production of live virus from cDNA using polymerase from a virus other than the one being rescued. In certain embodiments, hMPV is rescued from a cDNA using any of a number of polymerases, including, but not limited to, interspecies and intraspecies polymerases. In a certain embodiment, hMPV is rescued in a host cell expressing the minimal replication unit necessary for hMPV replication. For example, hMPV can be rescued from a cDNA using a number of polymerases, including, but not limited to, the polymerase of RSV, APV, MPV, or PIV. In a specific embodiment of the invention, hMPV is rescued using the polymerase of an RNA virus. In a more specific embodiment of the invention, hMPV is rescued using the polymerase of a negative stranded RNA virus. In an even more specific embodiment of the invention, hMPV is rescued using RSV polymerase. In another embodiment of the invention, hMPV is rescued using APV polymerase. In yet another embodiment of the invention, hMPV is rescued using an MPV polymerase. In another embodiment of the invention, hMPV is rescued using PIV polymerase.

In a more certain embodiment of the invention, hMPV is rescued from a cDNA using a complex of hMPV polymerase proteins. For example, the hMPV minireplicon can be rescued using a polymerase complex consisting of the L, P, N, and M2-1 proteins. In another embodiment of the invention, the polymerase complex consists of the L, P, and N proteins. In yet another embodiment of the invention, hMPV can be rescued from a cDNA using a polymerase complex consisting of polymerase proteins from other viruses, such as, but not limited to, RSV, PIV, and APV. In particular, hMPV can be rescued from a cDNA using a polymerase complex consisting of the L, P, N, and M2-1 proteins of RSV, PIV, APV, MPV, or any combination thereof. In yet another embodiment of the invention, the polymerase complex used to rescue hMPV from a cDNA consists of the L, P, and N proteins of RSV, PIV, APV, MPV, or any combination thereof. In even another embodiment of the invention, different polymerase proteins from various viruses can be used to form the polymerase complex. In such an embodiment, the polymerase used to rescue hMPV can be formed by different components of the RSV, PIV, APV, or MPV polymerases. By way of example, and not meant to limit the possible combination in forming a complex, the N protein can be encoded by the N gene of RSV, APV, PIV or MPV while the L protein is encoded by the L gene of RSV, APV, PIV or MPV and the P protein can be encoded by the P gene of RSV, APV, PIV or MPV. One skilled in the art would be able to determine the possible combinations that may be used to form the polymerase complex necessary to rescue the hMPV from a cDNA.

In certain embodiments, conditions for the propagation of virus are optimized in order to produce a robust and high-yielding cell culture (which would be beneficial, e.g., for manufacture the virus vaccine candidates of the invention). Critical parameters can be identified, and the production process can be first optimized in small-scale experiments to determine the scalability, robustness, and reproducibility and subsequently adapted to large scale production of virus. In certain embodiments, the virus that is propagated using the methods of the invention is hMPV. In certain embodiments, the virus that is propagated using the methods of the invention is a recombinant or a chimeric hMPV. In certain embodiments, the virus that is propagated using the methods of the invention is a virus of one of the following viral families Adenoviridae, Arenaviridae, Astroviridae, Baculoviridae, Bunyaviridae, Caliciviridae, Caulimovirus, Coronaviridae, Cystoviridae, Filoviridae, Flaviviridae, Hepadnaviridae, Herpesviridae, Hypoviridae, Idaeovirus, Inoviridae, Iridoviridae, Leviviridae, Lipothrixviridae, Luteovirus, Machlomovirus, Marafivirus, Microviridae, Myoviridae, Necrovirus, Nodaviridae, Orthomyxoviridae, Papovaviridae, Paramyxoviridae, Partitiviridae, Parvoviridae, Phycodnaviridae, Picornaviridae, Plasmaviridae, Podoviridae, Polydnaviridae, Potyviridae, Poxviridae, Reoviridae, Retroviridae, Rhabdoviridae, Sequiviridae, Siphoviridae, Sobemovirus, Tectiviridae, Tenuivirus, Tetraviridae, Tobamovirus, Tobravirus, Togaviridae, Tombusviridae, Totiviridae, Trichovirus, Mononegavirales. In certain embodiments, the virus that is propagated with the methods of the invention is an RNA virus. In certain embodiments, the virus is not a virus of the family Herpesviridae. In certain embodiments, the virus is not HSV.

In certain embodiments, a cell culture infected with a virus or a viral construct of interest is incubated at a lower post-infection incubation temperature as compared to the standard incubation temperature for the cells in culture. In a specific embodiment, a cell culture infected with a viral construct of interest is incubated at 33° C. or about 33° C. (e.g., 33±1° C.). In certain embodiments, the post-infection incubation temperature is about 25° C., 26° C., 27° C., 28° C., 29° C., 30° C., 31° C., 32° C., 33° C., 34° C., 35° C., 36° C. or 37° C.

In certain embodiments, virus is propagated by incubating a cells before infection with the virus at a temperature optimized for the growth of the cells and subsequent to infection of the cells with the virus, i.e., post-infection, the temperature is shifted to a lower temperature. In certain embodiments the shift is at least 1° C., 2° C., 3° C., 4° C., 5° C., 6° C., 7° C., 8° C., 8° C., 9° C., 10° C., 11° C., or at least 12° C. In certain embodiments the shift is at most 1° C., 2° C., 3° C., 4° C., 5° C., 6° C., 7° C., 8° C., 9° C., 10° C., 11° C., or at most 12° C. In a specific embodiment, the shift is 4° C.

In certain embodiments, the cells are cultured in a medium containing serum before infection with a virus or a viral construct of interest and the cells are cultured in a medium without serum after infection with the virus or viral construct. For a more detailed description of growing infected cells without serum, see the section entitled "Plasmid-Only Recovery of Virus in Serum Free Media." In a specific embodiment, the serum is fetal bovine serum and is present a concentration of 5% of culture volume, 2% of culture volume, or 0.5% of culture volume.

In certain embodiments, virus is propagated by incubating cells that are infected with the virus in the absence of serum. In certain embodiments, virus is propagated by incubating cells that are infected with the virus in a culture medium containing less than 5% of serum, less than 2.5% of serum, less than 1% of serum, less than 0.1% of serum, less than 0.01% of serum, or less than 0.001% of serum.

In certain embodiments, the cells are incubated before infection with the virus in medium containing serum. In certain embodiments, subsequent to infection of the cells with the virus, the cells are incubated in the absence of serum. In other embodiments, the cells are first incubated in medium containing serum; the cells are then transferred into medium without serum; and subsequently, the cells are infected with the virus and further incubated in the absence of virus.

In certain embodiments, the cells are transferred from medium containing serum into medium in the absence of serum, by removing the serum-containing medium from the cells and adding the medium without serum. In other embodiments, the cells are centrifuged and the medium containing serum is removed and medium without serum is added. In certain embodiments, the cells are washed with medium without serum to ensure that cells once infected with the virus are incubated in the absence of serum. In certain, more specific embodiments, the cells are washed with medium without serum at least one time, two times, three times, four times, five times, or at least ten times.

In yet other embodiments, cells are cultured in a medium containing serum and at a temperature that is optimal for the growth of the cells before infection with a virus or a viral construct, and the cell culture is incubated at a lower temperature (relative to the standard incubation temperature for the corresponding virus or viral vector) after infection with the viral construct of interest. In a specific embodiment, cells are cultured in a medium containing serum before infection with a viral construct of interest at 37° C., and the cell culture is incubated at 33° C. or about 33° C. (e.g., 33±1° C.) after infection with the viral construct of interest.

In even other embodiments, cells are cultured in a medium containing serum and at a temperature that is optimal for the growth of the cells before infection with a virus or a viral construct, and the cell culture is incubated without serum at a lower temperature (relative to the standard incubation temperature for the corresponding virus or viral vector) after infection with the viral construct of interest. In a specific embodiment, cells are cultured in a medium containing serum before infection with a viral construct of interest at 37° C., and the cell culture is incubated without serum at 33° C. or about 33° C. (e.g., 33±1° C.) after infection with the viral construct of interest.

The viral constructs and methods of the present invention can be used for commercial production of viruses, e.g., for vaccine production. For commercial production of a vaccine, it is preferred that the vaccine contains only inactivated viruses or viral proteins that are completely free of infectious virus or contaminating viral nucleic acid, or alternatively, contains live attenuated vaccines that do not revert to virulence. Contamination of vaccines with adventitious agents introduced during production should also be avoided. Methods known in the art for large scale production of viruses or viral proteins can be used for commercial production of a vaccine of the invention. In one embodiment, for commercial production of a vaccine of the invention, cells are cultured in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); and laboratory and commercial scale bioreactors from B. Braun Biotech International (B. Braun Biotech, Melsungen, Germany). In another embodiment, small-scale process optimization studies are performed before the commercial production of the virus, and the optimized conditions are selected and used for the commercial production of the virus.

Plasmid-Rescue in Serum-Free Medium

In certain embodiments of the invention, virus can be recovered without helper virus. More specifically, virus can be recovered by introducing into a cell a plasmid encoding the viral genome and plasmids encoding viral proteins required for replication and rescue. In certain embodiments, the cell is grown and maintained in serum-free medium. In certain embodiments, the plasmids are introduced into the cell by electroporation. In a specific embodiment, a plasmid encoding the antigenomic cDNA of the virus under the control of the T7 promoter, a plasmid encoding the T7 RNA polymerase, and plasmids encoding the N protein, P protein, and L protein, respectively, under control of the T7 promoter are introduced into SF Vero cells by electroporation. Vero cells were obtained from ATCC and adapted to grow in serum-free media according to the following steps (developed by Mike Berry's laboratory).

1. Thaw ATCC CCL-81 Vial in DMEM+5% v/v FBS in T-25 flask P121;
2. Expand 5 passages in DMEM+5% v/v FBS P126;
3. Directly transfer FBS grown cells to OptiPRO (Invitrogen Corporation) in T-225 flasks;
4. Expand 7 passages in OptiPRO;
5. Freeze down Pre-Master Cell Bank Stock at Passage 133-7;
6. Expand 4 passages in OptiPRO;
7. Freeze down Master Cell Bank Stock at Passage 137;
8. Expand 4 passages in OptiPRO;
9. Freeze down Working Cell Bank Stock at Passage 141; and
10. Thaw and expand for electroporation and virus amplification.

Methods for the rescue of viral particles are described in section 5.6 entitled "Rescue Of Recombinant Virus Particles".

In certain embodiments, the cells used for viral rescue are cells that can be grown and/or maintained without the addition of components derived from animals or humans. In certain embodiments, the cells used for viral rescue are cells that are adapted to growth without serum. In a specific embodiment, SF Vero cells are used for the rescue of virus. In certain embodiments, the cells are grown and/or maintained in OptiPRO SFM (Invitrogen Corporation) supplemented with 4 mM L-glutamine. In certain embodiments, the cells are grown in medium that is supplemented with serum but for rescue of viral particles the cells are transferred into serum-free medium. In a specific embodiment, the cells are washed in serum-free medium to ensure that the viral rescue takes place in a serum-free environment.

The plasmids are introduced into the cells by any method known to the skilled artisan that can be used with the cells, e.g., by calcium phosphate transfection, DEAE-Dextran transfection, electroporation or liposome mediated transfection (see Chapter 9 of Short Protocols in Molecular Biology, Ausubel et al. (editors), John Wiley & Sons, Inc., 1999). In specific embodiments, electroporation is used to introduce the plasmid DNA into the cells. SF Vero cells are resistant to lipofection. To select cells that have been transfected with the required plasmids, the plasmids can also carry certain markers. Such markers include, but are not limited to, resistancy to certain antibiotics (e.g., kanamycin, blasticidin, ampicillin, Hygromycin B, Puromycin and Zeocin™), makers that confer certain autotrophic properties on a cell that lacks this property without the marker, or a marker can also be a gene that is required for the growth of a cell but that is mutated in the cells into which the plasmid is introduced.

The transcription of the viral genome and/or the viral genes are under transcriptional control of a promoter. Thus, the sequences encoding the viral genome or the viral proteins are operatively linked to the promoter sequence. Any promoter/RNA polymerase system known to the skilled artisan can be used with the methods of the present invention. In certain embodiments, the promoter can be a promoter that allows transcription by an RNA polymerase endogenous to the cell, e.g., a promoter sequences that are recognized by a cellular DNA dependent RNA polymerases, such as RNA polymerase I (Pol I) or RNA polymerase II (Pol II). In certain embodiments, the promoter can be an inducible promoter. In certain embodiments, the promoter can be a promoter that allows transcription by an RNA polymerase that is not endogenous to the cell. In certain, more specific embodiments, the promoter is a T3 promoter, T7 promoter, SP6 promoter, or CMV promoter. Depending on the type of promoter used, a plasmid encoding the RNA polymerase that recognizes the promoter is also introduced into the cell to provide the appropriate RNA polymerase. In specific embodiments, the RNA polymerase is T3 RNA polymerase, T7 RNA polymerase, SP6 RNA polymerase, or CMV RNA polymerase. In a specific embodiment, the viral genes and the viral genome are transcribed under the control of a T7 promoter and a plasmid encoding the T7 RNA polymerase is introduced to provide the T7 RNA polymerase. The transcription of the polymerase can be under the control of any promoter system that would function in the cell type used. In a specific embodiment, the CMV promoter is used.

The viral genome can be in the plus or minus orientation. Thus, the viral genome can be transcribed from the genetic material to generate either a positive sense copy of the viral genome (antigenome copy) or a negative sense copy of the viral genome (genomic copy). In certain embodiments, the viral genome is a recombinant, chimeric and/or attenuated virus of the invention. In certain embodiments, the efficiency of viral replication and rescue may be enhanced if the viral genome is of hexamer length. In order to ensure that the viral genome is of the appropriate length, the 5' or 3' end may be defined using ribozyme sequences, including, Hepatitis Delta Virus (HDV) ribozyme sequence, Hammerhead ribozyme sequences, or fragments thereof, which retain the ribozyme catalytic activity.

In certain embodiments, the viral proteins required for replication and rescue include the N, P, and L gene. In certain, more specific, embodiments, the viral proteins required for replication and rescue include the N, P, M2-1 and L gene.

5.7 Attenuation of Recombinant Viruses

The recombinant viruses of the invention can be further genetically engineered to exhibit an attenuated phenotype. In particular, the recombinant viruses of the invention exhibit an attenuated phenotype in a subject to which the virus is administered as a vaccine. Attenuation can be achieved by any method known to a skilled artisan. Without being bound by theory, the attenuated phenotype of the recombinant virus can be caused, e.g., by using a virus that naturally does not replicate well in an intended host (e.g., using an APV in human), by reduced replication of the viral genome, by reduced ability of the virus to infect a host cell, or by reduced ability of the viral proteins to assemble to an infectious viral particle relative to the wild type strain of the virus. The viability of certain sequences of the virus, such as the leader and the trailer sequence can be tested using a minigenome assay (see section 5.8).

The attenuated phenotypes of a recombinant virus of the invention can be tested by any method known to the artisan (see, e.g., section 5.8). A candidate virus can, for example, be tested for its ability to infect a host or for the rate of replication in a cell culture system. In certain embodiments, a mimigenome system is used to test the attenuated virus when the gene that is altered is N, P, L, M2, F, G, M2-1, M2-2 or a combination thereof. In certain embodiments, growth curves at different temperatures are used to test the attenuated phenotype of the virus. For example, an attenuated virus is able to grow at 35° C., but not at 39° C. or 40° C. In certain embodiments, different cell lines can be used to evaluate the attenuated phenotype of the virus. For example, an attenuated virus may only be able to grow in monkey cell lines but not the human cell lines, or the achievable virus titers in different cell lines are different for the attenuated virus. In certain embodiments, viral replication in the respiratory tract of a small animal model, including but not limited to, hamsters, cotton rats, mice and guinea pigs, is used to evaluate the attenuated phenotypes of the virus. In other embodiments, the immune response induced by the virus, including but not limited to, the antibody titers (e.g., assayed by plaque reduction neutralization assay or ELISA) is used to evaluate the attenuated phenotypes of the virus. In a specific embodiment, the plaque reduction neutralization assay or ELISA is carried out at a low dose. In certain embodiments, the ability of the recombinant virus to elicit pathological symptoms in an animal model can be tested. A reduced ability of the virus to elicit pathological symptoms in an animal model system is indicative of its attenuated phenotype. In a specific embodiment, the candidate viruses are tested in a monkey model for nasal infection, indicated by mucous production.

The viruses of the invention can be attenuated such that one or more of the functional characteristics of the virus are impaired. In certain embodiments, attenuation is measured in comparison to the wild type strain of the virus from which the attenuated virus is derived. In other embodiments, attenuation is determined by comparing the growth of an attenuated virus in different host systems. Thus, for a non-limiting example, an APV is said to be attenuated when grown in a human host if the growth of the APV in the human host is reduced compared to the growth of the APV in an avian host.

In certain embodiments, the attenuated virus of the invention is capable of infecting a host, is capable of replicating in a host such that infectious viral particles are produced. In comparison to the wild type strain, however, the attenuated strain grows to lower titers or grows more slowly. Any technique known to the skilled artisan can be used to determine the growth curve of the attenuated virus and compare it to the growth curve of the wild type virus. For exemplary methods see Example section, infra. In a specific embodiment, the attenuated virus grows to a titer of less than $10^5$ pfu/ml, of less than $10^4$ pfu/ml, of less than $10^3$ pfu/ml, or of less than $10^2$ pfu/ml in Vero cells under conditions as described in, e.g., Example 22.

In certain embodiments, the attenuated virus of the invention (e.g., a chimeric mammalian MPV) cannot replicate in human cells as well as the wild type virus (e.g., wild type mammalian MPV) does. However, the attenuated virus can replicate well in a cell line that lack interferon functions, such as Vero cells.

In other embodiments, the attenuated virus of the invention is capable of infecting a host, of replicating in the host, and of causing proteins of the virus of the invention to be inserted into the cytoplasmic membrane, but the attenuated virus does not cause the host to produce new infectious viral particles. In certain embodiments, the attenuated virus infects the host, replicates in the host, and causes viral proteins to be inserted in the cytoplasmic membrane of the host with the same efficiency as the wild type mammalian virus. In other embodiments, the ability of the attenuated virus to cause viral proteins to be inserted into the cytoplasmic membrane into the host cell is reduced compared to the wild type virus. In certain embodiments, the ability of the attenuated mammalian virus to replicate in the host is reduced compared to the wild type virus. Any technique known to the skilled artisan can be used to determine whether a virus is capable of infecting a mammalian cell, of replicating within the host, and of causing viral proteins to be inserted into the cytoplasmic membrane of the host. For illustrative methods see section 5.8.

In certain embodiments, the attenuated virus of the invention is capable of infecting a host. In contrast to the wild type mammalian MPV, however, the attenuated mammalian MPV cannot be replicated in the host. In a specific embodiment, the attenuated mammalian virus can infect a host and can cause the host to insert viral proteins in its cytoplasmic membranes, but the attenuated virus is incapable of being replicated in the host. Any method known to the skilled artisan can be used to test whether the attenuated mammalian MPV has infected the host and has caused the host to insert viral proteins in its cytoplasmic membranes.

In certain embodiments, the ability of the attenuated mammalian virus to infect a host is reduced compared to the ability of the wild type virus to infect the same host. Any technique known to the skilled artisan can be used to determine whether a virus is capable of infecting a host. For illustrative methods see section 5.8.

In certain embodiments, mutations (e.g., missense mutations) are introduced into the genome of the virus to generated a virus with an attenuated phenotype. Mutations (e.g., missense mutations) can be introduced into the N-gene, the P-gene, the M-gene, the F-gene, the M2-gene, the S H-gene, the G-gene or the L-gene of the recombinant virus. Mutations can be additions, substitutions, deletions, or combinations thereof. In specific embodiments, a single amino acid deletion mutation for the N, P, L, F, G, M2-1, M2-2 or M2 proteins is introduced, which can be screened for functionality in the mini-genome assay system and be evaluated for predicted functionality in the virus. In more specific embodiments, the missense mutation is a cold-sensitive mutation. In other embodiments, the missense mutation is a heat-sensitive mutation. In one embodiment, major phosphorylation sites of P protein of the virus is removed. In another embodiment, a mutation or mutations are introduced into the L gene of the virus to generate a temperature sensitive strain. In yet another embodiment, the cleavage site of the F gene is mutated in such a way that cleavage does not occur or occurs at very low efficiency. In certain, more specific embodiments, the motif with the amino acid sequence RQSR (SEQ ID NO: 395) at amino acid postions 99 to 102 of the F protein of hMPV is mutated (see FIG. 9). A mutation can be, but is not limited to, a deletion of one or more amino acids, an addition of one or more amino acids, a substitution (conserved or non-conserved) of one or more amino acids or a combination thereof. In some strains of hMPV, the cleavage site is RQPR (SEQ ID NO:396) (see Example "P101S"). In certain embodiments, the cleavage site with the amino acid sequence is RQPR (SEQ ID NO:396) is mutated. In more specific embodiments, the cleavage site of the F protein of hMPV is mutated such that the infectivity of hMPV is reduced. In certain embodiments, the infectivity of hMPV is reduced by a factor of at least 5, 10, 50, 100, 500, $10^3$, $5\times10^3$, $10^4$, $5\times10^4$, $10^5$, $5\times10^5$, or at least $10^6$. In certain embodiments, the infectivity of hMPV is reduced by a factor of at most 5, 10, 50, 100, 500, $10^3$, $5\times10^3$, $10^4$, $5\times10^4$,$10^5$, $5\times10^5$, or at most $10^6$.

In other embodiments, deletions are introduced into the genome of the recombinant virus. In more specific embodiments, a deletion can be introduced into the N-gene, the P-gene, the M-gene, the F-gene, the M2-gene, the SH-gene, the G-gene or the L-gene of the recombinant virus. In specific embodiments, the deletion is in the M2-gene of the recombinant virus of the present invention. In other specific embodiments, the deletion is in the SH-gene of the recombinant virus of the present invention. In yet another specific embodiment, both the M2-gene and the SH-gene are deleted.

In certain embodiments, the intergenic region of the recombinant virus is altered. In one embodiment, the length of the intergenic region is altered. In another embodiment, the intergenic regions are shuffled from 5' to 3' end of the viral genome.

In other embodiments, the genome position of a gene or genes of the recombinant virus is changed. In one embodiment, the F or G gene is moved to the 3' end of the genome. In another embodiment, the N gene is moved to the 5' end of the genome.

In certain embodiments, attenuation of the virus is achieved by replacing a gene of the wild type virus with the analogous gene of a virus of a different species (e.g., of RSV, APV, PIV3 or mouse *pneumovirus*), of a different subgroup, or of a different variant. In illustrative embodiments, the N-gene, the P-gene, the M-gene, the F-gene, the M2-gene, the SH-gene, the G-gene or the L-gene of a mammalian MPV is replaced with the N-gene, the P-gene, the M-gene, the F-gene, the M2-gene, the SH-gene, the G-gene or the L-gene, respectively, of an APV. In other illustrative embodiments, the N-gene, the P-gene, the M-gene, the F-gene, the M2-gene, the SH-gene, the G-gene or the L-gene of APV is replaced with the N-gene, the P-gene, the M-gene, the F-gene, the M2-gene, the SH-gene, the G-gene or the L-gene, respectively, of a mammalian MPV. In a preferred embodiment, attenuation of the virus is achieved by replacing one or more polymerase associated genes (e.g., N, P, L or M2) with genes of a virus of a different species.

In certain embodiments, attenuation of the virus is achieved by replacing one or more specific domains of a protein of the wild type virus with domains derived from the corresponding protein of a virus of a different species. In an illustrative embodiment, the ectodomain of a F protein of APV is replaced with an ectodomain of a F protein of a mammalian MPV. In a preferred embodiment, one or more specific domains of L, N, or P protein are replaced with domains derived from corresponding proteins of a virus of a different species. In certain other embodiments, attenuation of the virus is achieved by deleting one or more specific domains of a protein of the wild type virus. In a specific embodiment, the transmembrane domain of the F-protein is deleted.

In certain embodiments of the invention, the leader and/or trailer sequence of the recombinant virus of the invention can be modified to achieve an attenuated phenotype. In certain, more specific embodiments, the leader and/or trailer sequence is reduced in length relative to the wild type virus by at least 1 nucleotide, at least 2 nucleotides, at least 3 nucleotides, at least 4 nucleotides, at least 5 nucleotides or at least 6 nucleotides. In certain other, more specific embodiments, the sequence of the leader and/or trailer of the recombinant virus is mutated. In a specific embodiment, the leader and the trailer sequence are 100% complementary to each other. In other embodiments, 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides are not complementary to each other where the remaining nucleotides of the leader and the trailer sequences are complementary to each other. In certain embodiments, the non-complementary nucleotides are identical to each other. In certain other embodiments, the non-complementary nucleotides are different from each other. In other embodiments, if the non-complementary nucleotide in the trailer is purine, the corresponding nucleotide in the leader sequence is also a purine. In other embodiments, if the non-complementary nucleotide in the trailer is pyrimidine, the corresponding nucleotide in the leader sequence is also a purine. In certain embodiments of the invention, the leader and/or trailer sequence of the recombinant virus of the invention can be replaced with the leader and/or trailer sequence of a another virus, e.g., with the leader and/or trailer sequence of RSV, APV, PIV3, mouse *pneumovirus*, or with the leader and/or trailer sequence of a human

*metapneumovirus* of a subgroup or variant different from the human *metapneumovirus* from which the protein-encoding parts of the recombinant virus are derived.

When a live attenuated vaccine is used, its safety must also be considered. The vaccine must not cause disease. Any techniques known in the art that can make a vaccine safe may be used in the present invention. In addition to attenuation techniques, other techniques may be used. One non-limiting example is to use a soluble heterologous gene that cannot be incorporated into the virion membrane. For example, a single copy of the soluble RSV F gene, a version of the RSV gene lacking the transmembrane and cytosolic domains, can be used. Since it cannot be incorporated into the virion membrane, the virus tropism is not expected to change.

Various assays can be used to test the safety of a vaccine. See section 5.8, infra. Particularly, sucrose gradients and neutralization assays can be used to test the safety. A sucrose gradient assay can be used to determine whether a heterologous protein is inserted in a virion. If the heterologous protein is inserted in the virion, the virion should be tested for its ability to cause symptoms even if the parental strain does not cause symptoms. Without being bound by theory, if the heterologous protein is incorporated in the virion, the virus may have acquired new, possibly pathological, properties.

In certain embodiments, one or more genes are deleted from the hMPV genome to generate an attenuated virus. In more specific embodiments, the M2-2 ORF, the M2-1 ORF, the M2 gene, the SH gene and/or the G2 gene is deleted.

In other embodiments, small single amino acid deletions are introduced in genes involved in virus replication to generate an attenuated virus. In more specific embodiments, a small single amino acid deletion is introduced in the N, L, or the P gene. In certain specific embodiments, one or more of the following amino acids are mutated in the L gene of a recombinant hMPV: Phe at amino acid position 456, Glu at amino acid position 749, Tyr at amino acid position 1246, Met at amino acid position 1094 and Lys at amino acid position 746 to generate an attenuated virus. A mutation can be, e.g., a deletion or a substitution of an amino acid. An amino acid substitution can be a conserved amino acid substitution or a non-conserved amino acid substitution. Illustrative examples for conserved amino acid exchanges are amino acid substitutions that maintain structural and/or functional properties of the amino acids' side-chains, e.g., an aromatic amino acid is substituted for another aromatic amino acid, an acidic amino acid is substituted for another acidic amino acid, a basic amino acid is substituted for another basic amino acid, and an aliphatic amino acid is substituted for another aliphatic amino acid. In contrast, examples of non-conserved amino acid exchanges are amino acid substitutions that do not maintain structural and/or functional properties of the amino acids' side-chains, e.g., an aromatic amino acid is substituted for a basic, acidic, or aliphatic amino acid, an acidic amino acid is substituted for an aromatic, basic, or aliphatic amino acid, a basic amino acid is substituted for an acidic, aromatic or aliphatic amino acid, and an aliphatic amino acid is substituted for an aromatic, acidic or basic amino acid. In even more specific embodiments Phe at amino acid position 456 is replaced by a Leu.

In certain embodiments, one nucleic acid is substituted to encode one amino acid exchange. In other embodiments, two or three nucleic acids are substituted to encode one amino acid exchange. It is preferred that two or three nucleic acids are substituted to reduce the risk of reversion to the wild type protein sequence.

In other embodiments, small single amino acid deletions are introduced in genes involved in virus assembly to generate an attenuated virus. In more specific embodiments, a small single amino acid deletion is introduced in the M gene or the M2 gene. In a preferred embodiment, the M gene is mutated.

In even other embodiments, the gene order in the genome of the virus is changed from the gene order of the wild type virus to generate an attenuated virus. In a more specific embodiment, the F, SH, and/or the G gene is moved to the 3' end of the viral genome. In another embodiment, the N gene is moved to the 5' end of the viral genome.

In other embodiments, one or more gene start sites (for locations of gene start sites see, e.g., Table 8) are mutated or substituted with the analogous gene start sites of another virus (e.g., RSV, PIV3, APV or mouse *pneumovirus*) or of a human *metapneumovirus* of a subgroup or a variant different from the human *metapneumovirus* from which the protein-encoding parts of the recombinant virus are derived. In more specific embodiments, the gene start site of the N-gene, the P-gene, the M-gene, the F-gene, the M2-gene, the SH-gene, the G-gene and/or the L-gene is mutated or replaced with the start site of the N-gene, the P-gene, the M-gene, the F-gene, the M2-gene, the SH-gene, the G-gene and/or the L-gene, respectively, of another virus (e.g., RSV, PIV3, APV or mouse *pneumovirus*) or of a human *metapneumovirus* of a subgroup or a variant different from the human *metapneumovirus* from which the protein-encoding parts of the recombinant virus are derived.

5.7.1 Attenuation by Substitution of Viral Genes

In certain embodiments of the invention, attenuation is achieved by replacing one or more of the genes of a virus with the analogous gene of a different virus, different strain, or different viral isolate. In certain embodiments, one or more of the genes of a *metapneumovirus*, such as a mammalian *metapneumovirus*, e.g., hMPV, or APV, is replaced with the analogous gene(s) of another *paramyxovirus*. In a more specific embodiment, the N-gene, the P-gene, the M-gene, the F-gene, the M2-gene, the M2-1 ORF, the M2-2 ORF, the SH-gene, the G-gene or the L-gene or any combination of two or more of these genes of a mammalian *metapneumovirus*, e.g., hMPV, is replaced with the analogous gene of another viral species, strain or isolate, wherein the other viral species can be, but is not limited to, another mammalian *metapneumovirus*, APV, or RSV.

In more specific embodiments, one or more of the genes of human *metapneumovirus* are replaced with the analogous gene(s) of another isolate of human *metapneumovirus*. E.g., the N-gene, the P-gene, the M-gene, the F-gene, the M2-gene, the M2-1 ORF, the M2-2 ORF, the SH-gene, the G-gene or the L-gene or any combination of two or more of these genes of isolate NL/1/99 (99-1), NL/1/00 (00-1), NL/17/00, or NL/1/94 is replaced with the analogous gene or combination of genes, i.e., the N-gene, the P-gene, the M-gene, the F-gene, the M2-gene, the M2-1 ORF, the M2-2 ORF, the SH-gene, the G-gene or the L-gene, of a different isolate, e.g., NL/1/99 (99-1), NL/1/00 (00-1), NL/17/00, or NL/1/94.

In certain embodiments, one or more regions of the genome of a virus is/are replaced with the analogous region(s) from the genome of a different viral species, strain or isolate. In certain embodiments, the region is a region in a coding region of the viral genome. In other embodiments, the region is a region in a non-coding region of the viral genome. In certain embodiments, two regions of two viruses are analogous to each other if the two regions support the same or a similar function in the two viruses. In certain other embodiments, two regions of two viruses are analogous if the two regions provide the same of a similar structural element in the two viruses. In more specific embodiments, two regions are analogous if they encode analogous protein domains in the two viruses, wherein analogous protein domains are domains that have the same or a similar function and/or structure.

In certain embodiments, one or more of regions of a genome of a *metapneumovirus*, such as a mammalian *metapneumovirus*, e.g., hMPV, or APV, is/are replaced with the analogous region(s) of the genome of another *paramyxovirus*. In certain embodiments, one or more of regions of the genome of a *paramyxovirus* is/are replaced with the analogous region(s) of the genome of a mammalian *metapneumovirus*, e.g., hMPV, or APV. In more specific embodiments, a region of the N-gene, the P-gene, the M-gene, the F-gene, the M2-gene, the M2-1 ORF, the M2-2 ORF, the SH-gene, the G-gene or the L-gene or any combination of two or more regions of these genes of a mammalian *metapneumovirus*, e.g., hMPV, is replaced with the analogous region of another viral species, strain or isolate. Another viral species can be, but is not limited to, another mammalian *metapneumovirus*, APV, or RSV.

In more specific embodiments, one or more regions of human *metapneumovirus* are replaced with the analogous region(s) of another isolate of human *metapneumovirus*. E.g., one or more region(s) of the N-gene, the P-gene, the M-gene, the F-gene, the M2-gene, the M2-1 ORF, the M2-2 ORF, the SH-gene, the G-gene or the L-gene or any combination of two or more regions of isolate NL/1/99 (99-1), NL/1/00 (00-1), NL/17/00, or NL/1/94 is replaced with the analogous region(s) of a different isolate of hMPV, e.g., NL/1/99 (99-1), NL/1/00 (00-1), NL/17/00, or NL/1/94.

In certain embodiments, the region is at least 5 nucleotides (nt) in length, at least 10 nt, at least 25 nt, at least 50 nt, at least 75 nt, at least 100 nt, at least 250 nt, at least 500 nt, at least 750 nt, at least 1 kb, at least 1.5 kb, at least 2 kb, at least 2.5 kb, at least 3 kb, at least 4 kb, or at least 5 kb in length. In certain embodiments, the region is at most 5 nucleotides (nt) in length, at most 10 nt, at most 25 nt, at most 50 nt, at most 75 nt, at most 100 nt, at most 250 nt, at most 500 nt, at most 750 nt, at most I kb, at most 1.5 kb, at most 2 kb, at most 2.5 kb, at most 3 kb, at most 4 kb, or at most 5 kb in length.

5.8 Assays for Use With the Invention

A number of assays may be employed in accordance with the present invention in order to determine the rate of growth of a chimeric or recombinant virus in a cell culture system, an animal model system or in a subject. A number of assays may also be employed in accordance with the present invention in order to determine the requirements of the chimeric and recombinant viruses to achieve infection, replication and packaging of virions.

The assays described herein may be used to assay viral titre over time to determine the growth characteristics of the virus. In a specific embodiment, the viral titre is determined by obtaining a sample from the infected cells or the infected subject, preparing a serial dilution of the sample and infecting a monolayer of cells that are susceptible to infection with the virus at a dilution of the virus that allows for the emergence of single plaques. The plaques can then be counted and the viral titre express as plaque forming units per milliliter of sample. In a specific embodiment of the invention, the growth rate of a virus of the invention in a subject is estimated by the titer of antibodies against the virus in the subject. Without being bound by theory, the antibody titer in the subject reflects not only the viral titer in the subject but also the antigenicity. If the antigenicity of the virus is constant, the increase of the antibody titer in the subject can be used to determine the growth curve of the virus in the subject. In a preferred embodiment, the growth rate of the virus in animals or humans is best tested by sampling biological fluids of a host at multiple time points post-infection and measuring viral titer.

The expression of heterologous gene sequence in a cell culture system or in a subject can be determined by any technique known to the skilled artisan. In certain embodiments, the expression of the heterologous gene is measured by quantifying the level of the transcript. The level of the transcript can be measured by Northern blot analysis or by RT-PCR using probes or primers, respectively, that are specific for the transcript. The transcript can be distinguished from the genome of the virus because the virus is in the antisense orientation whereas the transcript is in the sense orientation. In certain embodiments, the expression of the heterologous gene is measured by quantifying the level of the protein product of the heterologous gene. The level of the protein can be measured by Western blot analysis using antibodies that are specific to the protein.

In a specific embodiment, the heterologous gene is tagged with a peptide tag. The peptide tag can be detected using antibodies against the peptide tag. The level of peptide tag detected is representative for the level of protein expressed from the heterologous gene. Alternatively, the protein expressed from the heterologous gene can be isolated by virtue of the peptide tag. The amount of the purified protein correlates with the expression level of the heterologous gene. Such peptide tags and methods for the isolation of proteins fused to such a peptide tag are well known in the art. A variety of peptide tags known in the art may be used in the modification of the heterologous gene, such as, but not limited to, the immunoglobulin constant regions, polyhistidine sequence (Petty, 1996, Metal-chelate affinity chromatography, in Current Protocols in Molecular Biology, volume 1-3 (1994-1998). Ed. by Ausubel, F. M., Brent, R., Kunston, R. E., Moore, D. D., Seidman, J. G., Smith, J. A. and Struhl, K. Published by John Wiley and sons, Inc., USA, Greene Publish. Assoc. & Wiley Interscience), glutathione S-transferase (GST; Smith, 1993, Methods Mol. Cell Bio. 4:220-229), the *E. coli* maltose binding protein (Guan et al., 1987, Gene 67:21-30), various cellulose binding domains (U.S. Pat. Nos. 5,496,934; 5,202,247; 5,137,819; Tomme et al., 1994, Protein Eng. 7:117-123), and the FLAG epitope (Short Protocols in Molecular Biology, 1999, Ed. Ausubel et al., John Wiley & Sons, Inc., Unit 10.11) etc. Other peptide tags are recognized by specific binding partners and thus facilitate isolation by affinity binding to the binding partner, which is preferably immobilized and/or on a solid support. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

Samples from a subject can be obtained by any method known to the skilled artisan. In certain embodiments, the sample consists of nasal aspirate, throat swab, sputum or broncho-alveolar lavage.

5.8.1 Minireplicon Constructs

The production of live virus from cDNA provides a means for characterizing hMPV and also for producing attenuated vaccine strains and immunogenic compounds. In order to accomplish this goal, cDNA or minireplicon constructs that encode vRNAs containing a reporter gene can be used to rescue virus and also to identify the nucleotide sequences and proteins involved in amplification, expression, and incorporation of RNAs into virions. Any reporter gene known to the skilled artisan can be used with the invention (see section 5.8.2). For example, reporter genes that can be used include, but are not limited to, genes that encode GFP, HRP, LUC, and AP. (Also see section 5.8.2 for a more extensive list of examples of reporters) In one specific embodiment, the reporter gene that is used encodes CAT. In another specific embodiment of the invention, the reporter gene is flanked by leader and trailer sequences. The leader and trailer sequences that can be used to flank the reporter genes are those of any negative-sense virus, including, but not limited to, MPV, RSV, and APV. For example, the reporter gene can be flanked by the negative-sense hMPV or APV leader linked to the hepatitis delta ribozyme (Hep-d Ribo) and T7 polymerase termination (T-T7) signals, and the hMPV or APV trailer sequence preceded by the T7 RNA polymerase promoter.

In certain embodiments, the plasmid encoding the minireplicon is transfected into a host cell. In a more specific embodiment of the invention, hMPV is rescued in a host cell expressing T7 RNA polymerase, the N gene, the P gene, the L gene, and the M2.1 gene. In certain embodiments, the host cell is transfected with plasmids encoding T7 RNA polymerase, the N gene, the P gene, the L gene, and the M2.1 gene. In other embodiments, the plasmid encoding the minireplicon is transfected into a host cell and the host cell is infected with a helper virus.

The hMPV minireplicon can be rescued using a number of polymerases, including, but not limited to, interspecies and intraspecies polymerases. In a certain embodiment, the hMPV minireplicon is rescued in a host cell expressing the minimal replication unit necessary for hMPV replication. For example, hMPV can be rescued from a cDNA using a number of polymerases, including, but not limited to, the polymerase of RSV, APV, MPV, or PIV. In a specific embodiment of the invention, hMPV is rescued using the polymerase of an RNA virus. In a more specific embodiment of the invention, hMPV is rescued using the polymerase of a negative stranded RNA virus. In an even more specific embodiment of the invention, hMPV is rescued using RSV polymerase. In another embodiment of the invention, hMPV is rescued using APV polymerase. In yet another embodiment of the invention, hMPV is rescued using an MPV polymerase. In another embodiment of the invention, hMPV is rescued using PIV polymerase.

In another embodiment of the invention, hMPV is rescued from a cDNA using a complex of hMPV polymerase proteins. For example, the hMPV minireplicon can be rescued using a polymerase complex consisting of the L, P, N, and M2-1 proteins. In another embodiment of the invention, the polymerase complex consists of the L, P, and N proteins. In yet another embodiment of the invention, the hMPV minireplicon can be rescued using a polymerase complex consisting of polymerase proteins from other viruses, such as, but not limited to, RSV, PIV, and APV. In particular, the hMPV minireplicon can be rescued using a polymerase complex consisting of the L, P, N, and M2-1 proteins of RSV, PIV, or APV. In yet another embodiment of the invention, the polymerase complex used to rescue the hMPV minireplicon consists of the L, P, and N proteins of RSV, PIV, or APV. In even another embodiment of the invention, different polymerase proteins from various viruses can be used to form the polymerase complex. In such an embodiment, the polymerase used to rescue the hMPV minireplicon can be formed by different components of the RSV, PIV, or APV polymerases. By way of example, and not meant to limit the possible combination, in forming a complex, the N protein can be encoded by the N gene of RSV, APV, or PIV, while the L protein is encoded by the L gene of RSV, APV, or PIV, and P protein can be encoded by the P gene of RSV, APV, or PIV. One skilled in the art would be able to determine the possible combinations that may be used to form the polymerase complex necessary to rescue the hMPV minireplicon. In the minireplicon system, the expression of a reporter gene is measured in order to confirm the successful rescue of the virus and also to characterize the virus. The expression level of the reporter gene and/or its activity can be assayed by any method known to the skilled artisan, such as, but not limited to, the methods described in section 5.8.2.

In certain, more specific, embodiments, the minireplicon comprises the following elements, in the order listed: T7 RNA Polymerase or RNA polymerase I, leader sequence, gene start, GFP, trailer sequence, Hepatitis delta ribozyme sequence or RNA polymerase I termination sequence. If T7 is used as RNA polymerase, Hepatitis delta ribozyme sequence should be used as termination sequence. If RNA polymerase I is used, RNA polymerase I termination sequence may be used as a termination signal. Dependent on the rescue system, the sequence of the minireplicon can be in the sense or antisense orientation. In certain embodiments, the leader sequence can be modified relative to the wild type leader sequence of hMPV. The leader sequence can optionally be preceded by an AC. The T7 promoter sequence can be with or without a G-doublet or triplet, where the G-doublet or triplet provides for increased transcription.

In a specific embodiment, a cell is infected with hMPV at T0.24 hours later, at T24, the cell is transfected with a minireplicon construct. 48 hours after T0 and 72 hours after T0, the cells are tested for the expression of the reporter gene. If a fluorescent reporter gene product is used (e.g., GFP), the expression of the reporter gene can be tested using FACS.

In another embodiment, a cell is transfected with six plasmids at T=0 hours. Cells are then harvested at T=40 hours and T=60 hours and analyzed for CAT or GFP expression. (See FIG. 25.)

In another specific embodiment, a cell is infected with MVA-T7 at T0.1 hour later, at T1, the cell is transfected with a minireplicon construct. 24 hours after T0, the cell is infected with hMPV. 72 hours after T0, the cells are tested for the expression of the reporter gene. If a fluorescent reporter gene product is used (e.g., GFP), the expression of the reporter gene can be tested using FACS.

5.8.2 Reporter Genes

In certain embodiments, assays for measurement of reporter gene expression in tissue culture or in animal models can be used with the methods of the invention. The nucleotide sequence of the reporter gene is cloned into the virus, such as APV, hMPV, hMPV/APV or APV/hMPV, wherein (i) the position of the reporter gene is changed and (ii) the length of the intergenic regions flanking the reporter gene are varied. Different combinations are tested to determine the optimal rate of expression of the reporter gene and the optimal replication rate of the virus comprising the reporter gene.

In certain embodiments, minireplicon constructs are generated to include a reporter gene. The construction of minireplicon constructs is described herein.

The abundance of the reporter gene product can be determined by any technique known to the skilled artisan. Such techniques include, but are not limited to, Northern blot analysis or Western blot analysis using probes or antibodies, respectively, that are specific to the reporter gene.

In certain embodiments, the reporter gene emits a fluorescent signal that can be detected in a FACS. FACS can be used to detect cells in which the reporter gene is expressed.

Techniques for practicing the specific aspect of this invention will employ, unless otherwise indicated, conventional techniques of molecular biology, microbiology, and recombinant DNA manipulation and production, which are routinely practiced by one of skill in the art. See, e.g., Sambrook et al., Molecular cloning, a laboratory manual, second ed., vol. 1-3. (Cold Spring Harbor Laboratory, 1989), A Laboratory Manual, Second Edition; DNA Cloning, Volumes I and II (Glover, Ed. 1985); and Transcription and Translation (Hames & Higgins, Eds. 1984).

The biochemical activity of the reporter gene product represents the expression level of the reporter gene. The total level of reporter gene activity depends also on the replication rate of the recombinant virus of the invention. Thus, to determine the true expression level of the reporter gene from the recombinant virus, the total expression level should be divided by the titer of the recombinant virus in the cell culture or the animal model.

Reporter genes that can be used with the methods of invention include, but are not limited to, the genes listed in the Table 4 below:

TABLE 4

Reporter genes and the biochemical properties of the respective reporter gene products

| Reporter Gene | Protein Activity & Measurement |
|---|---|
| CAT (chloramphenicol acetyltransferase) | Transfers radioactive acetyl groups to chloramphenicol or detection by thin layer chromatography and autoradiography |
| GAL (b-galactosidase) | Hydrolyzes colorless galactosides to yield colored products. |
| GUS (b-glucuronidase) | Hydrolyzes colorless glucuronides to yield colored products. |
| LUC (luciferase) | Oxidizes luciferin, emitting photons |
| GFP (green fluorescent protein) | fluorescent protein without substrate |
| SEAP (secreted alkaline phosphatase) | luminescence reaction with suitable substrates or with substrates that generate chromophores |
| HRP (horseradish peroxidase) | in the presence of hydrogen oxide, oxidation of 3,3',5,5'-tetramethylbenzidine to form a colored complex |
| AP (alkaline phosphatase) | luminescence reaction with suitable substrates or with substrates that generate chromophores |

The abundance of the reporter gene can be measured by, inter alia, Western blot analysis or Northern blot analysis or any other technique used for the quantification of transcription of a nucleotide sequence, the abundance of its mRNA its protein (see Short Protocols in Molecular Biology, Ausubel et al., (editors), John Wiley & Sons, Inc., $4^{th}$ edition, 1999). In certain embodiments, the activity of the reporter gene product is measured as a readout of reporter gene expression from the recombinant virus. For the quantification of the activity of the reporter gene product, biochemical characteristics of the reporter gene product can be employed (see Table 4). The methods for measuring the biochemical activity of the reporter gene products are well-known to the skilled artisan. A more detailed description of illustrative reporter genes that can be used with the methods of the invention is set forth below.

5.8.3 Measurement of Incidence of Infection Rate

The incidence of infection can be determined by any method well-known in the art, for example, but not limited to, clinical samples (e.g., nasal swabs) can be tested for the presence of a virus of the invention by immunofluorescence assay (IFA) using an anti-APV-antigen antibody, an anti-hMPV-antigen antibody, an anti-APV-antigen antibody, and/or an antibody that is specific to the gene product of the heterologous nucleotide sequence, respectively.

In certain embodiments, samples containing intact cells can be directly processed, whereas isolates without intact cells should first be cultured on a permissive cell line (e.g. HEp-2 cells). In an illustrative embodiments, cultured cell suspensions should be cleared by centrifugation at, e.g., 300×g for 5 minutes at room temperature, followed by a PBS, pH 7.4 (Ca++ and Mg++ free) wash under the same conditions. Cell pellets are resuspended in a small volume of PBS for analysis. Primary clinical isolates containing intact cells are mixed with PBS and centrifuged at 300×g for 5 minutes at room temperature. Mucus is removed from the interface with a sterile pipette tip and cell pellets are washed once more with PBS under the same conditions. Pellets are then resuspended in a small volume of PBS for analysis. Five to ten microliters of each cell suspension are spotted per 5 mm well on acetone washed 12-well HTC supercured glass slides and allowed to air dry. Slides are fixed in cold (−20° C.) acetone for 10 minutes. Reactions are blocked by adding PBS-1% BSA to each well followed by a 10 minute incubation at room temperature. Slides are washed three times in PBS-0.1% Tween-20 and air dried. Ten microliters of each primary antibody reagent diluted to 250 ng/ml in blocking buffer is spotted per well and reactions are incubated in a humidified 37° C. environment for 30 minutes. Slides are then washed extensively in three changes of PBS-0.1% Tween-20 and air dried. Ten microliters of appropriate secondary conjugated antibody reagent diluted to 250 ng/ml in blocking buffer are spotted per respective well and reactions are incubated in a humidified 37° C. environment for an additional 30 minutes. Slides are then washed in three changes of PBS-0.1% Tween-20. Five microliters of PBS-50% glycerol-10 mM Tris pH 8.0-1 mM EDTA are spotted per reaction well, and slides are mounted with cover slips. Each reaction well is subsequently analyzed by fluorescence microscopy at 200× power using a B-2A filter (EX 450-490 nm). Positive reactions are scored against an autofluorescent background obtained from unstained cells or cells stained with secondary reagent alone. Positive reactions are characterized by bright fluorescence punctuated with small inclusions in the cytoplasm of infected cells.

5.8.4 Measurement of Serum Titer

Antibody serum titer can be determined by any method well-known in the art, for example, but not limited to, the amount of antibody or antibody fragment in serum samples can be quantitated by a sandwich ELISA. Briefly, the ELISA consists of coating microtiter plates overnight at 4° C. with an antibody that recognizes the antibody or antibody fragment in the serum. The plates are then blocked for approximately 30 minutes at room temperature with PBS-Tween-0.5% BSA. Standard curves are constructed using purified antibody or antibody fragment diluted in PBS-TWEEN-BSA, and samples are diluted in PBS-BSA. The samples and standards are added to duplicate wells of the assay plate and are incubated for approximately 1 hour at room temperature. Next, the non-bound antibody is washed away with PBS-TWEEN and the bound antibody is treated with a labeled secondary antibody (e.g., horseradish peroxidase conjugated goat-anti-human IgG) for approximately 1 hour at room temperature. Binding of the labeled antibody is detected by adding a chromogenic substrate specific for the label and measuring the rate of substrate turnover, e.g., by a spectrophotometer. The concentration of antibody or antibody fragment levels in the serum is determined by comparison of the rate of substrate turnover for the samples to the rate of substrate turnover for the standard curve at a certain dilution.

5.8.5 Serological Tests

In certain embodiments of the invention, the presence of antibodies that bind to a component of a mammalian MPV is detected. In particular the presence of antibodies directed to a protein of a mammalian MPV can be detected in a subject to diagnose the presence of a mammalian MPV in the subject. Any method known to the skilled artisan can be used to detect the presence of antibodies directed to a component of a mammalian MPV.

In another embodiment, serological tests can be conducted by contacting a sample, from a host suspected of being infected with MPV, with an antibody to an MPV or a component thereof, and detecting the formation of a complex. In such an embodiment, the serological test can detect the presence of a host antibody response to MPV exposure. The antibody that can be used in the assay of the invention to detect host antibodies or MPV components can be produced using any method known in the art. Such antibodies can be engineered to detect a variety of epitopes, including, but not limited to, nucleic acids, amino acids, sugars, polynucleotides, proteins, carbohydrates, or combinations thereof. In another embodiment of the invention, serological tests can be conducted by contacting a sample from a host suspected of being infected with MPV, with an a component of MPV, and detecting the formation of a complex. Examples of such methods are well known in the art, including but are not limited to, direct immunofluorescence, ELISA, western blot, immunochromatography.

In an illustrative embodiment, components of mammalian MPV are linked to a solid support. In a specific embodiment, the component of the mammalian MPV can be, but is not limited to, the F protein or the G protein. Subsequently, the material that is to be tested for the presence of antibodies directed to mammalian MPV is incubated with the solid support under conditions conducive to the binding of the antibodies to the mammalian MPV components. Subsequently, the solid support is washed under conditions that remove any unspecifically bound antibodies. Following the washing step, the presence of bound antibodies can be detected using any technique known to the skilled artisan. In a specific embodiment, the mammalian MPV protein-antibody complex is incubated with detectably labeled antibody that recognizes antibodies that were generated by the species of the subject, e.g., if the subject is a cotton rat, the detectably labeled antibody is directed to rat antibodies, under conditions conducive to the binding of the detectably labeled antibody to the antibody that is bound to the component of mammalian MPV. In a specific embodiment, the detectably labeled antibody is conjugated to an enzymatic activity. In another embodiment, the detectably labeled antibody is radioactively labeled. The complex of mammalian MPV protein-antibody-detectably labeled antibody is then washed, and subsequently the presence of the detectably labeled antibody is quantified by any technique known to the skilled artisan, wherein the technique used is dependent on the type of label of the detectably labeled antibody.

5.8.6 BIAcore Assay

Determination of the kinetic parameters of antibody binding can be determined for example by the injection of 250 μL of monoclonal antibody ("mAb") at varying concentration in HBS buffer containing 0.05% Tween-20 over a sensor chip surface, onto which has been immobilized the antigen. The antigen can be any component of a mammalian MPV. In a specific embodiment, the antigen can be, but is not limited to, the F protein or the G protein of a mammalian MPV. The flow rate is maintained constant at 75uL/min. Dissociation data is collected for 15 min, or longer as necessary. Following each injection/dissociation cycle, the bound mAb is removed from the antigen surface using brief, 1 min pulses of dilute acid, typically 10-100 mM HCl, though other regenerates are employed as the circumstances warrant.

More specifically, for measurement of the rates of association, $k_{on}$, and dissociation, $k_{off}$, the antigen is directly immobilized onto the sensor chip surface through the use of standard amine coupling chemistries, namely the EDC/NHS method (EDC=N-diethylaminopropyl)-carbodiimide). Briefly, a 5-100 nM solution of the antigen in 10 mM NaOAc, pH 4 or pH 5 is prepared and passed over the EDC/NHS-activated surface until approximately 30-50 RU's (Biacore Resonance Unit) worth of antigen are immobilized. Following this, the unreacted active esters are "capped" off with an injection of 1M Et-NH2. A blank surface, containing no antigen, is prepared under identical immobilization conditions for reference purposes. Once a suitable surface has been prepared, an appropriate dilution series of each one of the antibody reagents is prepared in HBS/Tween-20, and passed over both the antigen and reference cell surfaces, which are connected in series. The range of antibody concentrations that are prepared varies depending on what the equilibrium binding constant, $K_D$, is estimated to be. As described above, the bound antibody is removed after each injection/dissociation cycle using an appropriate regenerant.

Once an entire data set is collected, the resulting binding curves are globally fitted using algorithms supplied by the instrument manufacturer, BIAcore, Inc. (Piscataway, N.J.). All data are fitted to a 1:1 Langmuir binding model. These algorithm calculate both the $k_{on}$ and the $k_{off}$, from which the apparent equilibrium binding constant, $K_D$, is deduced as the ratio of the two rate constants (i.e. $k_{off}/k_{on}$). More detailed treatments of how the individual rate constants are derived can be found in the BIAevaluation Software Handbook (BIAcore, Inc., Piscataway, N.J.).

5.8.7 Microneutralization Assay

The ability of antibodies or antigen-binding fragments thereof to neutralize virus infectivity is determined by a microneutralization assay. This microneutralization assay is a modification of the procedures described by Anderson et al., (1985, J. Clin. Microbiol. 22:1050-1052, the disclosure of which is hereby incorporated by reference in its entirety). The procedure is also described in Johnson et al., 1999, J. Infectious Diseases 180:35-40, the disclosure of which is hereby incorporated by reference in its entirety.

Antibody dilutions are made in triplicate using a 96-well plate. $10^6$ $TCID_{50}$ of a mammalian MPV are incubated with serial dilutions of the antibody or antigen-binding fragments thereof to be tested for 2 hours at 37_C in the wells of a 96-well plate. Cells susceptible to infection with a mammalian MPV, such as, but not limited to Vero cells ($2.5\times10^4$) are then added to each well and cultured for 5 days at 37_C in 5% $CO_2$. After 5 days, the medium is aspirated and cells are washed and fixed to the plates with 80% methanol and 20% PBS. Virus replication is then determined by viral antigen, such as F protein expression. Fixed cells are incubated with a biotin-conjugated anti-viral antigen, such as anti-F protein monoclonal antibody (e.g., pan F protein, C-site-specific MAb 133-1H) washed and horseradish peroxidase conjugated avidin is added to the wells. The wells are washed again and turnover of substrate TMB (thionitrobenzoic acid) is measured at 450 nm. The neutralizing titer is expressed as the antibody concentration that causes at least 50% reduction in absorbency at 450 nm (the $OD_{450}$) from virus-only control cells.

The microneutralization assay described here is only one example. Alternatively, standard neutralization assays can be used to determine how significantly the virus is affected by an antibody.

5.8.8 Viral Fusion Inhibition Assay

This assay is in principle identical to the microneutralization assay, except that the cells are infected with the respective virus for four hours prior to addition of antibody and the read-out is in terms of presence of absence of fusion of cells (Taylor et al., 1992, J. Gen. Virol. 73:2217-2223).

5.8.9 Isothermal Titration Calorimetry

Thermodynamic binding affinities and enthalpies are determined from isothermal titration calorimetry (ITC) measurements on the interaction of antibodies with their respective antigen.

Antibodies are diluted in dialysate and the concentrations were determined by UV spectroscopic absorption measurements with a Perkin-Elmer Lambda 4B Spectrophotometer using an extinction coefficient of 217,000 $M^{-1}$ $cm^{-1}$ at the peak maximum at 280 nm. The diluted mammalian MPV-antigen concentrations are calculated from the ratio of the mass of the original sample to that of the diluted sample since its extinction coefficient is too low to determine an accurate concentration without employing and losing a large amount of sample.

ITC Measurements

The binding thermodynamics of the antibodies are determined from ITC measurements using a Microcal, Inc. VP Titration Calorimeter. The VP titration calorimeter consists of a matched pair of sample and reference vessels (1.409 ml) enclosed in an adiabatic enclosure and a rotating stirrer-syringe for titrating ligand solutions into the sample vessel. The ITC measurements are performed at 25° C. and 35° C. The sample vessel contained the antibody in the phosphate buffer while the reference vessel contains just the buffer solution. The phosphate buffer solution is saline 67 mM $PO_4$ at pH 7.4 from HyClone, Inc. Five or ten μl aliquots of the 0.05 to 0.1 mM RSV-antigen, PIV-antigen, and/or hMPV-antigen solution are titrated 3 to 4 minutes apart into the antibody sample solution until the binding is saturated as evident by the lack of a heat exchange signal.

A non-linear, least square minimization software program from Microcal, Inc., Origin 5.0, is used to fit the incremental heat of the i-th titration (ΔQ (i)) of the total heat, $Q_t$, to the total titrant concentration, $X_t$, according to the following equations (I), $$Q_t=nC_t\Delta H_{b^\circ}V\{1+X_t/nC_t+1/nK_bC_t-[(1+X_t/nC_t+1/nK_bC_t)^2-4X_t/nC_t]^{1/2}\}/2 \quad (1a)$$

$$\Delta Q(i)=Q(i)+dVi/2V\{Q(i)+Q(i-1)\}-Q(i-1) \quad (1b)$$

where $C_t$ is the initial antibody concentration in the sample vessel, V is the volume of the sample vessel, and n is the stoichiometry of the binding reaction, to yield values of $K_b$, $\Delta H_{b^\circ}$, and n. The optimum range of sample concentrations for the determination of $K_b$ depends on the value of $K_b$ and is defined by the following relationship.

$$C_tK_bn\leqq 500 \quad (2)$$

so that at 1 μM the maximum $K_b$ that can be determined is less than $2.5\times10^8$ $M^{-1}$. If the first titrant addition does not fit the binding isotherm, it was neglected in the final analysis since it may reflect release of an air bubble at the syringe opening-solution interface.

5.8.10 Immunoassays

Immunoprecipitation protocols generally comprise lysing a population of cells in a lysis buffer such as RIPA buffer (I % NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, 159 aprotinin, sodium vanadate), adding the antibody of interest to the cell lysate, incubating for a period of time (e.g., to 4 hours) at 4 degrees C., adding protein A and/or protein G sepharose beads to the cell lysate, incubating for about an hour or more at 4 degrees C., washing the beads in lysis buffer and re-suspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds., 1994, Current Protocols in Molecular Biology, Vol. 1, John Wiley & Sons, Inc., New York at pages 10, 16, 1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide get to a membrane such as nitrocellulose, PVDF or nylon, blocking the membrane, in blocking solution (e.g., PBS with 3% BSA or non-fat milk), washing the membrane in washing buffer (e.g., PBSTween20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{12}P$ or $^{121}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, GinTent Protocols in Molecular Biology, Vol. 1, John Wiley & Sons, Inc., New York at 10.8.1.

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). The parameters that can be modified to increase signal detection and other variations of ELISAs are well known to one of skill in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including a scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., $^{3}H$ or $^{121}I$) with the antibody of interest in the presence of increasing amounts of unlabeled antigen, and the detection of the antibody bound to the labeled antigen.

5.8.11 Sucrose Gradient Assay

The question of whether the heterologous proteins are incorporated into the virion can be further investigated by use of any biochemical assay known to the skilled artisan. In a specific embodiment, a sucrose gradient assay is used to determine whether a heterologous protein is incorporated into the virion.

Infected cell lysates can be fractionated in 20-60% sucrose gradients, various fractions are collected and analyzed for the presence and distribution of heterologous proteins and the vector proteins by, e.g., Western blot analysis. The fractions and the virus proteins can also be assayed for peak virus titers by plaque assay. If the heterologous protein co-migrates with the virion the heterologous protein is associated with the virion.

5.9 Methods to Identify New Isolates of MPV

The present invention relates to mammalian MPV, in particular hMPV. While the present invention provides the characterization of two serological subgroups of MPV, A and B, and the characterization of four variants of MPV A1, A2, B1 and B2, the invention is not limited to these subgroups and variants. The invention encompasses any yet to be identified isolates of MPV, including those which are characterized as belonging to the subgroups and variants described herein, or belonging to a yet to be characterized subgroup or variant.

Immunoassays can be used in order to characterize the protein components that are present in a given sample. Immunoassays are an effective way to compare viral isolates using peptides components of the viruses for identification. For example, the invention provides herein a method to identify further isolates of MPV as provided herein, the method comprising inoculating an essentially MPV-uninfected or specific-pathogen-free guinea pig or ferret (in the detailed description the animal is inoculated intranasally but other was of inoculation such as intramuscular or intradermal inoculation, and using an other experimental animal, is also feasible) with the prototype isolate I-2614 or related isolates. Sera are collected from the animal at day zero, two weeks and three weeks post inoculation. The animal specifically seroconverted as measured in virus neutralization (VN) assay (For an example of a VN assay, see Example 16) and indirect IFA (For an example of IFA, see Example 11 or 14) against the respective isolate I-2614 and the sera from the seroconverted animal are used in the immunological detection of said further isolates. As an example, the invention provides the characterization of a new member in the family of Paramyxoviridae, a human *metapneumovirus* or *metapneumovirus*-like virus (since its final taxonomy awaits discussion by a viral taxonomy committee the MPV is herein for example described as taxonomically corresponding to APV) (MPV) which may cause severe RTI in humans. The clinical signs of the disease caused by MPV are essentially similar to those caused by hRSV, such as cough, myalgia, vomiting, fever broncheolitis or pneumonia, possible conjunctivitis, or combinations thereof. As is seen with hRSV infected children, specifically very young children may require hospitalization. As an example an MPV which was deposited Jan. 19, 2001 as I-2614 with CNCM, Institute Pasteur, Paris or a virus isolate phylogenetically corresponding therewith is herewith provided. Therewith, the invention provides a virus comprising a nucleic acid or functional fragment phylogenetically corresponding to a nucleic acid sequence of SEQ. ID NO:19, or structurally corresponding therewith. In particular the invention provides a virus characterized in that after testing it in phylogenetic tree analysis wherein maximum likelihood trees are generated using 100 bootstraps and 3 jumbles it is found to be more closely phylogenetically corresponding to a virus isolate deposited as I-2614 with CNCM, Paris than it is related to a virus isolate of avian *pnuemovirus* (APV) also known as turkey rhinotracheitis virus (TRTV), the aetiological agent of avian rhinotracheitis. It is particularly useful to use an AVP-C virus isolate as outgroup in said phylogenetic tree analysis, it being the closest relative, albeit being an essentially non-mammalian virus.

5.9.1 Bioinformatics Alignment of Sequences

Two or more amino acid sequences can be compared by BLAST (Altschul, S. F. et al., 1990, J. Mol. Biol. 215:403-410) to determine their sequence homology and sequence identities to each other. Two or more nucleotide sequences can be compared by BLAST (Altschul, S. F. et al., 1990, J. Mol. Biol. 215:403-410) to determine their sequence homology and sequence identities to each other. BLAST comparisons can be performed using the Clustal W method (MacVector(tm)). In certain specific embodiments, the alignment of two or more sequences by a computer program can be followed by manual re-adjustment.

The determination of percent identity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide comparisons can be performed with the NBLAST program. BLAST amino acid sequence comparisons can be performed with the XBLAST program. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, 1988, CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table can be used. The gap length penalty can be set by the skilled artisan. The percent identity between two sequences can be determined using techniques similar to those described above, with or without allowing gaps. In calculating percent identity, typically only exact matches are counted.

5.9.2 Hybridization Conditions

A nucleic acid which is hybridizable to a nucleic acid of a mammalian MPV, or to its reverse complement, or to its complement can be used in the methods of the invention to determine their sequence homology and identities to each other. In certain embodiments, the nucleic acids are hybridized under conditions of high stringency. By way of example and not limitation, procedures using such conditions of high stringency are as follows. Prehybridization of filters containing DNA is carried out for 8 h to overnight at 65 C in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65 C in prehybridization mixture containing 100 μg/ml denatured salmon sperm DNA and 5-20×106 cpm of 32P-labeled probe. Washing of filters is done at 37 C for 1 h in a solution containing 2×SSC, 0.01% PVP, 0.01% Ficoll, and 0.01% BSA. This is followed by a wash in 0.1×SSC at 50 C for 45 min before autoradiography. Other conditions of high stringency which may be used are well known in the art. In other embodiments of the invention, hybridization is performed under moderate of low stringency conditions, such conditions are well-known to the skilled artisan (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols,© 1994-1997 John Wiley and Sons, Inc.).

5.9.3 Phylogenetic Analysis

This invention relates to the inference of phylogenetic relationships between isolates of mammalian MPV. Many methods or approaches are available to analyze phylogenetic relationship; these include distance, maximum likelihood, and maximum parsimony methods (Swofford, D L., et. al., Phylogenetic Inference. In Molecular Systematics. Eds. Hillis, D M, Mortiz, C, and Mable, B K. 1996. Sinauer Associates: Massachusetts, USA. pp. 407-514; Felsenstein, J., 1981, J. Mol. Evol. 17:368-376). In addition, bootstrapping techniques are an effective means of preparing and examining confidence intervals of resultant phylogenetic trees (Felsenstein, J., 1985, Evolution. 29:783-791). Any method or approach using nucleotide or peptide sequence information to compare mammalian MPV isolates can be used to establish phylogenetic relationships, including, but not limited to, distance, maximum likelihood, and maximum parsimony methods or approaches. Any method known in the art can be used to analyze the quality of phylogenetic data, including but not limited to bootstrapping. Alignment of nucleotide or peptide sequence data for use in phylogenetic approaches, include but are not limited to, manual alignment, computer pairwise alignment, and computer multiple alignment. One skilled in the art would be familiar with the preferable alignment method or phylogenetic approach to be used based upon the information required and the time allowed.

In one embodiment, a DNA maximum likehood method is used to infer relationships between hMPV isolates. In another embodiment, bootstrapping techniques are used to determine the certainty of phylogenetic data created using one of said phylogenetic approaches. In another embodiment, jumbling techniques are applied to the phylogenetic approach before the input of data in order to minimize the effect of sequence order entry on the phylogenetic analyses. In one specific embodiment, a DNA maximum likelihood method is used with bootstrapping. In another specific embodiment, a DNA maximum likelihood method is used with bootstrapping and jumbling. In another more specific embodiment, a DNA maximum likelihood method is used with 50 bootstraps. In another specific embodiment, a DNA maximum likelihood method is used with 50 bootstraps and 3 jumbles. In another specific embodiment, a DNA maximum likelihood method is used with 100 bootstraps and 3 jumbles.

In one embodiment, nucleic acid or peptide sequence information from an isolate of hMPV is compared or aligned with sequences of other hMPV isolates. The amino acid sequence can be the amino acid sequence of the L protein, the M protein, the N protein, the P protein, or the F protein. In another embodiment, nucleic acid or peptide sequence information from an hMPV isolate or a number of hMPV isolates is compared or aligned with sequences of other viruses. In another embodiment, phylogenetic approaches are applied to sequence alignment data so that phylogenetic relationships can be inferred and/or phylogenetic trees constructed. Any method or approach that uses nucleotide or peptide sequence information to compare hMPV isolates can be used to infer said phylogenetic relationships, including, but not limited to, distance, maximum likelihood, and maximum parsimony methods or approaches.

Other methods for the phylogenetic analysis are disclosed in International Patent Application PCT/NL02/00040, published as WO 02/057302, which is incorporated in its entirety herein. In particular, PCT/NL02/00040 discloses nucleic acid sequences that are suitable for phylogenetic analysis at page 12, line 27 to page 19, line 29, which is incorporated herein by reference.

For the phylogenetic analyses it is most useful to obtain the nucleic acid sequence of a non-MPV as outgroup with which the virus is to be compared, a very useful outgroup isolate can be obtained from avian *pneumovirus* serotype C (APV-C), see, e.g., FIG. 16.

Many methods and programs are known in the art and can be used in the inference of phylogenetic relationships, including, but not limited to BioEdit, ClustalW, TreeView, and NJPlot. Methods that would be used to align sequences and to generate phylogenetic trees or relationships would require the input of sequence information to be compared. Many methods or formats are known in the art and can be used to input sequence information, including, but not limited to, FASTA, NBRF, EMBL/SWISS, GDE protein, GDE nucleotide, CLUSTAL, and GCG/MSF. Methods that would be used to align sequences and to generate phylogenetic trees or relationships would require the output of results. Many methods or formats can be used in the output of information or results, including, but not limited to, CLUSTAL, NBRF/PIR, MSF, PHYLIP, and GDE. In one embodiment, ClustalW is used in conjunction with DNA maximum likelihood methods with 100 bootstraps and 3 jumbles in order to generate phylogenetic relationships.

5.10 Generation of Antibodies

The invention also relates to the generation of antibodies against a protein encoded by a mammalian MPV. In particular, the invention relates to the generation of antibodies against all MPV antigens, including the F protein, N protein, M2-1 protein, M2-2 protein, G protein, or P protein of a mammalian MPV. According to the invention, any protein encoded by a mammalian MPV, derivatives, analogs or fragments thereof, may be used as an immunogen to generate antibodies which immunospecifically bind such an immunogen. Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Examples of immunologically active portions of immunoglobulin molecules include F(ab) and F(ab')2 fragments which can be generated by treating the antibody with an enzyme such as pepsin or papain. In a specific embodiment, antibodies to a protein encoded by human MPV are produced. In another embodiment, antibodies to a domain a protein encoded by human MPV are produced.

Various procedures known in the art may be used for the production of polyclonal antibodies against a protein encoded by a mammalian MPV, derivatives, analogs or fragments thereof. For the production of antibody, various host animals can be immunized by injection with the native protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a protein encoded by a mammalian MPV, derivatives, analogs or fragments thereof, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for a protein encoded by a mammalian MPV, derivatives, analogs or fragments thereof together with genes from a human antibody molecule of appropriate biological activity can be used; such antibodies are within the scope of this invention.

According to the invention, techniques described for the production of single chain antibodies (U.S. Pat. No. 4,946,778) can be adapted to produce specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for a protein encoded by a mammalian MPV, derivatives, analogs or fragments thereof.

Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a protein encoded by a mammalian MPV, one may assay generated hybridomas for a product which binds to a fragment of a protein encoded by a mammalian MPV containing such domain.

The antibodies provided by the present invention can be used for detecting MPV and for therapeutic methods for the treatment of infections with MPV.

The specificity and binding affinities of the antibodies generated by the methods of the invention can be tested by any technique known to the skilled artisan. In certain embodiments, the specificity and binding affinities of the antibodies generated by the methods of the invention can be tested as described in sections 5.8.5, 5.8.6, 5.8.7, 5.8.8 or 5.8.9.

5.11 Screening Assays to Identify Antiviral Agents

The invention provides methods for the identification of a compound that inhibits the ability of a mammalian MPV to infect a host or a host cell. In certain embodiments, the invention provides methods for the identification of a compound that reduces the ability of a mammalian MPV to replicate in a host or a host cell. Any technique well-known to the skilled artisan can be used to screen for a compound that would abolish or reduce the ability of a mammalian MPV to infect a host and/or to replicate in a host or a host cell. In a specific embodiment, the mammalian MPV is a human MPV.

In certain embodiments, the invention provides methods for the identification of a compound that inhibits the ability of a mammalian MPV to replicate in a mammal or a mammalian cell. More specifically, the invention provides methods for the identification of a compound that inhibits the ability of a mammalian MPV to infect a mammal or a mammalian cell. In certain embodiments, the invention provides methods for the identification of a compound that inhibits the ability of a mammalian MPV to replicate in a mammalian cell. In a specific embodiment, the mammalian cell is a human cell. For a detailed description of assays that can be used to determine virus titer see section 5.7.

In certain embodiments, a cell is contacted with a test compound and infected with a mammalian MPV. In certain embodiments, a control culture is infected with a mammalian virus in the absence of a test compound. The cell can be contacted with a test compound before, concurrently with, or subsequent to the infection with the mammalian MPV. In a specific embodiment, the cell is a mammalian cell. In an even more specific embodiment, the cell is a human cell. In certain embodiments, the cell is incubated with the test compound for at least 1 minute, at least 5 minutes at least 15 minutes, at least 30 minutes, at least 1 hour, at least 2 hours, at least 5 hours, at least 12 hours, or at least 1 day. The titer of the virus can be measured at any time during the assay. In certain embodiments, a time course of viral growth in the culture is determined. If the viral growth is inhibited or reduced in the presence of the test compound, the test compound is identified as being effective in inhibiting or reducing the growth or infection of a mammalian MPV. In a specific embodiment, the compound that inhibits or reduces the growth of a mammalian MPV is tested for its ability to inhibit or reduce the growth rate of other viruses to test its specificity for mammalian MPV.

In certain embodiments, a test compound is administered to a model animal and the model animal is infected with a mammalian MPV. In certain embodiments, a control model animal is infected with a mammalian virus in without the administration of a test compound. The test compound can be administered before, concurrently with, or subsequent to the infection with the mammalian MPV. In a specific embodiment, the model animal is a mammal. In an even more specific embodiment, the model animal can be, but is not limited to, a cotton rat, a mouse, or a monkey. The titer of the virus in the model animal can be measured at any time during the assay. In certain embodiments, a time course of viral growth in the culture is determined. If the viral growth is inhibited or reduced in the presence of the test compound, the test compound is identified as being effective in inhibiting or reducing the growth or infection of a mammalian MPV. In a specific embodiment, the compound that inhibits or reduces the growth of a mammalian MPV in the model animal is tested for its ability to inhibit or reduce the growth rate of other viruses to test its specificity for mammalian MPV.

5.12 Formulations of Vaccines, Antibodies and Antivirals

In a preferred embodiment, the invention provides a proteinaceous molecule or *metapneumovirus*-specific viral protein or functional fragment thereof encoded by a nucleic acid according to the invention. Useful proteinaceous molecules are for example derived from any of the genes or genomic fragments derivable from a virus according to the invention. Such molecules, or antigenic fragments thereof, as provided herein, are for example useful in diagnostic methods or kits and in pharmaceutical compositions such as sub-unit vaccines. Particularly useful are the F, SH and/or G protein or antigenic fragments thereof for inclusion as antigen or subunit immunogen, but inactivated whole virus can also be used. Particularly useful are also those proteinaceous substances that are encoded by recombinant nucleic acid fragments that are identified for phylogenetic analyses, of course preferred are those that are within the preferred bounds and metes of ORFs useful in phylogenetic analyses, in particular for eliciting MPV specific antibody or T cell responses, whether in vivo (e.g. for protective purposes or for providing diagnostic antibodies) or in vitro (e.g. by phage display technology or another technique useful for generating synthetic antibodies).

Also provided herein are antibodies, be it natural polyclonal or monoclonal, or synthetic (e.g. (phage) library-derived binding molecules) antibodies that specifically react with an antigen comprising a proteinaceous molecule or MPV-specific functional fragment thereof according to the invention. Such antibodies are useful in a method for identifying a viral isolate as an MPV comprising reacting said viral isolate or a component thereof with an antibody as provided herein. This can for example be achieved by using purified or non-purified MPV or parts thereof (proteins, peptides) using ELISA, RIA, FACS or different formats of antigen detection assays (Current Protocols in Immunology). Alternatively, infected cells or cell cultures may be used to identify viral antigens using classical immunofluorescence or immunohistochemical techniques.

A pharmaceutical composition comprising a virus, a nucleic acid, a proteinaceous molecule or fragment thereof, an antigen and/or an antibody according to the invention can for example be used in a method for the treatment or prevention of a MPV infection and/or a respiratory illness comprising providing an individual with a pharmaceutical composition according to the invention. This is most useful when said individual comprises a human, specifically when said human is below 5 years of age, since such infants and young children are most likely to be infected by a human MPV as provided herein. Generally, in the acute phase patients will suffer from upper respiratory symptoms predisposing for other respiratory and other diseases. Also lower respiratory illnesses may occur, predisposing for more and other serious conditions. The compositions of the invention can be used for the treatment of immuno-compromised individuals including cancer patients, transplant recipients and the elderly.

The invention also provides methods to obtain an antiviral agent useful in the treatment of respiratory tract illness comprising establishing a cell culture or experimental animal comprising a virus according to the invention, treating said culture or animal with an candidate antiviral agent, and determining the effect of said agent on said virus or its infection of said culture or animal. An example of such an antiviral agent comprises a MPV-neutralising antibody, or functional component thereof, as provided herein, but antiviral agents of other nature are obtained as well. The invention also provides use of an antiviral agent according to the invention for the preparation of a pharmaceutical composition, in particular for the preparation of a pharmaceutical composition for the treatment of respiratory tract illness, specifically when caused by an MPV infection or related disease, and provides a pharmaceutical composition comprising an antiviral agent according to the invention, useful in a method for the treatment or prevention of an MPV infection or respiratory illness, said method comprising providing an individual with such a pharmaceutical composition.

In certain embodiments of the invention, the vaccine of the invention comprises mammalian *metapneumovirus* as defined herein. In certain, more specific embodiments, the mammalian *metapneumovirus* is a human *metapneumovirus*.

In a preferred embodiment, the mammalian *metapneumovirus* to be used in a vaccine formulation has an attenuated phenotype. For methods to achieve an attenuated phenotype, see section 5.6.

The invention provides vaccine formulations for the prevention and treatment of infections with PIV, RSV, APV, and/or hMPV. In certain embodiments, the vaccine of the invention comprises recombinant and chimeric viruses of the invention. In certain embodiments, the virus is attenuated.

In a specific embodiment, the vaccine comprises APV and the vaccine is used for the prevention and treatment for hMPV infections in humans. Without being bound by theory, because of the high degree of homology of the F protein of APV with the F protein of hMPV, infection with APV will result in the production of antibodies in the host that will cross-react with hMPV and protect the host from infection with hMPV and related diseases.

In another specific embodiment, the vaccine comprises hMPV and the vaccine is used for the prevention and treatment for APV infection in birds, such as, but not limited to, in turkeys. Without being bound by theory, because of the high degree of homology of the F protein of APV with the F protein of hMPV, infection with hMPV will result in the production of antibodies in the host that will cross-react with APV and protect the host from infection with APV and related diseases.

In a specific embodiment, the invention encompasses the use of recombinant and chimeric APV/hMPV viruses which have been modified in vaccine formulations to confer protection against APV and/or hMPV. In certain embodiments, APV/hMPV is used in a vaccine to be administered to birds, to protect the birds from infection with APV. Without being bound by theory, the replacement of the APV gene or nucleotide sequence with a hMPV gene or nucleotide sequence results in an attenuated phenotype that allows the use of the chimeric virus as a vaccine. In other embodiments the APV/hMPV chimeric virus is administered to humans. Without being bound by theory the APV viral vector provides the attenuated phenotype in humans and the expression of the hMPV sequence elicits a hMPV specific immune response.

In a specific embodiment, the invention encompasses the use of recombinant and chimeric hMPV/APV viruses which have been modified in vaccine formulations to confer protection against APV and/or hMPV. In certain embodiments, hMPV/APV is used in a vaccine to be administered to humans, to protect the human from infection with hMPV. Without being bound by theory, the replacement of the hMPV gene or nucleotide sequence with a APV gene or nucleotide sequence results in an attenuated phenotype that allows the use of the chimeric virus as a vaccine. In other embodiments the hMPV/APV chimeric virus is administered to birds. Without being bound by theory the hMPV backbone provides the attenuated phenotype in birds and the expression of the APV sequence elicits an APV specific immune response.

In certain preferred embodiments, the vaccine formulation of the invention is used to protect against infections by a *metapneumovirus* and related diseases. More specifically, the vaccine formulation of the invention is used to protect against infections by a human *metapneumovirus* and/or an avian *pneumovirus* and related diseases. In certain embodiments, the vaccine formulation of the invention is used to protect against infections by (a) a human *metapneumovirus* and a respiratory syncytial virus; and/or (b) an avian *pneumovirus* and a respiratory syncytial virus.

In certain embodiments, the vaccine formulation of the invention is used to protect against infections by (a) a human *metapneumovirus* and a human parainfluenza virus; and/or (b) an avian *pneumovirus* and a human parainfluenza virus, and related diseases.

In certain embodiments, the vaccine formulation of the invention is used to protect against infections by (a) a human *metapneumovirus*, a respiratory syncytial virus, and a human parainfluenza virus; and/or (b) an avian *pneumovirus*, a respiratory syncytial virus, and a human parainfluenza virus, and related diseases.

In certain embodiments, the vaccine formulation of the invention is used to protect against infections by a human *metapneumovirus*, a respiratory syncytial virus, and a human parainfluenza virus and related diseases. In certain other embodiments, the vaccine formulation of the invention is used to protect against infections by an avian *pneumovirus*, a respiratory syncytial virus, and a human parainfluenza virus and related diseases.

Due to the high degree of homology among the F proteins of different viral species, for exemplary amino acid sequence comparisons see FIG. 9, the vaccine formulations of the invention can be used for protection from viruses different from the one from which the heterologous nucleotide sequence encoding the F protein was derived. In a specific exemplary embodiment, a vaccine formulation contains a virus comprising a heterologous nucleotide sequence derived from an avian *pneumovirus* type A, and the vaccine formulation is used to protect from infection by avian *pneumovirus* type A and avian *pneumovirus* type B. The invention encompasses vaccine formulations to be administered to humans and animals which are useful to protect against APV, including APV-C and APV-D, hMPV, PIV, influenza, RSV, Sendai virus, mumps, laryngotracheitis virus, *simianvirus* 5, human *papillomavirus*, measles, mumps, as well as other viruses and pathogens and related diseases. The invention further encompasses vaccine formulations to be administered to humans and animals which are useful to protect against human *metapneumovirus* infections and avian *pneumovirus* infections and related diseases.

In one embodiment, the invention encompasses vaccine formulations which are useful against domestic animal disease causing agents including rabies virus, feline leukemia virus (FLV) and canine distemper virus. In yet another embodiment, the invention encompasses vaccine formulations which are useful to protect livestock against vesicular stomatitis virus, rabies virus, rinderpest virus, swinepox virus, and further, to protect wild animals against rabies virus.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain. For example, antigens of non-related viruses such as HIV (gp160, gp120, gp41) parasite antigens (e.g., malaria), bacterial or fungal antigens or tumor antigens can be engineered into the attenuated strain. Alternatively, epitopes which alter the tropism of the virus in vivo can be engineered into the chimeric attenuated viruses of the invention.

Virtually any heterologous gene sequence may be constructed into the chimeric viruses of the invention for use in vaccines. Preferably moieties and peptides that act as biological response modifiers. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to influenza and parainfluenza hemagglutinin neuraminidase and fusion glycoproteins such as the HN and F genes of human PIV3. In yet another embodiment, heterologous gene sequences that can be engineered into the chimeric viruses include those that encode proteins with immuno-modulating activities. Examples of immuno-modulating proteins include, but are not limited to, cytokines, interferon type 1, gamma interferon, colony stimulating factors, interleukin-1, -2, -4, -5, -6, -12, and antagonists of these agents.

In addition, heterologous gene sequences that can be constructed into the chimeric viruses of the invention for use in vaccines include but are not limited to sequences derived from a human immunodeficiency virus (HIV), preferably type 1 or type 2. In a preferred embodiment, an immunogenic HIV-derived peptide which may be the source of an antigen may be constructed into a chimeric PIV that may then be used to elicit a vertebrate immune response. Such HIV-derived peptides may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25), tat, rev, nef, vif, vpu, vpr, and/or vpx.

Other heterologous sequences may be derived from hepatitis B virus surface antigen (HBsAg); hepatitis A or C virus surface antigens, the glycoproteins of Epstein Barr virus; the glycoproteins of human *papillomavirus*; the glycoproteins of respiratory syncytial virus, parainfluenza virus, Sendai virus, *simianvirus* 5 or mumps virus; the glycoproteins of influenza virus; the glycoproteins of *herpesviruses*; VP1 of *poliovirus*; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Other heterologous sequences may be derived from tumor antigens, and the resulting chimeric viruses be used to generate an immune response against the tumor cells leading to tumor regression in vivo. These vaccines may be used in combination with other therapeutic regimens, including but not limited to chemotherapy, radiation therapy, surgery, bone marrow transplantation, etc. for the treatment of tumors. In accordance with the present invention, recombinant viruses may be engineered to express tumor-associated antigens (TAAs), including but not limited to, human tumor antigens recognized by T cells (Robbins and Kawakami, 1996, Curr. Opin. Immunol. 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, GAGE-1, N-acetylglucosaminyltransferase-V, p15; Tumor-specific mutated antigens, β-catenin, MUM-1, CDK4; Nonmelanoma antigens for breast, ovarian, cervical and pancreatic carcinoma, HER-2/neu, human *papillomavirus*-E6, -E7, MUC-1.

In even other embodiments, a heterologous nucleotide sequence is derived from a *metapneumovirus*, such as human *metapneumovirus* and/or avian *pneumovirus*. In even other embodiments, the virus of the invention contains two different heterologous nucleotide sequences wherein one is derived from a *metapneumovirus*, such as human *metapneumovirus* and/or avian *pneumovirus*, and the other one is derived from a respiratory syncytial virus. The heterologous nucleotide sequence encodes a F protein or a G protein of the respective virus. In a specific embodiment, a heterologous nucleotide sequences encodes a chimeric F protein, wherein the chimeric F protein contains the ectodomain of a F protein of a *metapneumovirus* and the transmembrane domain as well as the luminal domain of a F protein of a parainfluenza virus.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In a specific embodiment, the recombinant virus is non-pathogenic to the subject to which it is administered. In this regard, the use of genetically engineered viruses for vaccine purposes may desire the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication within the host. When used as a vaccine, the recombinant virus would go through limited replication cycle(s) and induce a sufficient level of immune response but it would not go further in the human host and cause disease. Recombinant viruses lacking one or more of the genes of wild type APV and hMPV, respectively, or possessing mutated genes as compared to the wild type strains would not be able to undergo successive rounds of replication. Defective viruses can be produced in cell lines which permanently express such a gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines. Alternatively, recombinant virus of the invention made from cDNA may be highly attenuated so that it replicates for only a few rounds.

In certain embodiments, the vaccine of the invention comprises an attenuated mammalian MPV. Without being bound by theory, the attenuated virus can be effective as a vaccine even if the attenuated virus is incapable of causing a cell to generate new infectious viral particles because the viral proteins are inserted in the cytoplasmic membrane of the host thus stimulating an immune response.

In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled. The resulting vaccine is usually inoculated intramuscularly.

Inactivated viruses may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG, Corynebacterium parvum, ISCOMS and virosomes.

Many methods may be used to introduce the vaccine formulations described above, these include but are not limited to oral, intradermal, intramuscular, intraperitoneal, intravenous, subcutaneous, percutaneous, and intranasal and inhalation routes. It may be preferable to introduce the chimeric virus vaccine formulation via the natural route of infection of the pathogen for which the vaccine is designed.

In certain embodiments, the invention relates to immunogenic compositions. The immunogenic compositions comprise a mammalian MPV. In a specific embodiment, the immunogenic composition comprises a human MPV. In certain embodiments, the immunogenic composition comprises an attenuated mammalian MPV or an attenuated human MPV. In certain embodiments, the immunogenic composition further comprises a pharmaceutically acceptable carrier.

5.13 Dosage Regimens, Administration and Formulations

The present invention provides vaccines and immunogenic preparations comprising MPV and APV, including attenuated forms of the virus, recombinant forms of MPV and APV, and chimeric MPV and APV expressing one or more heterologous or non-native antigenic sequences. The vaccines or immunogenic preparations of the invention encompass single or multivalent vaccines, including bivalent and trivalent vaccines. The vaccines or immunogenic formulations of the invention are useful in providing protections against various viral infections. Particularly, the vaccines or immunogenic formulations of the invention provide protection against respiratory tract infections in a host.

A recombinant virus and/or a vaccine or immunogenic formulation of the invention can be administered alone or in combination with other vaccines. Preferably, a vaccine or immunogenic formulation of the invention is administered in combination with other vaccines or immunogenic formulations that provide protection against respiratory tract diseases, such as but not limited to, respiratory syncytial virus vaccines, influenza vaccines, measles vaccines, mumps vaccines, rubella vaccines, pneumococcal vaccines, rickettsia vaccines, *staphylococcus* vaccines, whooping cough vaccines or vaccines against respiratory tract cancers. In a preferred embodiment, the virus and/or vaccine of the invention is administered concurrently with pediatric vaccines recommended at the corresponding ages. For example, at two, four or six months of age, the virus and/or vaccine of the invention can be administered concurrently with DtaP (IM), Hib (IM), Polio (IPV or OPV) and Hepatitis B (IM). At twelve or fifteen months of age, the virus and/or vaccine of the invention can be administered concurrently with Hib (IM), Polio (IPV or OPV), MMRII®(SubQ); Varivax®(SubQ), and hepatitis B (IM). The vaccines that can be used with the methods of invention are reviewed in various publications, e.g., The Jordan Report 2000, Division of Microbiology and Infectious Diseases, National Institute of Allergy and Infectious Diseases, National Institutes of Health, United States, the content of which is incorporated herein by reference in its entirety.

A vaccine or immunogenic formulation of the invention may be administered to a subject per se or in the form of a pharmaceutical or therapeutic composition. Pharmaceutical compositions comprising an adjuvant and an immunogenic antigen of the invention (e.g., a virus, a chimeric virus, a mutated virus) may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the immunogenic antigen of the invention into preparations which can be used pharmaceutically. Proper formulation is, amongst others, dependent upon the route of administration chosen.

When a vaccine or immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum hydroxide, aluminum phosphate gel, Freund's Complete Adjuvant, Freund's Incomplete Adjuvant, squalene or squalane oil-in-water adjuvant formulations, biodegradable and biocompatible polyesters, polymerized liposomes, triterpenoid glycosides or saponins (e.g., QuilA and QS-21, also sold under the trademark STIMULON, ISCOPREP), N-acetyl-muramyl-L-threonyl-D-isoglutamine (Threonyl-MDP, sold under the trademark TERMURTIDE), LPS, monophosphoryl Lipid A (3D-MLA sold under the trademark MPL).

The subject to which the vaccine or an immunogenic composition of the invention is administered is preferably a mammal, most preferably a human, but can also be a non-human animal, including but not limited to, primates, cows, horses, sheep, pigs, fowl (e.g., chickens, turkeys), goats, cats, dogs, hamsters, mice and rodents.

Many methods may be used to introduce the vaccine or the immunogenic composition of the invention, including but not limited to, oral, intradermal, intramuscular, intraperitoneal, intravenous, subcutaneous, percutaneous, intranasal and inhalation routes, and via scarification (scratching through the top layers of skin, e.g., using a bifurcated needle).

For topical administration, the vaccine or immunogenic preparations of the invention may be formulated as solutions, gels, ointments, creams, suspensions, etc. as are well-known in the art.

For administration intranasally or by inhalation, the preparation for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

Determination of an effective amount of the vaccine or immunogenic formulation for administration is well within the capabilities of those skilled in the art, especially in light of the detailed disclosure provided herein.

An effective dose can be estimated initially from in vitro assays. For example, a dose can be formulated in animal models to achieve an induction of an immunity response using techniques that are well known in the art. One having ordinary skill in the art could readily optimize administration to all animal species based on results described herein. Dosage amount and interval may be adjusted individually. For example, when used as an immunogenic composition, a suitable dose is an amount of the composition that when administered as described above, is capable of eliciting an antibody response. When used as a vaccine, the vaccine or immunogenic formulations of the invention may be administered in about 1 to 3 doses for a 1-36 week period. Preferably, 1 or 2 doses are administered, at intervals of about 2 weeks to about 4 months, and booster vaccinations may be given periodically thereafter. Alternate protocols may be appropriate for individual animals. A suitable dose is an amount of the vaccine formulation that, when administered as described above, is capable of raising an immunity response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 μg. Suitable dose range will vary with the route of injection and the size of the patient, but will typically range from about 0.1 mL to about 5 mL.

In a specific embodiment, the viruses and/or vaccines of the invention are administered at a starting single dose of at least $10^3$ $TCID_{50}$, at least $10^4$ $TCID_{50}$, at least $10^5$ $TCID_{50}$, at least $10^6$ $TCID_{50}$. In another specific embodiment, the virus and/or vaccines of the invention are administered at multiple doses. In a preferred embodiment, a primary dosing regimen at 2, 4, and 6 months of age and a booster dose at the beginning of the second year of life are used. More preferably, each dose of at least $10^5$ $TCID_{50}$, or at least $10^6$ $TCID_{50}$ is given in a multiple dosing regimen.

5.13.1 Challenge Studies

This assay is used to determine the ability of the recombinant viruses of the invention and of the vaccines of the invention to prevent lower respiratory tract viral infection in an animal model system, such as, but not limited to, cotton rats or hamsters. The recombinant virus and/or the vaccine can be administered by intravenous (IV) route, by intramuscular (IM) route or by intranasal route (IN). The recombinant virus and/or the vaccine can be administered by any technique well-known to the skilled artisan. This assay is also used to correlate the serum concentration of antibodies with a reduction in lung titer of the virus to which the antibodies bind.

On day 0, groups of animals, such as, but not limited to, cotton rats (*Sigmodon hispidis*, average weight 100 g) cynomolgous macacques (average weight 2.0 kg) are administered the recombinant or chimeric virus or the vaccine of interest or BSA by intramuscular injection, by intravenous injection, or by intranasal route. Prior to, concurrently with, or subsequent to administration of the recombinant virus or the vaccine of the invention, the animals are infected with wild type virus wherein the wild type virus is the virus against which the vaccine was generated. In certain embodiments, the animals are infected with the wild type virus at least 1 day, at least 2 days, at least 3 days, at least 4 days, at least 5 days, at least 6 days, 1 week or 1 or more months subsequent to the administration of the recombinant virus and/or the vaccine of the invention.

After the infection, cotton rats are sacrificed, and their lung tissue is harvested and pulmonary virus titers are determined by plaque titration. Bovine serum albumin (BSA) 10 mg/kg is used as a negative control. Antibody concentrations in the serum at the time of challenge are determined using a sandwich ELISA. Similarly, in macacques, virus titers in nasal and lung lavages can be measured.

5.13.2 Target Populations

In certain embodiments of the invention, the target population for the therapeutic and diagnostic methods of the invention is defined by age. In certain embodiments, the target population for the therapeutic and/or diagnostic methods of the invention is characterized by a disease or disorder in addition to a respiratory tract infection.

In a specific embodiment, the target population encompasses young children, below 2 years of age. In a more specific embodiment, the children below the age of 2 years do not suffer from illnesses other than respiratory tract infection.

In other embodiments, the target population encompasses patients above 5 years of age. In a more specific embodiment, the patients above the age of 5 years suffer from an additional disease or disorder including cystic fibrosis, leukaemia, and non-Hodgkin lymphoma, or recently received bone marrow or kidney transplantation.

In a specific embodiment of the invention, the target population encompasses subjects in which the hMPV infection is associated with immunosuppression of the hosts. In a specific embodiment, the subject is an immunocompromised individual.

In certain embodiments, the target population for the methods of the invention encompasses the elderly.

In a specific embodiment, the subject to be treated or diagnosed with the methods of the invention was infected with hMPV in the winter months.

5.13.3 Clinical Trials

Vaccines of the invention or fragments thereof tested in in vitro assays and animal models may be further evaluated for safety, tolerance and pharmacokinetics in groups of normal healthy adult volunteers. The volunteers are administered intramuscularly, intravenously or by a pulmonary delivery system a single dose of a recombinant virus of the invention and/or a vaccine of the invention. Each volunteer is monitored at least 24 hours prior to receiving the single dose of the recombinant virus of the invention and/or a vaccine of the invention and each volunteer will be monitored for at least 48 hours after receiving the dose at a clinical site. Then volunteers are monitored as outpatients on days 3, 7, 14, 21, 28, 35, 42, 49, and 56 postdose.

Blood samples are collected via an indwelling catheter or direct venipuncture using 10 ml red-top Vacutainer tubes at the following intervals: (1) prior to administering the dose of the recombinant virus of the invention and/or a vaccine of the invention; (2) during the administration of the dose of the recombinant virus of the invention and/or a vaccine of the invention; (3) 5 minutes, 10 minutes, 15 minutes, 20 minutes, 30 minutes, 1 hour, 2 hours, 4 hours, 8 hours, 12 hours, 24 hours, and 48 hours after administering the dose of the recombinant virus of the invention and/or a vaccine of the invention; and (4) 3 days, 7 days 14 days, 21 days, 28 days, 35 days, 42 days, 49 days, and 56 days after administering the dose of the recombinant virus of the invention and/or a vaccine of the invention. Samples are allowed to clot at room temperature and serum will be collected after centrifugation.

The amount of antibodies generated against the recombinant virus of the invention and/or a vaccine of the invention in the samples from the patients can be quantitated by ELISA. T-cell immunity (cytotoxic and helper responses) in PBMC and lung and nasal lavages can also be monitored.

The concentration of antibody levels in the serum of volunteers are corrected by subtracting the predose serum level (background level) from the serum levels at each collection interval after administration of the dose of recombinant virus of the invention and/or a vaccine of the invention. For each volunteer the pharmacokinetic parameters are computed according to the model-independent approach (Gibaldi et al., eds., 1982, Pharmacokinetics, 2nd edition, Marcel Dekker, New York) from the corrected serum antibody or antibody fragment concentrations.

5.14 Methods for Detecting and Diagnosing Mammalian MPV

The invention provides means and methods for the diagnosis and/or detection of MPV, said means and methods to be employed in the detection of MPV, its components, and the products of its transcription, translation, expression, propagation, and metabolic processes. More specifically, this invention provides means and methods for the diagnosis of an MPV infection in animals and in humans, said means and methods including but not limited to the detection of components of MPV, products of the life cycle of MPV, and products of a host's response to MPV exposure or infection.

The methods that can be used to detect MPV or its components, and the products of its transcription, translation, expression, propagation and metabolic processes are well known in the art and include, but are not limited to, molecular based methods, antibody based methods, and cell-based methods. Examples of molecular based methods include, but are not limited to polymerase chain reaction (PCR), reverse transcriptase PCR (RT-PCR), real time RT-PCR, nucleic acid sequence based amplification (NASBA), oligonucleotide probing, southern blot hybridization, northern blot hybridization, any method that involves the contacting of a sample with a nucleic acid that is complementary to an MPV or similar or identical to an MPV, and any combination of these methods with each other or with those in the art. Identical or similar nucleic acids that can be used are described herein, and are also well known in the art to be able to allow one to distinguish between MPV and the genomic material or related products of other viruses and organisms. Examples of antibody based methods include, but are not limited to, the contacting of an antibody with a sample suspected of containing MPV, direct immunofluorescence (DIF), enzyme linked immunoabsorbent assay (ELISA), western blot, immunochromatography. Examples of cell-based methods include, but are not limited to, reporter assays that are able to emit a signal when exposed to MPV, its components, or products thereof. In another embodiment, the reporter assay is an in vitro assay, whereby the reporter is expressed upon exposure to MPV, its components, or products thereof. Examples of the aforementioned methods are well-known in the art and also described herein. In a more specific embodiment, NASBA is used to amplify specific RNA or DNA from a pool of total nucleic acids.

In one embodiment, the invention provides means and methods for the diagnosis and detection of MPV, said means and methods including but not limited to the detection of genomic material and other nucleic acids that are associated with or complimentary to MPV, the detection of transcriptional and translational products of MPV, said products being both processed and unprocessed, and the detection of components of a host response to MPV exposure or infection.

In one embodiment, the invention relates to the detection of MPV through the preparation and use of oligonucleotides that are complimentary to nucleic acid sequences and transcriptional products of nucleic acid sequences that are present within the genome of MPV. Furthermore, the invention relates to the detection of nucleic acids, or sequences thereof, that are present in the genome of MPV and its transcription products, using said oligonucleotides as primers for copying or amplification of specific regions of the MPV genome and its transcripts. The regions of the MPV genome and its transcripts that can be copied or amplified include but are not limited to complete and incomplete stretches of one or more of the following: the N-gene, the P-gene, the M-gene, the F-gene, the M2-gene, the SH-gene, the G-gene, and the L-gene. In a specific embodiment, oligonucleotides are used as primers in conjunction with methods to copy or amplify the N-gene of MPV, or transcripts thereof, for identification purposes. Said methods include but are not limited to, PCR assays, RT-PCR assays, real time RT-PCR assays, primer extension or run on assays, NASBA and other methods that employ the genetic material of MPV or transcripts and compliments thereof as templates for the extension of nucleic acid sequences from said oligonucleotides. In another embodiment, a combination of methods is used to detect the presence of MPV in a sample. One skilled in the art would be familiar with the requirements and applicability of each assay. For example, PCR and RT-PCR would be useful for the amplification or detection of a nucleic acid. In a more specific embodiment, real time RT-PCR is used for the routine and reliable quantitation of PCR products.

In another embodiment, the invention relates to detection of MPV through the preparation and use of oligonucleotides that are complimentary to nucleic acid sequences and transcriptional products of nucleic acid sequences that are present within the genome of MPV. Furthermore, the invention relates to the detection of nucleic acids, or sequences thereof, that are present in or complimentary to the genome of MPV and its transcription products, using said oligonucleotide sequences as probes for hybridization to and detection of specific regions within or complimentary to the MPV genome and its transcripts. The regions of the MPV genome and its transcripts that can be detected using hybridization probes include but are not limited to complete and incomplete stretches of one or more of the following: the N-gene, the P-gene, the M-gene, the F-gene, the M2-gene, the SH-gene, the G-gene, and the L-gene. In a specific embodiment, oligonucleotides are used as probes in conjunction with methods to detect, anneal, or hybridize to the N-gene of MPV, or transcripts thereof, for identification purposes. Said methods include but are not limited to, Northern blots, Southern blots and other methods that employ the genetic material of MPV or transcripts and compliments thereof as targets for the hybridization, annealing, or detection of sequences or stretches of sequences within or complimentary to the MPV genome.

A nucleic acid which is hybridizable to a nucleic acid of a mammalian MPV, or to its reverse complement, or to its complement can be used in the methods of the invention to detect the presence of a mammalian MPV. In certain embodiments, the nucleic acids are hybridized under conditions of high stringency. By way of example and not limitation, procedures using such conditions of high stringency are as follows. Prehybridization of filters containing DNA is carried out for 8 h to overnight at 65 C in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65 C in prehybridization mixture containing 100 μg/ml denatured salmon sperm DNA and 5-20×106 cpm of 32P-labeled probe. Washing of filters is done at 37 C for 1 h in a solution containing 2×SSC, 0.01% PVP, 0.01% Ficoll, and 0.01% BSA. This is followed by a wash in 0.1×SSC at 50 C for 45 min before autoradiography. Other conditions of high stringency which may be used are well known in the art. In other embodiments of the invention, hybridization is performed under moderate of low stringency conditions, such conditions are well-known to the skilled artisan (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols,© 1994-1997 John Wiley and Sons, Inc.).

Any size oligonucleotides can be used in the methods of the invention. As described herein, such oligonucleotides are useful in a variety of methods, e.g., as primer or probes in various detection or analysis procedures. In preferred embodiments, oligonucleotide probes and primers are at least 5, at least 8, at least 10, at least 12, at least 15, at least 20, at least 25, at least 30, at least 35, at least 40, at least 45, at least 50, at least 55, at least 60, at least 70, at least 80, at least 100, at least 200, at least 300 at least 400, at least 500, at least 1000, at least 2000, at least 3000, at least 4000 or at least 5000 bases. In another more certain embodiments, oligonucleotide probes and primers comprise at least 5, at least 8, at least 10, at least 12, at least 15, at least 20, at least 25, at least 30, at least 35, at least 40, at least 45, at least 50, at least 55, at least 60, at least 70, at least 80, at least 100, at least 200, at least 300 at least 400, at least 500, at least 1000, at least 2000, at least 3000, at least 4000 or at least 5000 bases, that are at least 50%, at least 60%, at least 70%, at least 80%, at least 90%, at least 99%, at least 99.5% homologous to a target sequence, such as an MPV genomic sequence or complement thereof. In a another specific embodiment, the oligonucleotide that is used as a primer or a probe is of any length, and specifically hybridizes under stringent conditions through at least 8 of its most 3' terminal bases to a target sequence. In another specific embodiment, the oligonucleotide that is used as a primer or a probe is of any length, and specifically hybridizes under stringent conditions through at least 10 of its most 3' terminal bases to a target sequence. In another specific embodiment, the oligonucleotide that is used as a primer or a probe is of any length, and specifically hybridizes under stringent conditions through at least 12 of its most 3' terminal bases to a target sequence. In another specific embodiment, the oligonucleotide that is used as a primer or a probe is of any length, and specifically hybridizes under stringent conditions through at least 15 of its most 3' terminal bases to a target sequence. In another specific embodiment, the oligonucleotide that is used as a primer or a probe is of any length, and specifically hybridizes under stringent conditions through at least 20 of its most 3' terminal bases to a target sequence. In another specific embodiment, the oligonucleotide that is used as a primer or a probe is of any length, and specifically hybridizes under stringent conditions through at least 25 of its most 3' terminal bases to a target sequence. In another embodiment, a degenerate set of oligos is used so that a specific position or nucleotide is substituted. The degeneracy can occur at any position or at any number of positions, most preferably, at least at one position, but also at least at two positions, at least at three positions, at least ten positions, in the region that hybridizes under stringent conditions to the target sequence.

One skilled in the art would be familiar with the structural requirements imposed upon oligonucleotides by the assays known in the art. It is also possible to design oligonucleotide primers and probes using more systematic approaches. For example, one skilled in the art would be able to determine the appropriate length and sequence of an oligonucleotide primer or probe based upon preferred assay or annealing temperatures and the structure of the oligo, i.e., sequence. In addition, one skilled in the art would be able to determine the specificity of the assay employing an oligonucleotide primer or probe, by adjusting the temperature of the assay so that the specificity of the oligo for the target sequence is enhanced or diminished, depending upon the temperature. In a preferred embodiment, the annealing temperature of the primer or probe is determined, using methods known in the art, and the assay is performed at said annealing temperature. One skilled in the art would be familiar with methods to calculate the annealing temperature associated with an oligonucleotide for its specific target sequence. For example, annealing temperatures can be roughly calculated by, assigning 4° C. to the annealing temperature for each G or C nucleotide in the oligonucleotide that hybridizes to the target sequence. In another example, annealing temperatures can be roughly calculated by, assigning 2° C. to the annealing temperature for each A or T nucleotide in the oligonucleotide that hybridizes to the target sequence. The annealing temperature of the oligonucleotide is necessarily dependent upon the length and sequence of the oligonucleotide, as well as upon the complimentarily of the oligo for the target sequence, so that only binding events between the oligo primer or probe are factored into the annealing temperature. The examples described herein for the calculation of annealing temperature are meant to be examples and are not meant to limit the invention from other methods of determination for the annealing temperature. One skilled in the art would be familiar with other methods that can be used, and in addition, other more sophisticated methods of calculating annealing or melting temperatures for an oligonucleotide have been described herein. In a more specific embodiment, oligonucleotide probes and primers are annealed at a temperature of at least 30° C., at least 35° C., at least 40° C., at least 45° C., at least 50° C., at least 55° C., at least 60° C., at least 65° C., at least 70° C., at least 80° C., at least 90° C. or at least 99° C.

The invention provides cell-based and cell-free assays for the identification or detection of MPV in a sample. A variety of methods can be used to conduct the cell-based and cell-free assays of the invention, including but not limited to, those using reporters. Examples of reporters are described herein and can be used for the identification or detection of MPV using high-throughput screening and for any other purpose that would be familiar to one skilled in the art. There are a number of methods that can be used in the reporter assays of the invention. For example, the cell-based assays may be conducted by contacting a sample with a cell containing a nucleic acid sequence comprising a reporter gene, wherein the reporter gene is linked to the promoter of an MPV gene or linked to a promoter that is recognized by an MPV gene product, and measuring the expression of the reporter gene, upon exposure to MPV or a component of MPV. In a further embodiment of the cell-based assay, a host cell that is able to be infected by MPV, is transfected with a nucleic acid construct that encodes one or more reporter genes, such that expression from the reporter gene occurs in the presence of an MPV or an MPV component. In such an embodiment, expression of the reporter gene is operably linked to a nucleic acid sequence that is recognized by MPV or a component thereof, thereby causing expression of the reporter gene. The presence of MPV in the sample induces expression of the reporter gene that can be detected using any method known in the art, and also described herein (section 5.8.2). Examples of host cells that can be transfected and used in the cell-based detection assay, include, but are not limited to, Vero, tMK, COS7 cells. In another embodiment, the host cell is any cell that can be infected with MPV. The expression of the reporter gene is thereby indicative of the presence of an MPV or a component thereof. In a cell-free assay, a sample is contacted with a nucleic acid comprising a reporter gene that is operably linked to a nucleic acid sequence so that the presence of an MPV or a component thereof induces expression of the reporter gene in vitro. For example, the cell-free assay may be conducted by contacting a sample suspected of containing an MPV or a component thereof, with a nucleic acid that comprises a reporter gene, wherein the reporter gene is linked to the promoter of an MPV gene or linked to a promoter that is recognized by an MPV gene product, and measuring the expression of the reporter gene, upon exposure to MPV or a component of MPV. The expression of the reporter gene is thereby indicative of the presence of an MPV or a component thereof. While a large number of reporter compounds are known in the art, a variety of examples are provided herein (see, e.g., section 5.8.2).

In another embodiment, the invention relates to the detection of MPV infection using a minireplicon system. For example, a host cell can be transfected with an hMPV minireplicon construct that encodes one or more reporter genes, such that expression from the reporter gene occurs in the presence of hMPV or hMPV polymerase. Examples of reporter genes are described herein, in section 5.8.2. In such an embodiment, hMPV acts as a helper virus to promote the expression of the reporter gene or genes encoded by the minireplicon system. Without being bound by limitation, hMPV provides polymerase that drives rescue of the minireplicon system and therefore drives expression of the reporter gene or genes. In a certain embodiment, a host cell, that has been transfected with an hMPV minireplicon, encoding a reporter gene, is contacted with a sample suspected to contain hMPV. The presence of hMPV in the sample induces expression of the reporter gene that can be detected using any method known in the art, and also described herein (section 5.8.2). Examples of the host cell, include, but are not limited to, Vero, tMK, COS7 cells. In another embodiment, the host cell is any cell that can be infected with hMPV.

In another embodiment, the invention relates to the detection of an MPV infection in an animal or human host through the preparation and use of antibodies, e.g., monoclonal antibodies (MAbs), that are specific to and can recognize peptides or nucleic acids that are characteristic of MPV or its gene products. The epitopes or antigenic determinants recognized by said MAbs include but are not limited to proteinaceous and nucleic acid products that are synthesized during the life cycle and metabolic processes involved in MPV propagation. The proteinaceous or nucleic acid products that can be used as antigenic determinants for the generation of suitable antibodies include but are not limited to complete and incomplete transcription and expression products of one or more of the following components of MPV: the N-gene, the P-gene, the M-gene, the F-gene, the M2-gene, the SH-gene, the G-gene, and the L-gene. In one specific embodiment, MAbs raised against proteinaceous products of the G-gene or portions thereof are used in conjunction with other methods to detect or confirm the presence of the MPV expressed G peptide in a biological sample, e.g. body fluid. Said methods include but are not limited to ELISA, Radio-Immuno or Competition Assays, Immuno-precipitation and other methods that employ the transcribed or expressed gene products of MPV as targets for detection by MAbs raised against said targets or portions and relatives thereof. In another embodiment of the invention, the antibodies that can be used to detect hMPV, recognize the F, G, N, L, M, M2-1, P, and SH proteins of all four subtypes.

In another embodiment, the invention relates to the detection of factors that are associated with and characteristic of a host's immunologic response to MPV exposure or infection. Upon exposure or infection by MPV, a host's immune system illicits a response to said exposure or infection that involves the generation by the host of antibodies directed at eliminating or attenuating the effects and/or propagation of virus. This invention provides means and methods for the diagnosis of MPV related disease through the detection of said antibodies that may be produced as a result of MPV exposure to or infection of the host. The epitopes recognized by said antibodies include but are not limited to peptides and their exposed surfaces that are accessible to a host immune response and that can serve as antigenic determinants in the generation of an immune response by the host to the virus. Some of the proteinaceous and nuclear material used by a host immune response as epitopes for the generation of antibodies include but are not limited to products of one or more of the following components of MPV: the N-gene, the P-gene, the M-gene, the F-gene, the M2-gene, the SH-gene, the G-gene, and the L-gene. In one embodiment, antibodies to partially or completely accessible portions of the N-gene encoded peptides of MPV are detected in a host sample. In a specific embodiment, proteinaceous products of the G-gene or portions thereof are used in conjunction with other methods to detect the presence of the host derived antibodies in a biological sample, e.g. body fluid. Said methods include but are not limited to ELISA, Radio-Immuno or Competition Assays, and other methods that employ the transcribed or expressed gene products of MPV as targets for detection by host antibodies that recognize said products and that are found in biological samples.

This invention also provides means and methods for diagnostic assays or test kits and for methods to detect agents of an MPV infection from a variety of sources including but not limited to biological samples, e.g., body fluids. In one embodiment, this invention relates to assays, kits, protocols, and procedures that are suitable for identifying an MPV nucleic acid or a compliment thereof. In another embodiment, this invention relates to assays, kits, protocols, and procedures that are suitable for identifying an MPV expressed peptide or a portion thereof. In another embodiment, this invention relates to assays, kits, protocols, and procedures that are suitable for identifying components of a host immunologic response to MPV exposure or infection.

In addition to diagnostic confirmation of MPV infection of a host, the present invention also provides for means and methods to classify isolates of MPV into distinct phylogenetic groups or subgroups. In one embodiment, this feature can be used advantageously to distinguish between the different variant of MPV, variant A1, A2, B1 and B2, in order to design more effective and subgroup specific therapies. Variants of MPV can be differentiated on the basis of nucleotide or amino acid sequences of one or more of the following: the N-gene, the P-gene, the M-gene, the F-gene, the M2-gene, the SH-gene, the G-gene, and the L-gene. In a specific embodiment, MPV can be differentiated into a specific subgroup using the nucleotide or amino acid sequence of the G gene or glycoprotein and neutralization tests using monoclonal antibodies that also recognize the G glycoprotein.

In one embodiment, the diagnosis of an MPV infection in a human is made using any technique well known to one skilled in the art, e.g., immunoassays. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), sandwich immunoassays, immunoprecipitation assays, precipitin reactions, gel diffusion precipitation reactions, immunodiffusion assays, agglutination assays, complement-fixation assays, and fluorescent immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety) and non-limiting examples of immunoassays are described in section 5.8.

In one embodiment, the invention relates to the detection of an MPV infection using oligonucleotides in conjunction with PCR or primer extension methods to copy or amplify regions of the MPV genome, said regions including but not limited to genes or parts of genes, e.g., the N, M, F, G, L, M, P, and M2 genes. In a specific embodiment, oligonucleotides are used in conjunction with RT-PCR methods. In a further embodiment, the amplification products and/or genetic material can be probed with oligonucleotides that are complimentary to specific sequences that are either conserved between various hMPV strains or are distinct amongst various hMPV strains. The latter set of oligonucletides would allow for identification of the specific strain of hMPV responsible for the infection of the host.

The invention provides methods for distinguishing between different subgroups and variants of hMPV that are capable of infecting a host. In one specific embodiment, the hMPV that is responsible for a host infection is classified into a specific subgroup, e.g., subgroup A or subgroup B. In another specific embodiment, the hMPV that is responsible for a host infection is classified as a specific variant of a subgroup, e.g., variant A1, A2, B1, or B2. In another embodiment, the invention provides means and methods for the classification of an hMPV that is responsible for a host infection into a new subgroup and/or into a new variant of a new or existing subgroup. The methods that are able to distinguish hMPV strains into subgroups and/or variant groups would be known to one skilled in the art. In one embodiment, a polyclonal antibody is used to identify the etiological agent of an infection as a strain of hMPV, and a secondary antibody is used to distinguish said strain as characteristic of a new or known subgroup and/or new or known variant of hMPV. In one embodiment, antibodies that are selective for hMPV are used in conjunction with immunoreactive assays, e.g. ELISA or RIA, to identify the presence of hMPV exposure or infection in biological samples. In a further embodiment, secondary antibodies that are selective for specific epitopes in the peptide sequence of hMPV proteins are used to further classify the etiological agents of said identified hMPV infections into subgroups or variants. In one specific embodiment, an antibody raised against peptide epitopes that are shared between all subgroups of hMPV is used to identify the etiological agent of an infection as an hMPV. In a further specific embodiment, antibodies raised against peptide epitopes that are unique to the different subgroups and/or variants of hMPV are used to classify the hMPV that is responsible for the host infection into a known or new subgroup and/or variant. In one specific embodiment, the antibody that is capable of distinguishing between different subgroups and/or variants of hMPV recognizes segments of hMPV peptides that are unique to the subgroup or variant, said peptides including but not limited to those encoded by the N, M, F, G, L, M, P, and M2 genes. The peptides or segments of peptides that can be used to generate antibodies capable of distinguishing between different hMPV subgroups or variants can be selected using differences in known peptide sequences of various hMPV proteins in conjunction with hydrophilicity plots to identify suitable peptide segments that would be expected to be solvent exposed or accessible in a diagnostic assay. In one embodiment, the antibody that is capable of distinguishing between the different subgroups of hMPV recognizes differences in the F protein that are unique to different subgroups of hMPV, e.g. the amino acids at positions 286, 296, 312, 348, and 404 of the full length F protein. In another specific embodiment, the antibody that is capable of distinguishing between different subgroups and/or variants of hMPV recognizes segments of the G protein of hMPV that are unique to specific subgroups or variants, e.g., the G peptide sequence corresponding to amino acids 50 through 60 of SEQ ID:119 can be used to distinguish between subgroups A and B as well as between variants A1, A2, B1, and B2. In another embodiment of the invention, the nucleotide sequence of hMPV isolates are used to distinguish between different subgroups and/or different variants of hMPV. In one embodiment, oligonucleotide sequences, primers, and/or probes that are complimentary to sequences in the hMPV genome are used to classify the etiological agents of hMPV infections into distinct subgroups and/or variants in conjunction with methods known to one skilled in the art, e.g. RT-PCR, PCR, primer run on assays, and various blotting techniques. In one specific embodiment, a biological sample is used to copy or amplify a specific segment of the hMPV genome, using RT-PCR. In a further embodiment, the sequence of said segment is obtained and compared with known sequences of hMPV, and said comparison is used to classify the hMPV strain into a distinct subgroup or variant or to classify the hMPV strain into a new subgroup or variant. In another embodiment, the invention relates to diagnostic kits that can be used to distinguish between different subgroups and/or variants of hMPV.

In a preferred embodiment, diagnosis and/or treatment of a specific viral infection is performed with reagents that are most specific for said specific virus causing said infection. In this case this means that it is preferred that said diagnosis and/or treatment of an MPV infection is performed with reagents that are most specific for MPV. This by no means however excludes the possibility that less specific, but sufficiently crossreactive reagents are used instead, for example because they are more easily available and sufficiently address the task at hand. Herein it is for example provided to perform virological and/or serological diagnosis of MPV infections in mammals with reagents derived from APV, in particular with reagents derived from APV-C, in the detailed description herein it is for example shown that sufficiently trustworthy serological diagnosis of MPV infections in mammals can be achieved by using an ELISA specifically designed to detect APV antibodies in birds. A particular useful test for this purpose is an ELISA test designed for the detection of APV antibodies (e.g in serum or egg yolk), one commercially available version of which is known as APV-Ab SVANOVIR® which is manufactured by SVANOVA Biotech AB, Uppsal Science Park Glunten SE-751 83 Uppsala Sweden. The reverse situation is also the case, herein it is for example provided to perform virological and/or serological diagnosis of APV infections in mammals with reagents derived from MPV, in the detailed description herein it is for example shown that sufficiently trustworthy serological diagnosis of APV infections in birds can be achieved by using an ELISA designed to detect MPV antibodies. Considering that antigens and antibodies have a lock-and-key relationship, detection of the various antigens can be achieved by selecting the appropriate antibody having sufficient cross-reactivity. Of course, for relying on such cross-reactivity, it is best to select the reagents (such as antigens or antibodies) under guidance of the amino acid homologies that exist between the various (glyco)proteins of the various viruses, whereby reagents relating to the most homologous proteins will be most useful to be used in tests relying on said cross-reactivity.

For nucleic acid detection, it is even more straightforward, instead of designing primers or probes based on heterologous nucleic acid sequences of the various viruses and thus that detect differences between the essentially mammalian or avian *Metapneumoviruses*, it suffices to design or select primers or probes based on those stretches of virus-specific nucleic acid sequences that show high homology. In general, for nucleic acid sequences, homology percentages of 90% or higher guarantee sufficient cross-reactivity to be relied upon in diagnostic tests utilizing stringent conditions of hybridisation.

The invention for example provides a method for virologically diagnosing a MPV infection of an animal, in particular of a mammal, more in particular of a human being, comprising determining in a sample of said animal the presence of a viral isolate or component thereof by reacting said sample with a MPV specific nucleic acid a or antibody according to the invention, and a method for serologically diagnosing an MPV infection of a mammal comprising determining in a sample of said mammal the presence of an antibody specifically directed against an MPV or component thereof by reacting said sample with a MPV-specific proteinaceous molecule or fragment thereof or an antigen according to the invention. The invention also provides a diagnostic kit for diagnosing an MPV infection comprising an MPV, an MPV-specific nucleic acid, proteinaceous molecule or fragment thereof, antigen and/or an antibody according to the invention, and preferably a means for detecting said MPV, MPV-specific nucleic acid, proteinaceous molecule or fragment thereof, antigen and/or an antibody, said means for example comprising an excitable group such as a fluorophore or enzymatic detection system used in the art (examples of suitable diagnostic kit format comprise IF, ELISA, neutralization assay, RT-PCR assay). To determine whether an as yet unidentified virus component or synthetic analogue thereof such as nucleic acid, proteinaceous molecule or fragment thereof can be identified as MPV-specific, it suffices to analyse the nucleic acid or amino acid sequence of said component, for example for a stretch of said nucleic acid or amino acid, preferably of at least 10, more preferably at least 25, more preferably at least 40 nucleotides or amino acids (respectively), by sequence homology comparison with known MPV sequences and with known non-MPV sequences APV-C is preferably used) using for example phylogenetic analyses as provided herein. Depending on the degree of relationship with said MPV or non-MPV sequences, the component or synthetic analogue can be identified.

The invention also provides method for virologically diagnosing an MPV infection of a mammal comprising determining in a sample of said mammal the presence of a viral isolate or component thereof by reacting said sample with a cross-reactive nucleic acid derived from APV (preferably serotype C) or a cross-reactive antibody reactive with said APV, and a method for serologically diagnosing an MPV infection of a mammal comprising determining in a sample of said mammal the presence of a cross-reactive antibody that is also directed against an APV or component thereof by reacting said sample with a proteinaceous molecule or fragment thereof or an antigen derived from APV. Furthermore, the invention provides the use of a diagnostic kit initially designed for AVP or AVP-antibody detection for diagnosing an MPV infection, in particular for detecting said MPV infection in humans.

The invention also provides methods for virologically diagnosing an APV infection in a bird comprising determining in a sample of said bird the presence of a viral isolate or component thereof by reacting said sample with a cross-reactive nucleic acid derived from MPV or a cross-reactive antibody reactive with said MPV, and a method for serologically diagnosing an APV infection of a bird comprising determining in a sample of said bird the presence of a cross-reactive antibody that is also directed against an MPV or component thereof by reacting said sample with a proteinaceous molecule or fragment thereof or an antigen derived from MPV. Furthermore, the invention provides the use of a diagnostic kit initially designed for MPV or MPV-antibody detection for diagnosing an APV infection, in particular for detecting said APV infection in poultry such as a chicken, duck or turkey.

For diagnosis as for treatment, use can be made of the high degree of homology among different mammalian MPVs and between MPV and other viruses, such as, e.g., APV, in particular when circumstances at hand make the use of the more homologous approach less straightforward. Vaccinations that can not wait, such as emergency vaccinations against MPV infections can for example be performed with vaccine preparations derived from APV(preferably type C) isolates when a more homologous MPV vaccine is not available, and, vice versa, vaccinations against APV infections can be contemplated with vaccine preparations derived from MPV. Also, reverse genetic techniques make it possible to generate chimeric APV-MPV virus constructs that are useful as a vaccine, being sufficiently dissimilar to field isolates of each of the respective strains to be attenuated to a desirable level. Similar reverse genetic techniques will make it also possible to generate chimeric *paramyxovirus-metapneumovirus* constructs, such as RSV-MPV or P13-MPV constructs for us in a vaccine preparation. Such constructs are particularly useful as a combination vaccine to combat respiratory tract illnesses.

Since MPV CPE was virtually indistinguishable from that caused by hRSV or hPIV-1 in tMK or other cell cultures, the MPV may have well gone unnoticed until now. tMK (tertiary monkey kidney cells, i.e. MK cells in a third passage in cell culture) are preferably used due to their lower costs in comparison to primary or secondary cultures. The CPE is, as well as with some of the classical Paramyxoviridae, characterized by syncytium formation after which the cells showed rapid internal disruption, followed by detachment of the cells from the monolayer. The cells usually (but not always) displayed CPE after three passages of virus from original material, at day 10 to 14 post inoculation, somewhat later than CPE caused by other viruses such as hRSV or hPIV-1.

As an example, the invention provides a not previously identified *paramyxovirus* from nasopharyngeal aspirate samples taken from 28 children suffering from severe RTI. The clinical symptoms of these children were largely similar to those caused by hRSV. Twenty-seven of the patients were children below the age of five years and half of these were between 1 and 12 months old. The other patient was 18 years old. All individuals suffered from upper RTI, with symptoms ranging from cough, myalgia, vomiting and fever to broncheolitis and severe pneumonia. The majority of these patients were hospitalised for one to two weeks.

The virus isolates from these patients had the *paramyxovirus* morphology in negative contrast electron microscopy but did not react with specific antisera against known human and animal *paramyxoviruses*. They were all closely related to one another as determined by indirect immunofluorescence assays (IFA) with sera raised against two of the isolates. Sequence analyses of nine of these isolates revealed that the virus is somewhat related to APV. Based on virological data, sequence homology as well as the genomic organisation we propose that the virus is a member of *Metapneumovirus* genus. Serological surveys showed that this virus is a relatively common pathogen since the seroprevalence in the Netherlands approaches 100% of humans by the age of five years. Moreover, the seroprevalence was found to be equally high in sera collected from humans in 1958, indicating this virus has been circulating in the human population for more than 40 years. The identification of this proposed new member of the *Metapneumovirus* genus now also provides for the development of means and methods for diagnostic assays or test kits and vaccines or serum or antibody compositions for viral respiratory tract infections, and for methods to test or screen for antiviral agents useful in the treatment of MPV infections.

Methods and means provided herein are particularly useful in a diagnostic kit for diagnosing a MPV infection, be it by virological or serological diagnosis. Such kits or assays may for example comprise a virus, a nucleic acid, a proteinaceous molecule or fragment thereof, an antigen and/or an antibody according to the invention. Use of a virus, a nucleic acid, a proteinaceous molecule or fragment thereof, an antigen and/or an antibody according to the invention is also provided for the production of a pharmaceutical composition, for example for the treatment or prevention of MPV infections and/or for the treatment or prevention of respiratory tract illnesses, in particular in humans. Attenuation of the virus can be achieved by established methods developed for this purpose, including but not limited to the use of related viruses of other species, serial passages through laboratory animals or/and tissue/cell cultures, site directed mutagenesis of molecular clones and exchange of genes or gene fragments between related viruses.

Four distinct subtypes of hMPV have been described, referred to as subtypes A1, A2, B1 and B2. The invention relates to the detection of hMPV in a host using a single assay that is sensitive for all four subtypes. Any method known in the art can be used to detect the presence of hMPV in a host. In a more specific embodiment of the invention, a sensitive Taqman assay is used to detect the presence of hMPV in a host. One skilled in the art would be familiar with the requirements for the design of oligonucleotides and probes for use in such assays. Such oligonucleotides and probes can be designed to specifically recognize any region of the hMPV genome, transcripts or processed and unprocessed products thereof. In a more specific embodiment of the invention, the oligonucleotides and probes of the invention are complementary to or identical to, or similar to a sequence in all subtypes of hMPV, its transcripts, or processed and unprocessed products thereof, e.g., A1, B1, A2, and B2. In particular, the oligonucleotides and probes are at least 50%, 60%, 70%, 80%, 90%, 95%, 98%, 99%, or 99.5% identical to a negative or positive copy of the sequence in all four subtypes of hMPV, a transcript or processed and unprocessed products thereof. In another embodiment, it is complimentary to the negative or positive copy of the sequence in all four subtypes of hMPV. Any length oligonucleotides and probes can be used in the detection of assay of invention. Typical hybridization and washing conditions that may be used are known in the art. Preferably, the conditions are such as to enable the probe to bind specifically and to prevent the binding or easy removal of nonspecific binding. In yet another more specific embodiment of the invention, the oligonucleotides and probes of the invention are complementary to any of the open reading frames within the hMPV genome, including, but not limited to, the N-gene, P-gene, F-gene, M-gene, M2-gene, SH-gene, G-gene, and L-gene, or processed and unprocessed products thereof. In an even more specific embodiment of the invention, the oligonucleotides and probes of the invention recognize the N-gene, its transcripts, or processed and unprocessed products thereof. In yet another embodiment hMPV from all four subtypes are recognized with equal specificity.

Virus can be isolated from any biological sample obtainable from a host. In a more specific embodiment of the invention, nasopharyngeal samples are collected from a host for use in the detection assays of the invention. Virus can be propagated for detection purposes in a variety of cell lines that are able to support hMPV, including, but not limited to, Vero and tMK cells. The detection of viral RNA can be performed using a number of methods known to the skilled artisan. In one specific embodiment, viral RNA detection is performed using a Taqman PCR based method.

5.15 Compositions of the Invention and Components of Mammalian *Metapneumovirus*

The invention relates to nucleic acid sequences of a mammalian MPV, proteins of a mammalian MPV, and antibodies against proteins of a mammalian MPV. The invention further relates to homologs of nucleic acid sequences of a mammalian MPV and homologs of proteins of a mammalian MPV. The invention further relates to nucleic acid sequences encoding fusion proteins, wherein the fusion protein contains a protein of a mammalian MPV or a fragment thereof and one or more peptides or proteins that are not derived from mammalian MPV. In a specific embodiment, a fusion protein of the invention contains a protein of a mammalian MPV or a fragment thereof and a peptide tag, such as, but not limited to a polyhistidine tag. The invention further relates to fusion proteins, wherein the fusion protein contains a protein of a mammalian MPV or a fragment thereof and one or more peptides or proteins that are not derived from mammalian MPV. The invention also relates to derivatives of nucleic acids encoding a protein of a mammlian MPV. The invention also relates to derivatives of proteins of a mammalian MPV. A derivative can be, but is not limited to, mutant forms of the protein, such as, but not limited to, additions, deletions, truncations, substitutions, and inversions. A derivative can further be a chimeric form of the protein of the mammalian MPV, wherein at least one domain of the protein is derived from a different protein. A derivative can also be a form of a protein of a mammalian MPV that is covalently or non-covalently linked to another molecule, such as, e.g., a drug.

The viral isolate termed NL/1/00 (also 00-1) is a mammalian MPV of variant A1 and its genomic sequence is shown in SEQ ID NO:19. The viral isolate termed NL/17/00 is a mammalian MPV of variant A2 and its genomic sequence is shown in SEQ ID NO:20. The viral isolate termed NL/1/99 (also 99-1) is a mammalian MPV of variant B1 and its genomic sequence is shown in SEQ ID NO:18. The viral isolate termed NL/1/94 is a mammalian MPV of variant B2 and its genomic sequence is shown in SEQ ID NO:21. A list of sequences disclosed in the present application and the corresponding SEQ ID Nos is set forth in Table 14.

The protein of a mammalian MPV can be a an N protein, a P protein, a M protein, a F protein, a M2-1 protein or a M2-2 protein or a fragment thereof. A fragment of a protein of a mammlian MPV can be can be at least 25 amino acids, at least 50 amino acids, at least 75 amino acids, at least 100 amino acids, at least 125 amino acids, at least 150 amino acids, at least 175 amino acids, at least 200 amino acids, at least 225 amino acids, at least 250 amino acids, at least 275 amino acids, at least 300 amino acids, at least 325 amino acids, at least 350 amino acids, at least 375 amino acids, at least 400 amino acids, at least 425 amino acids, at least 450 amino acids, at least 475 amino acids, at least 500 amino acids, at least 750 amino acids, at least 1000 amino acids, at least 1250 amino acids, at least 1500 amino acids, at least 1750 amino acids, at least 2000 amino acids or at least 2250 amino acids in length. A fragment of a protein of a mammlian MPV can be can be at most 25 amino acids, at most 50 amino acids, at most 75 amino acids, at most 100 amino acids, at most 125 amino acids, at most 150 amino acids, at most 175 amino acids, at most 200 amino acids, at most 225 amino acids, at most 250 amino acids, at most 275 amino acids, at most 300 amino acids, at most 325 amino acids, at most 350 amino acids, at most 375 amino acids, at most 400 amino acids, at most 425 amino acids, at most 450 amino acids, at most 475 amino acids, at most 500 amino acids, at most 750 amino acids, at most 1000 amino acids, at most 1250 amino acids, at most 1500 amino acids, at most 1750 amino acids, at most 2000 amino acids or at most 2250 amino acids in length.

In certain embodiments of the invention, the protein of a mammalian MPV is a N protein, wherein the N protein is phylogenetically closer related to a N protein of a mammalian MPV, such as the N protein encoded by, e.g., the viral genome of SEQ ID NO:18, SEQ ID NO:19, SEQ ID NO:20, or SEQ ID NO:21, (see also Table 14 for a description of the SEQ ID Nos) than it is related to the N protein of APV type C. In certain embodiments of the invention, the protein of a mammalian MPV is a P protein, wherein the P protein is phylogenetically closer related to a P protein of a mammalian MPV, such as the P protein encoded by, e.g., the viral genome of SEQ ID NO:18, SEQ ID NO:19, SEQ ID NO:20, or SEQ ID NO:21, than it is related to the N protein of APV type C. In certain embodiments of the invention, the protein of a mammalian MPV is a M protein, wherein the M protein is closer related to a M protein of a mammalian MPV, such as the M protein encoded by, e.g., the viral genome of SEQ ID NO:18, SEQ ID NO:19, SEQ ID NO:20, or SEQ ID NO:21, than it is related to the M protein of APV type C. In certain embodiments of the invention, the protein of a mammalian MPV is a F protein, wherein the F protein is phylogenetically closer related to a F protein of a mammalian MPV, such as the F protein encoded by, e.g., the viral genome of SEQ ID NO:18, SEQ ID NO:19, SEQ ID NO:20, or SEQ ID NO:21, than it is related to the F protein of APV type C. In certain embodiments of the invention, the protein of a mammalian MPV is a M2-1 protein, wherein the M2-1 protein is phylogenetically closer related to a M2-1 protein of a mammalian MPV, such as the M2-1 protein encoded by, e.g., the viral genome of SEQ ID NO:18, SEQ ID NO:19, SEQ ID NO:20, or SEQ ID NO:21, than it is related to the M2-1 protein of APV type C. In certain embodiments of the invention, the protein of a mammalian MPV is a M2-2 protein, wherein the M2-2 protein is phylogenetically closer related to a M2-2 protein of a mammalian MPV, such as the M2-2 protein encoded by, e.g., the viral genome of SEQ ID NO:18, SEQ ID NO:19, SEQ ID NO:20, or SEQ ID NO:21, than it is related to the M2-2 protein of APV type C. In certain embodiments of the invention, the protein of a mammalian MPV is a G protein, wherein the G protein is phylogenetically closer related to a G protein of a mammalian MPV, such as the G protein encoded by, e.g., the viral genome of SEQ ID NO:18, SEQ ID NO:19, SEQ ID NO:20, or SEQ ID NO:21, than it is related to any protein of APV type C. In certain embodiments of the invention, the protein of a mammalian MPV is a SH protein, wherein the SH protein is phylogenetically closer related to a SH protein of a mammalian MPV, such as the SH protein encoded by, e.g., the viral genome of SEQ ID NO:18, SEQ ID NO:19, SEQ ID NO:20, or SEQ ID NO:21, than it is related to any protein of APV type C. In certain embodiments of the invention, the protein of a mammalian MPV is a L protein, wherein the L protein is phylogenetically closer related to a L protein of a mammalian MPV, such as the SH protein encoded by, e.g., the viral genome of SEQ ID NO:18, SEQ ID NO:19, SEQ ID NO:20, or SEQ ID NO:21, than it is related to any protein of APV type C.

In certain embodiments of the invention, the protein of a mammalian MPV is a N protein, wherein the N protein is at least 60%, at least 65%, at least 70%, at least 75%, at least 80%, at least 85%, at least 90%, at least 95%, at least 98%, at least 99%, or at least 99.5% identical to the amino acid sequence of a N protein encoded by the viral genome of SEQ ID NO:18, SEQ ID NO:19, SEQ ID NO:20, or SEQ ID NO:21 (the amino acid sequences of the respective N proteins are disclosed in SEQ ID NO:366-369; see also Table 14). In certain embodiments of the invention, the protein of a mammalian MPV is a N protein, wherein the P protein is at least 60%, at least 65%, at least 70%, at least 75%, at least 80%, at least 85%, at least 90%, at least 95%, at least 98%, at least 99%, or at least 99.5% identical to the amino acid sequence of a P protein encoded by the viral genome of SEQ ID NO:18, SEQ ID NO:19, SEQ ID NO:20, or SEQ ID NO:21 (the amino acid sequences of the respective P proteins are disclosed in SEQ ID NO:374-377; see also Table 14). In certain embodiments of the invention, the protein of a mammalian MPV is a M protein, wherein the M protein is at least 60%, at least 65%, at least 70%, at least 75%, at least 80%, at least 85%, at least 90%, at least 95%, at least 98%, at least 99%, or at least 99.5% identical to the amino acid sequence of a M protein encoded by the viral genome of SEQ ID NO:18, SEQ ID NO:19, SEQ ID NO:20, or SEQ ID NO:21 (the amino acid sequences of the respective M proteins are disclosed in SEQ ID NO:358-361; see also Table 14). In certain embodiments of the invention, the protein of a mammalian MPV is a F protein, wherein the F protein is at least 60%, at least 65%, at least 70%, at least 75%, at least 80%, at least 85%, at least 90%, at least 95%, at least 98%, at least 99%, or at least 99.5% identical to the amino acid sequence of a F protein encoded by the viral genome of SEQ ID NO:18, SEQ ID NO:19, SEQ ID NO:20, or SEQ ID NO:21 (the amino acid sequences of the respective F proteins are disclosed in SEQ ID NO:314-317; see also Table 14). In certain embodiments of the invention, the protein of a mammalian MPV is a M2-1 protein, wherein the M2-1 protein is at least 60%, at least 65%, at least 70%, at least 75%, at least 80%, at least 85%, at least 90%, at least 95%, at least 98%, at least 99%, or at least 99.5% identical to the amino acid sequence of a M2-1 protein encoded by the viral genome of SEQ ID NO:18, SEQ ID NO:19, SEQ ID NO:20, or SEQ ID NO:21 (the amino acid sequences of the respective M2-1 proteins are disclosed in SEQ ID NO:338-341; see also Table 14). In certain embodiments of the invention, the protein of a mammalian MPV is a M2-2 protein, wherein the M2-2 protein is at least 60%, at least 65%, at least 70%, at least 75%, at least 80%, at least 85%, at least 90%, at least 95%, at least 98%, at least 99%, or at least 99.5% identical to the amino acid sequence of a M2-2 protein encoded by the viral genome of SEQ ID NO:18, SEQ ID NO:19, SEQ ID NO:20, or SEQ ID NO:21 (the amino acid sequences of the respective M2-2 proteins are disclosed in SEQ ID NO:346-349; see also Table 14). In certain embodiments of the invention, the protein of a mammalian MPV is a G protein, wherein the G protein is at least 60%, at least 65%, at least 70%, at least 75%, at least 80%, at least 85%, at least 90%, at least 95%, at least 98%, at least 99%, or at least 99.5% identical to the amino acid sequence of a G protein encoded by the viral genome of SEQ ID NO:18, SEQ ID NO:19, SEQ ID NO:20, or SEQ ID NO:21 (the amino acid sequences of the respective G proteins are disclosed in SEQ ID NO:322-325; see also Table 14). In certain embodiments of the invention, the protein of a mammalian MPV is a SH protein, wherein the SH protein is at least 60%, at least 65%, at least 70%, at least 75%, at least 80%, at least 85%, at least 90%, at least 95%, at least 98%, at least 99%, or at least 99.5% identical to the amino acid sequence of a SH protein encoded by the viral genome of SEQ ID NO:18, SEQ ID NO:19, SEQ ID NO:20, or SEQ ID NO:21 (the amino acid sequences of the respective SH proteins are disclosed in SEQ ID NO:382-385; see also Table 14). In certain embodiments of the invention, the protein of a mammalian MPV is a L protein, wherein the L protein is at least 60%, at least 65%, at least 70%, at least 75%, at least 80%, at least 85%, at least 90%, at least 95%, at least 98%, at least 99%, or at least 99.5% identical to the amino acid sequence of a L protein encoded by the viral genome of SEQ ID NO:18, SEQ ID NO:19, SEQ ID NO:20, or SEQ ID NO:21 (the amino acid sequences of the respective L proteins are disclosed in SEQ ID NO:330-333; see also Table 14).

A fragment of a protein of mammalian MPV is at least 60%, at least 65%, at least 70%, at least 75%, at least 80%, at least 85%, at least 90%, at least 95%, at least 98%, at least 99%, or at least 99.5% identical to the homologous protein encoded by the virus of SEQ ID NO:18, SEQ ID NO:19, SEQ ID NO:20, or SEQ ID NO:21 over the portion of the protein that is homologous to the fragment. In a specific, illustrative embodiment, the invention provides a fragment of the F protein of a mammalian MPV that contains the ectodomain of the F protein and homologs thereof. The homolog of the fragment of the F protein that contains the ectodomain is at least 60%, at least 65%, at least 70%, at least 75%, at least 80%, at least 85%, at least 90%, at least 95%, at least 98%, at least 99%, or at least 99.5% identical to the corresponding fragment containing the ectodomain of the F protein encoded by a virus of SEQ ID NO:18, SEQ ID NO:19, SEQ ID NO:20, or SEQ ID NO:21 (the amino acid sequences of the respective F proteins are disclosed in SEQ ID NO:314-317; see also Table 14).

In certain embodiments, the invention provides a protein of a mammalian MPV of subgroup A and fragments thereof. The invention provides a N protein of a mammalian MPV of subgroup A, wherein the N protein is phylogenetically closer related to the N protein encoded by a virus of SEQ ID NO:19 or SEQ ID NO:20 than it is related to the N protein encoded by a virus encoded by SEQ ID NO:18 or SEQ ID NO:21. The invention provides a G protein of a mammalian MPV of subgroup A, wherein the G protein is phylogenetically closer related to the G protein encoded by a virus of SEQ ID NO:19 or SEQ ID NO:20 than it is related to the G protein encoded by a virus encoded by SEQ ID NO:18 or SEQ ID NO:21. The invention provides a P protein of a mammalian MPV of subgroup A, wherein the P protein is phylogenetically closer related to the P protein encoded by a virus of SEQ ID NO:19 or SEQ ID NO:20 than it is related to the P protein encoded by a virus encoded by SEQ ID NO:18 or SEQ ID NO:21. The invention provides a M protein of a mammalian MPV of subgroup A, wherein the M protein is phylogenetically closer related to the M protein encoded by a virus of SEQ ID NO:19 or SEQ ID NO:20 than it is related to the M protein encoded by a virus encoded by SEQ ID NO:18 or SEQ ID NO:21. The invention provides a N protein of a mammalian MPV of subgroup A, wherein the F protein is phylogenetically closer related to the F protein encoded by a virus of SEQ ID NO:19 or SEQ ID NO:20 than it is related to the F protein encoded by a virus encoded by SEQ ID NO:18 or SEQ ID NO:21. The invention provides a M2-1 protein of a mammalian MPV of subgroup A, wherein the M2-1 protein is phylogenetically closer related to the M2-1 protein encoded by a virus of SEQ ID NO:19 or SEQ ID NO:20 than it is related to the M2-1 protein encoded by a virus encoded by SEQ ID NO:18 or SEQ ID NO:21. The invention provides a M2-2 protein of a mammalian MPV of subgroup A, wherein the M2-2 protein is phylogenetically closer related to the M2-2 protein encoded by a virus of SEQ ID NO:19 or SEQ ID NO:20 than it is related to the M2-2 protein encoded by a virus encoded by SEQ ID NO:18 or SEQ ID NO:21. The invention provides a SH protein of a mammalian MPV of subgroup A, wherein the SH protein is phylogenetically closer related to the SH protein encoded by a virus of SEQ ID NO:19 or SEQ ID NO:20 than it is related to the SH protein encoded by a virus encoded by SEQ ID NO:18 or SEQ ID NO:21. The invention provides a L protein of a mammalian MPV of subgroup A, wherein the L protein is phylogenetically closer related to the L protein encoded by a virus of SEQ ID NO:19 or SEQ ID NO:20 than it is related to the L protein encoded by a virus encoded by SEQ ID NO:18 or SEQ ID NO:21.

In other embodiments, the invention provides a protein of a mammalian MPV of subgroup B or fragments thereof. The invention provides a N protein of a mammalian MPV of subgroup B, wherein the N protein is phylogenetically closer related to the N protein encoded by a virus of SEQ ID NO:18 or SEQ ID NO:21 than it is related to the N protein encoded by a virus encoded by SEQ ID NO:19 or SEQ ID NO:20. The invention provides a G protein of a mammalian MPV of subgroup A, wherein the G protein is phylogenetically closer related to the G protein encoded by a virus of SEQ ID NO:18 or SEQ ID NO:21 than it is related to the G protein encoded by a virus encoded by SEQ ID NO:19 or SEQ ID NO:20. The invention provides a P protein of a mammalian MPV of subgroup A, wherein the P protein is phylogenetically closer related to the P protein encoded by a virus of SEQ ID NO:18 or SEQ ID NO:21 than it is related to the P protein encoded by a virus encoded by SEQ ID NO:19 or SEQ ID NO:20. The invention provides a M protein of a mammalian MPV of subgroup A, wherein the M protein is phylogenetically closer related to the M protein encoded by a virus of SEQ ID NO:18 or SEQ ID NO:21 than it is related to the M protein encoded by a virus encoded by SEQ ID NO:19 or SEQ ID NO:20. The invention provides a N protein of a mammalian MPV of subgroup A, wherein the F protein is phylogenetically closer related to the F protein encoded by a virus of SEQ ID NO:18 or SEQ ID NO:21 than it is related to the F protein encoded by a virus encoded by SEQ ID NO:19 or SEQ ID NO:20. The invention provides a M2-1 protein of a mammalian MPV of subgroup A, wherein the M2-1 protein is phylogenetically closer related to the M2-1 protein encoded by a virus of SEQ ID NO:18 or SEQ ID NO:21 than it is related to the M2-1 protein encoded by a virus encoded by SEQ ID NO:19 or SEQ ID NO:20. The invention provides a M2-2 protein of a mammalian MPV of subgroup A, wherein the M2-2 protein is phylogenetically closer related to the M2-2 protein encoded by a virus of SEQ ID NO:18 or SEQ ID NO:21 than it is related to the M2-2 protein encoded by a virus encoded by SEQ ID NO:19 or SEQ ID NO:20. The invention provides a SH protein of a mammalian MPV of subgroup A, wherein the SH protein is phylogenetically closer related to the SH protein encoded by a virus of SEQ ID NO:18 or SEQ ID NO:21 than it is related to the SH protein encoded by a virus encoded by SEQ ID NO:19 or SEQ ID NO:20. The invention provides a L protein of a mammalian MPV of subgroup A, wherein the L protein is phylogenetically closer related to the L protein encoded by a virus of SEQ ID NO:18 or SEQ ID NO:21 than it is related to the L protein encoded by a virus encoded by SEQ ID NO:19 or SEQ ID NO:20.

The invention further provides proteins of a mammalian MPV of variant A1, A2, B1 or B2. In certain embodiments of the invention, the proteins of the different variants of mammalian MPV can be distinguished from each other by way of their amino acid sequence identities (see, e.g., FIG. 42*b*). A variant of mammalian MPV can be, but is not limited to, A1, A2, B1 or B2. The invention, however, also contemplates isolates of mammalian MPV that are members of another variant.

The invention provides a G protein of a mammalian MPV variant B 1, wherein the G protein of a mammalian MPV variant B1 is phylogenetically closer related to the G protein of the prototype of variant B1, isolate NL/1/99, than it is related to the G protein of the prototype of variant A1, isolate NL/1/00, the G protein of the prototype of A2, isolate NL/17/00, or the G protein of the prototype of B2, isolate NL/1/94. The invention provides a G protein of a mammalian MPV variant B1, wherein the amino acid sequence of the G protein is at least 66%, at least 70%, at least 75%, at least 80%, at least 85%, at least 90%, at least 95%, at least 98%, or at least 99% or at least 99.5% identical to the G protein of a mammalian MPV variant B1 as represented by the prototype NL/1/99 (SEQ ID NO:324). The invention provides a N protein of a mammalian MPV variant B1, wherein the N protein of a mammalian MPV variant B1 is phylogenetically closer related to the N protein of the prototype of variant B1, isolate NL/1/99, than it is related to the N protein of the prototype of variant A1, isolate NL/1/00, the N protein of the prototype of A2, isolate NL/17/00, or the N protein of the prototype of B2, isolate NL/1/94. The invention provides a N protein of a mammalian MPV variant B1, wherein the amino acid sequence of the N proteint is at least 98.5% or at least 99% or at least 99.5% identical to the N protein of a mammalian MPV variant B1 as represented by the prototype NL/1/99 (SEQ ID NO:368). The invention provides a P protein of a mammalian MPV variant B1, wherein the P protein of a mammalian MPV variant B1 is phylogenetically closer related to the P protein of the prototype of variant B1, isolate NL/1/99, than it is related to the P protein of the prototype of variant A1, isolate NL/1/00, the P protein of the prototype of A2, isolate NL/17/00, or the P protein of the prototype of B2, isolate NL/1/94. The invention provides a P protein of a mammalian MPV variant B1, wherein the amino acid sequence of the P protein is at least 96%, at least 98%, or at least 99% or at least 99.5% identical the P protein of a mammalian MPV variant B1 as represented by the prototype NL/1/99 (SEQ ID NO:376). The invention provides a M protein of a mammalian MPV variant B1, wherein the M protein of a mammalian MPV variant B1 is phylogenetically closer related to the M protein of the prototype of variant B1, isolate NL/1/99, than it is related to the M protein of the prototype of variant A1, isolate NL/1/00, the M protein of the prototype of A2, isolate NL/17/00, or the M protein of the prototype of B2, isolate NL/1/94. The invention provides a M protein of a mammalian MPV variant B1, wherein the amino acid sequence of the M protein is identical the M protein of a mammalian MPV variant B1 as represented by the prototype NL/1/99 (SEQ ID NO:360). The invention provides a F protein of a mammalian MPV variant B1, wherein the F protein of a mammalian MPV variant B1 is phylogenetically closer related to the F protein of the prototype of variant B1, isolate NL/1/99, than it is related to the F protein of the prototype of variant A1, isolate NL/1/00, the F protein of the prototype of A2, isolate NL/17/00, or the F protein of the prototype of B2, isolate NL/1/94. The invention provides a F protein of a mammalian MPV variant B1, wherein the amino acid sequence of the F protein is at least 99% identical to the F protein of a mammalian MPV variant B1 as represented by the prototype NL/1/99 (SEQ ID NO:316). The invention provides a M2-1 protein of a mammalian MPV variant B1, wherein the M2-1 protein of a mammalian MPV variant B1 is phylogenetically closer related to the M2-1 protein of the prototype of variant B1, isolate NL/1/99, than it is related to the M2-1 protein of the prototype of variant A1, isolate NL/1/00, the M2-1 protein of the prototype of A2, isolate NL/17/00, or the M2-1 protein of the prototype of B2, isolate NL/1/94. The invention provides a M2-1 protein of a mammalian MPV variant B1, wherein the amino acid sequence of the M2-1 protein is at least 98% or at least 99% or at least 99.5% identical the M2-1 protein of a mammalian MPV variant B1 as represented by the prototype NL/1/99 (SEQ ID NO:340). The invention provides a M2-2 protein of a mammalian MPV variant B1, wherein the M2-2 protein of a mammalian MPV variant B1 is phylogenetically closer related to the M2-2 protein of the prototype of variant B1, isolate NL/1/99, than it is related to the M2-2 protein of the prototype of variant A1, isolate NL/1/00, the M2-2 protein of the prototype of A2, isolate NL/17/00, or the M2-2 protein of the prototype of B2, isolate NL/1/94. The invention provides a M2-2 protein of a mammalian MPV variant B1, wherein the amino acid sequence of the M2-2 protein is at least 99% or at least 99.5% identical the M2-2 protein of a mammalian MPV variant B1 as represented by the prototype NL/1/99 (SEQ ID NO:348). The invention provides a SH protein of a mammalian MPV variant B1, wherein the SH protein of a mammalian MPV variant B1 is phylogenetically closer related to the SH protein of the prototype of variant B1, isolate NL/1/99, than it is related to the SH protein of the prototype of variant A1, isolate NL/1/00, the SH protein of the prototype of A2, isolate NL/17/00, or the SH protein of the prototype of B2, isolate NL/1/94. The invention provides a SH protein of a mammalian MPV variant B1, wherein the amino acid sequence of the SH protein is at least 83%, at least 85%, at least 90%, at least 95%, at least 98%, or at least 99% or at least 99.5% identical the SH protein of a mammalian MPV variant B1 as represented by the prototype NL/1/99 (SEQ ID NO:384). The invention provides a L protein of a mammalian MPV variant B1, wherein the L protein of a mammalian MPV variant B1 is phylogenetically closer related to the L protein of the prototype of variant B1, isolate NL/1/99, than it is related to the L protein of the prototype of variant A1, isolate NL/1/00, the L protein of the prototype of A2, isolate NL/17/00, or the L protein of the prototype of B2, isolate NL/1/94. The invention provides a L protein of a mammalian MPV variant B1, wherein the amino acid sequence of the L protein is at least 99% or at least 99.5% identical the L protein a mammalian MPV variant B1 as represented by the prototype NL/1/99 (SEQ ID NO:332).

The invention provides a G protein of a mammalian MPV variant A1, wherein the G protein of a mammalian MPV variant A1 is phylogenetically closer related to the G protein of the prototype of variant A1, isolate NL/1/00, than it is related to the G protein of the prototype of variant B1, isolate NL/1/99, the G protein of the prototype of A2, isolate NL/17/00, or the G protein of the prototype of B2, isolate NL/1/94. The invention provides a G protein of a mammalian MPV variant A1, wherein the amino acid sequence of the G protein is at least 66%, at least 70%, at least 75%, at least 80%, at least 85%, at least 90%, at least 95%, at least 98%, or at least 99% or at least 99.5% identical to the G protein of a mammalian MPV variant A1 as represented by the prototype NL/1/00 (SEQ ID NO:322). The invention provides a N protein of a mammalian MPV variant A1, wherein the N protein of a mammalian MPV variant A1 is phylogenetically closer related to the N protein of the prototype of variant A1, isolate NL/1/00, than it is related to the N protein of the prototype of variant B1, isolate NL/1/99, the N protein of the prototype of A2, isolate NL/17/00, or the N protein of the prototype of B2, isolate NL/1/94. The invention provides a N protein of a mammalian MPV variant A1, wherein the amino acid sequence of the N protein is at least 99.5% identical to the N protein of a mammalian MPV variant A1 as represented by the prototype NL/1/00 (SEQ ID NO:366). The invention provides a P protein of a mammalian MPV variant A1, wherein the P protein of a mammalian MPV variant A1 is phylogenetically closer related to the P protein of the prototype of variant A1, isolate NL/1/00, than it is related to the P protein of the prototype of variant B1, isolate NL/1/99, the P protein of the prototype of A2, isolate NL/17/00, or the P protein of the prototype of B2, isolate NL/1/94. The invention provides a P protein of a mammalian MPV variant A1, wherein the amino acid sequence of the P protein is at least 96%, at least 98%, or at least 99% or at least 99.5% identical to the P protein of a mammalian MPV variant A1 as represented by the prototype NL/1/00 (SEQ ID NO:374). The invention provides a M protein of a mammalian MPV variant A1, wherein the M protein of a mammalian MPV variant A1 is phylogenetically closer related to the M protein of the prototype of variant A1, isolate NL/1/00, than it is related to the M protein of the prototype of variant B1, isolate NL/1/99, the M protein of the prototype of A2, isolate NL/17/00, or the M protein of the prototype of B2, isolate NL/1/94. The invention provides a M protein of a mammalian MPV variant A1, wherein the amino acid sequence of the M protein is at least 99% or at least 99.5% identical to the M protein of a mammalian MPV variant A1 as represented by the prototype NL/1/00 (SEQ ID NO:358). The invention provides a F protein of a mammalian MPV variant A1, wherein the F protein of a mammalian MPV variant A1 is phylogenetically closer related to the F protein of the prototype of variant A1, isolate NL/1/00, than it is related to the F protein of the prototype of variant B1, isolate NL/1/99, the F protein of the prototype of A2, isolate NL/17/00, or the F protein of the prototype of B2, isolate NL/1/94. The invention provides a F protein of a mammalian MPV variant A1, wherein the amino acid sequence of the F protein is at least 98% or at least 99% or at least 99.5% identical to the F protein of a mammalian MPV variant A1 as represented by the prototype NL/1/00 (SEQ ID NO:314). The invention provides a M2-1 protein of a mammalian MPV variant A1, wherein the M2-1 protein of a mammalian MPV variant A1 is phylogenetically closer related to the M2-1 protein of the prototype of variant A1, isolate NL/1/00, than it is related to the M2-1 protein of the prototype of variant B1, isolate NL/1/99, the M2-1 protein of the prototype of A2, isolate NL/17/00, or the M2-1 protein of the prototype of B2, isolate NL/1/94. The invention provides a M2-1 protein of a mammalian MPV variant A1, wherein the amino acid sequence of the M2-1 protein is at least 99% or at least 99.5% identical to the M2-1 protein of a mammalian MPV variant A1 as represented by the prototype NL/1/00 (SEQ ID NO:338). The invention provides a M2-2 protein of a mammalian MPV variant A1, wherein the M2-2 protein of a mammalian MPV variant A1 is phylogenetically closer related to the M2-2 protein of the prototype of variant A1, isolate NL/1/00, than it is related to the M2-2 protein of the prototype of variant B1, isolate NL/1/99, the M2-2 protein of the prototype of A2, isolate NL/17/00, or the M2-2 protein of the prototype of B2, isolate NL/1/94. The invention provides a M2-2 protein of a mammalian MPV variant A1, wherein the amino acid sequence of the M2-2 protein is at least 96% or at least 99% or at least 99.5% identical to the M2-2 protein of a mammalian MPV variant A1 as represented by the prototype NL/1/00 (SEQ ID NO:346). The invention provides a SH protein of a mammalian MPV variant A1, wherein the SH protein of a mammalian MPV variant A1 is phylogenetically closer related to the SH protein of the prototype of variant A1, isolate NL/1/00, than it is related to the SH protein of the prototype of variant B1, isolate NL/1/99, the SH protein of the prototype of A2, isolate NL/17/00, or the SH protein of the prototype of B2, isolate NL/1/94. The invention provides a SH protein of a mammalian MPV variant A1, wherein the amino acid sequence of the SH protein is at least 84%, at least 90%, at least 95%, at least 98%, or at least 99% or at least 99.5% identical to the SH protein of a mammalian MPV variant A1 as represented by the prototype NL/1/00 (SEQ ID NO:382). The invention provides a L protein of a mammalian MPV variant A1, wherein the L protein of a mammalian MPV variant A1 is phylogenetically closer related to the L protein of the prototype of variant A1, isolate NL/1/00, than it is related to the L protein of the prototype of variant B1, isolate NL/1/99, the L protein of the prototype of A2, isolate NL/17/00, or the L protein of the prototype of B2, isolate NL/1/94. The invention provides a L protein of a mammalian MPV variant A1, wherein the amino acid sequence of the L protein is at least 99% or at least 99.5% identical to the L protein of a virus of a mammalian MPV variant A1 as represented by the prototype NL/1/00 (SEQ ID NO:330).

The invention provides a G protein of a mammalian MPV variant A2, wherein the G protein of a mammalian MPV variant A2 is phylogenetically closer related to the G protein of the prototype of variant A2, isolate NL/17/00, than it is related to the G protein of the prototype of variant B1, isolate NL/1/99, the G protein of the prototype of A1, isolate NL/1/00, or the G protein of the prototype of B2, isolate NL/1/94. The invention provides a G protein of a mammalian MPV variant A2, wherein the amino acid sequence of the G protein is at least 66%, at least 70%, at least 75%, at least 80%, at least 85%, at least 90%, at least 95%, at least 98%, at least 99% or at least 99.5% identical to the G protein of a mammalian MPV variant A2 as represented by the prototype NL/17/00 (SEQ ID NO:332). The invention provides a N protein of a mammalian MPV variant A2, wherein the N protein of a mammalian MPV variant A2 is phylogenetically closer related to the N protein of the prototype of variant A2, isolate NL/17/00, than it is related to the N protein of the prototype of variant B1, isolate NL/1/99, the N protein of the prototype of A1, isolate NL/1/00, or the N protein of the prototype of B2, isolate NL/1/94.

The invention provides a N protein of a mammalian MPV variant A2, wherein the amino acid sequence of the N protein at least 99.5% identical to the N protein of a mammalian MPV variant A2 as represented by the prototype NL/17/00 (SEQ ID NO:367). The invention provides a P protein of a mammalian MPV variant A2, wherein the P protein of a mammalian MPV variant A2 is phylogenetically closer related to the P protein of the prototype of variant A2, isolate NL/17/00, than it is related to the P protein of the prototype of variant B1, isolate NL/1/99, the P protein of the prototype of A1, isolate NL/1/00, or the P protein of the prototype of B2, isolate NL/1/94. The invention provides a P protein of a mammalian MPV variant A2, wherein the amino acid sequence of the P protein is at least 96%, at least 98%, at least 99% or at least 99.5% identical to the P protein of a mammalian MPV variant A2 as represented by the prototype NL/17/00(SEQ ID NO:375). The invention provides a M protein of a mammalian MPV variant A2, wherein the M protein of a mammalian MPV variant A2 is phylogenetically closer related to the M protein of the prototype of variant A2, isolate NL/17/00, than it is related to the M protein of the prototype of variant B1, isolate NL/1/99, the M protein of the prototype of A1, isolate NL/1/00, or the M protein of the prototype of B2, isolate NL/1/94. The invention provides a M protein of a mammalian MPV variant A2, wherein the amino acid sequence of the M protein is at least 99%, or at least 99.5% identical to the M protein of a mammalian MPV variant A2 as represented by the prototype NL/17/00(SEQ ID NO:359). The invention provides a F protein of a mammalian MPV variant A2, wherein the F protein of a mammalian MPV variant A2 is phylogenetically closer related to the F protein of the prototype of variant A2, isolate NL/17/00, than it is related to the F protein of the prototype of variant B1, isolate NL/1/99, the F protein of the prototype of A1, isolate NL/1/00, or the F protein of the prototype of B2, isolate NL/1/94. The invention provides a F protein of a mammalian MPV variant A2, wherein the amino acid sequence of the F protein is at least 98%, at least 99% or at least 99.5% identical to the F protein of a mammalian MPV variant A2 as represented by the prototype NL/17/00 (SEQ ID NO:315). The invention provides a M2-1 protein of a mammalian MPV variant A2, wherein the M2-1 protein of a mammalian MPV variant A2 is phylogenetically closer related to the M2-1 protein of the prototype of variant A2, isolate NL/17/00, than it is related to the M2-1 protein of the prototype of variant B1, isolate NL/1/99, the M2-1 protein of the prototype of A1, isolate NL/1/00, or the M2-1 protein of the prototype of B2, isolate NL/1/94. The invention provides a M2-1 protein of a mammalian MPV variant A2, wherein the amino acid sequence of the M2-1 protein is at least 99%, or at least 99.5% identical to the M2-1 protein of a mammalian MPV variant A2 as represented by the prototype NL/17/00 (SEQ ID NO: 339). The invention provides a M2-2 protein of a mammalian MPV variant A2, wherein the M2-2 protein of a mammalian MPV variant A2 is phylogenetically closer related to the M2-2 protein of the prototype of variant A2, isolate NL/17/00, than it is related to the M2-2 protein of the prototype of variant B1, isolate NL/1/99, the M2-2 protein of the prototype of A1, isolate NL/1/00, or the M2-2 protein of the prototype of B2, isolate NL/1/94. The invention provides a M2-2 protein of a mammalian MPV variant A2, wherein the amino acid sequence of the M2-2 protein is at least 96%, at least 98%, at least 99% or at least 99.5% identical to the M2-2 protein of a mammalian MPV variant A2 as represented by the prototype NL/17/00 (SEQ ID NO:347). The invention provides a SH protein of a mammalian MPV variant A2, wherein the SH protein of a mammalian MPV variant A2 is phylogenetically closer related to the SH protein of the prototype of variant A2, isolate NL/17/00, than it is related to the SH protein of the prototype of variant B1, isolate NL/1/99, the SH protein of the prototype of A1, isolate NL/1/00, or the SH protein of the prototype of B2, isolate NL/1/94. The invention provides a SH protein of a mammalian MPV variant A2, wherein the amino acid sequence of the SH protein is at least 84%, at least 85%, at least 90%, at least 95%, at least 98%, at least 99% or at least 99.5% identical to the SH protein of a mammalian MPV variant A2 as represented by the prototype NL/17/00(SEQ ID NO:383). The invention provides a L protein of a mammalian MPV variant A2, wherein the L protein of a mammalian MPV variant A2 is phylogenetically closer related to the L protein of the prototype of variant A2, isolate NL/17/00, than it is related to the L protein of the prototype of variant B1, isolate NL/1/99, the L protein of the prototype of A1, isolate NL/1/00, or the L protein of the prototype of B2, isolate NL/1/94. The invention provides a L protein of a mammalian MPV variant A2, wherein the amino acid sequence of the L protein is at least 99% or at least 99.5% identical to the L protein of a mammalian MPV variant A2 as represented by the prototype NL/17/00 (SEQ ID NO:331).

The invention provides a G protein of a mammalian MPV variant B2, wherein the G protein of a mammalian MPV variant B2 is phylogenetically closer related to the G protein of the prototype of variant B2, isolate NL/1/94, than it is related to the G protein of the prototype of variant B1, isolate NL/1/99, the G protein of the prototype of A1, isolate NL/1/00, or the G protein of the prototype of A2, isolate NL/17/00. The invention provides a G protein of a mammalian MPV variant B2, wherein the amino acid sequence of the G protein is at least 66%, at least 70%, at least 75%, at least 80%, at least 85%, at least 90%, at least 95%, at least 98%, or at least 99% or at least 99.5% identical to the G protein of a mammalian MPV variant B2 as represented by the prototype NL/1/94 (SEQ ID NO:325). The invention provides a N protein of a mammalian MPV variant B2, wherein the N protein of a mammalian MPV variant B2 is phylogenetically closer related to the N protein of the prototype of variant B2, isolate NL/1/94, than it is related to the N protein of the prototype of variant B1, isolate NL/1/99, the N protein of the prototype of A1, isolate NL/1/00, or the N protein of the prototype of A2, isolate NL/17/00. The invention provides a N protein of a mammalian MPV variant B2, wherein the amino acid sequence of the N protein is at least 99% or at least 99.5% identical to the N protein of a mammalian MPV variant B2 as represented by the prototype NL/1/94 (SEQ ID NO:369). The invention provides a P protein of a mammalian MPV variant B2, wherein the P protein of a mammalian MPV variant B2 is phylogenetically closer related to the P protein of the prototype of variant B2, isolate NL/1/94, than it is related to the P protein of the prototype of variant B1, isolate NL/1/99, the P protein of the prototype of A1, isolate NL/1/00, or the P protein of the prototype of A2, isolate NL/17/00. The invention provides a P protein of a mammalian MPV variant B2, wherein the amino acid sequence of the P protein is at least 96%, at least 98%, or at least 99% or at least 99.5% identical to the P protein of a mammalian MPV variant B2 as represented by the prototype NL/1/94 (SEQ ID NO:377). The invention provides a M protein of a mammalian MPV variant B2, wherein the M protein of a mammalian MPV variant B2 is phylogenetically closer related to the M protein of the prototype of variant B2, isolate NL/1/94, than it is related to the M protein of the prototype of variant B3, isolate NL/1/99, the M protein of the prototype of A1, isolate NL/1/00, or the M protein of the prototype of A2, isolate NL/17/00. The invention provides a M protein of a mammalian MPV variant B2, wherein the amino acid sequence of its M protein is identical to the M protein of a mammalian MPV variant B2 as represented by the prototype NL/1/94 (SEQ ID NO:361). The invention provides a F protein of a mammalian MPV variant B2, wherein the F protein of a mammalian MPV variant B2 is phylogenetically closer related to the F protein of the prototype of variant B2, isolate NL/1/94, than it is related to the F protein of the prototype of variant B1, isolate NL/1/99, the F protein of the prototype of A1, isolate NL/1/00, or the F protein of the prototype of A2, isolate NL/17/00. The invention provides a F protein of a mammalian MPV variant B2, wherein the amino acid sequence of the F protein is at least 99% or at least 99.5% identical to the F protein of a mammalian MPV variant B2 as represented by the prototype NL/1/94 (SEQ ID NO:317). The invention provides a M2-1 protein of a mammalian MPV variant B2, wherein the M2-1 protein of a mammalian MPV variant B2 is phylogenetically closer related to the M2-1 protein of the prototype of variant B2, isolate NL/1/94, than it is related to the M2-1 protein of the prototype of variant B1, isolate NL/1/99, the M2-1 protein of the prototype of A1, isolate NL/1/00, or the M2-1 protein of the prototype of A2, isolate NL/17/00. The invention provides a M2-1 protein of a mammalian MPV variant B2, wherein the amino acid sequence of the M2-1 protein is at least 98% or at least 99% or at least 99.5% identical to the M2-1 protein of a mammalian MPV variant B2 as represented by the prototype NL/1/94 (SEQ ID NO:341). The invention provides a M2-2 protein of a mammalian MPV variant B2, wherein the M2-2 protein of a mammalian MPV variant B2 is phylogenetically closer related to the M2-2 protein of the prototype of variant B2, isolate NL/1/94, than it is related to the M2-2 protein of the prototype of variant B1, isolate NL/1/99, the M2-2 protein of the prototype of A1, isolate NL/1/00, or the M2-2 protein of the prototype of A2, isolate NL/17/00. The invention provides a M2-2 protein of a mammalian MPV variant B2, wherein the amino acid sequence is at least 99% or at least 99.5% identical to the M2-2 protein of a mammalian MPV variant B2 as represented by the prototype NL/1/94 (SEQ ID NO:349). The invention provides a SH protein of a mammalian MPV variant B2, wherein the SH protein of a mammalian MPV variant B2 is phylogenetically closer related to the SH protein of the prototype of variant B2, isolate NL/1/94, than it is related to the SH protein of the prototype of variant B1, isolate NL/1/99, the SH protein of the prototype of A1, isolate NL/1/00, or the SH protein of the prototype of A2, isolate NL/17/00. The invention provides a SH protein of a mammalian MPV variant B2, wherein the amino acid sequence of the SH protein is at least 84%, at least 85%, at least 90%, at least 95%, at least 98%, or at least 99% or at least 99.5% identical to the SH protein of a mammalian MPV. variant B2 as represented by the prototype NL/1/94 (SEQ ID NO:385). The invention provides a L protein of a mammalian MPV variant B2, wherein the L protein of a mammalian MPV variant B2 is phylogenetically closer related to the L protein of the prototype of variant B2, isolate NL/1/94, than it is related to the L protein of the prototype of variant B1, isolate NL/1/99, the L protein of the prototype of A1, isolate NL/1/00, or the L protein of the prototype of A2, isolate NL/17/00. The invention provides a L protein of a mammalian MPV variant B2, wherein the and/or if the amino acid sequence of the L protein is at least 99% or at least 99.5% identical to the L protein of a mammalian MPV variant B2 as represented by the prototype NL/1/94 (SEQ ID NO:333).

In certain embodiments, the percentage of sequence identity is based on an alignment of the full length proteins. In other embodiments, the percentage of sequence identity is based on an alignment of contiguous amino acid sequences of the proteins, wherein the amino acid sequences can be 25 amino acids, 50 amino acids, 75 amino acids, 100 amino acids, 125 amino acids, 150 amino acids, 175 amino acids, 200 amino acids, 225 amino acids, 250 amino acids, 275 amino acids, 300 amino acids, 325 amino acids, 350 amino acids, 375 amino acids, 400 amino acids, 425 amino acids, 450 amino acids, 475 amino acids, 500 amino acids, 750 amino acids, 1000 amino acids, 1250 amino acids, 1500 amino acids, 1750 amino acids, 2000 amino acids or 2250 amino acids in length.

In certain, specific embodiments, the invention provides a G protein of a mammalian MPV wherein the G protein has one of the amino acid sequences set forth in SEQ ID NO:119-153; SEQ ID NO:322-325 or a fragment thereof. In certain, specific embodiments, the invention provides a F protein of a mammalian MPV wherein the F protein has one of the amino acid sequences set forth in SEQ ID NO:234-317. In certain, specific embodiments, the invention provides a L protein of a mammalian MPV wherein the L protein has one of the amino acid sequences set forth in SEQ ID NO:330-333 or a fragment thereof. In certain, specific embodiments, the invention provides a M2-1 protein of a mammalian MPV wherein the M2-1 protein has one of the amino acid sequences set forth in SEQ ID NO:338-341 or a fragment thereof. In certain, specific embodiments, the invention provides a M2-2 protein of a mammalian MPV wherein the M2-2 protein has one of the amino acid sequences set forth in SEQ ID NO:346-349 or a fragment thereof. In certain, specific embodiments, the invention provides a M protein of a mammalian MPV wherein the M protein has one of the amino acid sequences set forth in SEQ ID NO:358-361 or a fragment thereof. In certain, specific embodiments, the invention provides a N protein of a mammalian MPV wherein the N protein has one of the amino acid sequences set forth in SEQ ID NO:366-369 or a fragment thereof. In certain, specific embodiments, the invention provides a P protein of a mammalian MPV wherein the P protein has one of the amino acid sequences set forth in SEQ ID NO:374-377 or a fragment thereof. In certain, specific embodiments, the invention provides a SH protein of a mammalian MPV wherein the SH protein has one of the amino acid sequences set forth in SEQ ID NO:382-385 or a fragment thereof.

In certain embodiments of the invention, a fragment is at least 25 amino acids, 50 amino acids, 75 amino acids, 100 amino acids, 125 amino acids, 150 amino acids, 175 amino acids, 200 amino acids, 225 amino acids, 250 amino acids, 275 amino acids, 300 amino acids, 325 amino acids, 350 amino acids, 375 amino acids, 400 amino acids, 425 amino acids, 450 amino acids, 475 amino acids, 500 amino acids, 750 amino acids, 1000 amino acids, 1250 amino acids, 1500 amino acids, 1750 amino acids, 2000 amino acids or 2250 amino acids in length. In certain embodiments of the invention, a fragment is at most 25 amino acids, 50 amino acids, 75 amino acids, 100 amino acids, 125 amino acids, 150 amino acids, 175 amino acids, 200 amino acids, 225 amino acids, 250 amino acids, 275 amino acids, 300 amino acids, 325 amino acids, 350 amino acids, 375 amino acids, 400 amino acids, 425 amino acids, 450 amino acids, 475 amino acids, 500 amino acids, 750 amino acids, 1000 amino acids, 1250 amino acids, 1500 amino acids, 1750 amino acids, 2000 amino acids or 2250 amino acids in length.

The invention further provides nucleic acid sequences derived from a mammalian MPV. The invention also provides derivatives of nucleic acid sequences derived from a mammalian MPV. In certain specific embodiments the nucleic acids are modified.

In certain embodiments, a nucleic acid of the invention encodes a G protein, a N protein, a P protein, a M protein, a F protein, a M2-1 protein, a M2-2 protein, a SH protein, or a L protein of a mammalian MPV as defined above. In certain embodiments, a nucleic acid of the invention encodes a G protein, a N protein, a P protein, a M protein, a F protein, a M2-1 protein, a M2-2 protein, a SH protein, or a L protein of subgroup A of a mammalian MPV as defined above. In certain embodiments, a nucleic acid of the invention encodes a G protein, a N protein, a P protein, a M protein, a F protein, a M2-1 protein, a M2-2 protein, a SH protein, or a L protein of subgroup B of a mammalian MPV as defined above. In certain embodiments, a nucleic acid of the invention encodes a G protein, a N protein, a P protein, a M protein, a F protein, a M2-1 protein, a M2-2 protein, a SH protein, or a L protein of variant A1 of a mammalian MPV as defined above. In certain embodiments, a nucleic acid of the invention encodes a G protein, a N protein, a P protein, a M protein, a F protein, a M2-1 protein, a M2-2 protein, a SH protein, or a L protein of variant A2 of a mammalian MPV as defined above. In certain embodiments, a nucleic acid of the invention encodes a G protein, a N protein, a P protein, a M protein, a F protein, a M2-1 protein, a M2-2 protein, a SH protein, or a L protein of variant B1 of a mammalian MPV as defined above. In certain embodiments, a nucleic acid of the invention encodes a G protein, a N protein, a P protein, a M protein, a F protein, a M2-1 protein, a M2-2 protein, a SH protein, or a L protein of variant B2 of a mammalian MPV as defined above.

In certain embodiments, the invention provides a nucleotide sequence that is at least 50%, at least 55%, at least 60%, at least 65%, at least 70%, at least 75%, at least 75%, at least 80%, at least 85%, at least 90%, at least 95%, at least 98%, at least 99%, or at least 99.5% identical to the nucleotide sequence of SEQ ID NO:18, SEQ ID NO:19, SEQ ID NO:20, or SEQ ID NO:21. In certain embodiments, the nucleic acid sequence of the invention, is at least 50%, at least 55%, at least 60%, at least 65%, at least 70%, at least 75%, at least 75%, at least 80%, at least 85%, at least 90%, at least 95%, at least 98%, at least 99%, or at least 99.5% identical to a fragment of the nucleotide sequence of SEQ ID NO:18, SEQ ID NO:19, SEQ ID NO:20, or SEQ ID NO:21, wherein the fragment is at least 25 nucleotides, at least 50 nucleotides, at least 75 nucleotides, at least 100 nucleotides, at least 150 nucleotides, at least 200 nucleotides, at least 250 nucleotides, at least 300 nucleotides, at least 400 nucleotides, at least 500 nucleotides, at least 750 nucleotides, at least 1,000 nucleotides, at least 1,250 nucleotides, at least 1,500 nucleotides, at least 1,750 nucleotides, at least 2,000 nucleotides, at least 2,00 nucleotides, at least 3,000 nucleotides, at least 4,000 nucleotides, at least 5,000 nucleotides, at least 7,500 nucleotides, at least 10,000 nucleotides, at least 12,500 nucleotides, or at least 15,000 nucleotides in length. In a specific embodiment, the nucleic acid sequence of the invention is at least 50%, at least 55%, at least 60%, at least 65%, at least 70%, at least 75%, at least 75%, at least 80%, at least 85%, at least 90%, at least 95%, at least 98%, at least 99%, or at least 99.5% or 100% identical to one of the nucleotide sequences of SEQ ID NO:84-118; SEQ ID NO:154-233; SEQ ID NO:318-321; SEQ ID NO:326-329; SEQ ID NO:334-337; SEQ ID NO:342-345; SEQ ID NO:350-353; SEQ ID NO:354-357; SEQ ID NO:362-365; SEQ ID NO:370-373; SEQ ID NO:378-381; or SEQ ID NO:386-389.

In specific embodiments of the invention, a nucleic acid sequence of the invention is capable of hybridizing under low stringency, medium stringency or high stringency conditions to one of the nucleic acid sequences of SEQ ID NO:18, SEQ ID NO:19, SEQ ID NO:20, or SEQ ID NO:21. In specific embodiments of the invention, a nucleic acid sequence of the invention is capable of hybridizing under low stringency, medium stringency or high stringency conditions to one of the nucleic acid sequences of SEQ ID NO:84-118; SEQ ID NO:154-233; SEQ ID NO:318-321; SEQ ID NO:326-329; SEQ ID NO:334-337; SEQ ID NO:342-345; SEQ ID NO:350-353; SEQ ID NO:354-357; SEQ ID NO:362-365; SEQ ID NO:370-373; SEQ ID NO:378-381; or SEQ ID NO:386-389. In certain embodiments, a nucleic acid hybridizes over a length of at least 25 nucleotides, at least 50 nucleotides, at least 75 nucleotides, at least 100 nucleotides, at least 150 nucleotides, at least 200 nucleotides, at least 250 nucleotides, at least 300 nucleotides, at least 400 nucleotides, at least 500 nucleotides, at least 750 nucleotides, at least 1,000 nucleotides, at least 1,250 nucleotides, at least 1,500 nucleotides, at least 1,750 nucleotides, at least 2,000 nucleotides, at least 2,00 nucleotides, at least 3,000 nucleotides, at least 4,000 nucleotides, at least 5,000 nucleotides, at least 7,500 nucleotides, at least 10,000 nucleotides, at least 12,500 nucleotides, or at least 15,000 nucleotides with the nucleotide sequence of SEQ ID NO:18, SEQ ID NO:19, SEQ ID NO:20, or SEQ ID NO:21.

The invention further provides antibodies and antigen-binding fragments that bind specifically to a protein of a mammalian MPV. An antibody of the invention binds specifically to a G protein, a N protein, a P protein, a M protein, a F protein, a M2-1 protein, a M2-2 protein, a SH protein, or a L protein of a mammalian MPV. In specific embodiments, the antibody is a human antibody or a humanized antibody. In certain embodiments, an antibody of the invention binds specifically to a G protein, a N protein, a P protein, a M protein, a F protein, a M2-1 protein, a M2-2 protein, a SH protein, or a L protein of a virus of subgroup A of a mammalian MPV. In certain other embodiments, an antibody of the invention binds specifically to a G protein, a N protein, a P protein, a M protein, a F protein, a M2-1 protein, a M2-2 protein, a SH protein, or a L protein of a virus of subgroup B of a mammalian MPV. In certain, more specific, embodiments, an antibody of the invention binds specifically to a G protein, a N protein, a P protein, a M protein, a F protein, a M2-1 protein, a M2-2 protein, a SH protein, or a L protein of a virus of variant A1 of a mammalian MPV. In other embodiments, the antibody of the invention binds specifically to a G protein, a N protein, a P protein, a M protein, a F protein, a M2-1 protein, a M2-2 protein, a SH protein, or a L protein of a virus of subgroup A2 of a mammalian MPV. In certain embodiments, an antibody of the invention binds specifically to a G protein, a N protein, a P protein, a M protein, a F protein, a M2-1 protein, a M2-2 protein, a SH protein, or a L protein of a virus of subgroup B1 of a mammalian MPV. In certain other embodiments, an antibody of the invention binds specifically to a G protein, a N protein, a P protein, a M protein, a F protein, a M2-1 protein, a M2-2 protein, a SH protein, or a L protein of a virus of subgroup B2 of a mammalian MPV.

5.16 Inhibition of Virus Cell Fusion using Heptad Repeats

Virus-host cell fusion is a necessary step in the infectious life cycle of many enveloped viruses, including MPV. As such, the inhibition of virus cell fusion represents a new approach toward the control of these viruses. This method of inhibition represents an alternative means of preventing the propagation of MPV in a host and the infection by MPV of a host. The inhibition of virus-cell fusion is dependent upon the type of attachment protein required. Wang et al., Biochem Biophys Res Comm 302 (2003) 469-475. Consequently, in one embodiment of the invention, an assay is used to identify the dependency of virus cell fusion on various attachment proteins.

In certain embodiments, the invention provides methods for preventing, treating, or managing an hMPV infection in a subject, the method comprising administering a pharmaceutically effective amount of a heptad repeat (HR) peptide. In certain embodiments, a pharmaceutically effective amount reduces virus host cell fusion by at least 10%, at least 15%, at least 20%, at least 30%, at least 40%, at least 50%, at least 60%, at least 70%, at least 80%, at least 90%, at least 95%, at least 99%, at least 99.5%. In a specific embodiment, the HR is an HR of the virus that causes the infection in the subject. In a certain embodiment, the HR is that of an hMPV of the subtype A1. In a more specific embodiment, the HR sequence is one of the HR sequences of the F protein of hMPV, designated HRA or HRB, where HRA is the heptad repeat sequence near the N terminus of the peptide and HRB is near the C terminus. In certain embodiments, the HR that is administered to treat, prevent, or manage hMPV infection in the subject is an HR of hMPV subtype of A1, B1, A2, or B2.

In certain embodiments, the HR is at least 50%, 60%, 70%, 80%, 90%, 95%, 98%, 99%, or at least 99.5% identical to a HR of the virus that causes the infection in the subject. In certain embodiments, a derivative of a HR can be used to prevent viral fusion. Such derivatives include, but are not limited to, HR peptides that have been substituted with non native amino acids, truncated so that stretches of amino acids are removed, or lengthened, so that single amino acids or stretches thereof have been added. In yet another embodiment, single HR peptides are used to treat, manage, or prevent hMPV infection. In an even further embodiment, a combination of HR peptides is administered to treat, manage, or prevent hMPV infection.

The tests set forth below can be used to determine the effectiveness of a HR in preventing the fusion of an hMPV with a cell and can thus be used to determine which HRs or analogs or derivatives thereof are best suited for treating, preventing, or managing and hMPV infection in a subject.

In another embodiment of the invention, soluble synthesized HR peptides are assayed to determine whether the peptides are able to prevent viral-cell fusion. Any HR sequence can be used to inhibit hMPV viral-cell fusion, including but not limited to, HR sequences against RSV, PIV, APV, and hMPV. In a preferred embodiment, the HR sequence is that of hMPV. In a more specific embodiment, the HR sequence is one of the HR sequences of the F protein of hMPV, designated HRA or HRB, where HRA is the heptad repeat sequence near the N terminus of the peptide and HRB is near the C terminus. In another embodiment of the invention, the HRA and HRB derived peptides that are used to inhibit hMPV viral-cell fusion, include, but are not limited to HRA and HRB peptides from RSV, APV, and PIV. In even another embodiment of the invention, derivatives of HRA and HRB peptides are used to inhibit hMPV viral-cell fusion. For example, derivatives that are made by mutation of at least one amino acid residue in an HRA or HRB peptide are used to inhibit hMPV viral-cell fusion. In another embodiment of the invention, derivatives are made by truncation or resection of specific regions of an HRA or HRB peptide. In yet even another embodiment, the HRA or HRB peptide that is used is lengthened with respect to the endogenous HR sequence. In an even further embodiment, groups of short peptides that consist of sequences of different regions of an HRA or HRB peptide are used to inhibit hMPV viral-cell fusion. In another embodiment of the invention, hMPV HRA and HRB derived peptides are used against homologous strains of hMPV or against heterologous strains of hMPV. In yet another embodiment of the invention, HRA and HRB peptides, or analogs or derivatives thereof, are used together to inhibit viral-cell fusion. In a more preferred embodiment, either an HRA or HRB peptide or analog or derivative thereof is used alone. In another embodiment, the derivative of an HRA or HRB peptide that is used is at least 90%, 80%, 70%, 60%, or 50% identical to the endogenous HR peptide.

In order to examine the ability of the heptad repeat sequences to inhibit viral fusion, heptad repeat peptides can be expressed and purified so that they may be tested for their viral fusion inhibition ability. Soluble heptad repeat peptides can be expressed and purified and subsequently used in an assay to compete with endogenous heptad repeats in order to test for the blocking of viral fusion. In one embodiment of the invention, synthetic recombinant DNAs may be prepared that encode the heptad repeat sequences of the F protein of hMPV, designated HRA and HRB respectively. In another embodiment of the invention, synthetic recombinant DNAs may be prepared that encode heptad repeat peptides that also contain sequence tags useful in facilitating purification. In a preferred embodiment of the invention, the tag that facilitates purification of the heptad repeat peptide does not interfere with its activity. In yet another embodiment of the invention, the tag is composed of a series of histidine residues, e.g., six consecutive histidines at one of the peptide's termini, and is referred to as a histidine tag. There are a number of different approaches that can be used to express and purify soluble HRA and HRB. First, DNA vectors encoding the HRA and HRB are prepared using methods known to one skilled in the art. The plasmids are subsequently transformed into an appropriate expression host cell, such as, e.g., *E. coli* strain BL21 (DE3), and the protein is expressed and purified using methods routine in the art. For example, expression of a gene encoding an HR peptide with a histidine tag can be induced from a pET vector using IPTG. Cells can then be lysed and the expressed peptide can be isolated after immobilization on a Ni-chelated Sepharose affinity column following elution with a counter charged species, for e.g., imidazole.

In order to determine the potential effectiveness of the expressed heptad repeat peptides in inhibiting viral fusion, an assay can be used to confirm the assembly of a complex between HR peptides. This method would be advantageous over cell based assays in that it would allow for cell-free screening of peptides in order to determine efficacy in viral fusion inhibition. In one embodiment of the invention, HR peptides are incubated simultaneously for a period of time sufficient to allow complex formation. In a more specific embodiment, the amount of time allowed for complex formation is 1 h at 28° C. Complex formation can be detected using any method known in the art, including but not limited to, chromatography, Uv-vis spectroscopy, NMR spectroscopy, X-ray crystallography, centrifugation, or electrophoresis. In another specific embodiment of the invention, complex formation is detected using gel filtration methods coupled with electrophoresis in order to determine the molecular weight of the complex. In yet another embodiment of the invention, this complex formation assay is used to identify candidates that are useful in inhibiting viral fusion, e.g., the effectiveness of mutated HR peptides in the inhibition of viral fusion is determined. In yet even another embodiment of the invention, the effectiveness of derivatives of HR peptides in the inhibition of viral fusion is measured using this complex formation assay.

It is known that the heptad repeat segments of the peptides are helical in nature. For this reason, a number of methods can be used to determine whether expressed HR peptides form alpha helices in order to identify appropriate candidates for use in viral fusion inhibition. Such methods, include, but are not limited to, spectroscopy, X-ray crystallography, and microscopy. In one embodiment of the invention, CD (circular dichroism) spectroscopy is used to determine the structural features of the HR peptides.

A cell based assay can be used to determine the effectiveness of HR peptides in the inhibition of viral fusion. Any cell that can be infected with MPV can be used in the assay, including, but not limited to: tMK, Hep2, or Vero cells. In a specific embodiment, the type of cells that are used are Hep2 cells. Upon infection of a host cell with MPV, the cells are incubated with HR protein preparations and scored for fusion after incubation for an appropriate period of time. Cells are subsequently stained for synctium/polykaryon formation in order to determine whether viral-cell fusion was successful.

6. Virus Isolation and Characterization

6.1 EXAMPLE 1

Specimen Collection, Virus Isolation, Virus Characterization

Samples of nasopharyngeal aspirates were obtained from hosts to assay for the presence of viruses, and also to characterize those identified. Nasopharyngeal aspirates were collected from children suffering from respiratory tract infection (RTI). In order to determine the identity of the cause of illness, all nasopharyngeal aspirates were tested by direct immunofluorescence assays (DIF) (See method in Example 9), using fluorescence labeled antibodies against influenza virus types A and B, hRSV, and human parainfluenza virus (hPIV) types 1, 2, and 3. Viruses were also isolated from nasopharyngeal aspirates using rapid shell vial techniques, (Rothbarth et. al., 1999, J of Virol. Methods 78:163-169) on various cell lines, including VERO cells, tertiary cynomolgous monkey kidney (tMK) cells, human endothelial lung (HEL) cells and marbin dock kidney (MDCK) cells. Samples showing cytopathic effects (CPE) after two to three passages, that were negative in DIF assays, were tested by indirect immunofluorescence assays (IFA) (See method in Example 11), using virus specific antibodies against influenza virus types A, B and C, hRSV types A and B, measles virus, mumps virus, human parainfluenza virus (hPIV) types 1 to 4, sendai virus, simian virus type 5, and New-Castle disease virus. Although for many cases the aetiological agent could be identified, some specimens were negative for all of the viruses tested.

These 28 unidentified virus isolates grew slowly in tMK cells, poorly in VERO cells and A549 cells and barely in MDCK or chicken embryonated fibroblast cells. Most of the virus isolates induced CPE on tMK cells, between days ten and fourteen. This was somewhat later than the CPE caused by other viruses such as hRSV or hPIV. The CPE were virtually indistinguishable from that caused by hRSV or hPIV in tMK or other cell cultures, and were characterized by syncytium formation. Some of the effects observed on the cells included rapid internal disruption, followed by detachment of the cells from the monolayer.

The supernatants of infected tMK cells were used for Electron Microscopy (EM) analysis, and they revealed the presence of *paramyxovirus*-like virus particles ranging from 150 to 600 nanometers in diameter, with short envelope projections ranging from 13 to 17 nanometers. Consistent with the biochemical properties of enveloped viruses such as the Paramyxoviridae family of viruses, standard chloroform or ether treatment (Osterhaus et. al., 1985, Arch. of Virol. 86:239-25) resulted in a greater than $10^4$ $TCID_{50}$ reduction in infectivity of tMK cells. Virus-infected tMK cell culture supernatants did not display heamagglutinating activity with turkey, chicken and guinea pig erythrocytes. During culture, the virus replication appeared to be trypsin dependent. These combined virological data demonstrated that the newly identified virus was a taxonomic member of the Paramyxoviridae family.

RNA from tMK cells infected with 15 of the unidentified virus isolates was extracted for use in reverse transcription and polymerase chain reaction (RT-PCR) analyses, using primer-sets specific for Paramyxovirinae (K. B. Chua et al., 2000, Science 288:1432-1435) such as: hPIV 1-4, sendai virus, simian virus type 5, New-Castle disease virus, hRSV, morbilli, mumps, Nipah, Hendra, Tupaia and Mapuera viruses. RT-PCR assays were performed under conditions of low stringency in order to detect potentially related viruses. RNA isolated from homologous virus stocks was used as a control. Whereas the available controls reacted positive with the respective virus-specific primers, the newly identified virus isolates did not react with any primer set, indicating the virus was not closely related to the viruses tested.

Two of the virus-infected tMK cell culture supernatants were used to inoculate guinea pigs and ferrets intranasally. Sera samples were collected from these animals at day zero, two weeks, and three weeks post inoculation. The animals displayed no clinical symptoms, however, the seroconversion of all of the animals was detected and measured in virus neutralization (VN) (See method in Example 16) assays and indirect IFA against the homologous viruses. The sera did not react in indirect IFA with any of the known *paramyxoviruses* described above or with *pneumovirus* of mice (PVM). The so far unidentified virus isolates were screened, using the guinea pig and ferret pre- and post-infection sera. Of these, 28 were clearly positive by indirect IFA, with the post-infection sera suggesting that, the thus far unidentified viral isolates, were closely related or identical.

In order further characterize the virus, the phenotypic effects of virus infection on a cell line was examined. In short, tMK cells were cultured in 24 well plates containing glass slides (Costar, Cambridge, UK), with the medium described below supplemented with 10% fetal bovine serum (BioWhittaker, Vervier, Belgium). Before inoculation, the plates were washed with PBS and supplied with Eagle's MEM with Hanks' salt (ICN, Costa mesa, Calif.), of which 0.5 L was supplemented with 0.26 g of $NaHCO_3$, 0.025 M Hepes (Biowhittaker), 2 mM L-glutamine (Biowhittaker), 100 units penicillin, 100 μg streptomycin (Biowhittaker), 0.5 g lactalbumin (Sigma-Aldrich, Zwijndrecht, The Netherlands), 1.0 g D-glucose (Merck, Amsterdam, The Netherlands), 5.0 g peptone (Oxoid, Haarlem, The Netherlands) and 0.02% trypsin (Life Technologies, Bethesda, Md.). The plates were inoculated with the supernatant of the nasopharyngeal aspirate samples (0.2 ml per well in triplicate), followed by centrifuging at 840×g for one hour. After inoculation, the plates were incubated at 37° C. for a maximum of 14 days, and the medium was changed once a week while cultures were checked daily for CPE. After 14 days, the cells were scraped from the second passage and incubated for 14 days. This step was repeated for the third passage. The glass slides were used to demonstrate the presence of the virus by indirect IFA as described below.

CPE were generally observed after the third passage, between days 8 to 14, depending on the isolate. The CPE were virtually indistinguishable from that caused by hRSV or hPIV in tMK or other cell cultures, except that hRSV induces CPE at around day 4. CPE were characterized by syncytia formation, after which the cells showed rapid internal disruption, followed by detachment of the cells from the monolayer. For some isolates, CPE were difficult to observe, and IFA was used to confirm the presence of the virus in these cultures. The observation that the CPE were indistinguishable from those of other viruses indicated that diagnosis could not be made from a visual examination of clinical symptoms.

6.2 EXAMPLE 2

Seroprevalence in the Human Population

To study the seroprevalence of this virus in the human population, sera from humans in different age categories were analyzed by indirect IFA using tMK cells infected with one of the unidentified virus isolates. Studies revealed that antibodies to the virus could be detected in 25% of the children between six and twelve months. Furthermore, by the age of five, nearly 100% of the children were seropositive. In total, 56 sera samples examined by indirect IFA and by VN assay. For 51 of the samples or 91%, the results of the VN assay, i.e., a titer greater than 8, coincided with the results obtained with indirect IFA, i.e., a titer greater than 32. Four samples that were found to be positive by IFA, were negative by the VN assay, i.e., titer less than 8, whereas one serum sample was negative by IFA, i.e., titer less than 32, and was positive by the VN test, i.e., a titer of 16 (FIG. 2).

IFA conducted on 72 sera samples taken from humans in 1958, with ages ranging from 8-99 years, revealed a 100% seroprevalence rate, indicating the virus has been circulating in the human population for more than 40 years. In addition, a number of these sera samples were used in VN assays to confirm the IFA data (FIG. 2). The seroprevalence data indicate that the virus has been a significant source of infection in the human population for many years.

The repeated isolation of this virus from clinical samples from children with severe RTI indicates that the clinical and economic impact of MPV may be high. New diagnostic assays based on virus detection and serology would yield a more detailed analysis of the incidence rate and also of the clinical and economical impact of this viral pathogen.

The slight differences between the IFA and VN results (5 samples) may have been due to the fact that in the IFA, only IgG serum antibodies were detected, whereas the VN assay detects both classes and sub-classes of antibodies. Alternatively, differences may have been due to the differences in sensitivity between both assays. For IFA, a threshold value of 16 was used, whereas for VN a value of 8 was used.

Differences between results in the IFA and VN assays may also indicate possible differences between serotypes of this newly identified virus. Since MPV seems to be most closely related to APV, it was speculated that the human virus may have originated from birds. Analysis of serum samples taken from humans in 1958 revealed that MPV has been widespread in the human population for more then 40 years, indicating that a tentative zoonosis event must have taken place long before 1958.

6.3 EXAMPLE 3

Genomic Sequence of hMPV Isolate 00-1

In order to obtain sequence information for the unknown virus isolates, a random PCR amplification strategy known as RAP-PCR (Welsh et. al., 1992, NAR 20:4965-4970) (See Example 21). In short, tMK cells were infected with one of the virus isolates (isolate 00-1) as well as with hPIV-1 that served as a positive control. After both cultures displayed similar levels of CPE, virus in the culture supernatants was purified on continuous 20-60% sucrose gradients. The gradient fractions were inspected for virus-like particles by EM, and RNA was isolated from the fraction that contained approximately 50% sucrose, in which nucleocapsids were observed. Equivalent amounts of RNA isolated from both virus fractions were used for RAP-PCR, after which samples were run side by side on a 3% NuSieve agarose gel. Twenty differentially displayed bands specific for the unidentified virus were subsequently purified from the gel, cloned in plasmid pCR2.1 (Invitrogen) and sequenced (See Example 22) with vector-specific primers. A search for homologies against sequences in the Genbank database, using the BLAST program available through the National Library of Medicine, found that 10 out of 20 fragments displayed resemblance to APV/TRTV sequences.

These 10 fragments were located in the genes coding for the nucleoprotein (N; fragment 1 and 2), the matrix protein (M; fragment 3), the fusion protein (F; fragment 4, 5, 6, 7) and the polymerase protein (L; fragment 8, 9, 10) (FIG. 3). PCR primers were designed to complete the sequence information for the 3' end of the viral genome based on our RAP PCR fragments as well as published leader and trailer sequences for the *Pneumovirinae* (Randhawa, et.al., 1997, *J. Virol.* 71:9849-9854). Three fragments were amplified, of which fragment A spanned the extreme 3' end of the N open reading frame (ORF), fragment B spanned the phosphoprotein (F) ORF and fragment C closed the gap between the M and F ORFs (FIG. 16). Sequence analyses of these three fragments revealed the absence of NS1 and NS2 ORFs at the extreme 3' end of the viral genome and positioning of the F ORF immediately adjacent to the M ORF. This genomic organization resembled that of the *metapneumovirus* APV, which was also consistent with the sequence homology. Relation between different viruses could be deduced by comparing the amino acid sequence of FIG. 4 with the amino acid sequence of the respective N proteins of other viruses. Overall the translated sequences for the N, P, M and F ORFs showed an average of 30-33% homology with members of the genus *Pneumovirus* and 66-68% with members of the genus *Metapneumovirus*. For the SH and G ORFs, no discernable homology was found with members of either genera. The amino acid homologies found for the amino acid sequence of the N ORF showed about 40% homology with hRSV and 88% with APV-C, its closest relative genetically. The amino acid sequence for the P ORF showed about 25% homology with hRSV and about 66-68% with APV-C, the M ORF showed about 36-39% with hRSV and about 87-89% with APV-C, the F ORF showed about 40% homology with hRSV and about 81% with APV-C, the M2-1 ORF showed about 34-36% homology with *pneumoviruses* and 84-86% with APV-C, the M2-2 ORF showed 15-17% homology with *pneumoviruses* and 56% with APV-C and the fragments obtained from the L ORF showed an average of 44% with *pneumoviruses* and 64% with APV-C.

Genetic analyses of the N, M, P and F genes revealed that MPV has higher sequence homology to the recently proposed genus Metapneumovirinae as compared to the genus *Pneumovirinae* and thus demonstrates a genomic organization similar to and resembling that of APV/TRTV. In contrast to the genomic organization of the RSVs ('3-NS1-NS2-N-P-M-SH-G-F-M2-L-5'), *metapneumoviruses* lack NS1 and NS2 genes and also have a different genomic organization, specifically between the M and L ('3-N-P-M-F-M2-SH-G-L-5') genes. The lack of ORFs between the M and F genes in the virus isolates of the invention, the lack of NS1 and NS2 adjacent to N, and the high amino acid sequence homology found within APV led to the proposed classification of MPV isolated from humans as the first member of the *Metapneumovirus* genus of mammals, and more specifically of humans.

Phylogenetic analyses revealed that the nine MPV isolates, from which sequence information was obtained, are closely related. Although sequence information was limited, they appeared to be more closely related to one another than to any of the avian *metapneumoviruses*. Of the four serotypes of APV that have been described, serotype C appeared to be most closely related to MPV. This conclusion was based upon the nucleotide sequence similarities of the N, P, M and F genes. It should be noted however, that for serotype D, only partial sequences of the F gene were available from Genbank, and for serotype B, only M, N, and F sequences were available. Our MPV isolates formed two clusters in phylogenetic trees. For both hRSV and APV, different genetic and serological subtypes have been described. Whether the two genetic clusters of MPV isolates represent serogical subgroups that are also functionally different remains unknown at present. Our serological surveys showed that MPV is a common human pathogen.

6.4 EXAMPLE 4

Further Characterization of Associated Genes

Sequence analyses of the nucleoprotein (N), phosphoprotein (P), matrixprotein (M) and fusion protein (F) genes of MPV revealed the highest degree of sequence homology with APV serotype C, the avian *pneumovirus* found primarily in birds in the United States. These analyses also revealed the absence of non-structural proteins NS1 and NS2 at the 3'end of the viral genome and positioning of the fusion protein immediately adjacent to the matrix protein. The sequences of the 22K (M2) gene, the small hydrophobic (SH) gene, the attachment (G) gene, the polymerase (L) gene, the intergenic regions, and the trailer sequences were determined. In combination with the sequences described previously, the sequences presented here completed the genomic sequence of MPV with the exception of the extreme 12-15 nucleotides of the genomic termini and establish the genomic organization of MPV. Side by side comparisons of the sequences of the MPV genome with those of APV subtype A, B and C, RSV subtype A and B, PVM and other *paramyxoviruses* provides strong evidence for the classification of MPV in the *Metapneumovirus* genus.

GENE ENCODING THE NUCLEOPROTEIN (N): As shown above, the first gene in the genomic map of MPV codes for a 394 amino acid (aa) protein and shows extensive homology with the N protein of other *pneumoviruses*. The length of the N ORF is identical to the length of the N ORF of APV-C (Table 5) and is smaller than those of other *paramyxoviruses* (Barr et al., 1991, J Gen Virol 72:677-85). Analysis of the amino acid sequence revealed the highest homology with APV-C (88%), and only 7-11% with other *paramyxoviruses* (Table 6).

Three regions of similarity between viruses belonging to the order Mononegavirales were identified: A, B and C (FIG. 22) (Barr et al., 1991, J Gen Virol 72: 677-85). Although similarities are highest within a virus family, these regions are highly conserved between virus families observed. In all three regions MPV revealed 97% aa sequence identity with APV-C, 89% with APV-B, 92% with APV-A, and 66-73% with RSV and PYM. The region between aa residues 160 and 340 appears to be highly conserved among *metapneumoviruses* and to a somewhat lesser extent the *Pneumovirinae* (Miyahara et al., 1991, Arch Viral 124:255-68; Li et al., 1996, Virus Res 41:185-91; Barr, 1991, J Gen Virol 72:677-85).

GENE ENCODING THE PHOSPHOPROTEIN (P): The second ORF in the genome map codes for a 294 aa protein which shares 68% aa sequence homology with the P protein of APV-C, and only 22-26% with the P protein of RSV (Table 7). The P gene of MPV contains one substantial ORF and in that respect is similar to P from many other *paramyxoviruses* (Reviewed in Lamb et. al., Fields virology, (B. N. Knipe, Hawley, P. M., ed., LippencottRaven), Philadelphia, 1996; Sedlmeier et al., 1998, Adv Virus Res 50:101-39).

In contrast to APV A and B and PVM and similar to RSV and APV-C the MPV P ORF lacks cysteine residues. A region of high similarity between all *pneumoviruses* (amino acids 185-241) plays a role in either the RNA synthesis process or in maintaining the structural integrity of the nucleocapsid complex (Ling et al., 1995, Virus Res 36:247-57). This region of high similarity is also found in MPV (FIG. 6) specifically when conservative substitutions are taken into account, showing 100% similarity with APYC, 93% with APV-A and B, and approximately 81% with RSV. The C-terminus of the MPV P protein is rich in glutamate residues as has been described for APVs (Ling, et al., 1995, Virus Res 36:247-57).

GENE ENCODING THE MATRIX (M) PROTEIN: The third ORF of the MPV genome encodes a 254 aa protein, which resembles the M ORFs of other *pneumoviruses*. The M ORF of MPV has exactly the same size as the M ORFs of other *metapneumoviruses* and shows high aa sequence homology with the matrix proteins of APV (78-87%), lower homology with those of iRSV and PVM (37-38%), and 10% or less homology with those of other *paramyxoviruses* (Table 6).

The sequences of matrix proteins of all *pneumoviruses* were compared and a conserved heptadpeptide at residue 14 to 19 was found to also conserved in MPV (FIG. 7) (Easton et al. 1997, Virus Res, 48:27-33). For RSV, PVM and APV, small secondary ORFs within or overlapping with the major ORF of M have been identified (52 aa and 51 aa in bRSV, 75 aa in RSV, 46 aa in PVM and 51 aa in APV) (Yu et al., 1992, Virology 186:426-34; Easton et al., 1997, Virus Res 48:27-33; Samal et al., 1991, J Gen Virol 72:715-20; Satake et al., 1995, J Virol 50:92-9). One small ORF of 54 aa residues was found within the major M ORF (fragment 1, FIG. 8), starting at nucleotide 2281 and one small ORF of 33 aa residues was found overlapping with the major ORF of M starting at nucleotide 2893 (fragment 2, FIG. 8). Similar to the secondary ORFs of RSV and APV there is no significant homology between these secondary ORFs and secondary ORFs of the other *pneumoviruses*, and apparent start or stop signals are lacking. Furthermore, there have not been any report of protein synthesis occurring from these secondary ORFs.

GENE ENCODING THE FUSION PROTEIN: The F ORF of MPV is located adjacent to the M ORF, a feature that is characteristic of members of the *Metapneumovirus* genus. The F gene of MPV encodes a 539 aa protein, which is two aa residues longer than F of APV-C. Analysis of the aa sequence revealed 81% homology with APV-C, 67% with APV-A and B, 33-39% with *pneumovirus* F proteins and only 10-18% with other *paramyxoviruses* (Table 6). One of the conserved features among F proteins of *paramyxoviruses*, and also seen in MPV is the distribution of cysteine residues (Morrison et al., 1988, Virus Res 10:113-35; Yu et al., 1991, J. Gen Virol 72:75-81). The *metapneumoviruses* share 12 cysteine residues in E1 (7 are conserved among all *paramyxoviruses*), and two in E2 (1 is conserved among all *paramyxoviruses*). Of the 3 potential N-linked glycosylation sites present in the F ORF of MPV, none are shared with RSV and two (position 74 and 389) are shared with APV. The third, unique, potential N-linked glycosylation site for MPV is located at position 206 (FIG. 9).

Despite the low sequence homology with other paramyxoviruses, the F protein of MPV revealed typical fusion protein characteristics consistent with those described for the F proteins of other Paramyxoviridae family members (Morrison et. al., 1988, Virus Res 10:113-35). F proteins of Paramyxoviridae members are synthesized as inactive precursors (F0) that are cleaved by host cell proteases which generate amino terminal E2 subunits and large carboxy terminal F1 subunits. The proposed cleavage site (Collins et al., Fields virology, (B. N. Knipe, Howley, P.M., ed., Lippencott-Raven), Philadelphia, 1996) is conserved among all members of the Paramyxoviridae family. The cleavage site of MPV contains the residues RQSR (SEQ ID NO: 395). Both arginine (R) residues are shared with APV and RSV, but the glutamine (Q) and serine (S) residues are shared with other paramyxoviruses such as human parainfluenza virus type 1, Sendai virus and morbilliviruses.

The hydrophobic region at the amino terminus of F1 is thought to function as the membrane fusion domain and shows high sequence similarity among *paramyxoviruses* and *morbilliviruses* and to a lesser extent the *pneumoviruses* (Morrison et al., 1988, Virus Res 10:113-35). These 26 residues (position 137-163, FIG. 9) are conserved between MPV and APV-C, which is in agreement with this region being highly conserved among the *metapneumoviruses* (Naylor et al., 1998, J. Gen Virol 79:1393-1398; Seal et al., 2000, Virus Res 66:139-47).

As is seen for the F2 subunits of APV and other *paramyxoviruses*, MPV revealed a deletion of 22 aa residues compared with RSV (position 107-128, FIG. 9). Furthermore, for RSV and APV, the signal peptide and anchor domain were found to be conserved within subtypes and displayed high variability between subtypes (Plows et al., 1995, Virus Genes 11:37-45; Naylor et al., 1998, J. Gen Virol 79:1393-1398). The signal peptide of MPV (aa 10-35, FIG. 9) at the amino terminus of F2 exhibits some sequence similarity with APV-C (18 out of 26 aa residues are similar), and less conservation with other APVs or RSV. Much more variability between subtypes is seen in the membrane anchor domain at the carboxy terminus of E1, although some homology is still seen with APV-C.

GENE ENCODING THE M2 PROTEIN: The M2 gene is unique to the *Pneumovirinae* and two overlapping ORFs have been observed in all *pneumoviruses*. The first major ORF represents the M2-1 protein which enhances the processivity of the viral polymerase (Collins et al., 1995, Proc Natl Acad Sci U S A 92:11563-7; Collins et. al., Fields virology (B. N. Knipe, Howley, P. M., ed., Lippencott-Raven), Philadelphia, 1996) and its readthrough of intergenic regions (Hardy et al., 1998, J Virol 72:520-6; Fearns et al., 1999, J Virol 73:5852-64). The M2-1 gene for MPV, located adjacent to the F gene, encodes a 187 aa protein, and reveals the highest (84%) homology with M2-1 of APV-C. Comparison of all *pneumovirus* M2-1 proteins revealed the highest conservation in the amino-terminal half of the protein (Collins et al., 1990, J. Gen Virol 71:3015-20; Zamora et al., 1992, J. Gen Virol 73:737-41; Ahmadian et al., 1999, J. Gen Virol 80:2011-6), which is in agreement with the observation that MPV displays 100% similarity with APV-C in the first 80 aa residues of the protein (FIG. 10). The MPV M2-1 protein contains 3 cysteine residues located within the first 30 aa residues that are conserved among all *pneumoviruses*. Such a concentration of cysteines is frequently found in zinc-binding proteins (Cuesta et al., 2000, Gen Virol:74, 9858-67).

The secondary ORFs (M2-2) that overlap with the M2-1 ORFs of *pneumoviruses* are conserved in location but not in sequence and are thought to be involved in the control of the switch between virus RNA replication and transcription (Collins et al., 1985, J Virol 54:65-71; Elango et al., 1985, J Virol 55:101-10; Baybutt et. al., 1987, J Gen Virol 68:2789-96; Collins et al., 1990, J. Gen Virol 71:3015-20; Ling et al., 1992, J. Gen Virol 73:1709-15; Zamora et al., 1992, J. Gen Virol 73:737-41; Alansari et al., 1994, J. Gen Virol:75:401-404; Ahmadian et al., 1999, J. Gen Virol 80: 2011-6). For MPV, the M2-2 ORF starts at nucleotide 512 in the M2-1 ORF (FIG. 8), which is exactly the same start position as for APV-C. The length of the M2-2 ORFs are the same for APV-C and MPV, 71 aa residues. Sequence comparison of the M2-2 ORF (FIG. 10) revealed 64% aa sequence homology between MPV and APV-C and only 44-48% aa sequence homology between MPV and APV-A and B.

SMALL HYROPHOBIC (SH) GENE ORF: The gene located adjacent to M2 of hMPV probably encodes a 183 aa SH protein (FIG. 8). There is no discernible sequence identity between this ORF and other RNA virus genes or gene products. This is not surprising since sequence similarity between *pneumovirus* SH proteins is generally low. The aa composition of the SH ORF is relatively similar to that of APV, RSV and PVM, with a high percentage of threonine and serune residues (22%, 18%, 19%, 20.0%, 21% and 28% for hMPV, APV, RSV A, RSV B, bRSV and PVM respectively). The SH ORF of hMPV contains 10 cysteine residues, whereas APV SH contains 16 cysteine residues. The SH ORF of hMPV contains two potential N-linked glycosylation sites (aa 76 and 121), whereas APV has one, RSV has two or three and PVM has four.

The hydrophilicity profiles for the putative hMPV SH protein and SH of APV and RSV revealed similar characteristics (FIG. 1B). The SH ORFs of APV and hMPV have a hydrophilic N-terminus, a central hydrophobic domain which can serve as a potential membrane spanning domain (aa 30-53 for hMPV), a second hydrophobic domain (aa 155-170) and a hydrophilic C-terminus. In contrast, RSV SH appears to lack the C-terminal part of the APV and hMPV ORFs. In all *pneumovirus* SH proteins the hydrophobic domain is flanked by basic aa residues, which are also found in the SH ORF for hMPV (aa 29 and 54).

GENE ENCODING THE ATTACHMENT GLYCOPROTEIN (G): The putative G ORF of hMPV is located adjacent to the putative SH gene and encodes a 236 as protein (nt 6262-6972, FIG. 8). A secondary small ORF is found immediately following this ORF, potentially coding for 68 aa residues (nt 6973-7179) but lacking a start codon. A third potential ORF in the second reading frame of 194 aa residues is overlapping with both of these ORFs but also lacks a start codon (nt 6416-7000). This ORF is followed by a potential fourth ORF of 65 aa residues in the same reading frame (nt 7001-7198), again lacking a start codon. Finally, a potential ORF of 97 aa residues (but lacking a start codon) is found in the third reading frame (nt 6444-6737, FIG. 8). Unlike the first ORF, the other ORFs do not have apparent gene start or gene end sequences (see below). Although the 236 aa G ORF probably represents at least a part of the hMPV attachment protein it can not be excluded that the additional coding sequences are expressed as separate proteins or as part of the attachment protein through some RNA editing event. It should be noted that for APV and RSV no secondary ORFs after the primary G ORF have been identified but that both APV and RSV have secondary ORFs within the major ORF of G. However, evidence for expression of these ORFs is lacking and there is no sequence identity between the predicted aa sequences for different viruses (Ling et al., 1992, J Gen Virol 73:1709-15). The secondary ORFs in hMPV G do not reveal characteristics of other G proteins and whether the additional ORFs are expressed requires further investigation.

BLAST analyses with all ORFs revealed no discernible sequence identity at the nucleotide or aa sequence level with other known virus genes or gene products. This is in agreement with the low percentage sequence identity found for other G proteins such as those of hRSV A and B (53%) (Johnson et al., 1987, J Virol 61:163-6) and APV A and B (38%) (Juhasz and Easton, 1994, J Gen Virol 75:2873-80).

Whereas most of the hMPV ORFs resemble those of APV both in length and sequence, the putative G ORF of 236 aa residues of hMPV is considerably smaller than the G ORF of APV (Table 4). The aa sequence revealed a serine and threonine content of 34%, which is even higher than the 32% for RSV and 24% for APV. The putative G ORF also contains 8.5% proline residues, which is higher than the 8% for RSV and 7% for APV. The unusual abundance of proline residues in the G proteins of APV, RSV and hMPV has also been observed in glycoproteins where it is a major determinant of the proteins three dimensional structure (Collins and Wertz, 1983, PNAS 80:3208-12; Wertz et al., 1985, PNAS 82:4075-9; Jentoft, 1990, Trends Biochem Sci 15:291-4.). The G ORF of hMPV contains five potential N-linked glycosylation sites, whereas hRSV has seven, bRSV has five and APV has three to five.

The predicted hydrophilicity profile of hMPV G revealed characteristics similar to the other *pneumoviruses*. The N-terminus contains a hydrophilic region followed by a short hydrophobic area (aa 33-53 for hMPV) and a mainly hydrophilic C-terminus (FIG. 12B). This overall organization corresponds well with regions in the G protein of APV and RSV. The putative G ORF of hMPV contains only 1 cysteine residue in contrast to RSV and APV (5 and 20 respectively). Of note, only two of the four secondary ORFs in the G gene contained one additional cysteine residue and these four potential ORFs revealed 12-20% serine and threonine residues and 6-11% proline residues.

POLYMERASE GENE (L): In analogy to other negative strand viruses, the last ORF of the MPV genome is the RNA-dependent RNA polymerase component of the replication and transcription complexes. The L gene of MPV encodes a 2005 aa protein, which is one residue longer than the APV-A protein (Table 5). The L protein of MPV shares 64% homology with APV-A, 42-44% with RSV, and approximately 13% with other paramyxoviruses (Table 6). Six conserved domains within the L proteins of non-segmented negative strand RNA viruses were identified; it was found that the domain three contained the four core polymerase motifs that are thought to be essential for polymerase function (Poch et al., 1990, J Gen Virol 71:1153-62; Poch et al., 1989, EMBO J 8:3867-74). These motifs (A, B, C and D) are well conserved in the MPV L protein: in motifs A, B and C: MPV shares 100% similarity with all pneumoviruses and in motif D MPV shares 100% similarity with APV and 92% with RSVs. For all of domain III (aa 627-903 in the L ORF), MPV shares 77% identity with APV, 61-62% with RSV and 23-27% with other paramyxoviruses (FIG. 13). In addition to the polymerase motifs the pneumovirus L proteins contain a sequence which conforms to a consensus ATP binding motif $K(X)_{21}GEGAGN(X)_{20}K$ (SEQ ID NO: 397) ((Stec et al., 1991, Virology 183:273-87). The MPV L ORF contains a similar motif as APV, in which the spacing of the intermediate residues is shifted by one residue: $K(X)_{22}GEGAGN(X)_{19}K$ (SEQ ID NO: 398).

TABLE 5

LENGTHS OF THE ORFs OF MPV AND OTHER PARAMYXOVIRUSES

| | N[1] | P | M | F | M2-1 | M2-2 | SH | G | L |
|---|---|---|---|---|---|---|---|---|---|
| MPV | 394 | 294 | 254 | 539 | 187 | 71 | 183 | 236 | 2005 |
| APV A | 391 | 278 | 254 | 538 | 186 | 73 | 174 | 391 | 2004 |
| APV B | 391 | 279 | 254 | 538 | 186 | 73 | ** | 414 | ** |
| APV C | 394 | 294 | 254 | 537 | 184 | 71 | ** | ** | ** |
| APV D | ** | ** | ** | ** | ** | ** | ** | 389 | ** |
| hRSV A | 391 | 241 | 256 | 574 | 194 | 90 | 64 | 298 | 2165 |
| hRSV B | 391 | 241 | 249 | 574 | 195 | 93 | 65 | 299 | 2166 |
| bRSV | 391 | 241 | 256 | 569 | 186 | 93 | 81 | 257 | 2162 |
| PVM | 393 | 295 | 257 | 537 | 176 | 77 | 92 | 396 | ** |
| others[3] | 418-542 | 225-709 | 335-393 | 539-565 | **** | **** | **** | **** | 2183-2262 |

Legend for Table 5:
* = length in amino acid residues,
** = sequences not available,
*** = others: human parainfluenza virus 2, 3. Sendai virus, measles virus, nipah virus, phocine distemper virus, and New Castle Disease virus,
**** = ORF not present in viral genome.

TABLE 6

AMINO ACID SEQUENCE IDENTITY BETWEEN THE ORFs OF MPV AND THOSE OF OTHER PARAMYXOVIRUSES

| | N | P | M | F | M2-1 | M2-2 | L |
|---|---|---|---|---|---|---|---|
| APV A | 69 | 55 | 78 | 67 | 72 | 26 | 64 |
| APV B | 69 | 51 | 76 | 67 | 71 | 27 | ** |
| APV C | 88 | 68 | 87 | 81 | 84 | 56 | ** |
| hRSV A | 42 | 24 | 38 | 34 | 36 | 18 | 42 |
| hRSV B | 41 | 23 | 37 | 33 | 35 | 19 | 44 |
| bRSV | 42 | 22 | 38 | 34 | 35 | 13 | 44 |
| PVM | 45 | 26 | 37 | 39 | 33 | 12 | ** |
| others[3] | 7-11 | 4-9 | 7-10 | 10-18 | **** | **** | 13-14 |

Legend for Table 6:
* = No sequence homologies were found with known G and SH proteins and were thus excluded,
** = Sequences not available,
* = See list in table 4, denoted by same (*),
**** = ORF absent in viral genome.

6.5 EXAMPLE 5

Genomic Sequence of hMPV Isolate 1-99

Another isolate of hMPV (1-99) was also identified and sequenced. In order to do so, the hMPV isolate 1-99 was propagated on tertiary monkey kidney cells exactly as described before (van den Hoogen et al., 2001, Nature Medicine 7(6):719-724). Viral RNA was isolated using the MagnaPure LC isolation system (Roche Applied Science) and the total nucleic acid kit protocol. RNA was converted into cDNA using standard protocols, with random hexamers (Progema Inc. Leiden) as primers. This cDNA was kept at −20° C. or lower until used for sequence analysis. Primers used throughout this project were based on the sequences available from the prototype hMPV 1-00 strain, or obtained after sequence analysis using the hMPV strain 1-99.

PCR fragments were made ranging in size up to 1600 base-pairs to generate overlapping fragments. Sequence analysis was performed on the PCR fragments using standard technology and an ABI 3100 capillary sequence instrument (Applied Biosystems, Nieuwerkerk Issel). The nucleotide sequences generated were compared initially with the prototype hMPV strain 1-00 for comparison. Blast software was used for comparison with related sequences in the GenBank database. For further analysis of the sequences, DNASTAR software was used (DNASTAR Inc, Madison Wis., U.S.A.) and for phylogenetic analysis, the ClustalW software program was used.

Initially, sequences for the 1-99 isolate were obtained using primers that were designed based on sequence information from the 1-00 isolate. However, since some parts of the genome could not be sequenced based on the information from the 1-00 isolate, new primers based on sequence information from the 1-99 isolate, as well from information made available through the sequencing of the 3' and 5' end of the 1-00 isolate, were used.

The prototype sequence of the hMPV isolate 1-99 contained 13,223 base-pairs, sequenced in a total of 227 individual sequences, with an average length of 404 base-pairs. The sequence is SEQ ID NO:18.

The length of the open reading frames of hMPV 1-99 and other *Paramyxoviruses*, both in absolute size and percentage amino acid identity are shown in Table 7.

Most identity between the 1-99 and 1-00 strains was observed in the genes coding for N protein (95.2%), M (97.3%), F (93.7%), L (94.1%) and M2-1 (94.1%) with percentages homology of over 90%. The homology of the P and M2-2 genes between both strains was found to be 86.1 and 88.9% respectively. Also, the isolate is mostly related to the subtype C of the avian *Metapneumovirus*, with amino acid identities in the N protein (88.6%), M protein (87.1%) and M2-1 protein (84.3%). The identity with the P and M2-2 proteins is lower at 67.8% and 56.9% respectively.

The genes of the prototype 1-00 and 1-99 strains are identical on the genomic map, with the same number of amino acids for N, P, M, F, M21 and M2-2 protein. The putative SH gene is 6 amino acids shorter, the G protein is 12 amino acids shorter, and the L gene of the 1-00 and 1-99 strain are the same size.

Finally, the start of the genes on the genomic map and the non-coding sequences located between the genes, have been summarized in Table 8.

In summary, the sequence information of the 1-99 strain of the human *Metapneumovirus* clearly demonstrates the genetic relation of 1-99 with the prototype strain 1-00, sharing identical genomic map organization. Less phylogenetic relation is observed with the subtype C of APV.

TABLE 7

LENGTH OF THE ORFS OF HMPV 1-99 AND OTHER PARAMYXOVIRUSES (NO. OF AMINO ACID RESIDUES)

| | N | P | M | F | M21 | M22 | SH | G | L |
|---|---|---|---|---|---|---|---|---|---|
| 1-99 | 394 | 294 | 254 | 539 | 187 | 71 | 177 | 224 | 1937 |
| 1-00 | 394 | 294 | 254 | 539 | 187 | 71 | 183 | 236 | 2005 |
| APV-A | 391 | 278 | 254 | 538 | 186 | 73 | 174 | 391 | 2004 |
| APV-B | 391 | 279 | 254 | 538 | 186 | 73 | | 414 | |
| APV-C | 394 | 294 | 254 | 537 | 184 | 71 | | | |
| hRSV-A | 391 | 241 | 256 | 574 | 194 | 90 | 64 | 298 | 2165 |
| hRSV-B | 391 | 241 | 256 | 574 | 195 | 90 | 65 | 299 | 2166 |
| bRSV | 391 | 241 | 256 | 574 | 186 | 90 | 81 | 257 | 2162 |
| PVM | 393 | 295 | 257 | 537 | 176 | 98 | 92 | 396 | |

PERCENTAGE OF THE AMINO ACID SEQUENCE IDENTITY BETWEEN HMPV 1-99 AND OTHER PARAMYXOVIRUSES

| | N | P | M | F | M21 | M22 | SH | G | L |
|---|---|---|---|---|---|---|---|---|---|
| 1-00 | 95,2 | 86,1 | 97,3 | 93,7 | 94,1 | 88,9 | 59 | 32,4 | 94,1 |
| APV-A | 68,9 | 58,1 | 76,1 | 67,5 | 69 | 25 | 13,1 | 14,2 | 63,7 |
| APV-B | 69,1 | 53,9 | 76,5 | 66,8 | 65,8 | 26,4 | | | |
| APV-C | 88,6 | 67,8 | 87,1 | 80,5 | 84,3 | 56,9 | | | |
| bRSV | 41,1 | 28,1 | 36,9 | 35 | 32,6 | 9,7 | 12,2 | 15,6 | 46,5 |
| hRSV-A | 41,1 | 26 | 37,6 | 32,2 | 35,6 | | 6,2 | 16 | 46,9 |
| hRSV-B | 40,6 | 26 | 36,9 | 34,4 | 34 | 13,9 | 21,2 | 15,6 | 47 |
| PVM | 43,7 | 22,4 | 39,2 | 38,8 | | | 5,4 | 8 | |

TABLE 8

SUMMARY OF GENE START SEQUENCES ON THE GENOMIC MAP AND THE NON-CODING SEQUENCES LOCATED BETWEEN THE GENES.

| Pos. | ORF | Stop | Non-coding sequence | Gene start | Start | Pos | ORF |
|---|---|---|---|---|---|---|---|
| 1 | Le | | ACGAGAAAAAAACGCGUAUAAAUU | GGGACAAAUAAAA | AUG | 54 | N |
| | | | AAAUUCCAAACAAAAC | | | | |
| 1238 | N | UAA | UUAAAAAACU | GGGACAAGUCAAA | AUG | 1262 | P |
| 2146 | P | UAG | UUUAAUAAAAAUAAACAAU | GGGACAAGUCAAG | AUG | 2179 | M |
| 2943 | M | UAA | AAAUAACUGUCUUAAUCAAUAAUU | GGGACAAAUAAAA | AUG | 3065 | F |
| | | | GCUUAUAUAACUCUAG | | | | |
| | | | AGAUUAAUAAGCUUAUUAUUAUAG | | | | |
| | | | UUAUAUAAAAAUAAAU | | | | |
| | | | UAGAAUUAGAAGGGCAUCAAUAGA | | | | |
| | | | AAGC | | | | |
| 4684 | F | UAG | UUAAUUAAAAAAU | GGGACAAAUCAUC | AUG | 4711 | M2 |
| 5437 | M2 | UAG | UAAAAAAUAAAAAUAGAAU | GGGAUAAAUGACA | AUG | 5470 | SH |
| 6003 | SH | UAA | AAUAACACGGSUUUSAACAUUAAA | GGGACAAGUGGCU | AUG | 6210 | G |
| | | | AUSAGAACAACCUCCA | | | | |
| | | | CCCAGGUCUAUCAAUACAGUGGUU | | | | |
| | | | UAGCCAUUUAAAAACC | | | | |
| | | | GAAUAUUAUCUAGGCUGCACGACA | | | | |
| | | | CUUUGCAAUAAUAUGC | | | | |
| | | | AAUAGUCAAUAGUUAAACCACUGC | | | | |
| | | | UGCAAACUCAUCCAUA | | | | |
| | | | AUAUAAUCACUGAGUAAUACAAAA | | | | |
| | | | CAAGAAAAU | | | | |
| 6884 | G | UAG | AGAGGUGCAAAACUCAAAUGAGCA | GGGAUAAAUGACA | AUG | 7124 | L |
| | | | CAACACACAAACAUYC | | | | |
| | | | CAUCCAAGUAGUUAACAAAAAACC | | | | |
| | | | ACAAAAUAACCUUGAA | | | | |
| | | | AACCAAAAAACCAAAACAUAAACC | | | | |
| | | | CAGACCCAGAAAAACA | | | | |
| | | | UAGACACCAUAUGGAAGGUUCUAG | | | | |
| | | | CAUAUGCACCAAUGAG | | | | |
| | | | AUGGCAUCUGUUCAUGUAUCAAUA | | | | |
| | | | GCACCACCAUCAUUCA | | | | |
| | | | AGGAAUAAGAAGAGGCGAAAAUUU | | | | |
| | | | AA | | | | |
| 13009 | L | UGA | AUUAAACUAUGAUUUCUUUGAAGC | | AUG | 13243 | Tr |
| | | | AUUAGAGAACACAUAC | | | | |
| | | | CCCAAUAUGAUCAAGCUUAUAGAU | | | | |

TABLE 8-continued

SUMMARY OF GENE START SEQUENCES ON THE GENOMIC MAP AND THE NON-CODING SEQUENCES LOCATED BETWEEN THE GENES.

| Pos. | ORF Stop | Non-coding sequence | Gene start | Start | Pos | ORF |
|---|---|---|---|---|---|---|
| | | AAUUUGGGAAAUGCAG | | | | |
| | | AAAUAAAGAAACUAAUCMAGGUCM | | | | |
| | | CUGGGUAUAUGCUUGU | | | | |
| | | GAGUAAGAAGUAAUAAUAAUGAUA | | | | |
| | | AUGAUUAACCAUAAUC | | | | |
| | | UCMCMCMACUGAGAAAAUAAUCGU | | | | |
| | | CUAACAGUUUAGUUGA | | | | |
| | | UCAUUAGUUAUUUAAAAUUAUAAA | | | | |
| | | AUAGUAACUA | | | | |

6.6 EXAMPLE 6

Phylogenetic Relationships

Phylogenetic approaches can be used in order to identify the relationships among groups of viruses, i.e. between MPV and other viruses. Additionally, phylogenetic relationships can be determined for different isolates of the same type of virus. Phylogenetic trees were determined to determine relationships between MPV and other viruses, and also to determine relationships between the different isolates of hMPV. For example, phylogenetic trees can be generated, using nucleotide or protein sequence data, in order to illustrate the relationship between MPV and different viruses. Alternatively, phylogenetic trees can be generated, using nucleotide or protein sequence data, in order to illustrate the relationship between various isolates of hMPV.

PHYLOGENETIC RELATIONSHIPS BETWEEN hMPV AND DIFFERENT VIRUSES: Although BLAST searches using nucleotide sequences obtained from the unidentified virus isolates revealed homologies primarily with members of *Pneumovirinae*, homologies that were based on protein sequences revealed some resemblance with other *paramyxoviruses* as well. As an indication of the relationship between the newly identified virus isolates and members of *Pneumovirinae*, phylogenetic trees were constructed based on the N, P, M and F ORFs of these viruses. In all four phylogenetic trees, the newly identified virus isolate was most closely related to APV (FIG. 14). From the four serotypes of APV that have been described (Bayon-Auboyer et al., 2000, J Gen. Virol 81:2723-2733), APV serotype C, the *metapneumovirus* found primarily in birds in the USA, showed the closest resemblance to the newly identified virus. It should be noted however, that only partial sequence information for APV serotype D is available.

For all phylogenetic trees, DNA sequences were aligned using the ClustalW software package and maximum likelihood trees were generated using the DNA-ML software package of the Phylip 3.5 program using 50 or 100 bootstraps and 3 jumbles (Brandenburg et al., 1997, J Med Virol 52:97-104). Previously published sequences that were used for the generation of phylogenetic trees are available from Genbank under accessions numbers: For all ORFs: hRSV: NC001781; bRSV: NC001989; For the F ORF: PYM, D11128; MV-A, D00850; MV-B, Y14292; MV-C, AF187152; For the N ORF: PVM, D10331; MV-A, U39295; MV-B, U39296; MV-C, M176590; For the M ORF: PMV,U66893; MV-A, X58639; MV-B, U37586; MV-C, AE262571; For the P ORF: PVM, 09649; MV-A, U22110, MV-C, AF176591.

As an indicator of the relationship between MPV and members of the *Pneumovirinae*, phylogenetic trees based on the N, P, M, and F ORFs were constructed previously (van den Hoogen et al., 2001, Nat Med 7(6):19-24) and revealed a close relationship between MPV and APV-C. Because of the low homology of the MPV SH and G genes with those genes of other *paramyxoviruses*, reliable phylogenetic trees for these genes cannot be constructed. In addition, the distinct genomic organization between members of the *Pneumovirus* and *Metapneumovirus* genera make it impossible to generate phylogenetic trees based on the entire genomic sequence. Trees for the M2 and L genes were constructed in addition to those previously published. Both these trees confirmed the close relation between APV and MPV within the *Pneumovirinae* subfamily (FIG. 15).

To construct phylogenetic trees, DNA sequences were aligned using the ClustalW software package and maximum likelihood trees were generated using the DNA-ML software package of the Phylip 3.5 program using 100 bootstraps and 3 jumbles. Bootstrap values were computed for consensus trees created with the PHYLIP consensus package.

Based upon phylogenetic analyses of the different isolates of hMPV obtained so far, two major genotypes have been identified with virus isolate 00-1 being the prototype of genotype A and isolate 99-1 the prototype of genotype B.

It is hypothesized that the genotypes are related to subtypes and that re-infection with viruses from both subgroups occur in the presence of pre-existing immunity and the antigenic variation may not be strictly required to allow re-infection. Furthermore, hMPV appears to be closely related to avian *pneumovirus*, a virus primarily found in poultry. The nucleotide sequences of both viruses show high percentages of homology, with the exception of the SH and G proteins. The viruses appear to cross-react in tests that are based primarily on the nucleoprotein and matrixprotein, however, they respond differently in tests that are based on the attachment proteins. The differences in virus neutralization titer provide further proof that the two genotypes of hMPV are two different serotypes of one virus, where APV is a different virus.

PHYLOGENETIC RELATIONSHIPS BETWEEN DIFFERENT hMPV ISOLATES: Phylogenetic approaches can also be used in order to identify the relationships among different isolates of MPV. For example, phylogenetic trees can be generated, using nucleotide or protein sequence data of MPV, in order to illustrate the relationship between a number of MPV isolates that are obtained from different subjects. This approach is useful in understanding the differences that occur within the population of MPV viruses.

To determine the relationship of our various newly identified virus isolates, phylogenetic trees were constructed based on sequence information obtained from eight to nine isolates (8 for F, 9 for N, M and L). RT-PCR was used with primers designed to amplify short fragments in the N, M, F, P, SH and L ORFs, that were subsequently sequenced directly. The nine virus isolates that were previously found to be related in serological terms (see above) were also found to be closely related genetically. In fact, all nine isolates were more closely related to one another than to APV. Although the sequence information used for these phylogenetic trees was limited, it appears that the nine isolates can be divided in two groups, with isolate 94-1, 99-1 and 99-2 clustering in one group and the other six isolates (94-2; 93-1; 93-2; 93-3; 93-4; 00-1) in the other (FIG. 16).

An alignment of the F genes of different isolates of hMPV of all four variants, variant A1, A2, B1, or B2, is shown in FIG. 17.

An alignment of the F proteins of different isolates of hMPV of all four variants, variant A1, A2, B1, or B2, is shown in FIG. 18.

An alignment of the G genes of different isolates of hMPV of all four variants, variant A1, A2, B1, or B2, is shown in FIG. 19.

An alignment of the G proteins of different isolates of hMPV of all four variants, variant A1, A2, B1, or B2, is shown in FIG. 20.

A phylogenetic tree based on the F gene sequences showing the phylogenetic relationship of the different hMPV isolates and their association with the respective variants of hMPV is shown in FIG. 21. Further, a phylogenetic tree based on the G gene sequences showing the phylogenic relationship of the different hMPV isolates and their association with the respective variants of hMPV is shown in FIG. 22. The phylogenetic trees were calculated using DNA maximum likelihood with 50 bootstraps and 3 jumbles.

Sequence identities between different genes of hMPV isolate 00-1 with different genes of hMPV isolate 99-1, APV serotype C, and APV serotype A are listed in Table 9.

TABLE 9

ORF SEQUENCE IDENTITY BETWEEN HMPV ISOLATE 00-1 AND OTHER VIRUSES

| | N | P | M | F | M2.1 | M2.2 | SH | G | L |
|---|---|---|---|---|---|---|---|---|---|
| hMPV isolate 99-1 | 95 | 86 | 98 | 94 | 95 | 90 | 57 | 33 | 94 |
| APV serotype C | 88 | 68 | 87 | 81 | 84 | 56 | N.A. | N.A. | N.A. |
| APV serotype A | 69 | 55 | 78 | 68 | 72 | 25 | 18 | 9 | 64 |

Originally, phylogenetic relationships were inferred for only nine different isolates. Two potential genetic clusters were identified by analyses of partial nucleotide sequences in the N, M, F and L ORFs of virus isolates. Nucleotide identity of 90-100% was observed within a cluster, and 81-88% identity was observed between the clusters. Sequence information obtained on more virus isolates confirmed the existence of two genotypes. Virus isolate 00-1, as a prototype of cluster A, and virus isolate 99-1 as a prototype of cluster B, have been used in cross neutralization assays to test whether the genotypes are related to different serotypes or subgroups.

Using RT-PCR assays with primers located in the polymerase gene, thirty additional virus isolates were identified from nasopharyngeal aspirate samples. Sequence information of parts of the matrix and polymerase genes of these new isolates together with those of the previous nine isolates were used to construct phylogenetic trees (FIG. 15). Analyses of these trees confirmed the presence of two genetic clusters, with virus isolate 00-1, as the prototype virus in group A and virus isolate 99-1 as the prototype virus in group B. The nucleotide sequence identity within a group was more than 92%, while between the clusters the identity was 81-85%.

6.7 EXAMPLE 7

Leader Sequences of Human Metapneumovirus (hMPV) NL/1/00 Genomic RNA

While the majority of genomic composition was determined, the authentic terminal sequences at the extreme ends were lacking. Using ligation of the viral RNA and subsequent PCR amplification of the ligated junction and a combination of polyadenylation and 3' RACE methods, the authentic nucleotide sequences were determined (FIG. 54). The sequence analysis of PCR fragments generated by ligation of viral RNA ends revealed the Leader and Trailer sequences displayed in FIG. 26 (See, SEQ IDs 18-21). The trailer sequences obtained this way were consistent with the sequences expected from the trailer sequences of other *pramyxoviruses*, including APV. However, the leader sequence of only 2 out of 71 clones sequenced, contained AC as the terminal nucleotide residues that are found in all *paramyxoviruses* to date. Therefore, the terminal nucleotide sequences of the hMPV/NL/1/00 leader were subsequently confirmed using a combination of polyadenylation and 3' RACE methods. Furthermore, two extra nucleotides at the 3' leader terminus of hMPV NL/1/00 were identified.

Vero-grown hMPV NL/1/00 virus was used in this study. As a control, a related negative sense RNA virus, respiratory syncytial virus (RSV) A2, that has a similar genomic size with identified terminal sequences, was included. Viral RNA was isolated using the QIAamp Viral RNA Mini Kit (Qiagen), following the manufacturer's instructions.

Viral RNA was polyadenylated by incubating the viral RNA with poly (A) polymerase (Ambion) at 37° C. for 1 hr, followed by clean up using a NucAway spin column (Ambion). The viral RNA was then reverse transcribed using a primer complementary to the poly (A) tail region and the reverse transcriptase, Superscript I (Invitrogen). PCR and Nested PCR reactions were carried out using hMPV specific primers, juxtaposed to the terminal ends, to amplify the desired products with expected sizes for sequencing analysis. PCR products were further cloned into pCRII vector using a TA cloning kit (Invitrogen). To reveal the authentic nucleotide sequences for the terminus, direct sequencing of PCR DNA as well as the cloned PCR products were conducted.

Only hMPV data are shown in FIG. 55. Control experiments, using RSV-A2 RNA, indicated that the leader sequences of RSV-A2 remained intact and detectable with the same approach. Sequencing analyses on PCR products directly (FIG. 55) and on PCR clones both indicated that the leader region of hMPV consisted of 5' ACG CGA AAA AAA CGC GTA TA (SEQ ID NO: 394) (expressed as positive sense cDNA orientation) at the 3' most proximal 20 nucleotides in the leader sequence.

6.8 EXAMPLE 8

Stereotyping and Subgrouping of MPV Isolates

Virus neutralization assays (See, e.g., Example 16) were used to determine if the virus isolates of hMPV could be distinguished by serotype or genotype. Virus isolates 00-1 and 99-1 were used to inoculate ferrets in order to raise virus-specific antisera. For the 00-1 isolate, ferret and guinea pig specific antisera for the virus were generated by experimental intranasal infection of two specific pathogen free ferrets and two guinea pigs, housed in separate pressurized glove boxes. Two to three weeks later all the animals were bled by cardiac puncture, and their sera were used as reference sera. The sera were tested for all previous described viruses with indirect IFA as described below. These antisera, along with antisera prepared using the 99-1 isolate, were used in virus neutralization assays with both viruses (Table 10).

TABLE 10

VIRUS NEUTRALIZATION TITERS

| | ISOLATE 00-1 | ISOLATE 99-1 |
|---|---|---|
| PRESERUM FERRET A (00-1) | 2 | 2 |
| FERRET A 22 DPI (00-1) | 64 | 2 |
| PRESERUM FERRET B (99-1) | 2 | 2 |
| FERRET B 22 DPI (99-1) | 4 | 64 |
| For isolate 00-1 the titer differs 32 (64/2) fold | | |
| For isolate 99-1 the titer differs 16 (64/4) fold | | |

In addition, six guinea pigs were inoculated with either one of the viruses, i.e., 00-1 and 99-1). RT-PCR assays on nasophyeal aspirate samples showed virus replication from day 2 through day 10 post infection. At day 70 post infection the guinea pigs were challenged with either the homologous or the heterologous virus, and in all four cases virus replication was noticed.

Virus neutralization assays with anti sera after the first challenge showed essentially the same results as in the VN assays performed with the ferrets (>16-fold difference in VN titer).

The results presented in this example confirm the existence of two genotypes, that correspond to two serotypes of MPV, and show the possibility of repeated infection with heterologous and homologous virus (Table 11).

TABLE 11

| | primary infection | virus replication | secondary infection | virus replication |
|---|---|---|---|---|
| guinea pig 1-3 | 00-1 | 2 out of 3 | 99-1 | 1 out of 2 |
| guinea pig 4-6 | 00-1 | 3 out of 3 | 00-1 | 1 out of 3 |
| guinea pig 7-9 | 99-1 | 3 out of 3 | 00-1 | 2 out of 2 |
| guinea pig 10-12 | 99-1 | 3 out of 3 | 99-1 | 1 out of 3 |

Note: for the secondary infection guinea pig 2 and 9 were not there any more.

7 Diagnostic Assays/Detection Methods 7.1 EXAMPLE 9

Direct Immunofluoresence Assay (DIF) Method

Nasopharyngeal aspirateples from patients suffering from RTI were analyzed by DIF as described (Rothbarth et. al., 1999, J. of Virol. Methods 78:163-169). Samples were stored at −70° C. In short, nasopharyngeal aspirates were diluted with 5 ml Dulbecco MEM (BioWhittaker, Walkersville, Md.) and thoroughly mixed on a vortex mixer for one minute. The suspension was centrifuged for ten minutes at 840×g. The sediment was spread on a multispot slide (Nutacon, Leimuiden, The Netherlands) and the supernatant was used for virus isolation. After drying, the cells were fixed in acetone for one minute at room temperature. After the slides were washed, they were incubated for 15 minutes at 37° C. with commercially available FITC-labeled anti-sera specific for viruses such as influenza A and B, hRSV and hPIV 1 to 3 (Dako, Glostrup, Denmark). After three washings in PBS and one in tap water, the slides were submerged in a glycerol/PBS solution (Citifluor, UKO, Canterbury, UK) and covered. The slides were then analyzed using a Axioscop fluorescence microscope.

7.2 EXAMPLE 10

Virus Culture of MPV

The detection of the virus in a cultivated sample from a host is a direct indication of the host's current and/or past exposure or infection with the virus.

Samples that displayed CPE after the first passage were used to inoculate sub-confluent mono-layers of tMK cells in media in 24 well plates. Cultures were checked for CPE daily and the media was changed once a week. Since CPE differed for each isolate, all cultures were tested at day 12 to 14 with indirect IFA using ferret antibodies against the new virus isolate. Positive cultures were freeze-thawed three times, after which the supernatants were clarified by low-speed centrifugation, aliquoted and stored frozen at −70° C. The 50% tissue culture infectious doses ($TCID_{50}$) of virus in the culture supernatants were determined as described (Lennette, D. A. et al. In: Diagnostic Procedures For Viral, Rickettsial, And Chlamydial Infections, 7th ed. (eds. Lennette, E. H., Lennette, D. A. & Lennette, E. T.) 3-25; 37-138; 431-463; 481-494; 539-563 (American Public Health Association, Washington, 1995)).

7.3 EXAMPLE 11

Antigen Detection by Indirect Immunofluoresence Assays (IFA)

Antibodies can be used to visualize viral proteins in infected cells or tissues. Indirect immunofluorescence assay (IFA) is a sensitive approach in which a second antibody coupled to a fluorescence indicator recognizes a general epitope on the virus-specific antibody. IFA is more advantageous than DIF because of its higher level of sensitivity.

In order to perform the indirect IFA, collected specimens were diluted with 5 ml Dulbecco MEM medium (BioWhittaker, Walkersville, Md.) and thoroughly mixed on a vortex mixer for one minute. The suspension was then centrifuged for ten minutes at 840×g. The sediment was spread on a multispot slide. After drying, the cells were fixed in acetone for 1 minute at room temperature. Alternatively, virus was cultured on tMK cells in 24 well slides containing glass slides. These glass slides were washed with PBS and fixed in acetone for 1 minute at room temperature.

Two indirect IFAs were performed. In the first indirect IFA, slides containing infected tMK cells were washed with PBS, and then incubated for 30 minutes at 37° C. with virus specific antisera. Monoclonal antibodies against influenza A, B and C, hPIV type 1 to 3, and hRSV were used. For hPIV type 4, mumps virus, measles virus, sendai virus, simian virus type 5, and New-Castle Disease virus, polyclonal antibodies (RIVM) and ferret and guinea pig reference sera were used. After three washings with PBS and one wash with tap water, the slides were stained with secondary antibodies directed against the sera used in the first incubation. Secondary antibodies for the polyclonal antisera were goat-anti-ferret (KPL, Guilford, UK, 40 fold diluted), mouse-anti-rabbit (Dako, Glostrup, Denmark, 20 fold diluted), rabbit-anti-chicken (KPL, 20 fold dilution) and mouse-anti-guinea pig (Dako, 20 fold diluted).

In the second IFA, after washing with PBS, the slides were incubated for 30 minutes at 37° C. with 20 polyclonal antibodies at a dilution of 1:50 to 1:100 in PBS. Immunized ferrets and guinea pigs were used to obtain polyclonal antibodies, but these antibodies can be raised in various animals, and the working dilution of the polyclonal antibody can vary for each immunization. After three washes with PBS and one wash with tap water, the slides were incubated at 37° C. for 30 minutes with FITC labeled goat-anti-ferret antibodies (KPL, Guilford, UK, 40 fold diluted). After three washes in PBS and one in tap water, the slides were included in a glycerol/PBS solution (Citifluor, UKO, Canterbury, UK) and covered. The slides were analyzed using an Axioscop fluorescence microscope (Carl Zeiss B. V., Weesp, the Netherlands).

7.4 EXAMPLE 12

Haemagglutination Assays, Chloroform Sensitivity Tests and Electron Microscopy Different characteristics of a virus can be utilized for the detection of the virus. For example, many virus contain proteins that can bind to erythrocytes resulting in a lattice. This property is called hemagglutination and can be used in hemagglutination assays for detection of the virus. Virus may also be visualized under an electron microscope (EM) or detected by PCR techniques.

Hemagglutination assays and chloroform sensitivity tests were performed as described (Osterhaus et al., 1985, *Arch. of Virol* 86:239-25; Rothbarth et al., J of Virol Methods 78:163-169).

For EM analyses, virus was concentrated from infected cell culture supernatants in a micro-centrifuge at 4° C. at 17000× g, after which the pellet was resuspended in PBS and inspected by negative contrast EM.

7.5 EXAMPLE 13

Detection of hMPV/AVP Antibodies of IgC, IgA and IgM Classes

Specific antibodies to viruses rise during the course of infection/illness. Thus, detection of virus-specific antibodies in a host is an indicator of current and/or past infections of the host with that virus.

The indirect enzyme immunoassay (EIA) was used to detect the IgG class of hMPV antibodies. This assay was performed in microtitre plates essentially as described previously (Rothbarth et al., 1999, J. of Vir. Methods 78:163-169). Briefly, concentrated hMPV was solubilized by treatment with 1% Triton X-100. After determination of the optimal working dilution by checkerboard titration, it was coated for 16 hr at room temperature into microtitre plates in PBS. Subsequently, 100 ul volumes of 1:100 diluted human serum samples in EIA buffer were added to the wells and incubated for 1 hour at 37° C. Binding of human IgG was detected by adding a goat anti-human IgG peroxidase conjugate (Biosource, USA), adding TMB as substrate developed plates and Optical Density (OD) was measured at 450 nm. The results were expressed as the S(ignal)/N(egative) ratio of the OD. A serum was considered positive for IgG if the S/N ratio was beyond the negative control plus three times the standard.

The hMPV antibodies of the IgM and IgA classes were detected in sera by capture EIA essentially as described previously (Rothbarth et al., 1999, J Vir Methods 78:163-169). For the detection of IgA and IgM, commercially available microtiter plates coated with anti human IgM or IgA specific monoclonal antibodies were used. Sera were diluted 1:100. After incubation of 1 hour at 37° C., an optimal working dilution of hMPV was added to each well (100 μl) before incubation for 1 hour at 37° C. After washing, polyclonal anti-hMPV antibody labeled with peroxidase was added, and the plate was incubated 1 hour at 37° C. Adding TMB as a substrate the plates were developed, and OD was measured at 450 rim. The results were expressed as the S(ignal)/N(egative) ratio of the OD. A positive result was indicated for IgG when the S/N ratio was beyond the negative control plus three times the standard.

AVP antibodies were detected in an AVP inhibition assay. The protocol for the APV inhibition test is included in the APV-Ab SVANOVIR® enzyme immunoassay that is manufactured by SVANOVA Biotech AB, Uppsala Science Park Glunten SE-751 83 Uppsala Sweden. The results were expressed as the S(ignal)/N(egative ratio of the OD. A serum was considered positive for IgG, if the S/N ratio was beyond the negative control plus three times the standard.

7.6 EXAMPLE 14

Detection of Antibodies in Humans, Mammals, Ruminants or Other Animals by Indirect IFA For the detection of virus specific antibodies, infected tMK cells with MPV were fixed with acetone on coverslips (as described above), washed with PBS and incubated 30 minutes at 37° C. with serum samples at a 1 to 16 dilution. After two washes with PBS and one with tap water, the slides were incubated for 30 minutes at 37° C. with FITC-labeled secondary antibodies to the species used (Dako). Slides were processed as described above.

Antibodies can be labeled directly with a fluorescent dye, which will result in a direct immunofluorescence assay. FITC can be replaced with any fluorescent dye.

7.7 EXAMPLE 15

Detection of Antibodies in Humans, Mammals, Ruminants or Other Animals by ELISA In Paramyxoviridae, the N protein is the most abundant protein, and the immune response to this protein occurs early in infection. For these reasons, a recombinant source of the N proteins is preferably used for developing an ELISA assay for detection of antibodies to MPV. Antigens suitable for antibody detection include any MPV protein that combines with any MPV-specific antibody of a patient exposed to or infected with MPV virus. Preferred antigens of the invention include those that predominantly engender the immune response in patients exposed to MPV, thus, typically are recognized most readily by antibodies of a patient. Particularly preferred antigens include the N, F, M and G proteins of MPV. Antigens used for immunological techniques can be native antigens or can be modified versions thereof. Well known techniques of molecular biology can be used to alter the amino acid sequence of a MPV antigen to produce modified versions of the antigen that may be used in immunologic techniques.

Methods for cloning genes, for manipulating the genes to and from expression vectors, and for expressing the protein encoded by the gene in a heterologous host are well-known, and these techniques can be used to provide the expression vectors, host cells, and the for expressing cloned genes encoding antigens in a host to produce recombinant antigens for use in diagnostic assays. See e.g., MOLECULAR CLONING, A LABORATORY MANUAL AND CURRENT PROTOCOLS IN MOLECULAR BIOLOGY.

A variety of expression systems may be used to produce MPV antigens. For instance, a variety of expression vectors suitable to produce proteins in *E. Coli, B. subtilis*, yeast, insect cells, and mammalian cells have been described, any of which might be used to produce a MPV antigen suitable to detect anti-MPV antibodies in exposed patients.

The *baculovirus* expression system has the advantage of providing necessary processing of proteins, and is therefor preferred. The system utilizes the polyhedrin promoter to direct expression of MPV antigens. (Matsuura et al., 1987, J. Gen. Virol. 68:1233-1250).

Antigens produced by recombinant baculo-viruses can be used in a variety of immunological assays to detect anti-MPV antibodies in a patient. It is well established that recombinant antigens can be used instead of natural virus in practically any immunological assay for detection of virus specific antibodies. The assays include direct and indirect assays, sandwich assays, solid phase assays such as those using plates or beads among others, and liquid phase assays. Assays suitable include those that use primary and secondary antibodies, and those that use antibody binding reagents such as protein A. Moreover, a variety of detection methods can be used in the invention, including calorimetric, fluorescent, phosphorscent, chemiluminescent, luminescent and radioactive methods.

For example, an indirect IgG EIA using a recombinant N protein (produced with recombinant baculo-vuus in insect (Sf9) cells) as antigen can be performed. For antigen preparation, Sf9 cells are infected with the recombinant *baculovirus* and harvested 3-7 days post infection. The cell suspension is washed twice in PBS, pH 7.2, adjusted to a cell density of $5.0\times10^6$ cells/ml, and freeze-thawed three times. Large cellular debris is pelleted by low speed centrifugation (500×g for 15 minutes) and the supernatant is collected and stored at −70° C. until use. Uninfected cells are processed similarly for negative control antigen.

Once the antigen is prepared, 100 μl of a freeze-thaw lysate is used to coat microtiter plates at dilutions ranging from 1:50 to 1:1000. An uninfected cell lysate is run in duplicate wells and serves as a negative control. After incubation overnight, plates are washed twice with PBS/0.05% Tween. Test sera are diluted 1:50 to 1:200 in ELISA buffer (PBS, supplemented to 2% with normal goat sera, and with 0.5% bovine serum albumin and 0.1% milk), followed by incubation wells for 1 hour at 37° C.

Plates are washed two times with PBS/0.05% Tween. Horseradish peroxidase labeled goat anti-human (or against other species) IgG, diluted 1:3000 to 1:5000 in ELISA buffer, is added to wells, and incubated for 1 hour at 37° C. The plates are then washed two times with PBS/0.05% Tween and once with tap water, incubated for 15 minutes at room temperature with the enzyme substrate TMB, 3,3',5,5' tetramethylbenzidine, such as that obtained from Sigma, and the reaction is stopped with 100 μl of 2 M phosphoric acid. Colorimetric readings are measured at 450 nm using an automated microtiter plate reader.

7.8 EXAMPLE 16

Virus Neutralization Assay

When a subject is infected with a virus, an array of antibodies against the virus are produced. Some of these antibodies can bind virus particles and neutralize their infectivity. Virus neutralization assays (VN) are usually conducted by mixing dilutions of serum or monoclonal antibody with virus, incubating them, and assaying for remaining infectivity with cultured cells, embryonated eggs, or animals. Neutralizing antibodies can be used to define type-specific antigens on the virus particle, e.g., neutralizing antibodies could be used to define serotypes of a virus. Additionally, broadly neutralizing antibodies may also exist.

VN assays were performed with serial two-fold dilutions of human and animal sera starting at an eight-fold dilution. Diluted sera were incubated for one hour with 100 $TCID_{50}$ of virus before inoculation of tMK cells grown in 96 well plates, after which the plates were centrifuged at 840×g. The media was changed after three and six days and IFA was conducted with FTIC-labeled ferret antibodies against MPV 8 days after inoculation. The VN titre was defined as the lowest dilution of the serum sample resulting in negative IFA and inhibition of CPE in cell cultures.

7.9 EXAMPLE 17

RNA Isolation

The presence of viruses in a host can also be diagnosed by detecting the viral nucleic acids in samples taken from the host (See e.g., RT-PCR in Example 18 and RAP-PCR in Example 21).

RNA was isolated from the supernatants of infected cell cultures or sucrose gradient fractions using a High Pure RNA Isolation kit, according to instructions from the manufacturer (Roche Diagnostics, Ahnere, The Netherlands). RNA can also be isolated following other procedures known in the art (see, e.g., CURRENT PROTOCOLS IN MOLECULAR BIOLOGY, volume 1-3 (1994-1998). Ed. by Ausubel, F. M. et al., Published by John Wiley and sons, Inc., USA).

7.10 EXAMPLE 18

RT-PCR to Detect/Diagnose MPV

Detection of the virus in a biological sample can be done using methods that copy or amplify the genomic material of the virus. Virus-specific oligonucleotide sequences for RT-PCR assays on known *paramyxoviruses* are described below in this Example. A one-step RT-PCR was performed in 50 μl reactions containing 50 mM Tris.HCl pH 8.5, 50 mM NaCl, 4 mM $MgCl_2$, 2 mM dithiotreitol, 200 μM each dNTP, 10 units recombinant RNAsin (Promega, Leiden, the Netherlands), 10 units AMV RT (Promega, Leiden, The Netherlands), 5 units Amplitaq Gold DNA polymerase (PE Biosystems, Nieuwerkerk aan de Ijssel, The Netherlands) and 5 μl RNA. Cycling conditions were 45 min. at 42° C. and 7 min. at 95° C. once, 1 min at 95° C., 2 min. at 42° C. and 3 min. at 72° C. repeated 40 times and 10 min. at 72° C. once. Primers sequences are provided in the sequence listing. More specifically, the primers used for the nucleoprotein gene were N3 and N4, having nucleotide sequences corresponding to SEQ ID NOs:28 and 29 respectively, and were used to amplify a 151 nucleotide fragment. The primers used for the matrix protein gene were M3 and M4, having nucleotide sequences corresponding to SEQ ID NOs: 30 and 31 respectively, and were used to amplify a 252 nucleotide fragment. The primers used for the polymerase protein gene were L6 and L7, corresponding to SEQ ID NOs: 34 and 35 respectively, and were used to amplify a 173 nucleotide fragment. The primers used for the F protein gene were F7 and F8, corresponding to SEQ IS NOs: 32 and 33 respectively, and were used to amplify a 221 nucleotide fragment.

Furthermore, probes were used to confirm the presence of hMPV genome sequences. The probe used to detect the M gene had a nucleotide sequence corresponding to SEQ ID NO: 36. The probe used to detect the N gene had a nucleotide sequence corresponding to SEQ ID NO: 37. The probe used to detect the L gene had a nucleotide sequence corresponding to SEQ ID NO:38.

In another example, primers and probes can be designed based on MPV sequences that are known or obtained through sequencing. Likewise, different sequences of primers and difference buffer and assay conditions to be used for specific purposes would be known to one skilled in the art.

RT-PCR was used for the detection of known *paramyxoviruses* as well. Primers for hPIV-1 to 4, mumps, measles, Tupsia, Mapuera, and Hendra were developed in house and based on alignments of available sequences. Primers for New Castle Disease Virus were taken from Seal, J., J. et al; Clin. Microb., 2624-2630, 1995. Primers for Nipah and general *paramyxovirus*-PCR were taken from Chua, et al., 2000, *Science,* 288. The primers used to detect other known *paramyxoviruses* were as follows: hPIV-1 was detected with primers corresponding to the sequences of SEQ ID NO: 58 and 59 for the forward and reverse primers respectively, hPIV-2 was detected with primers corresponding to the sequences of SEQ ID NO: 60 and 61 for the forward and reverse primers respectively, hPIV-3 was detected with primers corresponding to the sequences of SEQ ID NO: 62 and 63 for the forward and reverse primers respectively, hPIV-4 was detected with primers corresponding to the sequences of SEQ ID NO: 64 and 65 for the forward and reverse primers respectively, Mumps was detected with primers corresponding to the sequences of SEQ ID NO: 66 and 67 for the forward and reverser primers respectively, NDV was detected with primers corresponding to the sequences of SEQ ID NO: 68 and 69 for the forward and reverse primers respectively, Tupaia was detected with primers corresponding to the sequences of SEQ ID NO: 70 and 71 for the forward and reverse primers respectively, Mapuera was detected with primers corresponding to the sequences of SEQ ID NO: 72 and 73 for the forward and reverse primers respectively, Hendra was detected with primers corresponding to the sequences of SEQ ID NO: 74 and 75 for the forward and reverse primers respectively, Nipah was detected with primers corresponding to the sequences of SEQ ID NO: 76 and 77 for the forward and reverse primers respectively, hRSV was detected with primers corresponding to the sequences of SEQ ID NO: 78 and 79 for the forward and reverse primers respectively, Measles was detected with primers corresponding to the sequences of SEQ ID NO: 80 and 81 for the forward and reverse primers respectively, and general Paramyxoviridae viruses were detected with primers corresponding to the sequences of SEQ ID NO: 82 and 83 for the forward and reverse primers respectively.

7.11 EXAMPLE 19

Detection of hMPV Using PCR

In order to detect the presence of hMPV in a sample, a rapid and simple PCR based assay was developed. Regular RT-PCR assays targeting L and N sequences of hMPV were performed with the following primer sets: L-forward (5'-CACCCCAGTCTTTCTTGAAA-3') (SEQ ID NO: 399) and L-reverse (5'-CATGCCCACTATAAAAGGTCAG-3') (SEQ ID NO: 34) and the primers N-forward (5'-CATGCTATATTAAAAGAGTCTC-3') (SEQ ID NO: 400) and N-reverse (5'-TCTGCAGCATATTTGTAATCA-3') (SEQ ID NO: 401). The reaction mixture (total volume 50 μl ) contained 5 μl RNA, 200 nM of each primer, AmpliTaq Gold buffer (Applied Biosystems, Nieuwerkerk a/d IJssel, The Netherlands), 600 μM dNTPs, 2 μM DTT, 2 mM MgCl2, 20 U RNAsin, 5 U Taq polymerase and 10 U AMV reverse transcriptase (all enzymes supplied by Promega). The RT-PCR parameters were: 60 min at 42° C. and 7 min at 95° C., followed by 40 cycles of 1 min at 95° C., 2 min at 45° C. and 3 min at 72° C. A final incubation at 72° C. for 10 min was included to ensure that elongation of all new DNA strands was completed.

Detection of PCR products was performed by transferring a 10 μl PCR reaction sample to a Hybond N+ membrane (Amersham Pharmacia biotech) and subsequent hybridization with a biotin-labeled probe (for both assays resp. N-probe (5'-ACAACTGCAGTGACACCTTCATCATTGCA-3') (SEQ ID NO: 402) and L-probe(5'-CTGTTAATATCCCACACCAGTGGCATGC-3') (SEQ ID NO: 403). Then the conjugate streptavidinperoxidase was bound to the probe and the detection reagent ECL (Amersham Pharmacia biotech) added. DNA fragments were visualized by exposing the blot to a x-ray film (FIG. 58). The results demonstrate that this RT-PCR based assay can be used to detect MPV strains from all four clades using one set of oligonucleotides for either the N or the L sequences.

7.12 EXAMPLE 20

Development of a Single Assay for the Detection of all Four Human Metapneumovirus Subtypes In order to allow for the detection of all hMPV subtypes, A1, A2, B1, and B2, a single sensitive assay was developed. This assay was advantageous because it allowed for the detection of hMPV strains from the various subtypes to be detected using a uniform set of diagnostic equipment and reagents. This new and sensitive Taqman assay was determined to be equally sensitive for all four subtypes.

Two sets of Taqman primers and probe were designed to identify all four subclades of hMPV on the basis of sequence information of the hMPV nucleocapsid gene from 53 clinical isolates. All four subtypes of hMPV were present within this panel of isolates. The selected primers and probes were located within the most conserved sequences in all subtypes. Designed Taqman primers for assay were Medi-N-forward (5'-CAACAACATAATGCTAGGACATGTATC-3') (SEQ ID NO: 404), Medi-N-reverse (5'CCGAGAACAACACTAGCAAAGTTG-3') (SEQ ID NO: 405) and probe Medi-N-probe (5'-FAM-TGGTGCGAGAAATGGGTCCT- GAATCTGG-TAMRA-3') (SEQ ID NO: 406). For assay NL-N the designed primers were RF930 (5'-CATATAAG-CATGCTATATTAAAAGAGTCTC-3') (SEQ ID NO: 407) and RF931 (5'-CCTATTTCTGCAGCATATTTGTAAT-CAG-3') (SEQ ID NO: 408) and probe RF928 (5'-FAM-TGYAATGATGAGGGTGTCACTGCGGTTG-TAMRA-3') (SEQ ID NO: 409) in which Y is either a C or a T residue.

HMPV isolates were obtained from frozen diagnostic nasopharyngeal samples. Viruses were grown on tMK cells and stored at −70° C. From all clinical hMPV isolates, four were chosen as prototype isolates, one for each subtype, to test the designed primers and probes. Full sequences of these prototype viruses can be obtained from the GenBank database: Prototype virus for hMPV subtype A1 (strain NL/01/00; accession number AF371337), A2 (strain NL/17/00; to be submitted), B1 (strain NL/99/01; to be submitted) and B2 (strain NL/94/01; to be submitted).

RNA runoff transcripts were made for generating a standard curve to be able to quantitate viral genomic copy numbers. The N sequence of the hMPV A1 prototype virus was cloned into a modified pCITE vector under the control of a T7 promoter. Runoff transcripts were generated using the Riboprobe System -T7 system (Promega), according to the manufacturer's instructions. Purity of the RNA runoff transcripts were checked by gel electrophoresis and quantitated by measuring A260 in a photospectrometer.

RNA was isolated with a high pure RNA isolation kit (Roche Diagnostics, Almere, The Netherlands) according to the manufacturers instructions. A 0.2 ml sample was used for RNA isolation. After binding to the column, DNase I digestion and washing, the RNA was eluted in 50 l nuclease-free double-distilled water. A 5 μl RNA sample was used for generation of cDNA with specific primers using the superscript III reverse-transcriptase enzyme (Invitrogen) in a final volume of 20 μl according to the manufacturers instruction. Aliquots of 5 μl cDNA were used for each real time PCT reaction.

Detection of viral RNA was performed using the Taqman universal PCR master mix (Applied Biosystems, Nieuwerkerk a/d IJessel, The Netherlands) following a separate RT step and according to the manufacturer's instructions. For the one step reactions the EZ RT-PCR kit (Applied Biosystems) was used. Amplification and detection were performed in the ABI Prism 7000 Taqman machine (Applied Biosystems). Each reaction mix contained 500 nm of forward primer (RF930), 250 nm reverse primer (RF931) and 500 nM endonuclease probe (RF928) labeled at the 5' end with FAM (6-carboxy-fluorescein) and at the 3' end with TAMRA (6-carboxy-tetramethyl-rhodamine). Amplification parameters were 5 min naturation/activation at 95° C. and 45 cycles of 30 sec at 95° C. and 1 min at 60° C. For the one-step reaction these cycle conditions were preceded by 2 min at 50° C. and 30 min at 60° C. for the RT step.

Two sets of primers and probe (for assays Medi-N and NL-N) were designed to detect all four subclades of hMPV. Primers and probes were targeted at the mostly conserved sequences within the nucleocapsid gene of hMPV and designed to hybridize with all four subclades of hMPV. Both assays were tested for their sensitivity to detect target sequences of the four prototype hMPV viruses. Runoff transcripts from the N sequences of the prototype virus strains were used to determine the sensitivity of both assays. A comparison between both assays (Medi-N and NL-N) revealed that both assays were able to detect target sequences from all four subclades of hMPV. Serial dilutions of runoff transcripts and virus isolates showed that the assay NL-N had a higher sensitivity in detecting target sequences of the A1 and A2 prototype virus strains. Therefore, the assay NL-N was chosen for further development and testing.

To test whether the primers and probe designed for assay NL-N were specific for hMPV, template RNA from 15 other common respiratory viral agents were used for real time RT-PCR analysis. These templates were isolated from virus stocks including RNA from measles virus, mumps, SV5, NDV, RSV A and B, APV-A, B, and C, HPIV-1, 2, 3, and 4, and Influenza virus A and B. The positive control sample was an hMPV A1 RNA template. None of the RNA templates isolated from the non hMPV virus stocks gave a positive signal, confirming that the designed primers and probe were specific for hMPV.

Different amounts of forward and reverse primers and of the probe were tested to obtain an optimal amplification signal. Preliminary experiments revealed that an asymmetric mix with twice the amount of forward primer (RF930) as compared to the reverse primer (RF931) give the most sensitive reaction mixture. To determine the sensitivity of our assay, serial dilutions of viral RNA from all four prototype viruses of hMPV were tested. Serial dilutions from the hMPV A1 and B1 prototype strains gave a positive result up to a dilution of $10^4$, while RNA from the higher titered virus stocks from the hMPV A2 and B2 prototype strains could be diluted as far as $10^5$ times (FIG. 59A). The assay proved to be equally sensitive for all four prototype viruses with a detection limit of at least 0.006 TCID50 for the hMPV A2 prototype virus and 0.01 TCID50 for the other prototype viruses. As a standard, RNA run-off transcripts from the hMPV A1 N sequence were generated. Upon quantitation of these RNA transcripts and making serial dilutions, as low as 5 RNA copies yielded a positive signal in our Taqman RT-PCR assay (FIG. 59 B).

Primers and probe for our new RT-PCR assay were based on sequences of the N gene from all four hMPV subtypes. Previously described assays, targeting the N (MacKay et. al., J. Clin. Microbiol. 41:100-105) or L (Van Den Hoogen, 2003 in press) sequences of hMPV, however used primers based on the sequence of the hMPV A1 prototype virus only. In FIG. 59 C, entropy plots of oligonucleotide annealing sites for the four prototype hMPV strains are shown for the different primer/probe sets tested. These assays were tested to determine whether they were able to detect all four subtypes of hMPV. The results from these assays on serial RNA dilutions of the prototype viruses showed that they did pick up the hMPV A viruses, albeit with a lower sensitivity than assay NL-N, but not the viruses from the B clades (FIG. 59 D).

7.13 EXAMPLE 21

RAP-PCR

The genetic material of MPV or another virus can be detected or amplified using primers that hybridize to regions within the genome and that extend in a particular direction so that the genetic material is amplified. This type of technique is useful when specific sequence information is unavailable or when performing an initial amplification of genetic material in a sample. One such technique is called RAP-PCR.

RAP-PCR was performed essentially as described (Welsh et al., 1992, *NAR* 20:4965-4970). For the RT reaction, 2 μl of RNA was used in a 10 μl reaction containing 10 ng/μl oligonucleotide, 10 mM dithiotreitol, 500 μm each dNTP, 25 mM Tris-HCl pH 8.3, 75 mM KCl and 3 mM $MgCl_2$. The reaction mixture was incubated for 5 minutes at 70° C. and 5 minutes at 37° C., after which 200 units Superscript RT enzyme (LifeTechnologies) were added. The incubation at 37° C. was continued for 55 minutes and the reaction was terminated by a 5 minute incubation at 72° C. The RT mixture was diluted to give a 50 μl PCR reaction containing 8 ng/μl oligonucleotide, 300 μl each dNTP, 15 mM Tris-HCl pH 8.3, 65 mM KCl, 3.0 mM $MgCL_2$ and 5 units Taq DNA polymerase (FE Biosystems). Cycling conditions were 5 minutes at 94° C., 5 minutes at 40° C., and 1 minute at 72° C. once, followed by 1 minute at 94° C., 2 minutes at 56° C. and 1 minute at 72° C. repeated 40 times, and 5 minutes at 72° C. once.

Primers used for RAP-PCR were: primer ZF1 with a nucleotide sequence corresponding to SEQ ID NO: 46, primer ZF4 with a nucleotide sequence corresponding to SEQ ID NO: 47, primer ZF7 with a nucleotide sequence corresponding to SEQ ID NO: 48, primer ZF10 with a nucleotide sequence corresponding to SEQ ID NO: 49, primer ZF13 with a nucleotide sequence corresponding to SEQ ID NO: 50, primer ZF16 with a nucleotide sequence corresponding to SEQ ID NO: 51, primer CS1 with a nucleotide sequence corresponding to SEQ ID NO: 52, CS4 with a nucleotide sequence corresponding to SEQ ID NO: 53, primer CS7 with a nucleotide sequence corresponding to SEQ ID NO: 54, primer CS10 with a nucleotide sequence corresponding to SEQ ID NO: 55, primer CS13 with a nucleotide sequence corresponding to SEQ ID NO: 56, and primer CS16 with a nucleotide sequence corresponding to SEQ ID NO: 57. Products were run side by side on a 3% NuSieve agarose gel (FMC BioProducts, Heerhugowaard, The Netherlands). Differentially displayed fragments specific for MPV were purified from the gel with a Qiaquick Gel Extraction kit (Qiagen, Leusden, The Netherlands) and cloned in pCR2.1 vector (Invitrogen, Groningen, The Netherlands), according to instructions from the manufacturer. Twenty fragments were successfully purified and sequenced. Sequence homology to APV was found in ten fragments, i.e. fragment 1 isolated using the ZF7 primer yielded a 335 bp fragment with homology to the N gene, fragment 2 isolated using the ZF10 primer yielded a 235 bp fragment with homology to the N gene, fragment 3 isolated using the ZF10 primer yielded a 800 bp fragment with homology to the M gene, fragment 4 isolated using the CS1 primer yielded a 1250 bp fragment with homology to the F gene, fragment 5 isolated using the CS10 primer yielded a 400 bp fragment with homology to the F gene, fragment 6 isolated using the CS13 primer yielded a 1450 bp fragment with homology to the F gene, fragment 7 isolated using primer CS13 yielded a 750 bp fragment with homology to the F gene, fragment 8 isolated using the ZF4 primer yielded a 780 bp fragment with homology to the L gene (protein level), fragment 9 isolated using the ZF10 primer yielded a 330 bp fragment with homology to the L gene (protein level), and fragment 10 isolated using the ZF10 primer yielded a 250 bp fragment with homology to the L gene (protein level).

TaqMan assays can be used to measure the level of expression of a gene. TaqMan assays were adapted to examine the expression of the L-gene and the N-gene. The primers that were used in these assays are not required to be specific to any one of the hMPV groups, however, examples are shown below. Reactions were carried out with a 500 nM concentration of a forward primer, 250 nM concentration of a reverse primer, 250 nM concentration of an oligonucleotide probe, 25 μl of a universal PCR mastermix (available from ABI), and 5 μl of cDNA in a 50 μl total reaction volume. Cycling conditions were: a first step of 10 minutes at 95° C., followed by a second step of 45 cycles consisting of 30 seconds at 95° C. and 60 seconds at 60° C. on an ABI 7000 sequence detection system.

Other examples of primers for the N gene of hMPV to be used in TaqMan assays are as follows: For isolates NL/1/00, BI/1/01, FI/4/01, NL/8/01, and FI/2/01, all of the subgroup A1, primers with the nucleotide sequence of SEQ ID NO: 39 could be used. For isolate NL/30/01, of the subgroup A1, a primer with the nucleotide sequence of SEQ ID NO: 40 could be used. For isolates NL/22/01 and NL/23/01, of the subgroup A2, a primer with the nucleotide sequence of SEQ ID NO: 41 could be used. For isolates NL/17/01, of the subgroup A2, a primer with the nucleotide sequence of SEQ ID NO: 42 could be used. For isolate NL/17/00, of the subgroup A2, a primer with the nucleotide sequence of SEQ ID NO: 43 could be used. For isolates NL/1/99, NL/5/01, NL/21/01, and NL/9/01, of the subgroup B1, a primer with the nucleotide sequence of SEQ ID NO: 44. For isolates FI/1/01 and FI/10/01, of subgroup B1, a primer with the nucleotide sequence of SEQ ID NO: 45 could be used.

A potential probe that can be used for the A1 subgroup corresponds to SEQ ID NO:390, a probe that can be used for the B1 subgroup corresponds to SEQ ID NO:391, and a probe that can be used for the B2 subgroup corresponds to SEQ ID NO:392.

7.14 EXAMPLE 22

Sequence Analysis of RAP-PCR Products

After segments are amplified using RAP-PCR, sequence information can be obtained on the amplified segments. In order to do so, it is advantageous to clone the generated fragments into vectors before sequencing.

RAP-PCR products cloned in vector pCR2.1 (Invitrogen) were sequenced with M13-specific oligonucleotides. DNA fragments obtained by RT-PCR were purified from agarose gels using Qiaquick Gel Extraction kit (Qiagen, Leusden, The Netherlands), and sequenced directly with the same oligonucleotides used for PCR. Sequence analyses were performed using a Dyenamic ET terminator sequencing kit (Amersham Pharmacia Biotech, Roosendaal, The Netherlands) and an ABI 373 automatic DNA sequencer (PE Biosystem). All techniques were performed according to the instructions of the manufacturer.

7.15 EXAMPLE 23

Generating Genomic Fragments by RT-PCR

The RAP-PCR method can leave gaps in the sequence that have not be amplified or copied. In order to obtain a complete sequence, the sequence information of the gaps can be obtained using RT-PCR.

To generate PCR fragments spanning gaps A, B and C between the RAP-PCR fragments (FIG. 3), RT-PCR assays were used as described previously on RNA samples isolated from virus isolate 00-1.

The following primers were used to generate fragment A: TR1 designed in the leader, corresponding to the nucleotide sequence of SEQ ID NO:22 and N1 designed at the 3' end of the RAP-PCR fragments obtained in N and corresponding to the sequence of SEQ ID NO:23. The following primers were used to generate fragment B: N2 designed at the 5' end of the RAP-PCR fragments obtained in N and corresponding to the nucleotide sequence of SEQ ID NO:24 and M1 designed at the 3' end of the RAP-PCR fragments obtained in M and corresponding to the nucleotide sequence of SEQ ID NO:25. The following primers were used to generate fragment C: M2 designed at the 5' end of the RAP-PCR fragment obtained in M and corresponding to the nucleotide sequence of SEQ ID NO:26 and F1 designed at the 3' end of the RAP-PCR fragments obtained in F and corresponding to the nucleotide sequence of SEQ ID NO: 27.

Fragments were purified after gel electrophoresis and cloned and sequenced as described previously.

7.16 EXAMPLE 24

Capture Anti-MPV IgM EIA Using a Recombinant Nucleoprotein

In order to detect the hMPV virus, an immunological assay that detects the presence of the antibodies in a variety of hosts. In one example, antibodies to the N protein are used because it is the most abundant protein that is produced. This feature is due the transcriptional gradient that occurs across the genome of the virus.

A capture IgM EIA using the recombinant nucleoprotein or any other recombinant protein as antigen can be performed by modification of assays as previously described by Erdman et al., 1990, J. Clin. Microb. 29: 1466-1471.

Affinity purified anti-human IgM capture antibody (or against other species), such as that obtained from Dako, is added to wells of a microtiter plate in a concentration of 250 ng per well in 0.1 M carbonate buffer pH 9.6. After overnight incubation at room temperature, the plates are washed two times with PBS/0.05% Tween. 100 μl of test serum diluted 1:200 to 1:1000 in ELISA buffer is added to triplicate wells and incubated for 1 hour at 37° C. The plates are then washed two times with in PBS/0.05% Tween.

The freeze-thawed (infected with recombinant virus) Sf21 cell lysate is diluted 1:100 to 1:500 in ELISA buffer is added to the wells and incubated for 2 hours at 37° C. Uninfected cell lysate serves as a negative control and is run in duplicate wells. The plates are then washed three times in PBS/0.05% Tween and incubated for 1 hour at 37° C. with 100 μl of a polyclonal antibody against MPV in a optimal dilution in ELISA buffer. After 2 washes with PBS/0.05% Tween, the plates are incubated with horseradish peroxide labeled secondary antibody (such as rabbit anti ferret), and the plates are incubated 20 minutes at 37° C.

The plates are then washed five times in PBS/0/05% Tween, incubated for 15 minutes at room temperature with the enzyme substrate TMB, 3,3,5,5 tetramethylbenzidine, as, for instance obtained from "Sigma", and the reaction is stopped with 100 μl of 2M phosphoric acid. Colormetric readings are measured at 450 nm using automated microtiter plate reader.

The sensitivities of the capture IgM EIAs using the recombinant nucleoprotein (or other recombinant protein) and whole MPV virus are compared using acute- and convalescent-phase serum pairs form persons with clinical MPV virus infection. The specificity of the recombinant nucleoprotein capture EIA is determined by testing serum specimens from healthy persons and persons with other *paramyxovirus* infections.

Potential for EIAs for using recombinant MPV fusion and glycoprotein proteins produced by the *baculovirus* expression.

The glycoproteins G and F are the two transmembranous envelope glycoproteins of the MPV virion and represent the major neutralisation and protective antigens. The expression of these glycoproteuns in a vector virus system sych as a baculovirus system provides a source of recombinant antigens for use in assays for detection of MPV specific antibodies. Moreover, their use in combination with the nucleoprotein, for instance, further enhances the sensitivity of enzyme immunoassays in the detection of antibodies against MPV.

A variety of other immunological assays (*Current Protocols in Immunology*, volume 1-3. Ed. by Coligan, J. E., Kruisbeek, A. M., Margulies, D. H., Shevach, E. M. and Strobe, W. Published by John Wiley and sons, Inc., USA) may be used as alternative methods to those described here.

In order to find virus isolates nasopharyngeal aspirates, throat and nasal swabs, broncheo alveolar lavages and throat swabs preferable from but not limited to humans, carnivores (dogs, cats, seals etc.), horses, ruminants (cattle, sheep, goats etc.), pigs, rabbits, birds (poultry, ostridges, etc) can be examined. From birds, cloaca and intestinal swabs and droppings can be examined as well. For all samples, serology (antibody and antigen detection etc.), virus isolation and nucleic acid detection techniques can be performed for the detection of virus. Monoclonal antibodies can be generated by immunizing mice (or other animals) with purified MPV or parts thereof (proteins, peptides) and subsequently using established hybridoma technology (*Current Protocols in Immunology*, Published by John Wiley and sons, Inc., USA). Alternatively, phage display technology can be used for this purpose (*Current Protocols in Immunology*, Published by John Wiley and sons, Inc., USA). Similarly, polyclonal antibodies can be obtained from infected humans or animals, or from immunised humans or animals (*Current Protocols in Immunology*, Published by John Wiley and sons, Inc., USA).

The detection of the presence or absence of NS1 and NS2 proteins can be performed using western-blotting, IFA, immuno precipitation techniques using a variety of antibody preparations. The detection of the presence or absence of NS1 and NS2 genes or homologues thereof in virus isolates can be performed using PCR with primer sets designed on the basis of known NS1 and/or NS2 genes as well as with a variety of nucleic acid hybridisation techniques.

To determine whether NS1 and NS2 genes are present at the 3' end of the viral genome, a PCR can be performed with primers specific for this 3' end of the genome. In our case, we used a primer specific for the 3' untranslated region of the viral genome and a primer in the N ORF. Other primers may be designed for the same purpose. The absence of the NS1/NS2 genes is revealed by the length and/or nucleotide sequence of the PCR product. Primers specific for NS1 and/or NS2 genes may be used in combination with primers specific for other parts of the 3' end of the viral genome (such as the untranslated region or N, M or F ORFs) to allow a positive identification of the presence of NS1 or NS2 genes. In addition to PCR, a variety of techniques such as molecular cloning, nucleic acid hybridisation may be used for the same purpose.

8. Cell Culture Systems and Animal Models for MPV and Recombinant Engineering of MPV

8.1 EXAMPLE 25 hMPV Growth in Different Cell Lines

Virus isolates can be cultured in different cell lines in order to examine characteristics of each virus. For example, the infectivity of different virus isolates can be characterized and distinguished on the basis of titer levels measured in culture. Alternatively, cells can be used to propagate or amplify strains of the virus in culture for further analysis.

In one example, tertiary monkey kidney cells were used to amplify hMPV. However, tertiary monkey kidney cells are derived from primary cells which may only be passaged a limited number of times and have been passaged three times in vivo. It was not known which kind of immortalized cell line would support hMPV virus growth to high titers. A number of monkey cell lines such as Vero, LLC-MK2, HEp-2, and lung fibroblast (LF1043) cells, were tested to see whether they could support hMPV virus replication (Table 12). Trypsin used was TPCK-trypsin (Worthington) at a concentration of 0.001 mg/ml. The growth of this virus in fertilized 10 day old chicken eggs was also tested. The infected eggs were incubated for 2 and 3 days at 37° C. prior to AF harvest. Virus titers were determined by plaque assay of infected cell lysates on Vero cells without trypsin, incubated for 10 days at 35° C., and immunostained using the guinea pig hMPV antiserum. The results showed that Vero cells and LLC-MK2 cells were the cell substrates most suitable for hMPV virus replication, resulting in virus stock titers of $10^6$-$10^7$ pfu/ml. These titers were similar to those obtained from tMK cells. The addition of trypsin at a concentration of 0.01 mg/ml did not increase virus titers appreciably (Table 12).

TABLE 12

HMPV VIRUS GROWTH IN DIFFERENT CELL LINES

| Cell Substrate | Trypsin used to grow virus | Virus titers on Vero cells (pfu/ml) |
|---|---|---|
| Vero | yes | $2.1 \times 10^7$ |
| | no | $1.1 \times 10^7$ |
| LLC-MK2 | yes | $2.3 \times 10^5$ |
| Hep-2 | yes | cells died |
| LF 1043 (HEL) | yes | no virus recovered |
| | no | no virus recovered |
| tMK | yes | $1.0 \times 10^7$ |
| eggs (10 days) | no | no virus recovered |

In order to study the virus kinetics of hMPV viral growth in Vero cells, a growth curve was performed using an MOI of 0.1 (FIG. 23). Cells and cell supernatants were harvested every 24 hours, and analyzed by plaque assay for quantification of virus titers. The results showed that at day 5, near peak titers of hMPV were observed. The absolute peak titer of 5.4 $\log_{10}$ pfu/ml was achieved on Day 8. The virus titer was very stable up to day 10. A growth curve carried out at the same time with solely the cell supernatants, showed only very low virus titers. This data demonstrated that hMPV replication, under the conditions used (MOI of 0.1) peaked on day 8 post-infection and that hMPV was largely, a cell-associated RNA virus.

TRANSFECTION OF 293 CELLS: 293 cells (human kidney epithelial cells) were passed in DMEM and supplemented with FCS (10%), L-Glutamine (1:100) and Pen/Strep (1:100) and split 1:10 every 3-4 days. Care was taken not to let the cells grow to confluency in order to enhance transfectability. Cells were not very adherent; a very brief (2 min. or less) incubation in Trypsin-EDTA was usually sufficient to release them from plastic surfaces. Cells were diluted in culture media immediately after trypsin-treatment.

Cells were split the day before transfection. Cell confluency approximated 50-75% when transfected. Gelatinized plasticware was used to prevent cells from detaching throughout the transfection procedure. Plates or flasks were covered with 0.1% gelatin (1:20 dilution of 2% stock) for 10 minutes and rinsed one time with PBS once. To achieve the correct cell density; cells were used at a concentration of $1\times10^7$ cells per T75 flask or 100 mm plate (in 10 ml) or $1\times10^6$ cells per well of a 6-well plate (in 2 ml).

Transfection lasted for a minimum of 7 hours, however, it was preferable to allow the transfection to occur overnight. The following were combined in a sterile tube: 30 mg DNA with 62 ml 2 M $CaCl_2$ and $H_2O$ to 500 ml (T75) or 3 mg DNA with 6.2 ml 2 M $CaCl_2$ and $H_2O$ to 50 ml (6-well plate); with brief mixing. Addition of 500 or 50 ml 2×HBS occurred dropwise and the solutions were allowed to mix for 5 minutes until a precipitate formed. Gentle care was used, i.e. no vortexing was applied. The old media was replaced with fresh prewarmed media (10 ml per T75 flask or 1 ml per well of a 6-well plate. The DNA was mixed carefully by blowing airbubles through the tube with a Gilson pipet and the precipitate was added dropwise to the media covering the cells. The cells were incubated in a 37°C $CO_2$ atmosphere.

The cells appeared to be covered with little specks (the precipitate). The transfection media was removed from the cells, and the cells were rinsed carefully with PBS, and then replaced with fresh media.

The cells were incubated in a 37°C $CO_2$ atmosphere until needed, usually between 8-24 hours.

A 10× stock of HBS was prepared with 8.18% NaCl, 5.94% Hepes and 0.2% $Na_2HPO_4$ (all w/v). The solution was filter sterilized and stored at 4°C. A 2× solution was prepared by diluting the 10× stock with $H_2O$ and adjusting the pH to 7.12 with 1 M NaOH. The solution was stored in aliquots at −20°C. Care was taken to exactly titrate the pH of the solution. The pH was adjusted immediately before the solution was used for the transfection procedure.

8.2 EXAMPLE 26

Minireplicon Construct of MPV

Minireplicon constructs can be generated to contain an antisense reporter gene. An example of a minireplicon, CAT-hMPV, is shown in FIG. 24. The leader and trailer sequences that were used for the generation of the minireplicon construct are shown in FIG. 26. For comparison, an alignment of APV, RSV and PIV3 leader and trailer sequences are also shown in FIG. 26.

Two versions of the minireplicon constructs were tested: one with terminal AC residues at the leader end (Le+AC), and one without terminal AC residues at the leader end (Le−AC). The two constructs were both functional in the assay (FIG. 25). It can be seen in FIG. 25 that much higher CAT expression occurred after 48 hours than after 24 hours. After 48 hours, around 14 ng CAT per 500,000 cells transfected was observed. This experiment was entirely plasmid driven: the minireplicon was cotransfected with a T7 polymerase plasmid, and the N, P, L, M2.1 genes were expressed from pCITE-2a/3a (the pCite plasmids have a T7 promoter followed by the IRES element derived from the encephalomyocarditis virus (EMCV)). The CAT expression was completely abolished when L, P and N were excluded. A significant reduction in CAT expression was noted when M2.1 expression was excluded from the vector.

The specificity (attributes to heterologous viruses) and the effect of the terminal residues of the leader (attributes to homologous virus) of the minireplicon system can also be tested by superinfecting the minireplicon-transfected cells with hMPV polymerase components (NL/1/00 and NL/1/99) or polymerase components from APV-A, APV-C, RSV or PIV. The different amount of each of the six plasmids can also be tested in order to determine the optimal conditions.

Other reporter genes can be used instead of CAT. In other examples, GFP can be inserted into the minireplicon construct instead of CAT.

8.3 EXAMPLE 27

Rescue of hMPV from a Minireplicon using RSV APV, MPV, or PIV Polymerase

In order to rescue hMPV, minireplicon constructs can be generated to contain a reporter gene. An example of a minireplicon, CAT-hMPV, is shown in FIG. 24. A cDNA encoding the reporter protein chloramphenicol acetyltransferase (CAT) can be cloned in negative-sense orientation between the 5' and 3' noncoding viral sequences. A T7 RNA polymerase promoter sequence and a recognition sequence for a restriction enzyme can flank the construct. In vitro transcription will yield virus-like RNA that will form reconstituted RNP complexes when mixed with purified polymerase proteins. The RNPs can be transfected into eucaryotic cells, for example, with helper virus. Alternatively, the rescue can be entirely plasmid driven, i.e., the minireplicon can be co-transfected with a T7 polymerase plasmid, and the N, P, L, and M2-1 genes expressed from pCITE-2a/3a. The polymerase components used to rescue hMPV can be those of RSV, APV, PIV, MPV, or any combination thereof (see section 5.8.1). Virus can be detected using any of a number of assays capable of detecting CAT activity. (See Example 24). In another alternative, rescue of hMPV using a minireplicon system can also be performed by superinfecting the minireplicon-transfected cells with hMPV polymerase components (NL/1/00 and NL/1/99) or polymerase components from MPV, APV, RSV, PIV, or any combination thereof.

In more detail, a cDNA of the leader region and the adjoining gene can be modified by mutagenesis using synthetic oligonucleotides. Similarly, a cDNA of the downstream end of another hMPV gene, e.g., the L gene, and adjoining trailer region, can be modified to contain an adjacent T7 RNA polymerase promoter. The leader and trailer fragments can be cloned into an expression vector, e.g., pUC19, on either side of an insert of the CAT gene. cDNAs encoding additional hMPV viral analogs can be constructed in the same way. Construct structures can be confirmed using sequencing. Examples of the leader and trailer sequences that can be used for the generation of the minireplicon construct are shown in FIG. 26. For comparison, an alignment of APV, RSV and PIV3 leader and trailer sequences are also shown in FIG. 26.

8.4 EXAMPLE 28

Generation of Full Length Infectious cDNA

Full length cDNAs that express the genes of the hMPV virus can be constructed so that infectious viruses can be produced. For example, a cDNA encoding all of the genes or all of the essential genes of hMPV can be constructed; the genome can then be expressed to produce infectious viruses.

In order to genetically manipulate hMPV, the genome of this RNA virus was cloned. For the 00-1 isolate of hMPV, eight PCR fragments varying in length from 1-3 kb were generated (FIG. 27). The PCR fragments were sequenced and analyzed for sequence errors by comparison to the hMPV sequence deposited in Genbank. Two silent mutations (nucleotide 5780 ile:ile in the SH gene, nucleotide 12219 cys:cys in the L gene) were not corrected. Another change in the L gene at nucleotide 8352 (trp:leu) was not changed since this mutation was observed in two independently generated PCR fragments (C and H), as well as in the hMPV 99-1 sequence. Similarly, a 5 nucleotide insertion at nucleotide 4715 in the F-M2 intergenic region was not corrected. Both of these changes may be reflected in the wild type sequence of hMPV. In contrast, at nucleotide 1242, a single A residue was removed in the N-P intergenic region; at nucleotide 3367, a ser:pro was corrected in the F gene; at nucleotide 6296, an asp:val was changed in the G gene; and at nucleotide 7332 a stop codon was changed to a glu in the L gene. Restriction maps of different isolates of hMPV are shown in FIG. 28. The restriction sites can be used to assemble the full-length construct.

The eight corrected PCR fragments were then assembled in sequence, taking advantage of unique restriction enzyme sites (FIG. 29). A genetic marker was introduced at nucleotide 75 generating an AflII restriction enzyme site without altering the amino acid sequence. A unique restriction enzyme site, XhoI, was added at the 3' end of the hMPV sequence. A phage T7 polymerase promoter followed by two G residues was also added to the 3' end of the hMPV sequence. At the 5' end of the hMPV genome, a Hepatitis delta ribozyme sequence and BssHII restriction enzyme site were added.

Helper plasmids encoding the hMPV L, N, P and M2-1 proteins in a pCITE plasmid were also generated. Once the full-length hMPV cDNA is generated, virus recovery by reverse genetics can be performed in Vero cells using fowlpox T7 or MVA-T7 as a source of T7 RNA polymerase, or a cell line or a plasmid expressing T7 RNA polymerase.

8.5 EXAMPLE 29 hMPV Recovery Employing the Pol I-Pol II Promoter System

Unlike the reverse genetics systems for non segmented RNA viruses which are based on plasmids with T7-promoter for expression of genomic RNA, systems employing the cellular transcription machinery may be more efficient and do not require the coexpression of the RNA polymerase derived from the bacteriophage T7. A unidirectional or bi-directional pol I-pol II transcription system can be used to express viral RNA molecule intracellularly. This systems proved to be very efficient for the generation of influenza virus from cloned cDNA (Hoffmann et. al., PNAS, 97 6108-6113 (2000). Unlike RNA polymerase II transcripts, RNA polymerase I transcripts do not contain cap structures at their 5'-end and do not have poly A tails at the 3'-end. Thus, systems employing the cellular transcription machinery are designed to express proteins from a pol II promoter and viral (−)vRNA or (+) cRNA which do not have a cap structure or a polyA tail from a pol I promoter. To provide virus-like primary transcripts which do not contain additional non viral sequences is critical because the terminal structures are crucial for viral replication and transcription.

In order to evaluate whether (−)vRNA or (+)cRNA transcription of hMPV cDNAs by RNA polymerase I is more efficient, a minigenome system may be designed to compare the replication efficiency of each. Replication efficiency can be measured by the transcription of a reporter molecule expressed by the minigenome, e.g., a CAT gene. In this approach, plasmids expressing the L, N, P, and M2-1 genes of hMPV, under the control of a pol II promoter, are cotransfected into a host cell together with a CAT-minigenome-plasmid. The relative efficiency of replication is measured by determining the relative level of expression of the CAT reporter molecule.

For example, RNA pol I can be used to synthesize positive strand copies of the hMPV viral genome (cRNA). In brief, the viral cDNA is inserted between an RNA pol I promoter and a terminator sequence. The whole pol I transcription unit is inserted in the positive-sense orientation between an RNA pol II promoter and a polyadenylation site. Two types of positive-sense RNAs are synthesized. From the pol II promoter, an mRNA with a 5'-cap structure is transcribed. From the pol I promoter full-length, positive-sense hMPV cRNA with a triphosphate group at the 5'end is transcribed by cellular RNA polymerase I. A cloning vector can be used for the insertion of arbitrary cDNA fragments, e.g., pHW 11 (Hoffmann & Webster, J. Gen Virol. 2000 December 81(Pt 12):2843-7) This plasmid contains the pol II promoter (immediate early promoter of the human *cytomegalovirus*) and the human pol I promoter that are upstream of a pol I terminator sequence and a poly(A) site.

In order to replicate the primary transcript representing viral cRNA, the viral polymerase proteins are provided by plasmid vectors with a pol II promoter, such as the immediate early promoter of human *cytomegalovirus*. These plasmids contain the cDNAs representing four gene segments of hMPV, i.e., the L-gene, the N-gene, the P-gene, and the M2-1 gene. Those four plasmids (1-5 μg) are cotransfected with the pol I/pol II plasmid (1-5 μg) representing the full length genome of hMPV into $10^6$-$10^7$ 293T cells, COS-7 or Vero cells. To improve the efficiency and reliability of the system, 293T cells can be cocultured with cells permissive for MPV, such as Vero or tMK cells. The addition of trypsin to the cell culture medium results in the generation of infectious virus particles. The coculturing of primate cells with MDCK cells was employed for the efficient rescue of influenza A virus (Hoffmann et. al., PNAS, 97 6108-6113 (2000). The supernatant after different times after transfection (i.e., 3 d to 10 d) is titrated and transferred to fresh Vero cells to determine the virus titer. The coexpression of all viral structural proteins (i.e., M, M2-2, SH, F, and G) from a pol II promoter may improve the efficiency of virus recovery.

Because from the pol I/pol II plasmids with the full length cDNA a capped and non-capped RNA is produced, it is expected that the first open reading frame representing the N-gene is translated into N-protein. Thus, by employing the pol I/pol II approach only four plasmids are needed for virus rescue: Three pol II-plasmids expressing L, P, and M2-1 protein and one pol I/pol II plasmid expressing the N-protein and the full length RNA of MPV.

8.6 EXAMPLE 30

Cell-Lines Expressing T7 RNA Polymerase for Recovery of Negative Strand Viruses A cell line expressing T7 RNA polymerase can be used for replication and packaging of recombinant MPV genomes. For example, Vero cells can be engineered to express T7 RNA polymerase under the control of a CMV promoter. This approach is useful because it eliminates the need for co-infection with a helper virus, such as a pox-virus expressing T7 RNA polymerase. Another advantage of this method is the elimination of the need for selection systems required to remove the helper virus.

In brief, cDNA encoding the L, N, P and M2-1 genes of hMPV are cloned and recombinantly engineered into expression vectors under the control of T7 promoter sequences. cDNA encoding the genome of the MPV, in either the positive or negative orientation, is cloned and recombinantly engineered into an expression vector under the control of T7 promoter sequences. These expression vectors may be concurrently transfected into the T7 expressing cell line, e.g., a BHK cell line that expresses T7 polymerase. The in vivo transcription of these cDNA constructs is mediated by T7 RNA polymerase. Viral titers can be determined by plaque assay of infected cell lysates.

8.7 EXAMPLE 31

Use of a Plasmid to Transiently Express T7 RNA Polymerase from a CMV or SV40 Promoter for hMPV Rescue A plasmid expressing T7 RNA polymerase under the control of a CMV or SV40 promoter can be engineered and transiently transfected into cells where it is used for replication and packaging of recombinant MPV genomes. For example, Vero and 293T cells can be engineered to express T7 RNA polymerase under the control of a CMV promoter. In one specific embodiment, a plasmid carrying the gene encoding T7 RNA polymerase under the control of the CMV MIE promoter can be used in combination with a selectable marker (e.g. Neomycin) driven by the T7 promoter. This would enable efficient selection of a cell line expressing T7 RNA polymerase. The approach using a cell line expressing T7 RNA polymerase is useful because it eliminates the need for co-infection with a helper virus, such as a poxvirus expressing T7 polymerase. Another advantage of this method is that eliminates the need for selection systems to eliminate contamination with the helper virus. Also, this approach allows the use of cell lines with high transfection efficiencies, such as 293T and COS-7 cells. Thus, cells transfected have multiple copies of T7-polymerase expressing plasmids resulting in a higher quantity of T7-polymerase protein per cell than transiently transfected cells compared to stable cell lines which only one copy In brief, cDNA encoding the L, N, P and M2-1 genes of hMPV are cloned and recombinantly engineered into expression vectors under the control of T7 promoter sequences. Alternatively, those four genes are expressed under the control of a RNA polymerase II promoter, such as the immediate early promoter of human *cytomegalovirus*. cDNA encoding the genome of the MPV, in either the positive or negative orientation, is cloned and recombinantly engineered into an expression vector under the control of T7 promoter sequences. These expression vectors are co-transfected together with the plasmid expressing T7 polymerase into cells that support hMPV replication, e.g., a Vero cell line, a tMK cell line, a 293T cell line, or a coculture of multiple cell lines. The in vivo transcription of these cDNA constructs is mediated by T7 RNA polymerase. Viral titers can be determined by plaque assay of infected cell lysates.

An alternative approach to supply T7, T3 or SP6 RNA polymerase consists of transfecting the T7 polymerase protein into cells before, concomitantly or after transfecting the cells with N, P, L, M2-1 and full-length genomic or antigenomic cDNA plasmids under the control of T7, T3 or SP6 promoters using lipid transfection reagents.

8.8 EXAMPLE 32

Rescue of hMPV

A successful system was developed to rescue recombinant hMPV. In brief, expression plasmids, encoding various polymerase proteins, were co-transfected with the cloned hMPV to be rescued into appropriate host cells. Upon collection and treatment, the cells and supernatant were then used to inoculate Vero cells. Infectious rescued virus was detected using immunostaining methods.

In order to rescue hMPV, confluent monolayers of 293T cells in a TC6-well plate were inoculated with fowl pox virus at a MOI (multiplicity of infection)=0.5. The cells were then incubated at 35C for 1 hour. The expression plasmids and the cloned hMPV to be rescued were mixed in 100 μl optiMEM (per well) in the following amounts: 0.4 μg of plasmid encoding the hMPV P gene (in pCITE 2a/3a, designated clone #41-6), 0.4 μg of plasmid encoding the hMPV N gene (in pCITE 2a/3a, designated clone #35-11), 0.3 μg of plasmid encoding the hMPV M2 gene (in pCITE 2a/3a, designated clone #25-6), 0.2 μg of plasmid encoding the L gene (in pCITE 2a/3a, designated clone #2), and 4 μg of hMPV plasmid clone #2 which has the leader and trailer like APV or clone #10 which has hMPV leader and trailer sequences. It is noteworthy that the expression plasmids used have the wild type sequence restored in the second amino acid position.

In the next step, the transfection reagent Lipofectamine 2000 (8 μl) was mixed into 100 μl of optiMEM and then added to the plasmid mixture. This combined mixture was applied to the 293T cells. Six days after transfection, the cells and supernatant were collected, frozen, thawed, and used to inoculate Vero cells. Nine days post inoculation, the infected cells were fixed in methanol, immunostained with a guinea pig polyclonal antibody followed by anti-guinea pig HRP and the DAKO AEC substrate. Plaque formation indicated that the rescued virus was infectious (FIG. 56). Positive red immunostaining was evident in the wells with both clone #2 and #10, though more immunostained cells were in the well with hMPV clone #2 which has the APV leader and trailer compared to the clone #10 with the hMPV leader and trailer. Positive immunostains are show in FIG. 57.

RT-PCR will be done on the virus that will be collected 10 days post infection to confirm the rescued sequence.

These results indicate that recombinant hMPV was successfully rescued and that infectious virus was produced.

8.9 EXAMPLE 33

Infection of Animal Hosts with Subtypes of hMPV

Animal hosts can be infected in order to characterize the virulence of MPV strains. For example, different hosts can be used in order to determine how infectious each strain is in an organism.

A small animal model for hMPV had not been identified. Balb/c mice, cotton rats, and Syrian Golden hamsters were infected with hMPV using a dose of $1.3\times10^6$ pfu/animal. The animals were inoculated intranasally with $1.3\times10^6$ pfu of hMPV in a 0.1 ml volume. The tissue samples were quantified by plaque assays that were immunostained on Day 9 with the hMPV guinea pig antiserum. Four days post-infection, the animals were sacrificed, and the nasal turbinates and lungs were isolated and quantified for hMPV titers by plaque assays that were immunostained (Table 13).

TABLE 13

HMPV TITERS IN INFECTED ANIMALS

| Animals | Number of animals | Mean virus titer on day 4 post-infection ($log_{10}$PFU/g tissue +/− Standard Error) Nasal turbinates | Lungs |
|---|---|---|---|
| mice (Balb c) | 6 | 2.7 +/− 0.4 | 2.2 +/− 0.6 |
| cotton rats | 5 | <1.7 +/− 0.0 | <1.8 +/− 0.0 |
| Syrian Golden hamsters | 6 | 5.3 +/− 0.2 | 2.3 +/− 0.6 |

The results showed that hMPV replicated to high titers in Syrian Golden hamsters. Titers of 5.3 and 2.3 log 10 pfu/g tissue were obtained in the nasal turbinates and lungs, respectively. hMPV did not replicate to any appreciable titer levels in the respiratory tracts of cotton rats. Mice showed titers of 2.7 and 2.2 $log_{10}$ pfu/g tissue in the upper and lower respiratory tracts, respectively. These results suggested that Syrian Golden hamsters would be a suitable small animal model to study hMPV replication and immunogenicity as well as to evaluate hMPV vaccine candidates.

INFECTION OF GUINEA PIGS. Two virus isolates, 00-1 (subtype A) and 99-1 (subtype B), were used to inoculate six guinea pigs per subtype (intratracheal, nose and eyes). Six guinea pigs were infected with hMPV 00-1 (10e6,5 TCID50). Six guinea pigs were infected with hMPV 99-1 (10e4,1 TCID50). The primary infection was allowed to progress for fifty-four days when the guinea pigs were inoculated with the homologous and heterologous subtypes (10e4 TCID50/ml), i.e., two guinea pigs had a primary infection with 00-1 and a secondary infection with 99-1 in order to achieve a heterologous infection, three guinea pigs had a primary infection with 00-1 and a secondary infection with 00-1 to achieve a homologous infection, two guinea pigs had a primary infection with 99-1 and a secondary infection with 00-1 to achieve a heterologous infection and three guinea pigs had a primary infection with 99-1 and a secondary infection with 99-1 to achieve a homologous infection.

Throat and nose swabs were collected for 12 days (primary infection) or 8 days (secondary infection) post infection, and were tested for the presence of the virus by RT-PCR assays. The results (FIG. 32) of the RT-PCR assays showed that guinea pigs inoculated with virus isolate 00-1 showed infection of the upper respiratory tract on days 1 through 10 post infection. Guinea pigs inoculated with 99-1 showed infection of the upper respiratory tract day 1 to 5 post infection. Infection of guinea pigs with 99-1 appeared to be less severe than infection with 00-1. A second inoculation of the guinea pigs with the heterologous virus, as commented on above, resulted in re-infection in 3 out of 4 of the guinea pigs. Likewise, reinfection in the case of the homologous virus occurred in 2 out of 6 guinea pigs. Little or no clinical symptoms were noted in those animals that became re-infected, and no clinical symptoms were seen in those animals that were protected against the re-infections, demonstrating that even with the wild-type virus, a protective effect due to the first infection may have occurred. This also showed that heterologous and homologous isolates could be used as a vaccine.

Both subtypes of hMPV were able to infect guinea pigs, although infection with subtype B (99-1) seemed less severe, i.e., the presence of the virus in nose and throat was for a shorter period than infection with subtype A (00-1). This may have been due to the higher dose given for subtype A, or to the lower virulence of subtype B. Although the presence of pre-existing immunity did not completely protect against re-infection with both the homologous and heterologous virus, the infection appeared to be less prominent, in that a shorter period of presence of virus was noted and not all animals became virus positive.

The serology of guinea pigs that were infected with both subtypes of hMPV was examined. At days 0, 52, 70, 80, 90, 110, 126 and 160, sera were collected from the guinea pigs and tested at a 1:100 dilution in a whole virus ELISA against 00-1 and 99-1 antigens. (See FIGS. 33A and B showing the IgG response against 00-1 and 99-1 for each individual guinea pig. See also FIG. 34 showing the specificity of the 00-1 and 99-1 ELISA but note that only data from homologous reinfected guinea pigs was used. See also FIG. 35 showing the mean IgG response against 00-1 and 99-1 ELISA of three homologous, i.e. 00-1 and 00-1, two homologous, i.e., 99-1 and 99-1, two heterologous, i.e., 99-1 and 00-1, and 2 heterologous, i.e., 00-1 and 99-1 infected guinea pigs).

Only a minor difference in response to the two different ELISAs was observed. Whole virus ELISA against 00-1 or 99-1 could not be used to discriminate between the two subtypes.

The reactivity of sera raised against hMPV in guinea pigs with APV antigen was examined. Sera were collected from the infected guinea pigs and tested with an APV inhibition ELISA. (See FIG. 36, showing the mean percentage of APV inhibition of hMPV infected guinea pigs). Sera raised against hMPV in guinea pigs reacted in the APV inhibition test in a manner similar to their reaction in the hMPV IgG ELISA's. Sera raised against 99-1 revealed a lower percentage of inhibition in the APV inhibition ELISA than sera raised against 00-1. Guinea pigs infected with 99-1 may have had a lower titer than that seen in the hMVP ELISAs. Alternatively, the cross-reaction of 99-1 with APV could have been less than that of 00-1. Nevertheless, the APV Ab inhibition ELISA could be used to detect hMPV antibodies in guinea pigs.

Virus neutralization assays were performed with sera raised against hMPV in guinea pigs. Sera were collected at day 0, day 52, day 70 and day 80 post infection and used in a virus cross-neutralization assay with 00-1, 99-1, and APV-C. The starting dilution used was 1 to 10 and 100 TCID50 virus per well. After neutralization, the virus was exposed to tMK cells (15 mm.) and centrifuged at 3500 RPM, after which the media was refreshed. The APV cultures were grown for 4 days and the hMPV cultures were grown for 7 days. Cells were fixed with 80% acetone, and IFAs were conducted with labeled monkey-anti hMPV. Wells that were negative upon staining were defined as the neutralizing titer. For each virus, a 10-log titration of the virus stock and a 2 fold titration of the working solution was included. (See FIG. 37 showing the virus neutralization titers of 00-01 and 99-1 infected guinea pigs against 00-1, 99-1, and APV-C).

INFECTION OF CYNOMOLOGOUS MACAGUES. Virus isolates 00-1 (subtype A) and 99-1 (subtype B) (1e5 TCID50) was used to inoculate two cynomologous macaques per subtype (intratracheal, nose and eyes). Six months after the primary infection, the macaques were inoculated for the second time with 00-1. Throat swabs were collected for 14 days (primary infection) or 8 days (secondary infection) post infection, and were tested for presence of the virus by RT-PCR assays (FIG. 38).

Cynomologous macaques inoculated with virus isolate 00-1 showed infection of the upper respiratory tract day 1 to 10 post infection. Clinical symptoms included a suppurative rhinitis. A second inoculation of the macaques with the homologous virus results in re-infection, as demonstrated by PCR, however, no clinical symptoms were seen.

Sera were collected from the macaques that received 00-1 during six months after the primary infection (re-infection occurred at day 240 for monkey 3 and day 239 for monkey 6). Sera were used to test for the presence of IgG (FIG. 39B) antibodies against either 00-1 or APV, and for the presence of IgA and IgM antibodies against 00-1 (FIG. 39A).

Two macaques were succesfully infected with 00-1 and in the presence of antibodies against 00-1 were reinfected with the homologous virus. The response to IgA and IgM antibodies showed the raise in IgM antibodies after the first infection, and the absence of it after the reinfection. IgA antibodies were only detected after the re-infection, showing the immediacy of the immune response after a first infection. Sera raised against hMPV in macaques that were tested in an APV inhibition ELISA showed a similar response as to the hMPV IgG ELISA.

Antibodies to hMPV in cynomologous macaques were detected with the APV inhibition ELISA using a similar sensitivity as that with the hMPV ELISA, and therefore the APV inhibition EIA was suitable for testing human samples for the presence of hMPV antibodies.

Virus cross-neutralization assays were preformed on sera collected from hMPV infected cynomologous macaques. The sera were taken from day 0 to day 229 post primary infection and showed only low virus neutralization titers against 00-1 (0-80), the sera taken after the secondary infection showed high neutralisation titers against 00-1, i.e., greater than 1280. Only sera taken after the secondary infection showed neutralization titers against 99-1 (80-640), and none of the sera were able to neutralize the APV C virus. There was no cross reaction between APV-C and hMPV in virus cross-neutralization assays, however, there was a cross reaction between 00-1 and 99-1 after a boost of the antibody response.

INFECTION OF HUMANS. The sera of patients ranging in ages under six months or greater than twenty years of age were previously tested using IFA and virus neutralization assays against 00-1. These sera were tested for the presence of IgG, IgM and IgA antibodies in an ELISA against 00-1. The samples were also tested for their ability to in inhibit the APV ELISA. A comparison of the use of the hMPV ELISA and the APV inhibition ELISA for the detection of IgG antibodies in human sera was made and a strong correlation between the IgG hMPV test and the APV-Ab test was noted, therefore the APV-Ab test was essentially able to detect IgG antibodies to hMPV in humans (FIG. 40).

INFECTION OF POULTRY. The APV inhibition ELISA and the 00-1 ELISA were used to test chickens for the presence of IgG antibodies against APV. Both the hMPV ELISA and the APV inhibition ELISA detected antibodies against APV.

8.10 EXAMPLE 34

APV as a Vaccine in Humans

APV can be used as a vaccine in humans to prevent infection by a human MPV, or to reduce the infectivity of human MPV in human hosts. The vaccine can be a whole APV or a chimeric or recombinant version or derivative thereof, that is comprised of heterologous sequences of another *metapneumovirus* in addition to sequences of APV. The genome of APV can be used as a backbone to create a recombinant virus vaccine. For example, a vaccine can be made where the F-gene and/or the G-gene of APV is substituted by the F-gene or the G-gene of human MPV. Alternatively, a vaccine can be made that includes sequences from PIV substituted for or added to sequences of an APV backbone. For more on the construction of a recombinant/chimeric vaccine, see, e.g., Construction of the Recombinant cDNA and RNA. The vaccine can be administered to a candidate by a variety of methods known to those skilled in the art, (see, Section 5.13, infra) including but not limited to, subcutaneous injection, intranasal administration, or inhalation. The viruses and/or vaccines of the invention are administered at a starting dosage of at least between $10^3$ $TCID_{50}$ and $10^6$ $TCID_{50}$. The viruses and/or vaccines are administered in either single or multiple dosages, e.g., a primary dose can be administered with one or more subsequent or booster doses administered at periodic time intervals throughout the host life. In a clinical trial, the replication rate of the virus can be used as an index to adjust the dosage of the vaccine so that an effective dosage regimen can be determined. A comparison can be made between the replication rate of the virus in the study population and a predetermined rate that is known to be effective.

The present invention is not to be limited in scope by the specific described embodiments that are intended as single illustrations of individual aspects of the invention, and any constructs, viruses or enzymes that are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

8.11 EXAMPLE 35

MPV as a Vaccine in Birds

Human MPV can be used as a vaccine in birds to prevent infection by an APV, or to reduce the infectivity of APV in avian hosts. The vaccine can be a whole MPV or a chimeric or recombinant version or derivative thereof, that is comprised of heterologous sequences of another *metapneumovirus* in addition to sequences of MPV. The genome of human MPV can be used as a backbone to create a recombinant virus vaccine. For example, a vaccine can be made where the F-gene and/or the G-gene of human MPV is substituted by the F-gene or the G-gene of APV. For more on the construction of a recombinant/chimeric vaccine, see, e.g., Construction of the Recombinant cDNA and RNA.

The vaccine can be administered to a candidate by a variety of methods, including but not limited to, subcutaneous injection, intranasal administration, or inhalation. The viruses and/or vaccines of the invention are administered at a starting dosage of at least between $10^3$ $TCID_{50}$ and $10^6$ $TCID_{50}$. The viruses and/or vaccines are administered in either single or multiple dosages, e.g., a primary dose can be administered with one or more subsequent or booster doses administered at periodic time intervals throughout the host life. In a clinical trial, the replication rate of the virus can be used as an index to adjust the dosage of the vaccine so that an effective dosage regimen can be determined. A comparison can be made between the replication rate of the virus in the study population and a predetermined rate that is known to be effective.

Various publications are cited herein, the disclosures of which are incorporated by reference in their entireties.

8.12 EXAMPLE 36

Inhibiting hMPV Fusion using hMPV F Protein Heptad Repeats

Inhibition of virus cell fusion represents a new approach toward the control of enveloped viruses. This approach would be advantageous in order to prevent the infection and/or propagation of the hMPV virus. During the fusion process, heptad repeat (HR) segments of the F protein are exposed. If soluble HR peptides are added to compete during the fusion process, then viral fusion will be blocked. Inhibition of hMPV-cell fusion by the HR peptides of the F protein is expected to show strong virus-cell fusion inhibition activity.

In order to examine the ability of hMPV F protein heptad repeats to inhibit viral fusion, HR peptides can be purified and used in a variety of assays to determine their effect on viral fusion. Genes encoding the HR segments of the hMPV F protein, i.e. designated HRA and HRB (see below) are cloned into expression vectors, e.g., pET 30a (Novagen). This cloning strategy would yield fusion proteins that correspond to the HR segments of the F protein of hMPV. For four isolates, the sequences of the HR segment near the amino terminal end of hMPV F protein, designated HRA, are postulated to be:

```
NL1/00 (SEQ ID NO:410):
KTIRLESEVTAIKNALKKTNEAVSTLGNGVRVLATAVRELKDFVSK

NL17/00 (SEQ ID NO:411):
KTIRLESEVTAIKNALKTTNEAVSTLGNGVRVLATAVRELKDFVSK

NL1/99 (SEQ ID NO:412):
KTIRLESEVNAIKGALKQTNEAVSTLGNGVRVLATAVRELKEFVSK

NL1/94 (SEQ ID NO:413):
KTIRLESEVNAIKGALKTTNEAVSTLGNGVRVLATAVRELKEFVSK.
```

Likewise, the sequences of the HR segment near the carboxy terminal end of the hMPV F protein, designated HRB, are postulated to be:

```
                                    (SEQ ID NO:414):
NL1/00:     NVALDQVFESIENSQALVDQSNRILSSAE

                                    (SEQ ID NO:415):
NL17/00:    NVALDQVFENIENSQALVDQSNRILSSAE

                                    (SEQ ID NO:416):
NL1/99:     NVALDQVFESIENSQALVDQSNKILNSAE

                                    (SEQ ID NO:417):
NL1/94:     NVALDQVFESIENSQALVDQSNKILNSAE.
```

Protein Expression and Purification

In order to examine the ability of the heptad repeat sequences to inhibit viral fusion, heptad repeat peptides can be expressed and purified so that they may be tested for their viral fusion inhibition ability. The recombinant expression vectors are transformed into a suitable bacterial host, e.g. *E. Coli* BL21 (DE3) and expression is induced at an optical density of 0.8-1.0 at 600 nm. Induction, using 1.0 mM IPTG, for 5 h at 25° C. is followed by harvesting and lysis of the bacterial cells by sonication in phosphate buffered saline. Triton X-100 is then added to a final concentration of 3% and the lysate is incubated for 30 min on ice and subsequently clarified by centrifugation at 12,000×g for 15 min at 4° C. The expressed HR proteins are subsequently purified.

Assembly of Complex and Analysis by Gel Filtration

In order to determine the potential effectiveness of the expressed heptad repeat peptides in inhibiting viral fusion, an assay can be used to confirm the assembly of a complex between HR peptides. In order to do so, equal molar amounts of HRA and HRB are mixed and incubated at room temperature for 1 h. The formation of the HRA/B complex with both HRA and HRB in the form of fusion proteins is evaluated. For gel filtration, samples are loaded on a Hiload Superdex G75 column (Pharmacia) running on Akta Explorer FPLC system (Amersham-Pharmacia). The fractions of the peak are collected and run on Tris-tricine SDS-PAGE. The peak molecular weight was estimated by comparison with the protein standards (Pharmacia) running on the same column.

CD Spectroscopy

It is known that the heptad repeat segments of the peptides are helical in nature. For this reason, a number of methods can be used to determine whether expressed HR peptides form alpha helices in order to identify appropriate candidates for use in viral fusion inhibition. CD spectra are performed on a spectrophotometer with proteins in PBS (10 mM sodium phosphate, pH 7.3; 150 mM NaCl). Wavelength spectra are recorded at 37° C. using a 0.1 cm path length cuvette. A protein concentration of approximately 20 μg/ml is used for the analysis.

Cell Fusion Assay

A cell based assay can be used to determine the effectiveness of HR peptides in the inhibition of viral fusion. In order to test for the inhibition of viral-cell fusion by the HRA and HRB peptides, an inhibition test is performed. Monolayers of Vero cells are infected with hMPV at 10-100 TCID50. Two hours post-infection, the supernatant is aspirated and the cells are washed in phosphate-buffered saline (PBS) to remove virus inoculum. Fresh medium (Iscove's Modified Dulbecco's Medium (IMDM) containing L-glutamine (2 mM), penicillin (100 U/ml), streptomycin (100 μg/ml) and 0.3% bovine serum albumin) is added and the cells are incubated at 37° C. HRA and HRB peptides are incubated individually with hMPV infected cells. Alternatively, different amounts of HRA and HRB peptides are incubated together with hMPV infected cells. Corresponding HR peptides from APV, RSV, or PIV, can also be used to inhibit hMPV viral fusion by incubation with hMPV infected cells. The cells are scored 24-72 hrs after incubation using immune fluorescence analysis (IFA). Staining for IFA is performed by incubating infected cells with guinea pig anti-hMPV serum in PBS for 1 hour, followed by a FITC-labeled rabbit anti-guinea pig polyclonal antibody preparation in PBS for 1 hour. Background staining is finally performed with eriochrome black before analysis under an immune fluorescence microscope. Infected cells were counted in 5 fields under high power magnification (320×)

Alternatively, cells are scored for cell to cell fusion an appropriate time after infection. After staining with crystal violet, cell fusion is measured by synctium/polykaryon formation and recorded as percentage of nuclei numbers in polykaryons to numbers of total nuclei. Five random different fields under a light microscope are counted and $IC_{50}$ are calculated according to Reed-Muench method.

9. Attenuated Viruses

9.1 EXAMPLE 36

Attenuation Resulting from Substitution of Viral Genes

Open reading frames of different viral genes are substituted in the cloned cDNA of the viral genome using standard recombinant DNA technology. For CAT activity of the different viral constructs see FIG. 60.

9.2 EXAMPLE 37

M2 Deletion Mutants

A map of the M2 gene of hMPV strain hMPV/NL/1/00 is shown in FIG. 61. In order to generate a deletion of the M2 gene, a Bsp E1 site is constructed at nucleotide position 4741 and a second Bsp E1 site is constructed at nucleotide position 5444. The restriction sites are constructed by site-specific mutagenesis. Restriction digestion of the recombinant genome at the two Bsp E1 sites using the restriction endonuclease Bsp E1 and subsequent ligation results in a deletion of the sequence between nucleotide position 4741 and nucleotide position 5444.

In order to generate a deletion of the M2-1 open reading frame of the M2 gene, Nhe I sites are introduced at nucleotide positions 4744 and 5241. The restriction sites are constructed by site-specific mutagenesis. Restriction digestion of the recombinant genome at the two Nhe I sites using the restriction endonuclease Nhe I and subsequent ligation results in a deletion of the sequence between nucleotide position 4744 and nucleotide position 5241.

In order to generate a deletion of the M2-2 open reading frame of the M2 gene, Swa I sites are introduced at nucleotide positions 5311 and 5453. The restriction sites are constructed by site-specific mutagenesis. Restriction digestion of the recombinant genome at the two Swa I sites using the restriction endonuclease Swa I and subsequent ligation results in a deletion of the sequence between nucleotide position 5311 and nucleotide position 5453.

The following primer sets were used:

primers used to introduce the restriction enzyme sites:

For putting BspEI into hMPV/NL/1/00 to make M2 deletion from 4741 to 5444:

```
primer set
"hMPV, BspEI, +4741"
gga caa atc ata acg t tcc gga ag gc tcc gtg c
(SEQ ID NO:418)

"hMPV, BspEI, -4741"
g cac gga gc ct tcc gga acgt tat gat ttg tcc
(SEQ ID NO:419)
and

primer set
"hMPV, BspEI, +5444"
cat agaaat tat at atg tcc gga ct ta ctt a agt tag
(SEQ ID NO:420)

"hMPV, Bsp EI, -5444"
cta act t aa g ta ag tcc gga cat at ata att tc
(SEQ ID NO:421).
```

For putting Nhe I sites into hMPV to make M2-1 deletion from 4744 to 5241 and change the start site from atg to acg at nt 4742:

```
primer set
"hMPV, Nhe I, +4744"
gga caa atc ata acggctagc aag gc t ccg tgc
(SEQ ID NO:422)

"hMPV, NheI, -4744
gca cgg agc ctt gct agc cgt tat gat ttg tcc
(SEQ ID NO:423)

primer set
"hMPV, NheI, +5241
ctt atc agc agg t gctagc a atg act ctt cat a tg c
(SEQ ID NO:424)

"hMPV, Nhe I, -5241
gcat atg aa g ag t ca t t gct a gc a cct gct gat
```

-continued

```
aag
(SEQ ID NO:425).
```

For putting SwaI sites into hMPV to make M2-2 deletion from 5311 to 5453:

```
primer set
"hMPV, SwaI, +5311"
c agt gag cat ggt cca a tt taa att act ata gag g
(SEQ ID NO:426)

"hMPV, SwaI, -5311"
c ctc tat agt aat tta aat tgg acc atg ctc act g
(SEQ ID NO:427)
and

primers
"hMPV, SwaI, +5453"
c ata gaa att ata tat gtc aag gct tat tta aa t tag
(SEQ ID NO:428)

"hMPV, SwaI, -5453"
cta att taa ata agc ctt gac ata tat aat ttc tat g
(SEQ ID NO:429).
```

For the generation of hMPV (strain hMPV/NL/1/00) with a deletion in SH, cloned with deletion from 5472 to 6026, has been recovered and grows well in Vero cell culture. The primer sets for cloning the hMPV/NL/1/00 virus with the SH deletion are as follows:

```
Primer set
hMPV SacII +5472
ggc tta ctt aag tta gta aaa aca ccgcgg agt ggg

ata aat gac
(SEQ ID NO:430)

hMPV SacII -5472
gtc att tat ccc act ccg cgg tgt ttt tac taa ctt

aag taa gcc
(SEQ ID NO:431)

primer set
hMPV SacII +6026
ct atc att acc caa ccgcgg aa acc caa tcc taa atg

tta ac
(SEQ ID NO:432)

r hMPV SacII -6026
gt taa cat tta gga ttg ggt tt ccgcgg ttg ggt aat

gat ag
(SEQ ID NO:433).
```

10. EXAMPLE

Plasmid-Only Recovery of hMPV in Serum Free Vero Cells by Electroporation

Introduction

This process allows recovery of recombinant hMPV using plasmids only, in the absence of helper viruses. The recovery of hMPV is carried out using SF Vero cells, which are propagated in the absence of animal and human derived products. This process allows recovery of recombinant hMPV with similar efficiency to previous methods using helper viruses (recombinant vaccinia or fowl-pox viruses expressing T7 polymerase). Because no helper viruses are needed in the recovery process, the vaccine viruses are free of contaminating agents, simplifying downstream vaccine production. The cells used for vaccine virus recovery are grown in media containing no animal or human derived products. This eliminates concerns about transmissible spongiform encephalopathies (e.g. BSE), for product end users.

This method enables generation of a recombinant vaccine seed that is completely free of animal or human derived components. The seed is also free of contaminating helper viruses.

Plasmid-based expression systems for rescue of viruses from cDNA are described, e.g., in R A Lerch et al., Wyeth Vaccines, Pearl River N.Y., USA (Abstract 206 from XII International Conference on Negative Strand Viruses, Jun. $14^{th}$-$19^{th}$ 2003, Pisa Italy) and G. Neumann et. al., J. Virol., 76, pp 406-410.

Methods and Results hMPV N plasmids (4 µg; marker: kanamycin resistancy), hMPV P plasmids (4 µg; marker: kanamycin resistancy), hMPV L plasmids (2 µg; marker: kanamycin resistancy), cDNA encoding hMPV antigenomic cDNA (5 µg; marker: kanamycin resistancy) and pADT7(N)DpT7 encoding T7 RNA polymerase (5 µg; marker: blasticidin) are introduced into SF Vero cells using electroporation in serum-free medium.

For the rescue of hMPV virus, 4 expression plasmids are used. They are for the genes N, P, L and also M2 of hMPV. In particular the following plasmids are used:

4 ug hMPV N pCITE plasmid, 4 ug hMPV P pCITE plasmid, 3 ug hMPV M2 pCITE plasmid, 2 ug hMPV L pCITE plasmid 5 ug T7 RNA polymerase plasmid, and 5 ug of the viral cDNA encoding the viral genome to be be rescued.

The pCITE plasmid has an internal ribosomal entry site that functions in the cytoplasm of the Vero cell so that the proteins for the N, P, M2 and L are made in the cytoplasm. These proteins form the viral polymerase complex.

The viral genome to be rescued is in a full length plasmid with a T7 promoter. Without being bound by theory, T7 DNA-dependent RNA polymerase transcribes a full length viral RNA genome using this full length plasmid. After the viral genome is made, the viral polymerase complex will transcribe the viral genome and generate viral messenger RNAs and virus is subsequently recovered.

The pulse for the electroporation is 220V and 950 microfarads. $5.5 \times 10^6$ SF Vero cells are used per electroporation. The electroporated cells are allowed to recover at 33° C. in the presence of OptiC (a custom formulation from GIBCO Invitrogen Corporation) overnight. Recovered cells are washed twice with 1 mL of PBS containing calcium and magnesium and overlayed with 2 mL of OptiC. Electroporated cells are further incubated at 33° C. for 5-7 days. At the end of the incubation period, cells are scraped into the media and total cell lysate is analyzed for presence of hMPV.

Virus recovery is confirmed by immunostaining of plaque assays using hMPV specific polyclonal antibodies.

11. EXAMPLE

A Proline to Serine Change in the Human *Metapneumovirus* F Protein Cleavage Site Abrogates Cleavage and Infectivity in Vero Cells Human *metapneumovirus* (hMPV), a recently described *paramyxovirus*, causes respiratory illness, which can include severe cough, bronchiolitis and pneumonia. Analogous to other members of the *Pneumovirus* subfamily, avian metapneumovirs (APV) and respiratory syncytiai virus (RSV), hMPV expresses two surface glycoproteins: an attachment glycoprotein (G) and a fusion protein (F). Although binding and entry studies of hMPV have not yet been reported, sequence alignment with other *paramyxovirus* F proteins have revealed conserved functional domains (see, e.g., FIG. 9). Without being bound by theory, cleavage of full-length fusion protein $F_0$ into $F_1$ and $F_2$ exposes a fusion peptide at the N terminus of the $F_1$ fragment, a prerequisite for fusion of the virus membrane with the host cell membrane.

While the strain hMPV/NL/1/00 (SEQ ID NO: 19) contains the sequence RQPR (SEQ ID NO:396) at the cleavage site of the F protein, the majority of other hMPV strains contain the amino acid sequence RQSR (SEQ ID NO:395) at the cleavage site of the F protein. The full-length hMPV/NL/1/00 with either proline or serine at amino acid position 101 of the F protein was cloned. Both viruses were rescued and amplified as described in Example 32 in the presence of trypsin (FIGS. 62 and 63). However, in the absence of trypsin, the serine substitution abrogated cleavage of the F protein (FIG. 64) and inhibited virus infectivity. Cleavage and subsequent infectivity could be restored with the addition of trypsin, albeit the plaque size of the 101S mutant was smaller than the 101P virus. These results demonstrate that cleavage of F is a prerequisite for infectivity of hMVP/NL/1/00.

Many other strains of hMPV that have been sequenced have serine at position 101 in the F protein and are likely to be cleaved. For example, the F protein of the strain CAN 99-81 has been shown to be cleaved using Western blot.

12. EXAMPLE

Growth Behavior of Recombinant hMPV

Several recombinant hMPV were constructed as described in Example 28. The different recombinant hMPV were rescued as described in Example 32. Growth curves of recombinant hMPV/NL/1/00 in the presence and absence of Trypsin are shown in FIG. 65. The cells (Vero cells) were infected at a MOI of 0.1.

Replication of wild type hMPV/NL/1/00 and recombinant hMPV/NL/1/00 in the upper and lower respiratory tract of hamsters are shown in FIG. 66. Hamsters were infected as described in Example 33.

A growth curve of a recombinant hMPV/NL/1/00 with an amino acid exchange of a glutamic acid to valine at amino acid position 93 of the F protein in the presence and absence of Trypsin are shown in FIG. 67. The cells (Vero cells) were infected at a MOI of 1.

13. Microneutralization Assay using hMPV/GFP2

When viruses are inoculated into an animal, an array of antibodies against the virus are produced. Some of these antibodies can bind virus particles and neutralize the infectivity of the viruses. In this example, a microneutralization assay was used to analyze the remaining infectivity of the viruses after the viruses were incubated with dilutions of serum containing antibodies. For serial dilutions, a 96-well plate is divided (i) into rows A (dilution 1:32); B (1:64); C (1:128); D (1:256); E (1:512); F (1:1024); G (1:2048); and H (No Antibody) and (ii) into columns 1 to 12 for the different samples (first sample: columns 1 to 3; second sample: columns 4 to 6; third sample: columns 7 to 9; and fourth sample: columns 10 to 12). 230 μl of sample dilution are added to row A. 115 μl of Opti-MEM are added to rows B-H. Then 115 μl of the 1:32 dilution of the first sample are added to wells 1B, 2B, and 3B, the second sample to wells 4B, 5B, and 6B, the third sample to wells 7B, 8B, and 9B, and the fourth sample to 10B, 11B, and 12B. Sera and medium are mixed gently by pipetting up and down three times. The steps are repeated for rows B to C, rows C to D, rows D to E, rows E to G. After diluted sample is added to row G and mixed, 115 μl are removed from row G and discarded.

Microneutralization assay was performed as follows: sera were serially diluted. Each test sample and each control was diluted by 1:32 by adding 22.5 μl of sera to 697.5 μl of Opti-MEM Medium (1×). Serum and medium were mixed gently by inversion three times and place on ice. Each dilution of serum was incubated with the virus hMPV/GFP2. Cells were washed with phosphate buffered saline ("PBS"). Vero cells from ATCC are maintained in MEM (JRH Biosciences) supplemented with 10% fetal bovine serum, 2 mM L-glutamine, nonessential amino acids, and 100 units/ml penicillin G, 100 μg/ml streptomycin sulfate. The virus/sera mixtures were added to cells and incubated for one hour at 35° C. All of the medium, which contained the virus, were removed, and cells were washed with PBS. Opti-MEM medium was added to the cells and the cell cultures were incubated for three days. Opti-MEM I Reduced-Serum Medium (1×) (GIBCO 31985-070) contains, among others, HEPES buffer, 2400 mg/L sodium bicarbonate, hypoxanthine, thymidine, sodium pyruvate, L-glutamine, trace elements, growth factors, and phenol red reduced to 1.1 mg/L. The remaining infectivity of the viruses was measured by quantifying eGFP green foci on the images captured with fluorescence microscope. Plaque reduction assay (see Example 16) using a wildtype virus, e.g., wildtype hMPV/NL/1/00, was also performed for comparing the sensitivity of the microneutralization assay. The results are presented in Table 16, Table 17, Table 18, Table 19 and FIG. 68.

The results demonstrate that the microneutralization assay using hMPV/GFP2 provides reliable and reproducible results. The use of hMPV-GFP in the microneutralization assay facilitates the high throughput screening of different vaccines and antibodies in animal model systems such as ferrets and monkeys. This technique also provides efficient means for diagnosing and monitoring infections in humans.

TABLE 16

Titers of ferret sera using hMPV/GFP2 microneutralization assay and plaque reduction assay. Complement from Guinea pig (add 100 ul in 20 ml of Opti-MEM) was used for plaque reduction assay. NT50 is 1/dilution that confers 50% neutralization of input virus. The numbers in the table indicate the titers of sera.

| | Plaque (NT50) | Microneutralization (NT50) | |
|---|---|---|---|
| Ferret sera | − trypsin<br>+ complement<br>Wildtype hMPV/NL/1/00 | − trypsin<br>− complement<br>hMPV/GFP2 | + trypsin<br>− complement<br>hMPV/GFP2 |
| 1 | 5.9 | 8.2 | 8.3 |
| 2 | 3.3 | 8.7 | 6.9 |
| 3 | 4.1 | 6.8 | 7.1 |
| 4 | 3.6 | 8.5 | 5.1 |
| 5 | 2.9 | 6.0 | 7.9 |

TABLE 17

Titers of Monkey sera using hMPV/GFP2 microneutralization assay and plaque reduction assay.

| Monkey sera | Plaque (NT50) − trypsin + complement Wildtype hMPV/NL/1/00 | Microneutralization (NT 50) + trypsin − complement hMPV/GFP2 |
|---|---|---|
| PreC23606M | 3.8 | <5 |
| PreC23611F | 2.1 | <5 |
| PreC23614F | 2.9 | <5 |
| Day28C23606M | 7 | 10 |
| Day28C23611F | 10 | 9 |
| Day28C23614F | 8 | 8.5 |
| Day35C23606M | NA | 10 |
| Day35C23611F | NA | 9.5 |
| Day35C23614F | NA | 10 |
| Day42C23606M | NA | 9.5 |
| Day42C23611F | NA | 10 |

TABLE 18

Linear Correlation between plaque reduction assay and microneutralization assay using hMPV/GFP2 (see also, FIG. 68)

| Serum | Correlation (no trypsin) | Correlation (with trypsin) |
|---|---|---|
| Ferret 1 | 0.924 | 0.911 |
| Ferret 3 | 0.935 | 0.992 |
| Ferret 5 | 0.943 | 0.87 |
| Ferret 6 | 0.773 | 0.910 |

TABLE 19

Titers of Hamster sera using plaque reduction assay and microneutralization assay.

| Challenge with | Plaque Reduction | Microneutralization |
|---|---|---|
| 50% Neutralization titer | Mean reciprocal $\log_2 \pm$ SE | Mean reciprocal $\log_2 \pm$ SE |
| Assay Virus | hMPV/NL/1/00 | hMPV/NL/1/00/GFP2 |
| b/h PIV3/hMPV-F2 | 7.4 ± 1.5 | 9.7 ± 0.6 |

| Assay Virus | hMPV/NL/1/00 | hMPV 99/1 | hMPV/NL/1/00/GFP2 |
|---|---|---|---|
| hMPV99-1 | 4.3 + 1.1 | 11.0 ± 2.1 | 10.6 ± 0.2 |
| hMPV001 | na | na | 9.7 ± 0.4 |

14. EXAMPLE

Evaluating the Efficacy and Immunogenicity of b/h PIV3 Expressing an Antigenic Protein of MPV in African Green Monkeys Bivalent MPV/RSV vaccine candidates, e.g., hMPV expressing an antigenic protein of RSV such as a soluble form of the F protein of human RSV ("hMPV/RSV $F^{SOL}$"), wherein the soluble form of the RSV F protein lacks the transmembrane and the luminal domains, are evaluated for efficacy and immunogenicity in a non-human primate model, such as African green monkeys.

Vero cells are maintained in Modified Eagle's Medium (MEM) (JRH Biosciences) supplemented with 2 mM L-glutamine, non-essential amino acids (NEAA), antibiotics, and 10% FBS. hMPV expressing an antigenic protein of RSV, e.g., hMPV/RSV $F^{SOL}$, wildtype MPV, e.g., hMPV/NL/100, and a wildtype RSV, e.g., wildtype RSV A2, are propagated in Vero cells. Cells are infected with the viruses at a multiplicity of infection (MOI) of 0.1 PFU/cell. Three to five days post-infection the cells and supernatant are collected and stabilized by adding 10×SPG (10×SPG is 2.18 M Sucrose, 0.038 M $KH_2PO_4$, 0.072 M $K_2HPO_4$, 0.054 M L-Glutamate) to a final concentration of 1×. The virus stocks are stored at −70° C. The virus titers are determined by plaque assays on Vero cells. Plaques are quantified after immunoperoxidase staining using PIV3 (VMRD) or MPV goat polyclonal antisera (Biogenesis).

MPV- and RSV-seronegative African Green monkeys (*Cercopithecus aethiops*) (3.5 to 6.5 years old, 2.6 to 5.8 kg) are identified using an MPV F IgG ELISA (Immuno-Biological Laboratories) and an RSV F IgG ELISA (Immuno-Biological Laboratories) for primate pre-sera collected on day 14 prior to the study start date. MPV F IgG ELISA is performed as follows: the primate sera from days 1, 28 and 56 from the vaccinated animals are analyzed for the presence of MPV F IgG using an ELISA kit (Immuno-Biological Laboratories, Hamburg, Germany) according to the manufacturer's instructions. The secondary monkey antiserum (Rockland Inc.) is used at a 1:1000 dilution. The MPV F IgG antibody titers are expressed as $\log_2$ IgG U/ml. The primate sera from days 1, 28 and 56 from the vaccinated animals are analyzed for the presence of RSV F IgG using an ELISA kit (Immuno-Biological Laboratories, Hamburg, Germany) according to the manufacturer's instructions. The secondary monkey antiserum (Rockland Inc.) is used at a 1:1000 dilution. The RSV F IgG antibody titers are plotted as $\log_2$ IgG U/ml.

The primates are housed in individual micro-isolator cages. The monkeys are anesthetized with a ketamine-valium mixture and infected intranasally and intratracheally with a hMPV vector expressing an antigenic protein of RSV, e.g., hMPV/RSV $F^{SOL}$, wildtype MPV, e.g., hMPV/NL/100, and a wildtype RSV, e.g., wildtype RSV A2, respectively. The nasal dose volume is 0.5 ml per nostril, and the intratracheal dose volume is 1 ml. On Day 1, each animal receives a dose of 2 ml containing 2-3×$10^5$ PFU of virus. The placebo animal group receives the same dose volume of Opti-MEM. On Day 28, all animals are challenged intratracheally and intranasally with 7×$10^5$ PFU of wildtype RSV A2 (1 ml at each site). Nasopharyngeal (NP) swabs are collected daily for 11 days and tracheal lavage (TL) specimens are collected on Days 1, 3, 5, 7 and 9 post-immunization and post-challenge. Blood samples obtained from the femoral vein are collected on Days 0, 7, 14, 21, 28, 35, 42, 49 and 56 for serological analysis. The animals are monitored for body temperature changes indicating a fever, signs of a cold, runny nose, sneezing, loss of appetite, and body weight. Virus present in the primate NP and TL specimens is quantitated by plaque assays using Vero cells that are immunostained with MPV goat polyclonal antiserum. Mean peak virus titers represent the mean of the peak virus titer measured for each animal on any of the 11 days following immunization or challenge.

Plaque reduction neutralization assays (PRNAs) are carried out for sera obtained on days 1, 28, and 56 post-dose from primates infected with a hMPV/RSV $F^{SOL}$. The primate sera are two-fold serially diluted, and incubated with 100 PFU of wildtype RSV A2 or wildtype MPV, e.g., hMPV/NL/100, respectively, in the presence of guinea pig complement for one hour at 4° C. The virus-serum mixtures are transferred to Vero cell monolayers and overlaid with 1% methyl cellulose in EMEM/L-15 medium (JRH Biosciences; Lenexa, Kans.) containing 2% FBS and 1% antibiotics. After 6 days of incubation at 35° C., the monolayers are immunostained using RSV goat polyclonal antiserum or hMPV goat polyclonal antiserum, respectively, for quantitation. Neutralization titers are expressed as the reciprocal $log_2$ of the highest serum dilution that inhibits 50% of viral plaques.

hMPV microneutralization assays and RSV A2 microneutralization assays, respectively, are performed on Vero cells. Serial two-fold dilutions of primate serum, starting at 1:4, are incubated at 37° C. for 60 min with 100 $TCID_{50}$ of hMPV or RSV A2, respectively. Subsequently, virus-serum mixtures are transferred to cell monolayers in 96-well plates and incubated at 37° C. for six days, after which all wells are observed for CPE. Neutralization titers are expressed as the reciprocal of the highest serum dilution that inhibited CPE. Neutralization antibody titers of ≦1:4 (the lowest serum dilution tested) are assigned a reciprocal $log_2$ titer of 2.

To study the replication efficiency of the bivalent MPV/RSV vaccine candidates, the experiment is designed as follows. On Day 1, MPV and RSV sero-negative African green monkeys, eight animals per group, are immunized intranasally and intratracheally with a MPV vaccine candidate, e.g., hMPV/RSV $F^{SOL}$, with a dose of 2-3×$10^5$ PFU. One positive control group is infected with wildtype MPV, e.g., hMPV/NL/100, another positive control group is infected with wildtype RSV A2, and the negative control group is administered placebo medium. On Day 28, each group is split into two sections, all animals of one section of each group are challenged intranasally and intratracheally with 7×$10^5$ PFU of wildtype MPV, e.g., hMPV/NL/100. All animals of the other section of each group are challenged intranasally and intratracheally with 7×$10^5$ PFU wildtype RSV A2. The animals are housed in micro-isolator cages for the duration of this study. Nasopharyngeal swabs are collected daily for 11 days post-immunization and post-challenge, and tracheal lavage samples are obtained on days 2, 4, 6, 8, and 10 post-immunization and post-challenge. Serum samples for antibody analyses are collected every seven days throughout the duration of the study.

In order to evaluate immune protection from MPV infection and RSV infection, respectively, the vaccinated primates are challenged with a high dose of wildtype MPV, e.g., hMPV/NL/100, and a high dose wildtype RSV A2, respectively, four weeks post-immunization. Efficacy is measured as a reduction in shed MPV challenge virus titer in the URT and LRT of the infected animals.

Efficacy of the MPV/RSV bivalent vaccine candidates is further evaluated by the levels of MPV neutralizing antibody titers and RSV F IgG serum antibody titers produced four weeks post-immunization. The MPV neutralizing antibody titers are determined using a 50% plaque reduction neutralization assay (PRNA). The immune responses elicited by the MPV/RSV bivalent vaccine candidates are also analyzed by measuring RSV F protein specific IgG levels at pre-dose (Day 1), four weeks post-dose (Day 28), and four weeks post-challenge (Day 56). The presence of RSV F IgG serum antibodies is determined using ELISA. The presence of MPV neutralizing activity in the serum can also be determined using an hMPV microneutralization assay.

In order to evaluate whether the MPV/RSV bivalent vaccines can protect from RSV infection, primate sera are also analyzed for the presence of RSV neutralization using a plaque reduction neutralization assay or a microneutralization assay.

TABLE 14

| LEGEND FOR SEQUENCE LISTING | |
|---|---|
| SEQ ID NO: 1 | Human metapneumovirus isolate 00-1 matrix protein (M) and fusion protein (F) genes |
| SEQ ID NO: 2 | Avian pneumovirus fusion protein gene, partial cds |
| SEQ ID NO: 3 | Avian pneumovirus isolate 1b fusion protein mRNA, complete cds |
| SEQ ID NO: 4 | Turkey rhinotracheitis virus gene for fusion protein (F1 and F2 subunits), complete cds |
| SEQ ID NO: 5 | Avian pneumovirus matrix protein (M) gene, partial cds and Avian pneumovirus fusion glycoprotein (F) gene, complete cds |
| SEQ ID NO: 6 | paramyxovirus F protein hRSV B |
| SEQ ID NO: 7 | paramyxovirus F protein hRSV A2 |
| SEQ ID NO: 8 | human metapneumovirus01-71 (partial sequence) |
| SEQ ID NO: 9 | Human metapneumovirus isolate 00-1 matrix protein(M) and fusion protein (F) genes |
| SEQ ID NO: 10 | Avian pneumovirus fusion protein gene, partial cds |
| SEQ ID NO: 11 | Avian pneumovirus isolate 1b fusion protein mRNA, complete cds |
| SEQ ID NO: 12 | Turkey rhinotracheitis virus gene for fusion protein (F1 and F2 subunits), complete cds |
| SEQ ID NO: 13 | Avian pneumovirus fusion glycoprotein (F) gene, complete cds |
| SEQ ID NO: 14 | Turkey rhinotracheitis virus (strain CVL14/1)attachment protien (G) mRNA, complete cds |
| SEQ ID NO: 15 | Turkey rhinotracheitis virus (strain 6574) attachment protein (G), complete cds |
| SEQ ID NO: 16 | Turkey rhinotracheitis virus (strain CVL14/1)attachment protein (G) mRNA, complete cds |
| SEQ ID NO: 17 | Turkey rhinotracheitis virus (strain 6574) attachment protein (G), complete cds |
| SEQ ID NO: 18 | isolate NL/1/99 (99-1) HMPV (Human Metapneumovirus)cDNA sequence |
| SEQ ID NO: 19 | isolate NL/1/00 (00-1) HMPV cDNA sequence |
| SEQ ID NO: 20 | isolate NL/17/00 HMPV cDNA sequence |
| SEQ ID NO: 21 | isolate NL/1/94 HMPV cDNA sequence |
| SEQ ID NO: 22 | RT-PCR primer TR1 |
| SEQ ID NO: 23 | RT-PCR primer N1 |
| SEQ ID NO: 24 | RT-PCR primer N2 |
| SEQ ID NO: 25 | RT-PCR primer M1 |
| SEQ ID NO: 26 | RT-PCR primer M2 |
| SEQ ID NO: 27 | RT-PCR primer F1 |
| SEQ ID NO: 28 | RT-PCR primer N3 |
| SEQ ID NO: 29 | RT-PCR primer N4 |
| SEQ ID NO: 30 | RT-PCR primer M3 |
| SEQ ID NO: 31 | RT-PCR primer M4 |
| SEQ ID NO: 32 | RT-PCR primer F7 |
| SEQ ID NO: 33 | RT-PCR primer F8 |
| SEQ ID NO: 34 | RT-PCR primer L6 |
| SEQ ID NO: 35 | RT-PCR primer L7 |
| SEQ ID NO: 36 | Oligonucleotide probe M |
| SEQ ID NO: 37 | Oligonucleotide probe N |
| SEQ ID NO: 38 | Oligonucleotide probe L |
| SEQ ID NO: 39 | TaqMan primer and probe sequences for isolates NL/1/00, BI/1/01, FI/4/01, NL/8/01, FI/2/01 |
| SEQ ID NO: 40 | TaqMan primer and probe sequences for isolates NL/30/01 |
| SEQ ID NO: 41 | TaqMan primer and probe sequences for isolates NL/22/01 and NL/23/01 |

TABLE 14-continued

| LEGEND FOR SEQUENCE LISTING | |
|---|---|
| SEQ ID NO: 42 | TaqMan primer and probe sequences for isolate NL/17/01 |
| SEQ ID NO: 43 | TaqMan primer and probe sequences for isolate NL/17/00 |
| SEQ ID NO: 44 | TaqMan primer and probe sequences for isolates NL/9/01, NL/21/01, and NL/5/01 |
| SEQ ID NO: 45 | TaqMan primer and probe sequences for isolates FI/1/01 and FI/10/01 |
| SEQ ID NO: 46 | Primer ZF1 |
| SEQ ID NO: 47 | Primer ZF4 |
| SEQ ID NO: 48 | Primer ZF7 |
| SEQ ID NO: 49 | Primer ZF10 |
| SEQ ID NO: 50 | Primer ZF13 |
| SEQ ID NO: 51 | Primer ZF16 |
| SEQ ID NO: 52 | Primer CS1 |
| SEQ ID NO: 53 | Primer CS4 |
| SEQ ID NO: 54 | Primer CS7 |
| SEQ ID NO: 55 | Primer CS10 |
| SEQ ID NO: 56 | Primer CS13 |
| SEQ ID NO: 57 | Primer CS16 |
| SEQ ID NO: 58 | Forward primer for amplification of HPIV-1 |
| SEQ ID NO: 59 | Reverse primer for amplification of HPIV-1 |
| SEQ ID NO: 60 | Forward primer for amplification of HPIV-2 |
| SEQ ID NO: 61 | Reverse primer for amplification of HPIV-2 |
| SEQ ID NO: 62 | Forward primer for amplification of HPIV-3 |
| SEQ ID NO: 63 | Reverse primer for amplification of HPIV-3 |
| SEQ ID NO: 64 | Forward primer for amplification of HPIV-4 |
| SEQ ID NO: 65 | Reverse primer for amplification of HPIV-4 |
| SEQ ID NO: 66 | Forward primer for amplification of Mumps |
| SEQ ID NO: 67 | Reverse primer for amplification of Mumps |
| SEQ ID NO: 68 | Forward primer for amplification of NDV |
| SEQ ID NO: 69 | Reverse primer for amplification of NDV |
| SEQ ID NO: 70 | Forward primer for amplification of Tupaia |
| SEQ ID NO: 71 | Reverse primer for amplification of Tupaia |
| SEQ ID NO: 72 | Forward primer for amplification of Mapuera |
| SEQ ID NO: 73 | Reverse primer for amplification of Mapuera |
| SEQ ID NO: 74 | Forward primer for amplification of Hendra |
| SEQ ID NO: 75 | Reverse primer for amplification of Hendra |
| SEQ ID NO: 76 | Forward primer for amplification of Nipah |
| SEQ ID NO: 77 | Reverse primer for amplification of Nipah |
| SEQ ID NO: 78 | Forward primer for amplification of HRSV |
| SEQ ID NO: 79 | Reverse primer for amplification of HRSV |
| SEQ ID NO: 80 | Forward primer for amplification of Measles |
| SEQ ID NO: 81 | Reverse primer for amplification of Measles |
| SEQ ID NO: 82 | Forward primer to amplify general paramyxoviridae viruses |
| SEQ ID NO: 83 | Reverse primer to amplify general paramyxoviridae viruses |
| SEQ ID NO: 84 | G-gene coding sequence for isolate NL/1/00 (A1) |
| SEQ ID NO: 85 | G-gene coding sequence for isolate BR/2/01 (A1) |
| SEQ ID NO: 86 | G-gene coding sequence for isolate FL/4/01 (A1) |
| SEQ ID NO: 87 | G-gene coding sequence for isolate FL/3/01 (A1) |
| SEQ ID NO: 88 | G-gene coding sequence for isolate FL/8/01 (A1) |
| SEQ ID NO: 89 | G-gene coding sequence for isolate FL/10/01 (A1) |
| SEQ ID NO: 90 | G-gene coding sequence for isolate NL/10/01 (A1) |
| SEQ ID NO: 91 | G-gene coding sequence for isolate NL/2/02 (A1) |
| SEQ ID NO: 92 | G-gene coding sequence for isolate NL/17/00 (A2) |
| SEQ ID NO: 93 | G-gene coding sequence for isolate NL/1/81 (A2) |
| SEQ ID NO: 94 | G-gene coding sequence for isolate NL/1/93 (A2) |
| SEQ ID NO: 95 | G-gene coding sequence for isolate NL/2/93 (A2) |
| SEQ ID NO: 96 | G-gene coding sequence for isolate NL/3/93 (A2) |
| SEQ ID NO: 97 | G-gene coding sequence for isolate NL/1/95 (A2) |
| SEQ ID NO: 98 | G-gene coding sequence for isolate NL/2/96 (A2) |
| SEQ ID NO: 99 | G-gene coding sequence for isolate NL/3/96 (A2) |
| SEQ ID NO: 100 | G-gene coding sequence for isolate NL/22/01 (A2) |
| SEQ ID NO: 101 | G-gene coding sequence for isolate NL/24/01 (A2) |
| SEQ ID NO: 102 | G-gene coding sequence for isolate NL/23/01 (A2) |
| SEQ ID NO: 103 | G-gene coding sequence for isolate NL/29/01 (A2) |
| SEQ ID NO: 104 | G-gene coding sequence for isolate NL/3/02 (A2) |
| SEQ ID NO: 105 | G-gene coding sequence for isolate NL/1/99 (B1) |
| SEQ ID NO: 106 | G-gene coding sequence for isolate NL/11/00 (B1) |
| SEQ ID NO: 107 | G-gene coding sequence for isolate NL/12/00 (B1) |
| SEQ ID NO: 108 | G-gene coding sequence for isolate NL/5/01 (B1) |
| SEQ ID NO: 109 | G-gene coding sequence for isolate NL/9/01 (B1) |
| SEQ ID NO: 110 | G-gene coding sequence for isolate NL/21/01 (B1) |
| SEQ ID NO: 111 | G-gene coding sequence for isolate NL/1/94 (B2) |
| SEQ ID NO: 112 | G-gene coding sequence for isolate NL/1/82 (B2) |

TABLE 14-continued

| LEGEND FOR SEQUENCE LISTING | |
|---|---|
| SEQ ID NO: 113 | G-gene coding sequence for isolate NL/1/96 (B2) |
| SEQ ID NO: 114 | G-gene coding sequence for isolate NL/6/97 (B2) |
| SEQ ID NO: 115 | G-gene coding sequence for isolate NL/9/00 (B2) |
| SEQ ID NO: 116 | G-gene coding sequence for isolate NL/3/01 (B2) |
| SEQ ID NO: 117 | G-gene coding sequence for isolate NL/4/01 (B2) |
| SEQ ID NO: 118 | G-gene coding sequence for isolate UK/5/01 (B2) |
| SEQ ID NO: 119 | G-protein sequence for isolate NL/1/00 (A1) |
| SEQ ID NO: 120 | G-protein sequence for isolate BR/2/01 (A1) |
| SEQ ID NO: 121 | G-protein sequence for isolate FL/4/01 (A1) |
| SEQ ID NO: 122 | G-protein sequence for isolate FL/3/01 (A1) |
| SEQ ID NO: 123 | G-protein sequence for isolate FL/8/01 (A1) |
| SEQ ID NO: 124 | G-protein sequence for isolate FL/10/01 (A1) |
| SEQ ID NO: 125 | G-protein sequence for isolate NL/10/01 (A1) |
| SEQ ID NO: 126 | G-protein sequence for isolate NL/2/02 (A1) |
| SEQ ID NO: 127 | G-protein sequence for isolate NL/17/00 (A2) |
| SEQ ID NO: 128 | G-protein sequence for isolate NL/1/81 (A2) |
| SEQ ID NO: 129 | G-protein sequence for isolate NL/1/93 (A2) |
| SEQ ID NO: 130 | G-protein sequence for isolate NL/2/93 (A2) |
| SEQ ID NO: 131 | G-protein sequence for isolate NL/3/93 (A2) |
| SEQ ID NO: 132 | G-protein sequence for isolate NL/1/95 (A2) |
| SEQ ID NO: 133 | G-protein sequence for isolate NL/2/96 (A2) |
| SEQ ID NO: 134 | G-protein sequence for isolate NL/3/96 (A2) |
| SEQ ID NO: 135 | G-protein sequence for isolate NL/22/01 (A2) |
| SEQ ID NO: 136 | G-protein sequence for isolate NL/24/01 (A2) |
| SEQ ID NO: 137 | G-protein sequence for isolate NL/23/01 (A2) |
| SEQ ID NO: 138 | G-protein sequence for isolate NL/29/01 (A2) |
| SEQ ID NO: 139 | G-protein sequence for isolate NL/3/02 (A2) |
| SEQ ID NO: 140 | G-protein sequence for isolate NL/1/99 (B1) |
| SEQ ID NO: 141 | G-protein sequence for isolate NL/11/00 (B1) |
| SEQ ID NO: 142 | G-protein sequence for isolate NL/12/00 (B1) |
| SEQ ID NO: 143 | G-protein sequence for isolate NL/5/01 (B1) |
| SEQ ID NO: 144 | G-protein sequence for isolate NL/9/01 (B1) |
| SEQ ID NO: 145 | G-protein sequence for isolate NL/21/01 (B1) |
| SEQ ID NO: 146 | G-protein sequence for isolate NL/1/94 (B2) |
| SEQ ID NO: 147 | G-protein sequence for isolate NL/1/82 (B2) |
| SEQ ID NO: 148 | G-protein sequence for isolate NL/1/96 (B2) |
| SEQ ID NO: 149 | G-protein sequence for isolate NL/6/97 (B2) |
| SEQ ID NO: 150 | G-protein sequence for isolate NL/9/00 (B2) |
| SEQ ID NO: 151 | G-protein sequence for isolate NL/3/01 (B2) |
| SEQ ID NO: 152 | G-protein sequence for isolate NL/4/01 (B2) |
| SEQ ID NO: 153 | G-protein sequence for isolate NL/5/01 (B2) |
| SEQ ID NO: 154 | F-gene coding sequence for isolate NL/1/00 |
| SEQ ID NO: 155 | F-gene coding sequence for isolate UK/1/00 |
| SEQ ID NO: 156 | F-gene coding sequence for isolate NL/2/00 |
| SEQ ID NO: 157 | F-gene coding sequence for isolate NL/13/00 |
| SEQ ID NO: 158 | F-gene coding sequence for isolate NL/14/00 |
| SEQ ID NO: 159 | F-gene coding sequence for isolate FL/3/01 |
| SEQ ID NO: 160 | F-gene coding sequence for isolate FL/4/01 |
| SEQ ID NO: 161 | F-gene coding sequence for isolate FL/8/01 |
| SEQ ID NO: 162 | F-gene coding sequence for isolate UK/1/01 |
| SEQ ID NO: 163 | F-gene coding sequence for isolate UK/7/01 |
| SEQ ID NO: 164 | F-gene coding sequence for isolate FL/10/01 |
| SEQ ID NO: 165 | F-gene coding sequence for isolate NL/6/01 |
| SEQ ID NO: 166 | F-gene coding sequence for isolate NL/8/01 |
| SEQ ID NO: 167 | F-gene coding sequence for isolate NL/10/01 |
| SEQ ID NO: 168 | F-gene coding sequence for isolate NL/14/01 |
| SEQ ID NO: 169 | F-gene coding sequence for isolate NL/20/01 |
| SEQ ID NO: 170 | F-gene coding sequence for isolate NL/25/01 |
| SEQ ID NO: 171 | F-gene coding sequence for isolate NL/26/01 |
| SEQ ID NO: 172 | F-gene coding sequence for isolate NL/28/01 |
| SEQ ID NO: 173 | F-gene coding sequence for isolate NL/30/01 |
| SEQ ID NO: 174 | F-gene coding sequence for isolate BR/2/01 |
| SEQ ID NO: 175 | F-gene coding sequence for isolate BR/3/01 |
| SEQ ID NO: 176 | F-gene coding sequence for isolate NL/2/02 |
| SEQ ID NO: 177 | F-gene coding sequence for isolate NL/4/02 |
| SEQ ID NO: 178 | F-gene coding sequence for isolate NL/5/02 |
| SEQ ID NO: 179 | F-gene coding sequence for isolate NL/6/02 |
| SEQ ID NO: 180 | F-gene coding sequence for isolate NL/7/02 |
| SEQ ID NO: 181 | F-gene coding sequence for isolate NL/9/02 |
| SEQ ID NO: 182 | F-gene coding sequence for isolate FL/1/02 |
| SEQ ID NO: 183 | F-gene coding sequence for isolate NL/1/81 |
| SEQ ID NO: 184 | F-gene coding sequence for isolate NL/1/93 |
| SEQ ID NO: 185 | F-gene coding sequence for isolate NL/2/93 |
| SEQ ID NO: 186 | F-gene coding sequence for isolate NL/4/93 |
| SEQ ID NO: 187 | F-gene coding sequence for isolate NL/1/95 |
| SEQ ID NO: 188 | F-gene coding sequence for isolate NL/2/96 |
| SEQ ID NO: 189 | F-gene coding sequence for isolate NL/3/96 |

TABLE 14-continued

LEGEND FOR SEQUENCE LISTING

| | |
|---|---|
| SEQ ID NO: 190 | F-gene coding sequence for isolate NL/1/98 |
| SEQ ID NO: 191 | F-gene coding sequence for isolate NL/17/00 |
| SEQ ID NO: 192 | F-gene coding sequence for isolate NL/22/01 |
| SEQ ID NO: 193 | F-gene coding sequence for isolate NL/29/01 |
| SEQ ID NO: 194 | F-gene coding sequence for isolate NL/23/01 |
| SEQ ID NO: 195 | F-gene coding sequence for isolate NL/17/01 |
| SEQ ID NO: 196 | F-gene coding sequence for isolate NL/24/01 |
| SEQ ID NO: 197 | F-gene coding sequence for isolate NL/3/02 |
| SEQ ID NO: 198 | F-gene coding sequence for isolate NL/3/98 |
| SEQ ID NO: 199 | F-gene coding sequence for isolate NL/1/99 |
| SEQ ID NO: 200 | F-gene coding sequence for isolate NL/2/99 |
| SEQ ID NO: 201 | F-gene coding sequence for isolate NL/3/99 |
| SEQ ID NO: 202 | F-gene coding sequence for isolate NL/11/00 |
| SEQ ID NO: 203 | F-gene coding sequence for isolate NL/12/00 |
| SEQ ID NO: 204 | F-gene coding sequence for isolate NL/1/01 |
| SEQ ID NO: 205 | F-gene coding sequence for isolate NL/5/01 |
| SEQ ID NO: 206 | F-gene coding sequence for isolate NL/9/01 |
| SEQ ID NO: 207 | F-gene coding sequence for isolate NL/19/01 |
| SEQ ID NO: 208 | F-gene coding sequence for isolate NL/21/01 |
| SEQ ID NO: 209 | F-gene coding sequence for isolate UK/11/01 |
| SEQ ID NO: 210 | F-gene coding sequence for isolate FL/1/01 |
| SEQ ID NO: 211 | F-gene coding sequence for isolate FL/2/01 |
| SEQ ID NO: 212 | F-gene coding sequence for isolate FL/5/01 |
| SEQ ID NO: 213 | F-gene coding sequence for isolate FL/7/01 |
| SEQ ID NO: 214 | F-gene coding sequence for isolate FL/9/01 |
| SEQ ID NO: 215 | F-gene coding sequence for isolate UK/10/01 |
| SEQ ID NO: 216 | F-gene coding sequence for isolate NL/1/02 |
| SEQ ID NO: 217 | F-gene coding sequence for isolate NL/1/94 |
| SEQ ID NO: 218 | F-gene coding sequence for isolate NL/1/96 |
| SEQ ID NO: 219 | F-gene coding sequence for isolate NL/6/97 |
| SEQ ID NO: 220 | F-gene coding sequence for isolate NL/7/00 |
| SEQ ID NO: 221 | F-gene coding sequence for isolate NL/9/00 |
| SEQ ID NO: 222 | F-gene coding sequence for isolate NL/19/00 |
| SEQ ID NO: 223 | F-gene coding sequence for isolate NL/28/00 |
| SEQ ID NO: 224 | F-gene coding sequence for isolate NL/3/01 |
| SEQ ID NO: 225 | F-gene coding sequence for isolate NL/4/01 |
| SEQ ID NO: 226 | F-gene coding sequence for isolate NL/11/01 |
| SEQ ID NO: 227 | F-gene coding sequence for isolate NL/15/01 |
| SEQ ID NO: 228 | F-gene coding sequence for isolate NL/18/01 |
| SEQ ID NO: 229 | F-gene coding sequence for isolate FL/6/01 |
| SEQ ID NO: 230 | F-gene coding sequence for isolate UK/5/01 |
| SEQ ID NO: 231 | F-gene coding sequence for isolate UK/8/01 |
| SEQ ID NO: 232 | F-gene coding sequence for isolate NL/12/02 |
| SEQ ID NO: 233 | F-gene coding sequence for isolate HK/1/02 |
| SEQ ID NO: 234 | F-protein sequence for isolate NL/1/00 |
| SEQ ID NO: 235 | F-protein sequence for isolate UK/1/00 |
| SEQ ID NO: 236 | F-protein sequence for isolate NL/2/00 |
| SEQ ID NO: 237 | F-protein sequence for isolate NL/13/00 |
| SEQ ID NO: 238 | F-protein sequence for isolate NL/14/00 |
| SEQ ID NO: 239 | F-protein sequence for isolate FL/3/01 |
| SEQ ID NO: 240 | F-protein sequence for isolate FL/4/01 |
| SEQ ID NO: 241 | F-protein sequence for isolate FL/8/01 |
| SEQ ID NO: 242 | F-protein sequence for isolate UK/1/01 |
| SEQ ID NO: 243 | F-protein sequence for isolate UK/7/01 |
| SEQ ID NO: 244 | F-protein sequence for isolate FL/10/01 |
| SEQ ID NO: 245 | F-protein sequence for isolate NL/6/01 |
| SEQ ID NO: 246 | F-protein sequence for isolate NL/8/01 |
| SEQ ID NO: 247 | F-protein sequence for isolate NL/10/01 |
| SEQ ID NO: 248 | F-protein sequence for isolate NL/14/01 |
| SEQ ID NO: 249 | F-protein sequence for isolate NL/20/01 |
| SEQ ID NO: 250 | F-protein sequence for isolate NL/25/01 |
| SEQ ID NO: 251 | F-protein sequence for isolate NL/26/01 |
| SEQ ID NO: 252 | F-protein sequence for isolate NL/28/01 |
| SEQ ID NO: 253 | F-protein sequence for isolate NL/30/01 |
| SEQ ID NO: 254 | F-protein sequence for isolate BR/2/01 |
| SEQ ID NO: 255 | F-protein sequence for isolate BR/3/01 |
| SEQ ID NO: 256 | F-protein sequence for isolate NL/2/02 |
| SEQ ID NO: 257 | F-protein sequence for isolate NL/4/02 |
| SEQ ID NO: 258 | F-protein sequence for isolate NL/5/02 |
| SEQ ID NO: 259 | F-protein sequence for isolate NL/6/02 |
| SEQ ID NO: 260 | F-protein sequence for isolate NL/7/02 |
| SEQ ID NO: 261 | F-protein sequence for isolate NL/9/02 |
| SEQ ID NO: 262 | F-protein sequence for isolate FL/1/02 |
| SEQ ID NO: 263 | F-protein sequence for isolate NL/1/81 |
| SEQ ID NO: 264 | F-protein sequence for isolate NL/1/93 |
| SEQ ID NO: 265 | F-protein sequence for isolate NL/2/93 |
| SEQ ID NO: 266 | F-protein sequence for isolate NL/4/93 |

TABLE 14-continued

LEGEND FOR SEQUENCE LISTING

| | |
|---|---|
| SEQ ID NO: 267 | F-protein sequence for isolate NL/1/95 |
| SEQ ID NO: 268 | F-protein sequence for isolate NL/2/96 |
| SEQ ID NO: 269 | F-protein sequence for isolate NL/3/96 |
| SEQ ID NO: 270 | F-protein sequence for isolate NL/1/98 |
| SEQ ID NO: 271 | F-protein sequence for isolate NL/17/00 |
| SEQ ID NO: 272 | F-protein sequence for isolate NL/22/01 |
| SEQ ID NO: 273 | F-protein sequence for isolate NL/29/01 |
| SEQ ID NO: 274 | F-protein sequence for isolate NL/23/01 |
| SEQ ID NO: 275 | F-protein sequence for isolate NL/17/01 |
| SEQ ID NO: 276 | F-protein sequence for isolate NL/24/01 |
| SEQ ID NO: 277 | F-protein sequence for isolate NL/3/02 |
| SEQ ID NO: 278 | F-protein sequence for isolate NL/3/98 |
| SEQ ID NO: 279 | F-protein sequence for isolate NL/1/99 |
| SEQ ID NO: 280 | F-protein sequence for isolate NL/2/99 |
| SEQ ID NO: 281 | F-protein sequence for isolate NL/3/99 |
| SEQ ID NO: 282 | F-protein sequence for isolate NL/11/00 |
| SEQ ID NO: 283 | F-protein sequence for isolate NL/12/00 |
| SEQ ID NO: 284 | F-protein sequence for isolate NL/1/01 |
| SEQ ID NO: 285 | F-protein sequence for isolate NL/5/01 |
| SEQ ID NO: 286 | F-protein sequence for isolate NL/9/01 |
| SEQ ID NO: 287 | F-protein sequence for isolate NL/19/01 |
| SEQ ID NO: 288 | F-protein sequence for isolate NL/21/01 |
| SEQ ID NO: 289 | F-protein sequence for isolate UK/11/01 |
| SEQ ID NO: 290 | F-protein sequence for isolate FL/1/01 |
| SEQ ID NO: 291 | F-protein sequence for isolate FL/2/01 |
| SEQ ID NO: 292 | F-protein sequence for isolate FL/5/01 |
| SEQ ID NO: 293 | F-protein sequence for isolate FL/7/01 |
| SEQ ID NO: 294 | F-protein sequence for isolate FL/9/01 |
| SEQ ID NO: 295 | F-protein sequence for isolate UK/10/01 |
| SEQ ID NO: 296 | F-protein sequence for isolate NL/1/02 |
| SEQ ID NO: 297 | F-protein sequence for isolate NL/1/94 |
| SEQ ID NO: 298 | F-protein sequence for isolate NL/1/96 |
| SEQ ID NO: 299 | F-protein sequence for isolate NL/6/97 |
| SEQ ID NO: 300 | F-protein sequence for isolate NL/7/00 |
| SEQ ID NO: 301 | F-protein sequence for isolate NL/9/00 |
| SEQ ID NO: 302 | F-protein sequence for isolate NL/19/00 |
| SEQ ID NO: 303 | F-protein sequence for isolate NL/28/00 |
| SEQ ID NO: 304 | F-protein sequence for isolate NL/3/01 |
| SEQ ID NO: 305 | F-protein sequence for isolate NL/4/01 |
| SEQ ID NO: 306 | F-protein sequence for isolate NL/11/01 |
| SEQ ID NO: 307 | F-protein sequence for isolate NL/15/01 |
| SEQ ID NO: 308 | F-protein sequence for isolate NL/18/01 |
| SEQ ID NO: 309 | F-protein sequence for isolate FL/6/01 |
| SEQ ID NO: 310 | F-protein sequence for isolate UK/5/01 |
| SEQ ID NO: 311 | F-protein sequence for isolate UK/8/01 |
| SEQ ID NO: 312 | F-protein sequence for isolate NL/12/02 |
| SEQ ID NO: 313 | F-protein sequence for isolate HK/1/02 |
| SEQ ID NO: 314 | F protein sequence for HMPV isolate NL/1/00 |
| SEQ ID NO: 315 | F protein sequence for HMPV isolate NL/17/00 |
| SEQ ID NO: 316 | F protein sequence for HMPV isolate NL/1/99 |
| SEQ ID NO: 317 | F protein sequence for HMPV isolate NL/1/94 |
| SEQ ID NO: 318 | F-gene sequence for HMPV isolate NL/1/00 |
| SEQ ID NO: 319 | F-gene sequence for HMPV isolate NL/17/00 |
| SEQ ID NO: 320 | F-gene sequence for HMPV isolate NL/1/99 |
| SEQ ID NO: 321 | F-gene sequence for HMPV isolate NL/1/94 |
| SEQ ID NO: 322 | G protein sequence for HMPV isolate NL/1/00 |
| SEQ ID NO: 323 | G protein sequence for HMPV isolate NL/17/00 |
| SEQ ID NO: 324 | G protein sequence for HMPV isolate NL/1/99 |
| SEQ ID NO: 325 | G protein sequence for HMPV isolate NL/1/94 |
| SEQ ID NO: 326 | G-gene sequence for HMPV isolate NL/1/00 |
| SEQ ID NO: 327 | G-gene sequence for HMPV isolate NL/17/00 |
| SEQ ID NO: 328 | G-gene sequence for HMPV isolate NL/1/99 |
| SEQ ID NO: 329 | G-gene sequence for HMPV isolate NL/1/94 |
| SEQ ID NO: 330 | L protein sequence for HMPV isolate NL/1/00 |
| SEQ ID NO: 331 | L protein sequence for HMPV isolate NL/17/00 |
| SEQ ID NO: 332 | L protein sequence for HMPV isolate NL/1/99 |
| SEQ ID NO: 333 | L protein sequence for HMPV isolate NL/1/94 |
| SEQ ID NO: 334 | L-gene sequence for HMPV isolate NL/1/00 |
| SEQ ID NO: 335 | L-gene sequence for HMPV isolate NL/17/00 |
| SEQ ID NO: 336 | L-gene sequence for HMPV isolate NL/1/99 |
| SEQ ID NO: 337 | L-gene sequence for HMPV isolate NL/1/94 |
| SEQ ID NO: 338 | M2-1 protein sequence for HMPV isolate NL/1/00 |
| SEQ ID NO: 339 | M2-1 protein sequence for HMPV isolate NL/17/00 |
| SEQ ID NO: 340 | M2-1 protein sequence for HMPV isolate NL/1/99 |
| SEQ ID NO: 341 | M2-1 protein sequence for HMPV isolate NL/1/94 |
| SEQ ID NO: 342 | M2-1 gene sequence for HMPV isolate NL/1/00 |
| SEQ ID NO: 343 | M2-1 gene sequence for HMPV isolate NL/17/00 |

TABLE 14-continued

| LEGEND FOR SEQUENCE LISTING | |
|---|---|
| SEQ ID NO: 344 | M2-1 gene sequence for HMPV isolate NL/1/99 |
| SEQ ID NO: 345 | M2-1 gene sequence for HMPV isolate NL/1/94 |
| SEQ ID NO: 346 | M2-2 protein sequence for HMPV isolate NL/1/00 |
| SEQ ID NO: 347 | M2-2 protein sequence for HMPV isolate NL/17/00 |
| SEQ ID NO: 348 | M2-2 protein sequence for HMPV isolate NL/1/99 |
| SEQ ID NO: 349 | M2-2 protein sequence for HMPV isolate NL/1/94 |
| SEQ ID NO: 350 | M2-2 gene sequence for HMPV isolate NL/1/00 |
| SEQ ID NO: 351 | M2-2 gene sequence for HMPV isolate NL/17/00 |
| SEQ ID NO: 352 | M2-2 gene sequence for HMPV isolate NL/1/99 |
| SEQ ID NO: 353 | M2-2 gene sequence for HMPV isolate NL/1/94 |
| SEQ ID NO: 354 | M2 gene sequence for HMPV isolate NL/1/00 |
| SEQ ID NO: 355 | M2 gene sequence for HMPV isolate NL/17/00 |
| SEQ ID NO: 356 | M2 gene sequence for HMPV isolate NL/1/99 |
| SEQ ID NO: 357 | M2 gene sequence for HMPV isolate NL/1/94 |
| SEQ ID NO: 358 | M protein sequence for HMPV isolate NL/1/00 |
| SEQ ID NO: 359 | M protein sequence for HMPV isolate NL/17/00 |
| SEQ ID NO: 360 | M protein sequence for HMPV isolate NL/1/99 |
| SEQ ID NO: 361 | M protein sequence for HMPV isolate NL/1/94 |
| SEQ ID NO: 362 | M gene sequence for HMPV isolate NL/1/00 |
| SEQ ID NO: 363 | M gene sequence for HMPV isolate NL/17/00 |
| SEQ ID NO: 364 | M gene sequence for HMPV isolate NL/1/99 |
| SEQ ID NO: 365 | M gene sequence for HMPV isolate NL/1/94 |
| SEQ ID NO: 366 | N protein sequence for HMPV isolate NL/1/00 |
| SEQ ID NO: 367 | N protein sequence for HMPV isolate NL/17/00 |

TABLE 14-continued

| LEGEND FOR SEQUENCE LISTING | |
|---|---|
| SEQ ID NO: 368 | N protein sequence for HMPV isolate NL/1/99 |
| SEQ ID NO: 369 | N protein sequence for HMPV isolate NL/1/94 |
| SEQ ID NO: 370 | N gene sequence for HMPV isolate NL/1/00 |
| SEQ ID NO: 371 | N gene sequence for HMPV isolate NL/17/00 |
| SEQ ID NO: 372 | N gene sequence for HMPV isolate NL/1/99 |
| SEQ ID NO: 373 | N gene sequence for HMPV isolate NL/1/94 |
| SEQ ID NO: 374 | P protein sequence for HMPV isolate NL/1/00 |
| SEQ ID NO: 375 | P protein sequence for HMPV isolate NL/17/00 |
| SEQ ID NO: 376 | P protein sequence for HMPV isolate NL/1/99 |
| SEQ ID NO: 377 | P protein sequence for HMPV isolate NL/1/94 |
| SEQ ID NO: 378 | P gene sequence for HMPV isolate NL/1/00 |
| SEQ ID NO: 379 | P gene sequence for HMPV isolate NL/17/00 |
| SEQ ID NO: 380 | P gene sequence for HMPV isolate NL/1/99 |
| SEQ ID NO: 381 | P gene sequence for HMPV isolate NL/1/94 |
| SEQ ID NO: 382 | SH protein sequence for HMPV isolate NL/1/00 |
| SEQ ID NO: 383 | SH protein sequence for HMPV isolate NL/17/00 |
| SEQ ID NO: 384 | SH protein sequence for HMPV isolate NL/1/99 |
| SEQ ID NO: 385 | SH protein sequence for HMPV isolate NL/1/94 |
| SEQ ID NO: 386 | SH gene sequence for HMPV isolate NL/1/00 |
| SEQ ID NO: 387 | SH gene sequence for HMPV isolate NL/17/00 |
| SEQ ID NO: 388 | SH gene sequence for HMPV isolate NL/1/99 |
| SEQ ID NO: 389 | SH gene sequence for HMPV isolate NL/1/94 |

What is claimed is:

1. An isolated infectious, replicating human metapneumovirus (hMPV) wherein the virus comprises at least one genetic modification resulting in at least one alteration from the RQSR sequence (SEQ ID# 395) at amino acid positions 99 to 102 of the F protein; Glu at amino acid position 749 of the L protein; Met at amino acid position 1094 of the L protein, and Lys at amino acid position 746 of the L protein.

2. The virus of claim 1, wherein the genetic modification is a deletion, a substitution or an addition.

3. The virus of claim 1, wherein at least one of the genetic alterations consists of 2 or 3 nucleotide substitutions or deletions per codon.

4. The virus of claim 1, wherein the amino acid at position 101 of the F protein is a proline.

5. The virus of claim 1 or 4, wherein the F protein of the virus is cleaved in the absence of trypsin.

6. The virus of claim 1 or 4, wherein the virus is infectious in the absence of trypsin, as tested by a plaque assay, wherein:

(i) recombinant hMPV is rescued in 293T cells, in OPTI-MEM media in the presence of LIPOFECTAMINE; and (ii) transfected 293T cells and supernatant are collected, frozen, thawed and used to inoculate Vero cells.

* * * * *